(12) United States Patent
Sato et al.

(10) Patent No.: US 10,626,095 B2
(45) Date of Patent: Apr. 21, 2020

(54) CYANOTRIAZOLE COMPOUNDS

(71) Applicant: OTSUKA PHARMACEUTICAL CO., LTD., Tokyo (JP)

(72) Inventors: Seiji Sato, Osaka (JP); Satoshi Matsuda, Osaka (JP); Chiharu Matsumura, Osaka (JP); Motohiro Itotani, Osaka (JP); Toshio Shinohara, Osaka (JP); Shigekazu Fujita, Osaka (JP); Yohji Sakurai, Osaka (JP); Kuninori Tai, Osaka (JP); Tae Fukushima, Osaka (JP); Naohide Kanemoto, Osaka (JP); Takashi Okamoto, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 262 days.

(21) Appl. No.: 14/905,310

(22) PCT Filed: Jul. 16, 2014

(86) PCT No.: PCT/JP2014/069501
§ 371 (c)(1),
(2) Date: Jan. 15, 2016

(87) PCT Pub. No.: WO2015/008872
PCT Pub. Date: Jan. 22, 2015

(65) Prior Publication Data
US 2016/0229816 A1    Aug. 11, 2016

Related U.S. Application Data

(60) Provisional application No. 61/928,267, filed on Jan. 16, 2014, provisional application No. 61/885,254, (Continued)

(51) Int. Cl.

| | | |
|---|---|---|
| *C07D 249/06* | (2006.01) |
| *C07D 403/12* | (2006.01) |
| *C07D 413/14* | (2006.01) |
| *C07D 401/12* | (2006.01) |
| *C07D 405/12* | (2006.01) |
| *C07D 417/12* | (2006.01) |
| *C07D 417/14* | (2006.01) |
| *C07D 249/04* | (2006.01) |
| *C07D 403/14* | (2006.01) |

(Continued)

(52) U.S. Cl.
CPC ......... *C07D 249/06* (2013.01); *C07D 249/04* (2013.01); *C07D 401/10* (2013.01); *C07D 401/12* (2013.01); *C07D 401/14* (2013.01); *C07D 403/10* (2013.01); *C07D 403/12* (2013.01); *C07D 403/14* (2013.01); *C07D 405/10* (2013.01); *C07D 405/12* (2013.01); *C07D 405/14* (2013.01); *C07D 409/10* (2013.01); *C07D 409/12* (2013.01); *C07D 409/14* (2013.01); *C07D 411/12* (2013.01); *C07D 411/14* (2013.01); *C07D 413/04* (2013.01); *C07D 413/10* (2013.01); *C07D 413/12* (2013.01); *C07D 413/14* (2013.01); *C07D 417/04* (2013.01); *C07D 417/12* (2013.01); *C07D 417/14* (2013.01); *C07D 471/04* (2013.01); *C07F 9/5456* (2013.01)

(58) Field of Classification Search
None
See application file for complete search history.

(56) References Cited

U.S. PATENT DOCUMENTS

| | | | |
|---|---|---|---|
| 3,826,803 A | 7/1974 | Tolman et al. |
| 3,928,373 A | 12/1975 | Beck et al. |

(Continued)

FOREIGN PATENT DOCUMENTS

| | | |
|---|---|---|
| CN | 1651418 A | 8/2005 |
| DE | 2126839 A | 12/1972 |

(Continued)

OTHER PUBLICATIONS

STN 39807-67-5, 1984 (Year: 1984).*

(Continued)

*Primary Examiner* — Jeffrey S Lundgren
*Assistant Examiner* — Michael J Schmitt
(74) *Attorney, Agent, or Firm* — Sughrue Mion, PLLC

(57) ABSTRACT

This invention relates to a cyanotriazole compound represented by the formula (1):

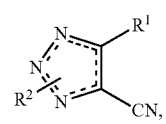

(1)

wherein each symbols are defined in the specification, or a salt thereof. The compound or a salt thereof stimulates the citric acid cycle activity and/or improves hyperglycemia with less side effects, and excellent safety, and therefore, it is useful for treating and/or preventing diseases or disorders on which citric acid cycle activation and/or improvement of hyperglycemia has a prophylactic and/or therapeutic effect, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure.

11 Claims, 2 Drawing Sheets

Related U.S. Application Data filed on Oct. 1, 2013, provisional application No. 61/847,268, filed on Jul. 17, 2013.

(51) Int. Cl.

| | |
|---|---|
| *C07D 411/14* | (2006.01) |
| *C07D 413/12* | (2006.01) |
| *C07D 411/12* | (2006.01) |
| *C07D 405/14* | (2006.01) |
| *C07D 401/14* | (2006.01) |
| *C07D 401/10* | (2006.01) |
| *C07D 403/10* | (2006.01) |
| *C07D 405/10* | (2006.01) |
| *C07D 409/10* | (2006.01) |
| *C07D 409/12* | (2006.01) |
| *C07D 409/14* | (2006.01) |
| *C07D 413/04* | (2006.01) |
| *C07D 413/10* | (2006.01) |
| *C07D 417/04* | (2006.01) |
| *C07D 471/04* | (2006.01) |
| *C07F 9/54* | (2006.01) |

(56) References Cited

U.S. PATENT DOCUMENTS

| | | | |
|---|---|---|---|
| 4,001,221 A * | 1/1977 | Gunther | C07C 317/00 548/224 |
| 4,039,531 A | 8/1977 | Günther et al. | |
| 4,431,589 A | 2/1984 | Chakrabarti et al. | |
| 4,489,072 A | 12/1984 | Sadaki et al. | |
| 4,935,505 A | 6/1990 | Townsend et al. | |
| 2006/0069013 A1 | 3/2006 | Ostergaard et al. | |
| 2006/0258561 A1 | 11/2006 | Balschmidt et al. | |

FOREIGN PATENT DOCUMENTS

| | | |
|---|---|---|
| DE | 3137854 A1 | 4/1982 |
| EP | 1 921 072 A1 | 5/2008 |
| JP | 51-53529 C | 5/1976 |
| JP | 57122087 A | 7/1982 |
| JP | 2006519791 A | 8/2006 |
| JP | 2007523842 A | 8/2007 |
| WO | 01/19770 A2 | 3/2001 |
| WO | 2006005683 A1 | 1/2006 |
| WO | 2006/082245 A1 | 8/2006 |
| WO | 2011/140296 A1 | 11/2011 |

OTHER PUBLICATIONS

STN 39807-70-0, 1984 (Year: 1984).*
STN 102109-15-9, 1986 (Year: 1986).*
STN REG No. 907202-66-8 (Year: 2006).*
STN REG No. 907202-65-7 (Year: 2006).*
STN REG No. 82549-49-3 (Year: 1984).*
STN REG No. 74336-28-0 (Year: 1984).*
Office Action dated Sep. 30, 2017 in corresponding Chinese Application No. 201480040496.3.
Office Action dated Nov. 17, 2016 from the State Intellectual Property Office of the P.R.C. in counterpart Chinese Application No. 201480040496.3.
Zachary T. Bloomgarden, MD, "World Congress on Insulin Resistance, Diabetes, and Cardiovascular Disease", Diabetes Care, Jul. 2011, vol. 34, pp. e115-e120 (part 1).
Zachary T. Bloomgarden, MD, "World Congress on Insulin Resistance, Diabetes, and Cardiovascular Disease", Diabetes Care, Aug. 2011, vol. 34, pp. e126-e131 (part 2).
Zachary T. Bloomgarden, MD, "World Congress on Insulin Resistance, Diabetes, and Cardiovascular Disease", Diabetes Care, Sep. 2011, vol. 34, pp. e140-e145 (part 3).
Zachary T. Bloomgarden, MD, "World Congress on Insulin Resistance, Diabetes, and Cardiovascular Disease", Diabetes Care, Oct. 2011, vol. 34, pp. e152-e157 (part 4).
IDF Diabetes Atlas Fifth Edition, 2011, 5th Ed, International Diabetes Federation, 143 pgs. total.
Antonio Ceriello, MD et al., "Postprandial Glucose Regulation and Diabetic Complications", Arch Intern Med, Oct. 25, 2004, vol. 164, pp. 2090-2095.
F. Cavalot et al., "Postprandial Blood Glucose Is a Stronger Predictor of Cardiovascular Events Than Fasting Blood Glucose in Type 2 Diabetes Mellitus, Particularly in Women: Lessons from the San Luigi Gonzaga Diabetes Study", The Journal of Clinical Endocrinology & Metabolism, 2006, vol. 91, No. 3, pp. 813-819.
Theodora S. Temelkova-Kurktschiev, MD, PhD et al., "Postchallenge Plasma Glucose and Glycemic Spikes Are More Strongly Associated With Atherosclerosis Than Fasting Glucose or $HbA_{1C}$ Level", Diabetes Care, Dec. 2000, vol. 23, No. 12, pp. 1830-1834.
Yaomin Hu et al., "Postchallenge plasma glucose excurions, carotid intima-media thickness, and risk factors for atherosclerosis in Chinese population with type 2 diabetes", Atherosclerosis, 2010, vol. 210, pp. 302-306.
James H. O'Keefe, MD et al., "Postprandial Hyperglycemia/Hyperlipidemia (Postprandial Dysmetabolism) Is a Cardiovascular Risk Factor", The American Journal of Cardiology, 2007, vol. 100, pp. 899-904.
Eunice Mah et al., "Postprandial Hyperglycemia on vascular endothelial function: mechanisms and consequences", Nutrition Research, vol. 32, 2012, pp. 727-740.
Jean-Louis Chiasson et al., "Acarbose for prevention of type 2 diabetes mellitus: the STOP-NIDDM randomised trial", Lancet, Jun. 15, 2002, vol. 359, pp. 2072-2077.
Jean-Louis Chiasson, MD et al., "Acarbose Treatment and the Risk of Cardiovascular Disease and Hypertension in Patients With Impaired Glucose Tolerance: The STOP-NIDDM Trial", JAMA, Jul. 23-30, 2003, vol. 290, No. 4, pp. 486-494.
The Navigator Study Group, "Effect of Nateglinide on the Incidence of Diabetes and Cardiovascular Events", The New England Journal of Medicine, Apr. 22, 2010, vol. 362, No. 16, pp. 1463-1476.
Benjamin M. Scirica, M.D., M.P.H. et al, "Saxagliptin and Cardiovascular Outcomes in Patients with Type 2 Diabetes Mellitus", The New England Journal of Medicine, Oct. 3, 2013, vol. 369, No. 14, pp. 1317-1326.
William B. White, M.D. et al., "Alogliptin after Acute Coronary Syndrome in Patients with Type 2 Diabetes", The New England Journal of Medicine, Oct. 3, 2013, vol. 369, No. 14, pp. 1327-1335.
Nancy T. Artinian, PhD et al., "Interventions to Promote Physical Activity and Dietary Lifestyle Changes for Cardiovascular Risk Factor Reduction in Adults: A Scientific Statement From the American Heart Association", Circulation, 2010, vol. 122, pp. 406-441 (37 pgs. total).
L. Busetto et al., "Obesity treatment in elderly outpatients: Predictors of efficacy and drop-out", Eating Weight Disord., 2009, vol. 14, No. 2-3, pp. e56-e65.
Biochimica et Biophysica Acta—Bioenergetics 1817, pp. S123.
International Search Report dated Nov. 18, 2014 in counterpart International Application No. PCT/JP2014/069501.
International Preliminary Report on Patentability dated Jan. 19, 2016 from the International Bureau in counterpart International Application No. PCT/JP2014/069501.
Jin et al., "One-Pot, Three-Component Synthesis of 1,4,5-Trisubstituted 1,2,3-Triazoles Starting from Primary Alcohols," Aug. 16, 2012 European Journal of Organic Chemistry, pp. 5446-5449.
Ponpandian et al., "Tandem Knoevenagel-[3+2] cycloaddition-elimination reactions: one-pot synthesis of 4,5-disubstituted 1,2,3-(NH)-triazoles," Tetrahedron Letters 53 (2012; available online Nov. 3, 2011) 59-63.
Nitsche et al., "Arylcyanoacrylamides as inhibitors of the Dengue and West Nile virus proteases", Bioorganic & Medicinal Chemistry vol. 19, No. 24 (2011) 7318-7337.

(56) References Cited

OTHER PUBLICATIONS

Fringuelli et al., "Amberlite IRA900F as a Solid Fluoride Source for a Variety of Organic Transformations under Solvent-Free Conditions", European Journal of Organic Chemistry (2008) pp. 3928-3932.

Cheng et al., "Synthesis and biological evaluation of 4-aryl-5-cyano-2H-1,2,3-triazoles as inhibitor of HER2 tyrosine kinase", Bioorganic & Medicinal Chemistry vol. 15, No. 3 (2007) 1533-1538.

Communication dated May 30, 2018 from the Australian Patent Office in counterpart Australian application No. 2014291142.

Piet, J.C., et al., "Reactions des Methylazide et Phenylazide Avec Quelques Alcynes et Olefines α-Nitrees. Synthese Regiospecifique des 1,2,3 Triazoles", Bulletin des Societes Chimiques Beiges, vol. 105, No. 1, 1996, pp. 33-44.

Nemeryuk, M., et al., "Transformations of Substituted 5-Aminopyrimidines Under Conditions of the Diazotization", Collection of Czechoslovak Chemical Communications, vol. 51, No. 1, 1986, pp. 215-233.

Gao, Y., et al., "[3+2] Cycloaddition Reactions in the Solid-Phase Synthesis of 1,2,3-Triazoles", Organic Letters, vol. 8, No. 15, 2006, pp. 3283-3285.

Database; C: \EPODATA\SEA\eplogf\ep14748306.log; pp. 1-15.

Communication dated Jan. 28, 2019 issued by the European Patent Office in European Application No. 14 748 306.9.

Communication dated Jun. 6, 2019 by the Indian Patent Office in application No. 201647004855.

\* cited by examiner

CYANOTRIAZOLE COMPOUNDS

CROSS REFERENCE TO RELATED APPLICATIONS

This application is a National Stage of International Application No. PCT/JP2014/069501 filed Jul. 16, 2014, claiming priorities based on United States Provisional Patent Application Nos. 61/847,268 filed Jul. 17, 2013, 61/885,254 filed Oct. 1, 2013, and 61/928,267 filed Jan. 16, 2014, the contents of all of which are incorporated herein by reference in their entirety.

TECHNICAL FIELD

This invention relates to cyanotriazole compounds which stimulate the citric acid cycle activity and/or improve hyperglycemia. The citric acid cycle activators are useful for treating and/or preventing diseases or disorders related to energy imbalance which comes from less energy output than calorie intake. Besides, the hypoglycemic agents are helpful for treating diabetes and impaired glucose tolerance accompanied by postprandial hyperglycemia. The compounds of this invention possessing activities of promoting the citric acid cycle and/or reducing blood glucose are applicable to, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure.

BACKGROUND ART

Overweight, obesity and insulin resistance associated with them are major risk factors for a number of chronic diseases including diabetes and cardiovascular diseases (non-patent documents 1-4), especially, the global pandemic of diabetes is serious problem for public health and puts a huge burden on healthcare system in the world (non-patent document 5). Although various oral and injectable hypoglycemic drugs have been developed and launched, the efforts to stop or to slow down the growth rate of diabetes-related mortality and morbidity are not still going well. Postprandial hyperglycemia (PPH) which is one of phenomenon of blood glucose dysregulation seen in diabetes and impaired glucose tolerance (IGT) is cautioned as an independent risk factor for cardiovascular disease (non-patent documents 6-7). Close relation between PPH and carotid intima-media thickness suggested that PPH was associated with atherosclerosis (non-patent documents 8-9). Some recent studies imply that PPH causes vascular inflammation and endothelial dysfunction through oxidative stress during PPH (non-patent documents 10-11). Three types of oral anti-diabetics, α-glucosidase inhibitors, glinides and DPP4 inhibitors, were developed aiming to lower PPH. Acarbose, a member of the α-glucosidase inhibitors class, showed a promising result that its treatment reduce both the risk of diabetes progression in patients with IGT and the incidence of cardiovascular disease in its clinical trial "STOP-NIDDM" (non-patent documents 12-13), however, another drug, a member of the glinides class, nateglinide failed to show its benefits in the trial "NAVIGATOR" (non-patent document 14). In addition, two DPP4 inhibitors, saxagliptin and alogliptin, did not have benefits for cardiovascular disease risk reduction in their clinical outcome trials, "SAVOR-TIMI 53" (non-patent document 15) and "EXAMIN" (non-patent document 16), respectively. Considering such a wavering situation, more efficacious and safer anti-diabetic agents having potency to lower PPH should be desirable for suppressing diabetes epidemic and also relieving diabetic vascular complications. Screening for new compounds with lowering PPH resulted in finding newly synthesized cyanotriazol compounds which reduced PPH after meal loading in Zucker Diabetic Fatty rats, one of type 2 diabetes model rats which show severe hyperglycemia and insulin resistance. This result demonstrated that the cyanotriazol compounds would be applicable to treating diabetes and preventing diabetic various complications.

When metabolic disorders including diabetes, obesity and so on are considered, they are highly involved in energy imbalance between energy expenditure and calorie intake. Although proper dietary restriction and exercise are best means for improving the metabolic disorders (non-patent document 17), it has been proved that the efficacy by themselves was insufficient (non-patent document 19) and drug intervention facilitated raising the probability of achieving clinical treatment target. Thus, modulation, particularly augmentation, of cellular energy expenditure is an attractive drug target to correct such energy imbalance-related disorders. The citric acid cycle has pivotal and mandatory roles in the aerobic metabolism, which mainly reduces $NAD^+$ to NADH and discharges carbon dioxide from metabolizing various energy substrates. We conceived that this cycle activation may lead to promote energy metabolism and expenditure, therefore we has conducted drug discovery screening to find synthetic chemical compounds with promoting citric acid cycle activity. Consequently, we found newly synthesized cyanotriazol compounds with strong efficacy on stimulating cellular citric acid cycle substrate consumption by measuring intracellular radiolabeled content derived from $[^{14}C]$-citrate. For further certification, we employed an extracellular flux analyzer (XF24-3; Seahorse Bioscience) to measure actual carbon dioxide evolution rate (CDER) in cultured cells treated by several screened compounds (non-patent document 19). The analysis proved that the tested compounds accelerated not only CDER and but also oxygen consumption rate (OCR), which indicates energy expenditure is highly stimulated by the compounds.

In this invention, we found that newly synthesized cyanotriazole compounds have strong efficacy to improve hyperglycemia and/or to stimulate the citric acid cycle activity. Not limiting the usage as an anti-obesity and/or diabetic drug, expected profits by a cyanotriazol compound are curative or preventive effects on diseases or disorders related to energy imbalance which comes from less energy output than calorie intake, for example, impaired glucose tolerance, insulin resistance, diabetic complication, dyslipidemia, hepatic steatosis, atherosclerosis and/or cardiovascular disease, as well as diseases or disorders that would benefit from stimulating energy expenditure.

Patent Document 1 discloses a production method of cyanotriazole compounds.

Patent Document 2 and Non-Patent Documents 20-21 disclose a cyanotriazole compound as a human epidermis growth factor receptor 2 tyrosinase inhibitor.

Patent Document 3 discloses a production method of cyanotriazole compounds.

Patent Document 4 discloses a cyanotriazole compound as an inhibitor of fatty acid synthase.

Document List

Patent Documents

[Patent Document 1] JP-A-51-53529
[Patent Document 2] CN 1651418 A

[Patent Document 3] U.S. Pat. No. 4,039,531
[Patent Document 4] WO 2011/140296

Non-Patent Documents

[Non-Patent Document 1] Diabetes Care, 2011, 34, e115-120'
[Non-Patent Document 2] Diabetes Care, 2011, 34, e126-131
[Non-Patent Document 3] Diabetes Care, 2011, 34, e140-145
[Non-Patent Document 4] Diabetes Care, 2011, 34, e152-157
[Non-Patent Document 5] IDF DIABETES ATLAS Fifth edition, 2011, 5$^{th}$ Ed, International Diabetes Federation
[Non-Patent Document 6] Arch Intern Med 164, 2090-2095
[Non-Patent Document 7] J Clin Endocrinol Metab 91, 813-819
[Non-Patent Document 8] Diabetes Care 23, 1830-1834
[Non-Patent Document 9] Atherosclerosis 210, 302-306
[Non-Patent Document 10] Am J Cardiol 100, 899-904
[Non-Patent Document 11] Nutr Res 32, 727-740
[Non-Patent Document 12] Lancet 359, 2072-2077
[Non-Patent Document 13] JAMA 250, 486-494
[Non-Patent Document 14] N Engl J Med 362, 1463-1476
[Non-Patent Document 15] N Engl J Med 369, 1317-1326
[Non-Patent Document 16] N Engl J Med 369, 1327-1335
[Non-Patent Document 17] Circulation 122, 406-441
[Non-Patent Document 18] Eat Weight Disord 14, e56-65
[Non-Patent Document 19] Biochimica et Biophysica Acta—Bioenergetics 1817, S123
[Non-Patent Document 20] Bioorganic Medicinal Chemistry, vol. 15, 2007, 1533-1538
[Non-Patent Document 21] Tetrahedron Letters, 53, 2012, 59-63

SUMMARY OF THE INVENTION

Problems to be Solved by the Invention

An object of the present invention is therefore to provide a compound which stimulates the citric acid cycle activity and/or improves hyperglycemia with less side effects, and excellent safety, and is useful for treating and/or preventing diseases or disorders on which citric acid cycle activation and/or improvement of hyperglycemia has a prophylactic and/or therapeutic effect, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure.

Means of Solving the Problems

The present inventors intensively conducted studies with the view to attaining the aforementioned object. As a result, they found that a cyanotriazole compound represented by the general formula (1) below and a salt thereof stimulates the citric acid cycle activity and/or improves hyperglycemia with less side effects, and excellent safety, and is useful for treating and/or preventing diseases or disorders on which citric acid cycle activation and/or improvement of hyperglycemia has a prophylactic and/or therapeutic effect, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure. The present invention has been achieved based on the finding.

The present invention provides a cyanotriazole compound represented by the formula (1):

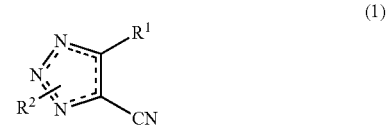

wherein
$R^1$ is a phenyl group, a thiazolyl group, a thienyl group, a pyridyl group or a quinolyl group, each of which is substituted (provided that the phenyl group is substituted with a lower alkyl group, a lower alkoxy group, a lower alkylthio group, a halogen atom, a phenoxy group or a carboxy group, then the phenyl group is substituted with additional one or more substituents); or an oxazolyl group, a furyl group, a pyrrolyl group, a piperidyl group, an indolyl group, a benzofuryl group, a benzothienyl group, a phenyl lower alkyl group, a pyrimidinyl group, a 2,3-dihydroindolyl group, an imidazolyl group, a benzothiazolyl group, an isoxazolyl group, a 2,3-dihydrobenzofuryl group, an isothiazolyl group, a dibenzofuryl group, a benzo[1,3]dioxolyl group, a carbazolyl group, a naphthyl group, a 2-oxo-1,2,3,4-tetrahydroquinolyl group, a 6-oxo-1,6-dihydropyrimidinyl group, an imidazo[1,2-a]pyridyl group, an oxadiazolyl group, a thiadiazolyl group, a benzoxazolyl group, a styryl group, a benzoyl group, a cycloalkyl group, a higher alkyl group, a 2-oxo-1,2-dihydroquinolyl group, a benzimidazolyl group, a 2,3-dihydro[1,4]benzodioxinyl group, a fluorenyl group, a bicyclo[2,2,1]hept-2-enyl group, a thieno[3,2-b]pyridyl group, an imidazo[1,2-a]benzimidazolyl group, a 3,4-dihydro-2H-[1,4]benzoxazinyl group, a 3,4-dihydro-2H-benzo[b][1,4]dioxepinyl group or an amino group, each of which is optionally substituted; and
$R^2$ is
(1) a hydrogen atom,
(2) a lower alkyl group optionally substituted with one or more substituents excluding an oxo group, or
(3) a heterocyclyl group optionally substituted with one or more substituents;
provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
methyl 4-[4-(4-cyano-1,2,3-triazol-5-yl)styryl]benzoate;
5-[4-(4-cyanostyryl)phenyl]-1,2,3-triazole-4-carbonitrile;
5-{4-[4-(N,N-dimethylamino)styryl]phenyl}-1,2,3-triazole-4-carbonitrile;
5-{4-[2-(biphenyl-4-yl)vinyl]phenyl}-1,2,3-triazole-4-carbonitrile;
5-{4-[4-(2-oxo-2H-chromen-3-yl)styryl]phenyl}-1,2,3-triazole-4-carbonitrile;
5-{4-[4-(benzo[d]oxazol-2-yl)styryl]phenyl}-1,2,3-triazole-4-carbonitrile;
5-{4-[2-(2-methoxynaphthalen-1-yl)vinyl]phenyl}-1,2,3-triazole-4-carbonitrile;

5-{4-[2-(4-methoxynaphthalen-1-yl)vinyl]phenyl}-1,2,3-triazole-4-carbonitrile;
5-{4-[2-(pyridin-4-yl)vinyl]phenyl}-1,2,3-triazole-4-carbonitrile;
5-{4-[2-(thiophen-2-yl)vinyl]phenyl}-1,2,3-triazole-4-carbonitrile;
5-{4-[2-(benzofuran-2-yl)vinyl]phenyl}-1,2,3-triazole-4-carbonitrile;
5-[4-(4-formylstyryl)phenyl]-1,2,3-triazole-4-carbonitrile;
5-{4-[2-(4'-formylbiphenyl-4-yl)vinyl]phenyl}-1,2,3-triazole-4-carbonitrile;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(3-fluoro-4-phenoxyphenyl)-5-cyano-1,2,3-triazole;
4-(4-fluoro-3-phenoxyphenyl)-5-cyano-1,2,3-triazole;
4-(4-fluoro-3-methoxyphenyl)-1,2,3-triazole-5-carbonitrile;
(5-(5-cyano-1,2,3-triazol-4-yl)furan-2-yl)methyl acetate;
2-[4-(4'-benzoxazole-2-yl-stilbene-4-yl)-5-cyano-1,2,3-triazole-N-yl]acetic acid methyl ester;
4-(4-(4-(1H-benzo[d]imidazol-2-yl)styryl)phenyl)-N-trityl-1,2,3-triazole-5-carbonitrile;
2-(4-(4-(1H-benzo[d]imidazol-2-yl)styryl)phenyl)-5-cyano-1,2,3-triazol-N-yl)acetamide;
2-(4-(4-(1H-benzo[d]imidazol-2-yl)styryl)phenyl)-5-cyano-1,2,3-triazol-N-yl)acetic acid;
4-(4-(4-(1H-benzo[d]imidazol-2-yl)styryl)phenyl)-N-(2-oxo-2-phenylethyl)-1,2,3-triazole-5-carbonitrile; and
4-(4'-benzoxazole-2-yl-stilbene-4-yl)-5-cyano-N-acetamide-1,2,3-triazole;
are excluded,
or a salt thereof (hereinafter to be referred to as Compound (1)).

In this embodiment, $R^1$ is preferably a group represented by formula:

-A-L1-B wherein
A is a divalent group selected from (A1) to (A45):
(A1) a phenylene group,
(A2) a thiazolediyl group,
(A3) an oxazolediyl group,
(A4) a thiophenediyl group,
(A5) a furandiyl group,
(A6) a pyrrolediyl group,
(A7) a pyridinediyi group,
(A8) a piperidinediyl group,
(A9) an indolediyl group,
(A10) a benzofurandiyl group,
(A11) a benzothiophenediyl group,
(A12) -lower alkylene-phenylene-,
(A13) a pyrimidinediyl group,
(A14) a quinolinediyl group,
(A15) a 2,3-dihydroindolediyl group,
(A16) an imidazolediyl group,
(A17) a benzothiazolediyl group,
(A18) an isoxazolediyl group,
(A19) a 2,3-dihydrobenzofurandiyl group,
(A20) an isothiazolediyl group,
(A21) a dibenzofurandiyl group,
(A22) a benzo[1,3]dioxolediyl group,
(A23) a carbazolediyl group,
(A24) a naphthalenediyl group,
(A25) a 2-oxo-1,2,3,4-tetrahydroquinolinediyl group,
(A26) a 6-oxo-1,6-dihydropyrimidinediyl group,
(A27) an imidazo[1,2-a]pyridinediyl group,
(A28) a [1,3,4]oxadiazolediyl group,
(A29) a [1,2,4]thiadiazolediyl group,
(A30) a benzoxazolediyl group,
(A31) a [1,3,4]thiadiazolediyl group,
(A32) a styrenediyl group,
(A33) —CO-phenylene-,
(A34) a cycloalkanediyl group,
(A35) a higher alkylene group,
(A36) a 2-oxo-1,2-dihydroquinolinediyl group,
(A37) a benzimidazolediyl group,
(A38) a 2,3-dihydro[1,4]benzodioxinediyl group,
(A39) a fluorenediyl group,
(A40) a bicyclo[2,2,1]hept-2-enediyl group,
(A41) a thieno[3,2-b]pyridinediyl group,
(A42) an imidazo[1,2-a]benzimidazolediyl group,
(A43) a 3,4-dihydro-2H-[1,4]benzoxazinediyl group,
(A44) a 3,4-dihydro-2H-benzo[b][1,4]dioxepinediyl group, and
(A45) —NH—,
each of (A1) to (A45) is optionally substituted with one or more members selected from the group consisting of
a halogen atom;
a lower alkyl group optionally substituted with one or more halogen atoms;
a lower alkenyl group;
a hydroxy group;
a lower alkoxy group optionally substituted with one or more halogen atoms;
a lower alkenyloxy group;
a lower alkynyloxy group;
a cyano group;
an amino group optionally mono- or di-substituted with members selected from the group consisting of a lower alkyl group, a lower alkyl-carbonyl group, a lower alkoxy-carbonyl group, and a lower alkylsulfonyl group;
a N,N-di-lower alkylamino lower alkyl group;
a N,N-di-lower alkylamino lower alkoxy group;
a cycloalkyl group optionally substituted with one or more halogen atoms;
a cycloalkoxy group optionally substituted with one or more halogen atoms;
a cycloalkyl lower alkyl group optionally substituted with one or more halogen atoms;
a cycloalkyl lower alkoxy group optionally substituted with one or more halogen atoms;
a lower alkoxy lower alkyl group optionally substituted with one or more halogen atoms;
a lower alkoxy lower alkoxy group optionally substituted with one or more halogen atoms;
a lower alkylthio group;
a phenyl group optionally substituted with one or more members selected from the group consisting of a halogen atom, a lower alkyl group optionally substituted with one or more halogen atoms, and a lower alkoxy group optionally substituted with one or more halogen atoms;
a phenoxy group optionally substituted with one or more members selected from the group consisting of a halogen atom, a lower alkyl group optionally substituted with one or more halogen atoms, and a lower alkoxy group optionally substituted with one or more halogen atoms;
a styryl group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenyl lower alkyl group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenyl lower alkoxy group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenoxy lower alkyl group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenoxy lower alkoxy group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a thienyl group;
an oxetanyl lower alkoxy group optionally substituted with one or more lower alkyl groups;
a furyl group;
a piperidyl group;
a pyrrolidinyl group; and
a morpholinyl group;
L1 is
a bond,
lower alkylene, lower alkenylene,
—O—, —O-lower alkylene, lower alkylene-O—, —O-lower alkenylene, lower alkenylene-O—, —O-lower alkylene-CO—, —CO-lower alkylene-O—,
—O-lower alkylene-O—, —O-lower alkenylene-O—, lower alkylene-O-lower alkylene, lower alkylene-C(OH)-lower alkylene,
—CO—, —CO-lower alkylene, lower alkylene-CO—,
—NH—, —NH-lower alkylene, lower alkylene-NH—, —N(phenyl)-, —N(lower alkyl)-, —N(lower alkyl)-lower alkylene, lower alkylene-N(lower alkyl)-,
—CONH—, —CONH-lower alkylene, lower alkylene-CONH—, —CO—N(lower alkyl)-, —CO—N(lower alkyl)-lower alkylene, lower alkylene-CO—N(lower alkyl)-,
—NHCO—, —N(lower alkyl)-CO—, —NHCO-lower alkylene, lower alkylene-NHCO—, —N(lower alkyl)-CO-lower alkylene, lower alkylene-N(lower alkyl)-CO—,
—$CO_2$—, —$CO_2$-lower alkylene, lower alkylene-$CO_2$—, —OCO—, —OCO-lower alkylene, lower alkylene-OCO—, —$NHCO_2$-lower alkylene, lower alkylene-$NHCO_2$—, —N(lower alkyl)-$CO_2$-lower alkylene, lower alkylene-N (lower alkyl)-$CO_2$—,
—OCONH-lower alkylene, lower alkylene-OCONH—, —OCO—N(lower alkyl)-lower alkylene, lower alkylene-OCO—N(lower alkyl)-,
—S—, lower alkylene-S—, —S-lower alkylene, lower alkylene-S-lower alkylene,
—$SO_2$—, lower alkylene-$SO_2$—, —$SO_2$-lower alkylene, lower alkylene-$SO_2$-lower alkylene, —$NHSO_2$-lower alkylene, lower alkylene-$NHSO_2$—, —N(lower alkyl)-$5O_2$-lower alkylene, lower alkylene-N(lower alkyl)-$SO_2$—,
—$SO_2$NH-lower alkylene, lower alkylene-$SO_2$NH—, —$SO_2$—N(lower alkyl)-lower alkylene, or lower alkylene-$SO_2$—N(lower alkyl)-;
and
B is a group or an atom selected from (B1) to (B65):
(B1) a phenyl group,
(B2) a naphthyl group,
(B3) a tetrahydronaphthyl group,
(B4) an imidazolyl group,
(B5) a [1,2,3]triazolyl group,
(B6) a thiazolyl group,
(B7) a pyrazolyl group,
(B8) a thienyl group,
(B9) a furyl group,
(B10) a tetrahydrofuryl group,
(B11) a pyrrolyl group,
(B12) a pyridyl group,
(B13) an imidazo[1,2-a]pyridyl group,
(B14) a pyrimidinyl group,
(B15) a pyridazyl group,
(B16) a pyrazyl group,
(B17) a pyrrolo[2,3-b]pyridyl group,
(B18) a pyrazolo[3,4-b]pyridyl group,
(B19) a piperidyl group,
(B20) a piperazinyl group,
(B21) a morpholinyl group,
(B22) a pyrrolidinyl group,
(B23) a quinolyl group,
(B24) an isoquinolyl group,
(B25) a 1,2,3,4-tetrahydroquinolyl group,
(B26) a 1,2,3,4-tetrahydroisoquinolyl group,
(B27) a 2-oxo-1,2,3,4-tetrahydroquinolyl group,
(B28) an indolyl group,
(B29) a 2,3-dihydroindolyl group,
(B30) an indanyl group,
(B31) a benzofuryl group,
(B32) a 2,3-dihydrobenzofuryl group,
(B33) a benzothienyl group,
(B34) a benzothiazolyl group,
(B35) a benzo[1,3]dioxolyl group,
(B36) a cycloalkyl group,
(B37) a cycloalkenyl group,
(B38) a tetrahydropyranyl group,
(B39) an oxetanyl group,
(B40) an oxiranyl group,
(B41) a 2,3-dihydro[1,4]benzodioxinyl group,
(B42) a 3,4-dihydro-2H-benzo[1,4]oxazinyl group,
(B43) a dibenzofuryl group,
(B44) a 4H-benzo[1,3]dioxinyl group,
(B45) a 1,2,4-oxadiazolyl group,
(B46) a 1,3,4-oxadiazolyl group,
(B47) an indazolyl group,
(B48) an isoxazolyl group,
(B49) a benzoisoxazolyl group,
(B50) a 2-oxo-1,2-dihydro-1H-benzimidazolyl group,
(B51) a 2-oxo-2,3-dihydro-3H-benzothiazolyl group,
(B52) a 2,3,4,5-tetrahydrobenzo[1,4]oxazepinyl group,
(B53) an isoindolinyl group,
(B54) a 2,4-dihydro-1H-benzo[1,3]oxazinyl group,
(B55) a 1,2,3,4-tetrahydrobenzo[1,4]oxazepinyl group,
(B56) a 2,3,4,5-tetrahydro-1H-benzoazepinyl group,
(B57) a tetrazolyl group,
(B58) a 2-oxo-1,2-dihydroquinolyl group,
(B59) a 3,4-dihydro-2H-benzodioxepinyl group,
(B60) a 3,6-dihydropyranyl group,
(B61) a 2-oxo-benzoxazolyl group,
(B62) an oxazolyl group,
(B63) a benzoxazolyl group,
(B64) a triphenylphosphonium group, and
(B65) a hydrogen atom,
each of (B1) to (B64) is optionally substituted on the ring(s) with one or more members selected from the group consisting of a halogen atom;
an oxo group;
a lower alkyl group optionally substituted with one or more members selected from the group consisting of a halogen atom, and a hydroxy group;
a higher alkyl group;
a hydroxy group;
a lower alkoxy group optionally substituted with one or more halogen atoms;
a cyano group;
a nitro group;
an amino group optionally mono- or di-substituted with lower alkyl groups;
a lower alkylsulfonylamino group;
a N,N-di-lower alkylamino-carbonyl group;
a N,N-di-lower alkylamino lower alkoxy group;
an acetylamino lower alkyl group;
a formyl group;
a lower alkyl-carbonyl group;
a lower alkylsulfonyl group;
a lower alkoxy-carbonyl group optionally substituted with one or more halogen atoms;
a phenyl group optionally substituted with one or more members selected from the group consisting of a halogen atom, a lower alkyl group optionally substituted with one or more halogen atoms, a lower alkoxy group optionally substituted with one or more halogen atoms, and a phenoxy group;
a phenoxy group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a styryl group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenyl lower alkyl group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenyl lower alkoxy group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a phenoxy lower alkyl group optionally substituted on the phenyl ring with one or more, members selected from the group consisting of a halogen atom, a lower alkyl group optionally substituted with one or more halogen atoms, and a lower alkoxy group optionally substituted with one or more halogen atoms;
a phenoxy lower alkoxy group optionally substituted on the phenyl ring with one or more members selected from the group consisting of a halogen atom, a lower alkyl group optionally substituted with one or more halogen atoms, and a lower alkoxy group optionally substituted with one or more halogen atoms;
a benzoyl group;
a lower alkylthio group optionally substituted with one or more halogen atoms;
a morpholinyl group;
a piperazinyl group optionally substituted with one or more lower alkyl groups;
a thienyl group;
a pyrrolyl group;
a pyrimidinyl group;
a pyrazolyl group optionally substituted with one or more lower alkyl groups optionally substituted with one or more halogen atoms;
a thiazolyl group optionally substituted with one or more lower alkyl groups;
a tetrahydropyranyloxy group;
a furyl group;
a pyrazinyl group optionally substituted with one or more lower alkyl groups;
a [1,2,4]oxadiazolyl group optionally substituted with one or more lower alkyl groups;
a [1,3,4]oxadiazolyl group optionally substituted with one or more lower alkyl groups;
a pyrrolidinyl group;
a pyridyl group optionally substituted with one or more lower alkyl groups optionally substituted with one or more halogen atoms;
an isoxazolyl group;
an imidazolyl group;
a cycloalkyl group;
a 2-oxo-pyrrolidinyl group; and
a [1,2,3]triazolyl group optionally substituted with one or more cyano groups.

The present invention also provides a cyanotriazole compound represented by the formula (1aa):

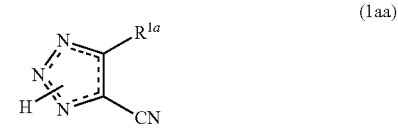

(1aa)

wherein
R$^{1a}$ is one of the following (1-1) to (1-34):
(1-1) a phenyl group substituted with one or more members selected from the group consisting of the following (1-1-1) to (1-1-108):
  (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
  (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
  (1-1-3) a lower alkoxy lower alkyl group optionally substituted with one or more members selected from the group consisting of a halogen atoms; and a cycloalkyl group,
  (1-1-4) a cycloalkyl group,
  (1-1-5) a cycloalkoxy group optionally substituted with one or more halogen atoms,
  (1-1-6) a cycloalkyl lower alkyl group,
  (1-1-7) a cycloalkyl lower alkoxy group optionally substituted on the cycloalkyl group with one or more members selected from the group consisting of a halogen atom; a lower alkyl group optionally substituted with one or more halogen atoms; and a phenyl group optionally substituted with one or more halogen atoms, (1-1-8) a cycloalkyl lower alkoxy lower alkyl group optionally substituted on the cycloalkyl group with one or more members selected from the group consisting of a hydroxy; and a lower alkoxy group, (1-1-9) a halogen atom (preferably provided that the phenyl group of (1-1) is substituted with one or more halogen atoms, then the phenyl group of (1-1) is substituted with additional one or more substituents excluding a phenoxy group), (1-1-10) a cyano group, (1-1-11) a phenyl group optionally substituted with one or more members selected from the group consisting of a halogen atom; a lower alkyl group optionally substituted with one or more halogen atoms; a lower alkoxy group optionally substituted with one or more halogen atoms; a lower alkoxy-carbonyl group; a lower alkylsulfonyl group; a phenyl group; a phenyl lower alkoxy group optionally substituted on the phenyl ring with one or more members selected from the group consisting of a halogen atom and a lower alkyl group optionally substituted with one or more halogen atoms; a phenoxy group; and a cyano group, (1-1-12) a phenyl lower alkyl group optionally substituted with one or more members selected from the group consisting of a halogen atom; a lower alkyl group optionally substituted with one or more halogen atoms; a lower alkoxy group optionally substituted with one or more halogen atoms; and a hydroxy group, (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; a halogen atom; and a 5-cyano-1H-1,2,3-triazol-4-yl group (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom), (1-1-14) a phenoxy group optionally substituted with one or more members selected from the group consisting of a halogen atom; a lower alkyl group optionally substituted with one or more halogen atoms; and a lower alkoxy group (preferably provided that the phenyl group of (1-1) is substituted with one or more phenoxy groups, then the phenyl group of (1-1) is substituted with additional one or more substituents excluding a halogen atom), (1-1-15) a phenoxy lower alkyl group optionally substituted on the phenyl ring with one or more members selected from the group consisting of a halogen atom; a lower alkyl group optionally substituted with one or more halogen atoms; and a lower alkoxy group optionally substituted with one or more halogen atoms, (1-1-16) a phenyl lower alkoxy group optionally substituted on the phenyl ring with one or more members selected from the group consisting of a halogen atom; a lower alkoxy group optionally substituted with one or more halogen atoms; a lower alkyl group optionally substituted with one or more halogen atoms; and a cyano group, (1-1-17) a phenylthio group optionally substituted with one or more members selected from the group consisting of a halogen atoms; and a lower alkyl group, (1-1-18) a benzylthio lower alkyl group optionally substituted on the phenyl ring with one or more members selected from the group consisting of a lower alkoxy group optionally substituted with one or more halogen atoms; and a lower alkyl group optionally substituted with one or more halogen atoms, (1-1-19) an N-lower alkyl-N-phenyl amino lower alkyl group optionally substituted on the phenyl ring with one or more members selected from the group consisting of a halogen atom; and a lower alkyl group optionally substituted with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more members selected from the group consisting of a halogen atom; a lower alkyl group optionally substituted with one or more halogen atoms; and a cyano group, (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms), (1-1-25) a pyrimidinyl group optionally substituted with one or more members selected from the group consisting of a halogen atom; a lower alkyl group optionally substituted with one or more halogen atoms; and a lower alkoxy group, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more members selected from the group consisting of a halogen atom; a lower alkyl group optionally substituted with one or more halogen atoms; and a phenyl group, (1-1-28) a benzoxazolyl group optionally substituted with one or more halogen atoms, (1-1-29) a benzofuryl group optionally substituted with one or more halogen atoms, (1-1-30) a benzofuryl lower alkoxy group optionally substituted on the benzofuran ring with one or more phenyl groups optionally substituted with one or more halogen atoms, (1-1-31) a thienyl group optionally substituted with one or more members selected from the group consisting of a halogen atom; a lower alkyl group optionally substituted with one or more halogen atoms; a lower alkylcarbonyl group; and a phenyl group optionally substituted with one or more members selected from the group consisting of a halogen atom, and a lower alkyl group optionally substituted with one or more halogen atoms,
(1-1-32) a benzothienyl group optionally substituted with one or more members selected from the group consisting of a halogen atom; a lower alkyl group optionally substituted with one or more halogen atoms; and a lower alkoxy group optionally substituted with one or more halogen atoms,
(1-1-33) a benzo[1,3]dioxolyl group optionally substituted with one or more halogen atoms,
(1-1-34) an indolinyl lower alkyl group,
(1-1-35) a benzothienylvinyl group,
(1-1-36) a benzo[1,3]dioxolylvinyl group optionally substituted on the benzo[1,3]dioxole ring with one or more halogen atoms,
(1-1-37) a lower alkoxy lower alkoxy group,
(1-1-38) a cycloalkoxy lower alkyl group optionally substituted on the cycloalkyl group with one or more lower alkyl groups,
(1-1-39) a cycloalkyl lower alkenyl group,
(1-1-40) a cycloalkenyloxy group,
(1-1-41) a cycloalkenylvinyl group,
(1-1-42) an oxiranyl group optionally substituted with one or more phenyl groups optionally substituted with one or more lower alkyl groups optionally substituted with one or more halogen atoms,
(1-1-43) an oxetanyl lower alkoxy group optionally substituted on the oxetane ring with one or more lower alkyl groups,
(1-1-44) a tetrahydropyranyl lower alkoxy group,
(1-1-45) a hydroxy group,
(1-1-46) a phenyl lower alkoxy lower alkyl group optionally substituted on the phenyl ring with one or more members selected from the group consisting of a halogen atom; a lower alkoxy group optionally substituted with one or more halogen atoms; a lower alkyl group optionally substituted with one or more halogen atoms; and a lower alkylthio group optionally substituted with one or more halogen atoms,
(1-1-47) a phenyl lower alkenyloxy group optionally substituted on the phenyl ring with one or more lower alkyl groups optionally substituted with one or more halogen atoms,
(1-1-48) a benzoyl group optionally substituted with one or more halogen atoms,
(1-1-49) a phenylthio lower alkyl group optionally substituted on the phenyl ring with one or more members selected from the group consisting of a halogen atoms; and a lower alkyl group optionally substituted with one or more halogen atoms,
(1-1-50) a phenylsulfonyl group optionally substituted with one or more lower alkyl groups,
(1-1-51) a phenylsulfonyl lower alkyl group optionally substituted on the phenyl ring with one or more halogen atoms,
(1-1-52) a naphthyl group optionally substituted with one or more halogen atoms,
(1-1-53) a naphthylvinyl group optionally substituted on the naphthyl ring with one or more halogen atoms,
(1-1-54) a tetrahydronaphthyloxy group,
(1-1-55) an indanyloxy group,
(1-1-56) an amino group optionally mono- or di-substituted with members selected from the group consisting of a lower alkyl group; a lower alkyl-carbonyl group; a lower alkoxy-carbonyl group; and a lower alkylsulfonyl group;
(1-1-57) an N-lower alkyl-N-phenyl amino group optionally substituted on the phenyl ring with one or more lower alkyl groups optionally substituted with one or more halogen atoms,
(1-1-58) an aminocarbonyl group optionally substituted with one or more members selected from the group consisting of a lower alkyl group; a cycloalkyl group; a cycloalkyl lower alkyl group; and a phenyl group optionally substituted with one or more halogen atoms,
(1-1-59) a pyridyl lower alkoxy group optionally substituted on the pyridine ring with one or more lower alkyl groups optionally substituted with one or more halogen atoms,
(1-1-60) a pyridyloxy group optionally substituted with one or more lower alkyl groups optionally substituted with one or more halogen atoms,
(1-1-61) a pyrrolo[2,3-b]pyridyl group optionally substituted with one or more lower alkyl groups,
(1-1-62) a pyrazolo[3,4-b]pyridyl group optionally substituted with one or more lower alkyl groups,
(1-1-63) an imidazo[1,2-a]pyridyl group optionally substituted with one or more members selected from the group consisting of a halogen atom; and a lower alkyl group optionally substituted with one or more halogen atoms,
11-1-64) a pyrimidinyl lower alkyl group optionally substituted on the pyrimidine ring with one or more lower alkyl groups optionally substituted with one or more halogen atoms,
(1-1-65) a pyrimidinyl lower alkoxy group optionally substituted on the pyrimidine ring with one or more members selected from the group consisting of a lower alkoxy group; a lower alkyl group optionally substituted with one or more halogen atoms; and a phenyl group,
(1-1-66) a pyrimidinyloxy group optionally substituted with one or more lower alkyl groups optionally substituted with one or more halogen atoms,
(1-1-67) a pyrimidinyloxy lower alkyl group optionally substituted on the pyrimidine ring with one or more lower alkyl groups optionally substituted with one or more halogen atoms,
(1-1-68) a pyrazinyl group optionally substituted with one or more lower alkyl groups,
(1-1-69) a pyridazinyl group optionally substituted with one or more members selected from the group consisting of a lower alkyl group; and a lower alkoxy group,
(1-1-70) a piperidyl lower alkyl group,
(1-1-71) a piperidylcarbonyl group,
(1-1-72) a piperazinyl group optionally substituted with one or more phenyl groups optionally substituted with one or more halogen atoms,
(1-1-73) an imidazolyl group,
(1-1-74) a pyrazolyl group optionally substituted with one or more lower alkyl groups,
(1-1-75) a pyrrolyl lower alkyl group,
(1-1-76) a thiazolyl group,
(1-1-77) a thiazolyl lower alkoxy group optionally substituted on the thiazole ring with one or more lower alkyl groups,
(1-1-78) a benzothiazolyl group optionally substituted with one or more halogen atoms,
(1-1-79) a furyl group,
(1-1-80) a furylvinyl group optionally substituted on the furan ring with one or more lower alkyl groups, (1-1-81) a benzofurylvinyl group (preferably the benzofurylvinyl group is bonded to the o- or m-position on the phenyl ring of (1-1)),
(1-1-82) a 2,3-dihydrobenzofuryl group,
(1-1-83) a thienyl lower alkoxy group,
(1-1-84) a thienylvinyl group optionally substituted on the thiophene ring with one or more halogen atoms (preferably the thienylvinyl group is bonded to the o- or m-position on the phenyl ring of (1-1)),
(1-1-85) a benzothienyl lower alkyl group optionally substituted on the benzothiophene ring with one or more halogen atoms,
(1-1-86) a benzothienyl lower alkoxy group optionally substituted on the benzothiophene ring with one or more members selected from the group consisting of a halogen atom; and a lower alkyl group optionally substituted with one or more halogen atoms,
(1-1-87) a benzo[1,3]dioxolyl lower alkyl group optionally substituted on the benzo[1,3]dioxole ring with one or more halogen atoms,
(1-1-88) a benzo[1,3]dioxolyl lower alkoxy group optionally substituted on the benzo[1,3]dioxole ring with one or more halogen atoms,
(1-1-89) a 4H-benzo[1,3]dioxinyl group optionally substituted with one or more halogen atoms,
(1-1-90) a 4H-benzo[1,3]dioxinylvinyl group optionally substituted on the benzo[1,3]dioxine ring with one or more halogen atoms,
(1-1-91) a quinolyl group,
(1-1-92) a quinolyl lower alkoxy group,
(1-1-93) a quinolylvinyl group,
(1-1-94) a 3,4-dihydro-2H-quinolyl group,
(1-1-95) a 3,4-dihydro-2H-quinolyl lower alkyl group,
(1-1-96) a 2-oxo-1,2,3,4-tetrahydroquinolyl group,
(1-1-97) a 2-oxo-1,2,3,4-tetrahydroquinolyl lower alkoxy group,
(1-1-98) a 2-oxo-1,2,3,4-tetrahydroquinolyloxy group optionally substituted with one or more lower alkyl groups,
(1-1-99) an isoquinolyl group,
(1-1-100) a 3,4-dihydro-1H-isoquinolyl group,
(1-1-101) a 3,4-dihydro-1H-isoquinolyl lower alkyl group,
(1-1-102) an indolyl group optionally substituted with one or more members selected from the group consisting of a halogen atom; a lower alkyl group; and a lower alkoxy-carbonyl group,
(1-1-103) an indolyl lower alkyl group,
(1-1-104) an indolylvinyl group optionally substituted on the indole ring with one or more lower alkyl groups,
(1-1-105) an indolinyl group,
(1-1-106) an indolinylcarbonyl group,
(1-1-107) a 1H-1,2,3-triazolyl group optionally substituted with one or more cyano groups, and
(1-1-108) a triphenylphosphonium lower alkyl group,
(1-2) a thiazolyl group substituted with one or more members selected from the group consisting of the following (1-2-1) to (1-2-26):
(1-2-1) a lower alkyl group optionally substituted with one or more halogen atoms,
(1-2-2) a lower alkoxy group,
(1-2-3) a cycloalkyl group,
(1-2-4) a halogen atom,
(1-2-5) a phenyl group optionally substituted with one or more members selected from the group consisting of a halogen atom; a lower alkyl group optionally substituted with one or more halogen atoms; a lower alkoxy group optionally substituted with one or more halogen atoms; a hydroxy group; and a cyano group,
(1-2-6) a styryl group optionally substituted on the phenyl ring with one or more lower alkyl groups optionally substituted with one or more halogen atoms,
(1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
(1-2-8) a benzyloxy group optionally substituted on the phenyl ring with one or more halogen atoms,
(1-2-9) a phenylthio group optionally substituted with one or more members selected from the group consisting of a halogen atom; and a lower alkyl group optionally substituted with one or more halogen atoms,
(1-2-10) an amino group optionally mono- or di-substituted with members selected from the group consisting of a lower alkyl group; a phenyl group optionally substituted with one or more members selected from the group consisting of a halogen atom, a lower alkyl group optionally substituted with one or more halogen atoms, and a lower alkoxy group optionally substituted with one or more halogen atoms; a benzyl group optionally substituted on the phenyl ring with one or more members selected from the group consisting of a halogen atom, and a lower alkyl group optionally substituted with one or more halogen atoms; and a benzoyl group optionally substituted with one or more halogen atoms,
(1-2-11) a pyridyl group optionally substituted with one or more members selected from the group consisting of a halogen atom; and a lower alkyl group optionally substituted with one or more halogen atoms,
(1-2-12) a lower alkenyl group,
(1-2-13) a cycloalkyl lower alkyl group,
(1-2-14) a phenyl lower alkyl group optionally substituted on the phenyl ring with one or more members selected from the group consisting of a halogen atom; a lower alkyl group optionally substituted with one or more halogen atoms; and a hydroxy group,
(1-2-15) a phenoxy lower alkyl group optionally substituted on the phenyl ring with one or more members selected from the group consisting of a halogen atom; a lower alkyl group optionally substituted with one or more halogen atoms; and a lower alkoxy group optionally substituted with one or more halogen atoms,
(1-2-16) a phenyl lower alkoxy lower alkyl group optionally substituted on the phenyl ring with one or more members selected from the group consisting of a halogen atom; a lower alkoxy group optionally substituted with one or more halogen atoms; and a lower alkyl group optionally substituted with one or more halogen atoms,
(1-2-17) a phenyl lower alkylsulfonyl lower alkyl group optionally substituted on the phenyl ring with one or more lower alkyl groups optionally substituted with one or more halogen atoms,
(1-2-18) a mono- or di-N-lower alkyl amino lower alkyl group;
(1-2-19) a piperidyl group optionally substituted with one or more members selected from the group consisting of a phenyl group optionally substituted with one or more members selected from the group consisting of a halogen atom, and a lower alkyl group optionally substituted with one or more halogen atoms; and a phenyl lower alkyl group optionally substituted on the phenyl ring with one or more members selected from the group consisting of a halogen atom, and a lower alkyl group optionally substituted with one or more halogen atoms, (1-2-20) a piperazinyl group optionally substituted with one or more phenyl groups optionally substituted with one or more members selected from the group consisting of a halogen atom, and a lower alkyl group optionally substituted with one or more halogen atoms, (1-2-21) an indolyl group, (1-2-22) a morpholinyl group, (1-2-23) a thienyl group, (1-2-24) a benzothienyl group optionally substituted with one or more lower alkyl groups optionally substituted with one or more halogen atoms, (1-2-25) a furyl group, and (1-2-26) a cyano group, (1-3) an oxazolyl group optionally substituted with one or more members selected from the group consisting of the following (1-3-1) to (1-3-12):

(1-3-1) a lower alkyl group optionally substituted with one or more halogen atoms, (1-3-2) a cycloalkyl group, (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms, (1-3-4) a lower alkoxy lower alkyl group, (1-3-5) a phenoxy lower alkyl group optionally substituted on the phenyl ring with one or more lower alkyl groups optionally substituted with one or more halogen atoms, (1-3-6) a naphthyl group, (1-3-7) a pyridyl group optionally substituted with one or more lower alkyl groups optionally substituted with one or more halogen atoms, (1-3-8) a furyl group, (1-3-9) a dihydrobenzofuryl group, (1-3-10) a thienyl group, (1-3-11) a benzothienyl group optionally substituted with one or more members selected from the group consisting of a halogen atom; a lower alkyl group optionally substituted with one or more halogen atoms; and a lower alkoxy group optionally substituted with one or more halogen atoms, and (1-3-12) a benzo[1,3]dioxolyl group optionally substituted with one or more halogen atoms, (1-4) a thienyl group substituted with one or more members selected from the group consisting of the following (1-4-1) to (1-4-14):

(1-4-1) a lower alkyl group optionally substituted with one or more halogen atoms, (1-4-2) a phenyl group optionally substituted with one or more members selected from the group consisting of a halogen atom; a lower alkyl group optionally substituted with one or more members selected from the group consisting of a halogen atom and a hydroxy group; a lower alkoxy group optionally substituted with one or more halogen atoms; a lower alkyl-carbonyl group; a lower alkoxy-carbonyl group; and a benzyloxy group optionally substituted on the phenyl ring with one or more members selected from the group consisting of a lower alkyl group optionally substituted with one or more halogen atoms, and a halogen atom, (1-4-3) a benzyl group optionally substituted on the phenyl ring with one or more halogen atoms, (1-4-4) a phenoxy group optionally substituted with one or more members selected from the group consisting of a lower alkyl group optionally substituted with one or more halogen atoms; and a halogen atom, (1-4-5) a styryl group optionally substituted on the phenyl ring with one or more members selected from the group consisting of a halogen atom; and a lower alkyl groups optionally substituted with one or more halogen atoms, (1-4-6) a cycloalkyl lower alkenyl group, (1-4-7) a halogen atom, (1-4-8) a pyridyl group optionally substituted with one or more members selected from the group consisting of a halogen atom; and a lower alkyl group optionally substituted with one or more halogen atoms, (1-4-9) a pyridyl lower alkyl group optionally substituted on the pyridine ring with one or more lower alkyl groups optionally substituted with one or more halogen atoms, (1-4-10) a pyrimidinyl group optionally substituted with one or more lower alkyl groups optionally substituted with one or more halogen atoms, (1-4-11) a thienyl group optionally substituted with one or more members selected from the group consisting of a halogen atom; and a phenyl group optionally substituted with one or more halogen atoms, (1-4-12) a thienylvinyl group, (1-4-13) a benzothienyl group optionally substituted with one or more members selected from the group consisting of a halogen atom; and a lower alkyl group optionally substituted with one or more halogen atoms, and (1-4-14) a benzo[1,3]dioxolyl group optionally substituted with one or more halogen atoms, (1-5) a furyl group optionally substituted with one or more members selected from the group consisting of the following (1-5-1) to (1-5-8):

(1-5-1) a phenyl group optionally substituted with one or more members selected from the group consisting of a halogen atom; a lower alkyl group optionally substituted with one or more halogen atoms; and a phenyl group, (1-5-2) a styryl group optionally substituted on the phenyl ring with one or more members selected from the group consisting of a halogen atom; a lower alkyl group optionally substituted with one or more halogen atoms; and a lower alkoxy group, (1-5-3) a lower alkyl group optionally substituted with one or more halogen atoms, (1-5-4) a naphthyl group, (1-5-5) a pyridyl group optionally substituted with one or more lower alkyl groups optionally substituted with one or more halogen atoms, (1-5-6) a quinolyl group, (1-5-7) a benzothienyl group-optionally substituted with one or more lower alkyl groups optionally substituted with one or more halogen atoms, and (1-5-8) a benzo[1,3]dioxolylvinyl group optionally substituted on the benzo[1,3]dioxole ring with one or more halogen atoms, (1-6) a pyrrolyl group optionally substituted with one or more members selected from the group consisting of the following (1-6-1) to (1-6-5):

(1-6-1) a lower alkyl group, (1-6-2) a phenyl group optionally substituted with one or more members selected from the group consisting of a halogen atom; a lower alkyl group optionally substituted with one or more halogen atoms; a lower alkoxy group optionally substituted with one or more halogen atoms; a phenoxy group; a benzyl group; and a benzoyl group,
- (1-6-3) a phenyl lower alkyl group optionally substituted on the phenyl ring with one or more members selected from the group consisting of a halogen atom; a lower alkyl group optionally substituted with one or more halogen atoms; a lower alkoxy group optionally substituted with one or more halogen atoms; a phenyl group; and a phenyl lower alkoxy group,
- (1-6-4) an indanyl group, and
- (1-6-5) a benzo[1,3]dioxolyl lower alkyl group, (1-7) a pyridyl group substituted with one or more members selected from the group consisting of the following (1-7-1) to (1-7-9):
- (1-7-1) a benzyloxy lower alkyl group optionally substituted on the phenyl ring with one or more members selected from the group consisting of a halogen atom; and a lower alkyl group optionally substituted with one or more halogen atoms,
- (1-7-2) a phenyl group optionally substituted with one or more members selected from the group consisting of a halogen atom; and a lower alkyl group optionally substituted with one or more halogen atoms,
- (1-7-3) a benzofuryl group,
- (1-7-4) a styryl group optionally substituted on the phenyl ring with one or more lower alkyl groups optionally substituted with one or more halogen atoms,
- (1-7-5) a naphthyl group,
- (1-7-6) a halogen atom,
- (1-7-7) a pyridyl group,
- (1-7-8) a benzothienyl group optionally substituted with one or more members selected from the group consisting of a halogen atom; and a lower alkyl group optionally substituted with one or more halogen atoms, and
- (1-7-9) a [1,2,3]triazolyl group optionally substituted with one or more cyano groups, (1-8) a piperidyl group optionally substituted with one or more members selected from the group consisting of the following (1-8-1) to (1-8-8):
- (1-8-1) a phenyl group optionally substituted with one or more members selected from the group consisting of a halogen atom; and a lower alkyl group optionally substituted with one or more halogen atoms,
- (1-8-2) a benzyl group optionally substituted on the phenyl ring with one or more members selected from the group consisting of a halogen atom; and a lower alkyl group optionally substituted with one or more halogen atoms,
- (1-8-3) a lower alkoxy-carbonyl group,
- (1-8-4) a benzoyl group optionally substituted on the phenyl ring with one or more lower alkyl groups optionally substituted with one or more halogen atoms,
- (1-8-5) a phenyl lower alkyl-carbonyl group optionally substituted on the phenyl ring with one or more halogen atoms,
- (1-8-6) a phenyl lower alkoxy-carbonyl group,
- (1-8-7) a phenoxycarbonyl group, and
- (1-8-8) a phenylsulfonyl group optionally substituted with one or more lower alkyl groups, (1-9) an indolyl group optionally substituted with one or more members selected from the group consisting of the following (1-9-1) to (1-9-8):
- (1-9-1) a lower alkyl group optionally substituted with one or more halogen atoms,
- (1-9-2) a phenyl group optionally substituted with one or more members selected from the group consisting of a halogen atom; a lower alkyl group optionally substituted with one or more halogen atoms; and a lower alkoxy group,
- (1-9-3) a cycloalkyl lower alkyl group,
- (1-9-4) a halogen atom,
- (1-9-5) a phenyl lower alkyl group optionally substituted on the phenyl ring with one or more members selected from the group consisting of a halogen atom; and a lower alkyl group optionally substituted with one or more halogen atoms,
- (1-9-6) a thienyl lower alkyl group,
- (1-9-7) a tetrahydrofuryl lower alkyl group, and
- (1-9-8) a benzo[1,3]dioxolyl group, (1-10) a benzofuryl group optionally substituted with one or more members selected from the group consisting of the following (1-10-1) to (1-10-7):
- (1-10-1) a halogen atom,
- (1-10-2) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-10-3) a lower alkyl group,
- (1-10-4) a benzyl group optionally substituted on the phenyl ring with one or more lower alkyl groups optionally substituted with one or more halogen atoms,
- (1-10-5) a styryl group optionally substituted on the phenyl ring with one or more lower alkyl groups optionally substituted with one or more halogen atoms,
- (1-10-6) a benzo[1,3]dioxolyl group optionally substituted with one or more halogen atoms, and
- (1-10-7) a pyrimidinyl group optionally substituted with one or more lower alkyl groups optionally substituted with one or more halogen atoms, (1-11) a benzothienyl group optionally substituted with one or more members selected from the group consisting of the following (1-11-1) to (1-11-7):
- (1-11-1) a phenyl group optionally substituted with one or more members selected from the group consisting of a halogen atom; and a lower alkyl group optionally substituted with one or more halogen atoms,
- (1-11-2) a lower alkyl group optionally substituted with one or more halogen atoms,
- (1-11-3) a phenyl lower alkoxy group optionally substituted on the phenyl ring with one or more lower alkyl groups optionally substituted with one or more halogen atoms,
- (1-11-4) a halogen atom,
- (1-11-5) a pyridyl group optionally substituted with one or more lower alkyl groups optionally substituted with one or more halogen atoms,
- (1-11-6) a pyrimidinyl group optionally substituted with one or more lower alkyl groups optionally substituted with one or more halogen atoms, and
- (1-11-7) a thienyl group, (1-12) a phenyl lower alkyl group optionally substituted on the phenyl ring with one or more members selected from the group consisting of the following (1-12-1) to (1-12-4):
- (1-12-1) a phenyl group optionally substituted with one or more lower alkyl groups optionally substituted with one or more halogen atoms,
- (1-12-2) a benzyloxy group optionally substituted on the phenyl ring with one or more lower alkyl groups optionally substituted with one or more halogen atoms, (1-12-3) a lower alkyl group optionally substituted with one or more halogen atoms, and
(1-12-4) a phenoxy group,
(1-13) a pyrimidinyl group optionally substituted with one or more members selected from the group consisting of the following (1-13-1) to (1-13-7):
- (1-13-1) a phenyl group optionally substituted with one or more lower alkyl groups optionally substituted with one or more halogen atoms,
- (1-13-2) a pyrrolidyl group,
- (1-13-3) a piperidyl group,
- (1-13-4) a lower alkyl group optionally substituted with one or more halogen atoms,
- (1-13-5) a lower alkoxy group,
- (1-13-6) a styryl group optionally substituted on the phenyl ring with one or more members selected from the group consisting of a halogen atom; and a lower alkyl group optionally substituted with one or more halogen atoms, and
- (1-13-7) a morpholinyl group, (1-14) a quinolyl group substituted with one or more members selected from the group consisting of the following (1-14-1) to (1-14-5):
- (1-14-1) a lower alkoxy group,
- (1-14-2) a phenyl group optionally substituted with one or more members selected from the group consisting of a halogen atom; and a lower alkyl group optionally substituted with one or more halogen atoms,
- (1-14-3) a phenyl lower alkoxy group optionally substituted on the phenyl ring with one or more lower alkyl groups optionally substituted with one or more halogen atoms,
- (1-14-4) a pyrrolidyl group, and
- (1-14-5) a thienyl group, (1-15) a 2,3-dihydro-1H-indolyl group optionally substituted with one or more members selected from the group consisting of the following (1-15-1) to (1-15-2):
- (1-15-1) a phenyl group optionally substituted with one or more members selected from the group consisting of a halogen atom; and a lower alkyl group optionally substituted with one or more halogen atoms, and
- (1-15-2) a benzyl group optionally substituted on the phenyl ring with one or more members selected from the group consisting of a halogen atom; and a lower alkyl group optionally substituted with one or more halogen atoms, (1-16) an imidazolyl group optionally substituted with one or more members selected from the group consisting of the following (1-16-1) to (1-16-4):
- (1-16-1) a lower alkyl group,
- (1-16-2) a halogen atom,
- (1-16-3) a phenyl group optionally substituted with one or more members selected from the group consisting of a halogen atom; and a lower alkyl group optionally substituted with one or more halogen atoms, and
- (1-16-4) a benzyl group optionally substituted on the phenyl ring with one or more members selected from the group consisting of a halogen atom; and a lower alkyl group optionally substituted with one or more halogen atoms, (1-17) a benzothiazolyl group optionally substituted with one or more members selected from the group consisting of the following (1-17-1) to (1-17-6):
- (1-17-1) a lower alkyl group optionally substituted with one or more halogen atoms,
- (1-17-2) a lower alkoxy group,
- (1-17-3) a halogen atom,
- (1-17-4) a phenyl group optionally substituted with one or more members selected from the group consisting of a halogen atom; and a lower alkyl group optionally substituted with one or more halogen atoms,
- (1-17-5) a phenoxy group optionally substituted with one or more members selected from the group consisting of a halogen atom; and a lower alkyl group optionally substituted with one or more halogen atoms, and
- (1-17-6) a pyridyl group optionally substituted with one or more lower alkyl groups optionally substituted with one or more halogen atoms, (1-18) an isoxazolyl group optionally substituted with one or more phenyl groups optionally substituted with one or more halogen atoms, (1-19) a 2,3-dihydrobenzofuryl group optionally substituted with one or more members selected from the group consisting of the following (1-19-1) to (1-19-3):
- (1-19-1) a halogen atom,
- (1-19-2) a phenyl group optionally substituted with one or more halogen atoms, and
- (1-19-3) a pyridyl group optionally substituted with one or more lower alkyl groups optionally substituted with one or more halogen atoms, (1-20) an isothiazolyl group optionally substituted with one or more phenyl groups optionally substituted with one or more members selected from the group consisting of a halogen atom, a lower alkyl group optionally substituted with one or more halogen atoms, and a lower alkoxy group optionally substituted with one or more halogen atoms, (1-21) a dibenzofuryl group, (1-22) a benzo[1,3]dioxolyl group optionally substituted with one or more members selected from the group consisting of the following (1-22-1) to (1-22-2):
- (1-22-1) a halogen atom, and
- (1-22-2) a pyridyl group optionally substituted with one or more lower alkyl groups optionally substituted with one or more halogen atoms, (1-23) a carbazolyl group optionally substituted with one or more lower alkyl groups, (1-24) a naphthyl group optionally substituted with one or more benzyloxy groups optionally substituted on the phenyl ring with one or more lower alkyl groups optionally substituted with one or more halogen atoms, (1-25) a 2-oxo-1,2,3,4-tetrahydroquinolyl group optionally substituted with one or more benzyl groups optionally substituted on the phenyl ring with one or more lower alkyl groups optionally substituted with one or more halogen atoms, (1-26) a 6-oxo-1,6-dihydropyrimidinyl group optionally substituted with one or more phenyl groups optionally substituted with one or more lower alkyl groups optionally substituted with one or more halogen atoms, (1-27) an imidazo[1,2-a]pyridyl group optionally substituted with one or more phenyl groups optionally substituted with one or more lower alkyl groups optionally substituted with one or more halogen atoms, (1-28) a [1,3,4]oxadiazolyl group optionally substituted with one or more phenyl groups optionally substituted with one or more lower alkyl groups optionally substituted with one or more halogen atoms, (1-29) a [1,2,4]thiadiazolyl group optionally substituted with one or more phenyl groups optionally substituted with one or more halogen, atoms, (1-30) a benzoxazolyl group optionally substituted with one or more members selected from the group consisting of the following (1-30-1) to (1-30-4):

(1-30-1) a lower alkyl group,
(1-30-2) a lower alkoxy group,
(1-30-3) a halogen atom, and
(1-30-4) a phenyl group,
(1-31) a [1,3,4]thiadiazolyl group optionally substituted with one or more phenyl groups optionally substituted with one or more halogen atoms;
(1-32) a styryl group optionally substituted on the phenyl ring with one or more benzyloxy groups optionally substituted on the phenyl ring with one or more lower alkyl groups optionally substituted with one or more halogen atoms,
(1-33) a benzoyl group optionally substituted with one or more benzyloxy groups optionally substituted on the phenyl ring with one or more lower alkyl groups optionally substituted with one or more halogen atoms,
and
(1-34) a cycloalkyl group optionally substituted with one or more members selected from the group consisting of a phenyl group optionally substituted with one of more members selected from the group consisting of a halogen atom and a benzyloxy group optionally substituted on the phenyl ring with one or more lower alkyl groups optionally substituted with one or more halogen atoms; and a benzyloxy groups optionally substituted on the phenyl ring with one or more lower alkyl groups optionally substituted with one or more halogen atoms; provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
5-{4-[2-(thiophen-2-yl)vinyl]phenyl}-1,2,3-triazole-4-carbonitrile;
5-{4-[2-(benzofuran-2-yl)vinyl]phenyl}-1,2,3-triazole-4-carbonitrile;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole; and
4-(4-fluoro-3-phenoxyphenyl)-5-cyano-1,2,3-triazole;
4-(2-fluorophenyl)-1,2,3-triazole-5-carbonitrile; and
4-(4-fluoro-3-methoxyphenyl)-1,2,3-triazole-5-carbonitrile;
are excluded,
or a salt thereof (hereinafter to be referred to as Compound (1aa)).

As preferable embodiment, $R^{1a}$ is one of the following (1-1) to (1-13):
(1-1) a phenyl group substituted with one or more members selected from the group consisting of the following (1-1-1) to (1-1-36):
(1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
(1-1-2) a lower alkoxy group optionally substituted with one or more halogen atoms (preferably provided that the phenyl group of (0.1-1) is substituted with one or more lower alkoxy groups, then the phenyl group of (1-1) is substituted with additional one or more substituents excluding a lower alkoxy group and a halogen atom),
(1-1-3) a lower alkoxy lower alkyl group,
(1-1-4) a cycloalkyl group,
(1-1-5) a cycloalkoxy group,
(1-1-6) a cycloalkyl lower alkyl group,
(1-1-7) a cycloalkyl lower alkoxy group,
(1-1-8) a cycloalkyl lower alkoxy lower alkyl group,
(1-1-9) a halogen atom (preferably provided that the phenyl group of (1-1) is substituted with one or more halogen atoms, then the phenyl group of (1-1) is substituted with additional one or more substituents excluding a phenoxy group),
(1-1-10) a cyano group,
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
(1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
(1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
(1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
(1-1-17) a phenylthio group optionally substituted with one or more halogen atoms, (1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms,
(1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of the following (1-6-1) to (1-6-3):

(1-6-1) a lower alkyl group,
(1-6-2) a phenyl group optionally substituted with one or more members selected from the group consisting of a halogen atom; and a lower alkyl group optionally substituted with one or more halogen atoms, and
(1-6-3) a phenyl lower alkyl group optionally substituted on the phenyl ring with one or more lower alkyl groups optionally substituted with one or more halogen atoms,
(1-7) a pyridyl group substituted with one or more members selected from the group consisting of the following (1-7-1) to (1-7-3):
　(1-7-1) a benzyloxy lower alkyl group optionally substituted on the phenyl ring with one or more lower alkyl groups optionally substituted with one or more halogen atoms,
　(1-7-2) a phenyl group optionally substituted with one or more lower alkyl groups optionally substituted with one or more halogen atoms, and
　(1-7-3) a benzofuryl group,
(1-8) a piperidyl group optionally substituted with one or more members selected from the group consisting of the following (1-8-1) to (1-8-2):
　(1-8-1) a phenyl group optionally substituted with one or more lower alkyl groups optionally substituted with one or more halogen atoms, and
　(1-8-2) a benzyl group optionally substituted on the phenyl ring with one or more halogen atoms,
(1-9) an indolyl group optionally substituted with one or more members selected from the group consisting of the following (1-9-1) to (1-9-2):
　(1-9-1) a lower alkyl group optionally substituted with one or more halogen atoms, and
　(1-9-2) a phenyl group optionally substituted with one or more halogen atoms,
(1-10) a benzofuryl group optionally substituted with one or more members selected from the group consisting of the following (1-10-1) to (1-10-2):
　(1-10-1) a halogen atom, and
　(1-10-2) a phenyl group optionally substituted with one or more halogen atoms,
(1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
　(1-12-1) a phenyl group optionally substituted with one or more lower alkyl groups optionally substituted with one or more halogen atoms; and
　(1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
　(1-13-1) a phenyl group,
　(1-13-2) a pyrrolidinyl group, and
　(1-13-3) a piperidyl group.

As another preferable embodiment, $R^{1a}$ is the following (1-1):
(1-1) a phenyl group substituted with one or more members selected from the group consisting of the following (1-1-1) to (1-1-36):
　(1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
　(1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
　(1-1-3) a lower alkoxy lower alkyl group,
　(1-1-4) a cycloalkyl group,
　(1-1-5) a cycloalkoxy group,
　(1-1-6) a cycloalkyl lower alkyl group,
　(1-1-7) a cycloalkyl lower alkoxy group,
　(1-1-8) a cycloalkyl lower alkoxy lower alkyl group,
　(1-1-9) a halogen atom (preferably provided that the phenyl group of (1-1) is substituted with one or more halogen atoms, then the phenyl group of (1-1) is substituted with additional one or more substituents excluding a phenoxy group),
　(1-1-10) a cyano group,
　(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
　(1-1-12) a phenyl lower alkyl group optionally substituted on the phenyl ring with one or more members selected from the group consisting of a halogen atom; and a lower alkyl group optionally substituted with one or more halogen atoms,
　(1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
　(1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
　(1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
　(1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
　(1-1-17) a phenylthio group optionally substituted with one or more halogen atoms, (1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms.

As another preferable embodiment, $R^{1a}$ is one of the following (1-2) to (1-13):
(1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms,
(1-7) a pyridyl group substituted with one or more members selected from the group consisting of the following (1-7-1) to (1-7-3):
  (1-7-1) a benzyloxy lower alkyl group optionally substituted on the phenyl ring with one or more lower alkyl groups optionally substituted with one or more halogen atoms,
  (1-7-2) a phenyl group optionally substituted with one or more lower alkyl groups optionally substituted with one or more halogen atoms, and
  (1-7-3) a benzofuryl group,
(1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms,
(1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms,
(1-10) a benzofuryl group optionally substituted with one or more members selected from the group consisting of the following (1-10-1) to (1-10-2):
  (1-10-1) a halogen atom, and
  (1-10-2) a phenyl group optionally substituted with one or more halogen atoms,
(1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms; and
  (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
  (1-13-1) a phenyl group,
  (1-13-2) a pyrrolidinyl group, and
  (1-13-3) a piperidyl group.

As another preferable embodiment, $R^{1a}$ is the following (1-2):
(1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms.

As another preferable embodiment, $R^{1a}$ is the following (1-3):
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms.

As another preferable embodiment, $R^{1a}$ is the following (1-5):
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms.

As another preferable embodiment, $R^{1a}$ is the following (1-13):
(1-13) a pyrimidinyl group optionally substituted with one or more members selected from the group consisting of the following (1-13-1) to (1-13-3):
  (1-13-1) a phenyl group,
  (1-13-2) a pyrrolidinyl group, and
  (1-13-3) a piperidyl group.

As another preferable embodiment, $R^{1a}$ is one of the following (1-1) to (1-7), (1-9), (1-10), (1-12) and (1-13):

(1-1) a phenyl group substituted with one or more (preferably 1 to 3) members selected from the group consisting of
- (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
- (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
- (1-1-9) a halogen atom (preferably provided that the phenyl group of (1-1) is substituted with one or more halogen atoms, then the phenyl group of (1-1) is substituted with additional one or more substituents excluding a phenoxy group),
- (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-1-12) a phenyl lower alkyl group optionally substituted on the phenyl ring with one or more members selected from the group consisting of a halogen atom; and a lower alkyl group optionally substituted with one or more halogen atoms,
- (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
- (1-1-14) a phenoxy group (preferably provided that the phenyl group of (1-1) is substituted with one or more phenoxy groups, then the phenyl group of (1-1) is substituted with additional one or more substituents excluding a halogen atom),
- (1-1-16) a phenyl lower alkoxy group optionally substituted on the phenyl ring with one or more lower alkyl groups optionally substituted with one or more halogen atoms,
- (1-1-19) an N-lower alkyl-N-phenyl amino lower alkyl group optionally substituted on the phenyl ring with one or more halogen atoms,
- (1-1-20) an N-benzyl-N-lower alkyl amino group optionally substituted on the phenyl ring with one or more lower alkyl groups optionally substituted with one or more halogen atoms,
- (1-1-21) a pyridyl group optionally substituted with one or more lower alkyl groups optionally substituted with one or more halogen atoms,
- (1-1-23) a pyridyloxy lower alkyl group optionally substituted on the pyridine ring with one or more lower alkyl groups optionally substituted with one or more halogen atoms,
- (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
- (1-1-25) a pyrimidinyl group optionally substituted with one or more lower alkyl groups optionally substituted with one or more halogen atoms,
- (1-1-26) a pyrimidinylvinyl group optionally substituted on the pyrimidine ring with one or more lower alkyl groups optionally substituted with one or more halogen atoms,
- (1-1-27) a piperidyl group optionally substituted with one or more lower alkyl groups optionally substituted with one or more halogen atoms,
- (1-1-31) a thienyl group,
- (1-1-32) a benzothienyl group,
- (1-1-33) a benzo[1,3]dioxolyl group optionally substituted with one or more halogen atoms,
- (1-1-35) a benzothienylvinyl group, and
- (1-1-36) a benzo[1,3]dioxolylvinyl group optionally substituted on the benzo[1,3]dioxole ring with one or more halogen atoms, (1-2) a thiazolyl group substituted with one or more members selected from the group consisting of
- (1-2-1) a lower alkyl group optionally substituted with one or more halogen atoms,
- (1-2-4) a halogen atom,
- (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
- (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of
- (1-3-1) a lower alkyl group,
- (1-3-2) a cycloalkyl group, and
- (1-3-3) a phenyl group optionally substituted with one or more members selected from the group consisting of a halogen atom; and a lower alkyl group optionally substituted with one or more halogen atoms, (1-4) a thienyl group substituted with one or more members selected from the group consisting of
- (1-4-2) a phenyl group optionally substituted with one or more lower alkyl groups optionally substituted with one or more halogen atoms, (1-5) a furyl group optionally substituted with one or more members selected from the group consisting of
- (1-5-1) a phenyl group optionally substituted with one or more halogen atoms, and
- (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of (1-6-1) a lower alkyl group, and
(1-6-2) a phenyl group optionally substituted with one or more members selected from the group consisting of a halogen atom; and a lower alkyl group optionally substituted with one or more halogen atoms,
(1-7) a pyridyl group substituted with one or more members selected from the group consisting of
(1-7-3) a benzofuryl group,
(1-9) an indolyl group optionally substituted with one or more members selected from the group consisting of
(1-9-1) a lower alkyl group optionally substituted with one or more halogen atoms,
(1-10) a benzofuryl group optionally substituted with one or more members selected from the group consisting of
(1-10-2) a phenyl group optionally substituted with one or more halogen atoms,
(1-12) a phenyl lower alkyl group optionally substituted on the phenyl ring with one or more members selected from the group consisting of
(1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of
(1-13-1) a phenyl group,
(1-13-2) a pyrrolidyl group, and
(1-13-3) a piperidyl group.

As another preferable embodiment, $R^{1a}$ is the following (1-1):
(1-1) a phenyl group substituted with one or more (preferably 1 to 3) members selected from the group consisting of
(1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
(1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
(1-1-9) a halogen atom (preferably provided that the phenyl group of (1-1) is substituted with one or more halogen atoms, then the phenyl group of (1-1) is substituted with additional one or more substituents excluding a phenoxy group),
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
(1-1-14) a phenoxy group (preferably provided that the phenyl group of (1-1) is substituted with one or more phenoxy groups, then the phenyl group of (1-1) is substituted with additional one or more substituents excluding a halogen atom),
(1-1-16) a phenyl lower alkoxy group optionally substituted on the phenyl ring with one or more lower alkyl groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-31) a thienyl group,
(1-1-32) a benzothienyl group,
(1-1-33) a benzo[1,3]dioxolyl group optionally substituted with one or more halogen atoms,
(1-1-35) a benzothienylvinyl group, and
(1-1-36) a benzo[1,3]dioxolylvinyl group optionally substituted on the benzo[1,3]dioxole ring with one or more halogen atoms.

As another preferable embodiment, $R^{1a}$ is one of the following (1-2) to (1-7), (1-9), (1-10), (1-12) and (1-13):
(1-2) a thiazolyl group substituted with one or more members selected from the group consisting of
(1-2-1) a lower alkyl group optionally substituted with one or more halogen atoms,
(1-2-4) a halogen atom,
(1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of
  (1-3-1) a lower alkyl group,
  (1-3-2) a cycloalkyl group, and
  (1-3-3) a phenyl group optionally substituted with one or more members selected from the group consisting of a halogen atom; and a lower alkyl group optionally substituted with one or more halogen atoms,
(1-4) a thienyl group substituted with one or more members selected from the group consisting of
  (1-4-2) a phenyl group optionally substituted with one or more lower alkyl groups optionally substituted with one or more halogen atoms,
(1-5) a furyl group optionally substituted with one or more members selected from the group consisting of
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of
  (1-6-1) a lower alkyl group, and
  (1-6-2) a phenyl group optionally substituted with one or more members selected from the group consisting of a halogen atom; and a lower alkyl group optionally substituted with one or more halogen atoms,
(1-7) a pyridyl group substituted with one or more members selected from the group consisting of (1-7-3) a benzofuryl group,
(1-9) an indolyl group optionally substituted with one or more members selected from the group consisting of
  (1-9-1) a lower alkyl group optionally substituted with one or more halogen atoms,
(1-10) a benzofuryl group optionally substituted with one or more members selected from the group consisting of
  (1-10-2) a phenyl group optionally substituted with one or more halogen atoms,
(1-12) a phenyl lower alkyl group optionally substituted on the phenyl ring with one or more members selected from the group consisting of
  (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of
  (1-13-1) a phenyl group,
  (1-13-2) a pyrrolidyl group, and
  (1-13-3) a piperidyl group.
As another preferable embodiment, $R^{1a}$ is the following (1-2):
(1-2) a thiazolyl group substituted with one or more members selected from the group consisting of
  (1-2-1) a lower alkyl group optionally substituted with one or more halogen atoms,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
  (1-2-11) a pyridyl group optionally substituted with one or more members selected from the group consisting of a halogen atom; and a lower alkyl group optionally substituted with one or more halogen atoms.
As another preferable embodiment, $R^{1a}$ is the following (1-3):
(1-3) an oxazolyl group optionally substituted with one or more members selected from the group consisting of
  (1-3-1) a lower alkyl group,
  (1-3-2) a cycloalkyl group, and
  (1-3-3) a phenyl group optionally substituted with one or more members selected from the group consisting of a halogen atom; and a lower alkyl group optionally substituted with one or more halogen atoms.
As another preferable embodiment, $R^{1a}$ is the following (1-5):
(1-5) a furyl group optionally substituted with one or more members selected from the group consisting of
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms.
As another preferable embodiment, $R^{1a}$ is the following (1-13):
(1-13) a pyrimidinyl group optionally substituted with one or more members selected from the group consisting of
  (1-13-1) a phenyl group,
  (1-13-2) a pyrrolidyl group, and
  (1-13-3) a piperidyl group.
The present invention also provides a cyanotriazole compound represented by the formula (1bb):

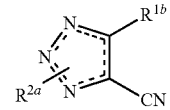

(1bb)

wherein
$R^{1b}$ is one of the following (1-1) to (1-13):
(1-1) a phenyl group optionally substituted with one or more members selected from the group consisting of the following (1-1-1) to (1-1-34):
  (1-1-1) a lower alkyl group optionally substituted with one or more halogen atoms,
  (1-1-2) a lower alkoxy group optionally substituted with one or more halogen atoms,
  (1-1-3) a lower alkoxy lower alkyl group,
  (1-1-4) a cycloalkyl group,
  (1-1-5) a cycloalkoxy group,
  (1-1-6) a cycloalkyl lower alkyl group,
  (1-1-7) a cycloalkyl lower alkoxy group,
  (1-1-8) a cycloalkyl lower alkoxy lower alkyl group,
  (1-1-9) a halogen atom,
  (1-1-10) a cyano group,
  (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group optionally substituted on the phenyl ring with one or more members selected from the group consisting of a lower alkoxy group; a lower alkyl group optionally substituted with one or more halogen atoms; a cyano group; and a halogen atom,
(1-1-14) a phenoxy group optionally substituted with one or more lower alkyl groups optionally substituted with one or more halogen atoms,
(1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
(1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
(1-1-17) a phenylthio group optionally substituted with one or more halogen atoms,
(1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms, and
(1-1-34) an indolinyl lower alkyl group,
(1-2) a thiazolyl group optionally substituted with one or more members selected from the group consisting of the following (1-2-1) to (1-2-11):
(1-2-1) a lower alkyl group optionally substituted with one or more halogen atoms,
(1-2-2) a lower alkoxy group,
(1-2-3) a cycloalkyl group,
(1-2-4) a halogen atom,
(1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-2-6) a styryl group optionally substituted on the phenyl ring with one or more lower alkyl groups optionally substituted with one or more halogen atoms,
(1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
(1-2-8) a benzyloxy group optionally substituted on the phenyl ring with one or more halogen atoms,
(1-2-9) a phenylthio group optionally substituted with one or more members selected from the group consisting of a halogen atom; and a lower alkyl group optionally substituted with one or more halogen atoms,
(1-2-10) an N-lower alkyl-N-phenyl amino group optionally substituted on the phenyl ring with one or more members selected from the group consisting of a halogen atom; and a lower alkyl group optionally substituted with one or more halogen atoms, and
(1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
(1-3-1) a lower alkyl group,
(1-3-2) a cycloalkyl group, and
(1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group optionally substituted with one or more members selected from the group consisting of the following (1-4-1) to (1-4-5):
(1-4-1) a lower alkyl group optionally substituted with one or more halogen atoms,
(1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms, (1-4-3) a benzyl group optionally substituted on the phenyl ring with one or more halogen atoms,
(1-4-4) a phenoxy group optionally substituted with one or more lower alkyl groups optionally substituted with one or more halogen atoms, and
(1-4-5) a styryl group optionally substituted on the phenyl ring with one or more lower alkyl groups optionally substituted with one or more halogen atoms, (1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms, (1-7) a pyridyl group optionally substituted with one or more members selected from the group consisting of the following (1-7-1) to (1-7-2):
  (1-7-1) a benzyloxy lower alkyl group optionally substituted on the phenyl ring with one or more lower alkyl groups optionally substituted with one or more halogen atoms, and
  (1-7-2) a phenyl group optionally substituted with one or more lower alkyl groups optionally substituted with one or more halogen atoms, (1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms, (1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms, (1-10) a benzofuryl group optionally substituted with one or more phenyl groups optionally substituted with one or more halogen atoms, (1-11) a benzothienyl group optionally substituted with one or more phenyl groups optionally substituted with one or more halogen atoms, (1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms, and
  (1-12-2) a benzyloxy group optionally substituted on the phenyl ring with one or more lower alkyl groups optionally substituted with one or more halogen atoms, and (1-13) a pyrimidinyl group optionally substituted with one or more members selected from the group consisting of the following (1-13-1) to (1-13-3):
  (1-13-1) a phenyl group,
  (1-13-2) a pyrrolidyl group, and
  (1-13-3) a piperidyl group; and $R^{2a}$ is one of the following (2-1) to (2-3):
(2-1) a lower alkyl group optionally substituted with one or more members selected from the group consisting of a hydroxy group; and a phenyl group optionally substituted with one or more lower alkyl groups optionally substituted with one or more halogen atoms,
(2-2) a 2-oxo-1,3-dioxolanyl group, and
(2-3) a group represented by the formula:

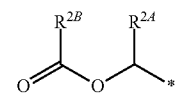

wherein
* is a bonding site;
$R^{2A}$ is one of the following (2A-1) to (2A-2):
  (2A-1) a hydrogen atom, and
  (2A-2) a lower alkyl group; and
$R^{2B}$ is one of the following (2B-1) to (2B-6):
  (2B-1) a lower alkoxy group optionally substituted with one or more members selected from the group consisting of a lower alkoxy group; a carboxy group; a lower alkoxycarbonyl group; a hydroxy group; a phenyl lower alkoxycarbonyl group; a lower alkenyloxy-carbonyl group; a morpholinyl group; a benzyloxycarbonyl group; and a tetrahydropyran-2-yloxy group,
  (2B-2) a lower alkyl group;
  (2B-3) a lower alkylamino group optionally substituted with one or more lower alkoxy-carbonyl groups;
  (2B-4) a cycloalkyl group;
  (2B-5) a cycloalkoxy group; and
  (2B-6) a phenyl group;

or a salt thereof (hereinafter to be referred to as Compound (1bb)).

As preferable embodiment, the cyanotriazole compound or salt is a compound represented by the formula (1bbA):

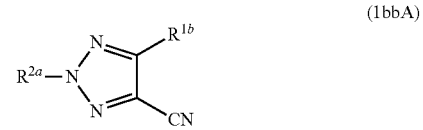

wherein each symbol is as defined in Compound (1bb), or a salt thereof (hereinafter to be referred to as Compound (1bbA)).

As another preferable embodiment, $R^{1b}$ is one of the following (1-1) to (1-5):
(1-1) a phenyl group optionally substituted with one or more members selected from:
  (1-1-1) a lower alkyl group optionally substituted with one or more halogen atoms, (1-1-2) a lower alkoxy group optionally substituted with one or more halogen atoms,
(1-1-9) a halogen atom,
(1-1-11) a phenyl group optionally substituted with one or more lower alkoxy groups optionally substituted with one or more halogen atoms,
(1-1-12) a phenyl lower alkyl group optionally substituted on the phenyl ring with one or more halogen atoms,
(1-1-13) a styryl group optionally substituted on the phenyl ring with one or more lower alkyl groups optionally substituted with one or more halogen atoms,
(1-1-16) a phenyl lower alkoxy group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-31) a thienyl group, and
(1-1-33) a benzo[1,3]dioxolyl group optionally substituted with one or more halogen atoms,
(1-2) a thiazolyl group optionally substituted with one or more members selected from:
   (1-2-1) a lower alkyl group optionally substituted with one or more halogen atoms,
   (1-2-4) a halogen atom,
   (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
   (1-2-11) a pyridyl group optionally substituted with one or more lower alkyl groups optionally substituted with one or more halogen atoms,
(1-3) an oxazolyl group optionally substituted with one or more members selected from:
   (1-3-1) a lower alkyl group,
   (1-3-2) a cycloalkyl group, and
   (1-3-3) a phenyl group optionally substituted with one or more members selected from the group consisting of a halogen atom; and a lower alkyl group optionally substituted with one or more halogen atoms,
(1-4) a thienyl group optionally substituted with one or more members selected from:
   (1-4-2) a phenyl group optionally substituted with one or more lower alkyl groups optionally substituted with one or more halogen atoms, and
(1-5) a furyl group optionally substituted with one or more members selected from:
   (1-5-1) a phenyl group optionally substituted with one or more halogen atoms; and $R^{2a}$ is one of the following groups:
a 1-(((2-carboxy-2,2-dimethylethoxy)carbonyl)oxy)ethyl group;
a 1-(((2-carboxy-1,1-dimethylethoxy) carbonyl)oxy)ethyl group;
a 1-(((2-hydroxyethoxy)carbonyl)oxy)ethyl group;
a 1-(butyryloxy)ethyl group;
a 1-(isobutyryloxy)ethyl group;
an acetoxymethyl group; and
a butyryloxymethyl group.

The present invention also provides a cyanotriazole compound selected from the group consisting of following compounds:
5-[3-methyl-5-(6-trifluoromethyl-pyridin-3-yl)-phenyl]-3H-[1,2,3]triazole-4-carbonitrile (Example 11),
5-[3-methyl-5-(6-trifluoromethyl-pyridin-3-yl)-phenyl]-2H-[1,2,3]triazole-4-carbonitrile,
5-[3-methyl-5-(6-trifluoromethyl-pyridin-3-yl)-phenyl]-1H-[1,2,3]triazole-4-carbonitrile,
5-[3-trifluoromethyl-5-(6-trifluoromethyl-pyridin-2-yl)-phenyl]-3H-[1,2,3]triazole-4-carbonitrile (Example 14),
5-[3-trifluoromethyl-5-(6-trifluoromethyl-pyridin-2-yl)-phenyl]-2H-[1,2,3]triazole-4-carbonitrile,
5-[3-trifluoromethyl-5-(6-trifluoromethyl-pyridin-2-yl)-phenyl]-1H-[1,2,3]triazole-4-carbonitrile,
5-[3-methoxy-5-(4-trifluoromethyl-pyridin-2-yl)-phenyl]-3H-[1,2,3]triazole-4-carbonitrile (Example 15),
5-[3-methoxy-5-(4-trifluoromethyl-pyridin-2-yl)-phenyl]-2H-[1,2,3]triazole-4-carbonitrile,
5-[3-methoxy-5-(4-trifluoromethyl-pyridin-2-yl)-phenyl])-1H-[1,2,3]triazole-4-carbonitrile,
5-[3-(4-trifluoromethyl-pyrimidin-2-yl)-phenyl]-3H-[1,2,3]triazole-4-carbonitrile (Example 21),
5-[3-(4-trifluoromethyl-pyrimidin-2-yl)-phenyl]-2H-[1,2,3]triazole-4-carbonitrile,
5-[3-(4-trifluoromethyl-pyrimidin-2-yl)-phenyl]-1H-([1,2,3]triazole-4-carbonitrile,
5-[3-methyl-5-(4-trifluoromethyl-pyrimidin-2-yl)-phenyl]-3H-[1,2,3]triazole-4-carbonitrile (Example 22),
5-[3-methyl-5-(4-trifluoromethyl-pyrimidin-2-yl)-phenyl]-2H-[1,2,3]triazole-4-carbonitrile,
5-[3-methyl-5-(4-trifluoromethyl-pyrimidin-2-yl)-phenyl]-1H-[1,2,3]triazole-4-carbonitrile,
5-[3-chloro-5-(4-trifluoromethyl-pyrimidin-2-yl)-phenyl]-3H-[1,2,3]triazole-4-carbonitrile (Example 23),
5-[(3-chloro-5-(4-trifluoromethyl-pyrimidin-2-yl)-phenyl]-2H-[1,2,3]triazole-4-carbonitrile,
5-[(3-chloro-5-(4-trifluoromethyl-pyrimidin-2-yl)-phenyl]-1H-[1,2,3]triazole-4-carbonitrile,
5-(5-chloro-4'-trifluoromethoxy-biphenyl-3-yl)-3H-[1,2,3]triazole-4-carbonitrile (Example 29),
5-(5-chloro-4'-trifluoromethoxy-biphenyl-3-yl)-2H-[1,2,3]triazole-4-carbonitrile,
5-(5-chloro-4'-trifluoromethoxy-biphenyl-3-yl)-1H-[1,2,3]triazole-4-carbonitrile,
5-{3-[(E)-2-(4-cyano-phenyl)-vinyl]-phenyl}-3H-[1,2,3]triazole-4-carbonitrile (Example 41),
5-{3-[(E)-2-(4-cyano-phenyl)-vinyl]-phenyl}-2H-[1,2,3]triazole-4-carbonitrile,
5-{3-[(E)-2-(4-cyano-phenyl)-vinyl]-phenyl}-1H-[1,2,3]triazole-4-carbonitrile,
5-{3-chloro-5-[(E)-2-(3-trifluoromethyl-phenyl)-vinyl]-phenyl}-3H-[1,2,3]triazole-4-carbonitrile (Example 47),
5-{3-chloro-5-[(E)-2-(3-trifluoromethyl-phenyl)-vinyl]-phenyl}-2H-[1,2,3]triazole-4-carbonitrile,
5-{3-chloro-5-[(E)-2-(3-trifluoromethyl-phenyl)-vinyl]-phenyl}-1H-[1,2,3]triazole-4-carbonitrile, 5-{3-[(E)-2-(5-trifluoromethyl-pyridin-3-yl)-vinyl]-phenyl}-3H-[1,2,3]triazole-4-carbonitrile (Example 49),
5-{3-[(E)-2-(5-trifluoromethyl-pyridin-3-yl)-vinyl]-phenyl}-2H-[1,2,3]triazole-4-carbonitrile,
5-{3-[(E)-2-(5-trifluoromethyl-pyridin-3-yl)-vinyl]-phenyl}-1H-[1,2,3]triazole-4-carbonitrile,
5-{3-[(E)-2-(4-trifluoromethyl-pyridin-2-yl)-vinyl]-phenyl}-3H-[1,2,3]triazole-4-carbonitrile (Example 50),
5-{3-[(E)-2-(4-trifluoromethyl-pyridin-2-yl)-vinyl]-phenyl}-2H-[1,2,3]triazole-4-carbonitrile,
5-{3-[(E)-2-(4-trifluoromethyl-pyridin-2-yl)-vinyl]-phenyl}-1H-[1,2,3]triazole-4-carbonitrile,
5-{3-trifluoromethyl-5-[(E)-2-(6-trifluoromethyl-pyridin-2-yl)-vinyl]-phenyl}-3H-[1,2,3]triazole-4-carbonitrile (Example 51),
5-{3-trifluoromethyl-5-[(E)-2-(6-trifluoromethyl-pyridin-2-yl)-vinyl]-phenyl}-2H-[1,2,3]triazole-4-carbonitrile,
5-{3-trifluoromethyl-5-[(E)-2-(6-trifluoromethyl-pyridin-2-yl)-vinyl]-phenyl}-1H-[1,2,3]triazole-4-carbonitrile,
5-{3-[(E)-2-(4-trifluoromethyl-pyrimidin-2-yl)-vinyl]-phenyl}-3H-[1,2,3]triazole-4-carbonitrile (Example 52),
5-{3-[(E)-2-(4-trifluoromethyl-pyrimidin-2-yl)-vinyl]-phenyl}-2H-[1,2,3]triazole-4-carbonitrile,
5-{3-[(E)-2-(4-trifluoromethyl-pyrimidin-2-yl)-vinyl]-phenyl}-1H-[1,2,3]triazole-4-carbonitrile,
5-[3-(4-trifluoromethyl-pyridin-2-yloxymethyl)-phenyl]-3H-[1,2,3]triazole-4-carbonitrile (Example 55),
5-[3-(4-trifluoromethyl-pyridin-2-yloxymethyl)-phenyl]-2H-([1,2,3]triazole-4-carbonitrile,
5-[3-(4-trifluoromethyl-pyridin-2-yloxymethyl)-phenyl]-1H-[1,2,3]triazole-4-carbonitrile,
5-[3-(2,5-bis-trifluoromethyl-benzyloxy)-phenyl]-3H-[1,2,3]triazole-4-carbonitrile (Example 60),
5-[3-(2,5-bis-trifluoromethyl-benzyloxy)-phenyl]-2H-[1,2,3]triazole-4-carbonitrile,
5-[3-(2,5-bis-trifluoromethyl-benzyloxy)-phenyl]-1H-[1,2,3]triazole-4-carbonitrile,
5-[4-(4-trifluoromethyl-pyrimidin-2-yl)-phenyl]-3H-[1,2,3]triazole-4-carbonitrile (Example 70),
5-[4-(4-trifluoromethyl-pyrimidin-2-yl)-phenyl]-2H-[1,2,3]triazole-4-carbonitrile,
5-[4-(4-trifluoromethyl-pyrimidin-2-yl)-phenyl]-1H-[1,2,3]triazole-4-carbonitrile,
5-[2-(4-chloro-phenyl)-thiazol-4-yl]-3H-[1,2,3]triazole-4-carbonitrile (Example 75),
5-[2-(4-chloro-phenyl)-thiazol-4-yl]-2H-[1,2,3]triazole-4-carbonitrile,
5-[2-(4-chloro-phenyl)-thiazol-4-yl]-1H-[1,2,3]triazole-4-carbonitrile,
5-[2-(3,4-dichloro-phenyl)-thiazol-4-yl]-3H-[1,2,3]triazole-4-carbonitrile (Example 77),
5-[2-(3,4-dichloro-phenyl)-thiazol-4-yl]-2H-[1,2,3]triazole-4-carbonitrile,
5-[2-(3,4-dichloro-phenyl)-thiazol-4-yl]-1H-[1,2,3]triazole-4-carbonitrile,
5-[2-(3-trifluoromethyl-phenyl)-thiazol-4-yl]-3H-[1,2,3]triazole-4-carbonitrile (Example 78),
5-[2-(3-trifluoromethyl-phenyl)-thiazol-4-yl]-2H-[1,2,3]triazole-4-carbonitrile,
5-[2-(3-trifluoromethyl-phenyl)-thiazol-4-yl]-1H-[1,2,3]triazole-4-carbonitrile,
5-[2-(3-trifluoromethoxy-phenyl)-thiazol-4-yl]-3H-[1,2,3]triazole-4-carbonitrile (Example 79),
5-[2-(3-trifluoromethoxy-phenyl)-thiazol-4-yl]-2H-[1,2,3]triazole-4-carbonitrile,
5-[2-(3-trifluoromethoxy-phenyl)-thiazol-4-yl]-1H-[1,2,3]triazole-4-carbonitrile,
5-[2-(3-chloro-4-fluoro-phenyl)-5-methyl-thiazol-4-yl]-3H-[1,2,3]triazole-4-carbonitrile (Example 90),
5-[2-(3-chloro-4-fluoro-phenyl)-5-methyl-thiazol-4-yl]-2H-[1,2,3]triazole-4-carbonitrile,
5-[2-(3-chloro-4-fluoro-phenyl)-5-methyl-thiazol-4-yl]-1H-[1,2,3]triazole-4-carbonitrile,
5-[5-methyl-2-(4-trifluoromethyl-phenyl)-thiazol-4-yl]-3H-[1,2,3]triazole-4-carbonitrile (Example 92),
5-[5-methyl-2-(4-trifluoromethyl-phenyl)-thiazol-4-yl]-2H-[1,2,3]triazole-4-carbonitrile,
5-[5-methyl-2-(4-trifluoromethyl-phenyl)-thiazol-4-yl]-1H-[1,2,3]triazole-4-carbonitrile,
5-[2-(4-chloro-phenyl)-5-ethyl-thiazol-4-yl]-3H-[1,2,3]triazole-4-carbonitrile (Example 98),
5-[2-(4-chloro-phenyl)-5-ethyl-thiazol-4-yl]-2H-[1,2,3]triazole-4-carbonitrile,
5-[2-(4-chloro-phenyl)-5-ethyl-thiazol-4-yl]-1H-[1,2,3]triazole-4-carbonitrile,
5-[5-ethyl-2-(5-trifluoromethyl-pyridin-2-yl)-thiazol-4-yl]-3H-[(1,2,3]triazole-4-carbonitrile (Example 100),
5-[5-ethyl-2-(5-trifluoromethyl-pyridin-2-yl)-thiazol-4-yl]-2H-[1,2,3]triazole-4-carbonitrile,
5-[5-ethyl-2-(5-trifluoromethyl-pyridin-2-yl)-thiazol-4-yl]-1H-[1,2,3]triazole-4-carbonitrile,
5-[5-chloro-2-(3-trifluoromethyl-phenyl-phenyl)-thiazol-4-yl]-3H-[1,2,3]triazole-4-carbonitrile (Example 108),
5-[5-chloro-2-(3-trifluoromethyl-phenyl)-thiazol-4-yl]-2H-[1,2,3]triazole-4-carbonitrile,
5-[5-chloro-2-(3-trifluoromethyl-phenyl)-thiazol-4-yl]-1H-[1,2,3]triazole-4-carbonitrile,
5-[5-cyclopropyl-2-(3-trifluoromethyl-phenyl)-oxazol-4-yl]-3H-[1,2,3]triazole-4-carbonitrile (Example 120),
5-[5-cyclopropyl-2-(3-trifluoromethyl-phenyl)-oxazol-4-yl]-2H-[1,2,3]triazole-4-carbonitrile,
5-[5-cyclopropyl-2-(3-trifluoromethyl-phenyl)-oxazol-4-yl]-1H-[1,2,3]triazole-4-carbonitrile,
5-[2-(4-chloro-phenyl)-5-isopropyl-oxazol-4-yl]-3H-[1,2,3]triazole-4-carbonitrile (Example 122),
5-[2-(4-chloro-phenyl)-5-isopropyl-oxazol-4-yl]-2H-([1,2,3]triazole-4-carbonitrile,
5-[2-(4-chloro-phenyl)-5-isopropyl-oxazol-4-yl]-1H-[1,2,3]triazole-4-carbonitrile,
5-{5-[(E)-2-(3-trifluoromethyl-phenyl)-vinyl]-furan-2-yl}-3H-[1,2,3]triazole-4-carbonitrile (Example 137),
5-{5-[(E)-2-(3-trifluoromethyl-phenyl)-vinyl]-furan-2-yl}-2H-[1,2,3]triazole-4-carbonitrile,
5-{5-[(E)-2-(3-trifluoromethyl-phenyl)-vinyl]-furan-2-yl}-1H-[1,2,3]triazole-4-carbonitrile,
5-[1-(4,4,4-trifluoro-butyl)-1H-indol-6-yl]-3H-([1,2,3]triazole-4-carbonitrile (Example 146),
5-[1-(4,4,4-trifluoro-butyl)-1H-indol-6-yl]-2H-[1,2,3]triazole-4-carbonitrile,
5-[1-(4,4,4-trifluoro-butyl)-1H-indol-6-yl]-1H-[1,2,3]triazole-4-carbonitrile,
5-[6-(4-fluoro-phenyl)-benzofuran-2-yl]-3H-[1,2,3]triazole-4-carbonitrile (Example 147),
5-[6-(4-fluoro-phenyl)-benzofuran-2-yl]-2H-[1,2,3]triazole-4-carbonitrile,
5-[6-(4-fluoro-phenyl)-benzofuran-2-yl]-1H-[1,2,3]triazole-4-carbonitrile,
5-(5'-fluoro-3'-trifluoromethyl-biphenyl-3-yl)-3H-[1,2,3]triazole-4-carbonitrile (Example 220),
5-(5'-fluoro-3'-trifluoromethyl-biphenyl-3-yl)-2H-[1,2,3]triazole-4-carbonitrile,
5-(5'-fluoro-3'-trifluoromethyl-biphenyl-3-yl)-1H-[1,2,3]triazole-4-carbonitrile, 5-(5-chloro-3',5'-bis-trifluoromethyl-biphenyl-3-yl)-3H-[1,2,3]triazole-4-carbonitrile (Example 275),
5-(5-chloro-3',5'-bis-trifluoromethyl-biphenyl-3-yl)-2H-[1,2,3]triazole-4-carbonitrile,
5-(5-chloro-3',5'-bis-trifluoromethyl-biphenyl-3-yl)-1H-[1,2,3]triazole-4-carbonitrile,
5-(5-chloro-3'-fluoro-4'-trifluoromethoxy-biphenyl-3-yl)-3H-[1,2,3]triazole-4-carbonitrile (Example 276),
5-(5-chloro-3'-fluoro-4'-trifluoromethoxy-biphenyl-3-yl)-2H-[1,2,3]triazole-4-carbonitrile,
5-(5-chloro-3'-fluoro-4'-trifluoromethoxy-biphenyl-3-yl)-1H-[1,2,3]triazole-4-carbonitrile,
5-(3'-fluoro-5,4'-bis-trifluoromethoxy-biphenyl-3-yl)-3H-[1,2,3]triazole-4-carbonitrile (Example 298),
5-(3'-fluoro-5,4'-bis-trifluoromethoxy-biphenyl-3-yl)-2H-[1,2,3]triazole-4-carbonitrile,
5-(3'-fluoro-5,4'-bis-trifluoromethoxy-biphenyl-3-yl)-1H-[1,2,3]triazole-4-carbonitrile,
5-[3-(3,4-bis-trifluoromethyl-benzyloxy)-phenyl]-3H-[1,2,3]triazole-4-carbonitrile (Example 423),
5-[3-(3,4-bis-trifluoromethyl-benzyloxy)-phenyl]-2H-[1,2,3]triazole-4-carbonitrile,
5-[3-(3,4-bis-trifluoromethyl-benzyloxy)-phenyl]-1H-[1,2,3]triazole-4-carbonitrile,
5-[3-(2,5-bis-trifluoromethyl-benzyloxy)-5-trifluoromethoxy-phenyl]-3H-[1,2,3]triazole-4-carbonitrile (Example 504),
5-[3-(2,5-bis-trifluoromethyl-benzyloxy)-5-trifluoromethoxy-phenyl]-2H-[1,2,3]triazole-4-carbonitrile,
5-[3-(2,5-bis-trifluoromethyl-benzyloxy)-5-trifluoromethoxy-phenyl]-1H-[1,2,3]triazole-4-carbonitrile,
5-{3-[(E)-2-(4-fluoro-2-trifluoromethyl-phenyl)-vinyl]-phenyl}-3H-[1,2,3]triazole-4-carbonitrile (Example 600),
5-{3-[(E)-2-(4-fluoro-2-trifluoromethyl-phenyl)-vinyl]-phenyl}-2H-[1,2,3]triazole-4-carbonitrile,
5-{3-[(E)-2-(4-fluoro-2-trifluoromethyl-phenyl)-vinyl]-phenyl}-1H-[1,2,3]triazole-4-carbonitrile,
5-{3-[(E)-2-(4-fluoro-3-methyl-phenyl)-vinyl]-phenyl}-3H-[1,2,3]triazole-4-carbonitrile (Example 607),
5-{3-[(E)-2-(4-fluoro-3-methyl-phenyl)-vinyl]-phenyl}-2H-[1,2,3]triazole-4-carbonitrile,
5-{3-[(E)-2-(4-fluoro-3-methyl-phenyl)-vinyl]-phenyl}-1H-[1,2,3]triazole-4-carbonitrile,
5-{3-[(E)-2-(3,5-bis-trifluoromethyl-phenyl)-vinyl]-5-chloro-phenyl}-3H-[1,2,3]triazole-4-carbonitrile (Example 610),
5-{3-[(E)-2-(3,5-bis-trifluoromethyl-phenyl)-vinyl]-5-chloro-phenyl}-2H-[1,2,3]triazole-4-carbonitrile,
5-{3-[(E)-2-(3,5-bis-trifluoromethyl-phenyl)-vinyl]-5-chloro-phenyl}-1H-[1,2,3]triazole-4-carbonitrile,
5-{3-[(E)-2-(3-trifluoromethyl-phenyl)-vinyl]-phenyl}-3H-[1,2,3]triazole-4-carbonitrile (Example 613),
5-{3-[(E)-2-(3-trifluoromethyl-phenyl)-vinyl]-phenyl}-2H-[1,2,3]triazole-4-carbonitrile,
5-{3-[(E)-2-(3-trifluoromethyl-phenyl)-vinyl]-phenyl}-1H-[1,2,3]triazole-4-carbonitrile,
5-{3-[(E)-2-(4-trifluoromethyl-phenyl)-vinyl]-phenyl}-3H-[1,2,3]triazole-4-carbonitrile (Example 617),
5-{3-[(E)-2-(4-trifluoromethyl-phenyl)-vinyl]-phenyl}-2H-[1,2,3]triazole-4-carbonitrile,
5-{3-[(E)-2-(4-trifluoromethyl-phenyl)-vinyl]-phenyl}-1H-[1,2,3]triazole-4-carbonitrile,
5-{3-trifluoromethyl-5-[(E)-2-(3-trifluoromethyl-phenyl)-vinyl]-phenyl}-3H-[1,2,3]triazole-4-carbonitrile (Example 620),
5-{3-trifluoromethyl-5-[(E)-2-(3-trifluoromethyl-phenyl)-vinyl]-phenyl}-2H-[1,2,3]triazole-4-carbonitrile,
5-{3-trifluoromethyl-5-[(E)-2-(3-trifluoromethyl-phenyl)-vinyl]-phenyl}-1H-[1,2,3]triazole-4-carbonitrile,
5-{3-chloro-5-[(E)-2-(4-fluoro-phenyl)-vinyl]-phenyl}-3H-[1,2,3]triazole-4-carbonitrile (Example 623),
5-{3-chloro-5-[(E)-2-(4-fluoro-phenyl)-vinyl]-phenyl}-2H-[1,2,3]triazole-4-carbonitrile,
5-{3-chloro-5-[(E)-2-(4-fluoro-phenyl)-vinyl]-phenyl}-1H-[1,2,3]triazole-4-carbonitrile,
5-{3-[(E)-2-(4-fluoro-phenyl)-vinyl]-5-methyl-phenyl}-3H-[1,2,3]triazole-4-carbonitrile (Example 627),
5-{3-[(E)-2-(4-fluoro-phenyl)-vinyl]-5-methyl-phenyl}-2H-[1,2,3]triazole-4-carbonitrile,
5-{3-[(E)-2-(4-fluoro-phenyl)-vinyl]-5-methyl-phenyl}-1H-[1,2,3]triazole-4-carbonitrile,
5-{3-[(E)-2-(4-fluoro-phenyl)-vinyl]-5-trifluoromethoxy-phenyl}-3H-[1,2,3]triazole-4-carbonitrile (Example 639),
5-{3-[(E)-2-(4-fluoro-phenyl)-vinyl]-5-trifluoromethoxy-phenyl}-2H-[1,2,3]triazole-4-carbonitrile,
5-{3-[(E)-2-(4-fluoro-phenyl)-vinyl]-5-trifluoromethoxy-phenyl}-1H-[1,2,3]triazole-4-carbonitrile,
5-{3-[(E)-2-(4-fluoro-phenyl)-vinyl]-phenyl}-3H-[1,2,3]triazole-4-carbonitrile (Example 640),
5-{3-[(E)-2-(4-fluoro-phenyl)-vinyl]-phenyl}-2H-[1,2,3]triazole-4-carbonitrile,
5-{3-[(E)-2-(4-fluoro-phenyl)-vinyl]-phenyl}-1H-[1,2,3]triazole-4-carbonitrile,
5-{3-ethoxy-5-[(E)-2-(3-trifluoromethyl-phenyl)-vinyl]-phenyl}-3H-[1,2,3]triazole-4-carbonitrile (Example 644),
5-{3-ethoxy-5-[(E)-2-(3-trifluoromethyl-phenyl)-vinyl]-phenyl}-2H-[1,2,3]triazole-4-carbonitrile,
5-{3-ethoxy-5-[(E)-2-(3-trifluoromethyl-phenyl)-vinyl]-phenyl}-1H-[1,2,3]triazole-4-carbonitrile,
5-{3-[(E)-2-(2,4-difluoro-phenyl)-vinyl]-5-trifluoromethyl-phenyl}-3H-[1,2,3]triazole-4-carbonitrile (Example 645),
5-{3-[(E)-2-(2,4-difluoro-phenyl)-vinyl]-5-trifluoromethyl-phenyl}-2H-[1,2,3]triazole-4-carbonitrile,
5-{3-[(E)-2-(2,4-difluoro-phenyl)-vinyl]-5-trifluoromethyl-phenyl}-1H-[1,2,3]triazole-4-carbonitrile,
5-{3-[(E)-2-(2,4-difluoro-phenyl)-vinyl]-phenyl}-3H-[1,2,3]triazole-4-carbonitrile (Example 646),
5-{3-[(E)-2-(2,4-difluoro-phenyl)-vinyl]-phenyl}-2H-[1,2,3]triazole-4-carbonitrile,
5-{3-[(E)-2-(2,4-difluoro-phenyl)-vinyl]-phenyl}-1H-[1,2,3]triazole-4-carbonitrile,
5-{3-chloro-5-[(E)-2-(3-trifluoromethoxy-phenyl)-vinyl]-phenyl}-3H-[1,2,3]triazole-4-carbonitrile (Example 649),
5-{3-chloro-5-[(E)-2-(3-trifluoromethoxy-phenyl)-vinyl]-phenyl}-2H-[1,2,3]triazole-4-carbonitrile,
5-{3-chloro-5-[(E)-2-(3-trifluoromethoxy-phenyl)-vinyl]-phenyl}-1H-[1,2,3]triazole-4-carbonitrile,
5-{3-methoxy-5-[(E)-2-(3-trifluoromethyl-phenyl)-vinyl]-phenyl}-3H-[1,2,3]triazole-4-carbonitrile (Example 657),
5-{3-methoxy-5-[(E)-2-(3-trifluoromethyl-phenyl)-vinyl]-phenyl}-2H-[1,2,3]triazole-4-carbonitrile,
5-{3-methoxy-5-[(E)-2-(3-trifluoromethyl-phenyl)-vinyl]-phenyl}-1H-[1,2,3]triazole-4-carbonitrile,
5-{3-[(E)-2-(3-fluoro-5-trifluoromethyl-phenyl)-vinyl]-phenyl}-3H-[1,2,3]triazole-4-carbonitrile (Example 659),
5-{3-[(E)-2-(3-fluoro-5-trifluoromethyl-phenyl)-vinyl]-phenyl}-2H-[1,2,3]triazole-4-carbonitrile,
5-{3-[(E)-2-(3-fluoro-5-trifluoromethyl-phenyl)-vinyl]-phenyl}-1H-[1,2,3]triazole-4-carbonitrile,
5-{3-[(E)-2-(4-fluoro-3-trifluoromethyl-phenyl)-vinyl]-phenyl}-3H-[1,2,3]triazole-4-carbonitrile (Example 663),
5-{3-[(E)-2-(4-fluoro-3-trifluoromethyl-phenyl)-vinyl]-phenyl}-2H-[1,2,3]triazole-4-carbonitrile, 5-{3-[(E)-2-(4-fluoro-3-trifluoromethyl-phenyl)-vinyl]-phenyl}-1H-[1,2,3]triazole-4-carbonitrile,
5-(3-benzo[b]thiophen-2-yl-5-chloro-phenyl)-3H-[1,2,3]triazole-4-carbonitrile (Example 718),
5-(3-benzo[b]thiophen-2-yl-5-chloro-phenyl)-2H-[1,2,3]triazole-4-carbonitrile,
5-(3-benzo[b]thiophen-2-yl-5-chloro-phenyl)-1H-[1,2,3]triazole-4-carbonitrile,
5-[3-(4-trifluoromethyl-pyridin-2-yl)-phenyl]-3H-[1,2,3]triazole-4-carbonitrile (Example 790),
5-[3-(4-trifluoromethyl-pyridin-2-yl)-phenyl]-2H-[1,2,3]triazole-4-carbonitrile,
5-[3-(4-trifluoromethyl-pyridin-2-yl)-phenyl]-1H-([1,2,3]triazole-4-carbonitrile,
5-[3-methyl-5-(5-trifluoromethyl-pyridin-2-yl)-phenyl]-3H-[1,2,3]triazole-4-carbonitrile (Example 807),
5-[3-methyl-5-(5-trifluoromethyl-pyridin-2-yl)-phenyl]-2H-[1,2,3]triazole-4-carbonitrile,
5-[3-methyl-5-(5-trifluoromethyl-pyridin-2-yl)-phenyl]-1H-[1,2,3]triazole-4-carbonitrile,
5-[3-(2,2-difluoro-benzo[1,3]dioxol-5-yl)-phenyl]-3H-[1,2,3]triazole-4-carbonitrile (Example 931),
5-[3-(2,2-difluoro-benzo[1,3]dioxol-5-yl)-phenyl]-28-[1,2,3]triazole-4-carbonitrile,
5-[3-(2,2-difluoro-benzo[1,3]dioxol-5-yl)-phenyl]-1H-[1,2,3]triazole-4-carbonitrile,
5-[3-(2,2-difluoro-benzo[1,3]dioxol-5-yl)-5-trifluoromethoxy-phenyl]-3H-[1,2,3]triazole-4-carbonitrile (Example 934),
5-[3-(2,2-difluoro-benzo[1,3]dioxol-5-yl)-5-trifluoromethoxy-phenyl]-2H-([1,2,3]triazole-4-carbonitrile,
5-[3-(2,2-difluoro-benzo[1,3]dioxol-5-yl)-5-trifluoromethoxy-phenyl]-1H-[1,2,3]triazole-4-carbonitrile,
5-[3-ethoxy-5-(4-trifluoromethyl-pyrimidin-2-yl)-phenyl]-38-[1,2,3]triazole-4-carbonitrile (Example 944),
5-[3-ethoxy-5-(4-trifluoromethyl-pyrimidin-2-yl)-phenyl]-2H-[1,2,3]triazole-4-carbonitrile,
5-[3-ethoxy-5-(4-trifluoromethyl-pyrimidin-2-yl)-phenyl]-1H-[1,2,3]triazole-4-carbonitrile,
5-[3-methyl-4-(4-trifluoromethyl-pyrimidin-2-yl)-phenyl]-3H-[1,2,3]triazole-4-carbonitrile (Example 989),
5-[3-methyl-4-(4-trifluoromethyl-pyrimidin-2-yl)-phenyl]-2H-[1,2,3]triazole-4-carbonitrile,
5-[3-methyl-4-(4-trifluoromethyl-pyrimidin-2-yl)-phenyl]-1H-[1,2,3]triazole-4-carbonitrile,
5-[3-((E)-2-benzo[b]thiophen-2-yl-vinyl)-phenyl]-3H-[1,2,3]triazole-4-carbonitrile (Example 1004),
5-[3-((E)-2-benzo[b]thiophen-2-yl-vinyl)-phenyl]-2H-[1,2,3]triazole-4-carbonitrile,
5-[3-((E)-2-benzo[b]thiophen-2-yl-vinyl)-phenyl]-1H-[1,2,3]triazole-4-carbonitrile,
5-{3-[(E)-2-(2,2-difluoro-benzo[1,3]dioxol-5-yl)-vinyl]-phenyl}-3H-[1,2,3]triazole-4-carbonitrile (Example 1017),
5-{3-[(E)-2-(2,2-difluoro-benzo[1,3]dioxol-5-yl)-vinyl]-phenyl}-2H-[1,2,3]triazole-4-carbonitrile,
5-{3-[(E)-2-(2,2-difluoro-benzo[1,3]dioxol-5-yl)-vinyl]-phenyl}-1H-[1,2,3]triazole-4-carbonitrile,
5-{3-[(E)-2-(6-trifluoromethyl-pyridin-2-yl)-vinyl]-phenyl}-3H-[1,2,3]triazole-4-carbonitrile (Example 1018),
5-{3-[(E)-2-(6-trifluoromethyl-pyridin-2-yl)-vinyl]-phenyl}-2H-[1,2,3]triazole-4-carbonitrile,
5-{3-[(E)-2-(6-trifluoromethyl-pyridin-2-yl)-vinyl]-phenyl}-1H-[1,2,3]triazole-4-carbonitrile,
5-[2-(4-chloro-2-fluoro-phenyl)-5-ethyl-thiazol-4-yl]-3H-[1,2,3]triazole-4-carbonitrile (Example 1248),
5-[2-(4-chloro-2-fluoro-phenyl)-5-ethyl-thiazol-4-yl]-2H-[1,2,3]triazole-4-carbonitrile,
5-[2-(4-chloro-2-fluoro-phenyl)-5-ethyl-thiazol-4-yl]-1H-[1,2,3]triazole-4-carbonitrile,
5-{5-[(E)-2-(4-fluoro-phenyl)-vinyl]-furan-2-yl}-3H-[1,2,3]triazole-4-carbonitrile (Example 1505),
5-{5-[(E)-2-(4-fluoro-phenyl)-vinyl]-furan-2-yl}-2H-[1,2,3]triazole-4-carbonitrile,
5-{5-[(E)-2-(4-fluoro-phenyl)-vinyl]-furan-2-yl}-1H-[1,2,3]triazole-4-carbonitrile,
5-(6-(benzofuran-2-yl)-pyridin-2-yl)-3H-[1,2,3]triazole-4-carbonitrile (Example 1573),
5-(6-(benzofuran-2-yl)-pyridin-2-yl)-2H-[1,2,3]triazole-4-carbonitrile,
5-(6-(benzofuran-2-yl)-pyridin-2-yl)-1H-[1,2,3]triazole-4-carbonitrile,
5-(2-phenyl-6-(piperidin-1-yl)-pyrimidin-4-yl)-3H-[1,2,3]triazole-4-carbonitrile (Example 1672),
5-(2-phenyl-6-(piperidin-1-yl)-pyrimidin-4-yl)-2H-[1,2,3]triazole-4-carbonitrile,
5-(2-phenyl-6-(piperidin-1-yl)-pyrimidin-4-yl)-1H-[1,2,3]triazole-4-carbonitrile,
5-(2-phenyl-6-(pyrrolidin-1-yl)-pyrimidin-4-yl)-3H-[1,2,3]triazole-4-carbonitrile (Example 1676),
5-(2-phenyl-6-(pyrrolidin-1-yl)-pyrimidin-4-yl)-2H-[1,2,3]triazole-4-carbonitrile,
5-(2-phenyl-6-(pyrrolidin-1-yl)-pyrimidin-4-yl)-1H-[1,2,3]triazole-4-carbonitrile,
3-(1-{4-[3-(2,5-bis-trifluoromethyl-benzyloxy)-phenyl]-5-cyano-2H-[1,2,3]triazol-2-yl}-ethoxycarbonyloxy)-2,2-dimethyl-propionic acid (Example 1806),
3-(1-{4-[3-chloro-5-(2,2-difluoro-benzo[1,3]dioxol-5-yl)-phenyl]-5-cyano-2H-[1,2,3]triazol-2-yl}-ethoxycarbonyloxy)-2,2-dimethyl-propionic acid (Example 1808),
3-(1-{4-[3-chloro-5-(4-trifluoromethyl-pyrimidin-2-yl)-phenyl]-5-cyano-2H-[1,2,3]triazol-2-yl}-ethoxycarbonyloxy)-2,2-dimethyl-propionic acid (Example 1810),
3-[1-(4-{3-chloro-5-[(E)-2-(3-trifluoromethyl-phenyl)-vinyl]-phenyl}-5-cyano-2H-[1,2,3]triazol-2-yl)-ethoxycarbonyloxy]-2,2-dimethyl-propionic acid (Example 1811),
3-(1-{4-cyano-5-[3-methoxy-5-(4-trifluoromethyl-pyridin-2-yl)-phenyl]-2H-[1,2,3]triazol-2-yl}-ethoxycarbonyloxy)-2,2-dimethyl-propionic acid (Example 1812),
3-[1-(4-cyano-5-{3-trifluoromethyl-5-[(E)-2-(6-trifluoromethyl-pyridin-2-yl)-vinyl]-phenyl}-2H-[1,2,3]triazol-2-yl)-ethoxycarbonyloxy]-2,2-dimethyl-propionic acid (Example 1813),
3-(1-{4-[2-(4-chloro-phenyl)-thiazol-4-yl]-5-cyano-2H-[(1,2,3]triazol-2-yl}-ethoxycarbonyloxy)-2,2-dimethyl-propionic acid (Example 1814),
3-[1-(4-cyano-5-{3-[(E)-2-(4-trifluoromethyl-pyridin-2-yl)-vinyl]-phenyl}-2H-[1,2,3]triazol-2-yl)-ethoxycarbonyloxy]-2,2-dimethyl-propionic acid (Example 1815),
3-[1-(4-cyano-5-{3-[(E)-2-(4-trifluoromethyl-pyrimidin-2-yl)-vinyl]-phenyl}-2H-[1,2,3]triazol-2-yl)-ethoxycarbonyloxy]-2,2-dimethyl-propionic acid (Example 1816),
3-(1-{4-[5-chloro-2-(3-trifluoromethyl-phenyl)-thiazol-4-yl]-5-cyano-2H-[1,2,3]triazol-2-yl}-ethoxycarbonyloxy)-2,2-dimethyl-propionic acid (Example 1817),
3-(1-{4-cyano-5-[2-(3-trifluoromethoxy-phenyl)-thiazol-4-yl]-2H-[1,2,3]triazol-2-yl}-ethoxycarbonyloxy)-2,2-dimethyl-propionic acid (Example 1818),
3-(1-{4-cyano-5-[2-(3,4-dichloro-phenyl)-thiazol-4-yl]-2H-[1,2,3]triazol-2-yl}-ethoxycarbonyloxy)-2,2-dimethyl-propionic acid (Example 1819), 3-(1-{4-cyano-5-[5-methyl-2-(4-trifluoromethyl-phenyl)-thiazol-4-yl]-2H-[1,2,3]triazol-2-yl}-ethoxycarbonyloxy)-2,2-dimethyl-propionic acid (Example 1820), 3-(1-{4-[2-(4-chloro-phenyl)-5-isopropyl-oxazol-4-yl]-5-cyano-2H-[1,2,3]triazol-2-yl}-ethoxycarbonyloxy)-2,2-dimethyl-propionic acid (Example 1822), 3-(1-{4-[2-(3-chloro-4-fluoro-phenyl)-5-methyl-thiazol-4-yl]-5-cyano-2H-[1,2,3]triazol-2-yl}-ethoxycarbonyloxy)-2,2-dimethyl-propionic acid (Example 1823), 3-(1-{4-cyano-5-[5-cyclopropyl-2-(3-trifluoromethyl-phenyl)-oxazol-4-yl]-2H-[1,2,3]triazol-2-yl}-ethoxycarbonyloxy)-2,2-dimethyl-propionic acid (Example 1824), 3-(1-{4-cyano-5-[3-methyl-5-(6-trifluoromethyl-pyridin-3-yl)-phenyl]-2H-[1,2,3]triazol-2-yl}-ethoxycarbonyloxy)-2,2-dimethyl-propionic acid (Example 1825), 3-(1-(4-cyano-5-[5-ethyl-2-(5-trifluoromethyl-pyridin-2-yl)-thiazol-4-yl]-2H-[1,2,3]triazol-2-yl)-ethoxycarbonyloxy)-2,2-dimethyl-propionic acid (Example 1826), 3-(1-{4-[3-(2,5-bis-trifluoromethylbenzyloxy)phenyl]-5-cyano-2H-[1,2,3]triazol-2-yl}ethoxycarbonyloxy)-3-methylbutyric acid (Example 1827), carbonic acid 1-{4-[3-(2,5-bis-trifluoromethylbenzyloxy)phenyl]-5-cyano-2H-[1,2,3]triazol-2-yl}ethyl ester-2-hydroxyethyl ester (Example 1828), acetic acid 4-cyano-5-[3-methyl-5-(4-trifluoromethylpyrimidin-2-yl)phenyl]-2H-[1,2,3]triazol-2-ylmethyl ester (Example 1829), acetic acid 4-{3-chloro-5-[(E)-2-(3-trifluoromethylphenyl)vinyl]phenyl}-5-cyano-2H-[1,2,3]triazol-2-ylmethyl ester (Example 1830), and butyric acid 4-[3-chloro-5-[(E)-2-(3-trifluoromethyl-phenyl)-vinyl]-phenyl]-5-cyano-2H-[(1,2,3]triazol-2-ylmethyl ester (Example 1831), or a salt thereof.

The present invention also provides a cyanotriazole compound represented by the formula (1'a):

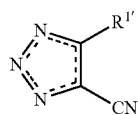

wherein

R$^{1'}$ is one of the following (1-1) to (1-12):

(1-1) a phenyl group optionally substituted with one or more (preferably 1 to 3) members selected from the group consisting of the following (1-1-1) to (1-1-34):

(1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents), (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom), (1-1-3) a lower alkoxy lower alkyl group,
(1-1-4) a cycloalkyl group,
(1-1-5) a cycloalkoxy group,
(1-1-6) a cycloalkyl lower alkyl group,
(1-1-7) a cycloalkyl lower alkoxy group,
(1-1-8) a cycloalkyl lower alkoxy lower alkyl group,
(1-1-9) a halogen atom (preferably provided that the phenyl group of (1-1) is substituted with one or more halogen atoms, then the phenyl group of (1-1) is substituted with additional one or more substituents excluding a phenoxy group),
(1-1-10) a cyano group,
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group optionally substituted on the phenyl ring with one or more members selected from the group consisting of a lower alkoxy group; a lower alkyl group optionally substituted with one or more halogen atoms; a cyano group; and halogen atoms (preferably provided that when the styryl group is bonded to the p-position on the phenyl ring of (1-1), then the styryl group is substituted on the phenyl ring with one or more members selected from the group consisting of a lower alkyl group substituted with one or more halogen atoms; and a fluoro atom),
(1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
(1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
(1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
(1-1-17) a phenylthio group optionally substituted with one or more halogen atoms,
(1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a 2,2-difluorobenzo[1,3]dioxolyl group, and
(1-1-34) an indolinyl lower alkyl group,
(1-2) a thiazolyl group optionally substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group optionally substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more lower alkyl groups optionally substituted with one or more halogen atoms,
(1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a benzyl group optionally substituted on the phenyl ring with one or more lower alkyl groups optionally substituted with one or more halogen atoms,
(1-7) a pyridyl group optionally substituted with one or more members selected from the group consisting of the following (1-7-1) to (1-7-2):
  (1-7-1) a benzyloxy lower alkyl group optionally substituted on the phenyl ring with one or more lower alkyl groups optionally substituted with one or more halogen atoms, and
  (1-7-2) a phenyl group optionally substituted with one or more lower alkyl groups optionally substituted with one or more halogen atoms,
(1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and (1-8-2) a benzyl group optionally substituted on the phenyl ring with one or more halogen atoms,
(1-9) an indolyl group optionally substituted with one or more members selected from the group consisting of the following (1-9-1) to (1-9-2):
 (1-9-1) a lower alkyl group optionally substituted with one or more halogen atoms, and
 (1-9-2) a phenyl group optionally substituted with one or more halogen atoms,
(1-10) a benzofuryl group optionally substituted with one or more phenyl groups optionally substituted with one or more halogen atoms,
(1-11) a benzothienyl group optionally substituted with one or more phenyl groups optionally substituted with one or more halogen atoms, and
(1-12) a phenyl lower alkyl group optionally substituted on the phenyl ring with one or more members selected from the group consisting of the following (1-12-1) to (1-12-2):
 (1-12-1) a phenyl group optionally substituted with one or more lower alkyl groups optionally substituted with one or more halogen atoms; and
 (1-12-2) a benzyloxy group optionally substituted on the phenyl ring with one or more lower alkyl groups optionally substituted with one or more halogen atoms;
provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
4-phenyl-5-cyano-1,2,3-triazole;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole; and
4-(4-fluoro-3-phenoxyphenyl)-5-cyano-1,2,3-triazole;
4-(2-fluorophenyl)-1,2,3-triazole-5-carbonitrile; and
4-(4-fluoro-3-methoxyphenyl)-1,2,3-triazole-5-carbonitrile;
 are excluded,
or a salt thereof (hereinafter to be referred to as Compound (1'a)).

The present invention also provides a cyanotriazole compound represented by the formula (1'b):

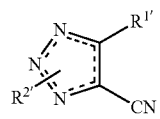

(1'b)

wherein
$R^{1'}$ is as defined in Compound (1'a); and
$R^{2'}$ is a group represented by the formula:

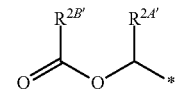

wherein
* is a bonding site;
$R^{2A'}$ is
 (2A-1) a hydrogen atom, or
 (2A-2) a lower alkyl group; and
$R^{2B'}$ is
 (2B-1) a lower alkoxy group optionally substituted with one or more members selected from the group consisting of a carboxy group; a lower alkoxy-carbonyl group; a hydroxy group; a phenyl lower alkoxy-carbonyl group; a lower alkenyloxy-carbonyl group; and a tetrahydropyran-2-yloxy group, or
 (2B-2) a lower alkyl group;
or a salt thereof (hereinafter to be referred to as Compound (1'b)).

The present invention also provides a cyanotriazole compound represented by the formula (1'bA):

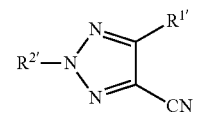

(1'bA)

wherein
$R^{1'}$ is as defined in Compound (1'a); and
$R^{2'}$ is as defined in Compound (1'b), or a salt thereof (hereinafter to be referred to as Compound (1'bA)).

Compound (1) encompasses Compound (1a) (mentioned below), Compound (1b) (mentioned below), Compound (1aa), Compound (1bb), Compound (1bbA), Compound (1'a), Compound (1'b), Compound (1'bA) and Compounds (1A)-(IC) (mentioned below).

In one embodiment, Compound (1) is used as a prophylactic and/or therapeutic agent for a disease or a disorder on which citric acid cycle activation and/or improvement of hyperglycemia has a prophylactic and/or therapeutic effect.

The present invention also provides a citric acid cycle activator comprising, as an active ingredient, Compound (1).

The present invention also provides a hypoglycemic agent comprising, as an active ingredient, Compound (1).

The present invention also provides a prophylactic and/or therapeutic agent for a disease or a disorder on which citric acid cycle activation and/or improvement of hyperglycemia has a prophylactic and/or therapeutic effect, comprising Compound (1) as an active ingredient. In one embodiment, the disease or disorder on which citric acid cycle activation and/or improvement of hyperglycemia has a prophylactic and/or therapeutic effect is selected from the group consisting of diabetes, impaired glucose tolerance, insulin resistance, diabetic complications, obesity, dyslipidemia, hepatic steatosis, atherosclerosis and cardiovascular disease.

The present invention also provides use of Compound (1) for manufacturing a prophylactic and/or therapeutic agent for a disease or a disorder on which citric acid cycle activation and/or improvement of hyperglycemia has a prophylactic and/or therapeutic effect.

The present invention also provides a method for preventing and/or treating a disease or a disorder on which citric acid cycle activation and/or improvement of hyperglycemia has a prophylactic and/or therapeutic effect, comprising administering an effective amount of Compound (1) to a patient.

Effect of the Invention

Since Compound (1) stimulates the citric acid cycle activity and/or improves hyperglycemia, it is useful for treating and/or preventing diseases or disorders on which citric acid cycle activation and/or improvement of hyperglycemia has a prophylactic and/or therapeutic effect, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure.

DESCRIPTION OF EMBODIMENTS

Figure 1:
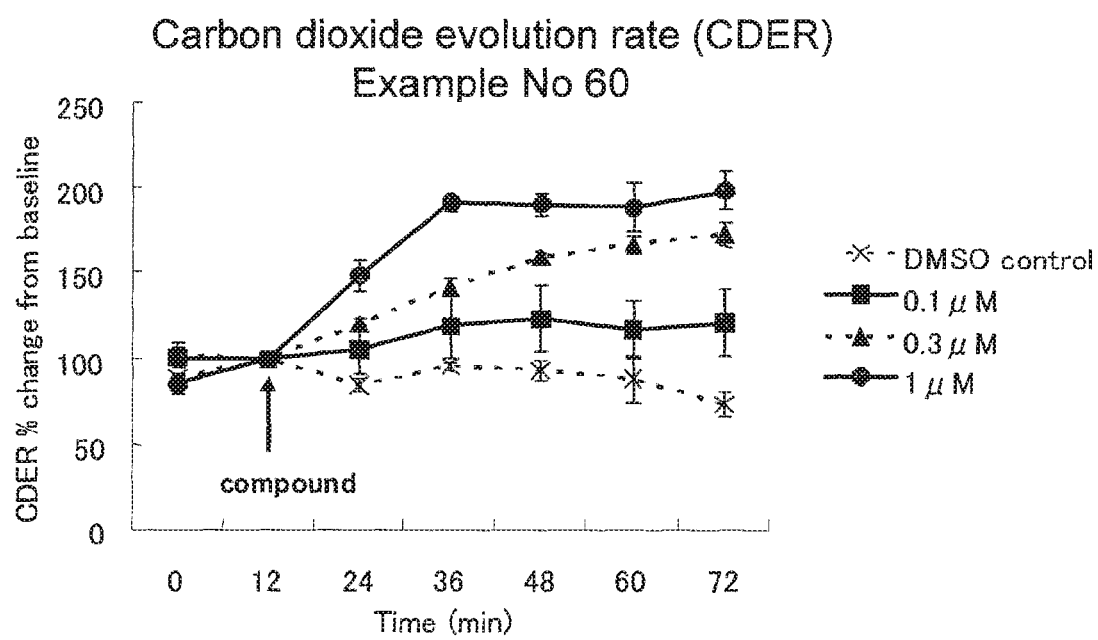
FIG. 1 shows carbon dioxide evolution rate (CDER) of the compound of Example 60.

Suitable examples and illustrations of the various definitions which the present invention includes within the scope thereof and which appear in the above and following description in the present specification are explained in detail as follows.

The term "lower" is intended to mean 1 to 6 carbon atom(s) unless otherwise indicated.

The term "higher" is intended to mean 7 to 20 carbon atom(s) unless otherwise indicated.

Examples of the "lower alkyl" include straight or branched ones such as methyl, ethyl, n-propyl, isopropyl, n-butyl, isobutyl, tert-butyl, sec-butyl, n-pentyl, neopentyl, n-hexyl, isohexyl, 3-methylpentyl and the like.

Examples of the "higher alkyl" include straight or branched ones such as n-heptyl, n-octyl, n-nonyl, n-decyl and the like.

Examples of the "lower alkyl group optionally substituted with one or more halogen atoms" include trifluoromethyl, 2,2,2-trifluoroethyl, 3,3,3-trifluoropropyl, 2,2-difluoropropyl, 2,2-dichloropropyl, 4,4,4-trifluorobutyl, 2,3-difluorobutyl, 2-chloro-3-fluorobutyl and the like, in which preferred is trifluoromethyl or 4,4,4-trifluorobutyl.

Examples of the "lower alkoxy" include straight or branched ones such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, 3-methylpentyloxy and the like, in which preferred is methoxy, ethoxy or isopropoxy.

Examples of the "lower alkoxy group optionally substituted with one or more halogen atoms" include difluoromethoxy, trifluoromethoxy, 2,2,2-trifluoroethoxy, 1,1,2,2-tetrafluoroethoxy, 3,3,3-trifluoropropoxy, 2,2-difluoropropoxy, 2,2-dichloropropoxy, 4,4,4-trifluorobutoxy, 2,3-difluorobutoxy, 2-chloro-3-fluorobutoxy and the like, in which preferred is trifluoromethoxy or 4,4,4-trifluorobutoxy.

Examples of the "lower alkoxy lower alkyl" include methoxymethyl, ethoxymethyl, propoxymethyl, methoxyethyl, ethoxyethyl, methoxypropyl and the like, in which preferred is ethoxymethyl.

Examples of the "lower alkoxy lower alkoxy" include methoxymethoxy, ethoxymethoxy, propoxymethoxy, methoxyethoxy, ethoxyethoxy, methoxypropoxy and the like, in which preferred is methoxymethoxy or ethoxymethoxy.

Examples of the "lower alkenyl" include linear or branched ones that have 1 to 3 double bonds such as vinyl (ethenyl), 1-methyetheyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like, in which preferred is vinyl or 1-methyetheyl.

Examples of the "lower alkenyloxy" include linear or branched ones that have 1 to 3 double bonds such as vinyloxy (ethenyloxy), 1-propenyloxy, 2-propenyloxy, 2-methyl-1-propenyloxy, 1-butenyloxy, 2-butenyloxy, 3-butenyloxy, 3-methyl-2-butenyoxyl, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy and the like, in which preferred is vinyloxy, 3-butenyloxy or 3-methyl-2-butenyoxyl.

Examples of the "lower alkynyloxy" include linear or branched ones that have 1 to 3 triple bonds such as ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy and the like, in which preferred is 2-butynyloxy.

Examples of the "lower alkylthio" include straight or branched ones such as methylthio, ethylthio, n-propylthio, isopropylthio, n-butylthio, isobutylthio, tert-butylthio, sec-butylthio, n-pentylthio, neopentylthio, n-hexylthio, isohexylthio, 3-methylpentylthio and the like in which preferred is methylthio or ethylthio.

Examples of the "lower alkyl-carbonyl" include straight or branched ones such as acetyl, ethylcarbonyl, propylcarbonyl, isopropylcarbonyl, butylcarbonyl, tert-butylcarbonyl, pentylcarbonyl, hexylcarbonyl and the like, in which preferred is acetyl or ethylcarbonyl.

Examples of the "lower alkoxy-carbonyl" include straight or branched ones such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like, in which preferred is methoxycarbonyl or ethoxycarbonyl.

Examples of the "lower alkenyloxy-carbonyl" include linear or branched ones that have 1 to 3 double bonds such as vinyloxycarbonyl (ethenyloxycarbonyl), 1-propenyloxycarbonyl, 2-propenyloxycarbonyl, 2-methyl-1-propenyloxycarbonyl, 1-butenyloxycarbonyl, 2-butenyloxycarbonyl, 3-butenyloxycarbonyl, 3-methyl-2-butenyoxylcarbonyl, 1-pentenyloxycarbonyl, 2-pentenyloxycarbonyl, 3-pentenyloxycarbonyl, 4-pentenyloxycarbonyl, 4-methyl-3-pentenyloxycarbonyl, 1-hexenyloxycarbonyl, 3-hexenyloxycarbonyl, 5-hexenyloxycarbonyl and the like, in which preferred is vinyloxycarbonyl, 2-propenyloxycarbonyl or 3-methyl-2-butenyoxylcarbonyl.

Examples of the "lower alkylsulfonyl" include straight or branched ones such as methylsulfonyl, ethylsulfonyl, propylsulfonyl, isopropylsulfonyl, butylsulfonyl, tert-butylsulfonyl, pentylsulfonyl, hexylsulfonyl and the like, in which preferred is methylsulfonyl.

Examples of the "cycloalkyl" include cyclopropyl, cyclobutyl, cyclopentyl, cyclohexyl, adamantyl, bicyclo[2.2.1]heptanyl and the like, in which preferred is cyclopropyl, adamantyl or bicyclo[2.2.1]heptanyl.

Examples of the "cycloalkoxy" include cyclopropoxy, cyclobutoxy, cyclopentyloxy, cyclohexyloxy, adamantyloxy, bicyclo[2.2.1]heptanyloxy and the like, in which preferred is cyclobutoxy.

Examples of the "cycloalkyl lower alkyl" include cyclopropylmethyl, cyclopropylethyl, cyclopentylmethyl, cyclohexylmethyl, cyclohexylethyl, adamantylmethyl, bicyclo[2.2.1]heptanylmethyl and the like, in which preferred is cyclopropylmethyl.

Examples of the "cycloalkyl lower alkoxy" include cyclopropylmethoxy, 1-cyclopropylethoxy, 2-cyclopropylethoxy, cyclopentylmethoxy, cyclohexylmethoxy, cycloheptylmethoxy, cyclooctylmethoxy, 2-cyclohexylethoxy, adamantylmethoxy, bicyclo[2.2.1]heptanylmethoxy and the like, in which preferred is cyclopropylmethoxy.

Examples of the "cycloalkyl lower alkoxy lower alkyl" include cyclopropylmethoxymethyl, cyclopropylmethoxyethyl, cyclopentylmethoxymethyl, cyclohexylmethoxymethyl, cycloheptylmethoxymethyl, cyclooctylmethoxyethyl, cyclohexylethoxymethyl, adamantylmethoxymethyl, bicyclo[2.2.1]heptanylmethoxymethyl and the like, in which preferred is cyclohexylmethoxymethyl.

Examples of the "cycloalkoxy lower alkyl" include cyclopropoxymethyl, cyclopropoxyethyl, cyclopentoxymethyl, cyclohexyloxymethyl, cycloheptoxymethyl, cyclooctoxymethyl, cyclohexyloxyethyl, adamantyloxymethyl, bicyclo[2.2.1]heptanyloxymethyl and the like, in which preferred is cyclopropoxymethyl or cyclopentoxymethyl.

Examples of the "cycloalkoxy lower alkoxy" include cyclopropoxymethoxy, cyclopropoxyethoxy, cyclopentoxymethoxy, cyclohexyloxymethoxy, adamantyloxymethoxy, bicyclo[2.2.1]heptanyloxymethoxy and the like, in which preferred is cyclopropoxymethoxy.

Examples of the "cycloalkyl lower alkenyl" include 2-cyclopropylvinyl, 3-cyclopropyl-1-propen-1-yl, 3-cyclopropyl-2-propen-1-yl, 3-cyclopropyl-2-methyl-1-propen-1-yl, 3-cyclopropyl-2-methyl-2-propen-1-yl, 4-cyclopropyl-1-buten-1-yl, 4-cyclopropyl-2-buten-1-yl, 4-cyclopropyl-3-buten-1-yl, 2-cyclobutylvinyl, 2-cyclopentylvinyl, 2-cyclohexylvinyl and the like, in which preferred is 2-cyclopropylvinyl.

Examples of the "cycloalkylvinyl" include 2-cyclopropylvinyl, 2-cyclobutylvinyl, 2-cyclopentylvinyl, 2-cyclohexylvinyl and the like, in which preferred is 2-cyclopropylvinyl.

Examples of the "cycloalkenyl" include 1-cyclopropenyl, 1-cyclobutenyl, 1-cyclopentenyl, 1-cyclohexenyl, bicyclo[2,2,1]hept-2-enyl and the like, in which preferred is 1-cyclopropenyl or bicyclo[2,2,1]hept-2-enyl.

Examples of the "cycloalkenyloxy" include 1-cyclopropenyloxy, 1-cyclobutenyloxy, 1-cyclopentenyloxy, 1-cyclohexenyloxy, bicyclo[2,2,1]hept-2-enyloxy and the like, in which preferred is 1-cyclopropenyloxy or 1-cyclohexenyloxy.

Examples of the "halogen" include fluoro, chloro, bromo and iodo, in which preferred is fluoro or chloro.

Examples of the "phenyl lower alkyl" include benzyl, 1-phenylethyl, phenethyl (2-phenylethyl), 3-phenylpropyl, 4-phenylbutyl, 5-phenylpentyl, 6-phenylhexyl and the like, in which preferred is benzyl or phenethyl.

Examples of the "phenoxy lower alkyl" include phenoxymethyl, 1-phenoxyethyl, 2-phenoxyethyl, 3-phenoxypropyl, 4-phenoxybutyl, 5-phenoxypentyl, 6-phenoxyhexyl and the like, in which preferred is phenoxymethyl.

Examples of the "phenyl lower alkoxy" include benzyloxy, 1-phenylethoxy, 2-phenylethoxy, 1-methyl-2-phenylethoxy, 3-phenylpropyloxy, 1-phenylbutyloxy, 4-phenylbutyloxy, 5-phenylpentyloxy, 6-phenylhexyloxy and the like, in which preferred is benzyloxy, 1-phenylethoxy or 1-methyl-2-phenylethoxy.

Examples of the "phenoxy lower alkoxy" include phenoxymethoxy, 1-phenoxyethoxy, 2-phenoxyethoxy, 3-phenoxypropoxy, 4-phenoxybutoxy, 5-phenoxypentoxy, 6-phenoxyhexoxy and the like, in which preferred is phenoxymethoxy or 2-phenoxyethoxy.

Examples of the "phenyl lower alkoxy lower alkyl" include benzyloxymethyl, 1-phenylethoxymethyl, 2-phenylethoxymethyl, 3-phenylpropoxymethyl, 4-phenylbutoxymethyl, 5-phenylpentoxymethyl, 6-phenylhexoxymethyl and the like, in which preferred is benzyloxymethyl.

Examples of the "phenyl lower alkenyl" include styryl, 3-phenyl-1-propen-1-yl, 3-phenyl-2-propen-1-yl, 3-phenyl-2-methyl-1-propen-1-yl, 3-phenyl-2-methyl-2-propen-1-yl, 4-phenyl-1-buten-1-yl, 4-phenyl-2-buten-1-yl, 4-phenyl-3-buten-1-yl and the like, in which preferred is styryl.

Examples of the "phenyl lower alkenyloxy" include styryloxy, 3-phenyl-1-propen-1-yloxy, 3-phenyl-2-propen-1-yloxy, 3-phenyl-2-methyl-1-propen-1-yloxy, 3-phenyl-2-methyl-2-propen-1-yloxy, 4-phenyl-1-buten-1-yloxy, 4-phenyl-2-buten-1-yloxy, 4-phenyl-3-buten-1-yloxy and the like, in which preferred is styryloxy.

Examples of the "phenylthio lower alkyl" include phenylthiomethyl, 1-phenylthioethyl, 2-phenylthioethyl, 3-phenylthiopropyl, 4-phenylthiobutyl, 5-phenylthiopentyl, 6-phenylthiohexyl and the like, in which preferred is phenylthiomethyl or 2-phenylthioethyl.

Examples of the "phenylsulfonyl lower alkyl" include phenylsulfonylmethyl, 1-phenylsulfonylethyl, 2-phenylsulfonylethyl, 3-phenylsulfonylpropyl, 4-phenylsulfonylbutyl, 5-phenylsulfonylpentyl, 6-phenylsulfonylhexyl and the like, in which preferred is phenylsulfonylmethyl or 2-phenylsulfonylethyl.

Examples of the "phenyl lower alkylsulfonyl lower alkyl" include benzylsulfonylmethyl, (1-phenylethylsulfonyl)methyl, (2-phenylethylsulfonyl)methyl, (3-phenylpropylsulfonyl)methyl and the like, in which preferred is benzylsulfonylmethyl.

Examples of the "phenyl lower alkyl-carbonyl" include benzylcarbonyl, 1-phenylethylcarbonyl, 2-phenylethylcarbonyl, 3-phenylpropylcarbonyl, 4-phenylbutylcarbonyl, 5-phenylpentylcarbonyl, 6-phenylhexylcarbonyl and the like, in which preferred is benzylcarbonyl or 2-phenylethylcarbonyl.

Examples of the "phenyl lower alkoxy-carbonyl" include benzyloxycarbonyl, 1-phenylethoxycarbonyl, 2-phenylethoxycarbonyl, 1-methyl-2-phenylethoxycarbonyl, 3-phenylpropyloxycarbonyl, 4-phenylbutyloxycarbonyl, 5-phenylpentyloxycarbonyl, 6-phenylhexyloxycarbonyl and the like, in which preferred is benzyloxycarbonyl, 1-phenylethoxycarbonyl or 1-methyl-2-phenylethoxycarbonyl.

Examples of the "benzyloxy lower alkyl" include benzyloxymethyl, 1-benzyloxyethyl, 2-benzyloxyethyl, 1-benzyloxypropyl, 3-benzyloxypropyl and the like, in which preferred is 1-benzyloxypropyl.

Examples of the "benzylthio lower alkyl" include benzylthiomethyl, 1-benzylthioethyl, 2-benzylthioethyl, 3-benzylthiopropyl and the like, in which preferred is benzylthiomethyl.

Examples of the "lower alkylamino" include straight or branched ones such as methylamino, ethylamino, n-propylamino, isopropylamino, n-butylamino, isobutylamino, tert-butylamino, sec-butylamino, n-pentylamino, neopentylamino, n-hexylamino, isohexylamino, 3-methylpentylamino and the like, in which preferred is methylamino or ethylamino.

Examples of the "N-lower alkyl-N-phenyl amino" include N-methyl-N-phenyl amino, N-ethyl-N-phenyl amino, N-propyl-N-phenyl amino, N-isopropyl-N-phenyl amino and the like, in which preferred is N-methyl-N-phenyl amino or N-ethyl-N-phenyl amino.

Examples of the "N-lower alkyl-N-phenyl amino lower alkyl" include N-methyl-N-phenyl amino methyl, N-ethyl-N-phenyl amino methyl, N-methyl-N-phenyl amino ethyl, N-methyl-N-phenyl amino propyl and the like, in which preferred is N-methyl-N-phenyl amino methyl.

Examples of the "N-benzyl-N-lower alkyl amino" include N-benzyl-N-methylamino, N-benzyl-N-ethylamino, N-benzyl-N-propylamino and the like, in which preferred is N-benzyl-N-methylamino.

Examples of the "mono- or di-N-lower alkyl amino lower alkyl" include mono- or di-N-methylaminomethyl, mono- or di-N-ethylaminomethyl, mono- or di-N-propylaminomethyl, mono- or di-N-methylaminoethyl, mono- or di-N-methylaminopropyl and the like, in which preferred is mono- or di-N-methylaminomethyl.

Examples of the "N,N-di-lower alkylamino lower alkyl" include N,N-di-methylaminomethyl, N,N-di-ethylaminomethyl, N,N-di-propylaminomethyl, N,N-di-methylaminoethyl, N,N-di-methylaminopropyl, N-ethyl-N-methylaminomethyl, N-ethyl-N-methylaminoethyl and the like, in which preferred is N,N-di-methylaminomethyl or N,N-di-ethylaminomethyl.

Examples of the "N,N-di-lower alkylamino lower alkoxy" include N,N-di-methylaminomethoxy, N,N-di-ethylaminomethoxy, N,N-di-propylaminomethoxy, N,N-di-methylaminoethoxy, N,N-dimethylaminopropoxy, N-ethyl-N-methylaminomethoxy, N-ethyl-N-methylaminoethoxy and the like, in which preferred is N,N-di-methylaminomethoxy, N,N-dimethylaminopropoxy or N,N-di-ethylaminomethoxy.

Examples of the "N,N-di-lower alkylamino-carbonyl" include N,N-di-methylaminocarbonyl, N,N-di-ethylaminocarbonyl, N,N-di-propylaminocarbonyl, N,N-di-butylaminocarbonyl, N,N-di-methylaminocarbonyl, N-ethyl-N-methylaminocarbonyl, N-ethyl-N-methylaminocarbonyl and the like, in which preferred is N,N-di-methylaminocarbonyl or N,N-di-ethylaminocarbonyl.

Examples of the "lower alkylsulfonylamino" include methylsulfonylamino, ethylsulfonylamino, propylsulfonylamino, isopropylsulfonylamino, butylsulfonylamino, isobutylsulfonylamino and the like, in which preferred is methylsulfonylamino or ethylsulfonylamino.

Examples of the "acetylamino lower alkyl" include acetylaminomethyl, 2-acetylaminoethyl, 3-acetylaminopropyl, 2-acetylamino-1-methylethyl, 4-acetylaminobutyl, 5-acetylaminopentyl, 6-acetylamino hexyl and the like, in which preferred is acetylaminomethyl or 2-acetylaminoethyl.

Examples of the "pyridyl lower alkyl" include (pyridin-2-yl)methyl, (pyridin-3-yl)methyl, 1-(pyridin-2-yl)ethyl, 2-(pyridin-2-yl)ethyl, 2-(pyridin-3-yl)ethyl, 3-(pyridin-2-yl)propyl and the like, in which preferred is 2-(pyridin-2-yl)ethyl.

Examples of the "pyridyl lower alkoxy" include (pyridin-2-yl)methoxy, (pyridin-3-yl)methoxy, 1-(pyridin-2-yl)ethoxy, 2-(pyridin-2-yl)ethoxy, 2-(pyridin-3-yl)ethoxy, 3-(pyridin-2-yl)propoxy and the like, in which preferred is (pyridin-2-yl)methoxy or 2-(pyridin-2-yl)ethoxy.

Examples of the "pyridyloxy lower alkyl" include (pyridin-2-yloxy)methyl, 1-(pyridin-2-yloxy)ethyl, 2-(pyridin-2-yloxy)ethyl, 3-(pyridin-2-yloxy)propyl and the like, in which preferred is (pyridin-2-yloxy)methyl or 2-(pyridin-2-yloxy)ethyl.

Examples of the "pyrimidinyl lower alkyl" include (pyrimidin-2-yl)methyl, (pyrimidin-4-yl)methyl, (pyrimidin-5-yl)methyl, 1-(pyrimidin-2-yl)ethyl, 2-(pyrimidin-2-yl)ethyl, 2-(pyrimidin-4-yl)ethyl, 3-(pyrimidin-2-yl)propyl and the like, in which preferred is (pyrimidin-2-yl)methyl or 2-(pyrimidin-2-yl)ethyl.

Examples of the "pyrimidinyl lower alkoxy" include (pyrimidin-2-yl)methoxy, (pyrimidin-4-yl)methoxy, (pyrimidin-5-yl)methoxy, 1-(pyrimidin-2-yl)ethoxy, 2-(pyrimidin-2-yl)ethoxy, 2-(pyrimidin-4-yl)ethoxy, 3-(pyrimidin-2-yl)propoxy and the like, in which preferred is (pyrimidin-2-yl)methoxy.

Examples of the "pyrimidinyloxy lower alkyl" include (pyrimidin-2-yloxy)methyl, (pyrimidin-4-yloxy)methyl, (pyrimidin-5-yloxy)methyl, 1-(pyrimidin-2-yloxy)ethyl, 2-(pyrimidin-2-yloxy)ethyl, 2-(pyrimidin-4-yloxy)ethyl, 3-(pyrimidin-2-yloxy)propyl and the like, in which preferred is (pyrimidin-2-yloxy)methyl.

Examples of the "benzofuryl lower alkoxy" include (benzofuran-2-yl)methoxy, (benzofuran-3-yl)methoxy, 1-(benzofuran-2-yl)ethoxy, 2-(benzofuran-2-yl)ethoxy, 3-(benzofuran-2-yl)propoxy and the like, in which preferred is (benzofuran-2-yl)methoxy.

Examples of the "indolinyl lower alkyl" include (indolin-1-yl)methyl, (indolin-2-yl)methyl, (indolin-3-yl)methyl, 1-(indolin-1-yl)ethyl, 2-(indolin-1-yl)ethyl, 3-(indolin-2-yl)propyl and the like, in which preferred is (indolin-1-yl)methyl.

Examples of the "oxetanyl lower alkoxy" include (oxetan-2-yl)methoxy, (oxetan-3-yl)methoxy, 1-(oxetan-2-yl)ethoxy, 2-(oxetan-2-yl)ethoxy, 1-(oxetan-3-yl)ethoxy, 2-(oxetan-3-yl)ethoxy, 3-(oxetan-2-yl)propoxy, 3-(oxetan-3-yl)propoxy and the like, in which preferred is (oxetan-2-yl)methoxy or (oxetan-3-yl)methoxy.

Examples of the "tetrahydrofuryl lower alkyl" include (tetrahydrofuran-2-yl)methyl, (tetrahydrofuran-3-yl)methyl, 1-(tetrahydrofuran-2-yl)ethyl, 2-(tetrahydrofuran-2-yl)ethyl, 3-(tetrahydrofuran-2-yl)propyl and the like, in which preferred is (tetrahydrofuran-2-yl)methyl.

Examples of the "tetrahydropyranyl lower alkoxy" include (tetrahydropyran-2-yl)methoxy, 1-(tetrahydropyran-2-yl)ethoxy, 2-(tetrahydropyran-2-yl)ethoxy, 3-(tetrahydropyran-2-yl)propyloxy and the like, in which preferred is (tetrahydropyran-2-yl)methoxy.

Examples of the "piperidyl lower alkyl" include (piperidin-1-yl)methyl, (piperidin-2-yl)methyl, (piperidin-3-yl)methyl, (piperidin-4-yl)methyl, 1-(piperidin-1-yl)ethyl, 2-(piperidin-1-yl)ethyl, 3-(piperidin-1-yl)propyl and the like, in which preferred is (piperidin-1-yl)methyl.

Examples of the "pyrrolyl lower alkyl" include (pyrrol-1-yl)methyl, (pyrrol-2-yl)methyl, (pyrrol-3-yl)methyl, 1-(pyrrol-1-yl)ethyl, 2-(pyrrol-1-yl)ethyl, 1-(pyrrol-2-yl)ethyl, 2-(pyrrol-2-yl)ethyl, 3-(pyrrol-1-yl)propyl and the like, in which preferred is (pyrrol-1-yl)methyl or (pyrrol-2-yl)methyl.

Examples of the "thiazolyl lower alkoxy" include (thiazol-2-yl)methoxy, (thiazol-4-yl)methoxy, (thiazol-5-yl)methoxy, 1-(thiazol-2-yl)ethoxy, 2-(thiazol-2-yl)ethoxy, 3-(thiazol-2-yl)propoxy and the like, in which preferred is (thiazol-2-yl)methoxy.

Examples of the "thienyl lower alkyl" include (thiophen-2-yl)methyl, (thiophen-3-yl)methyl, 1-(thiophen-2-yl)ethyl, 2-(thiophen-2-yl)ethyl, 3-(thiophen-2-yl)propyl and the like, in which preferred is (thiophen-2-yl)methyl or (thiophen-3-yl)methyl.

Examples of the "thienyl lower alkoxy" include (thiophen-2-yl)methoxy, (thiophen-3-yl)methoxy, 1-(thiophen-2-yl)ethoxy, 2-(thiophen-2-yl)ethoxy, 3-(thiophen-2-yl)propoxy and the like, in which preferred is (thiophen-2-yl)methoxy or (thiophen-3-yl)methoxy.

Examples of the "benzothienyl lower alkyl" include (benzothiophen-2-yl)methyl, (benzothiophen-3-yl)methyl, 1-(benzothiophen-2-yl)ethyl, 2-(benzothiophen-2-yl)ethyl, 3-(benzothiophen-2-yl)propyl and the like, in which preferred is (benzothiophen-2-yl)methyl or (benzothiophen-3-yl)methyl.

Examples of the "benzothienyl lower alkoxy" include (benzothiophen-2-yl)methoxy, (benzothiophen-3-yl)methoxy, 1-(benzothiophen-2-yl)ethoxy, 2-(benzothiophen-2-yl)ethoxy, 3-(benzothiophen-2-yl)propoxy and the like, in which preferred is (benzothiophen-2-yl)methoxy or (benzothiophen-3-yl)methoxy.

Examples of the "benzo[1,3]dioxolyl lower alkyl" include (benzo[1,3]dioxol-2-yl)methyl, (benzo[1,3]dioxol-4-yl)methyl, (benzo[1,3]dioxol-5-yl)methyl, 1-(benzo[1,3]dioxol-4-yl)ethyl, 2-(benzo[1,3]dioxol-4-yl)ethyl, 1-(benzo[1,3]dioxol-5-yl)ethyl, 2-(benzo[1,3]dioxol-5-yl)ethyl, 3-(benzo[1,3]dioxol-4-yl)propyl and the like, in which preferred is (benzo[1,3]dioxol-4-yl)methyl or (benzo[1,3]dioxol-5-yl)methyl.

Examples of the "benzo[1,3]dioxolyl lower alkoxy" include (benzo[1,3]dioxol-2-yl)methoxy, (benzo[1,3]dioxol-4-yl)methoxy, (benzo[1,3]dioxol-5-yl)methoxy, 1-(benzo[1,3]dioxol-4-yl)ethoxy, 2-(benzo[1,3]dioxol-4-yl)ethoxy, 1-(benzo[1,3]dioxol-5-yl) ethoxy, 2-(benzo[1,3]dioxol-5-yl) ethoxy, 3-(benzo[1,3]dioxol-4-yl)propoxy and the like, in which preferred is (benzo[1,3]dioxol-4-yl)methoxy or (benzo[1,3]dioxol-5-yl)methoxy.

Examples of the "quinolyl lower alkoxy" include (quinolin-2-yl)methoxy, (quinolin-3-yl)methoxy, (quinolin-4-yl)methoxy, (quinolin-5-yl)methoxy, (quinolin-6-yl)methoxy, (quinolin-7-yl)methoxy, (quinolin-8-yl)methoxy, 1-(quinolin-2-yl)ethoxy, 2-(quinolin-2-yl)ethoxy, 3-(quinolin-2-yl)propoxy and the like, in which preferred is (quinolin-2-yl)methoxy or 2-(quinolin-2-yl)ethoxy.

Examples of the "3,4-dihydro-2H-quinolyl lower alkyl" include (3,4-dihydro-2H-quinolin-1-yl)methyl, (3,4-dihydro-2H-quinolin-2-yl)methyl, (3,4-dihydro-2H-quinolin-3-yl)methyl, (3,4-dihydro-2H-quinolin-4-yl)methyl, (3,4-dihydro-2H-quinolin-5-yl)methyl, (3,4-dihydro-2H-quinolin-6-yl)methyl, (3,4-dihydro-2H-quinolin-7-yl)methyl, (3,4-dihydro-2H-quinolin-8-yl)methyl, 1-(3,4-dihydro-2H-quinolin-2-yl)ethyl, 2-(3,4-dihydro-2H-quinolin-2-yl)ethyl, 3-(3,4-dihydro-2H-quinolin-2-yl)propyl and the like, in which preferred is (3,4-dihydro-2H-quinolin-1-yl)methyl, (3,4-dihydro-2H-quinolin-2-yl)methyl or 2-(3,4-dihydro-2H-quinolin-2-yl)ethyl.

Examples of the "2-oxo-1,2,3,4-tetrahydroquinolyl lower alkoxy" include (2-oxo-1,2,3,4-tetrahydroquinolin-1-yl)methoxy, (2-oxo-1,2,3,4-tetrahydroquinolin-2-yl)methoxy, (2-oxo-1,2,3,4-tetrahydroquinolin-3-yl)methoxy, (2-oxo-1,2,3,4-tetrahydroquinolin-4-yl)methoxy, (2-oxo-1,2,3,4-tetrahydroquinolin-5-yl)methoxy, (2-oxo-1,2,3,4-tetrahydroquinolin-6-yl)methoxy, (2-oxo-1,2,3,4-tetrahydroquinolin-7-yl)methoxy, (2-oxo-1,2,3,4-tetrahydroquinolin-8-yl)methoxy, 1-(2-oxo-1,2,3,4-tetrahydroquinolin-2-yl)ethoxy, 2-(2-oxo-1,2,3,4-tetrahydroquinolin-2-yl)ethoxy, 3-(2-oxo-1,2,3,4-tetrahydroquinolin-2-yl)propoxy, 3-(2-oxo-1,2,3,4-tetrahydroquinolin-6-yl)propoxy and the like, in which preferred is (2-oxo-1,2,3,4-tetrahydroquinolin-2-yl)methoxy, 2-(2-oxo-1,2,3,4-tetrahydroquinolin-2-yl)ethoxy or 3-(2-oxo-1,2,3,4-tetrahydroquinolin-6-yl)propoxy.

Examples of the "3,4-dihydro-1H-isoquinolyl lower alkyl" include (3,4-dihydro-1H-isoquinolin-1-yl)methyl, (3,4-dihydro-1H-isoquinolin-2-yl)methyl, (3,4-dihydro-1H-isoquinolin-3-yl)methyl, (3,4-dihydro-1H-isoquinolin-4-yl)methyl, (3,4-dihydro-1H-isoquinolin-5-yl)methyl, (3,4-dihydro-1H-isoquinolin-6-yl)methyl, (3,4-dihydro-1H-isoquinolin-7-yl)methyl, (3,4-dihydro-1H-isoquinolin-8-yl)methyl, 1-(3,4-dihydro-1H-isoquinolin-1-yl)ethyl, 2-(3,4-dihydro-1H-isoquinolin-1-yl)ethyl, 3-(3,4-dihydro-1H-isoquinolin-1-yl)propyl and the like, in which preferred is (3,4-dihydro-1H-isoquinolin-1-yl)methyl, (3,4-dihydro-1H-isoquinolin-2-yl)methyl or 2-(3,4-dihydro-1H-isoquinolin-1-yl)ethyl.

Examples of the "indolyl lower alkyl" include (indol-1-yl)methyl, (indol-2-yl)methyl, (indol-3-yl)methyl, 1-(indol-1-yl)ethyl, 2-(indol-1-yl)ethyl, 3-(indol-2-yl)propyl and the like, in which preferred is (indol-1-yl)methyl.

Examples of the "triphenylphosphonium lower alkyl" include triphenylphosphonium methyl, 1-(triphenylphosphonium)ethyl, 2-(triphenylphosphonium)ethyl, 3-(triphenylphosphonium)propyl and the like, in which preferred is triphenylphosphonium methyl.

Examples of the "alkyl" include straight or branched ones having 1 to 10 carbon atoms, such as methyl, ethyl, n-propyl, isopropyl, n-butyl, isobutyl, tert-butyl, sec-butyl, n-pentyl, neopentyl, n-hexyl, isohexyl, 3-methylpentyl and the like.

Examples of the "aryl" include phenyl, 1-naphthyl, 2-naphthyl and the like.

Examples of the "aryl lower alkyl" include benzyl, 1-phenylethyl, phenethyl (2-phenylethyl), 3-phenylpropyl, 4-phenylbutyl, 5-phenylpentyl, 6-phenylhexyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, 3-(1-naphthyl)propyl, 3-(2-naphthyl)propyl, 4-(1-naphthyl)butyl, 4-(2-naphthyl)butyl and the like, in which preferred is benzyl or phenethyl.

Examples of the "aryl lower alkenyl" include styryl, 3-phenyl-1-propen-1-yl, 3-phenyl-2-propen-1-yl, 3-phenyl-2-methyl-1-propen-1-yl, 3-phenyl-2-methyl-2-propen-1-yl, 4-phenyl-1-buten-1-yl, 4-phenyl-2-buten-1-yl, 4-phenyl-3-buten-1-yl and the like, in which preferred is styryl.

Examples of the "acyl" include straight or branched alkylcarbonyl having 1 to 10 carbon atoms, preferably 1 to 6 carbon atoms, such as formyl, acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl and the like.

Examples of the "aroyl" include benzoyl, i-naphthoyl, 2-naphthoyl and the like, in which preferred is benzoyl.

Examples of the "lower alkylene" include linear or branched ones such as methylene, ethylene, 1-methylethylene, 2-methylethylene, trimethylene, 2-methyltrimethylene, 2,2 dimethyltrimethylene, 1-methyltrimethylene, methylmethylene, ethylmethylene, dimethylmethylene, tetramethylene, pentamethylene, hexamethylene and the like.

Examples of the "higher alkylene" include linear or branched ones such as heptamethylene, octamethylene, nonamethylene, decamethylene, dodecamethylene, tetradecamethylene, hexadecamethylene, octadecamethylene and the like.

Examples of the "lower alkenylene" include linear or branched ones that have 1 to 3 double bonds such as vinylene, 1-methylvinylene, 2-methylvinylene, 1,2-dimethylvinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene and the like.

Examples of the "phenylene" include 1,2-phenylene, 1,3-phenylene and 1,4-phenylene.

Examples of "heterocyclyl" include saturated or unsaturated monocyclic or polycyclic heterocyclyl containing at least one hetero atom selected from the group consisting of oxygen, sulfur and nitrogen. Examples of preferable heterocyclyl include the following (a) to (n):

(a) unsaturated 3 to 8-membered, preferably 5 or 6-membered heteromonocyclyl containing 1 to 4 nitrogen atoms, for example, pyrrolyl, pyrrolinyl, imidazolyl, pyrazolyl, pyridyl, and its N-oxide, tetrahydropyridyl (e.g., 1,2,3,6-tetrahydropyridyl), pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), dihydropyrimidinyl (e.g., 1,6-dihydrodihydropyrimidinyl), tetrahydropyrimidinyl (e.g., 1,2,3,6-tetrahydropyrimidiny) etc.;

(b) saturated 3 to 8-membered, preferably 5 to 7-membered heteromonocyclyl containing 1 to 4 nitrogen atoms, for example, azetidinyl, pyrrolidinyl, imidazolidinyl, piperidyl, pyrazolidinyl, piperazinyl, azepanyl, 1,4-diazepanyl, etc.;

(c) saturated or unsaturated condensed 7 to 12-membered heterocyclyl containing 1 to 5 nitrogen atoms, for example, decahydroquinolyl, indolyl, dihydroindolyl (e.g., 2,3-dihydroindolyl, etc.), isoindolyl, indolizinyl, benzimidazolyl, dihydrobenzimidazolyl (e.g., 2,3-dihydro-1H-benzo[d]imidazolyl, etc.), quinolyl, dihydroquinolyl (e.g. 1,4-dihydroquinolyl, 1,2-dihydroquinolyl, etc.), tetrahydroquinolyl (1,2,3,4-tetrahydroquinolyl, etc.), isoquinolyl, dihydroisoquinolyl (e.g., 3,4-dihydro-1H-isoquinolyl, 1,2-dihydroisoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl (e.g. benzo[d][1,2,3]triazolyl, etc.), tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, imidazo[4,5-c]pyridyl, imidazo[1,5-a]pyridyl, etc.), imidazobenzimidazolyl (e.g., imidazo[1,2-a]benzimidazolyl), naphthyridinyl, cinnolinyl, quinoxalinyl, quinazolinyl, pyrazolopyridyl (e.g., pyrazolo[2,3-a]pyridyl, etc.), tetrahydropyridoindolyl (e.g., 2,3,4,9-tetrahydro-1H-pyrido[3,4-b]indolyl, etc.), azabicyclooctanyl (e.g., (1R,5S)-8-azabicyclo[3.2.1]octanyl), carbazolyl etc.;

(d) saturated or unsaturated 3 to 8-membered, preferably 5 or 6-membered heteromonocyclyl containing 1 to 2 oxygen atoms, for example, furyl, tetrahydropyranyl (e.g., tetrahydro-2H-pyranyl, etc.), tetrahydrofuryl, etc.;

(e) unsaturated condensed 7 to 12-membered heterocyclyl containing 1 to 3 oxygen atoms, for example, benzofuryl, dihydrobenzofuryl (e.g. 2,3-dihydrobenzo[b]furyl, etc.), chromanyl, benzodioxolyl (e.g., 1,4-benzodioxanyl, etc.), benzodioxolyl (benzo[1,3]dioxolyl, etc.), dibenzofuryl, dihydrobenzodioxanyl, (e.g., 2,3-dihydro[1,4]benzodioxanyl), dihydrobenzodioxinyl (e.g., 2,3-dihydro[1,4]benzodioxinyl), dihydrobenzodioxepinyl (e.g., 3,4-dihydro-benzo[b][1,4]dioxepinyl) etc.;

(f) unsaturated 3 to 8-membered, preferably 5 or 6-membered heteromonocyclyl containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.;

(g) saturated 3 to 8-membered, preferably 5 or 6-membered heteromonocyclyl containing 1 to 2 oxygen atoms and 1 to 3 nitrogen atoms, for example, morpholinyl, etc.;

(h) unsaturated condensed 7 to 12-membered heterocyclyl containing 1 to 2 oxygen atoms and 1 to 3 nitrogen atoms, for example, benzoxazolyl, benzoxadiazolyl, benzisoxazolyl, dihydrobenzoxazinyl (e.g., 2,3-dihydrobenz-1,4-oxazinyl, etc.), furopyridyl (e.g., furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, etc.), furopyrrolyl (e.g., furo[3,2-b]pyrrolyl etc.), etc.;

(i) unsaturated 3 to 8-membered, preferably 5 or 6-membered heteromonocyclyl containing 1 to 2 sulfur atoms and 1 to 3 nitrogen atoms, for example, thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), isothiazolyl, etc.;

(j) saturated 3 to 8-membered, preferably 5 or 6-membered heteromonocyclyl containing 1 to 2 sulfur atoms and 1 to 3 nitrogen atoms, for example, thiazolidinyl, etc.;

(k) unsaturated 3 to 8-membered, preferably 5 or 6-membered heteromonocyclyl containing a sulfur atom, for example, thienyl, etc.;

(l) unsaturated condensed 7 to 12-membered heterocyclyl containing 1 to 3 sulfur atoms, for example, benzothienyl (e.g. benzo[b]thienyl, etc.);

(m) unsaturated condensed 7 to 12-membered heterocyclyl containing 1 to 2 sulfur atoms and 1 to 3 nitrogen atoms, for example, benzothiazolyl, benzothiadiazolyl, thienopyridyl (e.g., thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, thieno[3,2-b]pyridyl, 4,5,6,7-tetrahydrothieno[2,3-c]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc.; and (n) saturated or unsaturated 7- to 12-membered heterocyclic spiro groups containing 1 to 2 nitrogen atoms, for example, azaspiroundecanyl (e.g., 3-azaspiro[5.5]undecanyl), etc.

$R^1$ is preferably a group represented by formula:

-A-L1-B wherein each symbol is as defined above.

$R^1$ is more preferably one of the following (1-1) to (1-34):
(1-1) a phenyl group substituted with one or more members selected from the group consisting of the following (1-1-1) to (1-1-108):
    (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
    (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom), (1-1-3) a lower alkoxy lower alkyl group optionally substituted with one or more members selected from the group consisting of a halogen atoms; and a cycloalkyl group, (1-1-4) a cycloalkyl group, (1-1-5) a cycloalkoxy group optionally substituted with one or more halogen atoms, (1-1-6) a cycloalkyl lower alkyl group, (1-1-7) a cycloalkyl lower alkoxy group optionally substituted on the cycloalkyl group with one or more members selected from the group consisting of a halogen atom a lower alkyl group optionally substituted with one or more halogen atoms; and a phenyl group optionally substituted with one or more halogen atoms, (1-1-8) a cycloalkyl lower alkoxy lower alkyl group optionally substituted on the cycloalkyl group with one or more members selected from the group consisting of a hydroxy; and a lower alkoxy group, (1-1-9) a halogen atom (preferably provided that the phenyl group of (1-1) is substituted with one or more halogen atoms, then the phenyl group of (1-1) is substituted with additional one or more substituents excluding a phenoxy group), (1-1-10) a cyano group, (1-1-11) a phenyl group optionally substituted with one or more members selected from the group consisting of a halogen atom; a lower alkyl group optionally substituted with one or more halogen atoms; a lower alkoxy group optionally substituted with one or more halogen atoms; a lower alkoxy-carbonyl group; a lower alkylsulfonyl group; a phenyl group; a phenyl lower alkoxy group optionally substituted on the phenyl ring with one or more members selected from the group consisting of a halogen atom and a lower alkyl group optionally substituted with one or more halogen atoms; a phenoxy group; and a cyano group, (1-1-12) a phenyl lower alkyl group optionally substituted with one or more members selected from the group consisting of a halogen atom; a lower alkyl group optionally substituted with one or more halogen atoms; a lower alkoxy group optionally substituted with one or more halogen atoms; and a hydroxy group, (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; a halogen atom; and a 5-cyano-1H-1,2,3-triazol-4-yl group (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom), (1-1-14) a phenoxy group optionally substituted with one or more members selected from the group consisting of a halogen atom; a lower alkyl group optionally substituted with one or more halogen atoms; and a lower alkoxy group (preferably provided that the phenyl group of (1-1) is substituted with one or more phenoxy groups, then the phenyl group of (1-1) is substituted with additional one or more substituents excluding a halogen atom), (1-1-15) a phenoxy lower alkyl group optionally substituted on the phenyl ring with one or more members selected from the group consisting of a halogen atom; a lower alkyl group optionally substituted with one or more halogen atoms; and a lower alkoxy group optionally substituted with one or more halogen atoms, (1-1-16) a phenyl lower alkoxy group optionally substituted on the phenyl ring with one or more members selected from the group consisting of a halogen atom; a lower alkoxy group optionally substituted with one or more halogen atoms; a lower alkyl group optionally substituted with one or more halogen atoms; and a cyano group, (1-1-17) a phenylthio group optionally substituted with one or more members selected from the group consisting of a halogen atoms; and a lower alkyl group, (1-1-18) a benzylthio lower alkyl group optionally substituted on the phenyl ring with one or more members selected from the group consisting of a lower alkoxy group optionally substituted with one or more halogen atoms; and a lower alkyl group optionally substituted with one or more halogen atoms, (1-1-19) an N-lower alkyl-N-phenyl amino lower alkyl group optionally substituted on the phenyl ring with one or more members selected from the group consisting of a halogen atom; and a lower alkyl group optionally substituted with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more members selected from the group consisting of a halogen atom; a lower alkyl group optionally substituted with one or more halogen atoms; and a cyano group, (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms), (1-1-25) a pyrimidinyl group optionally substituted with one or more members selected from the group consisting of a halogen atom; a lower alkyl group optionally substituted with one or more halogen atoms; and a lower alkoxy group, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more members selected from the group consisting of a halogen atom; a lower alkyl group optionally substituted with one or more halogen atoms; and a phenyl group, (1-1-28) a benzoxazolyl group optionally substituted with one or more halogen atoms, (1-1-29) a benzofuryl group optionally substituted with one or more halogen atoms, (1-1-30) a benzofuryl lower alkoxy group optionally substituted on the benzofuran ring with one or more phenyl groups optionally substituted with one or more halogen atoms, (1-1-31) a thienyl group optionally substituted with one or more members selected from the group consisting of a halogen atom; a lower alkyl group optionally substituted with one or more halogen atoms; a lower alkyl-carbonyl group; and a phenyl group optionally substituted with one or more members selected from the group consisting of a halogen atom, and a lower alkyl group optionally substituted with one or more halogen atoms, (1-1-32) a benzothienyl group optionally substituted with one or more members selected from the group consisting of a halogen atom; a lower alkyl group optionally substituted with one or more halogen atoms; and a lower alkoxy group optionally substituted with one or more halogen atoms, (1-1-33) a benzo[1,3]dioxolyl group optionally substituted with one or more halogen atoms, (1-1-34) an indolinyl lower alkyl group, (1-1-35) a benzothienylvinyl group, (1-1-36) a benzo[1,3]dioxolylvinyl group optionally substituted on the benzo[1,3]dioxole ring with one or more halogen atoms, (1-1-37) a lower alkoxy lower alkoxy group, (1-1-38) a cycloalkoxy lower alkyl group optionally substituted on the cycloalkyl group with one or more lower alkyl groups, (1-1-39) a cycloalkyl lower alkenyl group, (1-1-40) a cycloalkenyloxy group, (1-1-41) a cycloalkenylvinyl group, (1-1-42) an oxiranyl group optionally substituted with one or more phenyl groups optionally substituted with one or more lower alkyl groups optionally substituted with one or more halogen atoms, (1-1-43) an oxetanyl lower alkoxy group optionally substituted on the oxetane ring with one or more lower alkyl groups, (1-1-44) a tetrahydropyranyl lower alkoxy group, (1-1-45) a hydroxy group, (1-1-46) a phenyl lower alkoxy lower alkyl group optionally substituted on the phenyl ring with one or more members selected from the group consisting of a halogen atom; a lower alkoxy group optionally substituted with one or more halogen atoms; a lower alkyl group optionally substituted with one or more halogen atoms; and a lower alkylthio group optionally substituted with one or more halogen atoms, (1-1-47) a phenyl lower alkenyloxy group optionally substituted on the phenyl ring with one or more lower alkyl groups optionally substituted with one or more halogen atoms, (1-1-48) a benzoyl group optionally substituted with one or more halogen atoms, (1-1-49) a phenylthio lower alkyl group optionally substituted on the phenyl ring with one or more members selected from the group consisting of a halogen atoms; and a lower alkyl group optionally substituted with one or more halogen atoms, (1-1-50) a phenylsulfonyl group optionally substituted with one or more lower alkyl groups, (1-1-51) a phenylsulfonyl lower alkyl group optionally substituted on the phenyl ring with one or more halogen atoms, (1-1-52) a naphthyl group optionally substituted with one or more halogen atoms, (1-1-53) a naphthylvinyl group optionally substituted on the naphthyl ring with one or more halogen atoms, (1-1-54) a tetrahydronaphthyloxy group, (1-1-55) an indanyloxy group, (1-1-56) an amino group optionally mono- or di-substituted with members selected from the group consisting of a lower alkyl group; a lower alkyl-carbonyl group; a lower alkoxy-carbonyl group; and a lower alkylsulfonyl group;

(1-1-57) an N-lower alkyl-N-phenyl amino group optionally substituted on the phenyl ring with one or more lower alkyl groups optionally substituted with one or more halogen atoms, (1-1-58) an aminocarbonyl group optionally substituted with one or more members selected from the group consisting of a lower alkyl group; a cycloalkyl group; a cycloalkyl lower alkyl group; and a phenyl group optionally substituted with one or more halogen atoms, (1-1-59) a pyridyl lower alkoxy group optionally substituted on the pyridine ring with one or more lower alkyl groups optionally substituted with one or more halogen atoms, (1-1-60) a pyridyloxy group optionally substituted with one or more lower alkyl groups optionally substituted with one or more halogen atoms, (1-1-61) a pyrrolo[2,3-b]pyridyl group optionally substituted with one or more lower alkyl groups, (1-1-62) a pyrazolo[3,4-b]pyridyl group optionally substituted with one or more lower alkyl groups, (1-1-63) an imidazo[1,2-a]pyridyl group optionally substituted with one or more members selected from the group consisting of a halogen atom; and a lower alkyl group optionally substituted with one or more halogen atoms, (1-1-64) a pyrimidinyl lower alkyl group optionally substituted on the pyrimidine ring with one or more lower alkyl groups optionally substituted with one or more halogen atoms, (1-1-65) a pyrimidinyl lower alkoxy group optionally substituted on the pyrimidine ring with one or more members selected from the group consisting of a lower alkoxy group; a lower alkyl group optionally substituted with one or more halogen atoms; and a phenyl group, (1-1-66) a pyrimidinyloxy group optionally substituted with one or more lower alkyl groups optionally substituted with one or more halogen atoms, (1-1-67) a pyrimidinyloxy lower alkyl group optionally substituted on the pyrimidine ring with one or more lower alkyl groups optionally substituted with one or more halogen atoms, (1-1-68) a pyrazinyl group optionally substituted with one or more lower alkyl groups, (1-1-69) a pyridazinyl group optionally substituted with one or more members selected from the group consisting of a lower alkyl group; and a lower alkoxy group, (1-1-70) a piperidyl lower alkyl group, (1-1-71) a piperidylcarbonyl group,
(1-1-72) a piperazinyl group optionally substituted with one or more phenyl groups optionally substituted with one or more halogen atoms,
(1-1-73) an imidazolyl group,
(1-1-74) a pyrazolyl group optionally substituted with one or more lower alkyl groups,
(1-1-75) a pyrrolyl lower alkyl group,
(1-1-76) a thiazolyl group,
(1-1-77) a thiazolyl lower alkoxy group optionally substituted on the thiazole ring with one or more lower alkyl groups,
(1-1-78) a benzothiazolyl group optionally substituted with one or more halogen atoms,
(1-1-79) a furyl group,
(1-1-80) a furylvinyl group optionally substituted on the furan ring with one or more lower alkyl groups,
(1-1-81) a benzofurylvinyl group (preferably the benzofurylvinyl group is bonded to the o- or m-position on the phenyl ring of (1-1)),
(1-1-82) a 2,3-dihydrobenzofuryl group,
(1-1-83) a thienyl lower alkoxy group,
(1-1-84) a thienylvinyl group optionally substituted on the thiophene ring with one or more halogen atoms (preferably the thienylvinyl group is bonded to the o- or m-position on the phenyl ring of (1-1)),
(1-1-85) a benzothienyl lower alkyl group optionally substituted on the benzothiophene ring with one or more halogen atoms,
(1-1-86) a benzothienyl lower alkoxy group optionally substituted on the benzothiophene ring with one or more members selected from the group consisting of a halogen atom; and a lower alkyl group optionally substituted with one or more halogen atoms,
(1-1-87) a benzo[1,3]dioxolyl lower alkyl group optionally substituted on the benzo[1,3]dioxole ring with one or more halogen atoms,
(1-1-88) a benzo[1,3]dioxolyl lower alkoxy group optionally substituted on the benzo[1,3]dioxole ring with one or more halogen atoms,
(1-1-89) a 4H-benzo[1,3]dioxinyl group optionally substituted with one or more halogen atoms,
(1-1-90) a 4H-benzo[1,3]dioxinylvinyl group optionally substituted on the benzo[1,3]dioxine ring with one or more halogen atoms,
(1-1-91) a quinolyl group,
(1-1-92) a quinolyl lower alkoxy group,
(1-1-93) a quinolylvinyl group,
(1-1-94) a 3,4-dihydro-2H-quinolyl group,
(1-1-95) a 3,4-dihydro-2H-quinolyl lower alkyl group,
(1-1-96) a 2-oxo-1,2,3,4-tetrahydroquinolyl group,
(1-1-97) a 2-oxo-1,2,3,4-tetrahydroquinolyl lower alkoxy group,
(1-1-98) a 2-oxo-1,2,3,4-tetrahydroquinolyloxy group optionally substituted with one or more lower alkyl groups,
(1-1-99) an isoquinolyl group,
(1-1-100) a 3,4-dihydro-1H-isoquinolyl group,
(1-1-101) a 3,4-dihydro-1H-isoquinolyl lower alkyl group,
(1-1-102) an indolyl group optionally substituted with one or more members selected from the group consisting of a halogen atom; a lower alkyl group; and a lower alkoxy-carbonyl group,
(1-1-103) an indolyl lower alkyl group,
(1-1-104) an indolylvinyl group optionally substituted on the indole ring with one or more lower alkyl groups,
(1-1-105) an indolinyl group,
(1-1-106) an indolinylcarbonyl group,
(1-1-107) a 1H-1,2,3-triazolyl group optionally substituted with one or more cyano groups, and
(1-1-108) a triphenylphosphonium lower alkyl group,
(1-2) a thiazolyl group substituted with one or more members selected from the group consisting of the following (1-2-1) to (1-2-26):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; a lower alkoxy group optionally substituted with one or more halogen atoms; a hydroxy group; and a cyano group,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an amino group optionally mono- or di-substituted with members selected from the group consisting of a lower alkyl group; a phenyl group optionally substituted with one or more members selected from the group consisting of a halogen atom, a lower alkyl group optionally substituted with one or more halogen atoms, and a lower alkoxy group optionally substituted with one or more halogen atoms; a benzyl group optionally substituted on the phenyl ring with one or more members selected from the group consisting of a halogen atom, and a lower alkyl group optionally substituted with one or more halogen atoms; and a benzoyl group optionally substituted with one or more halogen atoms,
  (1-2-11) a pyridyl group optionally substituted with one or more members selected from the group consisting of a halogen atom; and a lower alkyl group optionally substituted with one or more halogen atoms,
  (1-2-12) a lower alkenyl group,
  (1-2-13) a cycloalkyl lower alkyl group,
  (1-2-14) a phenyl lower alkyl group optionally substituted on the phenyl ring with one or more members selected from the group consisting of a halogen atom; a lower alkyl group optionally substituted with one or more halogen atoms; and a hydroxy group,
  (1-2-15) a phenoxy lower alkyl group optionally substituted on the phenyl ring with one or more members selected from the group consisting of a halogen atom; a lower alkyl group optionally substituted with one or more halogen atoms; and a lower alkoxy group optionally substituted with one or more halogen atoms,
  (1-2-16) a phenyl lower alkoxy lower alkyl group optionally substituted on the phenyl ring with one or more members selected from the group consisting of a halogen atom; a lower alkoxy group optionally substituted with one or more halogen atoms; and a lower alkyl group optionally substituted with one or more halogen atoms, (1-2-17) a phenyl lower alkylsulfonyl lower alkyl group optionally substituted on the phenyl ring with one or more lower alkyl groups optionally substituted with one or more halogen atoms, (1-2-18) a mono- or di-N-lower alkyl amino lower alkyl group;

(1-2-19) a piperidyl group optionally substituted with one or more members selected from the group consisting of a phenyl group optionally substituted with one or more members selected from the group consisting of a halogen atom, and a lower alkyl group optionally substituted with one or more halogen atoms; and a phenyl lower alkyl group optionally substituted on the phenyl ring with one or more members selected from the group consisting of a halogen atom, and a lower alkyl group optionally substituted with one or more halogen atoms, (1-2-20) a piperazinyl group optionally substituted with one or more phenyl groups optionally substituted with one or more members selected from the group consisting of a halogen atom, and a lower alkyl group optionally substituted with one or more halogen atoms, (1-2-21) an indolyl group, (1-2-22) a morpholinyl group, (1-2-23) a thienyl group, (1-2-24) a benzothienyl group optionally substituted with one or more lower alkyl groups optionally substituted with one or more halogen atoms, (1-2-25) a furyl group, and (1-2-26) a cyano group, (1-3) an oxazolyl group optionally substituted with one or more members selected from the group consisting of the following (1-3-1) to (1-3-12):

(1-3-1) a lower alkyl group optionally substituted with one or more halogen atoms, (1-3-2) a cycloalkyl group, (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms, (1-3-4) a lower alkoxy lower alkyl group, (1-3-5) a phenoxy lower alkyl group optionally substituted on the phenyl ring with one or more lower alkyl groups optionally substituted with one or more halogen atoms, (1-3-6) a naphthyl group, (1-3-7) a pyridyl group optionally substituted with one or more lower alkyl groups optionally substituted with one or more halogen atoms, (1-3-8) a furyl group, (1-3-9) a dihydrobenzofuryl group, (1-3-10) a thienyl group, (1-3-11) a benzothienyl group optionally substituted with one or more members selected from the group consisting of a halogen atom; a lower alkyl group optionally substituted with one or more halogen atoms; and a lower alkoxy group optionally substituted with one or more halogen atoms, and (1-3-12) a benzo[1,3]dioxolyl group optionally substituted with one or more halogen atoms, (1-4) a thienyl group substituted with one or more members selected from the group consisting of the following (1-4-1) to (1-4-14):

(1-4-1) a lower alkyl group optionally substituted with one or more halogen atoms, (1-4-2) a phenyl group optionally substituted with one or more members selected from the group consisting of a halogen atom; a lower alkyl group optionally substituted with one or more members selected from the group consisting of a halogen atom and a hydroxy group; a lower alkoxy group optionally substituted with one or more halogen atoms; a lower alkyl-carbonyl group; a lower alkoxy-carbonyl group; and a benzyloxy group optionally substituted on the phenyl ring with one or more members selected from the group consisting of a lower alkyl group optionally substituted with one or more halogen atoms, and a halogen atom, (1-4-3) a benzyl group optionally substituted on the phenyl ring with one or more halogen atoms, (1-4-4) a phenoxy group optionally substituted with one or more members selected from the group consisting of a lower alkyl group optionally substituted with one or more halogen atoms; and a halogen atom, (1-4-5) a styryl group optionally substituted on the phenyl ring with one or more members selected from the group consisting of a halogen atom; and a lower alkyl groups optionally substituted with one or more halogen atoms, (1-4-6) a cycloalkyl lower alkenyl group, (1-4-7) a halogen atom, (1-4-8) a pyridyl group optionally substituted with one or more members selected from the group consisting of a halogen atom; and a lower alkyl group optionally substituted with one or more halogen atoms, (1-4-9) a pyridyl lower alkyl group optionally substituted on the pyridine ring with one or more lower alkyl groups optionally substituted with one or more halogen atoms, (1-4-10) a pyrimidinyl group optionally substituted with one or more lower alkyl groups optionally substituted with one or more halogen atoms, (1-4-11) a thienyl group optionally substituted with one or more members selected from the group consisting of a halogen atom; and a phenyl group optionally substituted with one or more halogen atoms, (1-4-12) a thienylvinyl group, (1-4-13) a benzothienyl group optionally substituted with one or more members selected from the group consisting of a halogen atom; and a lower alkyl group optionally substituted with one or more halogen atoms, and (1-4-14) a benzo[1,3]dioxolyl group optionally substituted with one or more halogen atoms, (1-5) a furyl group optionally substituted with one or more members selected from the group consisting of the following (1-5-1) to (1-5-8):

(1-5-1) a phenyl group optionally substituted with one or more members selected from the group consisting of a halogen atom; a lower alkyl group optionally substituted with one or more halogen atoms; and a phenyl group, (1-5-2) a styryl group optionally substituted on the phenyl ring with one or more members selected from the group consisting of a halogen atom; a lower alkyl group optionally substituted with one or more halogen atoms; and a lower alkoxy group, (1-5-3) a lower alkyl group optionally substituted with one or more halogen atoms, (1-5-4) a naphthyl group, (1-5-5) a pyridyl group optionally substituted with one or more lower alkyl groups optionally substituted with one or more halogen atoms,
(1-5-6) a quinolyl group,
(1-5-7) a benzothienyl group optionally substituted with one or more lower alkyl groups optionally substituted with one or more halogen atoms, and
(1-5-8) a benzo[1,3]dioxolylvinyl group optionally substituted on the benzo[1,3]dioxole ring with one or more halogen atoms, (1-6) a pyrrolyl group optionally substituted with one or more members selected from the group consisting of the following (1-6-1) to (1-6-5):
(1-6-1) a lower alkyl group,
(1-6-2) a phenyl group optionally substituted with one or more members selected from the group consisting of a halogen atom; a lower alkyl group optionally substituted with one or more halogen atoms; a lower alkoxy group optionally substituted with one or more halogen atoms; a phenoxy group; a benzyl group; and a benzoyl group,
(1-6-3) a phenyl lower alkyl group optionally substituted on the phenyl ring with one or more members selected from the group consisting of a halogen atom; a lower alkyl group optionally substituted with one or more halogen atoms; a lower alkoxy group optionally substituted with one or more halogen atoms; a phenyl group; and a phenyl lower alkoxy group,
(1-6-4) an indanyl group, and
(1-6-5) a benzo[1,3]dioxolyl lower alkyl group, (1-7) a pyridyl group substituted with one or more members selected from the group consisting of the following (1-7-1) to (1-7-9):
(1-7-1) a benzyloxy lower alkyl group optionally substituted on the phenyl ring with one or more members selected from the group consisting of a halogen atom; and a lower alkyl group optionally substituted with one or more halogen atoms,
(1-7-2) a phenyl group optionally substituted with one or more members selected from the group consisting of a halogen atom; and a lower alkyl group optionally substituted with one or more halogen atoms,
(1-7-3) a benzofuryl group,
(1-7-4) a styryl group optionally substituted on the phenyl ring with one or more lower alkyl groups optionally substituted with one or more halogen atoms,
(1-7-5) a naphthyl group,
(1-7-6) a halogen atom,
(1-7-7) a pyridyl group,
(1-7-8) a benzothienyl group optionally substituted with one or more members selected from the group consisting of a halogen atom; and a lower alkyl group optionally substituted with one or more halogen atoms, and
(1-7-9) a [1,2,3]triazolyl group optionally substituted with one or more cyano groups, (1-8) a piperidyl group optionally substituted with one or more members selected from the group consisting of the following (1-8-1) to (1-8-8):
(1-8-1) a phenyl group optionally substituted with one or more members selected from the group consisting of a halogen atom; and a lower alkyl group optionally substituted with one or more halogen atoms,
(1-8-2) a benzyl group optionally substituted on the phenyl ring with one or more members selected from the group consisting of a halogen atom; and a lower alkyl group optionally substituted with one or more halogen atoms,
(1-8-3) a lower alkoxy-carbonyl group,
(1-8-4) a benzoyl group optionally substituted on the phenyl ring with one or more lower alkyl groups optionally substituted with one or more halogen atoms,
(1-8-5) a phenyl lower alkyl-carbonyl group optionally substituted on the phenyl ring with one or more halogen atoms,
(1-8-6) a phenyl lower alkoxy-carbonyl group,
(1-8-7) a phenoxycarbonyl group, and
(1-8-8) a phenylsulfonyl group optionally substituted with one or more lower alkyl groups, (1-9) an indolyl group optionally substituted with one or more members selected from the group consisting of the following (1-9-1) to (1-9-8):
(1-9-1) a lower alkyl group optionally substituted with one or more halogen atoms,
(1-9-2) a phenyl group optionally substituted with one or more members selected from the group consisting of a halogen atom; a lower alkyl group optionally substituted with one or more halogen atoms; and a lower alkoxy group,
(1-9-3) a cycloalkyl lower alkyl group,
(1-9-4) a halogen atom,
(1-9-5) a phenyl lower alkyl group optionally substituted on the phenyl ring with one or more members selected from the group consisting of a halogen atom; and a lower alkyl group optionally substituted with one or more halogen atoms,
(1-9-6) a thienyl lower alkyl group,
(1-9-7) a tetrahydrofuryl lower alkyl group, and
(1-9-8) a benzo[1,3]dioxolyl group, (1-10) a benzofuryl group optionally substituted with one or more members selected from the group consisting of the following (1-10-1) to (1-10-7):
(1-10-1) a halogen atom,
(1-10-2) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-10-3) a lower alkyl group,
(1-10-4) a benzyl group optionally substituted on the phenyl ring with one or more lower alkyl groups optionally substituted with one or more halogen atoms,
(1-10-5) a styryl group optionally substituted on the phenyl ring with one or more lower alkyl groups optionally substituted with one or more halogen atoms,
(1-10-6) a benzo[1,3]dioxolyl group optionally substituted with one or more halogen atoms, and
(1-10-7) a pyrimidinyl group optionally substituted with one or more lower alkyl groups optionally substituted with one or more halogen atoms, (1-11) a benzothienyl group optionally substituted with one or more members selected from the group consisting of the following (1-11-1) to (1-11-7):
(1-11-1) a phenyl group optionally substituted with one or more members selected from the group consisting of a halogen atom; and a lower alkyl group optionally substituted with one or more halogen atoms,
(1-11-2) a lower alkyl group optionally substituted with one or more halogen atoms,
(1-11-3) a phenyl lower alkoxy group optionally substituted on the phenyl ring with one or more lower alkyl groups optionally substituted with one or more halogen atoms,
(1-11-4) a halogen atom, (1-11-5) a pyridyl group optionally substituted with one or more lower alkyl groups optionally substituted with one or more halogen atoms,
(1-11-6) a pyrimidinyl group optionally substituted with one or more lower alkyl groups optionally substituted with one or more halogen atoms, and
(1-11-7) a thienyl group, (1-12) a phenyl lower alkyl group optionally substituted on the phenyl ring with one or more members selected from the group consisting of the following (1-12-1) to (1-12-4):
  (1-12-1) a phenyl group optionally substituted with one or more lower alkyl groups optionally substituted with one or more halogen atoms,
  (1-12-2) a benzyloxy group optionally substituted on the phenyl ring with one or more lower alkyl groups optionally substituted with one or more halogen atoms,
  (1-12-3) a lower alkyl group optionally substituted with one or more halogen atoms, and
  (1-12-4) a phenoxy group, (1-13) a pyrimidinyl group optionally substituted with one or more members selected from the group consisting of the following (1-13-1) to (1-13-7):
  (1-13-1) a phenyl group optionally substituted with one or more lower alkyl groups optionally substituted with one or more halogen atoms,
  (1-13-2) a pyrrolidyl group,
  (1-13-3) a piperidyl group,
  (1-13-4) a lower alkyl group optionally substituted with one or more halogen atoms,
  (1-13-5) a lower alkoxy group,
  (1-13-6) a styryl group optionally substituted on the phenyl ring with one or more members selected from the group consisting of a halogen atom; and a lower alkyl group optionally substituted with one or more halogen atoms, and
  (1-13-7) a morpholinyl group, (1-14) a quinolyl group substituted with one or more members selected from the group consisting of the following (1-14-1) to (1-14-5):
  (1-14-1) a lower alkoxy group,
  (1-14-2) a phenyl group optionally substituted with one or more members selected from the group consisting of a halogen atom; and a lower alkyl group optionally substituted with one or more halogen atoms,
  (1-14-3) a phenyl lower alkoxy group optionally substituted on the phenyl ring with one or more lower alkyl groups optionally substituted with one or more halogen atoms,
  (1-14-4) a pyrrolidyl group, and
  (1-14-5) a thienyl group, (1-15) a 2,3-dihydro-1H-indolyl group optionally substituted with one or more members selected from the group consisting of the following (1-15-1) to (1-15-2):
  (1-15-1) a phenyl group optionally substituted with one or more members selected from the group consisting of a halogen atom; and a lower alkyl group optionally substituted with one or more halogen atoms, and
  (1-15-2) a benzyl group optionally substituted on the phenyl ring with one or more members selected from the group consisting of a halogen atom; and a lower alkyl group optionally substituted with one or more halogen atoms, (1-16) an imidazolyl group optionally substituted with one or more members selected from the group consisting of the following (1-16-1) to (1-16-4):
  (1-16-1) a lower alkyl group,
  (1-16-2) a halogen atom,
  (1-16-3) a phenyl group optionally substituted with one or more members selected from the group consisting of a halogen atom; and a lower alkyl group optionally substituted with one or more halogen atoms, and
  (1-16-4) a benzyl group optionally substituted on the phenyl ring with one or more members selected from the group consisting of a halogen atom; and a lower alkyl group optionally substituted with one or more halogen atoms, (1-17) a benzothiazolyl group optionally substituted with one or more members selected from the group consisting of the following (1-17-1) to (1-17-6):
  (1-17-1) a lower alkyl group optionally substituted with one or more halogen atoms,
  (1-17-2) a lower alkoxy group,
  (1-17-3) a halogen atom,
  (1-17-4) a phenyl group optionally substituted with one or more members selected from the group consisting of a halogen atom; and a lower alkyl group optionally substituted with one or more halogen atoms,
  (1-17-5) a phenoxy group optionally substituted with one or more members selected from the group consisting of a halogen atom; and a lower alkyl group optionally substituted with one or more halogen atoms, and
  (1-17-6) a pyridyl group optionally substituted with one or more lower alkyl groups optionally substituted with one or more halogen atoms, (1-18) an isoxazolyl group optionally substituted with one or more phenyl groups optionally substituted with one or more halogen atoms, (1-19) a 2,3-dihydrobenzofuryl group optionally substituted with one or more members selected from the group consisting of the following (1-19-1) to (1-19-3):
  (1-19-1) a halogen atom,
  (1-19-2) a phenyl group optionally substituted with one or more halogen atoms, and
  (1-19-3) a pyridyl group optionally substituted with one or more lower alkyl groups optionally substituted with one or more halogen atoms, (1-20) an isothiazolyl group optionally substituted with one or more phenyl groups optionally substituted with one or more members selected from the group consisting of a halogen atom, a lower alkyl group optionally substituted with one or more halogen atoms, and a lower alkoxy group optionally substituted with one or more halogen atoms, (1-21) a dibenzofuryl group, (1-22) a benzo[1,3]dioxolyl group optionally substituted with one or more members selected from the group consisting of the following (1-22-1) to (1-22-2):
  (1-22-1) a halogen atom, and
  (1-22-2) a pyridyl group optionally substituted with one or more lower alkyl groups optionally substituted with one or more halogen atoms, (1-23) a carbazolyl group optionally substituted with one or more lower alkyl groups, (1-24) a naphthyl group optionally substituted with one or more benzyloxy groups optionally substituted on the phenyl ring with one or more lower alkyl groups optionally substituted with one or more halogen atoms, (1-25) a 2-oxo-1,2,3,4-tetrahydroquinolyl group optionally substituted with one or more benzyl groups optionally substituted on the phenyl ring with one or more lower alkyl groups optionally substituted with one or more halogen atoms, (1-26) a 6-oxo-1,6-dihydropyrimidinyl group optionally substituted with one or more phenyl groups optionally substituted with one or more lower alkyl groups optionally substituted with one or more halogen atoms, (1-27) an imidazo[1,2-a]pyridyl group optionally substituted with one or more phenyl groups optionally substituted with one or more lower alkyl groups optionally substituted with one or more halogen atoms, (1-28) a [1,3,4]oxadiazolyl group optionally substituted with one or more phenyl groups optionally substituted with one or more lower alkyl groups optionally substituted with one or more halogen atoms, (1-29) a [1,2,4]thiadiazolyl group optionally substituted with one or more phenyl groups optionally substituted with one or more halogen atoms, (1-30) a benzoxazolyl group optionally substituted with one or more members selected from the group consisting of the following (1-30-1) to (1-30-4):
- (1-30-1) a lower alkyl group,
- (1-30-2) a lower alkoxy group,
- (1-30-3) a halogen atom, and
- (1-30-4) a phenyl group, (1-31) a [1,3,4]thiadiazolyl group optionally substituted with one or more phenyl groups optionally substituted with one or more halogen atoms;

(1-32) a styryl group optionally substituted on the phenyl ring with one or more benzyloxy groups optionally substituted on the phenyl ring with one or more lower alkyl groups optionally substituted with one or more halogen atoms, (1-33) a benzoyl group optionally substituted with one or more benzyloxy groups optionally substituted on the phenyl ring with one or more lower alkyl groups optionally substituted with one or more halogen atoms, and (1-34) a cycloalkyl group optionally substituted with one or more members selected from the group consisting of a phenyl group optionally substituted with one or more members selected from the group consisting of a halogen atom and a benzyloxy group optionally substituted on the phenyl ring with one or more lower alkyl groups optionally substituted with one or more halogen atoms; and a benzyloxy groups optionally substituted on the phenyl ring with one or more lower alkyl groups optionally substituted with one or more halogen atoms.

$R^1$ is further more preferably one of the following (1-1) to (1-13):

(1-1) a phenyl group substituted with one or more members selected from the group consisting of the following (1-1-1) to (1-1-36):
- (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
- (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
- (1-1-3) a lower alkoxy lower alkyl group,
- (1-1-4) a cycloalkyl group,
- (1-1-5) a cycloalkoxy group,
- (1-1-6) a cycloalkyl lower alkyl group,
- (1-1-7) a cycloalkyl lower alkoxy group,
- (1-1-8) a cycloalkyl lower alkoxy lower alkyl group,
- (1-1-9) a halogen atom (preferably provided that the phenyl group of (1-1) is substituted with one or more halogen atoms, then the phenyl group of (1-1) is substituted with additional one or more substituents excluding a phenoxy group),
- (1-1-10) a cyano group,
- (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-1-12) a phenyl lower alkyl group optionally substituted on the phenyl ring with one or more members selected from the group consisting of a halogen atom; and a lower alkyl group optionally substituted with one or more halogen atoms,
- (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
- (1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
- (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
- (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
- (1-1-17) a phenylthio group optionally substituted with one or more halogen atoms,
- (1-1-18) a benzylthio lower alkyl group optionally substituted on the phenyl ring with one or more lower alkoxy groups optionally substituted with one or more halogen atoms,
- (1-1-19) an N-lower alkyl-N-phenyl amino lower alkyl group optionally substituted on the phenyl ring with one or more halogen atoms,
- (1-1-20) an N-benzyl-N-lower alkyl amino group optionally substituted on the phenyl ring with one or more lower alkyl groups optionally substituted with one or more halogen atoms,
- (1-1-21) a pyridyl group optionally substituted with one or more lower alkyl groups optionally substituted with one or more halogen atoms,
- (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms, (1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms, (1-4) a thienyl group substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more-lower alkyl groups optionally substituted with one or more halogen atoms, and
  (1-4-5) a styryl group optionally substituted on the phenyl ring with one or more lower alkyl groups optionally substituted with one or more halogen atoms, (1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms, (1-7) a pyridyl group substituted with one or more members selected from the group consisting of the following (1-7-1) to (1-7-3):
  (1-7-1) a benzyloxy lower alkyl group optionally substituted on the phenyl ring with one or more lower alkyl groups optionally substituted with one or more halogen atoms,
  (1-7-2) a phenyl group optionally substituted with one or more lower alkyl groups optionally substituted with one or more halogen atoms, and (1-7-3) a benzofuryl group,
(1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms,
(1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms,
(1-10) a benzofuryl group optionally substituted with one or more members selected from the group consisting of the following (1-10-1) to (1-10-2):
  (1-10-1) a halogen atom, and
  (1-10-2) a phenyl group optionally substituted with one or more halogen atoms,
(1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms; and
  (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
  (1-13-1) a phenyl group,
  (1-13-2) a pyrrolidinyl group, and
  (1-13-3) a piperidyl group.

In another embodiment, $R^1$ is further more preferably the following (1-1):
(1-1) a phenyl group substituted with one or more members selected from the group consisting of the following (1-1-1) to (1-1-36):
  (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
  (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
  (1-1-3) a lower alkoxy lower alkyl group,
  (1-1-4) a cycloalkyl group,
  (1-1-5) a cycloalkoxy group,
  (1-1-6) a cycloalkyl lower alkyl group,
  (1-1-7) a cycloalkyl lower alkoxy group,
  (1-1-8) a cycloalkyl lower alkoxy lower alkyl group,
  (1-1-9) a halogen atom (preferably provided that the phenyl group of (1-1) is substituted with one or more halogen atoms, then the phenyl group of (1-1) is substituted with additional one or more substituents excluding a phenoxy group),
  (1-1-10) a cyano group,
  (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-1-12) a phenyl lower alkyl group optionally substituted on the phenyl ring with one or more members selected from the group consisting of a halogen atom; and a lower alkyl group optionally substituted with one or more halogen atoms,
  (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group substituted on the phenyl ring with one or more members selected from the group consisting of a lower alkoxy group substituted with one or more halogen atoms; a lower alkyl group substituted with one or more halogen atoms; and a fluoro atom),
  (1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
  (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
  (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
  (1-1-17) a phenylthio group optionally substituted with one or more halogen atoms,
  (1-1-18) a benzylthio lower alkyl group optionally substituted on the phenyl ring with one or more lower alkoxy groups optionally substituted with one or more halogen atoms,
  (1-1-19) an N-lower alkyl-N-phenyl amino lower alkyl group optionally substituted on the phenyl ring with one or more halogen atoms,
  (1-1-20) an N-benzyl-N-lower alkyl amino group optionally substituted on the phenyl ring with one or more lower alkyl groups optionally substituted with one or more halogen atoms,
  (1-1-21) a pyridyl group optionally substituted with one or more lower alkyl groups optionally substituted with one or more halogen atoms,
  (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms.

In another embodiment, $R^1$ is further more preferably one of the following (1-2) to (1-13):
(1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms,
(1-7) a pyridyl group substituted with one or more members selected from the group consisting of the following (1-7-1) to (1-7-3):
  (1-7-1) a benzyloxy lower alkyl group optionally substituted on the phenyl ring with one or more lower alkyl groups optionally substituted with one or more halogen atoms, (1-7-2) a phenyl group optionally substituted with one or more lower alkyl groups optionally substituted with one or more halogen atoms, and (1-7-3) a benzofuryl group, (1-8) a piperidyl group optionally substituted with one or more members selected from the group consisting of the following (1-8-1) to (1-8-2):

(1-8-1) a phenyl group optionally substituted with one or more lower alkyl groups optionally substituted with one or more halogen atoms, and (1-8-2) a benzyl group optionally substituted on the phenyl ring with one or more halogen atoms, (1-9) an indolyl group optionally substituted with one or more members selected from the group consisting of the following (1-9-1) to (1-9-2):

(1-9-1) a lower alkyl group optionally substituted with one or more halogen atoms, and (1-9-2) a phenyl group optionally substituted with one or more halogen atoms, (1-10) a benzofuryl group optionally substituted with one or more members selected from the group consisting of the following (1-10-1) to (1-10-2):

(1-10-1) a halogen atom, and (1-10-2) a phenyl group optionally substituted with one or more halogen atoms, (1-11) a benzothienyl group optionally substituted with one or more phenyl groups optionally substituted with one or more halogen atoms, (1-12) a phenyl lower alkyl group optionally substituted on the phenyl ring with one or more members selected from the group consisting of the following (1-12-1) to (1-12-2):

(1-12-1) a phenyl group optionally substituted with one or more lower alkyl groups optionally substituted with one or more halogen atoms; and (1-12-2) a benzyloxy group optionally substituted on the phenyl ring with one or more lower alkyl groups optionally substituted with one or more halogen atoms, and (1-13) a pyrimidinyl group optionally substituted with one or more members selected from the group consisting of the following (1-13-1) to (1-13-3):

(1-13-1) a phenyl group, (1-13-2) a pyrrolidinyl group, and (1-13-3) a piperidyl group.

In another embodiment, $R^1$ is further more preferably the following (1-2):

(1-2) a thiazolyl group substituted with one or more members selected from the group consisting of the following (1-2-1) to (1-2-11):

(1-2-1) a lower alkyl group optionally substituted with one or more halogen atoms, (1-2-2) a lower alkoxy group, (1-2-3) a cycloalkyl group, (1-2-4) a halogen atom, (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, (1-2-6) a styryl group optionally substituted on the phenyl ring with one or more lower alkyl groups optionally substituted with one or more halogen atoms, (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms, (1-2-8) a benzyloxy group optionally substituted on the phenyl ring with one or more halogen atoms, (1-2-9) a phenylthio group optionally substituted with one or more members selected from the group consisting of a halogen atom; and a lower alkyl group optionally substituted with one or more halogen atoms, (1-2-10) an N-lower alkyl-N-phenyl amino group optionally substituted on the phenyl ring with one or more members selected from the group consisting of a halogen atom; and a lower alkyl group optionally substituted with one or more halogen atoms, and (1-2-11) a pyridyl group optionally substituted with one or more members selected from the group consisting of a halogen atom; and a lower alkyl group optionally substituted with one or more halogen atoms.

In another embodiment, $R^1$ is further more preferably the following (1-3):

(1-3) an oxazolyl group optionally substituted with one or more members selected from the group consisting of the following (1-3-1) to (1-3-3):

(1-3-1) a lower alkyl group, (1-3-2) a cycloalkyl group, and (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms.

In another embodiment, $R^1$ is further more preferably the following (1-5):

(1-5) a furyl group optionally substituted with one or more members selected from the group consisting of the following (1-5-1) to (1-5-2):

(1-5-1) a phenyl group optionally substituted with one or more halogen atoms, and (1-5-2) a styryl group optionally substituted on the phenyl ring with one or more members selected from the group consisting of a halogen atom; and a lower alkyl group optionally substituted with one or more halogen atoms.

In another embodiment, $R^1$ is further more preferably the following (1-13):

(1-13) a pyrimidinyl group optionally substituted with one or more members selected from the group consisting of the following (1-13-1) to (1-13-3):

(1-13-1) a phenyl group, (1-13-2) a pyrrolidinyl group, and (1-13-3) a piperidyl group.

$R^1$ is still more preferably one of the following (1-1) to (1-7), (1-9), (1-10), (1-12) and (1-13):

(1-1) a phenyl group substituted with one or more members selected from the group consisting of (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents), (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom), (1-1-9) a halogen atom (preferably provided that the phenyl group of (1-1) is substituted with one or more halogen atoms, then the phenyl group of (1-1) is substituted with additional one or more substituents excluding a phenoxy group), (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms, (1-1-12) a phenyl lower alkyl group optionally substituted on the phenyl ring with one or more members selected from the group consisting of a halogen atom; and a lower alkyl group optionally substituted with one or more halogen atoms, (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom), (1-1-14) a phenoxy group (preferably provided that the phenyl group of (1-1) is substituted with one or more phenoxy groups, then the phenyl group of (1-1) is substituted with additional one or more substituents excluding a halogen atom), (1-1-16) a phenyl lower alkoxy group optionally substituted on the phenyl ring with one or more lower alkyl groups optionally substituted with one or more halogen atoms, (1-1-19) an N-lower alkyl-N-phenyl amino lower alkyl group optionally substituted on the phenyl ring with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms), (1-1-25) a pyrimidinyl group optionally substituted with one or more lower alkyl groups optionally substituted with one or more halogen atoms, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more lower alkyl groups optionally substituted with one or more halogen atoms, (1-1-31) a thienyl group, (1-1-32) a benzothienyl group, (1-1-33) a benzo[1,3]dioxolyl group optionally substituted with one or more halogen atoms, (1-1-35) a benzothienylvinyl group, and (1-1-36) a benzo[1,3]dioxolylvinyl group optionally substituted on the benzo[1,3]dioxole ring with one or more halogen atoms, (1-2) a thiazolyl group substituted with one or more members selected from the group consisting of (1-2-1) a lower alkyl group optionally substituted with one or more halogen atoms, (1-2-4) a halogen atom, (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of (1-3-1) a lower alkyl group, (1-3-2) a cycloalkyl group, and (1-3-3) a phenyl group optionally substituted with one or more members selected from the group consisting of a halogen atom; and a lower alkyl group optionally substituted with one or more halogen atoms, (1-4) a thienyl group substituted with one or more members selected from the group consisting of (1-4-2) a phenyl group optionally substituted with one or more lower alkyl groups optionally substituted with one or more halogen atoms, (1-5) a furyl group optionally substituted with one or more members selected from the group consisting of (1-5-1) a phenyl group optionally substituted with one or more halogen atoms, and (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of (1-6-1) a lower alkyl group, and (1-6-2) a phenyl group optionally substituted with one or more members selected from the group consisting of a halogen atom; and a lower alkyl group optionally substituted with one or more halogen atoms, (1-7) a pyridyl group substituted with one or more members selected from the group consisting of (1-7-3) a benzofuryl group, (1-9) an indolyl group optionally substituted with one or more members selected from the group consisting of (1-9-1) a lower alkyl group optionally substituted with one or more halogen atoms, (1-10) a benzofuryl group optionally substituted with one or more members selected from the group consisting of (1-10-2) a phenyl group optionally substituted with one or more halogen atoms, (1-12) a phenyl lower alkyl group optionally substituted on the phenyl ring with one or more members selected from the group consisting of
- (1-12-2) a benzyloxy group optionally substituted on the phenyl ring with one or more lower alkyl groups optionally substituted with one or more halogen atoms, and (1-13) a pyrimidinyl group optionally substituted with one or more members selected from the group consisting of
- (1-13-1) a phenyl group,
- (1-13-2) a pyrrolidyl group, and
- (1-13-3) a piperidyl group.

In another embodiment, $R^1$ is still more preferably the following (1-1):

(1-1) a phenyl group substituted with one or more members selected from the group consisting of
- (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
- (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
- (1-1-9) a halogen atom (preferably provided that the phenyl group of (1-1) is substituted with one or more halogen atoms, then the phenyl group of (1-1) is substituted with additional one or more substituents excluding a phenoxy group),
- (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-1-12) a phenyl lower alkyl group optionally substituted on the phenyl ring with one or more members selected from the group consisting of a halogen atom; and a lower alkyl group optionally substituted with one or more halogen atoms,
- (1-1-13) a styryl group optionally substituted on the phenyl ring with one or more members selected from the group consisting of a lower alkoxy group optionally substituted with one or more halogen atoms; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkoxy group substituted with one or more halogen atoms; a lower alkyl group substituted with one or more halogen atoms; and a fluoro atom),
- (1-1-14) a phenoxy group (preferably provided that the phenyl group of (1-1) is substituted with one or more phenoxy groups, then the phenyl group of (1-1) is substituted with additional one or more substituents excluding a halogen atom),
- (1-1-16) a phenyl lower alkoxy group optionally substituted on the phenyl ring with one or more lower alkyl groups optionally substituted with one or more halogen atoms,
- (1-1-19) an N-lower alkyl-N-phenyl amino lower alkyl group optionally substituted on the phenyl ring with one or more halogen atoms,
- (1-1-20) an N-benzyl-N-lower alkyl amino group optionally substituted on the phenyl ring with one or more lower alkyl groups optionally substituted with one or more halogen atoms,
- (1-1-21) a pyridyl group optionally substituted with one or more lower alkyl groups optionally substituted with one or more halogen atoms,
- (1-1-23) a pyridyloxy lower alkyl group optionally substituted on the pyridine ring with one or more lower alkyl groups optionally substituted with one or more halogen atoms,
- (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
- (1-1-25) a pyrimidinyl group optionally substituted with one or more lower alkyl groups optionally substituted with one or more halogen atoms,
- (1-1-26) a pyrimidinylvinyl group optionally substituted on the pyrimidine ring with one or more lower alkyl groups optionally substituted with one or more halogen atoms,
- (1-1-27) a piperidyl group optionally substituted with one or more lower alkyl groups optionally substituted with one or more halogen atoms,
- (1-1-31) a thienyl group,
- (1-1-32) a benzothienyl group,
- (1-1-33) a benzo[1,3]dioxolyl group optionally substituted with one or more halogen atoms,
- (1-1-35) a benzothienylvinyl group, and
- (1-1-36) a benzo[1,3]dioxolylvinyl group optionally substituted on the benzo[1,3]dioxole ring with one or more halogen atoms.

In another embodiment, $R^1$ is still more preferably one of the following (1-2) to (1-7), (1-9), (1-10), (1-12) and (1-13):

(1-2) a thiazolyl group substituted with one or more members selected from the group consisting of
- (1-2-1) a lower alkyl group optionally substituted with one or more halogen atoms,
- (1-2-4) a halogen atom,
- (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
- (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of
- (1-3-1) a lower alkyl group,
- (1-3-2) a cycloalkyl group, and
- (1-3-3) a phenyl group optionally substituted with one or more members selected from the group consisting of a halogen atom; and a lower alkyl group optionally substituted with one or more halogen atoms, (1-4) a thienyl group substituted with one or more members selected from the group consisting of (1-4-2) a phenyl group optionally substituted with one or more lower alkyl groups optionally substituted with one or more halogen atoms, (1-5) a furyl group optionally substituted with one or more members selected from the group consisting of
- (1-5-1) a phenyl group optionally substituted with one or more halogen atoms, and
- (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of
- (1-6-1) a lower alkyl group, and
- (1-6-2) a phenyl group optionally substituted with one or more members selected from the group consisting of a halogen atom; and a lower alkyl group optionally substituted with one or more halogen atoms, (1-7) a pyridyl group substituted with one or more members selected from the group consisting of
- (1-7-3) a benzofuryl group, (1-9) an indolyl group optionally substituted with one or more members selected from the group consisting of
- (1-9-1) a lower alkyl group optionally substituted with one or more halogen atoms, (1-10) a benzofuryl group optionally substituted with one or more members selected from the group consisting of
- (1-10-2) a phenyl group optionally substituted with one or more halogen atoms, (1-12) a phenyl lower alkyl group optionally substituted on the phenyl ring with one or more members selected from the group consisting of
- (1-12-2) a benzyloxy group optionally substituted on the phenyl ring with one or more lower alkyl groups optionally substituted with one or more halogen atoms, and (1-13) a pyrimidinyl group optionally substituted with one or more members selected from the group consisting of
- (1-13-1) a phenyl group,
- (1-13-2) a pyrrolidyl group, and
- (1-13-3) a piperidyl group.

In another embodiment, $R^1$ is still more preferably the following (1-2):

(1-2) a thiazolyl group substituted with one or more members selected from the group consisting of
- (1-2-1) a lower alkyl group optionally substituted with one or more halogen atoms,
- (1-2-4) a halogen atom,
- (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
- (1-2-11) a pyridyl group optionally substituted with one or more members selected from the group consisting of a halogen atom; and a lower alkyl group optionally substituted with one or more halogen atoms.

In another embodiment, $R^1$ is still more preferably the following (1-3):

(1-3) an oxazolyl group optionally substituted with one or more members selected from the group consisting of
- (1-3-1) a lower alkyl group,
- (1-3-2) a cycloalkyl group, and
- (1-3-3) a phenyl group optionally substituted with one or more members selected from the group consisting of a halogen atom; and a lower alkyl group optionally substituted with one or more halogen atoms.

In another embodiment, $R^1$ is still more preferably the following (1-5):

(1-5) a furyl group optionally substituted with one or more members selected from the group consisting of
- (1-5-1) a phenyl group optionally substituted with one or more halogen atoms, and
- (1-5-2) a styryl group optionally substituted on the phenyl ring with one or more members selected from the group consisting of a halogen atom; and a lower alkyl group optionally substituted with one or more halogen atoms.

In another embodiment, $R^1$ is still more preferably the following (1-13):

(1-13) a pyrimidinyl group optionally substituted with one or more members selected from the group consisting of
- (1-13-1) a phenyl group,
- (1-13-2) a pyrrolidyl group, and
- (1-13-3) a piperidyl group.

In another embodiment, $R^1$ is preferably is one of the following (1-1) to (1-13):

(1-1) a phenyl group optionally substituted with one or more members selected from the group consisting of the following (1-1-1) to (1-1-34):
- (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
- (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
- (1-1-3) a lower alkoxy lower alkyl group,
- (1-1-4) a cycloalkyl group,
- (1-1-5) a cycloalkoxy group,
- (1-1-6) a cycloalkyl lower alkyl group,
- (1-1-7) a cycloalkyl lower alkoxy group,
- (1-1-8) a cycloalkyl lower alkoxy lower alkyl group,
- (1-1-9) a halogen atom (preferably provided that the phenyl group of (1-1) is substituted with one or more halogen atoms, then the phenyl group of (1-1) is substituted with additional one or more substituents excluding a phenoxy group),
- (1-1-10) a cyano group,
- (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-1-12) a phenyl lower alkyl group optionally substituted on the phenyl ring with one or more members selected from the group consisting of a halogen atom; and a lower alkyl group optionally substituted with one or more halogen atoms,
- (1-1-13) a styryl group optionally substituted on the phenyl ring with one or more members selected from the group consisting of a lower alkoxy group; a lower alkyl group optionally substituted with one or more halogen atoms; a cyano group; and a halogen atom (preferably provided that when the styryl group is bonded to the p-position on the phenyl ring of (1-1), then the styryl group is substituted on the phenyl ring with one or more members selected from the group consisting of a lower alkyl group substituted with one or more halogen atoms; and a fluoro atom), (1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom), (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms, (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms, (1-1-17) a phenylthio group optionally substituted with one or more halogen atoms, (1-1-18) a benzylthio lower alkyl group optionally substituted on the phenyl ring with one or more lower alkoxy groups optionally substituted with one or more halogen atoms, (1-1-19) an N-lower alkyl-N-phenyl amino lower alkyl group optionally substituted on the phenyl ring with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more lower alkyl groups optionally substituted with one or more halogen atoms, (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms), (1-1-25) a pyrimidinyl group optionally substituted with one or more lower alkyl groups optionally substituted with one or more halogen atoms, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more lower alkyl groups optionally substituted with one or more halogen atoms, (1-1-28) a benzoxazolyl group optionally substituted on the phenyl ring with one or more halogen atoms, (1-1-29) a benzofuryl group, (1-1-30) a benzofuryl lower alkoxy group, (1-1-31) a thienyl group, (1-1-32) a benzothienyl group, (1-1-33) a benzo[1,3]dioxolyl group optionally substituted with one or more halogen atoms, and (1-1-34) an indolinyl lower alkyl group, (1-2) a thiazolyl group optionally substituted with one or more members selected from the group consisting of the following (1-2-1) to (1-2-11):

(1-2-1) a lower alkyl group optionally substituted with one or more halogen atoms, (1-2-2) a lower alkoxy group, (1-2-3) a cycloalkyl group, (1-2-4) a halogen atom, (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, (1-2-6) a styryl group optionally substituted on the phenyl ring with one or more lower alkyl groups optionally substituted with one or more halogen atoms, (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms, (1-2-8) a benzyloxy group optionally substituted on the phenyl ring with one or more halogen atoms, (1-2-9) a phenylthio group optionally substituted with one or more members selected from the group consisting of a halogen atom; and a lower alkyl group optionally substituted with one or more halogen atoms, (1-2-10) an N-lower alkyl-N-phenyl amino group optionally substituted on the phenyl ring with one or more members selected from the group consisting of a halogen atom; and a lower alkyl group optionally substituted with one or more halogen atoms, and (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of the following (1-3-1) to (1-3-3):

(1-3-1) a lower alkyl group, (1-3-2) a cycloalkyl group, and (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms, (1-4) a thienyl group optionally substituted with one or more members selected from the group consisting of the following (1-4-1) to (1-4-5):

(1-4-1) a lower alkyl group optionally substituted with one or more halogen atoms, (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms, (1-4-3) a benzyl group optionally substituted on the phenyl ring with one or more halogen atoms, (1-4-4) a phenoxy group optionally substituted with one or more lower alkyl groups optionally substituted with one or more halogen atoms, and
(1-4-5) a styryl group optionally substituted on the phenyl ring with one or more lower alkyl groups optionally substituted with one or more halogen atoms, (1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms, (1-7) a pyridyl group optionally substituted with one or more members selected from the group consisting of the following (1-7-1) to (1-7-2):
  (1-7-1) a benzyloxy lower alkyl group optionally substituted on the phenyl ring with one or more lower alkyl groups optionally substituted with one or more halogen atoms, and
  (1-7-2) a phenyl group optionally substituted with one or more lower alkyl groups optionally substituted with one or more halogen atoms, (1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms, (1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms, (1-10) a benzofuryl group optionally substituted with one or more phenyl groups optionally substituted with one or more halogen atoms, (1-11) a benzothienyl group optionally substituted with one or more phenyl groups optionally substituted with one or more halogen atoms, (1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms, and
  (1-12-2) a benzyloxy group optionally substituted on the phenyl ring with one or more lower alkyl groups optionally substituted with one or more halogen atoms, and (1-13) a pyrimidinyl group optionally substituted with one or more members selected from the group consisting of the following (1-13-1) to (1-13-3):
  (1-13-1) a phenyl group,
  (1-13-2) a pyrrolidyl group, and
  (1-13-3) a piperidyl group.

In the above-mentioned embodiment, $R^1$ is more preferably one of the following (1-1) to (1-5):

(1-1) a phenyl group optionally substituted with one or more members selected from:
  (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
  (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
  (1-1-9) a halogen atom (preferably provided that the phenyl group of (1-1) is substituted with one or more halogen atoms, then the phenyl group of (1-1) is substituted with additional one or more substituents excluding a phenoxy group),
  (1-1-11) a phenyl group optionally substituted with one or more lower alkoxy groups optionally substituted with one or more halogen atoms,
  (1-1-12) a phenyl lower alkyl group optionally substituted on the phenyl ring with one or more halogen atoms,
  (1-1-13) a styryl group optionally substituted on the phenyl ring with one or more lower alkyl groups optionally substituted with one or more halogen atoms (preferably provided that when the styryl group is bonded to the p-position on the phenyl ring of (1-1), then the styryl group is substituted on the phenyl ring with one or more lower alkyl groups substituted with one or more halogen atoms),
  (1-1-16) a phenyl lower alkoxy group optionally substituted on the phenyl ring with one or more lower alkyl groups optionally substituted with one or more halogen atoms,
  (1-1-21) a pyridyl group optionally substituted with one or more lower alkyl groups optionally substituted with one or more halogen atoms,
  (1-1-23) a pyridyloxy lower alkyl group optionally substituted on the pyridine ring with one or more lower alkyl groups optionally substituted with one or more halogen atoms,
  (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
  (1-1-25) a pyrimidinyl group optionally substituted with one or more lower alkyl groups optionally substituted with one or more halogen atoms,
  (1-1-26) a pyrimidinylvinyl group optionally substituted on the pyrimidine ring with one or more lower alkyl groups optionally substituted with one or more halogen atoms,
  (1-1-31) a thienyl group, and (1-1-33) a benzo[1,3]dioxolyl group optionally substituted with one or more halogen atoms, (1-2) a thiazolyl group optionally substituted with one or more members selected from:
- (1-2-1) a lower alkyl group optionally substituted with one or more halogen atoms,
- (1-2-4) a halogen atom,
- (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
- (1-2-11) a pyridyl group optionally substituted with one or more lower alkyl groups optionally substituted with one or more halogen atoms, (1-3) an oxazolyl group optionally substituted with one or more members selected from:
- (1-3-1) a lower alkyl group,
- (1-3-2) a cycloalkyl group, and
- (1-3-3) a phenyl group optionally substituted with one or more members selected from the group consisting of a halogen atom; and a lower alkyl group optionally substituted with one or more halogen atoms, (1-4) a thienyl group optionally substituted with one or more members selected from:
- (1-4-2) a phenyl group optionally substituted with one or more lower alkyl groups optionally substituted with one or more halogen atoms, and (1-5) a furyl group optionally substituted with one or more members selected from:
- (1-5-1) a phenyl group optionally substituted with one or more halogen atoms.

In another embodiment, R is preferably one of the following (1-1) to (1-12):

(1-1) a phenyl group optionally substituted with one or more members selected from the group consisting of the following (1-1-1) to (1-1-34):
- (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
- (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom),
- (1-1-3) a lower alkoxy lower alkyl group,
- (1-1-4) a cycloalkyl group,
- (1-1-5) a cycloalkoxy group,
- (1-1-6) a cycloalkyl lower alkyl group,
- (1-1-7) a cycloalkyl lower alkoxy group,
- (1-1-8) a cycloalkyl lower alkoxy lower alkyl group,
- (1-1-9) a halogen atom (preferably provided that the phenyl group of (1-1) is substituted with one or more halogen atoms, then the phenyl group of (1-1) is substituted with additional one or more substituents excluding a phenoxy group),
- (1-1-10) a cyano group,
- (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
- (1-1-12) a phenyl lower alkyl group optionally substituted on the phenyl ring with one or more members selected from the group consisting of a halogen atom; and a lower alkyl group optionally substituted with one or more halogen atoms,
- (1-1-13) a styryl group optionally substituted on the phenyl ring with one or more members selected from the group consisting of a lower alkoxy group; a lower alkyl group optionally substituted with one or more halogen atoms; a cyano group; and halogen atoms (preferably provided that when the styryl group is bonded to the p-position on the phenyl ring of (1-1), then the styryl group is substituted on the phenyl ring with one or more members selected from the group consisting of a lower alkyl group substituted with one or more halogen atoms; and a fluoro atom),
- (1-1-14) a phenoxy group optionally substituted with one or more lower alkyl groups optionally substituted with one or more halogen atoms (preferably provided that the phenyl group of (1-1) is substituted with one or more phenoxy groups, then the phenyl group of (1-1) is substituted with additional one or more substituents excluding a halogen atom),
- (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
- (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
- (1-1-17) a phenylthio group optionally substituted with one or more halogen atoms,
- (1-1-18) a benzylthio lower alkyl group optionally substituted on the phenyl ring with one or more lower alkoxy groups optionally substituted with one or more halogen atoms,
- (1-1-19) an N-lower alkyl-N-phenyl amino lower alkyl group optionally substituted on the phenyl ring with one or more halogen atoms,
- (1-1-20) an N-benzyl-N-lower alkyl amino group optionally substituted on the phenyl ring with one or more lower alkyl groups optionally substituted with one or more halogen atoms,
- (1-1-21) a pyridyl group optionally substituted with one or more lower alkyl groups optionally substituted with one or more halogen atoms,
- (1-1-22) a pyridyl lower alkyl group optionally substituted on the pyridine ring with one or more lower alkyl groups optionally substituted with one or more halogen atoms,
- (1-1-23) a pyridyloxy lower alkyl group optionally substituted on the pyridine ring with one or more lower alkyl groups optionally substituted with one or more halogen atoms,
- (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a 2,2-difluorobenzo[1,3]dioxolyl group, and
(1-1-34) an indolinyl lower alkyl group,
(1-2) a thiazolyl group optionally substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group optionally substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more lower alkyl groups optionally substituted with one or more halogen atoms,
(1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a benzyl group optionally substituted on the phenyl ring with one or more lower alkyl groups optionally substituted with one or more halogen atoms,
(1-7) a pyridyl group optionally substituted with one or more members selected from the group consisting of the following (1-7-1) to (1-7-2):
  (1-7-1) a benzyloxy lower alkyl group optionally substituted on the phenyl ring with one or more lower alkyl groups optionally substituted with one or more halogen atoms, and
  (1-7-2) a phenyl group optionally substituted with one or more lower alkyl groups optionally substituted with one or more halogen atoms,
(1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms,
(1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms, (1-10) a benzofuryl group optionally substituted with one or more phenyl groups optionally substituted with one or more halogen atoms, (1-11) a benzothienyl group optionally substituted with one or more phenyl groups optionally substituted with one or more halogen atoms, and (1-12) a phenyl lower alkyl group optionally substituted on the phenyl ring with one or more members selected from the group consisting of the following (1-12-1) to (1-12-2):

(1-12-1) a phenyl group optionally substituted with one or more lower alkyl groups optionally substituted with one or more halogen atoms; and (1-12-2) a benzyloxy group optionally substituted on the phenyl ring with one or more lower alkyl groups optionally substituted with one or more halogen atoms.

In another embodiment, $R^1$ is preferably one of the following (1-1) to (1-6), (1-9) and (1-12):

(1-1) a phenyl group optionally substituted with one or more members selected from the group consisting of (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents), (1-1-2) a lower alkoxy group optionally substituted with one or more halogen atoms (preferably provided that the phenyl group of (1-1) is substituted with one or more lower alkoxy groups, then the phenyl group of (1-1) is substituted with additional one or more substituents excluding a lower alkoxy group and a halogen atom), (1-1-9) a halogen atom (preferably provided that the phenyl group of (1-1) is substituted with one or more halogen atoms, then the phenyl group of (1-1) is substituted with additional one or more substituents excluding a phenoxy group), (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms, (1-1-12) a phenyl lower alkyl group (preferably benzyl, 2-phenylethyl) optionally substituted on the phenyl ring with one or more members selected from the group consisting of a halogen atom; and a lower alkyl group optionally substituted with one or more halogen atoms, (1-1-13) a styryl group optionally substituted on the phenyl ring with one or more members selected from the group consisting of a lower alkyl group optionally substituted with one or more halogen atoms; and a cyano group (preferably provided that when the styryl group is bonded to the p-position on the phenyl ring of (1-1), then the styryl group is substituted on the phenyl ring with one or more lower alkyl groups substituted with one or more halogen atoms), (1-1-14) a phenoxy group (preferably provided that the phenyl group of (1-1) is substituted with one or more phenoxy groups, then the phenyl group of (1-1) is substituted with additional one or more substituents excluding a halogen atom), (1-1-16) a phenyl lower alkoxy group (preferably benzyloxy) optionally substituted on the phenyl ring with one or more lower alkyl groups optionally substituted with one or more halogen atoms, (1-1-19) an N-lower alkyl-N-phenyl amino lower alkyl group optionally substituted on the phenyl ring with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms), (1-1-25) a pyrimidinyl group optionally substituted with one or more lower alkyl groups optionally substituted with one or more halogen atoms, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more lower alkyl groups optionally substituted with one or more halogen atoms, (1-1-31) a thienyl group, and (1-1-33) a 2,2-difluorobenzo[1,3]dioxolyl group, (1-2) a thiazolyl group optionally substituted with one or more members selected from the group consisting of (1-2-1) a lower alkyl group, (1-2-4) a halogen atom, (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of (1-3-1) a lower alkyl group, (1-3-2) a cycloalkyl group, and (1-3-3) a phenyl group optionally substituted with one or more members selected from the group consisting of a halogen atom; and a lower alkyl group optionally substituted with one or more halogen atoms, (1-4) a thienyl group optionally substituted with one or more members selected from the group consisting of (1-4-2) a phenyl group optionally substituted with one or more lower alkyl groups optionally substituted with one or more halogen atoms, (1-5) a furyl group optionally substituted with one or more members selected from the group consisting of (1-5-1) a phenyl group optionally substituted with one or more halogen atoms, (1-6) a pyrrolyl group optionally substituted with one or more members selected from the group consisting of (1-6-1) a lower alkyl group, and (1-6-2) a phenyl group optionally substituted with one or more members selected from the group consisting of a halogen atom; and a lower alkyl group optionally substituted with one or more halogen atoms,
(1-9) an indolyl group optionally substituted with one or more members selected from the group consisting of
  (1-9-1) a lower alkyl group optionally substituted with one or more halogen atoms, and
(1-12) a phenyl lower alkyl group optionally substituted on the phenyl ring with one or more members selected from the group consisting of
  (1-12-2) a benzyloxy group optionally substituted on the phenyl ring with one or more lower alkyl groups optionally substituted with one or more halogen atoms.
In another embodiment, $R^1$ is preferably one of the following (1-1) to (1-3):
(1-1) a phenyl group optionally substituted with one or more members selected from the group consisting of
  (1-1-1) a lower alkyl group optionally substituted with one or more halogen atoms (preferably provided that the phenyl group of (1-1) is substituted with one or more lower alkyl groups, then the phenyl group of (1-1) is substituted with additional one or more substituents),
  (1-1-2) a lower alkoxy group (preferably provided that the phenyl group of (1-1) is substituted with one or more lower alkoxy groups, then the phenyl group of (1-1) is substituted with additional one or more substituents excluding a lower alkoxy group and a halogen atom),
  (1-1-9) a halogen atom (preferably provided that the phenyl group of (1-1) is substituted with one or more halogen atoms, then the phenyl group of (1-1) is substituted with additional one or more substituents excluding a phenoxy group),
  (1-1-11) a phenyl group optionally substituted with one or more lower alkoxy groups optionally substituted with one or more halogen atoms,
  (1-1-13) a styryl group optionally substituted on the phenyl ring with one or more lower alkyl groups optionally substituted with one or more halogen atoms (preferably provided that when the styryl group is bonded to the p-position on the phenyl ring of (1-1), then the styryl group is substituted on the phenyl ring with one or more lower alkyl groups substituted with one or more halogen atoms),
  (1-1-16) a phenyl lower alkoxy group optionally substituted on the phenyl ring with one or more lower alkyl groups optionally substituted with one or more halogen atoms,
  (1-1-21) a pyridyl group optionally substituted with one or more lower alkyl groups optionally substituted with one or more halogen atoms,
  (1-1-23) a pyridyloxy lower alkyl group optionally substituted on the pyridine ring with one or more lower alkyl groups optionally substituted with one or more halogen atoms,
  (1-1-24) a pyridylvinyl group optionally substituted on the pyridine ring with one or more lower alkyl groups optionally substituted with one or more halogen atoms (preferably a pyridylvinyl group substituted on the pyridine ring with one or more lower alkyl groups optionally substituted with one or more halogen atoms),
  (1-1-25) a pyrimidinyl group optionally substituted with one or more lower alkyl groups optionally substituted with one or more halogen atoms,
  (1-1-26) a pyrimidinylvinyl group optionally substituted on the pyrimidine ring with one or more lower alkyl groups optionally substituted with one or more halogen atoms, and
  (1-1-33) a 2,2-difluorobenzo[1,3]dioxolyl group,
(1-2) a thiazolyl group optionally substituted with one or more members selected from the group consisting of
  (1-2-1) a lower alkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
  (1-2-11) a pyridyl group optionally substituted with one or more lower alkyl groups optionally substituted with one or more halogen atoms, and
(1-3) an oxazolyl group optionally substituted with one or more members selected from the group consisting of
  (1-3-1) a lower alkyl group,
  (1-3-2) a cycloalkyl group, and
  (1-3-3) a phenyl group optionally substituted with one or more members selected from the group consisting of a halogen atom; and a lower alkyl group optionally substituted with one or more halogen atoms.
$R^2$ is preferably one of the following (2-1) to (2-4):
(2-1) a lower alkyl group optionally substituted with one or more members selected from the group consisting of a hydroxy group; and a phenyl group optionally substituted with one or more lower alkyl groups optionally substituted with one or more halogen atoms,
(2-2) a 2-oxo-1,3-dioxolanyl group, and
(2-3) a group represented by the formula:

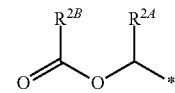

wherein
* is a bonding site;
$R^{2A}$ is one of the following (2A-1) to (2A-2):
  (2A-1) a hydrogen atom, and
  (2A-2) a lower alkyl group; and
$R^{2B}$ is one of the following (2B-1) to (2B-6):
  (2B-1) a lower alkoxy group optionally substituted with one or more members selected from the group consisting of a lower alkoxy group; a carboxy group; a lower alkoxycarbonyl group; a hydroxy group; a phenyl lower alkoxycarbonyl group; a lower alkenyloxy-carbonyl group; a morpholinyl group; a benzyloxycarbonyl group; and a tetrahydropyran-2-yloxy group,
  (2B-2) a lower alkyl group;
  (2B-3) a lower alkylamino group optionally substituted with one or more lower alkoxy-carbonyl groups;
  (2B-4) a cycloalkyl group;
  (2B-5) a cycloalkoxy group; and
  (2B-6) a phenyl group,
(2-4) a hydrogen atom.
$R^2$ is more preferably one of the following groups:
a hydrogen atom;
a 1-(((2-carboxy-2,2-dimethylethoxy)carbonyl)oxy)ethyl group;
a 1-(((2-carboxy-1,1-dimethylethoxy)carbonyl)oxy)ethyl group;

a 1-(((2-hydroxyethoxy)carbonyl)oxy)ethyl group;
a 1-(butyryloxy)ethyl group;
a 1-(isobutyryloxy)ethyl group;
an acetoxymethyl group; and
a butyryloxymethyl group.

In another embodiment, $R^2$ is preferably
a hydrogen atom, or
a group represented by the formula:

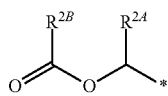

wherein
* is a bonding site;
$R^{2A}$ is one of the following (2A-1) to (2A-2):
(2A-1) a hydrogen atom, and
(2A-2) a lower alkyl group; and
$R^{2B}$ is one of the following (2B-1) to (2B-2):
(2B-1) a lower alkoxy group optionally substituted with one or more members selected from the group consisting of a carboxy group; a lower alkoxy-carbonyl group; a hydroxy group; a phenyl lower alkoxy-carbonyl group; a lower alkenyloxy-carbonyl group; and a tetrahydropyran-2-yloxy group, and
(2B-2) a lower alkyl group.

Compound (1) excludes the following compounds:
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
methyl 4-[4-(4-cyano-1,2,3-triazol-5-yl)styryl]benzoate;
5-[4-(4-cyanostyryl)phenyl]-1,2,3-triazole-4-carbonitrile;
5-{4-[4-(N,N-dimethylamino)styryl]phenyl}-1,2,3-triazole-4-carbonitrile;
5-{4-[2-(biphenyl-4-yl)vinyl]phenyl}-1,2,3-triazole-4-carbonitrile;
5-{4-[4-(2-oxo-2H-chromen-3-yl)styryl]phenyl}-1,2,3-triazole-4-carbonitrile;
5-{4-[4-(benzo[d]oxazol-2-yl)styryl]phenyl}-1,2,3-triazole-4-carbonitrile;
5-{4-[2-(2-methoxynaphthalen-1-yl)vinyl]phenyl}-1,2,3-triazole-4-carbonitrile;
5-{4-[2-(4-methoxynaphthalen-1-yl)vinyl]phenyl}-1,2,3-triazole-4-carbonitrile;
5-{4-[2-(pyridin-4-yl)vinyl]phenyl}-1,2,3-triazole-4-carbonitrile;
5-{4-[2-(thiophen-2-yl)vinyl]phenyl}-1,2,3-triazole-4-carbonitrile;
5-{4-[2-(benzofuran-2-yl)vinyl]phenyl}-1,2,3-triazole-4-carbonitrile;
5-[4-(4-formylstyryl)phenyl]-1,2,3-triazole-4-carbonitrile;
5-{4-[2-(4'-formylbiphenyl-4-yl)vinyl]phenyl}-1,2,3-triazole-4-carbonitrile;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(3-fluoro-4-phenoxyphenyl)-5-cyano-1,2,3-triazole;
4-(4-fluoro-3-phenoxyphenyl)-5-cyano-1,2,3-triazole;
4-(4-fluoro-3-methoxyphenyl)-1,2,3-triazole-5-carbonitrile;
(5-(5-cyano-1,2,3-triazol-4-yl)furan-2-yl)methyl acetate;
2-[4-(4'-benzoxazole-2-yl-stilbene-4-yl)-5-cyano-1,2,3-triazole-N-yl]acetic acid methyl ester;
4-(4-(4-(1H-benzo[d]imidazol-2-yl)styryl)phenyl)-N-trityl-1,2,3-triazole-5-carbonitrile;
2-(4-(4-(4-(1H-benzo[d]imidazol-2-yl)styryl)phenyl)-5-cyano-1,2,3-triazol-N-yl)acetamide;
2-(4-(4-(4-(1H-benzo[d]imidazol-2-yl)styryl)phenyl)-5-cyano-1,2,3-triazol-N-yl)acetic acid;
4-(4-(4-(1H-benzo[d]imidazol-2-yl)styryl)phenyl)-N-(2-oxo-2-phenylethyl)-1,2,3-triazole-5-carbonitrile; and
4-(4'-benzoxazole-2-yl-stilbene-4-yl)-5-cyano-N-acetamide-1,2,3-triazole;
and salts thereof.

Compound (1) is preferably Compound (1aa) or Compound (1bb).

Compound (1aa) excludes the following compounds:
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
5-{4-[2-(thiophen-2-yl)vinyl]phenyl}-1,2,3-triazole-4-carbonitrile;
5-{4-[2-(benzofuran-2-yl)vinyl]phenyl}-1,2,3-triazole-4-carbonitrile;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole; and
4-(4-fluoro-3-phenoxyphenyl)-5-cyano-1,2,3-triazole;
4-(2-fluorophenyl)-1,2,3-triazole-5-carbonitrile; and
4-(4-fluoro-3-methoxyphenyl)-1,2,3-triazole-5-carbonitrile;
and salts thereof.

Table 1 lists abbreviations, symbols and terms used in the preparations, Reference Examples, Examples, and Formulae in the above and subsequent descriptions of the present specification (including the tables) have the following meanings.

TABLE 1

| List of Abbreviation | |
|---|---|
| Abbreviation | Description |
| AcOEt | ethyl acetate |
| AcOK | potassium acetate |
| AcOH | acetic acid |
| BF₃ | boron trifluoride |
| BINAP | 2,2'-bis(diphenylphosphino)-1,1'-binaphthyl |
| DEAD | diethyl azodicarboxylate |
| DMF | N,N-dimethylformamide |
| DIPEA | N,N-diisopropylethylamine |
| DMA | dimethylacetamide |
| DME | 1,2-dimethoxyethane |

TABLE 1-continued

List of Abbreviation

| Abbreviation | Description |
|---|---|
| DMSO | dimethyl sulfoxide |
| Et$_2$O | diethyl ether |
| Et$_3$N | triethylamine |
| EtOH | ethyl alcohol |
| IBX | 2-iodoxybenzoic acid |
| MeOH | methyl alcohol |
| MsCl | methanesulfonyl chloride |
| MeI | iodomethane |
| n-BuLi | n-butyllithium |
| NBS | N-bromosuccinimide |
| NCS | N-chlorosuccinimide |
| NMP | N-methylpyrrolidone |
| Pd(OAc)$_2$ | palladium(II) acetate |
| Pd(PPh$_3$)$_4$ | tetrakis(triphenylphosphine)palladium(0) |
| Pd/C | palladium on carbon |
| PPh$_3$ | triphenylphosphine |
| SO$_3$Py | sulfur trioxide pyridine complex |
| TBME | tert-butyl methyl ether |
| TFA | trifluoroacetic acid |
| THF | tetrahydrofuran |
| tert-BuONa | sodium tert-butoxide |
| Ref. Ex. No. | Reference Example Number |
| Ex. No. | Example Number |
| STR | structure |
| m. p. | melting point |
| MS(M + H) | Mass spectrum data |

Compound (1) can be produced according to, for example, Reaction Schemes 1 to 7. However these reaction schemes are given for just example, and those skilled in the art will readily understand that these reaction schemes are not limited to the disclosed embodiment and that known variations and modifications can be used for these reaction schemes without departing from the scope and spirit of the present invention. All the starting materials and target compounds shown in Reaction Schemes 1 to 7 may be in the form of suitable salts. Examples of such salts are as described for Compound (1) below.

Compound (1a), which is Compound (1) wherein R$^2$ is a hydrogen atom, can be produced according to the following Reaction Scheme 1.

Reaction Scheme 1

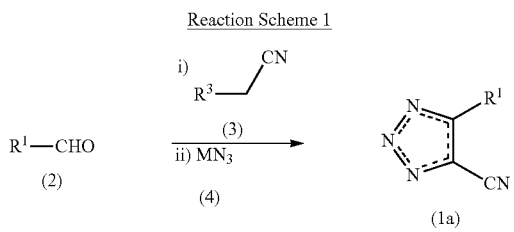

wherein R$^1$ is as defined above; R$^3$ is benzenesulfonyl nitro, etc; and MN$_3$ is sodium azide, lithium azide, potassium azide, trimethylsilyl azide, etc.

Compound (1a) can be produced by subjecting Compound (2) and Compound (3) to the Knoevenagel condensation in a suitable solvent, in the presence of a catalyst, and then subjecting the resulting compound to 1,3-dipolar addition with Compound (4), or by reacting Compound (2), Compound (3) and Compound (4) in a suitable solvent without catalyst.

Examples of the solvent include water, methanol, ethanol, N,N-dimethylformamide, N-methylpyrrolidone, acetonitrile, acetone, ethyl acetate, diethyl ether, tetrahydrofuran, hexane, benzene, toluene, mixed solvents thereof, etc.

Examples of the catalyst include piperidine, pyridine, acetic acid, benzoic acid, p-toluene sulfonic acid, sodium hydroxide, aluminum oxide, potassium fluoride, potassium acetate, N-benzyl-N, N,N-triethylammnonium chloride, tetrabutylammonium fluoride, mixed catalysts thereof, etc.

Compound (3) is usually used in an amount of at least about 1 mol, preferably about 1 to 2 mol, per 1 mol of Compound (2).

Compound (4) is usually used in an amount of at least 1 mol, preferably about 1 to 2 mol, per 1 mol of Compound (2).

The catalyst is usually used in an amount of about 0.1 to 2 mol, preferably about 0.5 to 1 mol, per 1 mol of Compound (2).

The reaction is usually carried out at about room temperature to 150° C., preferably about 80 to 110° C. The reaction is usually finished in about 1 to 12 hours.

Compound (1b), which is Compound (1) wherein R$^2$ is not a hydrogen atom, can be produced according to the following Reaction Scheme 2.

Reaction Scheme 2

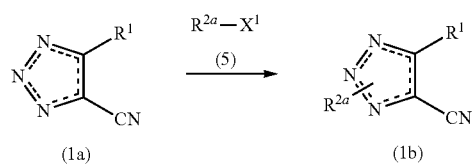

wherein R$^1$ is as defined above; R$^{2a}$ is a lower alkyl group or a heterocyclyl group, each of which is optionally substituted; and X$^1$ is a leaving group.

Examples of the leaving group for X$^1$ include a halogen atom, a lower alkanesulfonyloxy group optionally substituted with one or more halogen atoms (e.g., methanesulfonyloxy, trifluoromethanesulfonyloxy), an arenesulfonyloxy group (e.g., benzenesulfonyloxy) and the like, in which preferred is a halogen atom.

Compound (1b) can be produced by reacting Compound (1a) with Compound (5) in a suitable solvent, in the presence of a base.

Examples of the solvent include N,N-dimethylformamide, N-methylpyrrolidone, acetonitrile, acetone, ethyl acetate, diethyl ether, tetrahydrofuran, hexane, benzene, toluene, mixed solvents thereof, etc.

Examples of the base include sodium carbonate, sodium bicarbonate, sodium hydride, potassium tert-butoxide, triethylamine, diisopropylethylamine, 4-dimethylaminopyridine, etc.

Compound (5) is usually used in an amount of at least about 1 mol, preferably about 1 to 2 mol, per 1 mol of Compound (1a).

The base is usually used in an amount of at least about 1 mol, preferably about 1 to 2 mol, per 1 mol of Compound (1a).

The reaction is usually carried out at about room temperature to 150° C., preferably about 40 to 100° C. The reaction is usually finished in about 1 to 24 hours.

When R$^{2a}$ has carboxy group(s) and/or hydroxy group(s), a protecting group generally used in peptide chemistry and the like may be introduced into these groups. After the reaction, the objective compound can be obtained by removing the protecting group according to a method known per se.

Examples of the carboxy-protecting group include a benzyl group, an allyl group, a tert-butyl group, etc.

Examples of the hydroxy-protecting group include a tetrahydropyran-2-yl group, etc.

Compound (2) can be produced according to one of the following non-limiting Reaction Schemes 3 to 7, or the like.

Reaction Scheme 3

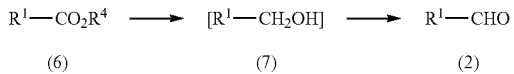

wherein $R^1$ is as defined above; and $R^4$ is a hydrogen atom, an alkyl group, an aryl group or an acyl group.

The reaction for producing Compound (2) or Compound (7) from Compound (6) can be carried out in a suitable solvent, in the presence of a suitable reducing agent.

Examples of the solvent include diethyl ether, dimethoxyethane, dioxane, methanol, ethanol, tetrahydrofuran, hexane, toluene, dichloromethane, 1,2-dichloroethane, mixed solvents thereof, etc.

Examples of the reducing agent include hydride reducing agents such as borane, sodium borohydride, lithium aluminium hydride, diisobutylaluminum (hydride, sodium bis(2-methoxyethoxy)aluminum hydride, etc.

The reducing agent is usually used in an amount of at least 0.25 to 10 mol, preferably about 1 to 5 mol, per 1 mol of Compound (6).

The reaction is usually carried out at about −78 to 100° C., preferably about −78 to 70° C. The reaction is usually finished in about 1 to about 12 hours.

The reaction for producing Compound (2) from Compound (7) can be carried out in a suitable solvent, in the presence of an oxidizing agent.

Examples of the solvent include N,N-dimethylformamide, dimethyl sulfoxide, ethyl acetate, dioxane, acetonitrile, acetone, dichloromethane, 1,2-dichloroethane, chloroform, mixed solvents thereof, etc.

Examples of the oxidizing agent include pyridinium dichlorochlomate, mangange(IV) oxide, 2,2,6,6-tetramethylpiperidine 1 oxyl (TEMPO)—oxidizing agents (sodium hypochlorite—potassium bromide, bromine, iodine, sodium nitrite, oxygen, etc.), 2-iodoxybenzoic acid, Dess-Martin reagent, dimethylsulfoxide (Swern oxidation, etc.), etc.

The oxidizing agent is usually used in an amount of at least 1 mol, preferably about 1 to 2 mol, per 1 mol of Compound (7).

The reaction is usually carried out at about −100 to 100° C./preferably about −80 to 70° C. The reaction is usually finished in about 1 to about 12 hours.

Reaction Scheme 4

wherein $R^1$ is as defined above; and $X^2$ is a halogen atom.

The reaction for producing Compound (2) from Compound (8) can be carried out by subjecting Compound (8) to a formylation reaction.

This formylation reaction can be carried out in a suitable solvent, in the presence of an organometal reagent and a formylating reagent.

Examples of the solvent include diethyl ether, tetrahydrofuran, toluene, hexane, pentane, mixed solvents thereof, etc.

Examples of the organometal reagent include organolithium reagents (n-butyllithium, etc), organo magnesium reagents (ethymagnesium bromide, isopropylmagnesium chloride, etc.), etc.

Examples of the formylating reagent include N,N-dimethylformamide, 1-formylpiperidine, 4-formylmorpholine, etc.

The organometal reagent is usually used in an amount of 1 mol per 1 mol of Compound (8).

The formylating reagent is usually used in an amount of at least 1 mol, preferably about 5 to 20 mol, per 1 mol of Compound (8).

The reaction is usually carried out at about −150 to 0° C., preferably about −90 to −40° C. The reaction is usually finished in about 1 to about 6 hours.

Reaction Scheme 5

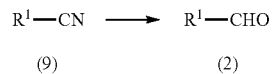

wherein $R^1$ is as defined above.

The reaction for producing Compound (2) from Compound (9) can be carried out in a suitable solvent, in the presence of a catalytic hydrogenation reducing agent.

Examples of the solvent include tetrahydrofuran, acetic acid, formic acid, water, mixed solvents thereof, etc.

Examples of the catalytic hydrogenation reducing agent include Raney nickel, etc.

The catalytic hydrogenation reducing agent is usually used in an amount of 0.3 to 5 mol per 1 mol of Compound (9).

The reaction is usually carried out at about 60 to 150° C., preferably about 90 to 110° C. The reaction is usually finished in about 1 to about 5 hours.

The reaction for producing Compound (2) from Compound (9) can also be carried out in a suitable solvent in the presence of a reducing agent.

Examples of solvent include tetrahydrofuran, toluene, dichloromethane, 1,2-dichloroethane, mixed solvents thereof, etc.

Examples of the reducing agent include diisobutylaluminium hydride, etc.

The reducing agent is usually used in an amount of at least 0.25 mol to 5 mol, preferably about 0.25 to 2 mol, per 1 mol of Compound (9).

The reaction is usually carried out at about −150 to 0° C., preferably about −90 to −40° C. The reaction is usually finished in about 1 to about 5 hours.

Reaction Scheme 6

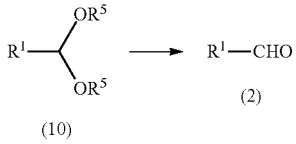

wherein $R^1$ is as defined above; and $R^5$ is a lower alkyl group.

The reaction for producing Compound (2) from Compound (10) can be carried out in a suitable solvent, in the presence of an acid.

Examples of the solvent include water, diethyl ether, dioxane, tetrahydrofuran, acetonitrile, ethyl acetate, acetone, N,N-dimethylformamide, methanol, ethanol, dichloromethane, toluene, etc.

Examples of the acid include inorganic acids such as hydrochloric acid, sulfuric acid, acetic acid, methanesulfonic acid, p-toluenesulfonic acid, trifluoroacetic acid, hydrochloric acid, etc.

The acid is usually used in an amount of 0.1 to 100 mol, preferably about 1 to 30 mol, per 1 mol of Compound (10).

The reaction is usually carried out at about 0 to 100° C. The reaction is usually finished in about 0.5 to about 12 hours.

Reaction Scheme 7

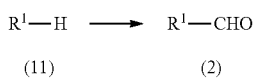

(11)    (2)

wherein $R^1$ is as defined above.

Compound (2) can be produced by subjecting Compound (11) to the Vilsmeier-Haack reaction in a suitable solvent, in the presence of the Vilsmeier reagent produced by a N,N-dimethylformamide and phosphorus oxychloride, etc.

Examples of the solvent include dichloromethane, chloroform, tetrachloromethane, 1,2-dichloroethane, N,N-dimethylformamide, toluene, etc.

The Vilsmeier reagent is usually used in an amount of 1-5 mol, preferably about 1 to 2 mol, per 1 mol of Compound (11).

The reaction is usually carried out at about 0 to 100° C. The reaction is usually finished in about 0.5 to about 12 hours.

Compound (1), intermediate compounds therefor and starting compounds therefor can be produced according to the above-mentioned reaction schemes. They can also be produced according to the synthesis methods described in the Reference Examples and Examples of the present specification and in consideration of the techniques known at the time of filing of the present application or known techniques.

The starting compounds and intermediate compounds shown in the above-mentioned reaction schemes can be subjected, where necessary before being applied to reactions, to protection of a functional group with a suitable protecting group by a known method, and to deprotection of the protecting group by a known method after completion of the reaction.

In addition, compounds in the form in which a solvate (for example, hydrate, ethanolate, etc.) was added to the starting material compounds and object compounds shown in each of the reaction formula are included in each of the formula.

Compound (1) encompasses isomers such as optical isomers, stereoisomers, positional isomers, rotational isomers and the like.

Compound (1) encompasses the following compounds: a compound represented by the formula (1A):

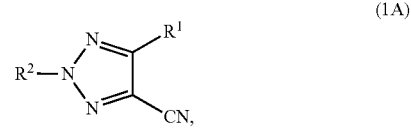

a compound represented by the formula (1B):

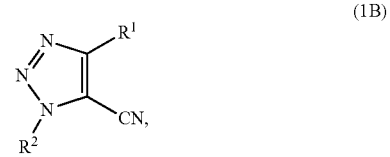

and a compound represented by the formula (1C):

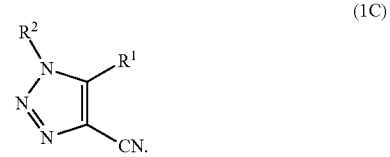

That is, Compound (1) encompasses 2H-[1,2,3]triazole-4-carbonitrile compound (2H-[1,2,3]triazole-5-carbonitrile compound) (Compound (1A)), 3H-[1,2,3]triazole-4-carbonitrile compound (1H-[1,2,3]triazole-5-carbonitrile compound) (Compound (1B)) and 1H-[1,2,3]triazole-4-carbonitrile compound (3H-[1,2,3]triazole-5-carbonitrile compound) (Compound (1C)).

When $R^2$ is not a hydrogen atom, Compound (1A) is preferable from among Compound (1).

The starting material compounds and object compounds shown in the above-mentioned reaction schemes can be used in an appropriate salt form.

Each of the object compounds obtained according to the above-mentioned reaction schemes can be isolated and purified from the reaction mixture by, for example, after cooling the reaction mixture, performing an isolation procedure such as filtration, concentration, extraction, etc., to separate a crude reaction product, and then subjecting the crude reaction product to a general purification procedure such as column chromatography, recrystallization, etc.

Among Compound (1), those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, AcOH, citric acid, tartaric acid, maleic acid, fumaric acid, malic acid, lactic acid and other organic acids, etc.

Among Compound (1), those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In Compound (1), one or more atoms can be substituted with one or more isotopic atoms. Examples of the isotopic atoms include deuterium ($^2H$), tritium ($^3H$), $^{13}C$, $^{14}N$, $^{18}O$, etc.

The following is an explanation of pharmaceutical preparations comprising Compound (1) as an active ingredient. Such pharmaceutical preparations are obtained by formulating Compound (1) into general pharmaceutical preparations, using typically employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, EtOH, propanol, simple syrup, glucose solutions, starch solutions, gelatin solutions, carboxymethyl cellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium lauryl sulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with general coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, EtOH and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, EtOH, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain general solubilizers, buffers, analgesic agents, etc., and further, if necessary, coloring agents, preservatives, flavors, sweetening agents, etc., and/or other medicines.

The proportion of Compound (1) in the pharmaceutical preparation is not limited and can be suitably selected from a wide range. It is typically preferable that the pharmaceutical preparation contain Compound (1) in a proportion of 1 to 70 wt %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally.

Injections are intravenously administered singly or as mixed with general injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is typically about 0.001 to about 100 mg/kg body weight/day, preferably 0.001 to 50 mg/kg body weight/day, in single or divided doses.

Hydrophobic penetrating cations, e.g. triphenylphosphonium derivatives and rodamine 123 derivatives, are known as carriers which lead various molecules toward mitochondria (non-patent documents: Trends Biotechnol 15, 326-330; PLoS One 8, e61902). Because the citric cycle exists within the mitochondria, the citric acid cycle activators are likely to be more potent by means of binding covalently to the hydrophobic penetrating cation or mixing with it.

EXAMPLES

Working examples of compounds used in the invention are shown below, being followed by the Pharmacological Test results of these compounds.

The following compounds of Reference Examples and Examples are shown as one tautomer, which are not limited, and the other two tautomers are also encompassed therein. For example, the compound of Example 1 encompasses the three tautomers:

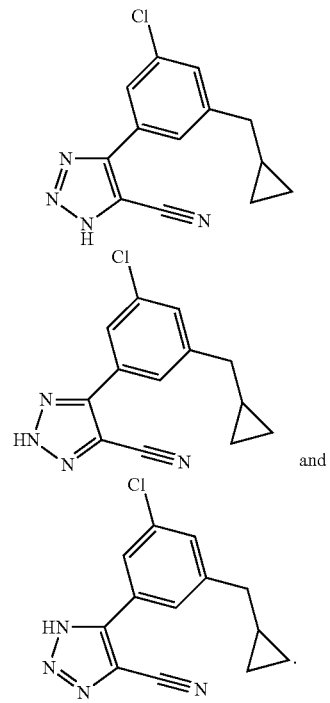

Reference Example 1

Synthesis of 3-bromo-2-oxo-pentanoic Acid methyl ester

To a suspension of copper(II) bromide (13.12 g, 58.7 mmol) in AcOEt (80 ml) was added 2-oxo-pentanoic acid methyl ester (2.55 g, 19.6 mmol) in chloroform (40 mil). The reaction mixture was refluxed for 8 hr. After cooling to room temperature, the reaction mixture was filtered through a pad of Celite. The filtrate was concentrated. The residue was purified by silica gel column chromatography (hexane/AcOEt=1/0 to 3/1) to give the title compound (3.30 g, 81%) as a colorless oil $^1$H-NMR (CDCl$_3$) δ: 1.08 (3H, t, J=7.3 Hz), 1.95-2.20 (2H, m), 3.93 (3H, s), 4.98 (1H, dd, J=6.2, 8.1 Hz).

Reference Example 2

Synthesis of 2-(6-trifluoromethyl-pyridin-2-yl)-thiazole-4-carboxylic Acid ethyl ester To a solution of 6-trifluoromethyl-pyridine-2-carbothioic acid amide (884 mg, 4.29 mmol) in EtOH (10 ml) was added ethyl bromopyruvate (0.656 ml, 5.23 mmol), and the reaction mixture was reflux for 4 hr. The reaction mixture was concentrated. The residue was purified by silica gel column chromatography (hexane/AcOEt=9/1 to 2/1) to give the title compound (1.13 g, 88%) as a pale yellow solid.

$^1$H-NMR (CDCl$_3$) δ: 1.44 (3H, t, J=7.1 Hz), 4.47 (2H, q, J=7.1 Hz), 7.73 (1H, d, J=7.9 Hz), 8.01 (1H, t, J=7.9 Hz), 8.31 (1H, s), 8.52 (1H, d, J=7.9 Hz).

Reference Example 3

Synthesis of 2-hexyl-thiazole-4-carboxylic Acid ethyl ester

The title compound was obtained using heptanethioic acid amide and ethyl bromopyruvate in the same manner as in Reference Example 2.

$^1$H-NMR (CDCl$_3$) δ: 0.86-0.91 (3H, m), 1.26-1.46 (9H, m), 1.75-1.85 (2H, m), 3.06 (2H, t, J=7.8 Hz), 4.42 (2H, q, J=7.1 Hz), 8.05 (1H, s).

Reference Example 4

Synthesis of 5-ethyl-2-(5-trifluoromethyl-pyridin-2-yl)-thiazole-4-carboxylic Acid methyl ester The title compound was obtained using 5-trifluoromethyl-pyridine-2-carbothioic acid amide and 3-bromo-2-oxo-pentanoic acid methyl ester in the same manner as in Reference Example 2.

$^1$H-NMR (CDCl$_3$) δ: 1.42 (3H, t, J=7.5 Hz), 3.34 (2H, q, J=7.5 Hz), 3.99 (3H, s), 8.03 (1H, dd, J=1.9, 8.4 Hz), 8.38 (1H, d, J=8.4 Hz), 8.84 (1H, d, J=1.9 Hz).

Reference Example 5

Synthesis of 5-ethyl-2-(3-trifluoromethyl-phenyl)-thiazole-4-carboxylic Acid methyl ester The title compound was obtained using 3-trifluoromethyl-thiobenzamide and 3-bromo-2-oxo-pentanoic acid methyl ester in the same manner as in Reference Example 2.

$^1$H-NMR (CDCl$_3$) δ: 1.40 (3H, t, J=7.5 Hz), 3.33 (2H, q, J=7.5 Hz), 3.98 (3H, s), 7.57 (1H, t, J=7.8 Hz), 7.68 (1H, d, J=7.8 Hz), 8.11 (1H, d, J=7.8 Hz), 8.19 (1H, s).

Reference Example 6

Synthesis of 5-ethyl-2-(6-trifluoromethyl-pyridin-3-yl)-thiazole-4-carboxylic Acid methyl ester The title compound was obtained using 6-trifluoromethyl-thionicotinamide and 3-bromo-2-oxo-pentanoic acid methyl ester in the same manner as in Reference Example 2.

$^1$H-NMR (CDCl$_3$) δ: 1.42 (3H, t, J=7.5 Hz), 3.35 (2H, q, J=7.5 Hz), 3.99 (3H, s), 7.77 (1H, dd, J=0.4, 8.2 Hz), 8.45-8.48 (1H, m), 9.19 (1H, d, J=2.0 Hz).

Reference Example 7

Synthesis of 5-methy-2-(5-trifluoromethyl-pyridin-2-yl)-thiazole-4-carboxylic Acid methyl ester The title compound was obtained using 5-trifluoromethyl-pyridine-2-carbothioic acid amide and 3-bromo-2-oxo-butyric acid methyl ester in the same manner as in Reference Example 2.

$^1$H-NMR (CDCl$_3$) δ: 2.86 (3H, s), 3.99 (3H, s), 8.03 (1H, dd, J=1.7, 8.3 Hz), 8.37 (1H, d, J=8.3 Hz), 8.84-8.85 (1H, m).

Reference Example 8

Synthesis of 2-(5-chloro-pyridin-2-yl)-5-methyl-thiazole-4-carboxylic Acid methyl ester The title compound was obtained using 5-chloro-pyridine-2-carbothioic acid amide and 3-bromo-2-oxo-butyric acid methyl ester in the same manner as in Reference Example 2.

$^1$H-NMR (CDCl$_3$) δ: 2.83 (3H, s), 3.97 (3H, s), 7.77 (1H, dd, J=2.4, 8.5 Hz), 8.20 (1H, dd, J=0.7, 8.5 Hz), 8.53 (1H, dd, J=0.7, 2.4 Hz).

Reference Example 9

Synthesis of 2-(3-trifluoromethyl-phenoxy)-thiazole-4-carboxylic Acid ethyl ester To a solution of 2-bromo-thiazole-4-carboxylic acid ethyl ester (300 mg, 1.27 mmol) in DMF (6 ml) were added m-hydroxybenzotrifluoride (227 mg, 1.398 mmol) and K$_2$CO$_3$ (527 mg, 3.81 mmol). The reaction mixture was stirred at 100° C. for 5 hr. After cooling to room temperature, the reaction was quenched by addition of water, and the mixture was extracted with AcOEt. The combined organic layers were washed with water and brine, dried over MgSO$_4$, and concentrated in vacuo to give the title compound (395 mg, 98%) as a pale yellow oil.

$^1$H-NMR (CDCl$_3$) δ: 1.38 (3H, t, J=7.1 Hz), 4.38 (2H, q, J=7.1 Hz), 7.54-7.58 (4H, m), 7.78 (1H, s).

Reference Example 10

Synthesis of 2-(4-chloro-phenylsulfanyl)-thiazole-4-carboxylic Acid ethyl ester

To a solution of 2-bromo-thiazole-4-carboxylic acid ethyl ester (250 mg, 1.27 mmol) in DMF (6 ml) were added p-chlorobenzenethiol (168 mg, 1.165 mmol) and K$_2$CO$_3$ (439 mg, 3.18 mmol). The reaction mixture was stirred at 100° C. for 1 hr. After cooling to room temperature, the reaction was quenched by addition of water, and the mixture was extracted with AcOEt. The combined organic layers were washed with water and brine, dried over MgSO$_4$, and concentrated in vacuo. The residue was purified by silica gel column chromatography (hexane/AcOEt=1/0 to 3/1) to give the title compound (259 mg, 82%) as a white solid.

$^1$H-NMR (CDCl$_3$) δ: 1.40 (3H, t, J=7.1 Hz), 4.42 (2H, q, J=7.1 Hz), 7.41-7.45 (2H, m), 7.58-7.62 (2H, m), 8.02 (1H, s).

Reference Example 11

Synthesis of 5-methyl-2-(3-trifluoromethyl-phenyl-sulfanyl)-thiazole-4-carboxylic Acid methyl ester The title compound was obtained using 2-bromo-5-methyl-thiazole-4-carboxylic acid methyl ester and 3-(trifluoromethyl)thiophenol in the same manner as in Reference Example 10.

$^1$H-NMR (CDCl$_3$) δ: 2.70 (3H, s), 3.94 (3H, s), 7.54 (1H, t, J=7.8 Hz), 7.67 (1H, d, J=7.8 Hz), 7.77 (1H, d, J=7.8 Hz), 7.86 (1H, s).

Reference Example 12

Synthesis of 2-[N-(4-chloro-phenyl)-N-methyl-amino]-thiazole-4-carboxylic Acid ethyl ester To a solution of 2-(4-chloro-phenylamino)-thiazole-4-carboxylic acid ethyl ester (116 mg, 0.41 mmol) in DMF (3 ml) was added NaH (21 mg, 0.533 mmol), and the reaction mixture was stirred at room temperature for 30 min, and then MeI (31 μl, 0.49 mmol) was added to the solution. The reaction mixture was stirred at room temperature overnight. After addition of water, the reaction mixture was extracted with AcOEt. The combined organic layers were washed with water and brine, dried over MgSO$_4$, and concentrated in vacuo. The residue was purified by silica gel column chromatography (hexane/AcOEt=9/1 to 3/1) to give the title compound (49 mg, 40%) as a white solid.

$^1$H-NMR (CDCl$_3$) δ: 1.38 (3H, t, J=7.1 Hz), 3.57 (3H, s), 4.37 (2H, q, J=7.1 Hz), 7.30-7.36 (2H, m), 7.38-7.42 (3H, m).

Reference Example 13

Synthesis of 2-[N-ethyl-N-(3-trifluoromethyl-phenyl)-amino]-thiazole-4-carboxylic Acid ethyl ester The title compound was obtained using 2-(3-trifluoromethyl-phenylamino)-thiazole-4-carboxylic acid ethyl ester and iodoethane in the same manner as in Reference Example 12.

$^1$H-NMR (CDCl$_3$) δ: 1.27 (3H, t, J=7.1 Hz), 1.38 (3H, t, J=7.1 Hz), 4.12 (2H, q, J=7.1 Hz), 4.36 (2H, q, J=7.1 Hz), 7.38 (1H, s), 7.56-7.57 (3H, m), 7.63 (1H, m).

Reference Example 14

Synthesis of 2-(3-chloro-4-fluoro-phenyl)-thiazole-4-carboxylic Acid ethyl ester To a solution of 2-bromo-thiazole-4-carboxylic acid ethyl ester (150 mg, 0.635 mmol) in 1,4-dioxane (3 ml), were added 3-chloro-4-fluorophenylboronic acid (111 mg, 0.635 mmol), [1,1'-bis(diphenylphosphino)ferrocene]palladium (II) dichloride (51.9 mg, 0.064 mmol) and potassium triphosphate (405 mg, 1.906 mmol). The reaction mixture was refluxed for 8 hr under nitrogen. 1 mol/l HCl was added to the reaction mixture, and the mixture was extracted with AcOEt. The combined organic layers were washed with brine, dried over MgSO$_4$, and concentrated in vacuo. The residue was purified by flash column chromatography (hexane/AcOEt=9/1 to 2/1) to give the title compound (113 mg, 62%) as a white solid.

$^1$H-NMR (CDCl$_3$) δ: 1.44 (3H, t, J=7.1 Hz), 4.46 (2H, q, J=7.1 Hz), 7.23 (1H, t, J=8.6 Hz), 7.87 (1H, ddd, J=2.3, 4.5, 8.6 Hz), 8.12 (1H, dd, J=2.3, 6.9 Hz), 8.17 (1H, s).

Reference Example 15

Synthesis of 2-(3-trifluoromethoxy-phenyl)-thiazole-4-carboxylic Acid ethyl ester The title compound was obtained using 2-bromo-thiazole-4-carboxylic acid ethyl ester and 3-(trifluoromethoxy)phenylboronic acid in the same manner as in Reference Example 14.

$^1$H-NMR (CDCl$_3$) δ: 1.44 (3H, t, J=7.1 Hz), 4.46 (2H, q, J=7.1 Hz), 7.30-7.34 (1H, m), 7.50 (1H, t, J=8.0 Hz), 7.90-7.94 (2H, m), 8.20 (1H, s).

Reference Example 16

Synthesis of 2-(4-chloro-phenyl)-5-(4-trifluoromethyl-phenyl)-thiazole-4-carboxylic Acid ethyl ester To a solution of p-bromo-alpha,alpha,alpha-trifluorotoluene (168 mg, 0.747 mmol) in toluene (5 ml) were added 2-(4-chloro-phenyl)-thiazole-4-carboxylic acid ethyl ester (200 mg, 0.747 mmol), cesium carbonate (608 mg, 1.868 mmol), rac-2,2'-Bis(diphenylphosphino)-1,1'-binaphthyl (46.5 mg, 0.075 mmol) and Pd(OAc)$_2$ (16.77 mg, 0.075 mmol). The reaction mixture was refluxed for 7 hr under nitrogen. Water was added to the reaction mixture, and the mixture was extracted with AcOEt. The combined organic layers were washed with brine, dried over MgSO$_4$, and concentrated in vacuo. The residue was purified by flash column chromatography (hexane/AcOEt=1/0 to 3/1) to give the title compound (169 mg, 55%) as a white solid.

$^1$H-NMR (CDCl$_3$) δ: 1.26 (3H, t, J=7.1 Hz), 4.32 (2H, q, J=7.1 Hz), 7.43-7.48 (2H, m), 7.65 (2H, d, J=8.3 Hz), 7.71 (2H, d, J=8.3 Hz), 7.92-7.97 (2H, m).

Reference Example 17

Synthesis of 2-[(E)-2-(3-trifluoromethyl-phenyl)-vinyl]-thiazole-4-carboxylic Acid ethyl ester To a solution of 2-formyl-thiazole-4-carboxylic acid ethyl ester (130 mg, 0.702 mmol) and (3-trifluoromethyl-benzyl)-phosphonic acid diethyl ester (239 mg, 0.807 mmol) in THF (3 ml) was added tert-BuONa (108 mg, 1.123 mmol) at 0° C. The reaction mixture was stirred overnight at room temperature. Water was added to the reaction mixture, and the mixture was extracted with AcOEt. The combined organic layers were washed with brine, dried over MgSO$_4$, and concentrated in vacuo. The residue was purified by flash column chromatography (hexane/AcOEt=1/0 to 3/1) to give the title compound (34 mg, 15%) as a white solid.

$^1$H-NMR (CDCl$_3$) δ: 1.43 (3H, t, J=7.1 Hz), 4.46 (2H, q, J=7.1 Hz), 7.45-7.61 (4H, m), 7.72 (1H, d, J=7.5 Hz), 7.77 (1H, s), 8.13 (1H, s).

Reference Example 18

Synthesis of 2-(3-trifluoromethyl-phenylamino)-thiazole-4-carboxylic Acid ethyl ester A mixture of 2-bromo-thiazole-4-carboxylic acid ethyl ester (300 mg, 1.271 mmol) and m-aminobenzotrifluoride (1 ml) was stirred for 6 hr at 140° C. 1 N HCl was added to the reaction mixture, and the mixture was extracted with Et$_2$O. The combined organic layers were washed with brine, dried over MgSO$_4$, and concentrated in vacuo. The residue was purified by flash column chromatography (hexane/AcOEt=4/1 to 3/2) to give the title compound (342 mg, 85%) as a pale yellow solid.

$^1$H-NMR (CDCl$_3$) δ: 1.39 (3H, t, J=7.1 Hz), 4.38 (2H, q, J=7.1 Hz), 7.35 (1H, d, J=7.5 Hz), 7.49 (1H, t, J=7.8 Hz), 7.53-7.62 (3H, m), 7.81 (1H, s).

Reference Example 19

Synthesis of [2-(6-trifluoromethyl-pyridin-2-yl)-thiazol-4-yl]-methanol

To a suspension of 2-(6-trifluoromethyl-pyridin-2-yl)-thiazole-4-carboxylic acid ethyl ester (500 mg, 1.65 mmol) and NaBH$_4$ (313 mg, 8.27 mmol) in DME (6 ml) was added dropwise MeOH (2.68 ml) at 50° C. The reaction mixture was stirred for 1.5 hr at 65° C. Water was added to the reaction mixture, and the mixture was extracted with AcOEt. The combined organic layers were washed with brine, dried over MgSO$_4$, and concentrated in vacuo to give the title compound (442 mg, quant.) as a white solid.

$^1$H-NMR (CDCl$_3$) δ: 2.22 (1H, t, J=5.9 Hz), 4.86 (2H, d, J=5.9 Hz), 7.37 (1H, t, J=0.8 Hz), 7.69 (1H, dd, J=0.8, 7.8 Hz), 7.97 (1H, t, J=7.8 Hz), 8.35 (1H, d, J=7.8 Hz).

Reference Example 20

Synthesis of [2-(3-trifluoromethyl-phenyl)-thiazol-4-yl]-methanol

The title compound was obtained using 2-(3-trifluoromethyl-phenyl)-thiazole-4-carboxylic acid ethyl ester in the same manner as in Reference Example 19.

$^1$H-NMR (CDCl$_3$) δ: 2.52 (1H, br), 4.85 (2H, s), 7.25 (1H, s), 7.56 (1H, t, J=7.8 Hz), 7.68 (1H, d, J=7.8 Hz), 8.10 (1H, d, J=7.8 Hz), 8.22 (1H, s).

Reference Example 21

Synthesis of [2-(3-chloro-4-fluoro-phenyl)-thiazol-4-yl]-methanol

The title compound was obtained using 2-(3-chloro-4-fluoro-phenyl)-thiazole-4-carboxylic acid ethyl ester in the same manner as in Reference Example 19.

$^1$H-NMR (CDCl$_3$) δ: 2.10-2.61 (1H, br), 4.83 (2H, s), 7.18-7.24 (2H, m), 7.79 (1H, ddd, J=2.3, 4.5, 8.6 Hz), 8.01 (1H, dd, J=2.3, 6.9 Hz).

Reference Example 22

Synthesis of [2-(4-chloro-phenylsulfanyl)-thiazol-4-yl]-methanol

The title compound was obtained using 2-(4-chloro-phenylsulfanyl)-thiazole-4-carboxylic acid ethyl ester in the same manner as in Reference Example 19.

$^1$H-NMR (CDCl$_3$) δ: 2.13-2.19 (1H, br), 4.73 (2H, d, J=5.1 Hz), 7.11 (1H, s), 7.38-7.41 (2H, m), 7.54-7.57 (2H, m).

Reference Example 23

Synthesis of [5-ethyl-2-(6-trifluoromethyl-pyridin-3-yl)-thiazol-4-yl]-methanol

The title compound was obtained using 5-ethyl-2-(6-trifluoromethyl-pyridin-3-yl)-thiazole-4-carboxylic acid methyl ester in the same manner as in Reference Example 19.

$^1$H-NMR (CDCl$_3$) δ: 1.36 (3H, t, J=7.5 Hz), 2.34 (1H, t, J=5.7 Hz), 2.92 (2H, q, J=7.5 Hz), 4.76 (2H, d, J=5.7 Hz), 7.75 (1H, d, J=8.2 Hz), 8.37 (1H, dd, J=1.8, 8.2 Hz), 9.19 (1H, d, J=1.8 Hz).

Reference Example 24

Synthesis of [5-methyl-2-(5-trifluoromethyl-pyridin-2-yl)-thiazol-4-yl]-methanol The title compound was obtained using 5-methyl-2-(5-trifluoromethyl-pyridin-2-yl)-thiazole-4-carboxylic acid methyl ester in the same manner as in Reference Example 19.

$^1$H-NMR (CDCl$_3$) δ: 2.33 (1H, brs), 2.53 (3H, s), 4.75 (2H, d, J=4.7 Hz), 7.99-8.01 (1H, m), 8.25 (1H, d, J=8.3 Hz), 8.82-8.83 (1H, m).

Reference Example 25

Synthesis of [2-(5-chloro-pyridin-2-yl)-5-methyl-thiazol-4-yl]-methanol

The title compound was obtained using 2-(5-chloro-pyridin-2-yl)-5-methyl-thiazole-4-carboxylic acid methyl ester in the same manner as in Reference Example 19.

$^1$H-NMR (CDCl$_3$) δ: 2.30 (1H, t, J=5.8 Hz), 2.50 (3H, s), 4.73 (2H, d, J=5.8 Hz), 7.74 (1H, dd, J=2.4, 8.5 Hz), 8.08 (1H, dd, J=0.6, 8.5 Hz), 8.52 (1H, dd, J=0.6, 2.4 Hz).

Reference Example 26

Synthesis of [2-(4-chloro-benzyloxy)-thiazol-4-yl]-methanol

To a solution of 4-chlorobenzyl alcohol (302 mg, 2.12 mmol) in THF (3 ml) was added NaH (119 mg, 2.97 mmol), and the reaction mixture was stirred at room temperature for 30 min. Then 2-bromo-thiazole-4-carboxylic acid ethyl ester (200 mg, 0.847 mmol) was added to the solution. The mixture was refluxed for 2 hr. The reaction was quenched by addition of water, and then the mixture was washed with AcOEt. The aqueous solution was acidified with HCl and extracted with AcOEt. The combined organic layers was washed with brine, dried over MgSO$_4$, and concentrated in vacuo. Triethylamine (0.142 ml, 1.02 mmol) and THF (20 ml) were added to the residue and then ethyl chlorocarbonate (0.089 ml, 0.932 mmol) was added to the solution at 0° C., and the mixture was stirred for 30 min. After filtration of precipitate, NaBH$_4$ (96 mg, 2.54 mmol) in water (1 ml) was added to the filtrate at 0° C. The mixture was stirred for 1 hr at same temperature. The reaction was quenched by addition of water, and the mixture was extracted with AcOEt. The combined organic layers were washed with water and brine, dried over MgSO$_4$, and concentrated in vacuo. The residue was purified by silica gel column chromatography (hexane/AcOEt=9/1 to 3/1) to give the title compound (118 mg, 54%) as a colorless oil.

$^1$H-NMR (CDCl$_3$) δ: 2.02-2.06 (1H, m), 4.58 (2H, d, J=5.4 Hz), 5.40 (2H, s), 6.56-6.58 (1H, m), 7.34-7.41 (4H, m).

Reference Example 27

Synthesis of [5-bromo-2-(4-chloro-phenyl)-thiazol-4-yl]-methanol

To a solution of [2-(4-chloro-phenyl)-thiazol-4-yl]-methanol (462 mg, 2.05 mmol) in DMF (4 ml) was added NBS (383 mg, 2.15 mmol). The reaction mixture was stirred overnight at room temperature. Water was added to the reaction mixture and the precipitate was filtered. The obtained solid was dissolved in AcOEt, and the solution was washed with water and brine, dried over MgSO$_4$, and concentrated in vacuo to give the title compound (560 mg, 90%) as a pale yellow solid.

$^1$H-NMR (CDCl$_3$) δ: 2.33-2.38 (1H, m), 4.75 (2H, d, J=6.1 Hz), 7.40-7.44 (2H, m), 7.78-7.82 (2H, m).

Reference Example 28

Synthesis of [5-bromo-2-(4-trifluoromethyl-phenyl)-thiazol-4-yl]-methanol

The title compound was obtained using [2-(4-trifluoromethyl-phenyl)-thiazol-4-yl]-methanol in the same manner as in Reference Example 27.

$^1$H-NMR (CDCl$_3$) δ: 2.43 (1H, t, J=6.1 Hz), 4.77 (2H, d, J=6.1 Hz), 7.70 (2H, d, J=8.2 Hz), 7.98 (2H, d, J=8.2 Hz).

Reference Example 29

Synthesis of [5-bromo-2-(3-trifluoromethyl-phenyl)-thiazol-4-yl]-methanol

The title compound was obtained using [2-(3-trifluoromethyl-phenyl)-thiazol-4-yl]-methanol in the same manner as in Reference Example 27.

$^1$H-NMR (CDCl$_3$) δ: 2.41 (1H, t, J=6.1 Hz), 4.77 (2H, d, J=6.1 Hz), 7.58 (1H, t, J=7.8 Hz), 7.70 (1H, d, J=7.8 Hz), 8.02 (1H, d, J=7.8 Hz), 8.15 (1H, s).

Reference Example 30

Synthesis of [5-bromo-2-(4-chloro-phenoxy)-thiazol-4-yl]-methanol

The title compound was obtained using [2-(4-chloro-phenoxy)-thiazol-4-yl]-methanol in the same manner as in Reference Example 27.

$^1$H-NMR (CDCl$_3$) δ: 2.07 (1H, t, J=6.3 Hz), 4.54 (2H, d, J=6.3 Hz), 7.19-7.24 (2H, m), 7.36-7.41 (2H, m).

Reference Example 31

Synthesis of [5-bromo-2-(3-chloro-4-fluoro-phenyl)-thiazol-4-yl]-methanol

The title compound was obtained using [2-(3-chloro-4-fluoro-phenyl)-thiazol-4-yl]-methanol in the same manner as in Reference Example 27.

$^1$H-NMR (CDCl$_3$) δ: 2.48 (1H, brs), 4.75 (2H, s), 7.21 (1H, t, J=8.6 Hz), 7.71 (1H, ddd, J=2.3, 4.4, 8.6 Hz), 7.96 (1H, dd, J=2.3, 6.9 Hz).

Reference Example 32

Synthesis of [5-bromo-2-(6-trifluoromethyl-pyridin-2-yl)-thiazol-4-yl]-methanol

The title compound was obtained using [2-(6-trifluoromethyl-pyridin-2-yl)-thiazol-4-yl]-methanol in the same manner as in Reference Example 27.

$^1$H-NMR (CDCl$_3$) δ: 2.35 (1H, t, J=6.0 Hz), 4.78 (2H, d, J=6.0 Hz), 7.70 (1H, dd, J=0.7, 7.9 Hz), 7.99 (1H, t, J=7.9 Hz), 8.31 (1H, d, J=7.9 Hz).

Reference Example 33

Synthesis of [5-propyl-2-(3-trifluoromethyl-phenyl)-thiazol-4-yl]-methanol

To a solution of [5-((E)-1-propen-1-yl)-2-(3-trifluoromethyl-phenyl)-thiazol-4-yl]-methanol (127 mg, 0.424 mmol) in EtOH (4 ml) was added 5% Pd/C-ethylenediamine complex (20 mg). The reaction mixture was stirred at room temperature for 1 hr under hydrogen. After filtration, the filtrate was concentrated to give the title compound (126 mg, 99%) as a pale yellow oil.

$^1$H-NMR (CDCl$_3$) δ: 1.01 (3H, t, J=7.3 Hz), 1.66-1.75 (2H, m), 2.40 (1H, t, J=5.9 Hz), 2.83 (2H, t, J=7.5 Hz), 4.73 (2H, d, J=5.9 Hz), 7.55 (1H, t, J=7.8 Hz), 7.65 (1H, d, J=7.8 Hz), 8.05 (1H, d, J=7.8 Hz), 8.17 (1H, s).

Reference Example 34

Synthesis of [2-(4-chloro-phenyl)-5-ethyl-thiazol-4-yl]-methanol

To a solution of [2-(4-chloro-phenyl)-5-vinyl-thiazol-4-yl]-methanol (72 mg, 0.286 mmol) in EtOH (4 ml) was added 5% Pd/C-ethylenediamine complex (20 mg). The reaction mixture was stirred at room temperature for 3 hr under hydrogen. After filtration, the filtrate was concentrated to give the title to compound (60 mg, 83%) as a white solid.

$^1$H-NMR (CDCl$_3$) δ: 1.32 (3H, t, J=7.5 Hz), 2.44-2.68 (1H, br), 2.86 (2H, q, J=7.5 Hz), 4.71 (2H, s), 7.37-7.40 (2H, m), 7.80-7.84 (2H, m).

Reference Example 35

Synthesis of [2-(4-chloro-phenyl)-5-propyl-thiazol-4-yl]-methanol

The title compound was obtained using [2-(4-chloro-phenyl)-5-((E)-1-propen-1-yl)-thiazol-4-yl]-methanol in the same manner as in Reference Example 34.

$^1$H-NMR (CDCl$_3$) δ: 1.00 (3H, t, J=7.3 Hz), 1.64-1.74 (2H, m), 2.43-2.49 (1H, br), 2.80 (2H, t, J=7.5 Hz), 4.70 (2H, d, J=4.0 Hz), 7.37-7.40 (2H, m), 7.80-7.84 (2H, m).

Reference Example 36

Synthesis of [2-(4-chloro-phenoxy)-5-ethyl-thiazol-4-yl]-methanol

The title compound was obtained using [2-(4-chloro-phenoxy)-5-vinyl-thiazol-4-yl]-methanol in the same manner as in Reference Example 34.
$^1$H-NMR (CDCl$_3$) δ: 1.24 (3H, t, J=7.6 Hz), 2.09-2.13 (1H, m), 2.73 (2H, q, J=7.6 Hz), 4.50 (2H, d, J=5.4 Hz), 7.19-7.23 (2H, m), 7.35-7.37 (2H, m).

Reference Example 37

Synthesis of [2-(4-chloro-phenyl)-5-isobutyl-thiazol-4-yl]-methanol

The title compound was obtained using [2-(4-chloro-phenyl)-5-(2-methyl-1-propen-1-yl)-thiazol-4-yl]-methanol in the same manner as in Reference Example 34.-(CDCl$_3$) δ: 0.98 (6H, d, J=6.6 Hz), 1.84-1.91 (1H, m), 2.29-2.60 (1H, br), 2.69 (2H, d, J=7.2 Hz), 4.69 (2H, s), 7.38-7.41 (2H, m), 7.82-7.85 (2H, m).

Reference Example 38

Synthesis of [2-(4-chloro-phenyl)-5-methyl-thiazol-4-yl]-methanol

To the solution of [5-bromo-2-(4-chloro-phenyl)-thiazol-4-yl]-methanol (200 mg, 0.657 mmol) in 1,4-dioxane (4 ml) were added methylboronic acid (59.0 mg, 0.985 mmol), Pd(Ph$_3$P)$_4$ (76 mg, 0.066 mmol) and K$_2$CO$_3$ (272 mg, 1.970 mmol). The reaction mixture was refluxed for 16 hr under nitrogen. After evaporation, water was added to the reaction mixture, and the mixture was extracted with AcOEt. The combined organic layers were washed with brine, dried over MgSO$_4$, and concentrated in vacuo. The residue obtained was purified by flash column chromatography (hexane/AcOEt=4/1 to 1/2) to give the title compound (130 mg, 83%) as a pale yellow solid.
$^1$H-NMR (CDCl$_3$) δ: 2.42 (1H, t, J=5.8 Hz), 2.47 (3H, s), 4.71 (2H, d, J=5.8 Hz), 7.36-7.41 (2H, m), 7.80-7.83 (2H, m).

Reference Example 39

Synthesis of [5-methyl-2-(4-trifluoromethyl-phenyl)-thiazol-4-yl]-methanol

The title compound was obtained using [5-bromo-2-(4-trifluoromethyl-phenyl)-thiazol-4-yl]-methanol in the same manner as in Reference Example 38.
$^1$H-NMR (CDCl$_3$) δ: 2.45-2.50 (4H, m), 4.73 (2H, d, J=5.8 Hz), 7.67 (2H, d, J=8.2 Hz), 7.99 (2H, d, J=8.2 Hz).

Reference Example 40

Synthesis of [5-methyl-2-(3-trifluoromethyl-phenyl)-thiazol-4-yl]-methanol

The title compound was obtained using [5-bromo-2-(3-trifluoromethyl-phenyl)-thiazol-4-yl]-methanol in the same manner as in Reference Example 38.
$^1$H-NMR (CDCl$_3$) δ: 2.49 (3H, s), 2.56 (1H, t, J=5.9 Hz), 4.73 (2H, d, J=5.9 Hz), 7.54 (1H, t, J=7.8 Hz), 7.64 (1H, d, J=7.8 Hz), 8.03 (1H, d, J=7.8 Hz), 8.15 (1H, s).

Reference Example 41

Synthesis of [2-(3-chloro-4-fluoro-phenyl)-5-methyl-thiazol-4-yl]-methanol

The title compound was obtained using [5-bromo-2-(3-chloro-4-fluoro-phenyl)-thiazol-4-yl]-methanol in the same manner as in Reference Example 38.
$^1$H-NMR (CDCl$_3$) δ: 2.38 (1H, t, J=5.8 Hz), 2.48 (3H, s), 4.71 (2H, d, J=5.8 Hz), 7.18 (1H, t, J=8.6 Hz), 7.73 (1H, ddd, J=2.3, 4.5, 8.6 Hz), 7.97 (1H, dd, J=2.3, 7.0 Hz).

Reference Example 42

Synthesis of [5-methyl-2-(6-trifluoromethyl-pyridin-2-yl)-thiazol-4-yl]-methanol The title compound was obtained using [5-bromo-2-(6-trifluoromethyl-pyridin-2-yl)-thiazol-4-yl]-methanol in the same manner as in Reference Example 38.
$^1$H-NMR (CDCl$_3$) δ: 2.30 (1H, t, J=5.8 Hz), 2.51 (3H, s), 4.74 (2H, d, J=5.8 Hz), 7.65 (1H, dd, J=0.8, 7.8 Hz), 7.94 (1H, t, J=7.8 Hz), 8.30 (1H, d, J=7.8 Hz).

Reference Example 43

Synthesis of [2-(4-chloro-phenyl)-5-vinyl-thiazol-4-yl]-methanol

To a solution of [5-bromo-2-(4-chloro-phenyl)-thiazol-4-yl]-methanol (200 mg, 0.657 mmol) in DME/H$_2$O=3/1 (4 ml) were added, 1,1'-bis(diphenylphosphino)ferrocene-palladium dichloride (16.21 mg, 0.020 mmol), sodium phosphate, tribasic (374 mg, 0.985 mmol) and vinylboronic acid pinacol cyclic ester (0.148 ml, 0.854 mmol). The reaction mixture was refluxed for 8 hr under nitrogen. Water was added to the reaction mixture, and the mixture was extracted with AcOEt. The combined organic layers were washed with brine, dried over MgSO$_4$, and concentrated in vacuo. The residue was purified by flash column chromatography (hexane/AcOEt=4/1 to 1/2) to give the title compound (104 mg, 63%) as a pale yellow solid.
$^1$H-NMR (CDCl$_3$) δ: 2.52 (1H, t, J=5.9 Hz), 4.79 (2H, d, J=5.9 Hz), 5.35 (1H, d, J=10.9 Hz), 5.56 (1H, d, J=17.2 Hz), 6.87 (1H, dd, J=10.9, 17.2 Hz), 7.40-7.43 (2H, m), 7.83-7.88 (2H, m).

Reference Example 44

Synthesis of [2-(4-chloro-phenyl)-5-((E)-1-propen-1-yl)-thiazol-4-yl]-methanol

The title compound was obtained using [5-bromo-2-(4-chloro-phenyl)-thiazol-4-yl]-methanol and trans-1-propen-1-ylboronic acid in the same manner as in Reference Example 43.
$^1$H-NMR (CDCl$_3$) δ: 1.92 (3H, dd, J=1.7, 6.7 Hz), 2.19-2.66 (1H, br), 4.76 (2H, s), 6.07 (1H, dq, J=15.4, 6.7 Hz), 6.55 (1H, dq, J=15.4, 1.7 Hz), 7.37-7.42 (2H, m), 7.81-7.86 (2H, m).

Reference Example 45

Synthesis of [5-((E)-1-propen-1-yl)-2-(3-trifluoromethyl-phenyl)-thiazol-4-yl]-methanol The title compound was obtained using [5-bromo-2-(3-trifluoromethyl-phenyl)-thiazol-4-yl]-methanol and trans-1-propen-1-ylboronic acid in the same manner as in Reference Example 43.

¹H-NMR (CDCl₃) δ: 1.93 (3H, dd, J=1.7, 6.7 Hz), 2.39 (1H, brs), 4.76-4.81 (2H, m), 6.11 (1H, dq, J=15.4, 6.7 Hz), 6.57 (1H, dq, J=15.4, 1.7 Hz), 7.55 (1H, t, J=7.8 Hz), 7.66 (1H, d, J=7.8 Hz), 8.06 (1H, d, 7.8 Hz), 8.18 (1H, s).

Reference Example 46

Synthesis of [2-(4-chloro-phenoxy)-5-vinyl-thiazol-4-yl]-methanol

The title compound was obtained using [5-bromo-2-(4-chloro-phenoxy)-thiazol-4-yl]-methanol and vinylboronic acid pinacol ester in the same manner as in Reference Example 43.

¹H-NMR (CDCl₃) δ: 2.14 (1H, t, J=6.2 Hz), 4.58 (2H, q, J=6.2 Hz), 5.19 (1H, d, J=10.9 Hz), 5.31 (1H, d, J=17.1 Hz), 6.77 (1H, dd, J=10.9, 17.1 Hz), 7.22-7.25 (2H, m), 7.37-7.40 (2H, m).

Reference Example 47

Synthesis of [2-(4-chloro-phenyl)-5-(2-methyl-1-propen-1-yl)-thiazol-4-yl]-methanol The title compound was obtained using [5-bromo-2-(4-chloro-phenyl)-thiazol-4-yl]-methanol and 2,2-dimethylethenylboronic acid pinacol ester in the same manner as in Reference Example 43.

¹H-NMR (CDCl₃) δ: 1.93 (3H, s), 1.97 (3H, s), 2.65 (1H, t, J=5.8 Hz), 4.73 (2H, d, J=5.8 Hz), 6.32 (1H, s), 7.38-7.41 (2H, m), 7.83-7.86 (2H, s).

Reference Example 48

Synthesis of 2-(4-chloro-phenylsulfanyl)-thiazole-4-carbaldehyde

To a solution of [2-(4-chloro-phenylsulfanyl)-thiazol-4-yl]-methanol (80 mg, 0.310 mmol) in DMSO (2 ml) was added IBX (104 mg, 0.372 mmol). The reaction mixture was stirred for 2 hr at room temperature. Water and AcOEt were added to the reaction mixture, and the precipitate was filtered. The filtrate was extracted with AcOEt. The combined organic layers were washed with water and brine, dried over MgSO₄, and concentrated in vacuo. The residue was purified by flash column chromatography (hexane/AcOEt=1/0 to 3/1) to give the title compound (62 mg, 78%) as a white solid.

¹H-NMR (CDCl₃) δ: 7.43-7.47 (2H, m), 7.60-7.64 (2H, m), 8.02 (1H, s), 9.95 (1H, s).

Reference Example 49

Synthesis of 2-(4-chloro-phenyl)-5-propyl-thiazole-4-carbaldehyde

The title compound was obtained using [2-(4-chloro-phenyl)-5-propyl-thiazol-4-yl]-methanol in the same manner as in Reference Example 48.

¹H-NMR (CDCl₃) δ: 1.04 (3H, t, J=7.3 Hz), 1.71-1.83 (2H, m), 3.26 (2H, t, J=7.6 Hz), 7.41-7.46 (2H, m), 7.85-7.90 (2H, m), 10.19 (1H, s).

Reference Example 50

Synthesis of 5-propyl-2-(3-trifluoromethyl-phenyl)-thiazole-4-carbaldehyde

The title compound was obtained using [5-propyl-2-(3-trifluoromethyl-phenyl)-thiazol-4-yl]-methanol in the same manner as in Reference Example 48.

¹H-NMR (CDCl₃) δ: 1.05 (3H, t, J=7.3 Hz), 1.76-1.83 (2H, m), 3.28 (2H, t, J=7.6 Hz), 7.60 (1H, t, J=7.8 Hz), 7.71 (1H, d, J=7.8 Hz), 8.11 (1H, d, J=7.8 Hz), 8.21 (1H, s), 10.22 (1H, s).

Reference Example 51

Synthesis of 2-(4-chloro-phenoxy)-5-ethyl-thiazole-4-carbaldehyde

The title compound was obtained using [2-(4-chloro-phenoxy)-5-ethyl-thiazol-4-yl]-methanol in the same manner as in Reference Example 48.

¹H-NMR (CDCl₃) δ: 1.31 (3H, t, J=7.5 Hz), 3.20 (2H, q, J=7.5 Hz), 7.25-7.28 (2H, m), 7.37-7.40 (2H, m), 9.98 (1H, s).

Reference Example 52

Synthesis of 2-(4-chloro-phenyl)-5-isobutyl-thiazole-4-carbaldehyde

The title compound was obtained using [2-(4-chloro-phenyl)-5-isobutyl-thiazol-4-yl]-methanol in the same manner as in Reference Example 48.

¹H-NMR (CDCl₃) δ: 1.02 (6H, d, J=6.6 Hz), 1.95-2.03 (1H, m), 3.17 (2H, d, J=7.2 Hz), 7.42-7.45 (2H, m), 7.86-7.89 (2H, m), 10.18 (1H, s).

Reference Example 53

Synthesis of 5-ethyl-2-(6-trifluoromethyl-pyridin-3-yl)-thiazole-4-carbaldehyde

The title compound was obtained using [5-ethyl-2-(6-trifluoromethyl-pyridin-3-yl)-thiazol-4-yl]-methanol in the same manner as in Reference Example 48.

¹H-NMR (CDCl₃) δ: 1.42 (3H, t, J=7.5 Hz), 3.37 (2H, q, J=7.5 Hz), 7.80 (1H, d, J=8.2 Hz), 8.44 (1H, dd, J=1.8, 8.2 Hz), 9.23 (1H, d, J=1.8 Hz), 10.24 (1H, s).

Reference Example 54

Synthesis of 5-methyl-2-(6-trifluoromethyl-pyridin-2-yl)-thiazole-4-carbaldehyde The title compound was obtained using [5-methyl-2-(6-trifluoromethyl-pyridin-2-yl)-thiazol-4-yl]-methanol in the same manner as in Reference Example 48.

¹H-NMR (CDCl₃) δ: 2.87 (3H, s), 7.72 (1H, dd, J=0.7, 7.9 Hz), 8.01 (1H, t, J=7.9 Hz), 8.40 (1H, d, J=7.9 Hz), 10.21 (1H, s).

Reference Example 55

Synthesis of 5-methyl-2-(5-trifluoromethyl-pyridin-2-yl)-thiazole-4-carbaldehyde The title compound was obtained using [5-methyl-2-(5-trifluoromethyl-pyridin-2-yl)-thiazol-4-yl]-methanol in the same manner as in Reference Example 48.

¹H-NMR (CDCl₃) δ: 2.89 (3H, s), 8.05-8.08 (1H, m), 8.35 (1H, d, J=8.3 Hz), 8.85-8.86 (1H, m), 10.22 (1H, s).

Reference Example 56

Synthesis of 2-(5-chloro-pyridin-2-yl)-5-methyl-thiazole-4-carbaldehyde

The title compound was obtained using [2-(5-chloro-pyridin-2-yl)-5-methyl-thiazol-4-yl]-methanol in the same manner as in Reference Example 48.
¹H-NMR (CDCl₃) δ: 2.86 (3H, s), 7.80 (1H, dd, J=2.3, 8.5 Hz), 8.17 (1H, dd, J=0.7, 8.5 Hz), 8.55 (1H, dd, J=0.7, 2.3 Hz), 10.19 (1H, s).

Reference Example 57

Synthesis of 5-methyl-2-(4-trifluoromethyl-phenyl)-thiazole-4-carbaldehyde

The title compound was obtained using [5-methyl-2-(4-trifluoromethyl-phenyl)-thiazol-4-yl]-methanol in the same manner as in Reference Example 48.
¹H-NMR (CDCl₃) δ: 2.87 (3H, s), 7.72 (2H, d, J=8.2 Hz), 8.05 (2H, d, J=8.2 Hz), 10.22 (1H, s).

Reference Example 58

Synthesis of 5-methyl-2-(3-trifluoromethyl-phenyl)-thiazole-4-carbaldehyde

The title compound was obtained using [5-methyl-2-(3-trifluoromethyl-phenyl)-thiazol-4-yl]-methanol in the same manner as in Reference Example 48.
¹H-NMR (CDCl₃) δ: 2.87 (3H, s), 7.60 (1H, t, J=7.8 Hz), 7.71 (1H, d, J=7.8 Hz), 8.09 (1H, d, J=7.8 Hz), 8.20 (1H, s), 10.22 (1H, s).

Reference Example 59

Synthesis of 2-(4-chloro-phenyl)-5-methyl-thiazole-4-carbaldehyde

The title compound was obtained using [2-(4-chloro-phenyl)-5-methyl-thiazol-4-yl]-methanol in the same manner as in Reference Example 48.
¹H-NMR (CDCl₃) δ: 2.84 (3H, s), 7.41-7.46 (2H, m), 7.84-7.89 (2H, m), 10.20 (1H, s).

Reference Example 60

Synthesis of 2-(4-chloro-benzyloxy)-thiazole-4-carbaldehyde

The title compound was obtained using [2-(4-chloro-benzyloxy)-thiazol-4-yl]-methanol in the same manner as in Reference Example 48.
¹H-NMR (CDCl₃) δ: 5.52 (2H, s), 7.36-7.43 (4H, m), 7.64 (1H, s), 9.74 (1H, s).

Reference Example 61

Synthesis of 2-(3-chloro-4-fluoro-phenyl)-5-methyl-thiazole-4-carbaldehyde

The title compound was obtained using [2-(3-chloro-4-fluoro-phenyl)-5-methyl-thiazol-4-yl]-methanol in the same manner as in Reference Example 48.

¹H-NMR (CDCl₃) δ: 2.85 (3H, s), 7.23 (1H, t, J=8.6 Hz), 7.78 (1H, ddd, J=2.3, 4.4, 8.6 Hz), 8.03 (1H, dd, J=2.3, 6.9 Hz), 10.19 (1H, s).

Reference Example 62

Synthesis of 2-(4-chloro-phenyl)-5-ethyl-thiazole-4-carbaldehyde

The title compound was obtained using [2-(4-chloro-phenyl)-5-ethyl-thiazol-4-yl]-methanol in the same manner as in Reference Example 48.
¹H-NMR (CDCl₃) δ: 1.39 (3H, t, J=7.5 Hz), 3.32 (2H, q, J=7.5 Hz), 7.41-7.46 (2H, m), 7.85-7.90 (2H, m), 10.19 (1H, s).

Reference Example 63

Synthesis of 5-methyl-2-(3-trifluoromethyl-phenyl-sulfanyl)-thiazole-4-carbaldehyde To a suspension of 5-methyl-2-(3-trifluoromethyl-phenyl-sulfanyl)-thiazole-4-carboxylic acid methyl ester (122 mg, 0.366 mmol) and NaBH₄ (69 mg, 8.27 mmol) in DME (4 ml) was added dropwise MeOH (0.38 ml) at 60° C. The reaction mixture was stirred for 1.5 hr at 60° C. Water was added to the reaction mixture, and the mixture was extracted with AcOEt. The combined organic layers were washed with brine, dried over Na₂SO₄, and concentrated in vacuo.

To a solution of the residue in DMSO (2 ml) was added IBX (123 mg, 0.439 mmol). The reaction mixture was stirred overnight at room temperature. Water and AcOEt were added to the reaction mixture, and the precipitate was filtered. The filtrate was extracted with AcOEt. The combined organic layers were washed with water and brine, dried over Na₂SO₄, and concentrated in vacuo. The residue was purified by flash column chromatography (hexane/AcOEt=1/0 to 4/1) to give the title compound (86 mg, 77%) as a white solid.
¹H-NMR (CDCl₃) δ: 2.73 (3H, s), 7.56 (1H, t, J=7.8 Hz), 7.68 (1H, d, J=7.8 Hz), 7.80 (1H, d, J=7.8 Hz), 7.88 (1H, s), 10.08 (1H, s).

Reference Example 64

Synthesis of 2-[(E)-2-(3-trifluoromethyl-phenyl)-vinyl]-thiazole-4-carbaldehyde

The title compound was obtained using 2-[(E)-2-(3-trifluoromethyl-phenyl)-vinyl]-thiazole-4-carboxylic acid ethyl ester in the same manner as in Reference Example 63.
¹H-NMR (CDCl₃) δ: 7.38 (1H, d, J=16.2 Hz), 7.51-7.63 (3H, m), 7.74 (1H, d, J=7.6 Hz), 7.80 (1H, s), 8.13 (1H, s), 10.06 (1H, s).

Reference Example 65

Synthesis of 2-(3-trifluoromethoxy-phenyl)-thiazole-4-carbaldehyde

The title compound was obtained using 2-(3-trifluoromethoxy-phenyl)-thiazole-4-carboxylic acid ethyl ester in the same manner as in Reference Example 63.
¹H-NMR (CDCl₃) δ: 7.34-7.37 (1H, m), 7.53 (1H, t, J=8.3 Hz), 7.90-7.93 (2H, m), 8.21 (1H, s), 10.12 (1H, s).

Reference Example 66

Synthesis of 2-(3-trifluoromethyl-phenoxy)-thiazole-4-carbaldehyde

The title compound was obtained using 2-(3-trifluoromethyl-phenoxy)-thiazole-4-carboxylic acid ethyl ester in the same manner as in Reference Example 63.
$^1$H-NMR (CDCl$_3$) δ: 7.56-7.61 (4H, m), 7.78 (1H, s), 9.79 (1H, s).

Reference Example 67

Synthesis of 2-[N-(4-chloro-phenyl)-N-methyl-amino]-thiazole-4-carbaldehyde

The title compound was obtained using 2-[N-(4-chloro-phenyl)-N-methyl-amino]-thiazole-4-carboxylic acid ethyl ester in the same manner as in Reference Example 63.
$^1$H-NMR (CDCl$_3$) δ: 3.57 (3H, s), 7.31-7.36 (2H, m), 7.40-7.44 (3H, m), 9.74 (1H, s).

Reference Example 68

Synthesis of 2-(4-chloro-phenyl)-5-(4-trifluoromethyl-phenyl)-thiazole-4-carbaldehyde The title compound was obtained using 2-(4-chloro-phenyl)-5-(4-trifluoromethyl-phenyl)-thiazole-4-carboxylic acid ethyl ester in the same manner as in Reference Example 63.
$^1$H-NMR (CDCl$_3$) δ: 7.46-7.50 (2H, m), 7.72-7.79 (4H, m), 7.95-7.99 (2H, m), 10.07 (1H, s).

Reference Example 69

Synthesis of 2-[N-ethyl-N-(3-trifluoromethyl-phenyl)-amino]-thiazole-4-carbaldehyde The title compound was obtained using 2-[N-ethyl-N-(3-trifluoromethyl-phenyl)-amino]-thiazole-4-carboxylic acid ethyl ester in the same manner as in Reference Example 63.
$^1$H-NMR (CDCl$_3$) δ: 1.29 (3H, t, J=7.1 Hz), 4.10 (2H, q, J=7.1 Hz), 7.39 (1H, s), 7.57-7.63 (4H, m), 9.75 (1H, s).

Reference Example 70

Synthesis of 2-hexyl-thiazole-4-carbaldehyde

The title compound was obtained using 2-hexyl-thiazole-4-carboxylic acid ethyl ester in the same manner as in Reference Example 63.
$^1$H-NMR (CDCl$_3$) δ: 0.87-0.92 (3H, m), 1.29-1.44 (6H, m), 1.78-1.88 (2H, m), 3.06 (2H, t, J=7.8 Hz), 8.07 (1H, s), 10.00 (1H, s).

Reference Example 71

Synthesis of 5-ethyl-2-(3-trifluoromethyl-phenyl)-thiazole-4-carbaldehyde

The title compound was obtained using 5-ethyl-2-(3-trifluoromethyl-phenyl)-thiazole-4-carboxylic acid methyl ester in the same manner as in Reference Example 63.
$^1$H-NMR (CDCl$_3$) δ: 1.40 (3H, t, J=7.5 Hz), 3.34 (2H, q, J=7.5 Hz), 7.59 (1H, t, J=7.8 Hz), 7.71 (1H, d, J=7.8 Hz), 8.11 (1H, d, J=7.8 Hz), 8.21 (1H, s), 10.22 (1H, s).

Reference Example 72

Synthesis of 5-ethyl-2-(5-trifluoromethyl-pyridin-2-yl)-thiazole-4-carbaldehyde

The title compound was obtained using 5-ethyl-2-(5-trifluoromethyl-pyridin-2-yl)-thiazole-4-carboxylic acid methyl ester in the same manner as in Reference Example 63.
$^1$H-NMR (CDCl$_3$) δ: 1.42 (3H, t, J=7.5 Hz), 3.36 (2H, q, J=7.5 Hz), 8.07 (1H, dd, J=2.1, 8.3 Hz), 8.35 (1H, d, J=8.3 Hz), 8.86 (1H, d, J=2.1 Hz), 10.21 (1H, s).

Reference Example 73

Synthesis of 5-bromo-2-(4-chloro-phenyl)-thiazole-4-carbaldehyde

To a solution of 2-(4-chloro-phenyl)-thiazole-4-carbaldehyde (600 mg, 2.68 mmol) in CH$_3$CN (10 ml) was added NBS (1.196 g, 6.44 mmol). The reaction mixture was stirred for 1 hr at 50° C. Additional NBS (645 mg, 3.62 mmol) was added to solution, and the mixture was refluxed for 1 hr. After concentration, the residue was purified by flash column chromatography (hexane/AcOEt=9/1 to 2/1) to give the title compound (89 mg, 11%) as pale yellow solid.
$^1$H-NMR (CDCl$_3$) δ: 7.44-7.48 (2H, m), 7.85-7.89 (2H, m), 10.10 (1H, s).

Reference Example 74

Synthesis of 2-(4-chloro-phenyl)-5-methoxy-thiazole-4-carbaldehyde

To a solution of 5-bromo-2-(4-chloro-phenyl)-thiazole-4-carbaldehyde (89 mg, 0.294 mmol) in MeOH (4 ml) was added sodium methoxide (284 mg, 1.471 mmol). The reaction mixture was stirred overnight at room temperature. Water was added to the reaction mixture and the precipitate was filtered. The obtained solid was dissolved in AcOEt, and the solution was dried over MgSO$_4$, and concentrated in vacuo. The residue was purified by flash column chromatography (hexane/AcOEt=2/1 to 1/1) to give the title compound (42 mg, 56%) as a white solid.
$^1$H-NMR (CDCl$_3$) δ: 4.21 (3H, s), 7.41-7.43 (2H, m), 7.80-7.83 (2H, m), 10.01 (1H, s).

Reference Example 75

Synthesis of 2-[(E)-2-(3-trifluoromethyl-phenyl)-vinyl]-thiazole-5-carboxylic Acid ethyl ester To a solution of ethyl 2-bromothiazole-5-carboxylate (500 mg, 2.118 mmol) in DME (10 ml) were added trans-2-(3-trifluoromethylphenyl)vinylboronic acid pinacol ester (663 mg, 2.224 mmol), 1,1'-bis(diphenylphosphino)ferrocene-palladium dichloride (86 mg, 0.106 mmol) and 2M sodium carbonate solution (3.18 ml, 6.35 mmol). The reaction mixture was stirred for 4 hr at 80° C. under nitrogen. Water was added to the reaction mixture, and the mixture was extracted with AcOEt. The combined organic layers were washed with brine, dried over MgSO$_4$, and concentrated in vacuo. The residue was purified by flash column chromatography (hexane/AcOEt=1/0 to 3/1) to give the title compound (512 mg, 74%) as a white solid.

¹H-NMR (CDCl₃) δ: 1.40 (3H, t, J=7.1 Hz), 4.39 (2H, q, J=7.1 Hz), 7.32 (1H, d, J=16.1 Hz), 7.53-7.62 (3H, m), 7.72-7.80 (2H, m), 8.39 (1H, s).

Reference Example 76

Synthesis of {2-[(E)-2-(3-trifluoromethyl-phenyl)-vinyl]-thiazol-5-yl}-methanol

To a suspension of LiAlH₄ (59 mg, 1.564 mmol) in THF (10 ml) was added dropwise 2-[(E)-2-(3-trifluoromethyl-phenyl)-vinyl]-thiazole-5-carboxylic acid ethyl ester (512 mg, 1.564 mmol) in THF (4 ml) at 0° C. 59 μl of water, 59 μl of 15% aqueous NaOH solution and 177 μp, of water were added to the reaction mixture at 0° C. After filtration of the precipitate, the filtrate was concentrated in vacuo to give the title compound (410 mg, 92%) as a yellow solid.
¹H-NMR (CDCl₃) δ: 2.13-2.17 (1H, m), 4.90 (2H, d, J=5.3 Hz), 7.30 (1H, d, J=16.3 Hz), 7.41 (1H, d, J=16.3 Hz), 7.47-7.59 (2H, m), 7.68-7.76 (2H, m), 7.76 (1H, s).

Reference Example 77

Synthesis of 2-trifluoromethyl-6-vinyl-pyridine

To a solution of 545 mg of 2-chloro-6-trifluoromethyl-pyridine and 554 mg of vinylboronic acid pinacol cyclic ester in 12 mL of 1,2-dimethoxyethane/water (3/1) were added 122 mg of 1,1'-bis(diphenylphosphino) ferrocene-palladium(II) dichloride CH₂Cl₂ complex and 1.71 g of sodium phosphate tribasic dodecahydrate. The reaction mixture was stirred at 80° C. under argon for 6 hr. The reaction was quenched by addition of water (15 mL), and extracted with AcOEt. The organic solution was dried over Na₂SO₄. After concentration, the dark red oil was purified by silica gel column (hexane->hexane/AcOEt 10%) to give the title compound (336 mg, 65%) as colorless oil.
¹H-NMR (CDCl₃) δ: 5.60 (1H, d, J=10.8 Hz), 6.31 (1H, d, J=17.4 Hz), 6.87 (1H, dd, J=10.8, 17.4 Hz), 7.53 (1H, d, J=7.9 Hz), 7.54 (1H, d, J=7.9 Hz), 7.82 (1H, t, J=7.9 Hz).

Reference Example 78

Synthesis of 4-trifluoromethyl-2-vinyl-pyridine

The title compound was obtained using 2-chloro-4-(trifluoromethyl)pyridine in the same manner as in Reference Example 77.
¹H-NMR (CDCl₃) δ: 5.61 (1H, d, J=10.8 Hz), 6.31 (1H, d, J=17.4 Hz), 6.87 (1H, dd, J=10.8, 17.4 Hz), 7.37 (1H, d, J=5.1 Hz), 7.53 (1H, s), 8.75 (1H, d, J=5.1 Hz).

Reference Example 79

Synthesis of 4-trifluoromethyl-2-vinyl-pyrimidine

The title compound was obtained using 2-chloro-4-(trifluoromethyl)pyrimidine in the same manner as in Reference Example 77.
¹H-NMR (CDCl₃) δ: 5.86 (1H, d, J=10.4 Hz), 6.77 (1H, d, J=17.3 Hz), 6.94 (1H, dd, J=10.4, 17.3 Hz), 7.45 (1H, d, J=5.0 Hz), 8.94 (1H, d, J=5.0 Hz).

Reference Example 80

Synthesis of 3-(1-methyl-2-phenyl-ethoxy)-5-trifluoromethyl-benzonitrile

To a solution of 187 mg of 3-hydroxy-5-trifluoromethyl-benzonitrile in 4 ml of tetrahydrofuran were added 289 mg of PPh₃, 136 mg of 1-phenyl-2-propanol and 0.58 ml of DEAD at 0° C. The reaction mixture was stirred at 0° C. for 1 hr and at room temperature for 24 hr. The reaction mixture was concentrated and the residue was purified by silica gel column chromatography (hexane/AcOEt 2%->hexane/AcOEt 20%) to give the title compound (205 mg, 67%) as a colorless oil.
¹H-NMR (CDCl₃) δ: 1.36 (3H, d, J=6.1 Hz), 2.91 (1H, dd, J=5.8, 13.9 Hz), 3.07 (1H, dd, J=6.7, 13.9 Hz), 4.60-4.66 (1H, m), 7.20-7.33 (7H, m), 7.42 (1H, s).

Reference Example 81

Synthesis of 3-methoxymethoxy-5-(4,4,5,5-tetramethyl-[1,3,2]dioxaborolan-2-yl)-benzonitrile To a solution of 360 mg of 3-methoxymethoxy-benzonitrile in 8 ml of tetrahydrofuran were added 29 mg of (1,5-cyclooctadiene)(methoxy)iridium(I) dimer, 24 mg of 4,4'-di-tert-butyl-2,2'-dipyridyl and 560 mg of bis(pinacolato)diboron. The resulting mixture was stirred under reflux for 16 hr. The dark red solution was concentrated to give the crude product (638 mg) as a wine red oil. This crude product was used for the next step without further purification.
¹H-NMR (CDCl₃) δ: 1.35 (12H, s), 3.48 (3H, s), 5.21 (2H, s), 7.38 (1H, s), 7.64 (1H, s), 7.72 (1H, s).

Reference Example 82

Synthesis of 3-(2,5-bis(trifluoromethyl)benzyloxy)-5-trifluoromethyl-benzonitrile To a suspension of 200 mg of 3-hydroxy-5-trifluoromethyl-benzonitrile and 265 mg of K₂CO₃ in 4 ml of CH₃CN was added 0.235 ml of 2,5-bis(trifluoromethyl)benzyl bromide. The reaction mixture was stirred at 80° C. for 2 hr. The mixture was filtered and the filtrate was concentrated to give the title compound (440 mg, quant.) as a white solid.
¹H NMR (CDCl₃) δ: 5.34 (2H, s), 7.43 (1H, s), 7.48 (1H, s), 7.59 (1H, s), 7.78 (1H, d, J=8.0 Hz), 7.90 (1H, d, J=8.0 Hz), 8.01 (1H, s).

Reference Example 83

Synthesis of 3-methoxy-5-(4-trifluoromethyl-pyridin-2-yl)-benzonitrile

To a solution of 218 mg of 2-chloro-4-(trifluoromethyl) pyridine and 373 mg of 3-methoxy-5-(4,4,5,5-tetramethyl-[1,3,2]dioxaborolan-2-yl)-benzonitrile in 5 ml of dimethoxyethane were added 49 mg of 1,1'-bis(diphenylphosphino)ferrocene-palladium(II) dichloride CH₂Cl₂ complex and 2 molar sodium carbonate aqueous solution, and the mixture was degassed. The reaction mixture was stirred at 80° C. under argon for 3 hr. The reaction was quenched by addition of water, and the mixture was extracted twice with TBME. The organic solution was concentrated and the residue was purified by silica gel column chromatography (hexane/AcOEt 5%->hexane/AcOEt 30%) to give the title compound (274 mg, 82%) as a white solid.
¹H-NMR (CDCl₃) δ: 3.94 (3H, s), 7.25 (1H, s), 7.53 (1H, d, J=5.0 Hz), 7.84 (1H, s), 7.91 (2H, s), 8.99 (1H, d, J=5.0 Hz).

Reference Example 84

Synthesis of 3-methoxymethoxy-5-(5-trifluoromethyl-pyridin-2-yl)-benzonitrile

The title compound was obtained using 3-methoxymethoxy-5-(4,4,5,5-tetramethyl-[1,3,2]dioxaborolan-2-yl)-benzonitrile and 2-chloro-5-trifluoromethyl-pyridine in the same manner as in Reference Example 83.

$^1$H-NMR (CDCl$_3$) δ: 3.52 (3H, s), 5.28 (2H, s), 7.43 (1H, s), 7.84 (1H, d, J=8.4 Hz), 7.97 (2H, s), 8.04 (1H, dd, J=2.2, 8.4 Hz), 8.97 (1H, s).

Reference Example 85

Synthesis of 1-methoxy-3-phenoxy-5-trifluoromethyl-benzene

A suspension of 1-methoxy-3-iodo-5-trifluoromethyl-benzene (600 mg, 2.0 mmol), cesium carbonate (1.4 g, 4.30 mmol), cuprous bromide (30 mg, 0.21 mmol), ethyl 2-cyclohexanonecarboxylate 70 mg (4.38 mmol) and phenol (240 mg, 4.38 mmol) in DMSO (1.5 ml) was heated to 80° C. for 8 hr under argon. The reaction mixture was allowed to cool to room temperature. After water was added to the reaction mixture, the mixture was extracted by hexane. After silica gel chromatography was charged with the resulting organic layers, it was eluted with AcOEt:hexane (1:10) to give the title compound (471 mg, 89%) as a colorless oil.

$^1$H-NMR (CDCl$_3$) δ: 3.81 (3H, s), 6.69 (1H, s), 6.82 (1H, s), 6.85 (1H, s), 7.03-7.05 (2H, m), 7.16-7.19 (1H, m), 7.36-7.39 (2H, m).

Reference Example 86

Synthesis of 3-(3-methoxy-5-trifluoromethyl-phenyl)-thiophene

The title compound was obtained using 1-iodo-3-methoxy-5-trifluoromethyl-benzene and thiophene-3-boronic acid in the same manner as in Reference Example 83.

$^1$H-NMR (CDCl$_3$) δ: 3.89 (3H, s), 7.05 (1H, s), 7.27 (1H, m), 7.36-7.44 (3H, m), 7.51 (1H, dd, J=1.4, 3.0 Hz).

Reference Example 87

Synthesis of trifluoromethanesulfonic Acid 3-phenoxy-5-trifluoromethylphenyl ester To a solution of 1-methoxy-3-phenoxy-5-trifluoromethyl benzene (471.2 mg, 1.76 mmol) in CH$_2$Cl$_2$ (2 ml) was added 1M boron tribromide in CH$_2$Cl$_2$ (6 ml, 6 mmol) at room temperature. The reaction mixture was stirred for 3 hr. Then water was added dropwise to the reaction mixture. After it was stirred for 0.5 hr, the organic layer was separated. After silica gel chromatography was charged with the resulting organic layer, it was eluted with AcOEt:hexane (1:10) to give 475.6 mg of 3-phenoxy-5-trifluoromethyl-phenol as a pale pink oil.

To a solution of 3-phenoxy-5-trifluoromethyl-phenol (475.6 mg) and DIPEA (0.60 ml) in CH$_2$Cl$_2$ (10 ml) was added trifluoromethanesulfonic anhydride (0.36 ml, 2.14 mmol) at 0° C. The reaction mixture was stirred at room temperature for 3 hr. Then water was added dropwise. After it was stirred for 10 min, the organic layer was separated. After silica gel chromatography was charged with the resulting organic layer, it was eluted with AcOEt:hexane (1:10) to give the title compound (639 mg, 94%) as a pale brown oil.

$^1$H-NMR (CDCl$_3$) δ: 7.04 (1H, s), 7.06-7.10 (2H, m), 7.21 (1H, s), 7.23 (1H, s), 7.25-7.29 (1H, m), 7.42-7.47 (2H, m).

Reference Example 88

Synthesis of trifluoromethanesulfonic Acid 3-(thiophen-3-yl)-5-trifluoromethylphenyl ester The title compound was obtained using 3-(3-methoxy-5-trifluoromethyl-phenyl)-thiophene in the same manner as in Reference Example 87.

$^1$H-NMR (CDCl$_3$) δ: 7.38 (1H, dd, J=1.3, 5.0 Hz), 7.43 (1H, s), 7.48 (1H, dd, J=3.0, 5.0 Hz), 7.60 (1H, dd, J=1.3, 3.0 Hz), 7.65 (1H, s), 7.85 (1H, s).

Reference Example 89

Synthesis of 3-phenoxy-5-trifluoromethyl-benzonitrile

A suspension of trifluoromethanesulfonic acid 3-phenoxy-5-trifluoromethylphenyl ester (638.7 mg, 1.65 mmol), zinc cyanide (300 mg, 2.56 mmol) and Pd(PPh$_3$)$_4$ (190 mg, 0.164 mmol) in DMF (6 ml) was heated to 80° C. for 8 hr under argon. The reaction mixture was allowed to cool to room temperature. The reaction mixture was filtered through a layer of Celite with AcOEt. The filtrate was washed twice with water and filtered through a column of silica gel. The eluate was concentrated in vacuo and the crude product was purified by flash chromatography on silica gel (AcOEt/hexane (0 to 10% gradient)) to give the title compound (348 mg, 80%) as a colorless oil.

$^1$H-NMR (CDCl$_3$) δ: 7.04-7.08 (2H, m), 7.26-7.30 (1H, m), 7.34 (1H, s), 7.42-7.48 (3H, m), 7.58 (1H, s).

Reference Example 90

Synthesis of 3-(thiophen-3-yl)-5-trifluoromethyl-benzonitrile

The title compound was obtained using trifluoromethanesulfonic acid 3-(thiophen-3-yl)-5-trifluoromethylphenyl ester in the same manner as in Reference Example 89.

$^1$H-NMR (CDCl$_3$) δ: 7.39 (1H, dd, J=1.3, 5.1 Hz), 7.49 (1H, dd, J=2.8, 5.1 Hz), 7.61 (1H, dd, J=1.3, 2.8 Hz), 7.82 (1H, s), 8.03 (2H, s).

Reference Example 91

Synthesis of 2-chloro-3-[(E)-2-(3-trifluoromethyl-phenyl)-vinyl]-benzonitrile

To a suspension of 19 mg of 1,1'-bis(diphenylphosphino)ferrocene-palladium(II) dichloride CH$_2$Cl$_2$ complex and 263 mg of sodium phosphate tribasic dodecahydrate in 1.5 ml of dimethoxyethane were added 100 mg of 3-bromo-2-chlorobenzonitrile and 165 mg of trans-2-(3-trifluoromethylphenyl)vinylboronic acid pinacol ester and 0.5 ml of water.

The reaction mixture was stirred at 80° C. under nitrogen for 7 hr. The reaction was quenched by addition of water and then AcOEt was added thereto. After separation the aqueous phase was extracted with AcOEt. The organic solution was filtered through a Na$_2$SO$_4$ and silica gel pad and concentrated. The residue was purified by silica gel column chromatography (hexane/AcOEt 5%->hexane/AcOEt 20%) to give the title compound (111 mg, 78%) as a white solid.
¹H-NMR (CDCl₃) δ: 7.15 (1H, d, J=16.5 Hz), 7.41 (1H, t, J=8.1 Hz), 7.50-7.64 (4H, m), 7.74-7.77 (2H, m), 7.90 (1H, dd, J=1.5, 8.1 Hz).

Reference Example 92

Synthesis of 3-cyclohexylmethoxymethyl-benzaldehyde

To a solution of cyclohexanemethanol (350 mg, 3.07 mmol) in DMF (5 ml) was added 60% NaH (120 mg, 3.0 mmol) at 0° C. under argon and the reaction mixture was stirred at 0° C. for 15 min. To the reaction mixture was added α-bromo-m-tolunitrile (590 mg, 3.0 mmol) at 0° C., and the reaction mixture was stirred at room temperature overnight. Water was added to the reaction mixture, and the mixture was extracted with AcOEt. The organic layers were washed twice with water, and then dried over anhydrous MgSO₄. The solvents were removed under reduced pressure to give crude product as a pale yellow oil. The crude material was purified by flash chromatography on silica gel (AcOEt/hexane (0 to 7% gradient)) to give 295.7 mg of 3-((cyclohexylmethoxy)methyl)benzonitrile as a colorless oil.

A suspension of 3-((cyclohexylmethoxy)methyl)benzonitrile (295.7 mg) and Raney Ni (1.0 g) in 88% formic acid (10 ml) was heated to 100° C. for 1.5 hr. The reaction mixture was allowed to cool to room temperature. The reaction mixture was diluted with diisopropyl ether and filtered through a layer of Celite. The filtrate was washed three times with water, and then dried over anhydrous MgSO₄. The solvents were removed under reduced pressure, and the resulting crude product was purified by flash chromatography on silica gel (AcOEt/hexane (0 to 7% gradient)) to give the title compound (262 mg, 38%) as a colorless oil.
¹H-NMR (CDCl₃) δ: 0.85-1.00 (2H, m), 1.00-1.40 (3H, m), 1.60-1.95 (6H, m), 3.30 (2H, d, J=6.5 Hz), 4.56 (2H, s), 7.51 (1H, t, J=7.5 Hz), 7.62 (1H, d, J=7.5 Hz), 7.80 (1H, d, J=7.5 Hz), 7.85 (1H, s), 10.03 (1H, s).

Reference Example 93

Synthesis of 3-(2,5-bis-trifluoromethyl-benzyloxy)-5-trifluoromethyl-benzaldehyde To a solution of 440 mg of 3-(2,5-bis-trifluoromethyl-benzyloxy)-5-trifluoromethyl-benzonitrile in 1 ml of THF were added 2 ml of formic acid (90%) and 250 mg of Raney Ni. The reaction mixture was stirred at 100° C. for 2 hr. After cooling to room temperature the mixture was diluted with AcOEt and filtered. The filtrate was concentrated. The residue was diluted with water and the mixture was extracted with CH₂Cl₂ twice. The organic solution was washed with water and brine, dried over MgSO₄, and concentrated to give the title compound (440 mg, quant.) as a white solid.
¹H-NMR (CDCl₃) δ: 5.38 (2H, s), 7.53 (1H, s), 7.67 (1H, s), 7.80-7.75 (2H, m), 7.89 (1H, d, J=8.2 Hz), 8.05 (1H, s), 10.05 (1H, s).

Reference Example 94

Synthesis of 3-(1-methyl-2-phenyl-ethoxy)-5-trifluoromethyl-benzaldehyde

The title compound was obtained using 3-(1-methyl-2-phenyl-ethoxy)-5-trifluoromethyl-benzonitrile in the same manner as in Reference Example 93.
¹H-NMR (CDCl₃) δ: 1.36 (3H, d, J=6.0 Hz), 2.90 (1H, dd, J=6.0, 13.8 Hz), 3.09 (1H, dd, J=6.5, 13.8 Hz), 4.67-4.73 (1H, m), 7.20-7.33 (6H, m), 7.49 (1H, s), 7.65 (1H, s), 9.97 (1H, s).

Reference Example 95

Synthesis of 3-methoxy-5-(4-trifluoromethyl-pyridin-2-yl)-benzaldehyde

The title compound was obtained using 3-methoxy-5-(4-trifluoromethyl-pyridin-2-yl)-benzonitrile in the same manner as in Reference Example 93.
¹H-NMR (CDCl₃) δ: 3.96 (3H, s), 7.50-7.53 (2H, m), 7.90 (1H, s), 7.99 (1H, s), 8.12 (1H, s), 8.90 (1H, d, J=5.0 Hz), 10.08 (1H, s).

Reference Example 96

Synthesis of 3-hydroxy-5-(5-trifluoromethyl-pyridin-2-yl)-benzaldehyde

The title compound was obtained using 3-methoxymethoxy-5-(5-trifluoromethyl-pyridin-2-yl)-benzonitrile in the same manner as in Reference Example 93.
¹H-NMR (DMSO-d₆) δ: 7.39 (1H, s), 7.90 (1H, s), 8.17 (1H, s), 8.25 (1H, d, J=8.5 Hz), 8.33 (1H, dd, J=2.2, 8.5 Hz), 9.08 (1H, s), 10.04 (1H, s).

Reference Example 97

Synthesis of 2-chloro-3-[(E)-2-(3-trifluoromethyl-phenyl)-vinyl]-benzaldehyde

The title compound was obtained using 2-chloro-3-[(E)-2-(3-trifluoromethyl-phenyl)-vinyl]-benzonitrile in the same manner as in Reference Example 93.
¹H-NMR (CDCl₃) δ: 7.13 (1H, d, J=16.2 Hz), 7.43 (1H, t, J=7.7 Hz), 7.53-7.65 (3H, m), 7.74-7.79 (2H, m), 7.87-7.93 (2H, m), 10.59 (1H, s).

Reference Example 98

Synthesis of 6-(tert-butyl-dimethyl-silyloxymethyl)-pyridine-2-carbaldehyde

To a solution of 610 mg of [6-(tert-butyl-dimethyl-silyloxymethyl)-pyridin-2-yl]-methanol in 8 ml of CH₃CN was added 876 mg of IBX. The reaction mixture was stirred at 70° C. for 1 hr. The reaction was diluted with isopropyl ether and the resulting suspension was filtered. The filtrate was concentrated to give the title compound (567 mg, 94%) as a colorless oil.
¹H-NMR (CDCl₃) δ: 0.16 (6H, s), 0.98 (9H, s), 4.93 (2H, s), 7.75-7.92 (3H, m), 10.03 (1H, s).

Reference Example 99

Synthesis of 1-[6-(tert-butyl-dimethyl-silyloxymethyl)-pyridin-2-yl]-propan-1-ol To a solution of 563 mg of 6-(tert-butyl-dimethyl-silyloxymethyl)-pyridine-2-carbaldehyde in 8 ml of THF was added 1.46 ml of 2 molar ethylmagnesium chloride at −20° C. The reaction mixture was stirred at same temperature for 2 hr and warmed to room temperature. The reaction was quenched by addition of saturated ammonium chloride aqueous solution, and the mixture was extracted twice with AcOEt. The organic solution was washed with water and brine, and concentrated. The residue was purified by silica gel column chromatography (hexane/AcOEt 5%->hexane/AcOEt 20%) to give the title compound (296 mg, 47%) as a pale pink solid.

$^1$H-NMR (CDCl$_3$) δ: 0.12 (6H, s), 0.92-0.98 (12H, m), 1.66-1.73 (1H, m), 1.83-1.89 (1H, m), 4.32 (1H, d, J=5.4 Hz), 4.64-4.68 (1H, m), 4.83 (2H, s), 7.09 (1H, d, J=7.8 Hz), 7.40 (1H, d, J=7.8 Hz), 7.69 (1H, t, J=7.8 Hz).

Reference Example 100

Synthesis of {6-[1-(4-trifluoromethyl-benzyloxy)-propyl]-pyridin-2-yl}-methanol

To a solution of 290 mg of 1-[6-(tert-butyl-dimethyl-silyloxymethyl)-pyridin-2-yl]-propan-1-ol and 0.175 ml of alpha'-bromo-alpha,alpha,alpha-trifluoro-p-xylene in 4 ml of DMF was added 50 mg of NaH (60 wt %) at 0° C. The reaction mixture was stirred at room temperature for 15 hr. The reaction was quenched by addition of 1 molar HCl, and the mixture was extracted twice with AcOEt. The organic solution was washed with water and brine, and concentrated. The residue was purified by silica gel column chromatography (hexane/AcOEt 20%->hexane/AcOEt 40%) to give the title compound (255 mg, 76%) as a white solid.

$^1$H-NMR (CDCl$_3$) δ: 0.96 (3H, t, J=7.4 Hz), 1.84-1.91 (2H, m), 3.86 (1H, t, J=5.0 Hz), 4.43-4.57 (3H, m), 4.76 (2H, d, J=5.0 Hz), 7.14 (1H, d, J=7.8 Hz), 7.35 (1H, d, J=7.8 Hz), 7.45 (2H, d, J=8.1 Hz), 7.60 (2H, d, J=8.1 Hz), 7.71 (1H, t, J=7.8 Hz).

Reference Example 101

Synthesis of 6-[1-(4-trifluoromethyl-benzyloxy)-propyl]-pyridine-2-carbaldehyde

To a solution of 250 mg of {6-[1-(4-trifluoromethyl-benzyloxy)-propyl]-pyridin-2-yl}-methanol in 4 ml of DMSO was added 280 mg of IBX. The reaction mixture was stirred at room temperature for 3 hr. The reaction was quenched by addition of water, and the mixture was extracted twice with AcOEt. The organic solution was washed with water and brine, and concentrated. The residue was filtered through a silica gel short column to give the title compound (249 mg, quant.) as a pale blue oil.

$^1$H-NMR (CDCl$_3$) δ: 0.99 (3H, t, J=7.5 Hz), 1.88-1.97 (2H, m), 4.49-4.59 (3H, m), 7.46 (2H, d, J=8.1 Hz), 7.60 (2H, d, J=8.1 Hz), 7.67-7.70 (1H, m), 7.89-7.90 (2H, m), 10.08 (1H, s).

Reference Example 102

Synthesis of (3-diethoxymethyl-phenyl)-methanol

To a solution of 3-(diethoxymethyl)benzaldehyde (2.51 g, 12.1 mmol) in EtOH (40 ml) was added NaBH$_4$ (0.68 g, 18.1 mmol) at 0° C. The reaction mixture was stirred overnight at room temperature. Water was added to the reaction mixture at 0° C., and the mixture was extracted twice with AcOEt. The combined organic layers were washed with water and brine, dried over Na$_2$SO$_4$, and concentrated in vacuo to give the title compound (2.45 g, 96%) as a colorless oil.

$^1$H-NMR (CDCl$_3$) δ: 1.22-1.27 (6H, m), 1.64 (1H, t, J=6.1 Hz), 3.51-3.66 (4H, m), 4.72 (2H, d, J=6.1 Hz), 5.50 (1H, s), 7.33-7.41 (3H, m), 7.48 (1H, s).

Reference Example 103

Synthesis of methanesulfonic Acid 2,5-bis-trifluoromethyl-benzyl ester

To a solution of 2,5-bis(trifluoromethyl)benzyl alcohol (1.50 g, 6.15 mmol) in AcOEt (30 ml) were added Et$_3$N (1.72 ml, 12.3 mmol) and MsCl (0.57 ml, 7.38 mmol) at 0° C. The reaction mixture was stirred overnight at room temperature. Water was added to the reaction mixture, and the mixture was extracted twice with AcOEt. The combined organic layers were washed with water and brine, dried over Na$_2$SO$_4$, and concentrated in vacuo to give the title compound (2.00 g, 100%) as a white solid.

$^1$H-NMR (CDCl$_3$) δ: 3.11 (3H, s), 5.45 (2H, s), 7.78 (1H, d, J=8.2 Hz), 7.87 (1H, d, J=8.2 Hz), 7.93 (1H, s).

Reference Example 104

Synthesis of methanesulfonic Acid 3-fluoro-5-trifluoromethyl-benzyl ester

The title compound was obtained using 3-fluoro-5-(trifluoromethyl)benzyl alcohol in the same manner as in Reference Example 103.

$^1$H-NMR (CDCl$_3$) δ: 3.06 (3H, s), 5.26 (2H, s), 7.32-7.39 (2H, m), 7.47 (1H, s).

Reference Example 105

Synthesis of methanesulfonic Acid 3-diethoxymethyl-benzyl ester

The title compound was obtained using 3-diethoxymethyl-benzyl alcohol in the same manner as in Reference Example 103.

$^1$H-NMR (CDCl$_3$) δ: 1.23-1.27 (6H, m), 2.93 (3H, s), 3.51-3.65 (4H, m), 5.26 (2H, s), 5.51 (1H, s), 7.34-7.40 (2H, m), 7.42-7.53 (2H, m).

Reference Example 106

Synthesis of methanesulfonic Acid 2,4-bis-trifluoromethyl-benzyl ester

To solution of 2,4-bistrifluoromethylbenzaldehyde (1.5 g, 6.20 mmol) in EtOH (20 ml) was added NaBH$_4$ (100 mg, 2.74 mmol) at room temperature, and the reaction mixture was stirred for 2 hr. The solvents were removed under reduced pressure. The residue that was diluted with AcOEt was washed with dilute HCl and water (3 times), and the organic layer was dried over anhydrous MgSO$_4$. The solvents were removed under reduced pressure to give 1.54 g of a crude (2,4-bis(trifluoromethyl)phenyl)methanol as a colorless oil.

To a solution of (2,4-bis(trifluoromethyl)phenyl)methanol (1.54 g) and Et$_3$N (1.2 ml, 8.63 mmol) in CH$_2$Cl$_2$ (50 ml) was added dropwise MsCl (0.55 ml, 7.11 mmol) at 0° C. The reaction mixture was stirred at 0° C. for 2 hr. Then water was added. The organic layers were separated and washed with diluted HCl and water (3 times), and then dried over anhydrous Na₂SO₄. The solvents were removed under reduced pressure to give the title compound (1.91 g, 96%) as a colorless oil.

¹H-NMR (CDCl₃) δ: 3.10 (3H, s), 5.46 (2H, s), 7.83-7.92 (2H, m), 7.97 (1H, s).

Reference Example 107

Synthesis of 3-trifluoromethyloxy-5-(5,5-dimethyl-[1,3,2]dioxaborinan-2-yl)-benzaldehyde To a solution of 3-bromo-5-trifluoromethoxy-benzaldehyde (1.20 g, 4.46 mmol) in DMSO (20 mL) were added bis(neopentylglycolato)diboron (1.11 g, 4.91 mmol), [1,1'-bis(diphenylphosphino)ferrocene]palladium(II) dichloride (0.11 g, 0.134 mmol) and AcOK (1.31, 13.4 mmol). The reaction mixture was stirred for 2.5 hr at 80° C. under nitrogen. Water was added to the reaction mixture, and the mixture was extracted twice with AcOEt. The combined organic layers were washed with water (twice) and brine, dried over Na₂SO₄, and concentrated in vacuo. The residue obtained was purified by silica gel flash column chromatography (Hexane:AcOEt=100:0-70:30) to give the title compound (0.72 g, 53%) as a colorless oil.

¹H-NMR (CDCl₃) δ: 1.04 (6H, s), 3.80 (4H, s), 7.77 (1H, s), 7.87 (1H, s), 8.22 (1H, s), 10.04 (1H, s).

Reference Example 108

Synthesis of 3-(4,4,5,5-tetramethyl-[1,3,2]dioxaborolan-2-yl)-5-trifluoromethyl-benzaldehyde The title compound was obtained using 3-bromo-5-trifluoromethylbenzaldehyde and bis(pinacolato)diboron in the same manner as in Reference Example 107.

¹H-NMR (CDCl₃) δ: 1.40 (12H, s), 8.24 (1H, s), 8.31 (1H, s), 8.49 (1H, s), 10.11 (1H, s).

Reference Example 109

Synthesis of 3-chloro-5-(5,5-dimethyl-[1,3,2]dioxaborinan-2-yl)-benzaldehyde

The title compound was obtained using 3-bromo-5-chloro-benzaldehyde and bis(neopentyl glycolato)diboron in the same manner as in Reference Example 107.

¹H-NMR (CDCl₃) δ: 1.04 (6H, s), 3.80 (4H, s), 7.90 (1H, s), 8.01 (1H, s), 8.16 (1H, s), 10.00 (1H, s).

Reference Example 110

Synthesis of 4-(5,5-dimethyl-[1,3,2]dioxaborinan-2-yl)-3-methyl-benzaldehyde

The title compound was obtained using 4-bromo-3-methyl-benzaldehyde and bis(neopentyl glycolato)diboron in the same manner as in Reference Example 107.

¹H-NMR (CDCl₃) δ: 1.05 (6H, s), 2.58 (3H, s), 3.80 (4H, s), 7.61-7.66 (2H, m), 7.85-7.89 (1H, m), 9.99 (1H, s).

Reference Example 111

Synthesis of 3-tert-butyl-5-(4,4,5,5-tetramethyl-[1,3,2]dioxaborolan-2-yl)-benzaldehyde The title compound was obtained using 3-bromo-5-tert-butyl-benzaldehyde and bis(pinacolato)diboron in the same manner as in Reference Example 107.

¹H-NMR (CDCl₃) δ: 1.39 (12H, s), 1.40 (9H, s), 8.02-8.04 (1H, m), 8.10-8.12 (1H, m), 8.13-8.15 (1H, m), 10.06 (1H, s).

Reference Example 112

Synthesis of 3-(3-hydroxy-phenyl)-thiophene-2-carbaldehyde

To a solution of 3-bromothiophene-2-carboxaldehyde (1.30 g, 6.81 mmol) in DME (26 ml) were added 3-hydroxyphenylboronic acid (1.03 g, 7.49 mmol), [1,1'-bis(diphenylphosphino)ferrocene]palladium(II) dichloride (0.17 g, 0.204 mmol) and 2M sodium carbonate solution (7.49 ml, 15.0 mmol). The reaction mixture was stirred for 2 hr at 80° C. under nitrogen. Water was added to the reaction mixture, and the mixture was extracted twice with AcOEt. The combined organic layers were washed with water and brine, dried over Na₂SO₄, and concentrated in vacuo. The residue obtained was purified by silica gel flash column chromatography (Hexane:AcOEt=65:35-50:50) to give the title compound (1.32 g, 95%) as a colorless oil.

¹H-NMR (CDCl₃) δ: 5.31 (1H, s), 6.92-6.96 (2H, m), 7.03-7.05 (1H, m), 7.22 (1H, d, J=5.0 Hz), 7.35 (1H, t, J=7.8 Hz), 7.74-7.75 (1H, m), 9.91 (1H, s).

Reference Example 113

Synthesis of 1-(3-diethoxymethyl-benzyloxy)-3,5-bis-trifluoromethyl-benzene

To a solution of 3-diethoxymethyl-benzyl bromide (0.50 g, 1.74 mmol) in DMF (8 ml) were added 3,5-bis(trifluoromethyl)phenol (0.42 g, 1.82 mmol) and K₂CO₃ (0.36 g, 2.60 mmol). The reaction mixture was stirred for 2 hr at 80° C. After cooling to room temperature, water was added to the reaction mixture, and the mixture was extracted twice with AcOEt. The combined organic layers were washed with water and brine, dried over Na₂SO₄, and concentrated in vacuo. The residue obtained was purified by silica gel flash column chromatography (Hexane:AcOEt=100:0-90:10) to give the title compound (0.25 g, 34%) as a colorless oil.

¹H-NMR (CDCl₃) δ: 1.24 (6H, t, J=7.0 Hz), 3.49-3.67 (4H, m), 5.16 (2H, s), 5.53 (1H, s), 7.38-7.49 (6H, m), 7.55 (1H, s).

Reference Example 114

Synthesis of (3,5-bis-trifluoromethyl-benzyl)-(3-([1,3]dioxolan-2-yl)-phenyl)-amine To a solution of 2-(3-bromophenyl)-1,3-dioxolane (2.00 g, 8.73 mmol) in toluene (40 ml) were added 3,5-bis(trifluoromethyl)benzylamine (2.12 g, 8.73 mmol), Pd(OAc)₂ (98 mg, 0.437 mmol), rac-BINAP (0.54 g 0.873 mmol) and tert-BuONa (0.92 g, 9.61 mmol). The reaction mixture was stirred for 2.5 hr at 100° C. under argon atmosphere. After cooling to room temperature, the mixture was filtered through a pad of Celite and concentrated in vacuo. The residue obtained was purified by silica gel flash column chromatography (Hexane:AcOEt=100:0-75:25) to give the title compound (2.74 g, 80%) as an orange solid.

¹H-NMR (CDCl₃) δ: 3.98-4.18 (4H, m), 4.19-4.32 (1H, m), 4.48 (2H, d, J=5.9 Hz), 5.74 (1H, s), 6.53-6.62 (1H, m), 6.77 (1H, s), 6.88 (1H, d, J=7.8 Hz), 7.19 (1H, t, J=7.8 Hz), 7.79 (1H, s), 7.84 (2H, s).

Reference Example 115

Synthesis of (3,5-bis-trifluoromethyl-benzyl)-(3-([1,3]dioxolan-2-yl)-phenyl)-methyl-amine To a solution of (3,5-bis-trifluoromethyl-benzyl)-(3-([1,3]dioxolan-2-yl)-phenyl)-amine (0.50 g, 1.28 mmol) in DMF (10 ml) was added NaH (61 mg, 1.53 mmol, 60 wt % in mineral oil) at 0° C. After the resulting suspension was stirred for 15 min, MeI (0.16 ml, 2.56 mmol) was added. The reaction mixture was stirred overnight at room temperature. Saturated aqueous NH$_4$Cl solution was added to the reaction mixture, and the mixture was extracted twice with AcOEt. The combined organic layers were washed with water and brine, dried over Na$_2$SO$_4$, and concentrated in vacuo. The residue obtained was purified by silica gel flash column chromatography (Hexane:AcOEt=100:0-85:15) to give the title compound (0.22 g, 42%) as a pale yellow oil.
$^1$H-NMR (CDCl$_3$) δ: 3.04 (3H, s), 4.01-4.16 (4H, m), 4.61 (2H, s), 5.78 (1H, s), 6.69-6.72 (1H, m), 6.89-6.91 (2H, m), 7.23-7.28 (1H, m), 7.71 (2H, s), 7.98 (1H, s).

Reference Example 116

Synthesis of 2-(3-bromo-5-chloro-phenyl)-[1,3]dioxolane

To a solution of 3-bromo-5-chloro-benzaldehyde (2.00 g, 9.13 mmol) in toluene (15 ml) were added ethylene glycol (0.76 ml, 9.13 mmol) and p-toluenesulfonic acid (87 mg, 0.457 mmol). The reaction mixture was refluxed for 6 hr using Dean-Stark apparatus. After cooling to room temperature, saturated aqueous NaHCO$_3$ solution was added to the reaction mixture at 0° C., and the mixture was extracted twice with AcOEt. The combined organic layers were washed with water and brine, dried over Na$_2$SO$_4$, and concentrated in vacuo. The residue obtained was purified by silica gel flash column chromatography (Hexane:AcOEt=100:0-90:10) to give the title compound (1.49 g, 62%) as a colorless oil.
$^1$H-NMR (CDCl$_3$) δ: 4.00-4.13 (4H, m), 5.76 (1H, s), 7.40 (1H, s), 7.50-7.51 (2H, m).

Reference Example 117

Synthesis of 1-(3-chloro-5-([1,3]dioxolan-2-yl)-phenyl)-4-trifluoromethyl-piperidine The title compound was obtained using 4-trifluoromethyl-piperidine and 2-(3-bromo-5-chloro-phenyl)-1,3-dioxolane in the same manner as in Reference Example 114.
$^1$H-NMR (CDCl$_3$) δ: 1.67-1.76 (2H, m), 1.94-1.98 (2H, m), 2.09-2.24 (1H, m), 2.70-2.77 (2H, m), 3.74-3.80 (2H, m), 4.00-4.15 (4H, m), 5.73 (1H, s), 6.85-6.87 (1H, m), 6.89-6.91 (1H, m), 6.95-6.96 (1H, m).

Reference Example 118

Synthesis of (3,5-bis-trifluoromethyl-benzyl)-triphenyl-phosphonium iodide

A suspension of 3,5-bis(trifluoromethyl)benzyl bromide (1.0 g, 3.26 mmol) and sodium iodide (1.0 g, 6.67 mmol) in acetone (10 ml) was stirred under reflux for 0.5 hr. The reaction mixture was filtered and the solvents were removed under reduced pressure. The residue was diluted with CH$_2$Cl$_2$ and was filtered. The solvents were removed under reduced pressure. To a solution of the resulting residue in CH$_3$CN was added PPh$_3$ (1.0 g, 3.81 mmol). The mixture was stirred under reflux for 1 hr. The reaction mixture was allowed to cool to room temperature. The solvents were removed under reduced pressure. To the residue was added AcOEt and hexane to give a suspension. The suspension was filtrated to give the title compound (1.89 g, 94%) as pale yellow prisms.
$^1$H-NMR (CDCl$_3$) δ: 5.84 (2H, d, J=14.9 Hz), 7.57-7.75 (9H, m), 7.75-7.90 (9H, m).

Reference Example 119

Synthesis of (3-trifluoromethyl-benzyl)-phosphonic Acid diethyl ester

A solution of 3-trifluoromethylbenzyl bromide (2.53 g, 10.6 mmol) and triethyl phosphite (3 ml, 17.5 mmol) was heated at 140° C. at 10 hr. The excess of reagents were removed in vacuo. The residue was purified by silica gel column chromatography (AcOEt:hexane=1:2) to give the title compound (2.82 g, 90%) as a colorless oil.
$^1$H-NMR (CDCl$_3$) δ: 1.22-1.29 (6H, m), 3.19 (2H, d, J=21.8 Hz), 3.98-4.14 (4H, m), 7.26-7.55 (4H, m).

Reference Example 120

Synthesis of (3-diethoxymethyl-benzyl)-phosphonic Acid diethyl ester

To a solution of potassium t-butoxide (1 g, 8.91 mmol) in tetrahydrofuran (8 ml) was added diethyl phosphite (1.1 ml, 8.54 mmol) at 0° C. under argon. The mixture was stirred at 0° C. for 45 min. To the reaction mixture was added a solution of 3-(diethoxymethyl)benzyl methanesulfonate (1.2 g, 4.2 mmol) in tetrahydrofuran (5 ml) at 0° C., and the mixture was stirred at room temperature overnight. Water was added to the reaction mixture, and the mixture was extracted with AcOEt-hexane (1:4). The organic layers were washed with brine, and dried over anhydrous Na$_2$SO$_4$. The solvents were removed under reduced pressure to give crude product as a colorless oil. The crude material was purified by silica gel (neutral) column chromatography (AcOEt/hexane=1:2) to give the title compound (977 mg, 70%) as a colorless oil.
$^1$H-NMR (CDCl$_3$) δ: 1.15-1.3 (12H, m), 3.16 (2H, d, J=21.5 Hz), 3.5-3.7 (4H, m), 3.9-4.05 (4H, m), 5.49 (1H, s), 7.25-7.4 (4H, m).

Reference Example 121

Synthesis of (6-bromo-benzofuran-2-yl)-methanol

The title compound was obtained using 6-bromo-benzofuran-2-carboxylic acid ethyl ester in the same manner as in Reference Example 19.
$^1$H-NMR (CDCl$_3$) δ: 4.76 (2H, s), 6.64 (1H, s), 7.33-7.43 (2H, m), 7.63 (1H, s).

Reference Example 122

Synthesis of 6-bromo-benzofuran-2-carbaldehyde

The title compound was obtained using (6-bromo-benzofuran-2-yl)-methanol in the same manner as in Reference Example 48.

¹H-NMR (CDCl₃) δ: 7.47-7.54 (2H, m), 7.63 (1H, d, J=8.4 Hz), 7.80 (1H, s), 9.88 (1H, s).

Reference Example 123

Synthesis of 2-(3'-trifluoromethyl-biphenyl-3-yl)-ethanol

The title compound was obtained using 3-bromophenethyl alcohol and 3-(trifluoromethyl)phenylboronic acid in the same manner as in Reference Example 91.

¹H-NMR (CDCl₃) δ: 1.44 (1H, t, J=6.0 Hz), 2.96 (2H, t, J=6.0 Hz), 3.93 (2H, q, J=6.0 Hz), 7.27-7.62 (6H, m), 7.75-7.83 (2H, m).

Reference Example 124

Synthesis of 4-hydroxy-3-[(E)-2-(3-trifluoromethyl-phenyl)-vinyl]-benzaldehyde

The title compound was obtained using 3-bromo-4-hydroxybenzaldehyde and (E)-2-(3-trifluoromethylphenyl)vinylboronic acid pinacol ester in the same manner as in Reference Example 91.

¹H-NMR (DMSO-d₆) δ: 7.07 (1H, d, J=8.4 Hz), 7.48 (1H, d, J=16.6 Hz), 7.57 (1H, d, J=16.6 Hz), 7.62-7.63 (2H, m), 7.72 (1H, dd, J=2.0, 8.4 Hz), 7.93 (2H, s), 8.19 (1H, d, J=2.0 Hz), 9.85 (1H, s).

Reference Example 125

Synthesis of trifluoromethanesulfonic Acid 4-formyl-2-[(E)-2-(3-trifluoromethyl-phenyl)-vinyl]-phenyl ester To a solution of 200 mg of 4-hydroxy-3-[(E)-2-(3-trifluoromethyl-phenyl)-vinyl]-benzaldehyde in CH₂Cl₂ were added 0.179 ml of DIPEA and 0.139 ml of trifluoromethanesulfonic anhydride at 0° C., and the mixture was stirred at room temperature for 18 hr. The reaction was quenched by addition of water. The aqueous phase was extracted twice with AcOEt. The organic layer were washed with water and brine, and concentrated. The residue was purified by silica gel column chromatography (hexane/AcOEt 5%=>hexane/AcOEt 20%) to give the title compound (74 mg, 26%) as a colorless oil.

¹H-NMR (CDCl₃) δ: 7.33 (1H, d, J=16.4 Hz), 7.38 (1H, d, J=16.4 Hz), 7.51-7.62 (3H, m), 7.74-7.78 (2H, m), 7.90 (1H, dd, J=2.0, 8.5 Hz), 8.30 (1H, d, J=2.0 Hz), 10.09 (1H, s).

Reference Example 126

Synthesis of {4-trifluoromethyl-3-[(E)-2-(3-trifluoromethyl-phenyl)-vinyl]-phenyl}-methanol The title compound was obtained using (3-bromo-4-trifluoromethyl-phenyl)-methanol and (E)-2-(3-trifluoromethylphenyl)vinylboronic acid pinacol ester in the same manner as in Reference Example 91.

¹H-NMR (CDCl₃) δ: 1.95 (1H, s), 4.82 (2H, s), 7.13 (1H, d, J=16.1 Hz), 7.38 (1H, d, J=8.1 Hz), 7.48-7.57 (3H, m), 7.67-7.79 (4H, m).

Reference Example 127

Synthesis of 2-(3-chloro-4-fluoro-phenyl)-4-trifluoromethyl-thiazole-5-carboxylic Acid ethyl ester The title compound was obtained using 2-bromo-4-trifluoromethyl-thiazole-5-carboxylic acid ethyl ester and 3-chloro-4-fluorophenylboronic acid in the same manner as in Reference Example 91.

¹H-NMR (CDCl₃) δ: 1.41 (3H, t, J=7.1 Hz), 4.42 (2H, q, J=7.1 Hz), 7.23-7.29 (1H, m), 7.86 (1H, ddd, J=2.3, 4.4, 8.6 Hz), 8.09 (1H, dd, J=2.3, 6.8 Hz).

Reference Example 128

Synthesis of 2-(4-trifluoromethoxy-phenyl)-oxazole-4-carboxylic Acid ethyl ester To the solution of 4-(trifluoromethoxy)benzamide (500 mg, 2.437 mmol) in EtOH (4 ml) was added ethyl bromopyruvate (0.918 ml, 7.31 mmol). The reaction mixture was stirred at 150° C. for 20 min by using a microwave reactor. After concentration, the residue was purified by flash column chromatography (hexane/AcOEt=9/1 to 2/1) to give the title compound (180 mg, crude) as a white solid.

¹H-NMR (CDCl₃) δ: 1.42 (3H, t, J=7.1 Hz), 4.44 (2H, q, J=7.1 Hz), 7.29-7.35 (2H, m), 8.14-8.19 (2H, m), 8.29 (1H, s).

Reference Example 129

Synthesis of 3-(5-fluoro-benzoxazol-2-yl)-benzoic Acid methyl ester

To a solution of methyl hydrogen isophthalate (1.5 g, 8.33 mmol) and 2-amino-4-fluorophenol (1.058 g, 8.33 mmol) in methanesulfonic acid (15 ml, 231 mmol) was added slowly phosphoric anhydride (5.91 g, 41.6 mmol). The reaction mixture was stirred for 2 hr at 80° C. After the reaction mixture was cooled to 0° C., saturated aqueous NaHCO₃ solution was added to the reaction mixture. The precipitate was collected by filtration, washed with water and CH₃CN:water (1:1) and air-dried at 60° C. to give the title compound (1.08 g, 48%) as a brown solid.

¹H-NMR (DMSO-d₆) δ: 3.94 (3H, s), 7.30-7.38 (1H, m), 7.72-7.92 (3H, m), 8.20-8.24 (1H, m), 8.43-8.48 (1H, m), 8.72-8.74 (1H, m).

Reference Example 130

Synthesis of [3-(5-fluoro-benzoxazol-2-yl)-phenyl]-methanol

To a solution of 3-(5-fluoro-benzoxazol-2-yl)-benzoic acid methyl ester (0.50 g, 1.84 mmol) in THF (10 ml) was added LiAlH₄ (0.07 g, 1.84 mmol) at 0° C. The reaction mixture was stirred for 3.5 hr at the same temperature. Water, 15% NaOH aqueous solution and water were added successively to the reaction mixture. The suspension was filtered through a pad of Celite. Water was added to the filtrate, and the mixture was extracted twice with AcOEt. The combined organic layers were washed with brine, dried over Na₂SO₄, and concentrated in vacuo to give the title compound (332 mg, 74%) as an orange solid.

¹H-NMR (DMSO-d₆) δ: 1.81 (1H, t, J=5.6 Hz), 4.82 (2H, d, J=5.6 Hz), 7.05-7.13 (1H, m), 7.43-7.60 (4H, m), 8.14-8.19 (1H, m), 8.25 (1H, s).

Reference Example 131

Synthesis of 3-[2-(2,5-bis-trifluoromethyl-benzyloxy)-phenyl]-propionic Acid methyl ester The title compound was obtained using methyl 3-(2-hydroxyphenyl)propionate and 2,5-bis(trifluoromethyl)benzyl bromide in the same manner as in Reference Example 82.

¹H-NMR (CDCl₃) δ: 2.65-2.70 (2H, m), 3.06 (2H, t, J=7.9 Hz), 3.67 (3H, s), 5.32 (2H, s), 6.88 (1H, d, J=8.3 Hz), 6.93 (1H, t, J=6.5 Hz), 7.19-7.26 (2H, m), 7.71 (1H, d, J=8.3 Hz), 7.65 (1H, d, J=8.3 Hz), 8.11 (1H, s).

Reference Example 132

Synthesis of 3-[2-(2,5-bis-trifluoromethyl-benzyloxy)-phenyl]-propan-1-ol

The title compound was obtained using 3-[2-(2,5-bis-trifluoromethyl-benzyloxy)-phenyl]-propionic acid methyl ester in the same manner as in Reference Example 19.

¹H-NMR (CDCl₃) δ: 1.38 (1H, t, J=5.6 Hz), 1.88-1.97 (2H, m), 2.83 (2H, t, J=7.3 Hz), 3.66-3.72 (2H, m), 5.32 (2H, s), 6.89 (1H, d, J=8.2 Hz), 6.98 (1H, t, J=7.4 Hz), 7.18-7.24 (2H, m), 7.71 (1H, d, J=8.2 Hz), 7.85 (1H, d, J=8.2 Hz), 8.14 (1H, s).

Reference Example 133

Synthesis of 2-(4-chloro-phenyl)-5-methyl-oxazole-4-carboxylic Acid methyl ester To a solution of methyl acetoacetate (0.108 ml, 1 mmol) in DMF (3 ml) were added 4-chlorobenzylamine (1.5 mmol), iodine (305 mg, 1.200 mmol), copper(II) acetate hydrate (19.96 mg, 0.100 mmol) and tert-butyl hydroperoxide (0.333 ml, 2.000 mmol). After the reaction mixture was stirred for 4 hr at room temperature, additional 4-chlorobenzylamine (0.5 mmol) was added to the reaction again. The reaction mixture was stirred for 14 hr at rt. The reaction was quenched by addition of water, and the mixture was extracted three times with AcOEt. The organic solution was washed with water, 10% sodium thiosulfate aqueous solution, and brine and concentrated. The residue was purified by silica gel column chromatography (hexane/AcOEt 5%->hexane/AcOEt 20%) to give the title compound (67 mg, 27%) as a white solid.

¹H-NMR (CDCl₃) δ: 2.71 (3H, s), 3.95 (3H, s), 7.42-7.45 (2H, m), 7.99-8.02 (2H, m).

Reference Example 134

Synthesis of [2-(4-chloro-phenyl)-5-methyl-oxazol-4-yl]-methanol

The title compound was obtained using 2-(4-chloro-phenyl)-5-methyl-oxazole-4-carboxylic acid methyl ester in the same manner as in Reference Example 19.

¹H-NMR (CDCl₃) δ: 2.40 (3H, s), 4.59 (2H, s), 7.39-7.42 (2H, m), 7.91-7.94 (2H, m).

Reference Example 135

Synthesis of 5-cyclopropyl-2-(3-trifluoromethyl-phenyl)-oxazole-4-carboxylic Acid methyl ester The title compound was obtained using 3-cyclopropyl-3-oxopropionic acid methyl ester and 3-(trifluoromethyl)benzylamine in the same manner as in Reference Example 133.

¹H-NMR (CDCl₃) δ: 1.21-1.28 (4H, m), 2.81-2.90 (1H, m), 3.98 (3H, s), 7.58 (1H, t, J=7.8 Hz), 7.71 (1H, d, J=7.8 Hz), 8.18 (1H, d, J=7.8 Hz), 8.25 (1H, s).

Reference Example 136

Synthesis of 2-(3-chloro-phenyl)-5-cyclopropyl-oxazole-4-carboxylic Acid methyl ester The title compound was obtained using methyl 3-cyclopropyl-3-oxopropionate and 3-chlorobenzylamine in the same manner as in Reference Example 133.

¹H-NMR (CDCl₃) δ: 1.19-1.23 (4H, m), 2.80-2.87 (1H, m), 3.97 (3H, s), 7.35-7.43 (2H, m), 7.88 (1H, dt, J=1.5, 7.5 Hz), 7.98 (1H, t, J=1.5 Hz).

Reference Example 137

Synthesis of [5-cyclopropyl-2-(3-trifluoromethyl-phenyl)-oxazol-4-yl]-methanol

The title compound was obtained using 5-cyclopropyl-2-(3-trifluoromethyl-phenyl)-oxazole-4-carboxylic acid methyl ester in the same manner as in Reference Example 19.

¹H-NMR (CDCl₃) δ: 0.99-1.10 (4H, m), 1.96-2.05 (1H, m), 2.20 (1H, s), 4.68 (2H, s), 7.56 (1H, t, J=7.7 Hz), 7.66 (1H, d, J=7.7 Hz), 8.13 (1H, d, J=7.7 Hz), 8.20 (1H, s).

Reference Example 138

Synthesis of 3-bromo-5-ethoxymethyl-benzaldehyde

To a solution of 1,3-dibromo-5-ethoxymethyl-benzene (1.42 g, 4.83 mmol) in dry Et₂O (28 ml) was added dropwise n-BuLi (1.907 ml, 5.07 mmol, 2.66 M solution in hexane) at −78° C. under nitrogen. The reaction mixture was stirred for 1 hr at the same temperature. DMF (3.72 ml, 48.3 mmol) was added to the reaction mixture, and stirring was continued for 1 hr. Saturated aqueous NH₄Cl solution was added to the reaction mixture, and the mixture was extracted twice with AcOEt. The combined organic layers were washed with water and brine, dried over Na₂SO₄, and concentrated in vacuo. The residue obtained was purified by silica gel flash column chromatography (Hexane:AcOEt=100:0-80:20) to give the title compound (978 mg, 83%) as a colorless oil.

¹H-NMR (CDCl₃) δ: 1.28 (3H, t, J=7.0 Hz), 3.59 (2H, q, J=7.0 Hz), 4.55 (2H, s), 7.76 (1H, s), 7.78 (1H, s), 7.92 (1H, s), 9.96 (1H, s).

Reference Example 139

Synthesis of (3-bromo-5-chloro-phenyl)-cyclopropyl-methanol

To a solution of 3-bromo-5-chloro-benzaldehyde (1.5 g, 6.83 mmol) in THF (20 mL) was added dropwise cyclopropylmagnesium bromide (11.7 mL, 8.20 mmol, 0.7 M solution in THF) at 0° C. The reaction mixture was stirred for 5 hr at the same temperature. Saturated aqueous NH$_4$Cl solution was added to the reaction mixture, and the mixture was extracted twice with AcOEt. The combined organic layers were washed with water and brine, dried over Na$_2$SO$_4$, and concentrated in vacuo. The residue obtained was purified by silica gel flash column chromatography (Hexane: AcOEt=100:0-85:15) to give the title compound (807 mg, 45%) as a colorless oil.

$^1$H-NMR (CDCl$_3$) δ: 0.40-0.52 (2H, m), 0.61-0.70 (2H, m), 1.11-1.19 (1H, m), 1.97 (1H, d, J=3.0 Hz), 3.94 (1H, dd, J=3.0, 8.5 Hz), 7.37 (1H, s), 7.42-7.43 (1H, m), 7.48 (1H, s).

Reference Example 140

Synthesis of 1-bromo-3-chloro-5-cyclopropylmethyl-benzene

To a solution of (3-bromo-5-chloro-phenyl)-cyclopropyl-methanol (493 mg, 1.89 mmol) in CH$_2$Cl$_2$ (15 ml) were added triethylsilane (0.90 ml, 5.65 mmol), BF$_3$-Et$_2$O complex (0.465 ml, 3.77 mmol) at 0° C. The reaction mixture was stirred for 2 hr at the same temperature. Saturated aqueous NaHCO$_3$ solution was added to the reaction mixture, and the mixture was extracted twice with CH$_2$Cl$_2$. The combined organic layers were washed with water and brine, dried over Na$_2$SO$_4$, and concentrated in vacuo. The residue obtained was purified by silica gel flash column chromatography (Hexane/AcOEt=100:0-95:5) to give the title compound (430 mg, 93%) as a colorless oil.

$^1$H-NMR (CDCl$_3$) δ: 0.18-0.22 (2H, m), 0.55-0.59 (2H, m), 0.91-0.98 (1H, m), 2.49 (2H, d, J=7.0 Hz), 7.19 (1H, s), 7.29 (1H, s), 7.34-7.35 (1H, m).

Reference Example 141

Synthesis of 1,3-dibromo-5-cyclopropyl-benzene

To a solution of diethyl zinc (12.6 ml, 13.8 mmol, 1.1 M solution in hexane) in 1,2-dichloroethane (25 ml) was added TFA (1.03 ml, 13.8 mmol) at 0° C. under nitrogen. After the reaction mixture was stirred for 20 min at the same temperature, diiodomethane (1.12 ml, 13.8 mmol) was added, and stirring was continued for 20 min. 1,3-Dibromo-5-vinyl-benzene (1.45 g, 5.54 mmol) in 1,2-dichloroethane (10 ml) was added dropwise to the resulting mixture, and stirring was continued for 4 hr at 80° C. under nitrogen. The reaction mixture was concentrated in vacuo. 1N NaOH aqueous solution was added to the residue, and the mixture was extracted twice with CH$_2$Cl$_2$. The combined organic layers were washed with brine, dried over Na$_2$SO$_4$, and concentrated in vacuo. The residue obtained was purified by silica gel flash column chromatography (Hexane:AcOEt=100:0-95:5) to give the title compound (1.13 g, 74%) as a colorless oil.

$^1$H-NMR (CDCl$_3$) δ: 0.67-0.71 (2H, m), 0.96-1.02 (2H, m), 1.79-1.85 (1H, m), 7.12 (1H, s), 7.13 (1H, s), 7.46-7.47 (1H, m).

Reference Example 142

Synthesis of 3-bromo-5-cyclopropyl-benzaldehyde

The title compound was obtained using 1,3-dibromo-5-cyclopropyl-benzene in the same manner as in Reference Example 138.

$^1$H-NMR (CDCl$_3$) δ: 0.74-0.79 (2H, m), 1.04-1.10 (2H, m), 1.91-1.98 (1H, m), 7.45-7.50 (2H, m), 7.75-7.78 (1H, m), 9.91 (1H, s).

Reference Example 143

Synthesis of 1,3-dibromo-5-cyclobutoxy-benzene

The title compound was obtained using 3,5-dibromo-phenol and cyclobutanol in the same manner as in Reference Example 80.

$^1$H-NMR (CDCl$_3$) δ: 1.64-1.74 (1H, m), 1.83-1.91 (1H, m), 2.10-2.19 (2H, m), 2.41-2.47 (2H, m), 4.55-4.62 (1H, m), 6.88 (1H, s), 6.89 (1H, s), 7.21-7.22 (1H, m).

Reference Example 144

Synthesis of 3-bromo-5-cyclobutoxy-benzaldehyde

The title compound was obtained using 1,3-dibromo-5-cyclobutoxy-benzene in the same manner as in Reference Example 138.

$^1$H-NMR (CDCl$_3$) δ: 1.67-1.77 (1H, m), 1.85-1.93 (1H, m), 2.12-2.22 (2H, m), 2.44-2.52 (2H, m), 4.68 (1H, quint, J=7.2 Hz), 7.20 (1H, s), 7.22 (1H, s), 7.56 (1H, s), 9.88 (1H, s).

Reference Example 145

Synthesis of 2-(4-chloro-phenyl)-4-ethyl-thiazole-5-carboxylic Acid methyl ester The title compound was obtained using 4-chlorothiobenzamide and methyl 2-chloro-3-oxopentanoate in the same manner as in Reference Example 2.

$^1$H-NMR (CDCl$_3$) δ: 1.34 (3H, t, J=7.5 Hz), 3.19 (2H, q, J=7.5 Hz), 3.90 (3H, s), 7.41-7.44 (2H, m), 7.90-7.93 (2H, m).

Reference Example 146

Synthesis of 3-[(Z)-2-(3,5-bis-trifluoromethyl-phenyl)-vinyl]-benzaldehyde

To solution of 3-(diethoxymethyl)benzaldehyde (0.18 ml, 0.885 mmol), 18-crown-6-ether (20 mg, 0.076 mmol) and (3,5-bis-trifluoromethyl-benzyl)triphenyl phosphonium iodide (500 mg, 0.812 mmol) in CH$_2$Cl$_2$ was slowly added potassium t-butoxide (200 mg, 1.78 mmol) at −78° C. After the reaction mixture was stirred at same temperature for 7 hr, water was added, and the mixture was acidified with 5N HCl. The layer of CH$_2$Cl$_2$ was separated. After silica gel chromatography was charged with the layer, the elution from AcOEt:hexane (1:10) gave a crude product. The crude product was purified by flash chromatography on silica gel (AcOEt/hexane (0 to 5% gradient)) to give the title compound (159 mg, 54%) as a colorless oil.

$^1$H-NMR (CDCl$_3$) δ: 6.72 (1H, d, J=12.2 Hz), 6.87 (1H, d, J=12.2 Hz), 7.40-7.47 (2H, m), 7.62 (2H, s), 7.71 (1H, s), 7.73 (1H, m), 7.76-7.81 (1H, m), 9.94 (1H, s).

Reference Example 147

Synthesis of 3-(5-fluoro-benzoxazol-2-yl)-benzaldehyde

To a solution of [3-(5-fluoro-benzoxazol-2-yl)-phenyl]-methanol (332 mg, 1.37 mmol) in DMSO (3.5 mL) was added IBX (573 mg, 2.05 mmol) at room temperature. The reaction mixture was stirred for 1.5 hr at the same temperature. Water and AcOEt were added to the reaction mixture, and the precipitate was filtered through a pad of Celite. The filtrate was extracted twice with AcOEt. The combined organic layers were washed with water, saturated aqueous sodium bicarbonate solution and brine, dried over $Na_2SO_4$, and concentrated in vacuo to give the title compound (268 mg, 81%) as a brown solid.

$^1$H-NMR (CDCl$_3$) δ: 7.10-7.17 (1H, m), 7.45-7.58 (2H, m), 7.73 (1H, t, J=8.0 Hz), 8.08 (1H, d, J=7.5 Hz), 8.50 (1H, d, J=7.5 Hz), 8.74 (1H, s), 10.14 (1H, s).

Reference Example 148

Synthesis of 3-[2-(2,5-bis-trifluoromethyl-benzyloxy)-phenyl]-propionaldehyde

The title compound was obtained using 3-[2-(2,5-bis-trifluoromethyl-benzyloxy)-phenyl]-propan-1-ol in the same manner as in Reference Example 147.

$^1$H-NMR (CDCl$_3$) δ: 2.78-2.83 (2H, m), 3.05 (2H, t, J=7.5 Hz), 5.32 (2H, s), 6.88 (1H, d, J=8.3 Hz), 6.97 (1H, t, J=7.5 Hz), 7.20-7.24 (2H, m), 7.72 (1H, d, J=8.3 Hz), 7.86 (1H, d, J=8.3 Hz), 8.05 (1H, s), 9.82 (1H, s).

Reference Example 149

Synthesis of 5-cyclopropyl-2-(3-trifluoromethyl-phenyl)-oxazole-4-carbaldehyde

The title compound was obtained using [5-cyclopropyl-2-(3-trifluoromethyl-phenyl)-oxazol-4-yl]-methanol in the same manner as in Reference Example 147.

$^1$H-NMR (CDCl$_3$) δ: 1.28-1.33 (4H, m), 2.68-2.77 (1H, m), 7.61 (1H, t, J=7.8 Hz), 7.73 (1H, d, J=7.8 Hz), 8.17 (1H, d, J=7.8 Hz), 8.23 (1H, s), 10.06 (1H, s).

Reference Example 150

Synthesis of 3-trifluoromethyl-5-[2-(6-trifluoromethyl-pyridin-2-yl)-ethyl]-benzaldehyde To a solution of 116 mg of 3-trifluoromethyl-5-[(E)-2-(6-trifluoromethyl-pyridin-2-yl)-vinyl]-benzaldehyde in 4 mL of EtOH was added 30 mg of 5% Pd/C-ethylenediamine complex, and the reaction mixture was stirred at 30° C. for 3 hr. After filtration, the filtrate was concentrated to give a mixture of the title compound and benzyl alcohol (109 mg) as a brown oil. To a solution of the mixture in 2 mL of DMSO was added IBX (141 mg, 0.504 mmol). The reaction mixture was stirred at room temperature for 2 hr. The reaction was quenched by addition of water, and then the mixture was extracted twice with TBME. The organic solution was washed with water and brine, and concentrated to give the title compound (100 mg, 86%) as a pale yellow oil.

$^1$H-NMR (CDCl$_3$) δ: 3.22-3.31 (4H, m), 7.26 (1H, d, J=7.6 Hz), 7.53 (1H, d, J=7.6 Hz), 7.70 (1H, s), 7.75 (1, t, J=7.6 Hz), 7.92 (1H, s), 7.96 (1H, s), 10.02 (1H, s).

Reference Example 151

Synthesis of 3-(3,5-bis-trifluoromethyl-phenoxymethyl)-benzaldehyde

To a solution of 1-(3-diethoxymethyl-benzyloxy)-3,5-bis-trifluoromethyl-benzene (0.25 g, 0.592 mmol) in THF (7.5 mL) was added 2N HCl (7.5 ml). The reaction mixture was stirred for 2.5 hr at room temperature. Saturated aqueous NaHCO$_3$ solution was added to the reaction mixture, and the mixture was extracted twice with AcOEt. The combined organic layers were washed with brine, dried over Na$_2$SO$_4$, and concentrated in vacuo to give the title compound (0.23 g, 100%) as a white solid.

$^1$H-NMR (CDCl$_3$) δ: 5.22 (2H, s), 7.41 (2H, s), 7.51 (1H, s), 7.61 (1H, t, J=7.6 Hz), 7.72 (1H, d, J=7.6 Hz), 7.90 (1H, d, J=7.6 Hz), 7.98 (1H, s), 10.07 (1H, s).

Reference Example 152

Synthesis of 3-[N-(3,5-bis-trifluoromethyl-benzyl)-N-methyl-amino]-benzaldehyde

The title compound was obtained using (3,5-bis-trifluoromethyl-benzyl)-(3-([1,3]dioxolan-2-yl)-phenyl)-methyl-amine in the same manner as in Reference Example 151.

$^1$H-NMR (CDCl$_3$) δ: 3.12 (3H, s), 4.68 (2H, s), 6.95-6.98 (1H, m), 7.23-7.29 (2H, m), 7.40 (1H, t, J=7.6 Hz), 7.68 (2H, s), 7.80 (1H, s), 9.95 (1H, s).

Reference Example 153

Synthesis of 5-(3-trifluoromethyl-phenoxy)-thiophene-2-carbaldehyde

To a solution of 5-bromothiophene-2-carboxaldehyde (0.85 g, 4.45 mmol) in NMP (10 ml) were added 3-hydroxy-benzotrifluoride (0.80 ml, 6.68 mmol) and cesium carbonate (2.18 g, 6.68 mmol). The reaction mixture was stirred for 5 hr at 110° C. Water was added to the reaction mixture, and the mixture was extracted twice with AcOEt. The combined organic layers were washed with water and brine, dried over Na$_2$SO$_4$, and concentrated in vacuo. The residue obtained was purified by silica gel flash column chromatography (Hexane:AcOEt=90:10-80:20) to give the title compound (0.89 g, 74%) as an orange oil.

$^1$H-NMR (CDCl$_3$) δ: 6.58 (1H, d, J=6.6 Hz), 7.35-7.38 (1H, m), 7.44 (1H, s), 7.49-7.57 (3H, m), 9.75 (1H, s).

Reference Example 154

Synthesis of 1-(3,4-difluoro-phenyl)-1H-indole-6-carbaldehyde

A suspension of indole-6-carbaldehyde (145 mg, 1.00 mmol), 1,2-difluoro-4-iodobenzene (200 μl, 1.66 mmol), copper(I) iodide (40 mg, 0.21 mmol), potassium phosphate (450 mg, 2.12 mmol) and N,N'-dimethylethylenediamine (40 μl, 0.37 mmol) in toluene 2 ml was stirring at 110° C. for 10 hr under argon. The reaction mixture was cooled to room temperature, diluted with hexane, and then purified by silica gel chromatography (AcOEt:hexane=1:10) to give the title compound (134 mg, 52%) as a white solid.

$^1$H-NMR (CDCl$_3$) δ: 6.77 (1H, dd, J=0.9, 3.3 Hz), 7.25-7.33 (1H, m), 7.33-7.43 (2H, m), 7.48 (1H, d, J=3.3 Hz), 7.72 (1H, dd, J=1.2, 8.4 Hz), 7.80 (1H, d, J=8.4 Hz), 7.99 (1H, m), 10.05 (1H, s).

Reference Example 155

Synthesis of 3-chloro-5-(4-trifluoromethyl-piperidin-1-yl)-benzaldehyde

The title compound was obtained using 1-(3-chloro-5-diethoxymethyl-phenyl)-4-trifluoromethyl-piperidine in the same manner as in Reference Example 151.

¹H-NMR (CDCl₃) δ: 1.67-1.78 (2H, m), 1.97-2.04 (2H, m), 2.16-2.31 (1H, m), 2.79-2.84 (2H, m), 3.82-3.88 (2H, m), 7.11-7.12 (1H, m), 7.26-7.29 (2H, m), 9.89 (1H, s).

Reference Example 156

Synthesis of (3'-trifluoromethyl-biphenyl-3-yl)-acetaldehyde

To a solution of 2-(3'-trifluoromethyl-biphenyl-3-yl)-ethanol (533 mg, 2 mmol) in CH₃CN (6 ml) was added IBX (728 mg, 2.60 mmol). The reaction mixture was stirred at 60° C. for 4 hr. The reaction was diluted with IPE and the resulting suspension was filtered. The filtrate was concentrated. The residue was purified by silica gel column chromatography (hexane/AcOEt 5%->20%) to give the title compound (354 mg, 67%) as a colorless oil.
¹H-NMR (CDCl₃) δ: 3.80 (2H, s), 7.26 (1H, d, J=7.2 Hz), 7.44 (1H, s), 7.48 (1H, t, J=7.6 Hz), 7.53-7.58 (2H, m), 7.62 (1H, d, J=7.6 Hz), 7.76 (1H, d, J=7.6 Hz), 7.82 (1H, s), 9.82 (1H, s).

Reference Example 157

Synthesis of 4-trifluoromethyl-3-[(E)-2-(3-trifluoromethyl-phenyl)-vinyl]-benzaldehyde The title compound was obtained using {4-trifluoromethyl-3-[(E)-2-(3-trifluoromethyl-phenyl)-vinyl]-phenyl}-methanol in the same manner as in Reference Example 48.
¹H-NMR (CDCl₃) δ: 7.23 (1H, d, J=16.1 Hz), 7.48-7.60 (3H, m), 7.73-7.88 (4H, m), 8.28 (1H, s), 10.14 (1H, s).

Reference Example 158

Synthesis of 2-(4-chloro-phenyl)-5-methyl-oxazole-4-carbaldehyde

The title compound was obtained using [2-(4-chloro-phenyl)-5-methyl-oxazol-4-yl]-methanol in the same manner as in Reference Example 48.
¹H-NMR (CDCl₃) δ: 2.72 (3H, s), 7.44-7.48 (2H, m), 7.97-8.01 (2H, m), 10.02 (1H, s).

Reference Example 159

Synthesis of 2-[(E)-2-(3-trifluoromethyl-phenyl)-vinyl]-thiazole-5-carbaldehyde

To the solution of {2-[(E)-2-(3-trifluoromethyl-phenyl)-vinyl]-thiazol-5-yl}-methanol (410 mg, 1.437 mmol) in AcOEt (16 ml) was added IBX (1.207 g, 4.31 mmol). The reaction mixture was refluxed for 1 hr. After filtration, the filtrate was concentrated. The residue was purified by flash column chromatography (hexane/AcOEt=9/1 to 3/2) to give the title compound (350 mg, 86%) as a yellow solid.
¹H-NMR (CDCl₃) δ: 7.37 (1H, d, J=16.1 Hz), 7.56-7.83 (5H, m), 8.42 (1H, s), 10.05 (1H, s).

Reference Example 160

Synthesis of 3-(2,3-dihydro-indol-1-ylmethyl)-benzaldehyde

A solution of indole (140 mg, 1.23 mmol), methanesulfonic acid 3-diethoxymethyl-benzyl ester (300 mg, 1.04 mmol) and DIPEA (0.35 ml) in CH₃CN (5 ml) was stirred at room temperature overnight and then heated to 80° C. for 8 hr. The solvents were removed under reduced pressure. The residue was purified by silica gel chromatography (AcOEt-hexane=1:4) to give a pale yellow oil.
To solution of the pale yellow oil in CH₃CN (2 ml) was added 1N HCl (1 ml) and the mixture was stirred at room temperature for 1 hr. The reaction mixture was basified with saturated NaHCO₃ aqueous solution and extracted with AcOEt, and the organic layer was dried over anhydrous Na₂SO₄. The solvents were removed under reduced pressure to give crude product as a pale brown oil. The crude material was purified by flash chromatography on silica gel (AcOEt/hexane (0 to 15% gradient)) to give the title compound (224 mg, 95%) as a pale yellow oil.
¹H-NMR (CDCl₃) δ: 3.00 (2H, t, J=8.2 Hz), 3.34 (2H, t, J=8.2 Hz), 4.32 (2H, s), 6.46 (1H, d, J=7.8 Hz), 6.70 (1H, dt, J=0.9, 7.4 Hz), 7.03-7.13 (2H, m), 7.51 (1H, t, J=7.6 Hz), 7.66 (1H, d, J=7.6 Hz), 7.80 (1H, d, J=7.6 Hz), 7.90 (1H, s), 10.02 (1H, s).

Reference Example 161

Synthesis of 3-(1-phenyl-ethoxy)-5-trifluoromethyl-benzaldehyde

The title compound was obtained using 3-hydroxy-5-trifluoromethyl-benzaldehyde and (1-bromoethyl)benzene in the same manner as in Reference Example 82.
¹H-NMR (CDCl₃) δ: 1.72 (3H, d, J=6.4 Hz), 5.45 (1H, q, J=6.4 Hz), 7.29-7.42 (6H, m), 7.51 (1H, s), 7.65 (1H, s), 9.94 (1H, s).

Reference Example 162

Synthesis of 3-(2,5-bis-trifluoromethyl-benzyloxy)-5-methoxy-benzaldehyde

The title compound was obtained using 3-hydroxy-5-methoxy-benzaldehyde and 2,5-bis(trifluoromethyl)benzyl bromide in the same manner as in Reference Example 82.
¹H-NMR (CDCl₃) δ: 3.87 (3H, s), 5.32 (2H, s), 6.81 (1H, s), 7.08-7.11 (2H, m), 7.72 (1H, d, J=8.1 Hz), 7.85 (1H, d, J=8.1 Hz), 8.06 (1H, s), 9.93 (1H, s).

Reference Example 163

Synthesis of 3-cyclopropylmethoxy-5-(5-trifluoromethyl-pyridin-2-yl)-benzaldehyde The title compound was obtained using 3-hydroxy-5-(5-trifluoromethyl-pyridin-2-yl)-benzaldehyde and cyclopropylmethyl bromide in the same manner as in Reference Example 82.
¹H-NMR (CDCl₃) δ: 0.37-0.43 (2H, m), 0.67-0.73 (2H, m), 1.26-1.33 (1H, m), 3.97 (2H, d, J=6.9 Hz), 7.50 (1H, s), 7.90-7.93 (2H, m), 7.99-8.02 (1H, m), 8.13 (1H, s), 8.97 (1H, s), 10.07 (1H, s).

Reference Example 164

Synthesis of 3-(3-trifluoromethyl-benzyloxy)-5-(5-trifluoromethyl-pyridin-2-yl)-benzaldehyde The title compound was obtained using 3-hydroxy-5-(5-trifluoromethyl-pyridin-2-yl)-benzaldehyde and 3-(trifluoromethyl)benzyl bromide in the same manner as in Reference Example 82.

¹H-NMR (CDCl₃) δ: 5.27 (2H, s), 7.48-7.68 (5H, m), 7.77 (1H, s), 7.93 (1H, d, J=8.3 Hz), 8.03-8.06 (2H, m), 8.18 (1H, s), 10.09 (1H, s).

Reference Example 165

Synthesis of 2-ethoxy-3-[(E)-2-(3-trifluoromethyl-phenyl)-vinyl]-benzaldehyde

The title compound was obtained using 2-hydroxy-3-[(E)-2-(3-trifluoromethyl-phenyl)-vinyl]-benzaldehyde and iodoethane in the same manner as in Reference Example 82.
¹H-NMR (CDCl₃) δ: 1.49 (3H, t, J=7.0 Hz), 4.08 (2H, q, J=7.0 Hz), 7.19 (1H, d, J=16.5 Hz), 7.27 (1H, t, J=7.7 Hz), 7.45 (1H, d, J=16.5 Hz), 7.50-7.57 (2H, m), 7.72 (1H, d, J=7.4 Hz), 7.76 (1H, s), 7.81 (1H, dd, J=1.7, 7.7 Hz), 7.88 (1H, dd, J=1.7, 7.7 Hz), 10.44 (1H, s).

Reference Example 166

Synthesis of 3-{[N-(4-fluoro-phenyl)-N-methyl-amino]-methyl}-benzaldehyde

To a suspension of 155 mg of 3-chloromethyl-benzaldehyde and 207 mg of K₂CO₃ in 4 ml of CH₃CN was added 150 mg of 4-fluoro-N-methylaniline. The reaction mixture was stirred at 80° C. for 2 hr and room temperature for 3 days. The mixture was filtered and then concentrated. The residue was purified by silica gel column chromatography (hexane/AcOEt 10%->20%) to give the title compound (240 mg, 99%) as a light yellow oil.
¹H-NMR (CDCl₃) δ: 2.99 (3H, s), 4.53 (2H, s), 6.66-6.70 (2H, m), 6.87-6.96 (2H, m), 7.49-7.51 (2H, m), 7.76-7.79 (2H, m), 10.00 (1H, s).

Reference Example 167

Synthesis of 3-(benzofuran-2-ylmethoxy)-benzaldehyde

The title compound was obtained using 2-bromomethyl-benzofuran and 3-hydroxybenzaldehyde in the same manner as in Reference Example 82.
¹H-NMR (CDCl₃) δ: 5.24 (2H, s), 6.83 (1H, s), 7.21-7.35 (3H, m), 7.45-7.59 (5H, m), 9.99 (1H, s).

Reference Example 168

Synthesis of 3-(2,5-bis-trifluoromethyl-benzyloxy)-benzaldehyde

The title compound was obtained using 3-hydroxybenzaldehyde and 2,5-bis(trifluoromethyl)benzyl bromide in the same manner as in Reference Example 82.
¹H-NMR (CDCl₃) δ: 5.35 (2H, s), 7.28-7.31 (1H, m), 7.49-7.56 (3H, m), 7.73 (1H, d, J=8.1 Hz), 7.86 (1H, d, J=8.1 Hz), 8.08 (1H, s), 10.01 (1H, s).

Reference Example 169

Synthesis of 3-fluoro-4-(3-trifluoromethyl-phenoxy)-benzaldehyde

To a solution of 3,4-difluorobenzaldehyde (0.45 g, 3.17 mmol) in NMP (5 ml) were added 3-hydroxybenzotrifluoride (0.45 ml, 3.80 mmol) and potassium carbonate (0.66 g, 4.75 mmol). The reaction mixture was stirred for 5 hr at 100° C. Water was added to the reaction mixture, and the mixture was extracted twice with AcOEt. The combined organic layers were washed with water (twice) and brine, dried over Na₂SO₄, and concentrated in vacuo to give the title compound (0.90 g, 100%) as a brown oil.
¹H-NMR (CDCl₃) δ: 7.13-7.40 (3H, m), 7.43-7.57 (2H, m), 7.64-7.77 (2H, m), 9.94 (1H, s).

Reference Example 170

Synthesis of 3-[3-(2,5-bis-trifluoromethyl-benzyloxy)-phenyl]-thiophene-2-carbaldehyde The title compound was obtained using 3-(3-hydroxyphenyl)-thiophene-2-carbaldehyde and methanesulfonic acid 2,5-bis-trifluoromethyl-benzyl ester in the same manner as in Reference Example 82.
¹H-NMR (CDCl₃) δ: 5.35 (2H, s), 7.08-7.14 (3H, m), 7.23 (1H, d, J=5.0 Hz), 7.44 (1H, t, J=8.0 Hz), 7.74-7.76 (2H, m), 7.85 (1H, d, J=8.0 Hz), 8.09 (1H, s), 9.88 (1H, s).

Reference Example 171

Synthesis of 5-fluoro-2-(3-fluoro-5-trifluoromethyl-benzyloxy)-3-methyl-benzaldehyde The title compound was obtained using methanesulfonic acid 3-fluoro-5-trifluoromethyl-benzyl ester and 5-fluoro-2-hydroxy-3-methyl-benzaldehyde in the same manner as in Reference Example 82.
¹H-NMR (DMSO-d₆) δ: 2.34 (3H, s), 5.12 (2H, s), 7.31-7.37 (1H, m), 7.51-7.58 (1H, m), 7.69-7.78 (3H, m), 10.16 (1H, s).

Reference Example 172

Synthesis of 3-(4,4,4-trifluoro-butoxy)-5-trifluoromethyl-benzaldehyde

The title compound was obtained using 3-hydroxy-5-trifluoromethyl-benzaldehyde and 1-bromo-4,4,4-trifluorobutane in the same manner as in Reference Example 82.
¹H-NMR (CDCl₃) δ: 2.07-2.16 (2H, m), 2.27-2.39 (2H, m), 4.14 (2H, t, J=6.0 Hz), 7.41 (1H, s), 7.55 (1H, s), 7.73 (1H, s), 10.02 (1H, s).

Reference Example 173

Synthesis of 3-(4-trifluoromethoxy-benzylsulfanyl-methyl)-benzaldehyde

To a solution of 3-chloromethyl-benzaldehyde (155 mg, 1 mmol) in THF (6 ml) were added potassium carbonate (166 mg, 1.200 mmol) and 4-(trifluoromethoxy)benzyl mercaptan (219 mg, 1.050 mmol). The reaction mixture was stirred at 70° C. for 5 hr. The mixture was filtered, and then the filtrate was concentrated. The residue was purified by silica gel column chromatography (hexane->hexane/AcOEt 20%) to give the title compound (188 mg, 58%) as a colorless oil.
¹H-NMR (CDCl₃) δ: 3.61 (2H, s), 3.68 (2H, s), 7.15 (2H, d, J=8.0 Hz), 7.26-7.30 (2H, m), 7.48-7.56 (2H, m), 7.76-7.78 (2H, m), 10.01 (1H, s).

Reference Example 174

Synthesis of 1-(2,4,5-trifluoro-benzyl)-piperidine-4-carbaldehyde

A suspension of 4-piperidinemethanol (260 mg, 2.257 mmol), potassium carbonate (390 mg, 2.82 mmol) and 2,4,5-trifluorobenzyl bromide (423 mg, 1.881 mmol) in N,N-dimethylformamide (5 ml) was stirred at room temperature for 2 hr. Water was added to the reaction mixture, and the mixture was extracted with AcOEt. The organic layers were washed with water (twice) and brine, and dried over anhydrous $Na_2SO_4$. The solvents were removed under reduced pressure to give a colorless oil. A solution of the colorless oil and IBX (632 mg, 2.26 mmol) was stirred at 40° C. for 2 hr. To reaction mixture was added water and AcOEt. The mixture was filtrated through a layer of Celite with AcOEt. The filtrate was separated, and the organic layer was washed with water (twice), and dried over $Na_2SO_4$. The solvents were removed under reduced pressure to give a colorless oil. The crude product was purified by flash chromatography on silica gel (AcOEt/hexane (0 to 50% gradient)) to give the title compound (241 mg, 50%) as a pale yellow oil.

$^1$H-NMR (CDCl$_3$) δ: 1.61-1.80 (2H, m), 1.87-1.97 (2H, m), 2.14-2.31 (3H, m), 2.77-2.86 (2H, m), 3.50 (2H, s), 6.85-6.93 (1H, m), 7.20-7.29 (1H, m), 9.65 (1H, d, J=0.9 Hz).

Reference Example 175

Synthesis of 3-(2-methoxy-benzyloxy)-5-trifluoromethyl-benzaldehyde

To a solution of 190 mg of 3-hydroxy-5-trifluoromethyl-benzaldehyde in 4 ml of CH$_3$CN were added 166 mg of K$_2$CO$_3$ and 0.149 ml of 2-methoxybenzyl chloride. The reaction mixture was stirred at 80° C. for 2 hr. 10 mg of NaI was added thereto, and the reaction was stirred at 80° C. for 1 h. After cooling to room temperature, the reaction mixture was filtered, and the filtrate was concentrated to give the title compound (368 mg, quant.) as a brown solid.

$^1$H-NMR (CDCl$_3$) δ: 3.90 (3H, s), 5.22 (2H, s), 6.93-7.00 (2H, m), 7.34 (1H, t, J=7.5 Hz), 7.44 (1H, d, J=7.5 Hz), 7.52 (1H, s), 7.67 (1H, s), 7.70 (1H, s), 10.00 (1H, s).

Reference Example 176

Synthesis of 3-(4-fluoro-phenyl)-benzo[b]thiophene-2-carbaldehyde

The title compound was obtained using 3-bromo-benzo[b]thiophene-2-carboxaldehyde and 4-fluorophenylboronic acid in the same manner as in Reference Example 91.

$^1$H-NMR (CDCl$_3$) δ: 7.24-7.32 (2H, m), 7.40-7.59 (4H, m), 7.75 (1H, d, J=8.0 Hz), 7.95 (1H, d, J=8.0 Hz), 9.93 (1H, s).

Reference Example 177

Synthesis of 2-(3-chloro-phenyl)-5-cyclopropyl-oxazole-4-carbaldehyde

The title compound was obtained using 2-(3-chloro-phenyl)-5-cyclopropyl-oxazole-4-carboxylic acid methyl ester in the same manner as in Reference Example 63.

$^1$H-NMR (CDCl$_3$) δ: 1.25-1.30 (4H, m), 2.67-2.74 (1H, m), 7.38-7.46 (2H, m), 7.87 (1H, dt, J=1.5, 7.5 Hz), 7.96 (1H, t, J=1.5 Hz), 10.04 (1H, s).

Reference Example 178

Synthesis of 2-(4-chloro-phenyl)-4-methyl-thiazole-5-carbaldehyde

The title compound was obtained using 2-(4-chloro-phenyl)-4-methyl-thiazole-5-carboxylic acid ethyl ester in the same manner as in Reference Example 63.

$^1$H-NMR (CDCl$_3$) δ: 2.79 (3H, s), 7.43-7.48 (2H, m), 7.93-7.97 (2H, m), 10.10 (1H, s).

Reference Example 179

Synthesis of 4-methyl-2-(3-trifluoromethyl-phenyl)-thiazole-5-carbaldehyde

The title compound was obtained using 4-methyl-2-(3-trifluoromethyl-phenyl)-thiazole-5-carboxylic acid ethyl ester in the same manner as in Reference Example 63.

$^1$H-NMR (CDCl$_3$) δ: 2.81 (3H, s), 7.62 (1H, t, J=7.8 Hz), 7.76 (1H, d, J=7.8 Hz), 8.15 (1H, d, J=7.8 Hz), 8.31 (1H, s), 10.13 (1H, s).

Reference Example 180

Synthesis of 2-(3-chloro-4-fluoro-phenyl)-4-trifluoromethyl-thiazole-5-carbaldehyde The title compound was obtained using 2-(3-chloro-4-fluoro-phenyl)-4-trifluoromethyl-thiazole-5-carboxylic acid ethyl ester in the same manner as in Reference Example 63.

$^1$H-NMR (CDCl$_3$) δ: 7.26-7.32 (1H, m), 7.91 (1H, ddd, J=2.3, 4.4, 8.6 Hz), 8.15 (1H, dd, J=2.3, 6.8 Hz), 10.23 (1H, d, J=0.8 Hz).

Reference Example 181

Synthesis of 2-(4-trifluoromethoxy-phenyl)-oxazole-4-carbaldehyde

The title compound was obtained using 2-(4-trifluoromethoxy-phenyl)-oxazole-4-carboxylic acid ethyl ester in the same manner as in Reference Example 63.

$^1$H-NMR (CDCl$_3$) δ: 7.33-7.37 (2H, m), 8.14-8.19 (2H, m), 8.34 (1H, s), 10.02 (1H, s).

Reference Example 182

Synthesis of 2-(4-chloro-phenyl)-4-ethyl-thiazole-5-carbaldehyde

The title compound was obtained using 2-(4-chloro-phenyl)-4-ethyl-thiazole-5-carboxylic acid methyl ester in the same manner as in Reference Example 63.

$^1$H-NMR (CDCl$_3$) δ: 1.44 (3H, t, J=7.5 Hz), 3.13 (2H, q, J=7.5 Hz), 7.43-7.47 (2H, m), 7.93-7.98 (2H, m), 10.11 (1H, s)

Reference Example 183

Synthesis of 3-(4-fluoro-benzyl)-5-trifluoromethoxy-benzaldehyde

To a solution of 3-(5,5-dimethyl-[1,3,2]dioxaborinan-2-yl)-5-trifluoromethoxy-benzaldehyde (0.33 g, 1.09 mmol) in DME (10 mL) were added 4-fluorobenzyl bromide (0.136 ml, 1.09 mmol), [1,1'-bis(diphenylphosphino) ferrocene]

palladium(II) dichloride (0.027 g, 0.033 mmol) and 2 M aqueous sodium carbonate solution (0.820 mL, 1.64 mmol). The reaction mixture was stirred for 1.5 hr at 80° C. under nitrogen. Water was added to the reaction mixture, and the mixture was extracted twice with AcOEt. The combined organic layers were washed with brine, dried over $Na_2SO_4$, and concentrated in vacuo. The residue obtained was purified by silica gel flash column chromatography (Hexane: AcOEt=100:0-85:15) to give the title compound (228 mg, 70%) as a colorless oil.

$^1$H-NMR (CDCl$_3$) δ: 4.14 (2H, s), 7.27-7.33 (3H, m), 7.56-7.64 (4H, m), 9.97 (1H, s).

Reference Example 184

Synthesis of 1-(4,4,4-trifluoro-butyl)-1H-indole-6-carbaldehyde

To a solution of indole-6-carbaldehyde (145 mg, 1.00 mmol) in DMF (1.5 ml) was added 60% NaH (50 mg, 3.5 mmol) at 0° C. under argon, and the reaction mixture was stirred at 0° C. for 0.5 hr. To the reaction mixture was added 1-bromo-4,4,4-trifluorobutane (191.9 mg, 1.00 mmol) at 0° C., and stirred at room temperature overnight. Water was added to the reaction mixture, and the mixture was extracted with AcOEt. The organic layer was washed twice with water, and then dried over anhydrous $Na_2SO_4$. The solvents were removed under reduced pressure to give crude product as a pale orange oil. The crude material was purified by flash chromatography on silica gel (AcOEt/hexane (0 to 15% gradient)) to give the title compound (195 mg, 76%) as a pale yellow oil.

$^1$H-NMR (CDCl$_3$) δ: 2.0-2.3 (4H, m), 4.32 (2H, t, J=6.8 Hz), 6.61 (1H, dd, J=0.8, 3.1 Hz), 7.32 (1H, d, J=3.1 Hz), 7.65 (1H, dd, J=1.3, 8.2 Hz), 7.74 (1H, d, J=8.2 Hz), 7.9 (1H, s), 10.08 (1H, s).

Reference Example 185

Synthesis of 1-(2,4-bis-trifluoromethyl-benzyl)-1H-pyrrole-2-carbaldehyde

The title compound was obtained using pyrrole-2-carboxaldehyde and methanesulfonic acid 2,4-bis-trifluoromethyl-benzyl ester in the same manner as in Reference Example 184.

$^1$H-NMR (CDCl$_3$) δ: 5.82 (2H, s), 6.39 (1H, dd, J=2.6, 4.0 Hz), 6.65 (1H, d, J=8.2 Hz), 6.96 (1H, m), 7.07 (1H, dd, J=1.7, 4.0 Hz), 7.65 (1H, d, J=8.2 Hz), 7.95 (1H, s), 9.58 (1H, d, J=0.9 Hz).

Reference Example 186

Synthesis of 3-(5-trifluoromethyl-pyridin-2-yloxymethyl)-benzaldehyde

To a solution of (3-diethoxymethyl-phenyl)-methanol (210 mg, 1 mmol) and 2-chloro-5-(trifluoromethyl)pyridine (0.154 ml, 1.200 mmol) in DMF (4 ml) was added NaH (60.0 mg, 1.500 mmol) at 0° C. and the mixture was stirred at room temperature for 20 hr. The reaction was quenched by addition of 1 molar HCl (2 ml) and THF (1 ml) at 0° C. The mixture was stirred for 30 min and extracted twice with AcOEt after diluted with water (5 ml). The organic solution was washed with water and brine, filtered through a $Na_2SO_4$ short column, and concentrated. The residue was purified by silica gel column chromatography (hexane/AcOEt 5%->hexane/AcOEt 20%) to give the title compound (277 mg, 98%) as a colorless oil.

$^1$H-NMR (CDCl$_3$) δ: 5.53 (2H, s), 6.92 (1H, d, J=8.7 Hz), 7.56 (1H, t, J=7.5 Hz), 7.71-7.87 (3H, m), 7.99 (1H, s), 8.46 (1H, s), 10.05 (1H, s).

Reference Example 187

Synthesis of 3-(4-trifluoromethyl-pyridin-2-yloxymethyl)-benzaldehyde

The title compound was obtained using (3-diethoxymethyl-phenyl)-methanol and 2-chloro-4-(trifluoromethyl)pyridine in the same manner as in Reference Example 186.

$^1$H-NMR (CDCl$_3$) δ: 5.52 (2H, s), 7.07 (1H, s), 7.11 (1H, d, J=5.3 Hz), 7.56 (1H, t, J=7.5 Hz), 7.73 (1H, d, J=7.5 Hz), 7.85 (1H, d, J=7.5 Hz), 7.99 (1H, s), 8.33 (1H, d, J=5.3 Hz), 10.05 (1H, s).

Reference Example 188

Synthesis of 4-[(E)-2-(3-formyl-phenyl)-vinyl]-benzonitrile

To a solution of (3-diethoxymethyl-benzyl)-phosphonic acid diethyl ester (367.6 mg, 1.11 mmol) and 4-cyanobenzaldehyde (170 mg, 1.30 mmol) in tetrahydrofuran (5 ml) was added 60% NaH (50 mg, 3.5 mmol) at 0° C. under argon, and the reaction mixture was stirred at room temperature overnight. The reaction mixture was acidified by 5N HCl at 0° C., and water was added. The reaction mixture was stirred overnight. The resulting suspension was filtered, and the white powder was washed with water. The resulting powder was purified by silica gel chromatography (CH$_2$Cl$_2$) to give the title compound (142 mg, 49%) as a colorless solid.

$^1$H-NMR (CDCl$_3$) δ: 7.19 (1H, d, J=16.3 Hz), 7.27 (H, d, J=16.3 Hz), 7.55-7.69 (5H, m), 7.76-7.84 (2H, m), 8.06 (1H, t, J=1.7 Hz), 10.07 (1H, s).

Reference Example 189

Synthesis of 3-[2-(5-trifluoromethyl-pyridin-2-yloxy)-ethyl]-benzaldehyde

To a solution of 2-chloro-5-(trifluoromethyl)pyridine (0.119 ml, 0.927 mmol) and 2-(3-[1,3]dioxolan-2-yl-phenyl)-ethanol (150 mg, 0.772 mmol) in 3 ml of DMF was added 46 mg of NaH (60 wt %) at 0° C. and the mixture was stirred at room temperature for 18 hr. The reaction was quenched by addition of 1N HCl and THF (1 ml) at 0° C. The mixture was stirred for 2 hr and extracted twice with TBME. The organic solution was washed with water and brine, filtered through a $Na_2SO_4$ short column, and concentrated. The residue was purified by silica gel column chromatography (hexane/AcOEt 5%->hexane/AcOEt 20%) to give the title compound (188 mg, 82%) as a colorless oil.

$^1$H-NMR (CDCl$_3$) δ: 3.19 (2H, t, J=6.6 Hz), 4.60 (2H, t, J=6.6 Hz), 6.95 (1H, s), 7.07 (1H, d, J=5.4 Hz), 7.50 (1H, t, J=7.5 Hz), 7.57-7.59 (1H, m), 7.75-7.78 (1H, m), 7.82 (1H, s), 8.29 (1H, d, J=5.4 Hz), 10.02 (1H, s).

Reference Example 190

Synthesis of 3-[(E)-2-(4-ethoxy-phenyl)-vinyl]-benzaldehyde

To a solution of (3-diethoxymethyl-benzyl)-phosphonic acid diethyl ester (150 mg, 0.45 mmol) and 4-ethoxybenzaldehyde (80 mg, 1.30 mmol) in tetrahydrofuran (5 ml) was added tert-BuONa (100 mg, 1.04 mmol) at 0° C., and the reaction mixture was stirred at room temperature for 3 days. The reaction was worked up and treated in the same manner as in Reference Example 188 to give the title compound (99 mg, 87%) as a yellow solid.

$^1$H-NMR (CDCl$_3$) δ: 1.43 (3H, t, J=7.0 Hz), 4.07 (2H, q, J=7.0 Hz), 6.90 (2H, d, J=8.8 Hz), 7.03 (1H, d, J=16.2 Hz), 7.16 (1H, d, J=16.2 Hz), 7.45-7.6 (3H, m), 7.7-7.8 (2H, m), 8.00 (1H, m), 10.05 (1H, s).

Reference Example 191

Synthesis of 3-chloro-5-cyclopropylmethyl-benzaldehyde

The title compound was obtained using 1-bromo-3-chloro-5-cyclopropylmethyl-benzene in the same manner as in Reference Example 138.

$^1$H-NMR (CDCl$_3$) δ: 0.22-0.25 (2H, m), 0.58-0.62 (2H, m), 0.96-1.01 (1H, m), 2.61 (2H, d, J=7.0 Hz), 7.52 (1H, s), 7.66 (1H, s), 7.69-7.70 (1H, m), 9.96 (1H, s).

Reference Example 192

Synthesis of 4-formyl-2-[(E)-2-(3-trifluoromethyl-phenyl)-vinyl]-benzonitrile

The title compound was obtained using trifluoromethanesulfonic acid 4-formyl-2-[(E)-2-(3-trifluoromethyl-phenyl)-vinyl]-phenyl ester in the same manner as in Reference Example 89.

$^1$H-NMR (CDCl$_3$) δ: 7.41-7.63 (4H, m), 7.80-7.82 (3H, m), 7.86 (1H, d, J=1.0 Hz), 8.30 (1H, s), 10.14 (1H, s).

Reference Example 193

Synthesis of 3-[2-(2,4-difluoro-phenyl)-ethyl]-benzaldehyde

The title compound was obtained using 3-[(E)-2-(2,4-difluoro-phenyl)-vinyl]-benzaldehyde in the same manner as in Reference Example 150.

$^1$H-NMR (CDCl$_3$) δ: 2.89-3.00 (4H, m), 6.73-6.82 (2H, m), 6.99-7.07 (1H, m), 7.39-7.47 (2H, m), 7.69-7.74 (2H, m), 9.99 (1H, s).

Reference Example 194

Synthesis of 3-methyl-5-(6-trifluoromethyl-pyridin-3-yl)-benzaldehyde

The title compound was obtained using 3-formyl-5-methylphenylboronic acid and 5-bromo-2-(trifluoromethyl)pyridine in the same manner as in Reference Example 112.

$^1$H-NMR (CDCl$_3$) δ: 2.55 (3H, s), 7.68 (1H, s), 7.77-7.81 (2H, m), 7.92 (1H, s), 8.06-8.12 (1H, m), 8.96-8.97 (1H, m), 10.08 (1H, s).

Reference Example 195

Synthesis of 5-ethoxymethyl-4'-fluoro-biphenyl-3-carbaldehyde

The title compound was obtained using 3-bromo-5-ethoxymethyl-benzaldehyde and 4-fluorophenylboronic acid in the same manner as in Reference Example 112.

$^1$H-NMR (CDCl$_3$) δ: 1.30 (3H, t, J=7.1 Hz), 3.62 (2H, q, J=7.1 Hz), 4.64 (2H, s), 7.14-7.18 (2H, m), 7.58-7.61 (2H, m), 7.80 (1H, s), 7.84 (1H, s), 7.96-7.97 (1H, m), 10.09 (1H, s).

Reference Example 196

Synthesis of 3-cyclopropyl-5-(6-trifluoromethyl-pyridin-3-yl)-benzaldehyde

The title compound was obtained using 3-bromo-5-cyclopropyl-benzaldehyde and 5-(4,4,5,5-tetramethyl-[1,3,2]dioxaborolan-2-yl)-2-trifluoromethyl-pyridine in the same manner as in Reference Example 112.

$^1$H-NMR (CDCl$_3$) δ: 0.82-0.86 (2H, m), 1.00-1.16 (2H, m), 2.05-2.11 (1H, m), 7.58 (1H, s), 7.63 (1H, s), 7.79 (1H, d, J=8.2 Hz), 7.86-7.88 (2H, m), 8.06-8.09 (1H, m), 1.07 (1H, s).

Reference Example 197

Synthesis of 3-cyclobutoxy-5-(6-trifluoromethyl-pyridin-3-yl)-benzaldehyde

The title compound was obtained using 3-bromo-5-cyclobutoxy-benzaldehyde and 5-(4,4,5,5-tetramethyl-[1,3,2]dioxaborolan-2-yl)-2-trifluoromethyl-pyridine in the same manner as in Reference Example 112.

$^1$H-NMR (CDCl$_3$) δ: 1.71-1.81 (1H, m), 1.90-1.97 (1H, m), 2.19-2.28 (2H, m), 2.50-2.58 (2H, m), 4.75-4.81 (1H, m), 7.31-7.33 (1H, m), 7.35-7.36 (1H, m), 7.66 (1H, t, J=1.5 Hz), 7.79 (1H, d, J=8.0 Hz), 8.07 (1H, dd, J=2.1, 8.2 Hz), 8.96 (1H, d, J=2.1 Hz), 10.04 (1H, s).

Reference Example 198

Synthesis of 2-ethoxy-5-(6-trifluoromethyl-pyridin-3-yl)-benzaldehyde

The title compound was obtained using 5-bromo-2-ethoxybenzaldehyde and 5-(4,4,5,5-tetramethyl-[1,3,2]dioxaborolan-2-yl)-2-trifluoromethyl-pyridine in the same manner as in Reference Example 112.

$^1$H-NMR (CDCl$_3$) δ: 1.54 (3H, t, J=7.0 Hz), 4.25 (2H, q, J=7.0 Hz), 7.14 (1H, d, J=8.8 Hz), 7.75 (1H, d, J=8.2 Hz), 7.80 (1H, dd, J=2.5, 8.8 Hz), 8.04 (1H, dd, J=2.1, 8.2 Hz), 8.09 (1H, d, J=2.5 Hz), 8.92-8.94 (1H, m), 10.56 (1H, s).

Reference Example 199

Synthesis of 4-isopropoxy-3-(6-trifluoromethyl-pyridin-3-yl)-benzaldehyde

The title compound was obtained using 3-bromo-4-isopropoxy-benzaldehyde and 5-(4,4,5,5-tetramethyl-[1,3,2]dioxaborolan-2-yl)-2-trifluoromethyl-pyridine in the same manner as in Reference Example 112.

$^1$H-NMR (CDCl$_3$) δ: 1.37 (6H, d, J=6.0 Hz), 4.74-4.80 (1H, m), 7.13 (1H, d, J=8.6 Hz), 7.75 (1H, d, J=8.1 Hz), 7.87 (1H, d, J=2.1 Hz), 7.93 (1H, dd, J=2.1, 8.6 Hz), 8.03 (1H, dd, J=2.1, 8.1 Hz), 8.92-8.93 (1H, m), 8.95 (1H, s).

Reference Example 200

Synthesis of 5-(3-fluoro-5-trifluoromethyl-phenyl)-thiophene-2-carbaldehyde

The title compound was obtained using 5-formyl-2-thiopheneboronic acid and 3-bromo-5-fluorobenzotrifluoride in the same manner as in Reference Example 112.

¹H-NMR (CDCl₃) δ: 7.36 (1H, d, J=8.1 Hz), 7.47 (1H, d, J=4.0 Hz), 7.54 (1H, d, J=9.1 Hz), 7.70 (1H, s), 7.78 (1H, d, J=4.0 Hz), 9.93 (1H, s).

Reference Example 201

Synthesis of 4-(4-trifluoromethyl-pyrimidin-2-yl)-benzaldehyde

The title compound was obtained using 4-formylphenylboronic acid and 2-chloro-4-(trifluoromethyl)pyrimidine in the same manner as in Reference Example 112.
¹H-NMR (CDCl₃) δ: 7.59 (1H, d, J=5.0 Hz), 8.03 (2H, d, J=8.1 Hz), 8.70 (2H, d, J=8.1 Hz), 9.11 (1H, d, J=5.0 Hz), 10.13 (1H, s).

Reference Example 202

Synthesis of 5'-fluoro-5-methyl-3'-trifluoromethyl-biphenyl-3-carbaldehyde

The title compound was obtained using 3-formyl-5-methylphenylboronic acid and 3-bromo-5-fluorobenzotrifluoride in the same manner as in Reference Example 112.
¹H-NMR (CDCl₃) δ: 2.53 (3H, s), 7.35 (1H, d, J=8.3 Hz), 7.50 (1H, d, J=9.3 Hz), 7.65 (2H, s), 7.75 (1H, s), 7.89 (1H, s), 10.07 (1H, s).

Reference Example 203

Synthesis of 2-(3,5-bis-trifluoromethyl-benzyl)-benzaldehyde

The title compound was obtained using 2-formylphenylboronic acid and 3,5-bis(trifluoromethyl)benzyl bromide in the same manner as in Reference Example 112.
¹H-NMR (CDCl₃) δ: 4.57 (2H, s), 7.29 (1H, d, J=7.4 Hz), 7.52-7.62 (4H, m), 7.70 (1H, s), 7.85-7.87 (1H, m), 10.11 (1H, s).

Reference Example 204

Synthesis of 3-(2,5-bis-trifluoromethyl-benzyl)-5-chloro-benzaldehyde

The title compound was obtained using 3-chloro-5-(5,5-dimethyl-[1,3,2]dioxaborinan-2-yl)-benzaldehyde and 2,5-bis(trifluoromethyl)benzyl bromide in the same manner as in Reference Example 112.
¹H-NMR (CDCl₃) δ: 4.30 (2H, s), 7.36 (1H, s), 7.44 (1H, s), 7.52 (1H, s), 7.67 (1H, d, J=8.2 Hz), 7.76 (1H, s), 7.86 (1H, d, J=8.2 Hz), 9.94 (1H, s).

Reference Example 205

Synthesis of 6-(4-fluoro-phenyl)-benzofuran-2-carbaldehyde

The title compound was obtained using 6-bromo-benzofuran-2-carbaldehyde and 4-fluorophenylboronic acid in the same manner as in Reference Example 112.

¹H-NMR (CDCl₃) δ: 7.18 (2H, t, J=8.7 Hz), 7.49-7.63 (4H, m), 7.75 (1H, s), 7.80 (1H, d, J=8.1 Hz), 9.88 (1H, s).

Reference Example 206

Synthesis of 2-((E)-styryl)-5-trifluoromethyl-benzaldehyde

The title compound was obtained using 2-bromo-5-(trifluoromethyl)benzaldehyde and trans-2-phenylvinylboronic acid in the same manner as in Reference Example 112.
¹H-NMR (CDCl₃) δ: 7.17 (1H, d, J=16 Hz), 7.37-7.46 (3H, m), 7.60-7.63 (2H, m), 7.84-7.87 (2H, m), 8.04 (1H, d, J=16 Hz), 8.13 (1H, s), 10.38 (1H, s).

Reference Example 207

Synthesis of 3-trifluoromethyl-5-(6-trifluoromethyl-pyridin-2-yl)-benzaldehyde

The title compound was obtained using 2-chloro-6-(trifluoromethyl)pyridine and 3-(4,4,5,5-tetramethyl-([1,3,2]dioxaborolan-2-yl)-5-trifluoromethyl-benzaldehyde in the same manner as in Reference Example 112.
¹H-NMR (CDCl₃) δ: 7.73-7.76 (1H, m), 8.04-8.06 (2H, m), 8.23 (1H, s), 8.61 (1H, s), 8.77 (1H, s), 10.20 (1H, s).

Reference Example 208

Synthesis of 4-[(E)-2-(3-trifluoromethyl-phenyl)-vinyl]-furan-2-carbaldehyde

The title compound was obtained using 4-bromo-2-furaldehyde and (E)-2-(3-trifluoromethylphenyl)vinylboronic acid pinacol ester in the same manner as in Reference Example 91.
¹H-NMR (CDCl₃) δ: 6.92-7.07 (2H, m), 7.47-7.53 (3H, m), 7.63 (1H, d, J=7.8 Hz), 7.71 (1H, s), 7.80 (1H, s), 9.70 (1H, s).

Reference Example 209

Synthesis of 3-[(E)-2-(2,4-difluoro-phenyl)-vinyl]-benzaldehyde

The title compound was obtained using 3-bromobenzaldehyde and 2-((E)-2-(2,4-difluorophenyl)vinyl)-4,4,5,5-tetramethyl-[1,3,2]-dioxaborolane in the same manner as in Reference Example 91.
¹H-NMR (CDCl₃) δ: 6.83-6.94 (2H, m), 7.16 (1H, d, J=16.5 Hz), 7.29 (1H, d, J=16.5 Hz), 7.53-7.61 (2H, m), 7.76-7.80 (2H, m), 8.02 (1H, s), 10.06 (1H, s).

Reference Example 210

Synthesis of 2-hydroxy-3-[(E)-2-(3-trifluoromethyl-phenyl)-vinyl]-benzaldehyde

The title compound was obtained using 3-bromo-2-hydroxybenzaldehyde and (E)-2-(3-trifluoromethylphenyl)vinylboronic acid pinacol ester in the same manner as in Reference Example 91.
¹H-NMR (CDCl₃) δ: 7.07 (1H, t, J=7.7 Hz), 7.27 (1H, d, J=16.5 Hz), 7.47-7.53 (4H, m), 7.72 (1H, d, J=7.4 Hz), 7.77 (1H, s), 7.83 (1H, dd, J=1.6, 7.7 Hz), 9.93 (1H, s), 11.6 (1H, s).

Reference Example 211

Synthesis of 5-chloro-2-[(E)-2-(3-trifluoromethyl-phenyl)-vinyl]-benzaldehyde

The title compound was obtained using 2-bromo-5-chloro-benzaldehyde and (E)-2-(3-trifluoromethylphenyl)vinylboronic acid pinacol ester in the same manner as in Reference Example 91.
$^1$H-NMR (CDCl$_3$) δ: 7.05 (1H, d, J=16.2 Hz), 7.49-7.58 (3H, m), 7.67 (1H, d, J=8.4 Hz), 7.74 (1H, s), 7.76 (1H, s), 7.82 (1H, d, J=2.3 Hz), 8.03 (1H, d, J=16.2 Hz), 10.26 (1H, s).

Reference Example 212

Synthesis of 3-chloro-5-(2,2-difluoro-benzo[1,3]dioxol-5-yl)-benzaldehyde

The title compound was obtained using 3-chloro-5-(5,5-dimethyl-[1,3,2]dioxaborinan-2-yl)-benzaldehyde and 5-bromo-2,2-difluoro-1,3-benzodioxole in the same manner as in Reference Example 91.
$^1$H-NMR (CDCl$_3$) δ: 7.15-7.18 (1H, m), 7.30-7.33 (2H, m), 7.75 (1H, s), 7.84 (1H, s), 7.90 (1H, s), 10.04 (1H, s).

Reference Example 213

Synthesis of 3-(4-trifluoromethyl-pyrimidin-2-yl)-benzaldehyde

The title compound was obtained using 3-formylphenylboronic acid and 2-chloro-4-(trifluoromethyl)pyrimidine in the same manner as in Reference Example 91.
$^1$H-NMR (CDCl$_3$) δ: 7.58-7.61 (1H, m), 7.70 (1H, t, J=7.7 Hz), 8.07-8.09 (1H, m), 8.79-8.82 (1H, m), 9.02 (1H, s), 9.10 (1H, d, J=5.0 Hz), 10.16 (1H, s).

Reference Example 214

Synthesis of 4-(3,5-bis-trifluoromethyl-phenyl)-thiophene-3-carbaldehyde

The title compound was obtained using 3-bromo-4-formylthiophene and 3,5-bis(trifluoromethyl)phenylboronic acid in the same manner as in Reference Example 91.
$^1$H-NMR (CDCl$_3$) δ: 7.41 (1H, d, J=3.2 Hz), 7.88-7.90 (3H, m), 7.31 (1H, d, J=3.2 Hz), 9.92 (1H, s).

Reference Example 215

Synthesis of 5-[(E)-2-(3-trifluoromethyl-phenyl)-vinyl]-thiophene-2-carbaldehyde The title compound was obtained using 5-bromothiophene-2-carboxaldehyde and (E)-2-(3-trifluoromethylphenyl)vinylboronic acid pinacol ester in the same manner as in Reference Example 91.
$^1$H-NMR (CDCl$_3$) δ: 7.13-7.21 (3H, m), 7.50-7.58 (2H, m), 7.66-7.70 (2H, m), 7.76 (1H, s), 9.88 (1H, s).

Reference Example 216

Synthesis of 3-chloro-5-(4-trifluoromethyl-pyrimidin-2-yl)-benzaldehyde

The title compound was obtained using 3-chloro-5-(5,5-dimethyl-[1,3,2]dioxaborinan-2-yl)-benzaldehyde and 2-chloro-4-(trifluoromethyl)pyrimidine in the same manner as in Reference Example 91.
$^1$H-NMR (CDCl$_3$) δ: 7.62 (1H, d, J=4.9 Hz), 8.00-8.04 (1H, m), 8.77-8.78 (1H, m), 8.91-8.92 (1H, m), 9.11 (1H, d, J=4.9 Hz), 10.12 (1H, s).

Reference Example 217

Synthesis of 3-chloro-5-[(E)-2-(3-trifluoromethyl-phenyl)-vinyl]-benzaldehyde

The title compound was obtained using 3-bromo-5-chloro-benzaldehyde and (E)-2-(3-trifluoromethylphenyl)vinylboronic acid pinacol ester in the same manner as in Reference Example 91.
$^1$H-NMR (CDCl$_3$) δ: 7.15 (1H, d, J=16.4 Hz), 7.23 (1H, d, J=16.4 Hz), 7.49-7.56 (2H, m), 7.59-7.78 (4H, m), 7.91 (1H, s), 10.01 (1H, s).

Reference Example 218

Synthesis of 3-(benzo[b]thiophen-3-yl)-5-chloro-benzaldehyde

The title compound was obtained using 3-bromo-5-chloro-benzaldehyde and benzothiophene-3-boronic acid in the same manner as in Reference Example 91.
$^1$H-NMR (CDCl$_3$) δ: 7.43-7.46 (2H, m), 7.52 (1H, s), 7.84-7.99 (5H, m), 10.06 (1H, s).

Reference Example 219

Synthesis of 5-[(E)-2-(3-trifluoromethyl-phenyl)-vinyl]-furan-2-carbaldehyde

The title compound was obtained using 5-bromo-2-furaldehyde and (E)-2-(3-trifluoromethylphenyl)vinylboronic acid pinacol ester in the same manner as in Reference Example 91.
$^1$H-NMR (CDCl$_3$) δ: 6.59 (1H, d, J=3.6 Hz), 7.00 (1H, d, J=16.4 Hz), 7.27 (1H, d, J=3.6 Hz), 7.41 (1H, d, J=16.4 Hz), 7.48-7.58 (2H, m), 7.66 (1H, d, J=7.6 Hz), 7.76 (1H, s), 9.63 (1H, s).

Reference Example 220

Synthesis of 3-(3,5-bis-trifluoromethyl-phenyl)-thiophene-2-carbaldehyde

The title compound was obtained using 3-bromothiophene-2-carboxaldehyde and 3,5-bis(trifluoromethyl)phenylboronic acid in the same manner as in Reference Example 91.
$^1$H-NMR (CDCl$_3$) δ: 7.27 (1H, d, J=5.0 Hz), 7.84 (1H, d, J=5.0 Hz), 7.93 (2H, s), 7.98 (1H, s), 9.84 (1H, s).

Reference Example 221

Synthesis of 2-fluoro-4-[(E)-2-(3-trifluoromethyl-phenyl)-vinyl]-benzaldehyde

The title compound was obtained using 4-bromo-2-fluorobenzaldehyde and (E)-2-(3-trifluoromethylphenyl)vinylboronic acid pinacol ester in the same manner as in Reference Example 91.
$^1$H-NMR (CDCl$_3$) δ: 6.90-7.33 (4H, m), 7.52-7.54 (1H, m), 7.55 (1H, d, J=7.8 Hz), 7.71 (1H, d, J=7.5 Hz), 7.79 (1H, s), 7.89 (1H, t, J=7.8 Hz), 10.35 (1H, s).

Reference Example 222

Synthesis of 1-(2,5-bis-trifluoromethyl-phenyl)-piperidine-4-carbaldehyde

A suspension of 4-((tetrahydro-2H-pyran-2-yloxy)methyl)piperidine (300 mg, 1.51 mmol), 2,5-bis(trifluoromethyl)bromobenzene (0.261 ml, 1.51 mmol), $Pd(OAc)_2$ (33.8 mg, 0.151 mmol), rac-BINAP (94 mg, 0.151 mmol) and tert-BuONa (730 mg, 7.60 mmol) in toluene (10 ml) was heated to 100° C. for 10 hr under argon. After the reaction mixture was allowed to cool to room temperature, the reaction mixture was filtered through a layer of Celite with AcOEt. The filtrate was concentrated in vacuo and the crude product was purified by flash chromatography on silica gel (AcOEt/hexane (0 to 7% gradient)) to give 1-(2,5-bis(trifluoromethyl)phenyl)-4-((tetrahydro-2H-pyran-2-yloxy)methyl)piperidine (251 mg, 50%) as a pale yellow oil.

$^1$H-NMR ($CDCl_3$) 1.4-1.9 (11H, m), 2.7-2.8 (2H, m), 3.1-3.2 (2H, m), 3.30 (1H, dd, J=6.3, 9.5 Hz), 3.5-3.6 (1H, m), 3.68 (1H, dd, J=6.6, 9.5 Hz), 3.85-3.95 (1H, m), 4.60 (1H, m), 7.43 (1H, d, J=8.3 Hz), 7.54 (1H, s), 7.73 (1H, d, J=8.3 Hz).

To a solution of 1-(2,5-bis(trifluoromethyl)phenyl)-4-((tetrahydro-2H-pyran-2-yloxy)methyl)piperidine (250.5 mg, 0.765 mmol) in THF (4 ml) was added 5N HCl, and the reaction mixture was stirred at room temperature for 3 hr. The reaction mixture was diluted with AcOEt and basified with 5N aqueous NaOH and saturated aqueous $NaHCO_3$ solution. The organic layer was washed twice with water, dried over anhydrous $Na_2SO_4$. The solvents were removed under reduced pressure to give a pale brown oil.

To a solution of the pale brown oil in DMSO (2 ml) was added IBX (210 mg, 0.498 mmol) and the reaction mixture was stirred at room temperature overnight. To the resulting suspension were added AcOEt and water, and the mixture was filtered through a layer of Celite with AcOEt. The organic layers were separated, and washed twice with water, dried over anhydrous $MgSO_4$. The solvents were removed under reduced pressure to give crude product as a pale brown oil. The crude material was purified by flash chromatography on silica gel (AcOEt/hexane (0 to 10% gradient)) to give the title compound (132 mg, 58%) as a colorless oil.

$^1$H-NMR ($CDCl_3$) δ: 1.8-1.95 (2H, m), 1.95-2.1 (2H, m), 2.3-2.5 (1H, m), 2.75-2.85 (2H, m), 3.1-3.2 (2H, m), 7.47 (1H, d, J=8.4 Hz), 7.54 (1H, s), 7.76 (1H, d, J=8.4 Hz), 9.73 (1H d, J=0.9 Hz).

Reference Example 223

Synthesis of 3-[(E)-2-(5-trifluoromethyl-pyridin-3-yl)-vinyl]-benzaldehyde

A reaction vessel was charged with $Pd(OAc)_2$ (0.024 g, 0.109 mmol), 3-dimethylaminopropionic acid hydrochloride (0.020 g, 0.131 mmol), $K_2CO_3$ (0.301 g, 2.179 mmol), 3-vinyl-benzaldehyde (0.144 g, 1.090 mmol), 3-bromo-5-(trifluoromethyl)pyridine (0.295 g, 1.308 mmol) and NMP (4 ml). The reaction mixture was stirred at 120° C. under argon for 9 hr. The reaction was quenched by addition of water, and then extracted with TBME (6 ml×2). The organic layer was washed with water and brine, and concentrated. The residue was purified by silica gel column chromatography (hexane/AcOEt 10%->30%) to give the title compound (250 mg, 80%) as a light yellow solid.

$^1$H-NMR ($CDCl_3$) δ: 7.22 (1H, d, J=16.4 Hz), 7.31 (1H, d, J=16.4 Hz), 7.59 (1H, t, J=7.6 Hz), 7.79-7.86 (2H, m), 8.08 (2H, s), 8.79 (1H, s), 8.93 (1H, s), 10.08 (1H, s).

Reference Example 224

Synthesis of 3-trifluoromethyl-5-[(E)-2-(6-trifluoromethyl-pyridin-2-yl)-vinyl]-benzaldehyde The title compound was obtained using 2-trifluoromethyl-6-vinyl-pyridine and 3-bromo-5-(trifluoromethyl)benzaldehyde in the same manner as in Reference Example 223.

$^1$H-NMR ($CDCl_3$) δ: 7.36 (1H, d, J=16.1 Hz), 7.60 (2H, d, J=7.7 Hz), 7.83-7.90 (2H, m), 8.08 (2H, s), 8.28 (1H, s), 10.11 (1H, s).

Reference Example 225

Synthesis of 3-[(E)-2-(5-trifluoromethyl-pyridin-2-yl)-vinyl]-benzaldehyde

The title compound was obtained using 5-trifluoromethyl-2-vinyl-pyridine and 3-bromobenzaldehyde in the same manner as in Reference Example 223.

$^1$H-NMR ($CDCl_3$) δ: 7.29 (1H, d, J=16.1 Hz), 7.59 (1H, d, J=8.3 Hz), 7.58 (1H, t, J=7.6 Hz), 7.81-7.93 (4H, m), 8.12 (1H, s), 8.87 (1H, s), 10.07 (1H, s).

Reference Example 226

Synthesis of 3-[(E)-2-(4-trifluoromethyl-pyridin-2-yl)-vinyl]-benzaldehyde

The title compound was obtained using 4-trifluoromethyl-2-vinyl-pyridine and 3-bromobenzaldehyde in the same manner as in Reference Example 223.

$^1$H-NMR ($CDCl_3$) δ: 7.30 (1H, d, J=16.1 Hz), 7.40 (1H, d, J=5.0 Hz), 7.55-7.60 (2H, m), 7.78-7.86 (3H, m), 8.11 (1H, s), 8.80 (1H, d, J=5.0 Hz), 10.07 (1H, s).

Reference Example 227

Synthesis of 3-[(E)-2-(4-trifluoromethyl-pyrimidin-2-yl)-vinyl]-benzaldehyde

The title compound was obtained using 3-bromobenzaldehyde and 4-trifluoromethyl-2-vinyl-pyrimidine in the same manner as in Reference Example 223.

$^1$H-NMR ($CDCl_3$) δ: 7.39 (1H, d, J=16.0 Hz), 7.46 (1H, d, J=5.0 Hz), 7.60 (1H, t, J=7.6 Hz), 7.88-7.91 (2H, m), 8.14-8.18 (2H, m), 8.98 (1H, d, J=5.0 Hz), 10.07 (1H, s).

Reference Example 228

Synthesis of 5-(3-fluoro-5-trifluoromethyl-phenyl)-1-methyl-1H-pyrrole-2-carbaldehyde A reaction vessel was charged with 3-bromo-5-fluorobenzotrifluoride (243 mg, 1 mmol), N-methylpyrrole-2-carboxaldehyde (218 mg, 2 mmol), AcOK (196 mg, 2 mmol), $Pd(OAc)_2$ (23 mg, 0.1 mmol) and DMA (3 ml). The reaction was carried out under microwave irradiation at 180° C. for 10 min and quenched by addition of water. The reaction mixture was extracted twice with AcOEt and the combined organic phase was washed with water, and concentrated. The residue was purified by silica gel column chromatography (hexane/AcOEt 10%->20%) to give the title compound (76 mg, 28%) as a brown oil.

$^1$H-NMR (CDCl$_3$) δ: 3.95 (3H, s), 6.37 (1H, d, J=4.1 Hz), 7.00 (1H, d, J=4.1 Hz), 7.32-7.40 (2H, m), 7.49 (1H, s), 9.63 (1H, s).

Reference Example 229

Synthesis of 3-phenoxy-5-trifluoromethyl-benzaldehyde

A suspension of 3-phenoxy-5-trifluoromethylbenzonitrile (347.8 mg, 1.32 mmol), Raney Ni (0.4 g) in 90% formic acid (3 ml) was heated to 100° C. for 1.5 hr. The reaction mixture was allowed to cool to room temperature. The reaction mixture was diluted with AcOEt and filtered through a layer of Celite. The filtrate was washed three times with water, and then dried over anhydrous Na$_2$SO$_4$. The solvents were removed under reduced pressure, and the resulting crude product was purified by flash chromatography on silica gel (AcOEt/hexane (0 to 30% gradient)) to give the title compound (307 mg, 87%) as a colorless oil.

$^1$H-NMR (CDCl$_3$) δ: 7.05-7.09 (2H, m), 7.22-7.26 (1H, m), 7.40-7.45 (2H, m), 7.50 (1H, s), 7.60 (1H, s), 7.83 (1H, s), 9.99 (1H, s).

Reference Example 230

Synthesis of 3-(thiophen-3-yl)-5-trifluoromethyl-benzaldehyde

The title compound was obtained using 3-(thiophen-3-yl)-5-trifluoromethyl-benzonitrile in the same manner as in Reference Example 229.

$^1$H-NMR (CDCl$_3$) δ: 7.46 (1H, dd, J=1.5, 5.0 Hz), 7.48 (1H, dd, J=3.0, 5.0 Hz), 7.64 (1H, dd, J=1.5, 3.0 Hz), 8.05 (1H, s), 8.08 (1H, s), 8.27 (1H, s), 10.12 (1H, s).

Reference Example 231

Synthesis of 3-(benzofuran-2-yl)-4-fluoro-benzaldehyde

The title compound was obtained using 3-bromo-4-fluorobenzaldehyde and benzo[b]furan-2-boronic acid in the same manner as in Reference Example 91.

$^1$H-NMR (CDCl$_3$) δ: 7.27-7.40 (4H, m), 7.57 (1H, d, J=7.7 Hz), 7.65 (1H, d, J=7.2 Hz), 7.86-7.91 (1H, m), 8.60 (1H, dd, J=2.1, 7.2 Hz), 10.08 (1H, s).

Reference Example 232

Synthesis of 3-methyl-4-(3-trifluoromethyl-benzyl)-benzaldehyde

The title compound was obtained using 4-(5,5-dimethyl-[1,3,2]dioxaborinan-2-yl)-3-methyl-benzaldehyde and 3-(trifluoromethyl)benzyl bromide in the same manner as in Reference Example 91.

$^1$H-NMR (CDCl$_3$) δ: 2.32 (3H, s), 4.11 (2H, s), 7.23-7.30 (2H, m), 7.37-7.44 (2H, m), 7.46-7.52 (1H, m), 7.66-7.73 (2H, m), 9.98 (1H, s).

Reference Example 233

Synthesis of 3-tert-butyl-5-(5-trifluoromethyl-pyridin-2-yl)-benzaldehyde

The title compound was obtained using 3-tert-butyl-5-(4,4,5,5-tetramethyl-[1,3,2]dioxaborolan-2-yl)-benzaldehyde and 2-chloro-5-(trifluoromethyl)pyridine in the same manner as in Reference Example 91.

$^1$H-NMR (CDCl$_3$) δ: 1.45 (9H, s), 7.93 (1H, d, J=8.1 Hz), 8.02-8.04 (2H, m), 8.32 (1H, s), 8.40-8.42 (1H, m), 8.99 (1H, s), 10.12 (1H, s).

Reference Example 234

Synthesis of 1-(2,5-bis-trifluoromethyl-phenyl)-1H-pyrrole-3-carbaldehyde

To a solution of 241 mg of 2,5-bis(trifluoromethyl)aniline in 1 ml of AcOH was added 160 mg of 2,5-dimethoxy-3-tetrahydrofurancarboxaldehyde and the reaction mixture was stirred at 90° C. for 2 hr. The reaction was quenched by addition of water, and the mixture was extracted with AcOEt. The organic solution was washed with water and 5 wt % NaHCO$_3$ aqueous solution, and concentrated to give the title compound (318 mg, quant.) as a brown oil.

$^1$H-NMR (CDCl$_3$) δ: 6.82-6.88 (2H, m), 7.46 (1H, s), 7.72 (1H, s), 7.89 (1H, d, J=8.2 Hz), 8.00 (1H, d, J=8.2 Hz), 9.87 (1H, s).

Reference Example 235

Synthesis of 3-methyl-5-(4-trifluoromethyl-pyrimidin-2-yl)-benzaldehyde

The title compound was obtained using 3-formyl-5-methylphenylboronic acid and 2-chloro-4-(trifluoromethyl)pyrimidine in the same manner as in Reference Example 91

$^1$H-NMR (CDCl$_3$) δ: 2.56 (3H, s), 7.58 (1H, d, J=5.0 Hz), 7.89 (1H, s), 8.61 (1H, s), 8.82 (1H, s), 9.09 (1H, d, J=5.0 Hz), 10.13 (1H, s).

Reference Example 236

Synthesis of 2-(4-chloro-phenyl)-5-propyl-oxazole-4-carboxylic Acid methyl ester The title compound was obtained using methyl 3-oxohexanoate and 4-chlorobenzylamine in the same manner as in Reference Example 133.

$^1$H NMR (CDCl$_3$) δ: 1.03 (3H, t, J=7.5 Hz), 1.76-1.83 (2H, m), 3.09 (2H, t, J=7.6 Hz), 3.94 (3H, s), 7.43-7.46 (2H, m), 8.00-8.03 (2H, m).

Reference Example 237

Synthesis of [2-(4-chloro-phenyl)-5-propyl-oxazol-4-yl]-methanol

The title compound was obtained using 2-(4-chloro-phenyl)-5-propyl-oxazole-4-carboxylic acid methyl ester in the same manner as in Reference Example 19.

$^1$H NMR (CDCl$_3$) δ: 0.99 (3H, t, J=7.4 Hz), 1.66-1.78 (2H, m), 2.71 (2H, t, J=7.4 Hz), 3.00 (1H, t, J=6.0 Hz), 4.59 (2H, d, J=6.0 Hz), 7.39-7.42 (2H, m), 7.91-7.94 (2H, m).

Reference Example 238

Synthesis of 2-(4-chloro-phenyl)-5-propyl-oxazole-4-carbaldehyde

The title compound was obtained using [2-(4-chloro-phenyl)-5-propyl-oxazol-4-yl]-methanol in the same manner as in Reference Example 147.

$^1$H NMR (CDCl$_3$) δ: 1.04 (3H, t, J=7.4 Hz), 1.77-1.87 (2H, m), 3.07 (2H, t, J=7.5 Hz), 7.45-7.47 (2H, m), 7.99-8.01 (2H, m), 10.02 (1H, s).

Reference Example 239

Synthesis of [2-(4-chloro-phenyl)-5-cyclopropyl-thiazol-4-yl]-methanol

The title compound was obtained using [5-bromo-2-(4-chloro-phenyl)-thiazol-4-yl]-methanol and cyclopropylboronic acid in the same manner as in Reference Example 38.

$^1$H NMR (CDCl$_3$) δ: 0.72-0.77 (2H, m), 1.08-1.15 (2H, m), 2.00-2.07 (1H, m), 2.44 (1H, t, J=5.8 Hz), 4.81 (2H, d, J=5.8 Hz), 7.36-7.40 (2H, m), 7.77-7.80 (2H, m).

Reference Example 240

Synthesis of 2-(4-chloro-phenyl)-5-cyclopropyl-thiazole-4-carbaldehyde

The title compound was obtained using [2-(4-chloro-phenyl)-5-cyclopropyl-thiazol-4-yl]-methanol in the same manner as in Reference Example 48.

$^1$H NMR (CDCl$_3$) δ: 0.85-0.90 (2H, m), 1.34-1.45 (2H, m), 3.07-3.15 (1H, m), 7.40-7.43 (2H, m), 7.80-7.40 (2H, m), 10.22 (1H, s).

Reference Example 241

Synthesis of [5-methyl-2-(4-trifluoromethoxy-phenoxy)-thiazol-4-yl]-methanol

The title compound was obtained using [5-bromo-2-(4-chloro-phenyl)-thiazol-4-yl]-methanol and methylboronic acid in the same manner as in Reference Example 38.

$^1$H NMR (CDCl$_3$) δ: 2.01 (1H, t, J=6.1 Hz), 2.34 (3H, s), 4.51 (2H, d, J=6.1 Hz), 7.28-7.36 (4H, m).

Reference Example 242

Synthesis of 5-methyl-2-(4-trifluoromethoxy-phenoxy)-thiazole-4-carbaldehyde

The title compound was obtained using [5-methyl-2-(4-trifluoromethoxy-phenoxy)-thiazol-4-yl]-methanol in the same manner as in Reference Example 48.

$^1$H NMR (CDCl$_3$) δ: 2.72 (3H, s), 7.26-7.38 (4H, m), 9.90 (1H, s).

Reference Example 243

Synthesis of 2-(4-chloro-phenyl)-5-isopropyl-oxazole-4-carboxylic Acid methyl ester The title compound was obtained using methyl isobutyrylacetate and 4-chlorobenzylamine in the same manner as in Reference Example 133.

$^1$H NMR (CDCl$_3$) δ: 1.36 (6H, d, J=7.2 Hz), 3.80-3.89 (1H, m), 3.94 (3H, s), 7.42-7.44 (2H, m), 7.99-8.02 (2H, m).

Reference Example 244

Synthesis of [2-(4-chloro-phenyl)-5-isopropyl-oxazol-4-yl]-methanol

The title compound was obtained using 2-(4-chloro-phenyl)-5-isopropyl-oxazole-4-carboxylic acid methyl ester in the same manner as in Reference Example 19.

$^1$H NMR (CDCl$_3$) δ: 1.34 (6H, d, J=7.2 Hz), 2.65 (1H, t, J=6.0 Hz), 3.13-3.22 (1H, m), 4.61 (2H, d, J=6.0 Hz), 7.40-7.43 (2H, m), 7.92-7.95 (2H, m).

Reference Example 245

Synthesis of 2-(4-chloro-phenyl)-5-isopropyl-oxazole-4-carbaldehyde

The title compound was obtained using [2-(4-chloro-phenyl)-5-isopropyl-oxazol-4-yl]-methanol in the same manner as in Reference Example 147.

$^1$H NMR (CDCl$_3$) δ: 1.41 (6H, d, J=6.9 Hz), 3.65-3.74 (1H, m), 7.44-7.49 (2H, m), 7.98-8.02 (2H, m), 10.04 (1H, s).

Reference Example 246

Synthesis of 5-ethyl-2-(3-trifluoromethyl-phenyl)-thiazole-4-carboxylic Acid methyl ester The title compound was obtained using 3-trifluoromethyl-thiobenzamide and 3-bromo-2-oxo-pentanoic acid methyl ester in the same manner as in Reference Example 2.

$^1$H NMR (CDCl$_3$) δ: 1.40 (3H, t, J=7.5 Hz), 3.33 (2H, q, J=7.5 Hz), 3.98 (3H, s), 7.57 (1H, t, J=7.8 Hz), 7.68 (1H, d, J=7.8 Hz), 8.11 (1H, d, J=7.8 Hz), 8.19 (1H, s).

Reference Example 247

Synthesis of 5-ethyl-2-(3-trifluoromethyl-phenyl)-thiazole-4-carbaldehyde

The title compound was obtained using 5-ethyl-2-(3-trifluoromethyl-phenyl)-thiazole-4-carboxylic acid methyl ester in the same manner as in Reference Example 63.

$^1$H NMR (CDCl$_3$) δ: 1.40 (3H, t, J=7.5 Hz), 3.34 (2H, q, J=7.5 Hz), 7.59 (1H, t, J=7.8 Hz), 7.71 (1H, d, J=7.8 Hz), 8.11 (1H, d, J=7.8 Hz), 8.21 (1H, s), 10.22 (1H, s).

Reference Example 248

Synthesis of 2-(3,4-difluoro-phenyl)-5-isobutyl-oxazole-4-carboxylic Acid methyl ester The title compound was obtained using 5-methyl-3-oxo-hexanoic acid methyl ester and 3,4-difluorobenzylamine in the same manner as in Reference Example 133.

¹H NMR (CDCl₃) δ: 1.00 (3H, s), 1.02 (3H, s), 2.10-2.19 (1H, m), 3.00 (2H, d, J=7.2 Hz), 3.95 (3H, s), 7.22-7.29 (1H, m), 7.81-7.86 (1H, m), 7.87-7.92 (1H, m).

Reference Example 249

Synthesis of 2-(3,4-difluoro-phenyl)-5-isobutyl-oxazole-4-carbaldehyde

The title compound was obtained using 2-(3,4-difluoro-phenyl)-5-isobutyl-oxazole-4-carboxylic acid methyl ester in the same manner as in Reference Example 63.
¹H NMR (CDCl₃) δ: 1.02 (3H, s), 1.03 (3H, s), 2.13-2.20 (1H, m), 2.97 (2H, d, J=7.1 Hz), 7.27-7.31 (1H, m), 7.81-7.91 (2H, m), 10.00 (1H, s).

Reference Example 250

Synthesis of 2-(4-trifluoromethoxy-phenoxy)-thiazole-4-carboxylic Acid ethyl ester The title compound was obtained using 2-bromo-thiazole-4-carboxylic acid ethyl ester and 4-(trifluoromethoxy)phenol in the same manner as in Reference Example 9.
¹H NMR (CDCl₃) δ: 1.38 (3H, t, J=7.1 Hz), 4.38 (2H, q, J=7.1 Hz), 7.26-7.29 (2H, m), 7.35-7.38 (2H, m), 7.75 (1H, s).

Reference Example 251

Synthesis of [2-(4-trifluoromethoxy-phenoxy)-thiazol-4-yl]-methanol

The title compound was obtained using 2-(4-trifluoromethoxy-phenoxy)-thiazole-4-carboxylic acid ethyl ester in the same manner as in Reference Example 19.
¹H NMR (CDCl₃) δ: 2.00 (1H, t, J=6.2 Hz), 4.59 (2H, d, J=6.2 Hz), 6.73 (1H, s), 7.23-7.34 (4H, m).

Reference Example 252

Synthesis of [5-bromo-2-(4-trifluoromethoxy-phenoxy)-thiazol-4-yl]-methanol

The title compound was obtained using [2-(4-trifluoromethoxy-phenoxy)-thiazol-4-yl]-methanol in the same manner as in Reference Example 27.
¹H NMR (CDCl₃) δ: 2.06 (1H, t, J=6.3 Hz), 4.55 (2H, d, J=6.3 Hz), 7.24-7.33 (4H, m).

Reference Example 318

Synthesis of (E)-3-[2,5-bis(trifluoromethyl)-phenyl]-prop-2-en-1-ol

To a solution of (E)-3-(2,5-bis-trifluoromethyl-phenyl)-acrylic acid ethyl ester (1.79 g, 5.74 mmol) in CH₂Cl₂ (35 ml) was added diisobutylaluminium hydride (0.94M in hexane) (13.4 ml, 12.6 mmol) at −30° C. under argon. After the reaction mixture was stirred at the same temperature for 45 min, methanol was added thereto in order to decompose the excess diisobutylaluminium hydride. Water, CH₂Cl₂ and Celite were added to the reaction mixture, and the mixture was filtered through a pad of Celite. The filtrate was extracted twice with CH₂Cl₂. The organic layer was washed with water and brine, dried over Na₂SO₄, and concentrated in vacuo to give the title compound (1.56 g, 100%).
¹H-NMR (CDCl₃) δ: 4.40-4.42 (2H, m), 6.41-6.47 (1H, m), 7.00-7.05 (1H, m), 7.61 (1H, d, J=8.2 Hz), 7.77 (1H, d, J=8.2 Hz), 7.87 (1H, s).

Reference Example 323

Synthesis of 5-phenoxy-2-phenyl-benzaldehyde

To a solution of 2-methyl-4-phenoxy-biphenyl (105.4 mg, 0.405 mmol) in CCl₄ (2 ml) were added NBS (180 mg, 1.0 mmol) and 2,2'-azodiisobutyronitrile (catalytic amount). After being stirred for 2 hr under reflux, the reaction mixture was cooled and filtrated. The filtrate was concentrated in vacuo to give a colorless oil. To a solution of the oil in 2-butanone (4 ml) and water (2 ml) was added silver nitrate (200 mg, 1.18 mmol). After being stirred for 1 hr under reflux, the reaction mixture was cooled, and extracted with AcOEt. The organic layer was washed with water, dried over anhydrous Na₂SO₄, and then concentrated in vacuo. The obtained residue was purified by TLC (AcOEt/hexane=1/20) to give the title compound (94.2 mg, 85%) as a colorless oil.
¹H-NMR (CDCl₃) δ: 7.06-7.10 (2H, m), 7.15-7.20 (1H, m), 7.30 (1H, dd, J=2.8, 8.4 Hz), 7.35-7.50 (8H, m), 7.59 (1H, d, J=2.7 Hz), 9.93 (1H, s).

Reference Example 342

Synthesis of 4-[2,5-bis(trifluoromethyl)-phenyl]-but-3-yn-1-ol

To a solution of 2,5-bis(trifluoromethyl)bromobenzene (2.0 g, 6.83 mmol) in THF (20 ml) were added 3-butyn-1-ol (0.62 ml, 8.19 mmol), PdCl₂(PPh₃)₂ (0.19 g, 0.273 mmol), Et₃N (1.90 ml, 13.7 mmol) and CuI (26 mg, 0.137 mmol). After the reaction mixture was refluxed for 2.5 hr, it was filtered through a pad of Celite. The filtrate was concentrated in vacuo and the residue was purified by silica gel column chromatography (hexane/AcOEt=9:1-4:1) to give the title compound (1.49 g, 77%).
¹H-NMR (CDCl₃) δ: 1.80 (1H, t, J=6.4 Hz), 2.75 (2H, t, J=6.2 Hz), 3.84-3.88 (2H, m), 7.63 (1H, d, J=8.2 Hz), 7.77 (1H, d, J=8.2 Hz), 7.82 (1H, s).

Reference Example 484

Synthesis of (E)-3-[3-[[2,5-bis(trifluoromethyl)-phenyl]-methoxy]-phenyl]-acrylaldehyde To a solution of 3-(2,5-bis-trifluoromethyl-benzyloxy)-benzaldehyde (1.00 g, 2.87 mmol) in toluene (20 ml) was added (triphenylphosphoranylidene)acetaldehyde (1.05 g, 3.45 mmol) and the reaction mixture was stirred at 100° C. overnight. The reaction mixture was concentrated in vacuo. The residue was purified by silica gel column chromatography (hexane/AcOEt=10:1-9:1) to give the title compound (0.49 g, 45%).
¹H-NMR (CDCl₃) δ: 5.33 (2H, s), 6.67-7.08 (1H, m), 7.09-7.23 (3H, m), 7.37-7.49 (2H, m), 7.73 (1H, d, J=8.3 Hz), 7.86 (1H, d, J=8.3 Hz), 8.08 (1H, s), 9.72 (1H, d, J=7.7 Hz).

Reference Example 597

Synthesis of 3-bromo-5-fluoro-phenol

To a solution of 3-bromo-5-fluoroanisole (7.0 g, 36.6 mmol) in AcOH (35 ml) was added 47% HBr aq. (35 ml).

The reaction mixture was stirred at 120° C. for 23.5 hr. The reaction was quenched by addition of water and AcOEt. After neutralized with saturated aqueous NaHCO$_3$ solution, the reaction mixture was extracted with AcOEt. The combined organic layers were washed with water and brine, dried over Na$_2$SO$_4$, and concentrated in vacuo. The obtained residue was purified by silica gel column chromatography (hexane/AcOEt-9/1) to give the title compound (7.69 g, quant.) as a pale yellow oil.

$^1$H-NMR (CDCl$_3$) δ: 6.11 (1H, brs), 6.53 (1H, dt, J=2.2, 10.0 Hz), 6.79-6.84 (2H, m).

Reference Example 600

Synthesis of [3,4-bis(trifluoromethyl)-phenyl]-methanol

To a solution of 3,4-bis(trifluoromethyl)benzoic acid (1.00 g, 3.87 mmol) in THF (20 ml) at 0° C. was added BH$_3$ THF complex (1.0M THF solution, 8.44 ml, 8.44 mmol). The reaction mixture was stirred at room temperature for 3 hr. The reaction was quenched by addition of 1N HCl aq. at 0° C., and the reaction mixture was extracted with AcOEt. The combined organic layers were washed with water and brine, dried over Na$_2$SO$_4$, and concentrated in vacuo. The obtained residue was purified by silica gel column chromatography (hexane/AcOEt=3/1) to give the title compound (820 mg, 87%) as a pale yellow oil.

$^1$H-NMR (CDCl$_3$) δ: 1.99 (1H, brs), 4.85 (2H, s), 7.67-7.69 (1H, m), 7.83-7.86 (2H, m).

Reference Example 618

Synthesis of 3-(difluoro-methoxy)-5-([1,3]dioxolan-2-yl)-phenol

To a solution of 2-(3-difluoromethoxy-5-[1,3]dioxolan-2-yl-phenyl)-5,5-dimethyl-[1,3,2]dioxaborinane (3.84 g, 11.7 mmol) in THF (40 ml) were added 3N NaOH (11.7 ml, 35.1 mmol) and 30% H$_2$O$_2$ (11.7 ml) at 0° C. After the reaction mixture was stirred at 0° C. for 30 min, it was warmed to room temperature and stirring was continued for 1 hr. The reaction mixture was acidified with 5N HCl, and extracted twice with AcOEt. The organic layer was washed with brine, dried over MgSO$_4$, and concentrated in vacuo to give the crude product of the title compound (3.73 g). This product was used in the next step without purification.

Reference Example 643

Synthesis of 3-(tetrahydro-pyran-2-yloxy)-adamantane-1-carboxylic Acid ethyl ester To a solution of 3-hydroxy-adamantane-1-carboxylic acid (1.0 g, 5.10 mmol) in DMF (10 ml) were added K$_2$CO$_3$ (1.0 g, 6.25 mmol) and iodoethane (0.6 ml, 6.58 mmol). After being stirred at room temperature for 3 days and at 60° C. for 1 hr, the reaction mixture was cooled and filtrated. The filtrate was concentrated in vacuo to give a colorless oil. To a solution of the oil in CH$_2$Cl$_2$ (20 ml) were added 3,4-dihydro-2H-pyran (0.6 ml, 6.58 mmol) and pyridinium p-toluensulfonate (catalytic amount). After the reaction mixture was stirred at room temperature for 5 hr, Et$_3$N (0.1 ml) was added to the reaction mixture. The reaction mixture was concentrated in vacuo. The obtained residue was purified by silica gel column chromatography (AcOEt/hexane=1/20) to give the title compound (1.26 g, 80%) as a colorless oil.

$^1$H-NMR (CDCl$_3$) δ: 1.24 (3H, t, J=7.1 Hz), 1.45-2.04 (18H, m), 2.21-2.28 (2H, m), 3.38-3.51 (1H, m), 3.89-4.01 (1H, m), 4.11 (2H, q, J=7.1 Hz), 4.82-4.93 (1H, m).

Reference Example 742

Synthesis of 2-phenyl-4-(phenylmethoxy-methyl)-pyrimidine

A mixture of 4-(benzyloxymethyl)-6-chloro-2-phenylpyrimidine (1.61 g, 5.18 mmol), AcONa (0.85 g, 10.36 mmol) and 10% Pd on carbon (160 mg) in DMF (20 ml) under hydrogen was stirred at room temperature for 45 min. The reaction mixture was filtered through a celite pad. To the filtrate was added water and the reaction mixture was extracted with AcOEt. The combined organic layers were washed with water and brine, dried over Na$_2$SO$_4$, and concentrated in vacuo. The obtained residue was triturated with hexane/EtOH to give the title compound (0.91 g, 64%) as a pale yellow powder.

$^1$H-NMR (CDCl$_3$) δ: 4.71 (2H, s), 4.73 (2H, s), 7.30-7.45 (6H, m), 7.46-7.53 (3H, m), 8.39-8.45 (2H, m), 8.79 (18, d, J=5.1 Hz).

Reference Example 750

Synthesis of (2-phenyl-pyrimidin-4-yl)-methanol

To a solution of 2-phenyl-4-(phenylmethoxy-methyl)-pyrimidine (0.90 g, 3.26 mmol) in CH$_2$Cl$_2$ (18 ml) at −10° C. was added BBr$_3$ (1.0M CH$_2$Cl$_2$ solution, 3.91 ml, 3.91 mmol). The reaction mixture was stirred at −10° C. for 0.5 hr. The reaction was quenched by addition of saturated aqueous NaHCO$_3$ solution and the reaction mixture was extracted with AcOEt. The combined organic layers were washed with water and brine, and dried over Na$_2$SO$_4$. The solution was purified by silica gel column chromatography (MeOH/CH$_2$Cl$_2$=0% to 5%) to give the title compound (0.38 g, 63%) as a yellow powder.

$^1$H-NMR (CDCl$_3$) δ: 3.72 (1H, t, J=5.1 Hz), 4.82 (2H, d, J=5.1 Hz), 7.18 (1H, dd, J=0.7, 5.1 Hz), 7.49-7.53 (3H, m), 8.43-8.49 (2H, m), 8.76 (1H, d, J=5.1 Hz).

Reference Example 760

Synthesis of 6-(phenylmethoxy-methyl)-2-[4-(trifluoromethyl)-phenyl]-3H-pyrimidin-4-one A mixture of 4-(trifluoromethyl)benzamidine hydrochloride (1.20 g, 4.60 mmol), ethyl 4-(benzyloxy)-3-oxobutanoate (1.09 g, 4.60 mmol) and 28% sodium methoxide (1.83 ml, 9.21 mmol) in MeOH (10 ml) was heated under reflux for 18 hr. After cooling to room temperature, the reaction mixture was concentrated in vacuo. To the residue was added water, and then the mixture was acidified with AcOH (pH=4). The resulting precipitate was filtered, and washed with water. The solid was triturated with isopropyl ether to give the title compound (1.21 g, 73%) as a beige powder.

$^1$H-NMR (CDCl$_3$) δ: 4.54 (2H, d, J=1.2 Hz), 4.72 (2H, s), 6.75 (1H, t, J=1.2 Hz), 7.31-7.45 (5H, m), 7.80-7.82 (2H, m), 8.33-8.36 (2H, m), 13.24 (1H, brs).

Reference Example 825

Synthesis of 3-[(E)-2-(2,2-difluoro-1,3-benzodioxol-5-yl)-vinyl]-benzaldehyde

To a solution of 3-vinyl-benzaldehyde (0.35 g, 2.65 mmol) in NMP (5.3 ml) were added 5-bromo-2,2-difluoro- 1,3-benzodioxole (0.63 g, 2.65 mmol), Pd(OAc)$_2$ (30 mg, 0.133 mmol), K$_2$CO$_3$ (0.73 g, 5.30 mmol) and N, N-dimethylglycine (14 mg, 0.133 mmol). After the reaction mixture was stirred at 100° C. overnight under argon, it was quenched by the addition of water and extracted with AcOEt. The organic layer was washed with water and brine, dried over Na$_2$SO$_4$, and concentrated in vacuo. The residue was purified by silica gel column chromatography (hexane/AcOEt=10:0-9:1) to give the title compound (563 mg, 74%).
$^1$H-NMR (CDCl$_3$) δ: 7.05 (1H, t, J=8.1 Hz), 7.13-7.22 (3H, m), 7.28 (1H, s), 7.54 (1H, t, J=7.6 Hz), 7.73-7.80 (2H, m), 8.02 (1H, s), 10.06 (1H, s).

Reference Example 831

Synthesis of 4-chloro-6-(phenylmethoxy-methyl)-2-[4-(trifluoromethyl)-phenyl]-pyrimidine A mixture of 6-(phenylmethoxy-methyl)-2-[4-(trifluoromethyl)-phenyl]-3H-pyrimidin-4-one (0.90 g, 2.50 mmol) and POCl$_3$ (0.70 ml, 7.49 mmol) in CH$_3$CN (18 ml) was stirred at 80° C. for 3 hr. After cooling to room temperature, the reaction mixture was poured into water, and extracted with AcOEt. The combined organic layers were washed with water and brine, dried over Na$_2$SO$_4$, and concentrated in vacuo to give the title compound (0.79 g, 84%) as a yellow oil.
$^1$H-NMR (CDCl$_3$) δ: 4.68-4.72 (4H, m), 7.09-7.23 (2H, m), 7.29-7.43 (3H, m), 7.53-7.54 (1H, m), 7.71-7.76 (2H, m), 8.52-8.59 (2H, m).

Reference Example 916

Synthesis of methyl 4-[bis(tert-butoxycarbonyl)amino]-3-bromobenzoate

To a solution of methyl 4-amino-3-bromobenzoate (1.00 g, 4.35 mmol) in THF (20 ml) were added di-tert-butyl dicarbonate (7.27 ml, 31.3 mmol) and N,N-dimethyl-4-aminopyridine (0.053 g, 0.435 mmol). After being stirred at room temperature for 8 hr, the reaction mixture was concentrated in vacuo. The residue was purified by flash column chromatography (AcOEt/hexane=20% to 50%) to give a white solid. The suspension of the obtained residue in hexane was filtrated to give the title compound (1.45 g, 78%) as a white powder.
$^1$H-NMR (CDCl$_3$) δ: 1.39 (18H, s), 3.94 (3H, s), 7.29 (1H, d, J=8.2 Hz), 7.99 (1H, dd, J=1.9, 8.2 Hz), 8.29 (1H, d, J=1.9 Hz).

Reference Example 924

Synthesis of 3-bromo-4-(tert-butoxycarbonylamino)-benzoic Acid

To a solution of methyl 4-(bis(tert-butoxycarbonyl)amino)-3-bromobenzoate (1.451 g, 3.37 mmol) in MeOH (30 ml) was added 1N NaOH (10.12 ml, 10.12 mmol). The reaction mixture was stirred at room temperature overnight, then at 50° C. for 1 hr. After acidified with 1N HCl, the reaction mixture was extracted with AcOEt. The organic layer was washed with brine, dried over anhydrous MgSO$_4$ and then concentrated in vacuo to give the title compound (927 mg, 87%) as a pale yellow solid.
$^1$H-NMR (DMSO-d$_6$) δ: 1.48 (9H, s), 7.78 (1H, d, J=8.5 Hz), 7.89 (1H, dd, J=1.9, 8.5 Hz), 8.08 (1H, d, J=1.9 Hz), 8.66 (1H, s), 13.14 (1H, brs).

Reference Example 934

Synthesis of (2-bromo-4-hydroxymethyl-phenyl)-carbamic Acid tert-butyl ester

To a solution of 3-bromo-4-(tert-butoxycarbonylamino)benzoic acid (927 mg, 2.93 mmol) in THF (20 ml) were added Et$_3$N (0.49 ml, 3.52 mmol) and ethyl chlorocarbonate (0.308 ml, 3.23 mmol) at 0° C. After being stirred at 0° C. for 30 min, the precipitate was filtrated off. To the filtrate was added a solution of NaBH$_4$ (333 mg, 8.80 mmol) in H$_2$O (4 ml) at 0° C. After being stirred at 0° C. for 1 hr, the reaction mixture was concentrated in vacuo. Water was added to the reaction mixture. The reaction mixture was extracted with AcOEt. The organic layer was washed with brine, dried over anhydrous MgSO$_4$, and then concentrated in vacuo to give the title compound (937 mg, quant.) as a pale yellow oil.
$^1$H-NMR (CDCl$_3$) δ: 1.53 (9H, s), 1.53-1.56 (1H, m), 4.62 (2H, s), 6.99 (1H, brs), 7.24-7.28 (1H, m), 7.55 (1H, d, J=2.0 Hz), 8.13 (1H, d, J=8.5 Hz).

Reference Example 935

Synthesis of N-[4-formyl-2-[3-(trifluoromethyl)phenyl]-phenyl]-N-methyl-acetamide To a solution of 6-(methylamino)-3'-(trifluoromethyl)biphenyl-3-carbaldehyde (46 mg, 0.165 mmol) in CH$_2$Cl$_2$ (4 ml) were added pyridine (0.054 ml, 0.658 mmol) and acetyl chloride (0.128 ml, 1.79 mmol) at room temperature overnight. Water was added to the reaction mixture. The reaction mixture was extracted with CH$_2$Cl$_2$. The organic layer was washed with 1N HCl and brine, dried over anhydrous MgSO$_4$, and then concentrated in vacuo. The residue was purified by flash column chromatography (AcOEt/hexane=40% to 75%) to give the title compound (21 mg, 39%) as a colorless oil.
$^1$H-NMR (CDCl$_3$) δ: 1.82 (3H, s), 3.04 (3H, s), 7.49-8.01 (7H, m), 10.11 (1H, s).

Reference Example 1014

Synthesis of 1-(3,4-difluoro-phenyl)-2,3-dihydro-1H-indole-4-carboxylic Acid methyl ester To a solution of 1-(3,4-difluoro-phenyl)-1H-indole-4-carboxylic acid methyl ester (0.20 g, 0.696 mmol) in TFA (2 ml) was added triethylsilane (0.1 ml, 0.63 mmol). The reaction mixture was stirred at room temperature for 3 days. To a reaction mixture was added triethylsilane (0.2 ml). After being stirred for 3 hr at 50° C., the reaction mixture was cooled, washed with water and saturated aqueous NaHCO$_3$ solution, dried over anhydrous Na$_2$SO$_4$, and then concentrated in vacuo. The obtained residue was purified by crystallization (hexane) to give the title compound (176 mg, 88%) as a white solid.
$^1$H-NMR (CDCl$_3$) δ: 3.51 (2H, t, J=8.5 Hz), 3.91 (3H, s), 3.94 (2H, t, J=8.5 Hz), 6.87-6.96 (1H, m), 7.05 (1H, ddd, J=2.8, 6.8, 12.4 Hz), 7.09-7.12 (3H, m), 7.40 (1H, dd, J=2.2, 6.8 Hz).

Reference Example 1123

Synthesis of 2-(4-chlorophenyl)-4-(trifluoromethyl)-thiazole-5-carboxylic Acid ethyl ester To a solution of ethyl 2-chloro-3-keto-4,4,4-trifluorobutyrate (200 mg, 0.915 mmol) in EtOH (4 ml) was added 4-chlorothiobenzamide (157 mg, 0.915 mmol). After being stirred at reflux temperature for 8 hr, the reaction mixture was concentrated in vacuo. The residue was purified by flash column chromatography (AcOEt/hexane=10% to 33%). To the obtained residue in EtOH (4 ml) was added p-toluenesulfonic acid monohydrate (17 mg, 0.092 mmol). After being stirred at reflux temperature for 16 hr, the reaction mixture was concentrated in vacuo. The residue was purified by flash column chromatography (AcCEt/hexane=10% to 33%) to give the title compound (101 mg, 33%) as a white powder.
$^1$H-NMR (CDCl$_3$) δ: 1.41 (3H, t, J=7.1 Hz), 4.42 (2H, q, J=7.2 Hz), 7.44-7.49 (2H, m), 7.91-7.96 (2H, m).

Reference Example 1173

Synthesis of 2-(morpholin-4-yl)-thiazole-4-carboxylic Acid ethyl ester

To a solution of ethyl 2-bromothiazole-4-carboxylate (200 mg, 0.847 mmol) in DMF (3 ml) was added morpholine (369 mg, 4.24 mmol). After the reaction mixture was stirred at 100° C. for 4 hr, water was added thereto. The reaction mixture was extracted with AcOEt. The organic layer was washed with brine, dried over anhydrous MgSO$_4$, and then concentrated in vacuo to give the title compound (186 mg, 91%) as a pale yellow solid.
$^1$H-NMR (CDCl$_3$) δ: 1.37 (3H, t, J=7.1 Hz), 3.51-3.54 (4H, m), 3.79-3.83 (4H, m), 4.36 (2H, q, J=7.1 Hz), 7.48 (1H, s).

Reference Example 1319

Synthesis of 5-fluoro-2-iodo-3-methyl-benzo[b]thiophene

To a solution of 5-fluoro-3-methylbenzo[b]thiophene (942 mg, 5.67 mmol) in THF (35 ml) was added n-butyllithium (3.97 ml, 6.23 mmol, 1.57 M in n-hexane) at −78° C. under argon. After the solution was stirred at −78° C. for 2 hr, iodine (1582 mg, 6.23 mmol) in THF (10 ml) was added to the reaction mixture. The resulting solution was stirred at 0° C. for 1 h. The reaction mixture was quenched with saturated aqueous solution of Na$_2$S$_2$O$_4$ and extracted with AcOEt. The organic layer was washed with saturated aqueous solution of Na$_2$S$_2$O$_4$ and brine, dried over Na$_2$SO$_4$, and concentrated in vacuo. The crude product was purified by silica gel chromatography (hexane/AcOEt=100:0-95:5) to give the title compound (1.41 g, 85%).
$^1$H-NMR (CDCl$_3$) δ: 2.37 (3H, s), 7.03-7.10 (1H, m), 7.33 (1H, dd, J=2.5, 9.6 Hz), 7.67 (1H, dd, J=4.9, 8.8 Hz).

Reference Example 1377

Synthesis of 2-[4-(trifluoromethyl)-phenyl]-imidazo[1,2-a]pyridine-7-carboxylic Acid methyl ester 4-Trifluoromethylphenacyl bromide (801 mg, 3 mmol), methyl 2-aminopyridine-4-carboxylate (456 mg, 3.00 mmol) and 2-butanone (7 mL) were charged into a reaction tube equipped with a condenser, and the mixture was heated to reflux and stirred for 14 hr. The formed precipitate was collected by filtration. The solid was then dissolved in saturated aqueous NaHCO$_3$ solution. The aqueous solution was extracted with AcOEt and the combined organic layers were dried over Na$_2$SO$_4$, filtered and concentrated in vacuo to give the title compound (504 mg, 52%) as a pale purple solid.
$^1$H-NMR (CDCl$_3$) δ: 3.98 (3H, s), 7.43 (1H, dd, J=1.8, 7.2 Hz), 7.72 (2H, d, J=8.1 Hz), 8.04 (1H, s), 8.10 (2H, d, J=8.1 Hz), 8.17-8.20 (1H, m), 8.39 (1H, s).

Reference Example 1415

Synthesis of 7-(trifluoromethyl)-benzo[b]thiophene-2-carboxylic Acid ethyl ester To a solution of 2-fluoro-3-trifluoromethyl benzaldehyde (3.53 g, 18.37 mmol) in DMSO (35 ml) were added Et$_3$N (7.64 ml, 55.1 mmol) and ethyl mercaptoacetate (2.208 ml, 20.21 mmol). After the resulting solution was stirred at 80° C. for 2 hr, it was quenched with water, and extracted twice with AcOEt. The organic layer was washed with water and brine, dried over Na$_2$SO$_4$, and concentrated in vacuo. The crude product was purified by silica gel column chromatography (hexane/AcOEt-100:0-75:25) to give the title compound (4.58 g, 91%).
$^1$H-NMR (CDCl$_3$) δ: 1.43 (3H, t, J=7.1 Hz), 4.43 (2H, q, J=7.1 Hz), 7.47-7.55 (1H, m), 7.76 (1H, d, J=7.5 Hz), 8.05 (1H, d, J=8.0 Hz), 8.12 (1H, s).

Reference Example 1477

Synthesis of 3-chloro-4-fluoro-thiobenzamide

To a solution of 3-chloro-4-fluorobenzonitrile (3.00 g, 19.3 mmol) in DMF (30 ml) was added 22% ammonium sulfide solution (11.95 g, 38.6 mmol). After the reaction mixture was stirred at 60-65° C. for 2 hr, and water was added thereto. After being filtered the precipitate, the obtained precipitate was dissolved in AcOEt. The solution was washed with water and brine, dried over anhydrous MgSO$_4$, and then concentrated in vacuo to give the title compound (2.24 g, 61%) as a pale yellow solid.
$^1$H-NMR (CDCl$_3$) δ: 7.01-7.24 (1H, br), 7.18 (1H, t, J=8.5 Hz), 7.54-7.88 (1H, br), 7.74-7.79 (1H, m), 7.98 (1H, dd, J=2.4, 6.9 Hz).

Reference Example 1494

Synthesis of 2-bromo-5-methyl-3H-imidazole-4-carboxylic Acid ethyl ester

To a solution of ethyl 4-methyl-5-imidazolecarboxylate (1 g, 6.49 mmol) in CHCl$_3$ (10 ml) and CH$_3$CN (10 ml) was added NBS (1.27 g, 7.14 mmol). The reaction mixture was stirred at room temperature for 19 hr. The reaction was quenched by addition of water and the reaction mixture was extracted with AcOEt. The combined organic layers were washed with water and brine, dried over Na$_2$SO$_4$, and concentrated in vacuo. The obtained residue was purified by silica gel column chromatography (CH$_2$Cl$_2$/MeOH=10/1) to give an orange powder. The powder was triturated with isopropyl ether/AcOEt to afford the title compound (0.47 g, 31%) as a pale orange powder.

$^1$H-NMR (CDCl$_3$) δ: 1.36 (3H, t, J=7.1 Hz), 2.51 (3H, brs), 4.35 (2H, q, J=7.1 Hz), 10.29-10.87 (1H, br).

Reference Example 1497

Synthesis of 6-[1-[[4-(trifluoromethyl)-phenyl]-methoxy]-ethyl]-pyridine-2-carboxylic Acid ethyl ester The mixture of 6-(1-(4-(trifluoromethyl)benzyloxy)ethyl) picolinonitrile (480 mg, 1.57 mmol) and 1N HCl/EtOH (6 ml, 6.00 mmol) was stirred under reflux for 18 hr. The reaction was quenched by addition of saturated aqueous NaHCO$_3$ solution and extracted with AcOEt. The combined organic layers were washed with water and brine, and concentrated in vacuo to give the title compound (420 mg, 76%) as a brown oil.
$^1$H-NMR (CDCl$_3$) δ: 1.44 (3H, t, J=6.9 Hz), 1.57 (3H, d, J=6.6 Hz), 4.45-4.54 (4H, m), 4.81 (1H, q, J=6.6 Hz), 7.45 (2H, d, J=8.3 Hz), 7.59 (2H, d, J=8.3 Hz), 7.70-7.73 (1H, m), 7.87 (1H, t, J=7.8 Hz), 8.02-8.05 (1H, m).

Reference Example 1643

Synthesis of 5-bromo-[1,3,4]oxadiazole-2-carboxylic Acid ethyl ester

The mixture of ethyl 5-amino-1,3,4-oxadiazole-2-carboxylate (1.00 g, 6.36 mmol) and cupric bromide (2.13 g, 9.55 mmol) in CH$_3$CN (20 ml) was stirred at room temperature for 15 min. To the reaction mixture was added tert-butyl nitrite (1.51 ml, 12.73 mmol) and the mixture was stirred at room temperature for 2 hr and at 50° C. for 0.5 hr. After concentration in vacuo, the reaction was quenched by addition of water and AcOEt. The resulting suspension was filtered. The filtrate was extracted with AcOEt. The combined organic layers were washed with water and brine, dried over Na$_2$SO$_4$, and concentrated in vacuo. The obtained residue was purified by silica gel column chromatography (hexane/AcOEt=4/1 to 1/1) to give the title compound (0.66 g, 47%) as a colorless oil.
$^1$H-NMR (CDCl$_3$) δ: 1.46 (3H, t, J=7.1 Hz), 4.53 (2H, q, J=7.1 Hz).

Reference Example 1666

Synthesis of acetic Acid [2-(4-chlorophenyl)-5-[(4-chlorophenyl)-methyl]-thiazol-4-yl]-methyl ester To a solution of (2-(4-chlorophenyl)thiazol-4-yl)methyl acetate (200 mg, 0.747 mmol) in toluene (2 ml) were added p-chlorobenzyl chloride (0.191 ml, 1.494 mmol), palladium acetate (8 mg, 0.037 mmol), 2-(diphenylphosphino)-2'-(N,N-dimethylamino)biphenyl (28 mg, 0.075 mmol), Cs$_2$CO$_3$ (365 mg, 1.12 mmol) and pivalic acid (0.017 ml, 0.149 mmol). After the reaction mixture was stirred at 110° C. for 8 hr under nitrogen, water was added thereto. The reaction mixture was extracted with AcOEt. The organic layer was washed with brine, dried over anhydrous MgSO$_4$, and then concentrated in vacuo. The residue was purified by flash column chromatography (AcOEt/hexane=0% to 30%) to give the title compound (162 mg, 55%) as a white powder.
$^1$H-NMR (CDCl$_3$) δ: 2.08 (3H, s), 4.21 (2H, s), 5.22 (2H, s), 7.15-7.18 (2H, m), 7.27-7.31 (2H, m), 7.36-7.40 (2H, m), 7.79-7.82 (2H, m).

Reference Example 1668

Synthesis of 4-formyl-piperidine-1-carboxylic Acid phenyl ester

To a solution of 4-piperidinemethanol (173 mg, 1.5 mmol) in saturated aqueous NaHCO$_3$ solution (5 ml) and CH$_2$Cl$_2$ (5 ml) was added phenyl chloroformate (0.188 ml, 1.500 mmol) by portions at 0° C. for 10 min. The reaction mixture was stirred at 0° C. for 1 hr. 2,2,6,6-Tetramethyl-piperidine 1-oxyl (10 mg, 0.064 mmol), KBr (15 mg, 0.126 mmol) and tetrabutylammonium bromide (20 mg, 0.062 mmol) were added to the reaction mixture, and then sodium hypochlorite (5% for Cl) (4 ml) were added dropwise thereto at 0° C. for 0.5 hr. After the reaction mixture was stirred for 10 min, the reaction was quenched by Na$_2$S$_2$O$_3$. The organic layer was separated, washed with water, dried over anhydrous Na$_2$SO$_4$, and then concentrated in vacuo. The obtained residue was purified by flash column chromatography (AcOEt/hexane=30% to 70%) to give the title compound (218 mg, 52%) as a pale yellow oil.
$^1$H-NMR (CDCl$_3$) δ: 1.61-1.79 (2H, m), 1.94-2.08 (2H, m), 2.46-2.58 (1H, m), 3.02-3.30 (2H, m), 4.05-4.25 (2H, m), 7.06-7.14 (2H, m), 7.16-7.27 (1H, m), 7.32-7.40 (2H, m), 9.72 (1H, s).

Reference Example 1729

Synthesis of [[[4-(trifluoromethyl)-benzoyl]amino]-carbamoyl]-formic Acid ethyl ester To a solution of 4-(trifluoromethyl)benzoic acid hydrazide (1.50 g, 7.35 mmol) in CH$_2$Cl$_2$ (30 ml) at 0° C. were added ethyl oxalyl chloride (0.90 ml, 8.08 mmol) and Et$_3$N (1.23 ml, 8.82 mmol). The reaction mixture was stirred at room temperature for 17 hr. The reaction was quenched by addition of water and the reaction mixture was extracted with AcOEt. The combined organic layers were washed with water and brine, dried over Na$_2$SO$_4$, and concentrated in vacuo. The obtained residue was triturated with isopropyl ether to give the title compound (1.85 g, 83%) as a white powder.
$^1$H-NMR (CDCl$_3$) δ: 1.41 (3H, t, J=7.2 Hz), 4.42 (2H, q, J=7.2 Hz), 7.71 (2H, d, J=8.2 Hz), 7.96 (2H, d, J=8.2 Hz), 9.70 (2H, brs).

Reference Example 1730

Synthesis of 5-[4-(trifluoromethyl)-phenyl]-[1,3,4] oxadiazole-2-carboxylic Acid ethyl ester To a solution of ethyl[[[4-(trifluoromethyl)-benzoyl] amino]-carbamoyl]-formic acid ethyl ester (1.60 g, 5.26 mmol) in CH$_2$Cl$_2$ (48 ml) were added a solution of 2-chloro-1,3-dimethylimidazolinium chloride (0.89 g, 5.26 mmol) in CH$_2$Cl$_2$ and Et$_3$N (1.47 ml, 10.52 mmol). The reaction mixture was stirred at room temperature for 22 hr. The reaction was quenched by addition of 0.5N HCl and the reaction mixture was extracted with CH$_2$Cl$_2$. The combined organic layers were washed with saturated aqueous NaHCO$_3$ solution and brine, dried over MgSO$_4$, and concentrated in vacuo. The obtained residue was purified by silica gel column chromatography (hexane/AcOEt=3/1) to give the title compound (0.78 g, 52%) as a white powder.
$^1$H-NMR (CDCl$_3$) δ: 1.50 (3H, t, J=7.2 Hz), 4.58 (2H, q, J=7.2 Hz), 7.83 (2H, d, J=8.3 Hz), 8.31 (2H, d, J=8.3 Hz).

Reference Example 1737

Synthesis of
1-(3,5-dibromo-phenyl)-3-methyl-butan-1-ol

To a stirred solution of 3,5-dibromobenzaldehyde (2.20 g, 8.34 mmol) in THF (44 ml) was added isobutyl magnesium bromide (10.0 ml, 10.0 mmol, 1M THF solution) at 0° C. The reaction mixture was gradually warmed to room temperature and stirred overnight. The reaction mixture was poured into saturated aqueous $NH_4Cl$ solution and extracted twice with AcOEt. The organic layer was washed with brine, dried over $Na_2SO_4$ and concentrated in vacuo. The residue was purified by silica gel column chromatography (hexane:AcOEt=100:0-75:25) to give the title compound (711 mg, 26%).
$^1$H-NMR (CDCl$_3$) δ: 0.95-0.98 (6H, m), 1.41-1.47 (1H, m), 1.64-1.78 (2H, m), 1.81 (1H, d, J=3.6 Hz), 4.67-4.72 (1H, m), 7.43-7.44 (2H, m), 7.56 (1H, s).

Reference Example 1752

Synthesis of
1,3-dibromo-5-(3-methyl-butyl)-benzene

To a solution of 1-(3,5-dibromophenyl)-3-methylbutan-1-one (1.24 g, 3.87 mmol) in diethylene glycol (15 ml) were added hydrazine hydrate (0.752 ml, 15.50 mmol) and potassium hydroxide (0.522 g, 9.30 mmol). After the reaction mixture was stirred at 150° C. for 5 hr, it was neutralized with 6N HCl and extracted twice with AcOEt. The organic layer was washed with water and brine, dried over $Na_2SO_4$, and concentrated in vacuo. The residue was purified by silica gel column chromatography (hexane:AcOEt=100:0-85:15) to give the title compound (917 mg, 77%).
$^1$H-NMR (CDCl$_3$) δ: 0.93 (6H, d, J=6.7 Hz), 1.45-1.51 (2H, m), 1.56-1.61 (1H, m), 2.53-2.57 (2H, m), 2.61 (2H, s), 7.46-7.49 (1H, m).

Reference Example 1863

Synthesis of 2-(4-chlorophenyl)-4-cyclopropyl-thiazole-5-carboxylic Acid methyl ester A solution of bromine (0.168 ml, 3.26 mmol) in CCl$_4$ (3 ml) was added dropwise to a suspension of methyl 3-cyclopropyl-3-oxopropionate (0.463 g, 3.26 mmol) and NaHCO$_3$ (0.821 g, 9.77 mmol) in CCl$_4$ (7 ml) at −10° C. for 1 hr. After being stirred for 20 min, to the reaction mixture were added 4-chloro-benzenecarbothioamide (0.559 g, 3.26 mmol) and EtOH (20 ml). The reaction mixture was stirred at room temperature for 0.5 h and then under reflux for 5 hr. After being cooled, the reaction mixture was filtrated. The obtained filtrate was concentrated in vacuo. The residue was purified by flash column chromatography (AcOEt/hexane=0% to 10%) to give the title compound (218 mg, 52%) as a pale yellow solid.
$^1$H-NMR (CDCl$_3$) δ: 1.09-1.14 (2H, m), 1.18-1.24 (2H, m), 3.02-3.08 (1H, m), 3.90 (3H, s), 7.38-7.42 (2H, m), 7.84-7.87 (2H, m).

Reference Example 1891

Synthesis of
2-amino-3-cyclopropyl-3-oxo-propionic Acid
methyl ester HCl

To a solution of methyl 3-cyclopropyl-3-oxopropanoate (1.0 g, 7.03 mmol) in AcOH (1 ml) was added slowly sodium nitrite (0.485 g, 7.03 mmol) in water (1.5 ml) at 0° C. After the reaction mixture was stirred at room temperature overnight, water was added thereto, and the mixture was extracted with AcOEt. The combined organic layers were washed with water, saturated aqueous NaHCO$_3$ solution, and brine, dried over $Na_2SO_4$, and concentrated in vacuo to give the crude product of 3-cyclopropyl-2-[(Z)-hydroxyimino]-3-oxo-propionic acid methyl ester (1.15 g). This product was used in the next step without purification.

The crude product of 3-cyclopropyl-2-[(Z)-hydroxyimino]-3-oxo-propionic acid methyl ester (1.15 g) was dissolved in EtOH (10 ml) and 4N HCl (AcOEt solution) (5.0 ml) was added thereto. The reaction mixture was stirred at room temperature for 10 hr under hydrogen (balloon) in the presence of 10% Pd—C (wet). The reaction mixture was filtered through a pad of Celite and the filtrate was concentrated in vacuo to give the title compound (1.17 g, 90%).
$^1$H-NMR (CDCl$_3$) δ: 0.96-1.09 (2H, m), 1.12-1.19 (2H, m), 2.42-2.47 (1H, m), 3.85 (3H, s), 5.60 (1H, s), 8.68 (3H, brs).

Reference Example 1892

Synthesis of 3-cyclopropyl-2-[(3,4-difluoro-benzoyl)amino]-3-oxo-propionic Acid methyl ester To a solution of 2-amino-3-cyclopropyl-3-oxo-propionic acid methyl ester HCl (480 mg, 2.479 mmol) in CH$_2$Cl$_2$ (15 ml) were added DIPEA (705 mg, 5.45 mmol) and 3,4-difluorobenzoyl chloride (0.348 ml, 2.97 mmol) at 0° C. After the reaction mixture was stirred at room temperature overnight, it was quenched by water and extracted with AcOEt. The organic layer was washed with brine, dried over $Na_2SO_4$ and concentrated in vacuo. The residue was purified by silica gel chromatography (hexane/AcOEt=100:0-75:25) to give the title compound (514 mg, 69%).
$^1$H-NMR (CDCl$_3$) δ: 1.07-1.30 (4H, m), 2.39-2.45 (1H, m), 3.87 (3H, s), 5.58 (1H, d, J=6.3 Hz), 7.22-7.33 (1H, m), 7.58-7.64 (1H, m), 7.69-7.75 (1H, m).

Reference Example 1899

Synthesis of 5-cyclopropyl-2-(3,4-difluoro-phenyl)-oxazole-4-carboxylic Acid methyl ester To a solution of triphenylphosphine (907 mg, 3.46 mmol) and iodine (878 mg, 3.46 mmol) in CH$_2$Cl$_2$ (10 ml) were added Et$_3$N (0.964 ml, 6.92 mmol) and 3-cyclopropyl-2-(3,4-difluoro-benzoylamino)-3-oxo-propionic acid methyl ester (514 mg, 1.729 mmol) in CH$_2$Cl$_2$ (10 ml). After the reaction mixture was stirred at room temperature overnight, it was quenched by saturated aqueous solution of Na$_2$S$_2$O$_3$ and extracted with CH$_2$Cl$_2$. The organic layer was washed with brine, dried over Na$_2$SO$_4$, and concentrated in vacuo. The residue was purified by silica gel column chromatography (hexane/AcOEt=100:0-75:25) to give the title compound (478 mg, 99%).
$^1$H-NMR (CDCl$_3$) δ: 1.16-1.25 (4H, m), 2.80-2.86 (1H, m), 3.97 (3H, s), 7.21-7.25 (1H, m), 7.73-7.78 (1H, m), 7.79-7.84 (1H, m).

Reference Example 2069

Synthesis of 3-[4-(trifluoromethyloxy)-phenyl]-isothiazole-5-carboxylic Acid ethyl ester To a solution of 5-(4-trifluoromethoxy-phenyl)-[1,3,4]oxathiazol-2-one (500 mg, 1.900 mmol) in xylene (7.5 ml)

was added ethyl propiolate (0.578 ml, 5.70 mmol). After the reaction mixture was stirred at 120° C. for 3 days, it was concentrated in vacuo. The residue was purified by silica gel chromatography (hexane/AcOEt=100:0-75:25) to give the title compound (132 mg, 21%) and 3-[4-(trifluoromethyl-oxy)-phenyl]-isothiazole-4-carboxylic acid ethyl ester (136 mg, 22%).

$^1$H-NMR (CDCl$_3$) δ: 1.27 (3H, t, J=7.1 Hz), 4.28 (2H, q, J=7.1 Hz), 7.28 (2H, d, J=8.2 Hz), 7.66-7.70 (2H, m), 9.38 (1H, s).

Reference Example 2079

Synthesis of 2-[(4-chloro-benzoyl)amino]-5-methyl-thiazole-4-carboxylic Acid methyl ester To a suspension of 2-amino-5-methylthiazole-4-carboxylic acid methyl ester (200 mg, 1.161 mmol) in CH$_2$Cl$_2$ at room temperature were added Et$_3$N (0.194 ml, 1.394 mmol) and 4-chlorobenzoyl chloride (0.162 ml, 1.278 mmol). The reaction mixture was stirred for 3 hr. Water and CH$_2$Cl$_2$ were added to the reaction mixture. The resulting precipitate was collected by filtration and dried to give the title compound (218 mg, 60%) as a colorless powder.

$^1$H-NMR (DMSO-d$_6$) δ: 2.66 (3H, s), 3.81 (3H, s), 7.60-7.64 (2H, m), 8.10-8.14 (2H, m), 12.94 (1H, brs).

Reference Example 2080

Synthesis of 5-cyclobutyl-2-[5-(trifluoromethyl)-pyridin-3-yl]-oxazole-4-carboxylic Acid ethyl ester To a solution of 5-cyclobutyl-oxazole-4-carboxylic acid ethyl ester (214 mg, 1.096 mmol) in diethylcarbonate (5 ml) were added 3-bromo-5-trifluoromethylpyridine (322 mg, 1.425 mmol), tri-o-tolylphosphine (66.7 mg, 0.219 mmol), cesium carbonate (714 mg, 2.192 mmol) and Pd(OAc)$_2$ (24.61 mg, 0.110 mmol). After the resulting suspension was stirred at 110° C. for 24 hr, it was filtered through a pad of Celite. The filtrate was concentrated in vacuo and the residue was purified by silica gel column chromatography (hexane/AcOEt=100:0-85:15) to give the title compound (165 mg, 44%).

$^1$H-NMR (CDCl$_3$) δ: 1.44 (3H, t, J=7.1 Hz), 1.99-2.07 (1H, m), 2.09-2.20 (1H, m), 2.40-2.52 (4H, m), 4.31-4.38 (1H, m), 4.44 (2H, q, J=7.1 Hz), 8.63 (1H, s), 8.97 (1H, s), 9.49 (1H, d, J=1.8 Hz).

Reference Example 2083

Synthesis of 5-Methyl-2-(4-trifluoromethyl-benzylamino)-thiazole-4-carboxylic Acid methyl ester To a suspension of 2-amino-5-methylthiazole-4-carboxylic acid methyl ester (200 mg, 1.161 mmol) in CH$_2$Cl$_2$ were added alpha,alpha,alpha-trifluoro-p-tolualdehyde (0.174 ml, 1.278 mmol) and AcOH (6.65 µl, 0.116 mmol) and the reaction mixture was stirred for 1 hr. After sodium triacetoxyborohydride (492 mg, 2.323 mmol) was added thereto, the reaction mixture was stirred for 3 days. The reaction was quenched by addition of saturated aqueous NaHCO$_3$ solution and organic layer was washed with water and brine, and concentrated. The obtained residue was purified by silica gel column chromatography (hexane/AcOEt=1/1) to give the title compound (87 mg, 22%) as a colorless powder.

$^1$H-NMR (CDCl$_3$) δ: 2.60 (3H, s), 3.88 (3H, s), 4.52 (2H, d, J=5.7 Hz), 5.66 (1H, brs), 7.47 (2H, d, J=8.0 Hz), 7.61 (2H, J=8.0 Hz).

Reference Example 2094

Synthesis of 2-amino-5-[4-(trifluoromethyl)-phenyl]-thiazole-4-carboxylic Acid methyl ester To a solution of alpha,alpha,alpha-trifluoro-p-tolualdehyde (2.87 ml, 20.98 mmol) and methyl dichloroacetate (2.17 ml, 20.98 mmol) in Et$_2$O was dropwise added sodium methoxide (3.88 ml, 19.51 mmol) for 20 min at 0° C., and the reaction mixture was stirred for 1 hr. The reaction was quenched by addition of brine and water. The organic layer was concentrated. To the obtained residue were added MeOH and thiourea (1.60 g, 20.96 mmol), the reaction mixture was refluxed overnight. The reaction mixture was concentrated. The residue was dissolved with AcOEt and washed with water and brine, and concentrated. The obtained solid was washed with EtOH and dried to give the title compound (4.74 g, 74%) as a pale brown powder.

$^1$H-NMR (DMSO-d$_6$) δ: 3.65 (3H, s), 7.42 (2H, s), 7.61 (2H, d, J=8.2 Hz), 7.73 (2H, d, J=8.2 Hz).

Reference Example 2143

Synthesis of 2-(2,2-difluoro-1,3-benzodioxol-5-yl)-oxazole-4-carboxylic Acid ethyl ester To a solution of ethyl oxazole-4-carboxylate (0.297 ml, 2.480 mmol) in dioxane (5 ml) were added 5-bromo-2,2-difluorobenzodioxole (588 mg, 2.480 mmol), 2-(dicylohexylphosphino)biphenyl (87 mg, 0.248 mmol), cesium carbonate (1616 mg, 4.96 mmol) and Pd(OAc)$_2$ (27.8 mg, 0.124 mmol). After the resulting suspension was stirred at 110° C. for 12 hr, it was filtered through a pad of Celite. The filtrate was concentrated in vacuo and the residue was purified by silica gel column chromatography (hexane/AcOEt=100:0-85:15) to give the title compound (350 mg, 47%).

$^1$H-NMR (CDCl$_3$) δ: 1.41 (3H, t, J=7.1 Hz), 4.44 (2H, q, J=7.1 Hz), 7.17 (1H, d, J=8.3 Hz), 7.83 (1H, d, J=1.5 Hz), 7.91 (1H, dd, J=1.5, 8.3 Hz), 8.27 (1H, s).

Reference Example 2160

Synthesis of (6-[4-(trifluoromethyl)-phenyl]-benzothiazol-2-yl)-amine

4'-Trifluoromethyl-biphenyl-4-ylamine (3.46 g, 14.57 mmol) and potassium thiocyanate (4.96 g, 51.0 mmol) were dissolved in acetic acid. To this solution was dropwise added a solution of bromine (0.826 ml, 16.03 mmol) in acetic acid, maintaining a reaction temperature below 25° C. After being stirred overnight, the reaction mixture was neutralized with 25% NH$_4$OH aq., and extracted with AcOEt. The combined organic layers were washed with brine and concentrated. The obtained residue was purified by silica gel column chromatography (hexane/AcOEt=3/2) to give the title compound (3.65 g, 85%) as a pale yellow powder.

$^1$H-NMR (DMSO-d$_6$) δ: 7.43 (1H, d, J=8.4 Hz), 7.60 (1H, dd, J=2.0, 8.4 Hz), 7.63 (2H, s), 7.78 (2H, d, J=8.2 Hz), 7.89 (2H, d, J=8.2 Hz), 8.09 (1H, d, J=2.0 Hz).

Reference Example 2161

Synthesis of 6-phenoxy-benzothiazole

6-Phenoxy-benzothiazol-2-ylamine (2.90 g, 11.97 mmol) was dissolved in hot 85% H$_3$PO$_4$, and the solution was cooled to −8° C. A solution of sodium nitrate (4.95 g, 71.8 mmol) in water was added slowly below −4° C. Then 50% hypophosphorous acid (29 ml) was added slowly thereto and the reaction mixture was stirred overnight. After cold water was added thereto, the reaction mixture was neutralized with 25% NH$_4$OH aq. and extracted with AcOEt. The combined organic layers were washed with brine and concentrated. The obtained residue was purified by silica gel column chromatography (hexane/AcOEt=6/1) was to give the title compound (1.03 g, 37%) as a red oil.

$^1$H-NMR (CDCl$_3$) δ: 7.04-7.07 (2H, m), 7.13-7.17 (1H, m), 7.24 (1H, dd, J=2.4, 8.8 Hz), 7.35-7.40 (2H, m), 7.51 (1H, d, J=2.4 Hz), 8.08 (1H, d, J=8.8 Hz), 8.91 (1H, s).

Reference Example 2162

Synthesis of 6-phenoxy-benzothiazole-2-carboxylic Acid methyl ester

A solution of 6-phenoxy-benzothiazole (1.03 g, 4.53 mmol) and Cs$_2$CO$_3$ (1.77 g, 5.44 mmol) in DMF was degassed and flushed with CO$_2$ twice. The reaction mixture was stirred for 21 hr at 125° C. under CO$_2$ gas. Then the reaction mixture was cooled to room temperature. Methyl iodide (0.850 ml, 13.60 mmol) was added to the mixture and stirred at 50° C. for 3 hr. Water was added to the reaction mixture and extracted with AcOEt. The combined organic layers were washed with water and brine and concentrated. The obtained residue was purified by silica gel column chromatography (hexane/AcOEt=4/1) to give the title compound (0.74 g, 57%) as a yellow powder.

$^1$H-NMR (CDCl$_3$) δ: 4.08 (3H, s), 7.08-7.11 (2H, m), 7.19-7.23 (1H, m), 7.30 (1H, dd, J=2.4, 9.0 Hz), 7.39-7.43 (3H, m), 8.17 (1H, d, J=9.0 Hz).

Reference Example 2192

Synthesis of 5-[4-(chloromethyl)-phenyl]-3H-[1,2,3]triazole-4-carbonitrile

To a solution of 5-[4-(hydroxymethyl)-phenyl]-3H-[1,2,3]triazole-4-carbonitrile (98.7 mg, 0.493 mmol) and pyridine (0.077 ml, 0.952 mmol) in CH$_2$Cl$_2$ (2 ml) was added thionyl chloride (0.072 ml, 0.986 mmol) at 0° C. After being stirred at room temperature, the reaction mixture was diluted with AcOEt, washed with HCl aq. and water, dried over anhydrous Na$_2$SO$_4$, and then concentrated in vacuo. The obtained residue was purified by flash column chromatography (AcOEt/hexane=0% to 30%) to give the title compound (65 mg, 63%) as a pale yellow solid.

$^1$H-NMR (CDCl$_3$) δ: 4.65 (2H, s), 7.56 (2H, d, J=8.3 Hz), 8.00 (2H, d, J=8.3 Hz), 12.06 (1H, br.).

Reference Example 2213

Synthesis of 2-(3-chlorophenyl)-4-([,3]dioxolan-2-yl)-5-iodo-thiazole

To a solution of 2-(3-chloro-phenyl)-4-[1,3]dioxolan-2-yl-thiazole (317 mg, 1.184 mmol) in THF (9 ml) was added n-BuLi (0.814 ml, 1.302 mmol, 1.6 M in n-hexane). After the reaction mixture was stirred for 1 hr, iodine (601 mg, 2.368 mmol) was added thereto, and stirring was continued for 3 hr. The reaction mixture was quenched with saturated aqueous solution of Na$_2$S$_2$O$_4$, and extracted twice with AcOEt. The organic layer was washed with water and brine, dried over Na$_2$SO$_4$ and concentrated in vacuo. The crude product was purified by silica gel column chromatography (hexane:AcOEt=100:0-75:25) to give the title compound (287 mg, 62%).

$^1$H-NMR (CDCl$_3$) δ: 4.07-4.15 (2H, m), 4.34-4.42 (2H, m), 6.11 (1H, s), 7.36 (1H, t, J=7.7 Hz), 7.38-7.42 (1H, m), 7.71-7.74 (1H, m), 7.91-7.92 (1H, m).

Reference Example 2214

Synthesis of 2-(3-chiorophenyl)-4-([1,3]dioxolan-2-yl)-5-(trifluoromethyl)-thiazole To a solution of 2-(3-chloro-phenyl)-4-[1,3]dioxolan-2-yl-5-iodo-thiazole (287 mg, 0.729 mmol) in DMF (4 ml) were added slowly methyl 2,2-difluoro-2-(fluorosulfonyl)acetate (0.650 ml, 5.10 mmol) and copper(I) iodide (167 mg, 0.875 mmol). The resulting suspension was stirred at 100° C. for 5 hr. After water was added to the reaction mixture, the resulting insoluble material was filtered through a pad of Celite. The filtrate was extracted with AcOEt. The organic layer was washed with water and brine, dried over Na$_2$SO$_4$, and concentrated in vacuo. The residue was purified by silica gel column chromatography (hexane:AcOEt=100:0-75:25) to give the title compound (223 mg, 91%).

$^1$H-NMR (CDCl$_3$) δ: 4.09-4.16 (2H, m), 4.32-4.39 (2H, m), 6.23 (1H, s), 7.40 (1H, t, J=7.9 Hz), 7.46-7.48 (1H, m), 7.78-7.80 (1H, m), 7.98 (1H, t, J=1.8 Hz).

The following compounds were synthesized in the same manner as in the above-mentioned Reference Examples or the below-mentioned Examples. The structures and $^1$H-NMR data thereof are shown in the following Table 2. The "ref." in Table 2 means "Reference Example No." or "Example No." which the compound was synthesized in reference to.

TABLE 2

| Ref. Ex. No | STR | 1H-NMR | ref. |
|---|---|---|---|
| 255 | | 1H-NMR (DMSO-d6) δ: 1.44 (3H, t, J = 7.1 Hz), 4.46 (2H, q, J = 7.1 Hz), 7.25-7.29 (1H, m), 7.55-7.57 (2H, m), 7.75 (1H, d, J = 8.7 Hz). | Ref. Ex. 125 |

TABLE 2-continued
| Ref. Ex. No | STR | 1H-NMR | ref. |
|---|---|---|---|
| 256 | 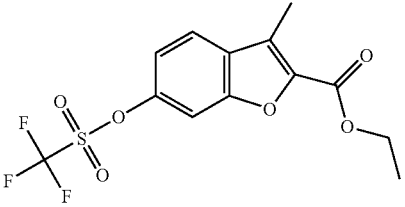 | 1H-NMR (DMSO-d6) δ: 1.45 (3H, t, J = 7.1 Hz). 2.60 (3H, s), 4.47 (2H, q, J = 7.1 Hz), 7.24-7.28 (1H, m), 7.51 (1H, d, J = 2.1 Hz), 7.70 (1H, d, J = 8.6 Hz). | Ref. Ex. 125 |
| 257 | 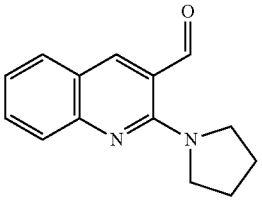 | 1H-NMR (CDCl3) δ: 1.96-2.01 (4H, m), 3.61-3.69 (4H, m), 7.21-7.25 (1H, m), 7.61-7.65 (1H, m), 7.71-7.73 (2H, m), 8.40 (1H, s), 10.21 (1H, s). | Ref. Ex. 1173 |
| 258 | 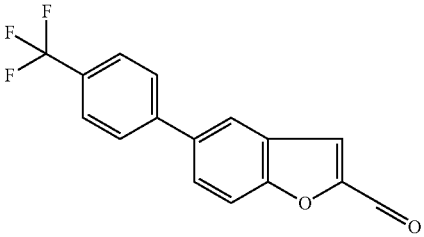 | 1H-NMR (CDCl3) δ: 7.63 (1H, s), 7.69-7.78 (6H, m), 7.95-7.96 (1H, m), 9.92 (1H, s). | Ref. Ex. 112 |
| 259 | 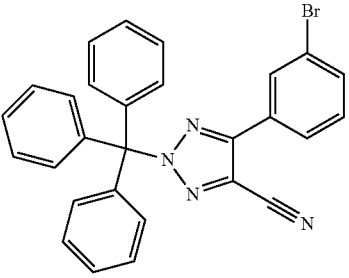 | 1H-NMR (CDCl3) δ: 7.04-7.10 (6H, m), 7.38-7.41 (9H, m), 7.54 (1H, t, J = 7.9 Hz), 7.74-7.76 (1H, m), 7.81 (1H, d, J = 7.9 Hz), 7.92 (1H, s). | Ref. Ex. 184 |
| 260 | 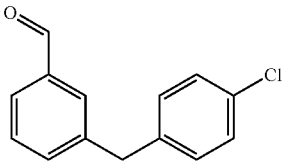 | 1H-NMR (CDCl3) δ: 4.03 (2H, s), 7.12 (2H, d, J = 8.2 Hz), 7.26-7.28 (2H, m), 7.43-7.46 (2H, m), 7.69 (1H, s), 7.74 (1H, d, J = 7.2 Hz), 9.98 (1H, s). | Ref. Ex. 38 |
| 261 | 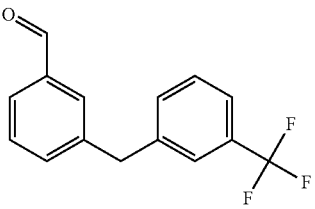 | 1H-NMR (CDCl3) δ: 4.12 (2H, s), 7.35-7.52 (6H, m), 7.71-7.77 (2H, m), 10.0 (1H, s). | Ref. Ex. 38 |
| 262 | 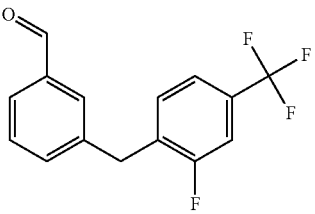 | 1H-NMR (CDCl3) δ: 4.12 (2H, s), 7.28-7.37 (3H, m), 7.48-7.49 (2H, m), 7.73 (1H, s), 7.75-7.77 (1H, m), 9.99 (1H, s). | Ref. Ex. 38 |

TABLE 2-continued

| Ref. Ex. No | STR | 1H-NMR | ref. |
|---|---|---|---|
| 263 | | 1H-NMR (CDCl3) δ: 5.38 (2H, s), 7.24-7.25 (1H, m), 7.26-7.55 (3H, m), 7.85-7.97 (3H, m), 9.99 (1H, s). | Ref. Ex. 82 |
| 264 | | 1H-NMR (DMSO-d6) δ: 2.01 (2H, t, J = 8.2 Hz), 2.40-2.43 (2H, m), 2.67 (2H, t, J = 7.5 Hz), 2.82 (2H, t, J = 7.5 Hz), 4.04 (2H, t, J = 6.2 Hz), 6.76 (1H, d, J = 8.2 Hz), 6.99 (1H, d, J = 8.2 Hz), 7.03 (1H, s), 7.28, (1H, d, J = 7.5 Hz), 7.41 (1H, s), 7.50-7.53 (2H, m), 9.97 (1H, s), 9.98 (1H, s). | Ref. Ex. 82 |
| 265 | | 1H-NMR (CDCl3) δ: 2.00-2.22 (4H, m), 4.26 (2H, t, J = 6.6 Hz), 6.70 (1H, d, J = 3.2 Hz), 7.18 (1H, d, J = 3.2 Hz), 7.40 (1H, d, J = 8.6 Hz), 7.80 (1H, dd, J = 1.5, 8.6 Hz), 8.16 (1H, d, J = 1.4 Hz), 10.04 (1H, s). | Ref. Ex. 184 |
| 266 | | 1H-NMR (CDCl3) δ: 5.29 (2H, s), 7.09 (1H, d, J = 8.5 Hz), 7.54-7.86 (5H, m), 7.96 (1H, s), 9.87 (1H, s). | Ref. Ex. 82 |
| 267 | | 1H-NMR (CDCl3) δ: 5.17 (2H, s), 6.66 (1H, t, J = 74.0 Hz), 7.35 (1H, d, J = 8.1 Hz), 7.38 (4H, s), 7.48-7.54 (1H, m), 7.55 (1H, s), 9.93 (1H, s). | Ref. Ex. 82 |

TABLE 2-continued
| Ref. Ex. No | STR | 1H-NMR | ref. |
|---|---|---|---|
| 268 | 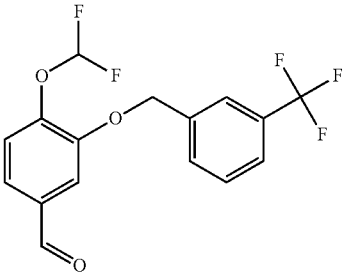 | 1H-NMR (CDCl3) δ: 5.25 (2H, s), 6.66 (1H, t, J = 73.7 Hz), 7.37 (1H, d, J = 8.2 Hz), 7.50-7.65 (5H, m), 7.73 (1H, s), 9.94 (1H, s). | Ref. Ex. 82 |
| 270 | 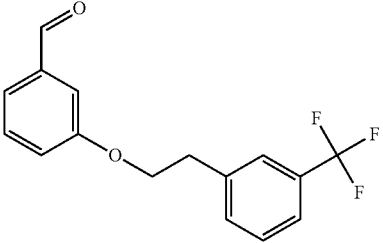 | 1H-NMR (CDCl3) δ: 3.18 (2H, t, J = 6.6 Hz). 4.25-4.27 (2H, m), 7.15-7.18 (1H, m), 7.37 (1H, s), 7.43-7.56 (6H, m), 9.96 (1H, s). | Ref. Ex. 80 |
| 271 | 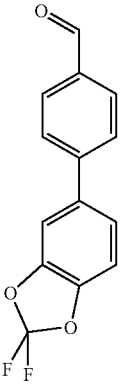 | 1H-NMR (CDCl3) δ: 7.17 (1H, d, J = 8.2 Hz), 7.33-7.36 (2H, m), 7.68 (2H, d, J = 8.2 Hz), 7.95-7.97 (2H, m), 10.07 (1H, s). | Ref. Ex. 75 |
| 273 | 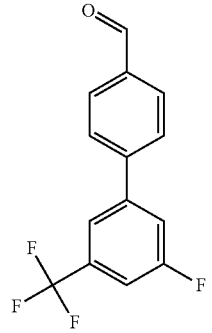 | 1H-NMR (CDCl3) δ: 7.35-7.39 (1H, m), 7.51-7.53 (1H, m), 7.68 (1H, s), 7.74-7.76 (2H, m), 7.99-8.02 (2H, m), 10.09 (1H, s). | Ref. Ex. 75 |

TABLE 2-continued

| Ref. Ex. No | STR | 1H-NMR | ref. |
|---|---|---|---|
| 274 | | 1H-NMR (CDCl3) δ: 5.84-6.06 (1H, m), 7.27-7.29 (1H, m), 7.47-7.56 (3H, m), 7.74-7.75 (2H, m), 7.96-7.98 (2H, m), 10.08 (1H, s) | Ref. Ex. 75 |
| 275 | | 1H-NMR (CDCl3) δ: 7.58-7.60 (4H, m), 7.91-7.93 (4H, m), 8.20 (2H, s), 8.27 (1H, s), 10.17 (1H, s). | Ref. Ex. 75 |
| 276 | | 1H-NMR (CDCl3) δ: 7.38-7.51 (4H, m), 7.75-7.76 (2H, m), 7.93-8.02 (3H, m), 10.10 (1H, s). | Ref. Ex. 75 |
| 277 | | 1H-NMR (CDCl3) δ: 7.39 (1H, d, J = 5.4 Hz), 7.52 (1H, d, J = 5.4 Hz), 7.64-7.66 (1H, m), 7.84-8.15 (5H, m), 8.15 (1H, s), 10.07 (1H, s). | Ref. Ex. 75 |

TABLE 2-continued

| Ref. Ex. No | STR | 1H-NMR | ref. |
| --- | --- | --- | --- |
| 278 | | 1H-NMR (CDCl3) δ: 7.52 (2H, d, J = 8.1 Hz), 7,61 (1H, s), 7.81 (1H, d, J = 8.1 Hz), 7.91-8.01 (3H, m), 10.10 (1H, s). | Ref. Ex. 75 |
| 279 | | 1H-NMR (CDCl3) δ: 7.36 (1H, t, J = 7.7 Hz), 7.66-7.73 (4H, m), 7.98-8.01 (2H, m), 10.09 (1H, s). | Ref. Ex. 75 |
| 280 | | 1H-NMR (DMSO-d6) δ: 7.51 (2H, d, J = 8.5 Hz), 7.58 (1H, d, J = 4.0 Hz), 7.64 (2H, s), 7.75 (2H, d, J = 8.5 Hz), 8.02 (1H, d, J = 4.0 Hz), 9.90 (1H, s). | Ref. Ex. 75 |
| 281 | | 1H-NMR (CDCl3) δ: 7.60-7.65 (3H, m), 7.80 (1H, d, J = 8.3 Hz), 7.85 (1H, s), 7.94-7.93 (2H, m), 10.08 (1H, s). | Ref. Ex. 75 |
| 282 | | 1H-NMR (CDCl3) δ: 7.77-7.87 (1H, m), 7.86-8.10 (4H, m), 10.10 (1H, s). | Ref. Ex. 75 |

TABLE 2-continued
| Ref. Ex. No | STR | 1H-NMR | ref. |
|---|---|---|---|
| 283 |  | 1H-NMR (CDCl3) δ: 4.19 (2H, s), 7.35 (2H, d, J = 8.0 Hz), 7.62 (2H, s), 7.77 (1H, s), 7.87 (2H, d, J = 8.0 Hz), 10.01 (1H, s). | Ref. Ex. 75 |
| 284 | 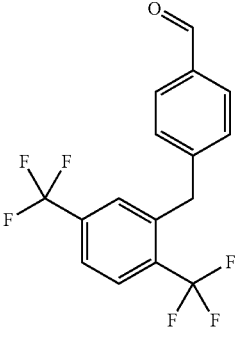 | 1H-NMR (CDCl3) δ: 4.32 (2H, s), 7.26-7.31 (2H, m), 7.44 (1H, s), 7.63-7.66 (1H, m), 7.83-7.86 (3H, m), 10.01 (1H, s). | Ref. Ex. 75 |
| 285 | 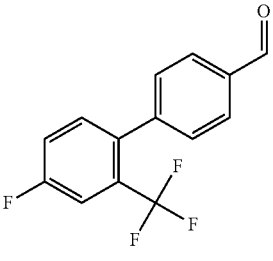 | 1H-NMR (CDCl3) δ: 7.30-7.33 (2H, m), 7.47-7.51 (3H, m), 7.93 (2H, d, J = 8.4 Hz), 10.09 (1H, s). | Ref. Ex. 75 |
| 286 | 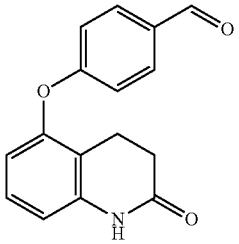 | 1H-NMR (CDCl3) δ: 2.40-2.43 (2H, m), 2.69-2.72 (2H, m), 6.71 (1H, d, J = 8.1 Hz), 6.81 (1H, d, J = 8.1 Hz), 7.05-7.07 (2H, m), 7.24 (1H, t, J = 8.1 Hz), 7.89-7.92 (2H, m), 9.91 (1H, s), 10.29 (1H, s). | Ref. Ex. 169 |
| 287 | 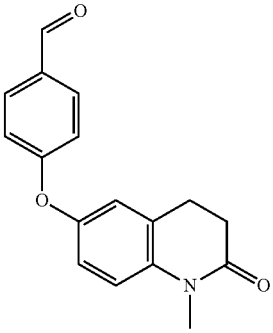 | 1H-NMR (CDCl3) δ: 2.67-2.70 (2H, m), 2.89-2.96 (2H, m), 3.40 (3H, s), 6.91-7.06 (5H, m), 7.84-7.86 (2H, m), 9.93 (1H, s). | Ref. Ex. 12 |

TABLE 2-continued
| Ref. Ex. No | STR | 1H-NMR | ref. |
|---|---|---|---|
| 288 | 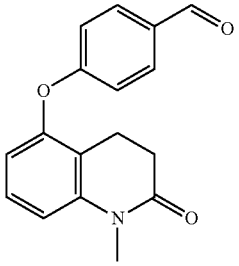 | 1H-NMR (CDCl3) δ: 2.59-2.62 (2H, m), 2.81-2.84 (2H, m), 3.40 (3H, s), 6.78 (1H, d, J = 8.1 Hz), 6.90 (1H, d, J = 8.1 Hz), 6.98-7.01 (2H, m), 7.28-7.32 (1H, m), 7.84-7.86 (2H, m), 9.92 (1H, s). | Ref. Ex. 12 |
| 289 | 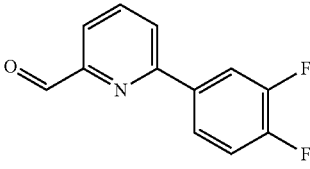 | 1H-NMR (CDCl3) δ: 7.27-7.33 (1H, m), 7.82-8.02 (5H, m), 10.15 (1H, s). | Ref. Ex. 75 |
| 290 | 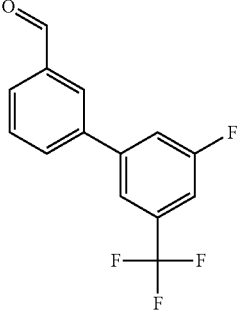 | 1H-NMR (CDCl3) δ: 7.37 (1H, d, J = 8.2 Hz), 7.52 (1H, d, J = 8.2 Hz), 7.66-7.69 (2H, m), 7.85-7.87 (1H, m), 7.94-7.96 (1H, m), 8.10 (1H, s), 10.12 (1H, s). | Ref. Ex. 75 |
| 291 | 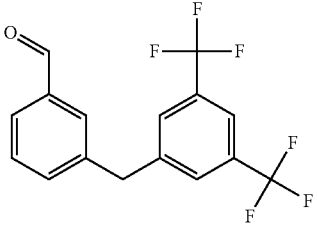 | 1H-NMR (CDCl3) δ: 4.19 (2H, s), 7.45 (1H, d, J = 7.6 Hz), 7.53 (1H, t, J = 7.6 Hz), 7.63 (2H, s), 7.76 (1H, s), 7.79 (1H, s), 7.80 (1H, d, J = 7.6 Hz), 10.01 (1H, s). | Ref. Ex. 75 |
| 292 | 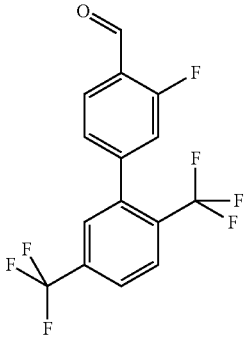 | 1H-NMR (CDCl3) δ: 7.18-7.25 (2H, m), 7.61 (1H, s), 7.82-7.84 (1H, m), 7.93-7.98 (2H, m), 10.43 (1H, s). | Ref. Ex. 75 |
| 293 | 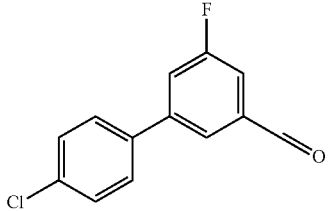 | 1H-NMR (CDCl3) δ: 7.45-7.87 (6H, m), 7.87 (1H, s), 10.05 (1H, s). | Ref. Ex. 75 |

TABLE 2-continued

| Ref. Ex. No | STR | 1H-NMR | ref. |
|---|---|---|---|
| 294 | | 1H-NMR (CDCl3) δ: 5.19 (2H, s), 7.02-7.04 (1H, m), 7.26-7.27 (2H, m), 7.42 (1H, t, J = 8.0 Hz), 7.51-7.67 (4H, m), 7.74 (2H, d, J = 8.0 Hz), 7.96 (2H, d, J = 8.0 Hz), 10.06 (1H, s). | Ref. Ex. 82 |
| 295 | | 1H-NMR (CDCl3) δ: 5.11 (2H, s), 7.00-7.02 (1H, m), 7.22-7.26 (1H, m), 7.37-7.42 (6H, m), 7.73 (2H, d, J = 8.3 Hz), 7.94-7.96 (2H, m), 10.06 (1H, s). | Ref. Ex. 82 |
| 296 | | 1H-NMR (CDCl3) δ: 7.43-7.63 (7H, m), 7.91 (1H, s), 10.06 (1H, s). | Ref. Ex. 75 |
| 297 | | 1H-NMR (CDCl3) δ: 7.40-7.58 (5H, m), 7.90 (1H, s), 10.03 (1H, s). | Ref. Ex. 75 |
| 298 | | 1H-NMR (CDCl3) δ: 7.30-7.50 (1H, m), 7.61-7.63 (2H, m), 7.66-7.67 (1H, m), 7.80-7.85 (2H, m), 10.46 (1H, s). | Ref. Ex. 75 |
| 299 | | 1H-NMR (CDCl3) δ: 7.41-7.42 (1H, m), 7.45-7.46 (1H, m), 7.58 (1H, s), 7.76 (1H, s), 7.82 (1H, s), 7.97 (1H, s), 10.02 (1H, s). | Ref. Ex. 75 |

TABLE 2-continued

| Ref. Ex. No | STR | 1H-NMR | ref. |
|---|---|---|---|
| 300 | | 1H-NMR (CDCl3) δ: 7.45-7.52 (3H, m), 7.61-7.71 (4H, m), 8.04 (1H, s), 10.08 (1H, s). | Ref. Ex. 75 |
| 301 | | 1H-NMR (CDCl3) δ: 7.42-7.43 (1H, m), 7.46-7.48 (1H, m), 7.60 (1H, s), 7.64 (1H, s), 7.67 (1H, s), 8.03 (1H, s), 10.06 (1H, s). | Ref. Ex. 75 |
| 302 | | 1H-NMR (CDCl3) δ: 7.47-7.49 (2H, m), 7.54-7.58 (2H, m), 7.65 (1H, s), 7.72 (1H, s), 8.00 (1H, s), 10.08 (1H, s). | Ref. Ex. 75 |
| 303 | | 1H-NMR(CDCl3) δ: 3.91 (3H, s), 7.12-7.21 (2H, m), 7.24-7.43 (4H, m). | Ref. Ex. 75 |
| 304 | | 1H-NMR (CDCl3) δ: 7.31-7.35 (2H, m), 7.35-7.42 (1H, m), 7.54 (1H, s), 7.62 (1H, s), 7.81 (1H, s). | Ref. Ex. 125 |

TABLE 2-continued

| Ref. Ex. No | STR | 1H-NMR | ref. |
|---|---|---|---|
| 305 | | 1H-NMR (CDCl3) δ: 6.94-7.05 0i, m), 7.40-7.46 (1H, m), 7.55 (1H, s), 7.63 (1H,s), 7.80 (1H, s), | Ref. Ex. 75, Ref. Ex. 750, Ref. Ex. 125 |
| 306 | | 1H-NMR (CDCl3) δ: 7.31-7.44 (3H, m), 7.92 (1H, s), 7.98 (2H, s). | Ref. Ex. 89 |
| 307 | | 1H-NMR (CDCl3) δ: 7.30-7.47 (3H, m), 8.02 (1H, s), 8.13 (1H, s), 8.22 (1H, s), 10.14 (1H, s). | Ref. Ex. 93 |
| 308 | | 1H-NMR (CDCl3) δ: 6.96-7.05 (2H, m), 7.26-7.45 (1H, m), 7.92 (1H, s), 7.99 (2H, s). | Ref. Ex. 89 |
| 309 | | 1H-NMR (CDCl3) δ: 7.79 (1H, s), 8.00 (1H, s), 8.20 (1H, s), 10.09 (1H, s). | Ref. Ex. 125 |

TABLE 2-continued

| Ref. Ex. No | STR | 1H-NMR | ref. |
|---|---|---|---|
| 310 | | 1H-NMR (CDCl3) δ: 6.80-6.81 (1H, m), 7.55-7.56 (1H, m), 7.91 (1H, s), 7.98 (1H, s), 8.04 (1H, s), 8.18 (1H, s), 10.13 (1H, s). | Ref. Ex. 75 |
| 311 | | 1H-NMR (CDCl3) δ: 6.96-7.06 (2H, m), 7.44-7.48 (1H, m), 8.01 (1H, s), 8.15 (1H, s), 8.20 (1H, s), 10.13 (1H, s). | Ref. Ex. 93 |
| 312 | | 1H-NMR (CDCl3) δ: 7.45-7.48 (2H, m), 7.53-7.56 (2H, m), 7.79 (1H, s), 7.84 (1H, s), 7.94 (1H, s), 10.03 (1H, s). | Ref. Ex. 75 |
| 313 | | 1H-NMR (CDCl3) δ: 7.27-7.34 (2H, m), 7.40-7.44 (1H, m), 7.76 (1H, s), 7.85 (1H, s), 7.91 (1H, s), 10.04 (1H, s). | Ref. Ex. 75 |
| 314 | | 1H-NMR (CDCl3) δ: 4.34 (2H, s), 7.40-7.43 (2H, m), 7.51-7.57 (1H, m), 7.64-7.67 (2H, m), 7.79-7.87 (2H, m), 10.01 (1H, s). | Ref. Ex. 75 |
| 315 | | 1H-NMR (CDCl3) δ: 4.02 (2H, s), 6.85-7.11 (3H, m), 7.42-7.51 (2H, m), 7.69-7.77 (2H, m), 9.99 (1H, s). | Ref. Ex. 75 |

TABLE 2-continued

| Ref. Ex. No | STR | 1H-NMR | ref. |
| --- | --- | --- | --- |
| 316 | | 1H-NMR (CDCl3) δ: 1.36 (3H, t, J = 7.2 Hz). 4.30 (2H, q, J = 7.2 Hz), 6.48 (1H, d, J = 15.8 Hz), 7.74 (1H, d, J = 8.2 Hz), 7.94 (1H, d, J = 8.2 Hz), 7.94 (1H, s), 8.04 (1H, dd, J = 2.1, 15.8 Hz). | Ref. Ex. 188 |
| 317 | | 1H-NMR (CDCl3) δ: 5.42 (2H, s), 7.03-7,15 (2H, m), 7.55-7.60 (1H, m), 7.75-7.77 (1H, m), 7.88-7.92 (2H, m), 8.11 (1H, s), 10.55 (1H, s). | Ref. Ex. 82 |
| 319 | | 1H-NMR (CDCl3) δ; 4.80-4.84 (2H, m), 6.46-6.51 (1H, m), 7.13-7.16 (1H, m), 7.24-7.26 (1H, m), 7.45-7.52 (3H, m), 7.63 (1H, d, J = 8.2 Hz), 7.78 (1H, d, J = 8.2 Hz), 7.90 (1H, s), 9.99 (1H, s). | Ref. Ex. 80 |
| 320 | | 1H-NMR (CDCl3) δ: 2.14-2.20 (2H m), 3.06-3.09 (2H, m), 4.12 (2H, s), 7.18-7.22 (1H, m), 7.39 (1H, s), 7.45-7.49 (2H, m), 7.59 (1H, d, J = 8.2 Hz), 7.64 (1H, s), 7.78 (1H, d, J = 8.2 Hz), 9.98 (1H, s). | Ref. Ex. 80 |
| 321 | | 1H-NMR (CDCl3) δ: 2.24 (3H, s), 6.87 (1H, dd, J = 2.5, 8.3 Hz), 6,92 (1H, d, J = 2.5 Hz), 7.05-7.08 (2H, m), 7.09-7.13 (1H, m), 7.18 (1H, d, J = 8.3 Hz), 7.30-7.43 (7H, m). | Ref. Ex. 75 |

| Ref. Ex. No | STR | 1H-NMR | ref. |
|---|---|---|---|
| 322 | | 1H-NMR (CDCl3) δ: 7.02 (1H, d, J = 5.0 Hz), 7.40-7.43 (2H, m), 7.45-7.48 (2H, m), 7.75 (1H, dd, J = 1.2, 5.0 Hz), 9.86 (1H, d, J = 1.2 Hz). | Ref. Ex. 75 |
| 324 | | 1H-NMR (CDCl3) δ: 7.41-7.45 (1H, m), 7.46-7.51 (2H, m), 7.58-7.81 (2H, m), 7.97-7.99 (2H, m), 8.02 (1H, t, J = 1.5 Hz), 10.03 (1H, s). | Ref. Ex. 75 |
| 325 | | 1H-NMR (CDCl3) δ: 3.82 (3H, m), 6.66-6.68 (1H, m), 6.80 (1H, s), 6.88 (1H, s), 6.94-7.01 (2H, m), 7.30-7.37 (2H, m). | Ref. Ex. 85 |
| 326 | | 1H-NMR (CDCl3) δ: 7.00-7.04 (2H, m), 7.05 (1H, t, J = 2.2 Hz), 7.22 (1H, s), 7.24 (1H, s), 7.39-7.43 (2H, m). | Ref. Ex. 87 |
| 327 | | 1H-NMR (CDCl3) δ: 7.00-7.04 (2H, m), 7.35 (1H, s), 7.40-7.44 (3H, m), 7.61 (1H, s). | Ref. Ex. 89 |
| 328 | | 1H-NMR (CDCl3) δ: 7.00-7.04 (2H, m), 7.37-7.41 (2H, m), 7.50 (1H, s), 7.59 (1H, s), 7.85 (1H, s), 10.00 (1H, s). | Ref. Ex. 229 |

TABLE 2-continued

| Ref. Ex. No | STR | 1H-NMR | ref. |
|---|---|---|---|
| 329 | | 1H-NMR (CDCl3) δ: 6.95 (1H, dd, J = 2.2, 8.5 Hz), 7.07-7.08 (1H, m), 7.21-7.24 (1H, m), 7.32-7.35 (1H, m), 7.47 (1H, s), 7.62 (1H, s), 7.89 (1H, s), 10.01 (1H, s). | Ref. Ex. 229 |
| 330 | | 1H-NMR (CDCl3) δ: 3.90 (3H, s), 7.12 (1H, s), 7.23 (1H, s), 7.38 (1H, s), 7.41-7.45 (2H, m), 7.49-7.53 (2H, m) | Ref. Ex. 75 |
| 331 | | 1H-NMR (CDCl3) δ: 3.87 (3H, s), 7.11 (1H, s), 7.15 (1H, s), 7.24 (1H, s), 7.27 (1H, d, J = 8.4 Hz), 7.33 (1H, dd, J = 2.0, 8.4 Hz), 7.51 (1H, d, J = 2.0 Hz). | Ref. Ex. 75 |
| 332 | | 1H-NMR (CDCl3) δ: 7.47-7.53 (5H, m), 7.63 (1H, s), 7.83 (1H, s). | Ref. Ex. 87 |
| 333 | | 1H-NMR (CDCl3) δ: 7.29 (1H, d, J = 8.2 Hz), 7.39 (1H, dd, J = 2.1, 8.2 Hz), 7.56-7.57 (3H, m), 7.71 (1H, s). | Ref. Ex. 87 |

TABLE 2-continued

| Ref. Ex. No | STR | 1H-NMR | ref. |
|---|---|---|---|
| 334 | | 1H-NMR (CDCl3) δ: 7.48-7.54 (4H, m), 7.90 (1H, s), 8.01 (2H, s). | Ref. Ex. 89 |
| 335 | | 1H-NMR (CDCl3) δ: 7.27 (1H, d, J = 8.3 Hz), 7.39 (1H, dd, J = 2.0, 8.3 Hz), 7.56 (1H, d, J = 2.0 Hz), 7.91 (2H, s), 7.95 (1H, s). | Ref. Ex. 89 |
| 336 | | 1H-NMR (CDCl3) δ: 7.47-7.51 (2H, m), 7.57-7.60 (2H, m), 8.05 (1H, s), 8.12 (1H, s), 8.25 (1H, s), 10.14 (1H, s). | Ref. Ex. 229 |
| 337 | | 1H-NMR (CDCl3) δ: 7.33 (1H, d, J = 8.2 Hz), 7.38 (1H, dd, J = 2.1, 8.2 Hz), 7.56 (1H, d, J = 2.1 Hz), 7.94 (1H, s), 8.12 (1H, s), 8.17 (1H, s), 10.12 (1H, s) | Ref. Ex. 229 |
| 338 | | 1H-NMR (CDCl3) δ: 3.89 (3H, s), 7.15 (2H, s), 7.28 (1H, s), 7.32-7.35 (3H, m), 7.46-7.49 (1H, m). | Ref. Ex. 75 |
| 339 | | 1H-NMR (CDCl3) δ: 7.34-7.41 (3H, m), 7.51-7.56 (2H, m), 7.60 (1H, s), 7.75 (1H, s). | Ref. Ex. 87 |

TABLE 2-continued

| Ref. Ex. No | STR | 1H-NMR | ref. |
|---|---|---|---|
| 340 | | 1H-NMR (CDCl3) δ: 7.32-7.53 (3H, m), 7.53-7.56 (1H, m), 7.94 (3H, s). | Ref. Ex. 89 |
| 341 | | 1H-NMR (CDCl3) δ: 7.36-7.41 (3H, m), 7.52-7.56 (1H, m), 7.98 (1H, s), 8.15-8.18 (2H, m), 10.13 (1H, s). | Ref. Ex. 229 |
| 343 | | 1H-NMR (CDCl3) δ: 1.23-1.28 (1H, m), 1.63-1.76 (4H, m), 2.86-2.89 (2H, m), 3.68-3.75 (2H, m), 7.55 (1H, d, J = 8.2 Hz), 7.81 (1H, s), 7.75 (1H, d, J = 8.2 Hz). | Ref. Ex. 33 |
| 344 | | 1H-NMR (CDCl3) δ: 1.84-1.95 (4H, m), 2.92-2.95 (2H, m), 4.06-4.11 (2H, m), 7.16-7.19 (1H, m), 7.38 (1H, s), 7.43-7.47 (2H, m), 7.56 (1H, d, J = 8.3 Hz), 7.63 (1H, s), 7.76 (1H, d, J = 8.3 Hz), 9.98 (1H, s). | Ref. Ex. 80 |
| 345 | | 1H-NMR (CDCl3) δ: 3.38 (2H, t, J = 6.5 Hz), 4.27 (2H, t, J = 6.5 Hz), 7.15-7.17 (1H, m), 7.36 (1H, s). 7.43-7.48 (2H, m), 7.63 (1H, d, J = 8.2 Hz), 7.78 (1H, s), 7.80 (1H, d, J = 8.2 Hz), 9.97 (1H, s). | Ref. Ex. 80 |

| Ref. Ex. No | STR | 1H-NMR | ref. |
| --- | --- | --- | --- |
| 346 | | 1H-NMR (CDCl3) δ: 5.25 (2H, s), 7,S3 (1H, a)f 7.68 (1H, s), 7.80 (1H, s), 7.91-7.94 (3H, m), 10.04 (1H, s). | Ref. Ex. 82, Ref. Ex. 93 |
| 347 | | 1H-NMR (CDCl3) δ: 4.00 (3H, s), 5.39 (2H, s), 7.05 (1H, d, J = 8.3 Hz), 7.47 (1H, s), 7.54-7.58 (1H, m), 7.71 (1H, d, J = 8.3 Hz), 7.84 (1H, d, J = 8.3 Hz), 8.18 (1H, s), 9.85 (1H, s). | Ref. Ex. 82 |
| 348 | | 1H-NMR (CDCl3) δ: 5.39 (2H, s), 6.98-6.99 (1H, m), 7.51-7.54 (1H, m), 7.76-7.90 (3H, m), 8.05 (1H, s), 10.47 (1H, s). | Ref. Ex. 82 |
| 349 | | 1H-NMR (CDCl3) δ: 3.83 (3H, s), 5.37 (2H, s), 6.95-6.99 (1H, m), 7.13-7.16 (1H, m), 7.39 (1H, s), 7.75 (1H, d, J = 8.2 Hz), 7.87 (1H, d, J = 8.2 Hz), 8.07 (1H, s), 10.62 (1H, s). | Ref. Ex. 82 |
| 350 | | 1H-NMR (CDCl3) δ: 4.72 (2H, s), 7.05 (1H, d, J = 7.3 Hz), 7.16 (1H, s), 7.50-7.61 (3H, m), 7.84-7.91 (2H, m), 10.15 (1H, s). | Ref. Ex. 75 |

TABLE 2-continued

| Ref. Ex. No | STR | 1H-NMR | ref. |
|---|---|---|---|
| 351 | | 1-HMR (CDCl3) δ: 5.55 (2H, s), 7.28-7.34 (1H, m), 7.46-7.49 (1H, m), 7.65-7.70 (1H, m), 7.77-7.89 (3H, m), 8.08-8.10 (2H, m), 9.29 (1H, d, J = 8.7 Hz), 11.00 (1H, s) | Ref. Ex. 82 |
| 352 | | 1H-NMR (CDCl3) δ: 5.39 (2H, s), 6.99-7.05 (1H, m), 7.27-7.31 (1H, m), 7.57-7.59 (1H, m), 7.76-7.78 (1H, m), 7.88-790 (1H, m), 8.05 (1H, s), 10.49 (1H, s). | Ref. Ex. 82 |
| 353 | | 1H-NMR (CDCl3) δ: 1.45-1.50 (3H, m), 4.12-4.17 (2H, m), 7.31 (1H, s), 7.39-7.44 (3H, m), 7.54 (1H, s), 7.68 (1H, s), 10.04 (1H, s). | Ref. Ex. 75 |
| 354 | | 1H-NMR (CDCl3) δ: 2.48 (3H, s), 7.39-7.68 (5H, m), 7.90 (1H, s), 10.03 (1H, s). | Ref. Ex. 75 |
| 355 | | 1H-NMR (CDCl3) δ: 3.62 (3H, s), 7.42-7.43 (4H, m), 7.68 (1H, s), 10.42 (1H, s). | Ref. Ex. 75 |
| 356 | | 1H-NMR (CDCl3) δ: 7.39-7.43 (2H, m), 7.73 (1H, s), 7.83-7.89 (2H, m), 8.09 (1H, s), 8.18 (1H, s), 8.37 (1H, s), 10.14 (1H, s), | Ref. Ex. 75 |

TABLE 2-continued
| Ref. Ex. No | STR | 1H-NMR | ref. |
|---|---|---|---|
| 357 | 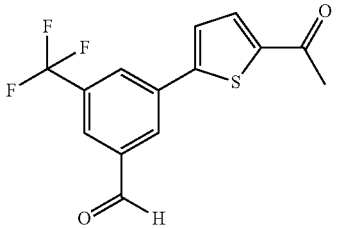 | 1H-NMR (CDCl3) δ: 1.56 (3H, s), 7.48-7.49 (1H, m), 7.71-7.72 (1H, m), 8.12 (2H, s), 8.31 (1H, s), 10.12 (1H, s). | Ref. Ex. 75 |
| 358 | 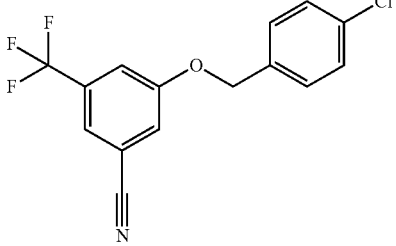 | 1H-NMR (CDCl3) δ: 5.10 (2H, s), 7.32-7.42 (6H, m), 7.52 (1H, s). | Ref. Ex. 82 |
| 359 | 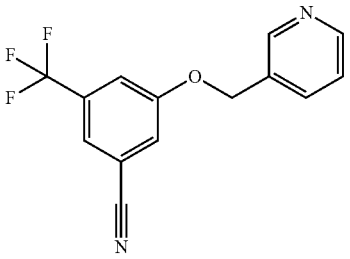 | 1H-NMR (CDCl3) δ: 5.15 (2H, s), 7.37-7.41 (2H, m), 7.45 (1H, s), 7.54 (1H, s), 7.76-7.79 (1H, s). 8.64-8.70 (2H, m). | Ref. Ex. 82 |
| 360 | 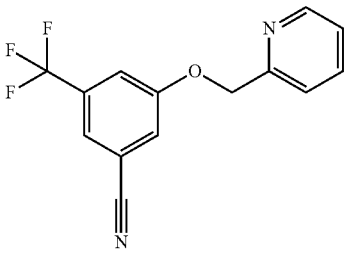 | 1H-NMR (CDCl3) δ: 5.27 (2H, s), 7.26-7.27 (1H, m), 7.42-7.51 (4H, m), 7.73-7.76 (1H, m), 4.62-464 (1H, s). | Ref. Ex. 82 |
| 361 | 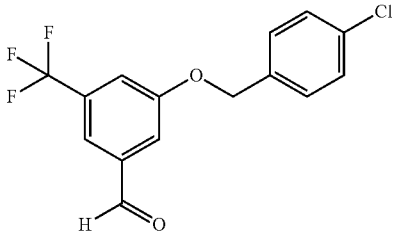 | 1H-NMR (CDCl3) δ: 5.14 (2H, s), 7.36-7.39 (4H, m), 7.48 (1H, s), 7.62 (1H, s), 7.74 (1H, s), 10.01 (1H, s). | Ref. Ex. 93 |
| 362 | 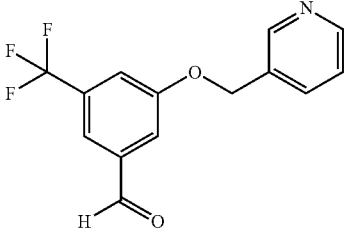 | 1H-NMR (CDCl3) δ: 5.19 (2H, s), 7.36-7.39 (1H, m), 7.49 (1H, s), 7.66 (1H, s), 7.76-7.78 (2H, m), 8.63-8.65 (1H, m), 8.72 (1H, s), 10.02 (1H, s). | Ref. Ex. 93 |

TABLE 2-continued
| Ref. Ex. No | STR | 1H-NMR | ref. |
|---|---|---|---|
| 363 |  | 1H-NMR (CDCl3) δ: 5.30 (2H, s), 7.24-7.27 (1H, m), 7.49-7.53 (2H, m), 7.67 (1H, s), 7.73-7.76 (2H, m), 8.63-8.65 (1H, m), 10.01 (1H, s). | Ref. Ex. 93 |
| 364 |  | 1H-NMR (CDCl3) δ: 7.14-7.19 (1H, m), 7.31-7.44 (4H, m), 7.54-7.57 (2H, m), 7.98 (1H, s), 8.00 (1H, s), 8.19 (1H, s), 10.10 (1H, s). | Ref. Ex. 112 |
| 365 |  | 1H-NMR (CDCl3) δ: 6.44 (1H, t, J = 54.7 Hz), 7.05-7.07 (1H, m), 7.23-7.26 (1H, m), 7.63-7.66 (2H, m), 7.79-7.80 (1H, m), 7.87 (1H, s), 7.97-7.99 (1H, m), 10.09 (1H, s). | Ref. Ex. 75 |
| 366 |  | 1H-NMR (CDCl3) δ: 6.70 (1H, t, J = 56.3 Hz), 7.26-7.31 (1H, m), 7.54 (1H, m), 7.63-7.67 (2H, m), 7.83-7.84 (1H, m), 7.93-7.95 (1H, m), 6.07 (1H, s), 10.10 (1H, s). | Ref. Ex. 75 |
| 367 |  | 1H-NMR (CDCl3) δ: 2.50 (3H, s), 7.41 (1H, s), 7.61 (1H, s), 7.65 (1H, s), 7.78 (1H, s), 7.79 (1H, d, J = 8.3 Hz), 7.92 (1H, d, J = 8.3 Hz), 10.04 (1H, s). | Ref. Ex. 75 |
| 368 |  | 1H-NMR (CDCl3) δ: 1.39-1.40 (6H, m), 4.66-4.71 (1H, m), 7.31 (1H, s), 7.38 (1H, s), 7.40-7.43 (2H, m), 7.53 (1H, s), 7.66 (1H, s), 10.01 (1H, s). | Ref. Ex. 75 |

TABLE 2-continued

| Ref. Ex. No | STR | 1H-NMR | ref. |
|---|---|---|---|
| 369 | | 1H-NMR (CDCl3) δ: 7.59 (1H, d, J = 8.8 Hz), 7.66-7.68 (1H, m), 7.93-7.95 (2H, m), 8.04 (2H, s), 10.09 (1H, s). | Ref. Ex. 75 |
| 370 | | 1H-NMR (CDCl3) δ: 7.63-7.81 (5H, m), 7.85 (1H, S), 8.05 (1H, s), 10.10 (1H, s). | Ref. Ex. 75 |
| 371 | | 1H-NMR (CDCl3) δ: 7.29-7.35 (2H, m), 7.41-7.45 (1H, m), 7.61 (1H, s), 7.73 (1H, s), 7.98 (1H, s), 10.08 (1H, s). | Ref. Ex. 75 |
| 372 | | 1H-NMR (CDCl3) δ: 7.05-7.13 (1H, m), 7.28-7.35 (1H, m), 7.62 (1H, s), 7.77 (1H, s), 7.95 (1H, s), 10.07 (1H, s). | Ref. Ex. 75 |
| 373 | | 1H-NMR (CDCl3) δ: 7.41 (1H, dd, J = 1.3, 5.0 Hz), 7.45 (1H, dd, J = 2.9, 5.0 Hz), 7.57 (1H, dd, J * 1.3, 3.9 Hz), 7.92 (1H, t, J * 1.6 Hz), 7.98 (1H, I, J - 1.7 Hz), 8.01 (1H, t, J= 1.5Hz)h 10.00 (1H, s). | Ref. Ex. 75 |

TABLE 2-continued

| Ref. Ex. No | STR | 1H-NMR | ref. |
|---|---|---|---|
| 374 | | 1H-NMR (CDCl3) δ: 7.45-7.49 (4H, m), 7.59-7.61 (2H, m), 8.01 (2H, d, J = 1.7 Hz), 8.08 (1H, t, J = 1.7 Hz), 10.12 (1H, s). | Ref. Ex. 75 |
| 375 | | 1H-NMR (CDCl3) δ: 7.41-7.45 (1H, m), 7.46 (1H, dd, J = 2.9, 5.0 Hz), 7.48-7.53 (3H, m), 7.61 (1H, dd, J = 1.4, 2.9 Hz), 7.65-7.69 (2H, m), 8.01 (1H, t, J = 1.6 Hz), 8.06 (1H, t, J = 1.7 Hz), 8.08 (1H, t, J = 1.6 Hz), 10.14 (1H, s). | Ref. Ex. 75 |
| 376 | | 1H-NMR (CDCl3) δ: 7.11-7.13 (2H, m), 7.19-7.23 (3H, m), 7.33-7.36 (2H, m), 7.44-7.48 (4H, m), 7.69-7.73 (2H, m), 9.90 (1H, s). | Ref. Ex. 75 |
| 377 | | 1H-NMR (CDCl3) δ: 7.10-7.15 (2H, m), 7.20-7.24 (3H, m), 7.31 (2H, d, J = 8.1 Hz), 7.42-7.49 (4H, m), 7.73 (2H, d, J = 8.1 Hz), 9.97 (1H, s). | Ref. Ex. 75 |
| 378 | | 1H-NMR (CDCl3) δ: 7.70 (1H, s), 7.83 (1H, s), 7.97 (1H, s), 8.04 (2H, s), 8.07 (1H, s), 10.12 (1H, s). | Ref. Ex. 75 |

TABLE 2-continued

| Ref. Ex. No | STR | 1H-NMR | ref. |
|---|---|---|---|
| 379 | | 1H-NMR (CDCl3) δ: 7.42-7.49 (2H, m), 7.57 (1H, s), 7.80-7.88 (1H, m), 7.94-7.99 (1H, m), 8.10 (1H, s), 8.17 (1H, s), 8.28 (1H, s), 10.13 (1H, s). | Ref. Ex. 75 |
| 380 | | 1H-NMR (CDCl3) δ: 7.17 (1H, dd, J = 3.7, 5.1 Hz), 7.44 (1H, dd, J = 1.1, 5.1 Hz), 7.49 (1H, dd, J = 1.1, 3.7 Hz), 8.04 (1H, s), 8.09 (1H, s), 8.28 (1H, s), 10.12 (1H, s). | Ref. Ex. 112 |
| 381 | | 1H-NMR (CDCl3) δ: 4.01 (3H, s), 7.78 (1H, s), 7.88 (1H, s), 7.95 (1H, s), 7.98 (1H, s), 8.15 (1H, s), 10.10 (1H, s). | Ref. Ex. 75 |
| 382 | | 1H-NMR (CDCl3) δ: 7.41-7.52 (2H, m), 7.67 (2H, d, J = 7.5 Hz), 7.79 (1H, s), 8.04 (1H, s), 10.13 (1H, s). | Ref. Ex. 75 |
| 383 | | 1H-NMR (CDCl3) δ: 7.31-7.32 (1H, m), 7.46 (1H, s), 7.54-7.55 (2H, m), 7.67 (1H, s), 7.75 (1H, s), 8.02 (1H, s), 10.09 (1H, s). | Ref. Ex. 75 |

TABLE 2-continued
| Ref. Ex. No | STR | 1H-NMR | ref. |
|---|---|---|---|
| 384 |  | 1H-NMR (CDCl3) δ: 7.37-7.39 (3H, m), 7.52-7.54 (1H, m), 7.60 (1H, s), 7.76 (1H, s), 7.90 (1H, s), 10.06 (1H, s). | Ref. Ex. 75 |
| 385 |  | 1H-MAR (CDCl3) δ: 5.34 (2H, s), 7.61 (1H, s), 7.70-7.87 (3H, m), 8.25 (1H, s), 10.18 (1H, s). | Ref. Ex. 82 |
| 386 |  | 1H-NMR (CDCl3) δ: 5.49 (2H, s), 7.20-7.23 (1H, m), 7.39-7.44 (1H, m), 7.66-7.68 (1H, m), 7.76 (1H, d, J = 8.2 Hz), 7.88 (1H, d, J = 8.2 Hz), 8.16 (1H, s), 10.33 (1H, s). | Ref. Ex. 82 |
| 387 |  | 1H-NMR (CDCl3) δ: 5.17 (2H, s), 7.27-7.28 (1H, m), 7.31 (1H, d, J = 8.5 Hz), 7.38 (1H, d, J = 8.5 Hz), 7.47-7.54 (4H, m), 10.00 (1H, s). | Ref. Ex. 80 |
| 388 |  | 1H-NMR (CDCl3) δ: 5.22 (2H, s), 6.96 (1H, d, J = 8.9 Hz), 7.34-7.38 (2H, m), 7.50-7.52 (2H, m), 7.85 (1H, s), 10.48 (1H, a). | Ref. Ex. 82 |

TABLE 2-continued

| Ref. Ex. No | STR | 1H-NMR | ref. |
|---|---|---|---|
| 389 | | 1H-NMR (CDCl3) δ: 5.22 (2H, s), 6.97-6.99 (1H, m), 7.27-7.29 (1H, m), 7.33-7.38 (2H, m), 7.49 (1H, s), 7.56-7.58 (1H, m), 10.50 (1H, s). | Ref. Ex. 82 |
| 390 | | 1H-NMR (CDCl3) δ: 2.27 (3H, s), 6.95-7.04 (2H, m), 7.18-7.21 (1H, m), 7.42 (1H, s), 7.72 (1H, s), 7.75 (1H, s), 10.05 (1H, s). | Ref. Ex. 75 |
| 391 | | 1H-NMR (CDCl3) δ: 6.07 (2H, s), 6.61 (1H, s), 7.17-7.20 (1H, m), 7.22-7.25 (1H, m), 7.37-7.42 (1H, m), 7.45-7.47(1H, m), 7.60 (1H, d, J = 6.1 Hz), 7.83 (1H, d, J = 8.1 Hz), 7.87 (1H, d, J = 8.2 Hz), 9.93 (1H, s). | Ref. Ex. 113 |
| 392 | | 1H-NMR (CDCl3) δ: 5.88 (2H, s), 7.09 (1H, d, J = 7.7 Hz), 7.19-7.24 (1H, m), 7.33-7.38 (3H, m), 7.39-7.43 (2H, m), 7.48 (1H, d, J = 7.7 Hz), 7.79 (1H, d, J = 8.0 Hz), 9.91 (1H, s). | Ref. Ex. 113 |
| 393 | | 1H-NMR (CDCl3) δ: 5.13 (2H, s), 7.19-7.24 (2H, m), 7.27-7.33 (1H, m), 7.49 (1H, s), 7.63 (1H, s), 7.77 (1H, s), 10.04 (1H, s). | Ref. Ex. 82 |
| 394 | | 1H-NMR (CDCl3) δ: 7.34-7.37 (2H, m), 7.51-7.60 (3H, m), 7.89-7.92 (1H, m), 8.32 (1H, s), 10.00 (1H, s). | Ref. Ex. 75 |

TABLE 2-continued

| Ref. Ex. No | STR | 1H-NMR | ref. |
|---|---|---|---|
| 395 | | 1H-NMR (CDCl3) δ: 3.91 (3H, s), 7.04-7.08 (2H, m), 7.32-7.37 (2H, m), 7.59-7.61 (1H, m), 7.86-7.89 (1H, m), 8.29 (1H, s), 10.03 (1H, s). | Ref. Ex. 75 |
| 396 | | 1H-NMR (CDCl3) δ: 7.40-7.41 (1H, m), 7.50-7.51 (1H, m), 7.65 (1H, s), 7.62 (1H, s), 7.91 (1H, s), 7.97 (1H, s), 10.06 (1H, s). | Ref. Ex. 75 |
| 397 | | 1H-NMR (CDCl3) δ: 7.36-7.40 (1H, m), 7.65-7.70 (2H, m), 7.80 (1H, s), 7.91-7.95 (2H, m), 10.04 (1H, s). | Ref. Ex. 75 |
| 398 | | 1H-NMR (CDCl3) δ: 5.84 (2H, s), 6.40 (1H, dd, J = 2.6, 4.1 Hz), 6.73 (1H, s), 6.97 (1H, s), 7.09 (1H, dd, J = 1.7, 4.1 Hz), 7.62 (1H, d, J = 8.2 Hz), 7.83 (1H, d, J = 8.2 Hz), 9.58 (1H, s). | Ref. Ex. 184 |
| 399 | | 1H-NMR (CDCl3) δ: 5.79 (2H, s), 7.02 (2H, d, J = 8.3 Hz), 7.18-7.23 (3H, m), 7.34-7.42 (3H, m), 7.76-7.78 (1H, m), 9.89 (1H, s). | Ref. Ex. 113 |

TABLE 2-continued

| Ref. Ex. No | STR | 1H-NMR | ref. |
|---|---|---|---|
| 400 | | 1H-NMR (CDCl3) δ: 7.59-7.71 (2H, m), 7.73 (1H, s), 7.82-7.84 (1H, m), 7.91-7.98 (2H, m), 10.03 (1H, s). | Ref. Ex. 75 |
| 401 | | 1H-NMR (CDCl3) δ: 3.86 (2H, s), 6.89-6.99 (2H, m), 7.09-7.14 (1H, m), 7.40 (1H, s), 7.56 (1H, s), 7.72 (1H, s), 9.94 (1H, s). | Ref. Ex. 75 |
| 402 | | 1H-NMR (CDCl3) δ: 7.61-7.63 (1H, m), 7.87 (2H, s), 7.98-8.00 (1H, m), 8.05 (1H, s), 8.36 (1H, s), 9.99 (1H, s). | Ref. Ex. 75 |
| 403 | | 1H-NMR (CDCl3) δ: 7.23 (1H, dd, J = 1.4, 5.0 Hz), 7.39 (1H, dd, J = 1.4, 3.0 Hz), 7.53 (1H, dd, J = 3.0, 5.0 Hz), 7.63-7.66 (1H, m), 7.66-7.89 (1H, m), 8.29 (1H, s), 10.15 (1H, s). | Ref. Ex. 112 |
| 404 | | 1H-NMR (CDCl3) δ: 6.63 (1H, s), 7.61-7.63 (3H, m), 7.85-7.89 (1H, m), 8.28 (1H, s), 10.10 (1H, s). | Ref. Ex. 112 |
| 405 | | 1H-NMR (CDCl3) δ: 7.11-7.16 (4H, m), 7.18-7.24 (1H, m), 7.34-7.45 (4H, m), 7.62 (1H, d, J = 8.1 Hz), 7.87-7.91 (1H, m), 8.31 (1H, s), 10.06 (1H, s). | Ref. Ex. 112 |

TABLE 2-continued

| Ref. Ex. No | STR | 1H-NMR | ref. |
|---|---|---|---|
| 406 | | 1H-NMR (DMSO-d6) δ: 5.33 (2H, s), 7.36-7.39 (1H, m), 7.71-7.84 (4H, m), 10.16 (1H, s). | Ref. Ex. 82 |
| 407 | | 1H-NMR (DMSO-d6) δ: 5.37 (2H, s), 7.29-7.34 (1H, m), 7.58 (1H, d, J = 7.8 Hz), 7.66-7.75 (4H, m), 10.23 (1H, s). | Ref. Ex. 82 |
| 408 | | 1H-NMR (DMSO-d6) δ: 5.25 (2H, s), 7.53-7.55 (1H, m), 7.73-7.77 (3H, m), 7.93-7.99 (1H, m), 10.12 (1H, s). | Ref. Ex. 82 |
| 409 | | 1H-NMR (CDCl3) δ: 5.22 (2H, s), 7.13-7.24 (4H, m) 7.35-7.40 (1H, m), 7.60-7.62 (1H, m), 10.29 (1H, s). | Ref. Ex. 82 |
| 410 | | 1H-NMR (CDCl3) δ: 5.37 (2H, s), 7.19-7.23 (1H, m), 7.39-7.43 (1H, m), 7.65-7.66 (1H, m), 7.90 (1H, s), 7.94 (2H, s), 10.35 (1H, s). | Ref. Ex. 82 |
| 411 | | 1H-NMR (CDCl3) δ: 5.21 (2H, s), 7.17-7.19 (1H, m), 7.39-7.42 (2H, m), 7.49 (1H, s), 7.65 (1H, s), 7.75 (1H, s), 10.03 (1H, s). | Ref. Ex. 82 |

TABLE 2-continued

| Ref. Ex. No | STR | 1H-NMR | ref. |
|---|---|---|---|
| 412 | | 1H-NMR (CDCl3) δ; 5.22 #H, s), 6.91 (1H, d, J = 8.9 Hz), 7.34-7.38 (2H, m), 7.49 (1H, s), 7.64-7.66 (1H, m), 7.98 (1H, s), 10.46 (1H, s). | Ref. Ex. 82 |
| 413 | | 1H-NMR (CDCl3) δ: 5.15 (2H, s), 7.36 (1H, d, J = 8.2 Hz), 7.43 (1H, d, J = 8.2 Hz), 7.52 (1H, s), 7.70 (1H, s), 7,74 (1H, 3), 10.18 (1H, s). | Ref. Ex. 82 |
| 414 | | 1H-NMR (CDCl3) δ: 1.06 (6H, s), 3.80 (4H, s), 7 60-7.62 (1H,m), 7.72-7.74 (1H, m), 8.08 (1H, s), 10.02 (1H, s). | Ref. Ex. 107 |
| 415 | | 1H-NMR (CDCl3) δ: 5.32 (2H, s), 7.13-7.18 (1H, m), 7.36-7.41 (1H, m), 7.51-7.55 (1H, m), 7.61-7.64 (3H, m), 7.69 (1H, s), 10.31 (1H, s). | Ref. Ex. 82 |
| 416 | | 1H-NMR (CDCl3) δ: 5.29 (2H, s), 7.12-7.28 (3H, m), 7.34-7.44 (3H, m), 7.60 (1H, d, J = 7.8 Hz), 10.29 (1H, s). | Ref. Ex. 82 |
| 417 | | 1H-NMR (CDCl3) δ: 2.73-2.77 (2H, m), 3.44-3.47 (2H, m), 5.37 (2H, S), 7.26 (1H, d, J = 6.0 Hz), 7.39 (1H, t, J = 8.0 Hz), 7.56 (1H, d, J = 8.0 Hz), 7.92 (2H, s), 8.01 (1H, s), 10.46 (1H, s). | Ref. Ex. 184 |

TABLE 2-continued
| Ref. Ex. No | STR | 1H-NMR | ref. |
|---|---|---|---|
| 418 | 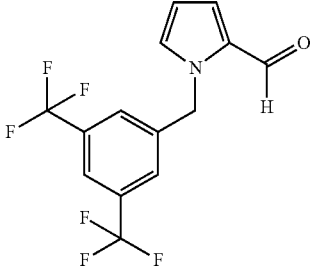 | 1H-NMR (CDCl3) δ: 5.67 (2H, s), 6.37 (1H, dd, J = 2.8, 3.9 Hz), 7.03-7.06 (2H, m), 7.53 (2H, s), 7.78 (1H, s), 9.54 (1H, d, J = 0.8 Hz). | Ref. Ex. 184 |
| 419 | 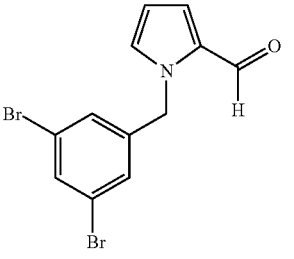 | 1H-NMR (CDCl3) δ: 5.51 (2H, s), 6.33 (1H, dd, J = 2.7, 4.0 Hz), 6.08 (2H, s), 7.01 (1H, d, J = 1.5, 4.0 Hz), 7.17 (1H, d, J = 1.3 Hz), 7.56 (1H, t, J = 1.5 Hz), 9.55 (1H, d, J = 0.8 Hz). | Ref. Ex. 184 |
| 420 | 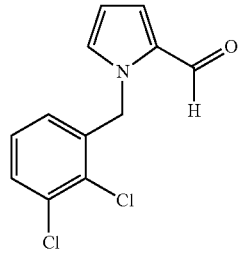 | 1H-NMR (CDCl3) δ: 5.69 (2H, s), 6.33 (1H, dd, J = 2.5, 4.0 Hz), 6.52-6.55 (1H, m), 6.99 (1H, s), 7.03 (1H, dd, J = 1.5, 4.0 Hz), 7.09 (1H, t, J = 7.9 Hz), 7.36-7.39 (1H, m), 9.57 (1H, s). | Ref. Ex. 184 |
| 421 | 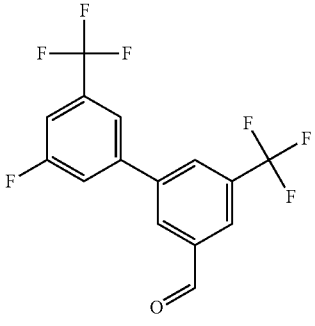 | 1H-NMR (CDCl3) δ: 7.44-7.47 (1H, m), 7.54-7.59 (1H, m), 7.71 (1H, s), 8.09 (1H, s), 8.22 (1H, s), 8.30 (1H, s), 10.19 (1H, s). | Ref. Ex. 81, Ref. Ex. 75 |
| 422 | 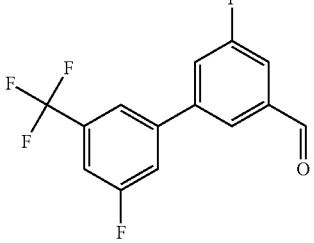 | 1H-NMR (CDCl3) δ: 7.40-7.41 (1H, m), 7.50-7.57 (2H, m), 7.62-7.66 (2H, m), 7.90 (1H, s), 10.07 (1H, s). | Ref. Ex. 75 |

TABLE 2-continued

| Ref. Ex. No | STR | 1H-NMR | ref. |
|---|---|---|---|
| 423 | | 1H-NMR (CDCl3) δ: 7.34 (1H, d, J = 8.5 Hz), 7.62-7.70 (3H, m), 7.83 (1H, d, J = 8.1 Hz), 7.95 (1H, d, J = 8.1 Hz), 10.04 (1H, s). | Ref. Ex. 75 |
| 424 | | 1H-NMR (CDCl3) δ: 7.08-7.10 (1H, m), 7.29-7.34 (1H, m), 7.48-7.51 (1H, m), 7.60-7.62 (1H, m), 7.81 (1H, s), 10.05 (1H, s). | Ref. Ex. 75 |
| 425 | | 1M-NMR (CDCl3) δ: 3.03 (3H, s), 5.24 (2H, s), 7.24-7.28 (1H, m), 7.62-7.67 (2H, m). | Ref. Ex. 103 |
| 426 | | 1H-NMR (CDCl3) δ: 5.17 (2H, s), 6.99-7.01 (1H, m), 7.26-7.29 (2H, m), 7.55-7.57 (1H, m), 7.63-7.65 (1H, m), 7.68-7.69 (1H, m), 10.48 (1H, s). | Ref. Ex. 82 |
| 427 | | 1H-NMR (CDCl3) δ: 5.40 (2H, s), 7.22-7.31 (1H, m), 7.38 (1H, t, J = 8.0 Hz), 7.62-7.63 (1H, m), 7.75 (1H, d, J = 8.0 Hz), 7.87 (1H, d, J = 8.0 Hz), 8.28 (1H, s), 10.57 (1H, s). | Ref. Ex. 82 |

TABLE 2-continued

| Ref. Ex. No | STR | 1H-NMR | ref. |
|---|---|---|---|
| 428 | | 1H-NMR (CDCl3) δ: 5.77-6.13 (1H, m), 7.30-7.45 (1H, m), 7.51-7.60 (5H, m), 7.89 (1H, s), 10.06 (1H, s). | Ref. Ex. 75 |
| 429 | | 1H-NMR (CDCl3) δ: 4.32 (2H, s), 7.06-7.09 (1H, m), 7.45-7.48 (2H, m), 7.60-7.88 (3H, m), 9.96 (1H, s). | Ref. Ex. 75 |
| 430 | | 1H-NMR (CDCl3) δ: 5.13 (2H, s), 6.92-7.05 (1H, m), 7.23-7.40 (2H, m), 7.47-7.52 (3H, m), 9.99 (1H, s). | Ref. Ex. 82 |
| 431 | | 1H-NMR (CDCl3) δ: 5.15 (3H, s), 7.16-7.25 (2H, m), 7.47-7.61 (3H, m), 10.00 (1H, s). | Ref. Ex. 82 |
| 432 | | 1H-NMR (CDCl3) δ: 5.27 (2H, s), 6.90-7.01 (1H, m), 7.10-7.19 (1H, m), 7.35-7.39 (2H, m), 7.60-7.83 (1H, m), 10.29 (1H, s). | Ref. Ex. 82 |
| 433 | | 1H-NMR (CDCl3) δ: 4.28 (2H, s), 7.66 (2H, s), 7.73 (1H, s), 7.82 (1H, s), 7.90 (1H, s), 8.08 (1H, s), 10.07 (1H, s). | Ref. Ex. 75 |

TABLE 2-continued
| Ref. Ex. No | STR | 1H-NMR | ref. |
|---|---|---|---|
| 434 | 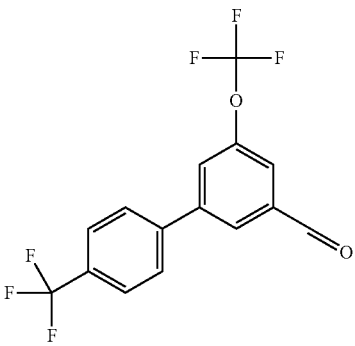 | 1H-NMR (CDCl3) δ: 7.69-7.79 (6H, m), 8.05 (1H, s), 10.10 (1H, s). | Ref. Ex. 75 |
| 435 | 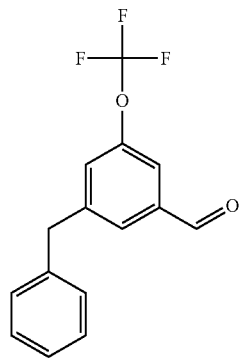 | 1H-NMR (CDCl3) δ: 4.08 (2H, s), 7.17-7.34 (6H, m), 7.57 (1H, s), 7.64 (1H, s), 9.96 (1H, s). | Ref. Ex. 75 |
| 436 | 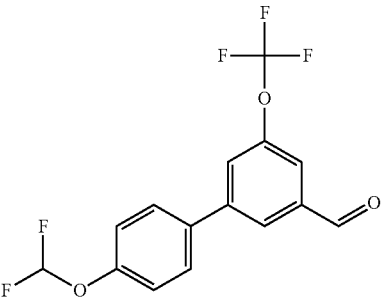 | 1H-NMR (CDCl3) δ: 6.58 (1H, t, J = 73.4 Hz), 7.24-7.27 (2H, m), 7.59-7.72 (4H, m), 8.01 (1H, s), 10.10 (1H, s). | Ref. Ex. 75 |
| 437 | 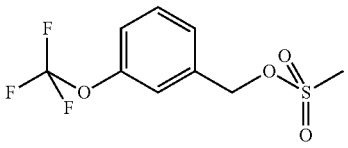 | 1H-NMR (CDCl3) δ: 2.99 (3H, s), 5.25 (2H, s), 7.25-7.29 (2H, m), 7.36 (1H, d, J = 7.8 Hz), 7.46 (1H, t, J = 7.9 Hz). | Ref. Ex. 106 |
| 438 | 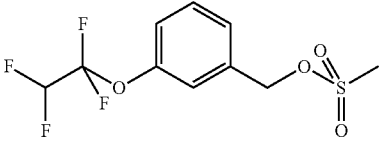 | 1H-NMR (CDCl3) δ: 2.97 (3H, s), 5.25 (2H, s), 5.92 (1H, tt, J = 2.8, 53.0 Hz), 7.24-7.28 (2H, m), 7.34 (1H, d, J = 7.7 Hz), 7.44 (1H, t, J = 7.7 Hz). | Ref. Ex. 106 |
| 439 | 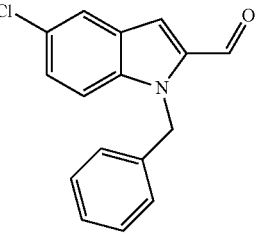 | 1H-NMR (CDCl3) δ: 5.82 (2H, s), 7.04-7.07 (2H, m), 7.20-7.28 (4H, m), 7.31-7.32 (2H, m), 7.74 (1H, t, J = 1.3 Hz), 9.91 (1H, s). | Ref. Ex. 113 |

TABLE 2-continued
| Ref. Ex. No | STR | 1H-NMR | ref. |
|---|---|---|---|
| 440 | 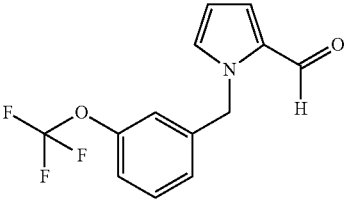 | 1H-NMR (CDCl3) δ: 5.58 (2H, s), 6.31 (1H, dd, J = 2.9, 3.7 Hz), 6.95 (1H, s), 6.98-7.02 (2H, m), 7.03-7.08 (1H, m), 7.08-7.14 (1H, m), 7.33 (1H, t, J = 8.0 Hz), 9.55 (1H, d, J = 0.8 Hz). | Ref. Ex. 184 |
| 441 | 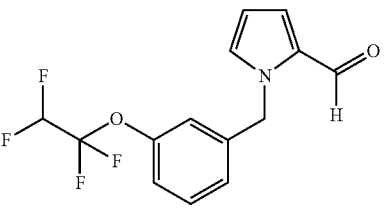 | 1H-NMR (CDCl3) δ: 5.58 (2H, s). 5.88 (1H, tt, J = 2.9, 53.0 Hz), 6.30 (1H, t, J = 3.3 Hz), 6.96 (1H, s), 6.98 (2H, d, J = 3.5 Hz), 7.02-7.07 (1H, m), 7.09-7.15 (1H, m), 7.32 (1H, t, J = 8.0 Hz), 9.55 (1H, s). | Ref. Ex. 184 |
| 442 | 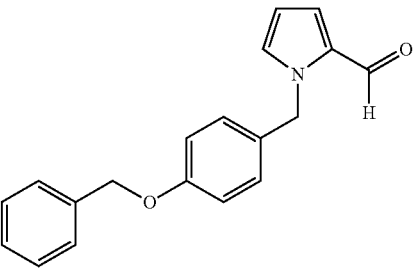 | 1H-NMR (CDCl3) δ: 5.03 (2H, s), 5.49 (2H, s), 6.24 (1H, t, J = 3.3 Hz), 6.88-6.94 (2H, m), 6.95 (2H, d, J = 3.5 Hz), 7.09-7.16 (2H, m), 7.29-7.44 (5H, m), 9.56 (1H, s). | Ref. Ex. 184 |
| 443 | 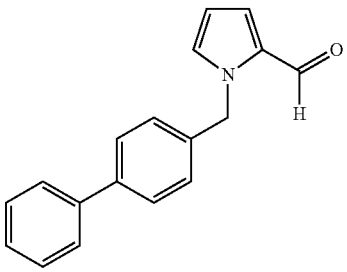 | 1H-NMR (CDCl3) δ: 5.61 (2H, s), 6.29 (1H, dd, J = 2.5, 4.0 Hz), 6.99 (1H, dd, J = 1.7, 4.0 Hz), 7.01-7.04 (1H, m), 7.20-7.25 (2H, m), 7.30-7.37 (1H, m), 7.38-7.46 (2H, m), 7.51-7.58 (4H, m), 9.53 (1H, d, J = 1.0 Hz). | Ref. Ex. 184 |
| 444 | 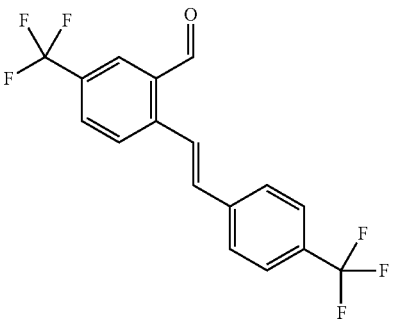 | 1H-NMR (CDCl3) δ: 7.38 (1H, d, J = 16.3 Hz), 7.65-7.72 (4H, m), 7.84-7.91 (2H, m), 8.12-8.21 (2H, m), 10.34 (1H, s). | Ref. Ex. 112 |
| 445 | 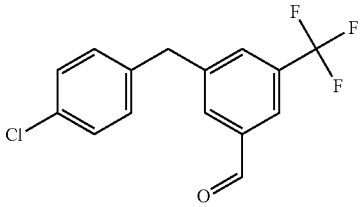 | 1H-NMR (CDCl3) δ: 4.12 (2H, s), 7.12-7.16 (2H, m), 7.29-7.35 (2H. m), 7.71 (1H, s), 7.98 (1H, s), 8.02 (1H, s), 10.05 (1H, s). | Ref. Ex. 81, Ref. Ex. 75 |

TABLE 2-continued
| Ref. Ex. No | STR | 1H-NMR | ref. |
|---|---|---|---|
| 446 | 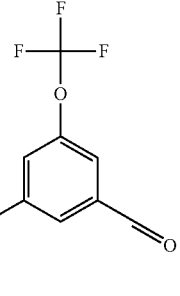 | 1H-NMR (CDCl3) δ: 7.35 (2H, d, J = 8.0 Hz), 7.63-7.66 (3H, m), 7.73 (1H, s), 8.02 (1H, s), 10.08 (1H, s). | Ref. Ex. 75 |
| 447 | 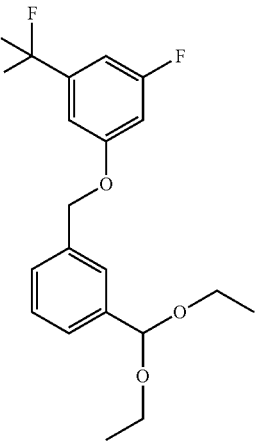 | 1H-NMR (CDCl3) δ: 1.24 (6H, t, J = 7.1 Hz), 3.51-3.65 (4H, m), 5.10 (2H, s), 5.52 (1H, s), 6.83-6.95 (2H, m), 7.03 (1H, s), 7.38-7.48 (3H, m), 7.53 (1H, s). | Ref. Ex. 82 |
| 448 | 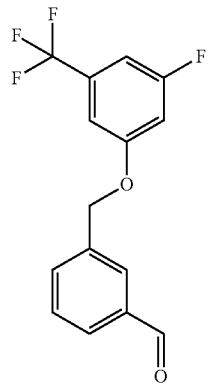 | 1H-NMR (CDCl3) δ: 5.16 (2H, s), 6.84-6.89 (1H, m), 6.97 (1H, d, J = 7.8 Hz), 7.05 (1H, s), 7.60 (1H, t, J = 7.6 Hz), 7.70 (1H, d, J = 7.6 Hz), 7.89 (1H, d, J = 7.6 Hz), 7.96 (1H, s), 10.06 (1H, s). | Ref. Ex. 151 |
| 449 | 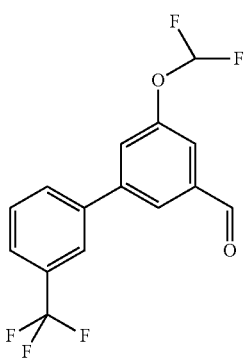 | 1H-NMR (CDCl3) δ: 6.65 (1H, t, J = 72.6 Hz), 7.61-7.72 (4H, m), 7.79-7.87 (2H, m), 7.97 (1H, s), 10.09 (1H, s). | Ref. Ex. 91 |

| Ref. Ex. No | STR | 1H-NMR | ref. |
|---|---|---|---|
| 450 | | 1H-NMR (CDCl3) δ: 6.64 (1H, t, J = 72.7 Hz), 7.11-7.31 (2H, m), 7.45-7.65 (4H, m), 7.94 (1H, s), 10.05 (1H, s). | Ref. Ex. 91 |
| 451 | | 1H-NMR (CDCl3) δ: 6.64 (1H, t, J = 72.8 Hz), 7.33-7.36 (2H, m), 7.58-7.66 (4H, m), 7.93 (1H, s), 10.07 (1H, s). | Ref. Ex. 91 |
| 452 | | 1H-NMR (CDCl3) δ: 1.04 (6H, s), 3.80 (4H, s), 6.58 (1H, t, J = 73.4 Hz), 7.66 (1H, s), 7.73 (1H, s), 8.14 (1H, s), 10.03 (1H, s). | Ref. Ex. 107 |
| 453 | | 1H-NMR (CDCl3) δ: 6.63 (1H, t, J 72.8 Hz), 7.45-7.63 (6H, m), 7.93 (1H, s), 10.06 (1H, s). | Ref. Ex. 91 |
| 454 | | 1H-NMR (CDCl3) δ: 6.67 (1H, t, J = 72.4 Hz), 7.63 (1H, s), 7.73 (1H, s), 7.96-8.10 (4H, m), 10.10 (1H, 5). | Ref. Ex. 91 |

TABLE 2-continued

| Ref. Ex. No | STR | 1H-NMR | ref. |
|---|---|---|---|
| 455 | | 1H-NMR (CDCl3) δ: 6.66 (1H, t, J = 72.5 Hz), 7.40-7.43 (1H, m), 7.52-7.56 (1H, m), 7.60 (1H, s), 7.65 (1H, s), 7.70 (1H, s), 7.95 (1H, s), 10.09 (1H, s). | Ref. Ex. 91 |
| 456 | | 1H-NMR (CDCl3) δ: 6.63 (1H, t, J = 72.6 Hz), 7.39 (1H, s), 7.60-7.73 (3H, m), 7.82-7.98 (2H, m), 10.05 (1H, s). | Ref. Ex. 91 |
| 457 | | 1H-NMR (CDCl3) δ: 7.85 (1H, s), 7.94-8.03 (6H, m), 10.08 (1H, s). | Ref. Ex. 91 |
| 458 | | 1H-NMR (DMSO-d6) δ: 5.39 (2H, s), 7.18 (2H, d, J = 3.8 Hz), 7.66 (1H, d, J = 4.0 Hz), 7.79 (2H, d, J = 8.8 Hz), 8.01 (1H, d, J = 4.0 Hz), 8.11 (1H, s), 8.20 (2H, s), 9.88 (1H, s). | Ref. Ex. 82 |
| 459 | | 1H-NMR (DMSO-d6) δ: 5.17 (2H, s), 7.18 (2H, d, J = 8.8 Hz), 7.30-7.59 (3H, m), 7.64 (1H, d, J = 4.0 Hz), 7.76 (2H, d, J = 8.8 Hz), 8.01 (1H, d, J = 4.0 Hz), 9.88 (1H, s). | Ref. Ex. 82 |

TABLE 2-continued

| Ref. Ex. No | STR | 1H-NMR | ref. |
|---|---|---|---|
| 460 | | 1H-NMR (DMSO-d6) δ: 5.40 (2H, s), 7.16 (2H, d, J = 8.7 Hz), 7.65 (1H, d, J = 4.0 Hz), 7.79 (2H, d, J = 8.7 Hz), 7.93-8.10 (3H, m), 8.19 (1H, s), 9.88 (1H, s). | Ref. Ex. 82 |
| 461 | | 1H-NMR (DMSO-d6) δ: 5.42 (2H, 5), 7.12-7.15 (1H, m), 7.43-7.48 (3H, m), 7.80 (1H, d, J = 4.0 Hz), 8.02-8.10 (3H, m), 8.22 (1H, s), 9.92 (1H, s). | Ref. Ex. 82 |
| 462 | | 1H-NMR (DMSO-d6) δ: 5.41 (2H, s), 7.13-7.17 (1H, m), 7.41-7.51 (3H, m), 7.79 (1H, d, J = 4.0 Hz), 8.06 (1H, d, J = 4.0 Hz), 8.11 (1H, s), 8.22 (2H, s), 9.92 (1H, s). | Ref. Ex. 82 |
| 463 | | 1H-NMR (CDCl3) δ: 2.28 (3H, s), 7.10-7.15 (2H, m), 7.24-7.26 (1H, m), 7.55 (1H, s), 7.70 (1H, s), 7.87 (1H, s), 10.02 (1H, s). | Ref. Ex. 91 |

TABLE 2-continued

| Ref. Ex. No | STR | 1H-NMR | ref. |
|---|---|---|---|
| 464 | | 1H-NMR (CDCl3) δ: 7.37-7.48 (3H, m), 7.78 (1H, s), 7.88 (1H, s), 7.93 (1H, s), 10.04 (1H, s). | Ref. Ex. 91 |
| 465 | | 1H-NMR (DMSO-d6) δ: 7.88 (1H, d, J = 8.4 Hz), 7.98 (1H, s), 8.11-3.19 (1H, m), 8.22-8.25 (2H, m), 8.29 (1H, s), 10.08 (1H, 8). | Ref. Ex. 91 |
| 466 | | 1H-NMR (CDCl3) δ: 5.76-6.13 (1H, m), 7.32-7.35 (2H, m), 7.60-7.64 (2H, m), 7.80-7.85 (2H, m), 7.95 (1H, s), 10.04 (1H, s). | Ref. Ex. 91 |
| 467 | | 1H-NMR (CDCl3) δ: 7.31-7.37 (1H, m), 7.76-7.83 (3H, m), 7.88 (1H, s), 7.94 (1H, s), 10.05 (1H, s). | Ref. Ex. 91 |
| 468 | | 1H-NMR (DMSO-d6) δ: 4.04 (2H, s), 7.16-7.21 (4H, m), 7.42 (1H, s), 7.58 (1H, s), 7.72 (1H, s), 9.94 (1H, s). | Ref. Ex. 112 |
| 469 | | 1H-NMR (CDCl3) δ: 6.57 (1H, t, J = 73.5 Hz), 7.23-7.24 (2H, m), 7.59-7.63 (2H, m), 7.79-7.84 (2H, m), 7.94 (1H, s), 10.04 (1H, s). | Ref. Ex. 91 |

TABLE 2-continued

| Ref. Ex. No | STR | 1H-NMR | ref. |
|---|---|---|---|
| 470 | | 1H-NMR (CDCl3) δ: 4.39 (2H, s), 7.45 (1H, s), 7.65-7.70 (2H, m), 7.80 (1H, s), 7.88 (1H, d, J = 8.2 Hz), 8.04 (1H, s), 10.3 (1H, s). | Ref. Ex. 81, Ref. Ex. 75 |
| 471 | | 1H-NMR (CDCl3) δ: 4.33 (2H, s), 7.19 (1H, d, J = 7.6 Hz), 7.44 (1H, t, J = 7.6 Hz), 7.51 (1H, t, J = 7.56 Hz), 7.66 (1H, s), 7.72 (1H, d, J = 7.6 Hz), 7.81 (1H, s), 8.01 (1H, s), 10.02 (1H, s). | Ref. Ex. 81, Ref. Ex. 75 |
| 472 | | 1H-NMR (CDCl3) δ: 5.22 (2H, s), 7.51-7.55 (2H, m), 7.63-7.65 (3H, m), 7.73 (1H, s), 7.76 (1H, s), 10.02 (1H, s). | Ref. Ex. 82 |
| 473 | | 1H-NMR (CDCl3) δ: 5.25 (2H, s), 7.23-7.28 (1H, m), 7.52 (1H, s), 7.64-7.69 (2H, m), 7.78 (1H, s), 7.83-7.85 (1H, m), 10.04 (1H, s). | Ref. Ex. 82 |
| 474 | | 1H-NMR (CDCl3) δ: 5.21 (2H, s), 7.33-7.39 (2H, m), 7.51 (2H, s), 7.64 (1H, s), 7.78 (1H, s), 10.03 (1H, s). | Ref. Ex. 82 |

TABLE 2-continued

| Ref. Ex. No | STR | 1H-NMR | ref. |
| --- | --- | --- | --- |
| 475 | | 1H-NMR (CDCl3) δ: 5.44 (2H, s), 7.53 (1H, s), 7.66 (1H, s), 7.82 (1H, s), 7.90-7.97 (2H, m), 8.02 (1H, s), 10.06 (1H, s). | Ref. Ex. 82 |
| 476 | | 1H-NMR (CDCl3) δ: 2.39 (3H, s), 5.14 (2H, s), 7.19-7.31 (3H, m), 7.40 (1H, d, J = 7.3 Hz), 7.49 (1H, s), 7.66 (1H, s), 7.74 (1H, s), 10.02 (1H, s). | Ref. Ex. 82 |
| 477 | | 1H-NMR (CDCl3) δ: 5.42 (2H, s), 7.31-7.36 (1H, m), 7.41-7.44 (2H, m), 7.53 (1H, s), 7.73 (1H, s), 7.79 (1H, s), 10.06 (1H, s). | Ref. Ex. 82 |
| 478 | | 1H-NMR (DMSO-d6) δ: 5.41 (2H, s), 7.18-7.24 (2H, m), 7.33 (1H, s), 7.42-7.49 (2H, m), 8.11(1H, s), 8.17-8.20 (3H, m), 9.80 (1H, s). | Ref. Ex. 82 |
| 479 | | 1H-NMR (DMSO-d6) δ: 5.32 (2H, s), 7.16-7.23 (2H, m), 7.30 (1H, s), 7.43-7.46 (2H, m), 7.67-7.72 (3H, m), 8.17 (1H, s), 9.79 (1H, s). | Ref. Ex. 82 |

TABLE 2-continued
| Ref. Ex. No | STR | 1H-NMR | ref. |
|---|---|---|---|
| 480 | 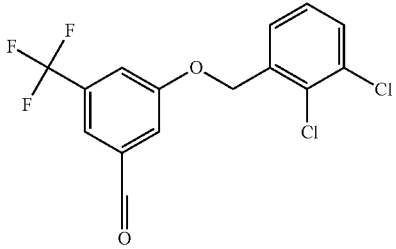 | 1H-NMR (CDCl3) δ: 5.29 (2H, s), 7.28-7.30 (1H, m), 7.49-7.53 (3H, m), 7.68 (1H, s), 7.80 (1H, s), 10.06 (1H, s). | Ref. Ex. 175 |
| 481 | 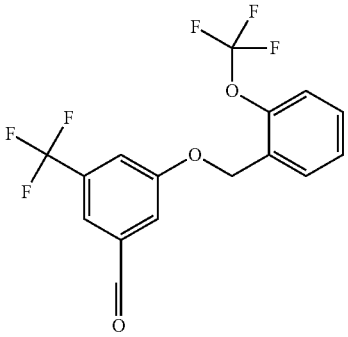 | 1H-NMR (CDCl3) δ: 5.24 (2H, s), 7.26-7.43 (3H, m), 7.48 (1H, s), 7.57-7.59 (1H, m), 7.64 (1H, s), 7.75 (1H, s), 10.02 (1H, s). | Ref. Ex. 82 |
| 482 | 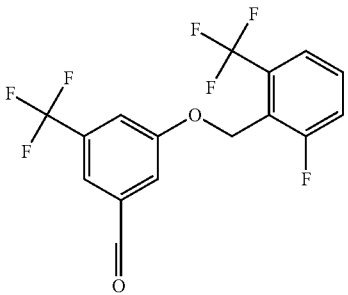 | 1H-NMR (CDCl3) δ: 5.32 (2H, s), 7.38-7.44 (1H, m), 7.50 (1H, s), 7.54-7.63 (1H, m), 7.70 (1H, s), 7.80 (1H, s), 10.06 (1H, s). | Ref. Ex. 82 |
| 483 | 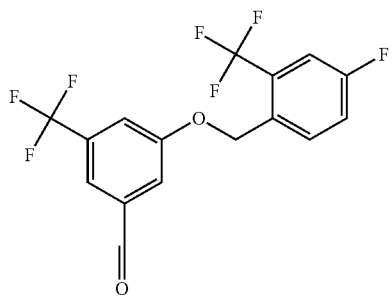 | 1H-NMR (CDCl3) δ: 5.30 (2H, s), 7.29-7.34 (1H, m), 7.44-7.47 (2H, m), 7.62 (1H, s), 7.68-7.73 (1H, m), 7.77 (1H, s), 10.02 (1H, s), | Ref. Ex. 82 |
| 485 | 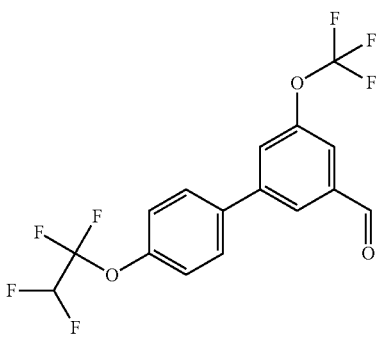 | 1H-NMR (CDCl3) δ: 5.77-6.13 (1H, m), 7.61 (2H, d, J = 8.7 Hz), 7.61-7.77 (4H, m), 8.02 (1H, s), 10.08 (1H, s). | Ref. Ex. 91 |

TABLE 2-continued
| Ref. Ex. No | STR | 1H-NMR | ref. |
|---|---|---|---|
| 486 | 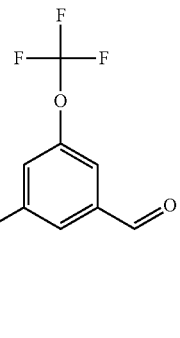 | 1H-NMR (CDCl3) δ: 7.40-7.48 (3H, m), 7.64 (1H, s), 7.76 (1H, s), 8.00 (1H, s), 10.08 (1H, s). | Ref. Ex. 91 |
| 487 | 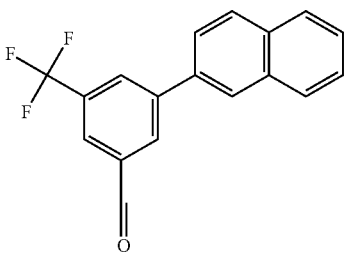 | 1H-NMR (CDCl3) δ: 7.55-7.58 (2H, m), 7.76-7.78 (1H, m), 7.89-7.99 (3H, m), 8.11-8.14 (2H, m), 8.22 (1H, s), 8.42 (1H, s), 10.18 (1H, s). | Ref. Ex. 75 |
| 488 | 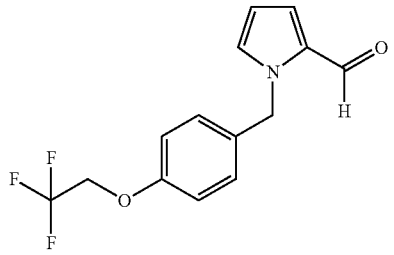 | 1H-NMR (CDCl3) δ: 4.31 (2H, q, J = 8.1 Hz), 5.51 (2H, s), 6.27 (1H, t, J = 3.3 Hz), 6.85-6.91 (2H, m), 6.97 (2H, d, J = 3.4 Hz), 7.11-7.17 (2H, m), 9.55(1H, s), | Ref. Ex. 113 |
| 489 | 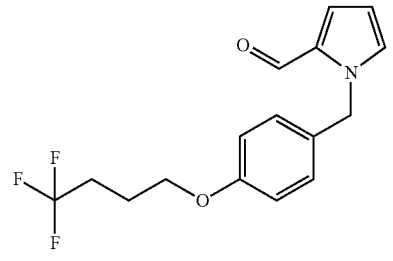 | 1H-NMR (CDCl3) δ: 1.07-2.09 (2H, m), 2.21-2.39 (2H, m), 3.98 (2H, t, J = 6.0 Hz), 5.49 (2H, s), 6.25 (1H, t, J = 3.3 Hz), 6.79-6.85 (2H, m), 8.96 (2H, d, J = 3.5 Hz), 7.10-7.15 (2H, m), 9.56 (1H, s). | Ref. Ex. 113 |
| 490 | 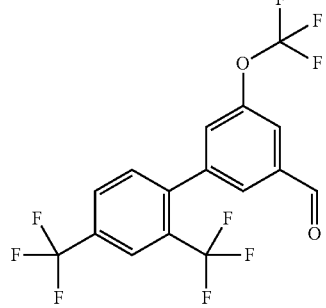 | 1H-NMR (CDCl3) δ: 7.47 (1H, s), 7.53 (1H, d J = 8.1 Hz), 7.78 (1H, s), 7.82 (1H, s), 7.85-7.92 (1H, m), 8.07 (1H, s), 10.06 (1H, s). | Ref. Ex. 91 |

TABLE 2-continued

| Ref. Ex. No | STR | 1H-NMR | ref. |
|---|---|---|---|
| 491 | | 1H-NMR (CDCl3) δ: 7.50 (1H, d J = 8.0 Hz), 7.68 (1H, s), 7.72 (1H, s), 7.89 (1H, d J = 8.0 Hz), 7.95 (1H, s), 8.06 (1H, s), 10.02 (1H, s). | Ref. Ex. 91 |
| 492 | | 1H-NMR (CDCl3) δ: 7.71-7.81 (2H, m), 7.92 (1H, s), 8.03 (1H, s), 8.07 (1H, s), 8.13 (1H, s), 8.35 (2H, s), 10.03 (1H, s). | Ref. Ex. 75 |
| 493 | | 1H-NMR (CDCl3) δ: 7.74-7.84 (3H, m), 7.98 (1H, s), 8.04 (1H, s), 8.22 (1H, s), 8.36 (2H, s), 10.07 (1H, s). | Ref. Ex. 75 |
| 494 | | 1H-NMR (CDCl3) δ: 4.00-4.13 (5H, m), 4.41-4.42 (2H, m), 5.75 (1H, s), 6.56-6.64 (1H, m), 6.76-6.78 (1H, m), 6.85 (1H, d, J = 7.6 Hz), 7.18 (1H, t, J = 7.6 Hz), 7.40-7.65 (4H, m). | Ref. Ex. 114 |

TABLE 2-continued

| Ref. Ex. No | STR | 1H-NMR | ref. |
|---|---|---|---|
| 495 | | 1H-NMR (CDCl3) δ: 3.02 (3H, s), 3.98-4.13 (4H, m), 4.54 (2H, s), 5.77 (1H, s), 6.68-6.75 (1H, m), 6.79-6.91 (2H, m), 7.18-7.37 (6H, m). | Ref. Ex. 12 |
| 496 | | 1H-NMR (CDCl3) δ: 3.03 (3H, s), 3.98-4.12 (4H, m), 4.54 (2H, s), 5.77 (1H, s), 6.70-6.73 (1H, m), 6.85-6.88 (2H, m), 7.20-7.26 (1H, m), 7.40-7.51 (4H, m). | Ref. Ex. 12 |
| 497 | | 1H-NMR (CDCl3) δ: 3.10 (3H, s), 4.60 (2H, s), 6.92-7.00 (1H, m), 7.18-7.35 (8H, m), 9.93 (1H, s). | Ref. Ex. 151 |
| 498 | | 1H-NMR (CDCl3) δ: 3.10 (3H, s), 4.64 (2H, s), 6.97-6.99 (1H, m), 7.22-7.25 (2H, m), 7.35-7.61 (5H, m), 9.94 (1H, s). | Ref. Ex. 151 |
| 499 | | 1H-NMR (CDCl3) δ: 5.18 (2H, s), 7.11-7.18 (1H, m), 7.20-7.26 (2H, m), 7.38-7.46 (1H, m), 7.59 (1H, t, J = 7.6 Hz). 7.70-7.75 (1H, m), 7.85-7.91 (1H, m), 7.97 (1H, s). 10.06 (1H s). | Ref. Ex. 113, Ref. Ex. 93 |

TABLE 2-continued

| Ref. Ex. No | STR | 1H-NMR | ref. |
|---|---|---|---|
| 500 | | 1H-NMR (CDCl3) δ: 5.19 (2H, s), 7.04 (2H, d, J = 8.5 Hz), 7.53-7.62 (3H, m), 7.68-7.75 (1H, m), 7.85-7.90 (1H, m), 7.96 (1H, s), 10.05 (1H, s). | Ref. Ex. 113, Ref. Ex. 93 |
| 501 | | 1H-NMR (CDCl3) δ: 5.23 (2H, s), 6.90-7.00 (2H, m), 7.17-7.24 (1H, m), 7.40 (1H, dd, J = 1.6, 7.8 Hz), 7.56 (1H, t, J = 7.7 Hz), 7.75-7.81 (1H, m), 7.84-7.88 (1H, m), 7.98 (1H, s), 10.05 (1H, s). | Ref. Ex. 113, Ref. Ex. 93 |
| 502 | | 1H-NMR (CDCl3) δ: 5.13 (2H, s), 6.84-6.89 (1H, m), 6.94-7.00 (2H, m), 7.22 (1H, t, J = 8.1 Hz), 7.58 (1H, t, J = 7.6 Hz), 7.69 (1H, d, J = 7.6 Hz); 7.86 (1H, d, J = 7.5 Hz), 7.95 (1H, s), 10.05 (1H, s). | Ref. Ex. 113, Ref. Ex. 93 |
| 503 | | 1H-NMR (CDCl3) δ: 5.23 (2H, s), 6.88 (1H, dd, J = 2.7, 6.9 Hz), 7.03-7.17 (2H, m), 7.59 (1H, t, J = 7.6 Hz), 7.76 (1H, d, J = 7.7 Hz), 7.87 (1H, d, J = 7.6 Hz), 7.97 (1H, s), 10.05 (1H, s). | Ref. Ex. 113, Ref. Ex. 93 |
| 504 | | 1H-NMR (CDCl3) δ: 5.11 (2H, s), 6.89 (2H, d, J = 1.8 Hz), 7.00 (1H, t, J = 1.8 Hz), 7.59 (1H, t, J = 7.6 Hz), 7.66-7.70 (1H, m), 7.65-7.90 (1H, m), 7.93 (1H, s), 10.05 (1H, s). | Ref. Ex. 113, Ref. Ex. 93 |
| 505 | | 1H-NMR (CDCl3) δ: 1.03-1.41 (5H, m), 1.77-1.89 (6H, m), 3.85 (2H, d, J = 6.0 Hz), 7.39 (1H, s), 7.55 (1H, s), 7.68 (1H, s), 10.00 (1H, s). | Ref. Ex. 175 |

TABLE 2-continued
| Ref. Ex. No | STR | 1H-NMR | ref. |
|---|---|---|---|
| 506 | 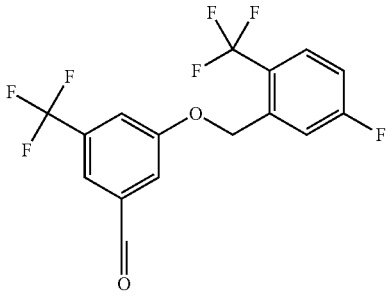 | 1H-NMR (CDCl3) δ: 5.34 (2H, s), 7.11-7.17 (1H, m), 7.44-7.49 (2H, m), 7.62 (1H, s), 7.71-7.77 (2H, m), 10.02 (1H, s). | Ref. Ex. 82 |
| 507 | 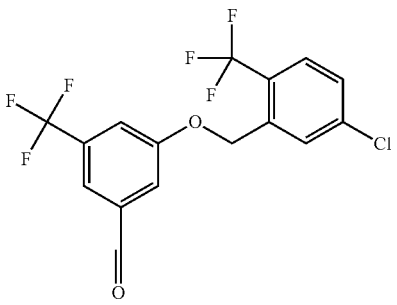 | 1H-NMR (CDCl3) δ: 5.31 (2H, s), 7.44-7.50 (2H, m), 7.59-7.68 (2H, m), 7.74 (1H, s), 7.78 (1H, s), 10.02 (1H, s). | Ref. Ex. 82 |
| 508 | 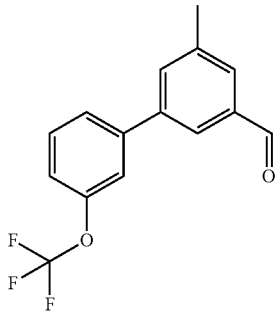 | 1H-NMR (CDCl3) δ: 2.52 (3H, s), 7.23-7.24 (1H, m), 7.46-7.57 (3H, m), 7.65 (1H, s), 7.71 (1H, s), 7.68 (1H, s), 10.06 (1H, s). | Ref. Ex. 91 |
| 509 | 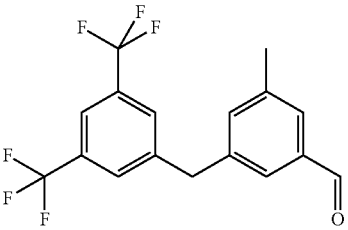 | 1H-NMR (CDCl3) δ: 2.43 (3H, s), 4.14 (2H, s), 7.25-7.26 (1H, m), 7.50 (1H, s), 7.60-7.62 (3H, m), 7.78 (1H, s), 9.97 (1H, s). | Ref. Ex. 91 |
| 510 | 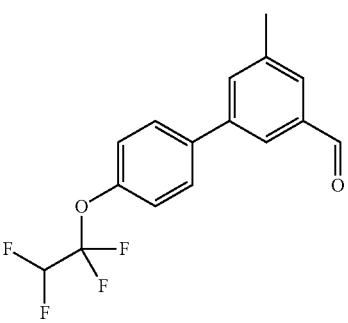 | 1H-NMR (CDCl3) δ: 2.51 (3H, s), 5.76-6.12 (1H, m), 7.24-7.33 (2H, m), 7.61-7.69 (4H, m), 7.87 (1H, s), 10.05 (1H, s). | Ref. Ex. 91 |

TABLE 2-continued

| Ref. Ex. No | STR | 1H-NMR | ref. |
| --- | --- | --- | --- |
| 511 | | 1H-NMR (CDCl3) δ: 5.17 (2H, s), 7.50 (1H, s), 7.55-7.57 (2H, m), 7.63 (1H, s), 7.76-7.79 (2H, m), 10.02 (1H, s). | Ref. Ex. 82 |
| 512 | | 1H-NMR (CDCl3) δ: 2.52 (3H, s), 7.40-7.48 (3H, m), 7.62 (1H, s), 7.72 (1H, s), 7.86 (1H, s), 10.06 (1H, s). | Ref. Ex. 91 |
| 513 | | 1H-NMR (CDCl3) δ: 0.87-1.05 (2H, m), 1.16-1.33 (4H, m), 1.46-1.57 (1H, m), 1.68-1.79 (6H, m), 4.09 (2H, t, J = 6.6 Hz), 7.38 (1H, s), 7.54 (1H, s), 7.68 (1H, s), 10.00 (1H, s). | Ref. Ex. 82 |
| 514 | | 1H-NMR (CDCl3) δ: 0.97 (3H, t, J = 7.3 Hz), 1.36-1.57 (2H, m), 1.83-1.89 (1H, m), 2.00-2.05 (1H, m), 5.18-5.23 (1H, m), 7.26-7.37 (6H, m), 7.46 (1H, s), 7.61 (1H, s), 9.69 (1H, s). | Ref. Ex. 82 |
| 515 | | 1H-NMR(CDCl3) δ: 2.35 (6H, s), 5.10 (2H, s), 7.11-7.13 (2H, m), 7.22 (1H, s), 7.49 (1H, 6), 7.66 (1H, s), 7.73 (1H, s), 10.02 (1H, s). | Ref. Ex. 82 |
| 516 | | 1H-NMR (CDCl3) δ: 2.34 (3H, s), 2.36 (3H, s), 5.10 (2H, s), 7.03-7.07 (2H, m), 7.29 (1H, s), 7.48 (1H, s), 7.65 (1H, s), 7.72 (1H, s), 10.01 (1H, s). | Ref. Ex. 82 |

TABLE 2-continued

| Ref. Ex. No | STR | 1H-NMR | ref. |
|---|---|---|---|
| 517 | | 1H-NMR (CDCl3) δ: 3.98-4.18 (4H, m), 5.79 (1H, s), 5.64 (1H, brs), 7.07-7.38 (6H, m). | Ref. Ex. 114 |
| 518 | | 1H-NMR (CDCl3) δ: 3.35 (3H, s), 4.00-4.13 (4H, m), 5.78 (1H, s), 7.07-7.35 (6H, m). | Ref. Ex. 12 |
| 519 | | 1H-NMR (CDCl3) δ: 3.36 (3H, s), 7.12-7.15 (4H, m), 7.33-7.40 (5H, m), 9.93 (1H, s). | Ref. Ex. 151 |
| 520 | | 1H-NMR (CDCl3) δ: 3.40 (3H, s), 7.24-7.30 (3H, m), 7.39-7.54 (5H, m), 9.97 (1H, s). | Ref. Ex. 151 |
| 521 | | 1H-NMR (CDCl3) δ: 1.35-1.57 (2H, m), 1.57-1.68 (4H, m), 1.83-1.87 (2H, m), 2.36-2.41 (1H, m), 3.89 (2H, d, J = 6.9 Hz), 7.31 (1H, s), 7.35 (1H, s), 7.47 (1H, s). | Ref. Ex. 80 |

TABLE 2-continued

| Ref. Ex. No | STR | 1H-NMR | ref. |
|---|---|---|---|
| 522 | | 1H-NMR (CDCl3) δ: 2.51 (3H, s), 7.31 (2H, d J = 8.0 Hz), 7.61-7.64 (3H, m), 7.69 (1H, s), 7.87 (1H, s), 10.06 (1H, s). | Ref. Ex. 91 |
| 523 | | 1H-NMR (CDCl3) δ: 2.53 (3H, s), 7.67-7.72 (2H, m), 7.73 (4H, s), 7.91 (1H, s), 10.07 (1H, s). | Ref. Ex. 91 |
| 524 | | 1H-NMR (CDCl3) δ: 2.51 (3H, s), 6.57 (1H, t J = 73.7 Hz), 7.70-7.32 (2H, m), 7.59-7.63 (3H, m), 7.68 (1H, s). 7.86 (1H, s), 10.05 (1H, s). | Ref. Ex. 91 |
| 525 | | 1H-NMR (CDCl3) δ: 2.52 (3H, s), 7.27-7.34 (1H, m), 7.62 (1H, s), 7.72 (1H, s), 7.76-7.86 (3H, m), 10.06 (1H, s). | Ref. Ex. 91 |
| 526 | | 1H-NMR (CDCl3) δ: 1.35-1.41 (2H, m), 1.62-1.68 (4H, m), 1.84-1.88 (2H, m), 2.35-2.40 (1H, m), 3.94 (2H, t, J = 6.9 Hz), 7.40 (1H, s), 7.53 (1H, s), 7.69 (1H, s), 10.01 (1H, s). | Ref. Ex. 229 |
| 527 | | 1H-NMR (CDCl3) δ: 1.66-1.75 (1H, m), 1.85-2.16 (5H, m), 4.92 (1H, bs), 5.83-5.87 (1H, m), 6.01-6.06 (1H, m), 7.40 (1H, s), 7.58 (1H, s), 7.68 (1H, s), 10.00 (1H, s). | Ref. Ex. 82 |

TABLE 2-continued

| Ref. Ex. No | STR | 1H-NMR | ref. |
|---|---|---|---|
| 528 | | 1H-NMR (CDCl3) δ: 5.34 (2H, s), 7.51-7.53 (2H, m), 7.66-7.68 (3H, m), 7.74-7.78 (2H, m), 10.03 (1H, s). | Ref. Ex. 82 |
| 529 | | 1H-NMR (CDCl3) δ: 5.29 (2H, s), 7.33-7.36 (2H, m), 7.45-7.48 (1H, m), 7.53-7.57 (2H, m), 7.68 (1H, s), 7.78 (1H, s), 10.05 (1H, s). | Ref. Ex. 82 |
| 530 | | 1H-NMR (CDCl3) δ: 5.20 (2H, 8), 6.89 (1H, d, J = 8.8 Hz), 7.17 (1H, dd, J = 2.5, 8.8 Hz), 7.40 (1H, d, J = 2.5 Hz), 7.56 (1H, t, J = 7.6 Hz), 7.75 (1H, d, J = 7.7 Hz), 7.86 (1H, d, J = 7.6 Hz), 7.96 (1H, s), 10.05 (1H, s). | Ref. Ex. 113, Ref. Ex. 93 |
| 531 | | 1H-NMR (CDCl3) δ: 5.11 (2H, s), 6.83 (1H, dd, J = 2.9, 8.9 Hz), 7.09 (1H, d, J = 2.9 Hz), 7.35 (1H, d, J = 8.9 Hz), 7.58 (1H, d, J = 7.6 Hz), 7.68 (1H, d, J = 7.7 Hz), 7.87 (1H, d, J = 7.5 Hz), 7.94 (1H, s), 10.05 (1H, s). | Ref. Ex. 113, Ref. Ex. 93 |
| 532 | | 1H-NMR (CDCl3) δ: 5.20 (2H, s), 6.91-6.98 (2H, m), 7.32 (1H, d, J = 8.4 Hz), 7.60 (1H, t, J = 7.6 Hz), 7.74-7.78 (1H, m), 7.86-7.90 (1H, m), 7.98 (1H, s), 10.06 (1H, s). | Ref. Ex. 113, Ref. Ex. 93 |
| 533 | | 1H-NMR (CDCl3) δ: 5.13 (2H, s), 7.02-7.08 (1H, m), 7.33 (2H, d, J = 8.0 Hz), 7.57-7.62 (1H, m), 7.85-7.91 (2H, m), 8.07 (1H, s), 10.07 (1H, s). | Ref. Ex. 113, Ref. Ex. 93 |

| Ref. Ex. No | STR | 1H-NMR | ref. |
|---|---|---|---|
| 534 | | 1H-NMR (CDCl3) δ: 5.10 (2H, s), 7.35 (2H, s), 7.59 (1H, t, J = 7.6 Hz), 7.81-7.86 (1H, m), 7.87-7.92 (1H, m), 8.04 (1H, s), 10.07 (1H, s). | Ref. Ex. 113, Ref. Ex. 93 |
| 535 | | 1H-NMR (CDCl3) δ: 7.70-7.75 (1H, m), 8.00-8.05 (1H, m), 8.30-8.35 (1H, m), 8.51 (1H, s), 10.12 (1H, s). | Ex. 1, Ref. Ex. 151 |
| 536 | | 1H-NMR (CDCl3) δ: 1.37-1.96 (14H, m), 3.50-3.60 (1H, m), 4.58 (2H, s), 7.50 (1H, t, J = 7.6 Hz), 7.60-7.65 (1H, m), 7.76-7.81 (1H, m), 7.86 (1H, s), 10.03 (1H, s). | Ref. Ex. 92 |
| 537 | | 1H-NMR (CDCl3) δ: 1.15-1.37 (2H, m), 1.45-1.65 (4H, m), 1.65-1.90 (2H, m), 2.15-2.35 (1H, m), 3.37 (2H, d, J = 7.0 Hz), 4.58 (2H, s), 7.51 (1H, t, J = 7.6 Hz), 7.63 (1H, d, J = 7.6 Hz), 7.80 (1H, d, J = 7.6 Hz), 7.86 (1H, s), 10.03 (1H, s). | Ref. Ex. 92 |
| 538 | | 1H-NMR (CDCl3) δ: 1.21-1.36 (2H, m), 1.40-1.75 (12H, m), 1.79-1.94 (1H, m), 3.27 (2H, d, J = 6.8 Hz), 4.57 (2H, s), 7.52 (1H, t, J = 7.6 Hz), 7.60-7.65 (1H, m), 7.77-7.82 (1H, m), 7.85 (1H, s), 10.03 (1H, s). | Ref. Ex. 92 |
| 539 | | 1H-NMR (CDCl3) δ: 1.49-1.92 (10H, m), 2.06-2.19 (4H, m), 3.54-3.61 (1H, m) 4.61 (2H, s), 7.51 (1H, t, J = 7.6 Hz), 7.64-7.69 (1H, m), 7.77-7.82 (1H, m) 7.89 (1H, s), 10.03 (1H, s). | Ref. Ex. 92 |
| 540 | | 1H-NMR (CDCl3) δ: 0.84 (3H, s), 0.86 (3H, s), 0.92 (3H, s) 1.10 (1H, dd, J = 3.3,13.0 Hz), 1.20-1.34 (2H, m), 1.64-1.80 (2H, m), 2.01-2.23 (2H, m), 3.67-3.76 (1H, m), 4.51 (1H, d, J = 12.6 Hz), 4.64 (1H, d, J = 12.6 Hz), 7.51 (1H, t, J = 7.6 Hz), 7.60-7.66 (1H, m), 7.76-7.82 (1H, m), 7.85 (1H, s), 10.03 (1H, s). | Ref. Ex. 92 |

TABLE 2-continued

| Ref. Ex. No | STR | 1H-NMR | ref. |
|---|---|---|---|
| 541 | | 1H-NMR (CDCl3) δ: 1.52-1.78 (12H, m), 1.93-2.02 (3H, m), 3.05 (2H, s), 4.56 (2H, s), 7.51 (1H, t, J = 7.6 Hz), 7.59-7.65 (1H, m), 7.76-7.82 (1H, m), 7.83 (1H, s), 10.03 (1H, s). | Ref. Ex. 92 |
| 542 | Chiral | 1H-NMR (CDCl3) δ: 0.72 (3H, d, J = 7.0 Hz), 0.91 (3H, d, J = 7.1 Hz), 0.95 (3H, d, J = 9.6 Hz), 0.79-1.06 (3H, m), 1.24-1.46 (2H, m), 1.60-1.71 (2H, m), 2.14-2.35 (2H, m), 3.15-3.25 (1H, m), 4.47 (1H, d, J = 11.6 Hz), 4.73 (1H, d, J = 11.8 Hz), 7.51 (1H, t, J = 7.6 Hz), 7.61-7.66 (1H, m), 7.77-7.82 (1H, m), 7.85 (1H, s), 10.03 (1H, s). | Ref. Ex. 92 |
| 543 | Chiral | 1H-NMR (CDCl3) δ: 0.73 (3H, d, J = 7.0 Hz), 0.91 (3H, d, J = 7.1 Hz), 0.95 (3H, d, J = 6.5 Hz), 0.78-1.06 (3H, m), 1.24-1.45 (2H, m), 1.60-1.73 (2H, m), 2.15-2.35 (2H, m), 3.15-3.26 (1H, m), 4.47 (1H, d, J = 11.8 Hz), 4.74 (1H, d, J = 11.8 Hz), 7.51 (1H, t, J = 7.6 Hz), 7.61-7.67 (1H, m), 7.76-7.82 (1H, m), 7.85 (1H, s), 10.03 (1H, s). | Ref. Ex. 92 |
| 544 | | 1H-NMR (CDCl3) δ: 2.51 (3H, s), 7.42-7.46 (2H, m), 7.53-7.57 (2H, m), 7.63 (1H, s), 7.68 (1H, s), 7.86 (1H, s), 10.06 (1H, s). | Ref. Ex. 91 |
| 545 | | 1H-NMR (CDCl3) δ: 2.27 (3H, s), 2.49 (3H, s), 7.10-7.24 (3H, m), 3.78 (1H, s), 7.70 (1H, s), 7.90 (1H, s), 10.03 (1H, s). | Ref. Ex. 91 |
| 546 | | 1H-NMR (CDCl3) δ: 2.53 (3H, s), 7.57-7.81 (5H, m), 7.86 (1H, s), 7.91 (1H, s), 10.07 (1H, s). | Ref. Ex. 91 |

TABLE 2-continued

| Ref. Ex. No | STR | 1H-NMR | ref. |
|---|---|---|---|
| 547 | | 1H-NMR (CDCl3) δ: 1.66-1.80 (12H, m), 2.04 (3H, bs), 3.55 (2H, s), 7.32 (1H, s), 7.35 (1H, s), 7.50 (1H, s). | Ref. Ex. 80 |
| 548 | | 1H-NMR (CDCl3) δ: 1.38-1.44 (2H, m), 1.52-1.62 (6H, m), 1.60-1.76 (4H, m), 2.02-2.07 (1H, m), 3.77 (2H, d, J = 6.6 Hz), 7.30 (1H, s), 7.34 (1H, s), 7.46 (1H, s). | Ref. Ex. 80 |
| 549 | | 1H-NMR (CDCl3) δ: 2.53 (3H, s), 7.41-7.50 (2H, m), 7.66-7.75 (3H, m), 7.89 (1H, s), 10.07 (1H, s). | Ref. Ex. 91 |
| 550 | | 1H-NMR (CDCl3) δ: 5.36 (2H, s), 7.42-7.44 (1H, m), 7.57-7.59 (3H, m), 8.01-8.02 (1H, m), 4.15-8.16 (1H, m), 10.00 (1H, s). | Ref. Ex. 82 |
| 551 | | 1H-NMR (CDCl3) δ: 1.24-1.75 (14H, m), 2.02-2.08 (1H, m), 3.74-3.83 (2H, m), 7.39 (1H, s), 7.55 (1H, s), 7.69 (1H, s), 10.01 (1H, s). | Ref. Ex. 93 |

TABLE 2-continued

| Ref. Ex. No | STR | 1H-NMR | ref. |
| --- | --- | --- | --- |
| 552 | | 1H-NMR (CDCl3) δ: 1.67-1.80 (12H, m), 2.04-2.05 (3H, m), 4.16 (2H, s), 7.56 (1H, s), 7.68 (1H, s), 8.02 (1H, s), 10.01 (1H, s). | Ref. Ex. 93 |
| 553 | | 1H-NMR (CDCl3) δ: 5.22 (2H, s), 7.28-7.31 (1H, m), 7.36 (1H, d, J = 6.5 Hz), 7.53 (1H, s), 7.57-7.58 (1H, m), 7.66 (1H, s), 7.78 (1H, s), 10.04 (1H, s). | Ref. Ex. 175 |
| 554 | | 1H-NMR (CDCl3) δ: 3.98-4.13 (4H, m), 4.22-4.33 (1H, m), 4.40 (2H, d, J = 5.5 Hz), 5.72 (1H, s), 6.41 (1H, s), 6.67-6.70 (2H, m), 7.44-7.61 (4H, m). | Ref. Ex. 114 |
| 555 | | 1H-NMR (CDCl3) δ: 7.87 (1H, s), 8.01-8.09 (4H, m), 10.01 (1H, s). | Ref. Ex. 91 |
| 556 | | 1H-NMR (CDCl3) δ: 7.15-7.18 (1H, m), 7.32-7.35 (2H, m), 7.63 (1H, t, J = 7.8 Hz), 7.70 (1H, d, J = 7.8 Hz), 7.88 (1H, d, J = 7.8 Hz), 8.03 (1H, s), 10.09 (1H, s). | Ref. Ex. 91 |

TABLE 2-continued

| Ref. Ex. No | STR | 1H-NMR | ref. |
|---|---|---|---|
| 557 | | 1H-NMR (CDCl3) δ: 3.05 (3H, s), 4.00-4.13 (4H, m), 4.58 (2H, s), 5.74 (1H, s), 6.50 (1H, s), 6.72 (1H, s), 6.76 (1H, s), 7.33-7.94 (4H, m). | Ref. Ex. 12 |
| 558 | | 1H-NMR (CDCl3) δ: 3.13 (3H, s), 4.65 (2H, s), 6.73 (1H, s), 7.07 (1H, s), 7.13 (1H, s), 7.32-7.51 (4H, m), 9.89 (1H, s). | Ref. Ex. 151 |
| 559 | | 1H-NMR (CDCl3) δ: 2.51 (3H, s), 6.95 (1H, d, J = 9.0 Hz), 7.15 (1H, d, J = 9.0 Hz), 7.21-7.33 (1H, m), 7.59 (1H, s), 7.69 (1H, s), 7.82 (1H, s), 10.05 (1H, s). | Ref. Ex. 91 |
| 560 | | 1H-NMR (CDCl3) δ: 2.55 (3H, s), 7.68 (1H, s), 7.78 (1H, s), 7.91 (1H, s), 7.92 (1H, s), 8.04 (2H, s), 10.09 (1H, s). | Ref. Ex. 91 |

TABLE 2-continued

| Ref. Ex. No | STR | 1H-NMR | ref. |
|---|---|---|---|
| 561 | | 1H-NMR (CDCl3) δ: 2.53 (3H, s), 7.07-7.10 (1H, m), 7.18 (1H, t, J = 8.0 Hz), 7.30-7.33 (1H, m), 7.73 (1H, s), 7.77 (1H, s), 7.98 (1H, s), 10.07 (1H, s). | Ref. Ex. 91 |
| 562 | | 1H-NMR (CDCl3) δ: 3.11 (2H, t, J = 6.7 Hz), 4.25 (2H, t, J = 6.7 Hz), 7.20-7.33 (4H, m), 7.36 (1H, s), 7.53 (1H, s), 7.69 (1H, s), 9.99 (1H, s). | Ref. Ex. 82 |
| 563 | | 1H-NMR (CDCl3) δ: 3.15 (2H, t, J = 6.9 Hz), 4.30 (2H, t, J = 6.9 Hz), 7.26-7.39 (6H, m), 7.54 (1H, s), 7.69 (1H, s), 10.00 (1H, s). | Ref. Ex. 82 |
| 564 | | 1H-NMR (CDCl3) δ: 1.02 (6H, s), 3.76 (4H, s), 7.02-7.04 (1H, m), 7.46 (1H, s), 7.54-7.57 (1H, m). | Ref. Ex. 107 |
| 565 | | 1H-NMR (CDCl3) δ: 7.17-7.24 (1H, m), 7.28-7.35 (2H, m), 7.61 (1H, s), 7.72 (1H, s), 7.97 (1H, s), 10.07 (1H, s). | Ref. Ex. 91 |
| 566 | | 1H-NMR (CDCl3) δ: 7.13 (1H, d, J = 8.3 Hz), 7.33 (1H, d, J = 4.0 Hz), 7.36-7.43 (2H, m), 7.74 (1H, d, J = 4.0 Hz), 9.90 (1H, s). | Ref. Ex. 91 |

TABLE 2-continued

| Ref. Ex. No | STR | 1H-NMR | ref. |
|---|---|---|---|
| 567 | | 1H-NMR (CDCl3) δ: 1.70 (3H, d, J = 6.4 Hz), 2.81 (3H, s), 6.05-6.12 (1H, m), 7.43-7.48 (1H, m), 7.61-7.68 (2H, m), 7.75 (1H, d, J = 7.8 Hz). | Ref. Ex. 103 |
| 568 | | 1H-NMR (CDCl3) δ: 1.06 (3H, t, J = 7.4 Hz), 1.90-2.03 (2H, m), 2.76 (3H, s), 5.82-5.87 (1H, m), 7.46-7.49 (1H, m), 7.64-7.73 (3H, m). | Ref. Ex. 103 |
| 569 | | 1H-NMR (CDCl3) δ: 2.49 (3H, s), 7.10-7.11 (1H, m), 7.51 (1H, s), 7.52 (1H, s), 7.73 (2H, s), 10.03 (1H, s). | Ref. Ex. 91 |
| 570 | | 1H-NMR (CDCl3) δ: 2.41 (3H, s), 4.27 (2H, s), 7.21 (1H, s), 7.44-7.47 (2H, m), 7.59-7.64 (2H, m), 7.83-7.85 (1H, m), 9.95 (1H, s). | Ref. Ex. 91 |
| 571 | | 1H-NMR (CDCl3) δ: 2.41 (3H, d, J = 6.2 Hz), 5.77-5.83 (1H, m), 7.37-7.42 (2H, m), 7.50-7.56 (2H, m), 7.68-7.71 (3H, m), 9.90 (1H, s). | Ref. Ex. 82 |

TABLE 2-continued

| Ref. Ex. No | STR | 1H-NMR | ref. |
|---|---|---|---|
| 572 | | 1H-NMR (CDCl3) δ: 1.15 (3H, t, J = 7.4 Hz), 1.91-2.00 (2H, m), 5.49-5.53 (1H, m), 7.36-7.41 (2H, m), 7.49-7.54 (2H, m), 7.62-7.71 (3H, m), 9.90 (1H, s). | Ref. Ex. 82 |
| 573 | | 1H-NMR (CDCl3) δ: 1.07 (6H, d, J = 6.7 Hz), 2.05-2.18 (1H, m), 3.82 (2H, d, J = 6.5 Hz), 7.40 (1H, s), 7.55 (1H, s), 7.69 (1H, s), 10.01 (1H, s). | Ref. Ex. 82 |
| 574 | | 1H-NMR (CDCl3) δ: 1.00 (6H, d, J = 6.6 Hz), 1.69-1.76 (2H, m), 1.84-1.88 (1H, m), 4.09 (2H, t, J = 6.5 Hz), 7.39 (1H, s), 7.55 (1H, s), 7.69 (1H, s), 10.01 (1H, s). | Ref. Ex. 82 |
| 575 | | 1H-NMR (CDCl3) δ: 4.01-4.14 (4H, m), 5.27 (2H, s), 5.78 (1H, s), 6.99-7.03 (2H, m), 7.15 (1H, s), 7.72 (1H, d, J = 8.1 Hz), 7.85 (1H, d, J = 8.1 Hz), 8.05 (1H, s). | Ref. Ex. 82 |
| 576 | | 1H-NMR (CDCl3) δ: 4.01-4.13 (4H, m), 5.16 (2H, s), 5.78 (1H, s), 6.99-7.02 (2H, m), 7.15 (1H, s), 7.87 (1H, s), 7.90 (2H, s) | Ref. Ex. 82 |
| 577 | | 1H-NMR (CDCl3) δ: 5.22 (2H, s), 7.28-7.32 (1H, m), 7.39 (1H, s), 7.52 (1H, s), 7.89 (1H, s), 7.91 (2H, s), 9.94 (1H, s). | Ref. Ex. 151 |

TABLE 2-continued

| Ref. Ex. No | STR | 1H-NMR | ref. |
|---|---|---|---|
| 578 | | 1H-NMR (CDCl3) δ: 5.33 (2H, s), 7.28-7.30 (1H, m), 7.39 (1H, s), 7.53 (1H, s), 7.76 (1H, d, J = 8.4 Hz), 7.88 (1H, d, J = 8.4 Hz), 8.04 (1H, s), 9.94 (1H, s). | Ref. Ex. 151 |
| 579 | | 1H-NMR (CDCl3) δ: 7.17-7.22 (1H, m), 7.35-7.37 (2H, m), 6.01 (1H, s), 8.13 (1H, s), 8.21 (1H, s), 10.14 (1H, s). | Ref. Ex. 112 |
| 580 | | 1H-NMR (CDCl3) δ: 7.14-7.17 (1H, m), 7.24-7.27 (1H, m), 7.33-7.37 (1H, m), 8.18 (2H, s), 8.38 (1H, s), 10.16 (1H, s). | Ref. Ex. 112 |
| 582 | | 1H-NMR (CDCl3) δ: 5.10 (2H, s), 7.07 (1H, d, J = 8.2 Hz), 7.14-7.25 (3H, m), 7.45-7.49 (3H, m), 9.98 (1H, s). | Ref. Ex. 82 |
| 583 | | 1H-NMR (CDCl3) δ: 2.12-2.21 (2H, m), 2.76-2.86 (2H, m), 4.00-4.09 (2H, m), 7.20-7.33 (5H, m), 7.39 (1H, s), 7.53 (1H, s), 7.70 (1H, s), 10.00 (1H, s). | Ref. Ex. 82 |

| Ref. Ex. No | STR | 1H-NMR | ref. |
|---|---|---|---|
| 584 | | 1H-NMR (CDCl3) δ: 2.35-2.42 (2H, m), 3.28-3.39 (1H, m), 4.21-4.25 (2H, m), 7.42 (1H, s), 7.57 (1H, s), 7.76 (1H, s), 10.02 (1H, s). | Ref. Ex. 82 |
| 585 | | 1H-NMR (CDCl3) δ: 6.05 (2H, s), 6.91-6.94 (1H, m), 7.08-7.11 (2H, m), 7.61 (1H, s), 7.66 (1H, s), 7.96 (1H, s), 10.06 (1H, s). | Ref. Ex. 91 |
| 586 | | 1H-NMR (CDCl3) δ: 4.04 (2H, s), 6.87-6.92 (2H, m), 6.99 (1H, d, J = 8.1 Hz), 7.45-7.48 (2H, m), 7.69 (1H, s), 7.75 (1H, d, J = 7.1 Hz), 9.99 (1H, s). | Ref. Ex. 91 |
| 587 | | 1H-NMR (CDCl3) δ: 5.41 (2H, s), 6.59 (1H, dd, J = 0.7, 3.2 Hz), 7.08-7.24 (4H, m), 7.29-7.34 (1H, m), 7.46 (1H, t, J = 7.6 Hz), 7.63-7.69 (2H, m), 7.76-7.80 (1H, m), 9.96 (1H, s). | Ref. Ex. 189 |
| 588 | | 1H-NMR (CDCl3) δ: 2.77 (2H, d, J = 5.9 Hz), 2.92 (2H, t, J = 5.8 Hz), 3.65 (2H, s), 3.76 (2H, s), 6.95-7.00 (1H, m), 7.07-7.14 (3H, m), 7.51 (1H, t, J = 7.6 Hz), 7.67-7.72 (1H, m), 7.78-7.83 (1H, m), 7.91 (1H, s), 10.03 (1H, s). | Ref. Ex. 160 |
| 589 | | 1H-NMR (CDCl3) δ: 2.00-2.10 (2H, m), 2.84 (2H, t, J = 6.4 Hz), 3.39 (2H, t, J = 6.2 Hz), 4.54 (2H, s), 6.44 (1H, d, J = 8.0 Hz), 6.57-6.64 (1H, m), 6.93-7.02 (2H, m), 7.48 (1H, t, J = 7.5 Hz), 7.52-7.58 (1H, m), 7.74-7.81 (2H, m), 10.00 (1H, s). | Ref. Ex. 160 |

TABLE 2-continued

| Ref. Ex. No | STR | 1H-NMR | ref. |
| --- | --- | --- | --- |
| 590 | | 1H-NMR (CDCl3) δ: 5.35 (2H, s), 7.13 (1H, s), 7.41 (1H, s), 7.44 (1H, s), 7.67-7.89 (2H, m), 6.03 (1H, s), 9.97 (1H, s). | Ref. Ex. 82 |
| 591 | | 1H-NMR (CDCl3) δ: 4.48 (2H, q, J = 7.8 Hz); 7.49 (1H, s), 7.62 (1H, s), 7.83 (1H, s), 10.04 (1H, s). | Ref. Ex. 82 |
| 592 | | 1H-NMR (CDCl3) δ: 5.24 (2H, s), 7.14 (1H, s), 7.40 (1H, s), 7.45 (1H, s), 7.87-7.92 (3H, m), 9.98 (1H, s). | Ref. Ex. 82 |
| 593 | | 1H-NMR (CDCl3) δ: 5.10 (2H, s), 7.10 (1H, s), 7.36 (1H, s), 7.41 (1H, s), 7.53-7.58 (2H, m), 7.65-7.69 (2H, m), 9.95 (1H, s). | Ref. Ex. 82 |
| 594 | | 1H-NMR (CDCl3) δ: 5.10 (2H, s), 7.07-7.18 (4H, m), 7.35-7.36 (1H, m), 7.39-7.40 (1H, m), 9.95 (1H, s). | Ref. Ex. 82 |

| Ref. Ex. No | STR | 1H-NMR | ref. |
|---|---|---|---|
| 595 | | 1H-NMR (CDCl3) δ: 5.18 (2H, s), 7.11 (1H, s), 7.33-7.36 (2H, m), 7.38 (1H, s), 7.42 (1H, s), 7.51 (1H, s), 9.96 (1H, s). | Ref. Ex. 82 |
| 596 | | 1H-NMR (CDCl3) δ: 5.13 (2H, s), 7.09 (1H, s), 7.28-7.59 (7H, m), 9.94 (1H, s). | Ref. Ex. 82 |
| 598 | | 1H-NMR (CDCl3) δ: 6.25 (1H, brs), 6.83 (1H, dt, J = 2.3, 8.8 Hz), 6.93-6.97 (2H, m). | Ref. Ex. 89 |
| 599 | | 1H-NMR (CDCl3) δ: 5.77 (1H, brs), 6.85 (1H, dt, J = 2.4, 9.5 Hz), 7.14-7.18 (2H, m), 9.90 (1H, d, J = 1.5 Hz). | Ref. Ex. 93 |
| 601 | | 1H-NMR (CDCl3) δ: 6.05 (1H, brs), 7.05-7.11 (1H, m), 7.14 (1H, dt, J = 1.9, 6.8 Hz). | Ref. Ex. 89 |
| 602 | | 1H-NMR (CDCl3) δ: 1.45-1.49 (2H, m), 1.73-2.00 (5H, m), 2.14-2.20 (2H, m), 3.92 (2H, d, J = 5.9 Hz), 7.39 (1H, s), 7.71 (1H, s), 7.85 (1H, s), 10.01 (1H, s). | Ref. Ex. 82 |

TABLE 2-continued

| Ref. Ex. No | STR | 1H-NMR | ref. |
|---|---|---|---|
| 603 | | 1H-NMR (CDCl3) δ: 1.48 (3H, t, J = 7.0 Hz), 4.16 (2H, t, J = 7.0 Hz), 7.38-7.42 (2H, m), 7.59-7.68 (3H, m), 7.78-7.85 (2H, m), 10.04 (1H, s). | Ref. Ex. 112 |
| 604 | | 1H-NMR (CDCl3) δ: 1.41 (6H, d, J = 6.1 Hz), 4.67-4.76 (1H, m), 7.37-7.41 (2H, m), 7.59-7.68 (3H, m), 7.76-7.85 (2H, m), 10.04 (1H, m). | Ref. Ex. 112 |
| 605 | | 1H-NMR (CDCl3) δ: 5.22 (2H, s), 7.00 (1H, dt, J = 2.4, 9.7 Hz), 7.24-7.27 (1H, m), 7.31-7.33 (1H, m), 7.89-7.91 (3H, m), 9.95 (1H, d, J = 1.4 Hz). | Ref. Ex. 82 |
| 606 | | 1H-NMR (CDCl3) δ: 5.23 (2H, s), 6.96 (1H, dt, J = 2.4, 9.8 Hz), 7.21-7.26 (1H, m), 7.30-7.32 (1H, m), 7.36-7.42 (1H, m), 7.47-7.49 (1H, m), 7.63-7.69 (1H, m), 9.94 (1H, d, J = 1.5 Hz). | Ref. Ex. 82 |
| 607 | | 1H-NMR (CDCl3) δ: 5.37 (2H, s), 6.96 (1H, dt, J = 2.4, 9.7 Hz), 7.23-7.26 (1H, m), 7.28-7.30 (1H, m), 7.85-7.92 (2H, m), 7.98-7.99 (1H, m), 9.94 (1H, d, J =1.5 Hz). | Ref. Ex. 82 |

TABLE 2-continued
| Ref. Ex. No | STR | 1H-NMR | ref. |
|---|---|---|---|
| 608 | 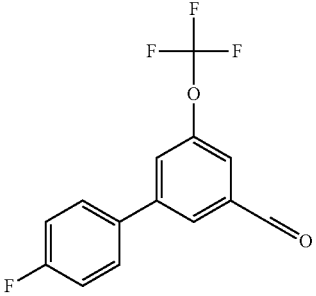 | 1H-NMR (CDCl3) δ: 7.17-7.22 (2H, m). 7.40-7.72 (4H, m), 7.99 (1H, s). 10.07 (1H, s). | Ref. Ex. 91 |
| 609 | 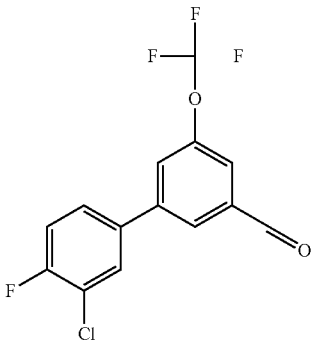 | 1H-NMR (CDCl3) δ: 7.19-7.31 (1H, m), 7.45-7.73 (4H, m), 7.98 (1H, s), 10.08 (1H, s). | Ref. Ex. 91 |
| 610 | 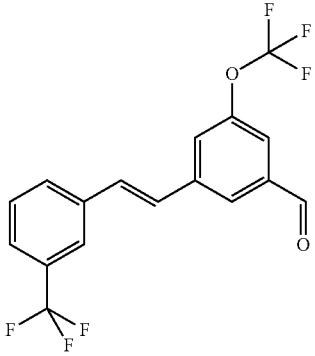 | 1H-NMR (CDCl3) δ: 6.90-7.29 (2H, m), 7.43-7.78 (6H, m), 7.98 (1H, s), 10.05 (1H, s). | Ref. Ex. 75 |
| 611 | 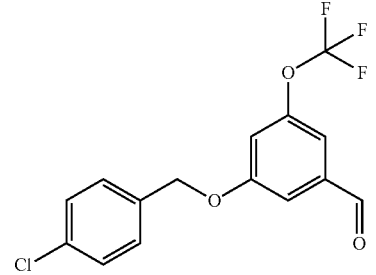 | 1H-NMR (CDCl3) δ: 5.10 (2H, s), 7.08 (1H, s), 7.32-7.40 (6H, m), 9.44 (1H, s). | Ref. Ex. 82 |
| 612 | 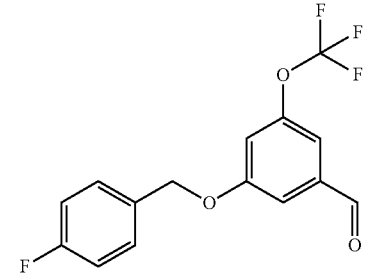 | 1H-NMR (CDCl3) δ: 5.09 (2H, s), 7.05-7.12 (3H, m), 7.34-7.43 (4H, m), 9.95 (1H, s). | Ref. Ex. 82 |

TABLE 2-continued

| Ref. Ex. No | STR | 1H-NMR | ref. |
|---|---|---|---|
| 613 | | 1H-NMR (CDCl3) δ: 7.28-7.31 (3H, m), 4.44-4.48 (2H, m), 8.26-8.28 (1H, m), 9.86 (1H, s). | Ref. Ex. 91 |
| 614 | | 1H-MMR (CDCl3) δ: 4.01-4.13 (4H, m), 5.78 (1H, s), 6.51 (1H, t, J = 73.1 Hz), 7.18 (1H, s), 7.29 (1H, s), 7.49 (1H, s). | Ref. Ex. 116 |
| 615 | | 1H-NMR (CDCl3) δ: 5.26 (2H, s), 6.94 (1H, dt, J = 2.4, 9.8 Hz), 7.21-7.24 (1H, m), 7.27-7.33 (2H, m), 7.45 (1H, dd, J = 2.7, 8.8 Hz), 7.70 (1H, dd, J = 5.3, 8.5 Hz), 9.93 (1H, d. J a 1.6 Hz). | Ref. Ex. 82 |
| 616 | | 1H-NMR (CDCl3) δ: 5.13 (2H, s), 6.96 (1H, dt, J = 2.4, 9.8 Hz), 7.21-7.25 (1H, m), 7.26-7.29 (1H, m), 7.55 (2H, d, J = 1.2 Hz), 7.76-7.78 (1H, m), 9.93 (1H, d, J = 1.5 Hz). | Ref. Ex. 82 |
| 617 | | 1H-NMR (CDCl3) δ: 1.02 (6H, s), 3.76 (4H, s), 4.01-4.16 (4H, m), 5.81 (1H, s), 6.53 (1H, t, J = 74.2 Hz), 7.30 (1H, s), 7.52 (1H, s), 7.75 (1H, 3). | Ref. Ex. 107 |
| 619 | | 1H-NMR(COCl3) δ: 5.61 (1H, brs), 6.56 (1H, t, J = 73.0 Hz), 6.89-6.90 (1H, m), 7.19-7.21 (2H, m), 9.91 (1H, s). | Ref. Ex. 151 |

TABLE 2-continued

| Ref. Ex. No | STR | 1H-NMR | ref. |
|---|---|---|---|
| 620 | | 1H-NMR (CDCl3) δ: 5.23 (2H, s), 6.59 (1H, t, J = 72.8 Hz), 7.05-7.06 (1H, m), 7.30 (1H, s), 7.36 (1H, s), 7.89 (1H, s), 7.92 (2H, s), 9.96 (1H, s). | Ref. Ex. 82 |
| 621 | | 1H-NMR (CDCl3) δ: 1.45 (3H, t, J = 7.0 Hz), 4.15 (2H, t, J = 7.0 Hz), 7.37-7.47 (5H, m), 7.60-7.68 (3H, m), 10.03 (1H, s). | Ref. Ex. 112 |
| 622 | | 1H-NMR (CDCl3) δ: 1.39 (6H, d, J = 6.1 Hz), 4.66-4.74 (1H, m), 7.36-7.47 (5H, m), 7.60-7.66 (3H, m), 10.03 (1H, s). | Ref. Ex. 112 |
| 623 | | 1H-NMR (CDCl3) δ: 7.58-7.59 (1H, m), 8.05 (1H, s), 8.24 (1H, s), 8.63 (1H, s), 8.74 (1H, s), 8.95 (1H, d, J = 5.0 Hz), 10.19 (1H, s). | Ref. Ex. 112 |
| 624 | | 1H-NMR (CDCl3) δ: 5.34 (2H, s), 6.59 (1H, t, J = 72.8 Hz), 7.05 (1H, m), 7.30 (1H, s), 7.36 (1H, s), 7.75 (1H, t, J = 8.4 Hz), 7.88 (1H, d J = 8.4 Hz), 8.04 (1H, s), 9.96 (1H, s). | Ref. Ex. 82 |

TABLE 2-continued

| Ref. Ex. No | STR | 1H-NMR | ref. |
|---|---|---|---|
| 625 | | 1H-NMR (CDCl3) δ: 5.13 (2H, s), 6.56 (1H, t, J = 73.1 Hz), 7.00-7.02 (1H, m), 7.23 (1H, s), 7.33-7.43 (6H, m), 9.93 (1H, s). | Ref. Ex. 82 |
| 626 | | 1H-NMR (CDCl3) δ: 5.19 (2H, s), 6.57 (1H, t, J = 72.9 Hz), 7.01 (1H, s), 7.33 (1H, s), 7.53-7.65 (1H, m), 7.56 (2H, d, J = 8.2 Hz), 7.68 (2H, d, J = 8.2 Hz), 9.94 (1H, s). | Ref. Ex. 82 |
| 627 | | 1H-NMR (CDCl3) δ: 5.09 (2H, s), 6.56 (1H, t, J = 72.9 Hz), 6.99 (1H, m), 7.24-7.38 (2H, m), 7.41 (4H, s), 9.93 (1H, s). | Ref. Ex. 82 |
| 628 | | 1H-NMR (CDCl3) δ: 5.08 (2H, s). 6.56 (1H, t, J = 73.0 Hz), 7.00 (1H, s), 7.10 (2H, t, J = 8.6 Hz), 7.24 (1H, s), 7.33 (1H, s), 7.39-7.43 (2H, m), 9.93 (1H, s). | Ref. Ex. 82 |
| 629 | | 1H-NMR (CDCl3) δ: 3.09 (3H, s), 5.33 (2H, s), 7.37-7.77 (1H, m), 7.88-7.93 (2H, m). | Ref. Ex. 103 |

TABLE 2-continued

| Ref. Ex. No | STR | 1H-NMR | ref. |
|---|---|---|---|
| 630 | | 1H-NMR (CDCl3) δ: 5.24 (2H, s), 7.27-7.30 (1H, m), 7.48-7.56 (3H, m), 7.75-7.80 (1H, m), 7.89-7.95 (2H, m), 10.00 (1H, s). | Ref. Ex. 82 |
| 631 | | 1H-NMR (CDCl3) δ: 5.23 (2H, s), 6.99 (1H, dt, J = 2.4, 9.7 Hz), 7.21-7.28 (1H, m), 7.30-7.33 (1H, m), 7.75-7.78 (1H, m), 7.90-7.93 (2H, m), 9.94 (1H, d, J = 1.4 Hz). | Ref. Ex. 82 |
| 632 | | 1H-NMR (CDCl3) δ: 5.82 (1H, s), 7.28-7.34 (1H, m), 7.36 (1H, dt, J = 1.8, 7.1 Hz), 9.86 (1H, d, J = 1.8 Hz). | Ref. Ex. 93 |
| 633 | | 1H-NMR (CDCl3) δ: 2.38 (3H, s), 7.65 (1H, s), 7.92 (3H, s), 9.90 (1H, s). | Ref. Ex. 91 |
| 634 | | 1H-NMR (CDCl3) δ: 7.99 (1H, d, J = 8.4 Hz), 8.08-8.11 (1H, m), 8.24 (1H, s), 8.63 (1H, S), 8.75 (1H, s), 9.01 (1H, s), 10.18 (1H, s). | Ref. Ex. 81, Ref. Ex. 75 |
| 635 | | 1H-NMR (CDCl3) δ: 7.65 (1H, d, J = 5.1 Hz), 8.32 (1H, s), 9.05 (1H, s), 9.14 (1H, d, J = 5.1 Hz), 9.21 (1H, s), 10.21 (1H, s). | Ref. Ex. 81, Ref. Ex. 75 |

TABLE 2-continued

| Ref. Ex. No | STR | 1H-NMR | ref. |
|---|---|---|---|
| 636 | | 1H-NMR (CDCl3) δ: 3.80 (3H, s), 5.06 (2H, s), 6.73-6.74 (1H, m), 6.78 (1H, s), 6.84 (1H, s), 7.37-7.42 (5H, m). | Ref. Ex. 82 |
| 637 | | 1H-NMR (CDCl3) δ: 3.84 (3H, s), 5.10 (2H, s), 6.78-6.80 (1H, m), 7.04 (1H, s), 7.10 (1H, s), 7.37-7.43 (5H, m), 9.90 (1H, s). | Ref. Ex. 93 |
| 638 | | 1H-NMR (CDCl3) δ: 7.64 (1H, d, J = 5.0 Hz), 7.91 (1H, s), 8.65 (1H, s), 8.98 (1H, s), 9.12 (1H, d, J = 5.0 Hz), 10.16 (1H, s). | Ref. Ex. 91 |
| 639 | | 1H-NMR (CDCl3) δ: 5.11 (2H, s), 6.58 (1H, t, J = 72.9 Hz), 7.01 (1H, m), 7.21-7.37 (5H, m), 9.94 (1H, s). | Ref. Ex. 82 |
| 640 | | 1H-NMR (CDCl3) δ: 5.14 (2H, s), 7.24-7.28 (1H, m), 7.47-7.48 (1H, m), 7.49-7.53 (2H, m), 7.55-7.57 (2H, m), 7.78-7.79 (1H, m), 10.00 (1H, s). | Ref. Ex. 82 |

TABLE 2-continued

| Ref. Ex. No | STR | 1H-NMR | ref. |
|---|---|---|---|
| 641 | | 1H-NMR (CDCl3) δ: 5.11 (2H, s), 6.95 (1H, dt, J = 2.4. 9.8 Hz), 7.21-7.25 (2H, m), 7.27-7.38 (3H, m). 9.93 (1H, d, J= 1.5 Hz). | Ref. Ex. 82 |
| 642 | | 1H-NMR (CDCl3) δ: 5.11 (2H, s), 7.21-7.26 (2H, m), 7.30-7.36 (2H, m), 7.45-7.51 (3H, m), 9.93 (1H, s). | Ref. Ex. 82 |
| 644 | | 1H-NMR (CDCl3) δ: 1.30 (1H, t, J = 6.1 Hz), 1.40-1.88 (18H, m), 2.19-2.27 (2H, m), 3.28 (2H, d, J = 6.1 Hz), 3.38-3.51 (1H, m), 3.90-4.01 (1H, m), 4.83-4.88 (1H, m). | Ref. Ex. 76 |
| 645 | | 1H-NMR (CDCl3) δ: 1.45-1.74 (13H, m), 2.18-2.27 (2H, m), 3.14 (2H, s), 4.56 (2H, S), 7.52 (1H, t, J = 7.5 Hz), 7.59-7.65 (1H, m), 7.77-7.85 (2H, m), 10.03 (1H, s). | Ref. Ex. 189 |
| 646 | | 1H-NMR (CDCl3) δ: 2.44 (3H, s), 5.21 (2H, s), 7.12 (1H, s), 7.29 (1H, s), 7.35 (1H, s), 7.87 (1H, s), 7.91 (2H, s), 9.96 (1H, s). | Ref. Ex. 82 |

TABLE 2-continued

| Ref. Ex. No | STR | 1H-NMR | ref. |
|---|---|---|---|
| 647 | | 1H-NMR (CDCl3) δ: 2.44 (3H, d, J = 0.3 Hz), 5.32 (2H, s), 7.12 (1H, s), 7.29 (1H, s), 7.36 (1H, s), 7.72 (1H, d, J = 8.2 Hz), 7.85 (1H, d, J = 8.2 Hz), 8.07 (1H, s), 9.95 (1H, s). | Ref. Ex. 82 |
| 648 | | 1H-NMR (CDCl3) δ: 1.33 (1H, s), 1.45-1.70 (12H, m), 2.17-2.25 (2H, m), 3.09 (2H, s), 4.01-4.20 (4H, m), 4.51 (2H, s), 5.82 (1H, s), 7.25-7.42 (4H, m). | Ref. Ex. 116 |
| 649 | | 1H-NMR (CDCl3) δ: 1.47-1.60 (8H, m), 1.68-1.72 (4H, m), 2.19-2.27 (2H, m), 3.14 (2H, s), 3.24 (3H, s), 4.57 (2H, s), 7.52 (1H, t, J = 7.6 Hz), 7.59-7.64 (1H, m), 7.77-7.85 (2H, m), 10.03 (1H, s). | Ref. Ex. 115, Ref. Ex. 151 |
| 650 | | 1H-NMR (CDCl3) δ: 5.31 (2H, s), 7.36-7.44 (2H, m), 7.90-7.94 (3H, m), 9.88 (1H, d, J = 1.5 Hz). | Ref. Ex. 82 |
| 651 | | 1H-NMR (CDCl3) δ: 5.09 (2H, s), 6.57 (1H, t, J = 72.9 Hz), 6.99 (1H, m), 7.07-7.18 (4H, m), 7.31 (1H, s), 9.94 (1H, s). | Ref. Ex. 82 |

TABLE 2-continued
| Ref. Ex. No | STR | 1H-NMR | ref. |
|---|---|---|---|
| 652 | 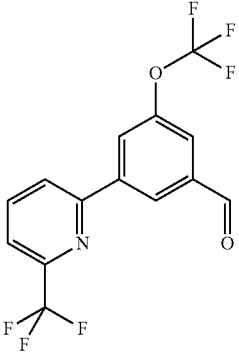 | 1H-NMR (CDCl3) δ: 7.59 (1H, d, J = 5.0 Hz), 7.70 (1H, t, J = 7.7 Hz), 8.08-8.09 (1H, m), 8.70-8.82 (1H, m), 9.02 (1H, s), 9.10 (1H, d, J = 5.0 Hz), 10.16 (1H, s). | Ref. Ex. 82 |
| 653 | 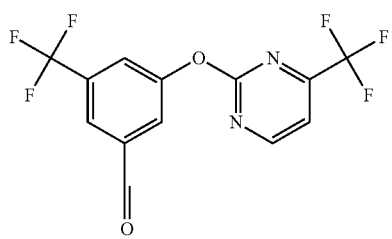 | 1H-NMR (CDCl3) δ: 7.46 (1H, d, J = 4.9 Hz), 7.78 (1H, s), 7.96 (1H, s), 8.07 (1H, s), 3.83 (1H, d, J = 4.9 Hz), 10.08 (1H, s). | Ref. Ex. 82 |
| 654 | 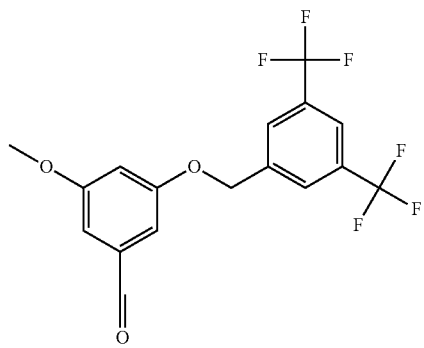 | 1H-NMR (CDCl3) δ: 3.85 (3H, s), 5.20 (2H, s), 6.80-6.82 (1H, m), 7.08-7.11 (2H, m), 7.87 (1H, s), 7.91 (2H, s), 9.93 (1H, s). | Ref. Ex. 82 |
| 655 | 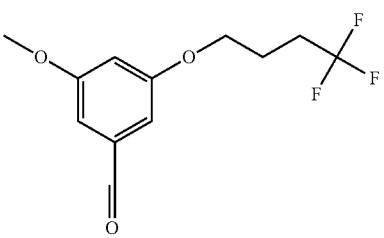 | 1H-NMR (CDCl3) δ: 2.03-2.12 (2H, m), 2.28-2.37 (2H, m), 3.85 (3H, s), 4.06 (2H, t, J = 5.9 Hz), 6.69-6.79 (1H, 3), 6.99-7.03 (2H, m), 9.91 (1H, s). | Ref. Ex. 82 |
| 656 | 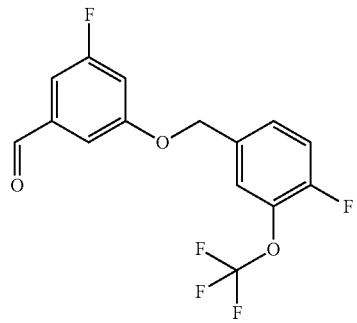 | 1H-NMR (CDCl3) δ: 5.09 (2H, s), 6.85 (1H, dt, J = 2.4, 9.8 Hz), 7.20-7.24 (1H, m), 7.25-7.31 (2H, m), 7.34-7.38 (1H, m), 7.38-7.42 (1H, m), 9.93 (1H, d, J = 1.5 Hz). | Ref. Ex. 82 |

| Ref. Ex. No | STR | 1H-NMR | ref. |
|---|---|---|---|
| 657 | | 1H-NMR (CDCl3) δ: 5.12 (2H, s), 6.95 (1H, dt, J = 2.4, 9.9 Hz), 7.01-7.09 (1H, m), 7.12-7.17 (1H, m), 7.18-7.22 (2H, m), 7.27-7.29 (1H, m), 7.34-7.41 (1H, m), 9.92 (1H, d, J = 1.6 Hz). | Ref. Ex. 82 |
| 658 | | 1H-NMR (CDCl3) δ: 5.08 (2H, s), 6.94 (1H, dt, J = 2.4, 10.0 Hz), 7.07-7.14 (2H, m), 7.18-7.21 (1H, m), 7.28-7.29 (1H, m), 7.39-7.44 (2H, m), 9.92 (1H, d, J = 1.6 Hz). | Ref. Ex. 82 |
| 659 | | 1H-NMR (CDCl3) δ: 5.11 (2H, s), 6.95 (1H, dt, J = 2.4, 9.8 Hz), 7.19-7.23 (1H, m), 7.24-7.29 (3H, m), 7.45-7.50 (2H, m), 9.92 (1H, d, J = 1.5 Hz). | Ref. Ex. 82 |
| 660 | | 1H-NMR (CDCl3) δ: 5.07 (2H, s), 6.97 (1H, dt, J = 2.4, 9.9 Hz), 7.20-7.24 (1H, m), 7-30-7.31 (1H, m), 7.52-7.71 (4H, m), 9.93 (1H, d, J = 1.5 Hz). | Ref. Ex. 82 |
| 661 | | 1H-NMR (CDCl3) δ: 5.19 (2H, s), 6.96 (1H, dt, J = 2.3, 9.8 Hz), 7.20-7.23 (1H, m), 7.28-7.30 (1H, m), 7.55-7.57 (2H, m), 7.66-7.69 (2H, m), 9.93 (1H d, J = 1.5 Hz). | Ref. Ex. 82 |
| 662 | | 1H-NMR (CDCl3) δ: 7.30 (1H, s), 7.80 (2H, s), 7.84 (1H, s), 7.63 (1H, s), 7.95 (1H, s), 10.06 (1H, s). | Ref. Ex. 91 |

TABLE 2-continued
| Ref. Ex. No | STR | 1H-NMR | ref. |
|---|---|---|---|
| 663 | 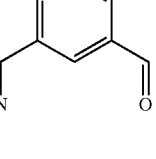 | 1H-NMR (CDCl3) δ: 7.28-7.31 (1H, m), 7.99 (1H, s), 8.73 (1H, s), 8.85-8.87 (3H,m), 10.10 (1H, s). | Ref. Ex. 91 |
| 664 | 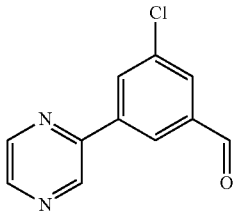 | 1H-NMR (CDCl3) δ: 7.97 (1H, s), 8.33 (1H, s), 8.43 (1H, s), 8.62 (1H, s), 8.69 (1H, s), 9.11 (1H, s), 10.09 (1H, s). | Ref. Ex. 91 |
| 665 |  | 1H-NMR (CDCl3) δ: 7.66-7.71 (2H, m), 7.97-8.01 (3H, m), 8.38-8.41 (1H, s), , 8.56 (1H, s), 10.14 (1H, s). | Ref. Ex. 83 |
| 666 |  | 1H-NMR (CDCl3) δ: 7.51-7.53 (1H, m), 7.70 (1H, t, J = 7.7 Hz), 7.99-8.01 (2H, m), 8.33-8.36 (1H, m), 8.56 (1H, s), 6.91 (1H, d, J = 5.0 Hz), 10.14 (1H, s). | Ref. Ex. 83 |
| 667 |  | 1H-NMR (CDCl3) δ: 7.26-7.28 (1H, m), 7.67 (1H, t, J = 7.7 Hz), 7.82-7.86 (3H, m), 7.91-7.94 (1H, m), 8.11 (1H, s), 10.11 (1H, s). | Ref. Ex. 83 |
| 668 |  | 1H-NMR (CDCl3) δ: 1.48 (3H, t, J = 7.0 Hz), 4.19 0H, q, J = 7.0 Hz), 7.56-7.58 (2H, m), 8.34-8.35 (1H. m), 8.60 (1H, s), 9.08 (1H, d, J = 4.9 Hz), 10.10 (1H, s). | Ref. Ex. 83 |

TABLE 2-continued

| Ref. Ex. No | STR | 1H-NMR | ref. |
|---|---|---|---|
| 669 | | 1H-NMR (CDCl3) δ: 1.39 (6H, d, J = 6.0 Hz), 4.69-4.81 (1H, m), 7.55-7.58 (2H, m), 8.33-8.34 (1H, m), 8.57 (1H, s), 9.07 (1H, d, J= 4.9 Hz), 10.10 (1H, s), | Ref. Ex. 83 |
| 670 | | 1H-NMR (CDCl3) δ: 5.10 (2H, s), 7.21-7.20 (2H, m), 7.34-7.40 (1H, m), 7.41-7.43 (1H, m), 7.46-7.47 (1H, m), 7.48-7.54 (2H, m), 9.99 (1H, s). | Ref. Ex. 82 |
| 671 | | 1H-NMR (CDCl3) δ: 5.10 (2H, s), 7.23-7.27 (1H, m), 7.33-7.40 (2H, m), 7.46-7.47 (1H, m), 7.49-7.54 (2H, m), 7.58-7.59 (1H, m), 9.99 (1H, s). | Ref. Ex. 82 |
| 672 | | 1H-NMR (CDCl3) δ: 5.10 (2H, s), 6.96 (1H, dt, J = 2.4, 9.8 Hz), 7.21-7.25 (1H, m), 7.27-7.29 (1H, m), 7.36-7.37 (2H, m), 7.57-7.58 (1H, m), 3.93 (1H, d, J = 1.5 Hz). | Ref. Ex. 82 |
| 673 | | 1H-NMR (CDCl3) δ: 5.11 (2H, s), 7.23-7.28 (1H, m), 7.32-7.36 (1H, m), 7.40-7.44 (1H,m), 7.44-7.47 (1H, m), 7.53-7.54 (3H, m), 10.01 (1H, s). | Ref. Ex. 82 |

TABLE 2-continued

| Ref. Ex. No | STR | 1H-NMR | ref. |
|---|---|---|---|
| 674 | | 1H-NMR (CDCl3) δ: 5.11 (2H, s), 6.95 (1H, dt, J = 2.4, 9.3 Hz), 7.20-7.24 (1H, m), 7.27-7.28 (1H, m), 7.31-7.34 (1H, m). 7.40-7.42 (1H, m), 7.51-7.53 (1H, m), 9.93 (1H, d, J = 1.5 Hz). | Ref. Ex. 82 |
| 675 | | 1H-NMR (CDCl3) δ: 5.09 (2H, s), 6.94 (1H, dt, J = 2.4, 9.8 Hz), 7.14-7.17 (1H, m), 7.20-7.29 (3H, m), 7.41-7.46 (1H, m), 9.92 (1H, d, J = 1.5 Hz). | Ref. Ex. 82 |
| 676 | | 1H-NMR (CDCl3) δ: 7.17 (1H, d, J = 16.2 Hz), 7.25-7.27 (1H, m), 7.37 (1H, d, J = 16.2 Hz), 7.71 (1H, d, J = 4.0 Hz), 7.80 (1H, s), 7.92 (2H, s), 9.80 (1H, s). | Ref. Ex. 75 |
| 677 | | 1H-NMR (DMSO-d6) δ: 3.28 (3H, s), 8.04-8.10 (2H, m), 8.13-8.17 (2H, m), 8.31 (1H, s), 8.44 (1H, s), 8.58 (1H, s), 10.20 (1H, s). | Ref. Ex. 91 |
| 678 | | 1H-WMR (CDCl3) δ: 3.93 (3H, s), 7.23 (1H, s), 7.68-7.71 (1H, m), 7.87-7.91 (3H, m), 7.96-7.99 (1H, m). | Ref. Ex. 83 |

TABLE 2-continued

| Ref. Ex. No | STR | 1H-NMR | ref. |
|---|---|---|---|
| 679 | | 1H-NMR (CDCl3) δ: 3.95 (3H, s), 7.31 (1H, s), 7.59-7.60 (1H, m), 8.30 (1H, s), 8.49 (1H, s), 9.07-9.09 (1H, m). | Ref. Ex. 83 |
| 680 | | 1H-NMR (CDCl3) δ: 3.90 (3H, s), 7.16 (1H, s), 7.29-7.31 (2H, m), 7.39 (1H, s), 7.43-7.51 (3H, s). | Ref. Ex. 83 |
| 681 | | 1H-NMR (CDCl3) δ: 1,34 (9H, s), 5.05 (2H, 3), 6.95 (1H, dt, J = 2.4, 10.0 Hz), 7.10-7.20 (1H, m), 7.29-7.30 (1H, m), 7.35-7.39 (2H, m), 7.42-7.46 (2H, m), 9.92 (1H, d, J = 1.6 Hz). | Ref. Ex. 82 |
| 682 | | 1H-NMR (CDCl3) δ: 3.96 (3H, s), 7.49 (1H, s), 7.66-7.69 (1H, m), 7,93-7.95 (1H, m), 7.96-7.99 (1H, m), 8.15 (1H, s), 10.09 (1H, s). | Ref. Ex. 93 |
| 683 | | 1H-NMR (CDCl3) δ: 7.27-7.31 (1H, m), 7.51-7.63 (3H, m), 7.77-7.90 (5H, m), 10.12 (1H, s). | Ref. Ex. 75 |
| 684 | | 1H-NMR (CDCl3) δ: 2.39 (3H, s), 7.11 (1H, d, J = 16.1 Hz), 7.23 (1H, d, J = 16.1 Hz), 7.50-7.66 (4H, m), 7.75 (1H, s), 9.83 (1H, s). | Ref. Ex. 75 |

TABLE 2-continued

| Ref. Ex. No | STR | 1H-NMR | ref. |
|---|---|---|---|
| 685 | | 1H-NMR (CDCl3) δ: 3.97 (3H, s), 7.57-7.59 (2H, m), 8.35-8.36 (1H, m), 8.62 (1H, s), 9.09 (1H, d, J = 4.0 Hz), 10.11 (1H, s). | Ref. Ex. 93 |
| 686 | | 1H-NMR (CDCl3) δ: 3.94 (3H, s), 7.23-7.36 (1H, m), 7.37-7.54 (5H, m), 7.67 (1H, s), 10.05 (1H, s). | Ref. Ex. 93 |
| 687 | | 1H-NMR (CDCl3) δ: 3.94 (3H, s), 7.24-7.26 (1H, m), 7.83-7.91 (3H, m), 8.02-8.06 (1H, m), 8.97 (1H, s). | Ref. Ex. 83 |
| 688 | | 1H-NMR (CDCl3) δ: 3.91 (3H, s), 7.20 (1H, s), 7.31 (1H, s), 7.37-7.45 (3H, m), 7.59 (1H, s). | Ref. Ex. 83 |
| 689 | | 1H-NMR (CDCl3) δ: 3.96 (3H, s), 7.51-7.52 (1H, m), 7.91-7.93 (2H, m), 8.01-8.03 (1H, m), 8.13 (1H, s), 8.97 (1H, s), 10.08 (1H, s). | Ref. Ex. 93 |

TABLE 2-continued

| Ref. Ex. No | STR | 1H-NMR | ref. |
|---|---|---|---|
| 690 | | 1H-NMR (CDCl3) δ: 3.93 (3H, s), 7.36-7.38 (2H, m), 7.44-7.52 (2H, m), 7.67 (2H, s), 10.06 (1H, s). | Ref. Ex. 93 |
| 691 | | 1H-NMR (CDCl3) δ: 7.24 (2H, d, J = 16.4 Hz), 7.49-7.58 (3H, m), 7.70 (1H, d, J = 7.6 Hz), 7.77-7.82 (3H, m), 8.05 (1H, s), 10.07 (1H, s). | Ref. Ex. 75 |
| 692 | | 1H-NMR (CDCl3) δ: 6.62 (1H, t, J = 72.9 Hz), 7.17-7.26 (2H, m), 7.51-7.58 (4H, m), 7.70 (1H, d, J = 7.6 Hz), 7.79 (1H, s), 7.90 (1H, s), 10.04 (1H, s). | Ref. Ex. 75 |
| 693 | | 1H-NMR (CDCl3) δ: 7.24-7.33 (2H, m), 7.59 (1H, t, J = 7.7 Hz), 7.79-7.86 (3H, m), 7.95 (2H, s), 8.08 (1H, s), 10.08 (1H, s). | Ref. Ex. 75 |
| 694 | | 1H-NMR (CDCl3) δ: 7.16 (1H, d, J = 16.4 Hz), 7.23 (1H, d, J = 16.4 Hz), 7.60-7.67 (4H, m), 7.76 (2H, s), 7.91 (1H, s), 10.01 (1H, s). | Ref. Ex. 91 |

| Ref. Ex. No | STR | 1H-NMR | ref. |
|---|---|---|---|
| 695 | | 1H-NMR (CDCl3) δ: 5.44 (2H, s), 7.03 (1H, dt, J = 2.4, 9.9 Hz), 7.18-7.23 (1H, m), 7.36-7.37 (1H, m), 7.55-7.61 (1H, m), 7.64 (1H, d, J = 8.5 Hz), 7.74-7.79 (1H, m), 7.84-7.87 (1H, m), 8.09-8.11 (1H, m), 8,23 (1H, d, J = 8.5 Hz), 9.91 (1H, d, J = 1.8 Hz). | Ref. Ex. 82 |
| 696 | | 1H-NMR (CDCl3) δ: 5.45 (2H, s), 7.29-7.36 (1H, m), 7.41-7.52 (2H, m), 7.54-7.61 (2H, m), 7.66 (1H, d, J = 8.5 Hz), 7.73-7.78 (1H, m), 7.84 (1H, dd, J = 1.1, 8.2 Hz), 8.09-8.12 (1H, m), 8.22 (1H, d, J = 8.5 Hz), 9.97 (1H, s). | Ref. Ex. 82 |
| 697 | | 1H-NMR (CDCl3) δ: 2.60 (6H, s), 7.64-7.70 (1H, m), 7.84-7.68 (1H, m), 7.97 (1H, dt, J = 1.4, 7.7 Hz), 8.11-8.12 (1H, m), 8.39 (1H, s), 10.11 (1H, s). | Ref. Ex. 91 |
| 698 | | 1H-NMR (CDCl3) δ: 4.08 (6H, s), 6.03 (1H, s), 7.64 (1H, t, J = 7.6 Hz), 8.00 (1H, dt, J = 1.5, 7.6 Hz), 8,72-8.76 (1H, m), 8.93-8.94 (1H, m), 10.14 (1H, s). | Ref. Ex. 91 |
| 699 | | 1H-NMR (CDCl3) δ: 4.22 (3H, s), 7.11 (1H, d, J = 9.2 Hz), 7.89 (1H, t, J = 7.7 Hz), 7.88 (1H, d, J = 9.2 Hz), 7.98 (1H, dt, J = 1.4, 7.7 Hz), 8.35-8.40 (1H, m), 8.50-8.51 (1H, m), 10.12 (1H, s). | Ref. Ex. 91 |
| 700 | | 1H-NMR(CDCl3) δ: 1.10-1.42 (6H, m), 1.62-1.88 (4H, m), 2.09-2.28 (1H, m), 6.25-6.38 (2H, m), 7.55 (1H, s), 7.65 (1H, s), 7.71 (1H, s), 9.95 (1H, s). | Ref. Ex. 91 |
| 701 | | 1H-NMR (CDCl3) δ: 7.63-7.65 (1H, m), 7.99-8.14 (2H, m), 8.41 (2H, s), 8.53 (1H, s), 10.13 (1H, s). | Ref. Ex. 91 |

TABLE 2-continued

| Ref. Ex. No | STR | 1H-NMR | ref. |
|---|---|---|---|
| 702 | | 1H-NMR (CDCl3) δ: 7.24-7.26 (2H, m), 7.56-7.63 (1H, m), 7.03 (4H, s), 7.77-7.82 (2H, m), 6.05 (1H, s), 10.07 (1H, s). | Ref. Ex. 91 |
| 703 | | 1H-NMR (CDCl3) δ: 7.47 (1H, s), 7.65 (1H, s), 7.69 (1H, d, J = 6.2 Hz), 8.01-8.03 (2H, m), 8.95 (1H, s), 9.41 (1H, s), 10.03 (1H, s). | Ref. Ex. 83 |
| 704 | | 1H-NMR (CDCl3) δ: 8.10 (1H, s), 8.17 (1H, s), 8.24 (1H, s), 8.31 (1H, s), 8.99 (1H, s), 9.10 (1H, s), 10.18 (1H, s). | Ref. Ex. 81, Ref. Ex. 75 |
| 705 | | 1H-NMR (CDCl3) δ: 5.22 (2H, s), 7.38-7.47 (5H, m), 7.59-7.50 (1H, m), 7.90-7.92 (1H, m), 8.00-8.02 2H, m), 8.15 (1H, s), 8.98 (1H, s), 10.07 (IK s). | Ref. Ex. 82 |
| 706 | | 1H-NMR (CDCl3) δ: 7.36 (1H, d, J = 16.0 Hz), 7.61-7.64 (1H, m), 7.82-7.94 (4H, m), 8.03 (2H, s), 10.12 (1H, s). | Ref. Ex. 75 |
| 707 | | 1H-NMR (CDCl3) δ: 5.14 (2H, s), 6.97 (1H, dt, J = 2.4, 9.7 Hz), 7.22-7.26 (1H, m), 7.29-7.30 (1H, m), 7.59-7.60 (1H, m), 7.61-7.63 (2H, m), 9.94 (1H, d, J = 1.5 Hz). | Ref. Ex. 82 |

TABLE 2-continued

| Ref. Ex. No | STR | 1H-NMR | ref. |
|---|---|---|---|
| 708 | | 1H-NMR (CDCl3) δ: 5.11 (2H, s), 6.96 (1H, dt, J = 2.4, 9.8 Hz), 7.20-7.26 (3H, m), 7.27-7.29 (1H, m), 7.38-7.39 (1H, m), 9.93 (1H, d, J = 1.5 Hz). | Ref. Ex. 82 |
| 709 | | 1H-NMR (CDCl3) δ: 5.09 (2H, s), 6.95 (1H, dt, J = 2.4, 9.8 Hz), 7.11 (2H, m), 7.20-7.25 (2H, m), 7.25-7.27 (1H, m), 9.93 (1H, d, J = 1.5 Hz). | Ref. Ex. 82 |
| 710 | | 1H-NMR (CDCl3) δ: 5.10 (2H, s), 7.25-7.30 (1H, m), 7.47-7.55 (3H, m), 7.60-7.64 (3H, m), 9.97 (1H, s). | Ref. Ex. 82 |
| 711 | | 1H-NMR (CDCl3) δ: 5.11 (2H, s), 7.21-7.22 (2H, m), 7.24-7.28 (1H, m), 7.39-7.40 (1H, m), 7.45-7.47 (1H, m), 7.49-7.54 (2H, m), 9.99 (1H, s). | Ref. Ex. 82 |
| 712 | | 1H-NMR (CDCl3) δ: 5.10 (2H, s), 7.05-7.09 (2H, m), 7.23-7.30 (2H, m), 7.44-7.46 (1H, m), 7.49-7.54 (2H, m), 9.99 (1H, s). | Ref. Ex. 82 |
| 713 | | 1H-NMR (DMSO-d6) δ: 2.68 (3H, s), 3.92 (3H, s), 7.60-7.61 (1H, m), 7.72 (1H, d, J = 8.5 Hz), 8.02-8.03 (1H, m), 8.14-8.15 (1H, m), 8.27 (1H, d, J = 8.8 Hz). | Ref. Ex. 83 |

TABLE 2-continued

| Ref. Ex. No | STR | 1H-NMR | ref. |
|---|---|---|---|
| 714 | | 1H-NMR (CDCl3) δ: 3.47 (3H, s), 5.16 (2H, s), 5.30 (1H, s), 6.77-6.78 (2H, m), 6.92 (1H, s). | Ref. Ex. 618 |
| 715 | | 1H-NMR (CDCl3) δ: 5.25 (1H, d, J = 10.9 Hz), 5.66 (1H, d, J = 17.5 = Hz), 6.63-6.69 (1H, m), 7.00 (1H, d, J = 8.3 Hz), 7.06-7.08 (1H, m), 7.15 1H, s). | Ref. Ex. 77 |
| 716 | | 1H-NMR (CDCl3) δ: 6.74-6.77 (1H, m), 7.02-7.05 (2H, m), 7.10 (2H, s), 7.73 (1H, s), 7.77 (1H, 3), 7.89 (1H, s), 10.01 (1H, s). | Ref. Ex. 91 |
| 717 | | 1H-NMR (CDCl3) δ: 7.98 (1H, s), 8.67 (1H, s), 8.71 (2H, s), 8.81 (1H, s), 10.09 (1H, s). | Ref. Ex. 91 |
| 718 | | 1H-NMR (CDCl3) δ: 6.72-6.77 (1H, m), 7.03-7.17 (4H, m), 7.54-7.58 (1H, m), 7.75-7.82 (2H, m), 8.03 (1H, s). 10.06 (1H, s). | Ref. Ex. 91 |
| 719 | | 1H-NMR (CDCl3) δ: 7.42-7.45 (3H, m), 7.88-8.23 (5H, m), 10.07 (1H, s). | Ref. Ex. 91 |
| 720 | | 1H-NMR (CDCl3) δ: 2.40 (3H, s), 5.10 (2H, s), 7.08 (1H, s). 7.27-7.47 (7H, m), 9.93 (1H, s). | Ref. Ex. 82 |

| Ref. Ex. No | STR | 1H-NMR | ref. |
|---|---|---|---|
| 721 | | 1H-NMR (CDCl3) δ: 2.41 (3H, s), 5.10 (2H, s), 6.98-7.08 (2H, m), 7 W,22 (2H, m), 7.25-7.28 (1H, m), 7.29-7.40 (2H, m), 9.93 (1H, s). | Ref. Ex. 82 |
| 722 | | 1H-NMR (CDCl3) δ: 2.41 (3H, s), 5.06 (2H, s), 7.04-7.12 (3H, m), 7.26-7.32 (2H, m), 7.38-7.44 (2H, m), 9.93 (1H, s). | Ref. Ex. 82 |
| 723 | | 1H-NMR (CDCl3) δ: 2.42 (3H, d, J = 0.4 Hz), 5.15 (2H, s), 7.08-7.12 (1H, m), 7.27-7.30 (1H, m), 7.31-7.34 (1H, m), 7.52 (1H, t, J = 7.6 Hz), 7.58-7.66 (2H, m), 7.72 (1H, s), 9.94 (1H, s). | Ref. Ex. 82 |
| 724 | | 1H-NMR (CDCl3) δ: 5.17 <2H, s)( 6.61-6.75 (2H, m), 7.56 (1H, t, J = 7.6 Hz), 7.73 (1H, d, J = 7.6 Hz), 7.86 (1H, d, J = 7.6 Hz), 7.94 (1H, s), 10.04 (1H, s). | Ref. Ex. 113, Ref. Ex. 229 |
| 725 | | 1H-NMR (CDCl3) δ: 2.40 (3H, s), 3.46 (3H, s), 3.74-3.79 (2H, m), 4.15-4.19 (2H, m), 7.04 (1H, s), 7.22 (1H, s), 7.28 (1H, s), 9.92 (1H, s). | Ref. Ex. 82 |
| 726 | | 1H-NMR (CDCl3) 6: 2.41 (3H, s), 5.11 (2H, s), 6.82-6.96 (2H, m), 7.07 (1H, s), 7.29 (1H, s), 7.52 (1H, s), 7.43-7.52 (1H, m), 9.94 (1H, s). | Ref. Ex. 82 |
| 727 | | 1H-NMR (CDCl3) δ: 2.43 (3H, d, J = 0.3 Hz), 5.15 (2H, s), 7.09 (1H, s), 7.26-7.38 (4H, m), 7.50 (1H, s), 9.94 (1H, s). | Ref. Ex. 82 |

| Ref. Ex. No | STR | 1H-NMR | ref. |
|---|---|---|---|
| 728 | 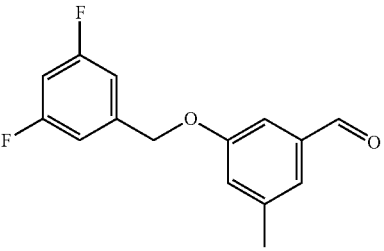 | 1H-NMR (CDCl3) δ: 2.42 (3H, s), 5.09 (2H, s), 6.72-6.82 (1H, m), 6.90-7.00 (2H, m), 7.07 (1H, s), 7.24 (1H, s), 7.32 (1H, s), 9.93 (1H, s). | Ref. Ex. 82 |
| 729 | 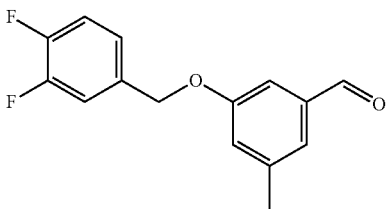 | 1H-NMR (CDCl3) δ: 2.41 (3H, s), 5.05 (2H, s), 7.08 (1H, s), 7.11-7.22 (2H, m), 7.22-7.29 (2H, m), 7.31 (1H, s), 9.93 (1H, s). | Ref. Ex. 82 |
| 730 | 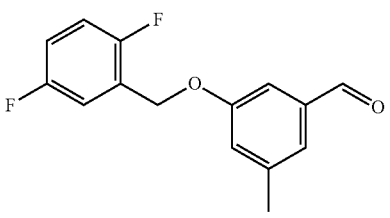 | 1H-NMR (CDCl3) δ: 2.42 (3H, s), 5.15 (2H, s), 6.90-7.09 (3H, m), 7.15-7.26 (1H, m), 7.28 (1H, s), 7.33 (1H, s), 9.94 (1H, s). | Ref. Ex. 82 |
| 731 | 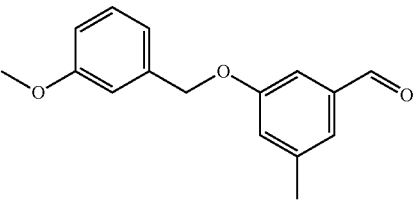 | 1H-NMR (CDCl3) δ: 2.41 (3H, s), 3.83 (3H, s), 5.08 (2H, s), 6.87 (1H, dd, J = 2.2, 8.1 Hz), 6.97-7.03 (2H, m), 7.08 (1H, s), 7.26-7.35 (3H, m), 9.93 (1H, s). | Ref. Ex. 82 |
| 732 | 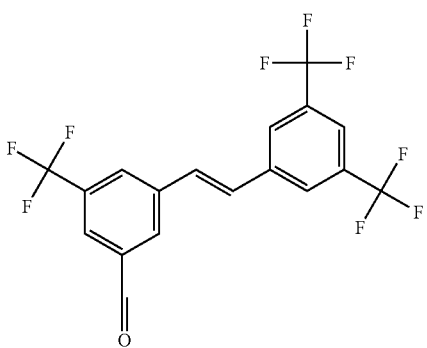 | 1H-NMR (CDCl3) δ: 7.34 (2H, s), 7.83 (1H, s), 7.98 (2H, s), 8.03 (1H, s), 8.08 (1H, s), 8.24 (1H, s), 10.12 (1H, s). | Ref. Ex. 75 |
| 733 | 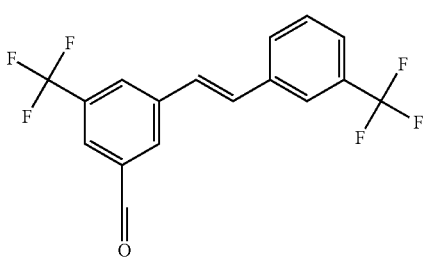 | 1H-NMR (CDCl3) δ: 7.22-7.34 (2H, m), 7.51-7.60 (2H, m), 7.72 (1H, d, J = 8.0 Hz), 7.81 (1H, s), 8.00 (1H, s), 8.04 (1H, s), 8.22 (1H, s), 10.11 (1H, s). | Ref. Ex. 75 |

TABLE 2-continued
| Ref. Ex. No | STR | 1H-NMR | ref. |
|---|---|---|---|
| 734 | 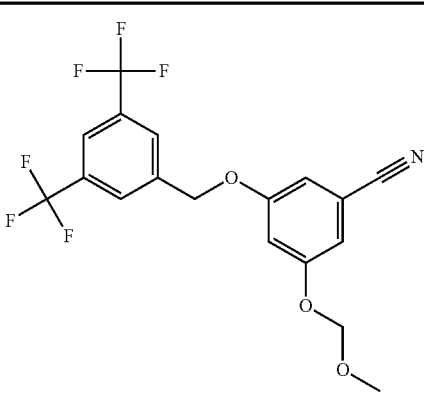 | 1H-NMR (CDCl3) δ: 3.48 (3H, s), 5.16 (2H, s), 5.19 (2H, s), 6.89-6.93 (2H, m), 7.01-7.02 (1H, m), 7.69 (3H, s). | Ref. Ex. 82 |
| 735 | 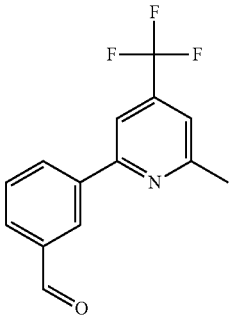 | 1H-NMR (CDCl3) δ: 2.74 (3H, s), 7.37 (1H, s), 7.68 (1H, t, J = 6.0 Hz), 7.80 (1H, s), 7.96-7.99 (1H, m), 8.31-8.34 (1H, m), 8.55 (1H, s), 10.12 (1H, s). | Ref. Ex. 83 |
| 736 | 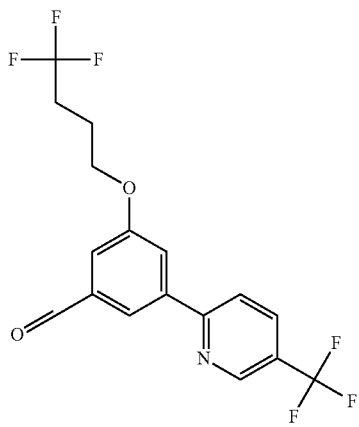 | 1H-NMR (CDCl3) δ: 2.09-2.18 (2H, m), 2.29-2.43 (2H, m), 4.14-4.21 (2H, m), 7.50 (1H, s), 7.91-7.93 (2H, m), 8.03-8.06 (1H, m), 8.14 (1H, s), 8.97 (1H, s), 10.08 (1H. s). | Ref. Ex. 82 |
| 737 | 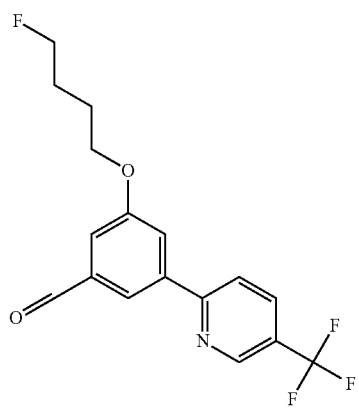 | 1H-NMR (CDCl3) δ: 1.87-2.02 (4H, m), 4.16-4.19 (2H, m), 4.46-4.50 (1H, m), 4.62-4.65 (1H, m), 7.50 (1H, s), 7.91-7.94 (2H, m), 8.02-8.06 (1H, m), 8.12 (1H, s), 8.97 (1H, s), 10.07 (1H, s). | Ref. Ex. 82 |

TABLE 2-continued

| Ref. Ex. No | STR | 1H-NMR | ref. |
|---|---|---|---|
| 738 | | 1H-NMR (CDCl3) δ: 7.18-7.31 (2H, m), 7.51-7.58 (2H, m), 7.67-7.73 (3H, m), 7.79 (1H, s), 7.90 (2H, d, J = 8.3 Hz), 10.02 (1H, s). | Ref. Ex. 75 |
| 739 | | 1H-NMR (CDCl3) δ: 7.00 (1H, d, J = 16.4 Hz), 7.09 (2H, t, J = 8.6 Hz), 7.17 (1H, d, J = 16.4 Hz), 7.49-7.52 (2H, m), 7.71-7.73 (2H, m), 7.88 (1H, s), 10.00 (1H, s). | Ref. Ex. 91 |
| 740 | | 1H-NMR (CDCl3) δ: 5.16 (2H, s), 6.97 (1H, dt, J = 2.4, 9.8 Hz), 7.22-7.25 (1H, m), 7.29-7.30 (1H, m), 7.32-7.38 (2H, m), 7.49-7.51 (1H, m), 9.94 (1H, d, J = 1.5 Hz). | Ref. Ex. 82 |
| 741 | | 1H-NMR (CDCl3) δ: 7.67 (1H, t, J = 7.7 Hz), 8.03 (1H, dt, J = 1.5, 7.7 Hz), 8.68 (1H, dt, J = 1.5, 7.7 Hz), 8.71 (2H, s), 8.91 (1H, t, J = 1.5 Hz), 10.14 (1H, s). | Ref. Ex. 91 |
| 743 | | 1H-NMR (CDCl3) δ: 5.18 (2H, s), 6.70-6.71 (1H, m), 7.01-7.04 (2H, m), 7.85-7.90 (3H, m), 8.37 (1H, m), 9.88 (1H, s). | Ref. Ex. 93 |

TABLE 2-continued

| Ref. Ex. No | STR | 1H-NMR | Ref. ref. |
|---|---|---|---|
| 744 | | 1H-NMR (CDCl3) δ: 1.84-1.98 (4H, m), 4.06-4.10 (2H, m), 4.44-4.48 (1H, m), 4.60-4.64 (1H, m), 5.20 (2H, s), 6.80-6.82 (1H, m), 7.07-7.10 (2H, m), 7.87 (1H, s), 7.91 (2H, s), 9.92 (1H, s). | Ref. Ex. 82 |
| 745 | | 1H-NMR (CDCl3) δ: 0.39-0.42 (2H, m), 0.67-0.73 (2H, m), 1.27-1.32 (1H, m), 3.89 (2H, d, J = 7.0 Hz), 5.22 (2H, s), 6.83-6.85 (1H, m), 7.09-7.12 (2H, m), 7.90 (1H, s), 7.93 (2H, s), 9.94 (1H, s). | Ref. Ex. 82 |
| 746 | | 1H-NMR (CDCl3) δ: 2.67 (3H, s), 3.91 (3H, s), 7.54-7.59 (1H, m), 7.79 (1H, d, J = 8.8 Hz), 7.98-7.99 (1H, m), 8.23-8.29 (2H, m), 10.08 (1H, s). | Ref. Ex. 93 |
| 747 | | 1H-NMR (CDCl3) δ: 0.55-0.58 (2H, m), 0.87-0.95 (2H, m), 1.58-1.61 (1H, m), 5.81-5.86 (1H, m), 6.46 (1H, d, J = 15.8 Hz), 7.50 (1H, s), 7.63 (1H, s), 7.66 (1H, s), 9.94 (1H, s). | Ref. Ex. 77 |

TABLE 2-continued

| Ref. Ex. No | STR | 1H-NMR | ref. |
|---|---|---|---|
| 748 | | 1H-NMR (CDCl3) δ: 7.19-7.27 (2H, m), 7.60 (1H, s), 7.63-7.67 (5H, m), 7.98 (1H, s), 10.05 (1H, s). | Ref. Ex. 91 |
| 749 | | 1H-NMR (CDCl3) δ: 6.62 (1H, t, J = 72.9 Hz), 7.21-7.25 (2H, m), 7.54 (2H, d, J = 11.0 Hz), 7.62-7.68 (4H, m), 7.90 (1H, s), 10.04 (1H, s). | Ref. Ex. 91 |
| 751 | | 1H-NMR (CDCl3) δ: 0.57-0.60 (2H, m), 0.88-0.92 (2H, m), 1.55-1.63 (1H, m), 5.86 (1H, dd, J = 9.2, 15.7 Hz), 6.50 (1H, d, J = 15.7 Hz), 7.36 (1H, s), 7.51 (1H, s), 7.73 (1H, s), 9.98 (1H, s). | Ref. Ex. 75 |
| 752 | | 1H-NMR (CDCl3) δ: 7.53-7.57 (3H, m), 7.69 (1H, d, J = 4.8 Hz), 8.53-8.57 (2H, m), 9.07 (1H, dd, J = 0.8, 4.8 Hz), 10.14 (1H, d, J = 0.8 Hz). | Ref. Ex. 159 |
| 753 | | 1H-NMR (CDCl3) δ: 3.17 (3H, s), 5.37 (2H, s), 7.36-7.38 (1H, m). 7.49-7.52 (3H, m), 8.42-8.46 (2H, m), 8.87 (1H, d, J = 5.1 Hz). | Ref. Ex. 103 |

TABLE 2-continued

| Ref. Ex. No | STR | 1H-NMR | ref. |
|---|---|---|---|
| 754 | | 1H-NWR (CDCl3) δ: 4.42 (2H, q, J = 8.0 Hz), 5.22 (2H, s), 6.88-6.89 (1H, m), 7.11 (1H, s), 7.20 (1H, s), 7.89 (1H, s), 7.91 (2H, s), 9.94 (1H, s). | Ref. Ex. 82 |
| 755 | | 1H-NMR (CDCl3) δ: 7.13-7.33 (3H, m), 7.58-7.70 (5H, m), 9.89 (1H, s). | Ref. Ex. 91 |
| 756 | | 1H-NMR (CDCl3) δ: 7.04 (1H, d, J = 16.3 Hz), 7.16 (1H, d, J = 16.3 Hz), 7.56-7.66 (4H, m), 7.72 (1H, s), 8.00 (1H, s), 9.97 (1H, s). | Ref. Ex. 91 |
| 757 | | 1H-NMR (CDCl3) δ: 5.31 (2H, s), 7.28-7.32 (1H, m), 7.43-7.45 (1H, m), 7.48-7.55 (6H, m), 8.45-8.49 (2H, m), 8.83 (1H, d, J = 5.1 Hz), 10.00 (1H, s). | Ref. Ex. 82 |
| 758 | | 1H-NMR (CDCl3) δ: 7.70-7.73 (1H, m), 7.94-8.02 (3H, m), 8.37 (1H, s), 8.44 (1H, s), 10.09 (1H, s). | Ref. Ex. 91 |

TABLE 2-continued

| Ref. Ex. No | STR | 1H-NMR | ref. |
| --- | --- | --- | --- |
| 759 | | 1H-NMR (CDCl3) δ: 7.85 (1H, d, J = 5.0 Hz), 8.05 (1H, s), 8.57 (1H, s), 8.63 (1H, s), 8.75 (1H, s), 9.01 (1H, d, J = 5.0 Hz), 10.11 (1H, s). | Ref. Ex. 91 |
| 761 | | 1H-NMR (CDCl3) δ: 1.49 (3H, t, J = 6.9 Hz), 4.20 (2H, q, J = 6.9 Hz), 7.49-7.50 (1H, m), 7.90-7.93 (2H, m), 8.02-8.05 (1H, m), 8.11-8.12 (1H, m), 8.97 (1H, s), 10.07 (1H, s). | Ref. Ex. 82 |
| 762 | | 1H-NMR (CDCl3) δ: 4.52 (2H, q, J = 8.0 Hz), 7.54-7.55 (1H, m), 7.94 (1H, d, J = 8.4 Hz), 8.01-8.02 (1H, m), 8.05-8.07 (1H, m), 8.23-8.24 (1H, m), 8.98 (1H, s), 10.09 (1H, s). | Ref. Ex. 82 |
| 763 | | 1H-NMR (CDCl3) δ: 0.92-1.05 (2H, m), 1.30-1.40 (2H, m), 1.43-1.56 (2H, m), 1.90-2.04 (5H, m), 3.48 (2H, d, J = 6.2 Hz). | Ref. Ex. 600 |
| 764 | | 1H-NMR (CDCl3) δ: 0.96-1.18 (2H, m), 1.24-1.43 (2H, m), 1.70-1.83 (1H, m), 1.93-2.04 (5H, m), 3.02 (3H, s), 4.06 (2H, d, J = 6.3 Hz). | Ref. Ex. 103 |
| 765 | | 1H-NMR (CDCl3) δ: 1.07-1.19 (2H, m), 1.33-1.47 (2H, m), 1.77-1.89 (1H, m), 1.96-2.11 (5H, m), 3.83 (2H, d, J = 6.2 Hz), 6.87 (1H, dt, J = 2.4, 10.1 Hz), 7.14-7.22 (2H, m), 9.92 (1H, d, J = 1.5 Hz). | Ref. Ex. 175 |

TABLE 2-continued

| Ref. Ex. No | STR | 1H-NMR | ref. |
|---|---|---|---|
| 766 | | 1H-NMR (CDCl3) δ: 1.08-1.20 (2H, m), 1.32-1.45 (2H, m), 1.77-1.88 (1H, m), 1.98-2.09 (5H, m), 3.84 (2H, d, J = 6.2 Hz), 7.15-7.20 (1H, m), 7.36-7.38 (1H, m), 7.44-7.48 (2H, m), 9.98 (1H, s). | Ref. Ex. 175 |
| 767 | | 1H-NMR (CDCl3) δ: 1.32 (1H, t, J = 4.7 Hz), 1.48-1.62 (4H, m), 1.64-1.74 (4H, m), 1.76-1.82 (1H, m), 2.05-2.17 (1H, m). 3.62 (2H, dd, J = 4.5, 7.1 Hz). | Ref. Ex. 600 |
| 768 | | 1H-NMR (CDCl3) δ: 1.55-1.77 (8H, m), 2.08-2.21 (2H, m), 3.03 (3H, s), 4.18 (2H, d, J = 7.5 Hz). | Ref. Ex. 103 |
| 769 | | 1H-NMR (CDCl3) δ: 1.61-1.70 (4H, m), 1.72-1.82 (4H, m), 2.15-2.18 (2H, m), 3.96 (2H, d, J = 7.2 Hz), 6.88 (1H, dt, J = 2.4, 10.1 Hz), 7.15-7.19 (1H, m), 7.21 (1H, dd, J = 1.3, 2.4 Hz), 9.93 (1H, d, J = 1.3 Hz). | Ref. Ex. 175 |
| 770 | | 1H-NMR (CDCl3) δ: 1.60-1.86 (8H, m), 2.14-2.18 (2H, m), 3.97 (2H, d, J = 7.3 Hz), 7.17-7.21 (1H, m), 7.39-7.40 (1H, m), 7.45-7.46 (1H, m), 7.47 (1H, d, J = 0.9 Hz), 9.99 (1H, s). | Ref. Ex. 175 |
| 771 | | 1H-NMR (CDCl3) δ: 0.58-0.60 (2H, m), 0.89-0.92 (2H, m), 1.52-1.65 (1H, m), 5.80-5.89 (1H, m), 6.60 (1H, d, J = 15.6 Hz), 6.92 (1H, d, J = 3.9 Hz), 7.59 (1H, d, J = 3.9 Hz), 9.80 (1H, s). | Ref. Ex. 77 |
| 772 | | 1H-NMR (CDCl3) δ: 0.39-0.47 (2H, m), 0.68-0.73 (2H, m), 1.24-1.36 (1H, m), 3.92 (2H, d, J = 7.0 Hz), 7.21-7.22 (1H, m), 7.63-7.70 (1H, m), 7.88-7.91 (3H, m), 7.99 (1H, t, J = 7.8 Hz). | Ref. Ex. 83 |

TABLE 2-continued
| Ref. Ex. No | STR | 1H-NMR | ref. |
|---|---|---|---|
| 773 | 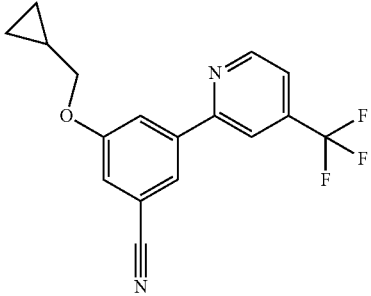 | 1H-NMR (CDCl3) δ: 0.38-0.42 (2H, m), 0.66-0.72 (2H, m), 1.26-1.34 (1H, m), 3.93 (2H, d, J = 7.0 Hz), 7.23-7.24 (1H, m), 7.52-7.54 (1H, m), 7.44-7.45 (1H, m), 7.91 (2H, s), 8.89 (1H, d, J = 5.0 Hz). | Ref. Ex. 83 |
| 774 | 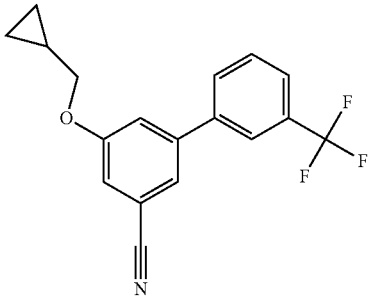 | 1H-NWR (CDCl3) δ: 0.38-0.42 (2H, m), 0.68-0.73 (2H, m), 1.27-1.34 (1H, m), 3.89 (2H, d, J = 6.9 Hz), 7.15-7.16 (1H, m), 7.34-7.35 (1H, m), 7.44-7.45 (1H, m), 7.59 (1H, t; J = 7.6 Hz), 7.73 (1H, d, J = 7.6 Hz), 7.80 (1H, d, J = 7.6 Hz), 7.78 (1H, s). | Ref. Ex. 83 |
| 775 | 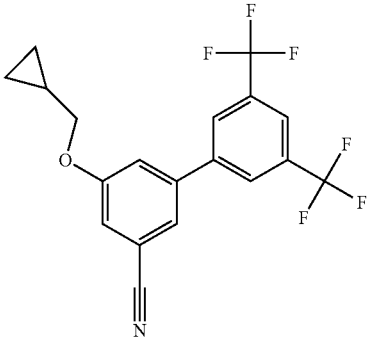 | 1H-NMR (CDCl3) δ: 0.38-0.42 (2H, m), 0.68-0.73 (2H, m), 1.27-1.34 (1H, m), 3.91 (2H, d, J = 7.0 Hz), 7.20-7.21 (1H, m), 7.34-7.35 (1H, m), 7.45-7.48 (1H, m), 7.93 (1H, s), 7.97 (2H, s). | Ref. Ex. 83 |
| 776 | 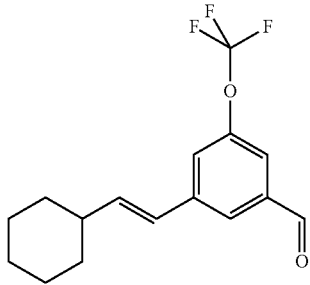 | 1H-NMR (CDCl3) δ: 1.17-1.36 (6H, m), 1.64-1.88 (4H, m), 2.10-2.28 (1H, m), 6.28-6.41 (2H, m), 7.40 (1H, s), 7.53 (1H, s), 7.78 (1H, s). 9.99 (1H, s). | Ref. Ex. 77 |
| 777 | 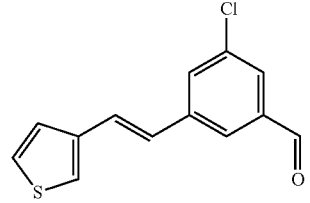 | 1H-NMR (CDCl3) δ: 6.92 (1H, d, J = 16.3 Hz), 7.23 (1H, d, J = 16.3 Hz), 7.35 (3H, s), 7.69-7.71 (2H, m), 7.85 (1H, s), 9.99 (1H, s). | Ref. Ex. 77 |

TABLE 2-continued

| Ref. Ex. No | STR | 1H-NMR | ref. |
|---|---|---|---|
| 778 | | 1H-NMR (CDCl3) δ: 7.04-7.17 (5H, m), 7.46-7.51 (2H, m), 7.66-7.71 (1H, m), 9.86 (1H, s). | Ref. Ex. 77 |
| 779 | | 1H-NMR (CDCl3) δ: 0.39-0.43 (2H, m), 0.68-0.72 (2H, m), 1.28-1.37 (1H, m), 3.96 (2H, d, J = 7.1 Hz), 7.46-7.47 (1H, m), 7.66-7.68 (1H, m), 7.95-7.98 (3H, m), 8.12-8.13 (1H, m), 10.07 (1H, s). | Ref. Ex. 93 |
| 780 | | 1H-MMR (CDCl3) δ: 0.39-0.43 (2H, m), 0.67-0.72 (2H, m), 1.30-1.36 (1H, m), 3.96 (2H, d, J = 6.9 Hz), 7.48-7.52 (2H, m), 7.90-7.91 (1H, m), 7.99 (1H, s), 8.12-8 13 (1H, m), 8.89 (1H, d, J = 5.0 Hz), 10.07 (1H, s). | Ref. Ex. 93 |
| 781 | | 1H-NMR (CDCl3) δ: 0.33-0.42 (2H, m), 0.68-0.72 (2H, m), 1.28-1.36 (1H, m), 3.94 (2H, d, J = 7.0 Hz), 7.40-7.43 (2H, m), 7.59 (1H, t, J = 7.6 Hz), 7.65-7.68 (2H, m), 7.80 (1H, d, J = 7.6 Hz), 7.86 (1H, s), 10.04 (1H, s). | Ref. Ex. 93 |
| 782 | | 1H-NMR (CDCl3) δ: 0.38-0.43 (2H, m), 0.68-0.73 (2H, m), 1.26-1.35 (1H, m), 3.95 (2H, d. J = 7.0 Hz), 7.42-7.43 (1H, m), 7.44-7.45 (1H, m), 7.68-7.69 (1H, m), 7.91 (1H, s), 8.04 (2H, s), 10.06 (1H, s). | Ref. Ex. 93 |
| 783 | | 1H-NMR (CDCl3) δ: 7.19 (1H, d, J = 16.3 Hz), 7.48 (1H, d, J = 5.1 Hz), 7.66 (4H, s), 7.71 (1H, d, J = 5.1 Hz), 7.81 (1H, d, J = 16.3 Hz), 10.21 (1H, s). | Ref. Ex. 77 |
| 784 | | 1H-NMR (CDCl3) δ: 7.04 (1H, d, J = 16.0 Hz), 7.12 (1H, d, J = 3.9 Hz), 7.18 (1H, d, J = 16.0 Hz), 7.31-7.37 (3H, m), 7.65 (1H, d, J = 3.9 Hz), 9.85 (1H, s). | Ref. Ex. 77 |

TABLE 2-continued
| Ref. Ex. No | STR | 1H-NMR | ref. |
|---|---|---|---|
| 785 | 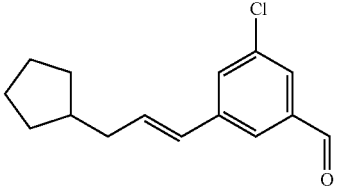 | 1H-NMR (CDCl3) δ: 1.15-1.32 (3H, m), 1.54-2.08 (6H, m), 2.23-2.27 (2H, m), 6.35-6.38 (2H, m), 7.55 (1H, s), 7.66 (1H, s), 7.71 (1H, s), 9.96 (1H, s). | Ref. Ex. 77 |
| 786 | 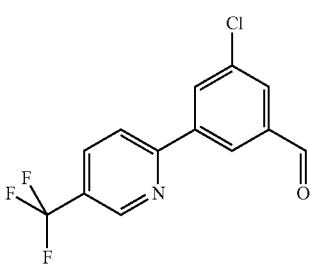 | 1H-NMR (CDCl3) δ: 7.92-7.97 (2H, m), 8.01 -8.10 (1H, m), 8.35-8.36 (1H, m), 8.43-8.44 (1H, m), 8.99 (1H, s), 10.09 (1H, s). | Ref. Ex. 91 |
| 787 | 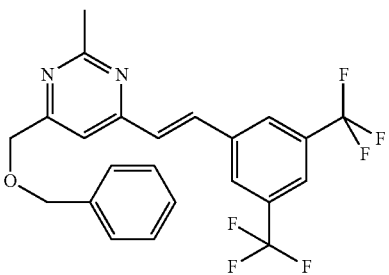 | 1H-NMR (CDCl3) δ: 2.74 (3H, s), 4.63 (2H, s), 4.70 (2H, s), 7.20 (1H, d, J = 16.0 Hz), 7.26 (1H, s), 7.32-7.43 (5H, m), 7.83 (1H, s), 7.93 (1H, d, J = 16.0 Hz), 8.02 (2H, s). | Ref. Ex. 75 |
| 788 | 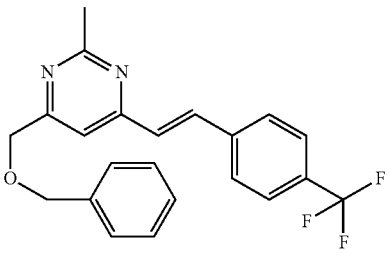 | 1H-NMR (CDCl3) δ: 2.74 (3H, s), 4.63 (2H, d, J = 0.5 Hz), 4.70 (2H, s), 7.15 (1H, d, J = 16.0 Hz), 7.32-7.43 (6H, m), 7.63-7.71 (4H, m), 7.87 (1H, d, J = 16.0 Hz). | Ref. Ex. 77 |
| 789 | 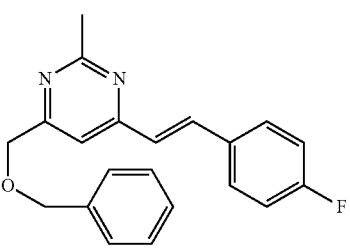 | 1H-NMR (CDCl3) δ: 2.72 (3H, s), 4.62 (2H, s), 4.69 (2H, s), 6.99 (1H, d, J = 16.1 Hz), 7.05-7.12 (2H, m), 7.31-7.43 (6H, m), 7.54-7.61 (2H, m), 7.81 (1H, d, J = 16.1 Hz). | Ref. Ex. 77 |
| 790 | 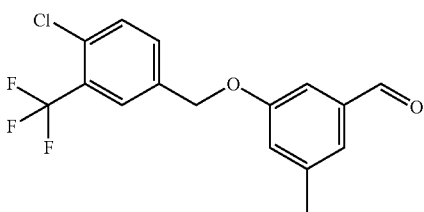 | 1H-NMR (CDCl3) δ: 2.42 (3H, s), 5.11 (2H, s), 7.08 (1H, s), 7.26 (1H, s), 7.33 (1H, s), 7.54 (2H, s), 7.78 (1H, s), 9.94 (1H, s). | Ref. Ex. 82 |

TABLE 2-continued

| Ref. Ex. No | STR | 1H-NMR | ref. |
|---|---|---|---|
| 791 | | 1H-NMR (CDCl3) δ: 1.33 (9H, s), 2.40 (3H, s), 5.06 (2H, s), 7.06 (1H, s), 7.28-7.31 (2H, m), 7.34-7.39 (2H, m), 7.40-7.45 (2H, m), 9.93 (1H, s) | Ref. Ex. 82 |
| 792 | | 1H-NMR (CDCl3) δ: 2.43 (3H, s), 5.21 (2H, s), 7.09 (1H, s), 7.29 (1H, s), 7.34 (1H, s), 7.73 (1H, d, J = 8.0 Hz), 7.97 (1H, dd, J = 1.2, 8.0 Hz), 8.81 (1H, d, J = 1.2 Hz), 9.95 (1H, s). | Ref. Ex. 82 |
| 793 | | 1H-NMR (CDCl3) δ: 5.06 (2H, s), 7.10-7.30 (4H, m), 7.34 (1H, dd, J = 1.3, 2.4 Hz), 7.47 (1H, dd, J = 1.3, 1.8 Hz), 9.92 (1H, s). | Ref. Ex. 82 |
| 794 | | 1H-NMR (CDCl3) δ: 5.10 (2H, s), 6.74-6.84 (1H, m), 6.91-7.01 (2H, m), 7.21-7.24 (1H, m), 7.32-7.35 (1H, m), 7.47-7.50 (1H, m), 9.92 (1H, s). | Ref. Ex. 82 |
| 795 | | 1H-NMR (CDCl3) δ: 5.11 (2H, s), 7.01-7.09 (1H, m), 7.12-7.25 (3H, m), 7.32-7.42 (2H, m), 7.46-7.48 (1H, m), 9.91 (1H, s). | Ref. Ex. 82 |
| 796 | | 1H-NMR (CDCl3) δ: 5.07 (2H, s), 7.06-7.14 (2H, m), 7.21-7.24 (1H, m), 7.34-7.36 (1H, m), 7.37-7.44 (2H, m), 7.45-7.47 (1H, m), 9.91 (1H, s). | Ref. Ex. 82 |

TABLE 2-continued
| Ref. Ex. No | STR | 1H-NMR | ref. |
|---|---|---|---|
| 797 | 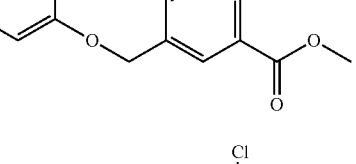 | 1H-NMR (CDCl3) δ: 3.94 (3H, s), 5.11 (2H, s), 7.11-7.15 (1H, m), 7.21-7.28 (2H, m), 7.42 (1H, t, J = 8.0 Hz), 7.64 (1H, s), 7.99 (2H, s). | Ref. Ex. 100 |
| 798 | 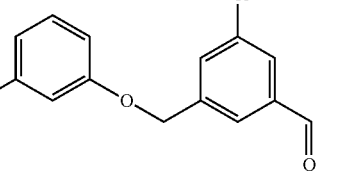 | 1H-NMR (CDCl3) δ: 5.15 (2H, s), 7.14 (1H, d, J = 8.3 Hz), 7.23 (1H, s), 7.29 (1H, s), 7.43 (1H, t, J = 7.9 Hz), 7.98 (1H, s), 8.12 (2H, s), 10.00 (1H, s). | Ref. Ex. 130, Ref. Ex. 159 |
| 799 | 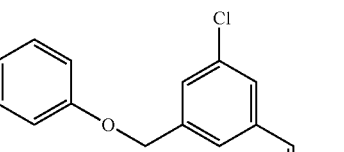 | 1H-NMR (CDCl3) δ: 5.10 (2H, s), 6.66-6.79 (3H, m), 7.21-7.30 (1H, m), 7.68-7.71 (1H, m), 7.81-7.84 (2H, m), 10.00 (1H, s). | Ref. Ex. 113, Ref. Ex. 130, Ref. Ex. 159 |
| 800 | 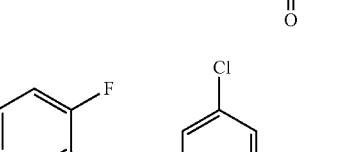 | 1H-NMR (CDCl3) δ: 5.14 (2H, s), 6.75-6.83 (1H, m), 6.85-7.00 (2H, m), 7.69-7.72 (1H, m), 7.81-7.83 (2H, m), 9.99 (1H, s). | Ref. Ex. 113, Ref. Ex. 130, Ref. Ex. 159 |
| 801 | 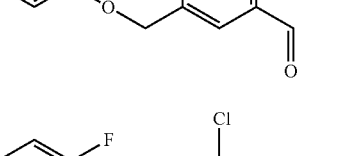 | 1H-NMR (CDCl3) δ: 5.14 (2H, s), 6.66-6.75 (2H, m), 7.72 (1H, s), 7.83 (2H, s), 9.99 (1H, s). | Ref. Ex. 113, Ref. Ex. 130, Ref. Ex. 159 |
| 802 | 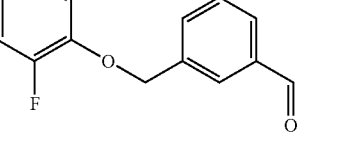 | 1H-NMR (CDCl3) δ: 3.03 (3H, s), 3.94 (3H, s), 5.24 (2H, s), 7.61 (1H, s), 7.96 (1H, s), 8.04 (1H, s). | Ref. Ex. 103 |
| 803 | 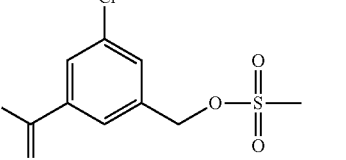 | 1H-NMR (CDCl3) δ: 7.20-7.29 (2H, m), 7.81 (1H, s), 7.93-7.97 (5H, m), 10.00 (1H, s). | Ref. Ex. 77 |

TABLE 2-continued

| Ref. Ex. No | STR | 1H-NMR | ref. |
|---|---|---|---|
| 804 | | 1H-NMR (CDCl3) δ: 1.54-1.77 (4H, m), 2.18-2.31 (4H, m), 6.02 (1H, brs), 6.43 (1H, d, J = 16.1 Hz), 6.87 (1H, d, J = 16.1 Hz), 7.45 (1H, s), 7.52 (1H, s), 7.82 (1H, s), 10.00 (1H, s). | Ref. Ex. 77 |
| 805 | | 1H-NMR (CDCl3) δ: 1.57-1.80 (4H, m), 2.15-2.30 (4H, m), 6.00 (1H, brs), 6.39 (1H, d, J = 16.1 Hz), 6.85 (1H, d, J = 16.1 Hz), 7.61 (1H, s), 7.65 (1H, s), 7.78 (1H, s), 9.96 (1H, s). | Ref. Ex. 77 |
| 806 | | 1H-NMR (CDCl3) δ: 7.14 (1H, d, J = 16.5 Hz), 7.23 (1H, d, J =16.5 Hz), 7.52 (1H, t, J = 7.8 Hz), 7.57 (1H, d, J = 7.8 Hz), 7.69 (1H, d, J = 7.8 Hz), 7.77 (1H, s), 7.91 (2H, s), 7.95 (1H, s), 9.99 (1H, s). | Ref. Ex. 77 |
| 807 | | 1H-NMR (CDCl3) δ: 2.35 (3H, s), 7.03-7.11 (4H, m), 7.47-7.52 (3H, m), 9.81 (1H, s). | Ref. Ex. 77 |
| 808 | | 1H-NMR (CDCl3) δ: 1.47 (3H, t, J = 7.0 Hz), 4.14 (2H, q, J = 7.0 Hz), 7.23 (2H, s), 7.31-7.32 (1H, m), 7.34-7.35 (1H, m), 7.64 (1H, s), 7.78 (1H, s), 7.93 (2H, s), 10.00 (1H, s). | Ref. Ex. 77 |
| 809 | | 1H-NMR (CDCl3) δ: 6.92-6.95 (1H, m), 7.04-7.07 (2H, m), 7.18 (2H, s), 7.98 (1H, s), 8.05 (1H, s), 8.19 (1H, s), 10.11 (1H, s). | Ref. Ex. 77 |

TABLE 2-continued

| Ref. Ex. No | STR | 1H-NMR | ref. |
|---|---|---|---|
| 810 | | 1H-NMR (CDCl3) δ: 0.57-0.61 (2H, m), 0.89-0.93 (2H, m), 1.59-1.64 (1H, m), 5.90 (1H, dd, J = 9.0, 15.3 Hz), 6.54 (1H, d, J = 15.3 Hz), 7.75 (1H, s), 7.91 (1H, s), 7.96 (1H, s), 10.04 (1H, s). | Ref. Ex. 77 |
| 811 | | 1H-NMR (CDCl3) δ: 7.25 (1H, d, J = 16.3 Hz), 7.31 (1H, d, J = 16.3 Hz), 7.66 (4H, s), 8.00 (1H, s), 8.05 (1H, s), 8.22 (1H, s), 10.11 (1H, s). | Ref. Ex. 77 |
| 812 | | 1H-NMR (CDCl3) δ: 2.70 (3H, s), 3.00-3.15 (4H, m), 4.56 (2H, d, J = 0.5 Hz), 4.63 (2H, s), 7.14 (1H, s), 7.31 (2H, d, J = 8.0 Hz), 7.30-7.59 (5H, m), 7.53 (2H, d, J = 8.0 Hz). | Ref. Ex. 33 |
| 813 | | 1H-NMR (CDCl3) δ: 2.69 (3H, s), 3.03-3.09 (2H, m), 3.17-3.22 (2H m), 4.57 (2H, s), 4.64 (2H, s), 7.15 (1H, brs), 7.32-7.38 (5H, m), 7.67 (2H, brs), 7.72 (1H, brs). | Ref. Ex. 33 |
| 814 | | 1H-NMR (CDCl3) δ: 2.80 (3H, s), 3.37 (1H, brs), 4.79 (2H, s), 7.15 (1H, d, J = 16.0 Hz), 7.21 (1H, brs), 7.65-7.73 (4H, m), 7.34 (1H, d, J = 16.0 Hz). | Ref. Ex. 750 |
| 815 | | 1H-NMR (CDCl3) δ: 2.77 (3H, s), 3.45 (1H, t, J = 5.0 Hz), 4.75 (2H, d, J = 5.0 Hz), 6.99 (1H, d, J =15.9 Hz), 7.09-7.14 (3H, m), 7.58-7.63 (2H, m), 7.65 (1H, d, J = 15.9 Hz). | Ref. Ex. 750 |

TABLE 2-continued

| Ref. Ex. No | STR | 1H-NMR | ref. |
|---|---|---|---|
| 816 | | 1H-NMR (CDCl3) δ: 2.88 (3H, s), 7.22 (1H, d, J = 16.1 Hz), 7.66-7.74 (5H, m), 7.96 (1H, d, J = 18.1 Hz), 10.04 (1H, s). | Ref. Ex. 159 |
| 817 | | 1H-NMR (CDCl3) δ: 7.05-7.20 (2H, m), 7.27-7.38 (3H, m), 7.52 (1H, s), 7.72-7.76 (2H, m), 7.89 (1H, s), 10.01 (1H, s). | Ref. Ex. 91 |
| 818 | | 1H-NMR (CDCl3) δ: 7.12 (1H, d, J = 16.3 Hz), 7.17 (1H, d, J = 16.3 Hz), 7.29-7.35 (2H, m), 7.40 (1H, d, J = 7.4 Hz), 7.54 (1H, s), 7.57 (1H, s), 7.63 (1H, s), 7.95 (1H, s), 10.04 (1H, s). | Ref. Ex. 91 |
| 819 | | 1H-NMR (CDCl3) δ: 5.32 (2H, s), 7.42-7.45 (2H, m), 7.67 (1H, s), 7.75 (1H, d, J = 8.1 Hz), 7.87 (1H, d, J = 8.1 Hz), 8.03 (1H, s), 9.93 (1H, s). | Ref. Ex. 82 |
| 820 | | 1H-NMR (CDCl3) δ: 5.24 (2H, s), 7.27-7.32 (1H, m), 7.38-7.39 (2H, m), 7.44 (1H, dd, J = 2.7, 8.8 Hz), 7.64 (1H, s), 7.67-7.70 (1H, m), 9.91 (1H, s). | Ref. Ex. 82 |

| Ref. Ex. No | STR | 1H-NMR | ref. |
|---|---|---|---|
| 821 | | 1H-NMR (CDCl3) δ: 0.36-0.40 (2H, m), 0.66-0.70 (2H, m), 1.26-1.31 (1H, m), 3.87 (2H, d, J = 7.2 Hz), 5.31 (2H, s), 6.83-6.84 (1H, m), 7.07-7.10 (2H, m), 7.73 (1H, d, J = 8.3 Hz), 7.85 (1H, d, J = 8.3 Hz), 8.07 (1H, s), 9.92 (1H, s). | Ref. Ex. 82 |
| 822 | | 1H-NMR (CDCl3) δ: 0.35-0.38 (2H, m), 0.65-0.69 (2H, m), 1.24-1.33 (1H, m), 3.85 (2H, d, J = 7.1 Hz), 5.14 (2H, s), 6.80-6.81 (1H, m), 7.04-7.05 (1H, m), 7.08-7.09 (1H, m), 7.46-7.65 (3H, m), 7.71 (1H, s), 9.90 (1H, s). | Ref. Ex. 82 |
| 823 | | 1H-NMR (CDCl3) δ: 2.86 (3H, s), 7.04-7.16 (3H, m), 7.57-7.63 (2H, m), 7.65 (1H, s), 7.90 (1H, d, J = 16.1 Hz), 10.03 (1H, s). | Ref. Ex. 159 |
| 824 | | 1H-NMR (CDCl3) δ: 7.03-7.21 (4H, m), 7.48-7.56 (3H, m), 7.73-7.73 (2H, m), 8.02 (1H, s), 10.06 (1H, s). | Ref. Ex. 91 |
| 826 | | 1H-NMR (CDCl3) δ: 7.13 (2H, s), 7.29-7.39 (3H, m), 7.56 (1H, t, J = 7.6 Hz), 7.74-7.83 (2H, m), 803 (1H, s), 10.06 (1H, s). | Ref. Ex. 825 |
| 827 | | 1H-NMR (CDCl3) δ: 7.05 (1H, d, J = 16.4 Hz), 7.17 (1H, d, J = 16.4 Hz), 7.35-7.38 (2H, m), 7.45-7.47 (2H, m), 7.71-7.74 (2H, m), 7.68 (1H, s), 10.00 (1H, s). | Ref. Ex. 825 |

TABLE 2-continued

| Ref. Ex. No | STR | 1H-NMR | ref. |
|---|---|---|---|
| 828 | | 1H-NMR (CDCl3) δ: 7.21 (1H, d, J = 18.1 Hz), 7.53-7.67 (3H, m), 7.81-7.87 (3H, m), 8.03 (2H, d, J = 5.4 Hz), 10.08 (1H, s). | Ref. Ex. 825 |
| 829 | | 1H-NMR (CDCl3) δ: 5.44 (1H, d, J = 10.9 Hz), 5.37 (1H, d, J = 17.5 Hz), 6.72 (1H, dd, J = 10.9, 17.5 Hz), 7.63 (1H, s), 7.69 (1H, s), 7.74 (1H, s), 9.98 (1H, s). | Ref. Ex. 77 |
| 830 | | 1H-NMR (CDCl3) δ: 5.47 (1H, d, J = 10.9 Hz), 5.90 (1H, d, J = 17.6 Hz), 6.76 (1H, dd, J = 10.9, 17.6 Hz), 7.48 (1H, s), 7.61 (1H, s), 7.85 (1H, s), 10.02 (1H, s). | Ref. Ex. 77 |
| 832 | | 1H-NMR (CDCl3) δ: 4.73 (2H, d, J = 0.5 Hz), 4.76 (2H, s), 7.31-7.45 (5H, m), 7.99-8.00 (1H, m), 8.02 (1H, brs), 8.58 (2H, s), 9.23 (1H, d, J = 1.3 Hz). | Ref. Ex. 91 |
| 833 | | 1H-NMR (CDCl3) δ: 4.72 (2H, s), 4.73 (2H, s), 7.32-7.43 (5H, m), 7.76 (1H, d, J = 5.0 Hz), 8.88 (1H, d, J = 5.0 Hz). | Ref. Ex. 742 |
| 834 | | 1H-NMR (CDCl3) δ: 3.13 (1H, t, J = 5.2 Hz), 4.91 (2H, dd, J = 0.6, 5.2 Hz), 7.88-7.89 (1H, m), 8.03-8.04 (1H, m), 8.59-8.60 (2H, m), 9.28 (1H, d, J = 1.3 Hz), | Ref. Ex. 750 |
| 835 | | 1H-NMR (CDCl3) δ: 2.94 (1H, t, J = 5.2 Hz), 4.90 (2H, d, J = 5.2 Hz), 7.63 (1H, d, J = 5.2 Hz), 8.89 (1H, d, J = 5.2 Hz). | Ref. Ex. 750 |

TABLE 2-continued

| Ref. Ex. No | STR | 1H-NMR | ref. |
|---|---|---|---|
| 836 | | 1H-NMR (CDCl3) δ: 7.10 (1H, d, J = 16.4 Hz), 7.17 (1H, s), 7.19 (1H, d, J = 1.0 Hz), 7.37 (1H, s), 7.40-7.48 (2H, m), 7.74-7.76 (2H, m), 7.90 (1H, s), 10.01 (1H, s). | Ref. Ex. 825 |
| 837 | | 1H-NMR (CDCl3) δ: 7.04 (1H, d, J = 17.2 Hz), 7.17-7.25 (3H, m), 7.55 (2H, d, J = 8.6 Hz), 7.73-7.74 (2H, m), 7.89 (1H, s), 10.00 (1H, s). | Ref. Ex. 825 |
| 838 | | 1H-NMR (CDCl3) δ: 6.99-7.21 (4H, m), 7.27-7.37 (2H, m), 7.73-7.89 (2H, m), 7.89 (1H, s), 10.01 (1H, s). | Ref. Ex. 75 |
| 839 | | 1H-NMR (CDCl3) δ: 7.00-7.22 (4H, m), 7.49-7.60 (4H, m), 7.94 (1H, s), 10.04 (1H, s). | Ref. Ex. 91 |
| 840 | | 1H-NMR (CDCl3) δ: 1.47 (3H, t, J = 7.0 Hz), 4.14 (2H, q, J = 7.0 Hz), 7.18-7.23 (2H, m), 7.30-7.32 (2H, m), 7.48-7.57 (2H, m), 7.63 (1H, s), 7.69 (1H, d, J = 7.7 Hz), 7.77 (1H, s), 9.89 (1H, s). | Ref. Ex. 77 |

TABLE 2-continued
| Ref. Ex. No | STR | 1H-NMR | ref. |
|---|---|---|---|
| 841 | 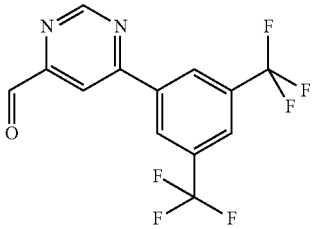 | 1H-NMR (CDCl3) δ 8.08 (1H, brs), 8.32 (1H, d, J = 1.4 Hz), 8.66 (2H, brs), 9.57 (1H, d, J = 1.4 Hz), 10.15 (1H, s). | Ref. Ex. 159 |
| 842 | 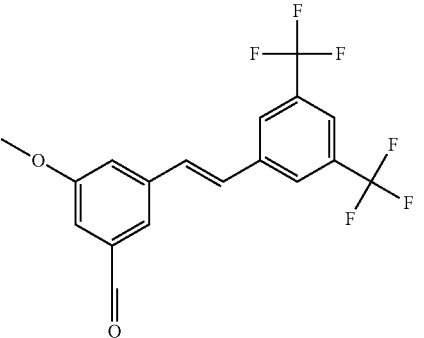 | 1H-NMR (CDCl3) δ: 3.92 (3H, s), 7.22-7.27 (2H, m), 7.31-7.32 (1H, m), 7.36-7.37 (1H, m), 7.66-7.67 (1H, m), 7.78 (1H, s), 7.94 (2H, s), 10.02 (1H, s). | Ref. Ex. 77 |
| 843 | 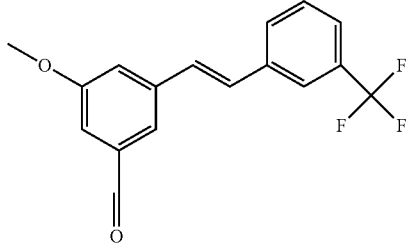 | 1H-NMR (CDCl3) δ: 3.91 (3H, s), 7.14-7.23 (2H, m), 7.29-7.30 (1H, m), 7.32-7.33 (1H, m), 7.48-7.53 (2H, m), 7.64 (1H, s), 7.68 (1H, d, J = 7.4 Hz), 7.77 (1H, s), 10.01 (1H, s). | Ref. Ex. 77 |
| 844 | 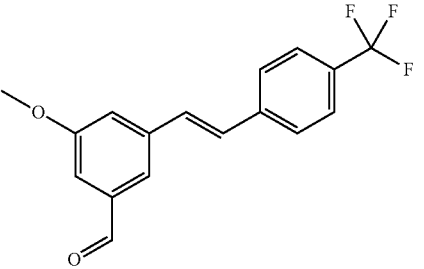 | 1H-NMR (CDCl3) δ: 3.91 (3H, s), 7.15-7.23 (2H, m), 7.29-7.30 (1H, m), 7.33-7.34 (1H, m), 7.61-7.64 (5H, m), 10.01 (1H, s). | Ref. Ex. 77 |
| 845 | 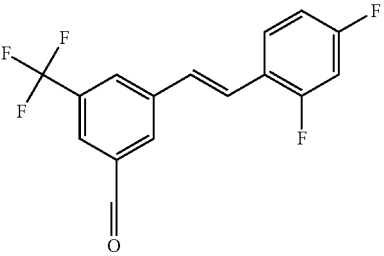 | 1H-NMR (CDCl3) δ: 6.85-6.96 (2H, m), 7.19 (1H, d, J = 16.6 Hz), 7.34 (1H, d, J = 16.6 Hz), 7.56-7.62 (1H, m), 7.97 (1H, s), 8.03 (1H, s), 8.19 (1H, s), 10.11 (1H, s). | Ref. Ex. 77 |
| 846 | 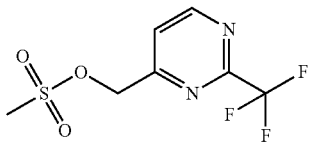 | 1H-NMR (C0Cl3) δ: 7.21 (1H, t, J = 9.1 Hz), 7.27-7.38 (2H, m), 7.50-7.59 (2H, m), 7.79-7.91 (3H, m), 8.07 (1H, s), 10.07 (1H, s). | Ref. Ex. 103 |

TABLE 2-continued
| Ref. Ex. No | STR | 1H-NMR | ref. |
|---|---|---|---|
| 847 |  | 1H-NMR (CDCl3) δ: 7.13 (1H, d, J = 16.3 Hz), 7.21 (1H, d, J = 16.3 Hz), 7.39-7.46 (4H, m), 7.59 (1H, s), 7.63 (1H, s), 7.96 (1H, s), 10.05 (1H, s). | Ref. Ex. 825 |
| 848 | 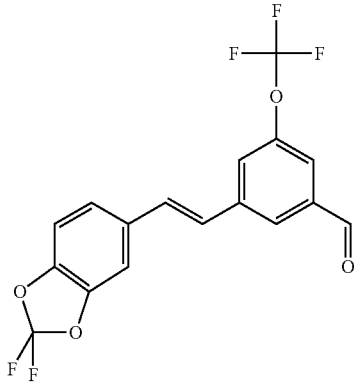 | 1H-NMR (CDCl3) δ: 7.01 (1H, d, J = 16.3 Hz), 7.07 (1H, d, J = 8.2 Hz), 7.18 (1H, d, J = 16.3 Hz), 7.20-7.29 (2H, m), 7.56 (1H, s), 7.62 (1H, s), 7.94 (1H, s), 10.04 (1H, s). | Ref. Ex. 825 |
| 849 | 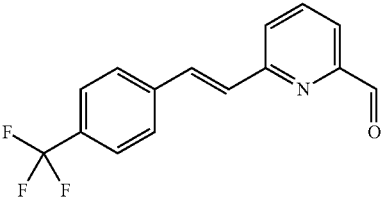 | 1H-NMR (CDCl3) δ: 7.31 (1H, d, J = 16.1 Hz), 7.61-7.91 (8H, m), 10.13 (1H, s). | Ref. Ex. 75 |
| 850 | 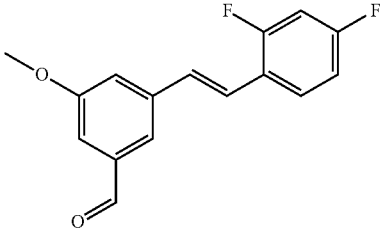 | 1H-NMR (CDCl3) δ: 3.91 (3H, s), 6.84-6.94 (2H, m), 7.11 (1H, d, J = 16.4 Hz), 7.24-7.32 (1H, m), 7.55-7.61 (1H, m), 7.63 (1H, s), 10.01 (1H, s). | Ref. Ex. 77 |
| 851 | 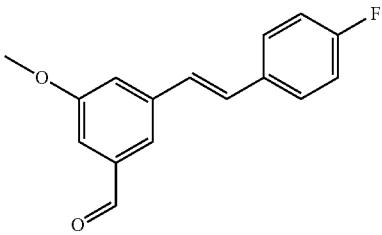 | 1H-NMR (CDCl3) δ: 3.90 (3H, s), 7.02 (1H, d, J = 16.3 Hz), 7.05-7.09 (2H, m), 7.15 (1H, d, J = 16.3 Hz), 7.26-7.30 (2H, m), 7.48-7.51 (2H, m), 7.61 (1H, s), 10.00 (1H, s). | Ref. Ex. 91 |

| Ref. Ex. No | STR | 1H-NMR | ref. |
|---|---|---|---|
| 852 | | 1H-NMR (CDCl3) δ: 7.06-7.12 (3H, m), 7.24 (1H, d, J = 15.5 Hz), 7.51-7.54 (2H, m), 7.96 (1H, s), 8.00 (1H, s), 8.17 (1H, s), 10.10 (1H, s). | Ref. Ex. 91 |
| 853 | | 1H-NMR (CDCl3) δ: 7.21 (1H, t, J = 9.1 Hz), 7.27-7.38 (2H, m), 7.50-7.59 (2H, m), 7.79-7.91 (3H, m), 8.07 (1H, s), 10.07 (1H, s). | Ref. Ex. 825 |
| 854 | | 1H-NMR (CDCl3) δ: 7.14-7.23 (2H, m), 7.51 (1H, d, J = 8.3 Hz), 7.56 (1H, t, J = 7.4 Hz), 7.62 (1H, dd, J = 2.1, 8.3 Hz), 7.75-7.82 (3H, m), 8.04-8.05 (1H, m), 10.06 (1H, s). | Ref. Ex. 825 |
| 855 | | 1H-NMR (CDCl3) δ: 7.10-7.24 (3H, m), 7.56 (1H, t, J = 7.6 Hz), 7.67-7.71 (1H, m), 7.75-7.82 (3H, m), 8.03 (1H, s), 10.06 (1H, s). | Ref. Ex. 825 |
| 856 | | 1H-NMR (CDCl3) δ: 7.25-7.29 (2H, m), 7.37 (1H, d, J = 16.6 Hz), 7.52-7.59 (2H, m), 7.79-7.84 (3H, m), 8.04 (1H, s), 10.07 (1H, s). | Ref. Ex. 825 |
| 857 | | 1H-NMR (CDCl3) δ: 2.03-2.14 (2H, m), 2.24-2.41 (2H, m), 4.08 (2H, t, J = 6.0 Hz), 7.16 (1H, dd, J = 2.0, 2.4 Hz), 7.27 (1H, dd, J - 1.3, 2.4 Hz), 7.45 (1H, dd, J= 1.3, 1.8 Hz), 9.92 (1H, s). | Ref. Ex. 82 |

TABLE 2-continued
| Ref. Ex. No | STR | 1H-NMR | ref. |
|---|---|---|---|
| 858 | 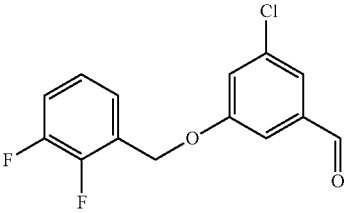 | 1H-NMR (CDCl3) δ: 5.19 (2H, s), 7.08-7.26 (4H, m), 7.38 (1H, dd, J = 1.3, 2.4 Hz), 7.49 (1H, dd, J = 1.3, 1.7 Hz), 9.93 (1H, s). | Ref. Ex. 82 |
| 859 | 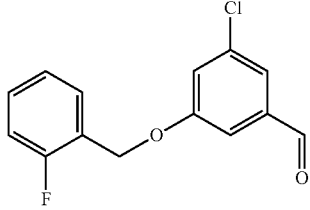 | 1H-NMR (CDCB) δ: 5.18 (2H, s), 7.08-7.22 (2H, m), 7.23-7.26 (1H, m), 7.31-7.41 (2H, m), 7.44-7.52 (2H, m), 9.92 (1H, s). | Ref. Ex. 82 |
| 860 | 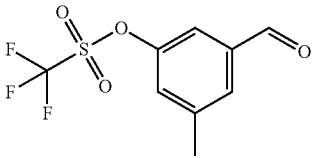 | 1H-NMR (CDCl3) δ: 2.51 (3H, s), 7.35 (1H, s), 7.59 (1H, s), 7.73 (1H, s), 9.99 (1H, s). | Ref. Ex. 125 |
| 861 | 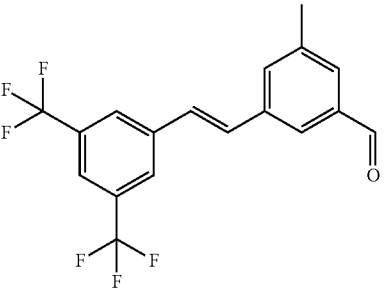 | 1H-NMR (CDCl3) δ: 2.49 (3H, s), 7.25 (2H, s), 7.61 (1H, s), 7.65 (1H, s), 7.78 (1H, s), 7.87 (1H, s), 7.94 (2H, s), 10.03 (1H, s). | Ref. Ex. 77 |
| 862 | 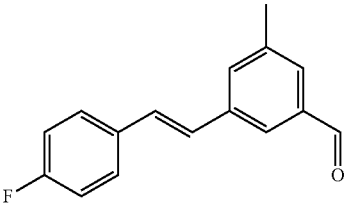 | 1H-NMR (CDCl3) δ: 2.46 (3H, s), 6.99-7.11 (3H, m), 7.16 (1H, d, J = 16.6 Hz), 7.47-7.52 (2H, m), 7.56 (1H, s), 7.58 (1H, s), 7.62 (1H, s), 10.02 (1H, s). | Ref. Ex. 91 |
| 863 | 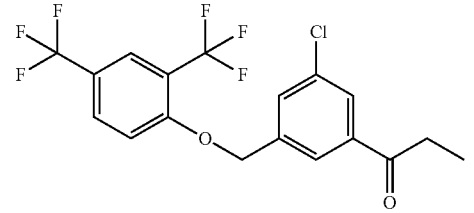 | 1H-NMR (CDCl3) δ: 3.94 (3H, s), 5.36 (2H, s), 7.10 (1H, d, J = 8.8 Hz), 7.64 (1H, s), 7.77 (1H, d, J = 8.8 Hz), 7.88 (1H, s), 7.96-8.00 (2H, m). | Ref. Ex. 82 |
| 864 | 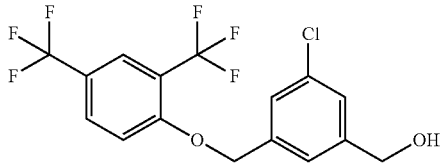 | 1H-NMR (CDCl3) δ: 4.68-4.71 (3H, m), 5.22 (2H, m), 7.09 (1H, d, J = 8.7 Hz), 7.26-7.35 (3H, m), 7.75 (1H, d, J = 8.5 Hz), 7.87 (1H, s). | Ref. Ex. 76 |

TABLE 2-continued

| Ref. Ex. No | STR | 1H-NMR | ref. |
|---|---|---|---|
| 865 | | 1H-NMR (CDCl3) δ: 4.64-4.80 (3H, m), 5.19 (2H, m), 7.26-7.37 (5H, m), 7.74 (1H, d, J = 8.1 Hz). | Ref. Ex. 113, Ref. Ex. 76 |
| 866 | | 1H-NMR (CDCl3) δ: 5.29 (2H, s), 7.12 (1H, d, J = 8.6 Hz), 7.70-7.72 (1H, m), 7.78-7.81 (1H, m), 7.63-7.85 (2H, m), 7.89 (1H, s), 10.00 (1H, s). | Ref. Ex. 48 |
| 867 | | 1H-NMR (CDCl3) δ: 5.27 (2H, s), 7.27 (1H, s), 7.37 (1H, d, J = 8.1 Hz), 7.70-7.72 (1H, m), 7.77 (1H, d, J = 8.1 Hz), 7.85 (2H, s), 10.00 (1H, s). | Ref. Ex. 48 |
| 868 | | 1H-NMR (CDCl3) δ: 2.46 (3H, s), 7.11 (1H, d, J = 16.4 Hz), 7.20 (1H, d, J = 16.4 Hz), 7.26-7.32 (1H, m), 7.35-7.41 (2H, m), 7.51-7.55 (2H, m), 7.58 (2H, s), 7.63 (1H, s), 10.02 (1H, s). | Ref. Ex. 91 |
| 869 | | 1H-NMR (CDCl3) δ: 5.10 (2H, s), 6.60-6.78 (3H, m), 7.21-7.30 (1H, m), 7.65 (1H, s), 7.87 (1H, s), 7.96 (1H, s), 9.98 (1H, s). | Ref. Ex. 113, Ref. Ex. 130, Ref. Ex. 159 |
| 870 | | 1H-NMR (CDCl3) δ: 5.15 (2H, s), 7.14 (1H, dd, J = 2.5, 8.2 Hz), 7.21-7.30 (2H, m), 7.43 (1H, t, J = 8.0 Hz), 7.87 (1H, s), 7.88 (1H, s), 8.00 (1H, s), 9.99 (1H, s). | Ref. Ex. 113, Ref. Ex. 130, Ref. Ex. 159 |
| 871 | | 1H-NMR (CDCl3) δ: 7.12 (1H, d, J = 16.1 Hz), 7.40 (1H, t, J = 7.6 Hz), 7.51-7.62 (3H, m), 7.69 (1H, d, J = 7.8 Hz), 7.76-7.85 (3H, m), 8.01 (1H, s), 10.07 (1H, s). | Ref. Ex. 186 |
| 872 | | (CDCl3) δ: 7.05 (1H, d, J = 16.4 Hz), 7.10 (1H, d, J = 16.4 Hz), 7.11-7.26 (2H, m), 7.35 (1H, ddd, J = 2.1, 7.6, 11.5 Hz), 7.54 (1H, t, J = 7.6 Hz), 7.71-7.76 (1H, m), 7.76-7.82 (1H. m), 8.01 (1H, s), 10.06 (1H, s). | Ref. Ex. 188 |

TABLE 2-continued

| Ref. Ex. No | STR | 1H-NMR | ref. |
|---|---|---|---|
| 873 | | 1H-NMR (CDCl3) δ: 7.19 (1H, ddd, J = 0.8, 4.8, 7.5 Hz), 7.27 (1H, d, J = 16.1 Hz), 7.40 (1H, d, J = 7.8 Hz), 7.55 (1H, t, J = 7.6 Hz), 7.66-7.75 (2H, m), 7.79-7.85 (2H, m), 8.10 (1H, s), 8.61-8.65 (1H, m), 10.06 (1H, s). | Ref. Ex. 186 |
| 874 | | 1H-NMR (CDCl3) δ: 7.15-7.25 (2H, m), 7.49-7.60 (3H, m), 7.73-7.84 (4H, m), 8.05 (1H, s), 10.07 (1H, s). | Ref. Ex. 17, Ref. Ex. 151 |
| 875 | | 1H-NMR (CDCl3) δ: 5.98 (2H, s), 6.81 (1H, d, J = 8.1 Hz), 6.95 (1H, dd, J = 1.6, 8.1 Hz), 6.98 (1H, d, J = 16.3 Hz), 7.07 (1H, d, J = 1.6 Hz), 7.11 (1H, d, J = 16.3 Hz), 7.50 (1H, t, J = 7.6 Hz), 7.69-7.76 (2H, m), 7.98 (1H, s), 10.04 (1H, s). | Ref. Ex. 17, Ref. Ex. 229 |
| 876 | | 1H-NMR (CDCl3) δ: 6.91-7.22 (5H, m)r 7.71-7.74 (2H( m), 7.87 {1H, s), 10.00 (1H, s). | Ref. Ex. 825 |
| 877 | | 1H-NMR (CDCl3) δ: 7.15-7.26 (3H, m), 7.39-7.41 (1H, m), 7.55-7.59 (2H, m), 7.76-7.84 (2H, m), 8.05 (1H, s), 10.07 (1H, s). | Ref. Ex. 107, Ref. Ex. 112 |
| 878 | | 1H-NMR (CDCl3) δ: 5.33 (2H, s), 7.27-7.31 (1H, m), 7.48-7.56 (3H, m), 7.80 (1H, d, J = 5.1 Hz), 8.95 (1H, d, J = 5.1 Hz), 10.00 (1H, s). | Ref. Ex. 82 |
| 879 | | 1H-NMR (CDCl3) δ: 7.02-7.19 (3H, m), 7.32-7.43 (1H, m), 7.56-7.59 (1H, m), 7.71-7.75 (2H, m), 7.87 (1H, s), 10.00 (1H, s). | Ref. Ex. 825 |

TABLE 2-continued

| Ref. Ex. No | STR | 1H-NMR | ref. |
|---|---|---|---|
| 880 | | 1H-NMR (CDCl3) δ: 7.06 (1H, d, J = 16.3 Hz), 7.19 (1H, d, J = 16.3 Hz), 7.20-7.23 (1H, m), 7.67-7.77 (4H, m), 7.89 (1H, s), 10.01 (1H, s). | Ref. Ex. 825 |
| 881 | | 1H-NMR (CDCl3) δ: 6.61 (1H, t, J = 73.0 Hz), 6.99-7.24 (4H, m), 7.49-7.53 (4H, m), 7.86 (1H, s), 10.03 (1H, s). | Ref. Ex. 825 |
| 882 | | 1H-NMR (CDCl3) δ: 6.93-6.97 (1H, m), 7.03-7.09 (1H, m), 7.19 (1H, d, J = 16.5 Hz), 7.28-7.33 2H, m), 7.56 (1H, t, J = 7.5 Hz), 7.77-7.82 (2H, m), 8.04 (1H, s), 10.07 (1H, s). | Ref. Ex. 825 |
| 883 | | 1H-NMR (CDCl3) δ: 6.94-7.00 (1H, m), 7.12 (1H, d, J = 16.5 Hz), 7.22-7.26 (1H, m), 7.39-7.45 (1H, m), 7.56 (1H, t, J = 7.6 Hz), 7.76-7.82 (2H, m), 8.03 (1H, s), 10.06 (1H, s). | Ref. Ex. 825 |
| 884 | | 1H-NMR (CDCl3) δ: 6.54 (1H, t, J = 73.7 Hz), 7.01-7.24 (4H, m), 7.52-7.54 (2H, m), 7.72-7.76 (2H, m), 7.88 (1H, s), 10.00 (1H, s). | Ref. Ex. 825 |

| Ref. Ex. No | STR | 1H-NMR | ref. |
|---|---|---|---|
| 885 | 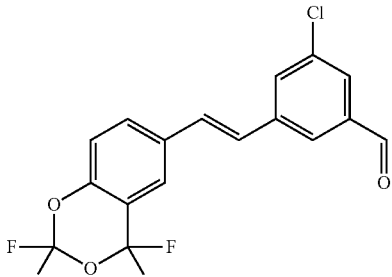 | 1H-NMR (CDCl3) δ: 7.06-7.22 (3H, m), 7.61-7.77 (4H, m), 7.80 (1H, s), 10.00 (1H, s). | Ref. Ex. 825 |
| 886 | 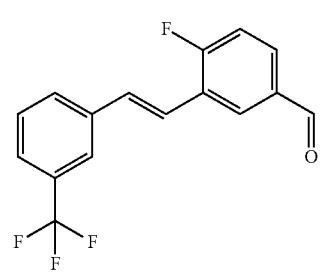 | 1H-NMR (CDCl3) δ: 7.24-7.27 (3H, m), 7.51-7.62 (2H, m), 7.71-7.82 (3H, m), 8.16-8.20 (1H, m), 10.01 (1H, s). | Ref. Ex. 77 |
| 887 | 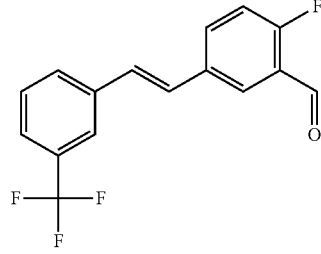 | 1H-NMR (CDCl3) δ: 7.14-7.24 (3H, m), 7.49-7.53 (2H, m), 7.66-7.77 (3H, m), 8.01-8.04 (1H, m), 10.40 (1H, s). | Ref. Ex. 825 |
| 888 | 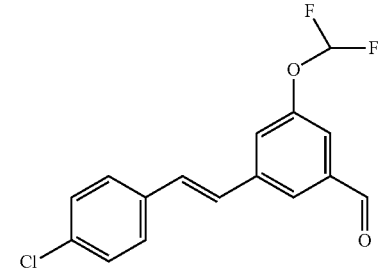 | 1H-NMR (CDCl3) δ: 6.61 (1H, t, J = 72.9 Hz), 7.08 (1H, d, J = 16.3 Hz), 7.17 (1H, d, J = 16.3 Hz), 7.35-7.52 (6H, m), 7.87 (1H, s), 10.03 (1H, s). | Ref. Ex. 825 |
| 889 | 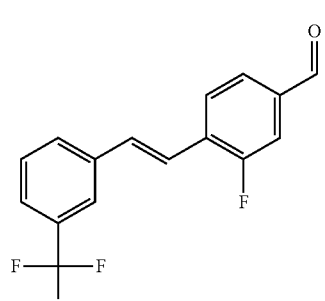 | 1H-NMR (CDCl3) δ: 7.35 (2H, s), 7.52-7.80 (7H, m), 9.98 (1H, s). | Ref. Ex. 825 |

TABLE 2-continued

| Ref. Ex. No | STR | 1H-NMR | ref. |
|---|---|---|---|
| 890 | | 1H-NMR (CDCl3) δ: 7.15-7.22 (2H, m), 7.44-7.54 (3H, m), 7.57 (1H, d, J = 7.6 Hz), 7.70 (1H, d, J = 7.6 Hz), 7.78 (1H, s), 7.83 (1H, s), 10.03 (1H, d, J = 1.7 Hz). | Ref. Ex. 75 |
| 891 | | 1H-NMR (CDCl3) δ: 3.94 (3H, s), 5.30 (2H, s), 7.18-7.45 (4H, m), 8.28 (1H, s). | Ref. Ex. 82 |
| 892 | | 1H-NMR (CDCl3) δ: 6.90-7.24 (1H, m), 7.28-7.34 (2H, m), 7.65 (4H, s), 7.79-7.85 (1H, m), 8.18-8.21 (1H, m), 10.02 (1H, s). | Ref. Ex. 91 |
| 893 | | 1H-NMR (CDCl3) δ: 7.06-7.27 (5H, m), 7.51-7.56 (2H, m), 7.75-7.77 (1H, m), 8.14-8.17 (1H, m), 10.00 (1H, s). | Ref. Ex. 825 |
| 894 | | 1H-NMR (CDCl3) δ: 7.29-7.39 (3H, m), 7.81-7.88 (2H, m), 7.97 (2H, s), 8.17-8.20 (1H, m), 10.02 (1H, s). | Ref. Ex. 77 |
| 895 | | 1H-NMR (CDCl3) δ: 4.64 (2H, s), 5.17 (2H, s), 7.21-7.29 (3H, m), 7.40-7.44 (1H, m), 7.64 (1H, s). | Ref. Ex. 19 |
| 896 | | 1H-NMR (CDCl3) δ: 5.25 (2H, s), 7.18-7.44 (4H, m), 8.31 (1.s), 9.97 (1H, s). | Ref. Ex. 159 |

TABLE 2-continued
| Ref. Ex. No | STR | 1H-NMR | ref. |
|---|---|---|---|
| 897 | 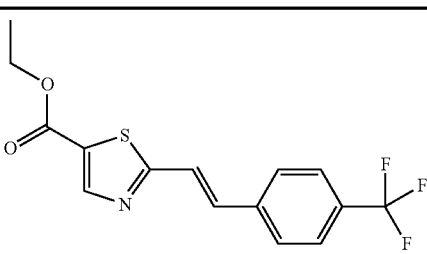 | 1H-NMR (CDCl3) δ: 1.40 (3H, t, J = 7.1 Hz), 4.39 (2H, q, J = 7.1 Hz), 7.33 (1H, d, J = 16.1 Hz), 7.59 (1H, d, J = 16.1 Hz), 7.66 (4H, s), 8.40 (1H, s). | Ref. Ex. 112 |
| 898 | 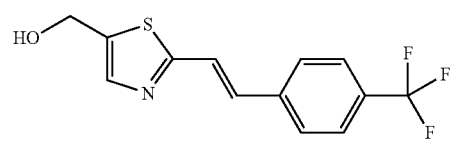 | 1H-NMR (CDCl3) δ: 2.05 (1H, brs), 4.90 (2H, d, J = 5.8 Hz), 7.31 (1H, d, J = 16.2 Hz), 7,41 (1H, d, J = 16.2 Hz), 7.63 (4H, s), 7.69 (1H, s). | Ref. Ex. 76 |
| 899 | 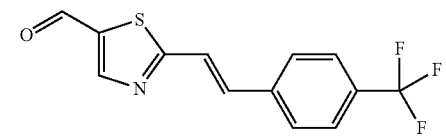 | 1H-NMR (CDCl3) δ: 7.38 (1H, d, J = 16.1 Hz), 7.68 (1H, d, J = 16.2 Hz), 7.68 (4H, s), 8.42 (1H, s), 10.05 (1H, s). | Ref. Ex. 159 |
| 900 | 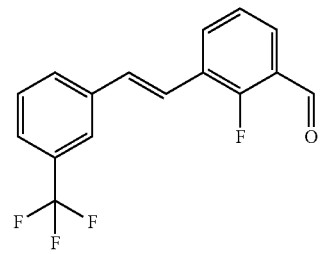 | 1H-NMR (CDCl3) δ: 7.28-7.56 (4H, m), 7.76-7.90 (4H, m), 7,96 (1H, s), 10.45 (1H, s). | Ref. Ex. 825 |
| 901 | 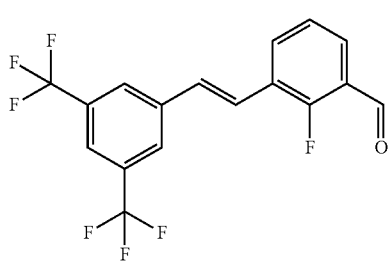 | 1H-NMR (CDCl3) δ: 7.26-7.44 (2H, m), 7.76-7.90 (4H, m), 7,96 (2H, s), 10.45 (1H, s). | Ref. Ex. 75 |
| 902 | 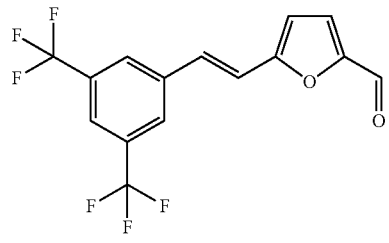 | 1H-NMR (CDCl3) δ: 6.65 (1H, d, J = 3.6Hz), 7.08 (1H, d, J = 16.3 Hz), 7.29 (1H, d, J = 3.6 Hz), 7.43 (1H, d, J = 16.3 Hz), 7.80-7.92 (3H, m), 9.66 (1H, s). | Ref. Ex. 75 |
| 903 | 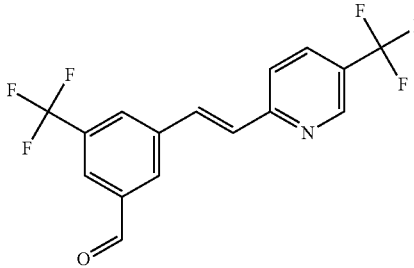 | 1H-NMR (CDCl3) δ: 7.35 (1H, d, J = 16.0 Hz), 7.51 (1H, d, J = 8.2 Hz), 7.88 (1H, d, J = 16.0 Hz), 7.94-7.97 (1H, m), 8.08-8.09 (2H, m), 6.28 (1H, s), 8.69 (1H, s), 10.12 (1H, s). | Ref. Ex. 825 |

TABLE 2-continued

| Ref. Ex. No | STR | 1H-NMR | ref. |
|---|---|---|---|
| 904 | | 1H-NMR (CDCl3) δ: 7.30 (1H, d, J = 16.0 Hz), 7.43-7.45 (1H, m), 7.61 (1H, s), 7.86 (1H, d, J = 16.0 Hz), 8.06-8.08 (2H, m), 8.26 (1H, s), 8.82 (1H, d, J = 5.0 Hz), 10.11 (1H, s). | Ref. Ex. 825 |
| 905 | | 1H-NMR (CDCl3) δ: 7.28 (1H, d, J = 16.0 Hz), 7.48 (1H, d, J = 8.3 Hz), 7.76-7.81 (3H, m), 7.92-7.98 (2H, m), 8.87 (1H, s), 10.01 (1H, s). | Ref. Ex. 825 |
| 906 | | 1H-NMR (CDCl3) δ: 7.39 (1H, d, J = 16.0 Hz), 7.41-7.43 (1H, m), 7.58 (1H, s), 7.73-7.80 (3H, m), 7.95-7.99 (1H, m), 8.80 (1H, d, J = 5.0 Hz), 10.09 (1H, s). | Ref. Ex. 825 |
| 907 | | 1H-NMR (CDCl3) δ: 7.06 (1H, d, J = 16.1 Hz), 7.28-7.31 (1H, m), 7.39-7.51 (2H, m), 7.57 (1H, t, J = 7.7 Hz), 7.75-7.84 (3H, m). 7.99-8.00 (1H, m), 10.07 (1H, s). | Ref. Ex. 825 |
| 908 | | 1H-NMR (CDCl3) δ: 7.05-7.15 (2H, m), 7.45-7.60 (3H, m), 7.67-7.72 (1H, m), 7.78-7.86 (2H, m), 8.01-8.02 (1H, m), 10.07 (1H, s). | Ref. Ex. 825 |

TABLE 2-continued

| Ref. Ex. No | STR | 1H-NMR | ref. |
|---|---|---|---|
| 909 | | 1H-NMR (CDCl3) δ: 7.26-7.45 (4H, m), 7.82-7.94 (2H, m), 7.96 (2H, s), 10.36 (1H, s). | Ref. Ex.75 |
| 910 | | 1H-NMR (CDCl3) δ: 6.61 (1H, d, J = 3.7 Hz), 7.03 (1H, d, J = 16.3 Hz), 7.28 (1H, d, J = 3.7 Hz), 7.43 (1H, d, J = 16.3 Hz), 7.62 (4H, m), 9.63 (1H, s). | Ref. Ex. 91 |
| 911 | | 1H-NMR (CDCl3) δ: 7.44-7.51 (2H, m), 8.13 (2H, s), 8.18 (1H, d, J = 16.0 Hz), 8.32 (1H, s), 9.01 (1H, d, J = 5.0 Hz), 10.12 (1H, s). | Ref. Ex. 825 |
| 912 | | 1H-NMR (CDCl3) δ: 7.55-7.61 (2H, m), 7.70 (1H, d, J = 8.5 Hz), 7.75-7.87 (3H, m), 8.10-8.16 (4H, m), 8.33-8.34 (1H, m), 10.15 (1H, s). | Ref. Ex. 825 |
| 913 | | 1H-NMR (CDCl3) δ: 1.81 (3H, s), 3.20 (3H. s), 3.96 (3H, s), 7.37 (1H, d, J = 8.2 Hz), 8.06 (1H, dd, J = 1.9, 8.1 Hz), 8.37 (1H, d, J = 1.9 Hz). | Ref. Ex. 12 |
| 914 | | 1H-NMR (CDCl3) δ: 2.07 (3H, s), 3.92 (3H, s), 7.61-7.68 (5H, m), 7.93 (1H, d, J = 1.7 Hz), 8.06-8.10 (1H, m), 8.40-8.50 (1H, br). | Ref. Ex. 112 |

TABLE 2-continued

| Ref. Ex. No | STR | 1H-NMR | ref. |
|---|---|---|---|
| 915 | | 1H-NMR (CDCl3) δ: 2.27 (3H, s), 3.94 (3H, s), 7.14-7.16 (2H, m), 7.52-7.76 (5H, m), 7.96-8.20 (3H, m). | Ref. Ex. 75 |
| 917 | | 1H-NMR (CDCl3) δ: 6.62 (1H, d, J = 3.7 Hz), 7.00 (1H, d, J = 16.3 Hz), 7.27 (1H, s), 7.28 (1H, d, J = 3.7 Hz), 7.35 (1H, s), 7.36 (1H, t, J = 16.3 Hz), 7.55 (1H, s), 9.64 (1H, s). | Ref. Ex. 825 |
| 918 | | 1H-NMR (CDCl3) δ: 6.55 (1H, d, J = 3.8 Hz), 7.83 (1H, d, J = 16.2 Hz), 7.07 (1H, d, J = 8.3 Hz), 7.19-7.29 (3H, m), 7.34 (1H, d, J = 16.2 Hz), 9.61 (1H, s). | Ref. Ex. 825 |
| 919 | | 1H-NMR (CDCl3) δ: 1.71 (1H, brs), 2.04 (3H, s), 4.72 (2H, d, J = 5.8 Hz), 6.90-6.95 (1H, br), 7.27-7.68 (6H, m), 8.14-8.16 (1H, m). | Ref. Ex. 76 |
| 920 | | 1H-NMR (CDCl3) δ: 2.26 (3H, s), 4.72 (2H, d, J = 5.6 Hz), 7.09-7.76 (10H, m). | Ref. Ex. 76 |
| 921 | | 1H-NMR (CDCl3) δ: 1.80 (3H, s), 3.03 (3H, s), 3.97 (3H, s), 7.37 (1H, d, J = 8.7 Hz), 7.50-7.67 (4H, m), 8.11-8.15 (2H, m). | Ref. Ex. 112 |

| Ref. Ex. No | STR | 1H-NMR | ref. |
|---|---|---|---|
| 922 |  | 1H-NMR (CDCl3) δ: 3.85 (3H, s), 6.55-5.63 (1H, m), 6.81-6.90 (2H, m), 7.04-7.19 (2H, m), 7.54-7.63 (2H, m), 7.95 (1H, s), 10.04 (1H, s). | Ref. Ex. 825 |
| 923 | 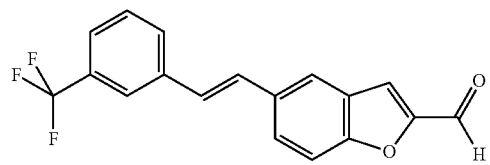 | 1H-NMR (CDCl) δ: 7.11-7.21 (2H, m), 7.45-7.77 (7H, m), 7.58 (1H, s), 9.89 (1H,s). | Ref. Ex. 77 |
| 925 | 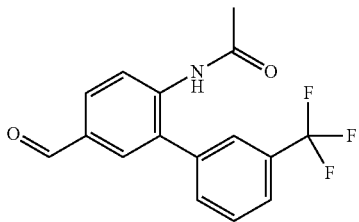 | 1H-NMR (CDCl3) δ: 2.08 (3H, s), 7.19 (1H, brs), 7.60-7.79 (5H, m), 7.93 (1H, dd, J = 1.9, 8.5 Hz), 8.59 (1H, d, J = 8.6 Hz), 9.98 (1H, s). | Ref. Ex. 159 |
| 926 | 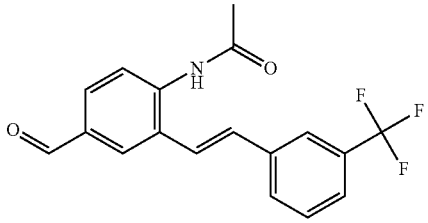 | 1H-NMR (CDCl3) δ: 2.28 (3H, s), 7.16 (2H, d, J = 4.3 Hz), 7.30-7.85 (6H, m), 8.03 (1H, s), 8.22-8.35 (1H, br), 9.98 (1H, s). | Ref. Ex. 159 |
| 927 | 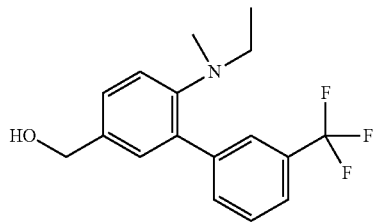 | 1H-NMR (CDCl3) δ: 0.86 (3H, t, J = 7.1 Hz), 2.56 (3H, s), 2.77 (2H, q, J = 7.1 Hz), 4.66 (2H, d, J = 5.8 Hz), 7.08 (1H, d, J = 6.2 Hz), 7.22-7.27 (2H, m), 7.43-7.61 (2H, m), 7 64-7.78 (1H, m), 7.87 (1H, s). | Ref. Ex. 76 |
| 928 | 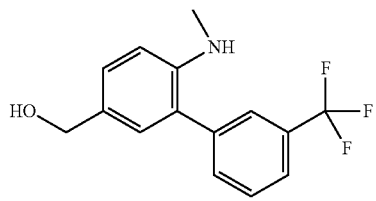 | 1H-NMR (CDCl3) δ: 1.49 (1H, t, J = 6.0 Hz), 2.81 (3H, s), 3.83 (1H, s), 4.61 (2H, d, J = 5.5 Hz), 6.70 (1H, d, J = 8.3 Hz), 7.10 (1H d, J = 2.1 Hz), 7.31 (1H, dd, J = 1.6, 7.8 Hz), 7.58-7.68 (4H, m). | Ref. Ex. 76 |

TABLE 2-continued
| Ref. Ex. No | STR | 1H-NMR | ref. |
|---|---|---|---|
| 929 | 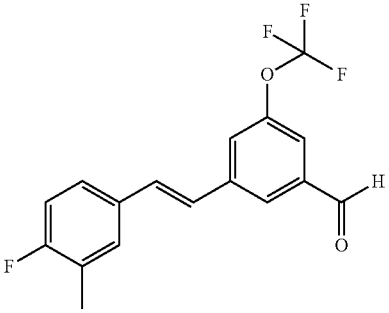 | 1H-NMR (CDCl3) δ: 2.32 (3H, s), 6.99-7.06 (2H, m), 7.16 (1H, d, J = 16.3 Hz), 7.31-7.38 (2H, m), 7.55-7.60 (2H, m), 7.93 (1H, s), 10.03 (1H, s). | Ref. Ex. 825 |
| 930 | 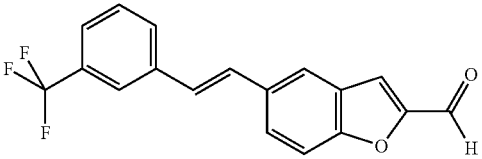 | 1H-NMR (CDCl3) δ: 7.59-7.81 (6H, m), 7.86 (1H, s), 7.96 (1H, s), 9.92 (1H, s). | Ref. Ex. 112 |
| 931 | 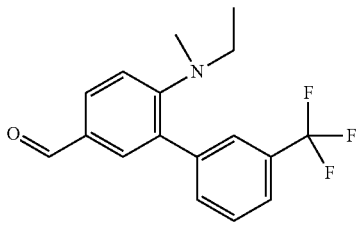 | 1H-NMR (CDCl3) δ: 0.94 (3H, t, J = 7.1 Hz), 2.68 (3H, s), 2.97 (2H, q, J = 7.1 Hz). 7.09 (1H, d, J = 8.6 Hz), 7.54-7.80 (6H, m), 9.87 (1H. s). | Ref. Ex. 48 |
| 932 | 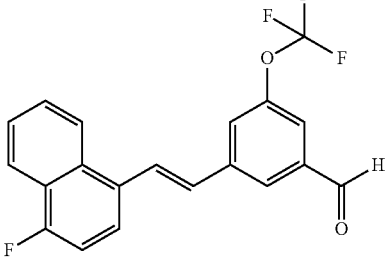 | 1H-NMR (CDCl3) δ: 7.11 (1H, d, J = 15.9 Hz), 7.16-7.26 (1H, m), 7.62-7.67 (5H, m), 7.94 (1H, d, J = 15.9 Hz), 8.03 (1H, s), 7.18-8.19 (2H, m), 10.08 (1H, s). | Ref. Ex. 825 |
| 933 | 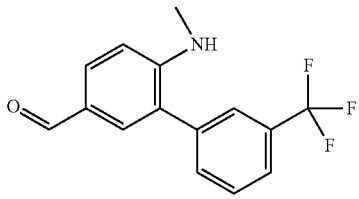 | 1H-NMR (CDCl3) δ: 2.91 (3H, d, J = 5.1 Hz), 4.45 (1H, brs), 6.74 (1H, d, J = 8.5 Hz), 7.59-7.69 (5H, m), 7.82 (1H, dd, J = 2.1, 8.6 Hz), 9.79 (1H, s). | Ref. Ex. 48 |
| 936 | 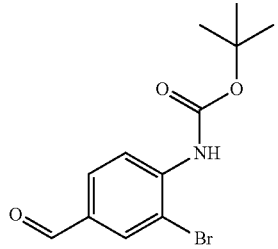 | 1H-NMR (CDCl3) δ: 1.55 (9H, s), 7.30 (1H, brs), 7.80 (1H, dd, J = 1.9, 8.6 Hz), 8.06 (1H, d, J = 1.9 Hz), 8.41 (1H, d, J = 8.8 Hz), 9.85 (1H, s). | Ref. Ex. 159 |

TABLE 2-continued

| Ref. Ex. No | STR | 1H-NMR | ref. |
|---|---|---|---|
| 937 | | 1H-NMR (CDCl3) δ: 1.56 (9H, s), 6.72 (1H, brs), 7.08-7.21 (2H, m), 7.54-7.84 (5H, m), 7.99 (1H, d, J = 2.0 Hz), 8.21 (1H, d, J = 8.6 Hz), 9.96 (1H, s), | Ref. Ex. 75 |
| 938 | | 1H-NMR (CDCl3) δ: 6.93 (1H, d, J = 3.7 Hz), 7.39 (1H, d, J = 3.7 Hz), 7.45-7.52 (2H, m), 7.91-7.94 (1H, m), 8.00 (1H, s), 8.28-8.31 (1H, m), 9.70 (1H, s). | Ref. Ex. 112 |
| 939 | | 1H-NMR (CDCl3) δ: 3.83 (3H, s), 6.51-6.62 (2H, m), 6.81-6.93 (3H, m), 7.26-7.27 (2H, m), 9.62 (1H, s). | Ref. Ex. 825 |
| 940 | | 1H-NMR (CDCl3) δ: 7.16 (2H, t, J = 8.6 Hz), 7.54-7.88 (5H, m), 8.39 (1H, s), 9.90 (1H, s). | Ref. Ex. 112 |
| 941 | | 1H-NMR (CDCl3) δ: 7.07 (1H, d, J = 16.3 Hz), 7.60 (1H, dd, J = 2.1, 8.4 Hz), 7.67 (1H, d, J = 8.4 Hz), 7.81 (1H, s), 7.84 (1H, d, J = 2.2 Hz), 7.96 (2H, m), 8.13 (1H, d, J = 16.3 Hz), 10.23 (1H, s). | Ref. Ex. 77 |
| 942 | | 1H-NMR (CDCl3) δ: 6.96 (1H, d, J = 8.3 Hz), 7.31 (1H, d, J = 16.4 Hz), 7.53 (1H, d, J = 16.4 Hz), 7.74-7.77 (2H, m), 7.86 (1H, s), 7.96 (2H, s), 8.12 (1H, d, J = 1.9 Hz), 9.93 (1H, s). | Ref. Ex. 77 |

TABLE 2-continued

| Ref. Ex. No | STR | 1H-NMR | ref. |
|---|---|---|---|
| 943 | | 1H-NMR (CDCl3) δ: 1.57 (9H, s), 3.26 (3H, s), 7.12-7.26 (2H, m), 7.30-7.74 (5H, m), 7.82 (1H, dd, J = 1.9, 8.1 Hz), 8.22 (1H, d, J = 1.9 Hz), 10.06 (1H, s). | Ref. Ex. 12 |
| 944 | | 1H-NMR (CDCl3) δ: 7.04-7.09 (2H, m), 7.21 (1H, d, J = 16.3 Hz), 7.72-7.78 (3H, m), 7.91 (2H, s), 9.96 (1H, s), 11.11 (1H, s). | Ref. Ex. 77 |
| 945 | | 1H-NMR (CDCl3) δ: 7.16 (1H, d, J = 16.3 Hz), 7.44 (1H, t, J = 7.9 Hz), 7.59 (1H, d, J = 16.3 Hz), 7.67 (1H, dd, J = 1.6, 7.9 Hz), 7.03 (1H, s), 7.90 (1H, dd, J = 1.4, 7.9 Hz), 7.96 (2H, s). | Ref. Ex. 77 |
| 946 | | 1H-NMR (CDCl3) δ: 7.15 (1H, d, J = 16.2 Hz), 7.45 (1H, t, J = 7.7 Hz), 7.79 (1H, d, J = 16.2 Hz), 7.62 (1H, s), 7.90-7.94 (2H, m), 7.97 (2H, s), 10.59 (1H, s). | Ref. Ex. 93 |
| 947 | | 1H-NMR (CDCl3) δ: 6.57 (1H, d, J = 3.7 Hz), 6.90-7.04 (2H, m), 7.19-7.38 (5H, m), 9.62 (1H, s). | Ref. Ex. 112 |
| 948 | | 1H-NMR (CDCl3) δ: 3.95 (3H, s), 6.56 (1H, d, J = 3.7 Hz), 6.80-6.97 (3H, m), 6.97-7.30 (2H, m), 9.61 (1H, s). | Ref. Ex. 825 |

TABLE 2-continued
| Ref. Ex. No | STR | 1H-NMR | ref. |
|---|---|---|---|
| 949 | 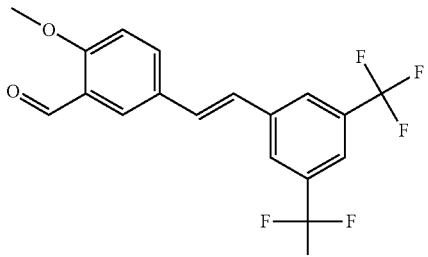 | 1H-NMR (CDCl3) δ: 3.99 (3H, s), 7.05 (1H, d, J = 8.7 Hz), 7.10 (1H, d, J = 16.4 Hz), 7.20 (1H, d, J = 16.4 Hz), 7.71-7.74 (2H, m), 7.90 (2H, s), 8.04 (1H, d, J = 2.4 Hz), 10.50 (1H, s). | Ref. Ex. 82 |
| 950 | 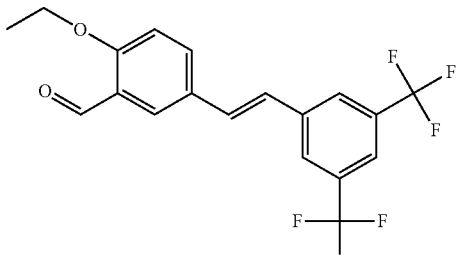 | 1H-NMR (CDCl3) δ: 1.53 (3H, t, J = 7.0 Hz), 7.20 (2H, q, J = 7.0 Hz), 7.02 (1H, d, J = 8.7 Hz), 7.09 (1H, d, J = 16.3 Hz), 7.20 (1H, d, J = 16.3 Hz), 7.65-7.73 (2H, m), 7.89 (2H, s), 8.04 (1H, d, J = 2.4 Hz), 10.53 (1H, s). | Ref. Ex. 82 |
| 951 | 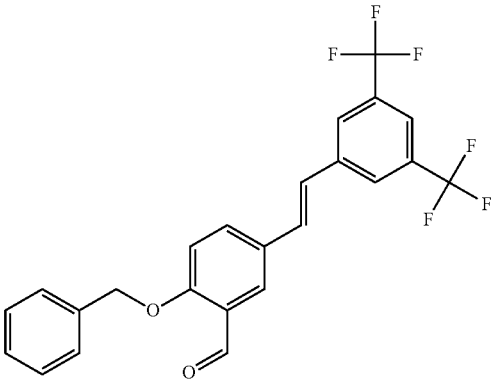 | 1H-NMR (CDCl3) δ: 5.25 (2H, s), 7.08-7.12 (2H, m), 7.20 (1H, d, J = 16.4 Hz), 7.42-7.47 (5H, m), 7.69-7.74 (2H, m), 7.90 (2H, s), 8.07 (1H, d, J = 2.4 Hz), 10.57 (1H, s). | Ref. Ex. 82 |
| 952 | 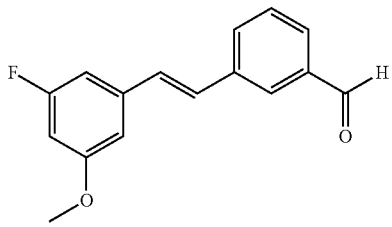 | 1H-NMR (CDCl3) δ: 3.85 (3H, s), 6.55-6.58 (1H, m), 6.84-6.87 (2H, m), 7.13 (2H, s), 7.55 (1H, t, J = 7.7 Hz), 7.74-7.80 (2H, m), 8.02 (1H, s), 10.06 (1H, s). | Ref. Ex. 825 |
| 953 | 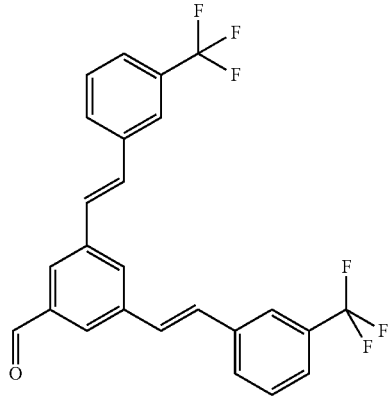 | 1H-NMR CDCl3) δ: 7.24 (2H, d, J = 16.2 Hz), 7.30 (2H, d, J = 16.2 Hz), 7.49-7.59 (4H, m), 7.72 (2H, d, J = 7.0 Hz). 7.81 (2H, s), 7.90 (1H, t, J = 1.6 Hz), 7.97 (2H, d, J = 1.6 Hz), 10.10 (1H, s). | Ref. Ex. 75 |

TABLE 2-continued

| Ref. Ex. No | STR | 1H-NMR | ref. |
|---|---|---|---|
| 954 | | 1H-NMR (CDCl3) δ: 6.97 (1H, d, J = 16.1 Hz), 7.03 (1H, dd, J = 3.5, 5.1 Hz), 7.12 (1H, d, J = 3.5 Hz), 7.22-7.25 (1H, m), 7.35 (1H, d, J = 16.1 Hz), 7.52 (1H, t, J = 7.6 Hz), 7.73 (1H, dt, J = 1.5, 7.8 Hz), 7.75 (1H, dt, J = 1.5, 7.6 Hz), 7.98 (1H, t, J = 1.7 Hz), 10.04 (1H, s). | Ref. Ex. 190 |
| 955 | | 1H-NMR (CDCl3) δ: 6.42 (1H, d, J = 3.3 Hz), 6.45 (1H, dd, J = 1.8, 3.3 Hz), 7.00 (1H, d, J = 16.3 Hz), 7.08 (1H, d, J = 16.3 Hz), 7.44 (1H, d, J = 1.6 Hz), 7.51 (1H, t, J = 7.5 Hz), 7.69-7.77 (2H, m), 7.98 (1H, t, J = 1.7 Hz), 10.04 (1H, s). | Ref. Ex. 190 |
| 956 | | 1H-NMR (CDCl3) δ: 7.21 (1H, d, J = 16.1 Hz), 7.51-7.58 (4H, m), 7.78-7 87 (5H, m), 8.00 (1H, d, J = 16.1 Hz), 8.12 (1H, s), 8.19-8.25 (1H, m), 10.09 (1H, s). | Ref. Ex. 825 |
| 957 | | 1H-NMR (CDCl3) δ: 3.85 (3H, s), 6.55-6.59 (1H, m), 6.84-6.88 (2H, m), 7.13 (2H, s), 7.55 (1H, t, J = 7.7 Hz), 7.74-7.80 (2H, m), 8.03 (1H, s), 10.06 (1H, s). | Ref. Ex. 825 |
| 958 | | 1H-NMR (CDCl3) δ: 7.59-7.68 (4H, m), 7.81-7.89 (4H, m), 9.91 (1H, s). | Ref. Ex. 112 |
| 959 | | 1H-NMR (CDCl3) δ: 2.50 (3H, s), 7.18-7.31 (3H, m), 7.52-7.59 (2H, m), 7.75-7.81 (3H, m), 8.03 (1H, s), 10.06 (1H, s). | Ref. Ex. 825 |

TABLE 2-continued

| Ref. Ex. No | STR | 1H-NMR | ref. |
|---|---|---|---|
| 960 | | 1H-NMR (CDCl3) δ: 1.56 (3H, t, J = 7.0 Hz), 4.26 (2H, q, J = 7.0 Hz), 7.04 (1H, d, J = 8.5 Hz), 7.29 (1H, d, J= 16.5 Hz), 7.56 (1H, d, J = 16.5 Hz), 7.76 (1H, s), 7.82 (1H, dd, J = 2.2, 8.6 Hz), 7.93 (2H, s), 8.12 (1H, d, J = 2.0 Hz), 9.94 (1H, s). | Ref. Ex. 82 |
| 961 | | 1H-NMR (CDCl3) δ: 5.04 (2H, s), 7.16 (1H, d, J = 16.5 Hz), 7.30 (1H, t, J = 7.7 Hz), 7.36-7.44 (6H, m), 7.49 (1H, d, J = 7.7 Hz), 7.54 (1H, d, J = 7.7 Hz), 7.59 (1H, d, J = 7.7 Hz), 7.69 (1H, s), 7.81 (1H, dd, J = 1.7, 7.7 Hz), 7.90 (1H, d, J = 1.5, 7.7 Hz) | Ref. Ex. 82 |
| 962 | | 1H-NMR (CDCl3) δ: 2.51 (3H, s), 7.09 (1H, d, J = 16.5 Hz), 7.20 (1H, d, J = 16.5 Hz), 7.26-7.33 (1H, m), 7.57 (1H, d, J = 7.5 Hz), 7.74-7.75 (3H, m), 7.89 (1H, s), 10.00 (1H, s). | Ref. Ex. 825 |
| 963 | | 1H-NMR (CDCl3) δ: 6.79-6.88 (3H, m), 7.18 (1H, d, J = 16.1 Hz), 7.52 (1H, t, J = 7.6 Hz), 7.66-7.69 (1H, m), 7.74-7.78 (1H, m), 7.96 (1H, s), 10.04 (1H, s). | Ref. Ex. 825 |
| 964 | | 1H-NMR (CDCl3) δ: 6.99-7.04 (1H, m), 7.10 (1H, d, J = 16.3 Hz), 7.17 (1H, d, J = 16.3 Hz), 7.22-7.25 (1H, m), 7.28-7.30 (1H, m), 7.33-7.39 (1H, m), 7.44-7.49 (2H, m), 7.81 (1H, s), 10.02 (1H, d, J = 1.7 Hz). | Ref. Ex. 91 |

TABLE 2-continued

| Ref. Ex. No | STR | 1H-NMR | ref. |
|---|---|---|---|
| 965 | | 1H-NMR (CDCl3) δ: 7.17 (1H, s), 7.28-7.38 (2H, m), 7.54-7.65 (2H, m), 7.81 (1H, s), 8.09 (1H, s), 8.23 (1H, s), 10.05 (1H, s). | Ref. Ex. 75 |
| 966 | | 1H-NMR (CDCl3) δ: 7.00 (1H, d, J = 16.3 Hz), 7.06-7.12 (2H, m), 7.17 (1H, d, J = 16.3 Hz), 7.43-7.46 (2H, m), 7.46-7.53 (2H, m), 7.80 (1H, s), 10.02 (1H, d, J = 1.7 Hz). | Ref. Ex. 75 |
| 967 | | 1H-NMR (CDCl3) δ: 7.17 (1H, d, J = 15.9 Hz), 7.58-7.60 (2H, m), 7.69 (1H, d, J = 7.9 Hz), 7.72 (1H, d, J = 8.4 Hz), 7.85 (1H, d, J = 2.3 Hz), 7.89 (1H, t, J = 7.9 Hz), 8.48 (1H, d, J = 15.9 Hz), 10.32 (1H, s). | Ref. Ex. 825 |
| 968 | | 1H-NMR (CDCl3) δ: 7.28 (1H, d, J = 16.2 Hz), 7.55-7.59 (2H, m), 7.72-7.90 (4H, m), 7.97 (1H, s), 10.00 (1H, s). | Ref. Ex. 825 |
| 969 | | 1H-NMR (CDCl3) δ: 1.55 (3H, t, J = 7.0 Hz), 4.23 (2H, q, J = 7.0 Hz), 7.02 (1H, d, J = 8.5 Hz), 7.26 (1H, d, J = 16.5 Hz), 7.47-7.54 (3H, m), 7.71 (1H, d, J = 7.3 Hz), 7.77-7.81 (2H, m), 8.13 (1H, d, J = 2.1 Hz), 9.93 (1H, s). | Ref. Ex. 82 |
| 970 | | 1H-NMR (CDCl3) δ: 6.81 (1H, d, J = 3.9 Hz), 7.33 (1H, d, J = 3.9 Hz), 7.32-7.43 (2H, m), 7.79-7.86 (3H, m), 9.68 (1H, s). | Ref. Ex. 75 |
| 971 | | 1H-NMR (CDCl3) δ: 3.61 (3H, s), 7.60 (1H, t, J = 7.7 Hz), 7.69 (1H, d, J = 7.8 Hz), 7.76-7.85 (3H, m), 7.96 (1H, d, J = 2.0 Hz), 9.97 (1H, s). | Ref. Ex. 112 |

TABLE 2-continued

| Ref. Ex. No | STR | 1H-NMR | ref. |
|---|---|---|---|
| 972 | | 1H-NMR (CDCl3) δ: 7.28-7.61 (5H, m), 7.74 (1H, s), 7.82 (1H, d, J = 8.1 Hz), 9.89 (1H, s). | Ref. Ex. 75 |
| 973 | | 1H-NMR (CDCl3) δ: 7.41 (1H, d, J = 15.9 Hz), 7.50 (1H, d, J = 5.1 Hz), 7.72 (2H, s), 8.07-8.15 (2H, m), 9.00 (1H, d, J = 5.1 Hz), 10.06 (1H, s). | Ref. Ex. 825 |
| 974 | | 1H-NMR (CDCl3) δ: 7.30-7.62 (4H, m), 7.74-7.96 (6H, m), 10.06 (1H, s). | Ref. Ex. 75 |
| 975 | | 1H-NMR (CDCl3) δ: 7.20-7.23 (1H, m), 7.34-7.39 (1H, m), 7.53-7.64 (2H, m), 7.72-7.78 (2H, m), 7.86-7.87 (1H, m), 7.93-7.95 (1H, m), 8.21 (1H, d, J = 7.7 Hz), 10.06 (1H, s). | Ref. Ex. 75 |
| 976 | | 1H-NMR (CDCl3) δ: 2.55-2.59 (2H, m), 2.87-2.92 (2H, m), 6.81 (1H, d, J = 7.5 Hz), 6.98 (1H, d, J = 7.5 Hz), 7.56-7.57 (1H, m), 7.68-7.72 (2H, m), 7.87-7.88 (1H, m), 10.03 (1H, s). | Ref. Ex. 75 |
| 977 | | 1H-NMR (CDCl3) δ: 7.36-7.76 (4H, m), 7.89-8.09 (3H, m), 8.56 (1H, d, J = 6.0 Hz), 9.36 (1H, s), 10.07 (1H, s). | Ref. Ex. 75 |

| Ref. Ex. No | STR | 1H-NMR | ref. |
|---|---|---|---|
| 978 | | 1H-NMR (CDCl3) δ: 7.29-7.41 (2H, m), 7.58-7.70 (3H, m), 7.89-8.03 (2H,m), 8.11-8.14 (1H, m), 10.16 (1H, s). | Ref. Ex. 75 |
| 979 | | 1H-NMR (CDCl3) δ: 7.01-7.07 (2H, m), 7.14 (1H, d, J = 16.7 Hz), 7.48-7.51 (2H, m), 7.65-7.70 (2H, m), 7.73-7.76 (2H, m), 9.95 (1H, s), 11.06 (1H, s). | Ref. Ex. 77 |
| 980 | | 1H-NMR (CDCl3) δ: 1.51 (3H, t, J = 7.0 Hz), 4.21 (2H, q, J = 7.0 Hz), 7.01 (1H, d, J = 8.5 Hz), 7.07 (1H, d, J = 16.4 Hz), 7.12 (1H, d, J = 16.4 Hz), 7.44-7.52 (2H, m), 7.64-7.71 (2H, m), 7.73 (1H, s), 8.01 (1H, d, J = 2.4 Hz), 10.52 (1H, s). | Ref. Ex. 82 |
| 981 | | 1H-NMR (CDCl3) δ: 7.62-7.97 (5H, m), 8.00-8.19 (2H, m), 8.37 (1H, s), 9.18 (1H, s), 10.10 (1H, s). | Ref. Ex. 75 |
| 982 | | 1H-NMR (CDCl3) δ: 1.49 (9H, s), 6.59 (1H, brs), 7.59-7.76 (5H, m), 7.90 (1H, dd, J = 2.0, 8.6 Hz), 8.41 (1H, d, J = 8.6 Hz), 9.95 (1H, s). | Ref. Ex. 75 |
| 983 | | 1H-NMR (CDCl3) δ: 7.08 (1H, d, J = 3.6 Hz), 7.40 (1H, d, J = 3.6 Hz), 7.60-7.65 (1H, m), 7.75-7.80 (1H, m), 7.92 (1H, d, J = 8.1 Hz), 8.14 (1H, d, J = 8.1 Hz), 8.64 (1H, s), 9.29 (1H, s), 9.73 (1H, s). | Ref. Ex. 75 |
| 984 | | 1H-NMR (CDCl3) δ: 7.52-7.58 (2H, m), 7.72-7.15 (1H, m), 7.85-8.12 (7H, m), 10.08 (1H, s). | Ref. Ex. 75 |

TABLE 2-continued
| Ref. Ex. No | STR | 1H-NMR | ref. |
|---|---|---|---|
| 985 | 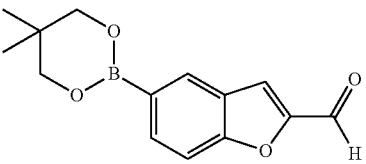 | 1H-NMR (CDCl3) δ: 1.03 (6H, s), 3.81 (4H, s), 7.57-7.59 (2H, m), 7.95-7.98 (1H, m), 8.24 (1H, s), 9.87 (1H, s). | Ref. Ex. 107 |
| 986 | 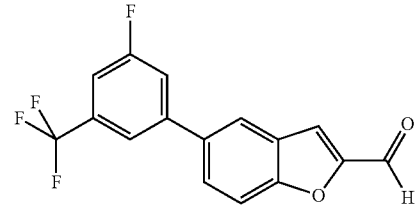 | 1H-NMR (CDCl3) δ: 7.35 (1H, d, J = 8.2 Hz), 7.50 (1H, d, J = 9.4 Hz), 7.63 (1H, s), 7.66 (1H, s), 7.72-7.74 (2H, m), 7.95 (1H, s), 9.93 (1H, s). | Ref. Ex. 75 |
| 987 | 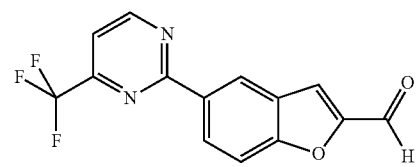 | 1H-NMR (CDCl3) δ: 7.54 (1H, d, J = 5.1 Hz), 7.68 (1H, s), 7.73 (1H, d, J = 8.7 Hz), 8.73-8.76 (1H, m), 8.98 (1H, s), 9.07 (1H, d, J = 5.1 Hz), 9.93 (1H, s). | Ref. Ex. 75 |
| 988 | 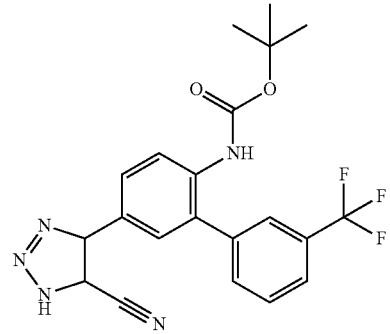 | 1H-NMR (CDCl3) δ: 1.25 (9H, s), 7.58 (1H, d, J = 8.5 Hz), 7.75 (4H, s), 7.87-7.90 (2H, m), 8.96 (1H, s). | Ex. 1 |
| 989 | 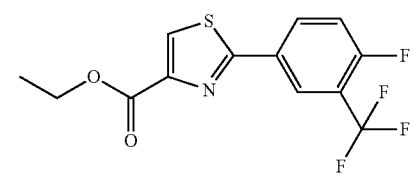 | 1H-NMR (CDCl3) δ:1.44 (3H, t, J = 7.1 Hz), 4.46 (2H, q, J = 7.1 Hz), 7.31 (1H, t, J = 9.2 Hz), 8.18-8.27 (3H, m). | Ref. Ex. 14 |
| 990 | 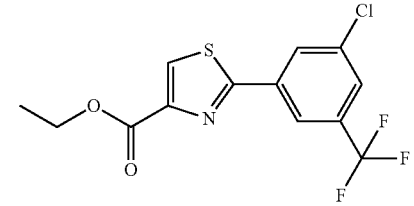 | 1H-NMR (CDCl3) δ: 1.45 (3H, t, J = 7.1 Hz), 4.47 (2H, q, J = 7.1 Hz), 7.70 (1H, s), 8.13 (1H, s), 8.21 (1H, s), 8.25 (1H, s). | Ref. Ex. 14 |
| 991 | 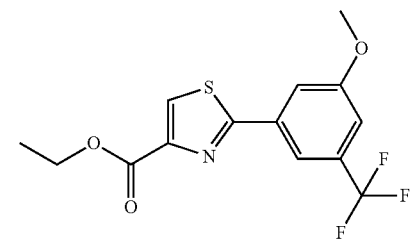 | 1H-NMR (CDCl3) δ: 1.44 (3H, t, J = 7.1 Hz), 3.94 (3H, s), 4.46 (2H, q, J = 7.1 Hz), 7.21-7.24 (1H, m), 7.73-7.74 (1H, m), 7.79-7.81 (1H, m), 8.21 (1H, s). | Ref. Ex. 14 |

TABLE 2-continued

| Ref. Ex. No | STR | 1H-NMR | ref. |
|---|---|---|---|
| 992 | | 1H-NMR (CDCl3) δ: 1.44 (3H, t, J = 7.1 Hz), 3.98 (3H, s), 4.45 (2H, q, J = 7.1 Hz), 7.08 (1H. d, J = 9.4 Hz), 8.14 (1H, s), 8.16-8.19 (2H, m). | Ref. Ex. 14 |
| 993 | | 1H-NMR (CDCl3) δ: 7.34 (1H, t, J = 9.2 Hz), 8.17-8.20 (1H, m), 8.22 (1H, s), 8.27 (1H, dd, J = 2.1, 6.5 Hz), 10.11 (1H, s). | Ref. Ex. 63 |
| 994 | | 1HNMR (CDCl3) δ: 7.21 (1H, s), 7.28-7.39 (1H, m), 7.51-7.72 (4H, m), 7.94 (1H, s), 8.29 (1H, s), 10.09 (1H, s). | Ref. Ex. 91 |
| 995 | | 1H-NMR (CDCl3) δ: 7.00 (1H, d, J = 16.2 Hz), 7.19 (1H, d, J = 16.2 Hz), 7.31-7.39 (3H, m), 7.52 (1H, t, J = 7.6 Hz), 7.70-7.77 (2H, m), 7.99 (1H, s), 10.05 (1H, s). | Ref. Ex. 190 |
| 996 | | 1H-NMR (CDCl3) δ: 2.37 (3H, s), 6.02-6.05 (1H, m), 6.30 (1H, d, J = 3.2 Hz), 6.91 (1H, d, J = 16.2 Hz), 6.99 (1H, d, J = 16.2 Hz), 7.50 (1H, t, J = 7.7 Hz), 7.66-7.74 (2H, m), 7.95 (1H, t, J = 1.7 Hz), 10.03 (1H, s). | Ref. Ex. 190 |
| 997 | | 1H-NMR (CDCl3) δ: 6.75 (1H, s), 7.12 (1H, d, J = 16.1 Hz), 7.22 (1H, dt, J = 1.1, 7.5 Hz), 7.31 (1H, dt, J = 1.4, 8.1 Hz), 7.35 (1H, d, J = 16.1 Hz), 7.47-7.58 (3H, m), 7.76-7.81 (2H, m), 8.05 (1H, t, J = 1.7 Hz), 10.06 (1H, s). | Ref. Ex. 190 |
| 998 | | 1H-NMR (CDCl3) δ: 7.03 (1H, d, J = 16.0 Hz), 7.31-7.37 (3H, m), 7.43 (1H, dd, J = 0.6, 16.0 Hz), 7.55 (1H, t, J = 7.7 Hz), 7.71-7.82 (4H, m), 8.03 (1H, t, J = 1.7 Hz), 10.06 (1H, s). | Ref. Ex. 190 |
| 999 | | 1H-NMR (CDCl3) δ: 7.24 (1H, d, J = 16.2 Hz), 7.38-7.53 (3H, m), 7.57 (1H, t, J = 7.6 Hz), 7.63 (1H, s), 7.78-7.83 (2H, m), 7.88-7.92 (1H, m), 8.02-8.06 (1H, m), 8.08 (1H, t, J = 1.7 Hz), 10.08 (1H, s). | Ref. Ex. 190 |

TABLE 2-continued

| Ref. Ex. No | STR | 1H-NMR | ref. |
|---|---|---|---|
| 1000 | | 1H-NMR (CDCl3) δ: 1.45 (3H, t, J = 7.0 Hz), 4.09 (2H, q, J = 7.0 Hz), 6.85 (1H, ddd, J = 0.9, 2.5, 8.2 Hz), 7.06-7.22 (4H, m), 7.26-7.32 (1H, m), 7.53 (1H, t, J = 7.7 Hz), 7.73-7.89 (2H, m), 8.21 (1H, t, J = 1.7 Hz), 10.06 (1H, s). | Ref. Ex. 188 |
| 1001 | | 1H-NMR (CDCl3) δ: 3.83 (3H, s), 7.13 (1H, d, J = 16.4 Hz), 7.12-7.38 (4H, m), 7.41 (1H, d, J = 16.4 Hz), 7.51 (1H, t, J = 7.7 Hz), 7.70 (1H, dt, J = 1.4, 7.7 Hz), 7.73-7.77 (1H, m), 7.89-8.03 (2H, m), 10.06 (1H, s). | Ref. Ex. 188 |
| 1002 | | 1H-NMR (CDCl3) δ: 3.92 (3H, s), 6.97 (1H, t, J = 8.5 Hz), 7.00 (1H, d, J = 16.3 Hz), 7.11 (1H, d, J = 16.3 Hz), 7.19-7.25 (1H, m), 7.31 (1H, dd, J = 2.1, 12.5 Hz), 7.53 (1H, t, J = 7.6 Hz), 7.70-7.79 (2H, m), 8.01 (1H, m), 10.05 (1H, s). | Ref. Ex. 190 |
| 1003 | | 1H-NMR (CDCl3) δ: 1.06 (3H, t, J = 7.4 Hz), 1.77-1.91 (2H, m), 3.97 (2H, t, J = 6.6 Hz), 6.82-6.87 (1H, m), 7.06-7.13 (2H, m), 7.13 (1H, d, J = 16.4 Hz), 7.18 (1H, d, J = 16.4 Hz), 7.29 (1H, t, J = 7.8 Hz), 7.53 (1H, t, J = 7.6 Hz), 7.72-7.79 (2H, m), 8.02 (1H, s), 10.05 (1H, s). | Ref. Ex. 100, Ref. Ex. 186 |
| 1004 | | 1H-NMR (CDCl3) δ: 6.81 (1H, dd, J = 0.8, 3.2 Hz), 7.57 (1H, d, J = 3.2 Hz), 7.68-7.84 (6H, m), 8.01 (1H, s), 10.05 (1H, s). | Ref. Ex. 154 |
| 1005 | | 1H-NMR (CDCl3) δ: 6.85 (1H, dd, J = 0.8, 3.4 Hz), 7.23-7.29 (1H, m), 7.31-7.41 (3H, m), 7.53 (1H, d, J = 8.6 Hz), 7.82 (1H, dd, J = 1.5, 8.6 Hz), 8.21-8.23 (1H, m), 10.07 (1H, s). | Ref. Ex. 154 |
| 1006 | | 1H-NMR (CDCl3) δ: 6.89 (1H, dd, J = 0.7, 3.3 Hz), 7.44 (1H, d, J = 3.3 Hz), 7.58 (1H, d, J = 8.7 Hz), 7.67-7.74 (3H, m), 7.77 (1H, s), 7.84 (1H, dd, J = 1.6, 8.7 Hz), 8.22-8.25 (1H, m), 10.08 (1H, s) | Ref. Ex. 154 |

TABLE 2-continued

| Ref. Ex. No | STR | 1H-NMR | ref. |
|---|---|---|---|
| 1007 | | 1H-NMR (CDCl3) δ: 4.01 (3H, s), 7.19-7.26 (1H, m), 7.28-7.41 (5H, m), 7.66 (1H, d, J = 8.2 Hz), 7.97 (1H, dd, J = 0.9, 7.5 Hz). | Ref. Ex. 154 |
| 1008 | | 1H-NMR (CDCl3) δ: 4.02 (3H, s), 7.30 (1H, t, J = 7.9 Hz), 7.39 (1H, dd, J = 0.8, 3.3 Hz), 7.47 (1H, d, J = 3.3 Hz), 7.63-7.73 (4H, m), 7.75-7.78 (1H, m), 7.99 (1H, dd, J = 0.9, 7.5 Hz). | Ref. Ex. 154 |
| 1009 | | 1H-NMR (CDCl3) δ: 5.37 (2H, s), 6.66 (1H, dd, J = 0.9, 3.3 Hz), 6.81-6.92 (2H, m), 7.06-7.16 (1H, m), 7.34 (1H, d, J = 3.2 Hz), 7.66 (1H, dd, J = 1.3, 8.2 Hz), 7.76 (1H, d, J = 8.2 Hz), 7.81 (1H, s), 10.02 (1H, s). | Ref. Ex. 184 |
| 1010 | | 1H-NMR (CDCl3): δ 5.47 (2H, s), 6.67 (1H, dd, J = 0.8, 3.2 Hz), 7.20 (1H, d, J = 7.6 Hz), 7.35 (1H, d, J = 3.2 Hz), 7.40-7.50 (2H, m), 7.56 (1H, d, J = 7.8 Hz), 7.67 (1H, dd, J = 1.3, 8.2 Hz), 7.77 (1H, d, J = 8.2 Hz), 7.82 (1H, s), 10.02 (1H, s). | Ref. Ex. 184 |
| 1011 | | 1H-NMR (CDCl3) δ: 6.77 (1H, d, J = 0.8, 3.2 Hz), 7.43-7.49 (2H, m), 7.51 (1H, d, J = 3.2 Hz), 7.52-7.57 (2H, m), 7.71 (1H, dd, J = 1.3, 8.2 Hz), 7.79 (1H, d, J = 8.2 Hz), 8.01 (1H, s), 10.04 (1H, s). | Ref. Ex. 154 |

TABLE 2-continued

| Ref. Ex. No | STR | 1H-NMR | ref. |
|---|---|---|---|
| 1012 | | 1H-NMR (CDCl3) δ: 3.90 (3H, s), 6.73 (1H, dd, J = 0.8, 3.2 Hz), 7.04-7.10 (2H, m), 7.38-7.44 (2H, m), 7.49 (1H, d, J = 3.2 Hz), 7.69 (1H, dd, J = 1.3, 8.2 Hz), 7.77 (1H, d, J = 8.2 Hz), 7.95 (1H, s), 10.01 (1H, s). | Ref. Ex. 154 |
| 1013 | | 1H-NMR (CDCl3) δ: 6.10 (2H, s), 6.72 (1H, dd, J = 0.8, 3.2 Hz), 6.94-6.98 (3H, m), 7.48 (1H, d, J = 3.2 Hz), 7.69 (1H, dd, J = 1.3, 8.2 Hz), 7.77 (1H, d, J = 8.2 Hz), 7.98 (1H, s), 10.03 (1H,s). | Ref. Ex. 154 |
| 1015 | | 1H-NMR (CDCl3) δ: 3.87 (1H, d, J = 1.7 Hz), 3.95 (1H, d, J = 1.7 Hz), 7.32-7.42 (5H, m), 7.52 (2H, d, J = 8.2 Hz), 7.90 (2H, d, J = 8.2 Hz), 10.03 (1H, s). | Ex. 952 |
| 1016 | | 1H-NMR (CDCl3) δ: 6.79 (1H, dd, J = 0.8, 3.3 Hz), 6.82-6.93 (1H, m), 7.05-7.13 (2H, m), 7.52 (1H, d, J = 3.3 Hz), 7.74 (1H, dd, J = 1.3, 8.2 Hz), 7.79 (1H, d, J = 8.2 Hz), 8.10 (1H, s), 10.07 (1H, s). | Ref. Ex. 154 |
| 1017 | | 1H-NMR (CDCl3) δ: 3.52 (2H, t, J = 8.6 Hz), 4.00 (2H, t, J = 8.6 Hz), 6.89-6.96 (1H, m), 7.01-7.09 (1H, ddd, J = 2.7, 6.8, 12.3 Hz), 7.10-7.31 (4H, m), 10.09 (1H, s.). | Ref. Ex. 76, Ref. Ex. 48 |

TABLE 2-continued

| Ref. Ex. No | STR | 1H-NMR | ref. |
|---|---|---|---|
| 1018 | | 1H-NMR (CDCl3) δ: 7.21-7.28 (1H, m), 7.30-7.43 (3H, m), 7.46 (1H, d, J = 3.2 Hz), 7.50-7.52 (1H, m), 7.69-7.75 (2H, m), 10.29 (1H, s). | Ref. Ex. 76, Ref. Ex. 48 |
| 1019 | | 1H-NMR (CDCl3) δ: 5.66 (2H, brs), 6.95 (1H, d, J = 8.5 Hz), 7.58 (1H, d, J = 2.2 Hz), 7.63 (1H, dd, J = 2.2, 8.4 Hz), 7.70-7.80 (4H, m). | Ex. 688 |
| 1020 | | 1H-NMR (CDCl3) δ: 7.73 (1H, s), 8.13-8.14 (1H, m), 8.19-8.20 (1H, m), 8.26 (1H, s), 10.12 (1H, s). | Ref. Ex. 63 |
| 1021 | | 1H-NMR (CDCl3) δ: 3.95 (3H, s), 7.23-7.28 (1H, m), 7.73 (1H, s), 7.80 (1H, s), 8.23 (1H, s), 10.12 (1H, s). | Ref. Ex. 63 |
| 1022 | | 1H-NMR (CDCl3) δ: 3.99 (3H, s), 7.11 (1H, d, J = 8.6 Hz), 8.14-8.21 (3H, m), 10.09 (1H, s). | Ref. Ex. 63 |
| 1023 | | 1H-NMR (CDCl3) δ: 1.06 (6H, s), 3.82 (4H, s), 7.15 (1H, t, J = 8.7 Hz), 7.93-7.98 (1H, m), 8.27-8.30 (1H, m), 9.98 (1H, s). | Ref. Ex. 107 |

TABLE 2-continued

| Ref. Ex. No | STR | 1H-NMR | ref. |
|---|---|---|---|
| 1024 | | 1H-NMR (CDCl3) δ: 7.37-7.43 (1H, m), 7.65 (1H, d, J = 5.0 Hz), 8.06-8.11 (1H, m), 8.72-8.75 (1H, m), 9.17 (1H, d, J = 5.0 Hz), 10.08 (1H, s). | Ref. Ex. 112 |
| 1025 | | 1H-NMR (CDCl3) δ: 6.93-6.96 (1H, m), 7.13-7.16 (1H, m), 7.20-7.31 (1H, m), 7.61 (1H, s), 7.67 (2H, s), 7.85-7.86 (1H, m), 9.91 (1H, s). | Ref. Ex. 75 |
| 1026 | | 1H-NMR (CDCl3) δ: 3.53 (2H, t, J = 8.5 Hz), 3.91 (3H, s), 4.03 (2H, t, J = 8.5 Hz), 7.13-7.31 (3H, m), 7.36-7.48 (4H, m). | Ref. Ex. 1014 |
| 1027 | | 1H-NMR (CDCl3) δ: 3.55 (2H, t, J = 8.6 Hz), 4.09 (2H, t, J = 8.6 Hz), 7.22-7.36 (4H, m), 7.37-7.50 (3H, m), 1010 (1H, s). | Ref. Ex. 76 Ref. Ex. 48 |
| 1028 | | 1H-NMR (CDCl3) δ: 7.21-7.26 (1H, m), 7.50-7.61 (4H, m), 7.72-7.81 (3H, m), 8.20 (1H, d, J = 2.2 Hz), 10.04 (1H, s). | Ref. Ex. 77 |
| 1029 | | 1H-NMR (CDCl3) δ: 3.05 (2H, t, J = 8.4 Hz), 3.42 (2H, t, J = 8.4 Hz), 3.88 (3H, s), 4.30 (2H, s), 6.96 (1H, dt, J = 6.4, 9.6 Hz), 7.10 (1H, d, J = 1.2 Hz), 7.11-7.24 (2H, m), 7.43 (1H, dd, J = 1.4, 7.5 Hz). | Ref. Ex. 113 |

TABLE 2-continued

| Ref. Ex. No | STR | 1H-NMR | ref. |
|---|---|---|---|
| 1030 | | 1H-NMR (CDCl3) δ: 3.04 (2H, t, J = 8.4 Hz), 3.36 (2H, t, J = 8.4 Hz), 3.87 (3H, s), 4.35 (2H, s), 7.11-7.18 (3H, m), 7.39-7.50 (2H, m), 7.52-7.58 (1H, m), 7.62 (1H, s). | Ref. Ex. 113 |
| 1031 | | 1H-NMR (CDCl3) δ: 7.40 (1H, dd, J = 7.4, 8.2 Hz), 7.54 (2H, s), 7.67-7.78 (6H, m), 10.30 (1H, s). | Ref. Ex. 76 Ref. Ex. 48 |
| 1032 | | 1H-NMR (CDCl3) δ: 5.36 (2H, s), 6.56-6.68 (1H, m), 6.99 (1H, dt, J = 6.4, 9.6 Hz), 7.32-7.41 (3H, m), 7.55 (1H, d, J = 8.2 Hz), 7.66 (1H, d, J = 7.3 Hz), 10.26 (1H, s). | Ref. Ex. 184 |
| 1033 | | 1H-NMR (CDCl3) δ: 3.09 (2H, t, J = 8.4 Hz), 3.47 (2H, t, J = 8.4 Hz), 4.32 (2H, s), 6.93 (1H, s), 6.96 (1H, dt, J = 6.4, 9.5 Hz), 7.14-7.26 (3H, m), 9.87 (1H, s). | Ref. Ex. 76 Ref. Ex. 48 |
| 1034 | | 1H-NMR (CDCl3) δ: 3.08 (2H, t, J = 8.4 Hz), 3.41 (2H, t, J = 8.4 Hz), 4.37 (2H, s), 6.96 (1H, s), 7.17-7.26 (2H, m), 7.47 (1H, t, J = 7.3 Hz), 7.51-7.58 (2H, m), 7.60 (1H, s), 9.87 (1H, s). | Ref. Ex. 76 Ref. Ex. 48 |
| 1035 | | 1H-NMR (CDCl3) δ: 1.37 (12H, s), 7.63-7.70 (1H, m), 7.73-7.77 (1H, m), 8.09 (1H, s), 10.02 (1H, d, J = 2.2 Hz). | Ref. Ex. 81 |

TABLE 2-continued

| Ref. Ex. No | STR | 1H-NMR | ref. |
|---|---|---|---|
| 1036 | | 1H-NMR (CDCl3) δ: 3.93 (3H, s), 5.37 (2H, s), 6.54-6.64 (2H, m), 6.99 (1H, dt, J = 6.4, 9 6 Hz), 7.28 (1H, d, J = 3.1 Hz), 7.67 (1H, dd, J = 0.5, 8.4 Hz), 7.83 (1H, dd, J = 1.4, 8.4 Hz), 8.06 (1H, s) | Ref. Ex. 184 |
| 1037 | | 1H-NMR (CDCl3) δ: 7.35-7.42 (2H, m), 7.68 (2H, s), 7.78 (1H, s), 7.81-7.89 (2H, m), 8.13 (1H, s), 10.08 (1H, s). | Ref. Ex. 91 |
| 1038 | | 1H-NMR (CDCl3) δ: 7.35-7.41 (2H, m), 7.80-8.02 (6H, m), 10.15 (1H, s). | Ref. Ex. 91 |
| 1039 | | 1H-NMR (CDCl3) δ: 4.12 (2H, s), 7.21 (1H, d, J = 8.8 Hz), 7.39-7.53 (4H, m), 7.70-7.83 (2H, m), 9.92 (1H, s). | Ref. Ex. 91 |
| 1040 | | 1H-NMR (CDCl3) δ: 4.09 (2H, s), 7.34-7.61 (6H, m), 7.72-7.74 (1H, m), 9.94 (1H, s). | Ref. Ex. 183 |

TABLE 2-continued

| Ref. Ex. No | STR | 1H-NMR | ref. |
|---|---|---|---|
| 1041 | | 1H-NMR (CDCl3) δ: 4.14 (2H, s), 7.27-7.55 (5H, m), 7.61-7.63 (2H, m), 9.97 (1H, s). | Ref. Ex. 183 |
| 1042 | | 1H-NMR (CDCl3) δ: 4.15 (2H, s), 7.32-7.57 (8H, m), 9.86 (1H, s). | Ref. Ex. 183 |
| 1043 | | 1H-NMR (CDCl3) δ: 7.15 (1H, s), 7.24-7.36 (3H, m), 7.55 (1H, d, J = 8.0 Hz), 7.63 (2H, t, J = 7.6 Hz), 7.87 (1H, d, J = 7.6 Hz), 8.13 (1H, d, J = 8.0 Hz), 10.11 (1H, s). | Ref. Ex. 91 |
| 1044 | | 1H-NMR (CDCl3) δ: 7.38 (1H, d, J = 16.2 Hz), 7.49 (1H, d, J = 5.1 Hz), 7.84-7.87 (2H, m), 8.01 (1H, s), 8.10 (1H, d, J = 16.2 Hz), 8.99 (1H, d, J = 4.8 Hz), 10.02 (1H, s). | Ref. Ex. 825 |
| 1045 | | 1H-NMR (CDCl3) δ: 1.47 (3H, t, J = 6.9 Hz), 4.14 (2H, q, J = 6.9 Hz), 7.34-7.42 (3H, m), 7.46 (1H, d, J = 5.1 Hz), 7.72 (1H, s), 8.11 (1H, d, J = 15.9 Hz), 6.98 (1H, d, J = 4.8 Hz), 10.01 (1H. s). | Ref. Ex. 825 |
| 1046 | | 1H-NMR (CDCl3) δ: 4.02 (3H, s), 7.15-7.24 (1H, m), 7.26-7.41 (4H. m), 7.55 (1H, dd, J = 0.9, 8.4 Hz), 7.61 (1H, dd, J = 0.9, 7.3 Hz). | Ex. 108 |

TABLE 2-continued

| Ref. Ex. No | STR | 1H-NMR | ref. |
|---|---|---|---|
| 1047 | | 1H-NMR (CDCl3) δ: 7.19-7.26 (1H, m), 7.29-7.43 (3H, m), 7.45 (1H, s), 7.63-7.68 (1H, m), 7.95-8.00 (1H, m), 11.27 (1H, s). | Ref. Ex. 76 Ref. Ex. 48 |
| 1048 | | 1H-NMR (CDCl3) δ: 3.91 (3H, s), 6.72 (1H, dd, J = 0.6, 3.2 Hz), 7.21-7.28 (2H, m), 7.41-7.50 (3H, m), 7.70 (1H, dd, J = 0.5, 8.4 Hz), 7.86 (1H, dd, J = 1.4, 8.4 Hz), 8.16 (1H, s). | Ref. Ex. 154 |
| 1049 | | 1H-NMR (CDCl3) δ: 3.92 (3H, s), 6.77 (1H, dd, J = 0.8, 3.3 Hz), 7.49 (1H, d, J = 3.3 Hz), 7.67-7.77 (5H, m), 7.90 (1H, dd, J = 1.4, 8.3 Hz), 8.32 (1H, dd, J = 0.6, 1.4 Hz). | Ref. Ex. 154 |
| 1050 | | 1H-NMR (CDCl3) δ: 3.17 (2H, t, J = 8.4 Hz), 3.87 (3H, s), 3.95 (2H, t, J = 8.4 Hz), 7.04-7.12 (2H, m), 7.15-7.24 (3H, m), 7.46 (1H, dd, J = 1.4, 7.6 Hz), 7.54 (1H, d, J = 1.1 Hz). | Ref. Ex. 1014 |
| 1051 | | 1H-NMR (CDCl3) δ: 3.21 (2H, t, J = 8.4 Hz), 3.89 (3H, s), 4.04 (2H, t, J = 8.4 Hz), 7.20-7.25 (2H, m), 7.38 (1H, s), 7.44-7.55 (3H, m), 7.74 (1H, d, J = 1.3 Hz). | Ref. Ex. 1014 |

TABLE 2-continued

| Ref. Ex. No | STR | 1H-NMR | ref. |
|---|---|---|---|
| 1052 | | 1H-NMR (CDCl3) δ: 3.20 (2H, t, J = 8.4 Hz), 3.98 (2H, t, J = 8.4 Hz), 7.04-7.13 (2H, m), 7.20-7.30 (4H, m), 7.37-7.39 (1H, m), 9.87 (1H, s). | Ref. Ex. 76 Ref. Ex. 48 |
| 1053 | | 1H-NMR (CDCl3) δ: 5.40 (2H, s), 6.58-6.68 (2H, m), 7.01 (1H, dt, J = 6.4, 9.5 Hz), 7.36 (1H, d, J = 3.1 Hz), 7.67 (1H, dd, J = 1.3, 8.2 Hz), 7.76 (1H, d, J = 8.2 Hz), 7.85 (1H, s), 10.05 (1H, s). | Ref. Ex. 76 Ref. Ex. 48 |
| 1054 | | 1H-NMR (CDCl3) δ: 7.43-7.59 (2H, m), 7.94-7.99 (2H, m), 8.12 (1H, d, J = 8.0 Hz), 8.36-8.39 (1H, m), 8.43-8.46 (1H, m), 10.09 (1H, s). | Ref. Ex. 112 |
| 1055 | | 1H-NMR (CDCl3) δ: 7.48-7.51 (1H, m), 7.70 (1H, t, J = 7.5 Hz), 7.93 (1H, d, J = 2.1 Hz), 8.00-8.05 (2H, m), 8.33-8.37 (1H, m), 8.56 (1H, s), 10.14 (1H, s). | Ref. Ex. 112 |
| 1056 | | 1H-NMR (CDCl3) δ: 1.39 (9H, s), 6.67 (1H, s), 7.29-7.41 (2H, m), 7.59 (1H, d, J = 8.4 Hz), 7.68 (1H, s), 7.84 (2H, s), 8.22 (1H, d, J = 8.4 Hz), 10.02 (1H, s). | Ref. Ex. 112 |
| 1057 | | 1H-NMR (CDCl3) δ: 7.63 (1H, d, J = 5.0 Hz), 7.72-7.94 (1H, m), 8.49-8.52 (1H, m), 8.84-8.85 (1H, m), 9.11 (1H, d, J = 5.0 Hz), 10.13 (1H, d, J = 2.1 Hz). | Ref. Ex. 75 |

TABLE 2-continued
| Ref. Ex. No | STR | 1H-NMR | ref. |
|---|---|---|---|
| 1058 |  | 1H-NMR (CDCl3) δ: 4.14 (2H, s), 7.29-7.32 (3H, m), 7.58-7.63 (4H, m), 9.97 (1H, s). | Ref. Ex. 183 |
| 1059 | 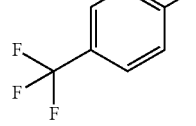 | 1H-NMR (CDCl3) δ: 7.25-7.40 (3H, m), 7.52-7.67 (2H, m), 8.59 (1H, s), 9.03 (1H, s), 9.33 (1H, s), 10.21 (1H, s). | Ref. Ex. 183 |
| 1060 |  | 1H-NMR (CDCl3) δ: 1.43 (3H, t, J = 7.1 Hz), 4.47 (2H, q, J = 7.1 Hz), 7.84-7 93, (2H, m), 8.06 (1H, s), 8.38 (1H, s). | Ref. Ex. 14 |
| 1061 | 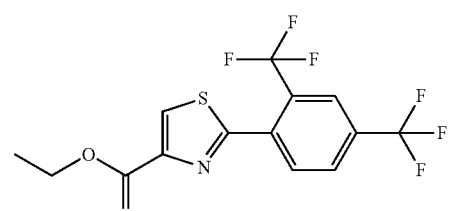 | 1H-NMR (CDCl3) δ: 7.87 (1H, d, J = 8.1 Hz), 7.95 (1H, d, J = 8.1 Hz), 8.10 (1H, s), 8.38 (1H, s), 10.14 (1H, s). | Ref. Ex. 63 |
| 1062 | 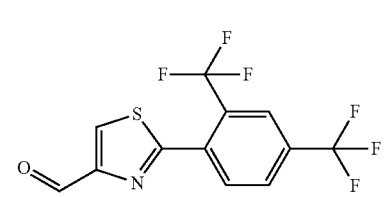 | 1H-NMR (CDCl3) δ: 4.01 (2H, s), 6.98-7.04 (2H, m), 7.10-7.16 (2H, m), 7.40 (1H, s), 7.56 (1H, s), 7.70 (1H, s), 9.93 (1H, s). | Ref. Ex. 183 |
| 1063 | 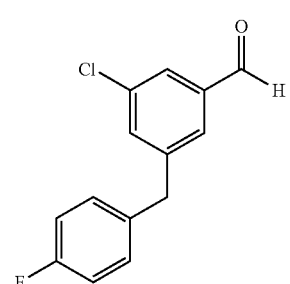 | 1H-NMR (CDCl3) δ: 2.39 (3H, s), 3.98 (2H, s), 6.96-7.02 (2H, m), 7.12-7.16 (2H, m), 7.25 (1H, s), 7.49 (1H, s), 7.54 (1H, s), 9.94(1H, s). | Ref. Ex. 183 |

TABLE 2-continued

| Ref. Ex. No | STR | 1H-NMR | ref. |
|---|---|---|---|
| 1064 | | 1H-NMR (CDCl3) δ: 2.40 (3H, s), 4.07 (2H, s), 7.25-7.32 (3H, m), 7.49-7.58 (4H, m), 9.96 (1H, s). | Ref. Ex. 183 |
| 1065 | | 1H-NMR (CDCl3) δ: 2.41 (3H, s), 4.07 (2H, s), 7.34-7.50 (6H, m), 7.56 (1H, s), 9.95 (1H, s). | Ref. Ex. 183 |
| 1066 | | 1H-NMR (CDCl3) δ: 4.09 (2H, s), 7.28-7.32 (2H, m), 7.42 (1H, s), 7.56-7.61 (3H, m), 7.73 (1H, s), 9.94 (1H, s). | Ref. Ex. 183 |
| 1067 | | 1H-NMR (CDCl3) δ: 1.44 (3H, t, J = 7.1 Hz), 4.47 (2H, q, J = 7.1 Hz), 7.74-7.77 (2H, m), 8.12-8.15 (2H, m), 8.25 (1H, s). | Ref. Ex. 14 |
| 1068 | | 1H-NMR (CDCl3) δ: 3.24 (2H, t, J = 8.4 Hz), 4.07 (2H, t, J = 8.4 Hz), 7.24-7.39 (4H, m), 7.45-7.58 (3H, m), 9.90 (1H, s). | Ref. Ex. 76<br>Ref. Ex. 48 |

TABLE 2-continued

| Ref. Ex. No | STR | 1H-NMR | ref. |
|---|---|---|---|
| 1069 | | 1H-NMR (CDCl3) δ: 3.92 (3H, s), 6.76 (1H, dd, J = 0.8, 3.3 Hz), 7.09-7.18 (1H, m), 7.22-7.35 (2H, m), 7.41 (1H, dd, J = 2.0, 3.3 Hz), 7.71 (1H, d, J = 8.3 Hz), 7.89 (1H, dd, J = 1.4, 8.3 Hz), 8.05 (1H, s), | Ref. Ex. 154 |
| 1070 | | 1H-NMR (CDCl3) δ: 6.78 (1H, dd, J = 0.8, 3.3 Hz), 7.15 (1H, dt, J = 0.9, 8.3 Hz), 7.22-7.23 (1H, m), 7.34 (1H, ddd, J = 0.9, 2.0, 8,0 Hz), 7.50-7.58 (2H, m), 7.72 (1H, dd, J = 1.3, 8.2 Hz), 7.79 (1H, d, J = 8.2 Hz), 8.07 (1H, s), 10.05 (1H, s). | Ref. Ex. 154 |
| 1071 | | 1H-NMR (CDCl3) δ: 6.82 (1H, dd, J = 0.8, 3.3 Hz), 7.57 (1H, d, J = 3.3 Hz), 7.66 (2H, J = 8.4 Hz), 7.74 (1H, dd, J = 1.3, 8.2 Hz), 7.81 (1H, d, J = 8.2 Hz), 7.85 (2H, d, J = 8.4 Hz), 8.09 (1H, s), 10.05 (1H, s). | Ref. Ex. 154 |
| 1072 | | 1H-NMR (CD3C) δ: 6.76 (1H, dd, J = 0.8, 3.2 Hz), 7.23-7.30 (2H, m), 7.44-7.51 (3H, m), 7.70 (1H, dd, J = 1.3, 8.2 Hz), 7.79 (1H, d, J = 8.2 Hz), 7.96 (1H, s), 10.03 (1H, s). | Ref. Ex. 76 Ref. Ex. 48 |
| 1073 | | 1H-NMR (CDCl3) δ: 3.21 (2H, t, J = 8.4 Hz), 3.87 (3H, s), 3.98 (2H, t, J = 8.4 Hz), 6.73-6.84 (1H, m), 7.02-7.16 (2H, m), 7.18-7.26 (2H, m), 7.51 (1H, dd, J = 1.4, 7.6 Hz). | Ref. Ex. 1014 |
| 1074 | | 1H-NMR (CDCl3) δ: 3.24 (2H, t, J = 8.4 Hz), 4.01 (2H, t, J = 8.4 Hz), 6.76-6.86 (1H, m), 7.03-7.19 (3H, m), 7.29-7.31 (2H, m), 9.88 (1H, s). | Ref. Ex. 76 Ref. Ex. 48 |

US 10,626,095 B2
473
474
TABLE 2-continued
| Ref. Ex. No | STR | 1H-NMR | ref. |
|---|---|---|---|
| 1075 | 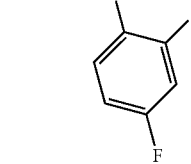 | 1H-NMR (CDCl3) δ: 6.79 (1H, dd, J = 0.8, 3.2 Hz), 7.04-7.15 (2H, m), 7.44 (1H, dd, J = 1.5, 3.2 Hz), 7.45-7.54 (1H, m), 7.71 (1H, dd, J = 1.3, 8.2 Hz), 7.76 (1H, s), 7.79 (1H, d, J = 8.2 Hz), 10.02 (1H, s). | Ref. Ex. 154 |
| 1076 | 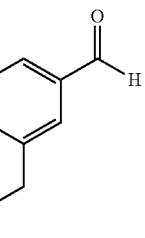 | 1H-NMR (CDCl3) δ: 4.09 (2H, s), 7.05 (1H, d, J = 9.1 Hz), 7.20-7.26 (2H, m), 7.41 (1H, s), 7.58 (1H, s), 7.76 (1H, s), 3.95 (1H, s). | Ref. Ex. 183 |
| 1077 | 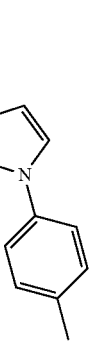 | 1H-NMR (CDCl3) δ: 2.46 (3H, s), 6.74 (1H, dd, J = 0.8, 3.2 Hz), 7.33-7.34 (4H, s), 7.53 (1H, d, J = 3.2 Hz), 7.70 (1H, dd, J = 1.3, 3.2 Hz), 7.78 (1H, d, J = 8.2 Hz), 8.01 (1H, s), 10.01 (1H, s). | Ref. Ex. 154 |
| 1078 | 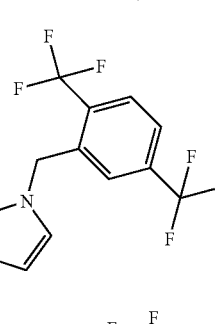 | 1H-NMR (CDCl3) δ: 5.67 (2H, s), 6.74 (1H, dd, J = 0.7, 3.2 Hz), 6.79 (1H, s), 7.35 (1H, d, J = 3.2 Hz), 7.64-7.74 (3H, m), 7.80 (1H, d, J = 8.2 Hz), 7.90 (1H, d, J = 8.3 Hz), 10.01 (1H, s). | Ref. Ex. 184 |
| 1079 | 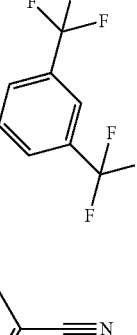 | 1H-NMR (CDCl3) δ: 5.54 (2H, s), 6.72 (1H, dd, J = 0.8, 3.2 Hz), 7.35 (1H, d, J = 3.2 Hz), 7.51 (2H, s), 7.69 (1H, dd, J = 1.2, 8.3 Hz), 7.78-7.84 (3H, m), 10.03 (1H, s). | Ref. Ex. 184 |
| 1080 |  | 1H-NMR (CDCl3) δ: 7.77-7.80 (2H, m), 8.11-8.15 (2H, m), 8.27 (1H, s), 10.13 (1H, s). | Ref. Ex. 63 |

TABLE 2-continued

| Ref. Ex. No | STR | 1H-NMR | ref. |
|---|---|---|---|
| 1081 | | 1H-NMR (CDCl3) δ: 4.14 (2H, s), 7.06 (1H, d, J = 8.7 Hz), 7.23-7.35 (3H, m), 7.63 (2H, s), 9.99 (1H, s). | Ref. Ex. 183 |
| 1082 | | 1H-NMR (CDCl3) δ: 7.50-7.54 (1H, m), 7.85 (1H, s), 7.94 (1H, s), 8.03 (1H, d, J = 8.7 Hz), 8.22 (1H, s), 8.46 (1H, s), 10.12 (1H, s). | Ref. Ex. 183 |
| 1083 | | 1H-NMR (CDCl3) δ: 3.92 (3H, s), 6.29 (1H, d, J = 4.2 Hz), 6.88-6.93 (1H, m), 8.97 (1H, d, J = 4.0 Hz), 7.13-7.31 (2H, m), 9.60 (1H, s). | Ref. Ex. 228 |
| 1084 | | 1H-NMR (CDCl3) δ: 5.31 (2H, s), 7.26-7.36 (3H, m), 7.61 (1H, t, J = 7.5 Hz), 7.75 (1H, d, J = 8.1 Hz), 7.89 (1H, d, J = 7.5 Hz), 7.97 (1H, s), 10.06 (1H, s). | Ref. Ex. 82 |
| 1085 | | 1H-NMR (CDCl3) δ: 3.93 (3H, s), 6.31 (1H, d, J = 3.9 Hz), 6.99 (1H, d, J = 3.9 Hz), 7.32 (2H, d, J = 8.1 Hz), 7.44-7.47 (2H, m), 9.60 (1H, s). | Ref. Ex. 228 |

TABLE 2-continued

| Ref. Ex. No | STR | 1H-NMR | ref. |
|---|---|---|---|
| 1086 | | 1H-NMR (CDCl3) δ: 7.38-7.46 (1H, m), 7.50-7.54 (1H, m), 7.95-7.96 (1H, m), 8.04-8.10 (2H, m), 8.95-8.98 (1H, m), 10.11 (1H, s). | Ref. Ex. 183 |
| 1087 | | 1H-NMR (CDCl3) δ: 3.17-3.22 (2H, m), 3.36-3.41 (2H, m), 7.15-7.30 (4H, m), 7.44-7.51 (2H, m), 8.91 (1H, d, J = 4.8 Hz), 9.99 (1H, s). | Ref. Ex. 34 |
| 1088 | | 1H-NMR (CDCl3) δ: 3.27-3.32 (2H, m), 3.41-3.46 (2H, m), 7.42-7.54 (3H, m), 7.70-7.73 (1H, m), 7.77 (1H, s), 7.92 (1H, d, J = 4.8 Hz), 9.99 (1H, s). | Ref. Ex. 48 |
| 1089 | | 1H-NMR (CDCl3) δ: 3.92 (3H, s), 6.82-6.84 (1H, m), 7.10-7.12 (3H, m), 7.27 (1H, s), 7.69-7.70 (1H, m), 9.88 (1H, s). | Ref. Ex. 234 |
| 1090 | | 1H-NMR (CDCl3) δ: 1.42 (3H, t, J = 7.2 Hz), 4.03-4.11 (4H, m), 6.97-6.98 (1H, m), 7.24-7.29 (4H, m), 7.55 (1H, s), 7.57 (1H, s), 9.92 (1H, s). | Ref. Ex. 183 |

TABLE 2-continued

| Ref. Ex. No | STR | 1H-NMR | ref. |
|---|---|---|---|
| 1091 | | 1H-NMR (CDCl3) δ: 3.99 (2H, s), 7.02-7.22 (3H, m), 7.40 (1H, s), 7.56 (1H, s), 7.73 (1H. s), 9.94 (1H, s). | Ref. Ex. 183 |
| 1092 | | 1H-NMR (CDCl3) δ: 6.80 (1H, dd, J = 0.6, 3.3 Hz), 7.11-7.20 (1H, m), 7.23-7.37 (2H, m), 7.48 (1H, dd, J = 1.9, 3.2 Hz), 7.73 (1H, dd, J = 1.3, 8.2 Hz), 7.80 (1H, d, J = 8.2 Hz), 7.65 (1H, s), 10.05 (1H, s). | Ref. Ex. 154 |
| 1093 | | 1H-NMR (CDCl3) δ: 4.12 (2H, s), 7.30-7.34 (3H, m), 7.55-7.63 (4H, m), 9.96 (1H, s). | Ref. Ex. 183 |
| 1094 | | 1H-NMR (CDCl3) δ: 1.45 (3H, t, J = 7.1 Hz), 4.47 (2H, q, J = 7.1 Hz), 7.54-7.58 (2H, m), 7.72-7.82 (6H, m). | Ref. Ex. 112 |
| 1095 | | 1H-NMR (CDCl3) δ: 1.45 (3H, t, J = 7.2 Hz), 4.47 (2H, q, J = 7.2 Hz), 7.55-7.59 (2H, m), 7.79-7.84 (2H, m), 7.89 (1H, s), 8.05 (2H, s). | Ref. Ex. 112 |

TABLE 2-continued

| Ref. Ex. No | STR | 1H-NMR | ref. |
|---|---|---|---|
| 1096 | | 1H-NMR (CDCl3) δ: 1.41 (3H, t, J = 7.1 Hz), 4.40 (2H, q, J = 7.1 Hz), 7.32 (2H, d, J = 8.1 Hz), 8.01-8.05 (2H, m), 8.42 (1H, s). | Ref. Ex. 14 |
| 1097 | | 1H-NMR (CDCl3) δ: 7.70-7.79 (3H, m), 8.09-8.15 (2H, m), 8.39 (1H, s), 9.10 (1H, s), 10.11 (1H, s). | Ref. Ex. 112 |
| 1098 | | 1H-NMR (CDCl3) δ: 7.59-7.63 (2H, m), 7.84 (1H, s), 7.89 (1H, s), 7.92 (1H, s), 8.07 (2H, s), 9.93 (1H, s). | Ref. Ex. 76 Ref. Ex. 48 |
| 1099 | | 1H-NMR (CDCl3) δ: 7.59-7.63 (2H, m), 7.75 (4H, s), 7.78-7.87 (2H, m), 9.91 (1H, s). | Ref. Ex. 76 Ref. Ex. 48 |
| 1100 | | 1H-NMR (CDCl3) δ: 4.13 (2H, s), 7.01-7.07 (1H, m), 7.33 (2H, d, J = 8.1 Hz), 7.54-7.61 (3H, m), 10.31 (1H, s). | Ref. Ex. 183 |
| 1101 | | 1H-NMR (CDCl3) δ: 7.34 (2H, dd, J = 0.8, 8.9 Hz), 8.06-8.11 (2H, m), 0.45 (1H, s), 10.06 (1H, s). | Ref. Ex. 63 |

TABLE 2-continued

| Ref. Ex. No | STR | 1H-NMR | ref. |
|---|---|---|---|
| 1102 | | 1H-NMR (CDCl3) δ: 3.74 (3H, s), 6.27 (1H, d, J = 3.9 Hz), 6.98 (1H, d, J = 3.8 Hz), 7.08-7.12 (1H, m), 7.25-7.31 (1H, m), 7.79-7.84 (1H, m), 9.81 (1H, s). | Ref. Ex. 228 |
| 1103 | | 1H-NMR (CDCl3) δ: 6.64-6.66 (1H, m), 7.28-7.31 (1H, m), 7.44-7.53 (2H, m), 7.66 (1H, s), 7.75 (1H, s), 7.91 (1H, s), 8.10 (1H, s), 8.29 (1H, brs), 10.09 (1H, s). | Ref. Ex. 112 |
| 1104 | | 1H-NMR (CDCl3) δ: 1.98-2.04 (2H, m), 2.07-2.13 (2H, m), 3.44 (2H, t, J = 6.8 Hz), 3.67 (2H, t, J = 6.8 Hz), 3.97 (3H, s), 6.98 (1H, s). | Ref. Ex. 1173 |
| 1107 | | 1H-NMR (CDCl3) δ: 3.92 (3H, s), 4.00 (2H, s), 6.94 (1H, d, J = 8.7 Hz), 7.29-7.36 (3H, m), 7.54 (2H, d, J = 8.7 Hz), 7.68 (1H, s), 10.45 (1H, s). | Ref. Ex. 183 |
| 1108 | | 1H-NMR (CDCl3) δ: 4.09 (2H, s), 6.96 (1H, d, J = 11.1 Hz), 7.10 (1H, d, J = 7.8 Hz), 7.30 (2H, d, J = 8.1 Hz), 7.59 (2H, d, J = 8.1 Hz), 7.82 (1H, t, J = 7.6 Hz), 10.32 (1H, s). | Ref. Ex. 183 |

TABLE 2-continued

| Ref. Ex. No | STR | 1H-NMR | ref. |
|---|---|---|---|
| 1109 | | 1H-NMR (CDCl3) δ: 6.68 (1H, s), 7.28-7.36 (3H, m), 7.49 (1H, d, J = 8.1 Hz), 7.73 (1H, s), 7.84 (1H, s), 8.15 (1H, s), 8.39 (1H, brs), 10.10 (1H, s). | Ref. Ex. 112 |
| 1110 | | 1H-NMR (CDCl3) δ: 7.37-7.40 (1H, m), 7.64 (1H, d, J = 1.9 Hz), 7.70-7.76 (2H, m), 8.07-8.10 (1H, m), 8.48-8.52 (1H, m), 8.73-8.75 (1H, m), 10.14 (1H, s). | Ref. Ex. 76<br>Ref. Ex. 48 |
| 1111 | | 1H-NMR (CDCl3) δ: 4.03 (2H, s), 6.79-6.80 (1H, m), 7.05-7.07 (1H, m), 7.20-7.35 (9H, m), 7.63-7.64 (1H, m), 9.85 (1H, s). | Ref. Ex. 234 |
| 1112 | | 1H-NMR (CDCl3) δ: 6.86-6.88 (1H, m), 7.19-7.21 (1H, m), 7.50-7.57 (4H, m), 7.61-7.68 (1H, m), 7.77-7.84 (3H, m), 7.94-7.99 (2H, m), 9.90 (1H, s). | Ref. Ex. 234 |
| 1113 | | 1H-NMR (CDCl3) δ: 6.79-6.81 (1H, m), 7.03-7.20 (6H, m), 7.35-7.41 (4H, m), 7.61-7.62 (1H, m), 9.85 (1H, s). | Ref. Ex. 234 |
| 1114 | | 1H-NMR (CDCl3) δ: 2.41 (3H, s), 4.02 (2H, s), 7.13-7.22 (5H, m), 7.51 (1H, s), 7.55 (1H, s), 9.95 (1H, s). | Ref. Ex. 183 |

| Ref. Ex. No | STR | 1H-NMR | ref. |
|---|---|---|---|
| 1115 | 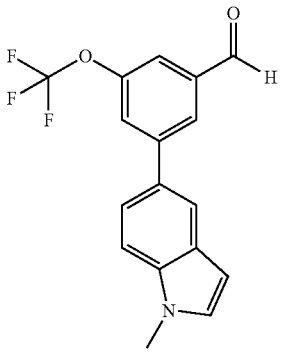 | 1H-NMR (CDCl3) δ: 3.86 (3H, s), 6.57-6.58 (1H, m), 7.13-7.14 (1H, m), 7.42-7.50 (2H, m), 7.65 (1H, s), 7.75 (1H, s), 7.88 (1H, s), 8.07-8.10 (1H, m), 10.07 (1H, s). | Ref. Ex. 112 |
| 1116 | 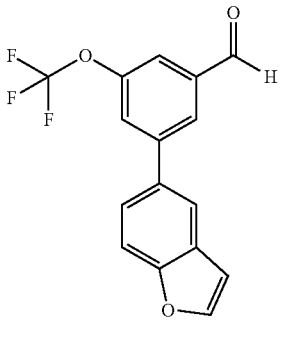 | 1H-NMR (CDCl3) δ: 6.85-6.86 (1H, m), 7.52-7.56 (1H, m), 7.63 (1H, d, J = 8.6 Hz), 7.69-7.73 (3H, m), 7.84 (1H, d, J = 1.8 Hz), 8.07 (1H, t, J = 1.5 Hz), 10.09 (1H, s). | Ref. Ex. 112 |
| 1117 | 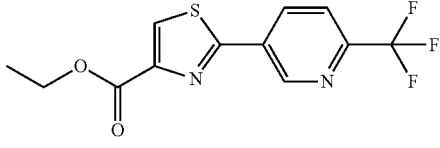 | 1H-NMR (CDCl3) δ: 1.45 (3H, t, J = 7.1 Hz), 4.48 (2H, q, J = 7.1 Hz), 7.81 (1H, d, J = 8.2 Hz), 8.30 (1H, s), 8.55 (1H, dd, J = 1.6, 8.2 Hz), 9.28 (1H, d, J = 1.9 Hz), | Ref. Ex. 2 |
| 1118 | 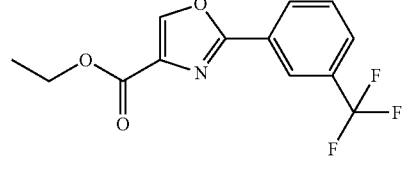 | 1H-NMR (CDCl3) δ: 1.42 (3H, t, J = 7.1 Hz), 4.45 (2H, q, J =7.1 Hz), 7.63 (1H, t, J = 7.8 Hz), 7.76 (1H, d, J = 7.7 Hz), 8.30-8.32 (2H, m), 8.41 (1H, s). | Ref. Ex. 2 |
| 1119 | 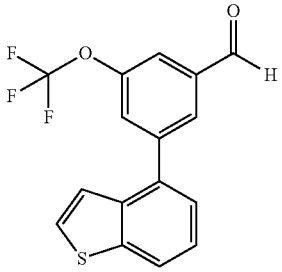 | 1H-NMR (CDCl3) δ: 7.37-7.40 (2H, m), 7.46 (1H, t, J = 7.7 Hz), 7.55 (1H, d, J = 5.6 Hz), 7.71 (1H, s), 7.78 (1H, s), 7.94-7.98 (1H, m), 8.04 (1H, t, J = 1.4 Hz), 10.10 (1H, s) | Ref. Ex. 112 |

TABLE 2-continued

| Ref. Ex. No | STR | 1H-NMR | ref. |
|---|---|---|---|
| 1120 | | 1H-NMR (CDCl3) δ: 7.40 (1H, d, J = 5.2 Hz), 7.55 (1H, d, J = 5.2 Hz), 7.61-7.64 (1H, m), 7.70-7.78 (2H, m), 7.94 (1H, d, J = 8.3 Hz), 8.11-8.15 (2H, m), 10.10 (1H, s). | Ref. Ex. 112 |
| 1121 | | 1H-NMR (CDCl3) δ: 3.30 (2H, t, J = 8.7 Hz), 4.66 (2H, t, J = 8.7 Hz), 6.89 (1H, d, J = 8.3 Hz), 7.36-7.40 (1H, m), 7.46 (1H, s), 7.63 (2H, s), 7.98 (1H, s), 10.06 (1H, s). | Ref. Ex. 112 |
| 1122 | | 1H-NMR (CDCl3) δ: 1.96-2.03 <4H. m), 3.57-3.67 (4H. m), 3.94 (3H, s), 6.45 (1H,s), 9.81 (1H, s). | Ref. Ex. 318 |
| 1124 | | 1H-NMR (CDCl3) δ: 1.42 (3H, t, J = 7.1 Hz), 4.44 (2H, q, J = 7.1 Hz), 7.64 (1H, t, J = 7.9 Hz), 7.79 (1H, d, J = 7.8 Hz), 8.18 (1H, d, J = 7.9 Hz), 8.25 (1H, s). | Ref. Ex. 1123 |
| 1125 | | 1H-NMR (CDCl3) δ: 7.84 (1H, d, J = 8.2 Hz), 8.32 (1H, s), 8.52 (1H, dd, J = 1.9, 8.1 Hz), 9.31 (1H, d, J = 1.8 Hz), 10.15 (1H, s). | Ref. Ex. 63 |
| 1126 | | 1H-NMR (CDCl3) δ: 6.85-6.87 (1H, m), 7.11-7.12 (1H, m), 7.62 (1H, s), 7 69-7.70 (1H, m), 7.76-7.79 (2H, m), 9.89 (1H, s). | Ref. Ex. 234 |

TABLE 2-continued

| Ref. Ex. No | STR | 1H-NMR | ref. |
|---|---|---|---|
| 1127 | | 1H-NMR (CDCl3) δ: 7.66 (1H, t, J = 7.8 Hz), 7.79 (1H, d, J = 7.8 Hz), 8.31 (1H, d, J = 7.8 Hz), 8.37 (1H, s), 8.40 (1H, s), 10.04 (1H, s). | Ref. Ex. 63 |
| 1128 | | 1H-NMR (CDCl3) δ: 1.93-2.01 (4H, m), 3.62 (4H, brs), 3.93 (3H, s), 3.94 (3H, s), 6.61 (1H, s). | Ref. Ex. 1173 |
| 1129 | | 1H-NMR (CDCl3) δ: 7.47-7.51 (2H, m), 7.96-8.01 (2H, m), 10.23 (1H, s). | Ref. Ex. 63 |
| 1130 | | 1H-NMR (CDCl3) δ: 7.67 (1H, t, J = 7.9 Hz), 7.83 (1H, d, J = 7.9 Hz), 8.21 (1H, d, J = 7.9 Hz), 8.31 (1H, s), 10.26 (1H, s). | Ref. Ex. 63 |
| 1131 | | 1H-NMR (CDCl3) δ: 5.17 (2H, s), 7.26-7.29 (2H, m), 7.48-7.50 (3H, m), 7.64 (1H, s), 7.75 (1H, s), 10.02 (1H, s). | Ref. Ex. 82 |
| 1132 | | 1H-NMR (CDCl3) δ: 0.90-0.94 (3H, m), 1.33-1.39 (4H, m), 1.46-1.48 (2H, m), 1.78-1.85 (2H, m), 4.06 (2H, t, J = 6.5 Hz), 7.39 (1H, s), 7.55 (1H, s), 7.69 (1H, s), 10.01 (1H, s). | Ref. Ex. 82 |

TABLE 2-continued

| Ref. Ex. No | STR | 1H-NMR | ref. |
| --- | --- | --- | --- |
| 1133 | | 1H-NMR (CDCl3) δ: 7.43 (1H, d, J = 5.5 Hz), 7.55 (1H, d, J = 5.5 Hz), 7.58-7.62 (1H, m), 7.70-7.74 (1H, m), 7.76 (1H, s), 8.01 (1H, d, J = 8.4 Hz), 8.07 (1H, d, J = 1.7 Hz), 8.12 (1H, t, J = 1.7 Hz), 10.10 (1H, s). | Ref. Ex. 112 |
| 1134 | | 1H-NMR (CDCl3) δ: 2.88-2.97 (4H, m), 7.32-7.55 (5H, m), 7.71 (1H, s), 7.71 (1H, s), 9.93 (1H, s). | Ref. Ex. 150 |
| 1135 | | 1H-NMR (CDCl3) δ: 7.18 (2H, t, J = 8.7 Hz), 7.60-7.67 (3H, m), 8.00 (1H, d, J = 8.4 Hz), 8.06 (2H, s), 10.13 (1H, s). | Ref. Ex. 112 |
| 1136 | | 1H-NMR (CDCl3) δ: 1.42-1.56 (2H, m), 1.75-1.80 (2H, m), 2.06-2.14 (1H, m), 3.42-3.51 (2H, m), 3.90-3.95 (2H, m), 4.02-4.07 (2H, m), 7.39 (1H, s), 7.55 (1H, s), 7.71 (1H, s), 10.01 (1H, s). | Ref. Ex. 82 |
| 1137 | | 1H-NMR (CDCl3) δ: 1.44 (3H, t, J = 7.1 Hz), 4.46 (2H, q, J = 7.1 Hz), 7.54 (1H, d, J = 8.4 Hz), 7.63 (1H, dd, J = 2.1, 8.4 Hz), 8.15 (1H, d, J = 2.1 Hz), 8.20 (1H, s). | Ref. Ex. 2 |
| 1138 | | 1H-NMR (CDCl3) δ: 5.40 (2H, s), 7.29-7.35 (1H, m), 7.52-7.60 (2H, m), 7.75 (1H, d, J = 8.7 Hz), 7.87 (1H, d, J = 8.2 Hz), 8.12 (1H, s), 9.93 (1H, s). | Ref. Ex. 82 |

TABLE 2-continued

| Ref. Ex. No | STR | 1H-NMR | ref. |
|---|---|---|---|
| 1139 | | 1H-NMR (CDCl3) δ: 5.39 (2H, s), 7.18-7.31 (2H, m), 7.50-7.55 (1H, m), 7.75 (1H, d, J = 7.9 Hz), 7.87 (1H, d, J = 7.9 Hz), 8.14 (1H, s), 10.42 (1H, s). | Ref. Ex. 82 |
| 1140 | | 1H-NMR (CDCl3) δ: 7.78 (2H, d, J = 8.2 Hz), 8.24 (2H, d, J = 8.2 Hz), 8.37 (1H, s), 10.40 (1H, s). | Ref. Ex. 63 |
| 1141 | | 1H-NMR (CDCl3) δ: 5.24 (2H, s), 7.13-7.25 (2H, m), 7.45-7.50 (1H, m), 7.58 (2H, d, J = 8.1 Hz), 7.68 (2H, d, J = 8.1 Hz), 10.40 (1H, s). | Ref. Ex. 82 |
| 1142 | | 1H-NMR (CDCl3) δ: 2.05 (4H, brs), 3.44 (2H, brs), 3.76 (2H, brs), 4.59 (2H, d, J = 0.7 Hz), 4.70 (2H, s), 6.48 (1H, s), 7.30-7.43 (5H, m), 7.66 (2H, d, J = 8.1 Hz), 8.50 (2H, d, J = 8.1 Hz). | Ref. Ex. 1173 |
| 1143 | | 1H-NMR (CDCl3) δ: 2.06 (4H, brs), 3.40 (2H, brs), 3.61 (1H, brs), 3.78 (2H, brs), 4.66 (2H, d, J = 2.0 Hz), 6.18 (1H, s), 7.69 (2H, d, J = 8.1 Hz), 8.54 (2H, d, J = 8.1 Hz). | Ref. Ex. 750 |

| Ref. Ex. No | STR | 1H-NMR | ref. |
|---|---|---|---|
| 1144 | | 1H-NMR (CDCl3) δ: 3.94 (3H, s), 6.34 (1H, d, J = 4.0 Hz), 6.99 (1H, d, J = 4.0 Hz), 7.27-7.29 (2H, m), 7.35-7.38 (1H, m), 7.48-7.53 (1H, m), 9.61 (1H, s). | Ref. Ex. 228 |
| 1145 | | 1H-NMR (CDCl3) δ: 3.05 (3H, s), 4.60 (2H, s), 6.72-6.77 (3H, m), 7.20-7.24 (2H, m), 7.49-7.51 (2H, m), 7.77 (2H, s), 10.00 (1H, s). | Ref. Ex. 82 |
| 1146 | | 1H-NMR (CDCl3) δ: 4.05 (2H, s), 6.78-6.79 (1H, m), 7.05-7.06 (1H, m), 7.20-7.24 (5H, m), 7.30-7.43 (4H, m), 7.63-7.64 (1H, m), 9.84 (1H, s). | Ref. Ex. 234 |
| 1147 | | 1H-NMR (CDCl3) δ: 2.97 (2H, t, J = 7.2 Hz), 4.10 (2H, t, J = 7.2 Hz), 5.94 (2H, s), 6 46-6.49 (1H, m), 6.53 (1H, s), 6.57-6.61 (2H, m), 7.71 (1H, d, J = 7.8 Hz), 7.13-7.14 (1H, m), 9.69 (1H, s). | Ref. Ex. 234 |
| 1148 | | 1H-NMR (CDCl3) δ: 2.05-2.13 (4H, m), 3.46-3.50 (2H, m), 3.79-3.83 (2H, m), 6.80 (1H, s), 7.72 (2H, d, J = 8.2 Hz), 8.60 (2H, d, J = 8.2 Hz), 10.02 (1H, s). | Ref. Ex. 159 |
| 1149 | | 1H-NMR (DMSO-d6) δ: 4.42 (2H, s), 5.53 (1H, brs), 6.42 (1H, brs), 7.88 (2H, d, J = 8.2 Hz), 8.32 (2H, d, J = 8.2 Hz), 12.68 (1H, brs). | Ref. Ex. 33 |

TABLE 2-continued

| Ref. Ex. No | STR | 1H-NMR | ref. |
|---|---|---|---|
| 1150 | 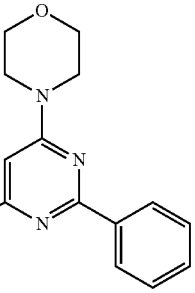 | 1H-NMR (CDCl3) δ: 3.69-3.76 (4H, m), 3.81-3.83 (4H, m), 4.61 (2H, s), 4.70 (2H, s), 6.66 (1H, s), 7.30-7.44 (8H, m), 8.34-8.38 (2H, m). | Ref. Ex. 1173 |
| 1151 | 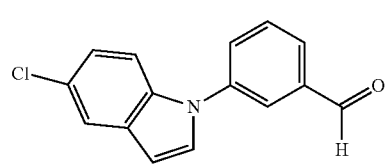 | 1H-NMR (CDCl3) δ: 6.67 (1H, d, J = 3.3 Hz), 7.20 (1H, dd, J = 2.0, 8.8 Hz), 7.39 (1H, d, J = 3.3 Hz), 7.49 (1H, d, J = 8.8 Hz), 7.67 (1H, d, J = 2.0 Hz), 7.69-7.80 (2H, m), 7.89 (1H, dt, J = 1.5, 7.2 Hz), 8.00 (1H, t, J = 1.6 Hz), 10.12 (1H, s). | Ref. Ex. 154 |
| 1152 | 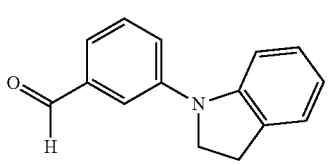 | 1H-NMR (CDCl3) δ: 3.17 (2H, t, J = 8.4 Hz), 4.02 (2H, t, J = 8.4 Hz), 6.81 (1H, dt, J = 1.0, 7.3 Hz), 7.08-7.15 (1H, m), 7.17-7.23 (2H, m), 7.41-7.55 (3H, m), 7.67-7.69 (1H, m), 10.00 (1H, s). | Ref. Ex. 114 Ref. Ex. 151 |
| 1153 | 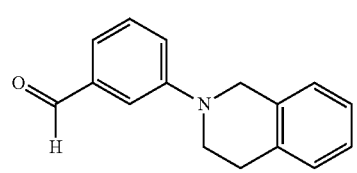 | 1H-NMR (CDCl3) δ: 3.02 (2H, t, J = 5.8 Hz), 3.64 (2H, t, J = 5.8 Hz), 4.49 (2H, s), 7.16-7.25 (5H, m), 7.26-7.31 (1H, m), 7.41-7.48 (2H, m), 9.99 (1H, s). | Ref. Ex. 114 Ref. Ex. 151 |
| 1154 | 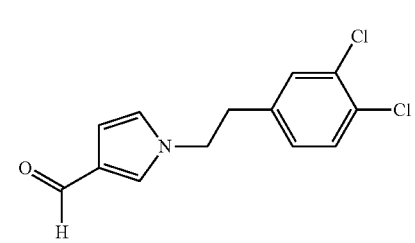 | 1H-NMR (CDCl3) δ: 3.03 (2H, t, J = 7.2 Hz), 4.13 (2H, t, J = 7.2 Hz), 6.56-6.63 (2H, m), 6.81 (1H, dd, J = 2.1, 8.2 Hz), 7.13-7.15 (2H, m), 7.34 (1H, d, J = 8.2 Hz), 9.70 (1H, s). | Ref. Ex. 234 |
| 1155 | 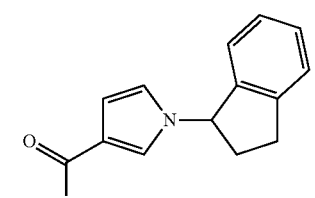 | 1HNMR (CDCl3) δ: 2.18-2.26 (1H, m), 2.70-2.76 (1H, m), 2.93-3.01 (1H, m), 3.10-3.20(1H, m), 5.61 (1H, t, J = 7.1 Hz), 6.64-6.69 (2H, m), 7.13 (1H, d, J = 7.5 Hz), 7.22-7.26 (2H, m), 7.33-7.35 (2H, m), 9.71 (1H, s). | Ref. Ex. 234 |
| 1156 | 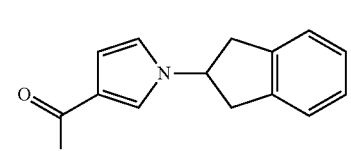 | 1H-NMR (CDCl3) δ: 3.23 (2H, dd, J = 5.1, 16.2 Hz), 3.54 (2H, dd, J = 7.5, 16.2 Hz), 4.89-4.98 (1H, m), 6.60-6.61 (1H, m), 6.66-6.69 (1H, m), 7.23-7.31 (5H, m), 9.70 (1H, s). | Ref. Ex. 234 |

TABLE 2-continued

| Ref. Ex. No | STR | 1H-NMR | ref. |
|---|---|---|---|
| 1157 | | 1H-NMR (CDCl3) δ: 5.23 (2H, s), 7.14-7.28 (2H, m), 7.45-7.68 (4H, m), 7.72 (1H, s), 10.40 (1H, s). | Ref. Ex. 82 |
| 1158 | | 1H-NMR (CDCl3) δ: 5.28 (2H, s), 7.18-7.36 (1H, m), 7.50-7.55 (1H, m), 7.89-7.94 (4H, m), 10.41 (1H, s). | Ref. Ex. 82 |
| 1159 | | 1H-NMR (CDCl3) δ: 1.38 (3H, t, J = 7.1 Hz), 4.38 (2H, q, J = 7.1 Hz), 7.24-7.29 (2H, m), 7.36-7.41 (2H, m), 7.73 (1H, s). | Ref. Ex. 9 |
| 1160 | | 1H-NMR (CDCl3) δ: 1.38 (3H, t, J = 7.1 Hz), 4.38 (2H, q, J = 7.1 Hz), 7.16-7.24 (2H, m), 7.34-7.39 (2H, m), 7.75 (1H, s). | Ref. Ex. 9 |
| 1161 | | 1H-NMR (CDCl3) δ: 1.38 (3H, t, J = 7.1 Hz), 4.38 (2H, q, J = 7.1 Hz), 7.16-7.24 (2H, m), 7.40 (1H, dd, J = 2.7, 6.0 Hz), 7.75 (1H, s). | Ref. Ex. 9 |

TABLE 2-continued

| Ref. Ex. No | STR | 1H-NMR | ref. |
|---|---|---|---|
| 1162 | | 1H-NMR (CDCl3) δ: 7.27-7.32 (2H, m), 7.39-7.44 (2H, m), 7.74 (1H, s), 9.79 (1H, s). | Ref. Ex. 63 |
| 1163 | | 1H-NMR (CDCl3) δ: 7.28-7.31 (2H, m), 7.38-7.43 (2H, m), 7.76 (1H, s), 9.79 (1H, s). | Ref. Ex. 63 |
| 1164 | | 1H-NMR (CDCl3) δ: 7.18-7.29 (2H, m), 7.44 (1H, dd, J = 2.7, 6.0 Hz), 7.76 (1H, s), 9.79 (1H, s). | Ref. Ex. 63 |
| 1165 | | 1H-NMR (CDCl3) δ: 7.05 (1H, s), 7.86 (2H, d, J = 8.3 Hz), 8.40 (2H, d, J = 8.3 Hz), 10.02 (1H, s). | Ref. Ex. 159 |
| 1166 | | 1H-NMR (CDCl3) δ: 5.42 (2H, m), 6.67 (1H, dd, J = 0.8, 3.2 Hz), 7.17 (2H, d, J = 7.9 Hz), 7.33-7.38 (2H, m), 7.54-7.61 (3H, m), 7.73 (1H, dd, J = 0.5, 8.2 Hz). | Ref. Ex. 184 |
| 1167 | | 1H-NMR (CDCl3) δ: 5.48 (2H, s), 6.67 (1H, dd, J = 0.7, 3.1 Hz), 7.19 (2H, d, J = 8.0 Hz), 7.37 (1H, d, J = 3.1 Hz), 7.57 (2H, d, J = 8.0 Hz), 7.66 (1H, dd, J = 1.3, 8.2 Hz), 7.77 (1H, d, J = 8.2 Hz), 7.81 (1H, s), 10.02 (1H, s). | Ref. Ex. 318 |

TABLE 2-continued

| Ref. Ex. No | STR | 1H-NMR | ref. |
|---|---|---|---|
| 1168 | | 1H-NMR (CDCl3) δ: 3.64 (1H, brs), 3.73-377 (4H, m), 3.82-3.84 (4H, m), 4.66 (2H, s), 6.36 (1H, s), 7.42-7.48 (3H, m), 8.33-8.43 (2H, m). | Ref. Ex. 750 |
| 1169 | | 1H-NMR (CDCl3) δ: 3.96 (3H, s), 5.86 (1H, s), 6.94-S.98 (1H, m), 7.04-7.08 (1H, m), 10.25 (1H, s). | Ref. Ex. 618 |
| 1170 | | 1H-NMR (CDCl3) δ: 4.00 (3H, s), 5.34 (2H, s), 6.92-6.98 (1H. m), 7.16-7.19 (1H, m). 7.77 (1H. d, J = 8.2 Hz), 7.89 (1H, d, J = 8.2 Hz), 8.13 (1H, s), 10.40 (1H, d, J = 3.4 Hz). | Ref. Ex. 82 |
| 1171 | | 1H-NMR (CDCl3) δ: 3.65-4.06 (8H, m), 6.97 (1H, s), 7.46-7.52 (3H, m), 8.41-8.48 (2H, m), 10.03 (1H, s). | Ref. Ex. 159 |
| 1172 | | 1H-NMR (CDCl3) δ: 4.00 (3H, s), 7.12-7.22 (1H, m), 7.35-7.38 (1H, m), 7.65 (1H, t, J = 7.8 Hz), 7.72-7.77 (1H, m), 8.22-8.26 (1H, m), 8.41-846 (1H, m), 8.89-8.91 (1H, m). | Ref. Ex. 129 |
| 1174 | | 1H-NMR (CDCl3) δ: 3.53-3.57 (4H, m), 3.81-3.84 (4H, m), 7.50 (1H, s). 9.72 (1H, s). | Ref. Ex. 63 |

TABLE 2-continued

| Ref. Ex. No | STR | 1H-NMR | ref. |
|---|---|---|---|
| 1175 | | 1HNMR (CDCl3) δ: 5.18 (2H, s), 7.24 (1H, s), 7.36 (1H, s), 7.48 (1H, s), 7.55 (2H, d, J = 7.8 Hz), 7.67 (2H, d, J = 7.8 Hz), 9.92 (1H, s). | Ref. Ex. 82 |
| 1176 | | 1H-NMR (CDCl3) δ: 5.16 (2H, s), 7.24-7.25 (1H, m), 7.37-7.38 (1H, m), 7.48 (1H, s), 7.55 (1H, d, J = 7.5 Hz), 7.59-7.65 (2H, m), 7.71 (1H, s), 9.92 (1H, s). | Ref. Ex. 82 |
| 1177 | | 1H-NMR (CDCl3) δ: 4.69 (2H, s), 4.71 (2H, s), 7.57 (1H, t, J = 7.5 Hz), 7.66 (1H, d, J = 7.5 Hz), 7.82-7.89 (5H, m), 10.05 (1H, s). | Ref. Ex. 100 |
| 1178 | | 1H-NMR (CDCl3) δ: 4.74 (2H, s), 4.82 (2H, s), 7.56 (1H, t, J = 7.7 Hz), 7.67 (2H, d, J = 7.7 Hz), 7.79 (1H, d, J = 8.1 Hz), 7.84-7.87 (1H, m), 7.90 (1H, s), 8.05 (1H, s), 10.05 (1H, s), | Ref. Ex. 100 |
| 1179 | | 1H-NMR (CDCl3) δ: 4.25 (2H, s), 7.34-7.36 (2H, m), 7.47-7.51 (3H, m), 7.60-7.62 (1H, m), 7.77-7.79 (1H, m), 7.86 (1H, s), 10.00 (1H, s). | Ref. Ex. 173 |

TABLE 2-continued

| Ref. Ex. No | STR | 1H-NMR | ref. |
|---|---|---|---|
| 1180 | | 1H-NMR (CDCl3) δ: 2.67 (3H, s), 7.57-7.68 (3H, m), 7.75-7.83 (3H, m), 7.88 (1H, s), 10.06 (1H, s). | Ref. Ex. 38, Ref. Ex. 19, Ref. Ex. 48 |
| 1181 | | 1H-NMR (CDCl3) δ: 2.65 (3H, s), 7.17 (2H, t, J = 8.7 Hz), 7.52-7.63 (3H, m), 7.69-7.75 (2H, m), 10.05 (1H, s). | Ref. Ex. 38, Ref. Ex. 19, Ref. Ex. 48 |
| 1182 | | 1H-NMR (CDCl3) δ: 3.05 (3H, 4.58 (2H, s), 6.53 (1H, dd, J = 3.0, 9.0 Hz), 6.78 (1H, d, J = 3.0 Hz), 7.21 (1H, d, J = 9.0 Hz), 7.44-7.54 (2H, m), 7.72 (1H, s), 7.79 (1H, d, J = 7.5 Hz), 10.00 (1H, m). | Ref. Ex. 82 |
| 1183 | | 1H-NMR (CDCl3) δ: 3.14 (3H, s), 4.66 (2H, s), 6.73 (2H, d, J = 8.4 Hz), 7.43-7.54 (4H, m), 7.73 (1H, s), 7.79 (1H, d, J = 7.2 Hz), 10.00 (1H, s). | Ref. Ex. 82 |
| 1184 | | 1H-NMR (CDCl3) δ: 5.16 (2H, s), 7.24-7.36 (4H, m), 7.50 (2H, s), 9.93 (1H, s). | Ref. Ex. 82 |

TABLE 2-continued
| Ref. Ex. No | STR | 1H-NMR | ref. |
|---|---|---|---|
| 1185 |  | 1H-NMR (CDCl3) δ: 7.49 (2H, d, J = 8.7 Hz), 7.59 (2H d, J = 8.7 Hz), 7.68 (1H, d, J = 8.5 Hz), 7.38 (1H, s), 7.92-7.96 (1H, m), 8.33 (1H, s), 10.10 (1H, s). | Ref. Ex. 147 |
| 1186 | 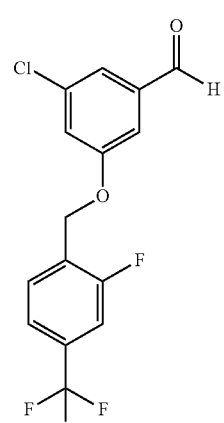 | 1H-NMR (CDCl3) δ: 5.23 (2H, s), 7-25-7.27 (1H, m), 7.37-7.44 (2H, m), 7.48-7.51 (2H, m), 7.62-7.69 (1H, m), 9.93 (1H, s). | Ref. Ex. 82 |
| 1187 |  | 1H-NMR (CDCl3) δ: 5.36 (2H, s), 7.24-7.27 <1H, m), 7.35-7.37 (1H, m), 7.51-7.52 (1H, m), 7.85-7.92 (2H, m), 7.83 (1H, s), 9.93 (1H, s). | Ref. Ex. 82 |
| 1188 | 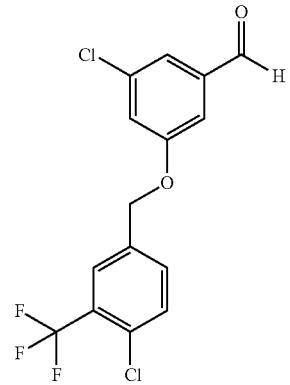 | 1H-NMR (CDCl3) δ: 5.12 (2H, s), 7.24-7.25 (1H, m), 7.35-7.36 (1H, m), 7.49-7.50 (1H, m), 7.55 (3H, s), 9.93 (1H, s) | Ref. Ex. 82 |

TABLE 2-continued

| Ref. Ex. No | STR | 1H-NMR | ref. |
|---|---|---|---|
| 1189 | | 1H-NMR (CDCl3) δ: 5.30 (2H, s), 7.51-7.61 (4H, m), 7.85-7.93 (2H, m), 9.95 (1H, s). | Ref. Ex. 82 |
| 1190 | | 1H-NMR (CDCl3) δ: 1.44 (3H, t, J = 7.1 Hz), 4.46 (2H, q, J = 7.1 Hz), 7.42-7.46 (2H, m), 7.50-7.58 (4H, m), 7.71-7.76 (2H, m). | Ref. Ex. 112 |
| 1191 | | 1H-NMR (CDCl3) δ: 1.05 (6H, s), 3.82 (4H, s), 7.64 (1H, d, J = 8.1 Hz), 7.92 (1H, d, J = 8.1 Hz), 8.03 (1H, s), 8.38 (1H, s), 10.12 (1H, s). | Ref. Ex. 75 |
| 1192 | | 1H-NMR (CDCl3) δ: 7.43-7.48 (2H, m), 7.54-7.60 (4H, m), 7.77 (1H, s), 7.79-7.83 (1H, m), 9.89 (1H, s). | Ref. Ex. 19, Ref. Ex. 147 |
| 1193 | | 1H-NMR (CDCl3) δ: 5.21 (2H, s), 7.13-7.17 (1H, m), 7.40 (1H, s), 7.51-7.66 (3H, m), 7.74 (1H, s), 7.85 (1H, d, J = 9.0 Hz), 7.95 (1H, s), 10.04 (1H, s). | Ref. Ex. 82 |
| 1194 | | 1H-NMR (CDCl3) δ: 5.39 (2H, s), 7.18 (1H, dd, J = 2.3, 8.8 Hz), 7.41 (1H, d, J = 2.3 Hz), 7.74 (1H, d, J = 8.4 Hz), 7.88 (2H, d, J = 6.8 Hz), 7.97 (1H, s), 8.09 (1H, s), 10.05 (1H, s). | Ref. Ex. 82 |

TABLE 2-continued

| Ref. Ex. No | STR | 1H-NMR | ref. |
|---|---|---|---|
| 1195 | | 1H-NMR (CDCl3) δ: 7.41 (1H, d, J = 9.0 Hz), 7.87 (1H, s), 7.80 (1H, d, J = 8.7 Hz), 7.87 (1H, s), 7.94 (1H, d, J = 8.3 Hz), 8.01 (1H, d, J = 8.3 Hz), 8.10 (1H, s), 10.15 (1H, s). | Ref. Ex. 91 |
| 1196 | | 1H-NMR (CDCl3) δ: 7.57 (1H, d, J = 5.0 Hz), 8.06-8.10 (2H, m), 8.60-8.63 (1H, m), 8.09 (1H, d, J = 5.0 Hz), 9.13 (1H, s), 10.16 (1H, s). | Ref. Ex. 91 |
| 1197 | | 1H-NMR (CDCl3) δ: 2.85-3.01 (4H, m), 6.85-6.95 (2H, m), 7.39-7.49 (2H, m), 7.69-7.75 (2H, m), 10.00 (1H, s). | Ref. Ex. 150 |
| 1198 | | 1H-NMR (CDCl3) δ: 2.99-3.05 (2H, m), 3.15-3.20 (2H, m), 7.45-7.52 (3H, m), 7.59 (1H, d, J = 7.8 Hz), 7.72-7.81 (3H, m), 10.02 (1H, s). | Ref. Ex. 150 |
| 1199 | | 1H-NMR (CDCl3) δ: 4.19 (4H, s), 7.03-7.06 (1H, m), 7.16-7.18 (2H, m), 7.38-7.41 (1H, m), 7.47 (1H, t, J = 7.8 Hz), 7.69-7.76 (2H, m), 10.00 (1H, s). | Ref. Ex. 150 |
| 1200 | | 1H-NMR (CDCl3) δ: 4.64 (2H, s), 4.68 (2H, s), 6.95-7.04 (2H, m), 7.16-7.22 (1H, m), 7.55 (1H, t, J = 7.5 Hz), 7.66 (1H, d, J = 7.5 Hz), 7.83 (1H, d, J = 7.5 Hz), 7.89 (1H, s), 10.04 (1H, s). | Ref. Ex. 100 |

TABLE 2-continued

| Ref. Ex. No | STR | 1H-NMR | ref. |
| --- | --- | --- | --- |
| 1201 | | 1H-NMR (CDCl3) δ: 5.05 (2H, s), 6.88-7.35 (4H, m), 7.47-7.50 (2H, m), 9.92 (1H, s). | Ref. Ex. 82 |
| 1202 | | 1H-NMR (CDCl3) δ: 1.39 (3H, t, J = 7.1 Hz), 4.39 (2H, q, J = 7.1 Hz), 7.21-7.25 (2H, m), 7.33-7.37 (2H, m), 7.51 (1H, brs), 7.55 (1H, s). | Ref. Ex. 184 |
| 1203 | | 1H-NMR (CDCl3) δ: 1.42 (3H, t, J = 7.1 Hz), 4.45 (2H, q, J = 7.1 Hz), 5.44 (2H, s), 7.16 (1H, dd, J = 2.6, 8.3 Hz), 7.25-7.30 (2H, m), 7.43 (1H, t, J = 8.0 Hz), 8.22 (1H, s). | Ref. Ex. 82 |
| 1204 | | 1H-NMR (CDCl3) δ: 1.42 (3H, t, J = 7.1 Hz), 4.45 (2H, q, J = 7.1 Hz), 5.40 (2H, s), 6.96-7.02 (2H, m), 7.16-7.19 (2H, m), 8.21 (1H, s). | Ref. Ex. 82 |
| 1205 | | 1H-NMR (CDCl3) δ: 5.45 (2H, s), 7.18 (1H, dd, J = 2.6, 8.2 Hz), 7.23-7.33 (2H, m), 7.45 (1H, t, J = 8.0 Hz), 8.23 (1H, s), 10.05 (1H, s). | Ref. Ex. 63 |
| 1206 | | 1H-NMR (CDCl3) δ: 5.40 (2H, s), 6.98-7.04 (2H, m), 7.17-7.20 (2H, m), 8.22 (1H, s), 10.04 (1H, s). | Ref. Ex. 63 |

TABLE 2-continued

| Ref. Ex. No | STR | 1H-NMR | ref. |
|---|---|---|---|
| 1207 | | 1H-NMR (CDCl3) δ: 4.66 (4H, s), 7.48-7.66 (6H, m), 7.82-7.85 (1H, m), 7.89 (1H, s), 10.04 (1H, s). | Ref. Ex. 100 |
| 1208 | | 1H-NMR (CDCl3) δ: 5.25 (2H, s), 7.32 (1H, d, J = 8.7 Hz), 7.41-7.50 (3H, m), 7.55 (1H, s), 7.60-7.63 (1H, m), 9.05 (1H, s). | Ref. Ex. 82 |
| 1209 | | 1H-NMR (CDCl3) δ: 5.31 (2H, s), 7.47-7.52 (2H, m), 7.63 (1H, d, J = 8.1 Hz), 7.88 (1H, s), 7.98 (2H, s), 9.96 (1H, s). | Ref. Ex. 82 |
| 1210 | | 1H-MMR (CDCl3) δ: 5.43 (2H, s), 7.48-7.50 (1H, m), 7.51 (1H, s), 7.63 (1H, d, J = 7.8 Hz), 7.74 (1H, d, J = 7.8 Hz), 7.86 (1H, d, J = 8.1 Hz), 8.26 (1H, s), 9.97 (1H, s). | Ref. Ex. 82 |

TABLE 2-continued
| Ref. Ex. No | STR | 1H-NMR | ref. |
|---|---|---|---|
| 1211 | 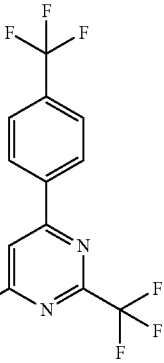 | 1H-NMR (CDCl3) δ: 4.75 (2H, s), 4.78 (2H, s), 7.32-7.43 (5H, m), 7.79 (2H, d, J = 8.2 Hz), 8.14 (1H, s), 8.29 (2H, d, J = 8.2 Hz). | Ref. Ex. 38 |
| 1212 | 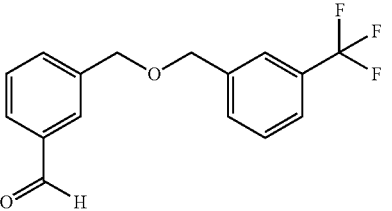 | 1H-NMR (CDCl3) δ: 4.65 (2H, s), 4.67 (2H, s), 7.46-7.67 (6H, m), 7.82-7.89 (2H, m), 10.04 (1H, s). | Ref. Ex. 100 |
| 1213 | 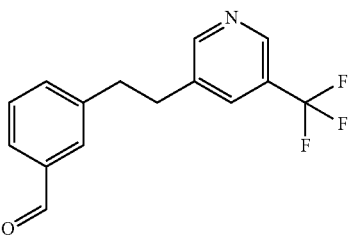 | 1H-NMR (CDCl3) δ: 3.05 (4H, s), 7.36-7.40 (1H, m), 7.47 (1H, t, J = 7.5 Hz), 7.65-7.76 (3H, m), 8.60 (1H, s), 6.74 (1H, s), 10.00 (1H, s). | Ref. Ex. 150 |
| 1214 | 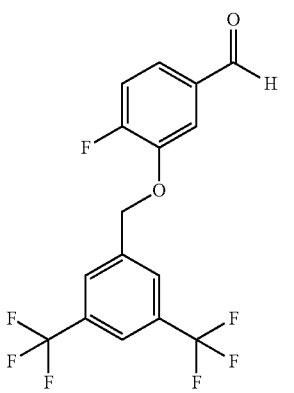 | 1H-NMR (CDCl3) δ: 5.29 (2H, s), 7.30-7.34 (1H, m), 7.51-7.61 (2H, m), 7.89 (1H, s), 7.94 (2H, s), 9.93 (1H, s). | Ref. Ex. 82 |
| 1215 | 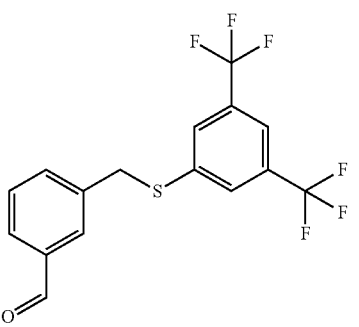 | 1H-NMR (CDCl3) δ: 4.26 (2H, s), 7.50-7.59 (2H, m), 7.65 (3H, s), 7.78-7.82 (2H, m), 10.00 (1H, s). | Ref. Ex. 173 |

TABLE 2-continued
| Ref. Ex. No | STR | 1H-NMR | ref. |
|---|---|---|---|
| 1216 | 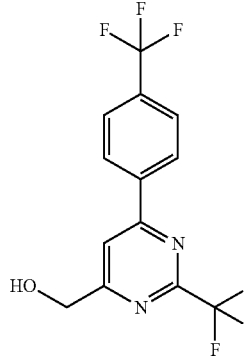 | 1H-NMR (CDCl3) δ: 2.76 (1H, t, J = 5.3 Hz), 4.96 (2H, d, J = 5.3 Hz), 7.81 (2H, d, J = 8,2 Hz), 8.04 (1H, s), 8.31 (2H, d, J = 8.2 Hz). | Ref. Ex. 750 |
| 1217 | 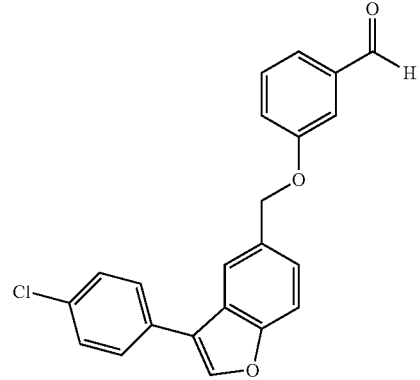 | 1H-NMR (CDCl3) δ: 5.23 (2H, s), 7.25-7.29 (1H, m), 7.43-7.60 (9H, m), 7.81 (1H, s), 7.86 (1H, s), 9.98 (1H, s). | Ref. Ex. 82 |
| 1218 | 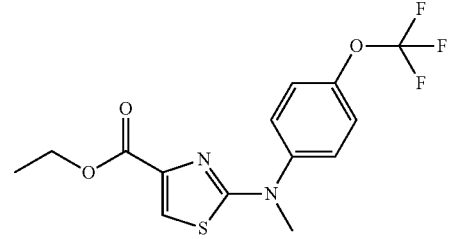 | 1H-NMR (CDCl3) δ: 1.38 (3H, t, J = 7.1 Hz), 3.59 (3H, s), 4.37 (2H, q, J = 7.1 Hz), 7.26-7.29 (2H, m), 7.39-7.44 (3H, m). | Ref. Ex. 12 |
| 1219 | 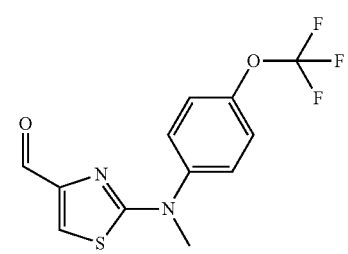 | 1H-NMR (CDCl3) δ: 3.59 (3H, s), 7.30 (2H, d, J = 8.9 Hz), 7.42-7.45 (3H, m), 9.75 (1H, s). | Ref. Ex. 63 |

TABLE 2-continued

| Ref. Ex. No | STR | 1H-NMR | ref. |
| --- | --- | --- | --- |
| 1220 | | 1H-NMR (CDCl3) δ: 7.84 (2H, d, J = 8.3 Hz), 8.37 (2H, d, J = 8.3 Hz), 8.42 (1H, s), 10.17 (1H, s). | Ref. Ex. 159 |
| 1221 | | 1H-NMR (CDCl3) δ: 0.90-1.10 (2H, m), 1.10-1.25 (3H, m), 1.57-1.58 (6H, m), 3.96 (2H, d, J = 7.2 Hz), 6.55 (1H, d, J = 3.1 Hz), 7.25-7.26 (1H, m), 7.32 (1H, dd, J = 1.2, 8.3 Hz), 7.64-7.68 (2H, m). | Ref. Ex. 184 |
| 1222 | | 1H-NMR (CDCl3) δ: 1.85-2.00 (4H, m), 2.00-2.15 (2H, m), 2.75-2.90 (1H, m), 4.15 (2H, d, J = 7.3 Hz), 6.55 (1H, dd, J = 0.7, 3.1 Hz), 7.27 (1H, d, J = 3.1 Hz), 7.33 (1H, dd, J = 1.4, 8.2 Hz), 7.64-7.69 (2H, m). | Ref. Ex. 184 |
| 1223 | | 1H-NMR (CDCl3) δ: 0.95-1.25 (5H, m), 1.55-1.80 (5H, m), 1.60-1.95 (1H, m), 4.02 (2H, d, J = 7.3 Hz), 6.55 (1H, dd, J = 0.6, 3.1 Hz), 7.30 (1H, d, J = 3.1 Hz), 7.61 (1H, dd, J = 1.3, 8.2 Hz), 7.72 (1H, d, J = 8.2 Hz), 7.91 (1H, s), 10.07 (1H, s). | Ref. Ex. 318 |
| 1224 | | 1H-NMR (CDCl3) δ: 1.76-1.99 (4H, m), 2.02-2.14 (2H, m), 2.78-2.94 (1H, m), 4.20 (2H, d, J = 7.3 Hz), 6.55 (1H, dd, J = 0.6, 3.1 Hz), 7.32 (1H, d, J = 3.1 Hz), 7.61 (1H, dd, J = 1.3, 8.2 Hz), 7.71 (1H, d, J = 8.2 Hz), 7.92 (1H, s), 10.07 (1H, s). | Ref. Ex. 318 |
| 1225 | | 1H-NMR (CDCl3) δ: 1.46-2.10 (4H, m), 3.70-3.87 (2H, m), 4.08-4.35 (3H, m), 6.57 (1H, d, J = 3.1 Hz), 7.31 (1H, dd, J = 1.3, 8.2 Hz), 7.38 (1H, d, J = 3.1 Hz), 7.66 (1H, d, J = 8.2 Hz), 7.73 (1H, s). | Ref. Ex. 184 |
| 1226 | | 1H-NMR (CDCl3) δ: 0.00-0.05 (2H, m), 0.40-0.47 (2H, m), 0.54-0.67 (1H, m), 1.75 (2H, q, J = 6.8 Hz), 4.30 (2H, t, J = 6.8 Hz), 6.56 (1H, dd, J = 0.6, 3.1 Hz), 7.35 (1H, d, J = 3.1 Hz), 7.61 (1H, dd, J = 1.3, 8.1 Hz), 7.72 (1H, d, J = 8.1 Hz), 7.93 (1H, s), 10.06 (1H, s). | Ref. Ex. 184 |

TABLE 2-continued

| Ref. Ex. No | STR | 1H-NMR | ref. |
|---|---|---|---|
| 1227 | | 1H-NMR (CDCl3) δ: 1.97 (3H, d, J = 7.1 Hz), 5.73 (1H, q, J = 7.1 Hz), 7.07-7.13 (2H, m), 7.21-7.32 (4H, m), 7.37 (1H, dd, J = 0.6, 3.2 Hz), 7.49 (1H, d, J * 8.2 Hz), 7.52 (1H, d, J = 3.2 Hz), 7.60 (1H, dd, J = 0.9, 7.3 Hz), 10.25 (1H, s). | Ref. Ex. 184 |
| 1228 | | 1H-NMR (CDCl3) δ: 2.63 (3H, s), 5.21 (2H, s), 7.12 (1H, d, J = 7.9 Hz), 7.35 (1H, t, J = 7.9 Hz), 7.50 (1H, dd, J = 1.0, 7.7 Hz), 7.88 (1H, s), 7.93 (2H, s), 10.35 (1H, s), | Ref. Ex. 76 Ref. Ex. 46 |
| 1229 | | 1H-NMR (CDCl3) δ: 2.65 (3H, s), 5.33 (2H, s), 7.12 (1H, d, J = 7.7 Hz), 7.33 (1H, t, J = 7.9 Hz), 7.51 (1H, dd, J = 1.0, 7.7 Hz), 7.73 (1H, d, J = 8.2 Hz), 7.86 (1H, d, J = 8.2 Hz), 8.11 (1H, s), 10.35 (1H, s). | Ref. Ex. 62, Ref. Ex. 46 |
| 1230 | | 1H-NMR (CDCl3) δ: 4.61 (2H, d, J = 0.7 Hz), 6.52 (1H, s), 7.29 (4H, s). | Ref. Ex. 318 |
| 1231 | | 1H-NMR (CDCl3) δ: 7.33-7.40 (4H, m), 7.53 (1H, s), 9.78 (1H, s). | Ref. Ex. 159 |
| 1232 | | 1H-NMR (CDCl3) δ: 2.40 (1H, brs), 4.62 (2H, s), 6.54 (1H, s), 7.20 (2H, d, J = 8.4 Hz), 7.36-7.41 (2H, m). | Ref. Ex. 318 |

TABLE 2-continued

| Ref. Ex. No | STR | 1H-NMR | ref. |
|---|---|---|---|
| 1233 | | 1H-NMR (CDCl3) δ: 7.27-7.29 (2H, m), 7.46 (1H, t, J = 2.1 Hz), 7.57-7.59 (1H, m), 7.73-7.75 (1H, m), 8.32 (1H, d, J = 5.3 Hz), 9.96 (1H, s). | Ref. Ex. 153 |
| 1234 | | 1H-NMR (CDCl3) δ: 4.11 (2H, s), 7.02 (1H, t, J = 8.4 Hz), 7.10-7.17 (1H, m), 7.33 (1H, dd, J = 2.1, 6.6 Hz), 7.44-7.51 (2H, m), 7.75-7.79 (2H, m), 9.99 (1H, s). | Ref. Ex. 173 |
| 1235 | | 1H-NMR (CDCl3) δ: 4.07 (2H, s), 6.71-6.86 (2H, m), 7.18-7.24 (1H, m), 7.40-7.48 (2H, m), 7.70-7.75 (2H, m), 9.96 (1H, s). | Ref. Ex. 173 |
| 1237 | | 1H-NMR (CDCl3) δ: 7.23-7.26 (2H, m), 7.44-7.50 (2H, m), 7.55 (1H, s), 9.79 (1H, s), | Ref. Ex. 48 |
| 1238 | | 1H-NMR (CDCl3) δ: 7.12-7.37 (2H, m), 7.70-7.76 (2H, m), 8.06 (1H, d, J = 7.5 Hz), 8.49 (1H, d, J = 7.5 Hz), 8.73 (1H, s), 10.14 (1H, s). | Ref. Ex. 130, Ref. Ex. 147 |

TABLE 2-continued

| Ref. Ex. No | STR | 1H-NMR | Ref. |
|---|---|---|---|
| 1240 | | 1H-NMR (CDCl3) δ: 5.16 (2H, s), 7.07 (1H, d, J = 8.4 Hz), 7.16-7.30 (3H, m), 7.46-7.57 (2H, m), 9.91 (1H, s). | Ref. Ex. 82 |
| 1241 | | 1H-NMR (CDCl3) δ: 1.43 (3H, t, J = 7.1 Hz), 4.47 (2H, q, J = 7.1 Hz), 7.88 (1H, d, J = 8.2 Hz), 7.94-7.97 (2H, m), 8.37 (1H, s). | Ref. Ex. 2 |
| 1242 | | 1H-NMR (CDCl3) δ: 7.90-8.02 (3H, m), 8.38 (1H, s), 10.14 (1H, s). | Ref. Ex. 63 |
| 1243 | | 1H-NMR (CDCl3) δ: 7.76 (1H, d, J = 7.8 Hz), 8.04 (1H, t, J = 7.7 Hz), 8.32 (1H, s), 8.48 (1H, d, J = 8.0 Hz), 10.11 (1H, s). | Ref. Ex. 48 |
| 1244 | | 1H-NMR (CDCl3) δ: 3.12-3.18 (2H, m), 3.24-3.29 (2H, m), 7.23-7.34 (3H, m), 7.43-7.48 (2H, m), 7.64-7.67 (1H, m), 7.72-7.78 (3H, m), 10.00 (1H, s). | Ref. Ex. 34 |

TABLE 2-continued

| Ref. Ex. No | STR | 1H-NMR | ref. |
|---|---|---|---|
| 1245 | | 1H-NMR (CDCl3) δ: 2.71 (2H, t, J = 7.5 Hz), 2.96 (2H, t, J = 7.5 Hz), 5.09 (2H, s), 5.15 (2H, s), 6.81-6-83 (3H, m), 7.18-7.24 (1H, m), 7.37-7.40 (2H, m), 7.51-7.66 (6H, m). | Ref. Ex. 82 |
| 1246 | | 1H-NMR (CDCl3) δ: 2.60 (2H, t, J = 7.5 Hz), 2.90 (2H, t, J = 7.5 Hz), 3.67 (3H, s), 5.10 (2H, s), 6.88-6.90 (2H, m), 7.12-7.15 (2H, m), 7.53-7.66 (4H, m) | Ref. Ex. 82 |
| 1247 | | 1H-NMR (CDCl3) δ: 1.35 (1H, t, J = 6.0 Hz), 2.82 (2H, t, J = 6.5 Hz), 3.83 (2H, q, J = 6.5 Hz), 5.11 (2H, s), 6.90-6.93 (2H, m), 7.14-7.18 (2H, m), 7.54 (2H, d, J = 8.2 Hz), 7.64 (2H, d, J = 8.2 Hz). | Ref. Ex. 76 |
| 1248 | | 1H-NMR (CDCl3) δ: 1.77 (1H, t, J = 5.9 Hz), 1.85-1.91 (2H, m), 2.70 (2H, t, J = 7.5 Hz), 3.65-3.70 (2H, m), 5.11 (2H, s), 6.78-6.84 (3H, m), 7.19-7.23 (1H, m), 7.48 (2H, d, J = 8.0 Hz), 7.55 (2H, d, J = 8.0 Hz). | Ref. Ex. 76 |

TABLE 2-continued

| Ref. Ex. No | STR | 1H-NMR | ref. |
|---|---|---|---|
| 1249 | | 1H-NMR (CDCl3) δ: 1.22 (1H, t, J = 5.3 Hz), 1.83-1.90 (2H, m), 2 66 (2H, t, J = 7.7 Hz), 3.65-3.69 (2H, m), 5.10 (2H, s), 6.88-6.90 (2H, m), 7.11-7.14 (2H, m), 7.54 (2H, d, J = 8.1 Hz), 7.63 (2H, d, J = 8.1 Hz). | Ref. Ex. 76 |
| 1250 | | 1H-NMR (CDCl3) δ: 3.65 (2H, s), 5.13 (2H, s), 6.95-6.98 (2H, m), 7.14-7.16 (2H, m), 7.55 (2H, d, J = 8.4 Hz), 7.65 (2H, d, J = 8.4 Hz), 9.73-9.74 (1H, m). | Ref. Ex. 156 |
| 1251 | | 1H-NMR (CDCl3) δ: 2.76-2.78 (2H, m), 2.92-2.97 (2H, m), 5.11 (2H, s), 6.79-6.84 (3H, m), 7.20-7.25 (1H, m), 7.55 (2H, d, J = 8.1 Hz), 7.65 (2H, d, J = 8.1 Hz), 9.82 (1H, s). | Ref. Ex. 156 |
| 1252 | | 1H-NMR (CDCl3) δ: 2.73-2.79 (2H, m), 2.89-2.94 (2H, m), 5.11 (2H, s), 6.87-6.92 (2H, m), 7.10-7.14 (2H, m), 7.54 (2H, d, J = 8.1 Hz), 7.64 (2H, d, J = 8.1 Hz), 9.82 (1H, s). | Ref. Ex. 156 |

TABLE 2-continued

| Ref. Ex. No | STR | 1H-NMR | ref. |
|---|---|---|---|
| 1253 | | 1H-NMR (CDCl3) δ: 5.13 (2H, s), 7.10 (1H, s), 7.38(1H, s), 7.42 (1H, s), 7.61-7.72 (3H, m), 9.96 (1H, s). | Ref. Ex. 82 |
| 1254 | | 1H-NMR (CDCl3) δ: 5.24 (2H, s), 7.11 (1H, s), 7.39 (1H, s), 7.40-7.51 (3H, m), 7.63-7.70 (1H, m), 9.96 | Ref. Ex. 82 |
| 1255 | | 1H-NMR (CDCl3) δ: 5.38 (2H, s), 7.10 (1H, s), 7.39-7.42 (2H, m), 7.86-7.93 (2H, m), 7.99 (1H, s), 9.96 (1H, s). | Ref. Ex. 82 |
| 1256 | | 1H-NMR (CDCl3) δ: 3.01 (3H, s), 5.27 (2H, s), 7.48 (2H, d, J = 8.1 Hz), 7.71 (2H, d, J = 8.1 Hz). | Ref. Ex. 103 |
| 1257 | | 1H-NMR (CDCl3) δ: 2.97 (3H, s), 3.21 (2H, t, J = 6.6 Hz), 4.48 (2H, t, J = 6.6 Hz), 7.71 (2H, s), 7.81 (1H, s). | Ref. Ex. 103 |

TABLE 2-continued

| Ref. Ex. No | STR | 1H-NMR | ref. |
|---|---|---|---|
| 1258 | | 1H-NMR (CDCl3) δ: 1.28 (3H, t, J = 7.1 Hz), 4.33 (2H, q, J = 7.1 Hz), 7.22 (1H, t, J = 8.6 Hz), 7.39-7.46 (3H, m), 7.60 (1H dd, J = 2.2, 6.9 Hz), 7.91-7.95 (2H, m). | Ref. Ex. 16 |
| 1259 | | 1H-MR(CDCl3) δ: 7.25-7.31 (1H, m), 7.45-7.54 (3H, m), 7.69 (1H, dd, J = 2.3, 6.8 Hz), 7.93-7.98 (2H, m), 10.06 (1H, s). | Ref. Ex. 63 |
| 1260 | | 1H-NMR (DMSO-d6) δ: 7.37 (1H, dd, J = 2.1, 8.6 Hz), 7.74 (1H, s), 7.90 (1H, d, J = 2.1 Hz), 8.00 (1H, d, J = 8.6 Hz). | Ref. Ex. 138 |
| 1261 | | 1H-NMR (CDCl3) δ: 7.30-7.34 (1H, m), 7.58 (1H, s), 7.63 (1H, t, J = 7.8 Hz), 7.77 (1H, d, J = 8.4 Hz), 7.76 (1H, s), 7.88 (1H, d, J = 7.8 Hz), 7.96 (1H, d, J = 8.4 Hz), 8.20 (1H, s), 10.10 (1H, s). | Ref. Ex. 75 |
| 1262 | | 1H-NMR (CDCl3) δ: 7.26-7.36 (1H, m), 7.59 (1H, s), 7.76-7.78 (2H, m), 7.83 (1H, s), 7.91 (1H, s), 8.06 (1H, s), 10.04 (1H, s). | Ref. Ex. 75 |
| 1263 | | 1H-NMR (CDCl3) δ: 2.51 (3H, s), 7.26-7.32 (1H, m), 7.56 (1H, s), 7.68-7.77 (4H, m), 8.00 (1H, s), 10.06 (1H, s). | Ref. Ex. 75 |

TABLE 2-continued

| Ref. Ex. No | STR | 1H-NMR | ref. |
|---|---|---|---|
| 1264 | | 1H-NMR (CDCl3) δ: 7.34-7.37 (1H, m), 7.61 (1H, s), 7.72 (1H, s), 7.77-7.81 (3H, m), 8.12 (1H, s), 10.08 (1H, s). | Ref. Ex. 75 |
| 1265 | | 1H-NMR (CDCl3) δ: 1.42 (3H, t, J = 7.1 Hz), 4.41-4.48 (4H, m), 7.43-7.46 (2H, m), 7.60-7.62 (2H, m), 8.09 (1H, s). | Ref. Ex. 2 |
| 1266 | | 1H-NMR (CDCl3) δ: 2.16 (1H, t, J = 6.0 Hz), 4.37 (2H, s), 4.76 (2H, d, J = 6.0 Hz), 7.10 (1H, s), 7.44 (2H, d, J = 8.1 Hz), 7.60 (2H, d, J = 8.2 Hz). | Ref. Ex. 19 |
| 1267 | | 1H-NMR (CDCl3) δ: 4.45 (2H, s), 7.46 (2H, d, J = 8.1 Hz), 7.63 (2H, d, J = 8.1 Hz), 8.10 (1H, s), 10.01 (1H, s). | Ref. Ex. 48 |
| 1268 | | 1H-NMR (CDCl3) δ: 3.77 (2H, s), 7.32-7.34 (2H, m), 7.54-7.62 (4H, m), 7.75-7.77 (1H, m), 7.82 (1H, s), 9.81 (1H, s). | Ref. Ex. 156 |
| 1269 | | 1H-NMR (CDCl3) δ: 4.62 (2H, s), 4.66 (2H, s), 7.42-7.44 (2H, m), 7.55 (1H, t, J = 7.7 Hz), 7.64-7.66 (3H, m), 7.82-7.84 (1H, m), 7.89 (1H, s), 10.04 (1H, s). | Ref. Ex. 100 |
| 1270 | | 1H-NMR (CDCl3) δ: 4.59 (2H, s), 4.64 (2H, s), 7.21 (2H, d, J = 7.8 Hz), 7.39-7.41 (2H, m), 7.54 (1H, t, J = 7.4 Hz), 7.63-7.66 (1H, m), 7.81-7.84 (1H, m), 7.89 (1H, s), 10.04 (1H, s). | Ref. Ex. 100 |

TABLE 2-continued

| Ref. Ex. No | STR | 1H-NMR | ref. |
|---|---|---|---|
| 1271 | | 1H-NMR (CDCl3) δ: 2.56 (3H, s), 5.20 (2H, s), 6.99-7.01 (2H, m), 7.55 (2H, d, J = 7.8 Hz), 7.66 (2H, d, J = 7.8 Hz), 7.94-7.96 (2H, m). | Ref. Ex. 82 |
| 1272 | | 1H-NMR (CDCl3) δ: 7.11-7.18 (1H, m), 7.46-7.50 (1H, m), 7.61 (1H, s), 7.74-7.84 (2H, m), 7.92 (1H, t, J = 1.8 Hz), 8.06 (1H, t, J = 1.5 Hz), 10.04 (1H, s). | Ref. Ex. 75 |
| 1273 | | 1H-NMR (CDCl3) δ: 7.12-7.18 (1H, m), 7.47-7.51 (1H, m), 7.63 (1H, s), 7.71 (1H, s), 7.75-7.82 (2H, m), 8.12 (1H, s), 10.08 (1H, s). | Ref. Ex. 75 |
| 1274 | | 1H-NMR (CDCl3) δ: 7.06-7.16 (1H, m), 7.42-7.97 (6H, m), 8.20 (1H, s), 10.10 (1H, s). | Ref. Ex. 75 |
| 1275 | | 1H-NMR (CDCl3) δ: 1.44 (3H, t, J = 7.1 Hz), 4.47 (2H, q, J = 7.1 Hz), 7.72 (2H, d, J = 8.2 Hz), 8.14 (2H, d, J = 8.1 Hz), 8.22 (1H, s). | Ref. Ex. 2 |
| 1276 | | 1H-NMR (CDCl3) δ: 1.50-1.65 (1H, m), 1.68-1.94 (2H, m), 1.95-2.09 (1H, m), 3.70-3.89 (2H, m), 4.17-4.39 (3H, m), 6.58 (1H, dd, J = 0.7, 3.1 Hz), 7.43 (1H, d, J = 3.1 Hz), 7.62 (1H, dd, J = 1.3, 8.2 Hz), 7.71 (1H, d, J = 8.2 Hz), 7.95 (1H, s), 10.06 (1H, s). | Ref. Ex. 318 |
| 1277 | | 1H-NMR (CDCl3) δ: 1.95 (3H, d, J = 7.1 Hz), 5.78 (1H, q, J = 7.1 Hz), 6.63 (1H, dd, J = 0.7, 3.2 Hz), 7.12-7.17 (2H, m), 7.22-7.35 (3H, m), 7.50 (1H, d, J = 3.2 Hz), 7.62 (1H, dd, J = 1.3, 8.2 Hz), 7.72 (1H, d, J = 8.2 Hz), 7.81 (1H, s), 9.98 (1H, s). | Ref. Ex. 318 |

TABLE 2-continued

| Ref. Ex. No | STR | 1H-NMR | ref. |
|---|---|---|---|
| 1278 | | 1H-NMR (CDCl3) δ: 2.54 (3H, s), 7.42-7.50 (3H, m), 7.54-7.60 (2H, m), 7.66 (1H, d, J = 7.7 Hz), 7.84-7.89 (1H, m), 10.38 (1H, s). | Ref. Ex. 600, Ref. Ex. 156 |
| 1279 | | 1H-NMR (CDCl3) δ: 2.55 (3H, s), 3.84 )3H, s), 6.80-6.83 (1H, m), 6.84-6.88 (1H, m), 6.93 (1H, ddd, J = 0.9, 2.6, 8.3 Hz), 7.31-7.43 (2H, m), 7.47 (1H, dd, J = 1.6, 7.6 Hz), 7.83 (1H, dd, J = 1.6, 7.5 Hz), 10.38 (1H, s). | Ref. Ex. 600, Ref. Ex. 156 |
| 1280 | | 1H-NMR (CDCl3) δ: 1.93 (3H, s), 2.34 (3H, s), 2.36 (3H, s), 6.93 (1H, dd, J = 1.7, 7.1 Hz), 7.11-7.22 (2H, m), 7.33-7.43 (2H, m), 7.83 (1H, dd, J = 2.1, 7.1 Hz). 10:38 (1H, s). | Ref. Ex. 600, Ref. Ex. 156 |
| 1281 | | 1H-NMR (CDCl3) δ: 2.21-2.31 (1H, br), 4.84 (2H, d, J = 4.4 Hz), 7.24-7.30 (2H, m), 7.47 (1H, t, J = 8.3 Hz), 7.83-7.86 (2H, m). | Ref. Ex. 19 |
| 1282 | | 1H-NMR (CDCl3) δ: 2.43 (1H, t, J = 6.1 Hz), 4.76 (2H, d, J = 6.0 Hz), 7.28-7.32 (1H, m), 7.47 (1H, t, J = 8.3 Hz), 7.74-7.77 (2H, m). | Ref. Ex. 27 |
| 1283 | | 1H-NMR (CDCl3) δ: 1.26 (1H, t, J = 5.8 Hz), 2.85 (2H, t, J = 6.9 Hz), 3.61-3.73 (2H, m), 7.21-7.24 (1H, m), 7.28-7.37 (3H, m), 7.52-7.63 (4H, m). | Ref. Ex. 77 |
| 1284 | | 1H-NMR (CDCl3) δ: 3.67 (2H, s), 7.28-7.32 (2H, m), 7.37-7.45 (3H, m), 7.52-7.56 (2H, m), 7.63-7.65 (1H, m), 9.66 (1H, s). | Ref. Ex. 156 |
| 1285 | | 1H-NMR (CDCl3) 6: 3.26 (2H, t, J = 6.3 Hz), 4.30 (2H, t, J = 6.3 Hz), 7.14-7.18 (1H, m), 7.37 (1H, s), 7.42-7.49 (2H, m). 7.77 (3H, s), 9.97 (1H, s). | Ref. Ex. 82 |

TABLE 2-continued

| Ref. Ex. No | STR | 1H-NMR | ref. |
|---|---|---|---|
| 1286 | | 1H-NMR (CDCl3) δ: 7.34-7.52 (2H, m), 7.02 (1H, t, J = 8.7 Hz), 7.76-8.02 (4H, m), 10.22 (1H, s). | Ref. Ex. 75 |
| 1287 | | 1H-NMR (CDCl3) δ: 7.29-7.41 (2H, m), 7.55-7.70 (4H, m), 8.12-8.16 (1H, m), 10.24 (1H, s). | Ref. Ex. 75 |
| 1288 | | 1H-NMR (CDCl3) δ: 2.47-2.51 (4H, m), 4.72 (2H, d, J = 5.8 Hz), 7.23-7.26 (1H, m), 7.44 (1H, t, J = 8.2 Hz), 7.76-7.78 (2H, m). | Ref. Ex. 38 |
| 1289 | | 1H-NMR (CDCl3) δ: 2.85 (3H, s), 7.29-7.33 (1H, m), 7.49 (1H, d, J = 8.2 Hz), 7.81-7.83 (2H, m), 10.21 (1H, s). | Ref. Ex. 48 |
| 1290 | | 1H-NMR (CDCl3) δ: 5.14 (1H, s), 7.10 (1H, s), 7.36-7.41 (2H, m), 7.56 (2H, s), 7.78 (1H, s), 9.56 (1H, s). | Ref. Ex. 82 |
| 1291 | | 1H-NMR (CDCl3) δ: 3.71 (4H, s), 7.47-7.51 (2H, m), 7.67 (2H, s), 7.73-7.79 (3H, m), 10.00 (1H, s). | Ref. Ex. 173 |
| 1292 | | 1H-NMR (CDCl3) δ: 1.31 (9H, s), 3.60 (2H, s), 3.69 (2H, s), 7.19-7.21 (2H, m), 7.31-7.35 (2H, m), 7.48 (1H, t, J = 7.5 Hz), 7.55-7.58 (1H, m), 7.75-7.79 (2H, m), 10.01 (1H, s). | Ref. Ex. 173 |

TABLE 2-continued
| Ref. Ex. No | STR | 1H-NMR | ref. |
|---|---|---|---|
| 1293 | 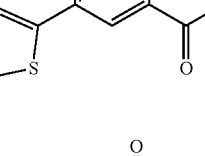 | 1H-NMR (CDCl3) δ: 2.51 (3H, s), 7.07-7.14 (1H, m), 7.44-7.48 (1H, m), 7.58 (1H, s), 7.68 (1H, s), 7.75-7.79 (2H, m), 8.00 (1H, s), 10.06 (1H, s). | Ref. Ex. 75 |
| 1294 | 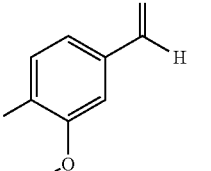 | 1H-NMR (CDCl3) δ: 5.20 (2H, s), 7.10-7.36 (1H, m), 7.49-7.61 (4H, m), 7.79 (1H, s), 9.92 (1H, s). | Ref. Ex. 82 |
| 1295 | 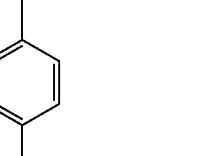 | 1H-NMR (CDCl3) δ: 1.05 (6H, s), 3.80 (4H, s), 7.30 (1H, dd, J = 1.9, 8.7 Hz), 7.72 (1H, s), 7.77-7.82 (2H, m). | Ref. Ex. 107 |
| 1296 |  | 1H-NMR (CDCl3) δ: 1.24 (3H, t, J = 7.2 Hz), 1.38 (3H, t, J = 7.1 Hz), 4.08 (2H, q, J = 7.1 Hz), 4.36 (2H, q, J = 7.1 Hz), 7.28-7.31 (2H, m), 7.35-7.40 (3H, m). | Ref. Ex. 12 |
| 1297 | 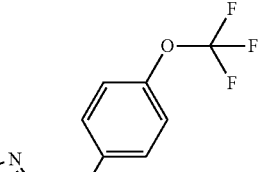 | 1H-NMR (CDCl3) δ: 2.10-2.27 (1H, br), 4.83 (2H, d, J = 4.4 Hz), 7.23 (1H, t, J = 0.8 Hz), 7.50 (1H, d, J = 8.4 Hz), 7.75 (1H, dd, J = 2.1, 8.4 Hz), 8.06 (1H, d, J = 2.1 Hz). | Ref. Ex. 19 |
| 1298 | 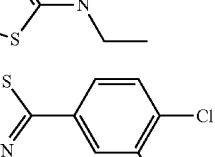 | 1H-NMR (CDCl3) δ: 2.49 (3H, s), 7.36-7.47 (2H, m), 7.64 (1H, t, J = 7.8 Hz), 7.74-7.92 (4H, m), 8.05 (1H, s), 10.10 (1H, s). | Ref. Ex. 75 |
| 1299 | 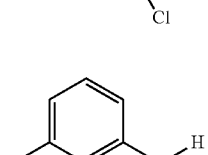 | 1H-NMR (CDCl3) δ: 7.32-7.37 (1H, m), 7.79-8.01 (6H, m), 10.14 (1H, s). | Ref. Ex. 75 |

TABLE 2-continued

| Ref. Ex. No | STR | 1H-NMR | ref. |
|---|---|---|---|
| 1300 | | 1H-NMR (CDCl3) δ: 1.27 (3H, t, J = 7.1 Hz), 4.06 (2H, q, J = 7.1 Hz), 7.29-7.33 (2H, m), 7.37-7.41 (3H, m), 9.73 (1H, s). | Ref. Ex. 63 |
| 1301 | | 1H-NMR (CDCl3) δ: 4.29 (2H, s), 7.07 (1H, s), 7.29-7.37 (2H, m), 7.53-7.55 (1H, m), 7.69-7.77 (4H, m), 9.95 (1H, s). | Ref. Ex. 112 |
| 1302 | | 1H-NMR (CDCl3) δ: 2.67 (3H, s), 2.81-3.18 (1H, br), 4.67 (2H, s). | Ref. Ex. 27 |
| 1303 | | 1H-NMR (CDCl3) δ: 2.45 (1H, t, J = 6.1 Hz), 4.75 (2H, d, J = 6.1 Hz), 7.51 (1H, d, J = 8.4 Hz), 7.67 (1H, dd, J = 2.1, 8.4 Hz), 7.99 (1H, d, J = 2.1 Hz). | Ref. Ex. 27 |
| 1304 | | 1H-NMR (CDCl3) δ: 7.08 (1H, d, J = 3.9 Hz), 7.16 (1H, d, J = 3.9 Hz), 7.56 (1H, t, J = 7.8 Hz), 7.75-7.82 (2H, m), 8.01-8.02 (1H, m), 10.05 (1H, s). | Ref. Ex. 91 |
| 1305 | | 1H-NMR (CDCl3) δ: 2.73-7.79 (2H, m), 3.03 (2H, t, J = 7.5 Hz), 5.15 (2H, s), 6.86-6.96 (2H, m), 7.17-7.22 (2H, m), 7.54 (2H, d, J = 8.1 Hz), 7.66 (2H, d, J = 8.1 Hz), 9.79 (1H, s). | Ref. Ex. 156 |
| 1306 | | 1H-NMR (CDCl3) δ: 1.26 (1H, t, J = 7.2 Hz), 1.85-1.94 (2H, m), 2.80 (2H, t, J = 7.5 Hz), 3.61-3.67 (2H, m), 5.15 (2H, s), 6.87-6.97 (2H, m), 7.15-7.21 (2H, m), 7.55-7.58 (2H, m), 7.65-7.67 (2H, m). | Ref. Ex. 82, Ref. Ex. 76 |

TABLE 2-continued

| Ref. Ex. No | STR | 1H-NMR | ref. |
|---|---|---|---|
| 1307 | | 1H-NMR (CDCl3) δ: 1.36 (1H, t, J = 5.8 Hz), 2.59 (2H, t, J = 6.3 Hz), 3.84-3.90 (2H, m), 5.13 (2H, s), 6.82-6.88 (3H, m), 7.22-7.27 (1H, m), 7.54-7.57 (2H, m), 7.64-7.68 (2H, m). | Ref. Ex. 82, Ref. Ex. 76 |
| 1308 | | 1H-NMR (CDCl3) δ: 3.67 (2H, s), 5.13 (2H, s), 6.84-6.93 (3H, m), 7.28-7.33 (1H, m), 7.55 (2H, d, J = 8.1 Hz), 7.65 (2H, d, J = 6.1 Hz), 9.75 (1H, s). | Ref. Ex. 156 |
| 1309 | | 1H-NMR (CDCl3) δ: 4.19 (2H, s), 5.23 (2H, s), 6.95 (1H, t, J = 7.3 Hz), 7.04 (1H, d, J = 8.2 Hz), 7.25-7.27 (2H, m), 7.49-7.51 (2H, m), 7.70 (2H, d, J = 8.1 Hz). | Ref. Ex. 82, Ref. Ex. 76 |
| 1310 | | 1H-NMR (CDCl3) δ: 3.73 (2H, s), 5.15 (2H, s), 6.93 (1H, d, J = 8.1 Hz), 7.00 (1H, t, J = 7.4 Hz), 7.19-7.21 (1H, m), 7.29-7.31 (1H, m), 7.50 (2H, d, J = 8.0 Hz), 7.65 (2H, d, J = 8.0 Hz), 9.74 (1H, s). | Ref. Ex. 48 |
| 1311 | | 1H-NMR (CDCl3) δ: 7.40 (1H, d, J = 3.9 Hz), 7.42 (1H, d, J = 3.9 Hz), 7.53-7.62 (3H, m), 7.80-7.84 (2H, m), 7.88-7.91 (2H, m), 8.14-8.15 (1H, m), 10.08 (1H, s). | Ref. Ex. 91 |
| 1312 | | 1H-NMR (CDCl3) δ: 7.08-7.14 (2H, m), 7.25-7.28 (1H, m), 7.38 (1H, d, J = 4.5 Hz), 7.55-7.63 (3H, m), 7.78-7.82 (1H, m), 7.86-7.90 (1H, m), 8.11-8.12 (1H, m), 10.08 (1H, s). | Ref. Ex. 91 |

TABLE 2-continued
| Ref. Ex. No | STR | 1H-NMR | ref. |
|---|---|---|---|
| 1313 |  | 1H-NMR (CDCl3) δ: 5.31 (2H, s), 7.04 (1H, s), 7.27-7.37 (5H, m), 7.67-7.76 (2H, m), 9.85 (1H, s). | Ref. Ex. 82 |
| 1314 | 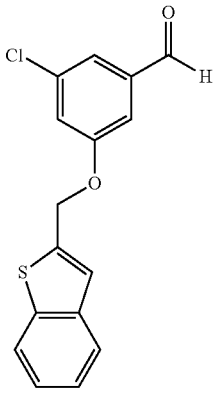 | 1H-NMR (CDCl3) δ: 5.39 (2H, s), 7.27-7.41 (5H, m), 7.48 (1H, s). 7.76-7.85 (2H, m), 9.92 (1H, s). | Ref. Ex. 82 |
| 1315 | 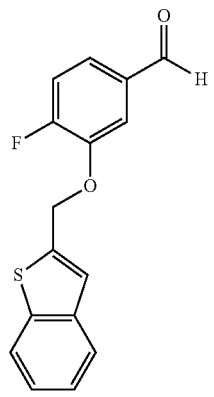 | 1H-NMR (CDCl3) δ: 5.47 (2H, s), 7.23-7.28 (4H, m), 7.47-7.52 (1H, m), 7.62-7.65 (1H, m), 7.75-7.84 (2H, m), 9.30 (1H, s). | Ref. Ex. 82 |
| 1316 | 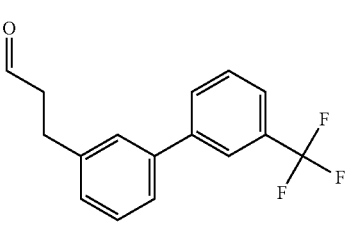 | 1H-NMR (CDCl3) δ: 2.83-2.89 (2H, m), 3.05 (2H, t, J = 7.5 Hz), 7.22-7.25 (1H, m), 7.38-7.47 (3H, m), 7.53-7.63 (2H, m), 7.74-7.81 (2H, m), 9.86 (1H, s). | Ref. Ex. 156 |

TABLE 2-continued

| Ref. Ex. No | STR | 1H-NMR | ref. |
|---|---|---|---|
| 1317 | | 1H-NMR (CDCl3) δ: 2.55-2.61 (2H, m), 2.89-2.94 (2H, m), 7.19-7.22 (1H, m), 7.26-7.36 (3H, m), 7.49-7.65 (4H, m), 9.66 (1H, m). | Ref. Ex. 156 |
| 1318 | | 1H-NMR (CDCl3) δ: 2.47 (3H, s), 7.36-7.40 (1H, m), 7.61-7.63 (1H, m), 7.74-7.79 (3H, m), 7.97 (1H, s), 10.09 (1H, s). | Ref. Ex. 75 |
| 1320 | | 1H-NMR (CDCl3) δ: 2.46 (3H, s), 7.14-7.21 (1H, m), 7.41-7.45 (1H, m), 7.64 (1H, s), 7.74-7.81 (2H, m), 7.97 (1H, t, J = 1.4 Hz), 10.08 (1H, s). | Ref. Ex. 75 |
| 1321 | | 1H-NMR (CDCl3) δ: 2.37 (1H, t, J = 5.9 HZ), 2.48 (3H, s), 4.71 (2H, d, J = 5.9 Hz), 7.48 (1H, d, J = 8.4 Hz), 7.69 (1H, dd, J = 2.1, 8.4 Hz), 8.00 (1H, d, J = 2.1 Hz). | Ref. Ex. 38 |
| 1322 | | 1H-NMR (CDCl3) δ: 2.60 (1H, brs), 2.74 (3H, s), 4.70 (2H, s), 7.57 (2H, d, J = 8.2 Hz), 7.69 (2H, d, J = 8.2 Hz). | Ref. Ex. 38 |
| 1323 | | 1H-NMR (CDCl3) δ: 2.85 (3H, s), 7.54 (1H, d, J = 8.4 Hz), 7.74 (1H, dd, J = 2.1, 8.4 Hz), 6.05 (1H, d, J = 2.1 Hz), 10.20 (1H, s). | Ref. Ex. 48 |

TABLE 2-continued

| Ref. Ex. No | STR | 1H-NMR | ref. |
|---|---|---|---|
| 1324 | | 1H-NMR (CDCl3) δ: 2.60 (3H, s), 7.66 (2H, d, J = 8.2 Hz), 7.75 (2H, d, J = 8.5 Hz), 9.34 (1H, s). | Ref. Ex. 48 |
| 1325 | | 1H-NMR (CDCl3) δ: 1.99-2.17 (4H, m), 3.50 (2H, t, J = 6.4 Hz), 3.82 (2H, t, J = 6.4 Hz), 4.03 (3H, s), 7.06 (1H, s), 7.95 (1H, s), 8.92 (2H, d, J = 0.43 Hz). | Ref. Ex. 38 |
| 1326 | | 1H-NMR (CDCl3) δ: 1.19-1.23 (2H, m), 1.61-1.64 (2H, m), 5.13 (4H, s). 6.91-6.94 (2H, m), 7.26-7.31 (4H, m), 7.54-7.58 (4H, m), 7.65 (2H, d, J = 6.1 Hz). | Ref. Ex. 82 |
| 1327 | | 1H-NMR (CDCl3) δ: 7.47-7.52 (1H, m), 7.58-7.67 (2H, m), 7.97-7.99 (1H, m), 8.01 (2H, s), 8.08 (1H, s), 9.91 (1H, s). | Ref. Ex. 75 |
| 1328 | | 1H-NMR (CDCl3) δ: 7.43-7.48 (1H m), 7.55-7.60 (1H, m), 7.69-7.75 (3H, m), 7.80-7.85 (2H, m), 7.95-7.99 (1H, m), 9.92 (1H, s). | Ref. Ex. 75 |

TABLE 2-continued

| Ref. Ex. No | STR | 1H-NMR | ref. |
|---|---|---|---|
| 1329 | | 1H-NMR (CDCl3) δ: 2.00-2.16 (4H, m), 3.49 (2H, t, J = 6.5 Hz), 3.82 (2H, t, J = 6.5 Hz), 6.83 (1H, s), 7.97 (1H, s), 3.96 (2H, s), 10.03 (1H, s). | Ref. Ex. 318 |
| 1330 | | 1H-NMR (CDCl3) δ: 1.98-2.14 (4H, m), 3.44 (2H, t, J = 6.8 Hz), 3.67 (2H, t, J = 6.8 Hz), 6.75 (1H, s), 9.84 (1H, s). | Ref. Ex. 318 |
| 1331 | | 1H-NMR (CDCl3) δ: 4.08 (3H, s), 7.81 (2H, d, J = 8.2 Hz), 8.30 (2H, d, J = 8.2 Hz), 8.40 (1H, s). | Ref. Ex. 38 |
| 1332 | | 1H-NMR (CDCl3) δ: 4.11 (3H, s), 7.60 (2H, d, J = 8.3 Hz), 7.85 (2H, d, J = 8.3 Hz), 8.39 (1H, s), 8.41 (2H, d, J =8.3 Hz), 8.75 (2H, d, J = 8.3 Hz). | Ref. Ex. 38 |

TABLE 2-continued

| Ref. Ex. No | STR | 1H-NMR | ref. |
|---|---|---|---|
| 1333 | | 1H-NMR (CDCl3) δ: 4.72 (2H, s), 4.73 (2H, d, J = 0.4 Hz), 7.30-7.36 (1H, m), 7.37-7.44 (4H, m), 7.50 (1H, d, J = 5.1 Hz), 7.73 (2H, d, J = 8.2 Hz), 8.55 (2H, d, J = 8.2 Hz), 8.82 (1H, d, J = 5.1 Hz). | Ref. Ex. 742 |
| 1334 | | 1H-NMR (CDCl3) δ: 2.45 (3H, s), 7.13-7.20 (1H, m), 7.40-7.44 (1H, m), 7.76-7.81 (2H, m), 7.88-7.92 (2H, m), 10.05 (1H, s). | Ref. Ex. 75 |
| 1335 | | 1H-NMR (CDCl3) δ: 7.11 (1H, d, J = 5.8 Hz), 7.24 (1H, d, J = 5.6 Hz), 7.72 (2H, s), 6.02 (1H, t, J = 1.4 Hz), 10.06 (1H, s). | Ref. Ex. 75 |
| 1336 | | 1H-NMR (CDCl3) δ: 2.45 (3H, s), 7.11-7.18 (1H, m), 7.39-7.43 (1H, m), 7.65 (1H, t, J = 7.7 Hz), 7.75-7.82 (2H, m), 7.90-7.94 (1H, m), 8.03-8.05 (1H, m), 10.10 (1H, s). | Ref. Ex. 75 |
| 1337 | | 1H-NMR (CDCl3) δ: 7.84 (4H, t, J = 8.7 Hz), 8.21 (1H, s), 8.41 (2H, d, J = 8.1 Hz), 8.78 (2H, d, J = 8.1 Hz), 10.22 (1H, s). | Ref. Ex. 318 |

TABLE 2-continued

| Ref. Ex. No | STR | 1H-NMR | ref. |
|---|---|---|---|
| 1338 | | 1H-NMR (CDCl3) δ: 1.97-2.05 (4H, m), 3.67-3.75 (4H, m), 4.00 (3H, s), 7.59 (1H, s), 7.73 (2H, d, J = 8.2 Hz), 8.23 (2H, d, J = 8.2 Hz). | Ref. Ex. 1173 |
| 1339 | | 1H-NMR (CDCl3) δ: 4.10 (3H, s), 8.10 (1H, s), 8.42 (1H, s), 8.62 (2H, s). | Ref. Ex. 38 |
| 1340 | | 1H-NMR (CDCl3) δ: 3.05 (2H, t, J = 6.6 Hz), 3.77-3.82 (2H, m), 4.62 (2H, s), 7:46-7.55 (2H, m), 7.69 (1H, s), 7.75-7.78 (4H, m), 10.01 (1H, s). | Ref. Ex. 189 |
| 1341 | | 1H-NMR (CDCl3) δ: 0.82-0.84 (4H, m), 1.78-1.80 (1H, m), 3.63 (2H, d, J = 5.7 Hz), 5.12 (2H, s), 6.90-6.93 (2H, m), 7.29-7.32 (2H, m), 7.48-7.56 (2H, m), 7.61-7.66 (2H, m). | Ref. Ex. 19 |
| 1342 | | 1H-NMR (CDCl3) δ: 1.36-1.40 (2H, m), 1.52-1.55 (2H, m), 5.13 (2H, s), 6.94-6.97 (2H, m), 7.22-7.25 (2H, m), 7.55 (2H, d, J = 8.1 Hz), 7.65 (2H, d, J = 8.1 Hz), 9.19 (1H, s). | Ref. Ex. 156 |

TABLE 2-continued

| Ref. Ex. No | STR | 1H-NMR | Ref. ref. |
|---|---|---|---|
| 1343 | | 1H-NMR (CDCl3) δ: 3.38 (1H, t, J = 4.8 Hz), 4.85 (2H, d, J = 4.8 Hz), 7.28 (1H, d, J = 5.1 Hz), 7.76 (2H, d, J = 8.2 Hz), 8.58 (2H, d, J = 8.2 Hz), 8.81 (1H, d, J = 5.1 Hz). | Ref. Ex. 750 |
| 1344 | | 1H-NMR (CDCl3) δ: 2.05 (4H, brs), 3.74 (4H, t, J = 6.7 Hz), 4.02 (3H, s), 7.60 (1H, s), 7.99 (1H, s), 8.56 (2H, s). | Ref. Ex. 1173 |
| 1345 | | 1H-NMR (CDCl3) δ: 1.06 (6H, s), 2.59 (3H, s), 3.81 (4H, s), 7.08-7.15 (1H, m), 7.37-7.41 (1H, m), 7.74-7.79 (1H, m). | Ref. Ex. 107 |
| 1346 | | 1H-NMR (CDCl3) δ: 1.05 (6H, s), 3.81 (4H, s), 7.08-7.15 (1H, m), 7.46-7.50 (1H, m), 7.74 (1H, s), 7.78-7.83 (1H, m). | Ref. Ex. 107 |
| 1347 | | 1H-NMR (CDCl3) δ: 7.76 (1H, d, J = 4.8 Hz), 7.79 (2H, d, J = 8.5 Hz), 8.68 (2H, dd, J = 0.7, 8.5 Hz), 9.11 (1H, dd, J = 0.7, 4.8 Hz), 10.15 (1H, d, J = 0.7 Hz). | Ref. Ex. 159 |
| 1348 | | 1H-NMR (CDCl3) δ: 2.05-2.08 (4H, m), 3.74 (4H, brs), 7.44 (1H, s), 7.73 (2H, d, J = 8.2 Hz), 8.23 (2H, d, J = 8.2 Hz), 9.93 (1H, s). | Ref. Ex. 318 |

TABLE 2-continued
| Ref. Ex. No | STR | 1H-NMR | ref. |
|---|---|---|---|
| 1349 | 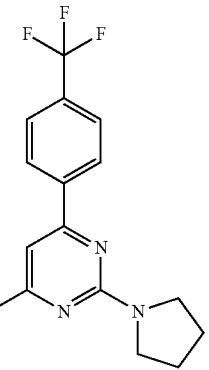 | 1H-NMR (CDCl3) δ: 1.98-2.10 (4H, m), 3.70 (4H, brs), 3.96 (1H, t, J = 4.7 Hz), 4.65 (2H, d, J = 4.7 Hz), 6.82 (1H, s), 7.71 (2H, d, J = 8.2 Hz), 8.16 (2H, d, J = 8.2 Hz). | Ref. Ex. 318 |
| 1350 | 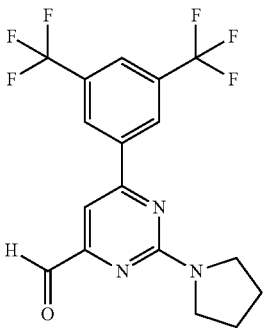 | 1H-NMR (CDCl3) δ: 2.04-2.10 (4H, m), 3.75 (4H, brs), 7.45 (1H, s), 7.99 (1H, s), 8.56 (2H, s), 9.93 (1H, s). | Ref. Ex. 318 |
| 1351 | 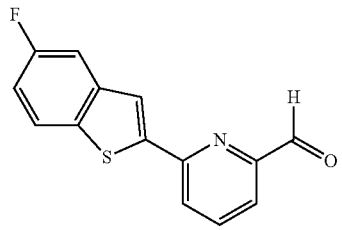 | 1H-NMR (CDCl3) δ: 7.12-7.19 (1H, m), 7.49-7.52 (1H, m), 7.80-7.85 (1H, m), 7.88-7.96 (3H, m), 7.96-8.02 (1H, m), 10.14 (1H, s). | Ref. Ex. 91 |
| 1352 | 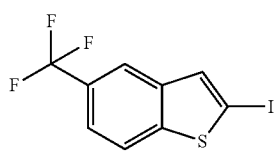 | 1H-NMR (CDCl3) δ: 7.52 (1H, dd, J = 1.3, 8.4 Hz), 7.62 (1H, s), 7.87 (1H, dd, J = 0.6, 8.4 Hz), 7.99 (1H, s). | Ref. Ex. 1319 |
| 1353 | 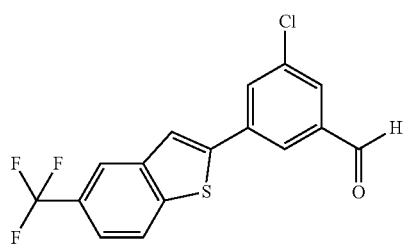 | 1H-NMR (CDCl3) δ: 7.59-7.62 (1H, m), 7.73 (1H, s), 7.86 (1H, s), 7.92-7.99 (2H, m), 8.09 (2H, s), 10.06 (1H, s). | Ref. Ex. 91 |
| 1354 | 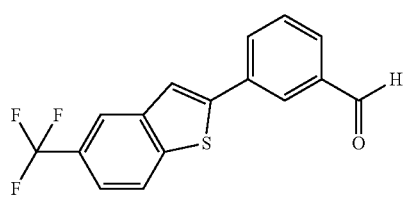 | 1H-NMR (CDCl3) δ: 7.55-7.60 (1H, m), 7.65 (1H, t, J = 7.7 Hz), 7.72 (1H, s), 7.88-7.92 (1H, m), 7.94-8.00 (2H, m), 8.08 (1H, s), 8.23 (1H, t, J = 1.4 Hz), 10.11 (1H, s). | Ref. Ex. 91 |

TABLE 2-continued
| Ref. Ex. No | STR | 1H-NMR | ref. |
|---|---|---|---|
| 1355 | 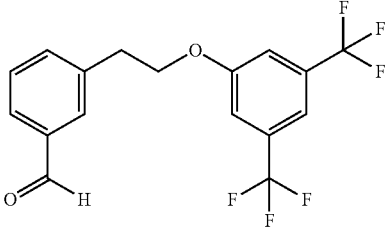 | 1H-NMR (CDCl3) δ: 3.23 (2H, t, J = 6.6 Hz), 4.30 (2H, t, J = 6.6 Hz), 7.26-7.28 (2H, m), 7.45 (1H, s), 7.53-7.60 (2H, m), 7.78-7.83 (2H, m), 10.03 (1H, s). | Ref. Ex. 80 |
| 1356 | 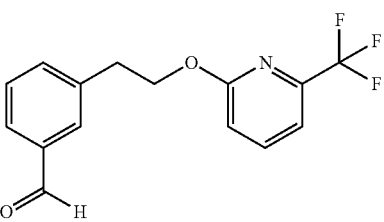 | 1H-NMR (CDCl3) δ: 3.18 (2H, t, J = 6.6 Hz), 4.61 (2H, t, J = 6.6 Hz), 6.89 (1H, d, J = 8.4 Hz), 7.24-7.26 (1H, m), 7.49 (1H, t, J = 7.5 Hz), 7.57-7.59 (1H, m), 7.67-7.78 (2H, m), 7.82 (1H, s), 10.02 (1H, s). | Ref. Ex. 189 |
| 1357 | 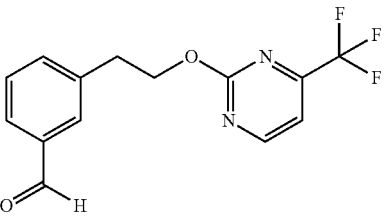 | 1H-NMR (CDCl3) δ: 3.25 (2H, t, J = 6.9 Hz), 4.69 (2H, t, J = 6.9 Hz), 7.26-7.28 (1H, m), 7.50 (1H, t, J = 7.5 Hz), 7.59-7.62 (1H, m), 7.75-7.79 (1H, m), 7.83 (1H, s), 8.76 (1H, d, J = 4.8 Hz), 10.02 (1H, s). | Ref. Ex. 189 |
| 1358 | 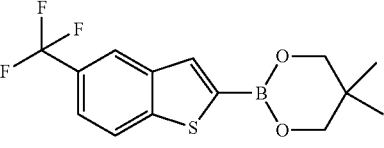 | 1H-NMR (CDCl3) δ: 1.06 (6H, s), 3.82 (4H, s). 7.54-7.58 (1H, m), 7.86 (1H, s), 7.99 (1H, d, J = 8.6 Hz), 8.10 (1H, s). | Ref. Ex. 107 |
| 1359 | 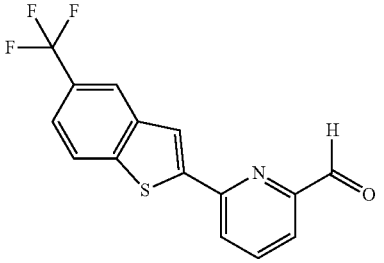 | 1H-NMR (CDCl3) δ: 7.59-7.68 (1H, m), 7.91-8.06 (5H, m), 8.12 (1H, s), 10.16 (1H, s). | Ref. Ex. 91 |
| 1360 | 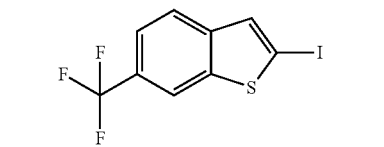 | 1H-NMR (CDCl3) δ: 7.52-7.57 (1H, m), 7.62 (1H, s), 7.81 (1H, d, J = 8.4 Hz), 8.04-8.07 (1H, m). | Ref. Ex. 1319 |
| 1361 | 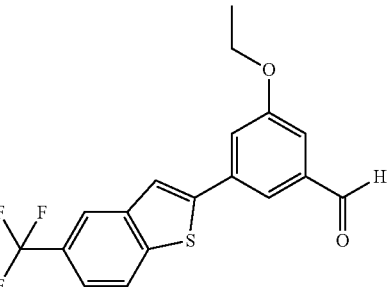 | 1HNMR (CDCl3) δ: 1.50 (3H, t, J = 7.0 Hz), 4.18 (2H, q, J = 7.0 Hz), 7.38-7.44 (1H, m), 7.48-7.50 (1H, m), 7.55-7.61 (1H, m), 7.69 (1H, s), 7.79 (1H, t, J = 1.4 Hz), 7.93-7.98 (1H, m), 8.07 (1H, s), 10.05 (1H, s). | Ref. Ex. 91 |

TABLE 2-continued

| Ref. Ex. No | STR | 1H-NMR | ref. |
|---|---|---|---|
| 1362 | | 1H-NMR (CDCl3) δ: 2.49 (3H, s), 7.16-7.23 (1H, m), 7.59-7.61 (2H, m), 7.74 (1H, d, J = 8.1 Hz), 7.80 (1H, s), 7.92 (1H, s), 8.07 (1H, s), 10.04 (1H, s). | Ref. Ex. 91 |
| 1363 | | 1H-NMR (CDCl3) δ: 7.59-7.68 (2H, m), 7.70 (1H, s), 7.88-7.93 (2H, m), 7.96-8.01 (1H, m), 8.14 (1H, s). 8.23 (1H, t, J = 1.5 Hz), 10.11 (1H, s). | Ref. Ex. 91 |
| 1364 | | 1H-NMR (CDCl3) δ: 2.67 (3H, s), 7.14-7.20 (1H, m), 7.43-7.47 (1H, m), 7.61-7.70 (1H, m), 7.76-7.81 (1H, m), 7.87-7.91 (1H, m), 10.23 (1H, s). | Ref. Ex. 91 |
| 1365 | | 1H-NMR (CDCl3) δ: 2.55 (3H, s), 7.49-7.53 (1H, m), 7.80 (1H, s), 8.00 (1H, s), 8.17 (1H, s), 8.33 (1H, s), 8.90 (1H, d, J = 5.1 Hz), 10.10 (1H, s). | Ref. Ex. 91 |
| 1366 | | 1H-NMR (CDCl3) δ: 7.57 (1H, d, J = 5.0 Hz), 7.83 (1H, s), 8.01 (1H, s), 8.24 (1H, s), 8.49 (1H, t, J = 1.4 Hz), 8.93 (1H, d, J = 5.0 Hz), 10.13 (1H, s). | Ref. Ex. 91 |

TABLE 2-continued

| Ref. Ex. No | STR | 1H-NMR | ref. |
|---|---|---|---|
| 1367 | | 1H-NMR (CDCl3) δ: 7.01-7.09 (1H, m), 7.31-7.38 (1H, m), 7.57-7.68 (3H, m), 7.87-7.98 (2H, m), 8.23 (1H, s), 10.10 (1H, s). | Ref. Ex. 91 |
| 1368 | | 1H-NMR (CDCl3) δ: 7.59-7.64 (1H, m), 7.90-8.05 (5H, m), 8.18 (1H, s), 10.16 (1H, s). | Ref. Ex. 107 Ref. Ex. 91 |
| 1369 | | 1H-NMR (CDCl3) δ: 2.71 (3H, s), 2.75 (3H, s), 4.12 (3H, s), 7.36 (1H, s), 7.67 (1H, t, J = 7.5 Hz), 7.93-7.96 (1H, m), 8.41-8.44 (1H, m), 8.61 (1H, s), 10.14 (1H, s). | Ref. Ex. 91 |
| 1370 | | 1H-NMR (CDCl3) δ: 6.85-6.90 (1H, m), 7.23-7.28 (1H, m), 7.69-7.74 (2H, m), 7.79 (1H, s), 7.83-7.87 (1H, m), 7.91-7.95 (1H, m), 8.10-8.11, (1H, m), 8.34-8.36 (1H, m), 10.11 (1H, s). | Ref. Ex. 91 |
| 1371 | | 1H-NMR (CDCl3) δ: 2.12 (3H, s), 2.45 (3H, s), 3.82 (3H, s), 5.15 (2H, s), 6.39 (1H, s), 7.32 (2H, s), 7.60 (1H, s) | Ref. Ex. 184 |
| 1372 | | 1HMIR (CDCl3) δ: 2.55 (3H, s), 7.81 (1H, s), 7.93 (1H, d, J = 8.2 Hz), 8.01-8.06 (1H, m), 8.18 (1H, s), 8.33 (1H, s), 8.98 (1H, s), 10.10 (1H, s). | Ref. Ex. 91 |

TABLE 2-continued

| Ref. Ex. No | STR | 1H-NMR | Ref. ref. |
|---|---|---|---|
| 1373 | | 1H-NMR (CDCl3) δ: 7.84 (1H, s), 7.95 (1H, d, J = 8.3 Hz), 8.07-8.10 (1H, m), 8.24 (1H, s), 8.50 (1H, t, J = 1.4 Hz), 9.00 (1H, s), 10.12 (1H, s). | Ref. Ex. 107 Ref. Ex. 14 |
| 1374 | | 1H-NMR (CDCl3) δ: 2.05 (6H, s), 4.52 (2H, d, J = 5.1 Hz), 5.11 (2H, s), 6.00 (1H, s), 7.31 (2H, s), 7.78 (1H, s). | Ref. Ex. 76 |
| 1375 | | 1H-NMR (CDCl3) δ: 7.37-7.40 (1H, m), 7.58 (1H, t, J = 7.5 Hz), 7.64-7.67 (1H, m), 7.75 (1H, d, J = 9.6 Hz), 8.01 (1H, s), 8.18-8.21 (1H, m), 8.26 (1H, s), 8.54 (1H, s). | Ref. Ex. 89 |
| 1376 | | 1H-NMR (CDCl3) δ: 7.06-7.13 (1H, m), 7.34-7.41 (1H, m), 7.63 (1H, d, J = 8.0 Hz), 7.69-7.73 (2H, m), 7.79 (1H, s), 8.14 (1H, s), 10.08 (1H, s). | Ref. Ex. 91 |

TABLE 2-continued
| Ref. Ex. No | STR | 1H-NMR | ref. |
|---|---|---|---|
| 1378 | 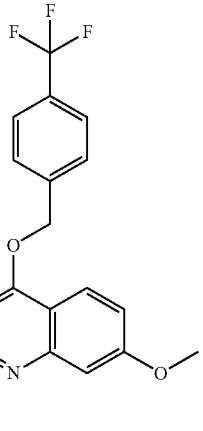 | 1H-NMR (CDCl3) δ: 4.09-4.24 (4H, m), 5.36 (2H, s), 5.90 (1H, s), 7.00 (1H, s), 7.16 (1H, dd, J = 2.5, 9.2 Hz), 7.45 (1H, d, J = 2.5 Hz), 7.63 (2H, d, J = 8.2 Hz), 7.70 (2H, d, J = 8.2 Hz), 8.12 (1H, d, J = 9.2 Hz). | Ref. Ex. 100 |
| 1379 | 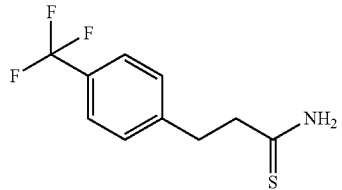 | 1H-NMR (CDCl3) δ: 2.90-2.95 (2H, m), 3.18-3.23 (2H, m). 6.44-6.79 (1H, br), 7.18-7.43 (1H, br), 7.35 (2H, d, J = 8.0 Hz), 7.55 (2H, d, J = 8.1 Hz). | Ref. Ex. 1477 |
| 1380 | 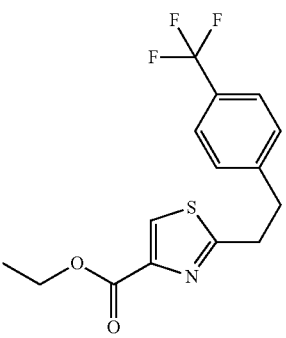 | 1H-NMR (CDCl3) δ: 1.41 (3H, t, J = 7.1 Hz), 3.17-3.23 (2H, m), 3.36-3.42 (2H, m), 4.44 (2H, q, J = 7.1 Hz), 7.32 (2H, d, J = 8.0 Hz), 7.55 (2H, d, J = 8.0 Hz), 8.05 (1H, s). | Ref. Ex. 2 |
| 1381 | 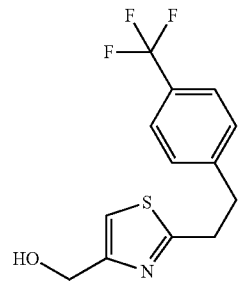 | 1H-NMR (CDCl3) δ: 2.15 (1H, bre), 3.15-3.20 (2H, m), 3.29-3.34 (2H, m), 4.76 (2H, s), 7.04 (1H, s), 7.32 (2H, d, J = 8.0 Hz), 7.55 (2H, d, J = 8.1 Hz). | Ref. Ex. 19 |
| 1382 | 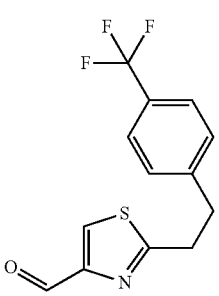 | 1H-NMR (CDCl3) δ: 3.23-3.28 (2H, m), 3.39-3.44 (2H, m), 7.35 (2H, d, J = 8.1 Hz), 7.58 (2H, d, J = 8.0 Hz), 8.07 (1H, s), 10.03 (1H, s). | Ref. Ex. 48 |

TABLE 2-continued
| Ref. Ex. No | STR | 1H-NMR | ref. |
|---|---|---|---|
| 1383 | 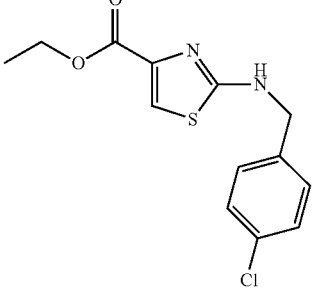 | 1H-NMR (CDCl3) δ: 1.35 (3H, t, J = 7.1 Hz), 4.33 (2H, q, J = 7.1 Hz), 4.50 (2H, d, J = 5.7 Hz), 7.31 (4H, s), 7.39 (1H, s) | Ref. Ex. 2 |
| 1384 | 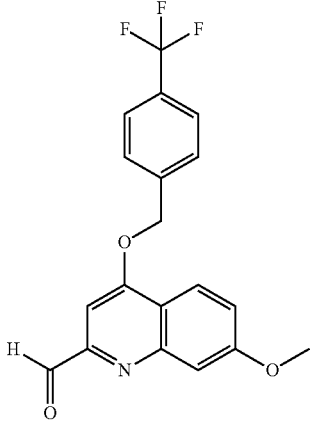 | 1H-NMR (CDCl3) δ: 3.99 (3H, s), 5.41 (2H, s), 7.30 (1H, dd, (J = 2.5, 9.2 Hz), 7.36 (1H, s), 7.51 (1H, d, J = 2.5 Hz), 7.64 (2H, d, J = 8.0 Hz), 7.71 (2H, d, J = 8.0 Hz), 8.20 (1H, d, J = 9.2 Hz), 10.13 (1H, s). | Ref. Ex. 151 |
| 1385 | 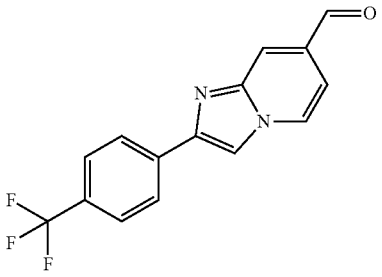 | 1H-NMR (CDCl3) δ: 7.36-7.39 (1H, m), 7.73 (2H, d, J = 8.1 Hz), 8.09-8.14 (4H, m), 8.23 (1H, d, J = 6.9 Hz), 10.02 (1H, s). | Ref. Ex. 48 |
| 1386 | 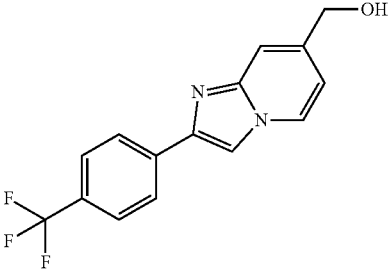 | 1H-NMR (CDCl3) δ: 4.75 (2H, s), 6.82-6.85 (1H, m), 7.61 (1H, s), 7.69 (2H, d, J = 8.1 Hz), 7.90 (1H, s), 8.04-8.11 (4H, m). | Ref. Ex. 76 |
| 1387 | 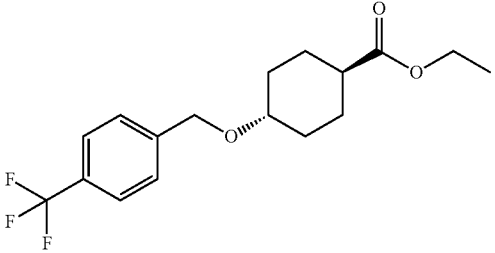 | 1H-NMR (CDCl3) δ: 1.25 (3H, t, J = 6.9 Hz), 1.33-1.55 (4H, m), 2.02-2.32 (5H, m), 3.31-3.39 (1H, m), 4.12 (2H, q, J = 6.9 Hz), 4.61 (2H, s), 7.45 (2H, d, J = 8.4 Hz), 7.60 (2H, d, J = 8.4 Hz). | Ref. Ex. 100 |

TABLE 2-continued

| Ref. Ex. No | STR | 1H-NMR | Ref. ref. |
|---|---|---|---|
| 1388 | | 1H-NMR (CDCl3) δ: 1.24-1.40 (2H, m), 1.19-1.54 (5H, m), 1.85-1.89 (2H, m), 2.13-2.16 (2H, m), 3.28-3.49 (2H, d, J = 8.4 Hz), 4.62 (2H, s), 7.45 (2H, d, J = 8.1 Hz), 7.60 (2H, d, J = 8.1 Hz). | Ref. Ex. 19 |
| 1389 | | 1H-NMR (CDCl3) δ: 1.30-1.48 (4H, m), 2.05-2.30 (5H, m), 3.32-3.39 (1H, m), 4.62 (2H, s), 7.46 (2H, d, J = 8.1 Hz), 7.60 (2H, d, J = 8.1 Hz), 9.66 (1H, s). | Ref. Ex. 156 |
| 1390 | | 1H-NMR (CDCl3) δ: 7.39 (1H, dd, J = 1.5, 9.3 Hz), 7.65 (1H, t, J = 7.8 Hz), 7.82 (1H, d, J = 9.3 Hz), 7.88-7.92 (1H, m), 8.05 (1H, s), 8.23-8.28 (1H, m), 8.44-8.45 (1H, m), 8.54-8.55 (1H, m), 10.12 (1H, s). | Ref. Ex. 93 |
| 1391 | | 1H-NMR (CDCl3) δ: 1.51 (3H, t, J = 7.2 Hz), 4.54 (2H, q, J = 7.2 Hz), 6.89 (1H, t, J = 7.2 Hz), 7.69 (2H, d, J = 8.1 Hz), 7.96-7.00 (2H, m), 8.14 (2H, d, J = 8.1 Hz), 8.30-8.32 (1H, m). | Ref. Ex. 1377 |
| 1392 | | 1H-NMR (DMSO-d6) δ: 4.00 (3H, s), 7.44 (1H, dd, J = 2.7, 9.3 Hz), 7.72 (1H, d, J = 2.7 Hz), 7.77 (1H, s), 7.79-7.83 (3H, m), 7.97 (2H, d, J = 8.1 Hz), 10.16 (1H, s). | Ref. Ex. 151 |

TABLE 2-continued

| Ref. Ex. No | STR | 1H-NMR | ref. |
|---|---|---|---|
| 1393 | | 1H-NMR (CDCl3) δ: 3.96 (3H, s), 4.11-4.26 (4H, m), 6.00 (1H, s), 7.18 (1H, dd, J = 2.6, 9.2 Hz), 7.46 (1H, s), 7.58 (1H, d, J = 2.6 Hz), 7.62 (2H, d, J = 8.0 Hz), 7.68 (1H, d, J = 9.2 Hz), 7.98 (2H, d, J = 8.1 Hz). | Ref. Ex. 38 |
| 1394 | | 1H-NMR (CDCl3) δ: 2.54 (3H, s), 7-65-7.71 (1H, m), 7.79 (1H s), 7.93-8.00 (2H, m), 8.21 (1H, s), 8.33 (1H, s), 10.10 (1H, s). | Ref. Ex. 75 |
| 1395 | | 1H-NMR (CDCl3) δ: 5.58 (2H, s), 7.30 (1H, d, J = 4.8 Hz), 7.56 (1H, t, J = 7.5 Hz), 7.77-7.81 (1H, m), 7.85-7.88 (1H, m), 8.04 (1H, s), 8.89 (1H, d, J = 4.8 Hz), 10.04 (1H, s). | Ref. Ex. 100 |
| 1396 | | 1H-NMR (CDCl3) δ: 5.51 (2H, s), 6.99 (1H, d, J = 8.4 Hz), 7.28 (1H, d, J = 7.5 Hz), 7.55 (1H, t, J = 7.5 Hz), 7.71-7.78 (2H, m), 7.83-7.86 (1H, m), 8.03 (1H, s), 10.04 (1H, s). | Ref. Ex. 100 |
| 1397 | | 1H-NMR (CDCl3) δ:1.37 (3H, t, J = 7.1 Hz), 3.05 (3H, s), 4.35 (2H, q, J = 7.1 Hz), 4.71 (2H, s), 7.20-7.23 (2H, m), 7.28-7.32 (2H, m), 7.40 (1H, s). | Ref. Ex. 12 |
| 1398 | | 1H-NMR (CDCl3) δ: 3.07 (3H, s), 4.73 (2H, s), 7.21-7.24 (2H, m), 7.30-7.33 (2H, m), 7.43 (1H, s), 9.73 (1H, s). | Ref. Ex. 63 |

TABLE 2-continued

| Ref. Ex. No | STR | 1H-NMR | ref. |
|---|---|---|---|
| 1399 | | 1H-NMR (CDCl3) δ: 2.14 (3H, s), 2.43 (3H, s), 5.18 (2H, s), 6.43 (1H, s), 7.34 (2H, s), 7.83 (1H, s), 9.88 (1H, s). | Ref. Ex. 48 |
| 1400 | | 1H-NMR (CDCl3) δ: 4.02 (3H, s), 7.21-7.25 (2H, m), 7.30 (1H, dd, J = 2.6, 9.3 Hz), 7.46-7.52 (2H, m), 7.02 (1H, d, J = 2.6 Hz), 7.83-7.85 (2H, m), 10.24 (1H, s). | Ref. Ex. 38 |
| 1401 | | 1H-NMR (CDCl3) δ: 6.90-6.98 (2H, m), 7.15-7.19 (1H, m), 7.37-7.41 (1H, m). | Ref. Ex. 1319 |
| 1402 | | 1H-NMR (CDCl3) δ: 4.73 (2H, s), 4.76 (2H, s), 7.41-7.46 (2H, m), 7.59 (1H, t, J = 7.8 Hz), 7.84 (3H, s). | Ref. Ex. 100 |
| 1403 | | 1H-NMR (CDCl3) δ: 4.69 (2H, S), 4.71 (2H, s), 7.39-7.84 (7H, m). | Ref. Ex. 100 |
| 1404 | | 1H-NMR (CDCl3) δ: 7.03-7.10 (1H, m), 7.14 (1H, s), 7.27-7-30 (1H, m), 7.46-7.50 (2H, m), 7.83 (1H, s), 8.07 (1H, s), 8.21 (1H, s), 10.05 (1H, s). | Ref. Ex. 75 |

TABLE 2-continued

| Ref. Ex. No | STR | 1H-NMR | ref. |
|---|---|---|---|
| 1405 | | 1H-NMR (CDCl3) δ: 7.43-7.49 (2H, m), 7.58-7.60 (1H, m), 7.68-7.72 (1H, m), 7.96 (1H, d, J = 8.7 Hz), 8.02 (1H, m), 8.11 (1H, s), 10.11 (1H, s). | Ref. Ex. 75 |
| 1406 | | 1H-NMR (CDCl3) δ: 4.78 (4H, s), 7.63-7.66 (1H, m), 7.72-7.74 (1H, m), 7.84-7.91 (4H, m). | Ref. Ex. 89 |
| 1407 | | 1H-NMR (CDCl3) δ: 4.73 (4H, s), 7.49-7.52 (2H, m), 7.61-7.65 (3H, m), 7.73-7.76 (1H, m), 7.86 (1H, t, J = 7.8 Hz), | Ref. Ex. 89 |
| 1408 | | 1H-NMR (CDCl3) δ: 6.86 (1H, d, J = 3.8 Hz), 7.33 (1H, d, J = 3.8 Hz), 7.80 (1H, d, J = 8.3 Hz), 7.82 (1H, s), 7.95 (1H, d, J = 8.3 Hz), 8.08 (1H, s), 9.71 (1H, s), | Ref. Ex. 43 |
| 1409 | | 1H-NMR (CDCl3) δ: 7.00-7.08 (1H, m), 7.11 (1H, s), 7.28-7.29 (1H, m), 7.45-7.49 (1H, m), 7.64 (1H, d, J = 7.6 Hz), 7.66-7.90 (1H, m), 8.08-8.12 (1H, m), 8.36 (1H, s), 10.11 (1H, s). | Ref. Ex. 75 |
| 1410 | | 1H-NMR (CDCl3) δ: 7.00-7.08 (1H, m), 7.11 (1H, s), 7.28-7.29 (1H, m), 7.45-7.49 (1H, m), 7.64 (1H, d, J = 7.6 Hz), 7.86-7.90 (1H, m), 8.08-8.12 (1H, m), 8.36 (1H, s), 10.11 (1H, s). | Ref. Ex. 93 |
| 1411 | | 1H-NMR (CDCl3) δ: 6.80-6.85 (1H, m), 7.18-7.24 (1H, m), 7.59-7.67 (2H, m), 7.84-7.87 (1H, m), 7.96 (1H, s), 8.14-8.17 (1H, m), 8.24-8.28 (1H, m), 8.45-8.46 (1H, m), 10.11 (1H, s). | Ref. Ex. 93 |

TABLE 2-continued

| Ref. Ex. No | STR | 1H-NMR | ref. |
|---|---|---|---|
| 1412 | | 1H-NMR (CDCl3) δ: 7.12-7.15 (1H, m), 7.59-7.65 (2H, m), 7.86-7.88 (1H, m), 7.97 (1H, s), 8.09-8.11 (1H, m), 8.22-8.25 (1H, m), 8.42-8.43 (1H, m), 10.11 (1H, s). | Ref. Ex. 19 |
| 1413 | | 1H-NMR (CDCl3) δ: 1.99 (1H, t, J = 6.2 Hz), 4.60 (2H, dd, J = 1.0, 6.2 Hz), 6.76 (1H, t, J = 1.0 Hz), 7.48-7.56 (4H, m). | Ref. Ex. 19 |
| 1414 | | 1H-NMR (CDCl3) δ: 2.05 (1H, t, J = 6.3 Hz), 4.55 (2H, d, J = 6.4 Hz), 7.46-7.55 (4H, m). | Ref. Ex. 27 |
| 1416 | | 1H-NMR (CDCl3) δ: 4.81 (2H, s), 4.85 (2H, s), 7.70-7.73 (1H, m), 7.83-7.93 (5H, m), 10.07 (1H, s). | Ref. Ex. 48 |
| 1417 | | 1H-NMR (CDCl3) δ: 2.01 (1H, t, J = 6.1 Hz), 2.33 (3H, s), 4.50 (2H, d, J = 6.0 Hz), 7.19-7.23 (2H, m), 7.33-7.37 (2H, m). | Ref. Ex. 38 |
| 1418 | | 1H-NMR (CDCl3) δ: 1.97-2.04 (1H, m), 2.35 (3H, s), 4.4W.52 (2H, m), 7.28-7.67 (4H. m). | Ref. Ex. 38 |
| 1419 | | 1H-NMR (CDCl3) δ: 2.71 (3H, s), 7.25-7.28 (2H, m), 7.36-7.40 (2H, m), 9.90 (1H, s). | Ref. Ex. 159 |
| 1420 | | 1H-NMR (CDCl3) δ: 2.73 (3H, s), 7.52-7.61 (4H, m), 9.90 (1H, s). | Ref. Ex. 159 |

TABLE 2-continued

| Ref. Ex. No | STR | 1H-NMR | ref. |
|---|---|---|---|
| 1421 | 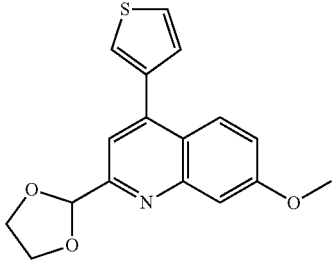 | 1H-NMR (CDCl3) δ: 3.96 (3H, s), 4.12-4.18 (2H, m), 4.19-4.25 (2H, m), 5.98 (1H, s), 7.18 (1H, dd, J = 2.7, 9.2 Hz), 7.33 (1H, dd, J = 1.3, 4.9 Hz), 7.49-7.51 (2H, m), 7.52-7.53 (H, m), 7.54 (1H, d, J = 2.7 Hz), 7.95 (1H, d, J = 9.2 Hz). | Ref. Ex. 38 |
| 1422 | 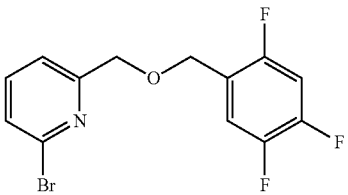 | 1H-NMR (CDCl3) δ: 4.64 (2H, s), 4.69 (2H, s), 6.89-6.97 (1H, m), 7.29-7.35 (1H, m), 7.39-7.46 (2H, m), 7.55-7.60 (1H, m). | Ref. Ex. 100 |
| 1423 | 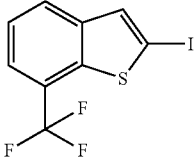 | 1H-NMR (CDCl3) δ: 7.37-7.44 (1H, m), 7.58 (1H, d, J = 7.5 Hz), 7.62 (1H, s), 7.87 (1H, d, J = 8.0 Hz). | Ref. Ex. 1319 |
| 1424 | 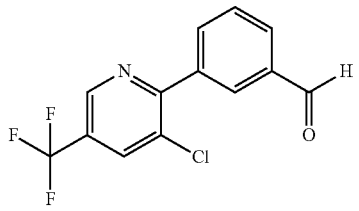 | 1H-NMR (CDCl3) δ: 7.68 (1H, t, J = 7.7 Hz), 7.99-8.10 (3H, m), 8.30 (1H, t, J = 1.5 Hz), 8.86-8.89 (1H, m), 10.11 (1H, s). | Ref. Ex. 75 |
| 1425 | 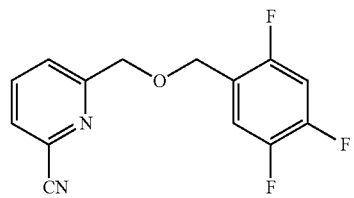 | 1H-NMR (CDCl3) δ: 4.66 (2H, s), 4.74 (2H, s), 6.90-6.99 (1H, m), 7.28-7.35 (1H, m), 7.62 (1H, d, J = 7.8 Hz), 7.72 (1H, d, J = 7.8 Hz), 7.87 (1H, t, J = 7.8 Hz). | Ref. Ex. 89 |
| 1426 | 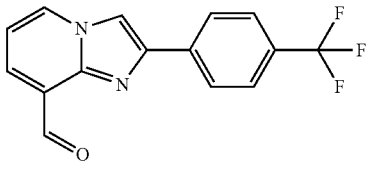 | 1H-NMR (CDCl3) δ: 6.99 (1H, t, J = 6.6 Hz), 7.72 (2H, d, J = 8.1 Hz), 7.85-7.88 (1H, m), 8.05 (1H, s), 8.14 (2H, d, J = 8.1 Hz), 8.37-8.39 (1H, m), 10.88 (1H, s). | Ref. Ex. 76<br>Ref. Ex. 48 |
| 1427 | 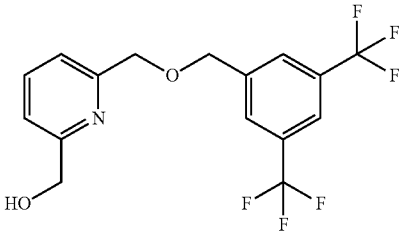 | 1H-NMR (CDCl3) δ: 3.60 (1H, t, J = 5.1 Hz), 4.77 (6H, s), 7.18 (1H, d, J = 7.8 Hz), 7.39 (1H, d, J = 7.8 Hz), 7.73 (1H, t, J = 7.8 Hz), 7.82-7.85 (3H, m). | Ref. Ex. 93 |

TABLE 2-continued

| Ref. Ex. No | STR | 1H-NMR | ref. |
|---|---|---|---|
| 1428 | | 1H-NMR (CDCl3) δ: 3.66-3.69 (1H, s), 4.72-4.76 (5H, m), 7.15-7.17 (1H, m), 7.36-7.41 (1H, m), 7.50-7.53 (2H, m), 7.62-7.74 (3H, m). | Ref. Ex. 93 |
| 1429 | | 1H-NMR (CDCl3) δ: 1.44 (3H, t, J = 7.2 Hz), 4.46 (2H, q, J = 7.2 Hz), 7.59-7.64 (1H, m), 7.89 (1H, s), 7.92 (1H, d, J = 8.7 Hz), 8.14-8.16 (1H, m), 8.20 (1H, s). | Ref. Ex. 14 |
| 1430 | | 1H-NMR (CDCl3) δ: 7.45-7.51 (1H, m), 7.60-7.67 (2H, m), 7.71 (1H, s), 7.87-7.91 (1H, m), 7.95-8.01 (2H, m), 8.24 (1H, t, J = 1.5 Hz), 10.10 (1H, s). | Ref. Ex. 75 |
| 1431 | | 1H-NMR (CDCl3) δ: 4.02 (3H, s), 7.32 (1H, dd, J = 2.6, 9.3 Hz), 7.35 (1H, dd, J = 1.3, 4.9 Hz), 7.52-7.57 (2H, m), 7.60 (1H, d, J = 2.6 Hz), 7.90 (1H, s), 8.06 (1H, d, J = 9.3 Hz), 10.23 (1H, s). | Ref. Ex. 151 |
| 1432 | | 1H-NMR (CDCl3) δ: 7.41 (1H, d, J = 3.9 Hz), 7.56-7.62 (1H, m), 7.65 (1H, s), 7.73 (1H, d, J = 4.0 Hz), 7.92 (1H, d, J = 8.3 Hz), 8.07 (1H, s), 9.92 (1H, s). | Ref. Ex. 43 |
| 1433 | | 1H-NMR (CDCl3) δ: 7.60-7.65 (1H, m), 7.89 (1H, s), 7.94 (1H, d, J = 8.4 Hz), 8.17 (1H, s), 8.22 (1H, s), 10.12 (1H, s). | Ref. Ex. 19, Ref. Ex. 48 |

TABLE 2-continued

| Ref. Ex. No | STR | 1H-NMR | ref. |
|---|---|---|---|
| 1434 | | 1H-NMR (CDCl3) δ: 7.45-7.52 (1H, m), 7.67-7.72 (2H, m), 7.85 (1H, s), 7.96-8.00 (2H, m), 8.11 (1H, s), 10.05 (1H, s). | Ref. Ex. 75 |
| 1435 | | 1H-NMR (CDCl3) δ: 7.12-7.18 (1H, m), 7.48-7.52 (1H, m), 7.58 (1H, s), 7.69 (1H, d, J = 8.2 Hz), 7.77-7.85 (2H, m), 8.08 (1H, d, J = 1.9 Hz), 10.04 (1H, s). | Ref. Ex. 75 |
| 1436 | | 1H-NMR (CDCl3) δ: 7.50-7.56 (1H, m), 7.80-7.88 (1H, m), 7.89 (1H, s), 8.26 (1H, s), 8.34 (1H, s), 8.58 (1H, s), 10.06 (1H, s). | Ref. Ex. 75 |
| 1437 | | 1H-NMR (CDCl3) δ: 3.96 (3H, s), 4.11-4.18 (2H, m), 4.19-4.27 (2H, m), 5.99 (1H, s), 7.17 (1H, dd, J = 2.6, 9.2 Hz), 7.42-7.47 (3H, m), 7.48-7.52 (2H, m), 7.55 (1H, d, J = 2.6 Hz), 7.72 (1H, d, J = 9.2 Hz). | Ref. Ex. 38 |
| 1438 | | 1H-NMR (DMSO-d6) δ: 4.00 (3H, s), 7.44 (1H, dd, J = 2.7, 9.3 Hz), 7.58-7.63 (2H, m), 7.65-7.68 (2H, m), 7.70 (1H, d, J = 2.7 Hz), 7.72 (1H, s), 7.83 (1H, d, J = 9.3 Hz), 10.15 (1H, s). | Ref. Ex. 151 |

TABLE 2-continued

| Ref. Ex. No | STR | 1H-NMR | ref. |
|---|---|---|---|
| 1439 | | 1H-NMR (CDCl3) δ: 4.69 (2H, s), 4.81 (2H, s), 6.90-6.98 (1H, m), 7.30-7.36 (1H, m), 7.70-7.73 (1H, m), 7.88-7.94 (2H, m), 10.06 (1H, | Ref. Ex. 318 |
| 1440 | | 1H-NMR (CDCl3) δ: 4.76 (2H, s), 4.80 (2H, s), 7.52 (2H, d, J = 8.1 Hz), 7.64 (2H, d, J = 8.1 Hz), 7.72-7.75 (1H, m), 7.87-7.94 (2H, m), 10.06 (1H, s). | Ref. Ex. 48 |
| 1441 | | 1H-NWR (CDCl3) δ: 6.92-6.99 (2H, m), 7.10-7.17 (1H, m), 7.28 (1H, d, J = 1.0 Hz). | Ref. Ex. 1319 |
| 1442 | | 1H-NMR (CDCl3) δ: 4.13 (2H, s), 7.42 (1H, s), 7.58 (1H, s), 7.65 (2H, s), 7.75 (1H, s), 8.62 (1H, s), 9.95 (1H, s). | Ref. Ex. 91 |
| 1443 | | 1H-NMR (CDCl3) δ: 5.22 (2H, s), 7.25-7.26 (1H, m), 7.38 (1H, s), 7.51 (1H, s), 7.75 (1H, d, J = 8.1 Hz), 7.97 (1H, d, J = 8.1 Hz), 8.81 (1H, s), 9.32 (1H, s). | Ref. Ex. 82 |
| 1444 | | 1H-NMR (CDCl3) δ: 4.05 (2H, s), 7.21-7.32 (1H, m), 7.41 (1H, s), 7.42-7.49 (1H, m), 7.58 (1H, s), 7.72 (1H, s), 8.51-8.53 (2H, m), 9.93 (1H, s). | Ref. Ex. 75 |
| 1445 | | 1H-NMR (CDCl3) δ: 7.03-7.22 (3H, m), 7.36-7.40 (1H, m), 7.65 (1H, t, J = 7.8 Hz), 7.88-7.91 (1H, m), 8.13-8.17 (1H, m), 8.34 (1H, s), 10.12 (1H, s). | Ref. Ex. 91 |

TABLE 2-continued
| Ref. Ex. No | STR | 1H-NMR | ref. |
|---|---|---|---|
| 1446 | 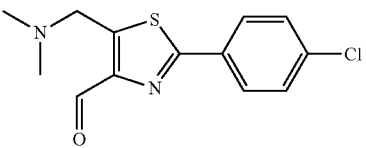 | 1H-NMR (CDCl3) δ: 2.38 (6H, s), 4.07 (2H, s), 7.42-7.45 (2H, m), 7.87-7.90 (2H, m), 10.19 (1H, s). | Ref. Ex. 1494, Ref. Ex. 1173 |
| 1447 | 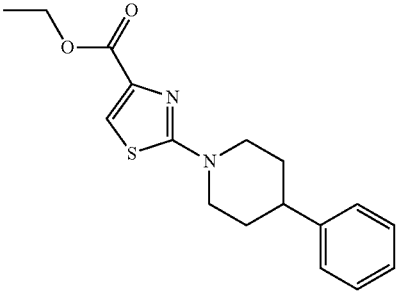 | 1H-NMR (CDCl3) δ: 1.38 (3H, t, J = 7.1 Hz), 1.76-2.04 (4H, m), 2.70-2.79 (1H, m), 3.15 (2H, dt, J = 3.0, 12.7 Hz), 4.17-4.21 (2H, m), 4.36 (2H, q, J = 7.1 Hz), 7.20-7.35 (5H, m), 7.43 (1H, s). | Ref. Ex. 184 |
| 1448 | 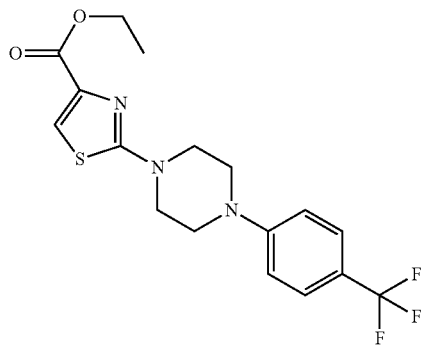 | 1H-NMR (CDCl3) δ: 1.38 (3H, t, J = 7.1 Hz), 3.39-3.43 (4H, m), 3.69-3.72 (4H, m), 4.37 (2H q, J = 7.1 Hz), 6.96 (2H, d, J = 8.7 Hz), 7.49 (1H, s), 7.51 (2H, d, J = 8.9 Hz). | Ref. Ex. 184 |
| 1449 | 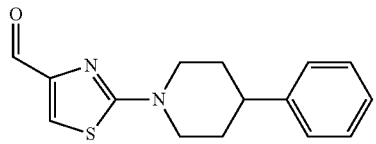 | 1H-NMR (CDCl3) δ: 1.77-2.00 (4H, m), 2.72-2.80 (1H, m), 3.19 (2H, dt, J = 3.0, 12.8 Hz), 4.21 (2H, dt, J = 12.9, 2.2 Hz), 7.21-7.35 (5H, m), 7.46 (1H, s), 9.71 (1H, s). | Ref. Ex. 63 |
| 1450 | 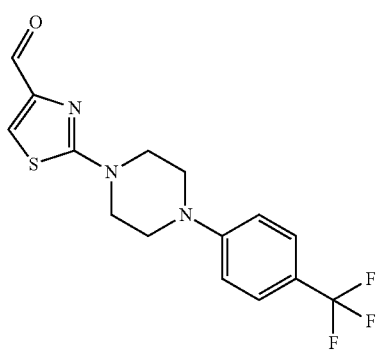 | 1H-NMR (CDCl3) δ: 3.40-3.44 (4H, m), 3.72-3.75 (4H, m), 6.97 (2H, d, J = 8.6 Hz), 7.51-7.54 (3H, m), 9.73 (1H, s). | Ref. Ex. 63 |

TABLE 2-continued

| Ref. Ex. No | STR | 1H-NMR | ref. |
|---|---|---|---|
| 1451 | | 1H-NMR (CDCl3) δ: 1.38 (3H, t, J = 7.1 Hz), 3.24-3.28 (4H, m), 3.67-3.71 (4H, m), 4.36 (2H, q, J = 7.1 Hz), 6.86-6.89 (2H, m), 7.22-7.25 (2H, m), 7.48 (1H, s). | Ref. Ex. 184 |
| 1452 | | 1H-NMR (CDCl3) δ: 3.25 (6H, s), 7.37-7.40 (2H, m), 7.73-7.76 (2H, m), 9.95 (1H, s). | Ref. Ex. 1173 |
| 1453 | | 1H-NMR (CDCl3) δ: 3.26-3.29 (4H, m), 3.70-3.74 (4H, m), 6.86-6.90 (2H, m), 7.22-7.26 (2H, m), 7.50 (1H, s), 9.72 (1H, s). | Ref. Ex. 63 |
| 1454 | | 1H-NMR (CDCl3) δ: 7.06-7.11 (1H, m), 7.17-7.22 (2H, m), 7.38-7.41 (1H, m), 7.35 (1H, s), 8.11 (1H, s), 8.25 (1H, s), 10.06 (1H, s). | Ref. Ex. 91 |
| 1455 | | 1H-NMR (CDCl3) δ: 1.42 (3H, t, J = 7.1 Hz), 7.42 (2H, q, J = 7.1 Hz), 7.30-7.35 (1H, m), 7.72 (1H, s), 7.86 (1H, d, J = 8.8 Hz), 8.04 (1H, s). | Ref. Ex. 1415 |
| 1456 | | 1H-NMR (CDCl3) δ: 4.15 (2H, s), 7.43-7.54 (2H, m), 7.63 (2H, s), 7.72 (1H, s), 7.78 (1H, d, J = 7.2 Hz), 8.62 (1H, s), 10.00 (1H, s). | Ref. Ex. 91 |

TABLE 2-continued

| Ref. Ex. No | STR | 1H-NMR | ref. |
|---|---|---|---|
| 1457 | | 1H-NMR (CDCl3) δ: 5.23 (2H, s), 7.24-7.28 (1H, m), 7.47-7.54 (3H, m), 7.74 (1H, d, J = 7.8 Hz), 7.08 (1H, d, J = 9.0 Hz), 8.82 (1H, s), 10.00 (1H, s). | Ref. Ex. 82 |
| 1458 | | 1H-NMR (CDCl3) δ: 1.53 (3H, d, J = 6.6 Hz), 4.56 (2H, s), 4.61-4.66 (1H, m), 7.39-7.47 (4H, m), 7.56-7.61 (3H, m). | Ref. Ex. 100 |
| 1459 | | 1H-NMR (CDCl3) δ: 1.56 (3H, d, J = 6.5 Hz), 4.55-4.73 (3H, m), 7.41-7.45 (2H, m), 7.60 (1H, t, J = 7.7 Hz), 7.78 (3H, s). | Ref. Ex. 100 |
| 1460 | | 1H-NMR (CDCl3) δ: 7.16-7.21 (1H, m), 7.54 (1H, s), 7.56-7.58 (1H, m), 7.76 (1H, d, J = 8.8 Hz). | Ref. Ex. 1319 |
| 1461 | | 1H-NMR (CDCl3) δ: 6.79-6.86 (1H, m), 7.22 (1H, dd, J = 2.2, 8.7 Hz), 7.50 (1H, d, J = 3.3 Hz). | Ref. Ex. 1319 |
| 1462 | | 1H-NMR (CDCl3) δ: 6.86-6.93 (1H, m), 7.29-7.33 (1H, m), 7.62-7.67 (2H, m), 7.89-7.97 (2H, m), 8.21 (1H, s), 10.10 (1H, s). | Ref. Ex. 91 |
| 1463 | | 1H-NMR (CDCl3) δ: 1.35 (3H, t, J = 7.5 Hz), 1.42 (3H, t, J = 7.2 Hz), 3.13 (2H, q, J = 7.5 Hz), 4.43 (2H, q, J = 7.2 Hz), 7.42-7.45 (2H, m), 8.01-8.03 (2H, m). | Ref. Ex. 133 |
| 1464 | | 1H-NMR (CDCl3) δ: 1.30 (3H, t, J = 7.5 Hz), 2.76 (2H, q, J = 7.5 Hz), 3.25 (1H, bs), 4.59 (2H, s), 7.39-7.43 (2H, m), 7.91-7.95 (2H, m). | Ref. Ex. 19 |

TABLE 2-continued

| Ref. Ex. No | STR | 1H-NMR | ref. |
|---|---|---|---|
| 1465 | | 1HNMR (CDCl3) δ: 7.22-7.25 (1H, m), 7.61-7.64 (3H, m), 7.87-7.98 (3H, m), 8.21 (1H, s), 10.10 (1H, s). | Ref. Ex. 91 |
| 1466 | | 1H-NMR (CDCl3) δ: 1.58 (3H, d, J = 6.6 Hz), 4.54-4.77 (3H, m), 7.63-7.66 (1H, m), 7.70-7.73 (1H, m), 7.79-7.81 (3H, m), 7.89 (1H, t, J = 7.8 Hz). | Ref. Ex. 89 |
| 1467 | | 1H-NMR (CDCl3) δ: 7.61-7.66 (3H, m), 7.85 (1H, d, J = 8.7 Hz), 7.87-7.90 (1H, m), 7.94-7.98 (1H, m), 8.21 (1H, t, J = 1.5 Hz), 10.10 (1H, s). | Ref. Ex. 91 |
| 1468 | | 1H-NMR (CDCl3) δ: 7.74 (2H, d, J = 8.2 Hz), 8.05 (2H, d, J = 8.1 Hz), 10.13 (1H, s). | Ref. Ex. 159 |
| 1469 | | 1H-NMR (CDCl3) δ: 7.62 (1H, t, J = 7.8 Hz), 7.76 (1H, d, J = 7.9 Hz), 8.10 (1H, d, J = 7.8 Hz), 8.20 (1H, s), 10.13 (1H, s). | Ref. Ex. 159 |
| 1470 | | 1H-NMR (CDCl3) δ: 7.34-7.37 (1H, m), 7.52 (1H, t, J = 8.2 Hz), 7.81-7.83 (2H, m), 10.12 (1H, s). | Ref. Ex. 159 |
| 1471 | | 1H-NMR (CDCl3) δ: 7.56 (1H, d, J = 8.4 Hz), 7.73 (1H, dd, J = 2.1, 8.4 Hz), 8.06 (1H, d, J = 2.1 Hz), 10.10 (1H, s). | Ref. Ex. 159 |
| 1472 | | 1H-NMR (CDCl3) δ: 1.58 (3H, t, J = 7.0 Hz), 4.38 (2H, q, J = 7.0 Hz), 7.39-7.42 (2H, m), 7.79-7.82 (2H, m), 10.00 (1H, s). | Ref. Ex. 184 |

TABLE 2-continued

| Ref. Ex. No | STR | 1H-NMR | ref. |
|---|---|---|---|
| 1473 | | 1H-NMR (CDCl3) δ: 4.23 (3H, s), 7.70 (2H, d, J = 8.2 Hz), 7.99 (2H, d, J = 8.1 Hz), 10.04 (1H, s). | Ref. Ex. 184 |
| 1474 | | 1H-NMR (CDCl3) δ: 4.23 (3H, s), 7.58 (1H, t, J = 7 8 Hz), 7.69 (1H, d, J = 7.9 Hz), 8.06 (1H, d, J = 7.9 Hz), 8.13 (1H, s), 10.04 (1H, s). | Ref. Ex. 184 |
| 1475 | | 1H-NMR (CDCl3) δ: 4.22 (3H, s), 7.26-7.31 (1H, m), 7.45-7.50 (1H, m), 7.76-7.80 (2H, m), 10.03 (1H, s). | Ref. Ex. 184 |
| 1476 | | 1H-NMR (CDCl3) δ: 4.22 (3H, s), 7.51 (1H, d, J = 8.4 Hz), 7.68 (1H, dd, J = 2.1, 8.4 Hz), 6.00 (1H, d, J = 2.1 Hz), 10.01 (1H, s). | Ref. Ex. 184 |
| 1478 | | 1H-NMR (CDCl3) δ: 1.62 (3H, d, J = 6.6 Hz), 4.57-4.67 (2H, m), 4.80 (1H, q, J = 6.6 Hz), 7.69-7.72 (1H, m), 7.80 (3H, s), 7.89-7.96 (2H, m). 10.07 (1H, s). | Ref. Ex. 318 |
| 1479 | | 1H-NMR (CDCl3) δ: 7.10-7.17 (1H, m), 7.38-7.39 (1H, m), 7.44-7.48 (1H, m), 7.55 (1H, s), 7.72-7.73 (2H, m), 9.91 (1H, s). | Ref. Ex. 91 |
| 1480 | | 1H-NMR (CDCl3) δ: 6.88-6.95 (1H, m), 7.30-7.40 (1H, m), 7.61-7.64 (1H, m), 7.85-7.86 (1H, m), 7.92-7.93 (1H, m), 8.07-8.08 (1H, m), 10.05 (1H, s). | Ref. Ex. 91 |
| 1481 | | 1H-NMR (CDCl3) δ: 4.01 (3H, s), 4.88 (2H, s), 4.91 (2H, s), 7.72-7.74 (1H, m), 7.83-7.98 (4H, m), 8.06-8.09 (1H, m). | Ref. Ex. 100 |

TABLE 2-continued

| Ref. Ex. No | STR | 1H-NMR | ref. |
|---|---|---|---|
| 1482 | | 1H-NMR (CDCl3) δ: 4.01 (3H, s), 4.89 (4H, s), 7.66-7.81 (3H, m), 7.91 (1H, t, J = 7.8 Hz), 8.07-8.10 (2H, m). | Ref. Ex. 100 |
| 1483 | | 1H-NMR (CDCl3) δ: 5.42 (2H, s), 7.28-7.31 (6H, m), 7.93 (1H, d, J = 8.7 Hz), 8.04 (1H, s), 9.99 (1H, s). | Ref. Ex. 80 |
| 1484 | | 1H-NMR (CDCl3) δ: 5.39 (2H, s), 6.84-6.91 (1H, m), 7.17-7.36 (3H, m), 7.46-7.54 (3H, m), 9.99 (1H, s). | Ref. Ex. 80 |
| 1485 | | 1H-NMR (CDCl3) δ: 1.52 (9H, s), 3.95 (3H, s), 7.42-7.45 (2H, m), 7.97-8.00 (2H, m). | Ref. Ex. 133 |

TABLE 2-continued

| Ref. Ex. No | STR | 1H-NMR | ref. |
|---|---|---|---|
| 1486 | | 1H-NMR (CDCl3) δ: 3.74 (1H, bs), 4.78 (4H, s), 4.91 (2H, s), 7.18 (1H, d, J = 8.1 Hz), 7.40 (1H, d, J = 8.1 Hz), 7.73 (1H, t, J = 8.1 Hz), 7.84 (1H, d, J = 8.1 Hz), 7.91 (1H, s), 7.98 (1H, d, J = 8.1 Hz). | Ref. Ex. 19 |
| 1487 | | 1H-NMR (CDCl3) δ: 3.66-3.68 (1H, m), 4.76-4.80 (4H, m), 4.89 (2H, s), 7.18 (1H, d, J = 8.4 Hz), 7.40 (1H, d, J = 8.4 Hz), 7.66-7.81 (3H, m), 8.10 (1H, s). | Ref. Ex. 19 |
| 1488 | | 1H-NMR (CDCl3) δ: 4.87 (2H, s), 4.94 (2H, s), 7.73-7.76 (1H, m), 7.84-7.99 (5H, m), 10.07 (1H, s). | Ref. Ex. 156 |
| 1489 | | 1H-NMR (CDCl3) δ: 4.88 (2H, s), 4.93 (2H, s), 7.67-7.75 (2H, m), 7.81 (1H, d, J = 8.4 Hz), 7.90-7.94 (2H, m), 8.10 (1H, s), 10.07 (1H, s). | Ref. Ex. 156 |
| 1490 | | 1H-NMR (CDCl3) δ: 1.53 (3H, d, J = 6.5 Hz), 4.54-4.60 (2H, m), 4.70 (1H, q, J = 6.5 Hz), 7.44-7.47 (2H, m), 7.60-7.64 (3H, m), 7.72-7.76 (1H, m), 7.87 (1H, t, J = 7.8 Hz). | Ref. Ex. 89 |
| 1491 | | 1H-NMR (CDCl3) δ: 1.38 (3H, t, J = 7.5 Hz), 3.12 (2H, q, J = 7.5 Hz), 7.45-7.48 (2H, m), 7.99-8.02 (2H, m), 10.03 (1H, s). | Ref. Ex. 48 |

TABLE 2-continued

| Ref. Ex. No | STR | 1H-NMR | ref. |
|---|---|---|---|
| 1495 | | 1H-NMR (CDCl3) δ: 7.66 (1H, d, J = 5.0 Hz), 7.72-7.76 (1H, m), 7.81-7.84 (1H, m), 8.33-8.38 (1H, m), 9.18 (1H, d, J = 5.0 Hz), 10.08 (1H, d, J = 1.6 Hz). | Ref. Ex. 91 |
| 1496 | | 1H-NMR (CDCl3) δ: 7.10-7.17 (1H, m), 7.46-7.50 (1H, m), 7.65 (1H, s), 7.76-7.81 (1H, m), 7.86 (2H, d, J = 8.4 Hz), 7.95 (2H, d, J = 8.4 Hz), 10.05 (1H, s). | Ref. Ex. 91 |
| 1498 | | 1H-NMR (CDCl3) δ: 1.55 (3H, d, J = 6.6 Hz), 3.87 (1H, bs), 4.52-4.55 (2H, m), 4.66 (1H, q, J = 6.6 Hz), 4.77 (2H, s), 7.15 (1H, d, J = 7.5 Hz), 7.39 (1H d, J = 7.5 Hz), 7.46 (2H, d, J = 7.8 Hz), 7.60 (2H, d, J = 7.8 Hz), 7.72 (1H, t, J = 7.5 Hz). | Ref. Ex. 19 |
| 1499 | | 1H-NMR (CDCl3) δ: 7.13-7.32 (1H, m), 7.68-7.69 (2H, m), 7.84-7.89 (3H, m), 7.95-7.98 (2H, m), 10.06 (1H, s). | Ref. Ex. 91 |
| 1500 | | 1H-NMR (CDCl3) δ: 7.63 (1H, d, J = 5.0 Hz), 7.99-8.05 (1H, m), 6.34-7.38 (1H, m), 8.45 (1H, d, J = 8.2 Hz), 9.12 (1H, d, J = 4.9 Hz), 10.46 (1H, s). | Ref. Ex. 91 |
| 1501 | | 1H-NMR (CDCl3) δ: 1.38 (3H, t, J = 7.1 Hz), 2.46 (3H, s), 3.86 (3H, s), 4.33 (2H, q, J = 7.1 Hz). | Ref. Ex. 12 |
| 1502 | | 1H-NMR (CDCl3) δ: 1.39 (3H, t, J = 7.1 Hz), 2.57 (3H, s), 3.55 (3H, s), 4.36 (2H, q, J = 7.1 Hz). | Ref. Ex. 12 |

TABLE 2-continued

| Ref. Ex. No | STR | 1H-NMR | ref. |
|---|---|---|---|
| 1503 | | 1H-NMR (CDCl3) δ: 4.32 (2H, s), 7.09 (1H, s), 7.30-7.34 (1H, m), 7.48-7.52 (2H, m), 7.62 (1H, d, J = 2.0 Hz), 7.75-7.80 (3H, m), 10.00 (1H, s). | Ref. Ex. 91 |
| 1504 | | 1H-NMR (CDCl3) δ: 5.32 (2H, s), 7.28-7.38 (2H, m), 7.42-7.59 (4H, m), 7.78-7.85 (2H, m), 10.00 (1H, s). | Ref. Ex. 82 |
| 1505 | | 1H-NMR (CDCl3) δ: 1.37 (6H, d, J = 7.2 Hz), 3.81-3.91 (1H, m), 3.96 (3H, s), 7.54 (1H, d, J = 8.5 Hz), 7.89-7.93 (1H, m), 8.17-8.18 (1H, m). | Ref. Ex. 133 |
| 1506 | | 1H-NMR (CDCl3) δ: 1.37 (6H, d, J = 6.9 Hz), 3.81-3.90 (1H, m), 3.95 (3H, s), 7.21-7.26 (1H, m), 7.94-7.99 (1H, m), 8.15 (1H, dd, J = 2.1, 7.2 Hz). | Ref. Ex. 133 |
| 1507 | | 1H-NMR (CDCl3) δ: 2.69 (3H, s), 7.60-7.63 (1H, m), 7.84-7.86 (2H, m), 8.14-8.17 (1H, m), 9.15 (1H, d, J = 4.8 Hz), 10.09 (1H, s). | Ref. Ex. 91 |
| 1508 | | 1H-NMR (CDCl3) δ: 1.34 (6H, d, J = 6.9 Hz), 2.67-2.71 (1H, m), 3.13-3.23 (1H, m), 4.61 (2H, d, J = 5.7 Hz), 7.51 (1H, d, J = 8.4 Hz), 7.62 (1H, dd, J = 2.1, 8.4 Hz), 8.07 (1H, d, J = 2.1 Hz). | Ref. Ex. 19 |
| 1509 | | 1H-NMR (CDCl3) δ: 1.41 (6H, d, J = 7.0 Hz), 3.67-3.74 (1H, m), 7.56 (1H, d, J = 8.4 Hz), 7.90 (1H, dd, J = 2.0, 8.4 Hz), 8.15 (1H, d, J = 2.0 Hz), 10.03 (1H, s). | Ref. Ex. 147 |

TABLE 2-continued

| Ref. Ex. No | STR | 1H-NMR | ref. |
|---|---|---|---|
| 1510 | | 1H-NMR (CDCl3) δ: 1.39 (6H, d, J = 6.9 Hz), 3.81-3.93 (1H, m), 3.97 (3H, s), 7.61 (1H, t, J = 7.8 Hz), 7.73 (1H, d, J = 7.8 Hz), 8.27 (1H, d, J = 7.8 Hz), 8.34 (1H, s). | Ref. Ex. 133 |
| 1511 | | 1H-NMR (CDCl3) δ: 1.36 (6H, d, J = 6.9 Hz), 2.27 (1H, t, J = 5.7 Hz), 3.15-3.24 (1H, m), 4.63 (2H, d, J = 5.7 Hz), 7.58 (1H, t, J = 7.8 Hz), 7.68 (1H, d, J = 7.8 Hz), 8.19 (1H, d, J = 7.8 Hz), 8.26 (1H, s). | Ref. Ex. 19 |
| 1512 | | 1H-NMR (CDCl3) δ: 1.43 (6H, d, J = 7.0 Hz), 3.69-3.76 (1H, m), 7.63 (1H, t, J = 7.8 Hz), 7.75 (1H, d, J = 7.8 Hz), 9.26 (1H, d, J = 7.8 Hz), 8.32 (1H, s), 10.06 (1H, s). | Ref. Ex. 147 |
| 1513 | | 1H-NMR (CDCl3) δ: 1.34 (6H, d, J = 6.9 Hz), 3.05-3.22 (2H, m), 4.61 (2H, d, J = 6.0 Hz), 7.20 (1H, t, J = 8.7 Hz), 7.85-7.91 (1H, m), 8.04 (1H, dd, J = 2.1, 7.2 Hz). | Ref. Ex. 19 |
| 1514 | | 1H-NMR (CDCl3) δ: 1.41 (6H, d, J = 7.0 Hz), 3.67-3.74 (1H, m), 7.24-7.28 (1H, m), 7.94-7.98 (1H, m), 8.13 (1H, dd, J = 2.2, 6.9 Hz), 10.03 (1H, s). | Ref. Ex. 147 |
| 1515 | | 1H-NMR (CDCl3) δ: 1.42 (9H, s), 2.87 (1H, d, J = 6.0 Hz), 4.70 (1H, d, J = 6.0 Hz), 7.40-7.42 (2H, m), 7.90-7.93 (2H, m). | Ref. Ex. 19 |
| 1516 | | 1H-NMR (CDCl3) δ: 1.54 (9H, s), 7.45-7.47 (2H, m), 8.00-8.02 (2H, m), 10.15 (1H, s). | Ref. Ex. 147 |
| 1517 | | 1H-NMR (CDCl3) δ: 7.67-7.72 (1H, m), 7.99-8.04 (4H, m), 8.23-8.28 (2H, m), 10.11 (1H, s). | Ref. Ex. 91 |

| Ref. Ex. No | STR | 1H-NMR | ref. |
|---|---|---|---|
| 1518 | | 1H-NMR (CDCl3) δ: 3.98 (3H, s), 7.18 (1H, dd, J = 4.7, 8.0 Hz), 7.50 (1H, s), 7.62 (1H, t, J = 7.6 Hz), 7.76-7.81 (1H, m), 7.88-7.93 (1H, m), 8.14 (1H, t, J = 1.7 Hz), 8.24 (1H, dd, J = 1.5, 8.0 Hz), 8.42 (1H, dd, J = 1.5, 4.7 Hz), 10.10 (1H, s). | Ref. Ex. 91 |
| 1519 | | 1H-NMR (CDCl3) δ: 7.55-7.57 (1H, m), 7.71-7.75 (1H, m), 7.81-7.84 (1H, m), 8.11 (1H, s), 8.27 (1H, t, J = 7.6 Hz), 8.95 (1H, d, J = 5.0 Hz), 10.07 (1H, d, J = 1.6 Hz). | Ref. Ex. 91 |
| 1520 | | 1H-NMR (CDCl3) δ: 2.53 (3H, s), 5.53 (2H s), 7.28 (2H, d, J = 8.1 Hz), 7.59 (2H, d, J = 8.1 Hz), 7.64 (1H, s), 9.81 (1H, d, J = 0.7 Hz). | Ref. Ex. 184 |
| 1521 | | 1H-NMR (CDCl3) δ: 2.46 (3H, s), 5.19 (2H, s), 7.18 (2H, d, J = 8.1 Hz), 7.55 (1H, s), 7.64 (2H, d, J = 8.1 Hz), 9.98 (1H s). | Ref. Ex. 184 |
| 1522 | | 1H-NMR (CDCl3) δ: 1.43 (3H, t, J = 7.1 Hz), 1.49 (18H, s), 4.44 (2H, q, J = 7.1 Hz), 5.52 (1H, s), 7.78 (2H, s), 8.07 (1H, s). | Ref. Ex. 2 |
| 1523 | | 1H-NMR (CDCl3) δ: 1.03 (3H, t, J = 7.2 Hz), 1.76-1.83 (2H, m), 3.09 (2H, t, J = 7.2 Hz), 3.95 (3H, s), 7.20-7.26 (1H, m), 7.94-7.99 (1H, m), 8.14-8.17 (1H, m). | Ref. Ex. 133 |

| Ref. Ex. No | STR | 1H-NMR | ref. |
|---|---|---|---|
| 1524 | | 1H-NMR (CDCl3) δ: 1.04 (3H, t, J = 7.5 Hz), 1.78-1.85 (2H, m), 3.12 (2H, t, J = 7.5 Hz), 3.97 (3H, s), 7.60 (1H, t, J = 7.8 Hz), 7.73 (1H, d, J = 7.8 Hz), 8.27 (1H, d, J = 7.8 Hz), 8.34 (1H, s). | Ref. Ex. 133 |
| 1525 | | 1H-NMR (CDCl3) : 2.16 (3H, s), 2.77-2.95 (1H, br), 4.79 (2H, d, J = 5.7 Hz), 6.19 (1H, s), 5.31 (1H, t, J = 1.4 Hz), 7.38-7.43 (2H, m), 7.83-7.67 (2H, m). | Ref. Ex. 43 |
| 1526 | | 1H-NMR (CDCl3) δ: 2.16 (3H, s), 2.80 (1H, t, J = 5.7 Hz), 4.79 (2H, d, J = 5.7 Hz), 5.20 (1H, s), 5.32 (1H, t, J = 1.3 Hz), 7.20 (1H, t, J = 8.6 Hz), 7.74-7.79 (1H, m), 7.99 (1H, dd, J = 2.2, 6.9 Hz). | Ref. Ex. 43 |
| 1527 | | 1H-NMR (CDCl3) δ: 1.49 (18H, a), 4.79 (2H, s), 7.06 (1H, s), 7.74 (2H, s). | Ref. Ex. 76 |
| 1528 | | 1H-NMR (CDCl3) δ: 0.99 (3H, t, J = 7.2 Hz), 1.66-1.79 (3H, m), 2.71 (2H, t, J = 7.2 Hz), 4.59 (2H, s), 7.21 (1H, t, J = 8.7 Hz), 7.85-7.91 (1H, m), 8.05 (1H, dd, J = 2.1, 7.2 Hz). | Ref. Ex. 19 |
| 1529 | | 1H-NMR (CDCl3) δ: 1.00 (3H, t, J = 7.5 Hz), 1.69-1.81 (2H, m), 2.34-2.38 (1H, m), 2.74 (2H, t, J = 7.5 Hz), 4.61 (2H, d, J = 5.4 Hz), 7.58 (1H, t, J = 7.8 Hz), 7.68 (1H, d, J = 7.8 Hz), 8.18 (1H, d, J = 7.8 Hz), 8.26 (1H, s). | Ref. Ex. 19 |
| 1530 | | 1H-NMR (CDCl3) δ: 1.40 (3H, t, J = 7.1 Hz), 2.53 (3H, s), 3.87 (3H, s), 4.36 (2H, q, J = 7.1 Hz), 7.43-7.46 (2H, m), 7.50-7.55 (2H, m). | Ref. Ex. 38 |
| 1531 | | 1H-NMR (CDCl3) δ: 1.41 (3H, t, J = 7.1 Hz), 2.53 (3H, s), 3.86 (3H, s), 4.36 (2H, q, J = 7.1 Hz), 7.14-7.20 (2H, m), 7.53-7.63 (2H, m). | Ref. Ex. 38 |

TABLE 2-continued

| Ref. Ex. No | STR | 1H-NMR | ref. |
|---|---|---|---|
| 1532 | 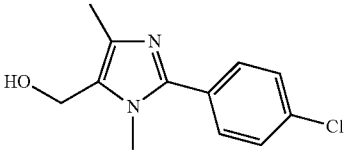 | 1H-NMR (CDCl3) δ: 1.54 (1H, brs), 2.27 (3H, s), 3.70 (3H, s), 4.68 (2H, a), 7.43 (2H, d, J = 8.6 Hz), 7.54 (2H, d, J = 8.6 Hz). | Ref. Ex. 76 |
| 1533 | 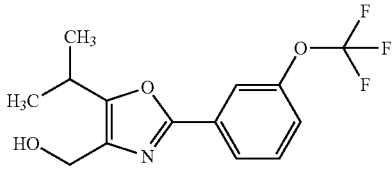 | 1H-NMR (CDCl3) δ: 1.34 (6H, d, J = 7.0 Hz), 2.71 (1H, t, J = 6.0 Hz), 3.13-3.23 (1H, m), 4.62 (2H, d, J = 6.0 Hz), 7.26-7.30 (2H, m), 8.01-8.06 (2H, m). | Ref. Ex. 133, Ref. Ex. 19 |
| 1534 | 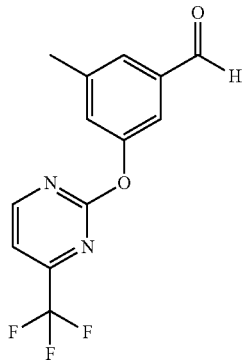 | 1H-NMR (CDCl3) δ: 2.49 (3H, s), 7.31 (1H, s), 7.41 (1H, d, J = 4.9 Hz), 7.54 (1H, s), 7.83 (1H, s), 8.79 (1H, d, J = 4.9 Hz), 9.99 (1H, s). | Ref. Ex. 113 |
| 1535 | 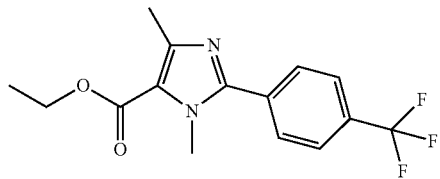 | 1H-NMR (CDCl3) δ: 1.41 (3H, t, J = 7.1 Hz), 2.55 (3H, s), 3.90 (3H, s), 4.37 (2H, q, J = 7.1 Hz), 7.74 (4H, s). | Ref. Ex. 38 |
| 1536 | 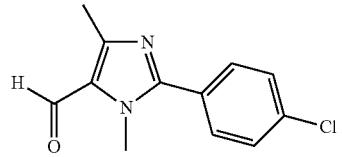 | 1H-NMR (CDCl3) δ: 2.55 (3H, s), 3.95 (3H, s), 7.47-7.51 (2H, m), 7.57-7.61 (2H, m), 9.88 (1H, s). | Ref. Ex. 159 |
| 1537 | 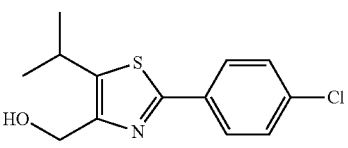 | 1H-NMR (CDCl3) δ: 1.34 (6H, d, J = 6.8 Hz), 2.44 (1H, t, J = 5.7 Hz), 3.28-3.37 (1H, m), 4.72 (2H, d, J = 5.6 Hz), 7.37-7.41 (2H, m), 7.81-7.85 (2H, m). | Ref. Ex. 34 |
| 1538 | 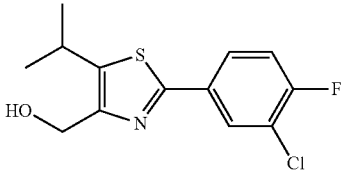 | 1H-NMR (CDCl3) δ: 1.35 (6H, d, J = 6.8 Hz), 2.35 (1H, t, J = 5.8 Hz), 3.30-3.35 (1H, m), 4.72 (2H, d, J = 5.8 Hz), 7.16-7.22 (1H, m), 7.77 (1H, m), 7.98 (1H, dd J = 2.3, 7.0 Hz). | Ref. Ex. 34 |
| 1539 | 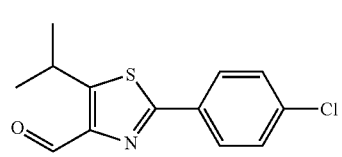 | 1H-NMR (CDCl3) δ: 1.39 (6H, d, J = 6.8 Hz), 4.10-4.19 (1H, m), 7.41-7.46 (2H, m), 7.86-7.90 (2H, m), 10.20 (1H, s). | Ref. Ex. 48 |

| Ref. Ex. No | STR | 1H-NMR | ref. |
|---|---|---|---|
| 1540 | | 1H-NMR (CDCl3) δ: 1.50 (18H, s), 5.37 (1H, s), 7.80 (2H, s), 8.09 (1H, s), 10.09 (1H, s). | Ref. Ex. 48 |
| 1541 | | 1H-NMR (CDCl3) δ: 1.39 (6H, d, J = 6.8 Hz), 4.10-4.19 (1H, m), 7.20-7.26 (1H, m), 7.77-7.82 (1H, m), 8.03 (1H, dd, J = 2.2, 6.9 Hz), 10.19 (1H, s). | Ref. Ex. 48 |
| 1542 | | 1H-NMR (CDCl3) δ: 1.40 (3H, t, J = 7.1 Hz), 2.62 (3H, s), 3.57 (3H, s), 4.39 (2H, q, J = 7.1 Hz), 7.12-7.17 (2H, m), 7.55-7.60 (2H, m). | Ref. Ex. 38 |
| 1543 | | 1H-NMR (CDCl3) δ: 1.49 (1H, t, J = 4.2 Hz), 2.26 (3H, s), 3.69 (3H, s), 4.67 (2H, d, J = 4.2 Hz), 7.11-7.18 (2H, m), 7.54-7.61 (2H, m). | Ref. Ex. 76 |
| 1544 | | 1H-NMR (CDCl3) δ: 1.68 (1H, brs), 2.28 (3H, s), 3.74 (3H, s), 4.63 (2H, s), 7.67-7.75 (4H, m). | Ref. Ex. 76 |
| 1545 | | 1H-NMR (CDCl3) δ: 1.44 (3H, t, J = 7.1 Hz), 4.43 (2H, s), 4.46 (2H, q, J = 7.1 Hz), 4.56 (2H, s), 7.56 (1H, t, J = 7.6 Hz), 7.67 (1H, d, J = 7.7 Hz), 7.78 (1H, d, J = 7.7 Hz), 7.86 (1H, s), 8.27 (1H, s). | Ref. Ex. 2 |
| 1546 | | 1H-NMR (CDCl3) δ: 2.54 (3H, s), 3.94 (3H, s), 7.16-7.23 (2H, m), 7.61-7.66 (2H, m), 9.88 (1H, s). | Ref. Ex. 159 |

| Ref. Ex. No | STR | 1H-NMR | ref. |
|---|---|---|---|
| 1547 | | 1H-NMR (CDCl3) δ: 2.56 (3H, s), 3.98 (3H, s), 7.74-7.84 (4H m), 9.91 (1H, s). | Ref. Ex. 159 |
| 1548 | | 1H-NMR (CDCl3) δ: 7.45-7.51 (2H, m), 7.73-7.80 (2H, m), 8.81 (1H, d, J = 4.8 Hz), 10.01 (1H, s). | Ref. Ex. 113 |
| 1549 | | 1H-NMR (CDCl3) δ: 2.41 (3H, s), 4.47 (2H, s), 7.06 (1H, s), 7.26-7.48 (5H, m), 7.75 (1H, d, J = 7.8 Hz), 10.11 (1H, s). | Ref. Ex. 91 |
| 1550 | | 1H-NMR (CDCl3) δ: 1.57-1.58 (3H, m), 4.57 (2H, s), 4.77 (1H, q, J = 6.6 Hz), 7.45-7.48 (2H, m), 7 60-7.62 (2H, m), 7.72-7.75 (1H, m), 7.88-7.92 (2H, m), 10.08 (1H, s). | Ref. Ex. 156 |
| 1551 | | 1H-NMR (CDCl3) δ: 4.45 (2H, s), 4.56 (2H, s), 7.58 (1H, t, J = 7.7 Hz), 7.69 (1H, d, J = 7.7 Hz), 7.78 (1H, d, J = 7.6 Hz), 7.84 (1H, s), 8.30 (1H, s), 10.10 (1H, s). | Ref. Ex. 63 |
| 1552 | | 1H-NMR (CDCl3) δ: 2.25 (3H, s), 5.44 (1H, s), 5.53 (1H, t, J = 1.3 Hz), 7.42-7.46 (2H, m), 7.90-7.95 (2H, m), 10.07 (1H, s). | Ref. Ex. 48 |
| 1553 | | 1H-NMR (CDCl3) δ: 2.48 (1H, t, J = 6.2 Hz), 4.95 (2H, d, J = 6.2 Hz), 7.45-7.46 (2H, m), 7.88-7.91 (2H, m). | Ref. Ex. 89 |

TABLE 2-continued

| Ref. Ex. No | STR | 1H-NMR | ref. |
|---|---|---|---|
| 1554 | | 1H-NMR (CDCl3) δ: 1.36 (6H, d, J = 6.9 Hz), 3.80-3.90 (1H, m), 3.95 (3H, s), 7.13-7.18 (2H, m), 8.05-8.09 (2H, m). | Ref. Ex. 133 |
| 1555 | | 1H-NMR (CDCl3) δ: 1.34 (6H, d, J = 6.9 Hz), 2.48 (1H, d, J = 6.0 Hz), 3.10-3.24 (1H, m), 4.61 (2H, d, J = 6.0 Hz), 7.10-7.16 (2H, m), 7.97-8.02 (2H, m). | Ref. Ex. 19 |
| 1556 | | 1H-NMR (CDCl3) δ: 1.41 (6H d, J = 6.9 Hz), 3.65-3.74 (1H, m), 7.15-7.21 (2H, m), 8.05-8.09 (2H, m), 10.04 (1H, s). | Ref. Ex. 147 |
| 1557 | | 1H-NMR (CDCl3) δ: 1.17-1.26 (4H, m), 2.79-2.88 (1H, m), 3.97 (3H, s), 7.40-7.43 (2H, m), 7.91-7.94 (2H, m). | Ref. Ex. 133 |
| 1558 | | 1H-NMR (CDCl3) δ: 0.96-1.05 (4H, m), 1.94-2.05 (1H, m), 2.22 (1H, bs), 4.66 (2H, s), 7.39-7.42 (2H, m), 7.87-7.90 (2H, m). | Ref. Ex. 19 |
| 1559 | | 1H-NMR (CDCl3) δ: 1.24-1.30 (4H, m), 2.65-2.74 (1H, m), 7.43-7.46 (2H, m), 7.90-7.93 (2H, m), 10.04 (1H, s). | Ref. Ex. 147 |
| 1560 | | 1H-NMR (CDCl3) δ: 1.38 (6H, d, J = 6.9 Hz), 3.80-3.90 (1H, m), 3.95 (3H, s), 7.21-7.30 (1H, m), 7.81-7.93 (2H, m). | Ref. Ex. 133 |
| 1561 | | 1H-NMR (CDCl3) δ: 1.34 (6H, d, J = 6.9 Hz), 2.35-2.38 (1H, m), 3.10-3.24 (1H, m), 4.60 (2H, d, J = 5.7 Hz), 7.19-7.28 (1H, m), 7.73-7.85 (2H, m). | Ref. Ex. 19 |

TABLE 2-continued

| Ref. Ex. No | STR | 1H-NMR | ref. |
|---|---|---|---|
| 1562 | | 1H-NMR (CDCl3) δ: 3.75 (3H, s), 3.89 (3H, s), 7.45 (1H, d, J = 1.1 Hz), 7.58 (1H, d, J = 1.1 Hz). | Ref. Ex. 12 |
| 1563 | | 1H-NMR (CDCl3) δ: 7.49-7.53 (2H, m), 7.93-7.98 (2H, m), 10.18 (1H, s). | Ref. Ex. 48 |
| 1564 | | 1H-NMR (CDCl3) δ: 7.77-7.83 (3H, m), 8.03-8.13 (3H, m), 9.00 (1H, s), 10.11 (1H, s). | Ref. Ex. 112 |
| 1565 | | 1H-NMR (CDCl3) δ: 1.20-1.27 (4H, m), 2.81-2.91 (1H, m), 3.98 (3H, s), 7.69-7.71 (2H, m), 8.10-8.13 (2H, m). | Ref. Ex. 133 |
| 1566 | | 1H-NMR (CDCl3) δ: 0.97-1.10 (4H, m), 1.97-2.06 (1H, m), 2.27-2.31 (1H, m), 4.68 (2H, d, J = 5.7 Hz), 7.69 (2H, d, J = 8.4 Hz), 8.06 (2H, d, J = 8.4 Hz). | Ref. Ex. 19 |
| 1567 | | 1H-NMR (CDCl3) δ: 1.27-1.33 (4H, m), 2.68-2.77 (1H, m), 7.73 (2H, d, J = 8.1 Hz), 8.10 (2H, d, J = 8.1 Hz), 10.06 (1H, s). | Ref. Ex. 147 |
| 1568 | | 1H-NMR (CDCl3) δ: 2.28 (3H, s), 2.97 (1H, brs), 3.54 (3H, s), 4.60 (2H, s), 7.12-7.17 (2H, m), 7.52-7.58 (2H, m). | Ref. Ex. 76 |
| 1569 | | 1H-NMR (CDCl3) δ: 1.40 (3H, t, J = 7.1 Hz), 2.62 (3H, s), 3.58 (3H, s), 4.40 (2H, q, J = 7.1 Hz), 7.39-7.45 (2H, m), 7.51-7.58 (2H, m). | Ref. Ex. 75 |

TABLE 2-continued

| Ref. Ex. No | STR | 1H-NMR | ref. |
|---|---|---|---|
| 1570 | | 1H-NMR (CDCl3) δ: 1.41 (3H, t, J = 7.1 Hz), 2.64 (3H, s), 3.62 (3H, s), 4.41 (2H, q, J = 7.1 Hz), 7.68-7.76 (4H, m). | Ref. Ex. 75 |
| 1571 | | 1H-NMR (CDCl3) δ: 2.62 (3H, s), 3.61 (3H, s), 7.15-7.22 (2H, m), 7.57-7.64 (2H, m), 9.99 (1H, s). | Ref. Ex. 159 |
| 1572 | | 1H-NMR (CDCl3) δ: 2.31 (3H, s), 2.53 (1H, t, J = 5.3 Hz), 3.61 (3H, s), 4.63 (2H, d, J = 5.3 Hz), 7.72 (4H, s). | Ref. Ex. 76 |
| 1573 | | 1H-NMR (CDCl3) δ: 2.29 (3H, s), 2.32 (1H, brs), 3.56 (3H, s), 4.61 (2H, d, J = 3.7 Hz), 7.41-7.45 (2H, m), 7.50-7.54 (2H, m). | Ref. Ex. 76 |
| 1574 | | 1H-NMR (CDCl3) δ: 1.02 (6H, s), 1.29 (6H, d, J = 6.9 Hz), 2.98-3.03 (1H, m), 3.80 (4H, s), 7.82-7.83 (1H, m), 7.93 (1H, s), 8.11 (1H, s), 10.03 (1H, s). | Ref. Ex. 107 |
| 1575 | | 1H-NMR (CDCl3) δ: 1.40 (3H, t, J = 7.1 Hz), 4.42 (2H, q, J = 7.1 Hz), 7.20-7.26 (1H, m), 7.54-7.59 (1H, m), 7.75 (1H, dd, J = 2.3, 6.8 Hz), 8.05 (1H, s). | Ref. Ex. 10 |
| 1576 | | 1H-NMR (CDCl3) δ: 1.41 (3H, t, J = 7.1 Hz), 4.43 (2H, q, J = 7.1 Hz), 7.58 (1H, t, J = 7.8 Hz), 7.71 (1H, d, J = 7.9 Hz), 7.83 (1H, d, J = 7.8 Hz), 7.92 (1H, s), 8.08 (1H, s). | Ref. Ex. 10 |

TABLE 2-continued
| Ref. Ex. No | STR | 1H-NMR | ref. |
|---|---|---|---|
| 1577 | 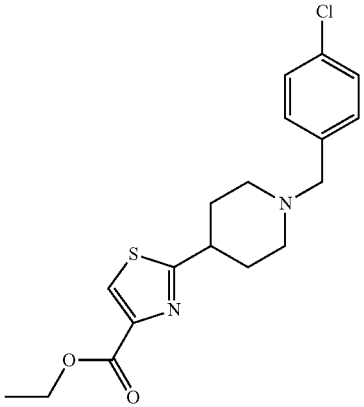 | 1H-NMR (CDCl3) δ: 1.40 (3H, t, J = 7.1 Hz), 1.77-1.89 (2H, m), 2.06-2.13 (4H, m), 2.94-2.98 (2H, m), 3.09-3.17 (1H, m), 3.49 (2H, s), 4.42 (2H, q, J = 7.1 Hz), 7.25-7.31 (4H, m), 8.07 (1H, s). | Ref. Ex. 113 |
| 1578 | 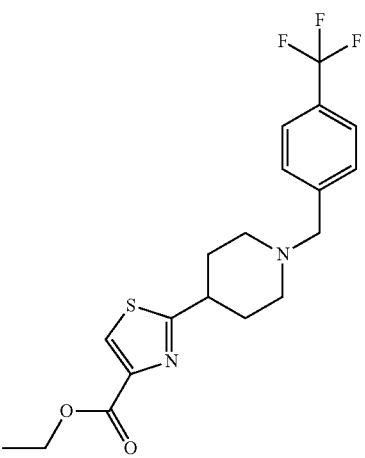 | 1H-NMR (CDCl3) δ: 1.40 (3H, t, J = 7.1 Hz), 1.80-1.92 (2H, m), 2.10-2.18 (4H, m), 2.95-2.99 (2H, m), 3.09-3.19 (1H, m), 3.58 (2H, s). 4.42 (2H, q, J = 7.1 Hz), 7.46 (2H, d, J = 8.1 Hz), 7.58 (2H, d, J = 8.0 Hz), 8.07 (1H, s). | Ref. Ex. 113 |
| 1579 | 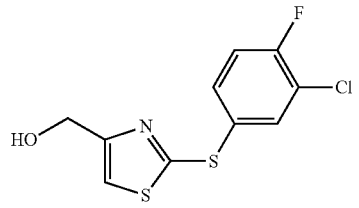 | 1H-NMR (CDCl3) δ: 2.11 (1H, brs), 4.74 (2H, d, J = 5.1 Hz), 7.13-7.22 (2H, m), 7.48-7.53 (1H, m), 7.67-7.71 (1H, m). | Ref. Ex. 19 |
| 1580 | 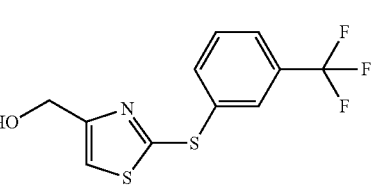 | 1H-NMR (CDCl3) δ: 2.00-2.28 (1H, br), 4.76 (2H, s), 7.18 (1H, s), 7.53 (1H, t, J = 7.8 Hz), 7.65 (1H, d, J = 7.9 Hz), 7.76 (1H, d, J = 7.7 Hz), 7.85 (1H, s). | Ref. Ex. 19 |
| 1581 | 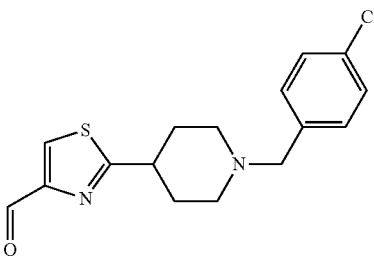 | 1H-NMR (CDCl3) δ: 1.82-1.95 (2H, m), 2.10-2.17 (4H, m), 2.95-3.13 (3H, m), 3.50 (2H, s), 7.26-7.32 (4H, m), 8.08 (1H, s), 10.00 (1H, s). | Ref. Ex. 63 |

TABLE 2-continued

| Ref. Ex. No | STR | 1H-NMR | ref. |
|---|---|---|---|
| 1582 | | 1H-NMR (CDCl3) δ: 1.84-1.97 (2H, m), 2.12-2.21 (4H, m), 2.96-3.13 (3H, m), 3.59 (2H, s), 7.47 (2H, d, J = 8.3 Hz), 7.58 (2H, d, J = 8.2 Hz), 8.08 (1H, s), 10.00 (1H, s). | Ref. Ex. 63 |
| 1583 | | 1H-NMR (CDCl3) δ: 2.62 (3H, s), 3.62 (3H, s), 7.46-7.49 (2H, m), 7.52-7.60 (2H, m), 9.99 (1H, s). | Ref. Ex. 159 |
| 1584 | | 1H-NMR (CDCl3) δ: 2.64 (3H, s), 3.66 (3H, s), 7.76 (4H, s), 10.01 (1H, s). | Ref. Ex. 159 |
| 1585 | | 1H-NMR (CDCl3) δ: 7.68 (1H, d, J = 5.1 Hz), 7.73-7.79 (1H, m), 8.05-8.11 (1H, m), 9.18 (1H, d, J = 5.1 Hz), 10.43 (1H, s). | Ref. Ex. 91 |
| 1586 | | 1H-NMR (CDCl3) δ: 1.35 (6H, d, J = 6.9 Hz), 3.03-3.10 (1H, m), 7.09-7.14 (1H, m), 7.45-7.48 (1H, m), 7.59 (1H, s), 7.75-7.80 (3H, m), 8.02 (1H, s), 10.07 (1H, s). | Ref. Ex. 91 |
| 1587 | | 1H-NMR (CDCl3) δ: 1.27 (6H, d, J = 6.9 Hz), 2.92-3.01 (1H, m), 4.10 (2H, s), 7.32-7.50 (6H, m), 7.63 (1H, s), 9.97 (1H, s). | Ref. Ex. 91 |

TABLE 2-continued

| Ref. Ex. No | STR | 1H-NMR | ref. |
|---|---|---|---|
| 1588 | | 1H-NMR (CDCl3) δ: 1.37 (6H, d, J = 6.9 Hz), 3.05-3.20 (1H, m), 7.57 (1H, d, J = 5.0 Hz), 7.95 (1H, s), 8.66 (1H, s), 8.63 (1H, s), 9.09 (1H, d, J = 5.0 Hz), 10.14 (1H, s). | Ref. Ex. 91 |
| 1589 | | 1H-NMR (CDCl3) δ: 1.40 (6H, d, J = 6.9 Hz), 3.65-3.75 (1H, m), 7.24-7.33 (1H, m), 7.81-7.92 (2H, m), 10.03 (1H, s). | Ref. Ex. 147 |
| 1590 | | 1H-NMR (CDCl3) δ: 1.18-1.25 (4H, m), 2.79-2.88 (1H, m), 3.97 (3H, s), 7.21 (1H, t, J = 8.4 Hz), 7.86-7.91 (1H, m), 8.05-8.08 (1H, m). | Ref. Ex. 133 |
| 1591 | | 1H-NMR (CDCl3) δ: 0.96-1.08 (4H, m), 1.95-2.01 (1H, m), 2.41 (1H, bs), 4.65 (2H, s), 7.19 (1H, t, J = 8.4 Hz), 7.80-7.86 (1H, m), 8.00 (1H, dd, J = 2.1, 8.4 Hz). | Ref. Ex. 19 |
| 1592 | | 1H-NMR (CDCl3) δ: 1.24-1.33 (4H, m), 2.65-2.74 (1H, m), 7.21-7.26 (1H, m), 7.85-7.90 (1H, m), 8.04 (1H, dd, J = 2.1, 6.9 Hz), 10.04 (1H, s). | Ref. Ex. 147 |
| 1593 | | 1H-NMR (CDCl3) δ: 7.25 (1H, t, J = 8.6 Hz), 7.57-7.61 (1H, m), 7.76 (1H, dd, J = 2.3, 6.8 Hz), 8.05 (1H, s), 9.96 (1H, s). | Ref. Ex. 48 |
| 1594 | | 1H-NMR (CDCl3) δ: 7.60 (1H, t, J = 7.9 Hz), 7.73 (1H, d, J = 7.9 Hz), 7.85 (1H, d, J = 7.7 Hz), 7.93 (1H, s), 8.08 (1H, s), 9.97 (1H, s). | Ref. Ex. 48 |

TABLE 2-continued

| Ref. Ex. No | STR | 1H-NMR | ref. |
|---|---|---|---|
| 1595 | | 1H-NMR (CDCl3) δ: 1.28 (3H, t, J = 7.6 Hz), 2.51 (3H, s), 2.63 (2H, q, J = 7.6 Hz), 5.50 (2H, s), 6.95-6.98 (2H, m), 7.24-7.29 (2H, m), 9.75 (1H, s). | Ref. Ex. 12 |
| 1596 | | 1H-NMR (CDCl3) δ: 1.30 (3H, t, J = 7.5 Hz), 2.45 (3H, s), 2.62 (2H, q, J = 7.5 Hz), 5.06 (2H, s), 6.85-6.89 (2H, m), 7.31-7.37 (2H, m), 9.96 (1H, s). | Ref. Ex. 12 |
| 1597 | | 1H-NMR (CDCl3) δ: 1.34 (6H, d, J = 6.9 Hz), 3.02-3.09 (1H, m), 7.16 (2H, t, J = 8.7 Hz), 7.56-7.62 (2H, m), 7.66 (1H, t, J = 1.6 Hz), 7.73 (1H, t, J = 1.6 Hz), 7.87 (1H, t, J = 1.6 Hz), 10.07 (1H, s). | Ref. Ex. 91 |
| 1598 | | 1H-NMR (CDCl3) δ: 1.42 (9H, s), 7.14-7.20 (2H, m), 7.56-7.61 (2H, m), 7.81-7.90 (3H, m), 10.08 (1H, s). | Ref. Ex. 91 |
| 1599 | | 1HNMR (CDCl3) δ: 1.39 (6H, d, J = 6.9 Hz), 3.83-3.92 (1H, m), 3.97 (3H, s), 7.76-7.74 (2H, m), 8.18-8.21 (2H, m). | Ref. Ex. 133 |
| 1600 | | 1H-NMR (CDCl3) δ: 0.91-0.99 (3H, m), 1.37-1.49 (5H, m), 1.69-1.79 (2H, m), 3.11 (2H, t, J = 7.8 Hz), 4.42 (2H, q, J = 7.2 Hz), 7.42-7.45 (2H, m), 8.00-8.03 (2H, m). | Ref. Ex. 133 |
| 1601 | | 1H-NMR (CDCl3) δ: 1.36 (6H, d, J = 6.9 Hz), 2.29 (1H, bs), 3.15-3.25 (1H, m), 4.63 (2H, bs), 7.69-7.72 (2H, m), 8.10-8.13 (2H, m). | Ref. Ex. 19 |

TABLE 2-continued

| Ref. Ex. No | STR | 1H-NMR | ref. |
|---|---|---|---|
| 1602 | | 1H-NMR (CDCl3) δ: 0.95 (3H, t, J = 7.5 Hz), 1.30-1.48 (2H, m), 1.63-1.73 (2H, m), 2.11-2.15 (1H, m), 2.73 (2H, t, J = 7.5 Hz), 4.59 (1H, d, J = 5.4 Hz), 7.40-7.43 (2H, m), 7.92-7.95 (2H, m). | Ref. Ex. 19 |
| 1603 | | 1H-NMR (CDCl3) δ: 1.43 (6H, d, J = 6.9 Hz), 3.68-3.78 (1H, m), 7.74-7.77 (2H, m), 8.18-8.20 (2H, m), 10.06 (1H, s). | Ref. Ex. 147 |
| 1604 | | 1H-NMR (CDCl3) δ: 0.97 (3H, t, J = 7.5 Hz), 1.38-1.50 (2H, m), 1.71-1.82 (2H, m), 3.09 (2H, t, J = 7.5 Hz), 7.45-7.46 (2H, m), 7.99-8.02 (2H, m), 10.02 (1H, s). | Ref. Ex. 147 |
| 1605 | | 1H-NMR (CDCl3) δ: 1.41 (3H, t, J = 7.1 Hz), 1.88-2.01 (2H, m), 2.26-2.29 (2H, m), 2.92-3.01 (2H, m), 3.27-3.36 (1H, m), 3.89-3.93 (2H, m), 4.43 (2H, q, J = 7.1 Hz), 6.96 (2H, d, J = 8.6 Hz), 7.49 (2H, d, J = 8.6 Hz), 8.09 (1H, s). | Ref. Ex. 16 |
| 1606 | | 1H-NMR (CDCl3) δ: 1.41 (3H, t, J = 7.1 Hz), 1.89-2.03 (2H, m), 2.25-2.29 (2H, m), 2.80-2.89 (2H, m), 3.21-3.31 (1H, m), 3.71-3.75 (2H, m), 4.43 (2H, q, J = 7.1 Hz), 6.85-6.91 (2H, m), 7.19-7.23 (2H, m), 8.09 (1H, s). | Ref. Ex. 16 |
| 1607 | | 1H-NMR (CDCl3) δ: 2.14 (3H, s), 5.25 (2H, s), 7.30 (1H, s), 7.40-7.44 (2H, m), 7.87-7.91 (2H, m). | Ref. Ex. 935 |
| 1608 | | 1H-NMR (CDCl3) δ: 1.93-2.06 (2H, m), 2.27-2.30 (2H, m), 2.85-2.93 (2H, m), 3.17-3.32 (1H, m), 3.72-3.78 (2H, m), 6.87-6.92 (2H, m), 7.20-7.23 (2H, m), 8.11 (1H, s), 10.01 (1H, s). | Ref. Ex. 63 |

TABLE 2-continued

| Ref. Ex. No | STR | 1H-NMR | ref. |
|---|---|---|---|
| 1609 | | 1H-NMR (CDCl3) δ: 1.94-2.08 (2H, m), 2.26-2.30 (2H, m), 2.84-2.93 (2H, m), 3.17-3.28 (1H, m), 3.72-3.76 (2H, m), 6.87-6.90 (2H, m), 7.20-7.23 (2H, m), 8.11 (1H, s), 10.01 (1H, s). | Ref. Ex. 63 |
| 1610 | | 1H-NMR (CDCl3) δ: 2.67 (3H, s), 3.93 (3H, s), 7.39-7.43 (2H, m), 7.54-7.57 (2H, m). | Ref. Ex. 10 |
| 1611 | | 1H-NMR (CDCl3) δ: 2.69 (3H, s), 3.93 (3H, s), 7.18-7.23 (1H, m), 7.49-7.54 (1H, m), 7.70 (1H, dd, J = 2.3, 6.8 Hz). | Ref. Ex. 10 |
| 1612 | | 1H-NMR (CDCl3) δ: 3.47 (3H, s), 3.98 (3H, s), 4.87 (2H, s), 7.44-7.47 (2H, m), 8.05-8.08 (2H, m). | Ref. Ex. 133 |
| 1613 | | 1H-NMR (CDCl3) δ: 3.47 (3H, s), 3.98 (3H, s), 4.87 (2H, s), 7.56 (1H, d, J = 8.4 Hz), 7.94-7.97 (1H, m), 8.24 (1H, s). | Ref. Ex. 133 |
| 1614 | | 1H-NMR (CDCl3) δ: 1.30 (6H, d, J = 6.9 Hz), 2.91-3.05 (1H, m), 5.22 (2H, s), 7.16-7.18 (1H, m), 7.30-7.32 (1H, m), 7.42 (1H, s), 7.87 (1H, s), 7.93 (2H, S), 9.98 (1H, s). | Ref. Ex. 82 |
| 1615 | | 1H-NMR (CDCl3) δ: 1.30 (6H, d, J = 7.2 Hz), 2.93-3.04 (1H, m), 5.33 (2H, s), 7.17 (1H, s), 7.30 (1H, s), 7.43 (1H, s), 7.73 (1H, d, J = 7.8 Hz), 7.86 (1H, d, J = 6.4 Hz), 8.09 (1H, s), 9.97 (1H, s). | Ref. Ex. 82 |

TABLE 2-continued

| Ref. Ex. No | STR | 1H-NMR | ref. |
| --- | --- | --- | --- |
| 1616 | | 1H-NMR (CDCl3) δ: 3.88 (3H, s), 3.95 (3H, s), 7.46-7.49 (2H, m), 7.56-7.59 (2H, m), 7.83 (1H, s). | Ref. Ex. 75 |
| 1617 | | 1H-NMR (CDCl3) δ: 1.39 (3H, t, J = 7.1 Hz), 3.04 (3H, s), 4.35 (2H, q, J = 7.1 Hz), 7.46-7.49 (2H, m), 7.55-7.59 (2H, m), 7.82 (1H, s). | Ref. Ex. 75 |
| 1618 | | 1H-NMR (CDCl3) δ: 1.36 (6H, d, J = 6.9 Hz), 3.04-3.14 (1H, m), 7.14 (1H, s), 7.23-7.35 (2H, m), 7.54-7.63 (2H, m), 7.74 (1H, s), 7.98-7.99 (1H, m), 8.18-8.19 (1H, m), 10.09 (1H, s). | Ref. Ex. 91 |
| 1619 | | 1H-NMR (CDCl3) δ: 2.57 (1H, bs), 3.43 (3H, s), 4.56 (2H, s), 4.69 (2H, bs), 7.42-7.45 (2H, m), 7.96-7.99 (2H, m). | Ref. Ex. 19 |
| 1620 | | 1H-NMR (CDCl3) δ: 2.46 (1H, bs), 3.44 (3H, s), 4.57 (2H, s), 4.69 (2H, s), 7.53 (1H, d, J = 8.4 Hz), 7.86 (1H, dd, J = 1.8, 8.4 Hz), 8.13 (1H, d, J = 1.8 Hz). | Ref. Ex. 19 |
| 1621 | | 1H-NMR (CDCl3) δ: 3.48 (3H, s), 4.84 (2H, s), 7.46-7.49 (2H, m), 8.03-8.06 (2H, m), 10.09 (1H, s). | Ref. Ex. 147 |
| 1622 | | 1H-NMR (CDCl3) δ: 3.49 (3H, s), 4.84 (2H, s), 7.58 (1H, d, J = 8.4 Hz), 7.94 (1H, dd, J = 2.1, 8.4 Hz), 8.21 (1H, d, J = 2.1 Hz), 10.09 (1H, s). | Ref. Ex. 147 |
| 1623 | | 1H-NMR (CDCl3) δ: 2.70 (3H, s), 7.40-7.43 (2H, m), 7.56-7.59 (2H, m), 10.06 (1H, s). | Ref. Ex. 63 |
| 1624 | | 1H-NMR (CDCl3) δ: 2.71 (3H, s), 7.19-7.25 (1H, m), 7.51-7.56 (1H, m), 7.72 (1H, dd, J = 2.3, 6.8 Hz), 10.06 (1H, s). | Ref. Ex. 63 |

TABLE 2-continued

| Ref. Ex. No | STR | 1H-NMR | ref. |
|---|---|---|---|
| 1625 | | 1H-NMR (CDCl3) δ: 1.36 (6H, d, J = 6.9 Hz), 3.04-3.14 (1H, m), 7.59-7.71 (3H, m), 7.77-7.86 (3H, m), 7.92 (1H, t, J = 1.6 Hz), 10,09 (1H, s). | Ref. Ex. 91 |
| 1626 | | 1H-NMR (CDCl3) δ: 0.89 (3H, t, J = 7.4 Hz), 1.30-1.40 (2H, m), 1.64-1.72 (2H, m), 2.61 (2H, t, J = 7.8 Hz), 5.51 (2H, s), 6.97-7.00 (2H, m), 7.26-7.32 (2H, m), 9.74 (1H, s). | Ref. Ex. 12 |
| 1627 | | 1H-NMR (CDCl3) δ: 0.89 (3H, t, J = 7.4 Hz), 1.30-1.40 (2H, m), 1.64-1.72 (2H, m), 2.58-2.62 (2H, m) 5.14 (2H, s), 6.96-7.02 (2H, m), 7.31-7.36 (2H, m), 9.92 (1H, s). | Ref. Ex. 12 |
| 1628 | | 1H-NMR (CDCl3) δ: 1.43 (3H, t, J = 6.9 Hz), 4.46 (2H, q, J = 6.9 Hz), 7.17-7.23 (2H, m), 7.46-7.49 (2H, m), 8.08-8.17 (4H, m). | Ref. Ex. 133 |
| 1629 | | 1H-NMR (CDCl3) δ: 7.80-7.86 (2H, m), 7.94-7.96 (1H, m), 7.99-8.01 (1H, m), 8.06-8.11 (1H, m), 8.97 (1H, d, J = 2.1 Hz), 10.07 (1H, s). | Ref. Ex. 91 |
| 1630 | | 1H-NMR (CDCl3) δ: 1.54 (9H, s), 3.97 (3H, s), 7.60 (1H, t, J = 7.8 Hz), 7.72 (1H, d, J = 7.8 Hz), 8.23 (1H, d, J = 7.8 Hz), 8.31 (1H, s). | Ref. Ex. 133 |

TABLE 2-continued

| Ref. Ex. No | STR | 1H-NMR | ref. |
|---|---|---|---|
| 1631 | | 1HJMMR (CDCl3) δ: 1.44 (9H, s), 2.66 (1H, s), 4.72 (2H, d, J = 5.7 Hz), 7.57 (1H, t, J = 7.9 Hz), 7.67 (1H, d, J = 7.8 Hz), 8.16 (1H, d, J = 7.8 Hz), 8.23 (1H, s). | Ref. Ex. 19 |
| 1632 | | 1H-NMR (CDCl3) δ: 7.55 (1H, d, J = 4.0 Hz), 7.77 (1H, d, J = 8.2 Hz), 7.82 (1H, d, J = 4.0 Hz), 8.09-8.13 (1H, m), 9.04 (1H, d, J = 1.8 Hz), 9.96 (1H, s). | Ref. Ex. 91 |
| 1633 | | 1H-NMR (CDCl3) δ: 7.22-7.27 (2H, m), 7.50-7.53 (2H, m), 8.08-8.11 (2H, m), 8.24-8.29 (2H, m), 10.15 (1H, s). | Ref. Ex. 19, Ref. Ex. 147 |
| 1634 | | 1H-NMR (CDCl3) δ: 1.56 (9H, s), 7.62 (1H, t, J = 7.8 Hz), 7.74 (1H, d, J = 7.8 Hz), 8.25-8.32 (2H, m), 10.17 (1H, s). | Ref. Ex. 147 |
| 1635 | | 1H-NMR (CDCl3) δ: 2.22-2.30 (1H, br), 4.63 (2H, s), 4.77 (2H, d, J = 5.7 Hz), 4.80 (2H, s), 7.20 (1H, s), 7.29-7.36 (4H, m). | Ref. Ex. 100, Ref. Ex. 19 |
| 1636 | | 1H-NMR (CDCl3) δ: 2.23-2.39 (1H, br), 4.72 (2H, s), 4.77 (2H, d, J = 5.9 Hz), 4.84 (2H, s), 7.21 (1H, s), 7.49 (2H, d, J = 6.0 Hz), 7.63 (2H, d, J = 8.2 Hz). | Ref. Ex. 100, Ref. Ex. 19 |
| 1637 | | 1H-NMR (CDCl3) δ: 2.13-2.32 (1H, br), 4.66 (2H, s), 4.77 (2H, s), 4.82 (2H, s), 7.19-7.23 (3H, m), 7.38-7.42 (2H, m). | Ref. Ex. 100, Ref. Ex. 19 |

TABLE 2-continued

| Ref. Ex. No | STR | 1H-NMR | ref. |
|---|---|---|---|
| 1638 | | 1H-NMR (CDCl3) δ: 1.93 (3H, dd, J = 1.7, 6.7 Hz), 2.45-2.61 (1H, br), 4.78 (2H, s), 6.11 (1H, dq, J = 15.5, 6.7 Hz), 6.57 (1H, dq, J = 15.4, 1.7 Hz), 7.67 (2H, d, J = 8.2 Hz), 8.00 (2H, d, J = 8.2 Hz). | Ref. Ex. 43 |
| 1639 | | 1H-NMR (CDCl3) δ: 1.92 (3H, dd, J = 1.8, 6.7 Hz), 2.49 (1H, brs), 4.77 (2H, s), 6.09 (1H, dq, J = 15.5, 6.7 Hz), 6.56 (1H, dq, J = 15.4, 1.7 Hz), 7.24-7.27 (1H, m), 7.45 (1H, t, J = 8.3 Hz), 7.78-7.81 (2H, m). | Ref. Ex. 43 |
| 1640 | | 1H-NMR (CDCl3) δ: 4.67 (2H, s), 4.86 (2H, s), 7.30-7.37 (4H, m), 8.19 (1H, s), 10.01 (1H, s). | Ref. Ex. 48 |
| 1641 | | 1H-NMR (CDCl3) δ: 4.76 (2H, s), 4.90 (2H, s), 7.50 (2H, d, J = 8.0 Hz), 7.64 (2H, d, J = 8.2 Hz), 8.20 (1H, s), 10.02 (1H, s). | Ref. Ex. 48 |
| 1642 | | 1H-NMR (CDCl3) δ: 4.70 (2H, s), 4.88 (2H, s), 7.23 (2H, d, J = 7.8 Hz), 7.42 (2H, d, J = 8.8 Hz), 8.20 (1H, s), 10.01 (1H, s). | Ref. Ex. 48 |
| 1644 | | 1H-NMR (CDCl3) δ: 7.67-7.70 (1H, m), 7.82 (1H, d, J = 8.3 Hz), 8.08-8.16 (4H, m), 9.03 (1H, s), 10.16 (1H, s). | Ref. Ex. 91 |
| 1645 | | 1H-NMR (CDCl3) δ: 1.37 (6H, d, J = 7.0 Hz), 3.82-3.89 (1H, m), 3.95 (3H, s), 7.29-7.32 (2H, m), 8.11-8.13 (2H, m). | Ref. Ex. 133 |

TABLE 2-continued

| Ref. Ex. No | STR | 1H-NMR | ref. |
|---|---|---|---|
| 1646 | | 1H-NMR (CDCl3) δ: 1.36 (6H, d, J = 7.0 Hz), 1.44 (3H, t, J = 7.0 Hz), 3.80-3.87 (1H, m), 3.94 (3H, s), 4.09 (2H, q, J = 7.0 Hz), 6.94-6.96 (2H, m), 7.99-8.01 (2H, m). | Ref. Ex. 133 |
| 1647 | | 1H-NMR (CDCl3) δ: 1.34 (6H, d, J 7.0 Hz), 2.27 (1H, bs), 3.13-3.23 (1H, m), 4.61 (2H, s), 7.26-7.30 (2H, m), 8.02-8.05 (2H, m). | Ref. Ex. 19 |
| 1648 | | 1H-NMR (CDCl3) δ: 1.41 (6H, d, J = 7.0 Hz), 3.66-3.76 (1H, m), 7.26-7.35 (2H, m), 8.10-8.13 (2H, m), 10.04 (1H, s). | Ref. Ex. 48 |
| 1649 | | 1H-NMR (CDCl3) δ: 1.33 (6H, d, J = 6.9 Hz), 1.44 (3H, t, J = 7.2 Hz), 2.24 (1H, bs), 3.11-3.20 (1H, m), 4.09 (2H, q, J = 7.2 Hz), 4.59 (2H, s), 6.93-6.96 (2H, m), 7.91-7.94 (2H, m). | Ref. Ex. 19 |
| 1650 | | 1H-NMR (CDCl3) δ: 1.40 (6H, d, J = 7.2 Hz), 1.44 (3H, t, J = 7.2 Hz), 3.63-3.72 (1H, m), 4.10 (2H, q, J = 7.2 Hz), 6.96-6.99 (2H, m), 7.97-8.00 (2H, m), 10.03 (1H, s). | Ref. Ex. 147 |
| 1651 | | 1HWMR (CDCl3) δ: 2.40 (3H, s), 7.66 (1H, s), 7.79 (1H, d, J = 8.1 Hz), 7.98 (1H, dd, J = 2.1, 8.1 Hz), 8.87 (1H, d, J = 2.1 Hz), 9.90 (1H, s). | Ref. Ex. 91 |
| 1652 | | 1H-NMR (CDCl3) δ: 7.06 (1H, d, J = 3.7 Hz), 7.37 (1H, d, J = 3.7 Hz), 7.78 (1H, d, J = 8.5 Hz), 8.27-8.32 (1H, m), 9.13 (1H, s), 9.74 (1H, s). | Ref. Ex. 91 |
| 1653 | | 1H-NMR (CDCl3) δ: 1.01 (3H, t, J = 7.3 Hz), 1.68-1.76 (2H, m), 243 (1H, t, J = 5.9 Hz), 2.83 (2H, t, J = 7.5 Hz), 4.73 (2H, d, J = 5.8 Hz), 7.68 (2H, d, J = 8.2 Hz), 8.00 (2H, d, J = 8.0 Hz). | Ref. Ex. 33 |

TABLE 2-continued
| Ref. Ex. No | STR | 1H-NMR | ref. |
|---|---|---|---|
| 1654 | 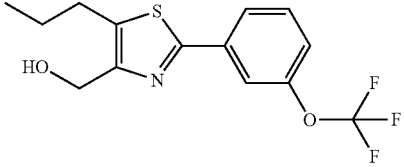 | 1H-NMR (CDCl3) δ: 1.01 (3H, t, J = 7.3 Hz), 1.65-1.77 (2H, m), 2.43 (1H, t, J = 5.9 Hz), 2.82 (2H, t, J = 7.5 Hz), 4.71 (2H, d, J = 5.8 Hz), 7.24-7.26 (1H, m), 7.45 (1H, t, J = 8.3 Hz), 7.78-7.80 (2H, m). | Ref. Ex. 33 |
| 1655 | 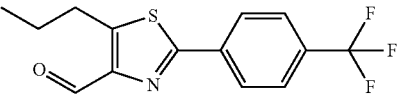 | 1H-NMR (CDCl3) δ: 1.06 (3H, t, J = 7.4 Hz), 1.73-1.66 (2H, m), 3.29 (2H, t, J = 7.6 Hz), 7.72 (2H, d, J = 8.2 Hz), 8.08 (2H, d, J = 8.1 Hz). 10.22 (1H, s). | Ref. Ex. 48 |
| 1656 | 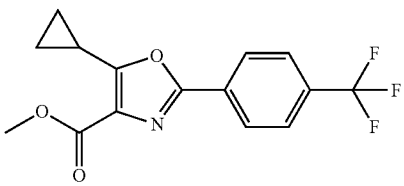 | 1H-NMR (CDCl3) δ: 1.16-1.28 (4H, m), 2.81-2.87 (1H, m), 3.97 (3H, s), 7.26-7.29 (2H, m), 8.02-8.04 (2H, m). | Ref. Ex. 133 |
| 1657 | 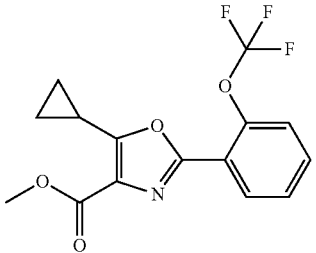 | 1H-NMR (CDCl3) δ: 1.19-1.21 (4H, m), 2.80-2.87 (1H, m), 3.97 (3H, s), 7.34-7.41 (2H, m), 7.47-7.51 (1H, m), 8.20-8.22 (1H, m). | Ref. Ex. 133 |
| 1658 | 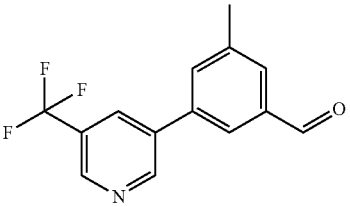 | 1H-NMR (CDCl3) δ: 2.55 (3H, s), 7.68 (1H, s), 7.79 (1H, s), 7.92 (1H, s), 8.13 (1H, s), 8.92 (1H, s), 9.06 (1H, s), 10.09 (1H, s). | Ref. Ex. 91 |
| 1659 | 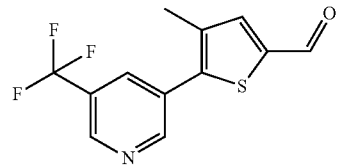 | 1H-NMR (CDCl3) δ: 2.39 (3H, s), 7.66 (1H, s), 8.02 (1H, s), 8.92-8.95 (2H, m), 9.90 (1H, s). | Ref. Ex. 91 |
| 1660 | 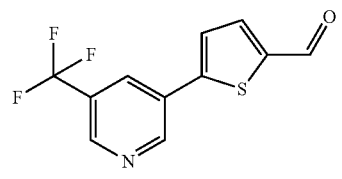 | 1H-NMR (CDCl3) δ: 7.54 (1H, d, J = 3.9 Hz), 7.82 (1H, d, J = 3.9 Kz), 8.14 (1H, s), 8.90 (1H, s), 9.12 (1H, s), 9.96 (1H, s). | Ref. Ex. 91 |
| 1661 | 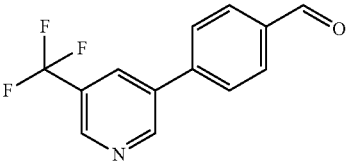 | 1H-NMR (CDCl3) δ: 7.79 (2H, d, J = 8.1 Hz). 8.03-8.06 (2H, m), 8.15 (1H, s), 8.95 (1H, s), 9.08 (1H, s), 10.11 (1H, s). | Ref. Ex. 91 |

TABLE 2-continued
| Ref. Ex. No | STR | 1H-NMR | ref. |
|---|---|---|---|
| 1662 | 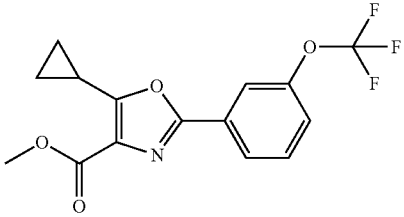 | 1H-NMR (CDCl3) δ: 1.14-1.27 (4H, m), 2.80-2.89 (1H, m), 3.97 (3H, s), 7.29-7.32 (1H, m), 7.48 (1H, t, J = 8.1 Hz), 7.83 (1H, s), 7.92-7.98 (1H, m). | Ref. Ex. 133 |
| 1663 | 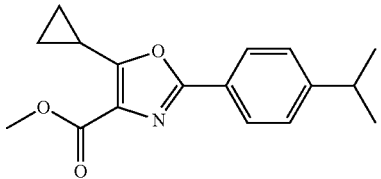 | 1H-NMR (CDCl3) δ: 1.18-1.28 (10H, m), 2.79-2.99 (2H, m), 3.96 (3H, s), 7.26-7.30 (2H, m), 7.90-7.93 (2H, m). | Ref. Ex. 133 |
| 1664 | 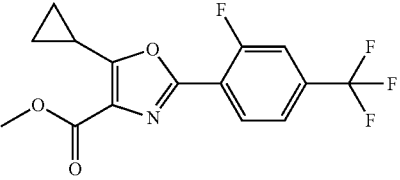 | 1H-NMR (CDCl3) δ: 1.21-1.26 (4H, m), 2.81-2.90 (1H, m), 3.98 (3H, s), 7.43-7.51 (2H, m), 7.20 (1H, t, J = 7.5 Hz). | Ref. Ex. 133 |
| 1665 | 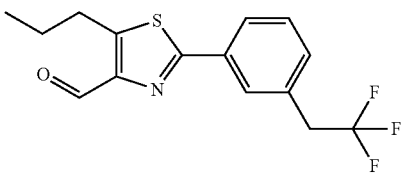 | 1H-NMR (CDCl3) δ: 1.05 (3H, t, J = 7.3 Hz), 1.72-1.85 (2H, m), 3.28 (2H, t, J = 7.6 Hz), 7.29-7.32 (1H, m), 7.49 (1H, t, J = 8.3 Hz), 7.82-7.85 (2H, m), 10.20 (1H, s). | Ref. Ex. 159 |
| 1667 | 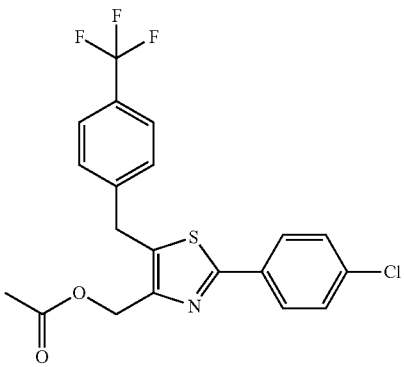 | 1H-NMR (CDCl3) δ: 2.07 (3H, s), 4.31 (2H, s), 5.23 (2H, s), 7.35-7.40 (4H, m), 7.59 (2H, d, J = 8.3 Hz), 7.79-7.83 (2H, m). | Ref. Ex. 1666 |
| 1669 | 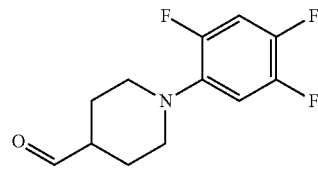 | 1H-NMR (CDCl3) δ: 1.78-1.94 (2H, m), 2.00-2.10 (2H, m), 2.34-2.45 (1H, m), 2.71-2.82 (2H, m), 3.26-3.36 (2H, m), 6.71-6.83 (1H, m), 6.85-6.97 (1H, m), 9.71 (1H, d, J = 0.9 Hz). | Ref. Ex. 114 Ref. Ex. 151 Ref. Ex. 48 |
| 1670 | 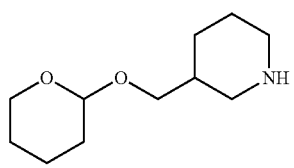 | 1H-NMR (CDCl3) δ: 1.0-2.0 (12H, m), 2.30-2.41 (1H, m), 2.50-2.60 (1H, m), 2.94-3.06 (1H, m), 3.09-3.27 (2H, m), 3.45-3.62 (2H, m), 3.78-3.91 (1H, m), 4.52-4.59 (1H, m). | Ref. Ex. 643 |

| Ref. Ex. No | STR | 1H-NMR | ref. |
|---|---|---|---|
| 1671 | 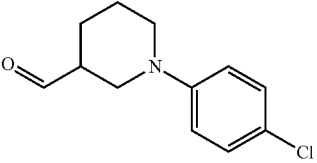 | 1H-NMR (CDCl3) δ: 1.66-1.89 (3H, m), 1.92-2.05 (1H, m), 2.54-2.62 (1H, m), 2.89-3.00 (1H, m), 3.16 (1H, dd, J = 8.0, 12.3 Hz), 3.22-3.33 (1H, m), 3.52 (1H, dd, J = 3.7, 12.3 Hz), 6.85-6.92 (2H, m), 7.17-7.24 (2H, m), 9.76 (1H, s). | Ref. Ex. 114 Ref. Ex. 151 Ref. Ex. 48 |
| 1672 | 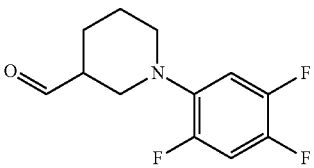 | 1H-NMR (CDCl3) δ: 1.70-1.97 (4H, m), 2.57-2.67 (1H, m), 2.78-2.88 (1H, m), 3.00-3.17 (2H, m), 3.31 (1H, dd, J = 3.5, 11.8 Hz), 6.74-6.97 (2H, m), 9.79 (1H, s). | Ref. Ex. 114 Ref. Ex. 151 Ref. Ex. 48 |
| 1673 | 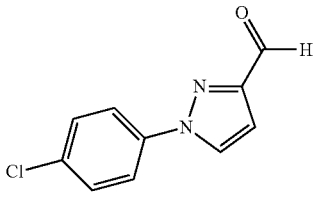 | 1H-NMR (CDCl3) δ: 7.00 (1H, d, J = 2.6 Hz), 7.48-7.52 (2H, m), 7.68-7.74 (2H, m), 7.95 (1H, dd, J = 0.7, 2.6 Hz), 10.08 (1H, s). | Ref. Ex. 76 Ref. Ex. 48 |
| 1674 | 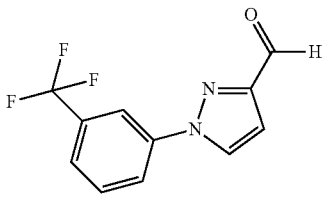 | 1H-NMR (CDCl3) δ: 7.03 (1H, d, J = 2.6 Hz), 7.64-7.68 (2H, m), 7.92-8.00 (1H, m), 8.04 (1H, dd, J = 0.7, 2.6 Hz), 8.95-8.08 (1H, m), 10.11 (1H, s). | Ref. Ex. 76 Ref. Ex. 48 |
| 1675 | 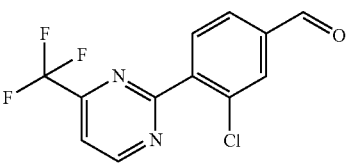 | 1H-NMR (CDCl3) δ: 7.69 (1H, d, J = 5.1 Hz), 7.90-7.93 (1H, m), 8.01-8.05 (2H, m), 9.18 (1H, d, J = 5.1 Hz), 10.07 (1H, s). | Ref. Ex. 91 |
| 1676 | 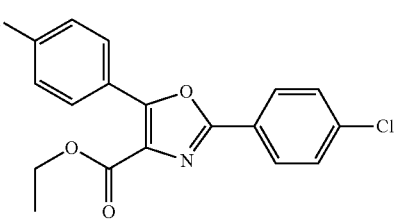 | 1H-NMR (CDCl3) δ: 1.44 (3H, t, J = 7.2 Hz), 4.46 (2H, q, J = 7.2 Hz), 7.47-7.50 (4H, m), 8.07-8.11 (4H, m). | Ref. Ex. 133 |
| 1677 | 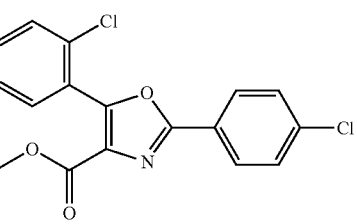 | 1H-NMR (CDCl3) δ: 1.26 (3H, t, J = 7.2 Hz), 4.33 (2H, q, J = 7.2 Hz), 7.26-7.61 (6H, m), 8.07-8.11 (2H, m). | Ref. Ex. 133 |

TABLE 2-continued

| Ref. Ex. No | STR | 1H-NMR | ref. |
|---|---|---|---|
| 1678 | | 1H-NMR (CDCl3) δ: 1.43 (18H, s), 4.04 (2H, s), 5.25 (1H, s), 6.76 (1H, brs), 7.02 (2H, s), 7.49 (1H, brs). | Ref. Ex. 1477 |
| 1679 | | 1H-NMR (CDCl3) δ: 1.39 (3H, t, J = 7.5 Hz), 3.31 (2H, q, J = 7.5 Hz), 3.97 (3H, s), 7.51 (1H, d, J = 8.4 Hz), 7.74 (1H, dd, J = 2.1, 8.4 Hz), 8.06 (1H, d, J = 2.1 Hz). | Ref. Ex. 2 |
| 1680 | | 1H-NMR (CDCl3) δ: 1.39 (3H, t, J = 7.5 Hz), 3.31 (2H, q, J = 7.5 Hz), 3.97 (3H, s), 7.34-7.42 (2H, m), 7.77-7.80 (1H, m), 7.95-7.97 (1H, m). | Ref. Ex. 2 |
| 1681 | | 1H-NMR (CDCl3) δ: 1.40 (3H, t, J = 7.5 Hz), 3.33 (2H, q, J = 7.5 Hz), 3.98 (3H, s), 7.70 (2H, d, J = 8.2 Hz), 8.05 (2H, d, J = 8.1 Hz). | Ref. Ex. 2 |
| 1682 | | 1H-NMR (CDCl3) δ: 4.68 (2H, s), 7.40-7.44 (4H, m), 7.60 (2H, d, J = 8.1 Hz), 7.81-7.86 (2H, m), 10.25 (1H, s). | Ref. 19 Ref. 159 |
| 1683 | | 1H-NMR (CDCl3) δ: 4.58 (2H, s), 7.22-7.26 (2H, m), 7.29-7.32 (2H, m), 7.39-7.43 (2H, m), 7.80-7.85 (2H, m), 10.24 (1H, s). | Ref. 19 Ref. 159 |

TABLE 2-continued

| Ref. Ex. No | STR | 1H-NMR | ref. |
|---|---|---|---|
| 1684 | | 1H-NMR (CDCl3) δ: 1.38-1.43 (21H, m), 4.29 (2H, s), 4.43 (2H, q, J = 7.1 Hz), 5.18 (1H, s), 7.11 (2H, s), 8.04 (1H, s). | Ref. Ex. 2 |
| 1685 | | 1H-NMR (CDCl3) δ: 1.39 (3H, t, J = 7.5 Hz), 3.32 (2H, q, J = 7.5 Hz). 7.53 (1H, d, J = 8.4 Hz), 7.75 (1H, dd, J = 2.1, 8.4 Hz), 8.06 (1H, d, J = 2.1 Hz), 10.19 (1H, s). | Ref. Ex. 63 |
| 1686 | | 1H-NMR (CDCl3) δ: 1.39 (3H, t, J = 7.5 Hz), 3.32 (2H, q, J = 7.5 Hz), 7.36-7.45 (2H, m), 7.79 (1H, dt, J = 6.9, 1.8 Hz), 7.95-7.97 (1H, m), 10.20 (1H, s). | Ref. Ex. 63 |
| 1687 | | 1H-NMR (CDCl3) δ: 1.40 (3H, t, J = 7.5 Hz), 3.34 (2H, q, J = 7.5 Hz), 7.72 (2H, d, J = 8.3 Hz), 8.06 (2H, d, J = 8.1 Hz), 10.22 (1H, s). | Ref. Ex. 63 |
| 1688 | | 1H-NMR (CDCl3) δ: 1.43 (18H, s), 4.28 (2H, s), 5.19 (1H, s), 7.11 (2H, s), 8.04 (1H, s), 10.01 (1H, s). | Ref. Ex. 63 |
| 1689 | | 1H-NMR (CDCl3) δ: 8.00 (1H, s), 8.07-8.09 (2H, m), 8.88 (1H, s), 9.06 (1H, s), 10.02 (1H, s). | Ref. Ex. 91 |
| 1690 | | 1H-NMR (CDCl3) δ: 1.03 (6H, s), 3.75 (4H, s), 8.02 (1H, s), 8.18 (1H, s), 9.93 (1H, s). | Ref. Ex. 107 |

TABLE 2-continued

| Ref. Ex. No | STR | 1H-NMR | ref. |
|---|---|---|---|
| 1691 | | 1H-NMR (CDCl3) δ: 7.65-7.85 (3H, m), 8.15 (1H, s), 8.96 (1H, s), 9.02 (1H, s), 10.06 (1H, s). | Ref. Ex. 91 |
| 1692 | | 1H-NMR (CDCl3) δ: 7.75 (1H, d, J = 8.3 Hz), 7.99 (1H, dd, J = 2.1, 8.3 Hz), 8.37-8.40 (2H, m), 8.90 (1H, s), 10.01 (1H, d, J = 1.1 Hz). | Ref. Ex. 91 |
| 1693 | | 1H-NMR (CDCl3) δ: 7.52 (1H, d, J = 5.0 Hz), 8.60 (1H, d, J = 1.3 Hz), 8.78 (1H, t, J = 1.3 Hz), 9.01 (1H d, J = 5.0 Hz), 10.02 (1H, d, J = 1.3 Hz). | Ref. Ex. 91 |
| 1694 | | 1H-NMR (CDCl3) δ: 1.37 (3H, t, J = 7.5 Hz), 2.39 (3H, s), 3.30 (2H, q, J = 7.5 Hz), 3.96 (3H, s), 7.23 (2H, d, J = 7.9 Hz), 7.82 (2H, d, J = 8.2 Hz). | Ref. Ex. 2 |
| 1695 | | 1H-NMR (CDCl3) δ: 1.38 (3H, t, J = 7.5 Hz), 3.30 (2H, q, J = 7.5 Hz), 3.96 (3H, s), 7.09-7.15 (2H, m), 7.89-7.94 (2H, m). | Ref. Ex. 2 |
| 1696 | | 1H-NMR (CDCl3) δ: 1.38 (3H, t, J = 7.5 Hz), 3.31 (2H, q, J = 7.5 Hz), 3.97 (3H, s), 7.20 (1H, t, J = 8.6 Hz), 7.76-7.81 (1H, m), 8.03 (1H, dd, J = 2.2, 6.9 Hz). | Ref. Ex. 2 |
| 1697 | | 1H-NMR (CDCl3) δ: 1.38 (3H, t, J = 7.5 Hz), 2.41 (3H, s), 3.31 (2H, q, J = 7.5 Hz), 7.26 (2H, d, J = 7.9 Hz), 7.82 (2H, d, J = 8.2 Hz), 10.20 (1H, s). | Ref. Ex. 63 |
| 1698 | | 1H-NMR (CDCl3) δ: 1.38 (3H, t, J = 7.5 Hz), 3.31 (2H, q, J = 7.5 Hz), 7.11-7.19 (2H, m), 7.89-7.96 (2H, m), 10.19 (1H, s). | Ref. Ex. 63 |
| 1699 | | 1H-NMR (CDCl3) δ: 1.39 (3H, t, J = 7.5 Hz), 3.32 (2H, q, J = 7.5 Hz), 7.19-7.26 (1H, m), 7.77-7.82 (1H, m), 8.03 (1H, dd, J = 2.1, 6.9 Hz), 10.19 (1H, s). | Ref. Ex. 63 |

TABLE 2-continued

| Ref. Ex. No | STR | 1H-NMR | ref. |
|---|---|---|---|
| 1700 | | 1H-NMR (CDCl3) δ: 3.91 (3H, s), 4.11 (2H, s). 7.23-7.27 (2H, m), 7.68 (1H, s), 7.99-8.03 (2H, m), 8.68 (1H, s), 8.76 (1H, s). | Ref. Ex. 91 |
| 1701 | | 1H-NMR (CDCl3) δ: 0.19-0.28 (2H, m), 0.58-0.60 (2H, m), 0.92-1.09 (1H, m), 1.35 (12H, s), 2.62 (2H, d, J = 6.9 Hz), 7.89 (1H, s), 7.92 (1H, s), 8.14 (1H, s), 10.04 (1H, s). | Ref. Ex. 81 |
| 1702 | | 1H-NMR (CDCl3) δ: 0.24-0.29 (2H, m), 0.57-0.63 (2H, m), 1.00-1.12 (1H, m), 2.69 (2H, d, J = 6.9 Hz), 7.13-7.19 (2H, m), 7.56-7.61 (2H, m), 7.69 (1H, s), 7.76 (1H, s), 7.89 (1H, s), 10.07 (1H, s). | Ref. Ex. 91 |
| 1703 | | 1H-NMR (CDCl3) δ: 0.26-0.31 (2H, m), 0.58-0.65 (2H, m), 1.00-1.16 (1H, m), 2.74 (2H, d, J = 6.9 Hz), 7.57 (1H, d, J = 4.9 Hz), 7.99 (1H, s), 8.67 (1H, s), 8.85 (1H, s), 9.08 (1H, d, J = 5.0 Hz), 10.15 (1H, s). | Ref. Ex. 91 |
| 1704 | | 1H-NMR (CDCl3) δ: 1.38 (3H, t, J = 7.5 Hz), 3.31 (2H, q, J = 7.5 Hz), 3.97 (3H, s), 7.50 (1H, d, J = 8.4 Hz), 7.74 (1H, dd, J = 2.1, 8.4 Hz), 8.06 (1H, d, J = 2.1 Hz). | Ref. Ex. 2 |
| 1705 | | 1H-NMR (CDCl3) δ: 1.39 (3H, t, J = 7.5 Hz), 3.32 (2H, q, J = 7.5 Hz), 3.97 (3H, s), 7.41 (1H, t, J = 1.9 Hz), 7.82 (2H, d, J = 1.9 Hz). | Ref. Ex. 2 |

TABLE 2-continued

| Ref. Ex. No | STR | 1H-NMR | ref. |
|---|---|---|---|
| 1706 | | 1H-NMR (CDCl3) δ: 1.39 (3H, t, J = 7.5 Hz), 3.32 (2H, q, J = 7.5 Hz), 3.97 (3H, s), 7.26-7.30 (1H, m), 7.46 (1H, t, J = 8.0 Hz), 7.81-7.86 (2H, m). | Ref. Ex. 2 |
| 1707 | | 1H-NMR (CDCl3) δ: 1.39 (3H, t, J = 7.5 Hz), 3.32 (2H, q, J = 7.5 Hz), 3.97 (3H, s), 7.25-7.31 (1H, m), 8.09-8.18 (2H, m). | Ref. Ex. 2 |
| 1708 | | 1H-NMR (CDCl3) δ: 1.39 (3H, t, J = 7.5 Hz), 3.33 (2H, q, J = 7.5 Hz), 7.53 (1H, d, J = 8.4 Hz), 7.75 (1H, dd, J = 2.1, 8.4 Hz), 8.06 (1H, d, J = 2.1 Hz), 10.19 (1H, s). | Ref. Ex. 63 |
| 1709 | | 1H-NMR (CDCl3) δ: 1.39 (3H, t, J = 7.5 Hz), 3.33 (2H, q, J = 7.5 Hz), 7.43 (1H, t, J = 1.9 Hz), 7.82 (2H, d, J = 1.9 Hz), 10.19 (1H, s). | Ref. Ex. 63 |
| 1710 | | 1H-NMR (CDCl3) δ: 1.39 (3H, t, J = 7.5 Hz), 3.33 (2H, q, J = 7.5 Hz), 7.29-7.33 (1H, m), 7.49 (1H, t, J = 8.3 Hz), 7.82-7.85 (2H, m), 10.21 (1H, s). | Ref. Ex. 63 |
| 1711 | | 1H-NMR (CDCl3) δ: 1.40 (3H, t, J = 7.5 Hz), 3.33 (2H, q, J = 7.5 Hz), 7.31 (1H, t, J = 9.2 Hz), 8.09-8.14 (1H, m), 8.19 (1H, dd, J = 2.3, 6.6 Hz), 10.20 (1H, s). | Ref. Ex. 63 |
| 1712 | | 1H-NMR (CDCl3) δ: 0.26-0.31 (2H, m), 0.59-0.66 (2H, m), 1.00-1.12 (1H, m), 2.73 (2H, d, J = 7.0 Hz), 7.76 (1H, s), 7.80 (1H, d, J = 6.1 Hz), 7.88 (1H, s), 7.95 (1H, s), 8.07-8.11 (1H, m), 8.99 (1H, s), 10.11 (1H, s). | Ref. Ex. 91 |

TABLE 2-continued

| Ref. Ex. No | STR | 1H-NMR | ref. |
|---|---|---|---|
| 1713 | | 1H-NMR (CDCl3) δ: 0.28-0.33 (2H, m), 0.60-0.66 (2H, m), 1.04-1.20 (1H, m), 2.75 (2H, d, J = 6.9 Hz), 7.91-7.97 (2H, m), 8.03-8.07 (1H, m), 8.27 (1H, s), 8.38 (1H, s), 8.99 (1H, s), 10.14 (1H, s). | Ref. Ex. 91 |
| 1715 | | 1H-NMR (CDCl3) δ: 3.88 (2H, s), 6.96-7.04 (2H, m), 7.08-7.15 (2H, m), 7.22-7.24 (2H, m), 7.51 (1H, t, J = 1.6 Hz). | Ref. Ex. 140 |
| 1716 | | 1H-NMR (CDCl3) δ: 4.00 (2H, s), 6.98-7.04 (2H, m), 7.11-7.16 (2H, m), 7.55-7.61 (2H, m), 7.65 (1H, s), 9.91 (1H, s). | Ref. Ex. 138 |
| 1717 | | 1H-NMR (CDCl3) δ: 1.40 (12H, s), 4.04 (2H, s), 6.97-7.03 (2H, m), 7.14-7.18 (2H, m), 7.79 (1H, s), 7.92 (1H, s), 8.18 (1H, s), 10.03 (1H, s). | Ref. Ex. 81 |
| 1718 | | 1H-NMR (CDCl3) δ: 7.44-7.56 (4H, m), 7.59-7.66 (2H, m), 8.10-8.13 (2H, m), 9.98 (1H, s). | Ref. Ex. 63 |
| 1719 | | 1H-NMR (CDCl3) δ: 7.50-7.54 (4H, m), 8.08-8.11 (2H, m), 8.18-8.21 (2H, m), 10.16 (1H, s). | Ref. Ex. 63 |

TABLE 2-continued

| Ref. Ex. No | STR | 1H-NMR | ref. |
|---|---|---|---|
| 1720 | | 1H-NMR (CDCl3) δ: 1.26-1.31 (4H, m), 2.67-2.76 (1H, m), 7.31-7.35 (1H, m), 7.51 (1H, t, J = 8.4 Hz), 7.82 (1H, s), 7.91-7.94 (1H, m), 10.05 (1H, s). | Ref. Ex. 63 |
| 1721 | | 1H-NMR (CDCl3) δ: 1.23-1.26 (10H, m), 2.64-2.73 (1H, m), 2.91-3.00 (1H, m), 7.30-7.33 (2H, m), 7.89-7.91 (2H, m), 10.05 (1H, s). | Ref. Ex. 63 |
| 1722 | | 1H-NMR (CDCl3) δ: 1.26-1.32 (4H, m), 2.71-2.80 (1H, m), 7.46-7.54 (2H, m), 8.13-8.18 (1H, m), 10.08 (1H, s). | Ref. Ex. 63 |
| 1723 | | 1H-NMR (CDCl3) δ: 4.11 (2H, s), 6.98-7.04 (2H, m), 7.16-7.21 (2H, m), 7.54-7.78 (5H, m), 7.83 (1H, s), 7.95 (1H, s), 10.06 (1H, s). | Ref. Ex. 91 |
| 1724 | | 1H-NMR (CDCl3) δ: 1.44 (9H, s), 7.85 (1H, t, J = 1.8 Hz), 7.92 (1H, t, J = 1.6 Hz), 8.01 (1H, t, J = 1.6 Hz), 8.12 (1H, s), 8.92 (1H, s), 9.05 (1H, d, J = 1.8 Hz), 10.11 (1H, s). | Ref. Ex. 91 |
| 1725 | | 1H-NMR (CDCl3) δ: 1.43 (9H, s), 7.80 (1H, d, J = 8.2 Hz), 7.85 (1H, t, J = 1.8 Hz), 7.91 (1H, t, J = 1.8 Hz), 8.01 (1H, t, J = 1.8 Hz), 8.06-8.10 (1H, m), 8.97 (1H, d, J = 2.1 Hz), 10.11 (1H, s). | Ref. Ex. 91 |

TABLE 2-continued

| Ref. Ex. No | STR | 1H-NMR | ref. |
|---|---|---|---|
| 1727 | | 1H-NMR (CDCl3) δ: 4.15 (2H, s), 7.35 (2H, d, J = 8.1 Hz), 7.70 (1H, s), 7.88 (2H, d, J = 8.1 Hz), 8.89 (1H, s), 8.78 (1H, s), 10.01 (1H, s). | Ref. Ex. 76, Ref. Ex. 147 |
| 1728 | | 1H-NMR (CDCl3) δ: 4.14 (2H, s), 6.97-7.05 (2H, m), 7.16-7.21 (2H, m), 7.78 (1H, s), 7.90 (1H, s), 8.00-8.04 (1H, m), 8.19 (1H, s), 8.37 (1H, s), 8.97 (1H, s), 10.08 (1H, s). | Ref. Ex. 91 |
| 1731 | | 1H-NMR (CDCl3) δ: 1.35 (3H, t, J = 7.6 Hz), 2.86 (2H, q, J = 7.6 Hz), 2.58 (1H, d, J = 5.0 Hz), 7.92 (1H, s), 8.63 (1H, s), 8.63 (1H, s), 9.09 (1H, d, J = 5.0 Hz), 10.14 (1H, s). | Ref. Ex. 91 |
| 1732 | | 1H-NMR (CDCl3) δ: 1.33 (3H, t, J = 7.7 Hz), 2.80 (2H, q, J = 7.7 Hz), 7.14-7.18 (2H, m), 7.57-7.60 (2H, m), 7.64 (1H, s), 7.70 (1H, s), 7.87 (1H, s), 10.07 (1H, s). | Ref. Ex. 91 |
| 1733 | | 1H-NMR (CDCl3) δ: 1.35 (3H, t, J = 7 6 Hz), 2.85 (2H, q, J = 7 6 Hz), 7.84 (1H, s), 7.93 (1H, d, J = 8.3 Hz), 8.04 (1H, dd, J = 2.0, 8.3 Hz), 8.20 (1H, s), 8.34-8.35 (1H, m), 8.98 (1H, s), 10.11 (1H, s). | Ref. Ex. 91 |
| 1734 | | 1H-NMR (CDCl3) δ: 1.92 (3H, dd, J = 1.7, 6.7 Hz), 2.39 (1H, t, J = 5.9 Hz), 4.76 (2H, d, J = 5.7 Hz), 6.03-6.12 (1H, m), 6.52-6.57 (1H, m), 7.19 (1H, t, J = 8.6 Hz), 7.73-7.77 (1H, m), 7.98 (1H, dd, J = 2.2, 7.0 Hz). | Ref. Ex. 43 |

TABLE 2-continued

| Ref. Ex. No | STR | 1H-NMR | ref. |
|---|---|---|---|
| 1735 | | 1H-NMR (CDCl3) δ: 0.53-0.57 (2H, m), 0.86-0.91 (2H, m), 1.53-1.62 (1H, m), 2.40 (1H, t, J = 5.9 Hz), 4.76 (2H, d, J = 5.8 Hz), 5.57 (1H, dd, J = 9.0, 15.4 Hz), 6.60 (1H, d, J = 15.4 Hz), 7.18 (1H, t, J = 8.6 Hz), 7.71-7.75 (1H, m), 7.97 (1H, dd, J = 2.2, 7.0 Hz). | Ref. Ex. 43 |
| 1736 | | 1H-NMR (CDCl3) δ: 1.22 (3H, t, J = 7.2 Hz), 2.96 (2H, q, J = 7.2 Hz), 7.85 (1H, t, J = 1.7 Hz), 8.00 (2H, d, J = 1.7 Hz). | Ref. Ex. 147 |
| 1738 | | 1H-NMR (CDCl3) δ: 0.99 (6H, d, J = 6.7 Hz), 2.24-2.32 (1H, m), 2.78 (2H, d, J = 6.9 Hz), 7.84 (1H, t, J = 1.6 Hz), 7.98 (2H, t, J = 1.6 Hz). | Ref. Ex. 48 |
| 1740 | | 1HNMR (CDCl3) δ: 0.96 (3H, t, J = 7.5 Hz), 1.68 (2H, q, J = 7.5 Hz), 2.65 (2H, t, J = 7.5 Hz), 7.59 (1H, s), 7.62 (1H, s), 7.83 (1H, s), 9.93 (1H, s). | Ref. Ex. 138 |
| 1741 | | 1H-NMR (CDCl3) δ: 0.53-0.56 (2H, m), 0.66-0.90 (2H, m), 1.54-1.61 (1H, m), 2.55-2.63 (1H, br), 4.76 (2H, d, J = 5.7 Hz), 5.55 (1H, dd, J = 9.1, 15.4 Hz), 6.60 (1H, d, J = 15.4 Hz), 7.37-7.40 (2H, m), 7.81 (2H, d, J = 8.5 Hz). | Ref. Ex. 77 |
| 1742 | | 1H-NMR (CDCl3) δ: 1.13 (9H, s), 2.48 (1H, t, J = 5.9 Hz), 4.77 (2H, d, J = 5.9 Hz), 6.10 (1H, d, J = 15.8 Hz), 6.43 (1H, d, J = 15.9 Hz), 7.39-7.41 (2H, m), 7.83-7.84 (2H, m). | Ref. Ex. 77 |
| 1743 | | 1H-NMR (CDCl3) δ: 1.00 (3H, t, J = 7.4 Hz), 1.66-1.74 (2H, m), 2.34 (1H, t, J = 5.9 Hz), 2.81 (2H, t, J = 7.5 Hz), 4.70 (2H, d, J = 5.9 Hz), 7.19 (1H, t, J = 8.6 Hz), 7.73-7.76 (1H, m), 7.98 (1H, dd, J = 2.2, 6.9 Hz). | Ref. Ex. 34 |
| 1744 | | 1H-NMR (CDCl3) δ: 0.07-0.10 (2H, m), 0.46-0.49 (2H, m), 0.71-0.77 (1H, m), 1.54-1.59 (2H, m), 2.42 (1H, t, J = 5.9 Hz), 2.93 (2H, t, J = 7.4 Hz), 4.72 (2H, d, J = 5.7 Hz), 7.18 (1H, t, J = 8.6 Hz), 7.72-7.75 (1H, m), 7.97 (1H, dd, J = 2.2, 7.0 Hz). | Ref. Ex. 34 |

TABLE 2-continued

| Ref. Ex. No | STR | 1H-NMR | ref. |
|---|---|---|---|
| 1745 | | 1H-NMR (CDCl3) δ: 1.05 (3H, t, J = 7.4 Hz), 1.74-1.82 (2H, m), 3.27 (2H, q, J = 7.8 Hz), 7.22-7.25 (1H, m), 7.78-7.81 (1H, m), 8.03 (1H, dd, J = 2.2, 6.9 Hz), 10.18 (1H, s). | Ref. Ex. 48 |
| 1746 | | 1H-NMR (CDCl3) δ: 0.07-0.10 (2H, m), 0.46-0.49 (2H, m), 0.71-0.77 (1H, m), 1.54-1.58 (2H, m), 2.41 (1H, t, J = 5.9 Hz), 2.93 (2H, t, J = 7.5 Hz), 4.72 (2H, d, J = 5.8 Hz), 7.38-7.40 (2H, m), 7.81-7.83 (2H, m). | Ref. Ex. 34 |
| 1747 | | 1H-NMR (CDCl3) δ: 0.09-0.12 (2H, m), 0.47-0.50 (2H, m), 0.74-0.82 (1H, m), 1.62-1.66 (2H, m), 3.38 (2H, t, J = 7.5 Hz), 7.23 (1H, t, J = 8.6 Hz), 7.78-7.81 (1H, m), 8.03 (1H, dd, J = 2.2, 6.9 Hz), 10.19 (1H, s). | Ref. Ex. 48 |
| 1748 | | 1H-NMR (CDCl3) δ: 0.09-0.12 (2H, m), 0.46-0.50 (2H, m), 0.74-0.82 (1H, m), 1.62-1.66 (2H, m), 3.38 (2H, t, J = 7.5 Hz), 7.42-7.45 (2H, m), 7.86-7.89 (2H, m), 10.19 (1H, s). | Ref. Ex. 48 |
| 1749 | | 1H-NMR (CDCl3) δ: 2.31 (1H, t, J = 6.7 Hz), 4.98 (2H, d, J = 6.7 Hz), 7.79 (2H, d, J = 8.2 Hz), 8.20 (2H, d, J = 8.2 Hz). | Ref. Ex. 19 |
| 1750 | | 1H-NMR (CDCl3) δ: 1.17-1.22 (4H, m), 2.32 (3H, s), 2.79-2.86 (1H, m), 3.96 (3H, s), 7.05 (1H, t, J = 8.9 Hz), 7.75-7.79 (1H, m), 7.86-7.88 (1H, m). | Ref. Ex. 133 |
| 1751 | | 1H-NMR (CDCl3) δ: 0.99 (3H, t, J = 7.3 Hz), 1.69-1.77 (2H, m), 2.74 (2H, t, J = 7.6 Hz), 7.16 (2H, t, J = 8.6 Hz), 7.56-7.60 (2H, m), 7.62 (1H, s), 7.68 (1H, s), 7.87 (1H, s), 10.06 (1H, s). | Ref. Ex. 91 |
| 1753 | | 1H-NMR (CDCl3) δ: 0.94 (3H, t, J = 7.3 Hz), 1.37 (12H, s), 1.64-1.72 (2H, m), 2.65-2.68 (2H, m), 7.80 (1H, s), 7.88 (1H, s), 8.12 (1H, s), 10.03 (1H, s). | Ref. Ex. 81 |

TABLE 2-continued

| Ref. Ex. No | STR | 1H-NMR | ref. |
|---|---|---|---|
| 1754 | | 1H-NMR (CDCl3) δ: 0.98 (9H, s), 1.54-1.58 (2H, m), 2.44 (1H, t, J = 5.8 Hz), 2.77-2.80 (2H, m), 4.70 (2H, d, J = 5.9 Hz), 7.38-7.40 (2H, m), 7.80-7.83 (2H, m) | Ref. Ex. 34 |
| 1755 | | 1H-NMR (CDCl3) δ: 1.00 (9H, s), 1.60-1.63 (2H, m), 3.24-3.28 (2H, m), 7.42-7.45 (2H, m), 7.85-7.88 (1H, m), 10.19 (1H, s). | Ref. Ex. 48 |
| 1756 | | 1H-NMR (CDCl3) δ: 1.23-1.28 (4H, m), 2.33 (3H, s), 2.79-2.86 (1H, m), 7.08 (1H, t, J = 8.9 Hz), 7.76-7.79 (1H, m), 7.84-7.88 (1H, m), 10.04 (1H, s). | Ref. Ex. 63 |
| 1757 | | 1H-NMR (CDCl3) δ: 1.18-1.23 (4H, m), 2.42 (3H, s), 2.80-2.86 (1H, m), 3.96 (3H, s), 7.28-7.30 (1H, m), 7.77-7.79 (1H, m), 7.96 (1H, s). | Ref. Ex. 133 |
| 1758 | | 1H-NMR (CDCl3) δ: 1.18-1.20 (4H, m), 1.25 (3H, t, J = 7.6 Hz), 2.68 (2H, q, J = 7.6 Hz), 2.80-2.86 (1H, m), 3.96 (3H, s), 7.25-7.27 (2H, m), 7.89-7.91 (2H, m). | Ref. Ex. 133 |
| 1759 | | 1H-NMR (CDCl3) δ: 1.25-1.29 (4H, m), 2.43 (3H, s), 2.66-2.73 (1H, m), 7.31-7.33 (1H, m), 7.76-7.78 (1H, m), 7.94 (1H, s), 10.04 (1H, s). | Ref. Ex. 63 |
| 1760 | | 1H-NMR (CDCl3) δ: 1.24-1.28 (7H, m), 2.65-2.73 (3H, m), 7.26-7.30 (2H, m), 7.88-7.90 (2H, m), 10.05 (1H, s). | Ref. Ex. 63 |

TABLE 2-continued

| Ref. Ex. No | STR | 1H-NMR | ref. |
|---|---|---|---|
| 1761 | | 1H-NMR (CDCl3) δ: 1.00 (3H, t, J = 7.3 Hz), 1.72-1.80 (2H, m), 2.78-2.81 (2H, m), 7.57 (1H, d, J = 5.0 Hz), 7.89 (1H, s), 8.60 (1H, s), 8.83 (1H, s), 9.09 (1H, d, J = 5.0 Hz), 10.14 (1H, s). | Ref. Ex. 91 |
| 1762 | | 1H-NMR (CDCl3) δ: 0.95 (6H, d, J = 6.5 Hz), 1.49-1.63 (3H, m), 2.65-2.69 (2H, m), 7.59 (1H, s), 7.62 (1H, s), 7.82 (1H, s), 9.93 (1H, s). | Ref. Ex. 138 |
| 1763 | | 1H-NMR (CDCl3) δ: 2.75 (3H, s), 5.19 (2H, d, J = 0.5 Hz), 6.96-7.02 (1H, m), 7.14-7.21 (2H, m), 7.31-7.32 (1H, m), 9.92 (1H, d, J = 1.6 Hz). | Ref. Ex. 82 |
| 1764 | | 1H-NMR (CDCl3) δ: 0.94 (6H, d, J = 6.5 Hz), 1.37 (12H, s), 1.49-1.63 (3H, m), 2.67-2.70 (2H, m), 7.81 (1H, s), 7.88 (1H, s), 8.11 (1H, s), 10.02 (1H, s). | Ref. Ex. 81 |
| 1765 | | 1H-NMR (CDCl3) δ: 1.36 (3H, t, J = 7.6 Hz), 2.85 (2H, q, J = 7.6 Hz), 7.69 (1H, s), 7.82 (1H, s), 7.94 (1H, s), 8.14 (1H, s), 8.92 (1H, s), 9.07 (1H, s), 10.10 (1H, s). | Ref. Ex. 91 |

TABLE 2-continued

| Ref. Ex. No | STR | 1H-NMR | ref. |
|---|---|---|---|
| 1766 | | 1H-NMR (CDCl3) δ: 1.00 (3H, t, J = 7.5 Hz), 1.71-1.79 (2H, m), 2.78 (2H, t, J = 7.5 Hz), 7.67 (1H, s), 7.79-7.81 (2H, m), 7.93 (1H, s), 8.08-8.10 (1H, m), 7.97 (1H, s), 10.10 (1H, s). | Ref. Ex. 91 |
| 1767 | | 1H-NMR (CDCl3) δ: 1.18-1.25 (4H, m), 2.80-2.87 (1H, m), 3.97 (3H, s), 7.52 (1H, d, J = 8.4 Hz), 7.81-7.84 (1H, m), 8.08 (1H, s). | Ref. Ex. 133 |
| 1768 | | 1H-NMR (CDCl3) δ: 1.15-1.24 (4H, m), 2.79-2.86 (1H, m), 3.97 (3H, s), 7.10-7.15 (2H, m), 7.97-8.01 (2H, m). | Ref. Ex. 133 |
| 1769 | | 1H-NMR (CDCl3) δ: 1.23-1.28 (4H, m), 2.65-2.72 (1H, m), 7.13-7.17 (2H, m), 7.96-8.00 (2H, m), 10.04 (1H, s). | Ref. Ex. 63 |
| 1770 | | 1H-NMR (CDCl3) δ: 1.23-1.32 (4H, m), 2.67-2.74 (1H, m), 7.54 (1H, d, J = 8.4 Hz), 7.82 (1H, dd, J = 2.0, 8.4 Hz), 8.06 (1H, d, J = 2.0 Hz). 10.04 (1H, s). | Ref. Ex. 63 |
| 1771 | | 1H-NMR (CDCl3) δ: 6.70 (1H, t, J = 55.9 Hz), 7.92 (1H, s), 7.96 (1H, s), 8.13 (1H, s), 10.01 (1H, s). | Ref. Ex. 138 |
| 1772 | | 1H-NMR (CDCl3) δ: 1.34-1.37 (3H, m), 2.83-2.87 (2H, m), 7.69 (1H, s), 7.79-7.82 (2H, m), 7.93 (1H, s). 8.09-8.10 (1H, m), 8.98 (1H, s). 10.10 (1H, s). | Ref. Ex. 91 |

TABLE 2-continued
| Ref. Ex. No | STR | 1H-NMR | ref. |
|---|---|---|---|
| 1773 | 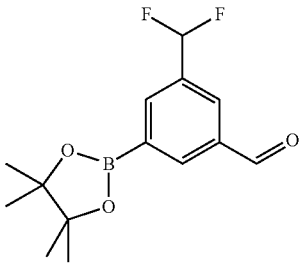 | 1H-NMR (CDCl3) δ: 1.27 (12H, s), 6.72 (1H, t, J = 56.0 Hz), 8.13 (1H, s), 8.19 (1H, s), 8.41 (1H, s), 10.09 (1H, s). | Ref. Ex. 81 |
| 1774 | 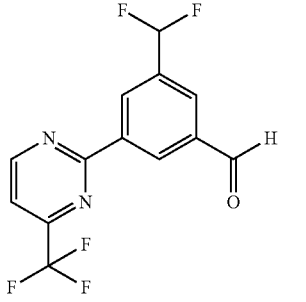 | 1H-NMR (CDCl3) δ: 6.84 (1H, t, J = 56.0 Hz), 7.64 (1H, d, J = 5.0 Hz), 8.23 (1H, s), 8.94 (1H, s), 9.13-9.15 (2H, m), 10.21 (1H, s). | Ref. Ex. 91 |
| 1775 | 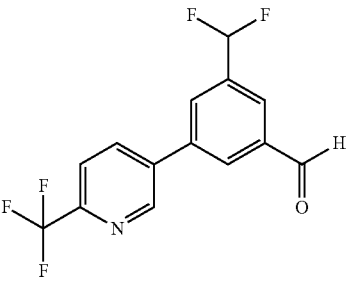 | 1H-NMR (CDCl3) δ: 6.83 (1H, t, J = 56.0 Hz), 7.84 (1H, d, J = 8.0 Hz), 8.01 (1H, s), 8.13 (2H, s), 8.24 (1H, s), 9.01 (1H, s), 10.17 (1H, s). | Ref. Ex. 91 |
| 1776 | 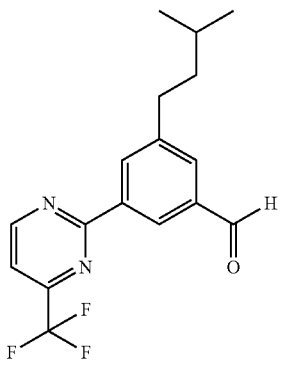 | 1H-NMR (CDCl3) δ: 0.97-0.99 (6H, m), 1.52-1.65 (3H, m), 2.80-2.83 (2H, m), 7.58 (1H, d, J = 5.0 Hz), 7.90 (1H, s), 8.60 (1H, s), 8.83 (1H, s), 9.09 (1H, d, J = 5.0 Hz), 10.14 (1H, s). | Ref. Ex. 91 |
| 1777 | 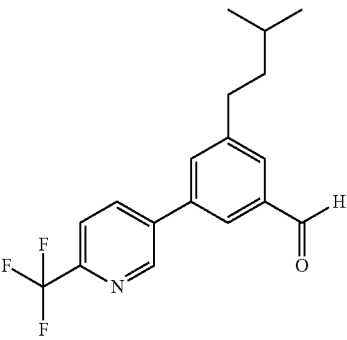 | 1H-NMR (CDCl3) δ: 0.97-0.99 (6H, m), 1.57-1.66 (3H, m), 2.78-2.81 (2H, m), 7.67 (1H, s), 7.79-7.81 (2H, m), 7.92 (1H, s), 8.08-8.10 (1H, m), 8.97 (1H, s), 10.09 (1H, s). | Ref. Ex. 91 |

TABLE 2-continued

| Ref. Ex. No | STR | 1H-NMR | ref. |
| --- | --- | --- | --- |
| 1778 | | 1H-NMR (CDCl3) δ: 3.46 (3H, s), 4.41-4.45 (1H, m), 7.52 (2H, s), 7.72 (1H, s). | Ref. Ex. 115 |
| 1779 | | 1H-NMR (CDCl3) δ: 1.45 (3H, t, J = 7.2 Hz), 4.47 (2H, q, J = 7.1 Hz), 8.07 (1H, dd, J = 1.9, 8.3 Hz), 8.32 (1H, s), 8.47 (1H, d, J = 8.3 Hz), 8.86-8.87 (1H, m). | Ref. Ex. 2 |
| 1780 | | 1H-NMR (CDCl3) δ: 8.10 (1H, dd, J = 2.2, 8.2 Hz), 8.34 (1H, s), 8.42 (1H, d, J = 8.3 Hz), 8.88-8.90 (1H, m), 10.12 (1H, s). | Ref. Ex. 63 |
| 1781 | | 1H-NMR (CDCl3) δ: 3.50 (3H, s), 4.54-4,58 (1H, m), 7.85 (1H, s), 7.88 (1H, s), 8.06 (1H, s), 9.99 (1H, s). | Ref. Ex. 138 |
| 1782 | | 1H-NMR (CDCl3) δ: 3.56 (3H, s), 4.68-4.73 (1H, m), 7.83 (1H, d, J = 8.0 Hz), 7.94 (1H, s), 8.04 (1H, s), 8.10-8.13 (1H, m), 8.17 (1H, t, J = 1.6 Hz), 8.99 (1H, d, J = 1.9 Hz). 10.15 (1H, s). | Ref. Ex. 112 |
| 1783 | | 1H-NMR (CDCl3) δ: 3.52 (3H, s), 4.64-4.68 (1H, m), 7.17-7.22 (2H, m), 7.59-7.62 (2H, m), 7.88 (1H, s), 7.92 (1H, s), 8.10 (1H, s), 10.11 (1H, s). | Ref. Ex. 112 |
| 1784 | | 1H-NMR (CDCl3) δ: 2.52 (3H, s), 7.50-7.54 (1H, m), 7.75 (1H, s), 7.79-7.82 (1H, m), 8.09 (1H, s), 8.23 (1H, s), 8.57 (1H, s), 10.08 (1H, s). | Ref. Ex. 112 |

TABLE 2-continued

| Ref. Ex. No | STR | 1H-NMR | ref. |
|---|---|---|---|
| 1785 | | 1H-NMR (CDCl3) δ: 2.53 (3H, s), 7.75-7.79 (3H, m), 8.11 (1H, s), 8.25 (1H, s), 8.67 (1H, s), 10.08 (1H, s). | Ref. Ex. 112 |
| 1786 | | 1H-NMR (CDCl3) δ: 1.45 (3H, t, J = 7.0 Hz), 4.45 (2H, q, J = 7.0 Hz), 7.86 (1H, d, J = 8.0 Hz), 8.18 (1H, d, J = 8.5 Hz), 8.24-8.26 (1H, m), 8.59 (1H, d, J = 6.0 Hz), 8.70 (1H, s), 9.42 (1H, s). | Ref. Ex. 112 |
| 1788 | | 1H-NMR (CDCl3) δ: 0.87 (1H, d, J = 8.4 Hz). 8.08-8.10 (1H, m), 8.27 (1H, d, J = 8.4 Hz), 8.52 (1H, m), 8.60-8.62 (1H, m). 9.44 (1H, m), 10.16 (1H, s). | Ref. Ex. 76, Ref. Ex. 147 |
| 1789 | | 1H-NMR (CDCl3) δ: 7.63-7.65 (1H, m), 7.82 (1H, s), 7.92 (1H, s), 7.97 (1H, s), 8.56 (1H, d, J = 2.5 Hz), 8.70 (1H, s), 10.06 (1H, s). | Ref. Ex. 112 |
| 1790 | | 1H-NMR (CDCl3) δ: 2.38 (1H, t, J = 5.8 Hz), 4.82 (2H, d, J = 5.8 Hz), 5.41 (1H, d, J = 11.0 Hz), 5.70 (1H, d, J = 17.2 Hz), 6.89 (1H, dd, J = 11.0, 17.2 Hz), 7.68 (1H, dd, J = 0.8, 7.8 Hz), 7.97 (1H, t, J = 7.8 Hz), 8.34 (1H, d, J = 7.8 Hz). | Ref. Ex. 77 |
| 1791 | | 1H-NMR (CDCl3) δ: 1.58 (3H, d, J = 6.5 Hz), 2.13 (1H, d, J = 3.6 Hz), 5.23-5.27 (1H, m), 6.93 (1H, d, J = 5.3 Hz), 7.23 (1H, d, J = 5.3 Hz). | Ref. Ex. 1737 |
| 1792 | | 1H-NMR (CDCl3) δ: 3.40 (3H, s), 4.40 (2H, s), 7.42 (2H, s), 7.58 (1H, s). | Ref. Ex. 115 |
| 1793 | | 1H-NMR (CDCl3) δ: 3.44 (3H, s), 4.51 (2H, s), 7.76 (1H, s), 7.77 (1H, s), 7.93 (1H, s), 9.96 (1H, s). | Ref. Ex. 138 |

| Ref. Ex. No | STR | 1H-NMR | ref. |
|---|---|---|---|
| 1794 | | 1H-NMR (CDCl3) δ: 7.48 (1H, d, J = 3.9 Hz), 7.64-7.67 (1H, m), 7.80 (1H, d, J = 3.9 Hz), 8.50 (1H, d, J = 2.6 Hz), 8.77 (1H, s), 9.94 (1H, s). | Ref. Ex. 112 |
| 1795 | | 1H-NMR (CDCl3) δ: 1.28 (3H, t, J = 7.0 Hz), 3.59 (2H, q, J = 7.0 Hz), 4.55 (2H, s), 7.76 (1H, s), 7.78 (1H, s), 7.92 (1H, s), 9.96 (1H. s). | Ref. Ex. 138 |
| 1796 | | 1H-NMR (CDCl3) δ: 1.31 (3H, t, J = 7.0 Hz), 3.65 (2H, q, J = 7.0 Hz), 4.67 (2H, s), 7.80 (1H, d, J = 8.1 Hz), 7.87 (1H, s), 7.95 (1H, s), 8.03 (1H, s), 8.10-8.12 (1H, m), 8.99 (1H, s), 10.12 (1H, s). | Ref. Ex. 112 |
| 1797 | | 1H-NMR (CDCl3) δ: 3.50 (3H, s), 4.63 (2H, s), 7.81 (1H, d, J = 8.1 Hz), 7.86 (1H, s), 7.95 (1H, s), 8.04 (1H, s), 8.09-8.12 (1H, m), 8.99 (1H, s), 10.12 (1H, s). | Ref. Ex. 112 |
| 1798 | | 1H-NMR (CDCl3) δ: 3.47 (3H, s), 4.59 (2H, s), 7.15-7.18 (2H, m), 7.58-7.62 (2H, m), 7.80 (1H, s), 7.82 (1H, s), 7.98 (1H, s), 10.09 (1H, s). | Ref. Ex. 112 |
| 1799 | | 1H-NMR (CDCl3) δ: 1.35 (3H, t, J = 7.5 Hz), 2.35 (1H, t, J = 5.8 Hz), 2.89 (2H, q, J = 7.5 Hz), 4.74 (2H, d, J = 5.8 Hz), 7.65 (1H, dd, J = 0.8, 7.8 Hz), 7.92-7.96 (1H, m), 8.31 (1H, d, J = 7.8 Hz). | Ref. Ex. 34 |

TABLE 2-continued

| Ref. Ex. No | STR | 1H-NMR | ref. |
|---|---|---|---|
| 1800 | | 1H-NMR (CDCl3) δ: 0.24-0.29 (1H, m), 0.45-0.52 (2H, m), 0.64-0.70 (1H, m), 1.04-1.10 (1H, m), 3.27 (3H, s), 3.46 (1H, d, J = 7.9 Hz), 7.27 (1H, s), 7.36 (1H, s), 7.44 (1H, s). | Ref. Ex. 115 |
| 1801 | | 1H-NMR (CDCl3) δ: 0.27-0.32 (1H, m), 0.47-0.57 (2H, m), 0.68-0.74 (1H, m), 1.07-1.15 (1H, m), 3.30 (3H, s), 3.60 (1H, d, J = 8.0 Hz), 7.60 (1H, s), 7.73 (1H, s), 7.78 (1H, s), 9.99 (1H, s). | Ref. Ex. 138 |
| 1802 | | 1H-NMR (CDCl3) δ: 1.42 (3H, t, J = 7.5 Hz), 3.34 (2H, q, J = 7.5 Hz), 7.72 (1H, dd, J = 0.7, 7.8 Hz), 8.01 (1H, t, J = 7.8 Hz), 8.41 (1H, d, J = 8.0 Hz), 10.20 (1H, s). | Ref. Ex. 48 |
| 1803 | | 1H-NMR (CDCl3) δ: 2.82 (3H, s), 3.97 (3H, s), 7.20 (1H, t, J = 8.6 Hz), 7.75-7.79 (1H, m), 8.02 (1H, dd, J = 2.2, 6.9 Hz). | Ref. Ex. 2 |
| 1804 | | 1H-NMR (CDCl3) δ: 1.26-1.34 (1H, m), 1.62-1.66 (1H, m), 2.05-2.13 (1H, m), 4.09-4.13 (2H, m), 7.19-7.21 (1H, m), 7.39 (1H, s), 7.45-7.50 (2H, m), 9.98 (1H, s). | Ref. Ex. 80 |
| 1805 | | 1H-NMR (CDCl3) δ: 2.25 (3H, s), 2.49 (3H, s), 7.08 (1H, d, J = 5.0 Hz), 7.49 (1H, s), 7.58 (1H, d, J = 5.0 Hz), 7.72 (1H, s), 7.74 (1H, s), 10.03 (1H, s). | Ref. Ex. 112 |

TABLE 2-continued

| Ref. Ex. No | STR | 1H-NMR | ref. |
|---|---|---|---|
| 1806 | | 1H-NMR (CDCl3) δ: 1.30 (3H, t, J = 7.0 Hz), 3.64 (2H, q, J = 7.0 Hz), 4.66 (2H, s), 7.74 (4H, s), 7.86 (1H, s), 7.90 (1H, s), 8.03 (1H, s), 10.11 (1H, s). | Ref. Ex. 112 |
| 1807 | | 1H-NMR (CDCl3) δ: 2.87 (3H, s), 3.99 (3H, s), 7.77 (1H, d, J = 8.2 Hz), 8.46 (1H, dd, J = 1.9, 8.2 Hz), 9.18 (1H, d, J = 1.9 Hz). | Ref. Ex. 2 |
| 1808 | | 1H-NMR (CDCl3) δ: 1.24-1.31 (1H, m), 1.57-1.65 (1H, m), 2.00-2.10 (1H, m), 3.96-4.05 (2H, m), 7.00 (2H, d, J = 1.6 Hz), 7.28 (1H, d, J = 1.6 Hz). | Ref. Ex. 80 |
| 1809 | | 1H-NMR (CDCl3) δ: 1.20-1.32 (1H, m), 1.61-1.67 (1H, m), 2.05-2.13 (1H, m), 4.09-4.14 (2H, m), 7.30-7.34 (2H, m), 7.61 (1H, s), 9.91 (1H, s). | Ref. Ex. 138 |
| 1810 | | 1H-NMR (CDCl3) δ: 1.58-1.67 (2H, m), 1.73-1.94 (6H, m), 4.68-4.72 (1H, m), 6.95 (2H, d, J = 1.5 Hz), 7.20 (1H, t, J = 1.5 Hz). | Ref. Ex. 80 |
| 1811 | | 1H-NMR (CDCl3) δ: 1.70-1.96 (8H, m), 4.79-4.82 (1H, m), 7.27-7.30 (2H, m), 7.54 (1H, s), 9.89 (1H, s). | Ref. Ex. 138 |
| 1812 | | 1H-NMR (CDCl3) δ: 1.42 (3H, s), 4.00 (2H, s), 4.46 (2H, d, J = 6.0 Hz), 4.58 (2H, d, J = 6.0 Hz), 7.04 (2H, d, J = 1.6 Hz), 7.28 (1H, t, J = 1.6 Hz). | Ref. Ex. 80 |

TABLE 2-continued

| Ref. Ex. No | STR | 1H-NMR | ref. |
|---|---|---|---|
| 1813 | | 1H-NMR (CDCl3) δ: 1.45 (3H, s), 4.09 (2H, s), 4.48 (2H, d, J = 6.0 Hz), 4.61 (2H, d, J = 6.0 Hz), 7.37-7.38 (2H, m), 7.61 (1H, s), 9.92 (1H, s). | Ref. Ex. 138 |
| 1814 | | 1H-NMR (CDCl3) δ: 1.32-1.36 (1H, m), 1.65-1.68 (1H, m), 2.12-2.16 (1H, m), 4.19 (2H, m), 7.42 (1H, s), 7.47 (1H, s), 7.71 (1H, s), 7.81 (1H, d, J = 8.0 Hz), 8.08-8.10 (1H, m), 8.98 (1H, s), 10.07 (1H, s). | Ref. Ex. 112 |
| 1815 | | 1H-NMR (CDCl3) δ: 1.66-2.02 (8H, m), 4.89-4.92 (1H, m), 7.36 (1H, s), 7.46 (1H, s), 7.64 (1H, s), 7.79 (1H, d, J = 8.5 Hz), 8.07-8.09 (1H, m), 8.97 (1H, s), 10.05 (1H, s). | Ref. Ex. 112 |
| 1816 | | 1H-NMR (CDCl3) δ: 1.49 (3H, s), 4.18 (2H, s), 4.52 (2H, d, J = 6.0 Hz), 4.66 (2H, d, J = 6.0 Hz), 7.45 (1H, s), 7.53 (1H, s), 7.72 (1H, s), 7.81 (1H, d, J = 8.0 Hz), 8.09-8.11 (1H, m), 8.98 (1H, s), 10.08 (1H, s). | Ref. Ex. 112 |
| 1817 | | 1H-NMR (CDCl3) δ: 1.65-1.69 (2H, m), 1.81-2.00 (6H, m), 4.88-4.91 (1H, m), 7.13-7.17 (2H, m), 7.31-7.35 (2H, m), 7.56-7.60 (3H, m), 10.02 (1H, s). | Ref. Ex. 112 |

TABLE 2-continued

| Ref. Ex. No | STR | 1H-NMR | ref. |
|---|---|---|---|
| 1818 | | 1H-NMR (CDCl3) δ: 2.63-2.70 (1H, m), 2.75-2.82 (1H, m), 4.10 (2H, d, J = 4.2 Hz), 4.62-4.66 (1H, m), 4.70-4.74 (1H, m), 5.09-5.13 (1H, m), 7.07 (2H, d, J = 1.6 Hz), 7.27 (1H, d, J = 1.6 Hz). | Ref. Ex. 80 |
| 1819 | | 1H-NMR (CDCl3) δ: 2.68-2.84 (2H, m), 4.16-4.21 (2H, m), 4.63-4.76 (2H, m), 5.12-5.17 (1H, m), 7.38-7.41 (2H, m), 7.61 (1H, s), 9.91 (1H, s). | Ref. Ex. 138 |
| 1820 | | 1H-NMR (CDCl3) δ: 1.49 (3H, t, J = 7.0 Hz), 4.18 (2H, q, J = 7.0 Hz), 7.38-7.39 (1H, m), 7.47-7.48 (1H, m), 7.67 (1H, t, J = 1.4 Hz). 7.80 (1H, d, J = 8.2 Hz), 8.07-8.09 (1H, m), 8.97 (1H, d, J = 2.0 Hz), 10.06 (1H, s). | Ref. Ex. 112 |
| 1821 | | 1H-NMR (CDCl3) δ: 1.41 (6H, d, J = 6.1 Hz), 4.70-4.75 (1H, m), 7.36-7.37 (1H, m), 7.46-7.47 (1H, m), 7.65 (1H, s), 7.80 (1H, d, J = 8.2 Hz), 8.07-8.09 (1H, m), 8.96 (1H, s), 10.05 (1H, s). | Ref. Ex. 112 |
| 1822 | | 1H-NMR (CDCl3) δ: 2.70-2.87 (2H, m), 4.25-4.31 (2H, m), 4.66-4.78 (2H, m), 5.18-5.23 (1H, m), 7.49 (1H, s), 7.54 (1H, s), 7.71 (1H, s), 7.80 (1H, d, J = 8.5 Hz), 8.08-8.10 (1H, m), 8.98 (1H, s), 10.07 (1H, s). | Ref. Ex. 112 |
| 1823 | | 1H-NMR (CDCl) δ: 4.22 (3H, s), 7.13 (1H, s), 7.37-7.42 (2H, m), 7.71-7.77 (2H, m), 9.90 (1H, s). | Ref. Ex. 48 |

TABLE 2-continued

| Ref. Ex. No | STR | 1H-NMR | ref. |
|---|---|---|---|
| 1824 | | 1H-NMR (CDCl3) δ: 1.71-1.79 (1H, m), 1.87-1.95 (1H, m), 2.17-2.26 (2H, m), 2.48-2.56 (2H, m), 4.72-4.80 (1H, m), 7.13-7.18 (2H, m), 7.24-7.28 (2H, m), 7.54-7.62 (3H, m), 10.01 (1H, s). | Ref. Ex. 112 |
| 1825 | | 1H-NMR (CDCl3) δ: 1.46 (6H, d, J = 6.1 Hz), 4.75-4.81 (1H, m), 7.15 (1H, d, J = 8.8 Hz), 7.75 (1H, d, J = 8.1 Hz), 7.78-7.80 (1H, m), 8.03-8.05 (1H, m), 8.09 (1H, d, J = 2.5 Hz), 8.93 (1H, d, J = 2.1 Hz), 10.54 (1H, s). | Ref. Ex. 112 |
| 1826 | | 1H-NMR (CDCl3) δ: 1.88-2.18 (8H, m), 4.43-4.48 (1H, m), 7.00 (2H, d, J = 1.6 Hz), 7.26-7.27 (1H, m). | Ref. Ex. 80 |
| 1827 | | 1H-NMR (CDCl3) δ: 1.36 (3H, t, J = 7.5 Hz), 2.30 (1H, t, J = 5.8 Hz), 2.91 (2H, q, J = 7.5 Hz), 4.76 (2H, d, J = 5.8 Hz), 8.00 (1H, dd, J = 1.8, 8.3 Hz), 8.26 (1H, d, J = 8.3 Hz), 8.82-8.83 (1H, m). | Ref. Ex. 19 |
| 1828 | | 1H-NMR (CDCl3) δ: 1.93-2.19 (8H, m), 4.58 (1H, m), 7.33 (2H, s), 7.59 (1H, s), 9.90 (1H, s). | Ref. Ex. 138 |
| 1829 | | 1H-NMR (CDCl3) δ: 1.92-2.18 (8H, m), 4.60 (1H, bis), 7.18-7.22 (1H, m), 7.40 (1H, s), 7.45-7.47 (2H, m), 9.98 (1H. s). | Ref. Ex. 80 |

TABLE 2-continued

| Ref. Ex. No | STR | 1H-NMR | ref. |
|---|---|---|---|
| 1830 | | 1H-NMR (CDCl3) δ: 1.94-2.24 (8H, m), 4.66-4.70 (1H, m), 7.40 (1H, t, J = 2.1 Hz), 7.48-7.49 (1H, m), 7.69 (1H, d, J = 1.4 Hz), 7.80 (1H, d, J = 8.1 Hz), 8.08 (1H, dd, J = 2.1, 8.1 Hz), 8.96 (1H, d, J = 2.1 Hz), 10.06 (1H, s). | Ref. Ex. 112 |
| 1831 | | 1H-NMR (CDCl3) δ: 1.96-2.20 (8H, m), 4.65 (1H, m), 7.15-7.18 (2H, m), 7.35-7.38 (2H, m), 7.56-7.59 (2H, m), 7.64 (1H, s), 10.03 (1H, s). | Ref. Ex. 112 |
| 1832 | | 1H-NMR (CDCl3) δ: 2.26 (1H, t, J = 5.8 Hz), 2.53 (3H, s), 4.76 (2H, d, J = 5.8 Hz), 7.74 (1H, d, J = 8.3 Hz), 8.35-8.37 (1H, m), 9.18 (1H, s). | Ref. Ex. 19 |
| 1833 | | 1H-NMR (CDCl3) δ: 2.89 (3H, s), 7.80 (1H, d, J = 8.2 Hz), 8.43 (1H, dd, J = 1.8, 8.2 Hz), 9.22 (1H, d, J = 1.8 Hz), 10.24 (1H, s). | Ref. Ex. 48 |
| 1834 | | 1H-NMR (CDCl3) δ: 1.17-1.23 (4H, m), 2.80-2.86 (1H, m), 3.97 (3H, s), 7.22-7.25 (1H, m), 7.78-7.81 (1H, m), 7.87-7.90 (1H, m). | Ref. Ex. 133 |
| 1835 | | 1H-NMR (CDCl3) δ: 1.18-1.24 (4H, m), 2.81-2.87 (1H, m), 3.97 (3H, s), 7.12-7.17 (1H, m), 7.39-7.44 (1H, m), 7.67-7.70 (1H, m), 7.77-7.80 (1H, m). | Ref. Ex. 133 |
| 1836 | | 1H-NMR (CDCl3) δ: 1.21-1.31 (4H, m), 2.89-2.74 (1H, m), 7.16-7.19 (1H, m), 7.42-7.47 (1H, m), 7.67 (1H, d, J = 8.0 Hz), 7.78 (1H, d, J = 8.0 Hz), 10.05 (1H, s). | Ref. Ex. 63 |
| 1837 | | 1H-NMR (CDCl3) δ: 1.22-1.30 (4H, m), 2.71-2.76 (1H, m), 7.28-7.30 (1H, m), 7.81-7.86 (2H, m), 10.06 (1H, s). | Ref. Ex. 63 |

TABLE 2-continued
| Ref. Ex. No | STR | 1H-NMR | ref. |
|---|---|---|---|
| 1838 |  | 1H-NMR (CDCl3) δ: 1.15-1.21 (4H, m), 2.78-2.84 (1H, m), 3.95 (3H, s), 6.03 (2H, s), 6.85 (1H, d, J = 8.2 Hz), 7.45 (1H, d, J = 1.6 Hz), 7.53 (1H, dd, J = 1.6, 8.2 Hz). | Ref. Ex. 133 |
| 1839 | 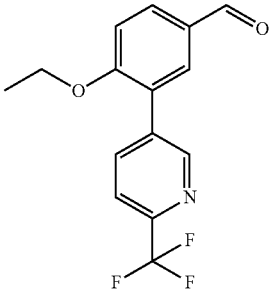 | 1H-NMR (CDCl3) δ: 1.43 (3H, t, J = 7.0 Hz), 4.20 (2H, q, J = 7.0 Hz), 7.14 (1H, d, J = 8.6 Hz), 7.76 (1H, d. J = 8.0 Hz), 7.88-7.89 (1H, m), 7.94 (1H, dd, J = 2.0, 8.6 Hz), 8.03-8.07 (1H, m), 8.94 (1H, s), 9.96 (1H, s). | Ref. Ex. 112 |
| 1840 |  | 1H-NMR (CDCl3) δ: 0.71-0.76 (1H, m), 1.07-1.60 (6H, m), 1.74-1.94 (1H, m), 2.22-2.37 (3H, m), 3.59-3.92 (2H, m), 6.98-7.00 (2H, m), 7.22-7.23 (1H, m). | Ref. Ex. 80 |
| 1841 | 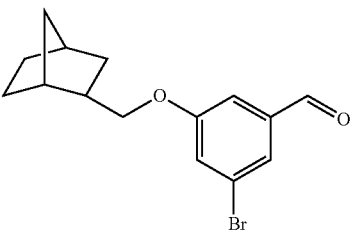 | 1H-NMR (CDCl3) δ: 0.74-0.88 (1H, m), 1.08-1.61 (6H, m), 1.78-2.00 (1H, m), 2.25-2.38 (3H, m), 3.70-4.00 (2H, m), 7.31-7.33 (2H, m), 7.56 (1H, s), 9.90 (1H, s). | Ref. Ex. 138 |
| 1842 | 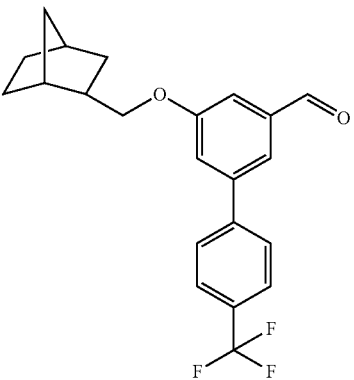 | 1H-NMR (CDCl3) δ: 0.76-0.82 (1H, m), 1.10-1.62 (6H, m), 1.80-2.04 (1H, m), 2.25-2.44 (3H, m), 3.77-4.10 (2H, m), 7.39-7.41 (1H, m), 7.46-7.50 (1H, m), 7.66-7.67 (1H, m), 7.80 (1H, d, J = 8.1 Hz), 8.07-8.10 (1H, m), 8.97-8.98 (1H, m), 10.05-10.07 (1H, m). | Ref. Ex. 112 |
| 1843 | 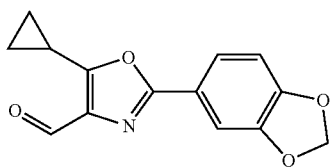 | 1H-NMR (CDCl3) δ: 1.22-1.28 (4H, m), 2.64-2.69 (1H, m), 6.04 (2H, m), 6.87 (1H, d, J = 8.5 Hz), 7.43 (1H, s), 7.51-7.53 (1H, m), 10.03 (1H, s). | Ref. Ex. 63 |

TABLE 2-continued

| Ref. Ex. No | STR | 1H-NMR | ref. |
|---|---|---|---|
| 1844 | | 1H-MdR (CDCl3) δ: 1.40 (3H, t, J = 7.5 Hz), 3.32 (2H, q, J = 7.5 Hz), 3.97 (3H, s), 7.77 (1H, dd; J = 2.4, 8.5 Hz), 8.20 (1H, dd, J = 0.6, 8.5 Hz), 8.53 (1H, dd, J = 0.6, 2.4 Hz). | Ref. Ex. 2 |
| 1845 | | 1H-NMR (CDCl3) δ: 1.15-1.25 (4H, m), 2.80-2.86 (1H, m), 3.97 (3H, s), 7.12 (1H, d, J = 8.3 Hz), 7.71 (1H, d, J = 1.7 Hz), 7.77 (1H, dd. J = 1.7, 8.3 Hz). | Ref. Ex. 133 |
| 1846 | | 1H-NMR (CDCl3) δ: 0.95 (3H, t, J = 7.4 Hz), 1.40 (3H, t, J = 7.1 Hz), 1.87-1.95 (2H, m), 4.37 (2H, q, J = 7.1 Hz), 4.55 (2H, t, J = 7.3 Hz), 7.09 (1H, s), 7.35-7.39 (2H, m), 7.72-7.75 (2H, m). | Ref. Ex. 113 |
| 1847 | | 1H-NMR (CDCl3) δ: 1.19 (3H, t, J = 7.0 Hz). 3.70 (2H, q, J = 7.0 Hz), 7.38 (1H, t, J = 7.7 Hz), 7.62-7.65 (1H, m), 7.80 (1H, d, J = 8.2 Hz), 7.95-7.97 (1H, m), 8.16 (1H, d, J = 7.7 Hz), 8.97 (1H, s), 10.47 (1H, s). | Ref. Ex. 112 |
| 1848 | | 1H-NMR (CDCl3) δ: 1.07 (6H, d, J = 6.1 Hz), 3.79-3.84 (1H, m), 7.36 (1H, t, J = 7.7 Hz), 7.61-7.63 (1H, m), 7.79 (1H, d, J = 8.1 Hz), 7.95-7.97 (1H, m), 8.14 (1H, d, J = 8.1 Hz), 8.96 (1H, s), 10.48 (1H, s). | Ref. Ex. 112 |
| 1849 | | 1H-NMR (CDCl3) δ: 1.22-1.31 (4H, m), 2.66-2.73 (1H, m), 7.14 (1H, d, J = 8.5 Hz), 7.69 (1H, d, J = 1.6 Hz), 7.75-7.77 (1H, m), 10.04 (1H, s). | Ref. Ex. 63 |
| 1850 | | 1H-NMR (CDCl3) δ: 1.34 (3H, t, J = 7.5 Hz), 2.36 (1H, t, J = 5.6 Hz), 2.89 (2H, q, J = 7.5 Hz), 4.73 (2H, d, J = 5.6 Hz), 7.74 (1H, dd, J = 2.4, 8.5 Hz), 8.09 (1H, dd, J = 0.6, 8.5 Hz), 8.52 (1H, dd, J = 0.6, 2.4 Hz). | Ref. Ex. 19 |
| 1851 | | 1H-NMR (CDCl3) δ: 3.37 (2H, t, J = 8.7 Hz), 4.85 (2H, t, J = 8.7 Hz), 7.67 (1H, s), 7.75 (1H, d, J = 8.1 Hz), 7.85 (1H, s), 8.01-8.03 (1H, s), 8.91 (1H, s), 10.28 (1H, s). | Ref. Ex. 112 |

TABLE 2-continued

| Ref. Ex. No | STR | 1H-NMR | ref. |
|---|---|---|---|
| 1852 | | 1H-NMR (CDCl3) δ: 1.20-1.31 (4H, m), 2.83-2.90 (1H, m), 3.98 (3H, s), 7.39-7.44 (1H, m), 7.85-7.90 (1H, m), 8.06 (1H, s). | Ref. Ex. 133 |
| 1853 | | 1H-NMR (CDCl3) δ: 1.20-1.31 (4H, m), 2.83-2.90 (1H, m), 3.98 (3H, s), 7.77 (1H, d, J = 8.2 Hz), 8.46 (1H, dd, J = 1.8, 8.2 Hz), 9.28 (1H, d, J = 1.8 Hz). | Ref. Ex. 133 |
| 1854 | | 1H-NMR (CDCl3) δ: 1.25-1.35 (4H, m), 2.70-2.76 (1H, m), 7.43 (1H, d, J = 8.3 Hz), 7.86 (1H, d, J = 8.7 Hz), 8.04 (1H, s), 10.05 (1H, s). | Ref. Ex. 63 |
| 1855 | | 1H-NMR (CDCl3) δ: 0.44-0.48 (2H, m), 0.49-0.55 (2H, m), 1.38-1.45 (4H, m), 4.37 (2H, q, J = 7.1 Hz), 4.47 (2H, d, J = 7.2 Hz), 7.11 (1H, s), 7.35-7.39 (2H, m), 7.73-7.77 (2H, m). | Ref. Ex. 113 |
| 1856 | | 1H-NMR (CDCl3) δ: 0.44-0.48 (2H, m), 0.52-0.57 (2H, m), 1.34-1.44 (1H, m), 4.44 (2H, d, J = 7.1 Hz), 7.15 (1H, s), 7.39 (2H, d, J = 8.4 Hz), 7.75 (2H, d, J = 8.4 Hz), 9.89 (1H, s). | Ref. Ex. 63 |
| 1857 | | 1H-NMR (CDCl3) δ: 1.46 (6H, d, J = 6.1 Hz), 4.76-4.81 (1H, m), 7.16 (1H, s), 7.21 (1H, d, J = 7.9 Hz), 7.80 (1H, d, J = 8.1 Hz), 7.97 (1H, d, J = 8.1 Hz), 8.04-8.07 (1H, m), 8.94 (1H, s), 10.53 (1H, s). | Ref. Ex. 112 |
| 1858 | | 1H-NMR (CDCl3) δ: 1.35 (6H, d, J = 6.1 Hz), 4.70-4.77 (1H, m), 7.50-7.56 (3H, m), 7.76 (1H, d, J = 8.0 Hz), 8.05-8.07 (1H, m), 8.92 (1H, s), 10.03 (1H, s). | Ref. Ex. 112 |

TABLE 2-continued

| Ref. Ex. No | STR | 1H-NMR | ref. |
|---|---|---|---|
| 1859 | | 1H-NMR (CDCl3) δ: 1.25-1.36 (4H, m), 2.73-2.78 (1H, m), 7.80 (1H, d, J = 8.5 Hz), 8.43-8.45 (1H, m), 9.29 (1H, s), 10.07 (1H, s). | Ref. Ex. 63 |
| 1860 | | 1H-NMR (CDCl3) δ: 1.41 (3H, t, J = 6.9 Hz), 4.18 (2H, q, J = 6.9 Hz), 7.50-7.53 (2H, m), 7.57-7.58 (1H, m), 7.76 (1H, d, J = 8.1 Hz), 8.07-8.09 (1H, m), 8.93 (1H, s), 10.04 (1H, s). | Ref. Ex. 112 |
| 1861 | | 1H-NMR (CDCl3) δ: 0.81 (3H, t, J = 7.4 Hz), 1.41 (3H, t, J = 7.0 Hz), 1.77-1.87 (2H, m), 4.13 (2H, t, J = 7.5 Hz), 4.43 (2H, q, J = 7.0 Hz), 6.80 (1H, s), 7.30-7.34 (2H, m), 7.44-7.48 (2H, m). | Ref. Ex. 184 |
| 1862 | | 1H-NMR (CDCl3) δ: 0.85 (3H, t, J = 7.4 Hz), 1.82-1.91 (2H, m), 4.13 (2H, t, J = 7.3 Hz), 6.79 (1H, s), 7.31-7.34 (2H, m), 7.45-7.49 (2H, m), 9.99 (1H, s). | Ref. Ex. 63 |
| 1864 | | 1H-NMR (CDCl3) δ: 1.17-1.21 (2H, m), 1.34-1.38 (2H, m), 2.48-2.54 (1H, m), 7.40-7.44 (2H, m), 7.78-7.91 (2H, m), 10.22 (1H, s). | Ref. Ex. 63 |
| 1865 | | 1H-NMR (CDCl3) δ: 1.54 (3H, t, J = 6.9 Hz), 4.26 (2H, q, J = 6.9 Hz), 7.15 (1H, s), 7.22-7.25 (1H, m), 7.80 (1H, d, J = 8.2 Hz), 7.97 (1H, d, J = 8.0 Hz), 8.05-8.08 (1H, m), 8.95 (1H, s), 10.56 (1H, s). | Ref. Ex. 112 |
| 1866 | | 1H-NMR (CDCl3) δ: 1.44 (6H, d, J = 5.9 Hz), 4.70-4.75 (1H, m), 7.07 (1H, d, J = 8.7 Hz), 7.10-7.13 (2H, m), 7.51-7.54 (2H, m), 7.71 (1H, dd, J = 2.6, 8.6 Hz), 8.01 (1H, d, J = 2.6 Hz), 10.53 (1H, s). | Ref. Ex. 112 |

TABLE 2-continued

| Ref. Ex. No | STR | 1H-NMR | ref. |
|---|---|---|---|
| 1867 | | 1H-NMR (CDCl3) δ: 1.51 (3H, t, J = 6.9 Hz), 4.19-4.23 (2H, m), 7.05 (1H, d, J = 8.6 Hz), 7.10-7.14 (2H, m), 7.51-7.54 (2H, m), 7.72 (1H, dd, J = 2.6, 8.6 Hz), 8.02 (1H, d, J = 2.5 Hz), 10.55 (1H, s). | Ref. Ex. 112 |
| 1868 | | 1H-NMR (CDCl3) δ: 1.40 (1H, t, J = 7.5 Hz), 3.33 (2H, q, J = 7.5 Hz), 7.80 (1H, dd, J = 2.4, 8.4 Hz), 8.18 (1H, dd, J = 0.6, 8.4 Hz), 8.55 (1H, dd, J = 0.6, 2.4 Hz), 10.19 (1H, s). | Ref. Ex. 48 |
| 1869 | | 1H-NMR (CDCl3) δ: 4.02 (3H, s), 7.17 (1H, d, J = 8.6 Hz), 7.76 (1H, d, J = 8.1 Hz), 7.83 (1H, dd, J = 2.5, 8.6 Hz), 8.03-8.05 (1H, m), 8.10 (1H, d, J = 2.5 Hz), 8.93 (1H, s), 10.54 (1H, s). | Ref. Ex. 112 |
| 1870 | | 1H-NMR (CDCl3) δ: 6.22 (2H, s), 7.42 (1H, d, J = 1.4 Hz), 7.68 (1H, d, J = 1.4 Hz), 7.80 (1H, d, J = 8.0 Hz), 8.22-8.25 (1H, m), 9.11 (1H, d, J = 1.8 Hz), 9.92 (1H, s). | Ref. Ex. 112 |
| 1871 | | 1H-NMR (CDCl3) δ: 3.31 (2H, t, J = 8.9 Hz), 4.80 (2H, t, J = 8.9 Hz), 7.10-7.14 (2H, m), 7.48-7.52 (2H, m), 7.60 (1H, s), 7.76 (1H, s), 10.25 (1H, s). | Ref. Ex. 112 |
| 1872 | | 1H-NMR (CDCl3) δ: 1.65-1.74 (1H, m), 1.84-1.92 (1H, m), 2.19-2.28 (2H, m), 2.42-2.50 (2H, m), 3.89 (3H, s), 4.64-4.70 (1H, m), 6.69 (1H, d, J = 8.8 Hz), 7.49 (1H, dd, J = 2.7, 8.8 Hz), 7.90 (1H, d, J = 2.7 Hz). | Ref. Ex. 80 |
| 1873 | | 1H-NMR (DMSO-d6) δ: 7.71 (1H, dd, J = 1.3, 5.1 Hz), 7.76 (1H, d, J = 1.3 Hz), 8.49 (1H, d, J = 5.1 Hz), 9.87 (1H, brs), 10.34 (1H, brs). | Ref. Ex. 1477 |

TABLE 2-continued

| Ref. Ex. No | STR | 1H-NMR | ref. |
|---|---|---|---|
| 1874 | | 1H-NMR (CDCl3) δ: 1.69-1.79 (1H, m), 1.88-1.96 (1H, m), 2.19-2.28 (2H, m), 2.46-2.53 (2H, m), 4.68-4.75 (1H, m), 6.72 (1H, d, J = 8.9 Hz), 7.57 (1H, dd, J = 2.7, 8.9 Hz), 7.92 (1H, d, J = 2.7 Hz), 10.41 (1H, s). | Ref. Ex. 76 Ref. Ex. 48 |
| 1875 | | 1H-NMR (CDCl3) δ: 1.74-1.84 (1H, m), 1.92-2.00 (1H, m), 2.25-2.35 (2H, m), 2.54-2.60 (2H, m), 4.80-4.86 (1H, m), 6.98 (1H, d, J = 8.7 Hz), 7.74-7.78 (2H, m), 8.02-8.04 (1H, m), 8.09 (1H, d, J = 2.5 Hz), 8.92 (1H, s), 10.55 (1H, s). | Ref. Ex. 112 |
| 1876 | | 1H-NMR (CDCl3) δ: 2.86 (3H, s), 3.99 (3H, s), 7.70 (1H, dd, J = 1.2, 5.2 Hz), 7.86 (1H, d, J = 1.2 Hz), 8.47 (1H, d, J = 5.2 Hz). | Ref. Ex. 2 |
| 1877 | | 1HWMR (CDCl3) δ: 1.41 (3H, t, J = 7.5 Hz), 3.34 (2H, q, J = 7.5 Hz), 3.99 (3H, s), 7.71 (1H, dd, J = 1.5, 5.2 Hz), 7.87 (1H, t, J = 0.7 Hz), 8.47 (1H, d, J = 5.2 Hz). | Ref. Ex. 2 |
| 1878 | | 1H-NMR (CDCl3) δ: 8.23 (1H, s), 9.09-9.10 (2H, m). | Ref. Ex. 89 |
| 1879 | | 1H-NMR (CDCl3) δ: 1.45 (6H, d, J = 6.1 Hz), 4.75-4.80 (1H, m), 7.11 (1H, s), 7.14-7.18 (3H, m), 7.54-7.58 (2H, m), 7.89 (1H, d, J = 8.0 Hz), 10.50 (1H, s). | Ref. Ex. 112 |
| 1881 | | 1H-NMR (CDCl3) δ: 1.41 (6H, d, J = 7.0 Hz), 3.67-3.73 (1H, m), 7.17 (1H, d, J = 8.4 Hz), 7.78 (1H, d, J = 1.8 Hz), 7.86 (1H, dd, J = 1.6, 8.4 Hz), 10.03 (1H, s). | Ref. Ex. 133, Ref. Ex. 63 |
| 1882 | | 1H-NMR (CDCl3) δ: 2.31 (1H, t, J = 5.9 Hz), 2.53 (3H, s), 4.75 (2H, d, J = 5.8 Hz), 7.65 (1H, dd, J = 1.5, 5.2 Hz), 7.81-7.82 (1H, m), 8.43-8.45 (1H, m). | Ref. Ex. 19 |
| 1883 | | 1H-NMR (CDCl3) δ: 1.35 (3H, t, J = 7.5 Hz), 2.35 (1H, t, J = 5.9 Hz), 2.92 (2H, q, J = 7.5 Hz), 4.75 (2H, d, J = 5.9 Hz), 7.66 (1H, dd, J = 1.3, 5.2 Hz), 7.82 (1H, d, J = 1.3 Hz), 8.44 (1H, d, J = 5.2 Hz). | Ref. Ex. 19 |

TABLE 2-continued

| Ref. Ex. No | STR | 1H-NMR | ref. |
|---|---|---|---|
| 1884 | | 1H-NMR (CDCl3) δ: 2.89 (3H, s), 7.71 (1H, dd, J = 1.5, 5.1 Hz), 7.86 (1H, dd, J = 0.5, 15 Hz), 8.50 (1H, dd, J = 0.5, 5.1 Hz), 10.22 (1H, s). | Ref. Ex. 48 |
| 1885 | | 1H-NMR (CDCl3) δ: 1.41 (3H, t, J = 7.5 Hz), 3.36 (2H, q, J = 7.5 Hz), 7.72 (1H, dd, J = 1.5, 5.2 Hz), 7.87-7.88 (1H, m), 8.50-8.51 (1H, m), 10.22 (1H, s). | Ref. Ex. 48 |
| 1886 | | 1H-NMR (CDCl3) δ: 1.29-1.44 (3H, m), 1.56-1.76 (3H, m), 1.81-1.87 (2H, m), 2.05-2.14 (2H, m), 2.82-2.89 (1H, m), 8.17 (1H, s), 9.92 (1H, s). | Ref. Ex. 63 |
| 1887 | | 1H-NMR (CDCl3) δ: 1.23-1.26 (4H, m), 2.87-2.93 (1H, m), 4.00 (3H, s), 7.50-7.57 (2H, m), 7.63-7.67 (1H, m), 7.89 (1H, d, J = 8.4 Hz), 7.96 (1H, d, J = 8.2 Hz), 8.08 (1H, d, J = 7.2 Hz), 9.09 (1H, d, J = 8.7 Hz). | Ref. Ex. 133 |
| 1888 | | 1H-NMR (CDCl3) δ: 1.30-1.32 (4H, m), 2.77-2.83 (1H, m), 7.52-7.60 (2H, m), 7.65-7.69 (1H, m), 7.91 (1H, d, J = 8.4 Hz), 7.98 (1H, d, J = 8.2 Hz), 8.07-8.09 (1H, m), 9.26 (1H, d, J = 8.6 Hz), 10.15 (1H, s). | Ref. Ex. 63 |
| 1889 | | 1H-NMR (CDCl3) δ: 1.46 (6H, d, J = 6.0 Hz), 4.75-4.80 (1H, m), 7.15 (1H, d, J = 8.5 Hz), 7.77-7.79 (1H, m), 8.09 (2H, s), 8.85 (1H, s), 9.01 (1H, s), 10.54 (1H, s). | Ref. Ex. 112 |
| 1893 | | 1H-NMR (CDCl3) δ: 1.05-1.27 (4H, m), 2.39-2.44 (1H, m), 3.85 (3H, s), 3.87 (3H, s), 5.61 (1H, d, J = 6.4 Hz), 7.06-7.09 (1H, m), 7.34-7.42 (4H, m). | Ref. Ex. 1892 |

TABLE 2-continued

| Ref. Ex. No | STR | 1H-NMR | ref. |
|---|---|---|---|
| 1894 | | 1H-NMR (CDCl3) δ: 1.19-1.23 (4H, m), 2.81-2.87 (1H, m), 3.96 (3H, s), 7.31-7.40 (2H, m), 7.46-7.49 (1H, m), 7.98-8.01 (1H, m). | Ref. Ex. 133 |
| 1895 | | 1H-NMR (CDCl3) δ: 1.25-1.30 (4H, m), 2.72-2.77 (1H, m), 7.35-7.43 (2H, m), 7.49-7.51 (1H, m), 7.95-7.97 (1H, m), 10.08 (1H, s). | Ref. Ex. 63 |
| 1896 | | 1H-NMR (CDCl3) δ: 7.28 (1H, brs), 7.77 (1H, brs), 8.45-8.46 (1H, m), 8.99 (1H, d, J = 1.2 Hr), 9.19 (1H, d, J = 1.8 Hz). | Ref. Ex. 1477 |
| 1897 | | 1H-NMR (CDCl3) δ: 7.21 (1H, brs), 7.68 (1H, brs), 8.24 (1H, t, J = 2.2 Hz), 8.68 (1H, d, J = 2.2 Hz), 8.87 (1H, d, J = 2.2 Hz). | Ref. Ex. 1477 |
| 1898 | | 1H-NMR (CDCl3) δ: 7.50 (1H, dd, J = 0.8, 7.8 Hz), 7.66 (1H, brs), 7.81 (1H, t, J = 7.8 Hz), 8.62 (1H, dd, J = 0.8, 7.8 Hz), 9.34 (1H, brs). | Ref. Ex. 1477 |
| 1900 | | 1H-NMR (CDCl3) δ: 1.18-1.23 (4H, m), 2.81-2.87 (1H, m), 3.87 (3H, s), 3.97 (3H, s), 6.98-7.01 (1H, m), 7.34 (1H, t, J = 7.9 Hz), 7.52-7.58 (2H, m). | Ref. Ex. 1899 |
| 1901 | | 1H-NMR (CDCl3) δ: 1.24-1.29 (4H, m), 2.66-2.73 (1H, m), 3.88 (3H, s), 7.00-7.04 (1H, m), 7.37 (1H, t, J = 7.9 Hz), 7.52-7.56 (2H, m), 10.06 (1H, s). | Ref. Ex. 63 |
| 1902 | | 1H-NMR (CDCl3) δ: 1.23-1.32 (4H, m), 2.66-2.73 (1H, m), 7.42-7.60 (1H, m), 7.64-7.84 (2H, m), 10.04 (1H, s). | Ref. Ex. 63 |

TABLE 2-continued

| Ref. Ex. No | STR | 1H-NMR | ref. |
|---|---|---|---|
| 1903 | | 1H-NMR (CDCl3) δ: 1.90-2.21 (8H, m), 2.41 (3H, s), 4.57 (1H, s), 7.01 (1H, s), 7.21 (1H, s), 7.28 (1H, s), 9.93 (1H, s). | Ref. Ex. 80 |
| 1904 | | 1H-NMR (CDCl3) δ: 1.41 (3H, t, J = 7.5 Hz), 1.46 (3H, t, J = 7.1 Hz), 3.32 (2H, q, J = 7.5 Hz), 4.46 (2H, q, J = 7.1 Hz), 8.03 (1H, dd, J = 1.7, 8.3 Hz), 8.40 (1H, d, J = 8.3 Hz), 8.82-8.84 (1H, m). | Ref. Ex. 2 |
| 1905 | | 1H-NMR (CDCl3) δ: 1.10-1.30 (4H, m), 2.41-2.46 (1H, m), 3.89 (3H, s), 5.62 (1H, d, J = 6.3 Hz), 7.41 (1H, d, J = 6.5 Hz), 7.64 (1H, d, J = 8.5 Hz), 7.91 (1H, s), 7.97 (1H, d, J = 8.5 Hz), 8.17 (1H, s). | Ref. Ex. 1892 |
| 1906 | | 1H-NMR (CDCl3) δ: 2.33 (1H, t, J = 5.8 Hz), 2.51 (3H, s), 4.74 (2H, d, J = 5.6 Hz), 8.21 (1H, t, J = 2.1 Hz), 8.58 (1H, d, J = 2.1 Hz), 8.93 (1H, d, J = 2.1 Hz). | Ref. Ex. 318 |
| 1907 | | 1H-NMR (CDCl3) δ: 2.87 (3H, s), 4.00 (3H, s), 8.51 (1H, dd, J = 1.5, 1.9 Hz), 8.93 (1H, d, J = 1.5 Hz), 9.28 (1H, d, J = 1.9 Hz). | Ref. Ex. 2 |
| 1908 | | 1H-NMR (CDCl3) δ: 1.42 (3H, t, J = 7.5 Hz), 3.35 (2H, q, J = 7.5 Hz), 4.00 (3H, s), 8.51-8.52 (1H, m), 8.93 (1H, d, J = 1.2 Hz), 9.28 (1H, d, J = 19 Hz). | Ref. Ex. 2 |
| 1909 | | 1H-NMR (CDCl3) δ: 1.46 (6H, d, J = 6.1 Hz), 4.77-4.83 (1H, m), 7.14 (1H, d, J = 6.9 Hz), 7.87 (1H, d, J = 8.4 Hz), 7.93-7.98 (1H, m), 8.36-8.39 (1H, m), 8.44 (1H, d, J = 2.5 Hz), 8.90 (1H, s), 10.54 (1H, s). | Ref. Ex. 112 |

TABLE 2-continued

| Ref. Ex. No | STR | 1H-NMR | ref. |
|---|---|---|---|
| 1910 | | 1H-NMR (CDCl3) δ: 1.22-1.28 (4H, m), 2.84-2.90 (1H, m), 3.98 (3H, s), 7.60-7.64 (1H, m), 7.91-7.94 (2H, m), 8.15 (1H, s). | Ref. Ex. 1899 |
| 1911 | | 1H-NMR (CDCl3) δ: 1.28-1.34 (4H, m), 2.72-2.78 (1H, m), 7.62-7.65 (1H, m), 7.90 (1H, s), 7.94 (1H, d, J = 8.4 Hz), 8.16 (1H, s), 10.06 (1H, s). | Ref. Ex. 63 |
| 1912 | | 1H-NMR (CDCl3) δ: 2.85 (3H, s), 3.99 (3H, s), 8.31 (1H, t, J = 2.1 Hz), 8.62 (1H, d, J = 2.1 Hz), 8.94 (1H, d, J = 2.1 Hz). | Ref. Ex. 2 |
| 1913 | | 1H-NMR (CDCl3) δ: 1.41 (3H, t, J = 7.5 Hz), 3.34 (2H, q, J = 7.5 Hz), 3.99 (3H, s), 8.31 (1H, t, J = 2.1 Hz), 8.62 (1H, d, J = 2.1 Hz), 8.96 (1H, d, J = 2.1 Hz). | Ref. Ex. 2 |
| 1914 | | 1H-NMR (CDCl3) δ: 2.84 (3H, s), 3.97 (3H, s), 7.35 (1H, dd, J = 0.7, 7.8 Hz), 7.75 (1H, t, J = 7.8 Hz), 8.17 (1H, dd, J = 0.7, 7.8 Hz). | Ref. Ex. 2 |
| 1915 | | 1H-NMR (CDCl3) δ: 1.40 (3H, t, J = 7.5 Hz), 3.32 (2H, q, J = 7.5 Hz), 3.97 (3H, s), 7.35 (1H, dd, J = 0.7, 7.8 Hz), 7.75 (1H, t, J = 7.8 Hz), 8.17 (1H, dd, J = 0.7, 7.8 Hz). | Ref. Ex. 2 |
| 1916 | | 1H-NMR (CDCl3) δ: 1.44 (3H, t, J = 7.0 Hz), 1.90-2.20 (8H, m), 4.05-4.10 (2H, m), 4.53-4.57 (1H, m). 6.71 (1H, t, J = 2.3 Hz), 7.00 (1H, s), 7.01 (1H, s), 9.89 (1H, s). | Ref. Ex. 80 |
| 1917 | | 1H-NMR (CDCl3) δ: 2.88 (3H, s), 8.28 (1H, t, J = 1.9 Hz), 8.64 (1H, d, J = 1.9 Hz), 8.97 (1H, d, J = 1.9 Hz), 10.22 (1H, s). | Ref. Ex. 318 |
| 1918 | | 1H-NMR (CDCl3) δ: 1.35 (3H, t, J = 7.5 Hz), 2.47 (1H, brs), 2.91 (2H, q, J = 7.5 Hz), 4.74 (2H, s), 8.22 (1H, t, J = 2.1 Hz), 8.58 (1H, d, J = 2.1 Hz), 8.95 (1H, d, J = 2.1 Hz). | Ref. Ex. 318 |

TABLE 2-continued

| Ref. Ex. No | STR | 1H-NMR | ref. |
|---|---|---|---|
| 1919 | | 1H-NMR (CDCl3) δ: 1.41 (3H, t, J = 7.5 Hz), 3.35 (2H, q, J = 7.5 Hz), 8.29 (1H, t, J = 2.1 Hz), 8.64 (1H, d, J = 2.1 Hz), 8.98 (1H, d, J = 2.1 Hz), 10.22 (1H, s). | Ref. Ex. 318 |
| 1920 | | 1H-NMR (CDCl3) δ: 2.29 (1H, t, J = 5.8 Hz), 2.50 (3H, s), 4.73 (2H, d, J = 5.8 Hz), 7.31 (1H, dd, J = 0.8, 7.8 Hz), 7.72 (1H, t, J = 7.8 Hz), 8.04 (1H, dd, J = 0.8, 7.8 Hz). | Ref. Ex. 318 |
| 1921 | | 1H-NMR (CDCl3) δ: 2.86 (3H, s), 7.38 (1H, dd, J = 0.7, 7.8 Hz), 7.78 (1H, t, J = 7.8 Hz), 8.14 (1H, dd, J = 0.7, 7.8 Hz), 10.19 (1H, s). | Ref. Ex. 318 |
| 1922 | | 1H-NMR (CDCl3) δ: 1.34 (3H, t, J = 7.5 Hz), 2.33 (1H, t, J = 5.8 Hz), 2.89 (2H, q, J = 7.5 Hz), 4.73 (2H, d, J = 5.8 Hz), 7.31 (1H, dd, J = 0.7, 7.8 Hz), 7.72 (1H, t, J = 7.8 Hz), 8.05 (1H, dd, J = 0.7, 7.8 Hz). | Ref. Ex. 318 |
| 1923 | | 1H-NMR (CDCl3) δ: 1.40 (3H, t, J = 7.5 Hz), 3.33 (2H, q, J = 7.5 Hz), 7.38 (1H, dd, J = 0.6, 7.8 Hz), 7.78 (1H, t, J = 7.8 Hz), 6.14 (1H, dd, J = 0.6, 7.8 Hz), 10.19 (1H, s). | Ref. Ex. 318 |
| 1924 | | 1H-NMR (CDCl3) δ: 1.13-1.29 (4H, m), 2.79-2.85 (1H, m), 3.24 (2H, t, J = 8.7 Hz), 3.95 (3H, s), 4.64 (2H, t, J = 8.7 Hz), 6.81 (1H, d, J = 8.4 Hz), 7.74-7.77 (1H, m), 7.86 (1H, s). | Ref. Ex. 133 |
| 1925 | | 1H-NMR (CDCl3) δ: 1.22-1.26 (4H, m), 2.64-2.70 (1H, m), 3.26 (2H, t, J = 8.8 Hz), 4.65 (2H, t, J = 8.8 Hz), 6.83 (1H, d, J = 8.4 Hz), 7.74-7.76 (1H, m), 7.84 (1H, s), 10.03 (1H, s). | Ref. Ex. 63 |
| 1926 | | 1H-NMR (CDCl3) δ: 2.80 (3H, s), 3.86 (3H, s), 3.96 (3H, s), 6.94 (2H, d, J = 8.7 Hz), 7.86 (2H, d, J = 8.7 Hz). | Ref. Ex. 2 |
| 1927 | | 1H-NMR (CDCl3) δ: 1.37 (3H, t, J = 7.5 Hz), 3.29 (2H, q, J = 7.5 Hz), 3.86 (3H, s), 3.96 (3H, s), 6.92-6.96 (2H, m), 7.85-7.89 (2H, m). | Ref. Ex. 2 |

TABLE 2-continued

| Ref. Ex. No | STR | 1H-NMR | ref. |
|---|---|---|---|
| 1928 | | 1H-NMR (CDCl3) δ: 2.82 (3H, s), 3.87 (3H, s), 6.95-6.99 (2H, m), 7.84-7.88 (2H, m), 10.19 (1H, s). | Ref. Ex. 318 |
| 1929 | | 1H-NMR (CDCl3) δ: 1.38 (3H, t, J = 7.5 Hz), 3.30 (2H, q, J = 7.5 Hz), 3.87 (3H, s), 6.95-6.99 (2H, m), 7.85-7.89 (2H, m), 10.18 (1H, s). | Ref. Ex. 318 |
| 1930 | | 1H-NMR (DMSO-d6) δ: 7.85-7.90 (1H, m), 8.57-8.60 (2H, m), 9.87 (1H, brs), 10.17 (1H, brs). | Ref. Ex. 1477 |
| 1931 | | 1H-NMR (CDCl3) δ: 7.77 (1H, dd, J = 0.9, 5.0 Hz), 7.93 (1H, s), 8.95 (1H, d, J = 5.0 Hz). | Ref. Ex. 89 |
| 1932 | | 1H-NMR (CDCl3) δ: 2.04-2.14 (4H, m), 3.35-3.39 (4H, m), 4.00-4.07 (2H, m), 4.10-4.16 (2H, m), 5.77 (1H, s), 6.93-6.96 (1H, m), 6.99 (1H, d, J = 7.6 Hz), 7.06 (1H, s). 7.29 (1H, d, J = 7.9 Hz). | Ref. Ex. 114 |
| 1933 | | 1H-NMR (CDCl3) δ: 2.04-2.12 (4H, m), 3.36-3.40 (4H, m), 4.01-4.12 (4H, m), 5.73 (1H, s), 6.88 (1H, t, J = 2.1 Hz), 6.91 (1H, s), 6.96 (1H, s). | Ref. Ex. 114 |
| 1934 | | 1H-NMR (CDCl3) δ: 2.06-2.14 (4H, m), 3.43-3.47 (4H, m), 7.12-7.14 (1H, m), 7.28-7.31 (2H, m), 9.90 (1H, s). | Ref. Ex. 151 |
| 1935 | | 1H-NMR (CDCl3) δ: 1.92-2.23 (8H, m), 4.64 (1H, m), 7.01 (2H, d, J = 8.7 Hz), 7.84 (2H, d, J = 8.7 Hz), 9.89 (1H, s). | Ref. Ex. 80 |

TABLE 2-continued

| Ref. Ex. No | STR | 1H-NMR | ref. |
|---|---|---|---|
| 1936 | | 1H-NMR (CDCl3) δ: 2.06-2.16 (4H, m), 3.42-3.46 (4H, m), 7.19-7.22 (1H, m), 7.34-7.37 (1H, m), 7.41-7.46 (2H, m), 9.97 (1H, s). | Ref. Ex. 151 |
| 1937 | | 1H-NMR (CDCl3) δ: 2.83 (3H, s), 3.97 (3H, s), 7.48-7.53 (1H, m), 8.28 (1H, dd, J = 4.5, 8.8 Hz), 8.44 (1H, d, J = 2.8 Hz). | Ref. Ex. 2 |
| 1938 | | 1H-NMR (CDCl3) δ: 1.40 (3H, t, J = 7.6 Hz), 3.31 (2H, q, J = 7.6 Hz), 3.97 (3H, s), 7.47-7.54 (1H, m), 8.28 (1H, dd, J = 4.5, 8.8 Hz), 8.44 (1H, d, J = 2.8 Hz). | Ref. Ex. 2 |
| 1939 | | 1H-NMR (CDCl3) δ: 1.42 (9H, s), 6.97-6.99 (1H, m), 7.81 (1H, s), 7.84 (1H, s), 7.96 (1H, s), 7.99-8.05 (1H, m), 10.08 (1H, s). | Ref. Ex. 112 |
| 1940 | | 1H-NMR (CDCl3) δ: 2.86 (3H, s), 7.46-7.56 (1H, m), 8.25 (1H, dd, J = 4.5, 8.7 Hz), 8.46 (1H, d, J = 2.8 Hz), 10.19 (1H, s). | Ref. Ex. 318, Ref. Ex. 48 |
| 1941 | | 1H-NMR (CDCl3) δ: 1.40 (3H, t, J = 7.5 Hz), 3.33 (2H, q, J = 7.5 Hz), 7.49-7.56 (1H, m), 8.18-8.30 (1H, m), 8.46 (1H, d, J = 2.8 Hz), 10.18 (1H, s). | Ref. Ex. 318, Ref. Ex. 48 |
| 1942 | | 1H-NMR (CDCl3) δ: 1.70-1.80 (2H, m), 1.94-2.00 (2H, m), 2.10-2.20 (1H, m), 2.68-275 (2H, m), 3.75-3.81 (2H, m), 4.00-4.07 (2H, m), 4.10-4.16 (2H, m), 5.78 (1H, s), 6.94 (1H, d, J = 8.0 Hz), 6.99 (1H, d, J = 7.4 Hz), 7.06 (1H, s), 7.28 (1H, d, J = 8.0 Hz). | Ref. Ex. 114 |
| 1943 | | 1H-NMR (CDCl3) δ: 1.71-1.80 (2H, m), 1.98-2.03 (2H, m), 2.16-2.25 (1H, m), 2.75-2.82 (2H, m), 3.82-3.88 (2H, m), 7.19-7.22 (1H, m), 7.33-7.36 (1H, m), 7.40-7.45 (2H, m), 9.96 (1H, s). | Ref. Ex. 151 |

TABLE 2-continued
| Ref. Ex. No | STR | 1H-NMR | ref. |
|---|---|---|---|
| 1944 | 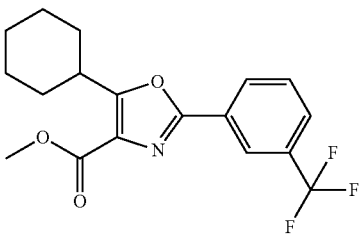 | 1H-NMR (CDCl3) δ: 1.27-1.98 (10H, m), 3.50-3.58 (1H, m), 3.97 (3H, s), 7.60 (1H, t, J = 7.8 Hz), 7.72 (1H, d, J = 7.8 Hz), 8.26 (1H, d, J = 7.8 Hz), 8.33 (1H, s). | Ref. Ex. 133 |
| 1945 | 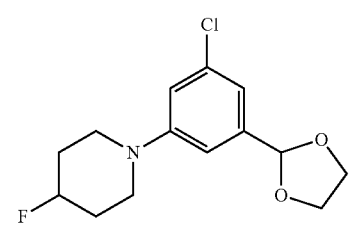 | 1H-NMR (CDCl3) δ: 1.92-2.05 (4H, m), 3.19-3.26 (2H, m), 3.35-3.42 (2H, m), 4.00-4.13 (4H, m), 4.75-4.90 (1H, m), 5.73 (1H, s), 6.86-6.94 (3H, m). | Ref. Ex. 114 |
| 1946 | 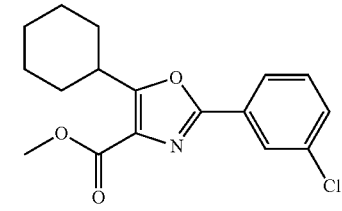 | 1H-NMR (CDCl3) δ: 1.27-1.99 (10H, m), 3.49-3.58 (1H, m), 3.95 (3H, s), 7.38-7.47 (2H, m), 7.95-7.98 (1H, m), 8.06-8.08 (1H, m). | Ref. Ex. 133 |
| 1947 | 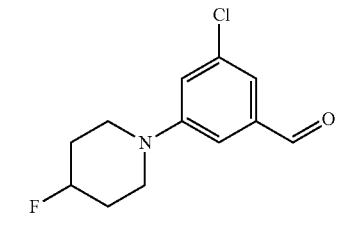 | 1H-NMR (CDCl3) δ: 1.95-2.05 (4H, m), 3.30-3.47 (4H, m), 4.81-4.92 (1H, m), 7.11-7.12 (1H, m), 7.27-7.28 (2H, m), 9.89 (1H, s). | Ref. Ex. 151 |
| 1948 | 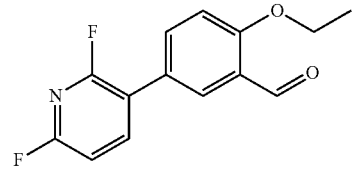 | 1H-NMR (CDCl3) δ: 1.53 (3H, t, J = 7.0 Hz), 4.23 (2H, q, J = 7.0 Hz), 6.92-6.94 (1H, m), 7.09 (1H, d, J = 8.8 Hz), 7.74-7.77 (1H, m), 7.95-8.01 (2H, m), 10.54 (1H, s). | Ref. Ex. 112 |
| 1949 | 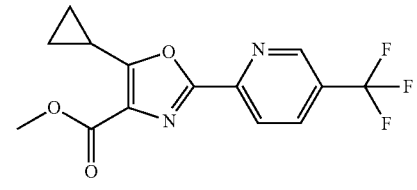 | 1H-NMR (CDCl3) δ: 1.23-1.35 (4H, m), 2.83-2.91 (1H, m), 3.98 (3H, s), 8.02-8.06 (1H, m), 8.29-8.33 (1H, m), 8.95 (1H, s). | Ref. Ex. 133 |
| 1950 | 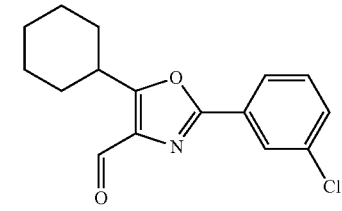 | 1H-NMR (CDCl3) δ: 1.33-1.50 (4H, m), 1.65-2.04 (6H, m), 3.34-3.39 (1H, m), 7.41-7.47 (2H, m), 7.95-7.97 (1H, m), 8.04-8.05 (1H, m), 10.04 (1H, s). | Ref. Ex. 63 |

TABLE 2-continued

| Ref. Ex. No | STR | 1H-NMR | ref. |
| --- | --- | --- | --- |
| 1951 | | 1H-NMR (CDCl3) δ: 1.31-1.99 (10H, m), 3.35-3.41 (1H, m), 7.63 (1H, t, J = 7.8 Hz), 7.74 (1H, d, J = 7.8 Hz), 8.26 (1H, d, J = 7.8 Hz), 8.31 (1H, s), 10.05 (1H, s). | Ref. Ex. 63 |
| 1953 | | 1H-NMR (CDCl3) δ: 1.72-1.94 (6H, m), 2.07-2.15 (2H, m), 3.92-4.00 (1H, m), 3.95 (3H, s), 7.36-7.47 (2H, m), 7.94-7.97 (1H, m), 8.05-8.07 (1H, m). | Ref. Ex. 133 |
| 1954 | | 1H-NMR (CDCl3) δ: 1.73-1.96 (6H, m), 2.08-2.16 (2H, m), 3.91-3.98 (1H, m), 3.96 (3H, s), 7.60 (1H, t, J = 7.7 Hz), 7.72 (1H, d, J = 7.7 Hz), 8.25 (1H, d, J = 7.7 Hz), 8.32 (1H, s). | Ref. Ex. 133 |
| 1955 | | 1H-NMR (CDCl3) δ: 1.85-2.52 (6H, m), 3.95 (3H, s), 4.30-4.38 (1H, m), 7.59-7.64 (1H, m), 7.74 (1H, d, J = 7.3 Hz), 8.30 (1H, d, J = 7.5 Hz), 8.37 (1H, s). | Ref. Ex. 133 |
| 1956 | | 1H-NMR (CDCl3) δ: 1.97-2.17 (2H, m), 2.37-2.50 (4H, m), 3.94 (3H, s), 4.29-4.37 (1H, m), 7.39-7.47 (2H, m), 7.99-8.02 (1H, m), 8.10-8.12 (1H, m). | Ref. Ex. 133 |
| 1957 | | 1H-NMR (CDCl3) δ: 1.76-2.00 (6H, m), 2.11-2.18 (2H, m), 3.75-3.81 (1H, m), 7.40-7.47 (2H, m), 7.94-7.96 (1H, m), 8.04-8.05 (1H, m), 10.03 (1H, s). | Ref. Ex. 63 |
| 1958 | | 1H-NMR (CDCl3) δ: 1.76-1.98 (6H, m), 2.12-2.20 (2H, m), 3.77-3.82 (1H, m), 7.63 (1H, t, J = 7.9 Hz), 7.75 (1H, d, J = 7.9 Hz), 8.25 (1H, d, J = 7.9 Hz), 8.31 (1H, s), 10.05 (1H, s). | Ref. Ex. 63 |

TABLE 2-continued

| Ref. Ex. No | STR | 1H-NMR | ref. |
|---|---|---|---|
| 1959 | | 1H-NMR (CDCl3) δ: 2.02-2.23 (2H, m), 2.40-2.56 (4H, m), 4.16-4.24 (1H, m), 7.64 (1H, t, J = 7.8 Hz), 7.76 (1H, d, J = 7.8 Hz), 8.29 (1H, d, J = 7.8 Hz), 8.35 (1H, s), 10.01 (1H, s). | Ref. Ex. 63 |
| 1960 | | 1H-NMR (CDCl3) δ: 2.00-2.22 (2H, m), 2.40-2.56 (4H, m), 4.17-4.26 (1H, m), 7.42-7.53 (2H, m), 7.98-8.03 (1H, m), 8.08-8.13 (1H, m), 9.99 (1H, s). | Ref. Ex. 63 |
| 1961 | | 1H-NMR (CDCl3) δ: 2.84 (3H, s), 3.98 (3H, s), 7.68 (2H, d, J = 8.2 Hz), 8.04 (2H, d, J = 8.2 Hz). | Ref. Ex. 2 |
| 1962 | | 1H-NMR (CDCl3) δ: 2.84 (3H, s), 3.98 (3H, s), 7.57 (1H, t, J = 7.8 Hz), 7.68 (1H, d, J = 7.8 Hz), 8.09 (1H, d, J = 7.8 Hz), 8.19 (1H, s). | Ref. Ex. 2 |
| 1963 | | 1H-NMR (CDCl3) δ: 1.98-2.20 (2H, m), 2.37-2.50 (4H, m), 3.94 (3H, s), 4.28-4.36 (1H, m), 7.22-7.25 (1H, m), 7.98-8.02 (1H, m), 8.17-8.20 (1H, m). | Ref. Ex. 133 |
| 1964 | | 1H-NMR (CDCl3) δ: 1.73-1.93 (6H, m), 2.07-2.15 (2H, m), 3.89-3.97 (1H, m), 3.95 (3H, s), 7.21-7.25 (1H, m), 7.93-7.97 (1H, m), 8.13 (1H, dd, J = 2.1, 7.0 Hz). | Ref. Ex. 133 |
| 1965 | | 1H-NMR (CDCl3) δ: 1.75-1.96 (6H, m), 2.11-2.17 (2H, m), 3.73-3.80 (1H, m), 7.24-7.27 (1H, m), 7.93-7.97 (1H, m), 8.11-8.12 (1H, m), 10.02 (1H, s). | Ref. Ex. 63 |
| 1966 | | 1H-NMR (CDCl3) δ: 2.00-2.21 (2H, m), 2.42-2.51 (4H, m), 4.14-4.22 (1H, m), 7.25-7.29 (1H, m), 7.98-8.01 (1H, m), 8.16-8.17 (1H, m), 9.98 (1H, s). | Ref. Ex. 63 |

TABLE 2-continued

| Ref. Ex. No | STR | 1H-NMR | ref. |
|---|---|---|---|
| 1967 | | 1H-NMR (CDCl3) δ: 1.24-1.69 (5H, m), 1.75-1.97 (5H, m), 3.48-3.55 (1H, m), 3.95 (3H, s), 7.21-7.24 (1H, m), 7.95-7.98 (1H, m), 8.14 (1H, dd, J = 2.2, 6.9 Hz). | Ref. Ex. 133 |
| 1968 | | 1H-NMR (CDCl3) δ: 1.25-1.49 (4H, m), 1.64-1.98 (6H, m), 3.32-3.38 (1H, m), 7.22-7.27 (1H, m), 7.94-7.98 (1H, m), 8.11-8.13 (1H, m), 10.03 (1H, s). | Ref. Ex. 63 |
| 1969 | | 1H-NMR (CDCl3) δ: 1.33 (12H, s), 1.69-1.80 (1H, m), 1.88-1.96 (1H, m), 2.18-2.32 (2H, m), 2.47-2.56 (2H, m), 4.76-4.82 (1H, m), 6.80 (1H, d, J = 8.4 Hz), 7.91 (1H, dd, J = 1.7, 8.4 Hz), 8.29 (1H, d, J = 1.7 Hz), 10.48 (1H, s). | Ref. Ex. 81 |
| 1970 | | 1H-NMR (CDCl3) δ: 1.73-1.83 (1H, m), 1.80-2.00 (1H, m), 2.25-2.35 (2H, m), 2.52-2.60 (2H, m), 4.83-4.90 (1H, m), 6.95 (1H, d, J = 8.8 Hz), 7.47 (1H, d, J = 4.9 Hz), 8.67 (1H, dd, J = 2.4, 8.8 Hz), 8.98 (1H, d, J = 2.4 Hz), 9.01 (1H, d, J = 4.9 Hz), 10.54 (1H, s). | Ref. Ex. 112 |
| 1971 | | 1H-NMR (CDCl3) δ: 1.75-1.83 (1H, m), 1.93-1.99 (1H, m), 2.25-2.34 (2H, m), 2.51-2.60 (2H, m), 4.82-4.89 (1H, m), 6.97 (1H, d, J = 8.8 Hz), 7.86 (1H, d, J = 8.2 Hz), 7.96-7.98 (1H, m), 8.34-8.36 (1H, m), 8.44 (1H, d, J = 2.4 Hz), 8.91 (1H, s), 10.54 (1H, s). | Ref. Ex. 112 |

TABLE 2-continued

| Ref. Ex. No | STR | 1H-NMR | ref. |
|---|---|---|---|
| 1972 | 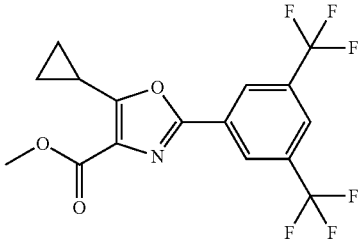 | 1H-NMR (CDCl3) δ: 1.24-1.31 (4H, m), 2.85-2.90 (1H, m), 3.99 (3H, s), 7.94 (1H, s), 8.42 (2H, s). | Ref. Ex. 133 |
| 1973 | 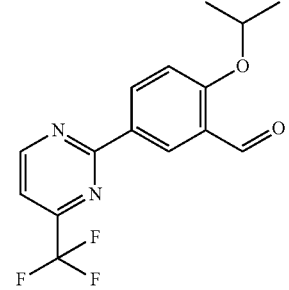 | 1H-NMR (CDCl3) δ: 1.46 (6H, d, J = 6.1 Hz), 4.79-484 (1H, m), 7.11 (1H, d, J = 9.0 Hz), 7.47 (1H, d, J = 4.9 Hz), 8.67-8.70 (1H, m), 8.98 (1H, d, J = 2.3 Hz), 9.01 (1H, d, J = 4.9 Hz), 10.54 (1H, s). | Ref. Ex. 112 |
| 1974 | 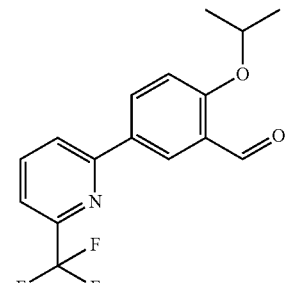 | 1H-NMR (CDCl3) δ: 1.45 (6H, d, J = 6.1 Hz), 4.76-4.81 (1H, m), 7.13 (1H, d, J = 8.8 Hz), 7.58 (1H, d, J = 7.4 Hz), 7.83-7.96 (1H, m), 8.41-8.45 (2H, m), 10.54 (1H, s). | Ref. Ex. 112 |
| 1975 | 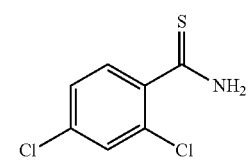 | 1H-NMR (CDCl3) δ: 7.22 (1H, brs), 7.29 (1H, dd, J = 2.0, 8.4 Hz), 7.40 (1H, d, J = 2.0 Hz), 7.67 (1H, d, J = 8.4 Hz), 8.00 (1H, brs). | Ref. Ex. 1477 |
| 1976 | 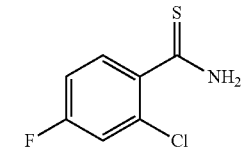 | 1H-NMR (CDCl3) δ: 6.95-7.09 (1H, m), 7.12 (1H, dd, J = 2.5, 8.5 Hz), 7.27 (1H, brs), 7.76 (1H, dd, J = 6.0, 8.5 Hz), 8.09 (1H, brs). | Ref. Ex. 1477 |
| 1977 | 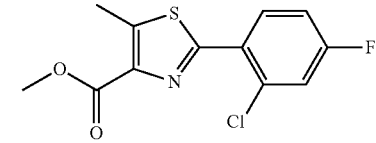 | 1H-NMR (CDCl3) δ: 2.83 (3H, s), 3.97 (3H, s), 7.02-7.12 (1H, m), 7.23 (1H, dd, J = 2.6, 8.6 Hz), 8.20 (1H, dd, J = 6.1, 8.6 Hz). | Ref. Ex. 2 |
| 1978 | 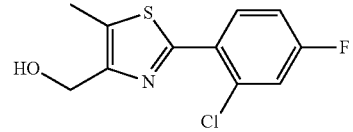 | 1H-NMR (CDCl3) δ: 2.40 (1H, t, J = 5.8 Hz), 2.50 (3H, s), 4.74 (2H, d, J = 5.8 Hz), 7.08-7.11 (1H, m), 7.23 (1H, dd. J = 2.6, 8.7 Hz), 8.17 (1H, dd, J = 6.2, 8.7 Hz). | Ref. Ex. 19 |

TABLE 2-continued

| Ref. Ex. No | STR | 1H-NMR | ref. |
|---|---|---|---|
| 1979 | | 1H-NMR (CDCl3) δ: 1.31-1.36 (4H, m), 2.71-2.77 (1H, m), 7.97 (1H, s), 8.41 (2H, s), 10.07 (1H, s). | Ref. Ex. 63 |
| 1980 | | 1H-NMR (CDCl3) δ: 1.72-1.93 (6H, m), 2.07-2.14 (2H, m), 3.89-3.94 (1H, m), 3.95 (3H, s), 7.22-7.28 (1H, m), 7.80-7.84 (1H, m), 7.86-7.91(1H, m). | Ref. Ex. 133 |
| 1981 | | 1H-NMR (CDCl3) δ: 2.86 (3H, s), 7.11-7.16 (1H, m), 7.24-7.31 (1H, m), 8.26 (1H, dd, J = 8.1, 8.9 Hz), 10.23 (1H, s). | Ref. Ex. 48 |
| 1982 | | 1H-NMR (CDCl3) δ: 1.99-2.20 (2H, m), 2.41-2.50 (4H, m), 3.96 (3H, s), 4.31-4.39 (1H, m), 7.81 (1H, d, J = 8.2 Hz), 8.55-8.59 (1H, m), 9.40-9.42 (1H, m). | Ref. Ex. 133 |
| 1983 | | 1H-NMR (CDCl3) δ: 2.83 (3H, s), 3.97 (3H, s), 7.35 (1H, dd, J = 2.1, 8.6 Hz), 7.50 (1H, d, J = 2.1 Hz), 8.19 (1H, d, J = 8.8 Hz). | Ref. Ex. 2 |
| 1984 | | 1H-NMR (CDCl3) δ: 1.40 (3H, t, J = 7.5 Hz), 3.33 (2H, q, J = 7.5 Hz), 3.97 (3H, s), 7.06-7.15 (1H, m), 7.23 (1H, dd, J = 2.6, 8.6 Hz), 8.20 (1H, dd, J = 6.1, 8.6 Hz). | Ref. Ex. 2 |
| 1985 | | 1H-NMR (CDCl3) δ: 3.99 (3H, s), 7.10-7.18 (1H, m), 7.24-7.30 (1H, m), 8.26-8.37 (2H, m). | Ref. Ex. 2 |
| 1986 | | 1H-NMR (CDCl3) δ: 2.02-2.24 (3H, m), 2.44-2.53 (5H, m), 4.18-4.25 (1H, m), 7.82 (1H, d, J = 8.2 Hz), 8.53-8.56 (1H, m), 9.41 (1H, s), 10.02 (1H, s). | Ref. Ex. 63 |

TABLE 2-continued

| Ref. Ex. No | STR | 1H-NMR | ref. |
|---|---|---|---|
| 1987 | | 1H-NMR (CDCl3) δ: 2.02-2.10 (1H, m), 2.13-2.23 (1H, m), 2.45-2.53 (4H, m), 4.18-4.26 (1H, m), 7.83 (1H, d, J = 8.2 Hz), 8.53-8.56 (1H, m), 9.41 (1H, s), 10.02 (1H, s). | Ref. Ex. 63 |
| 1988 | | 1H-NMR (CDCl3) δ: 1.09-1.15 (2H, m), 1.20-1.24 (2H, m), 3.01-3.07 (1H, m), 3.91 (3H, s), 7.20 (1H, t, J = 8.6 Hz), 7.77 (1H, ddd, J = 2.2, 4.5, 8.6 Hz), 8.00 (1H, dd, J = 2.2, 7.0 Hz). | Ref. Ex. 1863 |
| 1989 | | 1H-NMR (CDCl3) δ: 2.44 (1H, t, J = 5.8 Hz), 2.50 (3H, s), 4.74 (2H, d, J = 5.8 Hz), 7.34 (1H, dd, J = 2.1, 8.6 Hz), 7.50 (1H, d, J = 2.1 Hz), 8.16 (1H, d, J = 8.6 Hz). | Ref. Ex. 19 |
| 1990 | | 1H-NMR (CDCl3) δ: 2.32 (1H, t, J = 6.0 Hz), 4.86 (2H, d, J = 6.0 Hz), 7.05-7.13 (1H, m), 7.24-7.30 (1H, m), 7.34 (1H, s), 8.22 (1H, dd, J = 6.2, 8.9 Hz). | Ref. Ex. 19 |
| 1991 | | 1H-NMR (CDCl3) δ: 1.35 (3H, t, J = 7.5 Hz), 2.45 (1H, t, J = 5.8 Hz), 2.90 (2H, q, J = 7.5 Hz), 4.74 (2H, d, J = 5.8 Hz), 7.03-7.13 (1H, m), 7.23 (1H, dd, J = 2.6, 8.7 Hz), 8.17 (1H, dd, J = 6.2, 8.7 Hz). | Ref. Ex. 19 |
| 1992 | | 1H-NMR (CDCl3) δ: 1.01 (6H, d, J = 6.7 Hz), 2.11-2.20 (1H, m), 3.01 (2H, d, J = 7.2 Hz), 3.95 (3H, s), 7.38-7.47 (2H, m), 7.95-7.98 (1H, m), 8.07-8.09 (1H, m). | Ref. Ex. 133 |
| 1993 | | 1H-NMR (CDCl3) δ: 1.01 (6H, d, J = 6.5 Hz), 2.12-2.18 (1H, m), 3.00 (2H, d, J = 7.0 Hz), 3.94 (3H, s), 7.23 (1H, t, J = 8.5 Hz), 7.95-7.98 (1H, m), 8.14-8.16 (1H, m). | Ref. Ex. 133 |
| 1994 | | 1H-NMR (CDCl3) δ: 2.86 (3H, s), 7.39 (1H, dd, J = 2.1, 8.6 Hz), 7.53 (1H, d, J = 2.1 Hz); 8.24 (1H, d, J = 8.6 Hz), 10.23 (1H, s). | Ref. Ex. 48 |
| 1995 | | 1H-NMR (CDCl3) δ: 7.13-7.18 (1H, m), 7.28 (1H, dd, J = 2.6, 8.3 Hz), 8.30 (1H, s), 8.35 (1H, dd, J = 6.1, 8.9 Hz), 10.14 (1H, s). | Ref. Ex. 48 |

TABLE 2-continued
| Ref. Ex. No | STR | 1H-NMR | ref. |
|---|---|---|---|
| 1996 | 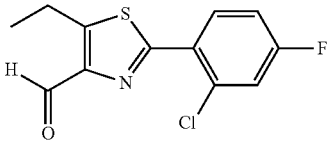 | 1H-NMR (CDCl3) δ: 1.41 (3H, t, J = 7.5 Hz), 3.34 (2H, q, J = 7.5 Hz), 7.07-7.16 (1H, m), 7.21-7.30 (1H, m), 8.26 (1H, dd, J = 6.1, 8.9 Hz), 10.23 (1H, s). | Ref. Ex. 48 |
| 1998 | 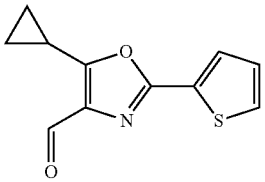 | 1H-NMR (CDCl3) δ: 1.22-1.28 (4H, m), 2.66-2.72 (1H, m), 7.10-7.13 (1H, m), 7.45-7.47 (1H, m), 7.63-7.65 (1H, m), 10.02 (1H, s). | Ref. Ex. 133, Ref. Ex. 63 |
| 1999 | 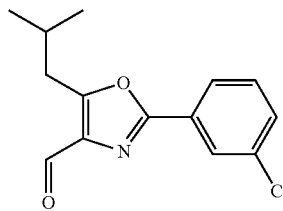 | 1H-NMR (CDCl3) δ: 1.02 (6H, d, J = 6.5 Hz), 2.12-2.32 (1H, m), 2.98 (2H, d, J = 6.0 Hz), 7.41-7.48 (2H, m), 7.96 (1H, d, J = 7.0 Hz), 8.06 (1H, s), 10.02 (1H, s). | Ref. Ex. 63 |
| 2000 | 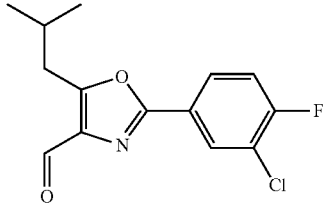 | 1H-NMR (CDCl3) δ: 1.02 (6H, d, J = 6.5 Hz), 2.13-2.19 (1H, m), 2.97 (2H, d, J = 7.0 Hz), 7.22-7.28 (1H, m), 7.94-7.98 (1H, m), 8.12-8.14 (1H, m), 10.00 (1H, s). | Ref. Ex. 63 |
| 2001 | 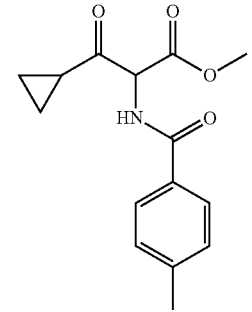 | 1H-NMR (CDCl3) δ: 1.05-1.27 (4H, m), 2.39-2.44 (1H, m), 2.41 (3H, s), 3.86 (3H, s), 5.62 (1H, d, J = 6.4 Hz), 7.24-7.27 (2H, m), 7.32-7.36 (1H, m), 7.74-7.76 (2H, m). | Ref. Ex. 1892 |
| 2002 | 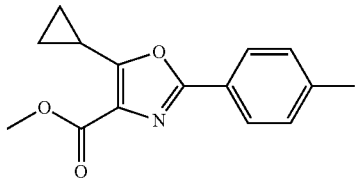 | 1H-NMR (CDCl3) δ: 1.17-1.22 (4H, m), 2.39 (3H, s), 2.80-2.87 (1H, m), 3.96 (3H, s), 7.24 (2H, d, J = 8.2 Hz), 7.88 (2H, d, J = 8.2 Hz). | Ref. Ex. 1899 |
| 2003 | 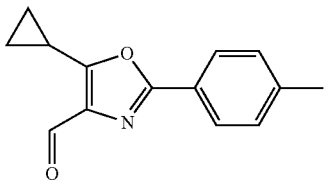 | 1H-NMR (CDCl3) δ: 1.25-1.27 (4H, m), 2.41 (3H, s), 2.66-2.72 (1H, m), 7.25-7.28 (2H, m), 7.85-7.88 (2H, m), 10.05 (1H, s). | Ref. Ex. 63 |

TABLE 2-continued

| Ref. Ex. No | STR | 1H-NMR | ref. |
|---|---|---|---|
| 2004 | | 1H-NMR (CDCl3) δ: 7.15 (1H, dd, J = 2.0, 12.1 Hz), 7.22-7.25 (1H, m), 7.71 (1H, bis), 7.93 (1H, brs), 8.35 (1H, t, J = 8.9 Hz). | Ref. Ex. 1477 |
| 2005 | | 1H-NMR (CDCl3) δ: 1.02 (6H, d, J = 6.7 Hz), 2.13-2.22 (1H, m), 3.03 (2H, d, J = 7.2 Hz), 3.98 (3H, s), 7.60 (1H, t, J = 7.8 Hz), 7.73 (1H, d, J = 7.8 Hz), 7.26 (1H, d, J = 7.8 Hz), 8.34 (1H, s). | Ref. Ex. 133 |
| 2006 | | 1H-NMR (CDCl3) δ: 7.13 (1H, brs), 7.22-7.25 (1H, m), 7.46-7.52 (1H, m), 7.60-7.61 (1H, m), 7.66 (1H, brs). | Ref. Ex. 1477 |
| 2007 | | 1H-NMR (CDCl3) δ: 3.99 (3H, s), 7.23-7.31 (2H, m), 8.30 (1H, s), 8.34-8.40 (1H, m). | Ref. Ex. 2 |
| 2008 | | 1H-NMR (CDCl3) δ: 1.47 (3H, t, J = 7.1 Hz), 4.50 (2H, q, J = 7.1 Hz), 6.62-6.63 (1H, m), 7.43 (1H, t, J = 7.8 Hz), 7.46-7.48 (1H, m), 7.64-7.66 (1H, m), 7.68-7.70 (1H, m), 8.05-8.07 (1H, m), 8.18 (1H, t, J = 1.6 Hz). | Ref. Ex. 133 |
| 2009 | | 1H-NMR (CDCl3) δ: 1.00-1.06 (6H, m), 2.13-2.22 (1H, m), 3.00 (2H, d. J = 7.0 Hz), 7.61-7.65 (1H, m), 7.75 (1H, d, J = 8.1 Hz), 8.26 (1H, d, J = 8.1 Hz), 8.33 (1H, s), 10.03 (1H, s). | Ref. Ex. 63 |
| 2010 | | 1H-NMR (CDCl3) δ: 2.83 (3H, s), 3.98 (3H, s), 7.21-7.29 (2H, m), 8.27 (1H, t, J = 8.3 Hz). | Ref. Ex. 2 |
| 2011 | | 1H-NMR (CDCl3) δ: 1.39 (3H, t, J = 7.5 Hz), 3.32 (2H, q, J = 7.5 Hz), 3.97 (3H, s), 7.20-7.26 (2H, m), 8.27 (1H, t, J = 8.4 Hz). | Ref. Ex. 2 |

TABLE 2-continued

| Ref. Ex. No | STR | 1H-NMR | ref. |
|---|---|---|---|
| 2012 |  | 1H-NMR (CDCl3) δ: 3.99 (3H, s), 7.18-7.23 (1H, m), 7.60-7.65 (1H, m), 7.81 (1H, t, J = 1.6 Hz), 8.24 (1H, s). | Ref. Ex. 2 |
| 2013 | 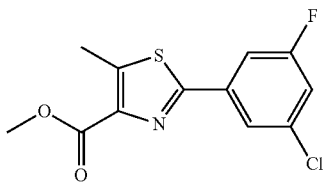 | 1H-NMR (CDCl3) δ: 2.83 (3H, s), 3.97 (3H, s), 7.14-7.17 (1H, m), 7.53-7.56 (1H, m), 7.72 (1H, t, J = 1.6 Hz). | Ref. Ex. 2 |
| 2014 | 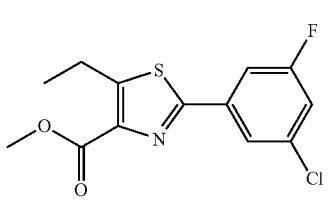 | 1H-NMR (CDCl3) δ: 1.39 (3H, t, J = 7.5 Hz), 3.32 (2H, q, J = 7.5 Hz), 3.97 (3H, s), 7.12-7.18 (1H, m), 7.54-7.57 (1H, m), 7.73-7.74 (1H, m). | Ref. Ex. 2 |
| 2015 | 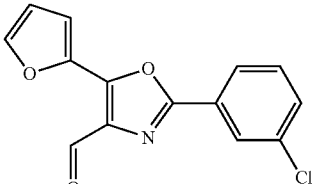 | 1H-NMR (CDCl3) δ: 6.66-6.67 (1H, m), 7.45 (1H, t, J = 7.8 Hz), 7.49-7.51 (1H, m), 7.57-7.58 (1H, m), 7.69-7.71 (1H, m), 8.04-8.07 (1H, m), 8.16 (1H, t, J = 1.7 Hz), 10.27 (1H, s). | Ref. Ex. 63 |
| 2016 | 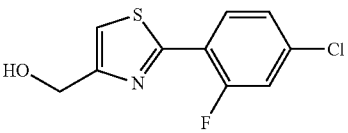 | 1H-NMR (CDCl3) δ: 2.36 (1H, t, J = 5.7 Hz), 4.86 (2H, d, J = 5.7 Hz), 7.23-7.26 (2H, m), 7.33 (1H, s), 8.23 (1H, t, J = 8.4 Hz). | Ref. Ex. 19 |
| 2017 | 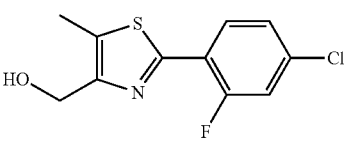 | 1H-NMR (CDCl3) δ: 2.45 (1H, t, J = 5.7 Hz), 2.49 (3H, s), 4.74 (2H, d, J = 5.7 Hz), 7.18-7.25 (2H, m), 8.19 (1H, t, J = 7.1 Hz). | Ref. Ex. 19 |
| 2018 | 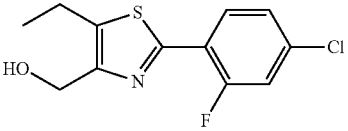 | 1H-NMR (CDCl3) δ: 1.34 (3H, t, J = 7.5 Hz), 2.44 (1H, t, J = 5.7 Hz), 2.89 (2H, q, J = 7.5 Hz), 4.74 (2H, d, J = 5.7 Hz), 7.17-7.25 (2H, m), 8.19 (1H, t, J = 8.4 Hz). | Ref. Ex. 19 |
| 2019 | 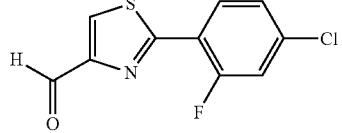 | 1H-NMR (CDCl3) δ: 7.28-7.36 (2H, m), 8.30 (1H, s), 8.35 (1H, t, J = 8.3 Hz), 10.13 (1H, s). | Ref. Ex. 48 |
| 2020 | 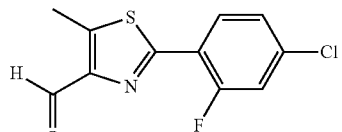 | 1H-NMR (CDCl3) δ: 2.85 (3H, s), 7.22-7.30 (2H, m), 8.27 (1H, t, J = 8.8 Hz), 10.23 (1H, s). | Ref. Ex. 48 |

TABLE 2-continued

| Ref. Ex. No | STR | 1H-NMR | ref. |
|---|---|---|---|
| 2021 | | 1H-NMR (CDCl3) δ: 1.40 (3H, t, J = 7.5 Hz), 3.33 (2H, q, J = 7.5 Hz), 7.18-7.34 (2H, m), 8.27 (1H, t, J = 8.3 Hz), 10.22 (1H, s). | Ref. Ex. 48 |
| 2022 | | 1H-NMR (CDCl3) δ: 2.38 (1H, t, J = 5.7 Hz), 4.84 (2H, d, J = 5.7 Hz), 7.11-7.19 (1H, m), 7 26-7.34 (1H, m), 7.55-7.61 (1H, m), 7.73-7.74 (1H, m). | Ref. Ex. 19 |
| 2023 | | 1H-NMR (CDCl3) δ: 2.36 (1H, 1, J = 5.9 Hz), 2.49 (3H, s), 4.72 (2H, d, J = 5.9 Hz), 7.10-7.15 (1H, m), 7.48-7.52 (1H, m), 7.67-7.69 (1H, m). | Ref. Ex. 19 |
| 2024 | | 1H-NMR (CDCl3) δ: 1.33 (3H, t, J = 7.5 Hz), 2.41 (1H, brs), 2.88 (2H, q, J = 7.5 Hz), 4.72 (2H, s), 7.10-7.13 (1H, m), 7.49-7.56 (1H, m), 7.68-7.69 (1H, m). | Ref. Ex. 19 |
| 2025 | | 1H-NMR (CDCl3) δ: 6.93-7.00 (1H, m), 7.14 (1H, brs), 7.35-7.41 (2H, m), 7.70 (1H, brs). | Ref. Ex. 1477 |
| 2026 | | 1H-NMR (CDCl3) δ: 7.00 (1H, brs), 7.15 (1H, t, J = 8.3 Hz), 7.64 (1H, brs), 7.80-7.84 (1H, m), 8.12 (1H, dd, J = 2.4, 6.4 Hz). | Ref. Ex. 1477 |
| 2027 | | 1H-NMR (CDCl3) δ: 1.31-1.39 (4H, m), 2.74-2.80 (1H, m), 8.06-8.08 (1H, m), 8.23 (1H, d, J = 8.5 Hz), 8.97 (1H, s), 10.09 (1H, s). | Ref. Ex. 318, Ref. Ex. 48 |
| 2028 | | 1H-NMR (CDCl3) δ: 7.20-7.23 (1H, m), 7.63-7.66 (1H, m), 7.81-7.83 (1H, m), 8.23 (1H, s), 10.10 (1H, s). | Ref. Ex. 48 |

TABLE 2-continued

| Ref. Ex. No | STR | 1H-NMR | ref. |
|---|---|---|---|
| 2029 | | 1H-NMR (CDCl3) δ: 2.66 (3H, s), 7.12-7.21 (1H, m), 7.54-7.57 (1H, m), 7.67-7.72 (1H, m), 10.20 (1H, s). | Ref. Ex. 48 |
| 2030 | | 1H-NMR (CDCl3) δ: 1.39 (3H, t, J = 7.5 Hz), 3.28 (2H, q, J = 7.5 Hz), 7.16-7.19 (1H, m), 7.55-7.61 (1H, m), 7.72-7.73 (1H, m), 10.19 (1H, s). | Ref. Ex. 48 |
| 2031 | | 1H-NMR (CDCl3) δ: 2.74 (3H, s), 3.97 (3H, s), 7.60 (1H, t, J = 7.8 Hz), 7.72 (1H, d, J = 7.8 Hz), 8.26 (1H, d, J = 7.8 Hz), 8.35 (1H, s). | Ref. Ex. 133 |
| 2032 | | 1H-NMR (CDCl3) δ: 2.74 (3H, s), 7.63 (1H, t, J = 7.8 Hr), 7.75 (1H, d, J = 7.9 Hz), 8.25 (1H, d, J = 7.8 Hz), 8.33 (1H, s), 10.00 (1H, s). | Ref. Ex. 63 |
| 2033 | | 1H-NMR (CDCl3) δ: 2.72 (3H, s), 3.96 (3H, s), 7.39 (1H, t, J = 7.8 Hz), 7.44 (1H, dt, J = 1.5, 8.0 Hz), 7.96 (1H, dt, J = 1.3, 7.6 Hz), 8.08 (1H, t, J = 1.7 Hz). | Ref. Ex. 133 |
| 2034 | | 1H-NMR (CDCl3) δ: 1.37 (3H, t, J = 7.6 Hz), 1.43 (3H, t, J = 7.1 Hz), 3.16 (2H, q, J = 7.6 Hz), 4.44 (2H, q, J = 7.1 Hz), 7.60 (1H, t, J = 8.0 Hz), 7.72 (1H, d, J = 8.0 Hz), 8.27 (1H, d, J = 8.0 Hz), 8.35 (1H, s). | Ref. Ex. 133 |
| 2035 | | 1H-NMR (CDCl3) δ: 1.57 (3H, t, J = 7.6 Hz), 3.15 (2H, q, J = 7.6 Hz), 7.63 (1H, t, J = 7.8 Hz), 7.75 (1H, d, J = 7.7 Hz), 8.26 (1H, d, J = 7.8 Hz), 8.33 (1H, s), 10.05 (1H, s). | Ref. Ex. 63 |

TABLE 2-continued

| Ref. Ex. No | STR | 1H-NMR | ref. |
|---|---|---|---|
| 2036 | | 1H-NMR (CDCl3) δ: 0.98-1.07 (4H, m), 1.96-2.00 (1H, m), 2.24 (1H, bs), 4.66 (2H, s), 7.26-7.28 (2H, m), 7.97-7.99 (2H, m). | Ref. Ex. 19 |
| 2037 | | 1H-NMR (CDCl3) δ: 1.01-1.05 (4H, m), 1.96-2.05 (1H, m), 2.13-2.16 (1H, m), 4.68 (2H, s), 7.33-7.40 (2H, m), 7.43-7.45 (1H, m), 8.08-8.11 (1H, m). | Ref. Ex. 19 |
| 2038 | | 1H-NMR (CDCl3) δ: 1.23-1.32 (4H, m), 2.67-2.74 (1H, m), 7.30-7.32 (2H, m), 8.01-8.03 (2H, m), 10.05 (1H, s). | Ref. Ex. 147 |
| 2039 | | 1H-NMR (CDCl3) δ: 1.26-1.28 (4H, m), 2.70-2.77 (1H, m), 7.37-7.44 (2H, m), 7.50-7.54 (1H, m), 8.18 (1H, dd, J = 1.7, 7.9 Hz), 10.07 (1H, s). | Ref. Ex. 147 |
| 2040 | | 1H-NMR (CDCl3) δ: 1.44 (3H, t, J = 7.0 Hz), 1.52 (9H, s), 4.43 (2H, q, J = 7.0 Hz), 7.23 (1H, t, J = 8.6 Hz), 7.92-7.95 (1H, m), 8.12 (1H, dd, J = 2.1, 6.9 Hz). | Ref. Ex. 133 |
| 2041 | | 1H-NMR (CDCl3) δ: 1.44 (3H, t, J = 7.2 Hz), 1.51 (9H, s), 4.43 (2H, q, J = 7.2 Hz), 7.22-7.28 (1H, m), 7.79-7.83 (1H, m), 7.85-7.89 (1H, m). | Ref. Ex. 133 |
| 2042 | | 1H-NMR (CDCl3) δ: 1.54 (9H, s), 7.23-7.25 (1H, m), 7.94-7.99 (1H, m), 8.12-8.15 (1H, m), 10.15 (1H, s). | Ref. Ex. 63 |

TABLE 2-continued

| Ref. Ex. No | STR | 1H-NMR | ref. |
|---|---|---|---|
| 2043 | | 1H-NMR (CDCl3) δ: 1.54 (9H, s), 7.25-7.31 (1H, m), 7.82-7.85 (1H, m), 7.86-7.91 (1H, m), 10.15 (1H, s). | Ref. Ex. 63 |
| 2044 | | 1H-NMR (CDCl3) δ: 3.99 (3H, s), 4.02-4.08 (2H, m), 7.46-7.48 (2H, m), 8.03-8.05 (2H, m). | Ref. Ex. 133 |
| 2045 | | 1H-NMR (CDCl3) δ: 4.01 (3H, s), 4.07 (2H, q, J = 9.8 Hz), 7.64 (1H, t, J = 7.9 Hz), 7.78 (1H, d, J = 7.7 Hz), 8.29 (1H, d, J = 7.9 Hz), 8.38 (1H, s). | Ref. Ex. 133 |
| 2046 | | 1H-NMR (CDCl3) δ: 3.97-4.03 (2H, m), 7.48-7.50 (2H, m), 8.01-8.03 (2H, m), 10.05 (1H, s). | Ref. Ex. 63 |
| 2047 | | 1H-NMR (CDCl3) δ: 4.00-4.06 (2H, m), 7.67 (1H, t, J = 7.9 Hz), 7.80 (1H, d, J = 7.9 Hz), 8.27 (1H, d, J = 7.9 Hz), 8.35 (1H, s), 10.07 (1H, s). | Ref. Ex. 63 |
| 2048 | | 1H-NMR (CDCl3) δ: 3.99 (3H, s), 4.05 (2H, q, J = 9.8 Hz), 7.25-7.28 (1H, m), 7.98-8.01 (1H, m), 8.19 (1H, dd, J = 2.1, 6.9 Hz). | Ref. Ex. 133 |

TABLE 2-continued

| Ref. Ex. No | STR | 1H-NMR | ref. |
|---|---|---|---|
| 2049 | | 1H-NMR (CDCl3) δ: 3.99 (3H, s), 4.0S (2H, q, J = 9.8 Hz), 7.30 (1H, t. J= 8.1 HZ). 7.86-7.88 (1H, m), 7.92-7.96 (1H, m). | Ref. Ex. 133 |
| 2050 | | 1H-NMR (CDCl3) δ: 3.95-4.03 (2H, m), 7.29-7.34 (1H, m), 7.84-7.93 (2H, m), 10.05 (1H, s). | Ref. Ex. 63 |
| 2051 | | 1H-NMR (CDCl3) δ: 3.97-4.03 (2H, m), 7.27-7.31 (1H, m), 7.96-7.99 (1H, m), 8.15-8.16 (1H, m), 10.05 (1H, s). | Ref. Ex. 63 |
| 2052 | | 1H-NMR (CDCl3) δ: 1.44 (9H, s), 7.93-7.95 (1H, m), 8.05 (1H, t, J = 1.6 Hz), 8.07 (1H, dd, J = 2.1, 8.3 Hz), 8.33 (1H, t, J = 1.6 Hz), 8.42 (1H, t, J = 1.8 Hz), 8.98-8.99 (1H, m), 10.12 (1H, s). | Ref. Ex. 43 |
| 2053 | | 1H-NMR (CDCl3) δ: 1.43 (9H, s), 7.22-7.24 (1H, m), 7.63 (1H, s), 7.66 (1H, s), 7.84 (1H, d, J = 8.5 Hz), 7.91-7.92 (1H, m), 7.96-7.97 (1H, m), 8.01-8.02 (1H, m), 10.09 (1H, s). | Ref. Ex. 43 |

TABLE 2-continued

| Ref. Ex. No | STR | 1H-NMR | ref. |
|---|---|---|---|
| 2054 | | 1H-NMR (CDCl3) δ: 1.43 (9H, s), 6.86-6.90 (1H, m), 7.31 (1H, dd, J = 2.2, 8.8 Hz), 7.60 (1H, d, J = 3.4 Hz), 7.92-7.93 (1H, m), 7.95-7.96 (1H, m), 8.01-8.02 (1H, m), 10.09 (1H, s). | Ref. Ex. 43 |
| 2055 | | 1H-NMR (CDCl3) δ: 1.41 (6H, d, J = 7.0 Hz), 3.67-3.74 (1H, m), 7.32-7.34 (2H, m), 8.10-8.12 (2H, m), 10.04 (1H, s). | Ref. Ex. 147 |
| 2056 | | 1H-NMR (CDCl3) δ: 3.99 (3H, s), 7.21 (1H, t, J = 8.3 Hz), 7.87-7.95 (1H, m), 8.19 (1H, s), 8.27 (1H, dd, J = 2.2, 6.4 Hz). | Ref. Ex. 2 |
| 2057 | | 1H-NMR (CDCl3) δ: 2.82 (3H, s), 3.97 (3H, s), 7.18 (1H, t, J = 8.3 Hz), 7.79-7.83 (1H, m), 8.17 (1H, dd, J = 2.2, 6.4 Hz). | Ref. Ex. 2 |
| 2058 | | 1H-NMR (CDCl3) δ: 1.38 (3H, t, J = 7.5 Hz), 3.31 (2H, q, J = 7.5 Hz), 3.97 (3H, s), 7.18 (1H, t, J = 8.3 Hz), 7.81-7.85 (1H, m), 8.18 (1H, dd, J = 2.2, 6.5 Hz). | Ref. Ex. 2 |
| 2059 | | 1H-NMR (CDCl3) δ: 2.23 (1H, t, J = 6.0 Hz), 4.83 (2H, d, J = 6.0 Hz), 7.19 (1H, t, J = 8.4 Hz), 7.21 (1H, s), 7.83-7.86 (1H, m), 8.19 (1H, dd, J = 2.2, 6.5 Hz). | Ref. Ex. 19 |
| 2060 | | 1H-NMR (CDCl3) δ: 2.37 (1H, t, J = 5.9 Hz), 2.48 (3H, s), 4.71 (2H, d, J = 5.9 Hz), 7.16 (1H, t, J = 8.4 Hz), 7.75-7.79 (1H, m), 8.12 (1H, dd, J = 2.2, 6.5 Hz). | Ref. Ex. 19 |
| 2061 | | 1H-NMR (CDCl3) δ: 1.33 (3H, t, J = 7.5 Hz), 2.34 (1H, t, J = 5.9 Hz), 2.87 (2H, q, J = 7.5 Hz), 4.71 (2H, d, J = 5.9 Hz), 7.16 (1H, t, J = 8.4 Hz), 7.77-7.80 (1H, m), 8.13 (1H, dd, J = 2.2, 6.5 Hz). | Ref. Ex. 19 |

TABLE 2-continued
| Ref. Ex. No | STR | 1H-NMR | ref. |
|---|---|---|---|
| 2062 | 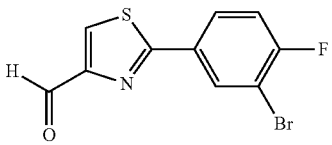 | 1H-NMR (CDCl3) δ: 7.24 (1H, t, J = 8.4 Hz), 7.90-7.94 (1H, m), 8.19 (1H, s), 8.26 (1H, dd, J = 2.2, 6.4 Hz), 10.09 (1H, s). | Ref. Ex. 48 |
| 2063 | 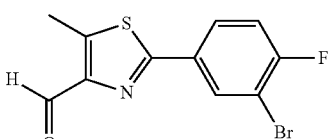 | 1H-NMR (CDCl3) δ: 2.84 (3H, s), 7.21 (1H, t, J = 8.3 Hz), 7.81-7.85 (1H, m), 8.18 (1H, dd, J = 2.2, 6.4 Hz), 10.19 (1H, s). | Ref. Ex. 48 |
| 2064 | 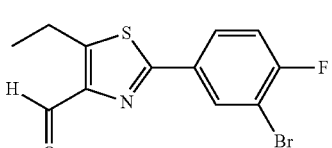 | 1H-NMR (CDCl3) δ: 1.39 (3H, t, J = 7.5 Hz), 3.32 (2H, q, J = 7.5 Hz), 7.21 (1H, t, J = 8.3 Hz), 7.82-7.86 (1H, m), 8.18 (1H, dd, J = 2.2, 6.5 Hz), 10.19 (1H, s). | Ref. Ex. 48 |
| 2066 | 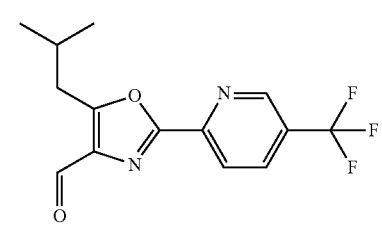 | 1H-NMR (CDCl3) δ: 1.02 (6H, d, J = 6.7 Hz), 2.19-2.26 (1H, m), 3.04 (2H, d, J = 7.2 Hz), 8.09-8.12 (1H, m), 8.32 (1H, d, J = 8.3 Hz), 9.01 (1H, s), 10.07 (1H, s). | Ref. Ex. 133, Ref. Ex. 318, Ref. Ex. 48 |
| 2067 | 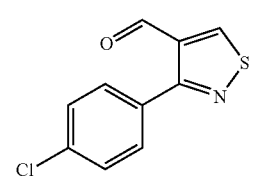 | 1H-NMR (CDCl3) δ: 7.50-7.52 (2H, m), 7.61-7.64 (2H, m), 9.49 (1H, s), 10.00 (1H, s). | Ref. Ex. 63 |
| 2068 | 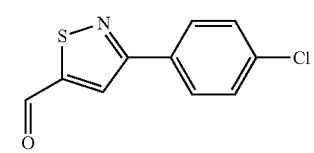 | 1H-NMR (CDCl3) δ: 7.46-7.48 (2H, m), 7.91-7.93 (2H, m), 8.07 (1H, s), 10.17 (1H, s). | Ref. Ex. 63 |
| 2070 | 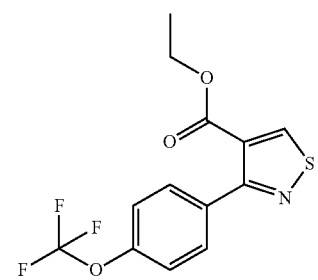 | 1H-NMR (CDCl3) δ: 1.27 (3H, t, J = 7.2 Hz), 4.28 (2H, q, J = 7.2 Hz), 7.28 (2H, d, J = 8.3 Hz), 7.66-7.70 (2H, m), 9.38 (1H, s). | Ref. Ex. 2069 |
| 2071 | 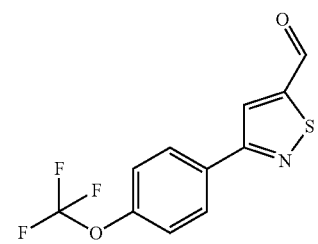 | 1H-NMR (CDCl3) δ: 7.34 (2H, d, J = 8.7 Hz), 8.01-8.03 (2H, m), 8.08 (1H, s), 10.18 (1H, s). | Ref. Ex. 63 |

TABLE 2-continued

| Ref. Ex. No | STR | 1H-NMR | ref. |
|---|---|---|---|
| 2072 | | 1H-NMR (CDCl3) δ: 1.05 (3H, t, J = 7.4 Hz), 1.80-1.89 (2H, m), 3.09 (2H, t, J = 7.4 Hz), 7.63 (1H, t, J = 7.8 Hz), 7.75 (1H, d, J = 7.8 Hz), 8.26 (1H, d, J = 7.8 Hz), 8.33 (1H, s), 10.04 (1H, s). | Ref. Ex. 147 |
| 2073 | | 1H-NMR (CDCl3) δ: 1.04 (3H, t, J = 7.4 Hz), 1.78-1.87 (2H, m), 3.07 (2H, t, J = 7.4 Hz), 7.24-7.28 (1H, m), 7.94-7.98 (1H, m), 8.13 (1H, dd, J = 2.2, 7.0 Hz), 10.01 (1H, s). | Ref. Ex. 147 |
| 2074 | | 1H-NMR (CDCl3) δ: 7.37-7.38 (2H, m), 7.72-7.75 (2H, m), 9.50 (1H, s), 10.02 (1H, s). | Ref. Ex. 63 |
| 2075 | | 1H-NMR (CDCl3) δ: 7.46-7.48 (2H, m), 7.91-7.93 (2H, m), 8.07 (1H, s), 10.17 (1H, s). | Ref. Ex. 63 |
| 2076 | | 1H-NMR (CDCl3) δ: 7.78-7.82 (4H, m), 9.52 (1H, s), 10.03 (1H, s) | Ref. Ex. 63 |
| 2077 | | 1H-NMR (CDCl3) δ: 7.76 (2H, d, J = 8.5 Hz), 8.10 (2H, d, J = 8.5 Hz), 8.15 (1H, s), 10.19 (1H, s). | Ref. Ex. 63 |

TABLE 2-continued

| Ref. Ex. No | STR | 1H-NMR | ref. |
|---|---|---|---|
| 2078 | | 1H-NMR (CDCl3) δ: 7.43-7.51 (2H, m), 8.24 (1H, d, J = 7.5 Hz), 8.36 (1H, s), 10.20 (1H, s). | Ref. Ex. 318 |
| 2081 | | 1H-NMR (DMSO-d6) δ: 2.72 (3H, s), 7.60-7.63 (2H, m), 8.10-8.13 (2H, m), 9.99 (1H, s), 12.94 (1H, brs). | Ref. Ex. 63 |
| 2082 | | 1H-NMR (CDCl3) δ: 1.43 (3H, t, J = 7.1 Hz), 1.98-2.18 (2H, m), 2.38-2.52 (4H, m), 4.29-4.36 (1H, m), 4.42 (2H, d, J = 7.1 Hz), 7.28-7.31 (1H, m), 7.70 (1H, s), 7.88 (1H, d, J = 8.8 Hz), 7.99 (1H, s). | Ref. Ex. 2080 |
| 2084 | | 1H-NMR (CDCl3) δ: 1.24 (3H, t, J = 7.5 Hz), 3.11 (2H, q, J = 7.5 Hz), 3.88 (3H, s), 4.53 (2H, d, J = 5.8 Hz), 5.57 (1H, brs), 7.47 (2H, d, J = 8.0 Hz), 7.62 (2H, J = 8.0 Hz). | Ref. Ex. 2083 |
| 2085 | | 1H-NMR (CDCl3) δ: 2.60 (3H, s), 4.54 (2H, s), 7.30 (4H, s), 9.82 (1H, s). | Ref. Ex. 63 |
| 2086 | | 1H-NMR (CDCl3) δ: 2.60 (3H, s), 4.66 (2H, s), 7.49 (2H, d, J = 8.0 Hz), 7.54 (1H, brs), 7.59 (2H, d, J = 8.0 Hz), 9.82 (1H, s). | Ref. Ex. 63 |

TABLE 2-continued

| Ref. Ex. No | STR | 1H-NMR | ref. |
|---|---|---|---|
| 2087 | | 1H-NMR (CDCl3) δ: 1.28 (3H, t, J = 7.5 Hz), 3.04 (2H, q, J = 7.5 Hz), 4.70 (2H, s), 7.50 (2H, d, J = 8.1 Hz), 7.58 (2H, d, J = 8.1 Hz), 8.58 (1H, s), 9.79 (1H, s). | Ref. Ex. 63 |
| 2088 | | 1H-NMR (CDCl3) δ: 2.00-2.20 (2H, m), 2.43-2.53 (4H, m), 4.19-4.24 (1H, m), 7.30-7.34 (1H, m), 7.72 (1H, s), 7.89 (1H, d, J = 8.8 Hz), 7.99 (1H, s), 10.00 (1H, s). | Ref. Ex. 63 |
| 2089 | | 1H-NMR (CDCl3) δ: 7.67 (1H, t, J = 7.9 Hz), 7.77 (1H, d, J = 7.4 Hz), 8.01 (1H, s). 8.48 (1H, s), 8.50 (1H, d, J = 7.9 Hz), 10.15 (1H, s). | Ref. Ex. 63 |
| 2090 | | 1H-NMR (CDCl3) δ: 7.45-7.51 (2H, m), 7.97 (1H, s), 8.14-8.16 (1H, m), 8.18-8.20 (1H, m), 10.13 (1H, s). | Ref. Ex. 63 |
| 2091 | | 1H-NMR (DMSO-d6) δ: 1.27 (3H, t, J = 7.5 Hz), 3.16 (2H, q, J = 7.5 Hz), 3.82 (3H, s), 7.61-7.63 (2H, m), 8.11-8.13 (2H, m), 12.94 (1H, brs). | Ref. Ex. 2079 |
| 2092 | | 1H-NMR (CDCl3) δ: 7.30 (1H, t, J = 8.6 Hz), 7.96 (1H, s), 8.22-8.25 (1H, m), 8.35-8.36 (1H, m), 10.11 (1H, s). | Ref. Ex. 63 |

TABLE 2-continued

| Ref. Ex. No | STR | 1H-NMR | ref. |
|---|---|---|---|
| 2093 | | 1H-NMR (DMSO-d6) δ: 1.23 (3H, t, J = 7.5 Hz), 2.96 (2H, q, J = 7.5 Hz), 3.91 (3H, s), 3.96 (3H, s), 7.54-7.56 (2H, m), 8.20-8.22 (2H, m). | Ref. Ex. 12 |
| 2095 | | 1H-NMR (CDCl3) δ: 1.43 (3H, t, J = 7.6 Hz), 2.92 (2H, q, J = 7.6 Hz), 3.96 (3H, s), 7.61 (1H, t, J = 7.7 Hz), 7.70 (1H, d, J = 7.7 Hz), 8.33 (1H, d, J = 7.7 Hz), 8.36 (1H, s). | Ref. Ex. 2080 |
| 2096 | | 1H-NMR (CDCl3) δ: 3.86 (3H, s), 7.61 (2H, d, J = 8.2 Hz), 7.71 (2H, d, J = 8.2 Hz). | Ref. Ex. 1643 |
| 2097 | | 1H-NMR (CDCl3) δ: 3.99 (3H, s), 6.89-6.94 (1H, m), 7.49-7.58 (2H, m), 8.23 (1H, s). | Ref. Ex. 2 |
| 2098 | | 1H-NMR (CDCl3) δ: 2.83 (3H, s), 3.97 (3H, s), 6.85-6.93 (1H, m), 7.42-7.50 (2H, m). | Ref. Ex. 2 |
| 2099 | | 1H-NMR (CDCl3) δ: 1.39 (3H, t, J = 7.5 Hz), 3.31 (2H, q, J = 7.5 Hz), 3.97 (3H, s), 6.85-6.93 (1H, m), 7.41-7.51 (2H, m). | Ref. Ex. 2 |
| 2100 | | 1H-NMR (CDCl3) δ: 1.45 (3H, t, J = 7.6 Hz), 2.93 (2H, q, J = 7.6 Hz), 7.65 (1H, t, J = 7.8 Hz), 7.74 (1H, d, J = 7.8 Hz), 8.37 (1H, s), 8.43 (1H, d, J = 8.1 Hz), 10.09 (1H, s). | Ref. Ex. 63 |

TABLE 2-continued

| Ref. Ex. No | STR | 1H-NMR | ref. |
|---|---|---|---|
| 2102 | | 1H-NMR (CDCl3) δ: 1.42 (3H, t, J = 7.6 Hz), 3.12 (2H, q, J = 7.6 Hz), 4.14 (3H, s), 7.41-7.44 (2H, m), 8.26-6.29 (2H, m), 9.96 (1H, s). | Ref. Ex. 63 |
| 2103 | | 1H-NMR (CDCl3) δ: 7.68 (2H, d, J = 8.2 Hz), 7.76 (2H, d, J = 8.2 Hz), 9.94 (1H, s). | Ref. Ex. 63 |
| 2104 | | 1H-NMR (CDCl3) δ: 2.04-2.23 (2H, m), 2.44-2.55 (4H, m), 4.19-4.26 (1H, m), 8.60 (1H, s), 9.00 (1H, s), 9.50 (1H, s), 10.02 (1H, s). | Ref. Ex. 63 |
| 2105 | | 1H-NMR (CDCl3) δ: 2.24 (1H, t, J = 6.0 Hz), 4.84 (2H, dd, J = 0.8, 6.0 Hz), 6.85-6.90 (1H, m). 7.26 (1H, s). 7.45-7.52 (2H, m). | Ref. Ex. 19 |
| 2106 | | 1H-NMR (CDCl3) δ: 2.39 (1H, t, J = 5.9 Hz), 2.49 (3H, s), 4.72 (2H, d, J = 5.9 Hz), 6.80-6.88 (1H, m). 7.37-7.44 (2H, m). | Ref. Ex. 19 |
| 2107 | | 1H-NMR (CDCl3) δ: 1.33 (3H, t, J = 7.5 Hz), 2.51 (1H, t, J = 5.8 Hz), 2.88 (2H, q, J = 7.5 Hz), 4.71 (2H, d, J = 5.8 Hz), 6.81-6.86 (1H, m), 7.38-7.44 (2H, m). | Ref. Ex. 19 |
| 2108 | | 1H-NMR (CDCl3) δ: 1.35 (3H, t, J = 7.6 Hz), 1.42 (3H, t, J = 7.1 Hz), 3.13 (2H, q, J = 7.6 Hz), 4.43 (2H, q, J = 7.1 Hz), 7.23 (1H, t, J = 8.6 Hz), 7.95-7.98 (1H, m), 8.16 (1H, dd, J = 2.1, 6.9 Hz). | Ref. Ex. 133 |
| 2109 | | 1H-NMR (CDCl3) δ: 1.42 (3H, t, J = 7.1 Hz), 2.71 (3H, s), 4.43 (2H, q, J = 7.1 Hz), 7.23 (1H, t, J = 8.5 Hz), 7.95-7.98 (1H, m), 8.16 (1H, dd, J = 2.2, 6.9 Hz). | Ref. Ex. 133 |

TABLE 2-continued

| Ref. Ex. No | STR | 1H-NMR | ref. |
|---|---|---|---|
| 2110 | | 1H-NMR (CDCl3) δ: 1.44 (3H, t, J = 7.5 Hz), 2.91 (2H, q, J = 7.5 Hz), 7.43-7.48 (2H, m), 8.06-8.09 (2H, m), 10.08 (1H, s). | Ref. Ex. 2080, Ref. Ex. 48 |
| 2111 | | 1H-NMR (CDCl3) δ: 2.72 (3H, s), 7.24-7.28 (1H, m), 7.94-7.97 (1H, m), 8.13-8.15 (1H, m), 10.02 (1H, s). | Ref. Ex. 63 |
| 2112 | | 1H-NMR (CDCl3) δ: 1.38 (3H, t, J = 7.5 Hz), 3.12 (2H, q, J = 7.5 Hz), 7.05-7.32 (1H, m), 7.95-7.98 (1H, m), 8.13-8.15 (1H, m), 10.02 (1H, s). | Ref. Ex. 63 |
| 2113 | | 1H-NMR (CDCl3) δ: 1.37 (3H, t, J = 7.6 Hz), 1.43 (3H, t, J = 7.2 Hz), 3.16 (2H, q, J = 7.6 Hz), 4.44 (2H, q, J = 7.2 Hz), 7.72 (2H, d, J = 8.3 Hz), 8.20 (2H, d, J = 8.3 Hz). | Ref. Ex. 133 |
| 2114 | | 1H-NMR (CDCl3) δ: 1.43 (3H, t, J = 7.1 Hz), 2.74 (3H, s), 4.44 (2H, q, J = 7.1 Hz), 7.72 (2H, d, J = 8.4 Hz), 8.20 (2H, d, J = 8.4 Hz). | Ref. Ex. 133 |
| 2115 | | 1H-NMR (CDCl3) δ: 1.35 (3H, t, J = 7.6 Hz), 1.42 (3H, t, J = 7.2 Hz), 3.14 (2H, q, J = 7.6 Hz), 4.43 (2H, q, J = 7.2 Hz), 7.54 (1H, d, J = 8.4 Hz), 7.91 (1H, dd, J = 2.0, 8.4 Hz), 8.18 (1H, d, J = 1.9 Hz). | Ref. Ex. 133 |
| 2116 | | 1H-NMR (CDCl3) δ: 2.75 (3H, s), 7.75 (2H, d, J = 8.2 Hz), 8.18 (2H, d, J = 8.2 Hz), 10.05 (1H, s). | Ref. Ex. 63 |
| 2117 | | 1H-NMR (CDCl3) δ: 1.40 (3H, t, J = 7.6 Hz), 3.15 (2H, q, J = 7.6 Hz), 7.75 (2H, d, J = 8.2 Hz), 8.19 (2H, d, J = 8.2 Hz), 10.05 (1H, s). | Ref. Ex. 63 |
| 2118 | | 1H-NMR (CDCl3) δ: 1.39 (3H, t, J = 7.6 Hz), 3.12 (2H, q, J = 7.6 Hz), 7.57 (1H, d, J = 8.4 Hz), 7.90 (1H, dd, J = 1.9, 8.4 Hz), 8.16 (1H, d, J = 1.9 Hz), 10.02 (1H, s). | Ref. Ex. 63 |

TABLE 2-continued

| Ref. Ex. No | STR | 1H-NMR | ref. |
|---|---|---|---|
| 2119 | | 1H-NMR (CDCl3) δ: 2.73 (3H, s), 7.57 (1H, d, J = 8.4 Hz), 7.89 (1H, dd, J = 2.0, 8.4 Hz), 8.16 (1H, d, J = 2.0 Hz), 10.02 (1H, s). | Ref. Ex. 63 |
| 2120 | | 1H-NMR (CDCl3) δ: 6.92-6.97 (1H, m), 7.52-7.58 (2H, m), 8.23 (1H, s), 10.11 (1H, s). | Ref. Ex. 48 |
| 2121 | | 1H-NMR (CDCl3) δ: 2.85 (3H, s), 6.88-6.93 (1H, m), 7.43-7.49 (2H, m), 10.20 (1H, s). | Ref. Ex. 48 |
| 2122 | | 1H-NMR (CDCl3) δ: 1.39 (3H, t, J = 7.5 Hz), 3.33 (2H, q, J = 7.5 Hz), 6.83-6.93 (1H, m), 7.41-7.57 (2H, m), 10.19 (1H, s). | Ref. Ex. 48 |
| 2123 | | 1H-NMR (CDCl3) δ: 1.38 (3H, t, J = 7.5 Hz), 1.44 (3H, t, J = 7.2 Hz), 3.18 (2H, q, J = 7.5 Hz), 4.45 (2H, q, J = 7.2 Hz), 7.80 (1H, d, J = 8.5 Hz), 8.56 (1H, dd, J = 1.9, 8.5 Hz), 9.37 (1H, d, J = 1.9 Hz). | Ref. Ex. 2080 |
| 2124 | | 1H-NMR (CDCl3) δ: 1.43 (3H, t, J = 7.2 Hz), 1.98-2.18 (2H, m), 2.40-2.50 (4H, m), 4.30-4.35 (1H, m), 4.42 (2H, q, J = 7.1 Hz), 6.93-6.97 (1H, m), 7.34-7.37 (1H, m), 7.97 (1H, d, J = 3.2 Hz). | Ref. Ex. 2080 |

TABLE 2-continued

| Ref. Ex. No | STR | 1H-NMR | ref. |
|---|---|---|---|
| 2125 | | 1H-NMR (CDCl3) δ: 3.27-3.29 (4H, m), 3.69-3.71 (4H, m), 3.80 (3H, s), 6.87-6.91 (2H, m), 7.24-7.26 (2H, m), 7.58 (2H, d, J = 8.2 Hz), 7.64 (2H, d, J = 8.2 Hz). | Ref. Ex. 184 |
| 2126 | | 1H-NMR (CDCl3) δ: 1.35 (3H, t, J = 7.5 Hz), 1.42 (3H, t, J = 7.1 Hz), 3.14 (2H, q, J = 7.5 Hz), 4.43 (2H, q, J = 7.1 Hz), 7.38-7.45 (2H, m), 7.95-7.98 (1H, m), 8.08-8.09 (1H, m). | Ref. Ex. 133 |
| 2127 | | 1H-NMR (CDCl3) δ: 1.41 (3H, t, J = 7.6 Hz), 3.17 (2H, q, J = 7.6 Hz), 7.82 (1H, d, J = 8.3 Hz), 8.53 (1H, d, J = 8.3 Hz), 9.38 (1H, s), 10.06 (1H, s). | Ref. Ex. 318, Ref. Ex. 48 |
| 2128 | | 1H-NMR (CDCl3) δ: 1.39 (3H, t, J = 7.6 Hz), 3.13 (2H, q, J = 7.6 Hz), 7.40-7.48 (2H, m), 7.94-7.97 (1H, m), 8.06 (1H, d, J = 1.6 Hz), 10.03 (1H, s). | Ref. Ex. 63 |
| 2129 | | 1H-NMR (CDCl3) δ: 2.72 (3H, s), 7.15-7.19 (2H, m), 8.04-8.08 (2H, m), 10.02 (1H, s). | Ref. Ex. 63 |
| 2130 | | 1H-NMR (CDCl3) δ: 1.44 (3H, t, J = 7.1 Hz), 2.76 (3H, s), 4.45 (2H, q, J = 7.1 Hz), 7.80 (1H, d, J = 8.2 Hz), 8.53-8.57 (1H, m), 9.37 (1H, s). | Ref. Ex. 2080 |
| 2131 | | 1H-NMR (CDCl3) δ: 1.42 (3H, t, J = 7.2 Hz), 2.71 (3H, s), 4.43 (2H, q, J = 7.2 Hz), 7.13 (1H, d, J = 8.3 Hz), 7.79 (1H, d, J = 1.6 Hz), 7.86 (1H, dd, J = 1.6, 8.3 Hz). | Ref. Ex. 2080 |

TABLE 2-continued
| Ref. Ex. No | STR | 1H-NMR | ref. |
|---|---|---|---|
| 2132 | 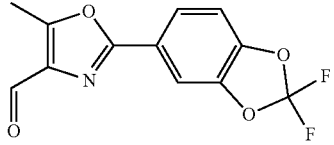 | 1H-NMR (CDCl3) δ: 2.72 (3H, s), 7.17 (1H, d, J = 8.4 Hz), 7.77 (1H, d, J = 1.7 Hz), 7.85 (1H, dd, J = 1.7, 8.4 Hz), 10.01 (1H, s). | Ref. Ex. 63 |
| 2133 | 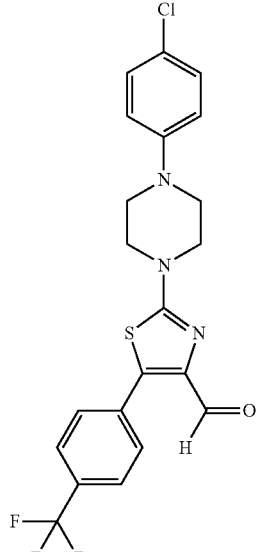 | 1H-NMR (CDCl3) δ: 3.27-3.30 (4H, m), 3.74-3.77 (4H, m), 6.87-6.91 (2H, m), 7.23-7.27 (2H, m), 7.61 (2H, d, J = 8.0 Hz), 7.71 (2H, d, J = 8.0 Hz), 9.74 (1H, s). | Ref. Ex. 63 |
| 2134 | 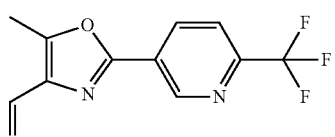 | 1H-NMR (CDCl3) δ: 2.78 (3H, s), 7.82 (1H, d, J = 8.2 Hz), 8.52 (1H, dd, J = 1.6, 8.2 Hz), 9.37 (1H, d, J = 1.6 Hz), 10.06 (1H, s). | Ref. Ex. 318, Ref. Ex. 48 |
| 2135 | 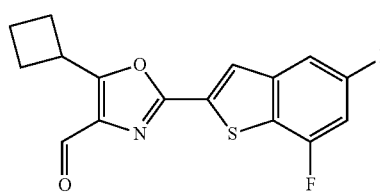 | 1H-NMR (CDCl3) δ: 2.01-2.21 (2H, m), 2.42-2.55 (4H, m), 4.17-4.25 (1H, m), 6.95-6.99 (1H, m), 7.37 (1H, dd, J = 2.1, 8.5 Hz), 7.96 (1H, d, J = 3.2 Hz), 10.00 (1H, s). | Ref. Ex. 63 |
| 2136 | 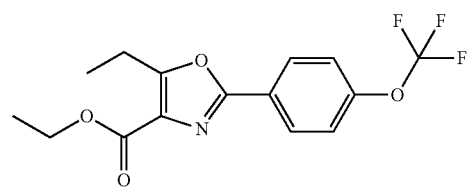 | 1H-NMR (CDCl3) δ: 1.35 (3H, t, J = 7.5 Hz), 1.42 (3H, t, J = 7.1 Hz), 3.14 (2H, q, J = 7.5 Hz), 4.43 (2H, q, J = 7.1 Hz), 7.30 (2H, d, J = 8.7 Hz), 8.12 (2H, d, J = 8.7 Hz). | Ref. Ex. 133 |
| 2137 | 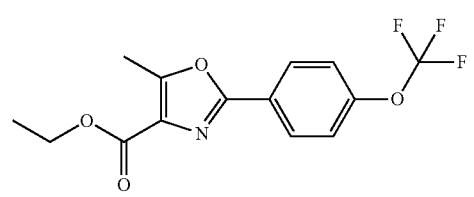 | 1H-NMR (CDCl3) δ: 1.43 (3H, t, J = 7.1 Hz), 2.72 (3H, s), 4.43 (2H, q, J = 7.1 Hz), 7.30 (2H, d, J = 8.2 Hz), 8.10-8.13 (2H, m). | Ref. Ex. 133 |

TABLE 2-continued

| Ref. Ex. No | STR | 1H-NMR | ref. |
|---|---|---|---|
| 2138 | | 1H-NMR (CDCl3) δ: 1.38 (3H, t, J = 7.6 Hz), 3.13 (2H, q, J = 7.6 Hz), 7.33 (2H, d, J = 8.1 Hz), 8.10-8.13 (2H, m), 10.03 (1H, s). | Ref. Ex. 63 |
| 2139 | | 1H-NMR (CDCl3) δ: 2.73 (3H, s), 7.33 (2H, d, J = 8.2 Hz), 8.08-8.12 (2H, m), 10.03 (1H, s). | Ref. Ex. 63 |
| 2140 | | 1H-NMR (CDCl3) δ: 4.00 (3H, s), 7.45 (1H, dd, J = 0.6, 8.4 Hz), 8.26 (1H, s), 8.31 (1H, dd, J = 2.5, 8.4 Hz), 8.96 (1H, dd, J = 0.6, 2.5 Hz). | Ref. Ex. 2 |
| 2141 | | 1H-NMR (CDCl3) δ: 2.84 (3H, s), 3.98 (3H, s), 7.42 (1H, dd, J = 0.6, 8.4 Hz), 8.23 (1H, dd, J = 2.5, 8.4 Hz), 8.86 (1H, dd, J = 0.6, 2.5 Hz). | Ref. Ex. 2 |
| 2142 | | 1H-NMR (CDCl3) δ: 1.40 (3H, t, J = 7.5 Hz), 3.33 (2H, q, J = 7.5 Hz), 3.98 (3H, s), 7.42 (1H, d, J = 8.4 Hz), 8.24 (1H, dd, J = 2.5, 8.4 Hz), 8.88 (1H, d, J = 2.5 Hz). | Ref. Ex. 2 |
| 2144 | | 1H-NMR (CDCl3) δ: 7.19 (1H, d, J = 8.3 Hz), 7.83 (1H, d, J = 1.8 Hz), 7.91 (1H, dd, J = 1.6, 8.3 Hz), 8.32 (1H, s), 10.01 (1H, s). | Ref. Ex. 63 |
| 2145 | | 1H-NMR (CDCl3) δ: 1.43 (3H, t, J = 7.1 Hz), 4.46 (2H, q, J = 7.1 Hz), 7.83 (1H, d, J = 8.2 Hz), 8.38 (1H, s), 8.58-8.62 (1H, m), 9.43 (1H, s). | Ref. Ex. 2080 |
| 2146 | | 1H-NMR (CDCl3) δ: 2.18 (1H, t, J = 5.7 Hz), 4.85 (2H, d, J = 5.7 Hz), 7.29 (1H, t, J = 0.7 Hz), 7.42 (1H, dd, J = 0.7, 8.3 Hz), 8.20 (1H, dd, J = 2.5, 8.3 Hz), 8.93 (1H, dd, J = 0.7, 2.5 Hz). | Ref. Ex. 19 |
| 2147 | | 1H-NMR (CDCl3) δ: 1.57 (1H, brs), 2.50 (3H, s), 4.73 (2H, s), 7.39 (1H, dd, J = 0.5, 8.3 Hz), 8.15 (1H, dd, J = 2.5, 8.3 Hz), 8.85 (1H, dd, J = 0.5, 2.5 Hz). | Ref. Ex. 19 |

TABLE 2-continued

| Ref. Ex. No | STR | 1H-NMR | ref. |
|---|---|---|---|
| 2148 | | 1H-NMR (CDCl3) δ: 1.36 (3H, t, J = 7.6 Hz), 1.43 (3H, t, J = 7.1 Hz), 3.15 (2H, q, J = 7.6 Hz), 4.44 (2H, q, J = 7.1 Hz), 7.30-7.34 (1H, m), 7.50 (1H, t, J = 8.1 Hz), 7.93 (1H, s), 8.01-8.04 (1H, m). | Ref. Ex. 2080 |
| 2149 | | 1H-NMR (CDCl3) δ: 1.33 (3H, t, J = 7.5 Hz), 3.25 (2H, q, J = 7.5 Hz), 3.93 (3H, s). | Ref. Ex. 1643 |
| 2150 | | 1H-NMR (CDCl3) δ: 1.41 (3H, t, J = 7.2 Hz), 4.44 (2H, q, J = 7.2 Hz), 6.59 (1H, t, J = 73.1 Hz), 7.22 (2H, d, J = 8.9 Hz), 8.13 (2H, d, J = 8.9 Hz), 8.27 (1H, s). | Ref. Ex. 2080 |
| 2151 | | 1H-NMR (CDCl3) δ: 1.39 (3H, t, J = 7.6 Hz), 3.13 (2H, q, J = 7.6 Hz), 7.33-7.36 (1H, m), 7.53 (1H, t, J = 8.0 Hz), 7.92 (1H, s), 8.00-8.03 (1H, m), 10.04 (1H, s). | Ref. Ex. 63 |
| 2152 | | 1H-NMR (CDCl3) δ: 1.28 (3H, t, J = 7.5 Hz), 2.17 (1H, t, J = 6.2 Hz), 2.82 (2H, q, J = 7.5 Hz), 4.62 (2H, d, J = 6.2 Hz). | Ref. Ex. 19 |
| 2153 | | 1H-NMR (CDCl3) δ: 1.34 (3H, t, J = 7.5 Hz), 2.30 (1H, t, J = 5.8 Hz), 2.89 (2H, q, J = 7.5 Hz), 4.73 (2H, d, J = 5.8 Hz), 7.39 (1H, dd, J = 0.6, 8.3 Hz), 8.16 (1H, dd, J = 2.5, 8.3 Hz), 8.87 (1H, dd, J = 0.6, 2.5 Hz). | Ref. Ex. 19 |
| 2154 | | 1H-NMR (CDCl3) δ: 6.60 (1H, t, J = 73.3 Hz), 7.24-7.26 (2H, m), 8.12 8.14 (2H, m), 8.32 (1H, s), 10.01 (1H, s). | Ref. Ex. 63 |
| 2155 | | 1H-NMR (CDCl3) δ: 7.85 (1H, d, J = 8.2 Hz), 8.43 (1H, s), 8.58-8.60 (1H, m), 9.43 (1H, s), 10.05 (1H, s). | Ref. Ex. 63 |
| 2156 | | 1H-NMR (CDCl3) δ: 7.48 (1H, dd, J = 0.6, 8.4 Hz), 8.25 (1H, s), 8.29 (1H, dd, J = 2.5, 8.4 Hz), 8.99 (1H, dd, J = 0.6, 2.5 Hz), 10.12 (1H, s). | Ref. Ex. 48 |

TABLE 2-continued

| Ref. Ex. No | STR | 1H-NMR | ref. |
|---|---|---|---|
| 2157 | | 1H-NMR (CDCl3) δ: 2.87 (3H, s), 7.45 (1H, dd, J = 0.6, 8.4 Hz), 8.22 (1H, dd, J = 2.5, 8.4 Hz), 8.89 (1H, dd, J = 0.6, 2.5 Hz), 10.21 (1H, s). | Ref. Ex. 48 |
| 2158 | | 1H-NMR (CDCl3) δ: 1.40 (3H, t, J = 7.5 Hz), 3.34 (2H, q, J = 7.5 Hz), 7.45 (1H, dd, J = 0.5, 8.3 Hz), 8.23 (1H, dd, J = 2.5, 8.3 Hz), 8.90 (1H, dd, J = 0.5, 2.5 Hz), 10.21 (1H, s). | Ref. Ex. 48 |
| 2159 | | 1H-NMR (CDCl3) δ: 1.33 (3H, t, J = 7.5 Hz), 3.25 (2H, q, J = 7.5 Hz), 10.04 (1H, s). | Ref. Ex. 48 |
| 2163 | | 1H-NMR (CDCl3) δ: 3.06 (1H, t, J = 6.1 Hz), 5.05 (2H, d, J = 6.1 Hz), 7.02-7.06 (2H, m), 7.12-7.16 (1H, m), 7.19 (1H, dd, J = 2.4, 8.9 Hz), 7.34-7.39 (2H, m), 7.45 (1H, d, J = 2.4 Hz), 7.92 (1H, d, J = 8.9 Hz). | Ref. Ex. 19 |
| 2164 | | 1H-NMR (CDCl3) δ: 7.09-7.12 (2H, m), 7.20-7.24 (1H, m), 7.33 (1H, dd, J = 2.4, 9.0 Hz), 7.40-7.45 (3H, m), 8.18 (1H, d, J = 9.0 Hz), 10.11 (1H, s). | Ref. Ex. 48 |
| 2165 | | 1H-NMR (CDCl3) δ: 7.24-7.78 (5H, m), 8.18 (1H, d, J = 1.6 Hz), 8.23 (1H, dd, J = 0.3, 8.5 Hz), 9.05 (1H, s). | Ref. Ex. 2161 |
| 2166 | | 1H-NMR (CDCl3) δ: 4.11 (3H, s), 7.74-7.79 (4H, m), 7.82 (1H, dd, J = 1.8, 8.6 Hz), 8.19 (1H, dd, J = 0.4, 1.8 Hz), 8.33 (1H, d, J = 0.4, 8.6 Hz). | Ref. Ex. 2162 |
| 2167 | | 1H-NMR (CDCl3) δ: 2.91 (1H, t, J = 6.1 Hz), 5.12 (2H, d, J = 6.1 Hz), 7.70-7.76 (5H, m), 8.07 (1H, d, J = 8.5 Hz), 8.11 (1H, d, J = 1.6 Hz). | Ref. Ex. 19 |

TABLE 2-continued

| Ref. Ex. No | STR | 1H-NMR | ref. |
|---|---|---|---|
| 2168 | 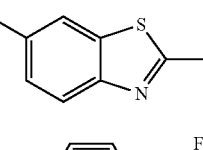 | 1H-NMR (CDCl3) δ: 7.75-7.80 (4H, m), 7.85 (1H, dd, J = 1.8, 8.6 Hz), 8.22 (1H, d, J = 1.8 Hz), 8.33 (1H, d, J = 8.6 Hz), 10.19 (1H, s). | Ref. Ex. 48 |
| 2169 | 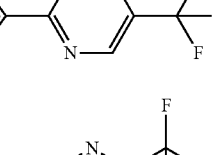 | 1H-NMR (CDCl3) δ: 2:23 (1H, t, J = 5.6 Hz), 4.87 (2H, d, J = 5.6 Hz), 7.40 (1H, t, J = 0.8 Hz), 8.02-8.08 (1H, m), 8.30 (1H, d, J = 8.3 Hz), 8.85-8.86 (1H, m). | Ref. Ex. 19 |
| 2170 | 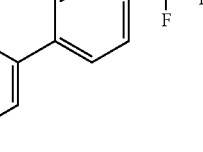 | 1H-NMR (CDCl3) δ: 7.44 (1H, dd, J = 1.6, 10.9 Hz), 7.54 (1H, dd, J = 1.2, 8.1 Hz), 7.82-7.84 (1H, m), 8.02-8.06 (1H, m), 8.07-8.12 (1H, m), 8.97 (1H, d, J = 2.1 Hz), 10.43 (1H, d, J = 0.4 Hz). | Ref. Ex. 112 |
| 2171 | 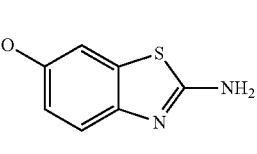 | 1H-NMR (CDCl3) δ: 5.23 (2H, brs), 7.02-7.06 (3H, m), 7.31 (1H, d, J = 2.4 Hz), 7.53-7.57 (3H, m). | Ref. Ex. 2160 |
| 2172 | 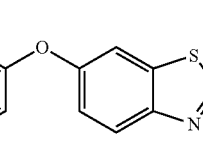 | 1H-NMR (CDCl3) δ: 7.14 (2H, d, J = 8.4 Hz), 7.26 (1H, dd, J = 2.4, 8.8 Hz), 7.60-7.62 (3H, m), 8.13 (1H, d, J = 8.8 Hz), 8.97 (1H, s). | Ref. Ex. 2161 |
| 2173 | 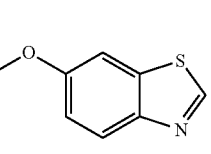 | 1H-NMR (CDCl3) δ: 6.96-7.00 (2H, m), 7.23 (1H, dd, J = 2.4, 8.9 Hz), 7.30-7.34 (2H, m), 7.51 (1H, d, J = 2.4 Hz), 8.09 (1H, d, J = 8.9 Hz), 8.93 (1H, s). | Ref. Ex. 2161 |
| 2174 | 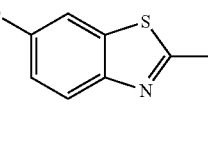 | 1H-NMR (CDCl3) δ: 4.09 (3H, s), 7.14 (2H, d, J = 8.4 Hz), 7.32 (1H, dd, J = 2.4, 9.0 Hz), 7.56 (1H, d, J = 2.4 Hz), 7.65 (2H, d, J = 8.4 Hz), 8.23 (1H, d, J = 9.0 Hz). | Ref. Ex. 2162 |
| 2175 | 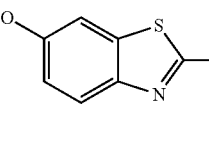 | 1H-NMR (CDCl3) δ: 2.73 (1H, t, J = 6.1 Hz), 5.08 (2H, d, J = 6.1 Hz), 7.08 (2H, d, J = 8.4 Hz), 7.22 (1H, dd, J = 2.4, 8.6 Hz), 7.55 (1H, d, J = 2.4 Hz), 7.60 (2H, d, J = 8.4 Hz), 7.98 (1H, d, J = 8.8 Hz). | Ref. Ex. 19 |
| 2176 | 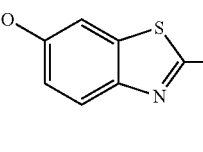 | 1H-NMR (CDCl3) δ: 7.16 (2H, d, J = 8.4 Hz), 7.35 (1H, dd, J = 2.4, 9.0 Hz), 7.56 (1H, d, J = 2.4 Hz), 7.66 (2H, d, J = 8.4 Hz), 8.23 (1H, d, J = 9.0 Hz), 10.14 (1H, s). | Ref. Ex. 48 |

TABLE 2-continued

| Ref. Ex. No | STR | 1H-NMR | ref. |
|---|---|---|---|
| 2177 | 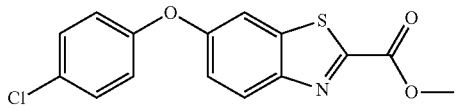 | 1H-NMR (CDCl3) δ: 4.08 (3H, s), 7.00-7.05 (2H, m), 7.28 (1H, dd, J = 2.4, 9.0 Hz), 7.34-7.38 (2H, m), 7.44 (1H, d, J = 2.4 Hz), 8.18 (1H, d, J = 9.0 Hz). | Ref. Ex. 2162 |
| 2178 | 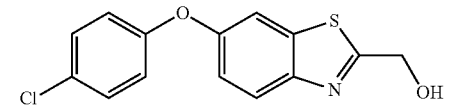 | 1H-NMR (CDCl3) δ: 3.03 (1H, t, J = 6.1 Hz), 5.06 (2H, d, J = 6.1 Hz), 6.95-6.99 (2H, m), 7.17 (1H, dd, J = 2.4, 8.9 Hz), 7.30-7.34 (2H, m), 7.45 (1H, d, J = 2.4 Hz), 7.93 (1H, d, J = 8.9 Hz). | Ref. Ex. 19 |
| 2179 | 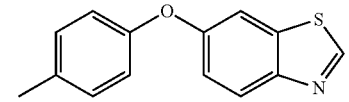 | 1H-NMR (CDCl3) δ: 2.36 (3H, s), 6.95-6.98 (2H, m), 7.18 (2H, d, J = 8.1 Hz), 7.22 (1H, dd, J = 2.4, 8.9 Hz), 7.46 (1H, d, J = 2.4 Hz), 8.06 (1H, d, J = 8.9 Hz), 8.89 (1H, s). | Ref. Ex. 2161 |
| 2180 | 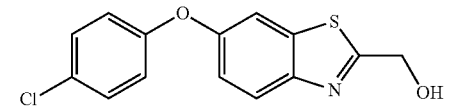 | 1H-NMR (CDCl3) δ: 7.02-7.06 (2H, m), 7.31 (1H, dd, J = 2.4, 9.0 Hz), 7.36-7.40 (2H, m), 7.45 (1H, d, J = 2.4 Hz), 8.19 (1H, d, J = 9.0 Hz), 10.1 (1H, s). | Ref. Ex. 48 |
| 2181 | 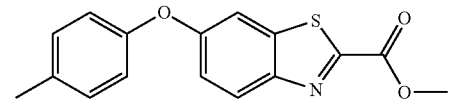 | 1H-NMR (CDCl3) δ: 2.37 (3H, s), 4.07 (3H, s), 6.98-7.00 (2H, m), 7.21 (2H, d, J = 8.1 Hz), 7.28 (1H, dd, J = 2.5, 9.0 Hz), 7.37 (1H, d, J = 2.5 Hz), 6.15 (1H, d, J = 9.0 Hz). | Ref. Ex. 2162 |
| 2182 | 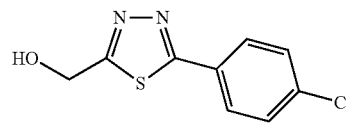 | 1H-NMR (CDCl3) δ: 2.61 (1H, brs), 5.13 (2H, d, J = 6.2 Hz), 7.45-7.49 (2H, m), 7.89-7.96 (2H, m). | Ref. Ex. 38 |
| 2183 | 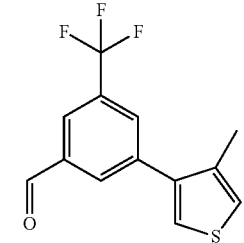 | 1H-NMR (CDCl3) δ: 2.29 (3H, d, J = 0.8 Hz), 7.10-7.11 (1H, m), 7.34 (1H, d, J = 3.2 Hz), 7.89-7.90 (1H, m), 8.09-8.10 (2H, m), 10.12 (1H, s). | Ref. Ex. 112 |
| 2184 | 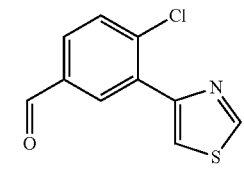 | 1H-NMR (CDCl3) δ: 7.66 (1H, d, J = 8.3 Hz), 7.83 (1H, dd, J = 2.0, 8.3 Hz), 0.01 (1H, d, J = 2.0 Hz), 8.52 (1H, d, J = 2.0 Hz), 8.93 (1H, d, J = 2.0 Hz), 10.06 (1H, s). | Ref. Ex. 112 |
| 2185 | 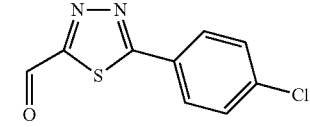 | 1H-NMR (CDCl3) δ: 7.49-7.54 (2H, m), 8.00-6.03 (2H, m), 10.25 (1H, s). | Ref. Ex. 46 |
| 2186 | 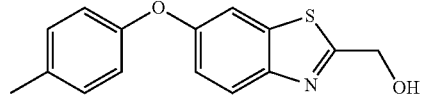 | 1H-NMR (CDCl3) δ: 2.35 (3H, s), 2.75 (1H, t, J = 6.1 Hz), 5.04 (2H, d, J = 6.1 Hz), 6.93-6.97 (2H, m), 7.15-7.19 (3H, m), 7.40 (1H, d, J = 2.4 Hz), 7.9 (1H, d, J = 8.9 Hz). | Ref. Ex. 19 |

TABLE 2-continued
| Ref. Ex. No | STR | 1H-NMR | ref. |
|---|---|---|---|
| 2187 |  | 1H-NMR (CDCl3) δ: 2.48 (6H, s), 6.75 (1H, d, J = 0.7 Hz), 7.86-7.87 (1H, m), 8.05 (2H, d, J = 1.5 Hz), 10.10 (1H, 2). | Ref. Ex. 112 |
| 2188 | 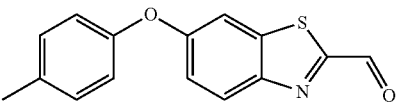 | 1H-NMR (CDCl3) δ: 2.36 (3H, s), 6.99-7.02 (2H, m), 7.22 (2H, d, J = 8.1 Hz), 7.31 (1H, dd, J = 2.4, 9.0 Hz), 7.38 (1H, d, J = 2.4 Hz), 8.15 (1H, d, J = 9.0 Hz), 10.11 (1H, s). | Ref. Ex. 46 |
| 2189 | 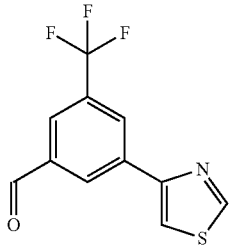 | 1H-NMR (CDCl3) δ: 7.75 (1H, d, J = 1.9 Hz), 8.12 (1H, s), 8.49 (1H, s), 8.82 (1H, s), 8.95 (1H, d, J = 1.9 Hz), 10.15 (1H, s). | Ref. Ex. 112 |
| 2190 | 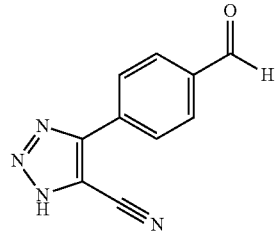 | 1H-NMR (DMSO-d6) δ: 8.10-6.15 (4H, m), 10.09 (1H, s) | Ex. 125 |
| 2191 | 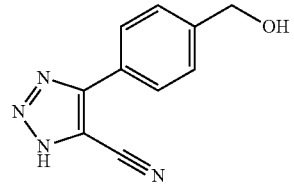 | 1H-NMR (DMSO-d6) δ: 4.58 (2H, s), 5.36 (1H, br.), 7.54 (2H, d, J = 8.4 Hz), 7.84 (2H, d, J = 8.4 Hz). | Ref. Ex. 102 |
| 2193 | 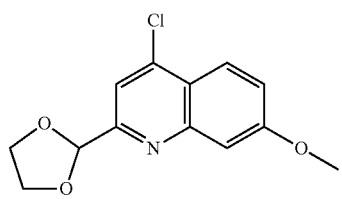 | 1H-NMR (CDCl3) δ: 3.95 (3H, s), 4.12-4.17 (2H, m), 4.19-4.24 (2H, m), 5.93 (1H, s), 7.28-7.30 (1H, m), 7.49 (1H, d, J = 2.5 Hz), 7.60 (1H, s), 8.11 (1H, d, J = 9.2 Hz). | Ref. Ex. 116 |
| 2194 | 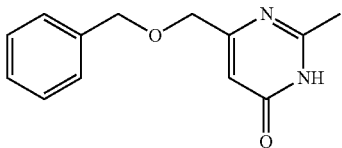 | 1H-NMR (CDCl3) δ: 2.47 (3H, s), 4.41 (2H, d, J = 1.1 Hz), 4.65 (2H, s), 6.56 (1H, s), 7.31-7.33 (1H, m), 7.35-7.39 (4H, m), 12.98 (1H, brs). | Ref. Ex. 760 |

TABLE 2-continued

| Ref. Ex. No | STR | 1H-NMR | ref. |
|---|---|---|---|
| 2195 | | 1H-NMR (CDCl3) δ: 2.68 (3H, s), 4.58 (2H, s), 4.67 (2H, s), 7.32-7.33 (1H, m), 7.34-7.40 (5H, m). | Ref. Ex. 831 |
| 2196 | | 1H-NMR (CDCl3) δ: 4.57 (2H, s), 4.75 (2H, s), 6.72 (1H, s), 7.31-7.34 (1H, m), 7.37-7.42 (4H, m), 7.52-7.58 (3H, m), 8.13-8.15 (2H, m). | Ref. Ex. 760 |
| 2197 | | 1H-NMR (CDCl3) δ: 4.67 (2H, s), 4.69 (2H, s), 7.31-7.50 (9H, m), 8.40-8.44 (2H, m). | Ref. Ex. 831 |
| 2198 | | 1H-NMR (CDCl3) δ: 1.63-1.73 (6H, m), 3.74 (4H, brs), 4.64 (2H, s), 4.75 (2H, s), 6.71 (1H, s), 7.31-7.43 (8H, m), 8.35-8.37 (2H, m). | Ref. Ex. 1173 |
| 2199 | | 1H-NMR (CDCl3) δ: 1.63-1.75 (6H, m), 3.73 (4H, brs), 3.78 (1H, brs), 4.70 (2H, s), 6.39 (1H, s), 7.43-7.46 (3H, m), 8.39-8.42 (2H, m). | Ref. Ex. 750 |
| 2200 | | 1H-NMR (CDCl3) δ: 1.67-1.69 (4H, m), 1.70-1.75 (2H, m), 3.94 (4H, brs), 7.01 (1H, s), 7.47-7.48 (3H, m), 8.45-8.47 (2H, m), 10.09 (1H, s). | Ref. Ex. 159 |

TABLE 2-continued

| Ref. Ex. No | STR | 1H-NMR | ref. |
|---|---|---|---|
| 2201 | | 1H-NMR (CDCl3) δ: 2.03-2.04 (4H, m), 3.44 (2H, brs), 3.76 (2H, brs), 4.60 (2H, d, J = 0.5 Hz), 4.70 (2H, s), 6.44 (1H, s), 7.29-7.44 (8H, m), 8.38-8.40 (2H, m). | Ref. Ex. 1173 |
| 2202 | | 1H-NMR (CDCl3) δ: 2.04 (4H, brs), 3.38 (2H, brs), 3.78 (2H, brs), 3.84 (1H, brs), 4.64 (2H, s), 6.11 (1H, s), 7.43-7.46 (3H, m), 8.43-8.46 (2H, m). | Ref. Ex. 750 |
| 2203 | | 1H-NMR (CDCl3) δ: 2.05 (2H, brs), 2.10 (2H, brs), 3.46 (2H, brs), 3.81 (2H, brs), 6.80 (1H, s), 7.46-7.49 (3H, m), 8.48-8.50 (2H, m), 10.02 (1H, s). | Ref. Ex. 159 |
| 2204 | | 1H-NMR (CDCl3) δ: 4.54 (2H, s), 4.68 (2H, s), 6.97 (1H, s), 7.31-7.35 (1H, m), 7.37-7.40 (4H, m). | Ref. Ex. 760 |
| 2205 | | 1H-NMR (CDCl3) δ: 4.68 (4H, s), 7.33-7.45 (5H, m), 7.84 (1H, s). | Ref. Ex. 831 |
| 2206 | | 1H-NMR (CDCl3) δ: 1.61-1.65 (4H, m), 1.68-1.73 (2H, m), 3.68 (4H, brs), 4.53 (2H, s), 4.63 (2H, s), 6.78 (1H, s), 7.30-7.33 (1H, m), 7.34-7.39 (4H, m). | Ref. Ex. 1173 |

TABLE 2-continued

| Ref. Ex. No | STR | 1H-NMR | ref. |
|---|---|---|---|
| 2207 | | 1H-NMR (CDCl3) δ: 1.62-1.66 (4H, m), 1.69-1.75 (2H, m), 2.85 (1H, t, J = 5.4 Hz), 3.69 (4H, bre), 4.64 (2H, d, J= 5.4 Hz), 6.62 (1H.s). | Ref. Ex. 750 |
| 2208 | | 1H-NMR (CDCl3) δ: 1.65-1.69 (4H, m), 1.73-1.78 (2H, m), 3.49-3.99 (4H. m), 7.12 (1H, s), 9.94 (1H, s). | Ref. Ex. 159 |
| 2209 | | 1H-NMR (CDCl3) δ: 3.13 (3H, s), 3.99 (3H, s), 3.99 (3H, s), 5.13 (2H, d, J = 0.8 Hz), 6.52 (1H, t, J = 0.8 Hz). | Ref. Ex. 103 |
| 2210 | | 1H-NMR (CDCl3) δ: 3.97 (3H, s), 4.01 (3H, m), 5.07 (2H, d, J = 0.9 Hz), 6.56 (1H, t, J = 0.9 Hz), 7.23-7.26 (1H, m), 7.44-7.45 (1H, m), 7.48-7.53 (2H, m), 9.98 (1H, s). | Ref. Ex. 82 |
| 2211 | | 1H-NMR (CDCl3) δ: 6.59 (1H, t, J = 73.4 Hz), 7.21-7.23 (1H, m), 7.37 (1H, s), 7.46-7.52 (2H, m), 7.66 (1H, s), 7.74 (1H, s), 8.02 (1H, s), 10.09 (1H, s). | Ref. Ex. 75 |

TABLE 2-continued

| Ref. Ex. No | STR | 1H-NMR | ref. |
|---|---|---|---|
| 2212 | | 1H-NMR (CDCl3) δ: 4.05-4.13 (2H, m), 4.15-4.23 (2H, m), 6.08 (1H, s), 7.34-7.41 (2H, m), 7.45 (1H, d, J = 0.4 Hz), 7.81-7.84 (1H, m), 8.00-8.01 (1H, m). | Ref. Ex. 116 |
| 2215 | | 1H-NMR (CDCl3) δ: 7.46 (1H, t, J = 7.8 Hz), 7.52-7.54 (1H, m), 7.85-7.87 (1H, m), 8.04 (1H, t, J = 1.8 Hz), 10.21 (1H, s). | Ref. Ex. 151 |
| 2216 | | 1H-NMR (CDCl3) δ: 5.37 (2H, s), 7.48-7.53 (2H, m), 7.60-7.65 (2H, m), 7.72-7.78 (3H, m), 10.03 (1H, s). | Ref. Ex. 82 |

Example 1

Synthesis of 5-(3-chloro-5-cyclopropylmethyl-phenyl)-3H-[1,2,3]triazole-4-carbonitrile To a solution of 3-chloro-5-cyclopropylmethyl-benzaldehyde (238 mg, 1.223 mmol) in toluene (7 ml) were added phenylsulfonylacetonitrile (222 mg, 1.223 mmol) and AcOK (120 mg, 1.223 mmol). After the reaction mixture was stirred for 1.5 hr at 80° C., it was concentrated in vacuo. DMF (1.5 ml) and sodium azide (119 mg, 1.834 mmol) were added to the residue and stirring was continued for 1 hr at 110° C. Saturated aqueous NH$_4$Cl solution was added to the reaction mixture, and the mixture was extracted twice with AcOEt. The combined organic layers were washed with water (twice) and brine, dried over Na$_2$SO$_4$, and concentrated in vacuo. The residue obtained was purified by silica gel flash column chromatography (Hexane:AcOEt=90:10-35:65) to give the title compound (296 mg, 94%) as a brown oil.

$^1$H-NMR (CDCl$_3$) δ: 0.24-0.27 (2H, m), 0.59-0.63 (2H, m), 0.99-1.06 (1H, m), 2.62 (2H, d, J=7.0 Hz), 7.38-7.40 (1H, m), 7.79-7.83 (2H, m).

Example 2

Synthesis of 5-[3-(4,4,4-trifluoro-butoxy)-5-trifluoromethyl-phenyl]-3H-[1,2,3]triazole-4-carbonitrile To a solution of 220 mg of 3-(4,4,4-trifluoro-butoxy)-5-trifluoromethyl-benzaldehyde in 4 mL of toluene were added 139 mg of phenylsulfonylacetonitrile and 36.0 mg of AcOK. The reaction mixture was stirred at 80° C. for 2 hr. After cooling to 40° C., 2 mL of NMP and 57.2 mg of sodium azide were added and the reaction mixture was stirred at 80° C. for 2 hr. The reaction was quenched by addition of 5 wt % aqueous NaHCO$_3$ solution, and then the mixture was washed with toluene. The aqueous solution was acidified with 5N HCl and extracted with TBME. The organic phase was washed with water and brine, and concentrated to give a dark red oil. The oil was purified by silica gel column chromatography (Hexane/AcOEt 5%->Hexane/AcOEt 40%) to give the title compound (232 mg) as a white solid. The white solid was recrystallized (hexane/CH$_2$Cl$_2$) to afford the title compound (164 mg, 61%) as a white powder.

Melting point 84-87° C.

Example 3

Synthesis of 5-(3-cyclohexylmethoxymethyl-phenyl)-3H-[1,2,3]triazole-4-carbonitrile The title compound was obtained using 3-cyclohexylmethoxymethyl-benzaldehyde in the same manner as in Example 1.

white powder

Melting point 101.3-104.8° C.

Example 4

Synthesis of 5-(4-chloro-3'-trifluoromethyl-biphenyl-2-yl)-3H-[1,2,3]triazole-4-carbonitrile The title compound was obtained using 4-chloro-3'-trifluoromethyl-biphenyl-2-carbaldehyde in the same manner as in Example 2.

white solid (hexane/AcOEt)

Melting point 156-159° C.

Example 5

Synthesis of 5-[2-(3,5-bis-trifluoromethyl-benzyl)-phenyl]-3H-[1,2,3]triazole-4-carbonitrile The title compound was obtained using 2-(3,5-bis-trifluoromethyl-benzyl)-benzaldehyde in the same manner as in Example 1.
white powder (hexane)
$^1$H-NMR (DMSO-$d_6$) δ: 4.26 (2H, s), 7.47-7.60 (6H, m), 7.89 (1H, s).

Example 6

Synthesis of 5-[2-((E)-styryl)-5-trifluoromethyl-phenyl]-3H-[1,2,3]triazole-4-carbonitrile The title compound was obtained using 2-((E)-styryl)-5-trifluoromethyl-benzaldehyde in the same manner as in Example 1.
white solid
Melting point 206.0-206.3° C.

Example 7

Synthesis of 5-(2-phenethyl-5-trifluoromethyl-phenyl)-3H-[1,2,3]triazole-4-carbonitrile To a solution of 138 mg of 5-[2-((E)-styryl)-5-trifluoromethyl-phenyl]-3H-[1,2,3]triazole-4-carbonitrile in 4 ml of EtOH was added 40 mg of 5% Pd/C (56% wet). The reaction mixture was stirred at room temperature under hydrogen for 2 hr and then filtered through a Celite pad followed by concentration to give a crude product. The crude product was purified by silica gel column chromatography (Hexane/AcOEt 10%->Hexane/AcOEt 30%) to give the title compound as a white solid. The white solid was recrystallized (hexane/AcOEt) to afford the title compound (88 mg, 64%) as a white powder.
Melting point 121-124° C.

Example 8

Synthesis of 5-{5-chloro-2-[(E)-2-(3-trifluoromethyl-phenyl)-vinyl]-phenyl}-3H-[1,2,3]triazole-4-carbonitrile The title compound was obtained using 5-chloro-2-[(E)-2-(3-trifluoromethyl-phenyl)-vinyl]-benzaldehyde in the same manner as in Example 2.
white solid (hexane/AcOEt)
Melting point 151-154° C.

Example 9

Synthesis of 5-[5-fluoro-2-(3-fluoro-5-trifluoromethyl-benzyloxy)-3-methyl-phenyl]-3H-[1,2,3]triazole-4-carbonitrile The title compound was obtained using 5-fluoro-2-(3-fluoro-5-trifluoromethyl-benzyloxy)-3-methyl-benzaldehyde in the same manner as in Example 1.
beige powder (hexane-AcOEt)
$^1$H-NMR (DMSO-$d_6$) δ: 2.39 (3H, s), 4.77 (2H, s), 7.28-7.43 (4H, m), 7.60-7.63 (1H, m).

Example 10

Synthesis of 5-(3-(thiophen-3-yl)-5-trifluoromethyl-phenyl)-3H-[1,2,3]triazole-4-carbonitrile The title compound was obtained using 3-(thiophen-3-yl)-5-trifluoromethyl-benzaldehyde in the same manner as in Example 1.
white powder (hexane)
Melting point 126.9-129.4° C.

Example 11

Synthesis of 5-[3-methyl-5-(6-trifluoromethyl-pyridin-3-yl)-phenyl]-3H-[1,2,3]triazole-4-carbonitrile The title compound was obtained using 3-methyl-5-(6-trifluoromethyl-pyridin-3-yl)-benzaldehyde in the same manner as in Example 1.
white powder (AcOEt-hexane)
Melting point 229-230° C.

Example 12

Synthesis of 5-[3-cyclopropyl-5-(6-trifluoromethyl-pyridin-3-yl)-phenyl]-3H-[1,2,3]triazole-4-carbonitrile The title compound was obtained using 3-cyclopropyl-5-(6-trifluoromethyl-pyridin-3-yl)-benzaldehyde in the same manner as in Example 1.
pale brown powder (AcOEt-hexane)
$^1$H-NMR (DMSO-$d_6$) δ: 0.88-0.93 (2H, m), 1.07-1.11 (2H, m), 2.10-2.17 (1H, m), 7.66 (1H, s), 7.71 (1H, s), 8.01-8.03 (1H, m), 8.05-8.07 (1H, m), 8.41-8.45 (1H, m), 8.15 (1H, d, J=1.9 Hz).

Example 13

Synthesis of 5-[3-tert-butyl-5-(5-trifluoromethyl-pyridin-2-yl)-phenyl]-3H-[1,2,3]triazole-4-carbonitrile The title compound was obtained using 3-tert-butyl-5-(5-trifluoromethyl-pyridin-2-yl)-benzaldehyde in the same manner as in Example 1.
white powder (AcOEt-hexane)
Melting point 171-174° C.

Example 14

Synthesis of 5-[3-trifluoromethyl-5-(6-trifluoromethyl-pyridin-2-yl)-phenyl]-3H-[1,2,3]triazole-4-carbonitrile The title compound was obtained using 3-trifluoromethyl-5-(6-trifluoromethyl-pyridin-2-yl)-benzaldehyde in the same manner as in Example 2.
white powder (hexane/AcOEt)
Melting point 151-154° C.

Example 15

Synthesis of 5-[3-methoxy-5-(4-trifluoromethyl-pyridin-2-yl)-phenyl]-3H-[1,2,3]triazole-4-carbonitrile The title compound was obtained using 3-methoxy-5-(4-trifluoromethyl-pyridin-2-yl)-benzaldehyde in the same manner as in Example 1.
white powder
Melting point 209-211° C.

Example 16

Synthesis of 5-[2-ethoxy-5-(6-trifluoromethyl-pyridin-3-yl)-phenyl]-3H-[1,2,3]triazole-4-carbonitrile The title compound was obtained using 2-ethoxy-5-(6-trifluoromethyl-pyridin-3-yl)-benzaldehyde in the same manner as in Example 1.
pale brown powder (AcOEt-hexane)
Melting point 207-209° C.

Example 17

Synthesis of 5-[4-isopropoxy-3-(6-trifluoromethyl-pyridin-3-yl)-phenyl]-3H-[(1,2,3]triazole-4-carbonitrile The title compound was obtained using 4-isopropoxy-3-(6-trifluoromethyl-pyridin-3-yl)-benzaldehyde in the same manner as in Example 1.
pale brown powder (AcOEt-hexane)
Melting point 239-242° C.

Example 18

Synthesis of 5-[3-cyclopropylmethoxy-5-(5-trifluoromethyl-pyridin-2-yl)-phenyl]-3H-[0,1,2,3]triazole-4-carbonitrile The title compound was obtained using 3-cyclopropylmethoxy-5-(5-trifluoromethyl-pyridin-2-yl)-benzaldehyde in the same manner as in Example 1.
white powder (IPA/hexane)
Melting point 168-171° C.

Example 19

Synthesis of 5-[3-cyclobutoxy-5-(6-trifluoromethyl-pyridin-3-yl)-phenyl]-3H-[1,2,3]triazole-4-carbonitrile The title compound was obtained using 3-cyclobutoxy-5-(6-trifluoromethyl-pyridin-3-yl)-benzaldehyde in the same manner as in Example 1.
white powder (AcOEt-hexane)
Melting point 222-224° C.

Example 20

Synthesis of 5-[3-(3-trifluoromethyl-benzyloxy)-5-(5-trifluoromethyl-pyridin-2-yl)-phenyl]-3H-[1,2,3]triazole-4-carbonitrile The title compound was obtained using 3-(3-trifluoromethyl-benzyloxy)-5-(5-trifluoromethyl-pyridin-2-yl)-benzaldehyde in the same manner as in Example 1.
pale yellow powder (hexane/$CH_2Cl_2$)
Melting point 210-212° C.

Example 21

Synthesis of 5-[3-(4-trifluoromethyl-pyrimidin-2-yl)-phenyl]-3H-[1,2,3]triazole-4-carbonitrile The title compound was obtained using 3-(4-trifluoromethyl-pyrimidin-2-yl)-benzaldehyde in the same manner as in Example 1.
beige powder ($CH_3CN$)
$^1$H-NMR (DMSO-$d_6$) δ: 7.84 (1H, t, J=7.8 Hz), 8.04 (1H, d, J=5.0 Hz), 8.13 (1H, d, J=7.8 Hz), 8.57 (1H, d, J=7.8 Hz), 9.00 (1H, s), 9.35 (1H, d, J=5.0 Hz).

Example 22

Synthesis of 5-[3-methyl-5-(4-trifluoromethyl-pyrimidin-2-yl)-phenyl]-3H-[1,2,3]triazole-4-carbonitrile The title compound was obtained using 3-methyl-5-(4-trifluoromethyl-pyrimidin-2-yl)-benzaldehyde in the same manner as in Example 1.
beige powder ($CH_3CN$)
$^1$H-NMR (CDCl$_3$) δ: 2.53 (3H, s), 7.94 (1H, s), 8.02 (1H, d, J=5.0 Hz), 8.38 (1H, s), 8.80 (1H, s), 9.32 (1H, d, J=5.0 Hz).

Example 23

Synthesis of 5-[3-chloro-5-(4-trifluoromethyl-pyrimidin-2-yl)-phenyl]-3H-[1,2,3]triazole-4-carbonitrile The title compound was obtained using 3-chloro-5-(4-trifluoromethyl-pyrimidin-2-yl)-benzaldehyde in the same manner as in Example 1.
beige powder (hexane-AcOEt)
$^1$H-NMR (DMSO-$d_6$) δ: 8.09 (1H, d, J=5.0 Hz), 8.15 (1H, s), 8.48 (1H, s), 8.92 (1H, s), 9.36 (1H, d, J=5.0 Hz).

Example 24

Synthesis of 5-[3-chloro-5-(4-trifluoromethyl-piperidin-1-yl)-phenyl]-3H-[1,2,3]triazole-4-carbonitrile The title compound was obtained using 3-chloro-5-(4-trifluoromethyl-piperidin-1-yl)-benzaldehyde in the same manner as in Example 1.
brown amorphous
$^1$H-NMR (CDCl$_3$) δ: 1.70-1.78 (2H, m), 2.00 (2H, d, J=12.5 Hz), 2.20-2.25 (1H, m), 2.84 (2H, t, J=12.5 Hz), 3.85 (2H, d, J=12.5 Hz), 6.99 (1H, s), 7.38 (1H, s), 7.40 (1H, s).

Example 25

Synthesis of 5-(3-(benzo[b]thiophen-3-yl)-5-chloro-phenyl)-3H-[1,2,3]triazole-4-carbonitrile The title compound was obtained using 3-(benzo[b]thiophen-3-yl)-5-chloro-benzaldehyde in the same manner as in Example 1.
beige powder (hexane-AcOEt)
$^1$H-NMR (DMSO-$d_6$) δ: 7.47-7.49 (2H, m), 7.87-7.88 (1H, m), 7.97-8.02 (2H, m), 8.08-8.14 (3H, m).

Example 26

Synthesis of 5-(3-(benzofuran-2-yl)-4-fluoro-phenyl)-3H-[1,2,3]triazole-4-carbonitrile The title compound was obtained using 3-(benzofuran-2-yl)-4-fluoro-benzaldehyde in the same manner as in Example 1.
pink powder (AcOEt-hexane)
Melting point 224-225° C.

Example 27

Synthesis of 5-[3-(5-fluoro-benzoxazol-2-yl)-phenyl]-3H-[1,2,3]triazole-4-carbonitrile The title compound was obtained using 3-(5-fluoro-benzoxazol-2-yl)-benzaldehyde in the same manner as in Example 1.
beige powder (AcOEt)
Melting point 292° C.

Example 28

Synthesis of 5-(5-fluoro-3'-trifluoromethyl-biphenyl-3-yl)-3H-[1,2,3]triazole-4-carbonitrile The title compound was obtained using 5-fluoro-3'-trifluoromethyl-biphenyl-3-carbaldehyde in the same manner as in Example 1.
white powder (hexane-AcOEt)
$^1$H-NMR (DMSO-$d_6$) δ: 7.71-7.90 (4H, m), 8.10-8.12 (3H, m).

Example 29

Synthesis of 5-(5-chloro-4'-trifluoromethoxy-biphenyl-3-yl)-3H-[1,2,3]triazole-4-carbonitrile The title compound was obtained using 5-chloro-4'-trifluoromethoxy-biphenyl-3-carbaldehyde in the same manner as in Example 1.
beige amorphous
$^1$H-NMR (DMSO-$d_6$) δ: 7.54 (2H, d, J=8.2 Hz), 7.90-7.98 (4H, m), 8.12-8.13 (1H, m).

Example 30

Synthesis of 5-[3-chloro-5-(2,2-difluoro-benzo[1,3]dioxol-5-yl)-phenyl]-3H-[1,2,3]triazole-4-carbonitrile The title compound was obtained using 3-chloro-5-(2,2-difluoro-benzo[1,3]dioxol-5-yl)-benzaldehyde in the same manner as in Example 1.
beige powder (hexane-AcOEt)
$^1$H-NMR (DMSO-$d_6$) δ: 7.56-7.65 (2H, m), 7.89-7.91 (2H, m), 7.96 (1H, s), 8.11 (1H, s).

Example 31

Synthesis of 5-(5'-fluoro-5-methyl-3'-trifluoromethyl-biphenyl-3-yl)-3H-[1,2,3]triazole-4-carbonitrile The title compound was obtained using 5'-fluoro-5-methyl-3'-trifluoromethyl-biphenyl-3-carbaldehyde in the same manner as in Example 1.
white granules (hexane-AcOEt)
$^1$H-NMR (DMSO-$d_6$) δ: 2.49 (3H, s), 7.75 (1H, s), 7.76 (1H, s), 7.86 (1H, s), 7.95 (1H, s), 7.98 (1H, s), 8.06 (1H, s).

Example 32

Synthesis of 5-(3',4'-difluoro-6-methoxy-biphenyl-3-yl)-3H-[1,2,3]triazole-4-carbonitrile The title compound was obtained using 3',4'-difluoro-6-methoxy-biphenyl-3-carbaldehyde in the same manner as in Example 1.
white powder (EtOH)
Melting point 266-267° C.

Example 33

Synthesis of 5-(5-ethoxymethyl-4'-fluoro-biphenyl-3-yl)-3H-[1,2,3]triazole-4-carbonitrile The title compound was obtained using 5-ethoxymethyl-4'-fluoro-biphenyl-3-carbaldehyde in the same manner as in Example 1.
pale brown powder (AcOEt-hexane)
Melting point 138-140° C.

Example 34

Synthesis of 5-[3-(4-fluoro-benzyl)-5-trifluoromethoxy-phenyl]-3H-[1,2,3]triazole-4-carbonitrile The title compound was obtained using 3-(4-fluoro-benzyl)-5-trifluoromethoxy-benzaldehyde in the same manner as in Example 1.
colorless oil
$^1$H-NMR (CDCl$_3$) δ: 4.05 (2H, s), 6.99-7.06 (2H, m), 7.14-7.20 (3H, m), 7.70 (1H, s), 7.76 (1H, s).

Example 35

Synthesis of 5-[3-(2,5-bis-trifluoromethyl-benzyl)-5-chloro-phenyl]-3H-[1,2,3]triazole-4-carbonitrile The title compound was obtained using 3-(2,5-bis-trifluoromethyl-benzyl)-5-chloro-benzaldehyde in the same manner as in Example 1.
white powder (hexane)
$^1$H-NMR (DMSO-$d_6$) δ: 4.40 (2H, s), 7.50 (1H, s), 7.52 (1H, s), 7.76 (1H, s), 7.91 (1H, d, J=8.3 Hz), 7.93 (1H, s), 8.03 (1H, d, J=8.3 Hz).

Example 36

Synthesis of 5-[3-(2,3-dihydro-indol-1-ylmethyl)-phenyl]-3H-[1,2,3]triazole-4-carbonitrile The title compound was obtained using 3-(2,3-dihydro-indol-1-ylmethyl)-benzaldehyde in the same manner as in Example 1.
pale brown powder ($CH_2Cl_2$-hexane)
$^1$H-NMR ($CDCl_3$) δ: 3.01 (2H, t, J=8.3 Hz), 3.38 (2H, t, J=8.3 Hz), 4.34 (2H, s), 6.50 (1H, d, J=7.7 Hz), 6.70 (1H, t, J=7.5 Hz), 7.06 (1H, t, J=7.7 Hz), 7.12 (1H, d, J=7.5 Hz), 7.50-7.52 (2H, m), 7.86-7.89 (1H, m), 7.95 (1H, s).

Example 37

Synthesis of 5-(3-phenoxy-5-trifluoromethyl-phenyl)-3H-[1,2,3]triazole-4-carbonitrile The title compound was obtained using 3-phenoxy-5-trifluoromethyl-benzaldehyde in the same manner as in Example 1.
white powder (toluene-hexane)
$^1$H-NMR ($CDCl_3$) δ: 7.10 (2H, m), 7.24 (1H, m), 7.34 (1H, s), 7.44 (2H, t, J=7.9 Hz), 7.77 (1H, s), 7.94 (1H, s).

Example 38

Synthesis of 5-[3-(4-chloro-phenylsulfanyl)-phenyl]-3H-[1,2,3]triazole-4-carbonitrile The title compound was obtained using 3-(4-chloro-phenylsulfanyl)-benzaldehyde in the same manner as in Example 1.
brown prisms (hexane-$Et_2O$)
Melting point 134-138° C.

Example 39

Synthesis of 5-{3-trifluoromethyl-5-[2-(6-trifluoromethyl-pyridin-2-yl)-ethyl]-phenyl}-3H-[1,2,3]triazole-4-carbonitrile The title compound was obtained using 3-trifluoromethyl-5-[2-(6-trifluoromethyl-pyridin-2-yl)-ethyl]-benzaldehyde in the same manner as in Example 2.
brown amorphous (hexane/$CH_2Cl_2$)
$^1$H-NMR (DMSO-$d_6$) δ: 3.25 (4H, s), 7.62 (1H, d, J=7.8 Hz), 7.72 (1H, d, J=7.8 Hz), 7.78 (1H, s), 7.97-8.01 (2H, m), 8.05 (1H, s).

Example 40

Synthesis of 5-{3-[2-(2,4-difluoro-phenyl)-ethyl]-phenyl}-3H-[1,2,3]triazole-4-carbonitrile The title compound was obtained using 3-[2-(2,4-difluoro-phenyl)-ethyl]-benzaldehyde in the same manner as in Example 2.
pale yellow solid (hexane/AcOEt)
Melting point 146-147° C.

Example 41

Synthesis of 5-{3-[(E)-2-(4-cyano-phenyl)-vinyl]-phenyl}-3H-[1,2,3]triazole-4-carbonitrile The title compound was obtained using 4-[(E)-2-(3-formyl-phenyl)-vinyl]-benzonitrile in the same manner as in Example 1.
pale yellow powder (AcOEt-hexane)
Melting point 215.5-217.6° C.

Example 42

Synthesis of 5-{2-chloro-3-[(E)-2-(3-trifluoromethyl-phenyl)-vinyl]-phenyl}-3H-[1,2,3]triazole-4-carbonitrile The title compound was obtained using 2-chloro-3-[(E)-2-(3-trifluoromethyl-phenyl)-vinyl]-benzaldehyde in the same manner as in Example 2.
light pink solid (hexane/AcOEt)
Melting point 187-190° C.

Example 43

Synthesis of 5-{2-ethoxy-3-[(E)-2-(3-trifluoromethyl-phenyl)-vinyl]-phenyl}-3H-[1,2,3]triazole-4-carbonitrile The title compound was obtained using 2-ethoxy-3-[(E)-2-(3-trifluoromethyl-phenyl)-vinyl]-benzaldehyde in the same manner as in Example 2.
white solid (hexane/AcOEt)
Melting point 192-194° C.

Example 44

Synthesis of 5-{3-[(E)-2-(4-ethoxy-phenyl)-vinyl]-phenyl}-3H-[1,2,3]triazole-4-carbonitrile The title compound was obtained using 3-[(E)-2-(4-ethoxy-phenyl)-vinyl]-benzaldehyde in the same manner as in Example 1.
white powder (AcOEt-hexane)
$^1$H-NMR ($CDCl_3$) δ: 1.44 (3H, t, J=7.0 Hz), 4.07 (2H, d, J=7.0 Hz), 6.89-6.94 (2H, m), 7.02 (1H, d, J=16.3 Hz), 7.16 (1H, d, J=16.3 Hz), 7.45-7.53 (3H, m), 7.60-7.65 (1H, m), 7.80-7.85 (1H, m), 8.07 (1H, brs).

Example 45

Synthesis of 5-{4-cyano-3-[(E)-2-(3-trifluoromethyl-phenyl)-vinyl]-phenyl}-3H-[1,2,3]triazole-4-carbonitrile The title compound was obtained using 4-formyl-2-[(E)-2-(3-trifluoromethyl-phenyl)-vinyl]-benzonitrile in the same manner as in Example 2.
light brown solid (hexane/AcOEt)
$^1$H-NMR (DMSO-$d_6$) δ: 7.60 (1H, d, J=16.4 Hz), 7.70 (1H, d, J=16.4 Hz), 7.70-7.76 (2H, m), 7.97 (1H, dd, J=1.7, 6.4 Hz), 8.02-8.04 (2H, m), 8.15 (1H, d, J=8.1 Hz), 8.46 (1H, d, J=1.6 Hz).

Example 46

Synthesis of 5-{4-trifluoromethyl-3-[(E)-2-(3-trifluoromethyl-phenyl)-vinyl]-phenyl}-3H-[1,2,3]triazole-4-carbonitrile The title compound was obtained using 4-trifluoromethyl-3-[(E)-2-(3-trifluoromethyl-phenyl)-vinyl]-benzaldehyde in the same manner as in Example 2.

white solid (hexane/AcOEt)

Melting point 196-199° C.

Example 47

Synthesis of 5-{3-chloro-5-[(E)-2-(3-trifluoromethyl-phenyl)-vinyl]-phenyl}-3H-[1,2,3]triazole-4-carbonitrile The title compound was obtained using 3-chloro-5-[(E)-2-(3-trifluoromethyl-phenyl)-vinyl]-benzaldehyde in the same manner as in Example 1.

white powder (hexane-AcOEt)

$^1$H-NMR (DMSO-$d_6$) δ: 7.53-7.57 (2H, m), 7.64-7.68 (2H, m), 7.82 (1H, s), 7.94-7.96 (2H, m), 8.02 (1H, s), 8.05 (1H, s).

Example 48

Synthesis of 5-{3-[(E)-2-(5-trifluoromethyl-pyridin-2-yl)-vinyl]-phenyl}-3H-[1,2,3]triazole-4-carbonitrile The title compound was obtained using 3-[(E)-2-(5-trifluoromethyl-pyridin-2-yl)-vinyl]-benzaldehyde in the same manner as in Example 2.

white solid (hexane/AcOEt)

Melting point 185-187° C.

Example 49

Synthesis of 5-{3-[(E)-2-(5-trifluoromethyl-pyridin-3-yl)-vinyl]-phenyl}-3H-[1,2,3]triazole-4-carbonitrile The title compound was obtained using 3-[(E)-2-(5-trifluoromethyl-pyridin-3-yl)-vinyl]-benzaldehyde in the same manner as in Example 2.

light orange powder (hexane/AcOEt)

Melting point 209-211° C.

Example 50

Synthesis of 5-(3-[(E)-2-(4-trifluoromethyl-pyridin-2-yl)-vinyl]-phenyl)-3H-(1,2,3)triazole-4-carbonitrile The title compound was obtained using 3-[(E)-2-(4-trifluoromethyl-pyridin-2-yl)-vinyl]-benzaldehyde in the same manner as in Example 2.

pale yellow solid (hexane/AcOEt)

Melting point 192-196° C.

Example 51

Synthesis of 5-{3-trifluoromethyl-5-[(E)-2-(6-trifluoromethyl-pyridin-2-yl)-vinyl]-phenyl}-3H-[1,2,3]triazole-4-carbonitrile The title compound was obtained using 3-trifluoromethyl-5-[(E)-2-(6-trifluoromethyl-pyridin-2-yl)-vinyl]-benzaldehyde in the same manner as in Example 2.

light brown solid (hexane/AcOEt)

Melting point 213-216° C.

Example 52

Synthesis of 5-{3-[(E)-2-(4-trifluoromethyl-pyrimidin-2-yl)-vinyl]-phenyl}-3H-[1,2,3]triazole-4-carbonitrile The title compound was obtained using 3-[(E)-2-(4-trifluoromethyl-pyrimidin-2-yl)-vinyl]-benzaldehyde in the same manner as in Example 2.

pale yellow solid (hexane/AcOEt)

Melting point 201-204° C.

Example 53

Synthesis of 5-{3-[(Z)-2-(3,5-bis-trifluoromethyl-phenyl)-vinyl]-phenyl}-3H-[1,2,3]triazole-4-carbonitrile The title compound was obtained using 3-[(Z)-2-(3,5-bis-trifluoromethyl-phenyl)-vinyl]-benzaldehyde in the same manner as in Example 1.

white powder (CH$_2$Cl$_2$-hexane)

Melting point 143.9-146.7° C.

Example 54

Synthesis of 5-(3-{[N-(4-fluoro-phenyl)-N-methyl-amino]-methyl}-phenyl)-3H-[1,2,3]triazole-4-carbonitrile The title compound was obtained using 3-{[N-(4-fluoro-phenyl)-N-methyl-amino]-methyl}-benzaldehyde in the same manner as in Example 2.

white solid (hexane/CH$_2$Cl$_2$)

Melting point 122-124° C.

Example 55

Synthesis of 5-[3-(4-trifluoromethyl-pyridin-2-yloxymethyl)-phenyl]-3H-[1,2,3]triazole-4-carbonitrile The title compound was obtained using 3-(4-trifluoromethyl-pyridin-2-yloxymethyl)-benzaldehyde in the same manner as in Example 2.

pale yellow solid (AcOEt-hexane)

Melting point 147.3-147.4° C.

Example 56

Synthesis of 5-[3-(5-trifluoromethyl-pyridin-2-yloxymethyl)-phenyl]-3H-[1,2,3]triazole-4-carbonitrile The title compound was obtained using 3-(5-trifluoromethyl-pyridin-2-yloxymethyl)-benzaldehyde in the same manner as in Example 2.
light yellow solid (AcOEt-hexane)
Melting point 134.4-134.6° C.

Example 57

Synthesis of 5-[3-(3,5-bis-trifluoromethyl-phenoxymethyl)-phenyl]-3H-[1,2,3]triazole-4-carbonitrile The title compound was obtained using 3-(3,5-bis-trifluoromethyl-phenoxymethyl)-benzaldehyde in the same manner as in Example 1.
slightly brown powder (hexane-AcOEt)
$^1$H-NMR (DMSO-$d_6$) δ: 5.43 (2H, s), 7.64-7.70 (5H, m), 7.87-7.91 (1H, m), 8.03 (1H, s).

Example 58

Synthesis of 5-{3-[N-(3,5-bis-trifluoromethyl-benzyl)-N-methyl-amino]-phenyl}-3H-[1,2,3]triazole-4-carbonitrile The title compound was obtained using 3-[N-(3,5-bis-trifluoromethyl-benzyl)-N-methyl-amino]-benzaldehyde in the same manner as in Example 1.
white powder (CH$_3$CN)
$^1$H-NMR (DMSO-$d_6$) δ: 3.13 (3H, s), 4.84 (2H, s), 6.93-6.97 (1H, m), 7.18 (1H, t, J=7.6 Hz), 7.21-7.22 (1H, m), 7.40 (1H, t, J=7.6 Hz), 7.88 (2H, s), 8.00 (1H, s).

Example 59

Synthesis of 5-[3-(benzofuran-2-ylmethoxy)-phenyl]-3H-[1,2,3]triazole-4-carbonitrile The title compound was obtained using 3-(benzofuran-2-ylmethoxy)-benzaldehyde in the same manner as in Example 1.
beige powder (AcOEt-hexane)
Melting point 176-177° C.

Example 60

Synthesis of 5-[3-(2,5-bis-trifluoromethyl-benzyl oxy)-phenyl]-3H-[1,2,3]triazole-4-carbonitrile The title compound was obtained using 3-(2,5-bis-trifluoromethyl-benzyloxy)-benzaldehyde in the same manner as in Example 1.
slightly yellow granules (CH$_3$CN)
Melting point 180° C.

Example 61

Synthesis of 5-[3-(2-methoxy-benzyloxy)-5-trifluoromethyl-phenyl]-3H-[1,2,3]triazole-4-carbonitrile The title compound was obtained using 3-(2-methoxy-benzyloxy)-5-trifluoromethyl-benzaldehyde in the same manner as in Example 2.
white solid (hexane/CH$_2$Cl$_2$)
$^1$H-NMR (DMSO-$d_6$) δ: 3.84 (3H, s), 5.23 (2H, s), 7.02 (1H, d, J=7.4 Hz), 7.08 (1H, d, J=8.2 Hz), 7.38 (1H, t, J=8.2 Hz), 7.45 (1H, d, J=7.4 Hz), 7.55 (1H, s), 7.77 (2H, s).

Example 62

Synthesis of 5-[3-(2,5-bis-trifluoromethyl-benzyloxy)-5-methoxy-phenyl]-3H-[1,2,3]triazole-4-carbonitrile The title compound was obtained using 3-(2,5-bis-trifluoromethyl-benzyloxy)-5-methoxy-benzaldehyde in the same manner as in Example 2.
white powder (hexane/TBME)
Melting point 168-169° C.

Example 63

Synthesis of 5-[3-(2,5-bis-trifluoromethyl-benzyloxy)-5-trifluoromethyl-phenyl]-3H-[1,2,3]triazole-4-carbonitrile The title compound was obtained using 3-(2,5-bis-trifluoromethyl-benzyloxy)-5-trifluoromethyl-benzaldehyde in the same manner as in Example 1.
white powder (hexane/AcOEt)
Melting point 125° C.

Example 64

Synthesis of 5-[3-(1-phenyl-ethoxy)-5-trifluoromethyl-phenyl]-3H-[1,2,3]triazole-4-carbonitrile The title compound was obtained using 3-(1-phenyl-ethoxy)-5-trifluoromethyl-benzaldehyde in the same manner as in Example 2.
light yellow powder (hexane/CH$_2$Cl$_2$)
Melting point 105-108° C.

Example 65

Synthesis of 5-[3-(4-trifluoromethoxy-benzylsulfanylmethyl)-phenyl]-3H-[1,2,3]triazole-4-carbonitrile The title compound was obtained using 3-(4-trifluoromethoxy-benzylsulfanylmethyl)-benzaldehyde in the same manner as in Example 2.
light brown solid (hexane/CH$_2$Cl$_2$)
Melting point 95-97° C.

Example 66

Synthesis of 5-{3-[2-(5-trifluoromethyl-pyridin-2-yloxy)-ethyl]-phenyl}-3H-[1,2,3]triazole-4-carbonitrile
The title compound was obtained using 3-[2-(5-trifluoromethyl-pyridin-2-yloxy)-ethyl]-benzaldehyde in the same manner as in Example 2.
pale yellow solid (hexane/CH$_2$Cl$_2$)
Melting point 115.2-115.3° C.

Example 67

Synthesis of 5-[3-(1-methyl-2-phenyl-ethoxy)-5-trifluoromethyl-phenyl]-3H-[1,2,3]triazole-4-carbonitrile The title compound was obtained using 3-(1-methyl-2-phenyl-ethoxy)-5-trifluoromethyl-benzaldehyde in the same manner as in Example 2.
colorless oil
$^1$H-NMR (CDCl$_3$) δ: 1.41 (3H, d, J=6.1 Hz), 2.94 (1H, dd, J=6.2, 7.8 Hz), 3.15 (1H, dd, J=6.2, 7.8 Hz), 4.71-4.77 (1H, m), 7.22-7.33 (6H, m), 7.69 (1H, s), 7.79 (1H, s).

Example 68

Synthesis of 5-(3'-trifluoromethyl-biphenyl-4-yl)-3H-[1,2,3]triazole-4-carbonitrile The title compound was obtained using 3'-trifluoromethyl-biphenyl-4-carbaldehyde in the same manner as in Example 1.
slightly brown flakes (CH$_3$CN)
Melting point 248° C.

Example 69

Synthesis of 5-[4-(4-trifluoromethyl-pyridin-2-yl)-phenyl]-3H-[1,2,3]triazole-4-carbonitrile The title compound was obtained using 4-(4-trifluoromethyl-pyridin-2-yl)-benzaldehyde in the same manner as in Example 1.
colorless flakes (AcOEt)
Melting point 252-253° C.

Example 70

Synthesis of 5-[4-(4-trifluoromethyl-pyrimidin-2-yl)-phenyl]-3H-[1,2,3]triazole-4-carbonitrile The title compound was obtained using 4-(4-trifluoromethyl-pyrimidin-2-yl)-benzaldehyde in the same manner as in Example 1.
white granules (CH$_3$CN)
Melting point 236-237° C.

Example 71

Synthesis of 5-[3-methyl-4-(3-trifluoromethyl-benzyl)-phenyl]-3H-[1,2,3]triazole-4-carbonitrile The title compound was obtained using 3-methyl-4-(3-trifluoromethyl-benzyl)-benzaldehyde in the same manner as in Example 1.
pale brown powder (AcOEt-hexane)
Melting point 160-162° C.

Example 72

Synthesis of 5-[3-fluoro-4-(3-trifluoromethyl-phenoxy)-phenyl]-3H-[1,2,3]triazole-4-carbonitrile The title compound was obtained using 3-fluoro-4-(3-trifluoromethyl-phenoxy)-benzaldehyde in the same manner as in Example 1.
beige powder (hexane-AcOEt)
Melting point 149-151° C.

Example 73

Synthesis of 5-{2-fluoro-4-[(E)-2-(3-trifluoromethyl-phenyl)-vinyl]-phenyl}-3H-[1,2,3]triazole-4-carbonitrile The title compound was obtained using 2-fluoro-4-[(E)-2-(3-trifluoromethyl-phenyl)-vinyl]-benzaldehyde in the same manner as in Example 1.
white granules (AcOEt)
$^1$H-NMR (DMSO-d$_6$) δ: 7.56-7.85 (7H, m), 7.94-7.96 (1H, m), 8.00 (1H, s).

Example 74

Synthesis of 5-[4-(4-trifluoromethoxy-phenyl)-thiazol-2-yl]-3H-[1,2,3]triazole-4-carbonitrile The title compound was obtained using 4-(4-trifluoromethoxy-phenyl)-thiazole-2-carbaldehyde in the same manner as in Example 1.
pale yellow solid
$^1$H-NMR (DMSO-d$_6$) δ: 7.52-7.55 (2H, m), 8.17-8.20 (2H, m), 8.49 (1H, s).

Example 75

Synthesis of 5-[2-(4-chloro-phenyl)-thiazol-4-yl]-3H-[1,2,3]triazole-4-carbonitrile The title compound was obtained using 2-(4-chloro-phenyl)-thiazole-4-carbaldehyde in the same manner as in Example 1.
pale brown solid (AcOEt-hexane)
Melting point 221.3-223.8° C.

Example 76

Synthesis of 5-[2-(3-chloro-4-fluoro-phenyl)-thiazol-4-yl]-3H-[1,2,3]triazole-4-carbonitrile The title compound was obtained using 2-(3-chloro-4-fluoro-phenyl)-thiazole-4-carbaldehyde in the same manner as in Example 1.
white solid (AcOEt-hexane)
Melting point 233.8-236.2° C.

Example 77

Synthesis of 5-[2-(3,4-dichloro-phenyl)-thiazol-4-yl]-3H-[1,2,3]triazole-4-carbonitrile The title compound was obtained using 2-(3,4-dichloro-phenyl)-thiazole-4-carbaldehyde in the same manner as in Example 1.
white solid (AcOEt-hexane)
Melting point 237.7-243.2° C.

Example 78

Synthesis of 5-[2-(3-trifluoromethyl-phenyl)-thiazol-4-yl]-3H-[1,2,3]triazole-4-carbonitrile The title compound was obtained using 2-(3-trifluoromethyl-phenyl)-thiazole-4-carbaldehyde in the same manner as in Example 2.
white solid (AcOEt-hexane)
Melting point 212.8-217.1° C.

Example 79

Synthesis of 5-[2-(3-trifluoromethoxy-phenyl)-thiazol-4-yl]-3H-[1,2,3]triazole-4-carbonitrile The title compound was obtained using 2-(3-trifluoromethoxy-phenyl)-thiazole-4-carbaldehyde in the same manner as in Example 1.
white solid (AcOEt-hexane)
Melting point 222.3-224.2° C.

Example 80

Synthesis of 5-[2-(4-trifluoromethoxy-phenyl)-thiazol-4-yl]-3H-[1,2,3]triazole-4-carbonitrile The title compound was obtained using 2-(4-trifluoromethoxy-phenyl)-thiazole-4-carbaldehyde in the same manner as in Example 1.
white solid (AcOEt-hexane)
Melting point 191.1-192.8° C.

Example 81

Synthesis of 5-{2-[(E)-2-(3-trifluoromethyl-phenyl)-vinyl]-thiazol-4-yl}-3H-[1,2,3]triazole-4-carbonitrile The title compound was obtained using 2-[(E)-2-(3-trifluoromethyl-phenyl)-vinyl]-thiazole-4-carbaldehyde in the same manner as in Example 1.
white solid (AcOEt-hexane)
Melting point 206.8-211.2° C.

Example 82

Synthesis of 5-[2-(4-chloro-benzyloxy)-thiazol-4-yl]-3H-[1,2,3]triazole-4-carbonitrile The title compound was obtained using 2-(4-chloro-benzyloxy)-thiazole-4-carbaldehyde in the same manner as in Example 1.
white solid
$^1$H-NMR (DMSO-$d_6$) δ: 5.54 (2H, s), 7.48 (2H, d, J=8.4 Hz), 7.61 (2H, d, J=8.4 Hz), 7.71 (1H, s).

Example 83

Synthesis of 5-{2-[N-(4-chloro-phenyl)-N-methyl-amino]-thiazol-4-yl}-3H-[1,2,3]triazole-4-carbonitrile The title compound was obtained using 2-[N-(4-chloro-phenyl)-N-methyl-amino]-thiazole-4-carbaldehyde in the same manner as in Example 1.
white solid (AcOEt-hexane)
$^1$H-NMR (DMSO-$d_6$) δ: 3.55 (3H, s), 7.45 (1H, s), 7.50-7.53 (2H, m), 7.63-7.66 (2H, m).

Example 84

Synthesis of 5-{2-[N-ethyl-N-(3-trifluoromethyl-phenyl)-amino]-thiazol-4-yl}-3H-[1,2,3]triazole-4-carbonitrile The title compound was obtained using 2-[N-ethyl-N-(3-trifluoromethyl-phenyl)-amino]-thiazole-4-carbaldehyde in the same manner as in Example 1.
white solid (AcOEt-hexane)
Melting point 163.3-165.3° C.

Example 85

Synthesis of 5-[2-(3-trifluoromethyl-phenoxy)-thiazol-4-yl]-3H-[1,2,3]triazole-4-carbonitrile The title compound was obtained using 2-(3-trifluoromethyl-phenoxy)-thiazole-4-carbaldehyde in the same manner as in Example 1.
pale yellow solid
$^1$H-NMR (DMSO-$d_6$) δ: 7.71-7.78 (2H, m), 7.80-7.89 (2H, m), 7.93 (1H, s).

Example 86

Synthesis of 5-[2-(4-chloro-phenylsulfanyl)-thiazol-4-yl]-3H-[1,2,3]triazole-4-carbonitrile The title compound was obtained using 2-(4-chloro-phenylsulfanyl)-thiazole-4-carbaldehyde in the same manner as in Example 1.
white solid (AcOEt-hexane)
Melting point 192.7-194.7° C.

Example 87

Synthesis of 5-(2-hexyl-thiazol-4-yl)-3H-[1,2,3]triazole-4-carbonitrile

The title compound was obtained using 2-hexyl-thiazole-4-carbaldehyde in the same manner as in Example 1.
white solid
Melting point 87.3-89.7° C.

Example 88

Synthesis of 5-(2-(adamantan-1-yl)-thiazol-4-yl)-3H-[1,2,3]triazole-4-carbonitrile The title compound was obtained using 2-(adamantan-1-yl)-thiazole-4-carbaldehyde in the same manner as in Example 1.
white solid
Melting point 180.1-183.5° C.

Example 89

Synthesis of 5-[2-(4-chloro-phenyl)-5-methyl-thiazol-4-yl]-3H-[1,2,3]triazole-4-carbonitrile The title compound was obtained using 2-(4-chloro-phenyl)-5-methyl-thiazole-4-carbaldehyde in the same manner as in Example 1.
white solid (AcOEt-hexane)
$^1$H-NMR (DMSO-$d_6$) δ: 2.78 (3H, s), 7.61-7.64 (2H, m), 7.96-7.99 (2H, m).

Example 90

Synthesis of 5-[2-(3-chloro-4-fluoro-phenyl)-5-methyl-thiazol-4-yl]-3H-[1,2,3]triazole-4-carbonitrile The title compound was obtained using 2-(3-chloro-4-fluoro-phenyl)-5-methyl-thiazole-4-carbaldehyde in the same manner as in Example 1.
white solid (AcOEt-hexane)
Melting point 210.1-211.4° C.

Example 91

Synthesis of 5-[5-methyl-2-(3-trifluoromethyl-phenyl)-thiazol-4-yl]-3H-[1,2,3]triazole-4-carbonitrile The title compound was obtained using 5-methyl-2-(3-trifluoromethyl-phenyl)-thiazole-4-carbaldehyde in the same manner as in Example 1.
white solid (AcOEt-hexane)
Melting point 217.9-219.9° C.

Example 92

Synthesis of 5-[5-methyl-2-(4-trifluoromethyl-phenyl)-thiazol-4-yl]-3H-[1,2,3]triazole-4-carbonitrile The title compound was obtained using 5-methyl-2-(4-trifluoromethyl-phenyl)-thiazole-4-carbaldehyde in the same manner as in Example 1.
white solid (AcOEt-hexane)
Melting point 288.3-292.0° C.

Example 93

Synthesis of 5-[5-methyl-2-(5-trifluoromethyl-pyridin-2-yl)-thiazol-4-yl]-3H-[1,2,3]triazole-4-carbonitrile The title compound was obtained using 5-methyl-2-(5-trifluoromethyl-pyridin-2-yl)-thiazole-4-carbaldehyde in the same manner as in Example 1.
colorless powder (AcOEt)
$^1$H-NMR (DMSO-$d_6$) δ: 2.82 (3H, s), 8.29 (1H, d, J=8.3 Hz), 8.49 (1H, dd, J=1.8, 8.3 Hz), 9.06-9.07 (1H, m).

Example 94

Synthesis of 5-[5-methyl-2-(6-trifluoromethyl-pyridin-2-yl)-thiazol-4-yl]-3H-[1,2,3]triazole-4-carbonitrile The title compound was obtained using 5-methyl-2-(6-trifluoromethyl-pyridin-2-yl)-thiazole-4-carbaldehyde in the same manner as in Example 1.
beige powder
$^1$H-NMR (DMSO-$d_6$) δ: 2.82 (3H, s), 7.98 (1H, d, J=7.6 Hz), 8.31 (1H, t, J=7.6 Hz), 8.37 (1H, d, J=7.6 Hz).

Example 95

Synthesis of 5-[2-(5-chloro-pyridin-2-yl)-5-methyl-thiazol-4-yl]-3H-[1,2,3]triazole-4-carbonitrile The title compound was obtained using 2-(5-chloro-pyridin-2-yl)-5-methyl-thiazole-4-carbaldehyde in the same manner as in Example 1.
colorless powder (AcOEt)
$^1$H-NMR (DMSO-$d_6$) δ: 2.80 (3H, s), 8.12 (1H, dd, J=0.5, 8.5 Hz), 8.21 (1H, dd, J=2.4, 8.5 Hz), 8.73 (1H, dd, J=0.5, 2.4 Hz).

Example 96

Synthesis of 5-[5-methyl-2-(4-trifluoromethoxy-phenoxy)-thiazol-4-yl]-3H-[1,2,3]triazole-4-carbonitrile The title compound was obtained using 5-methyl-2-(4-trifluoromethoxy-phenoxy)-thiazole-4-carbaldehyde in the same manner as in Example 1.
pale yellow solid
$^1$H-NMR (DMSO-$d_6$) δ: 2.62 (3H, s), 7.45-7.48 (2H, m), 7.61-7.66 (2H, m).

Example 97

Synthesis of 5-[5-methyl-2-(3-trifluoromethyl-phenylsulfanyl)-thiazol-4-yl]-3H-[1,2,3]triazole-4-carbonitrile The title compound was obtained using 5-methyl-2-(3-trifluoromethyl-phenylsulfanyl)-thiazole-4-carbaldehyde in the same manner as in Example 1.
white solid
Melting point 118.5-121.7° C.

Example 98

Synthesis of 5-[2-(4-chloro-phenyl)-5-ethyl-thiazol-4-yl]-3H-[1,2,3]triazole-4-carbonitrile The title compound was obtained using 2-(4-chloro-phenyl)-5-ethyl-thiazole-4-carbaldehyde in the same manner as in Example 1.
white solid (AcCEt-hexane)
Melting point 253.4-255.8° C.

Example 99

Synthesis of 5-[5-ethyl-2-(3-trifluoromethyl-phenyl)-thiazol-4-yl]-3H-[1,2,3]triazole-4-carbonitrile The title compound was obtained using 5-ethyl-2-(3-trifluoromethyl-phenyl)-thiazole-4-carbaldehyde in the same manner as in Example 1.
white solid (AcOEt-hexane)
Melting point 185.7-188.5° C.

Example 100

Synthesis of 5-[5-ethyl-2-(5-trifluoromethyl-pyridin-2-yl)-thiazol-4-yl]-3H-[1,2,3]triazole-4-carbonitrile The title compound was obtained using 5-ethyl-2-(5-trifluoromethyl-pyridin-2-yl)-thiazole-4-carbaldehyde in the same manner as in Example 1.
white solid (AcOEt-hexane)
$^1$H-NMR (DMSO-$d_6$) δ: 1.35 (3H, t, J=7.5 Hz), 3.27 (2H, q, J=7.5 Hz), 8.28 (1H, d, J=8.3 Hz), 8.48-8.50 (1H, m), 9.05 (1H, s).

Example 101

Synthesis of 5-[5-ethyl-2-(6-trifluoromethyl-pyridin-3-yl)-thiazol-4-yl]-3H-[1,2,3]triazole-4-carbonitrile The title compound was obtained using 5-ethyl-2-(6-trifluoromethyl-pyridin-3-yl)-thiazole-4-carbaldehyde in the same manner as in Example 1.
beige powder
$^1$H-NMR (DMSO-$d_6$) δ: 1.32 (3H, t, J=7.9 Hz), 3.28-3.45 (2H, m), 8.00-8.08 (1H, m), 8.54 (1H, dd, J=4.6, 10.7 Hz), 9.30-9.31 (1H, m).

Example 102

Synthesis of 5-[2-(4-chloro-phenoxy)-5-ethyl-thiazol-4-yl]-3H-([1,2,3]triazole-4-carbonitrile The title compound was obtained using 2-(4-chloro-phenoxy)-5-ethyl-thiazole-4-carbaldehyde in the same manner as in Example 1.
white solid
$^1$H-NMR (DMSO-$d_6$) δ: 1.21-1.25 (3H, m), 3.07-3.11 (2H, m), 7.52-7.57 (4H, m).

Example 103

Synthesis of 5-[2-(4-chloro-phenyl)-5-propyl-thiazol-4-yl]-3H-[1,2,3]triazole-4-carbonitrile The title compound was obtained using 2-(4-chloro-phenyl)-5-propyl-thiazole-4-carbaldehyde in the same manner as in Example 1.
white solid (AcOEt-hexane)
Melting point 222.5-222.8° C.

Example 104

Synthesis of 5-[5-propyl-2-(3-trifluoromethyl-phenyl)-thiazol-4-yl]-3H-[1,2,3]triazole-4-carbonitrile The title compound was obtained using 5-propyl-2-(3-trifluoromethyl-phenyl)-thiazole-4-carbaldehyde in the same manner as in Example 1.
white solid
Melting point 177.0-178.2° C.

Example 105

Synthesis of 5-[2-(4-chloro-phenyl)-5-cyclopropyl-thiazol-4-yl]-3H-[1,2,3]triazole-4-carbonitrile The title compound was obtained using 2-(4-chloro-phenyl)-5-cyclopropyl-thiazole-4-carbaldehyde in the same manner as in Example 1.
white solid (AcOEt-hexane)
Melting point 268.0-271.2° C.

Example 106

Synthesis of 5-[2-(4-chloro-phenyl)-5-isobutyl-thiazol-4-yl]-3H-[1,2,3]triazole-4-carbonitrile The title compound was obtained using 2-(4-chloro-phenyl)-5-isobutyl-thiazole-4-carbaldehyde in the same manner as in Example 1.
white solid
$^1$H-NMR (DMSO-$d_6$) δ: 0.96 (6H, d, J=6.6 Hz), 1.94-2.00 (1H, m), 3.16 (2H, d, J=6.8 Hz), 7.63 (2H, d, J=8.5 Hz), 8.01 (2H, d, J=8.5 Hz).

Example 107

Synthesis of 5-[2-(4-chloro-phenyl)-5-(4-trifluoromethyl-phenyl)-thiazol-4-yl]-3H-[1,2,3]triazole-4-carbonitrile The title compound was obtained using 2-(4-chloro-phenyl)-5-(4-trifluoromethyl-phenyl)-thiazole-4-carbaldehyde in the same manner as in Example 1.
white solid (AcOEt-hexane)
Melting point 275.7-278.4° C.

Example 108

Synthesis of 5-[5-chloro-2-(3-trifluoromethyl-phenyl)-thiazol-4-yl]-3H-[1,2,3]triazole-4-carbonitrile To the solution of 5-[2-(3-trifluoromethyl-phenyl)-thiazol-4-yl]-3H-[1,2,3]triazole-4-carbonitrile (24 mg, 0.075 mmol) in $CH_3CN$ (4 ml) was added NCS (10.9 mg, 0.082 mmol). The reaction mixture was stirred at 50° C. for 5 hr. After concentration, saturated aqueous $NaHCO_3$ solution was added to the residue and the mixture was washed with toluene. Then the aqueous solution was acidified with 5N HCl and extracted with AcOEt. The combined organic layers were washed with brine, dried over $MgSO_4$, and concentrated in vacuo. The residue obtained was purified by Solid Phase Extraction (SAX) (AcOEt) to give the title compound (10 mg, 38%) as a white solid.
Melting point 204.1-205.5° C.

Example 109

Synthesis of 5-[5-chloro-2-(4-trifluoromethoxy-phenoxy)-thiazol-4-yl]-3H-[1,2,3]triazole-4-carbonitrile To a solution of 2-(4-trifluoromethoxy-phenoxy)-thiazole-4-carbaldehyde (118 mg, 0.408 mmol) in toluene (4 ml) were added phenylsulfonylacetonitrile (78 mg, 0.428 mmol) and AcOK (40 mg, 0.408 mmol). After the reaction mixture was refluxed for 1 hr, it was concentrated in vacuo. DMF (1.5 ml) and sodium azide (119 mg, 1.834 mmol) were added to the residue and stirring was continued for 0.5 hr at 50° C. and for 2 hr at room temperature. Aqueous HCl solution was added to the reaction mixture, and the mixture was extracted with AcOEt. The combined organic layers were washed with water and brine, dried over $MgSO_4$, and concentrated in vacuo. NCS (75 mg, 0.563 mmol) and DMF (4 ml) were added to the residue, and the reaction mixture was stirred for 3 days at room temperature. Water was added to the reaction mixture, and the mixture was extracted with AcOEt. The combined organic layers were washed with water and brine, dried over MgSO$_4$, and concentrated in vacuo. The residue was purified by flash column chromatography (Hexane:AcCEt=1:1-1:4) to give the title compound (66 mg, 42%) as a white solid.
Melting point 143.5-145.1° C.

Example 110

Synthesis of 5-[2-(4-chloro-phenyl)-5-methoxy-thiazol-4-yl]-3H-[1,2,3]triazole-4-carbonitrile The title compound was obtained using 2-(4-chloro-phenyl)-5-methoxy-thiazole-4-carbaldehyde in the same manner as in Example 1.
white solid (AcOEt-hexane)
$^1$H-NMR (DMSO-d$_6$) δ: 4.19 (3H, s), 7.62 (2H, d, J=8.5 Hz), 7.93 (2H, d, J=8.5 Hz).

Example 111

Synthesis of 5-[2-(3-trifluoromethyl-phenyl)-thiazol-5-yl]-3H-[1,2,3]triazole-4-carbonitrile The title compound was obtained using 2-(3-trifluoromethyl-phenyl)-thiazole-5-carbaldehyde in the same manner as in Example 1.
white solid
Melting point 196.8-198.6° C.

Example 112

Synthesis of 5-{2-[(E)-2-(3-trifluoromethyl-phenyl)-vinyl]-thiazol-5-yl}-3H-[1,2,3]triazole-4-carbonitrile The title compound was obtained using 2-[(E)-2-(3-trifluoromethyl-phenyl)-vinyl]-thiazole-5-carbaldehyde in the same manner as in Example 1.
pale yellow solid
$^1$H-NMR (DMSO-d$_6$) δ: 7.62-7.78 (4H, m), 8.06 (1H, d, J=7.5 Hz), 8.13 (1H, s), 8.20 (1H, s).

Example 113

Synthesis of 5-[2-(4-chloro-phenyl)-4-methyl-thiazol-5-yl]-3H-[1,2,3]triazole-4-carbonitrile The title compound was obtained using 2-(4-chloro-phenyl)-4-methyl-thiazole-5-carbaldehyde in the same manner as in Example 1.
white solid
Melting point 239.8-245.0° C.

Example 114

Synthesis of 5-[4-methyl-2-(3-trifluoromethyl-phenyl)-thiazol-5-yl]-3H-[1,2,3]triazole-4-carbonitrile The title compound was obtained using 4-methyl-2-(3-trifluoromethyl-phenyl)-thiazole-5-carbaldehyde in the same manner as in Example 1.
white solid
Melting point 188.2-192.0° C.

Example 115

Synthesis of 5-[2-(4-chloro-phenyl)-4-ethyl-thiazol-5-yl]-1H-[1,2,3]triazole-4-carbonitrile The title compound was obtained using 2-(4-chloro-phenyl)-4-ethyl-thiazole-5-carbaldehyde in the same manner as in Example 1.
white powder (EtOH-water)
Melting point 205.2-208.7° C.

Example 116

Synthesis of 5-[2-(3-chloro-4-fluoro-phenyl)-4-trifluoromethyl-thiazol-5-yl]-3H-[1,2,3]triazole-4-carbonitrile The title compound was obtained using 2-(3-chloro-4-fluoro-phenyl)-4-trifluoromethyl-thiazole-5-carbaldehyde in the same manner as in Example 1.
pale yellow solid
$^1$H-NMR (DMSO-d$_6$) δ: 7.65 (1H, t, J=8.9 Hz), 8.06-8.12 (1H, m), 8.27 (1H, dd, J=2.2, 7.0 Hz).

Example 117

Synthesis of 5-[2-(4-trifluoromethoxy-phenyl)-oxazol-4-yl]-3H-[1,2,3]triazole-4-carbonitrile The title compound was obtained using 2-(4-trifluoromethoxy-phenyl)-oxazole-4-carbaldehyde in the same manner as in Example 1.
white solid
Melting point 179.6-183.4° C.

Example 118

Synthesis of 5-[2-(4-chloro-phenyl)-5-methyl-oxazol-4-yl]-3H-[1,2,3]triazole-4-carbonitrile The title compound was obtained using 2-(4-chloro-phenyl)-5-methyl-oxazole-4-carbaldehyde in the same manner as in Example 2.
light brown solid (hexane/CH$_2$Cl$_2$)
$^1$H-NMR (DMSO-d$_6$) δ: 2.68 (3H, s), 7.64-7.67 (2H, m), 7.97-8.00 (2H, m).

Example 119

Synthesis of 5-[2-(4-chloro-phenyl)-5-propyl-oxazol-4-yl]-3H-[1,2,3]triazole-4-carbonitrile The title compound was obtained using 2-(4-chloro-phenyl)-5-propyl-oxazole-4-carbaldehyde in the same manner as in Example 2.
yellow solid (AcOEt-hexane)
$^1$H-NMR (DMSO-d$_6$) δ: 0.97 (3H, t, J=7.4 Hz), 1.72-1.82 (2H, m), 3.07 (2H, t, J=7.4 Hz), 7.66-7.68 (2H, m), 8.00-8.02 (2H, m).

Example 120

Synthesis of 5-[5-cyclopropyl-2-(3-trifluoromethyl-phenyl)-oxazol-4-yl]-3H-[1,2,3]triazole-4-carbonitrile The title compound was obtained using 5-cyclopropyl-2-(3-trifluoromethyl-phenyl)-oxazole-4-carbaldehyde in the same manner as in Example 2.
white solid (AcOEt-hexane)
Melting point 195.6-195.7° C.

Example 121

Synthesis of 5-[2-(3-chloro-phenyl)-5-cyclopropyl-oxazol-4-yl]-3H-[1,2,3]triazole-4-carbonitrile The title compound was obtained using 2-(3-chloro-phenyl)-5-cyclopropyl-oxazole-4-carbaldehyde in the same manner as in Example 2.
white solid (AcOEt-hexane)
Melting point 174.2-174.9° C.

Example 122

Synthesis of 5-[2-(4-chloro-phenyl)-5-isopropyl-oxazol-4-yl]-3H-[1,2,3]triazole-4-carbonitrile The title compound was obtained using 2-(4-chloro-phenyl)-5-isopropyl-oxazole-4-carbaldehyde in the same manner as in Example 2.
white solid (hexane/$CH_2Cl_2$)
Melting point 197-199° C.

Example 123

Synthesis of 5-[2-(4-fluoro-phenyl)-5-isopropyl-oxazol-4-yl]-3H-[1,2,3]triazole-4-carbonitrile The title compound was obtained using 2-(4-fluoro-phenyl)-5-isopropyl-oxazole-4-carbaldehyde in the same manner as in Example 2.
white solid (AcOEt-hexane)
Melting point 183-185° C.

Example 124

Synthesis of 5-[5-isopropyl-2-(4-trifluoromethoxy-phenyl)-oxazol-4-yl]-3H-[1,2,3]triazole-4-carbonitrile The title compound was obtained using 5-isopropyl-2-(4-trifluoromethoxy-phenyl)-oxazole-4-carbaldehyde in the same manner as in Example 2.
white solid (AcOEt-hexane)
Melting point 190.8-191.1° C.

Example 125

Synthesis of 5-[2-(3,4-difluoro-phenyl)-5-isobutyl-oxazol-4-yl]-3H-[1,2,3]triazole-4-carbonitrile To a solution of 2-(3,4-difluoro-phenyl)-5-isobutyl-oxazole-4-carbaldehyde (92.9 mg, 0.350 mmol) in DMF (3 ml) were added (phenylsulfonyl)acetonitrile (63.5 mg, 0.350 mmol) and sodium azide (34.2 mg, 0.525 mmol). After the reaction mixture was stirred for 1.5 hr at 80° C., saturated aqueous $NH_4Cl$ solution was added to the reaction mixture, and the mixture was extracted twice with AcOEt. The combined organic layers were washed with water twice and brine, dried over $Na_2SO_4$, and concentrated in vacuo. The crude product obtained was recrystallized from hexane-AcOEt to give the title compound (61.8 mg, 54%) as a pale brown powder.
pale brown powder (AcOEt-hexane)
$^1$H-NMR (CDCl$_3$) δ: 0.96 (6H, d, J=6.7 Hz), 2.12-2.17 (1H, m), 2.99 (2H, d, J=7.0 Hz), 7.66-7.71 (1H, m), 7.84-7.89 (1H, m), 7.93-7.97 (1H, m).

Example 126

Synthesis of 5-[3-(3,5-bis-trifluoromethyl-phenyl)-thiophen-2-yl]-3H-[1,2,3]triazole-4-carbonitrile The title compound was obtained using 3-(3,5-bis-trifluoromethyl-phenyl)-thiophene-2-carbaldehyde in the same manner as in Example 1.
brown powder (hexane-AcOEt)
$^1$H-NMR (DMSO-d$_6$) δ: 7.58 (1H, d, J=5.2 Hz), 8.00 (2H, s), 8.00-8.02 (1H, m), 8.10 (1H, s).

Example 127

Synthesis of 5-{3-[3-(2,5-bis-trifluoromethyl-benzyloxy)-phenyl]-thiophen-2-yl}-3H-[1,2,3]triazole-4-carbonitrile The title compound was obtained using 3-[3-(2,5-bis-trifluoromethyl-benzyloxy)-phenyl]-thiophene-2-carbaldehyde in the same manner as in Example 1.
pale yellow amorphous
$^1$H-NMR (DMSO-d$_6$) δ: 5.27 (2H, s), 6.89-6.91 (2H, m), 7.04 (1H, d, J=7.1 Hz), 7.34 (1H, t, J=7.6 Hz), 7.41 (1H, d, J=4.7 Hz), 7.94-8.10 (4H, m).

Example 128

Synthesis of 5-(4-phenyl-5-trifluoromethyl-thiophen-2-yl)-3H-[1,2,3]triazole-4-carbonitrile To a solution of 250 mg of (4-phenyl-5-trifluoromethyl-thiophen-2-yl)methanol and 1 ml of TEA in 2 ml of DMSO, 400 mg of $SO_3Py$ complex was added portionwise and the mixture was stirred at room temperature for 2 hr. Water was added to the reaction mixture, and the mixture was extracted with n-hexane. The organic layer was washed with water 3 times and purified by column chromatography on silica gel (n-hexane:AcOEt=9:1 to 2:1) to give 242 mg of colorless oil. The oil was dissolved in 3 ml of toluene, and then 110 mg of AcOK and 185 mg of phenylsulfonylacetonitrile were added to the solution. The mixture was stirred at 100° C. for 2 hr, and then concentrated. The residue was dissolved in 3 ml of DMF, and 180 mg of NaN$_3$ was added to the solution. The mixture was stirred at 110° C. for 2 hr. Saturated aqueous $NH_4Cl$ solution was added to the reaction mixture, and the mixture was extracted twice with AcOEt. The combined organic layers were washed with water (twice) and brine, dried over $Na_2SO_4$, and concentrated in vacuo. The residue obtained was purified by silica gel flash column chromatography (Hexane:AcOEt=9:1 to 2:1) to give the title compound (198 mg, 62%) as a white powder.
Melting point 140.6-142.10° C.

Example 129

Synthesis of 5-[5-(3-fluoro-5-trifluoromethyl-phenyl)-thiophen-2-yl]-3H-[1,2,3]triazole-4-carbonitrile The title compound was obtained using 5-(3-fluoro-5-trifluoromethyl-phenyl)-thiophene-2-carbaldehyde in the same manner as in Example 1.
slightly yellow powder ($CH_3CN$)
Melting point 189-192° C.

Example 130

Synthesis of 5-[4-methyl-5-(4-trifluoromethyl-phenyl)-thiophen-2-yl]-3H-[1,2,3]triazole-4-carbonitrile The title compound was obtained using 4-methyl-5-(4-trifluoromethyl-phenyl)-thiophene-2-carbaldehyde in the same manner as in Example 1.
white powder (hexane-AcCEt)
$^1$H-NMR (DMSO-$d_6$) δ: 2.39 (3H, s), 7.62 (1H, s), 7.80-7.85 (4H, m).

Example 131

Synthesis of 5-[5-(4-chloro-benzyl)-thiophen-2-yl]-3H-[1,2,3]triazole-4-carbonitrile The title compound was obtained using 5-(4-chloro-benzyl)-thiophene-2-carbaldehyde in the same manner as in Example 1.
brown powder ($CH_3CN$)
Melting point 173-175° C.

Example 132

Synthesis of 5-[5-(3-trifluoromethyl-phenoxy)-thiophen-2-yl]-3H-[1,2,3]triazole-4-carbonitrile The title compound was obtained using 5-(3-trifluoromethyl-phenoxy)-thiophene-2-carbaldehyde in the same manner as in Example 1.
brown powder (hexane-i-$Pr_2O$)
$^1$H-NMR (DMSO-$d_6$) δ: 6.89 (1H, d, J=4.0 Hz), 7.49 (1H, d, J=4.0 Hz), 7.52-7.55 (2H, m), 7.58 (1H, d, J=8.0 Hz), 7.66 (1H, t, J=8.0 Hz).

Example 133

Synthesis of 5-{5-[(E)-2-(3-trifluoromethyl-phenyl)-vinyl]-thiophen-2-yl}-3H-[1,2,3]triazole-4-carbonitrile The title compound was obtained using 5-[(E)-2-(3-trifluoromethyl-phenyl)-vinyl]-thiophene-2-carbaldehyde in the same manner as in Example 1.
yellow needles ($CH_3CN$)
$^1$H-NMR (DMSO-$d_6$) δ: 7.22 (1H, d, J=16.4 Hz), 7.39-7.40 (1H, m), 7.60-7.63 (3H, m), 7.76 (1H, d, J=16.4 Hz), 7.93-7.94 (1H, m), 8.01 (1H, s).

Example 134

Synthesis of 5-[4-(3,5-bis-trifluoromethyl-phenyl)-thiophen-3-yl]-3H-[1,2,3]triazole-4-carbonitrile The title compound was obtained using 4-(3,5-bis-trifluoromethyl-phenyl)-thiophene-3-carbaldehyde in the same manner as in Example 1.
pale yellow powder (hexane-AcOEt)
$^1$H-NMR (DMSO-$d_6$) δ: 7.88 (2H, s), 8.08 (1H, s), 8.17 (1H, d, J=3.2 Hz), 8.20 (1H, d, J=3.2 Hz).

Example 135

Synthesis of 5-{4-[(E)-2-(3-trifluoromethyl-phenyl)-vinyl]-furan-2-yl}-3H-[1,2,3]triazole-4-carbonitrile The title compound was obtained using 4-[(E)-2-(3-trifluoromethyl-phenyl)-vinyl]-furan-2-carbaldehyde in the same manner as in Example 1.
brown powder (hexane-AcOEt)
$^1$H-NMR (DMSO-$d_6$) δ: 7.25 (1H, d, J=16.5 Hz), 7.36 (1H, d, J=16.5 Hz), 7.48 (1H, s), 7.61-7.63 (2H, m), 7.87-7.89 (1H, m), 7.92 (1H, s), 8.19 (1H, s).

Example 136

Synthesis of 5-[5-(4-chloro-phenyl)-furan-2-yl]-3H-[1,2,3]triazole-4-carbonitrile The title compound was obtained using 5-(4-chloro-phenyl)-furan-2-carbaldehyde in the same manner as in Example 1.
pale yellow powder (AcOEt)
$^1$H-NMR (DMSO-$d_6$) δ: 7.23 (1H, d, J=3.6 Hz), 7.32 (1H, d, J=3.6 Hz), 7.59 (2H, d, J=8.7 Hz), 7.86 (2H, d, J=8.7 Hz).

Example 137

Synthesis of 5-{5-[(E)-2-(3-trifluoromethyl-phenyl)-vinyl]-furan-2-yl}-3H-[1,2,3]triazole-4-carbonitrile The title compound was obtained using 5-[(E)-2-(3-trifluoromethyl-phenyl)-vinyl]-furan-2-carbaldehyde in the same manner as in Example 1.
brown powder (hexane-AcOEt)
$^1$H-NMR (DMSO-$d_6$) δ: 6.86 (1H, d, J=3.6 Hz), 7.18 (1H, d, J=3.6 Hz), 7.24 (1H, d, J=16.4 Hz), 7.46 (1H, d, J=16.4 Hz), 7.60-7.65 (2H, m), 7.89-7.93 (1H, m), 7.94 (1H, s).

Example 138

Synthesis of 5-[1-(2,4-bis-trifluoromethyl-benzyl)-1H-pyrrol-2-yl]-3H-[1,2,3]triazole-4-carbonitrile The title compound was obtained using 1-(2,4-bis-trifluoromethyl-benzyl)-1H-pyrrole-2-carbaldehyde in the same manner as in Example 1.
white powder ($CH_2Cl_2$-hexane)
Melting point 120.5-123.0° C.

Example 139

Synthesis of 5-[5-(3-fluoro-5-trifluoromethyl-phenyl)-1-methyl-1H-pyrrol-2-yl]-3H-[1,2,3]triazole-4-carbonitrile The title compound was obtained using 5-(3-fluoro-5-trifluoromethyl-phenyl)-1-methyl-1H-pyrrole-2-carbaldehyde in the same manner as in Example 2.
brown solid (hexane/AcOEt)
Melting point 164-167° C.

Example 140

Synthesis of 5-[1-(2,5-bis-trifluoromethyl-phenyl)-1H-pyrrol-3-yl]-3H-[1,2,3]triazole-4-carbonitrile The title compound was obtained using 1-(2,5-bis-trifluoromethyl-phenyl)-1H-pyrrole-3-carbaldehyde in the same manner as in Example 2.
pale brown solid (hexane/AcOEt)
Melting point 171-174° C.

Example 141

Synthesis of 5-[6-(3-trifluoromethyl-phenyl)-pyridin-2-yl]-3H-[1,2,3]triazole-4-carbonitrile The title compound was obtained using 6-(3-trifluoromethyl-phenyl)-pyridine-2-carbaldehyde in the same manner as in Example 1.
brown powder ($CH_3CN$)
$^1$H-NMR (DMSO-$d_6$) δ: 7.78 (1H, t, J=7.8 Hz), 7.85 (1H, d, J=7.8 Hz), 8.05 (1H, d, J=7.8 Hz), 8.17 (1H, t, J=7.9 Hz), 8.30 (1H, d, J=7.9 Hz), 8.59 (1H, d, J=7.9 Hz), 8.77 (1H, s).

Example 142

Synthesis of 5-{6-[1-(4-trifluoromethyl-benzyloxy)-propyl]-pyridin-2-yl}-3H-[1,2,3]triazole-4-carbonitrile The title compound was obtained using 6-[1-(4-trifluoromethyl-benzyloxy)-propyl]-pyridine-2-carbaldehyde in the same manner as in Example 2.
dark blue oil
$^1$H-NMR (CDCl$_3$) δ: 0.98 (3H, t, J=7.4 Hz), 1.87-2.05 (2H, m), 4.50-4.61 (3H, m), 7.45 (2H, d, J=8.1 Hz), 7.50 (1H, d, J=7.8 Hz), 7.61 (2H, d, J=8.1 Hz), 7.93 (1H, t, J=7.8 Hz), 8.07 (1H, d, J=7.8 Hz).

Example 143

Synthesis of 5-[6-(3-trifluoromethyl-phenyl)-pyridin-3-yl]-3H-[1,2,3]triazole-4-carbonitrile The title compound was obtained using 6-(3-trifluoromethyl-phenyl)-pyridine-3-carbaldehyde in the same manner as in Example 1.
colorless flakes ($CH_3CN$)
Melting point 201-202° C.

Example 144

Synthesis of 5-[1-(2,5-bis-trifluoromethyl-phenyl)-piperidin-4-yl]-3H-[1,2,3]triazole-4-carbonitrile The title compound was obtained using 1-(2,5-bis-trifluoromethyl-phenyl)-piperidine-4-carbaldehyde in the same manner as in Example 1.
white powder (AcOEt-hexane)
Melting point 201.4-203.1° C.

Example 145

Synthesis of 5-[1-(3,4-difluoro-phenyl)-1H-indol-6-yl]-3H-[1,2,3]triazole-4-carbonitrile The title compound was obtained using 1-(3,4-difluoro-phenyl)-1H-indole-6-carbaldehyde in the same manner as in Example 1.
pale yellow powder (AcOEt-hexane)
$^1$H-NMR (CDCl$_3$-DMSO-$d_6$) δ: 6.74 (1H, dd, J=0.8, 3.3 Hz), 7.26-7.50 (4H, m), 7.79 (2H, s), 8.15 (1H, s).

Example 146

Synthesis of 5-[1-(4,4,4-trifluoro-butyl)-1H-indol-6-yl]-3H-[1,2,3]triazole-4-carbonitrile The title compound was obtained using 1-(4,4,4-trifluoro-butyl)-1H-indole-6-carbaldehyde in the same manner as in Example 1.
pale brown powder (AcOEt-hexane)
Melting point 197.3-200.3° C.

Example 147

Synthesis of 5-[6-(4-fluoro-phenyl)-benzofuran-2-yl]-3H-[1,2,3]triazole-4-carbonitrile The title compound was obtained using 6-(4-fluoro-phenyl)-benzofuran-2-carbaldehyde in the same manner as in Example 1.
brown powder (hexane-AcOEt)
Melting point 233° C.

Example 148

Synthesis of 5-[3-(4-fluoro-phenyl)-benzo[b]thiophen-2-yl]-3H-[1,2,3]triazole-4-carbonitrile The title compound was obtained using 3-(4-fluoro-phenyl)-benzo[b]thiophene-2-carbaldehyde in the same manner as in Example 1.
beige powder (hexane)
$^1$H-NMR (DMSO-$d_6$) δ: 7.31-7.58 (6H, m), 7.65-7.70 (1H, m), 8.17 (1H, d, J=7.3 Hz).

Example 149

Synthesis of 5-(3'-trifluoromethyl-biphenyl-3-ylmethyl)-3H-[1,2,3]triazole-4-carbonitrile The title compound was obtained using (3'-trifluoromethyl-biphenyl-3-yl)-acetaldehyde in the same manner as in Example 2.
colorless oil
$^1$H-NMR (DMSO-$d_6$) δ: 4.32 (2H, s), 7.30 (1H, d, J=7.7 Hz), 7.49 (1H, t, J=7.7 Hz), 7.66-7.76 (4H, m), 7.97-7.99 (2H, m).

Example 150

Synthesis of 5-{2-[2-(2,5-bis-trifluoromethyl-benzyloxy)-phenyl]-ethyl}-3H-[1,2,3]triazole-4-carbonitrile The title compound was obtained using 3-[2-(2,5-bis-trifluoromethyl-benzyloxy)-phenyl]-propionaldehyde in the same manner as in Example 2.
colorless oil
$^1$H-NMR (DMSO-d$_6$) δ: 2.97-3.07 (4H, m), 5.31 (2H, s), 6.92 (1H, t, J=7.4 Hz), 7.07-7.10 (2H, m), 7.23-7.27 (1H, m), 7.99 (1H, d, J=8.3 Hz), 8.07 (1H, d, J=8.3 Hz), 8.12 (1H, s), 15.88 (1H, s).

Example 151

Synthesis of 5-[1-(2,4,5-trifluoro-benzyl)-piperidin-4-yl]-3H-[1,2,3]triazole-4-carbonitrile The title compound was obtained using 1-(2,4,5-trifluoro-benzyl)-piperidine-4-carbaldehyde in the same manner as in Example 1.
pale yellow powder (CH$_2$Cl$_2$-hexane)
$^1$H-NMR (CDCl$_3$-CD$_3$OD) δ: 1.8-2.0 (4H, m), 2.23-2.31 (2H, m), 2.9-3.3 (3H, m), 3.62 (2H, s), 6.92-7.00 (1H, m), 7.23-7.26 (1H, m).

The structures of the compounds of Examples 1-151 are shown in the following Table 3. The compounds of Examples in Table 3 are shown as one tautomer, which are not limited, and the other two tautomers are also encompassed therein.

TABLE 3

| Ex. No. | STR |
|---|---|
| 1 | 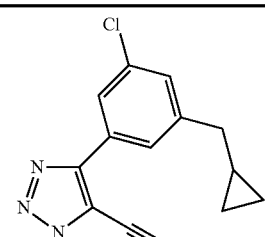 |
| 2 | 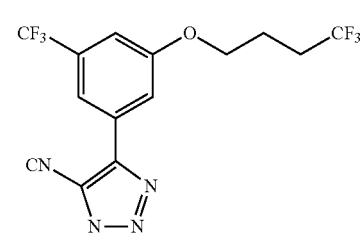 |
| 3 | 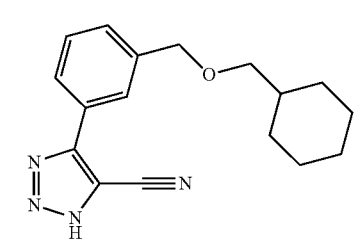 |
| 4 | 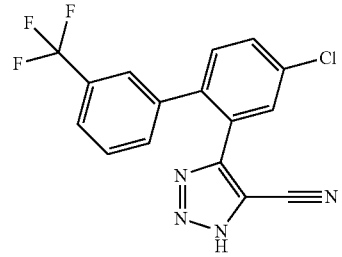 |
| 5 | 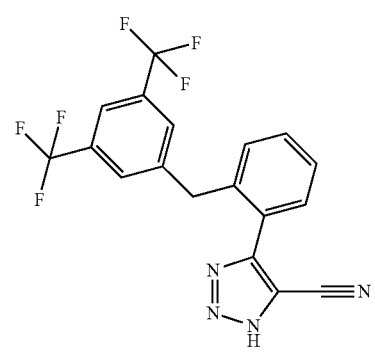 |
| 6 | 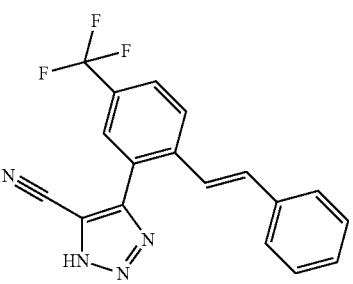 |
| 7 | 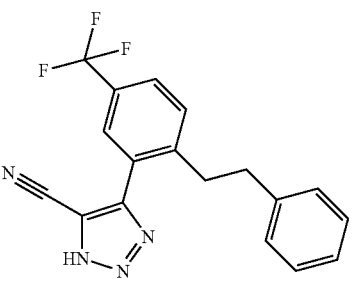 |
| 8 | 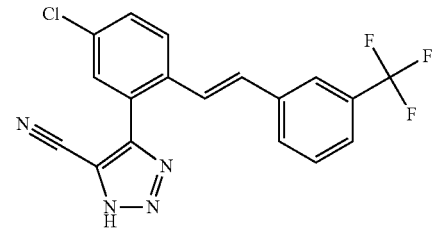 |

TABLE 3-continued

| Ex. No. | STR |
|---|---|
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |

TABLE 3-continued
| Ex. No. | STR |
|---|---|
| 19 | 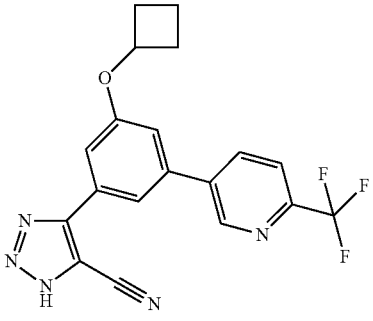 |
| 20 | 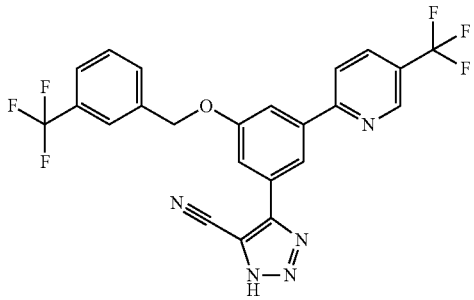 |
| 21 | 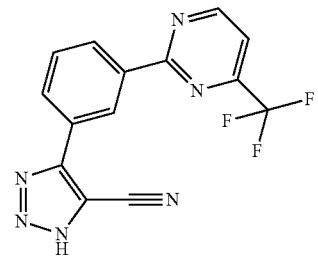 |
| 22 | 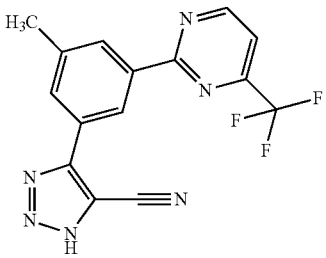 |
| 23 | 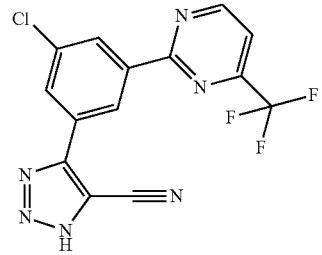 |
| 24 | 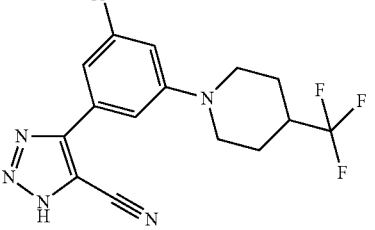 |
| 25 | 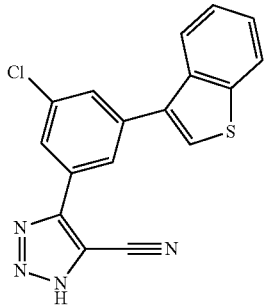 |
| 26 | 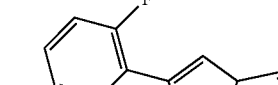 |
| 27 | 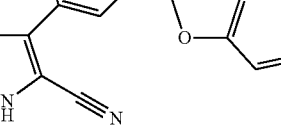 |
| 28 | 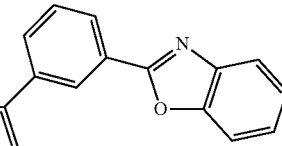 |
| 29 | 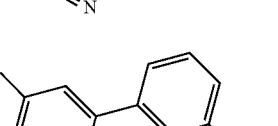 |

TABLE 3-continued

| Ex. No. | STR |
|---|---|
| 30 | |
| 31 | |
| 32 | |
| 33 | |
| 34 | |
| 35 | |
| 36 | |
| 37 | |
| 38 | |
| 39 | |

TABLE 3-continued

| Ex. No. | STR |
| --- | --- |
| 40 | |
| 41 | |
| 42 | |
| 43 | |
| 44 | |
| 45 | |
| 46 | |
| 47 | |
| 48 | |
| 49 | |

TABLE 3-continued

| Ex. No. | STR |
|---|---|
| 50 | |
| 51 | |
| 52 | |
| 53 | |
| 54 | |

TABLE 3-continued

| Ex. No. | STR |
|---|---|
| 55 | |
| 56 | |
| 57 | |
| 58 | |
| 59 | |

US 10,626,095 B2
TABLE 3-continued
| Ex. No. | STR |
|---|---|
| 60 | 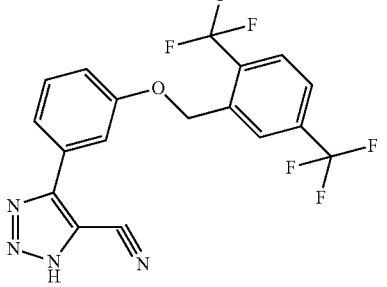 |
| 61 | 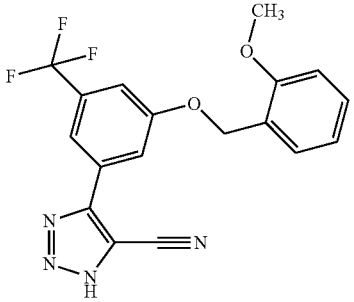 |
| 62 | 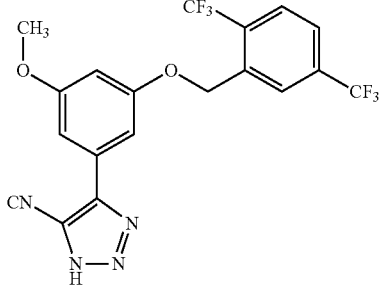 |
| 63 | 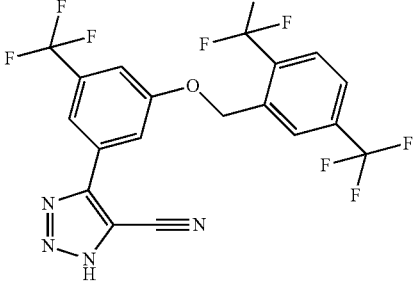 |
| 64 | 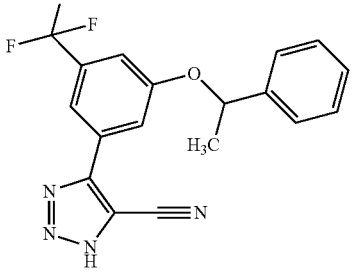 |
TABLE 3-continued
| Ex. No. | STR |
|---|---|
| 65 | 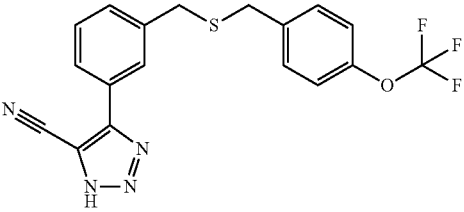 |
| 66 | 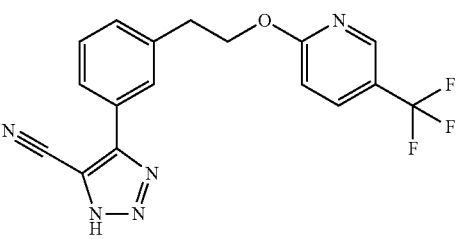 |
| 67 | 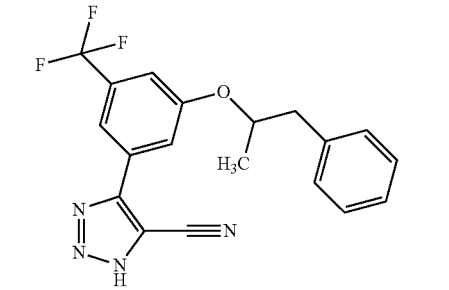 |
| 68 | 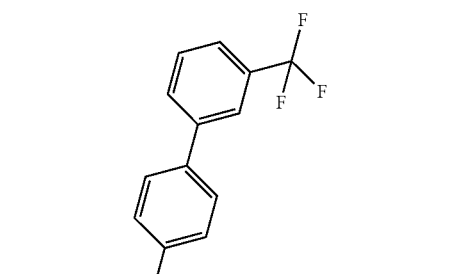 |
| 69 | 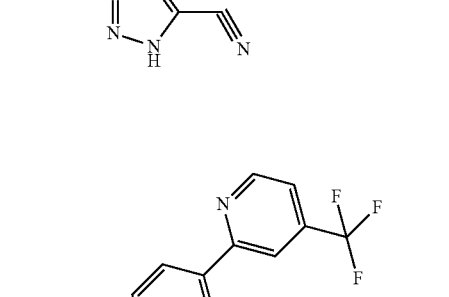 |

TABLE 3-continued
| Ex. No. | STR |
|---|---|
| 70 | 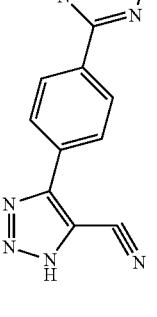 |
| 71 | |
| 72 | |
| 73 | |
| 74 | 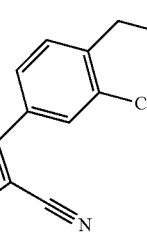 |
| 75 | |
| 76 | |
| 77 | |
| 78 | |
| 79 | |
| 80 | |

TABLE 3-continued
| Ex. No. | STR |
|---|---|
| 81 | 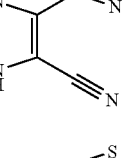 |
| 82 | |
| 83 | |
| 84 | |
| 85 | |
| 86 | |
| 87 | |
| 88 | 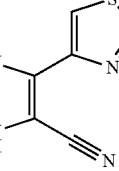 |
| 89 | |
| 90 | |
| 91 | |
| 92 | |
| 93 | |
| 94 | |

TABLE 3-continued
| Ex. No. | STR |
|---|---|
| 95 | 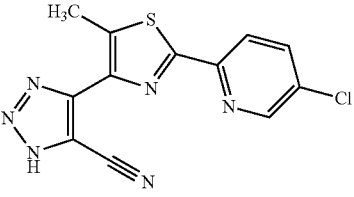 |
| 96 | 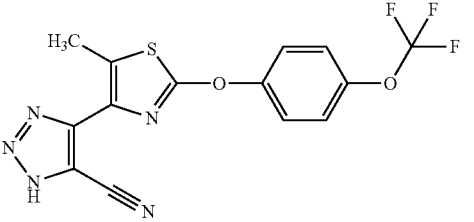 |
| 97 | 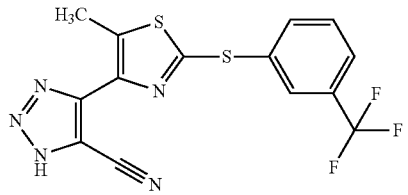 |
| 98 | 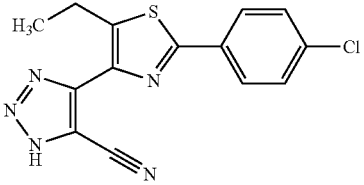 |
| 99 | 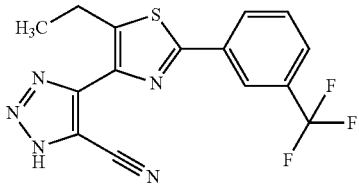 |
| 100 | 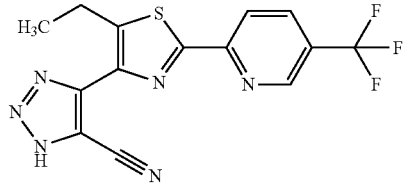 |
| 101 | 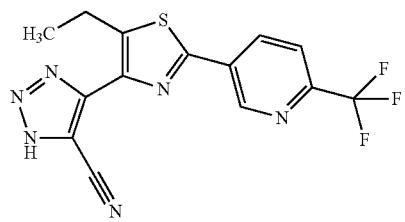 |
| 102 | 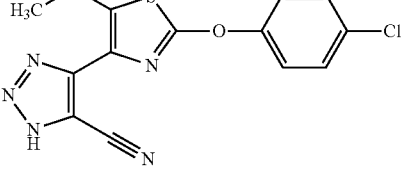 |
| 103 | 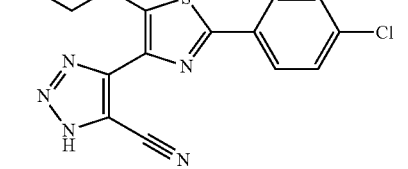 |
| 104 | 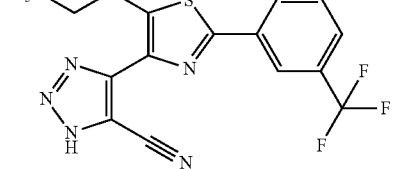 |
| 105 | 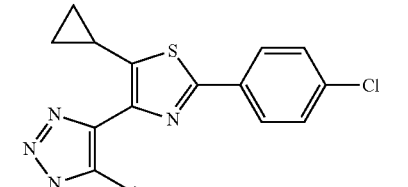 |
| 106 | 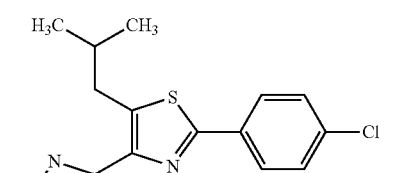 |
| 107 | 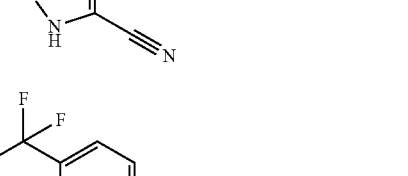 |
| 108 | 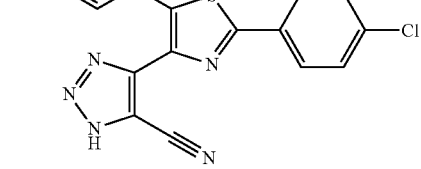 |

TABLE 3-continued
| Ex. No. | STR |
|---|---|
| 109 | 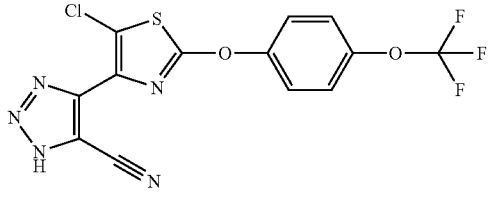 |
| 110 | 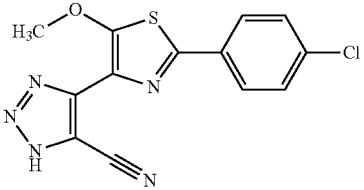 |
| 111 | 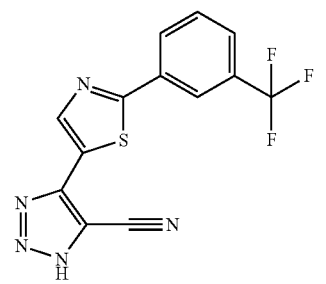 |
| 112 | 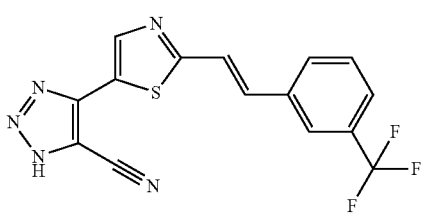 |
| 113 | 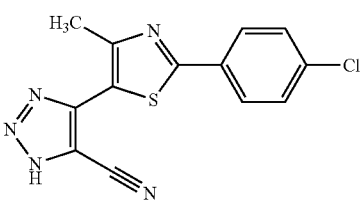 |
| 114 | 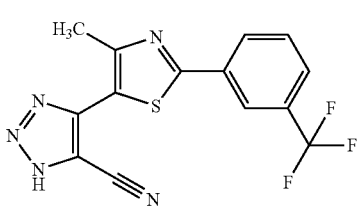 |
| 115 | 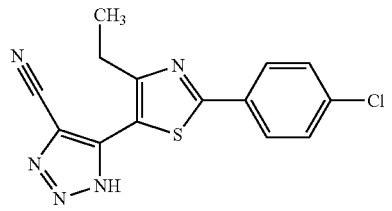 |
| 116 | 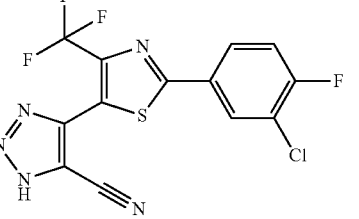 |
| 117 | 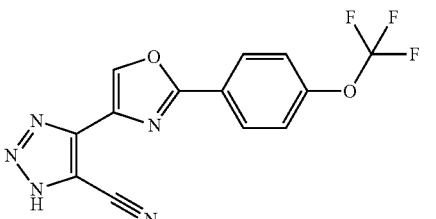 |
| 118 | 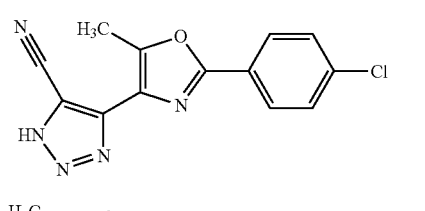 |
| 119 | 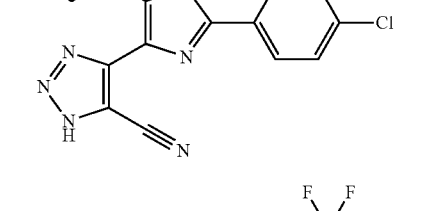 |
| 120 | 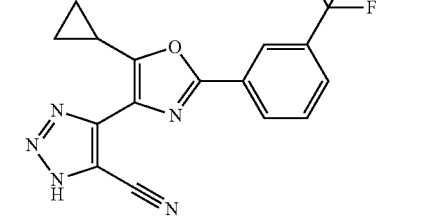 |
| 121 | 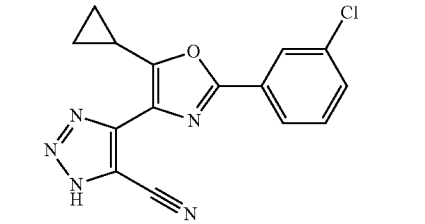 |
| 122 | 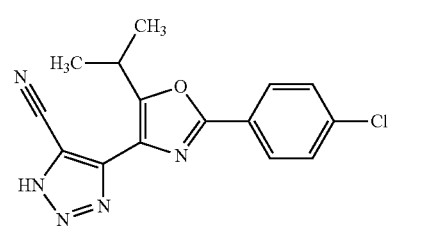 |

TABLE 3-continued
| Ex. No. | STR |
|---|---|
| 123 | 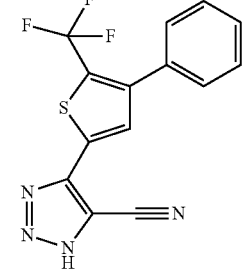 |
| 124 | 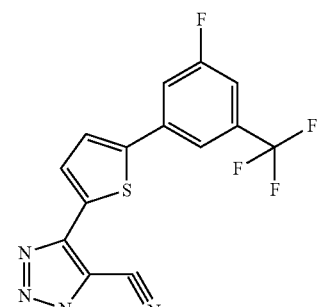 |
| 125 | 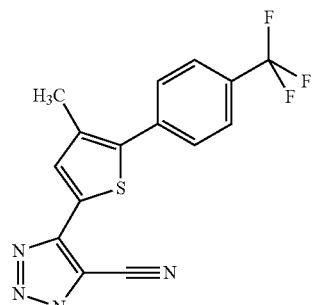 |
| 126 | 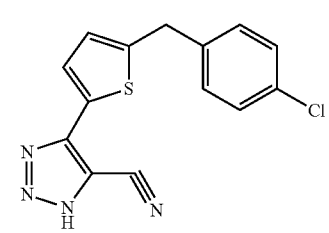 |
| 127 | 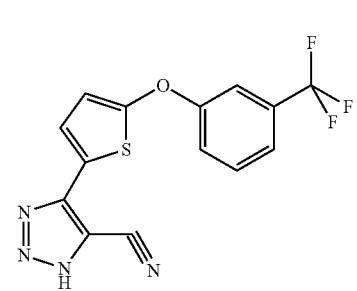 |
| 128 | |
| 129 | |
| 130 | |
| 131 | |
| 132 | |

TABLE 3-continued

| Ex. No. | STR |
|---|---|
| 133 | |
| 134 | |
| 135 | |
| 136 | |
| 137 | |
| 138 | |
| 139 | |
| 140 | |
| 141 | |
| 142 | |

TABLE 3-continued

| Ex. No. | STR |
|---|---|
| 143 | 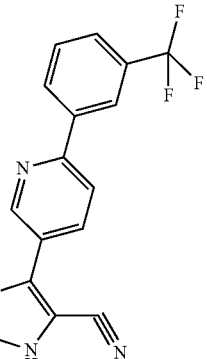 |
| 144 | |
| 145 | |
| 146 | |
| 147 | |

TABLE 3-continued

| Ex. No. | STR |
|---|---|
| 148 | 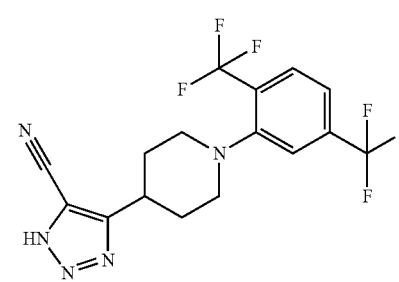 |
| 149 | |
| 150 | |
| 151 | |

Example 191

Synthesis of 5-[3-(2,2-dimethyl-propoxy)-5-trifluoromethyl-phenyl]-3H-[1,2,3]triazole-4-carbonitrile To a solution of 5-[3-(2,2-dimethyl-propoxy)-5-(trifluoromethyl)-phenyl]-2-trityl-2H-[1,2,3]triazole-4-carbonitrile (285 mg, 0.503 mmol) in THF (2 ml) and H$_2$O (0.5 ml) was added AcOH (1 ml). After being stirred for 6 hr under reflux, the reaction mixture was concentrated, and the residue was purified by flash column chromatography (AcOEt/hexane=5% to 50%) to give a colorless oil (119 mg). The oil was crystallized (hexane/CH$_2$Cl$_2$) to give the title compound (86 mg, 53%) as a white powder.

$^1$H-NMR (CDCl$_3$) δ: 1.07 (9H, s), 3.71 (2H, s), 7.26 (1H, s), 7.70 (1H, s), 7.81 (1H, s).

Example 316

Synthesis of 5-(6-dimethylamino-3'-trifluoromethyl-biphenyl-3-yl)-3H-[1,2,3]triazole-4-carbonitrile

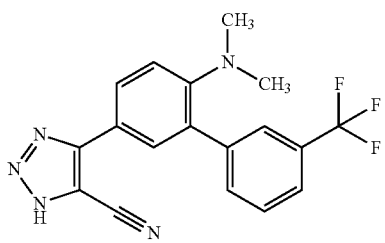 [SMILES: CN(C)c1ccc(-c2nn[nH]c2C#N)cc1-c1cccc(C(F)(F)F)c1]

Sodium cyanoborohydride (19.08 mg, 0.304 mmol) was added to a solution of 5-[4-amino-3-[3-(trifluoromethyl)phenyl]-phenyl]-3H-[1,2,3]triazole-4-carbonitrile (50 mg, 0.152 mmol), formaldehyde (0.5 ml, 18.15 mmol) and AcOH (20 µl, 0.349 mmol) in MeOH (3 ml). After being stirred at room temperature for 2 hr, the reaction mixture was concentrated in vacuo. Water was added to the reaction mixture. The reaction mixture was extracted with AcOEt. The organic layer was washed with brine, dried over anhydrous MgSO$_4$, and then concentrated in vacuo. The obtained residue was purified by flash column chromatography (hexane/AcOEt=4/1 to 1/1), and crystallized (AcOEt-hexane) to give the title compound (30 mg, 55%) as a yellow solid.

$^1$H-NMR (DMSO-d$_6$) δ: 2.58 (6H, s), 7.29 (1H, d, J=8.6 Hz), 7.72-7.74 (3H, m), 7.83 (1H, dd, J=2.3, 8.5 Hz), 7.87-7.89 (2H, m).

Example 688

Synthesis of 5-{4-amino-3-[(E)-2-(3-trifluoromethyl-phenyl)-vinyl]-phenyl}-3H-[1,2,3]triazole-4-carbonitrile

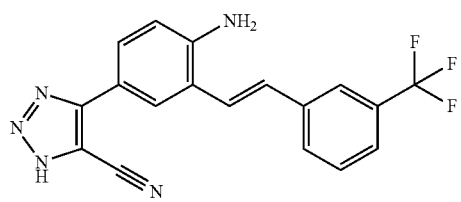 [SMILES: N#Cc1[nH]nnc1-c1ccc(N)c(/C=C/c2cccc(C(F)(F)F)c2)c1]

To a solution of {4-(5-cyano-1H-[1,2,3]triazol-4-yl)-2-[(E)-2-(3-trifluoromethyl-phenyl)-vinyl]-phenyl}-carbamic acid tert-butyl ester (228 mg, 0.501 mmol) in CH$_2$Cl$_2$ (4 ml) was added TFA (2 ml). After being stirred at room temperature for 1 hr, the reaction mixture was concentrated in vacuo, neutralized with aqueous NaHCO$_3$ solution, and extracted with AcOEt. The organic layer was separated, washed with brine, dried over anhydrous MgSO$_4$, and then concentrated in vacuo. The obtained residue was purified by flash column chromatography (hexane/AcOEt=3/2 to 1/4) and crystallized (IPA-hexane) to give the title compound (90 mg, 51%) as a yellow solid.

$^1$H-NMR (DMSO-d$_6$) δ: 6.06-6.40 (2H, br), 6.83 (1H, d, J=8.5 Hz), 7.15 (1H, d, J=16.0 Hz), 7.52-7.64 (4H, m), 7.89-8.05 (3H, m).

Example 693

Synthesis of N-{4-(5-cyano-1H-[1,2,3]triazol-4-yl)-2-[(E)-2-(3-trifluoromethyl-phenyl)-vinyl]-phenyl}-methanesulfonamide

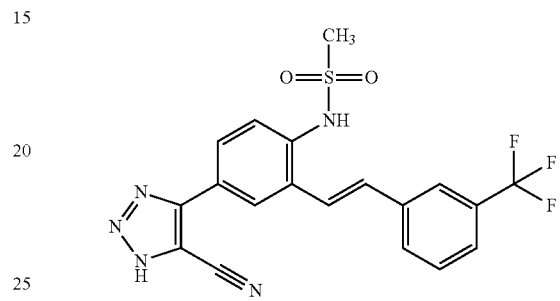

To a solution of 5-{4-amino-3-[(E)-2-(3-trifluoromethyl-phenyl)-vinyl]-phenyl}-3H-[1,2,3]triazole-4-carbonitrile (40 mg, 0.113 mmol) in CH$_2$Cl$_2$ (2 ml) were added pyridine (30 µl) and mesyl chloride (20 µl, 1.292 mmol). The reaction mixture was stirred at room temperature overnight. To the reaction mixture were added pyridine (80 µl) and mesyl chloride (130 µl). After being stirred at room temperature overnight, water was added to the reaction mixture. The reaction mixture was extracted with AcOEt. The organic layer was washed with brine, dried over anhydrous MgSO$_4$ and then concentrated in vacuo. To the obtained residue in acetonitrile (2 ml) was added N,N-dimethylethylendiamine (0.5 ml). After being stirred at room temperature overnight, the reaction mixture was concentrated in vacuo, the residue was acidified with HCl, and the mixture was extracted with AcOEt. The organic layer was washed with brine, dried over anhydrous MgSO$_4$, and then concentrated in vacuo. The suspension of the obtained residue in IPE was filtrated to give the title compound (17 mg, 35%) as a white solid.

$^1$H-NMR (DMSO-do) δ: 3.10 (3H, s), 7.39 (1H, d, J=16.2 Hz), 7.62-7.85 (5H, m), 7.96-8.01 (2H, m), 8.31 (1H, d, J=2.1 Hz), 9.78 (1H, s).

Example 952

Synthesis of 5-{3-chloro-5-[3-(3-trifluoromethyl-phenyl)-oxiran-2-yl]-phenyl}-3H-[1,2,3]triazole-4-carbonitrile

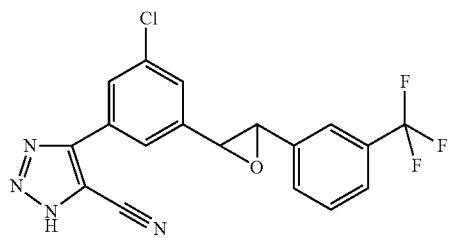 [SMILES: N#Cc1[nH]nnc1-c1cc(Cl)cc(C2OC2c2cccc(C(F)(F)F)c2)c1]

To a solution of 5-{3-Chloro-5-[(E)-2-(3-trifluoromethyl-phenyl)-vinyl]-phenyl}-3H-[1,2,3]triazole-4-carbonitrile (200 mg, 0.534 mmol) in CH$_2$Cl$_2$ (4 ml) and MeOH (0.2 ml) was added 70% m-chloroperoxybenzoic acid (140 mg). After the reaction mixture was stirred at room temperature for 3 days, 70% m-chloroperoxybenzoic acid (140 mg) was added thereto. The reaction mixture was stirred at 40° C. for 4 hr, then at room temperature for 3 days. To the reaction mixture were added saturated aqueous NaHCO$_3$ solution and Na$_2$S$_2$O$_3$. After being stirred for 10 min, the reaction mixture was diluted with AcOEt. The organic layer were separated, washed with diluted aqueous HCl solution and brine, and then dried over anhydrous Na$_2$SO$_4$. After diluted with hexane, the organic layer was purified by silica gel column chromatography (hexane/AcOEt=1/1) to give a pale yellow amorphous solid. The obtained amorphous solid was recrystallized (Et$_2$O/hexane) to give the title compound (40 mg, 19%) as a white powder.

$^1$H-NMR (CDCl$_3$) δ: 3.94 (1H, d, J=1.7 Hz), 3.97 (1H, d, J=1.7 Hz), 7.47 (1H, d, J=1.7 Hz), 7.49-7.57 (2H, m), 7.59-7.65 (2H, m), 7.88 (1H, t, J=1.5 Hz), 7.96 (1H, d, J=1.7 Hz).

Example 1110

Synthesis of N-(4-chloro-phenyl)-3-(5-cyano-1H-[1,2,3]triazol-4-yl)-N-methyl-benzamide

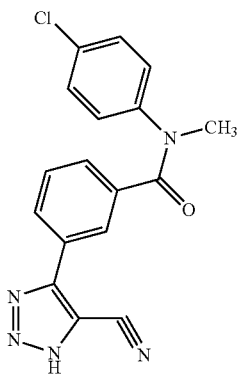 [SMILES: CN(C(=O)c1cccc(-c2nn[nH]c2C#N)c1)c1ccc(Cl)cc1]

To a solution of 3-(5-cyano-1H-[1,2,3]triazol-4-yl)-benzoic acid (0.37 g, 1.73 mmol) in DMF (7 ml) were added 4-chloro-N-methylanilene (0.29 g, 2.07 mmol), WSC (0.40 g, 2.07 mmol) and HOBt (0.32 g, 2.09 mmol). The reaction mixture was stirred at room temperature for 3 hr, then at 40° C. for 4 hr. The reaction mixture was concentrated in vacuo, and the residue was diluted with CH$_2$Cl$_2$ and water. After the reaction mixture was acidified with HCl, the organic layer was separated, washed with water and brine, dried over anhydrous Na$_2$SO$_4$, and then concentrated in vacuo. The obtained residue was purified by silica gel thin layer chromatography (hexane/AcOEt=1/2) and recrystallized (Et$_2$O-hexane) give the title compound (87 mg, 21%) as a beige powder.

Melting point 185-189° C.

Example 1145

Synthesis of 5-[3-(3,4-dichloro-benzenesulfonylmethyl)-phenyl]-3H-[1,2,3]triazole-4-carbonitrile

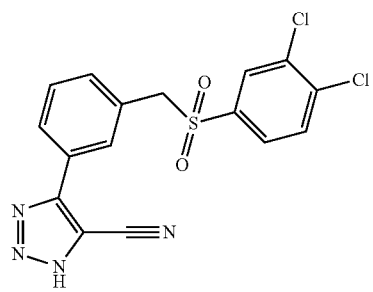 [SMILES: N#Cc1[nH]nnc1-c1cccc(CS(=O)(=O)c2ccc(Cl)c(Cl)c2)c1]

To a solution of 5-[3-[[(3,4-dichlorophenyl)sulfanyl]-methyl]-phenyl]-3-trityl-3H-[1,2,3]triazole-4-carbonitrile (102.6 mg, 1.7 mmol) in CH$_2$Cl$_2$ (2 ml) was added 70% m-chloroperoxybenzoic acid (100 mg) at 0° C. The reaction mixture was stirred at room temperature for 3 hr. To a reaction mixture were added saturated aqueous NaHCO$_3$ solution and Na$_2$S$_2$O$_3$. After being stirred for 10 min, the organic layer was purified by silica gel column chromatography (CH$_2$CH$_2$) to give a white solid. The white solid was stirred in TFA (4 ml) for 7 hr. The reaction mixture was concentrated, and the residue was stirred in water. The precipitate was collected by filtration. The obtained white powder was recrystallized (AcOEt/hexane) to give the title compound (52 mg, 77%) as a white powder.

$^1$H-NMR (CDCl$_3$-DMSO-d$_6$) δ: 4.42 (2H, s), 7.28 (1H, d, J=7.8 Hz), 7.45-7.52 (2H, m), 7.57 (1H, d, J=8.4 Hz), 7.70-7.75 (2H, m), 8.01 (1H, d, J=7.8 Hz).

Example 1473

Synthesis of 5-{5-[4-(1-hydroxy-ethyl)-phenyl]-thiophen-2-yl}-3H-[1,2,3]triazole-4-carbonitrile

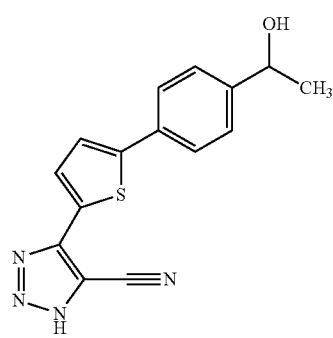 [SMILES: CC(O)c1ccc(-c2ccc(-c3nn[nH]c3C#N)s2)cc1]

To a solution of 5-[5-(4-acetyl-phenyl)-thiophen-2-yl]-3H-[1,2,3]triazole-4-carbonitrile (0.15 g, 0.51 mmol) in EtOH (4.5 ml) was added NaBH$_4$ (58 mg, 1.53 mmol) at 0° C. The reaction mixture was stirred at room temperature for 1.5 hr. After water was added, the reaction mixture was acidified with HCl, and extracted with AcOEt. The organic layer was washed with brine, dried over anhydrous MgSO$_4$ and then concentrated in vacuo. The suspension of the obtained residue in acetonitrile was filtrated to give the title compound (86 mg, 57%) as a yellow powder.

$^1$H-NMR (DMSO-$d_6$) δ: 1.33 (3H, d, J=6.4 Hz), 4.71-4.77 (1H, m), 5.22 (1H, brs), 7.40 (2H, d, J=8.3 Hz), 7.51 (1H, d, J=3.8 Hz), 7.54 (1H, d, J=3.8 Hz), 7.65 (2H, d, J=8.3 Hz).

Example 1779

Synthesis of 5-[3-(4-trifluoromethyl-benzyloxy)-benzoyl]-3H-[1,2,3]triazole-4-carbonitrile

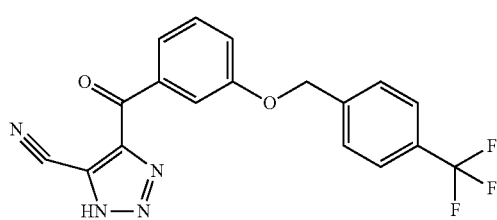 [SMILES: N#Cc1[nH]nnc1C(=O)c1cccc(OCc2ccc(C(F)(F)F)cc2)c1]

To a solution of 1-(3-(4-(trifluoromethyl)benzyloxy)phenyl)ethanone (589 mg, 2.00 mmol) in DMSO (3 ml) was added 48% HBr (0.91 ml, 8.00 mmol). The reaction mixture was stirred at 70° C. for 16 hr. The reaction was quenched by addition of water, and the mixture was extracted with AcOEt. The combined organic layers were washed with water and brine, dried over $Na_2SO_4$, and concentrated in vacuo. The residue was purified by silica gel column chromatography (hexane/AcOEt 4/1 to 3/2) to give a mixture of 2,2-dihydroxy-1-(3-(4-(trifluoremethyl)benzyloxy)phenyl)ethanone (414 mg) as a yellow oil.

To a solution of 2,2-dihydroxy-1-(3-(4-(trifluoromethyl)benzyloxy)phenyl)ethanone (414 mg) in toluene (3 ml) were added phenylsulfonylacetonitrile (241 mg, 1.33 mmol) and Potassium acetate (12.45 mg, 0.13 mmol). The reaction mixture was stirred at 30° C. for 2 days. NMP and $NaN_3$ were added to the reaction mixture, and the reaction was stirred at 30° C. for 15 hr. The reaction was quenched by addition of 5% $NaHCO_3$ aq. and then washed with toluene. The aqueous solution was acidified with 1N HCl aq. and extracted with TBME. The combined organic layers were washed with water and brine, filtered through a silica gel short column, and concentrated in vacuo. The yellow solid was recrystallized (hexane/$CH_2Cl_2$) to give the title compound (102 mg, 22%) as a light yellow solid.

Example 1802

Synthesis of [4-(5-cyano-1H-[1,2,3]triazol-4-yl)-benzyl]-triphenyl-phosphonium chloride

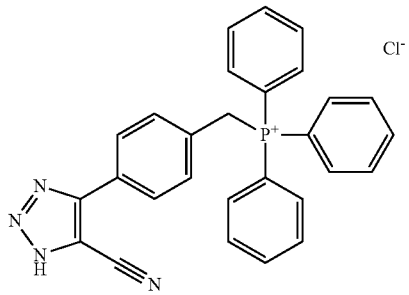 [SMILES: N#Cc1[nH]nnc1-c1ccc(C[P+](c2ccccc2)(c2ccccc2)c2ccccc2)cc1 ; [Cl-]]

To a solution of 5-[4-(chloromethyl)-phenyl]-3H-[1,2,3] triazole-4-carbonitrile (63.6 mg, 0.291 mmol) in toluene (1 ml) was added triphenylphosphine (500 mg, 1.906 mmol). The reaction mixture was stirred at 110° C. for 5 hr. After cooling to room temperature, the precipitate was collected by filtration. The obtained solid was recrystallized (MeOH/IPA) to give the title compound (100 mg, 71%) as a pale yellow powder.

$^1$H-NMR (DMSO-$d_6$) δ: 5.29 (2H, d, J=16.1 Hz), 7.18 (2H, dd, J=2.3, 8.4 Hz), 7.68-7.80 (14H, m), 7.89-7.95 (3H, m).

The following compounds were synthesized in the same manner as in the above-mentioned Examples. The structures and physical property thereof (melting point, $^1$H-NMR data mass spectrum etc.) are shown in the following Table 4. The "ref." in Table 4 means "Example No." or "Reference Example No." which the compound was synthesized in reference to.

TABLE 4
| Ex. No. | STR | m.p. | Ex. ref. |
|---|---|---|---|
| 152 | 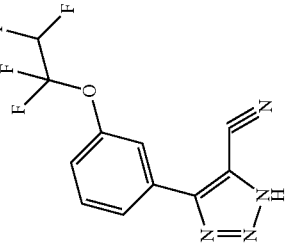 | 112-114 | Ex. 1 |
| 153 | 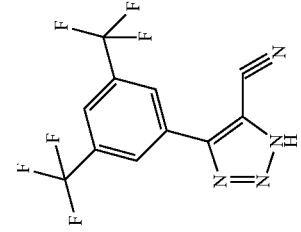 | 183-184 | Ex. 1 |
| 154 | 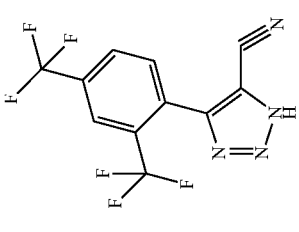 | 79-81 | Ex. 1 |

TABLE 4-continued

| | | | |
|---|---|---|---|
| 155 | [structure] | 124-126 | Ex. 1 |
| 156 | [structure] | 180-183 | Ex. 1 |
| 157 | [structure] | 167-171 | Ex. 1 |
| 158 | [structure] | 209-210 | Ex. 1 |

TABLE 4-continued

| | | | |
|---|---|---|---|
| 159 | [structure: 4-chloro-3-fluorophenyl triazole carbonitrile] | 202-203 | Ex. 1 |
| 160 | [structure: 3-chloro-2-fluoro-5-(trifluoromethyl)phenyl triazole carbonitrile] | 113-115 | Ex. 1 |
| 161 | [structure: 2,5-bis(trifluoromethyl)phenyl triazole carbonitrile] | 115-118 | Ex. 1 |

TABLE 4-continued

| Ex. No. | STR | 1H-NMR | ref. |
|---|---|---|---|
| 162 | (4-(difluoromethoxy)-3-hydroxyphenyl triazole carbonitrile structure) | 1H-NMR (DMSO-d6) δ: 7.16 (1H, t, J = 74.5 Hz), 7.34 (2H, s), 7.51 (1H, s), 10.51 (1H, s). | Ex. 1 |
| 163 | (3,5-bis(trifluoromethyl)phenyl triazole carbonitrile structure) | 1H-NMR (CDCl3) δ: 7.92 (1H, d, J = 8.6 Hz), 8.01 (1H, d, J = 8.6 Hz), 8.06 (1H, s). | Ex. 1 |
| 164 | (4-fluoro-3-(trifluoromethyl)phenyl triazole carbonitrile structure) | 1H-NMR (DMSO-d6) δ: 7.77-7.84 (1H, m), 8.23-8.28 (2H, m). | Ex. 1 |

TABLE 4-continued

| | Structure | 1H-NMR | Ex. |
|---|---|---|---|
| 165 | 2-phenoxyphenyl-triazole-carbonitrile | 1H-NMR (CDCl3) δ: 6.9-7.0 (1H, m), 7.1-7.2 (2H, m), 7.2-7.3 (2H, m), 7.4-7.5 (3H, m), 8.20 (1H, d, J = 7.4 Hz), 13.0 (1H, br). | Ex. 128 |
| 166 | 3-(2-phenylethyl)-5-(trifluoromethyl)phenyl-triazole-carbonitrile | 1H-NMR (CDCl3) δ: 2.99-3.14 (4H, m), 7.18-7.34 (5H, m), 7.53 (1H, s), 8.00 (1H, s), 8.10 (1H, s). | Ex. 7 |
| 167 | 3-bromo-5-(trifluoromethyl)phenyl-triazole-carbonitrile | 1H-NMR (CDCl3) δ: 7.92 (1H, s), 8.24 (1H, s), 8.37 (1H, s). | Ex. 1 |

TABLE 4-continued

| | Structure | NMR | Ex. |
|---|---|---|---|
| 168 | (3-hydroxy-5-(trifluoromethyl)phenyl triazole carbonitrile) | 1H-NMR (DMSO-d6) δ: 7.22 (1H, s), 7.59 (1H, s), 7.63 (1H, s), 10.72 (1H, s). | Ex. 1 |
| 169 | (3-(cyclohexylmethoxy)-5-(trifluoromethyl)phenyl triazole carbonitrile) | 1H-NMR (CDCl3) δ: 1.07-1.34 (6H, m), 1.70-1.91 (5H, m), 3.87 (2H, d, J = 6.0 Hz), 7.24 (1H, s), 7.69 (1H, s), 7.80 (1H, s). | Ex. 2 |
| 170 | (3-(cyclopropylmethoxy)-5-(trifluoromethyl)phenyl triazole carbonitrile) | 1H-NMR (CDCl3) δ: 0.42-0.45 (2H, m), 0.69-0.75 (2H, m), 1.32-1.37 (1H, m), 3.96 (2H, d, J = 7.0 Hz), 7.28 (1H, s), 7.74 (1H, s), 7.83 (1H, s). | Ex. 2 |

TABLE 4-continued

| # | Structure | 1H-NMR | Ex. |
|---|---|---|---|
| 171 | (3-(2-cyclohexylethoxy)-5-(trifluoromethyl)phenyl triazole) | 1H-NMR (CDCl3) δ: 0.99-1.07 (2H, m), 1.22-1.32 (3H, m), 1.56-1.82 (8H, m), 4.14 (2H, t, J = 6.6 Hz), 7.27 (1H, s), 7.72 (1H, s), 7.83 (1H, s). | Ex. 2 |
| 172 | (3-(4-phenyl... methyl)... trifluoromethyl phenyl triazole) | 1H-NMR (CDCl3) δ: 0.99 (3H, t, J = 7.4 Hz), 1.41-1.65 (2H, m), 1.86-1.91 (1H, m), 2.06-2.13 (1H, m), 5.23-5.27 (1H, m), 7.26-7.43 (6H, m), 7.66 (1H, s), 7.75 (1H, s). | Ex. 2 |
| 173 | (3-(cyclohexylmethoxy)phenyl triazole) | 1H-NMR (DMSO-d6) δ: 1.06-1.34 (7H, m), 1.59-1.91 (4H, m), 3.82 (2H, d, J = 6.0 Hz), 7.03 (1H, d, J = 8.0 Hz), 7.39-7.54 (3H, m). | Ex. 1 |
| 174 | (3-cyclohexyloxyphenyl triazole) | 1H-NMR (DMSO-d6) δ: 1.25-1.63 (6H, m), 1.73-2.07 (4H, m), 4.40-4.44 (1H, m), 7.12-7.15 (1H, m), 7.41-7.53 (3H, m). | Ex. 1 |

TABLE 4-continued

| | Structure | NMR | Ex. |
|---|---|---|---|
| 175 | (cyclopentyl-CH2-O-CH2-phenyl)-triazole-CN | 1H-NMR (CDCl3) δ: 1.50-1.80 (8H, m), 4.07-4.15 (1H, m), 4.59 (2H, s), 7.44-7.53 (2H, m), 7.83-7.92 (1H, m), 7.98 (1H, s), 13.0 (1H, br.). | Ex. 1 |
| 176 | (cyclohexyl-O-CH2-phenyl)-triazole-CN | 1H-NMR (CDCl3) δ: 1.16-1.61 (6H, m), 1.72-1.88 (2H, m), 2.00-2.11 (2H, m), 3.45-3.58 (1H, m), 4.70 (2H, s), 7.41-7.51 (2H, m), 7.80-7.89 (1H, m), 8.01 (1H, s), 13.0 (1H, br.). | Ex. 1 |
| 177 | (cyclooctyl-O-CH2-phenyl)-triazole-CN | 1H-NMR (CDCl3) δ: 1.38-2.01 (14H, m), 3.62-3.73 (1H, m), 4.64 (2H, s), 7.42-7.51 (2H, m), 7.81-7.90 (1H, m), 7.99 (1H, s), 13.0 (1H, br.). | Ex. 1 |
| 178 | (cyclopentyl-CH2-O-CH2-phenyl)-triazole-CN | 1H-NMR (CDCl3) δ: 1.20-1.34 (2H, m), 1.48-1.86 (6H, m), 2.20-2.32 (1H, m), 3.44 (2H, d, J = 7.1 Hz), 4.63 (2H, s), 7.45-7.55 (2H, m), 7.86-7.94 (1H, m), 7.99 (1H, s), 13.0 (1H, br.). | Ex. 1 |

TABLE 4-continued
| | | | |
|---|---|---|---|
| 179 | 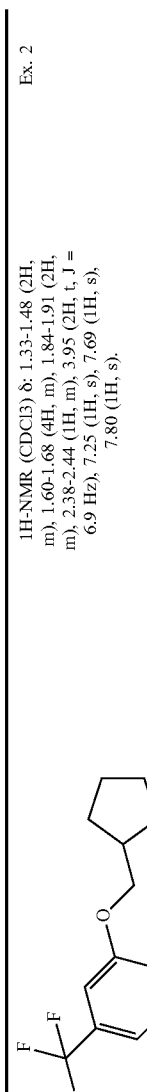 | 1H-NMR (CDCl3) δ: 1.33-1.48 (2H, m), 1.60-1.68 (4H, m), 1.84-1.91 (2H, m), 2.38-2.44 (1H, m), 3.95 (2H, t, J = 6.9 Hz), 7.25 (1H, s), 7.69 (1H, s), 7.80 (1H, s). | Ex. 2 |
| 180 | 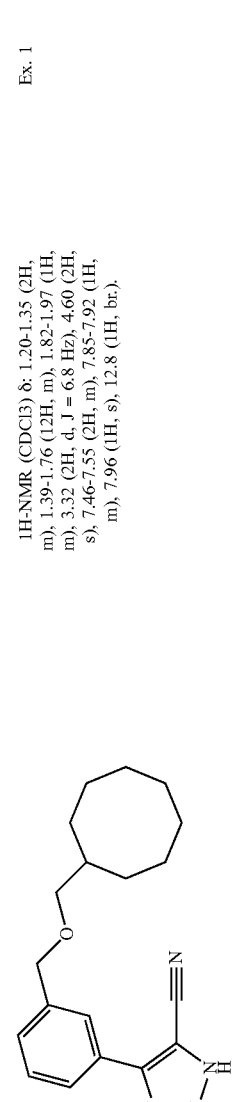 | 1H-NMR (CDCl3) δ: 1.20-1.35 (2H, m), 1.39-1.76 (12H, m), 1.82-1.97 (1H, m), 3.32 (2H, d, J = 6.8 Hz), 4.60 (2H, s), 7.46-7.55 (2H, m), 7.85-7.92 (1H, m), 7.96 (1H, s), 12.8 (1H, br.). | Ex. 1 |
| 181 | 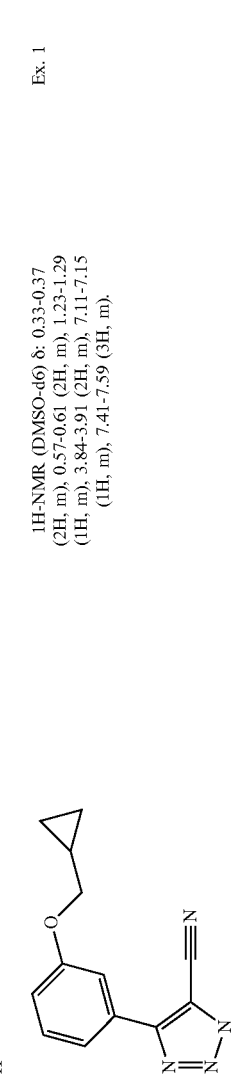 | 1H-NMR (DMSO-d6) δ: 0.33-0.37 (2H, m), 0.57-0.61 (2H, m), 1.23-1.29 (1H, m), 3.84-3.91 (2H, m), 7.11-7.15 (1H, m), 7.41-7.59 (3H, m). | Ex. 1 |
| 182 | 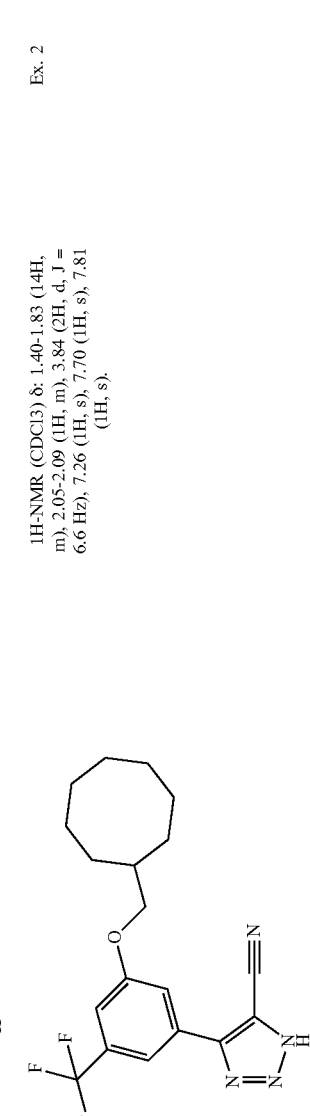 | 1H-NMR (CDCl3) δ: 1.40-1.83 (14H, m), 2.05-2.09 (1H, m), 3.84 (2H, d, J = 6.6 Hz), 7.26 (1H, s), 7.70 (1H, s), 7.81 (1H, s). | Ex. 2 |

TABLE 4-continued

| | | | |
|---|---|---|---|
| 183 | [structure: 3-cyclopentyloxy-5-trifluoromethylphenyl triazole with CN] | 1H-NMR (CDCl3) δ: 1.65-1.99 (8H, m), 4.85-4.90 (1H, m), 7.22 (1H, s), 7.68 (1H, s), 7.77 (1H, s). | Ex. 2 |
| 184 | [structure: 3-cyclohexyloxy-5-trifluoromethylphenyl triazole with CN] | 1H-NMR (CDCl3) δ: 1.33-1.47 (3H, m), 1.56-1.63 (3H, m), 1.82-1.86 (2H, m), 2.02-2.05 (2H, m), 4.36-4.41 (1H, m), 7.24 (1H, s), 7.71 (1H, s), 7.78 (1H, s). | Ex. 7 |
| 185 | [structure: 3-(2-phenylethoxy)-5-trifluoromethylphenyl triazole with CN] | 1H-NMR (CDCl3) δ: 3.16 (2H, t, J = 6.9 Hz), 4.30 (2H, t, J = 6.9 Hz), 7.26-7.37 (6H, m), 7.69 (1H, s), 7.80 (1H, s). | Ex. 1 |
| 186 | [structure: 3-(3-methylbutoxy)-5-trifluoromethylphenyl triazole with CN] | 1H-NMR (CDCl3) δ: 0.99 (6H, d, J = 6.6 Hz), 1.70-1.92 (3H, m), 4.11 (2H, t, J = 6.5 Hz), 7.24 (1H, s), 7.70 (1H, s), 7.81 (1H, s). | Ex. 2 |

TABLE 4-continued

| | Structure | NMR | Ref |
|---|---|---|---|
| 187 | [structure with isobutyl ether, CF3-phenyl, triazole-CN] | 1H-NMR (CDCl3) δ: 1.07 (6H, d, J = 6.7 Hz), 2.10-2.19 (1H, m), 3.84 (2H, d, J = 6.5 Hz), 7.26 (1H, s), 7.70 (1H, s), 7.81 (1H, s). | Ex. 2 |
| 188 | [structure with 3-phenylpropoxy, CF3-phenyl, triazole-CN] | 1H-NMR (CDCl3) δ: 2.12-2.21 (2H, m), 2.82-2.87 (2H, m), 4.06-4.10 (2H, m), 7.18-7.33 (6M, m), 7.71 (1H, s), 7.82 (1H, s). | Ex. 2 |
| 189 | [structure with CF3/CF3 alkyl ether, CF3-phenyl, triazole-CN] | 1H-NMR (CDCl3) δ: 2.36-2.42 (2H, m), 3.30-3.41 (1H, m), 4.23-4.27 (2H, m), 7.26 (1H, s), 7.72 (1H, s), 7.89 (1H, s). | Ex. 2 |
| 190 | [structure with OCH2CF3, CF3-phenyl, triazole-CN] | 1H-NMR (CDCl3) δ: 4.49 (2H, q, J = 7.9 Hz), 7.33 (1H, s), 7.78 (1H, s), 7.92 (1H, s). | Ex. 2 |

TABLE 4-continued

| | Structure | 1H-NMR | Ref. |
|---|---|---|---|
| 192 | (3-methyl-5-(4,4,4-trifluorobutoxy)phenyl triazole carbonitrile) | 1H-NMR (CDCl3) δ: 2.02-2.15 (2H, m), 2.25-2.40 (2H, m), 2.41 (3H, s), 4.08 (2H, t, J = 5.9 Hz), 6.86 (1H, s), 7.29 (1H, s), 7.38 (1H, s), 12.2 (1H, br.). | Ref. Ex. 82, Ex. 1 |
| 193 | (3-methyl-5-(2-methoxyethoxy)phenyl triazole carbonitrile) | 1H-NMR (CDCl3) δ: 2.39 (3H, s), 3.55 (3H, s), 3.83-3.87 (2H, m), 4.19-4.23 (2H, m), 6.83 (1H, s), 7.36 (2H, br.s), 12.7 (1H, br.). | Ex. 1 |
| 194 | (3-methoxy-5-(4,4,4-trifluorobutoxy)phenyl triazole carbonitrile) | 1H-NMR (CDCl3) δ: 2.06-2.11 (2H, m), 2.30-2.38 (2H, m), 3.87 (3H, s), 4.08 (2H, t, J = 5.9 Hz), 6.58 (1H, s), 7.11 (2H, bs). | Ex. 2 |
| 195 | (3-chloro-5-(4,4,4-trifluorobutoxy)phenyl triazole carbonitrile) | 1H-NMR (CDCl3) δ: 2.04-2.17 (2H, m), 2.25-2.43 (2H, m), 4.09 (2H, t, J = 6.0 Hz), 7.03 (1H, t, J = 2.0 Hz), 7.43 (1H, s), 7.59 (1H, s), 12.0 (1H, br.). | Ex. 1 |

TABLE 4-continued

| | Structure | NMR | Ex. |
|---|---|---|---|
| 196 | (3-cyclopropylphenyl-triazole-carbonitrile) | 1H-NMR (CDCl3) δ: 0.76-0.80 (2H, m), 1.02-1.07 (2H, m), 1.95-2.02 (1H, m), 7.20-7.22 (1H, m), 7.41 (1H, t, J = 7.8 Hz), 7.65 (1H, s), 7.72 (1H, d, J = 7.8 Hz). | Ex. 2 |
| 197 | (3-phenethylphenyl-triazole-carbonitrile) | 1H-NMR (DMSO-d6) δ: 2.92-3.00 (4H, m), 7.16-7.29 (5H, m), 7.42 (1H, d, J = 7.7 Hz), 7.51 (1H, t, J = 7.7 Hz), 7.71 (1H, d, J = 7.7 Hz), 7.78 (1H, s). | Ex. 1 |
| 198 | (3-hexyloxy-5-trifluoromethylphenyl-triazole-carbonitrile) | 1H-NMR (DMSO-d6) δ: 0.87-0.90 (3H, m), 1.29-1.34 (4H, m), 1.40-1.46 (2H, m), 1.73-1.80 (2H, m), 4.14 (2H, t, J = 6.5 Hz), 7.45 (1H, s), 7.70 (1H, s), 7.75 (1H, s). | Ex. 2 |

TABLE 4-continued
| Ex. No. | STR | m.p. | ref. |
|---|---|---|---|
| 199 | 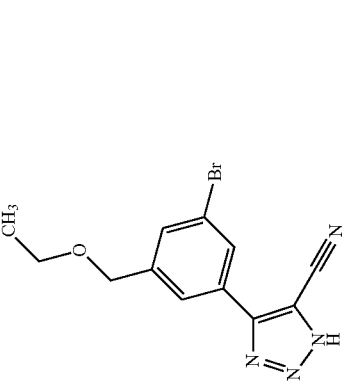 | | 1H-NMR (CDCl3) δ: 1.30 (3H, t, J = 7.0 Hz), 3.62 (2H, q, J = 7.0 Hz), 4.58 (2H, s), 7.64 (1H, s), 7.92 (1H, s), 8.03 (1H, s). Ex. 1 |
| 200 | 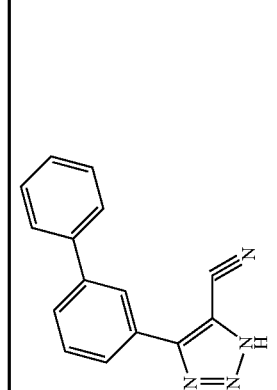 | 119-121 | Ex. 1 |
| 201 | 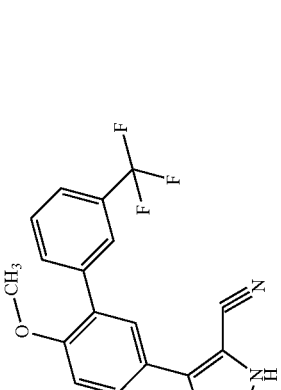 | 223-225 | Ex. 1 |

TABLE 4-continued

| | | | |
|---|---|---|---|
| 202 | [structure: 2,5-bis(trifluoromethyl)biphenyl triazole carbonitrile] | 173-175 | Ex. 1 |
| 203 | [structure: 4-chloro-3-(trifluoromethyl)biphenyl triazole carbonitrile] | 197-198 | Ex. 1 |
| 204 | [structure: 2,4,5-trifluorobiphenyl triazole carbonitrile] | 197-198 | Ex. 1 |

TABLE 4-continued

| | | | |
|---|---|---|---|
| 205 | (structure) | 175-176 | Ex. 1 |
| 206 | (structure) | 104-108 | Ex. 1 |
| 207 | (structure) | 167-169 | Ex. 1 |

TABLE 4-continued

| | | | |
|---|---|---|---|
| 208 | (3-chloro-5-(3,4-difluorophenyl)phenyl-triazole-carbonitrile structure) | 193-194 | Ex. 1 |
| 209 | (3-(trifluoromethyl)-5-(4-(trifluoromethoxy)phenyl)phenyl-triazole-carbonitrile structure) | 142.9-143.5 | Ex. 1 |
| 210 | (3-(1-methylethyl)-5-(4-fluorophenyl)phenyl-triazole-carbonitrile structure) | 128-130 | Ex. 1 |

TABLE 4-continued

| Ex. No. | STR | ref. | 1H-NMR |
|---|---|---|---|
| 211 | [structure: 3-(methoxymethyl)-5-[4-(trifluoromethyl)phenyl]phenyl-triazole-carbonitrile] | 142-149 | Ex. 1 |
| 212 | [structure: 3-cyclobutoxy-5-(4-fluorophenyl)phenyl-triazole-carbonitrile] | 153-160 | Ex. 1 |
| 213 | [structure: 4'-chloro-biphenyl-triazole-carbonitrile] | Ref. Ex. 271, Ex. 1 | 1H-NMR (DMSO-d6) δ: 7.59 (2H, d, J = 8.6 Hz), 7.72 (1H, t, J = 7.8 Hz), 7.77 (2H, d, J = 8.6 Hz), 7.86-7.90 (2H, m), 8.16 (1H, s). |

TABLE 4-continued
| | | | |
|---|---|---|---|
| 214 |  | 1H-NMR (CDCl3) δ: 7.41-7.67 (3H, m), 7.73-7.75 (1H, m), 7.83 (1H, d, J = 7.7 Hz), 7.89 (1H, s), 8.03 (1H, d, J = 7.7 Hz), 8.21 (1H, s). | Ref. Ex. 271, Ex. 1 |
| 215 |  | 1H-NMR (CDCl3) δ: 7.62-7.66 (1H, m), 7.78-7.86 (2H, m), 7.95-7.99 (3H, m), 8.09-8.11 (1H, m). | Ex. 1 |
| 216 | 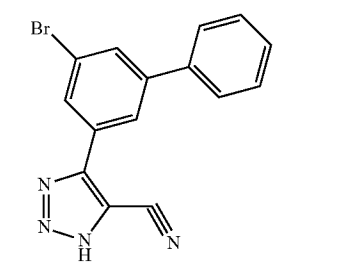 | 1H-NMR (DMSO-d6) δ: 7.44-7.58 (3H, m), 7.74-7.79 (2H, m), 8.02-8.08 (2H, m), 8.15-8.18 (1H, m). | Ex. 1 |
| 217 | 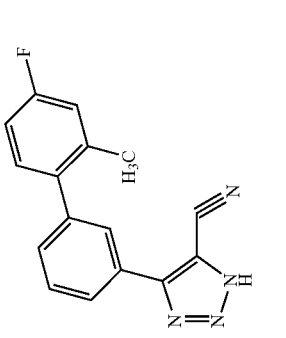 | 1H-NMR (DMSO-d6) δ: 2.29 (3H, s), 7.13-7.17 (1H, m), 7.21-7.24 (1H, m), 7.30-7.33 (1H, m), 7.55 (1H, d, J = 7.8 Hz), 7.70 (1H, t, J = 7.8 Hz), 7 83 (1H, s), 7.90 (1H, d, J = 7.8 Hz). | Ex. 1 |

TABLE 4-continued

| | Structure | 1H-NMR | |
|---|---|---|---|
| 218 | 3-(trifluoromethyl)-5-phenyl-phenyl triazole carbonitrile | 1H-NMR (CDCl3) δ: 7.4-7.6 (3H, m), 7.6-7.7 (2H, m), 7.96 (1H, s), 8.21 (1H, s), 8.42 (1H, s). | Ex. 1 |
| 219 | 3',4'-difluorobiphenyl triazole carbonitrile | 1H-NMR (DMSO-d6) δ: 7.58-7.62 (2H, m), 7.22 (1H, t, J = 7.8 Hz), 7.84-7.90 (3H, m), 8.17 (1H, s). | Ex. 1 |
| 220 | 3-fluoro-5-(trifluoromethyl)biphenyl triazole carbonitrile | 1H-NMR (DMSO-d6) δ: 7.75-7.78 (2H, m), 7.95-8.03 (4H, m), 8.27 (1H, s). | Ex. 1 |

TABLE 4-continued
| | | | |
|---|---|---|---|
| 221 |  | 1H-NMR (DMSO-d6) δ: 3.90 (3H, s), 7.76 (1H, t, J = 7.8 Hz), 7.90-7.96 (4H, m), 8.10 (2H, d, J = 8.3 Hz), 8.23 (1H, s). | Ex. 1 |
| 222 | 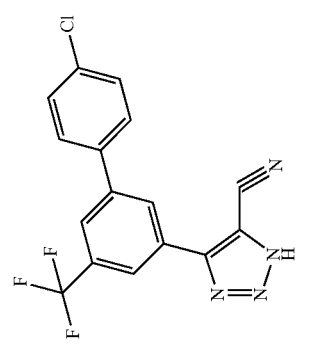 | 1H-NMR (CDCl3) δ: 7.45-7.50 (2H, m), 7.60-7.65 (2H, m), 7.92 (1H, s), 8.24 (1H, s), 8.39 (1H, s). | Ex. 1 |
| 223 |  | 1H-NMR (DMSO-d6) δ: 7.58-7.61 (2H, m), 7.67-7.69 (1H, m), 7.76-7.82 (3H, m), 8.02 (1H, s). | Ex. 1 |

TABLE 4-continued

| | Structure | 1H-NMR | |
|---|---|---|---|
| 224 | 2-chlorobiphenyl with 5-CF3 and triazole-carbonitrile | 1H-NMR (CDCl3) δ: 7.36-7.42 (3H, m), 7.52-7.55 (1H, m), 7.85 (1H, s), 8.27 (1H, s), 8.29 (1H, s), 12.1 (1H, br). | Ex. 1 |
| 225 | 2,4-dichlorobiphenyl with 5-CF3 and triazole-carbonitrile | 1H-NMR (CDCl3) δ: 7.33-7.40 (2H, m), 7.58 (1H, d, J = 1.7 Hz), 7.81 (1H, s), 8.26 (1H, s), 8.28 (1H, s), 12.0 (1H, br). | Ex. 1 |
| 226 | 2-fluorobiphenyl with 5-CF3 and triazole-carbonitrile | 1H-NMR (CDCl3) δ: 7.23-7.26 (1H, m), 7.30-7.33 (1H, m), 7.40-7.45 (1H, m), 7.52-7.56 (1H, m) 7.95 (1H, s), 8.26 (1H, s), 8.40 (1H, s). | Ex. 1 |

| | | | |
|---|---|---|---|
| 227 | 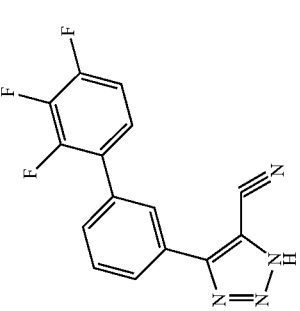 | 1H-NMR (DMSO-d6) δ: 7.48-7.51 (2H, m), 7.76-7.77 (2H, m), 7.97 (1H, m), 8.07 (1H, s). | Ex. 1 |
| 228 | 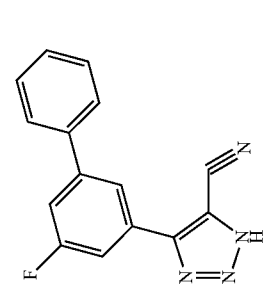 | 1H-NMR (DMSO-d6) δ: 7.47 (1H, t, J = 7.3 Hz), 7.55 (2H, t, J = 7.3 Hz), 7.68 (1H, d, J = 9.1 Hz), 7.77-7.79 (3H, m), 8.04 (1H, s). | Ex. 1 |
| 229 | 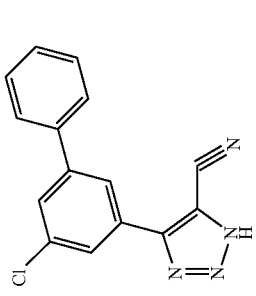 | 1H-NMR (DMSO-d6) δ: 7.47 (1H, t, J = 7.4 Hz), 7.55 (2H, t, J = 7.4 Hz), 7.78 (2H, d, J = 7.4 Hz), 7.90 (1H, s), 7.94 (1H, s), 8.13 (1H, s). | Ex. 1 |

| | | | |
|---|---|---|---|
| 230 |  | 1H-NMR (CDCl3) δ: 7.43-7.45 (2H, m), 7.54-7.57 (1H, m), 7.64 (1H, s), 7.93 (1H, s), 8.26 (1H, s), 8.39 (1H, s). | Ex. 1 |
| 231 |  | 1H-NMR (CDCl3) δ: 7.27-7.51 (3H, m), 7.89 (1H, s), 8.25 (1H, s), 8.36 (1H, s). | Ex. 1 |
| 232 |  | 1H-NMR (CDCl3) δ: 8.98-7.05 (2H, m), 7.48-7.56 (1H, m), 7.91 (1H, s), 8.27 (1H, s), 8.36 (1H, s). | Ex. 1 |

TABLE 4-continued
| | | | |
|---|---|---|---|
| 233 |  | 1H-NMR (DMSO-d6) δ: 7.77-7.85 (2H, m), 7.94-7.96 (1H, m), 8.05-8.12 (3H, m), 8.19 (1H, s). | Ex. 1 |
| 234 | 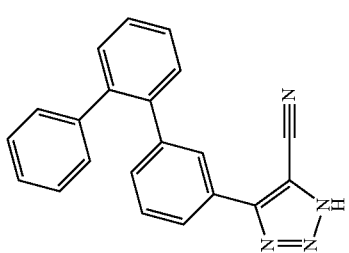 | 1H-NMR (CDCl3) δ: 7.15-7.18 (2H, m), 7.21-7.25 (4H, m), 7.33-7.37 (1H, m), 7.45-7.50 (4H, m), (7.70-7.83 (2H, m), 12.0 (1H, br.). | Ex. 1 |
| 235 |  | 1H-NMR (DMSO-d6) δ: 7.68-7.76 (2H, m), 7.92-7.96 (2H, m), 8.08-8.13 (2H, m), 8.21 (1H, s). | Ex. 1 |

TABLE 4-continued

| | | | |
|---|---|---|---|
| 236 | [structure: 2'-fluoro-5'-(difluoromethyl)biphenyl triazole carbonitrile] | 1H-NMR (DMSO-d6) δ: 7.12 (1H, t, J = 55.7 Hz), 7.56 (1H, t, J = 8.8 Hz), 7.72-7.85 (4H, m), 7.96-8.10 (1H, m), 8.10 (1H, s). | Ex. 1 |
| 237 | [structure: 5'-fluoro-2'-(difluoromethyl)biphenyl triazole carbonitrile] | 1H-NMR (DMSO-d6) δ: 6.89 (1H, t, J = 54.4 Hz), 7.36-7.38 (1H, m), 7.46-7.50 (1H, m), 7.59 (1H, d, J = 7.8 Hz), 7.75 (1H, t, J = 7.8 Hz), 7.84-7.87 (1H, m), 7.90 (1H, s), 7.99 (1H, d, J = 8.0 Hz). | Ex. 1 |
| 238 | [structure: 2'-(trifluoromethyl)-5'-(trifluoromethyl)-3-methylbiphenyl triazole carbonitrile] | 1H-NMR (DMSO-d6) δ: 2.47 (3H, s), 7.42 (1H, s), 7.69 (1H, s), 7.82 (1H, s), 7.85 (1H, s), 8.07 (1H, d, J = 8.3 Hz), 8.15 (1H, d, J = 8.3 Hz). | Ex. 1 |

TABLE 4-continued

| | Structure | 1H-NMR | |
|---|---|---|---|
| 239 | 3,5-bis(trifluoromethyl)-5'-fluoro-biphenyl triazole carbonitrile | 1H-NMR (DMSO-d6) δ: 7.77-7.79 (1H, m), 8.06 (1H, t, J = 9.9 Hz), 8.19-8.21 (2H, m), 8.48 (2H, s). | Ex. 1 |
| 240 | 3',4'-difluoro-5-(trifluoromethoxy)biphenyl triazole carbonitrile | 1H-NMR (DMSO-d6) δ: 7.62-7.67 (2H, m), 7.85 (1H, m), 7.93 (1H, s), 7.94-7.96 (1H, m), 8.20 (1H, s). | Ex. 1 |
| 241 | 3'-(trifluoromethyl)-5-(trifluoromethoxy)biphenyl triazole carbonitrile | 1H-NMR (DMSO-d6) δ: 7.78-7.86 (2H, m), 7.89 (1H, s), 8.02 (1H, s), 8.12 (1H, d, J = 7.8 Hz), 8.15 (1H, s), 8.28 (1H, s). | Ex. 1 |

TABLE 4-continued

| | Structure | 1H-NMR | |
|---|---|---|---|
| 242 | (3'-fluoro-5'-(trifluoromethyl)-5-(trifluoromethoxy)biphenyl-3-yl triazole carbonitrile) | 1H-NMR (DMSO-d6) δ: 7.82 (1H, d, J = 8.8 Hz), 7.90 (1H, s), 8.04 (2H, s), 8.07 (1H, s), 8.31 (1H, s) | Ex. 1 |
| 243 | (3',4'-difluoro-5-(trifluoromethoxy)biphenyl-3-yl triazole carbonitrile) | 1H-NMR (DMSO-d6) δ: 7.75–7.90 (4H, m), 8.08 (1H, s). | Ex. 1 |
| 244 | (3',5'-bis(trifluoromethyl)-5-(trifluoromethoxy)biphenyl-3-yl triazole carbonitrile) | 1H-NMR (DMSO-d6) δ: 7.93 (1H, s), 8.19 (1H, s), 8.22 (1H, s), 8.36 (1H, s), 8.51 (2H, s). | Ex. 1 |

TABLE 4-continued

| | Structure | 1H-NMR | Ex. |
|---|---|---|---|
| 245 | (3-OCF3-phenyl / 5-OCF3-phenyl biphenyl triazole carbonitrile) | 1H-NMR (DMSO-d6) δ: 7.47 (1H, d, J = 8.2 Hz), 7.68 (1H, t, J = 8.0 Hz), 7.73 (1H, s), 7.75 (1H, s), 7.81 (1H, d, J = 8.2 Hz), 7.83 (1H, s), 8.19 (1H, s). | Ex. 1 |
| 246 | (3-OCF3-phenyl / 5-F biphenyl triazole carbonitrile) | 1H-NMR (DMSO-d6) δ: 7.48 (1H, d, J = 8.3 Hz), 7.68 (1H, t, J = 8.3 Hz), 7.71-7.73 (1H, m), 7.79 (1H, s), 7.83-7.85 (2H, m), 8.07 (1H, s). | Ex. 1 |
| 247 | (2-Cl-phenyl / 5-OCF3 biphenyl triazole carbonitrile) | 1H-NMR (DMSO-d6) δ: 7.48-7.65 (5H, m), 7.88 (1H, s), 7.97 (1H, s). | Ex. 1 |

TABLE 4-continued

| | | | |
|---|---|---|---|
| 248 | structure | 1H-NMR (DMSO-d6) δ: 7.80 (1H, d, J = 8.6 Hz), 7.97 (1H, s), 8.02 (1H, s), 8.04-8.06 (1H, m), 8.12 (1H, s), 8.22 (1H, s). | Ex. 1 |
| 249 | structure | 1H-NMR (DMSO-d6) δ: 7.58 (1H, t, J = 7.8 Hz), 7.89-7.91 (2H, m), 7.98-8.02 (1H, m), 8.01 (1H, s), 8.05 (1H, s). | Ex. 1 |
| 250 | structure | 1H-NMR (DMSO-d6) δ: 7.73 (1H, s), 7.84 (1H, s), 7.94 (1H, s), 8.04 (1H, s), 8.09 (1H, d, J = 8.2 Hz), 8.16 (1H, d, J = 8.2 Hz). | Ex. 1 |

TABLE 4-continued

| | Structure | 1H-NMR | |
|---|---|---|---|
| 251 | (4-fluoro-2-methylphenyl / trifluoromethoxyphenyl / triazole-carbonitrile) | 1H-NMR (DMSO-d6) δ: 2.30 (3H, s), 7.15-7.19 (1H, m), 7.24-7.27 (1H, m), 7.36-7.39 (1H, m), 7.59 (1H, s), 7.85-7.89 (2H, m). | Ex. 1 |
| 252 | (4-trifluoromethylphenyl / 3-trifluoromethylphenyl / triazole-carbonitrile) | 1H-NMR (DMSO-d6) δ: 7.93 (2H, d, J = 8.2 Hz), 8.07 (2H, d, J = 8.2 Hz), 8.25 (1H, s), 8.27 (1H, s), 8.51 (1H, s). | Ex. 1 |
| 253 | (3-fluoro-5-trifluoromethylphenyl / 3-fluorophenyl / triazole-carbonitrile) | 1H-NMR (DMSO-d6) δ: 7.73-7.77 (1H, m), 7.78-7.82 (1H, m), 7.94-7.98 (1H, m), 8.01-8.07 (2H, m), 8.14 (1H, t, J = 1.4 Hz). | Ex. 1 |

TABLE 4-continued

| | Structure | 1H-NMR | |
|---|---|---|---|
| 254 | (structure) | 1H-NMR (DMSO-d6) δ: 7.52-7.57 (1H, m), 7.74 (1H, s), 7.80-7.84 (1H, m), 7.93 (1H, s), 8.09 (1H, d, J = 8.4 Hz), 8.16 (1H, d, J = 8.4 Hz). | Ex. 1 |
| 255 | (structure) | 1H-NMR (DMSO-d6) δ: 7.66 (1H, d, J = 9.5 Hz), 7.73-7.89 (3H, m), 7.94 (1H, s). | Ex. 1 |
| 256 | (structure) | 1H-NMR (DMSO-d6) δ: 7.82 (1H, d, J = 8.6 Hz), 8.10-8.14 (2H, m), 8.25 (1H, s), 8.38 (1H, s), 8.54 (1H, s). | Ex. 1 |

TABLE 4-continued

| | Structure | 1H-NMR | |
|---|---|---|---|
| 257 | (2'-trifluoromethyl-5-trifluoromethyl-biphenyl triazole carbonitrile) | 1H-NMR (CDCl3) δ: 7.41 (1H, d, J = 7.3 Hz), 7.59-7.67 (2H, m), 7.76 (1H, s), 7.84 (1H, d, J = 7.3 Hz), 8.20 (1H, m), 8.33 (1H, s). | Ex. 1 |
| 258 | (3-(hexafluoroisopropoxy)-5-fluoro-biphenyl triazole carbonitrile) | 1H-NMR (DMSO-d6) δ: 6.68-7.01 (1H, m), 7.40-7.41 (1H, m), 7.62-7.88 (5H, m), 8.05-8.08 (1H, m). | Ex. 1 |
| 259 | (3'-trifluoromethyl-5-trifluoromethyl-biphenyl triazole carbonitrile) | 1H-NMR (CDCl3) δ: 7.62-7.73 (2H, m), 7.84-7.89 (2H, m), 7.95 (1H, s), 8.28 (1H, s), 8.42 (1H, s). | Ex. 1 |

TABLE 4-continued

| | Structure | 1H-NMR | |
|---|---|---|---|
| 260 | (structure: 4'-(trifluoromethyl)-5-(trifluoromethoxy)biphenyl triazole carbonitrile) | 1H-NMR (DMSO-d6) δ: 7.90-8.04 (6H, m), 8.26 (1H, s). | Ex. 1 |
| 261 | (structure: 4'-(trifluoromethyl)-5-fluoro biphenyl triazole carbonitrile) | 1H-NMR (DMSO-d6) δ: 7.73-7.76 (1H, m), 7.85 (1H, s), 7.91 (2H, d, J = 8.1 Hz), 8.01 (2H, d, J = 8.1 Hz), 8.09 (1H, s). | Ex. 1 |
| 262 | (structure: 4'-(difluoromethoxy)-5-(trifluoromethoxy)biphenyl triazole carbonitrile) | 1H-NMR (DMSO-d6) δ: 7.34 (1H, t, J = 73.7 Hz), 7.35 (2H, d, J = 8.6 Hz), 7.83 (2H, s), 7.56 (2H, d, J = 8.6 Hz), 6.20 (1H, s). | Ex. 1 |

TABLE 4-continued

| | Structure | 1H-NMR | |
|---|---|---|---|
| 263 | 4-[3-(4-trifluoromethoxyphenyl)-5-fluorophenyl]-1H-1,2,3-triazole-5-carbonitrile | 1H-NMR (DMSO-d6) δ: 7.54 (2H, d, J = 8.0 Hz), 7.69-7.82 (2H, m), 7.89-7.92 (2H, m), 8.03-8.04 (1H, m). | Ex. 1 |
| 264 | 4-[3-(4-trifluoromethoxyphenyl)-5-trifluoromethoxyphenyl]-1H-1,2,3-triazole-5-carbonitrile | 1H-NMR (DMSO-d6) δ: 7.55 (2H, d, J = 8.0 Hz), 7.82-7.98 (4H, m), 8.22 (1H, s). | Ex. 1 |
| 265 | 4-[3-(4-trifluoromethoxyphenyl)-5-difluoromethoxyphenyl]-1H-1,2,3-triazole-5-carbonitrile | 1H-NMR (DMSO-d6) δ: 7.46 (1H, t, J = 73.5 Hz), 7.55 (2H, d, J = 8.1 Hz), 7.68-7.70 (2H, m), 7.91 (2H, d, J = 8.8 Hz), 8.06 (1H, s). | Ex. 1 |

TABLE 4-continued

| | Structure | 1H-NMR | |
|---|---|---|---|
| 266 | 3-(difluoromethoxy)-5'-(trifluoromethyl)biphenyl with triazole-carbonitrile | 1H-NMR (DMSO-d6) δ: 7.48 (1H, t, J = 73.5 Hz), 7.64-7.86 (4H, m), 7.94-8.09 (3H, m). | Ex. 1 |
| 267 | 3'-(difluoromethoxy)-5-(trifluoromethoxy)biphenyl with triazole-carbonitrile | 1H-NMR (DMSO-d6) δ: 7.30 (1H, d, J = 8.1 Hz), 7.38 (1H, t, J = 74.0 Hz), 7.58-7.67 (3H, m), 7.86 (1H, s), 7.94 (1H, s), 8.23 (1H, s). | Ex. 1 |
| 268 | 3-chloro-4'-(trifluoromethyl)biphenyl with triazole-carbonitrile | 1H-NMR (DMSO-d6) δ: 7.90 (2H, d, J = 8.4 Hz), 7.97-8.05 (4H, m), 8.18 (1H, s). | Ex. 1 |

| | | | |
|---|---|---|---|
| 269 | 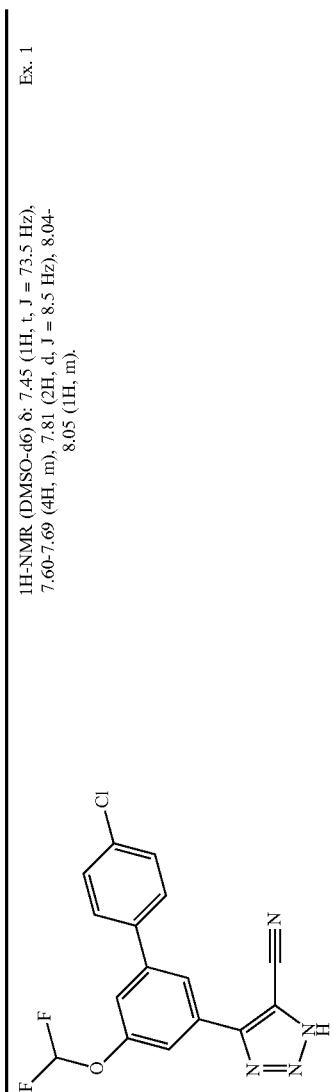 | 1H-NMR (DMSO-d6) δ: 7.45 (1H, t, J = 73.5 Hz), 7.60-7.69 (4H, m), 7.81 (2H, d, J = 8.5 Hz), 8.04-8.05 (1H, m). | Ex. 1 |
| 270 | 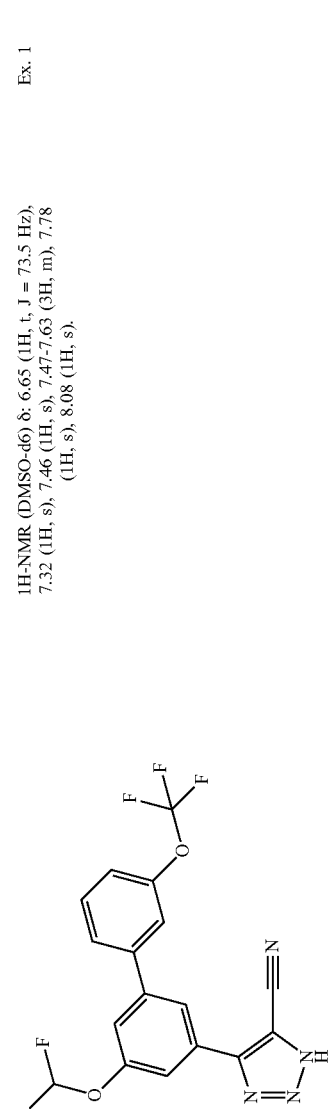 | 1H-NMR (DMSO-d6) δ: 6.65 (1H, t, J = 73.5 Hz), 7.32 (1H, s), 7.46 (1H, s), 7.47-7.63 (3H, m), 7.78 (1H, s), 8.08 (1H, s). | Ex. 1 |
| 271 | 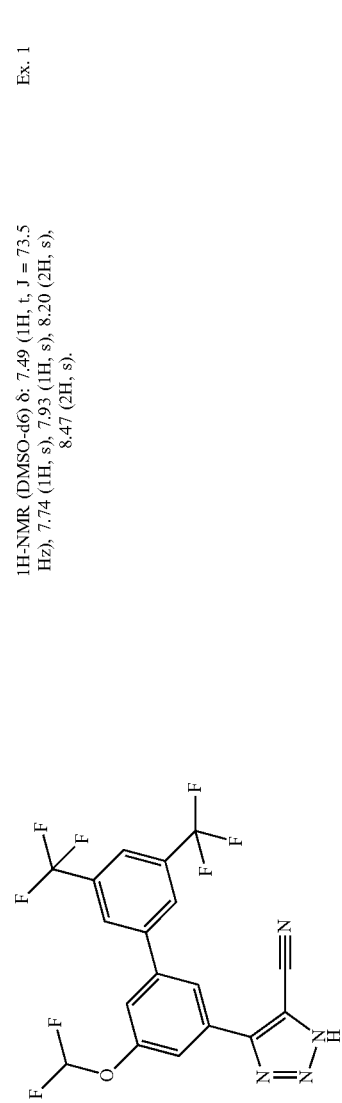 | 1H-NMR (DMSO-d6) δ: 7.49 (1H, t, J = 73.5 Hz), 7.74 (1H, s), 7.93 (1H, s), 8.20 (2H, s), 8.47 (2H, s). | Ex. 1 |

TABLE 4-continued

| | Structure | 1H-NMR | |
|---|---|---|---|
| 272 | 3'-(difluoromethoxy)-5'-(triazol-cyano), 5-fluoro-3-(trifluoromethyl)biphenyl | 1H-NMR (DMSO-d6) δ: 7.47 (1H, t, J = 73.4 Hz), 7.54-7.72 (3H, m), 8.02-8.05 (2H, m), 8.15 (1H, s). | Ex. 1 |
| 273 | 3'-(difluoromethoxy)-5'-(triazol-cyano)-2,5-bis(trifluoromethyl)biphenyl | 1H-NMR (DMSO-d6) δ: 7.41 (1H, t, J = 73.2 Hz), 7.45 (1H, s), 7.77-7.79 (2H, m), 7.92 (1H, s), 8.08-8.18 (2H, m). | Ex. 1 |
| 274 | 3-chloro-3'-(trifluoromethoxy)biphenyl triazole-cyano | 1H-NMR (DMSO-d6) δ: 7.48 (1H, d, J = 8.1 Hz), 7.68 (1H, t, J = 8.1 Hz), 7.80 (1H, s), 7.84 (1H, d, J = 8.1 Hz), 7.94 (1H, s), 8.03 (1H, s), 8.17 (1H, s). | Ex. 1 |

TABLE 4-continued
| | | | |
|---|---|---|---|
| 275 | 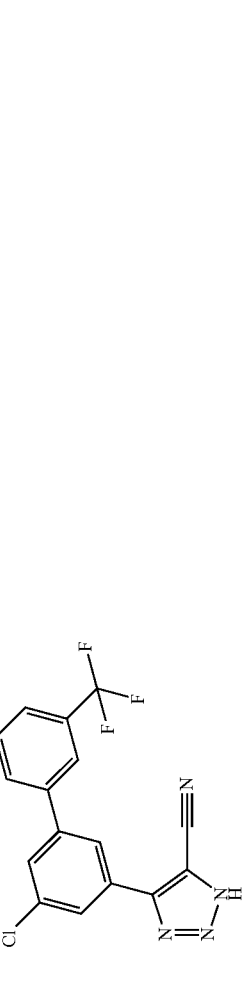 | 1H-NMR (DMSO-d6) δ: 7.99 (1H, s), 8.20 (1H, s), 8.23 (1H, s), 8.28 (1H, s), 8.48 (2H, s). | Ex. 1 |
| 276 |  | 1H-NMR (DMSO-d6) δ: 7.71-7.75 (2H, m), 7.94-8.16 (3H, m), 8.16 (1H, s). | Ex. 1 |
| 277 |  | 1H-NMR (DMSO-d6) δ: 7.93 (1H, d, J = 11.1 Hz), 7.96 (1H, s), 8.07-8.08 (2H, m), 8.18-8.20 (2H, m). | Ex. 1 |

TABLE 4-continued
| | | | |
|---|---|---|---|
| 278 | 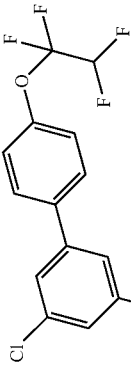 | 1H-NMR (DMSO-d6) δ: 6.68-7.02 (1H, m), 7.45 (2H, d, J = 8.7 Hz), 7.86-7.94 (4H, m), 8.12 (1H, t, J = 1.5 Hz) | Ex. 1 |
| 279 | 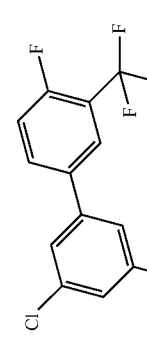 | 1H-NMR (DMSO-d6) δ: 7.70 (1H, t, J = 10.1 Hz), 7.94 (1H, s), 8.07 (1H, s), 8.14-8.16 (3H, m). | Ex. 1 |
| 280 | 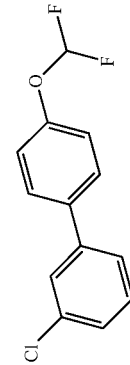 | 1H-NMR (DMSO-d6) δ: 7.33 (1H, t, J = 73.9 Hz), 7.34 (2H, d, J = 8.6 Hz), 7.84 (2H, d, J = 8.6 Hz), 7.90 (1H, s), 7.95 (1H, s), 8.11 (1H, s). | Ex. 1 |
| 281 | 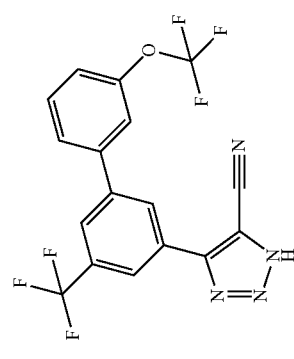 | 1H-NMR (DMSO-d6) δ: 7.47 (1H, d, J = 8.0 Hz), 7.68 (1H, t, J = 8.0 Hz), 7.85-7.88 (2H, m), 8.19 (1H, s), 8.24 (1H, s), 8.46 (1H, s). | Ex. 2 |

TABLE 4-continued

| | Structure | 1H-NMR | |
|---|---|---|---|
| 282 | (structure with OCF2CHF2, OCF3, triazole-CN) | 1H-NMR (DMSO-d6) δ: 7.85 (1H, t, J = 51.8 Hz), 7.47 (2H, d, J = 8.5 Hz), 7.83-7.91 (4H, m), 8.21 (1H, s). | Ex. 1 |
| 283 | (structure with 2,4-bis(CF3)phenyl, Cl, triazole-CN) | 1H-NMR (DMSO-d6) δ: 7.70 (1H, s), 7.79-7.83 (2H, m), 8.05-8.06 (1H, m), 8.19-8.22 (2H, m). | Ex. 1 |
| 284 | (structure with OCF3, CH3, Cl, triazole-CN) | 1H-NMR (DMSO-d6) δ: 2.33 (3H, s), 7.31-7.47 (3H, m), 7.68 (1H, s) 7.80 (1H, m), 7.95 (1H, s). | Ex. 1 |

TABLE 4-continued

| | Structure | NMR | Ex. |
|---|---|---|---|
| 285 | 2,4-bis(trifluoromethyl)phenyl - 3-(trifluoromethoxy)phenyl - triazole-CN | 1H-NMR (DMSO-d6) δ: 7.65 (1H, s), 7.82 (1H, d, J = 8.5 Hz), 7.91 (1H, s), 7.98 (1H, s), 8.21-8.23 (2H, m). | Ex. 1 |
| 286 | 3-(trifluoromethoxy)phenyl - 3-methylphenyl - triazole-CN | 1H-NMR (DMSO-d6) δ: 2.51 (3H, s), 7.42-7.45 (1H, m), 7.64-7.80 (5H, m), 8.00 (1H, s). | Ex. 1 |
| 287 | 4-(1,1,1,3,3,3-hexafluoroisopropoxy)phenyl - 3-methylphenyl - triazole-CN | 1H-NMR (DMSO-d6) δ: 2.48 (3H, s), 6.66-7.03 (1H, m), 7.43 (2H, d, J = 8.6 Hz), 7.71 (2H, s), 7.80-7.84 (2H, m), 7.97 (1H, s). | Ex. 1 |

TABLE 4-continued
| | | | |
|---|---|---|---|
| 288 |  | 1H-NMR (DMSO-d6) δ: 2.48 (3H, s), 7.59-7.77 (4H, m), 7.88-7.95 (1H, m), 8.00 (1H, s). | Ex. 1 |
| 289 | 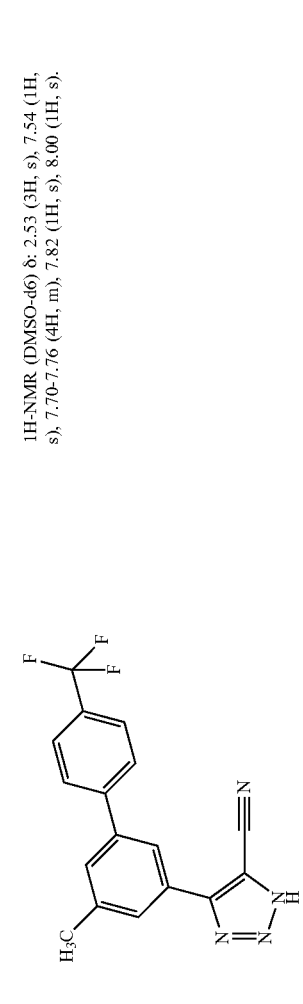 | 1H-NMR (DMSO-d6) δ: 2.53 (3H, s), 7.54 (1H, s), 7.70-7.76 (4H, m), 7.82 (1H, s), 8.00 (1H, s). | Ex. 1 |
| 290 | 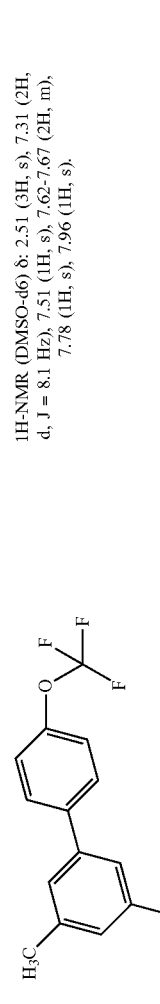 | 1H-NMR (DMSO-d6) δ: 2.51 (3H, s), 7.31 (2H, d, J = 8.1 Hz), 7.51 (1H, s), 7.62-7.67 (2H, m), 7.78 (1H, s), 7.96 (1H, s). | Ex. 1 |

TABLE 4-continued

| # | Structure | 1H-NMR | Ex. |
|---|---|---|---|
| 291 | (biphenyl with OCHF2 and CH3 substituents, triazole-CN) | 1H-NMR (DMSO-d6) δ: 2.48 (3H, s), 7.31-7.34 (2H, m), 7.32 (1H, t, J = 74.0 Hz), 7.69 (2H, s), 7.77-7.80 (2H, m), 7.95 (1H, s). | Ex. 1 |
| 292 | (biphenyl with F, CF3 and CH3 substituents, triazole-CN) | 1H-NMR (DMSO-d6) δ: 2.51 (3H, s), 7.65-7.72 (1H, m), 7.73 (1H, s), 7.79 (1H, s), 8.00 (1H, s), 8.07-8.12 (2H, m). | Ex. 1 |
| 293 | (biphenyl with Cl and CH3 substituents, triazole-CN) | 1H-NMR (DMSO-d6) δ: 2.61 (3H, s), 7.58 (2H, d, J = 8.6 Hz), 7.71 (2H, s), 7.76 (2H, d, J = 8.6 Hz), 7.96 (1H, s). | Ex. 1 |
| 294 | (biphenyl with CF3 and CH3 substituents, triazole-CN) | 1H-NMR (DMSO-d6) δ: 2.50 (3H, s), 7.75-7.81 (4H, m), 8.03-8.06 (3H, m). | Ex. 1 |

TABLE 4-continued

| | Structure | 1H-NMR | |
|---|---|---|---|
| 295 | (3-methyl-5-(3-fluoro-4-(trifluoromethyl)phenyl)phenyl triazole carbonitrile) | 1H-NMR (DMSO-d6) δ: 2.50 (3H, s), 7.78-7.80 (2H, m), 7.84 (1H, s), 7.91-7.95 (2H, m), 8.06 (1H, s). | Ex. 1 |
| 296 | (3-methyl-5-(2-methyl-4-(trifluoromethoxy)phenyl)phenyl triazole carbonitrile) | 1H-NMR (DMSO-d6) δ: 2.31 (3H, s), 2.46 (3H, s), 7.29-7.40 (4H, m), 7.67 (1H, s), 7.75 (1H, s). | Ex. 1 |
| 297 | (3-methyl-5-(3,5-bis(trifluoromethyl)phenyl)phenyl triazole carbonitrile) | 1H-NMR (DMSO-d6) δ: 2.55 (3H, s), 7.54 (1H, s), 7.88-7.90 (2H, m), 7.99 (1H, s), 8.05 (2H, s). | Ex. 1 |

TABLE 4-continued

| | Structure | 1H-NMR | |
|---|---|---|---|
| 298 | (3-fluoro-4-(trifluoromethoxy)phenyl / 3-(trifluoromethoxy)phenyl triazole carbonitrile) | 1H-NMR (DMSO-d6) δ: 7.43-7.56 (4H, m), 7.90 (1H, s), 8.14 (1H, s). | Ex. 1 |
| 299 | (3-chloro-4-fluorophenyl / 3-(trifluoromethoxy)phenyl triazole carbonitrile) | 1H-NMR (DMSO-d6) δ: 7.56-7.62 (1H, m), 7.77-7.82 (3H, m), 8.01-8.05 (1H, m), 8.17 (1H, s). | Ex. 1 |
| 300 | (4-fluorophenyl / 3-(trifluoromethoxy)phenyl triazole carbonitrile) | 1H-NMR (DMSO-d6) δ: 7.39 (2H, t, J = 8.9 Hz), 7.83 (1H, s) 7.82-7.86 (2H, m), 7.87 (1H, s), 8.19 (1H, s). | Ex. 1 |

TABLE 4-continued

| | | | |
|---|---|---|---|
| 301 | [structure: 3'-CF3-biphenyl with OCH2CH3 and triazole-CN] | 1H-NMR (CDCl3) δ: 1.48 (3H, t, J = 7.0 Hz), 4.19 (2H, t, J = 7.0 Hz), 7.25 (1H, s), 7.52-7.61 (3H, m), 7.76-7.86 (3H, m). | Ex. 2 |
| 302 | [structure: 3'-CF3-biphenyl with OCH(CH3)2 and triazole-CN] | 1H-NMR (CDCl3) δ: 1.43 (6H, d, J = 6.1 Hz), 4.68-4.76 (1H, m), 7.23 (1H, s), 7.56-7.66 (3H, m), 7.74 (1H, s), 7.80-7.86 (2H, m). | Ex. 2 |
| 303 | [structure: biphenyl with OCH2CH3 and triazole-CN] | 1H-NMR (CDCl3) δ: 1.48 (3H, t, J = 7.0 Hz), 4.18 (2H, t, J = 7.0 Hz), 7.25 (1H, s), 7.39-7.49 (4H, m), 7.62-7.65 (2H, m), 7.77 (1H, bs). | Ex. 2 |

TABLE 4-continued

| | | | |
|---|---|---|---|
| 304 | (structure) | 1H-NMR (CDCl3) δ: 1.42 (6H, d, J = 6.1 Hz), 4.67-4.75 (1H, m), 7.25 (1H, s), 7.39-7.49 (4H, m), 7.62-7.65 (2H, m), 7.75 (1H, bs). | Ex. 2 |
| 305 | (structure) | 1H-NMR (DMSO-d6) δ: 3.26 (3H, m), 7.75 (1H, t, J = 7.8 Hz), 7.93-8.07 (6H, m), 8.21-8.22 (1H, m). | Ex. 1 |
| 306 | (structure) | 1H-NMR (DMSO-d6) δ: 3.28 (3H, m), 8.06-8.12 (4H, m), 8.24 (1H, s), 8.26 (1H, s), 8.49 (1H, s). | Ex. 1 |

TABLE 4-continued

| | Structure | 1H-NMR | |
|---|---|---|---|
| 307 | 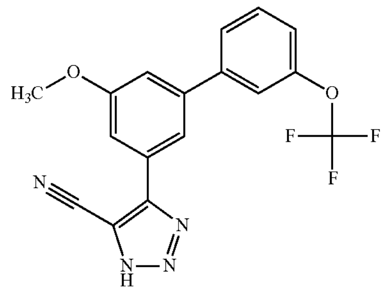 [SMILES: COc1cc(-c2cccc(OC(F)(F)F)c2)cc(-c2nn[nH]c2C#N)c1] | 1H-NMR (CDCl3) δ: 3.95 (3H, s), 7.22-7.35 (2H, m), 7.47-7.57 (4H, m), 7.78 (1H, s). | Ex. 1 |
| 308 | 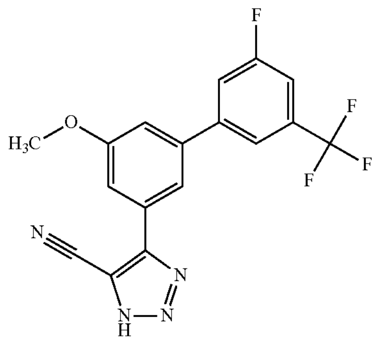 [SMILES: COc1cc(-c2cc(F)cc(C(F)(F)F)c2)cc(-c2nn[nH]c2C#N)c1] | 1H-NMR (CDCl3) δ: 3.96 (3H, s), 7.22-7.23 (1H, m), 7.36 (1H, d, J = 8.6 Hz), 7.50-7.53 (1H, m), 7.58 (1H, s), 7.67 (1H, s), 7.76 (1H, s). | Ex. 1 |
| 309 | 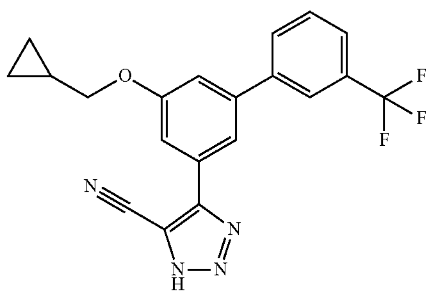 [SMILES: N#Cc1[nH]nnc1-c1cc(OCC2CC2)cc(-c2cccc(C(F)(F)F)c2)c1] | 1H-NMR (CDCl3) δ: 0.40-0.44 (2H, m), 0.68-0.73 (2H, m), 1.31-1.39 (1H, m), 3.96 (2H, d, J = 7.0 Hz), 7.27-7.28 (1H, m), 7.54 (1H, s), 7.59 (1H, t, J = 7.8 Hz), 7.65 (1H, d, J = 7.8 Hz), 7.78 (1H, s), 7.62 (1H, d, J = 7.6 Hz), 7.86 (1H, s). | Ex. 2 |

TABLE 4-continued

| | Structure | 1H-NMR | Ex. |
|---|---|---|---|
| 310 | (3,5-bis(trifluoromethyl)phenyl with cyclopropylmethoxy, triazole-CN) | 1H-NMR (CDCl3) δ: 0.41-0.45 (2H, m), 0.69-0.74 (2H, m), 1.30-1.39 (1H, m), 3.97 (2H, d, J = 7.0 Hz), 7.26-7.27 (1H, m), 7.59 (1H, s), 7.78 (1H, s), 7.91 (1H, s), 8.05 (2H, s). | Ex. 2 |
| 311 | (acetamido biphenyl-CF3, triazole-CN) | 1H-NMR (DMSO-d6) δ: 1.91 (3H, s), 7.73-7.80 (5H, m), 7.89-7.92 (2H, m), 9.64 (1H, s), 16.15-16.84 (1H, br). | Ex. 1 |
| 312 | (N,N-diethylamino biphenyl-CF3, triazole-CN) | 1H-NMR (DMSO-d6) δ: 0.83 (3H, t, J = 7.0 Hz), 2.62 (3H, s), 2.83 (2H, q, J = 6.9 Hz), 7.32 (1H, d, J = 8.6 Hz), 7.72-7.74 (3H, m), 7.82-7.91 (3H, m). | Ex. 1 |

TABLE 4-continued

| | Structure | 1H-NMR | Ex. |
|---|---|---|---|
| 313 | (structure) | 1H-NMR (DMSO-d6) δ: 1.68 (3H, 2.95 (3H, s), 7.74-8.03 (7H, m). | Ex. 1 |
| 314 | (structure) | 1H-NMR (CDCl3) δ: 3.59 (3H, s), 7.60 (1H, t, J = 7.7 Hz), 7.63 (1H, d, J = 8.2 Hz), 7.80 (1H, d, J = 7.7 Hz), 7.89-7.90 (2H, m), 8.06 (1H, d, J = 2.2 Hz). | Ex. 1 |
| 315 | (structure) | 1H-NMR (DMSO-d6) δ: 7.76-7.80 (1H, m), 7.85-7.90 (4H, m), 7.94-7.97 (2H, m). | Ex. 2 |
| 317 | (structure) | 1H-NMR (DMSO-d6) δ: 0.88 (6H, t, J = 7.0 Hz), 2.92 (4H, q, J = 7.0 Hz), 7.37 (1H, d, J = 8.5 Hz), 7.72-7.76 (3H, m), 7.82-7.89 (2H, m), 7.93 (1H, s). | Ex. 316 |

TABLE 4-continued

| | Structure | 1H-NMR | Ex. |
|---|---|---|---|
| 318 | 3-(trifluoromethyl)phenyl-2-methylphenyl-triazole-carbonitrile | 1H-NMR (CDCl3) δ: 2.21 (3H, s), 7.37-7.69 (7H, m), 11.8 (1H, br.). | Ex. 1 |
| 319 | 3-methoxyphenyl-2-methylphenyl-triazole-carbonitrile | 1H-NMR (CDCl3) δ: 2.23 (3H, s), 3.85 (3H, s), 6.85-6.89 (1H, m), 6.89-6.96 (2H, m), 7.32-7.46 (4H, m). | Ex. 1 |
| 320 | 2,3-dimethylphenyl-2-methylphenyl-triazole-carbonitrile | 1H-NMR (CDCl3) δ: 1.99 (3H, s), 2.05 (3H, s), 2.35 (3H, s), 6.98 (1H, dd, J = 2.0, 7.0 Hz), 7.12-7.22 (2H, m), 7.30 (1H, dd, J = 1.7, 7.4 Hz), 7.38 (1H, t, J = 7.4 Hz), 7.43 (1H, dd, J = 1.7, 7.6 Hz). | Ex. 1 |
| 321 | 4-fluorophenyl-dimethyl-triazole-carbonitrile | 1H-NMR (DMSO-d6) δ: 1.43 (9H, s), 7.13-7.20 (2H, m), 7.57-7.63 (2H, m), 7.67-7.69 (1H, m), 7.94 (1H, t, J = 1.6 Hz), 7.99 (1H, t, J = 1.6 Hz). | Ex. 1 |

TABLE 4-continued

| | Structure | NMR | Ex. |
|---|---|---|---|
| 322 | (3-trifluoromethylphenyl-phenyl with CH(CH3)2 and triazole-CN) | 1H-NMR (DMSO-d6) δ: 1.37 (6H, d, J = 6.9 Hz), 3.05-3.14 (1H, m), 7.54-7.68 (3H, m), 7.78-7.90 (3H, m), 8.00 (1H, t, J = 1.7 Hz). | Ex. 1 |
| 323 | (4-fluorophenyl-phenyl with cyclopropylmethyl and triazole-CN) | 1H-NMR (DMSO-d6) δ: 0.25-0.32 (2H, m), 0.58-0.65 (2H, m), 1.02-1.15 (1H, m), 2.69 (2H, d, J = 6.9 Hz), 7.12-7.20 (2H, m), 7.55-7.63 (3H, m), 7.87 (1H, s), 7.97 (1H, s). | Ex. 1 |
| 324 | (4-fluorophenyl-phenyl with CH2CH3 and triazole-CN) | 1H-NMR (CDCl3) δ: 1.34 (3H, d, J = 7.6 Hz), 2.81 (2H, q, J = 7.6 Hz), 7.13-7.19 (2H, m), 7.51 (1H, s), 7.58-7.63 (2H, m), 7.77 (1H, s), 7.95 (1H, s). | Ex. 1 |

TABLE 4-continued

| No. | Structure | NMR | Ex. |
|---|---|---|---|
| 325 | (4-fluorobiphenyl with propyl and triazole-CN) | 1H-NMR (DMSO-d6) δ: 0.95 (3H, t, J = 7.3 Hz), 1.66-1.74 (2H, m), 2.72 (2H, t, J = 7.3 Hz), 7.34-7.38 (2H, m), 7.67 (1H, s), 7.70 (1H, s), 7.75-7.79 (2H, m), 7.95-7.97 (1H, m). | Ex. 1 |
| 326 | (4-fluorobiphenyl with CF3-CH(OMe) and triazole-CN) | 1H-NMR (CDCl3) δ: 3.54 (3H, s), 4.54-4.69 (1H, m), 7.17-7.21 (2H, m), 7.61-7.65 (2H, m), 7.75 (1H, s), 8.00 (1H, s), 8.22 (1H, s). | Ex. 1 |
| 327 | (4-fluorobiphenyl with CH2OMe and triazole-CN) | 1H-NMR (DMSO-d6) δ: 3.36 (3H, s), 4.59 (2H, s), 7.35-7.39 (2H, m), 7.77-7.80 (3H, m), 7.84 (1H, s), 8.07 (1H, s). | Ex. 1 |

| | | | |
|---|---|---|---|
| 328 | [structure: 4'-fluorobiphenyl with cyclopentyloxy and triazole-carbonitrile] | 1H-NMR (DMSO-d6) δ: 1.62-1.70 (2H, m), 1.78-2.50 (8H, m), 4.90 (1H, m), 7.12-7.19 (3H, m), 7.44-7.46 (1H, m), 7.56-7.61 (2H, m), 7.69 (1H, s). | Ex. 1 |
| 329 | [structure: 4'-fluorobiphenyl with methoxymethoxy and triazole-carbonitrile] | 1H-NMR (DMSO-d6) δ: 1.41 (3H, t, J = 6.9 Hz), 4.23 (2H, q, J = 6.9 Hz), 7.28-7.35 (3H, m), 7.70-7.75 (2H, m), 7.81-7.87 (2H, m). | Ex. 1 |
| 330 | [structure: 4'-fluorobiphenyl with isopropoxy and triazole-carbonitrile] | 1H-NMR (DMSO-d6) δ: 1.35 (6H, d, J = 6.0 Hz), 4.79-4.86 (1H, m), 7.28-7.35 (3H, m), 7.70-7.75 (2H, m), 7.80-7.85 (2H, m). | Ex. 1 |

TABLE 4-continued

| Ex. No. | STR | m.p. | ref. |
|---|---|---|---|
| 331 | | 173-177 | Ex. 1 |
| 332 | | 296-298 | Ex. 1 |

TABLE 4-continued
| | | | |
|---|---|---|---|
| 333 | 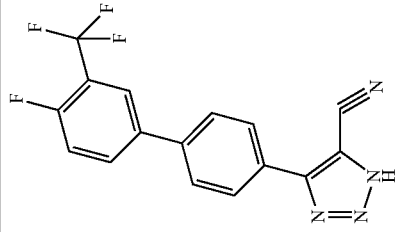 | 285-290 | Ex. 1 |
| 334 | 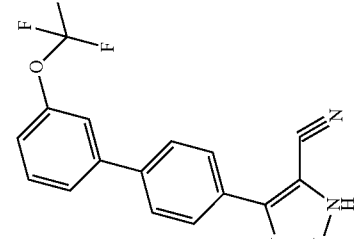 | 211-212 | Ex. 1 |

TABLE 4-continued

| | | | |
|---|---|---|---|
| 335 | 209 | Ex. 1 | 2',4'-dichloro biphenyl triazole carbonitrile structure |
| 336 | 242-245 | Ex. 1 | 3',4',5'-trifluoro biphenyl triazole carbonitrile structure |

TABLE 4-continued
| | | | |
|---|---|---|---|
| 337 | 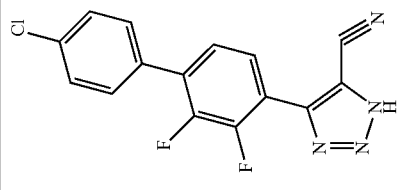 | 210-211 | Ex. 1 |
| 338 | 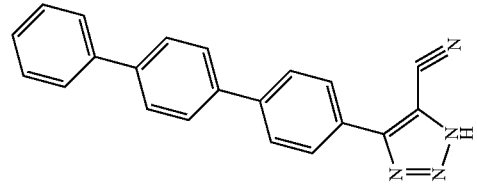 | 292-293 | Ex. 1 |

TABLE 4-continued
| | | | |
|---|---|---|---|
| 339 | 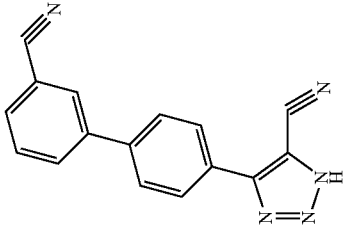 | 271-274 | Ex. 1 |
| 340 | 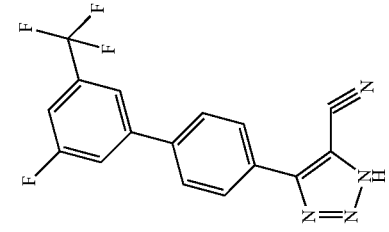 | 256 | Ex. 1 |
| 341 | 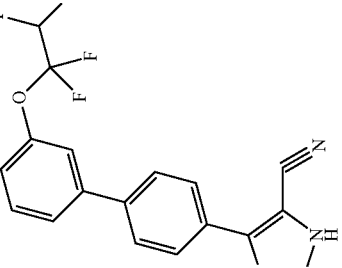 | 168-170 | Ex. 1 |

TABLE 4-continued
| 342 | 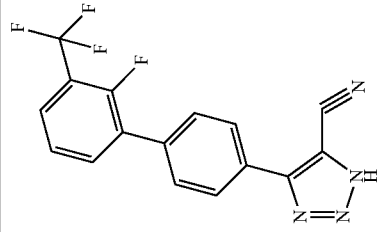 | 206-207 | Ex. 1 |
| 343 | 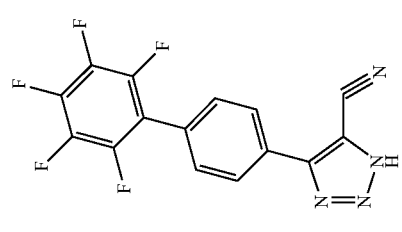 | 237-241 | Ex. 1 |

TABLE 4-continued
| | | | |
|---|---|---|---|
| 344 | 156-159 | 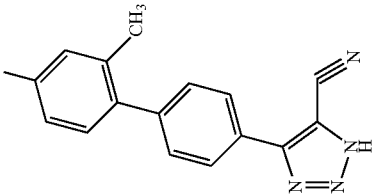 | Ex. 1 |
| 345 | 224 | 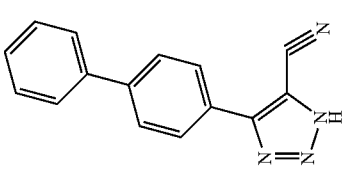 | Ex. 1 |

TABLE 4-continued
| | | | |
|---|---|---|---|
| 346 | 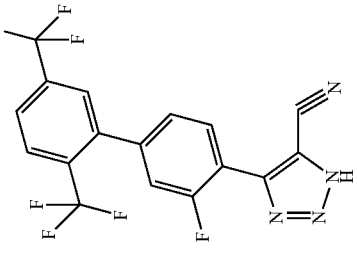 | 127-128 | Ex. 1 |
| 347 | 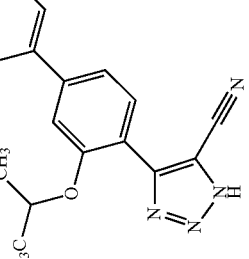 | 216-218 | Ex. 1 |

TABLE 4-continued
| Ex. No. | STR | 1H-NMR | ref. |
|---|---|---|---|
| 348 | 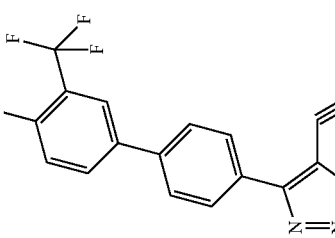 | 1H-NMR (DMSO-d6) δ: 7.86 (1H, d, J = 8.4 Hz), 8.02 (4H, m), 8.09 (1H, d, J = 8.4 Hz), 8.16 (1H, s). | Ex. 1 |
| 349 | 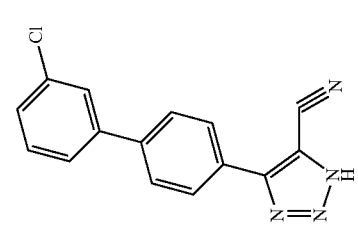 | 1H-NMR (DMSO-d6) δ: 7.48-7.54 (2H, m), 7.74-7.76 (1H, m), 7.83-7.84 (1H, m) 7.96-8.01 (4H, m). | Ex. 1 |

TABLE 4-continued
| | | | |
|---|---|---|---|
| 350 |  | 1H-NMR (DMSO-d6) δ: 7.64 (2H, d, J = 8.1 Hz), 7.86 (1H, s), 7.99 (2H, d, J = 8.1 Hz), 6.06 (1H, d, J = 8.3 Hz), 8.14 (1H, d, J = 8.3 Hz). | Ex. 1 |
| 351 | 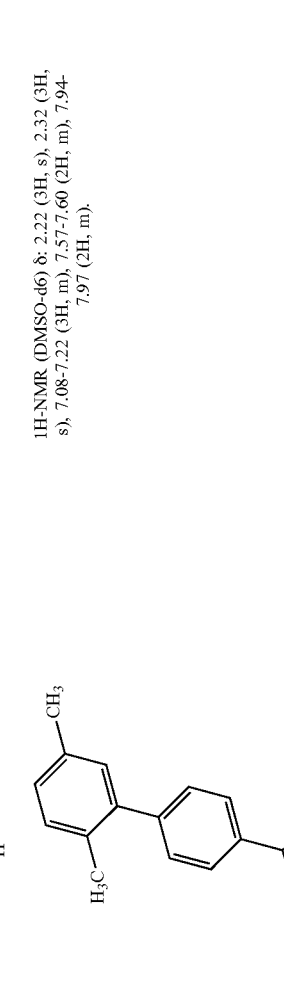 | 1H-NMR (DMSO-d6) δ: 2.22 (3H, s), 2.32 (3H, s), 7.08-7.22 (3H, m), 7.57-7.60 (2H, m), 7.94-7.97 (2H, m). | Ex. 1 |

TABLE 4-continued

| | | | |
|---|---|---|---|
| 352 | [structure: 2,3,4,5-tetrafluorophenyl-phenyl-triazole-carbonitrile] | 1H-NMR (DMSO-d6) δ: 7.79 (2H, d, J = 8.3 Hz), 7.94-8.03 (1H, m), 8.08 (2H, d, J = 8.3 Hz). | Ex. 1 |
| 353 | [structure: 4-fluoro-2-trifluoromethylphenyl-phenyl-triazole-carbonitrile] | 1H-NMR (DMSO-d6) δ: 7.55-7.58 (3H, m), 7.64-7.68 (1H, m), 7.78-7.80 (1H, m), 7.96 (2H, d, J = 8.2 Hz). | Ex. 1 |

TABLE 4-continued

| Ex. No. | STR | m.p. | 1H-NMR | ref. |
|---|---|---|---|---|
| 354 | | | 1H-NMR (DMSO-d6) δ: 7.38-7.40 (1H, m), 7.51-7.53 (1H, m), 7.60-7.66 (2H, m), 7.85-7.88 (1H, m), 7.94-7.96 (1H, m). | Ex. 1 |
| 355 | | | 1H-NMR (CDCl3) δ: 7.14-7.17 (2H, m), 7.20-7.26 (2H, m), 7.29-7.32 (2H, m), 7.46 (4H, s), 7.83 (2H, d, J = 8.0 Hz), 12.2 (1H, br). | Ex. 1 |
| 356 | | 138.6-139.4 | | Ex. 1 |

TABLE 4-continued

| | | | |
|---|---|---|---|
| 357 | (structure: 4'-chloro-biphenyl with CF3 and triazole-carbonitrile) | 141.3-142.4 | Ex. 1 |
| 358 | (structure: 4'-methoxy-biphenyl with CF3 and triazole-carbonitrile) | 118.8-119.3 | Ex. 1 |
| 359 | (structure: 3'-trifluoromethoxy-biphenyl with CF3 and triazole-carbonitrile) | 117.5-118.2 | Ex. 1 |

TABLE 4-continued

| Ex. No. | STR | 1H-NMR | ref. |
|---|---|---|---|
| 360 | | 91.7-92.9 | Ex. 1 |
| 361 | | 1H-NMR (CDCl3) δ: 7.15-7.21 (2H, m), 7.37 (3H, br. s), 7.49-7.63 (2H, m), 7.57-7.63 (1H, t, J = 7.3 Hz), 7.73 (1H, br.s), 11.5 (1H, br.). | Ex. 1 |
| 362 | | 1H-NMR (CDCl3) δ: 7.08-7.13 (2H, m), 7.29-7.35 (2H, m), 7.48-7.68 (4H, m), 11.8 (1H, br.). | Ex. 1 |
| 363 | | 1H-NMR (DMSO-d6) δ: 7.06-7.11 (2H, m), 7.13-7.35 (8H, m), 7.42-7.50 (2H, m), 7.54-7.61 (1H, m). | Ex. 1 |

TABLE 4-continued

| | Structure | NMR | Ex. |
|---|---|---|---|
| 364 | (biphenyl with CF3 and triazole-CN) | 1H-NMR (DMSO-d6) δ: 7.15-7.19 (2H, m), 7.35-7.40 (3H, m), 7.81 (1H, d, J = 8.5 Hz), 8.03-8.05 (2H, m). | Ex. 1 |
| 365 | (phenoxyphenyl with CF3 and triazole-CN) | 1H-NMR (CDCl3) δ: 6.96-7.00 (2H, m), 7.03-7.05 (2H, m), 7.12-7.17 (3H, m), 7.33-7.40 (2H, m), 7.68 (1H, d, J = 7.8 Hz), 7.85-7.87 (2H, m). | Ex. 1 |
| 366 | (bis-CF3 biphenyl with triazole-CN) | 1H-NMR (DMSO-d6) δ: 7.43 (2H, d, J = 8.0 Hz), 7.76 (2H, d, J = 8.0 Hz), 7.87 (1H, d, J = 8.6 Hz), 8.08-8.10 (2H, m). | Ex. 1 |

TABLE 4-continued
| Ex. No. | STR | m.p. | ref. |
|---|---|---|---|
| 367 | 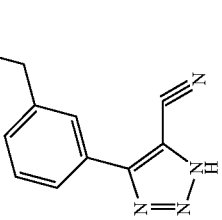 | 153 | Ex. 1 |
| 368 | 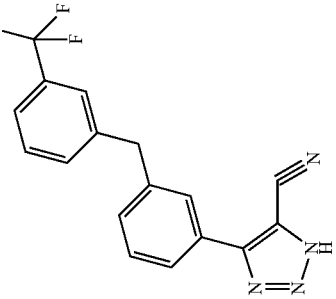 | 127-131 | Ex. 1 |

TABLE 4-continued

| | | | |
|---|---|---|---|
| 369 | 4-[3-(2-fluoro-4-(trifluoromethyl)benzyl)phenyl]-1H-1,2,3-triazole-5-carbonitrile | 117-118 | Ex. 1 |
| 370 | 4-[3-(4-chlorobenzyl)-4-methoxyphenyl]-1H-1,2,3-triazole-5-carbonitrile | 216 | Ex. 1 |
| 371 | 4-[3-(3,4-difluorobenzyl)phenyl]-1H-1,2,3-triazole-5-carbonitrile | 138-140 | Ex. 1 |

TABLE 4-continued

| | | | |
|---|---|---|---|
| 372 | [structure] | 139-141 | Ex. 1 |
| 373 | [structure] | 123-134 | Ex. 1 |
| 374 | [structure] | 123-125 | Ex. 1 |
| 375 | [structure] | 141-142 | Ex. 1 |

TABLE 4-continued

| | | | |
|---|---|---|---|
| 376 | [structure: 4-fluorobenzyl, 3-chloro-5-(4-cyano-1H-1,2,3-triazol-5-yl)phenyl] | 98-101 | Ex. 1 |
| 377 | [structure: 4-fluorobenzyl, 3-methyl-5-(4-cyano-1H-1,2,3-triazol-5-yl)phenyl] | 119 | Ex. 1 |
| 378 | [structure: 4-(trifluoromethyl)benzyl, 3-chloro-5-(4-cyano-1H-1,2,3-triazol-5-yl)phenyl] | 108-112 | Ex. 1 |

TABLE 4-continued

| | | | |
|---|---|---|---|
| 379 | (structure) | 106-109 | Ex. 1 |
| 380 | (structure) | 134-136 | Ex. 1 |
| 381 | (structure) | 124-127 | Ex. 1 |

TABLE 4-continued

| | | | |
|---|---|---|---|
| 382 | [structure: 3,5-dichloro-4'-fluoro benzyl phenyl triazole carbonitrile] | 136-139 | Ex. 1 |
| 383 | [structure: 4-(trifluoromethyl)benzyl, 2-methoxy phenyl triazole carbonitrile] | 199 | Ex. 1 |
| 384 | [structure: 2,5-bis(trifluoromethyl)benzyl phenyl triazole carbonitrile] | 226-227 | Ex. 1 |

TABLE 4-continued

| Ex. No. | STR | 1H-NMR | ref. |
|---|---|---|---|
| 385 | (structure) | 1H-NMR (DMSO-d6) δ: 4.29 (2H, s), 7.53-7.59 (2H, m), 7.74 (1H, d, J = 7.5 Hz), 7.82 (1H, s), 7.96 (1H, s), 8.05 (2H, s). | Ex. 1 |
| 386 | (structure) | 1H-NMR (DMSO-d6) δ: 4.06 (2H, s), 7.15-7.17 (1H, m), 7.34-7.58 (2H, m), 7.71 (1H, s), 7.72-7.75 (2H, m). | Ex. 1 |
| 387 | (structure) | 1H-NMR (DMSO-d6) δ: 4.39 (2H, s), 7.96 (1H, s), 8.00 (1H, s), 8.05 (1H, s), 8.11 (1H, s), 8.13 (2H, s). | Ex. 1 |

TABLE 4-continued

| | Structure | 1H-NMR | Ex. |
|---|---|---|---|
| 388 | (3-fluoro-5-(2,5-bis(trifluoromethyl)benzyl)phenyl triazole carbonitrile) | 1H-NMR (DMSO-d6) δ: 4.40 (2H, s), 7.28 (1H, d, J = 8.7 Hz), 7.43 (1H, s), 7.56 (1H, d, J = 8.7 Hz), 7.90 (1H, d, J = 8.2 Hz), 7.91 (1H, s), 8.02 (1H, d, J = 8.2 Hz). | Ex. 1 |
| 389 | (3-benzyl-5-trifluoromethoxyphenyl triazole carbonitrile) | 1H-NMR (DMSO-d6) δ: 4.08 (2H, s), 7.17 (1H, s), 7.21-7.36 (5H, m), 7.78 (1H, s), 8.08 (1H, s). | Ex. 1 |
| 390 | (3-(4-chlorobenzyl)-5-trifluoromethylphenyl triazole carbonitrile) | 1H-NMR (DMSO-d6) δ: 4.16 (2H, s), 7.33-7.39 (4H, m), 7.85 (1H, s), 8.04 (2H, s). | Ex. 1 |

TABLE 4-continued

| # | Structure | 1H-NMR | Ex. |
|---|---|---|---|
| 391 | (3-CF3, 4-F benzyl derivative) | 1H-NMR (CDCl3) δ: 4.21 (2H, s), 7.28-7.44 (3H, m), 7.61 (1H, s), 8.07 (1H, s), 8.14 (1H, s). | Ex. 1 |
| 392 | (2,5-bis-CF3 benzyl derivative) | 1H-NMR (CDCl3) δ: 4.40 (2H, s), 7.51 (2H, s), 7.67-7.69 (1H, m), 7.88 (1H, d, J = 8.2 Hz), 7.94 (1H, s), 8.18 (1H, s). | Ex. 2 |
| 393 | (2-CF3 benzyl derivative) | 1H-NMR (CDCl3) δ: 4.31 (2H, s), 7.23-7.26 (1H, m), 7.35-7.41 (1H, m), 7.50 (2H, s), 7.71 (1H, d, J = 7.3 Hz), 7.93 (1H, s), 8.09 (1H, s). | Ex. 2 |

TABLE 4-continued

| | | | |
|---|---|---|---|
| 394 | *[structure: 3-chloro-5-(4-trifluoromethoxybenzyl)phenyl triazole carbonitrile]* | 1H-NMR (DMSO-d6) δ: 4.10 (2H,s), 7.29 (1H, s), 7.32 (1H, s), 7.43 (2H, d, J = 8.6 Hz), 7.58 (1H, s), 7.75 (2H, d, J = 8.6 Hz). | Ex. 1 |
| 395 | *[structure: 3-methyl-5-(3,5-bis(trifluoromethyl)benzyl)phenyl triazole carbonitrile]* | 1H-NMR (DMSO-d6) δ: 2.37 (3H, s), 4.24 (2H, s), 7.36 (1H, s), 7.55 (1H, s), 7.60 (1H, s), 7.95 (1H, s), 8.03 (2H, s). | Ex. 1 |

TABLE 4-continued
| | | | |
|---|---|---|---|
| 396 | 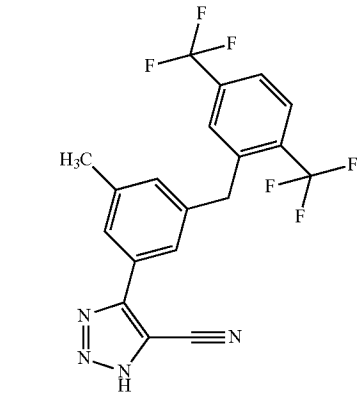 [SMILES: Cc1cc(Cc2cc(C(F)(F)F)ccc2C(F)(F)F)cc(-c2nn[nH]c2C#N)c1] | 1H-NMR (DMSO-d6) δ: 2.37 (3H, s), 4.33 (2H, s), 7.22 (1H, s), 7.40 (1H, s), 7.58 (1H, s), 7.83 (1H, s), 7.88 (1H, d, J = 8.5 Hz), 8.02 (1H, d, J = 8.5 Hz). | Ex. 1 |
| 397 |  | 1H-NMR (DMSO-d6) δ: 4.12 (2H, s), 7.16 (1H, s), 7.38-7.56 (4H, m), 7.73 (1H, s), 7.77 (1H, s). | Ex. 1 |
| 398 | 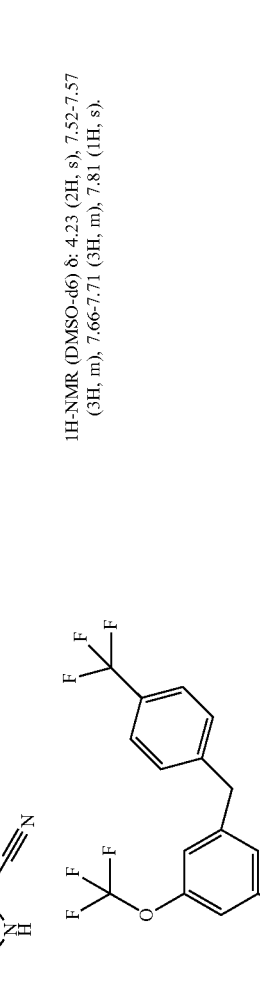 | 1H-NMR (DMSO-d6) δ: 4.23 (2H, s), 7.52-7.57 (3H, m), 7.66-7.71 (3H, m), 7.81 (1H, s). | Ex. 1 |

TABLE 4-continued

| Ex. No. | STR | m.p. | 1H-NMR (DMSO-d6) δ: 2.35 (3H, s), 4.10 (2H, s), 7.52-7.65 (7H, m). | ref. |
|---|---|---|---|---|
| 399 | (3-CF3-benzyl)-5-methyl-phenyl triazole carbonitrile structure | | 1H-NMR (DMSO-d6) δ: 2.35 (3H, s), 4.10 (2H, s), 7.52-7.65 (7H, m). | Ex. 1 |
| 400 | (4-CF3-benzyl)-phenyl triazole carbonitrile structure | 209-210 | | Ex. 1 |
| 401 | (4-CF3-benzyl)-3-fluoro-phenyl triazole carbonitrile structure | 195-197 | | Ex. 1 |

TABLE 4-continued

| Ex. No. | STR | | ref. |
|---|---|---|---|
| 402 | (4-(trifluoromethyl)benzyl structure with difluoro phenyl triazole carbonitrile) | 144-146 | Ex. 1 |
| 403 | (3-methyl-5-(4-(trifluoromethoxy)benzyl)phenyl triazole carbonitrile) | 1H-NMR (DMSO-d6) δ: 2.32-2.38 (3H, m) 4.00-4.05 (2H, m), 7.22-7.41 (5H, m), 7.53-7.63 (2H, m). | Ex. 1 |
| 404 | (3-(trifluoromethyl)-5-(trifluoromethoxy)benzyl phenyl triazole carbonitrile) | 1H-NMR (DMSO-d6) δ: 4.14 (2H, s), 7.01-7.19 (2H, m), 7.20-7.30 (2H, m), 7.75-7.80 (2H, m). | Ex. 1 |

TABLE 4-continued

| | | | |
|---|---|---|---|
| 405 | 5-(3-(trifluoromethylbenzyl)phenyl with CH(CH3) group, triazole-carbonitrile | 1H-NMR (DMSO-d6) δ: 1.28 (6H, d, J = 6.9 Hz), 2.91-3.02 (1H, m), 4.10 (2H, s), 7.19 (1H, s), 7.40-7.51 (4H, m), 7.57 (1H, s), 7.70 (1H, s). | Ex. 1 |
| 406 | 5-bromo-3-(4-fluorobenzyl)phenyl triazole-carbonitrile | 1H-NMR (DMSO-d6) δ: 4.00 (2H, s), 6.97-7.05 (2H, m), 7.15-7.20 (2H, m), 7.43 (1H, s), 7.74 (1H, s), 7.95-7.98 (1H, m). | Ex. 1 |
| 407 | 4-(3,5-bis(trifluoromethyl)benzyl)phenyl triazole-carbonitrile | 1H-NMR (DMSO-d6) δ: 4.27 (2H, s), 7.57 (2H, d, J = 8.1 Hz), 7.84 (2H, d, J = 8.1 Hz), 7.96 (1H, s), 8.05 (2H, s). | Ex. 1 |

TABLE 4-continued
| Ex. No. | STR | | 1H-NMR | |
|---|---|---|---|---|
| 408 |  | | 1H-NMR (DMSO-d6) δ: 4.17 (2H, s), 7.16-7.58 (4H, m), 7.65-7.80 (3H, m). | Ex. 1 |
| Ex. No. | STR | | m.p. | ref. |
|---|---|---|---|---|
| 409 | 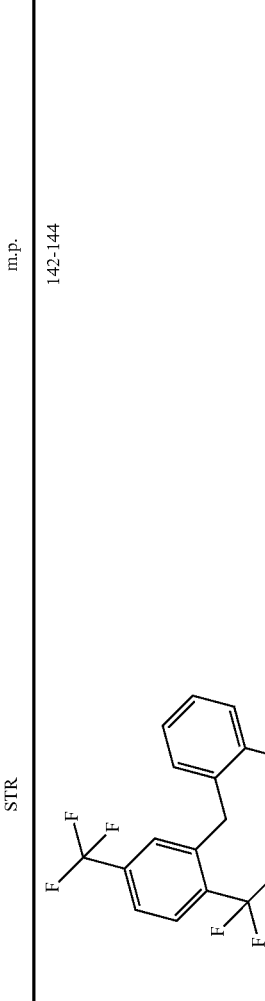 | | 142-144 | Ex. 1 |
| Ex. No. | STR | | 1H-NMR | ref. |
|---|---|---|---|---|
| 410 | 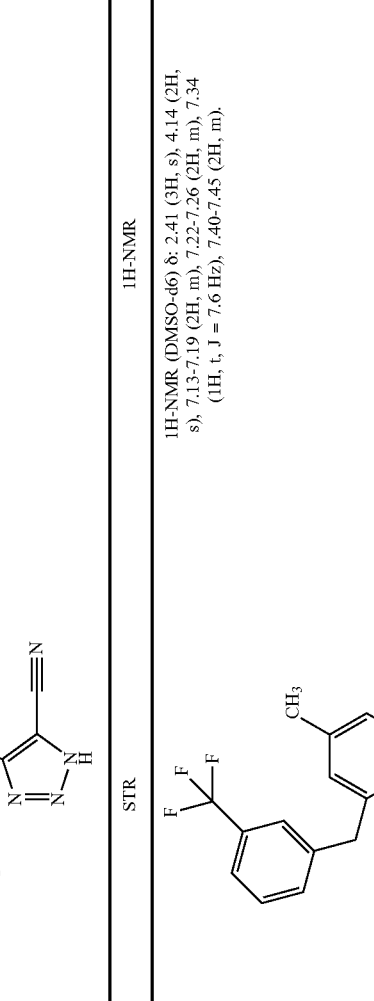 | | 1H-NMR (DMSO-d6) δ: 2.41 (3H, s), 4.14 (2H, s), 7.13-7.19 (2H, m), 7.22-7.26 (2H, m), 7.34 (1H, t, J = 7.6 Hz), 7.40-7.45 (2H, m). | Ex. 1 |

TABLE 4-continued

| Ex. No. | STR | m.p. | ref. |
|---|---|---|---|
| 411 | | 119-123 | Ex. 1 |
| 412 | | 177 | Ex. 1 |
| 413 | | 171-172 | Ex. 1 |

TABLE 4-continued

| | | | |
|---|---|---|---|
| 414 | [structure] | 140-142 | Ex. 1 |
| 415 | [structure] | 134-135 | Ex. 1 |
| 416 | [structure] | 195-197 | Ex. 1 |

TABLE 4-continued

| Ex. No. | STR | | 1H-NMR | ref. |
|---|---|---|---|---|
| 417 | (structure: 3,4-difluorobenzyloxy-5-(trifluoromethyl)phenyl triazole carbonitrile) | 141.9-142.3 | | Ex. 1 |
| 418 | (structure: 3,5-bis(trifluoromethyl)benzyloxy-5-fluorophenyl triazole carbonitrile) | | 1H-NMR (CDCl3) δ: 5.24 (2H, s), 6.86 (1H, dt, J = 2.3, 10.0 Hz), 7.38-7.43 (1H, m), 7.45-7.47 (1H, m), 7.89 (1H, s), 7.94 (2H, s), 12.20 (1H, brs). | Ex. 2 |
| 419 | (structure: 2-fluoro-4-(trifluoromethyl)benzyloxy-5-fluorophenyl triazole carbonitrile) | | 1H-NMR (CDCl3) δ: 5.24 (2H, s), 6.84 (1H, dt, J = 2.3, 10.1 Hz), 7.35-7.41 (2H, m), 7.45-7.50 (2H, m), 7.66-7.71 (1H, m). | Ex. 2 |

TABLE 4-continued

| | Structure | 1H-NMR | |
|---|---|---|---|
| 420 | 3-fluoro-5-[(2,4-bis(trifluoromethyl)benzyl)oxy]phenyl triazole carbonitrile | 1H-NMR (CDCl3) δ: 5.38 (2H, s), 6.82 (1H, dt, J = 2.3, 10.1 Hz), 7.36-7.41 (1H, m), 7.43-7.44 (1H, m), 7.86-7.98 (3H, m), 12.16 (1H, brs). | Ex. 2 |
| 421 | 3-fluoro-5-[(2-trifluoromethyl-4-fluorobenzyl)oxy]phenyl triazole carbonitrile | 1H-NMR (CDCl3) δ: 5.27 (2H, s), 6.80 (1H, dt, J = 2.3, 10.1 Hz), 7.30-7.34 (1H, m), 7.34-7.38 (1H, m), 7.42-7.46 (2H, m), 7.70-7.57 (1H, m), 12.12 (1H, brs). | Ex. 2 |
| 422 | 3-fluoro-5-[(3-trifluoromethyl-4-chlorobenzyl)oxy]phenyl triazole carbonitrile | 1H-NMR (CDCl3) δ: 5.14 (2H, s), 6.82 (1H, dt, J = 2.3, 10.1 Hz), 7.31-7.40 (1H, m), 7.40-7.44 (1H, m), 7.54-7.61 (2H, m), 7.77-7.79 (1H, m), 12.40 (1H, brs). | Ex. 2 |
| 423 | 3-[(3,4-bis(trifluoromethyl)benzyl)oxy]phenyl triazole carbonitrile | 1H-NMR (CDCl3) δ: 5.26 (2H, s), 7.11-7.14 (1H, m), 7.46-7.51 (1H, m), 7.59-7.51 (1H, m), 7.62-7.68 (1H, m), 7.77-7.83 (1H, m), 7.89-7.96 (2H, m), 12.19 (1H, brs). | Ex. 2 |

TABLE 4-continued

| | Structure | 1H-NMR | |
|---|---|---|---|
| 424 | 3-fluoro-5-[(3,4-bis(trifluoromethyl)benzyl)oxy]phenyl triazole carbonitrile | 1H-NMR (CDCl3) δ: 5.25 (2H, s), 6.84 (1H, dt, J = 2.3, 10.0 Hz), 7.37-7.41 (1H, m), 7.44-7.45 (1H, m), 7.78-7.81 (1H, m), 7.90-7.94 (2H, m). | Ex. 2 |
| 425 | 3-[(4-chloro-3-(trifluoromethyl)benzyl)oxy]phenyl triazole carbonitrile | 1H-NMR (CDCl3) δ: 5.16 (2H, s), 7.09-7.13 (1H, m), 7.47 (1H, t, J = 8.0 Hz), 7.53-7.64 (4H, m), 7.79-7.80 (1H, m). | Ex. 2 |
| 426 | 3-fluoro-5-[(3-fluoro-4-(trifluoromethoxy)benzyl)oxy]phenyl triazole carbonitrile | 1H-NMR (CDCl3) δ: 5.30 (2H, s), 6.81 (1H, dt, J = 2.3, 10.1 Hz), 7.24-7.29 (1H, m), 7.30-7.38 (3H, m), 7.41-7.42 (1H, m). | Ex. 2 |
| 427 | 3-[(3-fluoro-4-(trifluoromethoxy)benzyl)oxy]phenyl triazole carbonitrile | 1H-NMR (CDCl3) δ: 5.14 (2H, s), 7.08-7.12 (1H, m), 7.24-7.29 (1H, m), 7.31-7.37 (2H, m), 7.47 (1H, t, J = 8.0 Hz), 7.56-7.58 (1H, m), 7.61-7.64 (1H, m). | Ex. 2 |

TABLE 4-continued

| | Structure | NMR | Ex. |
|---|---|---|---|
| 428 | (3,4-difluoro-5-((3,5-bis(trifluoromethyl)benzyl)oxy)phenyl triazole carbonitrile) | 1H-NMR (CDCl3) δ: 5.34 (2H, s), 7.51-7.59 (2H, m), 7.88-7.90 (1H, m), 7.95-7.97 (2H, m), 12.90 (1H, brs). | Ex. 2 |
| 429 | (3-((4-fluoro-3-(trifluoromethoxy)benzyl)oxy)-5-fluorophenyl triazole carbonitrile) | 1H-NMR (CDCl3) δ: 5.10 (2H, s), 6.81 (1H, dt, J = 2.3, 10.2 Hz), 7.22-7.28 (1H, m), 7.34-7.43 (4H, m). | Ex. 2 |
| 430 | (3-((3-fluorobenzyl)oxy)-5-fluorophenyl triazole carbonitrile) | 1H-NMR (CDCl3) δ: 5.14 (2H, s), 6.81 (1H, dt, J = 2.2, 10.2 Hz), 7.02-7.08 (1H, m), 7.16-7.20 (1H, m), 7.21-7.25 (1H, m), 7.32-7.39 (2H, m), 7.41-7.43 (1H, m). | Ex. 2 |
| 431 | (3-((4-fluorobenzyl)oxy)-5-fluorophenyl triazole carbonitrile) | 1H-NMR (CDCl3) δ: 5.10 (2H, s), 6.81 (1H, dt, J = 2.3, 10.3 Hz), 7.07-7.14 (2H, m), 7.30-7.36 (1H, m), 7.41-7.46 (3H, m). | Ex. 2 |

TABLE 4-continued

| | Structure | 1H-NMR | |
|---|---|---|---|
| 432 | 3-fluoro-5-((4-(trifluoromethoxy)benzyl)oxy)phenyl triazole carbonitrile | 1H-NMR (CDCl3) δ: 5.13 (2H, s), 6.82 (1H, dt, J = 2.3, 10.2 Hz), 7.25-7.28 (2H, m), 7.33-7.37 (1H, m), 7.42-7.43 (1H, m), 7.48-7.51 (2H, m). | Ex. 2 |
| 433 | 3-fluoro-5-((3-(trifluoromethyl)benzyl)oxy)phenyl triazole carbonitrile | 1H-NMR (CDCl3) δ: 5.18 (2H, s), 6.83 (1H, dt, J = 2.3, 10.2 Hz), 7.34-7.38 (1H, m), 7.43-7.45 (1H, m), 7.52-7.57 (1H, m), 7.61-7.67 (2H, m), 7.72-7.73 (1H, m). | Ex. 2 |
| 434 | 3-fluoro-5-((4-(trifluoromethyl)benzyl)oxy)phenyl triazole carbonitrile | 1H-NMR (CDCl3) δ: 5.20 (2H, s), 6.82 (1H, dt, J = 2.2, 10.1 Hz), 7.34-7.37 (1H, m), 7.42-7.43 (1H, m), 7.57-7.59 (2H, m), 7.66-7.69 (2H, m), 12.10 (1H, brs). | Ex. 2 |
| 435 | 3-((4-fluoro-3-(trifluoromethoxy)benzyl)oxy)phenyl triazole carbonitrile | 1H-NMR (CDCl3) δ: 5.12 (2H, s), 7.09-7.13 (1H, m), 7.21-7.27 (1H, m), 7.37-7.40 (1H, m), 7.42-7.49 (2H, m), 7.57-7.58 (1H, m), 7.61-7.64 (1H, m). | Ex. 2 |

TABLE 4-continued

| | Structure | 1H-NMR | |
|---|---|---|---|
| 436 | 3-chloro-4-(trifluoromethoxy)benzyloxy phenyl triazole carbonitrile | 1H-NMR (CDCl3) δ: 5.12 (2H, s), 7.09-7.13 (1H, m), 7.34-7.42 (2H, m), 7.44-7.49 (1H, m), 7.57-7.58 (1H, m), 7.60-7.64 (2H, m). | Ex. 2 |
| 437 | fluoro analog | 1H-NMR (CDCl3) δ: 5.11 (2H, s), 6.81 (1H, dt, J = 2.3, 10.1 Hz), 7.35-7.42 (4H, m), 7.59-7.60 (1H, m). | Ex. 2 |
| 438 | isomer | 1H-NMR (CDCl3) δ: 5.13 (2H, s), 7.06-7.12 (1H, m), 7.33-7.39 (1H, m), 7.43-7.44 (1H, m), 7.46-7.52 (2H, m), 7.56-7.58 (1H, m), 7.61-7.64 (1H, m). | Ex. 2 |
| 439 | fluoro isomer | 1H-NMR (CDCl3) δ: 5.12 (2H, s), 6.81 (1H, dt, J = 2.3, 10.1 Hz), 7.34-7.38 (2H, m), 7.41-7.43 (2H, m), 7.50-7.53 (1H, m). | Ex. 2 |

TABLE 4-continued

| | Structure | NMR | Ex. |
|---|---|---|---|
| 440 | (3-fluoro-5-(4-tert-butylbenzyloxy)phenyl triazole carbonitrile) | 1H-NMR (CDCl3) δ: 1.33 (9H, s), 5.09 (2H, s), 6.83 (1H, dt, J = 2.3, 10.4 Hz), 7.29-7.33 (1H, m), 7.37-7.40 (2H, m), 7.42-7.46 (3H, m). | Ex. 2 |
| 441 | (3-fluoro-5-(3-chloro-5-trifluoromethylbenzyloxy)phenyl triazole carbonitrile) | 1H-NMR (CDCl3) δ: 5.16 (2H, s), 6.83 (1H, dt, J = 2.3, 10.1 Hz), 7.36-7.41 (1H, m), 7.42-7.43 (1H, m), 7.60-7.61 (2H, m), 7.65-7.66 (1H, m). | Ex. 2 |
| 442 | (3-fluoro-5-(3-chloro-5-trifluoromethoxybenzyloxy)phenyl triazole carbonitrile) | 1H-NMR (CDCl3) δ: 5.12 (2H, s), 6.82 (1H, dt, J = 2.3, 10.1 Hz), 7.21-7.23 (2H, m), 7.36-7.42 (3H, m), 11.89 (1H, brs). | Ex. 2 |
| 443 | (3-fluoro-5-(3-chloro-5-fluorobenzyloxy)phenyl triazole carbonitrile) | 1H-NMR (DMSO-d6) δ: 5.25 (2H, s), 7.20 (1H, dt, J = 2.2, 10.9 Hz), 7.28-7.38 (3H, m), 7.44-7.47 (2H, m). | Ex. 2 |

TABLE 4-continued

| | Structure | 1H-NMR | |
|---|---|---|---|
| 444 | 3-chloro-5-(trifluoromethyl)benzyloxy phenyl triazole carbonitrile | 1H-NMR (CDCl3) δ: 5.17 (2H, s), 7.09-7.14 (1H, m), 7.48 (1H, t, J = 8.0 Hz), 7.60-7.67 (5H, m). | Ex. 2 |
| 445 | 3-chloro-5-(trifluoromethoxy)benzyloxy phenyl triazole carbonitrile | 1H-NMR (CDCl3) δ: 5.13 (2H, s), 7.08-7.12 (1H, m), 7.20-7.25 (2H, m), 7.41-7.42 (1H, m), 7.44-7.50 (1H, m), 7.57-7.58 (1H, m), 7.61-7.65 (1H, m). | Ex. 2 |
| 446 | 3-chloro-5-fluorobenzyloxy phenyl triazole carbonitrile | 1H-NMR (CDCl3) δ: 5.11 (2H, s), 7.04-7.11 (3H, m), 7.25-7.27 (1H, m), 7.46 (1H, t, J = 8.0 Hz), 7.55-7.57 (1H, m), 7.61-7.64 (1H, m). | Ex. 2 |
| 447 | 3-fluoro-5-(trifluoromethyl)benzyloxy phenyl triazole carbonitrile | 1H-NMR (DMSO-d6) δ: 5.33 (2H, s), 7.20-7.25 (1H, m), 7.29-7.33 (1H, m), 7.39-7.40 (1H, m), 7.69-7.77 (3H, m). | Ex. 2 |

TABLE 4-continued

| Ex. No. | STR | m.p. | ref. |
|---|---|---|---|
| 448 | (structure) | 167-168 | Ex. 1 |
| 449 | (structure) | 107-109 | Ex. 1 |
| 450 | (structure) | 142-144 | Ex. 1 |
| 451 | (structure) | 129-130 | Ex. 1 |

TABLE 4-continued
| | | | |
|---|---|---|---|
| 452 | 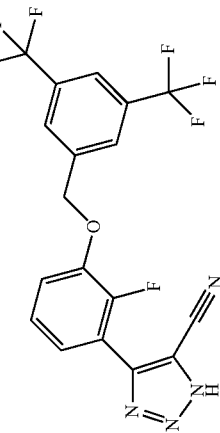 | 153 | Ex. 1 |
| 453 |  | 167 | Ex. 1 |
| 454 |  | 146-148 | Ex. 1 |
| 455 | 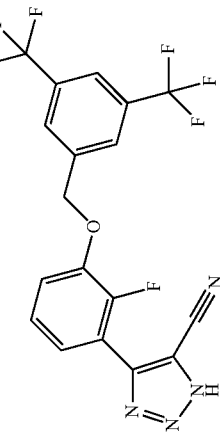 | 175-176 | Ex. 1 |

TABLE 4-continued

| | | | |
|---|---|---|---|
| 456 | [structure] | 175-177 | Ex. 1 |
| 457 | [structure] | 168 | Ex. 1 |
| 458 | [structure] | 168 | Ex. 1 |
| 459 | [structure] | 133-135 | Ex. 1 |

TABLE 4-continued

| | | | |
|---|---|---|---|
| 460 | 189-191 | Ex. 1 | |
| 461 | 220-222 | Ex. 1 | |
| 462 | 202-203 | Ex. 1 | |
| 463 | 183-184 | Ex. 1 | |

TABLE 4-continued

| | Structure | Range | Ex. |
|---|---|---|---|
| 464 | (structure) | 109-111 | Ex. 1 |
| 465 | (structure) | 121 | Ex. 1 |
| 466 | (structure) | 139-140 | Ex. 1 |

TABLE 4-continued

| | | | |
|---|---|---|---|
| 467 | [structure with 4-chloro-3-(trifluoromethyl)benzyloxy and trifluoromethoxy substituents on phenyl-triazole-carbonitrile] | 128-129 | Ex. 1 |
| 468 | [structure with 3,5-bis(trifluoromethyl)benzyloxy and 1-methylethyl substituents on phenyl-triazole-carbonitrile] | 115-116 | Ex. 1 |
| 469 | [structure with 2,5-bis(trifluoromethyl)benzyloxy and 1-methylethyl substituents on phenyl-triazole-carbonitrile] | 135-136 | Ex. 1 |

TABLE 4-continued

| Ex. No. | STR | 1H-NMR | ref. |
|---|---|---|---|
| 470 | 3-(benzyloxy)-5-(trifluoromethyl)phenyl triazole carbonitrile | 1H-NMR (CDCl3) δ: 5.21 (2H, s), 7.37-7.51 (6H, m), 7.81 (1H, s), 7.87 (1H, s). | Ex. 1 |
| 471 | 3,5-bis(trifluoromethyl)benzyloxy phenyl triazole carbonitrile | 1H-NMR (CDCl3) δ: 5.31 (2H, s), 7.40 (1H, s), 7.84 (1H, s), 7.92-7.97 (4H, m). | Ex. 1 |
| 472 | 4-chlorobenzyloxy-(trifluoromethyl)phenyl triazole carbonitrile | 1H-NMR (CDCl3) δ: 5.16 (2H, s), 7.33 (1H, s), 7.37-7.43 (4H, m), 7.78 (1H, s), 7.87 (1H, s). | Ex. 1 |

TABLE 4-continued

| | Structure | 1H-NMR | |
|---|---|---|---|
| 473 | 3-fluoro-5-(trifluoromethyl)benzyl ether phenyl triazole carbonitrile | 1H-NMR (DMSO-d6) δ: 5.32 (2H, s), 7.24-7.26 (1H, m), 7.50-7.58 (3H, m), 7.69 (2H, d, J = 9.1 Hz), 7.74 (1H, s). | Ex. 1 |
| 474 | 2-(trifluoromethyl)benzyl ether 3-(trifluoromethyl)phenyl triazole carbonitrile | 1H-NMR (CDCl3) δ: 5.39 (2H, s), 7.36 (1H, s), 7.50 (1H, t, J = 7.6 Hz), 7.63 (1H, t, J = 7.6 Hz), 7.74-7.81 (3H, m), 7.90 (1H, s). | Ex. 1 |
| 475 | 2,5-bis(trifluoromethyl)benzyl ether chloro phenyl triazole carbonitrile | 1H-NMR (DMSO-d6) δ: 5.51 (2H, s), 7.27-7.32 (1H, m), 7.56 (2H, d, J = 4.5 Hz), 8.03 (1H, d, J = 8.3 Hz), 8.10 (1H, d, J = 8.3 Hz), 8.30 (1H, s). | Ex. 1 |

| | Structure | 1H-NMR | |
|---|---|---|---|
| 476 | 3-((2,3,4,5-tetrafluorobenzyl)oxy)phenyl triazole carbonitrile | 1H-NMR (DMSO-d6) δ: 5.26 (2H, s), 7.26-7.29 (1H, m), 7.51-7.66 (4H, m). | Ex. 1 |
| 477 | 3-((2,4,5-trifluorobenzyl)oxy)phenyl triazole carbonitrile | 1H-NMR (DMSO-d6) δ: 5.19 (2H, s), 7.25-7.28 (1H, m), 7.50-7.77 (5H, m). | Ex. 1 |
| 478 | 3,5-bis(trifluoromethyl)benzyloxy phenyl triazole carbonitrile | 1H-NMR (CDCl3) δ: 5.23 (2H, s), 7.36 (1H, s), 7.52-7.57 (1H, m), 7.62-7.68 (2H, m), 7.75 (1H, s), 7.81 (1H, s), 7.89 (1H, s). | Ex. 2 |

TABLE 4-continued

| | Structure | NMR | Ref |
|---|---|---|---|
| 479 | (2-fluoro-5-(trifluoromethyl)benzyl ether) | 1H-NMR (CDCl3) δ: 5.29 (2H, s), 7.25-7.28 (1H, m), 7.40 (1H, s), 7.68-7.71 (1H, m), 7.85-7.89 (2H, m), 7.94 (1H, s). | Ex. 2 |
| 480 | (2,4-bis(trifluoromethyl)benzyl ether) | 1H-NMR (CDCl3) δ: 5.22 (2H, s), 7.32-7.42 (3H, m), 7.54 (1H, s), 7.80 (1H, s), 7.91 (1H, s). | Ex. 2 |
| 481 | (2-methylbenzyl ether) | 1H-NMR (CDCl3) δ: 2.43 (3H, s), 5.18 (2H, s), 7.23-7.32 (3H, m), 7.38 (1H, s), 7.44 (1H, d, J = 7.2 Hz), 7.83 (1H, s), 7.88 (1H, s). | Ex. 2 |

TABLE 4-continued

| | | | |
|---|---|---|---|
| 482 | structure: 3-(2,6-dichlorobenzyloxy)-5-(trifluoromethyl)phenyl triazole carbonitrile | 1H-NMR (CDCl3) δ: 5.42 (2H, s), 7.31-7.34 (1H, m), 7.40-7.43 (3H, m), 7.87 (1H, s), 7.91 (1H, s). | Ex. 2 |
| 483 | structure: 3-(3-chlorobenzyloxy)phenyl triazole carbonitrile | 1H-NMR (CDCl3) δ: 5.12 (2H, s), 7.09-7.12 (1H, m) 7.30-7.35 (3H, m), 7.43-7.48 (2H, m), 7.55-7.62 (2H, m). | Ex. 2 |
| 484 | structure: 3-(2,5-dichlorobenzyloxy)phenyl triazole carbonitrile | 1H-NMR (CDCl3) δ: 5.20 (2H, s), 7.14 (1H, ddd, J = 0.8, 2.6, 8.4 Hz), 7.23-7.27 (1H, m), 7.35 (1H, d, J = 8.4 Hz), 7.48 (1H, t, J = 8.0 Hz), 7.58-7.66 (3H, m). | Ex. 2 |

TABLE 4-continued

| | Structure | 1H-NMR | Ref. |
|---|---|---|---|
| 485 | 3-[(3,5-bis(trifluoromethyl)benzyl)oxy]phenyl triazole carbonitrile | 1H-NMR (CDCl3) δ: 5.25 (2H, s), 7.15 (1H, ddd, J = 1.0, 2.6, 8.3 Hz), 7.49 (1H, d, J = 8.0 Hz), 7.61-7.68 (2H, m), 7.87 (1H, s), 7.94 (2H, s). | Ref. Ex. 82, Ex. 1 |
| 486 | 3-fluoro-5-(trifluoromethyl)benzyloxy phenyl-trifluoromethyl triazole carbonitrile | 1H-NMR (CDCl3) δ: 5.45 (2H, s), 7.36 (1H, s), 7.81 (1H, s), 7.89-8.01 (4H, m). | Ex. 1 |
| 487 | 2,3-dichlorobenzyloxy-trifluoromethylphenyl triazole carbonitrile | 1H-NMR (CDCl3) δ: 5.24 (2H, s), 7.22-7.27 (2H, m), 7.43-7.48 (2H, m), 7.77 (1H, s), 7.87 (1H, s). | Ex. 1 |

TABLE 4-continued

| | Structure | 1H-NMR | |
|---|---|---|---|
| 488 | 3-(trifluoromethyl)-5-((2-(trifluoromethoxy)benzyl)oxy)phenyl triazole-carbonitrile | 1H-NMR (DMSO-d6) δ: 5.35 (2H, s), 7.45-7.49 (2H, m), 7.53-7.60 (2H, m), 7.72-7.75 (1H, m), 7.79 (1H, s), 7.81 (1H, s). | Ex. 2 |
| 489 | 3-(trifluoromethyl)-5-((2-fluoro-6-(trifluoromethyl)benzyl)oxy)phenyl triazole-carbonitrile | 1H-NMR (DMSO-d6) δ: 5.35 (2H, s), 7.66-7.84 (6H, m). | Ex. 2 |
| 490 | 3-(trifluoromethyl)-5-((4-fluoro-2-(trifluoromethyl)benzyl)oxy)phenyl triazole-carbonitrile | 1H-NMR (DMSO-d6) δ: 5.40 (2H, s), 7.61-7.67 (2H, m), 7.72-7.78 (2H, m), 7.83 (1H, s), 7.88-7.93 (1H, m). | Ex. 2 |

TABLE 4-continued

| | Structure | 1H-NMR | |
|---|---|---|---|
| 491 | 5-[3-(trifluoromethyl)-5-[[2-(trifluoromethyl)-5-fluorophenyl]methoxy]phenyl]-1H-1,2,3-triazole-4-carbonitrile | 1H-NMR (CDCl3) δ: 5.36 (2H, s), 7.11-7.17 (1H, m), 7.33 (1H, s), 7.47-7.51 (1H, m), 7.71-7.78 (2H, m), 7.90 (1H, s). | Ex. 2 |
| 492 | 5-[3-(trifluoromethyl)-5-[[2-(trifluoromethyl)-5-chlorophenyl]methoxy]phenyl]-1H-1,2,3-triazole-4-carbonitrile | 1H-NMR (CDCl3) δ: 5.33(2H, s), 7.34 (1H, s), 7.45 (1H, d, J = 8.5 Hz), 7.66 (1H, d, J = 8.5 Hz), 7.76 (1H, s), 7.79 (1H, s), 7.90 (1H, s). | Ex. 2 |
| 493 | 5-[3-(trifluoromethyl)-5-[[4-chloro-3-(trifluoromethyl)phenyl]methoxy]phenyl]-1H-1,2,3-triazole-4-carbonitrile | 1H-NMR (CDCl3) δ: 5.22 (2H, s), 7.37 (1H, s), 7.57-7.65 (2H, m), 7.81-7.83 (2H, m), 7.92 (1H, s). | Ex. 2 |

TABLE 4-continued

| | Structure | 1H-NMR | Ex. |
|---|---|---|---|
| 494 | 5-(3-((2,5-dimethylbenzyl)oxy)-5-(trifluoromethyl)phenyl)-1H-1,2,3-triazole-4-carbonitrile | 1H-NMR (CDCl3) δ: 2.34 (3H, s), 2.36 (3H, s), 5.12 (2H, s), 7.11-7.15 (2H, m), 7.24 (1H, s), 7.35 (1H, s), 7.80 (1H, s), 7.85 (1H, s). | Ex. 1 |
| 495 | 5-(3-((2,4-dimethylbenzyl)oxy)-5-(trifluoromethyl)phenyl)-1H-1,2,3-triazole-4-carbonitrile | 1H-NMR (CDCl3) δ: 2.36 (3H, s), 2.40 (3H, s), 5.14 (2H, s), 7.06-7.10 (2H, m), 7.30-7.36 (2H, m), 7.81 (1H, s), 7.87 (1H, s). | Ex. 2 |
| 496 | 5-(3-((4-(trifluoromethyl)benzyl)oxy)-5-(trifluoromethyl)phenyl)-1H-1,2,3-triazole-4-carbonitrile | 1H-NMR (CDCl3) δ: 5.25 (2H, s), 7.34 (1H, s), 7.60 (2H, d, J = 8.1 Hz), 7.68 (2H, d, J = 8.1 Hz), 7.79 (1H, s), 7.88 (1H, s). | Ex. 2 |

TABLE 4-continued

| | Structure | NMR | Ref |
|---|---|---|---|
| 497 | 3-((2-cyanobenzyl)oxy)-5-(trifluoromethyl)phenyl triazole carbonitrile | 1H-NMR (CDCl3) δ: 5.36 (2H, s), 7.36 (1H, s), 7.48-7.53 (1H, m), 7.67-7.77 (3H, m), 7.81 (1H, s), 7.89 (1H, s). | Ex. 191 |
| 498 | 3-((2-chlorobenzyl)oxy)-5-(trifluoromethyl)phenyl triazole carbonitrile | 1H-NMR (CDCl3) δ: 5.30 (2H,s), 7.33-7.38 (3H, m), 7.45-7.48 (1H, m), 7.58-7.61 (1H, m), 7.83 (1H, s), 7.90 (1H, s). | Ex. 2 |
| 499 | 3-((3-chloro-2-fluoro-5-(trifluoromethyl)benzyl)oxy)phenyl triazole carbonitrile | 1H-NMR (DMSO-d6) δ: 5.34 (2H, s), 7.25-7.33 (1H, m), 7.48-7.62 (3H, m), 8.00-8.20 (2H, m). | Ex. 2 |

TABLE 4-continued

| | Structure | 1H-NMR | Ex. |
|---|---|---|---|
| 500 | 2,5-dichlorobenzyl ether of 3-CF3-5-(triazolyl-CN)phenol | 1H-NMR (CDCl3) δ: 5.23 (2H, s), 7.25-7.38 (3H, m), 7.59 (1H, s), 7.81 (1H, s), 7.90 (1H, s). | Ex. 2 |
| 501 | 3,5-bis(trifluoromethyl)benzyl ether of 3-chloro-5-(triazolyl-CN)phenol | 1H-NMR (DMSO-d6) δ: 5.24 (2H, s), 7.15 (1H, t, J = 2.1 Hz), 7.54 (1H, t, J = 1.5 Hz), 7.66 (1H, t, J = 1.5 Hz), 7.89 (1H, s), 7.93 (2H, s). | Ex. 1 |
| 502 | 2,5-bis(trifluoromethyl)benzyl ether of 3-chloro-5-(triazolyl-CN)phenol | 1H-NMR (DMSO-d6) δ: 5.44 (2H, s), 7.45 (1H, t, J = 2.0 Hz), 7.50 (1H, t, J = 1.5 Hz), 7.56 (1H, t, J = 1.5 Hz), 8.03 (1H, d, J = 8.4 Hz), 8.09 (1H, d, J = 8.4 Hz), 8.24 (1H, s). | Ex. 1 |

TABLE 4-continued

| | | | |
|---|---|---|---|
| 503 | [structure: 3-chloro-5-(benzyloxy)phenyl triazole carbonitrile] | 1H-NMR (CDCl3) δ: 5.14 (2H, s), 7.03-7.12 (1H, m), 7.32-7.48 (5H, m), 7.51 (1H, s), 7.80 (1H, s). | Ex. 1 |
| 504 | [structure: 3-(2,5-bis(trifluoromethyl)benzyloxy)-5-(trifluoromethoxy)phenyl triazole carbonitrile] | 1H-NMR (DMSO-d6) δ: 5.47 (2H, s), 7.36 (1H, s), 7.49 (1H, s), 7.57 (1H, s), 8.02 (1H, d, J = 8.1 Hz), 8.09 (1H, d, J = 8.1 Hz), 8.25 (1H, s). | Ex. 1 |
| 505 | [structure: 3-(3,5-bis(trifluoromethyl)benzyloxy)-5-(trifluoromethoxy)phenyl triazole carbonitrile] | 1H-NMR (DMSO-d6) δ: 5.26 (2H, s), 7.00 (1H, s), 7.55 (1H, s), 7.60 (1H, s), 7.89 (1H, s), 7.94 (2H, s). | Ex. 2 |

TABLE 4-continued

| | Structure | 1H-NMR | |
|---|---|---|---|
| 506 | (3-fluoro-5-(2,5-bis(trifluoromethyl)benzyloxy)phenyl triazole carbonitrile) | 1H-NMR (CDCl3) δ: 5.35 (2H, s), 6.81-6.89 (1H, m), 7.36-7.43 (1H, m), 7.44-7.48 (1H, m), 7.72-7.77 (1H, m), 7.85-7.90 (1H, m), 8.03-8.07 (1H, m). | Ex. 1 |
| 507 | (3,5-bis(trifluoromethoxy/4-trifluoromethylbenzyloxy)phenyl triazole carbonitrile) | 1H-NMR (DMSO-d6) δ: 5.37 (2H, s), 7.29 (1H, s), 7.46 (1H, s), 7.56 (1H, d, J = 1.6 Hz), 7.72 (2H, d, J = 8.2 Hz), 7.79 (2H, d, J = 8.2 Hz). | Ex. 1 |
| 508 | (3-methyl-5-(2,5-bis(trifluoromethyl)benzyloxy)phenyl triazole carbonitrile) | 1H-NMR (CDCl3) δ: 2.44 (3H, s), 5.34 (2H, s), 6.97 (1H, s), 7.39 (1H, s), 7.46 (1H, s), 7.72 (1H, d, J = 8.1 Hz), 7.85 (1H, d, J = 8.1 Hz), 8.09 (1H, s), 12.0 (1H, br.). | Ex. 1 |

TABLE 4-continued

| | Structure | NMR | Ex. |
|---|---|---|---|
| 509 | 3,5-bis(trifluoromethyl)benzyloxy-5-methylphenyl triazole carbonitrile | 1H-NMR (CDCl3) δ: 2.44 (3H, s), 5.23 (2H, s), 6.97 (1H, s), 7.41 (1H, s), 7.46 (1H, s), 7.87 (1H, s), 7.94 (2H, s), 12.0 (1H, br). | Ex. 1 |
| 510 | 3-benzyloxy-5-(trifluoromethoxy)phenyl triazole carbonitrile | 1H-NMR (DMSO-d6) δ: 5.24 (2H, s), 7.26 (1H, s), 7.36-7.51 (6H, m), 7.55 (1H, s). | Ex. 1 |
| 511 | 3-(4-chlorobenzyloxy)-5-(trifluoromethoxy)phenyl triazole carbonitrile | 1H-NMR (DMSO-d6) δ: 5.25 (2H, s), 7.27 (1H, s), 7.44 (1H, s), 7.47-7.55 (5H, m). | Ex. 1 |

TABLE 4-continued

| | Structure | 1H-NMR | Ex. |
|---|---|---|---|
| 512 | 4-fluorobenzyloxy / trifluoromethoxy phenyl triazole carbonitrile | 1H-NMR (DMSO-d6) δ: 5.22 (2H, s), 7.22-7.26 (3H, m), 7.44 (1H, s), 7.55-7.58 (3H, m). | Ex. 1 |
| 513 | 3-fluoro-5-(trifluoromethyl)benzyloxy / trifluoromethoxy phenyl triazole carbonitrile | 1H-NMR (DMSO-d6) δ: 5.37 (2H, s), 7.32 (1H, s), 7.47 (1H, s), 7.57 (1H, s), 7.68-7.73 (2H, m), 7.76 (1H, s). | Ex. 1 |
| 514 | 3,5-bis(trifluoromethyl)benzyloxy / difluoromethoxy phenyl triazole carbonitrile | 1H-NMR (DMSO-d6) δ: 5.42 (2H, s), 7.14 (1H, t, J = 2.1 Hz), 7.31 (1H, s), 7.35 (1H, t, J = 73.5 Hz), 7.44 (1H, s), 8.13 (1H, s), 8.22 (2H, s). | Ex. 1 |

TABLE 4-continued

| | Structure | NMR | Ex. |
|---|---|---|---|
| 515 | 3-methyl-5-(benzyloxy)phenyl-triazole-carbonitrile | 1H-NMR (CDCl3) δ: 2.41 (3H, s), 5.13 (2H, s), 6.95 (1H, s), 7.30-7.49 (7H, m), 12.2 (1H, br.). | Ex. 1 |
| 516 | 3-methyl-5-(3-fluorobenzyloxy)phenyl-triazole-carbonitrile | 1H-NMR (CDCl3) δ: 2.41 (3H, s), 5.12 (2H, s), 6.93 (1H, s), 6.98-7.07 (1H, m), 7.15-7.26 (2H, m), 7.32-7.41 (3H, m). | Ex. 1 |
| 517 | 3-methyl-5-(4-fluorobenzyloxy)phenyl-triazole-carbonitrile | 1H-NMR (CDCl3) δ: 2.41 (3H, s), 5.09 (2H, s), 6.93 (1H, s), 7.04-7.12 (2H, m), 7.34-7.48 (4H, m). | Ex. 1 |
| 518 | 3-methyl-5-(3-trifluoromethylbenzyloxy)phenyl-triazole-carbonitrile | 1H-NMR (CDCl3) δ: 2.43 (3H, s), 5.17 (2H, s), 6.96 (1H, s), 7.35-7.46 (2H, m), 7.52 (1H, t, J = 7.8 Hz), 7.57-7.67 (2H, m), 7.73 (1H, s), 12.2 (1H, br.). | Ex. 1 |

TABLE 4-continued

| | | | |
|---|---|---|---|
| 519 | structure | 1H-NMR (DMSO-d6) δ: 5.21 (2H, s), 7.07 (1H, d, J = 2.1 Hz), 7.27 (1H, s), 7.34 (1H, t, J = 73.5 Hz), 7.36-7.50 (6H, m). | Ex. 1 |
| 520 | structure | 1H-NMR (DMSO-d6) δ: 5.43 (2H, s), 7.13-7.15 (1H, m), 7.32, (1H, s), 7.36 (1H, t, J = 73.5 Hz), 7.41-7.43 (1H, m), 8.02 (1H, d, J = 8.7 Hz), 8.09 (1H, d, J = 8.7 Hz), 8.23 (1H, s). | Ex. 1 |
| 521 | structure | 1H-NMR (DMSO-d6) δ: 5.34 (2H, s), 7.09-7.10 (1H, m), 7.29 (1H, s), 7.35 (1H, t, J = 73.5 Hz), 7.41-7.42 (1H, m), 7.71 (2H, d, J = 8.2 Hz), 7.79 (2H, d, J = 8.2 Hz). | Ex. 1 |

TABLE 4-continued

| # | Structure | 1H-NMR | Ex. |
|---|---|---|---|
| 522 | (3,5-disubstituted phenyl with OCHF2 and OCH2-4-chlorophenyl, triazole-CN) | 1H-NMR (DMSO-d6) δ: 5.22 (2H, s), 7.06 (1H, s), 7.07-7.53 (7H, m). | Ex. 1 |
| 523 | (3,5-disubstituted phenyl with OCHF2 and OCH2-4-fluorophenyl, triazole-CN) | 1H-NMR (DMSO-d6) δ: 5.20 (2H, s), 7.07 (1H, s), 7.20-7.27 (3H, m), 7.35 (1H, t, J = 73.1 Hz), 7.40 (1H, s), 7.55 (2H, t, J = 6.3 Hz). | Ex. 1 |
| 524 | (3-methyl-5-(2,4-difluorobenzyloxy)phenyl triazole-CN) | 1H-NMR (CDCl3) δ: 2.42 (3H, s), 5.13 (2H, s), 6.82-6.97 (3H, m), 7.34-7.55 (3H, m). | Ex. 1 |

TABLE 4-continued

| | Structure | 1H-NMR | Ref. |
|---|---|---|---|
| 525 | (3-methyl-5-((2-fluoro-5-(trifluoromethyl)benzyl)oxy)phenyl triazole carbonitrile) | 1H-NMR (CDCl3) δ: 2.44 (3H, s), 5.21 (2H, s), 6.97 (1H, s), 7.18-7.26 (1H, m), 7.40 (1H, s), 7.44 (1H, s), 7.59-7.67 (1H, m), 7.83-7.90 (1H, m). | Ref. Ex. 82, Ex. 1 |
| 526 | (3-(difluoromethoxy)-5-((3-fluoro-4-(trifluoromethoxy)benzyl)oxy)phenyl triazole carbonitrile) | 1H-NMR (DMSO-d6) δ: 5.27 (2H, s), 710 (1H, s), 7.28-7.66 (6H, m). | Ex. 1 |
| 527 | (3-(benzyloxy)-5-methoxyphenyl triazole carbonitrile) | 1H-NMR (DMSO-d6) δ: 3.80 (3H, s), 5.15 (2H, s), 6.77-6.79 (1H, m), 7.02-7.03 (1H, m), 7.09-7.10 (1H, m), 7.32-7.47 (5H, m). | Ex. 1 |

TABLE 4-continued

| | Structure | 1H-NMR | Ex. |
|---|---|---|---|
| 528 | 3-methyl-5-[(3-fluoro-5-(trifluoromethyl)benzyl)oxy]phenyl triazole-CN | 1H-NMR (CDCl3) δ: 2.43 (3H, s), 5.17 (2H, s), 6.95 (1H, s), 7.26-7.34 (1H, m), 7.37-7.44 (3H, m), 7.52 (1H, s). | Ex. 1 |
| 529 | 3-methyl-5-[(3,5-difluorobenzyl)oxy]phenyl triazole-CN | 1H-NMR (CDCl3) δ: 2.42 (3H, s), 5.12 (2H, s), 6.72-6.81 (1H, m), 6.93 (1H, s), 6.95-7.01 (2H, m), 7.35 (1H, s), 7.42 (1H, s), 11.9 (1H, br.). | Ex. 2 |
| 530 | 3-methoxy-5-[(3,5-bis(trifluoromethyl)benzyl)oxy]phenyl triazole-CN | 1H-NMR (CDCl3) δ: 3.13 (3H, s), 5.22 (2H, s), 6.67-6.68 (1H, m), 7.21 (2H, s), 7.87 (1H, s), 7.93 (2H, s). | Ex. 2 |
| 531 | 3-methyl-5-[(2,5-difluorobenzyl)oxy]phenyl triazole-CN | 1H-NMR (CDCl3) δ: 2.43 (3H, s), 5.16 (2H, s), 6.95 (1H, s), 6.95-7.15 (2H, m), 7.20-7.29 (1H, m), 7.38 (1H, s), 7.42 (1H, s), 11.9 (1H, br.). | Ex. 2 |

TABLE 4-continued

| | Structure | NMR | Ex. |
|---|---|---|---|
| 532 | 3-methyl-5-[(3,4-difluorobenzyl)oxy]phenyl triazole carbonitrile | 1H-NMR (CDCl3) δ: 2.42 (3H, s), 5.07 (2H, s), 6.92 (1H, s), 7.15-7.21 (2H, m), 7.25-7.32 (1H, m), 7.35 (1H, s), 7.41 (1H, s), 11.9 (1H, br). | Ex. 1 |
| 533 | 3-methyl-5-[(4-chloro-3-trifluoromethylbenzyl)oxy]phenyl triazole carbonitrile | 1H-NMR (CDCl3) δ: 2.43 (3H, s), 5.13 (2H, s), 6.94 (1H, s), 7.37 (1H, s), 7.43 (1H, s), 7.53 (1H, d, J = 8.4 Hz), 7.58 (1H, dd, J = 1.7, 8.4 Hz), 7.79 (1H, d, J = 1.7 Hz), 12.0 (1H, br). | Ex. 1 |
| 534 | 3-methyl-5-[(4-tert-butylbenzyl)oxy]phenyl triazole carbonitrile | 1H-NMR (CDCl3) δ: 1.33 (9H, s), 2.41 (3H, s), 5.08 (2H, s), 6.95 (1H, s), 7.37-7.45 (6H, m), 12.0 (1H, br). | Ex. 1 |
| 535 | 3-methyl-5-[(3-methoxybenzyl)oxy]phenyl triazole carbonitrile | 1H-NMR (CDCl3) δ: 2.41 (3H, s), 3.83 (3H, s), 5.10 (2H, s), 6.87 (1H, dd, J = 2.5, 8.3 Hz), 6.95 (1H, s), 6.99-7.06 (2H, m), 7.31 (1H, t, J = 7.8 Hz), 7.37 (2H, s), 12.1 (1H, br). | Ex. 1 |

| | | |
|---|---|---|
| 536 | [structure] | 1H-NMR (CDCl3) δ: 5.11 (2H, s), 6.80 (1H, dt, J = 2.3, 10.1 Hz), 7.16-7.21 (1H, m), 7.25-7.31 (1H, m), 7.33-7.38 (1H, m), 7.41-7.46 (2H, m). | Ex. 1 |
| 537 | [structure] | 1H-NMR (CDCl3) δ: 5.08 (2H, s), 7.08 (1H, t, J = 2.0 Hz), 7.15-7.22 (2H, m), 7.26-7.32 (1H, m), 7.49 (1H, t, J = 1.9 Hz), 7.61 (1H, t, J = 2.0 Hz), 12.1 (1H, br.). | Ex. 1 |
| 538 | [structure] | 1H-NMR (CDCl3) δ: 5.11 (2H, s), 6.74-6.83 (1H, m), 6.94-7.03 (2H, m), 7.09 (1H, t, J = 1.9 Hz), 7.49 (1H, s), 7.62 (1H, s), 12.1 (1H, br.). | Ex. 1 |
| 539 | [structure] | 1H-NMR (CDCl3) δ: 5.13 (2H, s), 7.00-7.08 (1H, m), 7.11 (1H, t, J = 2.0 Hz), 7.14-7.24 (2H, m), 7.33-7.42 (1H, m), 7.50 (1H, s), 7.60 (1H, s). | Ex. 1 |

TABLE 4-continued

TABLE 4-continued

| | Structure | 1H-NMR | |
|---|---|---|---|
| 540 | 3-chloro-5-(4-fluorobenzyloxy)phenyl triazole carbonitrile | 1H-NMR (CDCl3) δ: 5.09 (2H, s), 7.06-7.13 (3H, m), 7.40-7.46 (2H, m), 7.49-7.51 (1H, m), 7.59 (1H, t, J = 1.6 Hz). | Ex. 1 |
| 541 | 3,5-bis(trifluoromethyl)benzyloxy / 4-fluorobutoxy phenyl triazole carbonitrile | 1H-NMR (CDCl3) δ: 1.85-1.98 (4H, m), 4.07-4.10 (2H, m), 4.47-4.50 (1H, m), 4.59-4.51 (1H, m), 5.22 (2H, s), 6.67-6.68 (1H, m), 7.21 (2H, bs), 7.87 (1H, s), 7.93 (2H, s). | Ex. 1 |
| 542 | 3,5-bis(trifluoromethyl)benzyloxy / cyclopropylmethoxy phenyl triazole carbonitrile | 1H-NMR (CDCl3) δ: 0.38-0.39 (2H, m), 0.67-0.69 (2H, m), 1.25-1.35 (1H, m), 3.88 (2H, d, J = 7.4 Hz), 5.22 (2H, s), 6.69 (1H, t, J = 2.2 Hz), 7.20 (2H, bs), 7.86 (1H, s), 7.93 (2H, s). | Ex. 1 |

TABLE 4-continued

| | Structure | NMR | Ex. |
|---|---|---|---|
| 543 | 3-chloro-5-(2,3-difluorobenzyloxy)phenyl triazole carbonitrile | 1H-NMR (CDCl3) δ: 5.20 (2H, s), 7.09-7.29 (4H, m), 7.52 (1H, s), 7.62 (1H, s), 12.3 (1H, br). | Ex. 1 |
| 544 | 3,5-bis(trifluoromethyl)... 2,2,2-trifluoroethoxy phenyl triazole carbonitrile | 1H-NMR (CDCl3) δ: 4.43 (2H, q, J = 7.9 Hz), 5.24 (2H, s), 6.45 (1H, t, J = 2.3 Hz), 7.24 (1H, s), 7.35 (1H, s), 7.88 (1H, s), 7.93 (2H, s). | Ex. 1 |
| 545 | 3-chloro-5-(2-fluorobenzyloxy)phenyl triazole carbonitrile | 1H-NMR (CDCl3-DMSO-d6) δ: 5.18 (2H, s), 7.06-7.14 (2H, m), 7.19 (1H, t, J = 8.0 Hz), 7.32-7.38 (1H, m), 7.48-7.55 (2H, m), 7.61 (1H, s). | Ex. 2 |

TABLE 4-continued

| | Structure | 1H-NMR | |
|---|---|---|---|
| 546 | 2,5-bis(trifluoromethyl)benzyl ether of 3-bromo-5-(triazolyl-cyano)phenol | 1H-NMR (DMSO-d6) δ: 5.43 (2H, s), 7.53-7.54 (1H, m), 7.57-7.68 (1H, m), 7.69-7.70 (1H, m), 8.03 (1H, d, J = 8.4 Hz), 8.09 (1H, d, J = 8.4 Hz), 8.24 (1H, s). | Ex. 2 |
| 547 | 2-fluoro-5-(trifluoromethyl)benzyl ether analog | 1H-NMR (DMSO-d6) δ: 5.32 (2H, s), 7.49-7.53 (2H, m), 7.61-7.68 (2H, m), 7.74 (1H, dd, J = 2.7, 9.2 Hz), 8.87 (1H, dd, J = 5.5, 8.5 Hz). | Ex. 2 |
| 548 | 3-(trifluoromethyl)benzyl ether analog | 1H-NMR (DMSO-d6) δ: 5.33 (2H, s), 7.51-7.54 (2H, m), 7.65-7.69 (2H, m), 7.74 (1H, d, J = 7.7 Hz), 7.80 (1H, d, J = 7.5 Hz), 7.86 (1H, s). | Ex. 2 |

TABLE 4-continued

| | Structure | 1H-NMR | |
|---|---|---|---|
| 549 | 3,5-bis(trifluoromethyl)benzyl / cyclopropylmethyl ether triazole-CN | 1H-NMR (DMSO-d6) δ: 0.33-0.36 (2H, m), 0.57-0.62 (2H, m), 1.21-1.31 (1H, m), 3.90 (2H, d, J = 7.1 Hz), 5.39 (2H, s), 6.85-6.86 (1H, m), 7.08-7.11 (2H, m), 8.01 (1H, d, J = 8.3 Hz), 8.08 (1H, d, J = 8.3 Hz), 8.21 (1H, s). | Ex. 2 |
| 550 | 3-(trifluoromethyl)benzyl / cyclopropylmethyl ether triazole-CN | 1H-NMR (DMSO-d6) δ: 0.32-0.36 (2H, m), 0.57-0.61 (2H, m), 1.18-1.30 (1H, m), 3.89 (2H, d, J = 7.1 Hz), 5.29 (2H, s), 6.82-6.84 (1H, m), 7.05-7.06 (1H, m), 7.11-7.12 (1H, m), 7.66 (1H, t, J = 7.7 Hz), 7.72 (1H, J = 7.9 Hz), 7.79 (1H, d, J = 7.7 Hz), 7.85 (1H, s). | Ex. 2 |
| 551 | 4-(trifluoromethoxy)benzyl / 3-(trifluoromethyl)phenyl triazole-CN | 1H-NMR (DMSO-d6) δ: 5.34 (2H, s), 7.42 (2H, d, J = 7.9 Hz), 7.59 (1H, s), 7.64-7.66 (2H, m), 7.79-7.80 (2H, m). | Ex. 2 |

TABLE 4-continued

| | | | |
|---|---|---|---|
| 552 | (structure) | 1H-NMR (CDCl3) δ: 2.34 (3H, s), 5.36 (2H, s), 7.06 (1H, d, J = 7.9 Hz), 7.13 (1H, d, J = 7.6 Hz), 7.33 (1H, t, J = 7.9 Hz), 7.71-7.77 (1H, m), 7.87 (1H, d, J = 8.0 Hz), 8.13 (1H, s), 12.4 (1H, br). | Ex. 1 |
| 553 | (structure) | 1H-NMR (DMSO-d6) δ: 5.47 (2H, s), 7.42 (1H, t, J = 2.0 Hz), 7.48 (1H, t, J = 2.0 Hz), 7.56 (1H, t, J = 1.5 Hz), 8.04-8.20 (3H, m). | Ex. 1 |
| 554 | (structure) | 1H-NMR (CDCl3) δ: 2.32 (3H, s), 5.24 (2H, s), 7.05 (1H, d, J = 6.3 Hz), 7.13 (1H, d, J = 7.6 Hz), 7.33 (1H, t, J = 7.9 Hz), 7.88 (1H, s), 7.94 (2H, s). | Ex. 1 |

TABLE 4-continued

| | Structure | 1H-NMR | |
|---|---|---|---|
| 555 | 4-fluoro-3-[(3,5-bis(trifluoromethyl)benzyl)oxy]phenyl triazole carbonitrile | 1H-NMR (DMSO-d6) δ: 5.48 (2H, s), 7.53 (1H, s), 7.55 (1H, s), 7.75 (1H, d, J = 7.9 Hz), 8.13 (1H, s), 8.21 (2H, m). | Ex. 1 |
| 556 | 3-[(2,6-dichlorobenzyl)oxy]phenyl triazole carbonitrile | 1H-NMR (CDCl3) δ: 5.36 (2H, s), 7.15-7.19 (1H, m), 7.27 (1H, dd, J = 7.5, 8.6 Hz), 7.37-7.40 (2H, m), 7.48 (1H, t, J = 8.2 Hz), 7.61-7.65 (2H, m), 12.2 (1H, br). | Ex. 1 |
| 557 | 3-[(2,6-difluorobenzyl)oxy]phenyl triazole carbonitrile | 1H-NMR (CDCl3) δ: 5.20 (2H, s), 6.90-7.01 (2H, m), 7.11-7.17 (1H, m), 7.30-7.41 (1H, m), 7.46 (1H, t, J = 8.2 Hz), 7.58-7.64 (2H, m). | Ex. 1 |
| 558 | 4-fluoro-3-[(4-chloro-3-(trifluoromethyl)benzyl)oxy]phenyl triazole carbonitrile | 1H-NMR (DMSO-d6) δ: 5.37 (2H, s), 7.51 (1H, s), 7.54 (1H, s), 7.73 (1H, d, J = 8.2 Hz), 7.75-7.82 (2H, m), 7.99 (1H, s). | Ex. 1 |

TABLE 4-continued

| Ex. No. | STR | m.p. | ref. |
|---|---|---|---|
| 559 | (structure) | 153-156 | Ex. 1 |
| 560 | (structure) | 170-171 | Ex. 1 |
| 561 | (structure) | 123-126 | Ex. |

TABLE 4-continued
| Ex. No. | STR | 1H-NMR | ref. |
|---|---|---|---|
| 562 | 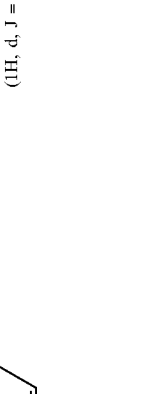 | 1H-NMR (CDCl3) δ: 5.72 (2H, s), 7.21-7.24 (2H, m), 7.42-7.50 (5H, m), 7.51-7.57 (1H, m), 8.25 (1H, d, J = 7.6 Hz), 13.0 (1H, br). | Ex. 1 |
| 563 | 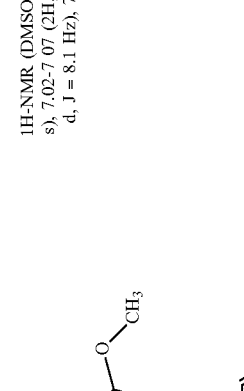 | 1H-NMR (DMSO-d6) δ: 3.87 (3H, s), 5.44 (2H, s), 7.02-7.07 (2H, m), 7.67 (1H, brs), 7.81 (1H, d, J = 8.1 Hz), 7.88 (1H, s), 7.93 (1H, d, J = 8.1 Hz). | Ex. 1 |
| 564 | 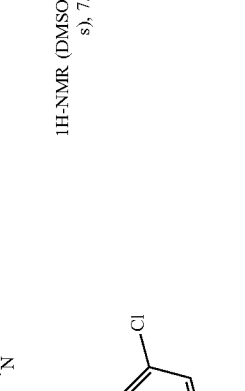 | 1H-NMR (DMSO-d6) δ: 5.09 (2H, s), 7.67 (1H, s), 7.93-7.96 (4H, m). | Ex. 1 |

TABLE 4-continued

| | Structure | 1H-NMR | |
|---|---|---|---|
| 565 | 2-fluoro-6-[2-fluoro-... triazole-cyano structure with 2,5-bis(trifluoromethyl)benzyloxy | 1H-NMR (DMSO-d6) δ: 5.31 (2H, s), 7.36-7.44 (2H, m), 7.57-7.61 (1H, m), 7.83 (1H, s), 7.93-7.97 (2H, m). | Ex. 1 |
| 566 | triazole-cyano with 4-fluoro substituted phenyl and 3,5-bis(trifluoromethyl)benzyloxy | 1H-NMR (DMSO-d6) δ: 5.36 (2H, s), 7.29-7.82 (4H, m), 7.82 (2H, s). | Ex. 1 |
| 567 | triazole-cyano with 4-chloro substituted phenyl and 3,5-bis(trifluoromethyl)benzyloxy | 1H-NMR (DMSO-d6) δ: 5.38 (2H, s), 7.31 (1H, d, J = 9.0 Hz), 7.58-7.69 (5H, m). | Ex. 1 |
| 568 | triazole-cyano with 3-fluoro substituted phenyl and 3,5-bis(trifluoromethyl)benzyloxy | 1H-NMR (DMSO-d6) δ: 5.19 (2H, s), 7.34-7.43 (4H, m), 7.56-7.62 (2H, m). | Ex. 1 |

TABLE 4-continued

| | Structure | 1H-NMR | |
|---|---|---|---|
| 569 | 3-Cl, 5-F phenyl with 3-F,5-CF3 benzyloxy, triazole-CN | 1H-NMR (DMSO-d6) δ: 4.95 (2H, s), 7.37 (1H, d, J = 9.1 Hz), 7.42 (1H, s), 7.50-7.53 (1H, m), 7.62 (1H, d, J = 9.1 Hz), 7.85-7.87 (1H, m). | Ex. 1 |
| 570 | 3,5-diF phenyl with 3-F,5-CF3 benzyloxy, triazole-CN | 1H-NMR (DMSO-d6) δ: 5.12 (2H, s), 7.34-7.37 (2H, m), 7.39 (1H, s), 7.62 (1H, d, J = 8.7 Hz), 7.67-7.72 (1H, m). | Ex. 1 |
| 571 | 3,5-diCl phenyl with 3-F,5-CF3 benzyloxy, triazole-CN | 1H-NMR (DMSO-d6) δ: 4.97 (2H, s), 7.39 (1H, d, J = 9.1 Hz), 7.43 (1H, s), 7.62 (1H, d, J = 9.1 Hz), 7.67 (1H, d, J = 2.6 Hz), 7.97 (1H, d, J = 2.6 Hz). | Ex. 1 |
| 572 | 3-F phenyl with 3,4-diF benzyloxy, triazole-CN | 1H-NMR (DMSO-d6) δ: 5.02 (2H, s), 6.97 (1H, m), 7.09-7.17 (1H, m), 7.28-7.38 (3H, m), 7.51-7.57 (1H, m). | Ex. 1 |

TABLE 4-continued

| | Structure | 1H-NMR | |
|---|---|---|---|
| 573 | 4-(3-fluoro-2-((3,5-bis(trifluoromethyl)benzyl)oxy)phenyl)-1H-1,2,3-triazole-5-carbonitrile | 1H-NMR (DMSO-d6) δ: 5.29 (2H, s), 7.35-7.44 (2H, m), 7.54-7.61 (1H, m), 7.90 (2H, s), 8.04 (1H, s). | Ex. 1 |
| 574 | 4-(5-bromo-2-((3-fluoro-5-(trifluoromethyl)benzyl)oxy)phenyl)-1H-1,2,3-triazole-5-carbonitrile | 1H-NMR (DMSO-d6) δ: 5.38 (2H, s), 7.25 (1H, d, J = 8.9 Hz), 7.59 (1H, d, J = 9.4 Hz), 7.65 (1H, s), 7.66 (1H, s), 7.73-7.79 (1H, m), 7.80 (1H, s). | Ex. 1 |
| 575 | 4-(3-fluoro-2-((3-(trifluoromethoxy)benzyl)oxy)phenyl)-1H-1,2,3-triazole-5-carbonitrile | 1H-NMR (DMSO-d6) δ: 5.12 (2H, s), 7.14 (1H, s), 7.20 (1H, d, J = 7.6 Hz), 7.28 (1H, d, J = 8.2 Hz), 7.32-7.43 (3H, m), 7.53-7.58 (1H, m). | Ex. 1 |
| 576 | 4-(3-fluoro-2-((3-(trifluoromethyl)benzyl)oxy)phenyl)-1H-1,2,3-triazole-5-carbonitrile | 1H-NMR (DMSO-d6) δ: 5.15 (2H, s), 7.30-7.83 (7H, m). | Ex. 1 |

TABLE 4-continued

| Ex. No. | STR | m.p. | 1H-NMR | ref. |
|---|---|---|---|---|
| 577 | (3,5-bis(trifluoromethyl)benzyloxy-5-fluorophenyl triazole carbonitrile structure) | | 1H-NMR (DMSO-d6) δ: 5.44 (2H, s), 7.32-7.37 (1H, m), 7.43-7.54 (2H, m), 8.08 (1H, s), 8.11 (2H, s). | Ex. 1 |
| 578 | (3-(trifluoromethyl)-4-fluorobenzyloxy-5-fluorophenyl triazole carbonitrile structure) | | 1H-NMR (DMSO-d6) δ: 5.29 (2H, s), 7.30-7.54 (4H, m), 7.73-7.83 (2H, m). | Ex. 1 |
| 579 | (2,4,5-trifluorobenzyloxy-3-fluorophenyl triazole carbonitrile structure) | | 1H-NMR (DMSO-d6) δ: 5.04 (2H, s), 7.27-7.42 (4H, m), 7.54-7.59 (1H, m). | Ex. 1 |
| 580 | (4-chlorobenzyloxy-3-chlorophenyl triazole carbonitrile structure) | 244-246 | | Ex. 1 |

TABLE 4-continued
| | | | |
|---|---|---|---|
| 581 | 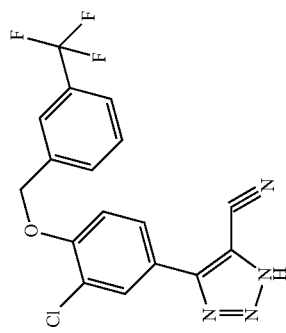 | 219-220 | Ex. 1 |
| 582 | 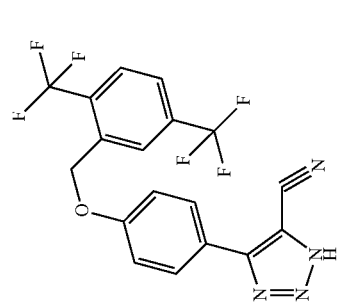 | 260-262 | Ex. 1 |
| 583 | 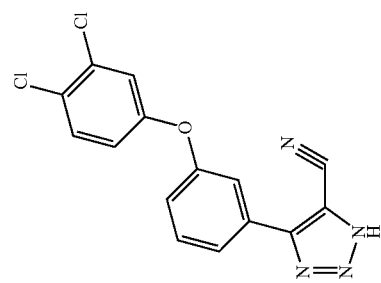 | 176-177 | Ex. 1 |

TABLE 4-continued

| | | | |
|---|---|---|---|
| 584 | [4-methoxyphenoxy-phenyl-triazole-carbonitrile structure] | 139-142 | Ex. 1 |
| 585 | [3,5-dichlorophenoxy-phenyl-triazole-carbonitrile structure] | 153 | Ex. 1 |

TABLE 4-continued

| | | | |
|---|---|---|---|
| 587 | [structure: 4-chloro-3-methylphenoxy phenyl triazole carbonitrile] | 144-147 | Ex. 1 |
| 588 | [structure: 3-(trifluoromethyl)phenoxy phenyl triazole carbonitrile] | 129 | Ex. 1 |

TABLE 4-continued

| Ex. No. | STR | 1H-NMR | ref. |
|---|---|---|---|
| 586 | (2,4-dichlorophenoxy)phenyl triazole carbonitrile | 1H-NMR (DMSO-d6) δ: 7.17-7.19 (1H, m), 7.28 (1H, d, J = 8.8 Hz), 7.44-7.45 (1H, m), 7.48-7.51 (1H, m), 7.62-7.82 (2H, m), 7.83 (1H, s). | Ex. 1 |
| 589 | (4-chlorophenoxy)phenyl triazole carbonitrile | 1H-NMR (DMSO-d6) δ: 7.12-7.16 (2H, m), 7.22-7.24 (1H, m), 7.46-7.50 (2H, m), 7.51 (1H, t, J = 1.8 Hz), 7.63-7.69 (2H, m). | Ex. 1 |
| 590 | trifluoromethyl (4-chlorophenoxy)phenyl triazole carbonitrile | 1H-NMR (CDCl3) δ: 7.0-7.1 (2H, m), 7.33 (1H, s), 7.3-7.4 (2H, m), 7.77 (1H, s), 7.97 (1H, s). | Ex. 1 |
| 591 | trifluoromethyl (3-chlorophenoxy)phenyl triazole carbonitrile | 1H-NMR (CDCl3) δ: 6.95-7.0 (1H, m), 7.06 (1H, s), 7.15-7.25 (1H, m), 7.3-7.4 (2H, m), 7.79 (1H, s), 8.00 (1H, s). | Ex. 1 |

TABLE 4-continued

| Ex. No. | STR | m.p. | ref. |
|---|---|---|---|
| 592 | 4-[4-(3-trifluoromethylphenoxy)phenyl]-1H-1,2,3-triazole-5-carbonitrile | 166-167 | Ex. 1 |
| 593 | 4-[4-(4-chlorophenoxy)phenyl]-1H-1,2,3-triazole-5-carbonitrile | 174-176 | Ex. 1 |
| 594 | 4-[4-(4-chlorophenoxy)-3-trifluoromethylphenyl]-1H-1,2,3-triazole-5-carbonitrile | 130-135 | Ex. 1 |

TABLE 4-continued
| Ex. No. | STR | 1H-NMR | ref. |
|---|---|---|---|
| 595 | 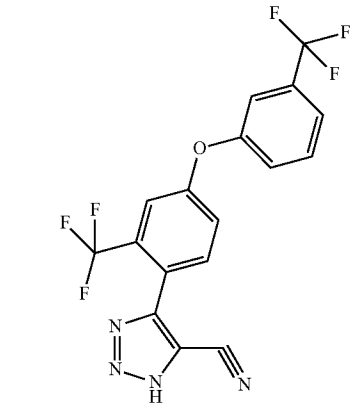 | 92-93 | Ex. 1 |
| 596 |  | 1H-NMR (DMSO-d6) δ: 7.36 (1H, d, J = 8.7 Hz), 7.45-7.47 (1H, m), 7.54 (1H, s), 7.64 (1H, d, J = 7.8 Hz), 7.71 (1H, t, J = 7.8 Hz), 8.16-8.30 (1H, m), 8.30 (1H, s). | Ex. 1 |
| 597 |  | 1H-NMR (DMSO-d6) δ: 7.33-7.35 (1H, m), 7.37 (1H, d, J =8.6 Hz), 7.43 (1H, s), 7.57 (1H, d, J = 8.0 Hz), 7.67 (1H, d, J = 8.0 Hz), 7.93-7.95 (1H, m), 8.26 (1H, s). | Ex. 1 |

TABLE 4-continued
| Ex. No. | STR | m.p. | ref. |
|---|---|---|---|
| 598 | 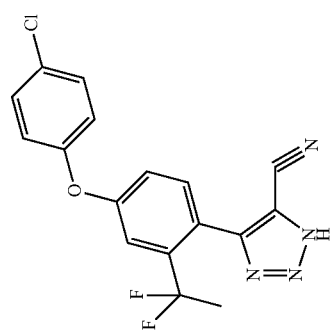 | 1H-NMR (DMSO-d6) δ: 7.27 (2H, d, J = 8.1 Hz), 7.41-7.57 (4H, m), 7.74 (1H, d, J = 8.4 Hz). | Ex. 1 |
| 599 | | 1H-NMR (DMSO-d6) δ: 7.35-7.45 (3H, m), 7.58 (1H, d, J = 7.8 Hz), 7.67 (1H, t, J = 7.8 Hz), 7.90 (1H, d, J = 8.5 Hz), 8.12 (1H, s). | Ex. 1 |
| 600 | 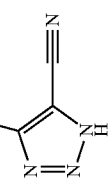 | 189-192 | Ex. 2 |

TABLE 4-continued

| | | | |
|---|---|---|---|
| 601 | (structure) | 191-194 | Ex. 2 |
| 602 | (structure) | 231-234 | Ex. 2 |
| 603 | (structure) | 284-286 | Ex. 2 |

TABLE 4-continued

| | | | |
|---|---|---|---|
| 604 | [structure] | 269-272 | Ex. 2 |
| 605 | [structure] | 243-244 | Ex. 2 |
| 606 | [structure] | 196 | Ex. 1 |

TABLE 4-continued

| Ex. No. | STR | 1H-NMR | ref. |
|---|---|---|---|
| 607 | (structure: 4-fluoro-3-methylstyryl phenyl triazole carbonitrile) | 194-196 | Ex. 1 |
| 608 | (structure: 3,5-disubstituted (3-fluorostyryl, fluoro) phenyl triazole carbonitrile) | 1H-NMR (DMSO-d6) δ: 7.13-7.18 (1H, m), 7.43-7.47 (4H, m), 7.52-7.54 (1H, m), 7.58-7.63 (1H, m), 7.71-7.73 (1H, m), 7.92 (1H, brs). | Ex. 2 |
| 609 | (structure: 3-styryl-5-trifluoromethyl phenyl triazole carbonitrile) | 1H-NMR (DMSO-d6) δ: 7.31-7.36 (1H, m), 7.41-7.59 (4H, m), 7.67-7.69 (2H, m), 8.06 (1H, s), 8.17 (1H, s), 8.37 (1H, s). | Ex. 1 |

TABLE 4-continued

| | Structure | NMR | Ex. |
|---|---|---|---|
| 610 | 3,5-bis(trifluoromethyl)phenyl-CH=CH-(3-chloro-5-yl)phenyl-triazole-CN | 1H-NMR (DMSO-d6) δ: 7.67 (1H, d, J = 16.4 Hz), 7.79 (1H, d, J = 16.4 Hz), 7.85 (1H, s), 7.94 (1H, s), 8.01 (1H, s), 8.07 (1H, s), 8.36 (2H, s). | Ex. 1 |
| 611 | 3,5-bis(trifluoromethyl)phenyl-CH=CH-(3-trifluoromethoxy-5-yl)phenyl-triazole-CN | 1H-NMR (DMSO-d6) δ: 7.68-7.88 (4H, m), 8.02 (1H, s), 8.15 (1H, s), 8.37 (2H, s). | Ex. 1 |
| 612 | 3-(trifluoromethyl)phenyl-CH=CH-(3-trifluoromethoxy-5-yl)phenyl-triazole-CN | 1H-NMR (DMSO-d6) δ: 7.59-7.69 (4H, m), 7.75 (1H, s), 7.87 (1H, s), 7.96-7.98 (1H, m), 8.04 (1H, s), 8.15 (1H, s). | Ex. 1 |

TABLE 4-continued

| | Structure | NMR | Ex. |
|---|---|---|---|
| 613 | 3-(trifluoromethyl)styryl-phenyl triazole carbonitrile | 1H-NMR (DMSO-d6) δ: 7.47 (1H, d, J = 16.5 Hz), 7.58 (1H, d, J = 16.5 Hz), 7.63-7.68 (3H, m), 7.79-7.85 (2H, m), 7.96-7.98 (1H, m), 8.02 (1H, s), 8.13 (1H, s). | Ex. 1 |
| 614 | difluoromethoxy-3-(trifluoromethyl)styryl-phenyl triazole carbonitrile | 1H-NMR (DMSO-d6) δ: 7.39 (1H, t, J = 73.5 Hz), 7.51-7.67 (6H, m), 7.96-7.99 (2H, m), 8.01 (1H, d, J = 10.1 Hz). | Ex. 1 |
| 615 | 3,5-bis(trifluoromethyl)styryl-phenyl triazole carbonitrile | 1H-NMR (DMSO-d6) δ: 7.58 (1H, d, J = 16.5 Hz), 7.68 (1H, t, J = 7.8 Hz), 7.79-7.86 (3H, m), 7.99 (1H, s), 8.14 (1H, s), 8.37 (2H, s). | Ex. 1 |

TABLE 4-continued

| | Structure | 1H-NMR | |
|---|---|---|---|
| 616 | 3-chloro-5-[(E)-2-(4-trifluoromethylphenyl)vinyl]phenyl triazole-carbonitrile | 1H-NMR (DMSO-d6) δ: 7.52 (1H, d, J = 16.6 Hz), 7.57 (1H, d, J = 16.6 Hz), 7.77 (2H, d, J = 8.3 Hz), 7.82-7.87 (3H, m), 7.97 (1H, s), 8.07 (1H, s). | Ex. 1 |
| 617 | 3-[(E)-2-(4-trifluoromethylphenyl)vinyl]phenyl triazole-carbonitrile | 1H-NMR (DMSO-d6) δ: 7.46 (1H, d, J = 16.5 Hz), 7.65 (1H, d, J = 16.5 Hz), 7.65 (1H, d, J = 7.8 Hz), 7.75-7.88 (6H, m), 8.13 (1H, s). | Ex. 1 |
| 618 | 3-chloro-5-[(E)-2-(3,5-difluorophenyl)vinyl]phenyl triazole-carbonitrile | 1H-NMR (DMSO-d6) δ: 7.16-7.22 (1H, m), 7.39-7.56 (4H, m), 7.83 (1H, s), 7.91 (1H, s), 8.02 (1H, s). | Ex. 1 |

TABLE 4-continued

| | Structure | 1H-NMR | |
|---|---|---|---|
| 619 | 3,5-bis(trifluoromethyl)styryl-phenyl triazole carbonitrile | 1H-NMR (CDCl3) δ: 7.29-7.38 (2H, m), 7.82 (1H, s), 7.92 (1H, s), 7.99 (2H, s), 8.21 (1H, s), 3.38 (1H, s). | Ex. 1 |
| 620 | 3-(trifluoromethyl)styryl-(3-trifluoromethylphenyl) triazole carbonitrile | 1H-NMR (CDCl3) δ: 7.22-7.38 (2H, m), 7.50-7.59 (2H, m), 7.73 (1H, d, J = 8.0 Hz), 7.81 (1H, s), 7.89 (1H, s), 8.16 (1H, s), 8.34 (1H, s). | Ex. 1 |
| 621 | 3,5-difluorostyryl-phenyl triazole carbonitrile | 1H-NMR (DMSO-d6) δ: 7.13-7.19 (1H, m), 7.31-7.83 (7H, m), 8.08 (1H, s). | Ex. 1 |

TABLE 4-continued

| | | | |
|---|---|---|---|
| 622 | [structure: styryl-phenyl triazole carbonitrile] | 1H-NMR (DMSO-d6) δ: 7.31-7.44 (5H, m), 7.63-7.67 (3H, m), 7.77-7.80 (2H, m), 8.09 (1H, s). | Ex. 1 |
| 623 | [structure: 4-fluorostyryl-3-chlorophenyl triazole carbonitrile] | 1H-NMR (DMSO-d6) δ: 7.26 (2H, t, J = 7.2 Hz), 7.31 (1H, d, J = 16.4 Hz), 7.47 (1H, d, J = 16.4 Hz), 7.68-7.71 (2H, m), 7.79 (1H, s), 7.91 (1H, s), 8.01 (1H, s). | Ex. 1 |
| 624 | [structure: 4-trifluoromethylstyryl-3-trifluoromethoxyphenyl triazole carbonitrile] | 1H-NMR (DMSO-d6) δ: 7.59 (2H, s), 7.76-7.89 (6H, m), 8.15 (1H, s). | Ex. 1 |

TABLE 4-continued

| | Structure | 1H-NMR | |
|---|---|---|---|
| 625 | 3-(difluoromethoxy)-5-[(E)-2-[4-(trifluoromethyl)phenyl]vinyl]phenyl triazole-carbonitrile | 1H-NMR (DMSO-d6) δ: 7.39 (1H, t, J = 73.4 Hz), 7.55-7.60 (3H, m), 7.70 (1H, s), 7.77 (2H, d, J = 8.2 Hz), 7.88 (2H, d, J = 8.2 Hz), 8.01 (1H, s). | Ex. 1 |
| 626 | 3-methyl-5-[(E)-2-[3,5-bis(trifluoromethyl)phenyl]vinyl]phenyl triazole-carbonitrile | 1H-NMR (CDCl3) δ: 2.49 (3H, s), 7.18-7.32 (2H, m), 7.50 (1H, s), 7.55 (1H, s), 7.77 (1H, s), 7.94-7.97 (3H, m), 12.1 (1H, br.). | Ex. 1 |
| 627 | 3-methyl-5-[(E)-2-(4-fluorophenyl)vinyl]phenyl triazole-carbonitrile | 1H-NMR (CDCl3) δ: 2.47 (3H, s), 7.00-7.18 (4H, m), 7.45-7.54 (3H, m), 7.67 (1H, s), 7.90 (1H, s), 12.2 (1H, br.). | Ex. 1 |

TABLE 4-continued
| | | | |
|---|---|---|---|
| 628 | 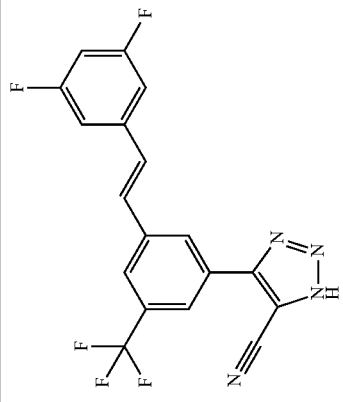 | 1H-NMR (DMSO-d6) δ: 7.17-7.23 (1H, m), 7.40-7.45 (2H, m), 7.54 (1H, d, J = 16.5 Hz), 7.64 (1H, d, J = 16.5 Hz), 8.10 (1H, s), 8.16 (2H, s), 8.34 (1H, s). | Ex. 2 |
| 629 | 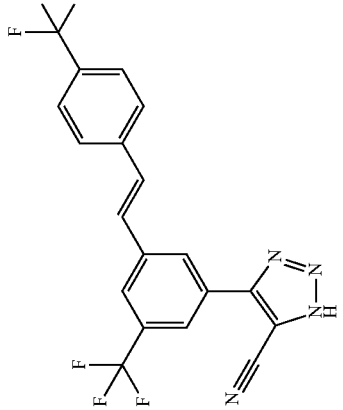 | 1H-NMR (DMSO-d6) δ: 7.66 (2H, s), 7.79 (2H, d, J = 8.2 Hz), 7.89 (2H, d, J = 8.2 Hz), 8.11 (1H, s), 6.24 (1H, s), 8.41 (1H, s). | Ex. 2 |
| 630 | 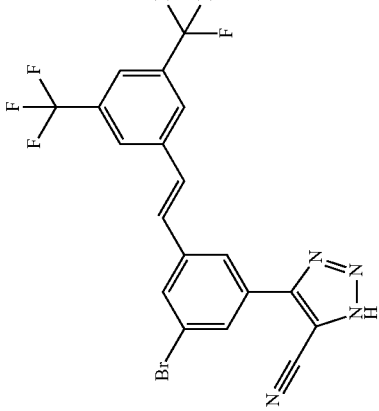 | 1H-NMR (DMSO-d6) δ: 7.57 (1H, d, J = 16.5 Hz), 7.80 (1H, d, J = 16.5 Hz), 7.98-8.01 (2H, m), 6.09-8.10 (2H, m), 0.35 (2H, s). | Ex. 2 |

TABLE 4-continued

| # | Structure | 1H-NMR | Ex. |
|---|---|---|---|
| 631 | 3-bromo-5-[3-(trifluoromethyl)styryl]phenyl triazole carbonitrile | 1H-NMR (DMSO-d6) δ: 7.25-7.61 (2H, m), 7.63-7.69 (2H, m), 7.95-7.96 (2H, m), 8.02 (1H, s), 8.09-8.10 (2H, m). | Ex. 2 |
| 632 | 3-ethoxy-5-[3,5-bis(trifluoromethyl)styryl]phenyl triazole carbonitrile | 1H-NMR (DMSO-d6) δ: 1.41 (3H, t, J = 7.0 Hz), 4.18 (2H, q, J = 7.0 Hz), 7.40 (1H, s), 7.44 (1H, s), 7.60 (1H, d, J = 16.4 Hz), 7.74 (1H, d, J = 16.4 Hz), 7.99 (1H, s), 8.34 (2H, s). | Ex. 2 |
| 633 | 3-methyl-5-styrylphenyl triazole carbonitrile | 1H-NMR (CDCl3) δ: 2.47 (3H, s), 7.12 (1H, d, J = 16.4 Hz), 7.20 (1H, d, J = 16.4 Hz), 7.25-7.32 (1H, m), 7.34-7.42 (2H, m), 7.48 (1H, s), 7.51-7.57 (2H, m), 7.66 (1H, s), 7.90 (1H, s), 12.0 (1H, br.). | Ex. 1 |

TABLE 4-continued

| # | Structure | 1H-NMR | Ref |
|---|---|---|---|
| 634 | (4-methoxyphenyl-vinyl-phenyl-triazole-carbonitrile) | 1H-NMR (CDCl3) δ: 3.85 (3H, s), 6.88-6.95 (2H, m), 7.02 (1H, d, J = 16.3 Hz), 7.17 (1H, d, J = 16.3 Hz), 7.45-7.54 (3H, m), 7.59-7.66 (1H, m), 7.79-7.88 (1H, m), 8.07 (1H, s), 12.0 (1H, br.). | Ex. 1 |
| 635 | (4-chlorophenyl-vinyl-phenyl-triazole-carbonitrile) | 1H-NMR (DMSO-d6) δ: 7.32-7.38 (2H, m), 7.46 (2H, d, J = 8.5 Hz), 7.61-7.69 (3H, m), 7.80 (2H, t, J = 7.8 Hz), 8.09 (1H, s). | Ex. 1 |
| 636 | (3-chlorophenyl-vinyl-phenyl-triazole-carbonitrile) | 1H-NMR (DMSO-d6) δ: 7.33-7.51 (4H, m), 7.59-7.67 (2H, m), 7.76-7.83 (3H, m), 8.10 (1H, s). | Ex. 1 |
| 637 | (3-chlorophenyl-vinyl-(3-chlorophenyl)-triazole-carbonitrile) | 1H-NMR (DMSO-d6) δ: 7.39-7.46 (4H, m), 7.55-7.60 (1H, m), 7.76 (1H, s), 7.81 (1H, s), 7.92 (1H, s), 6.03 (1H, s). | Ex. 1 |

TABLE 4-continued

| | Structure | 1H-NMR | Ex. |
|---|---|---|---|
| 638 | 3-chlorostyryl, 5-(trifluoromethoxy)phenyl triazole-carbonitrile | 1H-NMR (DMSO-d6) δ: 7.37-7.52 (4H, m), 7.61 (1H, d, J = 7.6 Hz), 7.74 (1H, s), 7.77 (1H, s), 7.84 (1H, s), 8.12 (1H, s). | Ex. 1 |
| 639 | 4-fluorostyryl, 5-(trifluoromethoxy)phenyl triazole-carbonitrile | 1H-NMR (DMSO-d6) δ: 7.27 (2H, t, J = 8.9 Hz), 7.32 (1H, t, J = 16.6 Hz), 7.38 (1H, d, J = 16.6 Hz), 7.70-7.73 (3H, m), 7.82 (1H, s), 8.10 (1H, s). | Ex. 1 |
| 640 | 4-fluorostyryl phenyl triazole-carbonitrile | 1H-NMR (DMSO-d6) δ: 7.24 (2H, t, J = 8.9 Hz), 7.34 (2H, d, J = 4.4 Hz), 7.60-7.81 (5H, m), 8.08 (1H, s). | Ex. 1 |

TABLE 4-continued

| | Structure | 1H-NMR | Ex. |
|---|---|---|---|
| 641 | 3-fluoro-4-(trifluoromethoxy)phenyl styryl triazole-carbonitrile | 1H-NMR (DMSO-d6) δ: 7.38 (1H, d, J = 16.5 Hz), 7.51 (1H, d, J = 16.5 Hz), 7.57-7.68 (2H, m), 7.80-7.88 (4H, m), 8.09 (1H, s). | Ex. 1 |
| 642 | 3-chloro-5-(4-chlorostyryl)phenyl triazole-carbonitrile | 1H-NMR (DMSO-d6) δ: 4.37 (1H, d, J = 16.5 Hz), 7.44-7.49 (3H, m), 7.67 (2H, d, J = 8.5 Hz), 7.79 (1H, s), 7.91 (1H, s), 8.02 (1H, s). | Ex. 1 |
| 643 | 2,4-bis(trifluoromethyl)phenyl styryl triazole-carbonitrile | 1H-NMR (DMSO-d6) δ: 7.46 (1H, d, J = 14.1 Hz), 7.68-7.90 (5H, m), 8.02 (1H, d, J = 8.3 Hz), 8.18 (1H, s), 8.41 (1H, s). | Ex. 1 |

TABLE 4-continued

| | Structure | 1H-NMR | |
|---|---|---|---|
| 644 | 3-(trifluoromethyl)styryl-5-(2-methoxyethoxy)phenyl triazole carbonitrile | 1H-NMR (DMSO-d6) δ: 1.40 (3H, t, J = 6.9 Hz), 4.18 (2H, q, J = 6.9 Hz), 7.34-7.35 (1H, m), 7.43-7.44 (1H, m), 7.51 (2H, s), 7.64-7.66 (2H, m), 7.69 (1H, s), 7.94-7.96 (1H, m), 8.00 (1H, s). | Ex. 2 |
| 645 | 2,4-difluorostyryl-3-(trifluoromethyl)phenyl triazole carbonitrile | 1H-NMR (DMSO-d6) δ: 7.17-7.23 (1H, m), 7.32-7.38 (1H, m), 7.48-7.57 (2H, m), 7.88-7.94 (1H, m), 8.09 (1H, s), 8.19(1H, s), 8.41 (1H, s). | Ex. 2 |
| 646 | 2,4-difluorostyryl-phenyl triazole carbonitrile | 1H-NMR (DMSO-d6) δ: 7.15-7.20 (1H, m), 7.30-7.44 (3H, m), 7.64 (1H, t, J = 7.8 Hz), 7.80-7.82 (2H, m), 7.88-7.94 (1H, m), 8.12 (1H, s). | Ex. 2 |

TABLE 4-continued

| | Structure | 1H-NMR | |
|---|---|---|---|
| 647 | 3-methoxyphenyl styryl phenyl triazole carbonitrile | 1H-NMR (CDCl3) δ: 3.91 (3H, s), 6.90-7.02 (2H, m), 7.17 (1H, d, J = 16.5 Hz), 7.24-7.32 (1H, m), 7.46-7.65 (3H, m), 7.69 (1H, d, J = 7.9 Hz), 7.84 (1H, d, J = 7.7 Hz), 8.08 (1H, s), 12.0 (1H, br). | Ex. 1 |
| 648 | 4-trifluoromethoxyphenyl chlorostyryl phenyl triazole carbonitrile | 1H-NMR (DMSO-d6) δ: 7.36-7.54 (4H, m), 7.76-7.80 (3H, m), 7.92 (1H, s), 8.03 (1H, s). | Ex. 1 |
| 649 | 3-trifluoromethoxyphenyl chlorostyryl phenyl triazole carbonitrile | 1H-NMR (DMSO-d6) δ: 7.31 (1H, d, J = 8.3 Hz), 7.45-7.58 (3H, m), 7.67-7.70 (2H, m), 7.81 (1H, s), 7.93 (1H, s), 8.04 (1H, s). | Ex. 1 |
| 650 | 3-fluorophenyl styryl phenyl triazole carbonitrile | 1H-NMR (DMSO-d6) δ: 7.05-7.20 (1H, m), 7.34-7.56 (5H, m), 7.64 (1H, t, J = 7.7 Hz), 7.78-7.83 (2H, m), 8.09 (1H, s). | Ex. 1 |

TABLE 4-continued

| | Structure | 1H-NMR | Ex. |
|---|---|---|---|
| 651 | 3-chloro-5-fluorostyryl triazole carbonitrile | 1H-NMR (DMSO-d6) δ: 7.14-7.18 (1H, m), 7.43-7.54 (5H, m), 7.81 (1H, s), 7.92 (1H, s), 8.03 (1H, s). | Ex. 1 |
| 652 | 3,4-difluorostyryl triazole carbonitrile | 1H-NMR (CDCl3) δ: 6.90 (1H, d, J = 16.5 Hz), 7.12 (1H, d, J = 16.5 Hz), 7.12-7.26 (2H, m), 7.32-7.41 (1H, m), 7.53 (1H, t, J = 7.7 Hz), 7.60-7.66 (1H, m), 7.84-7.96 (1H, m), 8.11 (1H, s), 12.0 (1H, br.). | Ex. 1 |
| 653 | 2-trifluoromethylstyryl triazole carbonitrile | 1H-NMR (CDCl3) δ: 7.14 (1H, d, J = 16.0 Hz), 7.40 (1H, t, J = 7.6 Hz), 7.53-7.62 (3H, m), 7.67-7.73 (2H, m), 7.81 (1H, d, J = 7.9 Hz), 7.89-7.96 (1H, m), 8.10 (1H, s), 12.0 (1H, br.). | Ex. 1 |
| 654 | 3-methoxystyryl triazole carbonitrile | 1H-NMR (CDCl3) δ: 3.87 (3H, s), 6.82-6.89 (1H, m), 7.05-7.24 (4H, m), 7.30 (1H, t, J = 7.9 Hz), 7.52 (1H, t, J = 7.7 Hz), 7.65 (1H, d, J = 7.8 Hz), 7.83-7.92 (1H, m), 8.10 (1H, s), 12.3 (1H, br.). | Ex. 1 |

TABLE 4-continued
| | | | |
|---|---|---|---|
| 655 | 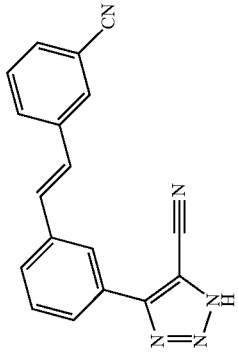 | 1H-NMR (DMSO-d6) δ: 7.41 (1H, d, J = 16.5 Hz), 7.57 (1H, t, J = 16.5 Hz), 7.59-7.69 (2H, m), 7.76 (1H, d, J = 7.7 Hz), 7.78-7.85 (2H, m), 7.97 (1H, d, J = 7.9 Hz), 8.10 (1H, s), 8.17 (1H, s). | Ex. 1 |
| 656 | 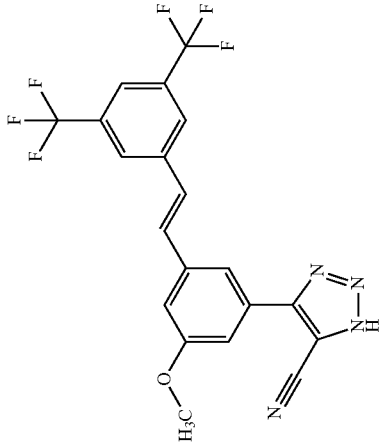 | 1H-NMR (DMSO-d6) δ: 3.91 (3H, s), 7.39-7.40 (1H, m), 7.46 (1H, s), 7.61 (1H, d, J = 16.5 Hz), 7.72-7.79 (2H, m), 8.00 (1H, s), 8.36 (1H, s). | Ex. 2 |
| 657 | 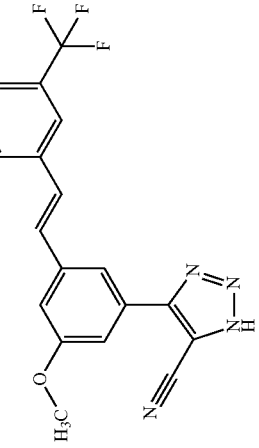 | 1H-NMR (DMSO-d6) δ: 3.90 (3H, s), 7.36-7.37 (1H, m), 7.44-7.45 (1H, m), 7.47-7.56 (2H, m), 7.64-7.67 (2H, m), 7.71 (1H, s), 7.95-7.97 (1H, m), 6.01 (1H, s). | Ex. 2 |

TABLE 4-continued

| | Structure | 1H-NMR | Ex. |
|---|---|---|---|
| 658 | 3-methoxy-5-[(E)-2-[4-(trifluoromethyl)phenyl]ethenyl]phenyl triazole-carbonitrile | 1H-NMR (DMSO-d6) δ: 3.90 (3H, s), 7.37-7.38 (1H, m), 7.45-7.54 (3H, m), 7.72-7.77 (3H, m), 7.85-7.87 (2H, m). | Ex. 2 |
| 659 | 3-[(E)-2-[3-fluoro-5-(trifluoromethyl)phenyl]ethenyl]phenyl triazole-carbonitrile | 1H-NMR (DMSO-d6) δ: 7.48 (1H, d, J = 16.3 Hz), 7.58-7.69 (3H, m), 7.82-7.91 (4H, m), 8.11 (1H, s). | Ex. 2 |
| 660 | 3-(trifluoromethoxy)-5-[(E)-2-[3-(trifluoromethoxy)phenyl]ethenyl]phenyl triazole-carbonitrile | 1H-NMR (DMSO-d6) δ: 7.32 (1H, d, J = 7.7 Hz), 7.52 7.59 (3H, m), 7.69-7.71 (2H, m), 7.74 (1H, s), 7.83 (1H, s), 8.13 (1H, s). | Ex. 1 |

TABLE 4-continued

| | Structure | 1H-NMR | |
|---|---|---|---|
| 661 | 4-F, 5-CF3 phenyl stilbene triazole | 1H-NMR (DMSO-d6) δ: 7.45 (1H, d, J = 16.5 Hz), 7.52 (1H, t, J = 9.5 Hz), 7.64-7.76 (3H, m), 7.83-7.88 (2H, m), 8.17 (1H, s), 8.26-8.28 (1H, m). | Ex. 2 |
| 662 | 4-Cl, 3-CF3 phenyl stilbene triazole | 1H-NMR (DMSO-d6) δ: 7.48 (1H, d, J = 16.6 Hz), 7.59 (1H, d, J = 16.6 Hz), 7.66 (1H, t, J = 7.6 Hz), 7.76 (1H, d, J = 8.3 Hz), 7.80-7.85 (2H, m), 7.97-8.00 (1H, m), 8.11 (2H, s). | Ex. 2 |
| 663 | 4-F, 3-CF3 phenyl stilbene triazole | 1H-NMR (DMSO-d6) δ: 7.46 (1H, d, J = 16.5 Hz), 7.52 (1H, d, J = 16.5 Hz), 7.54-7.59 (1H, m), 7.65 (1H, t, J = 7.8 Hz), 7.79-7.83 (2H, m), 8.03-8.06 (2H, m), 8.10 (2H, s). | Ex. 2 |
| 664 | 2-F, 3-CF3 phenyl stilbene triazole | 1H-NMR (DMSO-d6) δ: 7.44-7.49 (2H, m), 7.58 (1H, d, J = 16.7 Hz), 7.67 (1H, t, J = 7.9 Hz), 7.73 (1H, t, J = 7.2 Hz), 7.83-7.87 (2H, m), 8.17-8.23 (2H, m). | Ex. 2 |

TABLE 4-continued

| | | | |
|---|---|---|---|
| 665 | structure with 2,4-difluorophenyl vinyl, methoxy, triazole-CN | 1H-NMR (DMSO-d6) δ: 3.89 (3H, s), 7.15-7.20 (1H, m), 7.30-7.39 (5H, m), 7.71 (1H, s), 7.86-7.92 (1H, m). | Ex. 2 |
| 666 | structure with 4-chlorophenyl vinyl, OCHF2, triazole-CN | 1H-NMR (DMSO-d6) δ: 7.13-7.49 (5H, m), 7.56 (1H, s), 7.63-7.70 (3H, m), 7.96 (1H, s). | Ex. 1 |
| 667 | structure with 4-fluorophenyl vinyl, CF3, triazole-CN | 1H-NMR (DMSO-d6) δ: 7.26-7.29 (2H, m), 7.43 (1H, d, J = 16.5 Hz), 7.56 (1H, d, J = 16.5 Hz), 7.71-7.75 (2H, m), 8.06 (1H, s), 8.16 (1H, s), 8.35 (1H, s). | Ex. 2 |

| | | | |
|---|---|---|---|
| 668 | 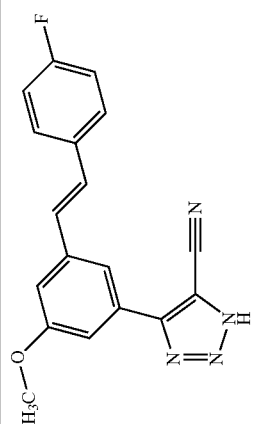 | 1H-NMR (DMSO-d6) δ: 3.89 (3H, s), 7.22-7.40 (6H, m), 7.66-7.71 (3H, m). | Ex. 2 |
| 669 | 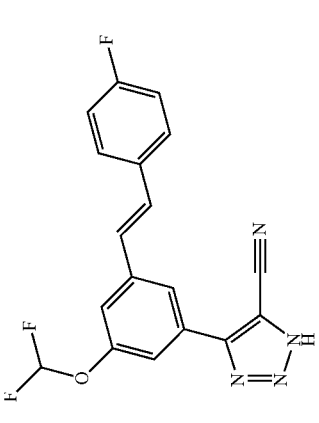 | 1H-NMR (DMSO-d6) δ: 7.14-7.47 (5H, m), 7.55 (1H, s), 7.63 (1H, s), 7.63-7.73 (2H, m), 7.95 (1H, s). | Ex. 1 |
| 670 | 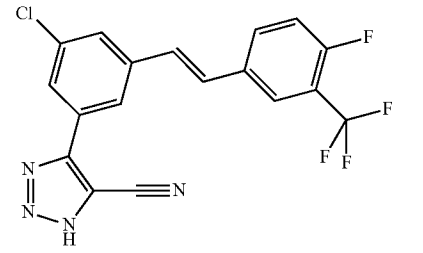 [SMILES: N#Cc1[nH]nnc1-c1cc(Cl)cc(/C=C/c2ccc(F)c(C(F)(F)F)c2)c1] | 1H-NMR (DMSO-d6) δ: 7.46-7.61 (3H, m), 7.82 (1H, s), 7.93 (1H, s), 8.00-8.06 (3H, m). | Ex. 1 |
| 671 | 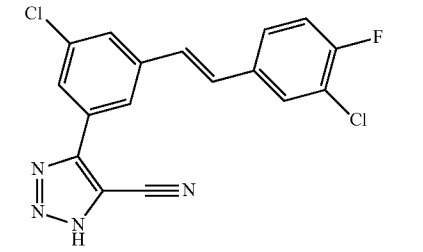 [SMILES: N#Cc1[nH]nnc1-c1cc(Cl)cc(/C=C/c2ccc(F)c(Cl)c2)c1] | 1H-NMR (DMSO-d6) δ: 7.38-7.50 (3H, m), 7.63-7.68 (1H, m), 7.81 (1H, s), 7.90-7.94 (2H, m), 8.01 (1H, s). | Ex. 1 |

TABLE 4-continued

| | Structure | 1H-NMR | Ex. |
|---|---|---|---|
| 672 | (2,5-difluorophenyl vinyl-phenyl triazole carbonitrile) | 1H-NMR (DMSO-d6) δ: 7.18-7.24 (1H, m), 7.30-7.40 (2H, m), 7.55 (1H, d, J = 16.3 Hz), 7.65 (1H, t, J = 7.7 Hz), 7.74-7.78 (1H, m), 7.81-7.84 (2H, m), 8.14 (1H, s). | Ex. 2 |
| 673 | (3,4,5-trifluorophenyl vinyl-phenyl triazole carbonitrile) | 1H-NMR (DMSO-d6) δ: 7.33 (1H, d, J = 16.6 Hz), 7.50 (1H, d, J = 16.6 Hz), 7.59-7.67 (2H, m), 7.80-7.84 (2H, m), 8.01-8.08 (1H, m), 8.12 (1H, s). | Ex. 2 |
| 674 | (4-difluoromethoxyphenyl vinyl-3-chlorophenyl triazole carbonitrile) | 1H-NMR (DMSO-d6) δ: 7.04-7.53 (5H, m), 7.71 (2H, d, J = 8.7 Hz), 7.79 (1H, s), 7.91 (1H, s), 8.02 (1H, s). | Ex. 1 |
| 675 | (3-trifluoromethylphenyl vinyl-4-fluorophenyl triazole carbonitrile) | 1H-NMR (DMSO-d6) δ: 7.48-7.67 (5H, m), 7.83-7.86 (1H, m), 7.99-8.04 (2H, m), 8.29 (1H, dd, J = 2.2, 7.2 Hz). | Ex. 1 |

TABLE 4-continued

| | | | |
|---|---|---|---|
| 676 | (structure: 2-fluoro-5-[(E)-2-(3-trifluoromethylphenyl)vinyl]phenyl triazole carbonitrile) | 1H-NMR (DMSO-d6) δ: 7.45 (1H, d, J = 16.6 Hz), 7.53-7.57 (2H, m), 7.63-7.65 (2H, m), 7.90-7.94 (2H, m), 7.99 (1H, s), 8.03-8.05 (1H, m). | Ex. 1 |
| 677 | (structure: 2-fluoro-5-[(E)-2-(4-trifluoromethylphenyl)vinyl]phenyl triazole carbonitrile) | 1H-NMR (DMSO-d6) δ: 7.52-7.59 (2H, m), 7.77 (1H, d, J = 8.2 Hz), 7.83-7.92 (5H, m), 8.29-8.33 (1H, m). | Ex. 1 |
| 678 | (structure: 2-fluoro-5-[(E)-2-(4-fluorophenyl)vinyl]phenyl triazole carbonitrile) | 1H-NMR (DMSO-d6) δ: 7.22-7.28 (2H, m), 7.34-7.56 (3H, m), 7.71-7.81 (3H, m), 8.26 (1H, dd, J = 2.2, 7.1 Hz). | Ex. 1 |

TABLE 4-continued

| | | | |
|---|---|---|---|
| 679 | (structure: 5-(4-fluoro-3-(3,5-bis(trifluoromethyl)styryl)phenyl)-1H-1,2,3-triazole-4-carbonitrile) | 1H-NMR (DMSO-d6) δ: 7.53-7.59 (1H, m), 7.61 (1H, d, J = 16.7 Hz), 7.77 (1H, d, J = 16.7 Hz), 7.86-7.89 (1H, m), 8.02 (1H, s), 8.27-8.30 (1H, m), 8.42 (2H, s). | Ex. 1 |
| 680 | (structure: 5-(3-fluoro-5-(3-(trifluoromethyl)styryl)phenyl)-1H-1,2,3-triazole-4-carbonitrile) | 1H-NMR (DMSO-d6) δ: 7.49-7.59 (3H, m), 7.62-7.68 (3H, m), 7.95-7.97 (2H, m), 8.02 (1H, brs). | Ex. 2 |
| 681 | (structure: 5-(2-fluoro-3-(3,5-bis(trifluoromethyl)styryl)phenyl)-1H-1,2,3-triazole-4-carbonitrile) | 1H-NMR (DMSO-d6) δ: 7.51 (1H, t, J = 7.8 Hz), 7.65 (1H, d, J = 16.7 Hz), 7.72-7.77 (1H, m), 7.81 (1H, d, J = 16.7 Hz), 8.02 (2H, s), 8.44 (2H, s). | Ex. 1 |

TABLE 4-continued

| | Structure | 1H-NMR | Ex. |
|---|---|---|---|
| 682 | (3-(trifluoromethyl)phenyl vinyl, 2-fluorophenyl, triazole-CN) | 1H-NMR (DMSO-d6) δ: 7.45-7.86 (5H, m), 8.02 (2H, s), 8.43 (2H, s). | Ex. 1 |
| 683 | (3-(trifluoromethyl)phenyl vinyl, acetamido phenyl, triazole-CN) | 1H-NMR (DMSO-d6) δ: 2.17 (3H, s), 7.35 (1H, d, J = 16.2 Hz), 7.59-7.69 (3H, m), 7.78 (1H, dd, J = 2.0, 8.4 Hz), 7.87 (1H, d, J = 8.4 Hz), 7.97-7.99 (2H, m), 8.25 (1H, d, J = 2.0 Hz), 9.86 (1H, s). | Ex. 1 |
| 684 | (3-fluoro-5-methoxyphenyl vinyl, 3-(trifluoromethoxy)phenyl, triazole-CN) | 1H-NMR (DMSO-d6) δ: 3.83 (3H, s), 6.77-6.82 (1H, m), 7.08-7.14 (2H, m), 7.44 (1H, d, J = 16.6 Hz), 7.52 (1H, d, J = 16.6 Hz), 7.74 (1H, s), 7.82 (1H, s), 8.10 (1H, s). | Ex. 1 |

TABLE 4-continued

| | Structure | 1H-NMR | |
|---|---|---|---|
| 685 | (structure: 4-fluoro-3-methylphenyl vinyl linked to 3-(trifluoromethoxy)phenyl-triazole-carbonitrile) | 1H-NMR (DMSO-d6) δ: 2.28 (3H, s), 7.19 (1H, t, J = 9.1 Hz), 7.34 (1H, d, J = 16.4 Hz), 7.44 (1H, d, J = 16.4 Hz), 7.49-7.53 (1H, m), 7.61 (1H, d, J = 7.7 Hz), 7.71 (1H, s), 7.80 (1H, s), 8.09 (1H, s). | Ex. 1 |
| 686 | (structure: Boc-NH-phenyl vinyl-3-(trifluoromethyl)phenyl with triazole-carbonitrile) | 1H-NMR (DMSO-d6) δ: 1.50 (9H, s), 7.30 (1H, d, J = 16.2 Hz), 7.61-7.68 (3H, m), 7.76-7.77 (2H, m), 7.87-7.96 (1H, m), 7.98 (1H, s), 8.22 (1H, s), 9.32 (1H, s). | Ex. 1 |
| 687 | (structure: Boc-N(CH3)-phenyl vinyl-3-(trifluoromethyl)phenyl with triazole-carbonitrile) | 1H-NMR (DMSO-d6) δ: 1.06-1.69 (9H, br), 3.22 (3H, s), 7.17-7.32 (1H, m), 7.43 (1H, d, J = 16.4 Hz), 7.56 (1H, d, J = 8.2 Hz), 7.66-7.68 (2H, m), 7.84 (1H, dd, J = 2.1, 8.2 Hz), 7.87-7.99 (2H, br), 8.30 (1H, d, J = 2.2 Hz). | Ex. 1 |

TABLE 4-continued

| | Structure | NMR | Ex. |
|---|---|---|---|
| 689 | 3-ethoxyphenyl stilbene triazole-carbonitrile | 1H-NMR (CDCl3) δ: 1.45 (3H, t, J = 7.0 Hz), 4.09 (2H, q, J = 7.0 Hz), 6.85 (1H, ddd, J = 0.8, 2.5, 8.1 Hz), 7.07-7.16 (3H, m), 7.18 (1H, d, J = 16.5 Hz), 7.30 (1H, t, J = 7.8 Hz), 7.52 (1H, t, J = 7.8 Hz), 7.65 (1H, d, J = 7.9 Hz), 7.86 (1H, d, J = 7.8 Hz), 8.09 (1H, s). | Ex. 1 |
| 690 | 3,5-bis(trifluoromethyl)stilbene-2-chloro triazole-carbonitrile | 1H-NMR (DMSO-d6) δ: 7.17 (1H, d, J = 16.3 Hz), 7.48 (1H, d, J = 7.6 Hz), 7.54 (1H, dd, J = 1.8, 7.6 Hz), 7.69 (1H, d, J = 16.3 Hz), 7.81 (1H, s), 7.86 (1H, dd, J = 1.7, 7.7 Hz), 7.97 (2H, s). | Ex. 2 |
| 691 | 3,5-bis(trifluoromethyl)stilbene benzyloxy triazole-carbonitrile | 1H-NMR (DMSO-d6) δ: 5.32 (2H, s), 7.30-7.46 (7H, m), 7.70 (1H, d, J = 16.8 Hz), 7.81 (1H, d, J = 7.4 Hz), 7.90 (1H, d, J = 2.2 Hz), 7.95 (1H, s), 8.28 (2H, s). | Ex. 2 |

TABLE 4-continued

| | Structure | 1H-NMR | Ref |
|---|---|---|---|
| 692 | (structure with isopropylamino, 3-(trifluoromethyl)styryl, and cyanotriazole) | 1H-NMR (DMSO-d6) δ: 1.25 (6H, d, J = 6.1 Hz), 3.68-3.90 (1H, m), 5.86-5.97 (1H, m), 6.86 (1H, d, J = 8.7 Hz), 7.14 (1H, d, J = 16.3 Hz), 7.60-7.68 (4H, m), 7.97-8.00 (3H, m). | Ex. 316 |
| 694 | (structure with 2-hydroxy, 3-(trifluoromethyl)styryl, and cyanotriazole) | 1H-NMR (DMSO-d6) δ: 7.10 (1H, t, J = 7.7 Hz), 7.38 (1H, d, J = 16.3 Hz), 7.52 (1H, dd, J = 1.5, 7.7 Hz), 7.64-7.67 (2H, m), 7.78 (1H, d, J = 16.3 Hz), 7.86-7.88 (1H, m), 7.93-7.95 (1H, m), 8.01 (1H, s). | Ex. 2 |
| 695 | (structure with benzyloxy, 3-(trifluoromethyl)styryl, and cyanotriazole) | 1H-NMR (DMSO-d6) δ: 4.68 (2H, s), 7.15-7.17 (2H, m), 7.26-7.32 (3H, m), 7.43 (1H, t, J = 7.7 Hz), 7.49 (2H, s), 7.55 (1H, dd, J = 1.6, 7.7 Hz), 7.61-7.67 (2H, m), 7.84 (2H, bs), 8.01-8.03 (1H, m). | Ex. 2 |

TABLE 4-continued
| | Structure | 1H-NMR | Ex. |
|---|---|---|---|
| 696 | 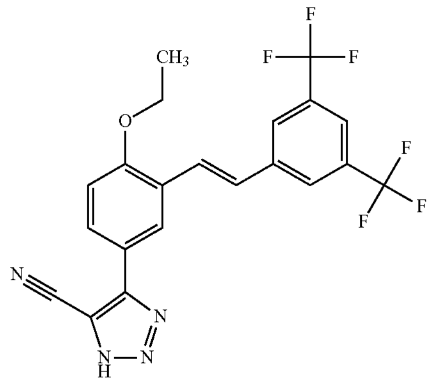 [SMILES: CCOc1ccc(-c2nn[nH]c2C#N)cc1/C=C/c1cc(C(F)(F)F)cc(C(F)(F)F)c1] | 1H-NMR (DMSO-d6) δ: 1.46 (3H, t, J = 7.0 Hz), 4.26 (2H, q, J = 7.0 Hz), 7.30-7.34 (1H, m), 7.54 (1H, d, J = 16.2 Hz), 7.72 (1H, d, J = 16.2 Hz), 7.82 (1H, d, J = 7.7 Hz), 7.99 (1H, s), 8.15 (1H, s), 8.28 (2H, s). | Ex. 2 |
| 697 | 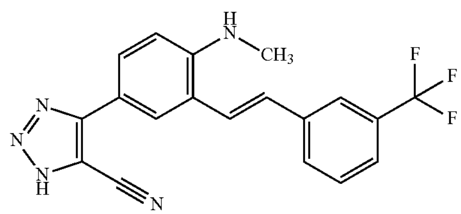 [SMILES: CNc1ccc(-c2nn[nH]c2C#N)cc1/C=C/c1cccc(C(F)(F)F)c1] | 1H-NMR (DMSO-d6) δ: 2.85 (3H, d, J = 3.5 Hz), 6.50 (1H, brs), 6.77 (1H, d, J = 8.8 Hz), 7.17 (1H, d, J = 15.9 Hz), 7.56-7.72 (4H, m), 7.89-7.94 (1H, m), 8.00-8.04 (2H, m). | Ex. 690 |
| 698 | 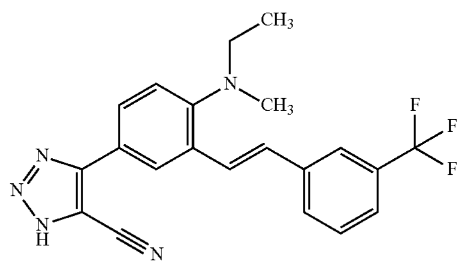 [SMILES: CCN(C)c1ccc(-c2nn[nH]c2C#N)cc1/C=C/c1cccc(C(F)(F)F)c1] | 1H-NMR (DMSO-d6) δ: 1.11 (3H, t, J = 7.1 Hz), 2.80 (3H, s), 3.07 (2H, q, J = 7.1 Hz), 7.23 (1H, d, J = 3.5 Hz), 7.31 (1H, d, J = 4.4 Hz), 7.47 (1H, d, J = 16.4 Hz), 7.54-7.66 (2H, m), 7.78 (1H, dd, J = 2.2, 8.4 Hz), 7.90-7.98 (2H, m), 8.12 (1H, d, J = 2.2 Hz). | Ex. 316 |
| 699 | 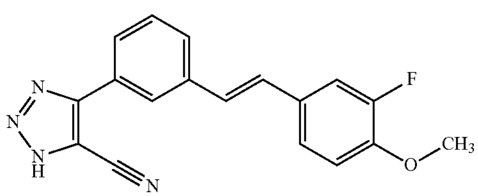 [SMILES: COc1ccc(/C=C/c2cccc(-c3nn[nH]c3C#N)c2)cc1F] | 1H-NMR (CDCl3) δ: 3.92 (3H, s), 6.95 (1H, t, J = 8.6 Hz), 6.99 (1H, d, J = 16.3 Hz), 7.09 (1H, d, J = 16.3 Hz), 7.20-7.24 (1H, m), 7.30 (1H, dd, J = 2.0, 12.5 Hz), 7.50 (1H, t, J = 7.7 Hz), 7.59-7.63 (1H, m), 7.83-7.87 (1H, m), 8.07 (1H, s). | Ex. 1 |

TABLE 4-continued

| # | Structure | 1H-NMR | Ref |
|---|---|---|---|
| 700 | (3-(2-ethoxyphenyl)vinyl-phenyl triazole carbonitrile) | 1H-NMR (CDCl3) δ: 1.07 (3H, t, J = 7.4 Hz), 1.78-1.91 (2H, m), 3.98 (2H, t, J = 6.6 Hz), 6.82-6.87 (1H, m), 7.07-7.16 (3H, m), 7.19 (1H, d, J = 16.2 Hz), 7.28 (1H, t, J = 7.8 Hz), 7.52 (1H, t, J = 7.8 Hz), 7.62-7.67 (1H, m), 7.87-7.89 (1H, m), 8.08-8.10 (1H, m). | Ex. 1 |
| 701 | (4-methyl-3-trifluoromethylphenyl vinyl phenyl triazole carbonitrile) | 1H-NMR (DMSO-d6) δ: 2.46 (3H, s), 7.41-7.50 (3H, m), 7.64 (1H, t, J = 7.8 Hz), 7.78-7.87 (3H, m), 7.91 (1H, s), 8.11 (1H, s). | Ex. 1 |
| 702 | (4-methyl-3-trifluoromethylphenyl vinyl chlorophenyl triazole carbonitrile) | 1H-NMR (DMSO-d6) δ: 2.45 (3H, s), 7.39-7.55 (3H, m), 7.78 (1H, s), 7.83 (1H, d, J = 8.2 Hz), 7.90 (2H, s), 8.02 (1H, s). | Ex. 1 |
| 703 | (methylsulfonamide trifluoromethylphenyl vinyl phenyl triazole carbonitrile) | 1H-NMR (DMSO-d6) δ: 3.17 (3H, s), 3.27 (3H, s), 7.47 (1H, d, J = 16.5 Hz), 7.61 (1H, d, J = 16.6 Hz), 7.66-7.70 (2H, m), 7.81 (1H, d, J = 8.3 Hz), 7 87-7.95 (3H, m), 8.37 (1H, d, J = 1.9 Hz). | Ex. 693 |

TABLE 4-continued

| | Structure | 1H-NMR | Ex. |
|---|---|---|---|
| 704 | 4-hydroxy-3-[(E)-2-(3-trifluoromethylphenyl)vinyl]phenyl triazole carbonitrile | 1H-NMR (DMSO-d6) δ: 7.11 (1H, d, J = 8.2 Hz), 7.39 (1H, d, J = 16.3 Hz), 7.58 (1H, d, J = 16.3 Hz), 7.63-7.68 (3H, m), 7.91-7.93 (2H, m), 8.12 (1H, d, J = 2.3 Hz), 10.68 (1H, bs). | Ex. 2 |
| 705 | 4-methoxymethoxy-3-[(E)-2-(3-trifluoromethylphenyl)vinyl]phenyl triazole carbonitrile | 1H-NMR (DMSO-d6) δ: 1.45 (3H, t, J = 7.0 Hz), 4.23 (2H, q, J = 7.0 Hz), 7.31 (1H, d, J = 8.7 Hz), 7.42 (1H, d, J = 16.5 Hz), 7.57 (1H, d, J = 16.5 Hz), 7.64-7.66 (2H, m), 7.80 (1H, dd, J = 2.3, 8.7 Hz), 7.90-7.94 (2H, m), 8.17 (1H, d, J = 2.3 Hz). | Ex. 2 |
| 706 | 4-hydroxy-3-[(E)-2-(3-trifluoromethylphenyl)vinyl]phenyl triazole carbonitrile | 1H-NMR (DMSO-d6) δ: 7.08 (1H, d, J = 8.6 Hz), 7.25 (1H, d, J = 16.7 Hz), 7.43 (1H, d, J = 16.7 Hz), 7.50-7.61 (2H, m), 7.69 (1H, dd, J = 2.1, 8.6 Hz), 7.82 (1H, d, J = 2.1 Hz), 7.87-7.92 (2H, m). | Ex. 2 |

TABLE 4-continued
| | | | |
|---|---|---|---|
| 707 | 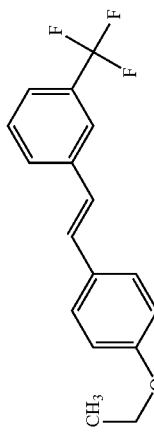 | 1H-NMR (DMSO-d6) δ: 1.39 (3H, t, J = 6.9 Hz), 4.21 (2H, q, J = 6.9 Hz), 7.28-7.35 (2H, m), 7.47 (1H, d, J = 16.5 Hz), 7.60-7.64 (2H, m), 7.80 (1H, dd, J = 2.2, 8.7 Hz), 7.87-7.94 (3H, m). | Ex. 2 |
| 708 | 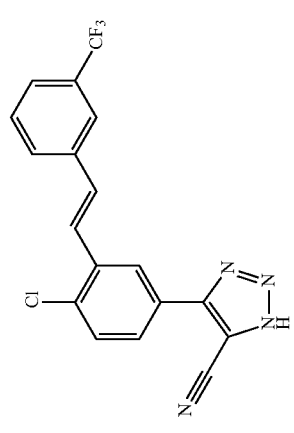 | 1H-NMR (DMSO-d6) δ: 7.49 (1H, d, J = 16.2 Hz), 7.83-7.72 (3H, m), 7.78 (1H, d, J = 8.3 Hz), 7.83 (1H, dd, J = 2.2, 8.3 Hz), 8.00-8.02 (2H, m), 8.34 (1H, d, J = 2.2 Hz). | Ex. 2 |
| 709 | 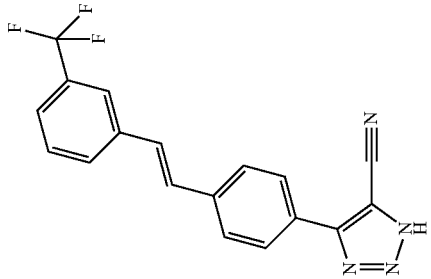 | 1H-NMR (DMSO-d6) δ: 7.53 (2H, s), 7.64-7.66 (2H, m), 7.88-8.00 (6H, m). | Ex. 1 |

TABLE 4-continued

| | Structure | 1H-NMR | Ex. |
|---|---|---|---|
| 710 | 3-(trifluoromethyl)phenyl-vinyl-fluorophenyl-triazole-carbonitrile | 1H-NMR (DMSO-d6) δ: 7.51 (1H, d, J = 16.6 Hz), 7.59 (1H, d, J = 16.6 Hz), 7.65-7.81 (4H, m), 8.00-8.08 (3H, m). | Ex. 1 |
| 711 | 3,5-bis(trifluoromethyl)phenyl-vinyl-fluorophenyl-triazole-carbonitrile | 1H-NMR (DMSO-d6) δ: 7.84-7.90 (5H, m), 8.06 (1H, s), 8.34 (2H, s). | Ex. 1 |

TABLE 4-continued
| | | | |
|---|---|---|---|
| 712 |  | 1H-NMR (DMSO-d6) δ: 7.62 (1H, d, J = 16.5 Hz), 7.77 (1H, d, J = 16.5 Hz), 7.86-8.00 (5H, m), 8.41 (2H, s). | Ex. 1 |
| 713 | 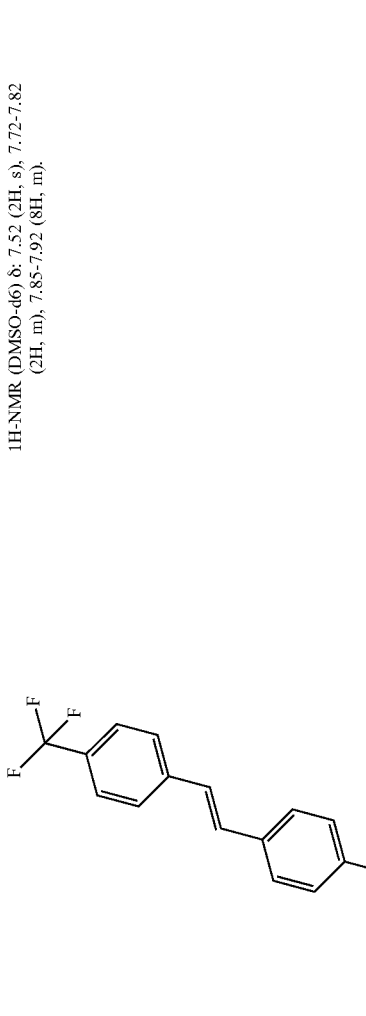 | 1H-NMR (DMSO-d6) δ: 7.52 (2H, s), 7.72-7.82 (2H, m), 7.85-7.92 (8H, m). | Ex. 1 |

TABLE 4-continued

| Ex. No. | STR | m.p. | 1H-NMR | ref. |
|---|---|---|---|---|
| 714 | (4-fluorostyryl phenyl triazole carbonitrile structure) | | 1H-NMR (DMSO-d6) δ: 7.22-7.32 (3H, m), 7.42 (1H, d, J = 16.7 Hz), 7.68-7.73 (2H, m), 7.32 (2H, d, J = 8.4 Hz), 7.91 (2H, d, J = 8.4 Hz). | Ex. 1 |
| 717 | (trifluoromethyl styryl trifluoromethyl phenyl triazole carbonitrile structure) | | 1H-NMR (DMSO-d6) δ: 7.38 (1H, d, J = 16.3 Hz), 7.57 (1H, d, J = 16.3 Hz), 7.73-7.82 (4H, m), 7.98-8.00 (2H, m), 8.24 (1H, d, J = 8.9 Hz). | Ex. 1 |
| 715 | (styryl trifluoromethyl phenyl triazole carbonitrile structure) | 206.0-206.3 | | Ex. 1 |

TABLE 4-continued

| | | | |
|---|---|---|---|
| 716 | (structure) | 210-213 | Ex. 2 |
| 718 | (structure) | 231-233 | Ex. 1 |
| 719 | (structure) | 225-227 | Ex. 1 |

TABLE 4-continued

| | | | |
|---|---|---|---|
| 720 | [structure] | 255-258 | Ex. 1 |
| 721 | [structure] | 235-237 | Ex. 1 |
| 722 | [structure] | 253-255 | Ex. 1 |
| 723 | [structure] | 251 | Ex. 1 |

TABLE 4-continued
| | | | |
|---|---|---|---|
| 724 |  | 208-209 | Ex. 1 |
| 725 |  | 253 | Ex. 1 |
| 726 |  | 243-247 | Ex. 1 |

TABLE 4-continued

| | | | |
|---|---|---|---|
| 727 | [5-(trifluoromethyl)benzothiophen-2-yl / 3-chloro phenyl / triazole-CN structure] | 258-259 | Ex. 1 |
| 728 | [5-methylbenzothiophen-2-yl / 3-chloro phenyl / triazole-CN structure] | 265-266 | Ex. 1 |
| 729 | [5-(trifluoromethyl)benzothiophen-2-yl / 3-methoxymethyl phenyl / triazole-CN structure] | 220-221 | Ex. 1 |

TABLE 4-continued
| | | | |
|---|---|---|---|
| 730 |  | 219-220 | Ex. 1 |
| 732 |  | 256-257 | Ex. 1 |
| 733 |  | 270-271 | Ex. 1 |
| 734 |  | 267-268 | Ex. 1 |

TABLE 4-continued

| | | | |
|---|---|---|---|
| 735 | [structure: 5-chloro-3-(6-(trifluoromethoxy)benzothiophen-2-yl)phenyl triazole carbonitrile] | 204-205 | Ex. 1 |
| 736 | [structure: 3-(1-ethyl)-5-(5-fluorobenzothiophen-2-yl)phenyl triazole carbonitrile] | 179-183 | Ex. 1 |
| 737 | [structure: 2-(1-ethoxy)-4-(6-(trifluoromethoxy)benzothiophen-2-yl)phenyl triazole carbonitrile] | 182-191 | Ref. Ex. 112, Ex. 1 |
| 738 | [structure: 3-(2-methylpropan-2-yl)-5-(6-(trifluoromethoxy)benzothiophen-2-yl)phenyl triazole carbonitrile] | 147.1-149.7 | Ex. 125 |

TABLE 4-continued

| Ex. No. | STR | 1H-NMR | ref. |
|---|---|---|---|
| 731 | | 1H-NMR (DMSO-d6) δ: 7.65 (1H, t, J = 8.1 Hz), 7.76 (1H, t, J = 7.8 Hz), 7.83 (1H, d, J = 7.3 Hz), 7.94 (1H, d, J = 7.8 Hz), 8.06 (1H, d, J = 7.3 Hz), 8.16 (1H, s), 8.23 (1H, d, J = 7.8 Hz), 8.30-8.33 (1H, m). | Ex. 1 |
| 739 | | 1H-NMR (DMSO-d6) δ: 7.42-7.45 (2H, m), 7.91-7.95 (1H, m), 8.05-8.08 (1H, m), 8.17 (1H, s), 8.21 (1H, s), 8.33 (1H, s), 8.48 (1H, s). | Ex. 1 |
| 740 | | 1H-NMR (DMSO-d6) δ: 7.45 (1H, dd, J = 2.0, 8.6 Hz), 7.93 (1H, s), 7.97 (1H, d, J = 2.0 Hz), 8.05 (1H, s), 8.08-8.10 (1H, m), 8.11 (1H, s), 8.17 (1H, s). | Ex. 1 |
| 741 | | 1H-NMR (DMSO-d6) δ: 7.25-7.33(1H, m), 7.69-7.81 (2H, m), 7.89-8.02 (3H, m), 8.05-8.12 (1H, m), 8.25-8.29 (1H, m). | Ex. 1 |

TABLE 4-continued

| | Structure | NMR | Ex. |
|---|---|---|---|
| 742 | 5-fluorobenzothiophen-2-yl attached to 3-chloro-phenyl linked to triazole-carbonitrile | 1H-NMR (DMSO-d6) δ: 7.28-3.36 (1H, m), 7.69-7.74 (1H, m), 7.93 (1H, t, J = 1.6 Hz), 8.06-8.13 (3H, m), 8.18 (1H, t, J = 1.6 Hz). | Ex. 1 |
| 743 | 5-fluorobenzothiophen-2-yl attached to 3-trifluoromethoxy-phenyl linked to triazole-carbonitrile | 1H-NMR (DMSO-d6) δ: 7.29-7.36 (1H, m), 7.71-7.76 (1H, m), 7.85-7.88 (1H, m), 8.01-8.04 (1H, m), 8.08-8.15 (2H, m), 8.24-8.27 (1H, m). | Ex. 1 |
| 744 | 5-fluorobenzothiophen-2-yl attached to 3-methyl-phenyl linked to triazole-carbonitrile | 1H-NMR (DMSO-d6) δ: 2.52 (3H, s), 7.06-7.14 (1H, m), 7.44-7.48 (1H, m), 7.58 (1H, s), 7.64 (1H, s), 7.73-7.80 (2H, m), 8.13 (1H, s). | Ex. 1 |
| 745 | 3-methylbenzothiophen-2-yl attached to phenyl linked to triazole-carbonitrile | 1H-NMR (DMSO-d6) δ: 2.52 (3H, s), 7.42-7.50 (2H, m), 7.75-7.78 (2H, m), 7.87 (1H, d, J = 7.9 Hz), 7.93-7.96 (1H, m), 8.02 (1H, d, J = 7.9 Hz), 8.10 (1H, s). | Ex. 1 |

TABLE 4-continued

| | Structure | 1H-NMR | Ex. |
|---|---|---|---|
| 746 | (5-chloro-3-methylbenzothiophene-2-yl with 3-(trifluoromethoxy)phenyl-triazole-carbonitrile) | 1H-NMR (DMSO-d6) δ: 2.51 (3H, s), 7.49 (1H, dd, J = 2.0, 8.5 Hz), 7.78 (1H, s), 7.92 (1H, s), 7.98 (1H, d, J = 2.0 Hz), 8.04-8.12 (2H, m). | Ex. 1 |
| 747 | (5-(trifluoromethyl)benzothiophene-2-yl phenyl triazole carbonitrile) | 1H-NMR (DMSO-d6) δ: 7.68-7.73 (1H, m), 7.77 (1H, t, J = 7.9 Hz), 7.92-7.97 (1H, m), 8.00-8.05 (1H, m), 8.12 (1H, s), 8.28-8.34 (3H, m). | Ex. 1 |
| 748 | (6-(trifluoromethyl)benzothiophene-2-yl phenyl triazole carbonitrile) | 1H-NMR (DMSO-d6) δ: 7.70-7.81 (2H, m), 7.92-7.97 (1H, m), 8.03-8.15 (3H, m), 8.31 (1H, s), 8.59 (1H, s). | Ex. 1 |
| 749 | (7-fluorobenzothiophene-2-yl phenyl triazole carbonitrile) | 1H-NMR (DMSO-d6) δ: 7.26-7.33 (1H, m), 7.44-7.52 (1H, m), 7.72-7.80 (2H, m), 7.91-7.96 (1H, m), 8.01-8.06 (1H, m), 8.09 (1H, J = 3.7 Hz), 8.30 (1H, t, J = 1.7 Hz). | Ex. 1 |

TABLE 4-continued

| | Structure | 1H-NMR | Ex. |
|---|---|---|---|
| 750 | (7-trifluoromethyl-benzothiophen-2-yl)-(3-chloro-5-(triazolyl-carbonitrile)phenyl) | 1H-NMR (DMSO-d6) δ: 7.93 (1H, d, J = 7.6 Hz), 8.02-8.10 (2H, m), 7.25 (1H, t, J = 7.8 Hz), 8.35-8.43 (3H, m). | Ex. 1 |
| 751 | (5,7-difluoro-benzothiophen-2-yl)-(3-chloro-5-(triazolyl-carbonitrile)phenyl) | 1H-NMR (DMSO-d6) δ: 7.42-7.51 (1H, m), 7.64-7.70 (1H, m), 7.97 (1H, t, J = 1.7 Hz), 8.15 (1H, t, J = 1.7 Hz), 8.18 (1H, d, J = 3.6 Hz), 8.22 (1H, t, J = 1.5 Hz). | Ex. 1 |
| 752 | (5,7-difluoro-benzothiophen-2-yl)-(3-tert-butyl-5-(triazolyl-carbonitrile)phenyl) | 1H-NMR (DMSO-d6) δ: 1.42 (9H, s), 7.39-7.45 (1H, m), 7.64-7.67 (1H, m), 7.99-8.02 (2H, m), 8.08-8.13 (2H, m). | Ex. 125 |

TABLE 4-continued

| Ex. No. | STR | m.p. | ref. |
|---|---|---|---|
| 753 | (5-fluorobenzothiophen-2-yl)-phenyl-triazole-carbonitrile | 294-296 | Ex. 1 |
| 754 | (5-trifluoromethoxybenzothiophen-2-yl)-phenyl-triazole-carbonitrile | 281-282 | Ex. 1 |

TABLE 4-continued

| Ex. No. | STR | | 1H-NMR | ref. |
|---|---|---|---|---|
| 755 | (structure: 3-thienyl, trifluoromethoxy-substituted phenyl, triazole-carbonitrile) | 111-113 | | Ex. 1 |
| 756 | (structure: 3-thienyl, fluoro-substituted phenyl, triazole-carbonitrile) | 190-191 | | Ex. 1 |
| 757 | (structure: 3-thienyl, fluoro-substituted phenyl, triazole-carbonitrile) | | 1H-NMR (DMSO-d6) δ: 7.59 (1H, d, J = 8.9 Hz), 7.65 (1H, d, J = 5.0 Hz), 7.73-7.75 (1H, m), 7.83 (1H, d, J = 10.1 Hz), 8.08-8.09 (2H, m). | Ex. 1 |
| 758 | (structure: 3-thienyl, fluoro-substituted phenyl, triazole-carbonitrile) | | 1H-NMR (DMSO-d6) δ: 7.49 (1H, t, J = 7.8 Hz), 7.55-7.56 (1H, m), 7.70-7.75 (2H, m), 7.93-7.96 (2H, m). | Ex. 1 |

TABLE 4-continued

| | Structure | 1H-NMR | Ex. |
|---|---|---|---|
| 759 | 3-chloro-5-(thiophen-3-yl)phenyl triazole carbonitrile | 1H-NMR (DMSO-d6) δ: 7.65-7.66 (1H, m), 7.73-7.74 (1H, m), 7.82 (1H, s), 8.02 (1H, s), 8.11 (1H, s), 8.17 (1H, s). | Ex. 1 |
| 760 | 4-fluoro-3-(thiophen-3-yl)phenyl triazole carbonitrile | 1H-NMR (DMSO-d6) δ: 7.54-7.61 (2H, m), 7.75-7.77 (1H, m), 7.85-7.88 (1H, m), 7.95-7.96 (1H, m), 8.21-8.23 (1H, m). | Ex. 1 |
| 761 | 2-methoxy-5-(thiophen-3-yl)phenyl triazole carbonitrile | 1H-NMR (DMSO-d6) δ: 3.93 (3H, s), 7.30 (1H, d, J = 8.8 Hz), 7.56-7.57 (1H, m), 7.66-7.67 (1H, m), 7.84-7.85 (1H, m), 7.90-7.95 (1H, m), 7.99 (1H, s). | Ex. 1 |
| 762 | 3-(thiophen-3-yl)phenyl triazole carbonitrile | 1H-NMR (CDCl3) δ: 7.43-7.47 (2H, m), 7.54-7.56 (2H, m), 7.73-7.75 (1H, m), 7.89-7.94 (1H, m), 8.23 (1H, s). | Ex. 1 |

TABLE 4-continued

| | | | |
|---|---|---|---|
| 763 | [structure: 3-bromo-5-(thiophen-3-yl)phenyl triazole carbonitrile] | 1H-NMR (DMSO-d6) δ: 7.64-7.67 (1H, m), 7.73-7.75 (1H, m), 7.95 (1H, s), 8.11-8.12 (1H, m), 8.15 (1H, s), 8.21 (1H, s). | Ex. 1 |
| 764 | [structure: 3-phenyl-5-(thiophen-3-yl)phenyl triazole carbonitrile] | 1H-NMR (DMSO-d6) δ: 7.43-7.49 (1H, m), 7.52-7.58 (2H, m), 7.70-7.76 (2H, m), 7.81-7.86 (2H, m), 8.06-8.08 (1H, m), 8.11-8.13 (1H, m), 8.16-8.20 (2H, m). | Ex. 1 |
| 765 | [structure: 3-ethoxy-5-(thiophen-3-yl)phenyl triazole carbonitrile] | 1H-NMR (DMSO-d6) δ: 1.40 (3H, t, J = 7.0 Hz), 4.19 (2H, q, J = 7.0 Hz), 7.34 (1H, s), 7.45 (1H, s), 7.60-7.62 (1H, m), 7.70-7.71 (1H, m), 7.78 (1H, s), 8.80-8.01 (1H, m). | Ex. 1 |

TABLE 4-continued

| | Structure | 1H-NMR | |
|---|---|---|---|
| 766 | (3-thiophen-3-yl-5-fluoro-2-methoxyphenyl triazole carbonitrile) | 1H-NMR (DMSO-d6) δ: 3.28 (3H, s), 7.47-7.49 (1H, m), 7.59-7.60 (1H, m), 7.68-7.72 (2H, m), 8.02 (1H, s). | Ex. 1 |
| 767 | (3-thiophen-3-yl-5-(1-ethoxy)phenyl triazole carbonitrile) | 1H-NMR (DMSO-d6) δ: 1.35 (6H, d, J = 6.0 Hz), 4.76-4.86 (1H, m), 7.32-7.33 (1H, m), 7.43-7.44 (1H, m), 7.60-7.61 (1H, m), 7.69-7.70 (1H, m), 7.75-7.76 (1H, m), 7.99-8.01 (1H, m). | Ex. 1 |
| 768 | (3-thiophen-3-yl-5-methylphenyl triazole carbonitrile) | 1H-NMR (DMSO-d6) δ: 2.45 (3H, s), 7.58-7.62 (2H, m), 7.70-7.72 (1H, m), 7.76 (1H, s), 7.95 (1H, s), 8.01 (1H, s). | Ex. 1 |
| 769 | (3-(2-trifluoromethylthiophen-3-yl)-5-methylphenyl triazole carbonitrile) | 1H-NMR (DMSO-d6) δ: 2.46 (3H, s), 7.34-7.36 (1H, m), 7.45 (1H, s), 7.77-7.85 (2H, m), 8.06 (1H, d, J = 5.1 Hz). | Ex. 1 |

TABLE 4-continued

| | Structure | 1H-NMR | |
|---|---|---|---|
| 770 | 3-(trifluoromethoxy)-5-(2-chlorothiophen-3-yl)phenyl triazole-carbonitrile | 1H-NMR (DMSO-d6) δ: 7.38 (1H, d, J = 5.8 Hz), 7.67 (1H, d, J = 5.8 Hz), 7.79 (1H, s), 7.87 (1H, s), 8.18 (1H, t, J = 1.5 Hz). | Ex. 1 |
| 771 | 3-methyl-5-(2-acetylthiophen-3-yl)phenyl triazole-carbonitrile | 1H-NMR (DMSO-d6) δ: 2.20 (3H, s), 2.46 (3H, s), 7.24 (1H, d, J = 5.0 Hz), 7.48 (1H, s), 7.73 (1H, s), 7.76 (1H, s), 8.01 (1H, d, J = 5.0 Hz). | Ex. 1 |
| 772 | 3-(thiophen-2-yl)phenyl triazole-carbonitrile | 1H-NMR (DMSO-d6) δ: 7.11-7.13 (1H, m), 7.34 (1H, d, J = 1.0 Hz), 7.35 (1H, d, J = 1.0 Hz), 7.42-7.43 (1H, m), 7.53-7.56 (1H, m), 7.73-7.75 (1H, m), 8.23 (1H, s). | Ex. 1 |

TABLE 4-continued

| | Structure | 1H-NMR | |
|---|---|---|---|
| 773 | 3-(acetylthiophen-2-yl)-5-(3-(trifluoromethyl)phenyl)-1H-1,2,3-triazole-4-carbonitrile | 1H-NMR (DMSO-d6) δ: 2.57 (3H, s), 7.93 (1H, d, J = 4.0 Hz), 8.03 (1H, d, J = 4.0 Hz), 8.18 (1H, s), 8.30 (1H, s), 8.47 (1H, s). | Ex. 1 |
| 774 | 4-(3-(thiophen-2-yl)-5-(trifluoromethyl)phenyl)-1H-1,2,3-triazole-5-carbonitrile | 1H-NMR (DMSO-d6) δ: 7.25 (1H, dd, J = 3.7, 5.0 Hz), 7.74 (1H, dd, J = 1.0, 5.0 Hz), 7.82 (1H, dd, J = 1.0, 3.7 Hz), 8.10 (1H, s), 8.18 (1H, s), 8.41 (1H, s). | Ex. 1 |
| 776 | 4-(3-methyl-5-(6-(trifluoromethyl)pyridin-2-yl)phenyl)-1H-1,2,3-triazole-5-carbonitrile | 1H-NMR (DMSO-d6) δ: 2.52 (3H, s), 7.84 (1H, s), 7.92 (1H, d, J = 7.8 Hz), 8.12 (1H, s), 8.25 (1H, t, J = 8.0 Hz), 8.34 (1H, d, J = 8.0 Hz), 8.47 (1H, s). | Ex. 1 |

TABLE 4-continued

| Ex. No. | STR | m.p. | ref. |
|---|---|---|---|
| 775 | (5-(trifluoromethyl)pyridin-2-yl / trifluoromethoxy phenyl triazole carbonitrile) | 144-145 | Ex. 1 |
| 777 | (3-chloro-5-(trifluoromethyl)pyridin-2-yl phenyl triazole carbonitrile) | 190 | Ex. 1 |
| 778 | (3-(trifluoromethyl)pyridin-2-yl phenyl triazole carbonitrile) | 197 | Ex. 1 |
| 779 | (5-fluoropyridin-2-yl chloro phenyl triazole carbonitrile) | 242-244 | Ex. 1 |

TABLE 4-continued
| | | | |
|---|---|---|---|
| 780 | 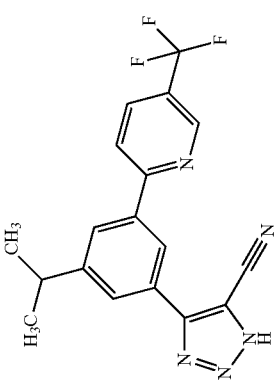 | 128-130 | Ref. Ex. 91, Ex. 1 |
| 781 | 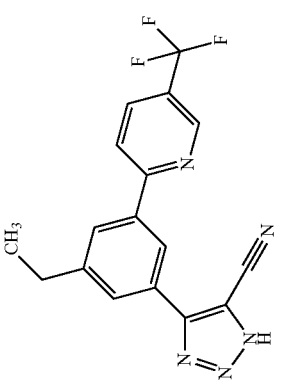 | 180-183 | Ex. 1 |
| 782 | 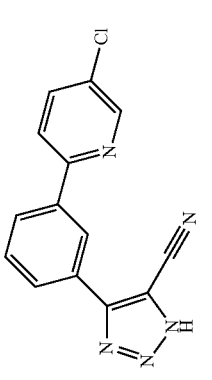 | 253-255 | Ex. 1 |
| 783 | 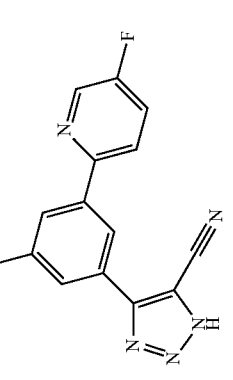 | 225-228 | Ex. 1 |

TABLE 4-continued

| Ex. No. | STR | 1H-NMR | ref. |
|---|---|---|---|
| 784 | | 220-223 | Ex. 125 |
| 785 | | 166-171 | Ex. 125 |
| 786 | | 1H-NMR (CDCl3) δ: 7.53-7.55 (1H, m), 8.03 (1H, s), 8.34 (1H, s), 8.42 (1H, s), 8.84 (1H, s), 8.92 (1H, d, J = 5.0 Hz). | Ex. 2 |

TABLE 4-continued
| 787 |  | 1H-NMR (DMSO-d6) δ: 8.31 (1H, s), 8.40-8.43 (2H, m), 8.62 (1H, s), 8.95 (1H, s), 9.13 (1H, s). | Ex. 2 |
| --- | --- | --- | --- |
| 788 | 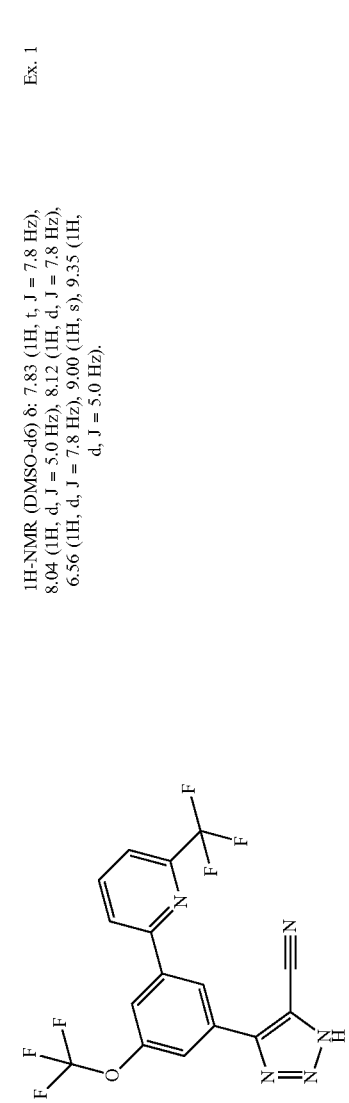 | 1H-NMR (DMSO-d6) δ: 7.83 (1H, t, J = 7.8 Hz), 8.04 (1H, d, J = 5.0 Hz), 8.12 (1H, d, J = 7.8 Hz), 6.56 (1H, d, J = 7.8 Hz), 9.00 (1H, s), 9.35 (1H, d, J = 5.0 Hz). | Ex. 1 |
| 789 |  | 1H-NMR (CDCl3) δ: 7.59-7.65 (2H, m), 7.96-8.06 (3H, m), 8.17-8.20 (1H, m), 8.62 (1H, s). | Ex. 1 |

TABLE 4-continued
| | | | |
|---|---|---|---|
| 790 | 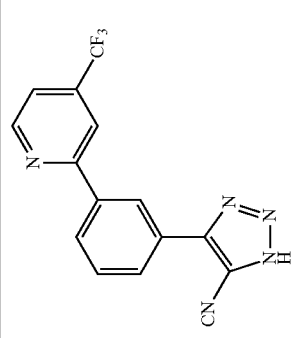 | 1H-NMR (CDCl3) δ: 7.47 (1H, d, J = 5.0 Hz), 7.63 (1H, t, J = 7.8 Hz), 8.01 (1H, s), 8.07 (1H, d, J = 7.8 Hz), 8.15 (1H, d, J = 7.8 Hz), 8.62 (1H, s), 8.67 (1H, d, J = 6.0 Hz). | Ex. 1 |
| 791 | 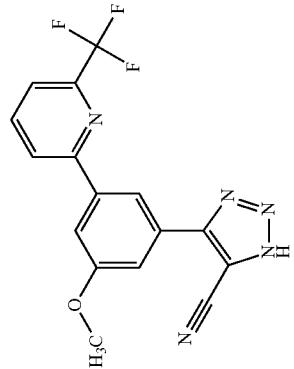 | 1H-NMR (CDCl3) δ: 3.96 (3H, s), 7.57 (1H, s), 7.68-7.74 (2H, m), 7.98-8.03 (2H, m), 8.16 (1H, s). | Ex. 1 |
| 792 | 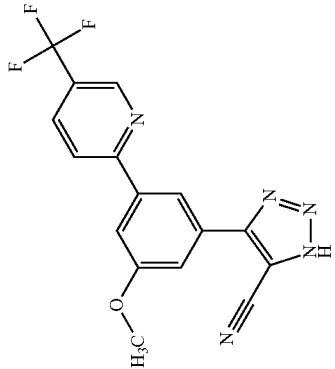 | 1H-NMR (DMSO-d6) δ: 3.95 (3H, s), 7.57-7.58 (1H, m), 7.87-7.88 (1H, m), 8.28-8.31 (2H, m), 8.37-8.39 (1H, m), 9.11 (1H, s). | Ex. 1 |

TABLE 4-continued
| | | | |
|---|---|---|---|
| 793 | 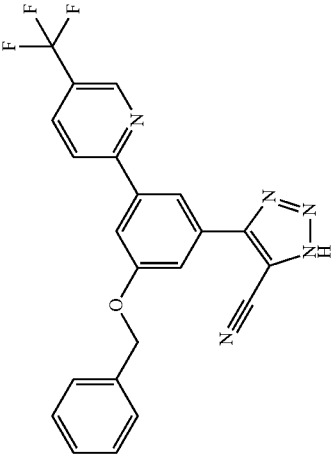 | 1H-NMR (CDCl3) δ: 5.24 (2H, s), 7.35-7.44 (3H, m), 7.49-7.51 (2H, m), 7.74 (2H, s), 7.92 (1H, c, J = 8.4 Hz), 8.08-8.11 (1H, m), 8.30 (1H, s), 9.01 (1H, s). | Ex. 1 |
| 794 | 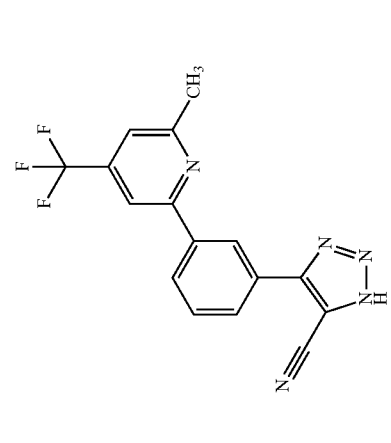 | 1H-NMR (DMSO-d6) δ: 2.68 (3H, s), 7.71 (1H, s), 7.77 (1H, t, J = 8.0 Hz), 7.99-8.01 (1H, m), 8.18 (1H, s), 8.35-8.38 (1H, m), 8.72-8.73 (1H, m). | Ex. 1 |
| 795 | 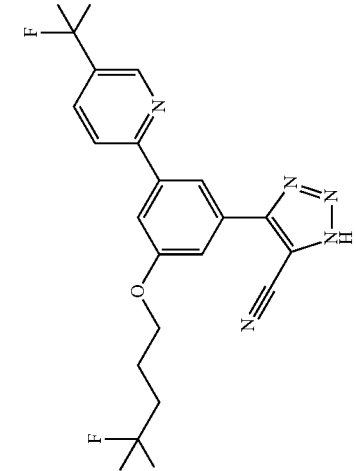 | 1H-NMR (CDCl3) δ: 2.10-2.17 (2H, m), 2.32-2.42 (2H, m), 4.20 (2H, t, J = 5.9 Hz), 7.65-7.66 (1H, m), 7.72-7.73 (1H, m), 7.95 (1H, d, J = 8.4 Hz), 8.06-8.09 (1H, m), 8.28 (1H, s), 8.99 (1H, s). | Ex. 1 |

| | Structure | 1H-NMR | |
|---|---|---|---|
| 796 | (pyridine with CF3, phenyl with O-butyl-F, triazole-CN) | 1H-NMR (CDCl3) δ: 1.88-2.05 (4H, m), 4.17-4.21 (2H, m), 4.46-4.50 (1H, m), 4.62-4.65 (1H, m), 7.56 (2H, s), 7.95 (1H, d, J = 8.4 Hz), 8.09-8.12 (1H, m), 8.28 (1H, s), 9.01 (1H, s). | Ex. 1 |
| 797 | (2-CF3-pyridine, Cl-phenyl, triazole-CN) | 1H-NMR (DMSO-d6) δ: 7.98 (1H, d, J = 7.6 Hz), 8.05-8.06 (1H, m), 8.29 (1H, t, J = 8.0 Hz), 8.35-8.36 (1H, m), 8.44 (1H, d, J = 8.0 Hz), 8.65 (1H, s). | Ex. 1 |
| 798 | (4-CF3-pyridine, Cl-phenyl, triazole-CN) | 1H-NMR (DMSO-d6) δ: 7.85 (1H, d, J = 4.4 Hz), 8.03 (1H, s), 8.48 (1H, s), 8.51 (1H, s), 8.71 (1H, s), 9.02 (1H, d, J = (4.4 Hz), | Ex. 1 |

TABLE 4-continued

| | Structure | 1H-NMR | |
|---|---|---|---|
| 799 | 5-(trifluoromethyl)pyridine-phenyl(OCH2CH3)-triazole-CN | 1H-NMR (CDCl3) δ: 1.50 (3H, t, J = 7.3 Hz), 4.21 (2H, q, J = 7.3 Hz), 7.62-7.63 (1H, m), 7.65-7.66 (1H, m), 7.95 (1H, d, J = 8.3 Hz), 8.11 (1H, dd, J = 1.8, 8.5 Hz), 8.29 (1H, s), 9.01-9.02 (1H, m). | Ex. 1 |
| 800 | 5-(trifluoromethyl)pyridine-phenyl(OCH2CF3)-triazole-CN | 1H-NMR (DMSO-d6) δ: 5.02 (2H, q, J = 8.9 Hz), 7.68 (1H, s), 8.01 (1H, s), 8.34-8.43 (3H, m), 9.21 (1H, s). | Ex. 1 |
| 801 | 5-(trifluoromethyl)pyridine-phenyl(Cl)-triazole-CN | 1H-NMR (DMSO-d6) δ: 8.05 (1H, d, J = 1.8 Hz), 8.06-8.43 (3H, m), 8.67 (1H, s), 0.13 (1H, s). | Ex. 1 |

TABLE 4-continued

| | Structure | 1H-NMR | |
|---|---|---|---|
| 802 | 3-(cyclopropylmethoxy)-5-[6-(trifluoromethyl)pyridin-2-yl]phenyl triazole carbonitrile | 1H-NMR (DMSO-d6) δ: 0.38-0.41 (2H, m), 0.60-0.65 (2H, m), 1.29-1.34 (1H, m), 4.03 (2H, d, J = 6.9 Hz), 7.55-7.57 (1H, m), 7.82-7.83 (1H, m), 7.92-7.95 (1H, m), 8.23-8.27 (2H, m), 8.39 (1H, d, J = 8.0 Hz). | Ex. 2 |
| 803 | 3-(cyclopropylmethoxy)-5-[4-(trifluoromethyl)pyridin-2-yl]phenyl triazole carbonitrile | 1H-NMR (DMSO-d6) δ: 0.38-0.42 (2H, m), 0.60-0.65 (2H, m), 1.28-1.35 (1H, m), 4.04 (2H, d, J = 7.0 Hz), 7.53-7.54 (1H, m), 7.80-7.82 (1H, m), 7.91-7.92 (1H, m), 8.30-8.31 (1H, m), 8.43 (1H, s), 8.99 (1H, d, J = 4.9 Hz). | Ex. 2 |
| 804 | 3-(trifluoromethoxy)-5-[6-methyl-4-(trifluoromethyl)pyridin-2-yl]phenyl triazole carbonitrile | 1H-NMR (DMSO-d6) δ: 5.26 (3H, s), 7.72-7.80 (2H, m), 7.83-7.87 (1H, m), 7.96-8.01 (2H, m). | Ex. 1 |

TABLE 4-continued

| | Structure | 1H-NMR | |
|---|---|---|---|
| 805 | 4-(3-methyl-5-(4-(trifluoromethyl)pyridin-2-yl)phenyl)-1H-1,2,3-triazole-5-carbonitrile | 1H-NMR (DMSO-d6) δ: 2.52 (3H, s), 7.78-7.84 (2H, m), 8.24 (1H, s), 8.38 (1H, s), 8.53 (1H, s), 8.99 (1H, d, J = 5.0 Hz). | Ex. 1 |
| 806 | 4-(3-(trifluoromethoxy)-5-(4-(trifluoromethyl)pyridin-2-yl)phenyl)-1H-1,2,3-triazole-5-carbonitrile | 1H-NMR (DMSO-d6) δ: 7.88 (1H, d, J = 4.5 Hz), 7.97 (1H, s), 8.42 (1H, s), 8.54 (1H, s), 8.79 (1H, t, J = 1.5 Hz), 9.03 (1H, d, J = 4.5 Hz). | Ex. 1 |
| 807 | 4-(3-methyl-5-(5-(trifluoromethyl)pyridin-2-yl)phenyl)-1H-1,2,3-triazole-5-carbonitrile | 1H-NMR (DMSO-d6) δ: 2.52 (3H, s), 7.84 (1H, s), 8.18 (1H, s), 8.25 (1H, d, J = 6.4 Hz), 8.37 (1H, dd, J = 2.0, 8.4 Hz), 8.49 (1H, s), 9.09 (1H, s). | Ex. 1 |

TABLE 4-continued

| | | | |
|---|---|---|---|
| 809 | (structure: cyclopropylmethyl and 5-(trifluoromethyl)pyridin-2-yl substituted benzene linked to triazole-carbonitrile) | 1H-NMR (DMSO-d6) δ: 0.27-0.34 (2H, m), 0.52-0.59 (2H, m), 1.02-1.15 (1H, m), 2.72 (2H, d, J = 6.8 Hz), 7.97 (1H, s), 8.22 (1H, s), 8.27 (1H, d, J = 8.5 Hz), 8.35-8.40 (1H, m), 8.51-8.53 (1H, m), 8.09-9.11 (1H, m). | Ex. 1 |
| 810 | (structure: methyl and 5-chloropyridin-2-yl substituted benzene linked to triazole-carbonitrile) | 1H-NMR (DMSO-d6) δ: 2.51 (3H, s), 7.79 (1H, s), 8.06-8.10 (3H, m), 8.41 (1H, s), 8.75-8.77 (1H, m). | Ex. 1 |
| 811 | (structure: isopropoxy and 5-(trifluoromethyl)pyridin-2-yl substituted benzene linked to triazole-carbonitrile) | 1H-NMR (DMSO-d6) δ: 1.37 (6H, d, J = 6.0 Hz), 4.86-4.92 (1H, m), 7.42 (1H, d, J = 9.0 Hz), 8.22 (1H, d, J = 8.5 Hz), 8.28-8.31 (1H, m), 8.33-8.37 (1H, m), 8.39 (1H, d, J = 2.3 Hz), 9.03 (1H, s). | Ex. 1 |

TABLE 4-continued

| Ex. No. | STR | m.p. | ref. |
|---|---|---|---|
| 812 | [structure: 3,5-disubstituted phenyl with tert-butyl group and pyridine-CN, triazole-CN] | 1H-NMR (DMSO-d6) δ: 1.42 (9H, s), 8.09 (1H, t, J = 1.5 Hz), 8.31-8.34 (2H, m), 8.46-8.51 (2H, m), 9.16-9.17 (1H, m). | Ex.125 |
| 808 | [structure: 3-(5-trifluoromethylpyridin-2-yl)phenyl triazole-CN] | 168-169 | Ex. 1 |
| 813 | [structure: 3-chloro-5-(6-trifluoromethylpyridin-3-yl)phenyl triazole-CN] | 204-206 | Ex. 1 |
| 814 | [structure: 3-(6-trifluoromethylpyridin-3-yl)phenyl triazole-CN] | 198-200 | Ex. 1 |

TABLE 4-continued
| | | | |
|---|---|---|---|
| 815 | 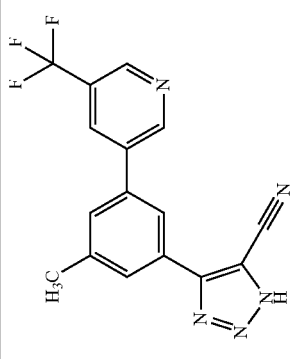 | 243-244 | Ex. 1 |
| 816 | 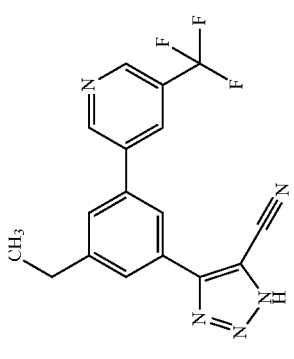 | 204-208 | Ex. 1 |
| 817 | 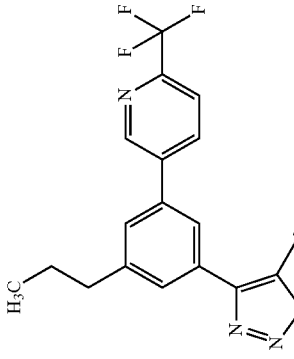 | 185-186 | Ex. 1 |

TABLE 4-continued

| Ex. No. | STR | | 1H-NMR | |
|---|---|---|---|---|
| 818 | (structure: 3-methyl-5-(6-(trifluoromethyl)pyridin-3-yl)phenyl triazole carbonitrile) | 213-217 | | Ex. 1 |
| 819 | (structure: 3-chloro-5-(5-fluoropyridin-3-yl)phenyl triazole carbonitrile) | | 1H-NMR (DMSO-d6) δ: 7.97-7.99 (1H, m), 8.11-8.13 (1H, m), 8.20-8.24 (2H, m), 8.68 (1H, d, J = 2.6 Hz), 8.90 (1H, s). | Ex. 1 ref. |
| 820 | (structure: 3-(ethoxymethoxymethyl)-5-(6-(trifluoromethyl)pyridin-3-yl)phenyl triazole carbonitrile) | | 1H-NMR (DMSO-d6) δ: 1.21 (3H, t, J = 7.0 Hz), 3.59 (2H, q, J = 7.0 Hz), 4.66 (2H, s), 7.94 (1H, s), 7.98 (1H, s), 8.08 (1H, d, J = 8.2 Hz), 8.21 (1H, s), 8.43-8.46 (1H, m), 9.16 (1H, q, J = 1.9 Hz). | Ex. 1 |

TABLE 4-continued

| Ex. No. | STR | m.p. | ref. |
|---|---|---|---|
| 821 | | 180-203 | Ex. 1 |
| 822 | | 158-161 | Ex. 1 |
| 823 | | 243-247 | Ex. 1 |

TABLE 4-continued

| | | | |
|---|---|---|---|
| 824 | [structure] | 183-185 | Ex. 1 |
| 825 | [structure] | 220-222 | Ex. 1 |
| 826 | [structure] | 197-200 | Ex. 1 |
| 827 | [structure] | 250-254 | Ex. 1 |

TABLE 4-continued

| Ex. No. | STR | | 1H-NMR | ref. |
|---|---|---|---|---|
| 828 | (structure: 4-[2-(propan-2-yloxy)-5-[5-(trifluoromethyl)pyridin-3-yl]phenyl]-1H-1,2,3-triazole-5-carbonitrile) | 169-174 | | Ex. 1 |
| 829 | (structure: 4-[3-(2-methylpropan-2-yl)-5-(2,6-difluoropyridin-3-yl)phenyl]-1H-1,2,3-triazole-5-carbonitrile) | | 1H-NMR (DMSO-d6) δ: 1.43 (9H, s), 6.96-6.99 (1H, m), 7.67-7.69 (1H, m), 7.90-7.94 (1H, m), 8.00-8.10 (2H, m). | Ex. 1 |
| 830 | (structure: 4-[3-[5-(trifluoromethyl)pyridin-3-yl]phenyl]-1H-1,2,3-triazole-5-carbonitrile) | | 1H-NMR (CDCl3) δ: 7.72-7.78 (2H, m), 8.17-8.21 (1H, m), 8.26 (1H, s), 8.37 (1H, s), 8.96 (1H, s), 9.25 (1H, s). | Ex. 1 |

TABLE 4-continued

| | Structure | 1H-NMR | Ex. |
|---|---|---|---|
| 831 | 3,5-bis(trifluoromethyl)pyridyl-phenyl-triazole-CN | 1H-NMR (CDCl3) δ: 7.92 (1H, s), 8.18 (1H, s), 8.37 (1H, s), 8.44 (1H, s), 8.97 (1H, s), 9.12 (1H, s). | Ex. 1 |
| 832 | 6-(trifluoromethyl)pyridyl-(cyclopropylmethyl)phenyl-triazole-CN | 1H-NMR (DMSO-d6) δ: 0.28-0.34 (2H, m), 0.51-0.59 (2H, m), 1.03-1.15 (1H, m), 2.70 (2H, d, J = 7.0 Hz), 7.92 (2H, d, J = 8.5 Hz), 8.07 (1H, d, J = 8.5 Hz), 8.11 (1H, s), 8.40-8.46 (1H, m), 9.13-9.17 (1H, m). | Ex. 1 |
| 833 | 5-(trifluoromethyl)pyridyl-(tert-butyl)phenyl-triazole-CN | 1H-NMR (DMSO-d6) δ: 1.42 (9H, s), 8.01-8.04 (2H, m), 8.09-8.11 (1H, m), 8.57 (1H, s), 9.03 (1H, s), 9.28 (1H, s). | Ex. 1 |

TABLE 4-continued

| | Structure | 1H-NMR | |
|---|---|---|---|
| 834 | 3,5-disubstituted phenyl: tert-butyl and 1H-1,2,3-triazole-4-carbonitrile; pyridyl bears CF₃ | 1H-NMR (DMSO-d6) δ: 1.42 (9H, s), 7.95-7.99 (1H, m), 8.03-8.10 (3H, m), 8.42-8.48 (1H, m), 9.14-9.17 (1H, m). | Ex. 1 |
| 835 | 3,5-disubstituted phenyl: sec-butyl-like chain (CH(CH₃)CH₂CH₂–) and 1H-1,2,3-triazole-4-carbonitrile; pyridyl bears CF₃ | 1H-NMR (DMSO-d6) δ: 0.95 (6H, d, J = 6.2 Hz), 1.55-1.65 (3H, m), 2.78 (2H, t, J = 7.6 Hz), 7.83 (1H, s), 7.86 (1H, s), 8.06 (1H, d, J = 8.2 Hz), 8.09 (1H, t, J = 1.5 Hz), 8.43 (1H, dd, J = 2.0, 8.2 Hz), 9.15 (1H, d, J = 2.0 Hz). | Ex. 1 |
| 836 | 3,5-disubstituted phenyl: CHF₂ and 1H-1,2,3-triazole-4-carbonitrile; pyridyl bears CF₃ | 1H-NMR (DMSO-d6) δ: 7.26 (1H, t, J = 55.5 Hz), 8.11 (1H, d, J = 8.5 Hz), 8.18 (1H, s), 8.22 (1H, s), 8.46 (1H, s), 8.49-8.51 (1H, m), 9.20 (1H, s). | Ex. 1 |

TABLE 4-continued

| Ex. No. | STR | m.p. | 1H-NMR | ref. |
|---|---|---|---|---|
| 837 | | | 1H-NMR (DMSO-d6) δ: 3.60 (3H, s), 5.26-5.35 (1H, m), 8.06 (1H, s), 8.10 (2H, d, J = 7.5 Hz), 8.37 (1H, s), 8.45 (1H, d, J = 7.5 Hz), 9.16 (1H, s). | Ex. 1 |
| 838 | | 227-229 | | Ex. 1 |
| 839 | | 179-182 | | Ex. 1 |

TABLE 4-continued
| | | | |
|---|---|---|---|
| 841 | 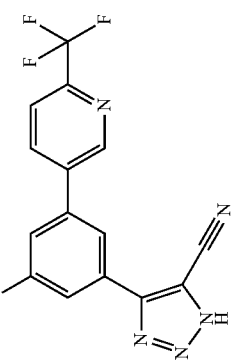 | 236-238 | Ex. 1 |
| 843 | | 231-232 | Ex. 1 |
| 844 | 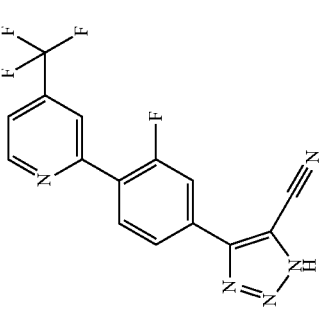 | 218-220 | Ex. 1 |

TABLE 4-continued

| Ex. No. | STR | 1H-NMR | ref. |
|---|---|---|---|
| 840 | (structure: 4-[3-(cyclopentyloxy)-5-(6-(trifluoromethyl)pyridin-3-yl)phenyl]-1H-1,2,3-triazole-5-carbonitrile) | 1H-NMR (DMSO-d6) δ: 1.59-1.85 (6H, m), 1.97-2.07 (2H, m), 5.02-5.07 (1H, m), 7.50 (1H, s), 7.52 (1H, s), 7.82 (1H, s), 8.05 (1H, d, J = 8.3 Hz), 8.44 (1H, dd, J = 2.0, 8.3 Hz), 9.15 (1H, d, J = 2.0 Hz). | Ex. 1 |
| 842 | (structure: 4-[3-(2,6-difluoropyridin-3-yl)-6-ethoxyphenyl]-1H-1,2,3-triazole-5-carbonitrile) | 1H-NMR (DMSO-d6) δ: 1.41 (3H, t, J = 7.0 Hz), 4.25 (2H, q J = 7.0 Hz), 7.31-7.34 (1H, m), 7.38 (1H, d, J = 8.8 Hz), 7.76-7.82 (2H, m), 8.32-8.38 (1H, m). | Ex. 1 |
| 845 | (structure: 4-[4-(6-(trifluoromethyl)pyridin-2-yl)phenyl]-1H-1,2,3-triazole-5-carbonitrile) | 1H-NMR (DMSO-d6) δ: 7.93 (1H, d, J = 7.6 Hz), 8.07 (2H, d, J = 8.4 Hz), 8.25 (1H, t, J = 7.6 Hz), 8.38 (2H, d, J = 8.4 Hz), 8.41 (1H, d, J = 8.2 Hz). | Ex. 1 |

TABLE 4-continued

| Ex. No. | STR | m.p. | ref. |
|---|---|---|---|
| 846 | ![structure] | 300-303 | Ex. 1 |
| 847 | ![structure] | 218-220 | Ex. 1 |

TABLE 4-continued
| | | | |
|---|---|---|---|
| 848 |  | 278 | Ex. 1 |
| 849 |  | 248-249 | Ex. 1 |
| 850 | 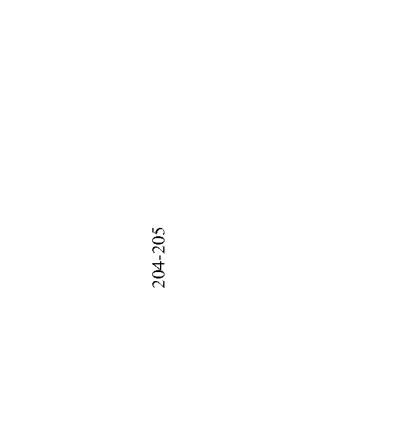 | 204-205 | Ex. 1 |

TABLE 4-continued
| | | | |
|---|---|---|---|
| 851 | 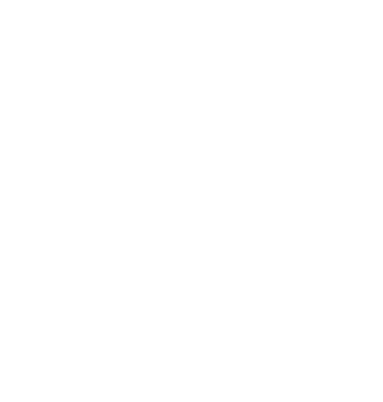 | 201-206 | Ex. 1 |
| 852 | 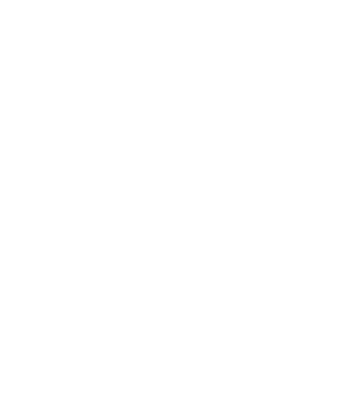 | 170-173 | Ex. 1 |

TABLE 4-continued
| Ex. No. | STR | | ref. |
|---|---|---|---|
| 853 |  | 177-178 | Ex. 1 |
| Ex. No. | STR | 1H-NMR | ref. |
|---|---|---|---|
| 854 | 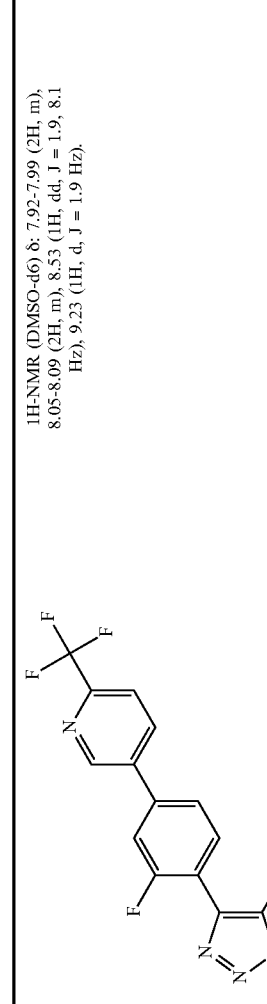 | 1H-NMR (DMSO-d6) δ: 7.92-7.99 (2H, m), 8.05-8.09 (2H, m), 8.53 (1H, dd, J = 1.9, 8.1 Hz), 9.23 (1H, d, J = 1.9 Hz). | Ex. 125 |
| 855 |  | 1H-NMR (DMSO-d6) δ: 8.01-8.06 (4H, m), 8.17-8.21 (1H, m), 8.63 (1H, d, J = 2.5 Hz), 8.91 (1H, s). | Ex. 1 |

TABLE 4-continued
| | | | |
|---|---|---|---|
| 856 | 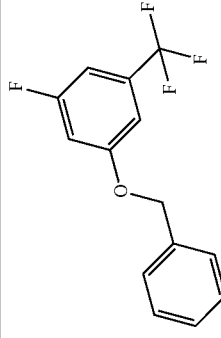 | 1H-NMR (DMSO-d6) δ: 5.34 (2H, s), 7.25-7.35 (3H, m), 7.66 (2H, d, J = 7.7 Hz), 7.86-7.90 (1H, m), 8.01 (1H, s). | Ex. 1 |
| 857 | 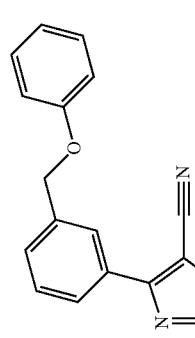 | 1H-NMR (CDCl3) δ: 5.16 (2H, s), 6.94-7.04 (3H, m), 7.27-7.34 (2H, m), 7.52-7.62 (2H, m), 7.92-7.97 (1H, m), 8.05 (1H, s). | Ex. 1 |
| 858 | 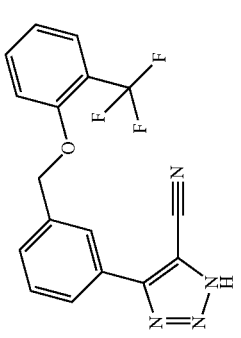 | 1H-NMR (CDCl3) δ: 5.27 (2H, s), 7.01-7.07 (2H, m), 7.46-7.65 (4H, m), 7.93-7.98 (1H, m), 8.04 (1H, s), 12.0 (1H, br.). | Ex. 1 |
| 859 | 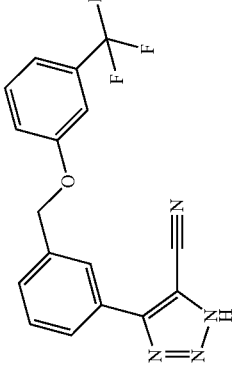 | 1H-NMR (CDCl3) δ: 5.18 (2H, s), 7.16 (1H, dd, J = 2.4, 8.4 Hz), 7.23-7.26 (2H, m), 7.38-7.45 (1H, m), 7.54-7.61 (2H, m), 7.96-8.00 (1H, m), 8.07 (1H, s). | Ex. 1 |

TABLE 4-continued

| # | Structure | 1H-NMR | Ref. |
|---|---|---|---|
| 860 | (4-trifluoromethylphenyl methoxy)-phenyl triazole carbonitrile | 1H-NMR (CDCl3) δ: 5.20 (2H, s), 7.06 (2H, d, J = 8.5 Hz), 7.54-7.59 (4H, m), 7.94-8.00 (1H, m), 8.06 (1H, s), 12.0 (1H, br.) | Ex. 1 |
| 861 | (2-chlorophenoxymethyl)phenyl-pyrazole carbonitrile | 1H-NMR (CDCl3) δ: 5.24 (2H, s), 6.93-7.02 (2H, m), 7.19-7.22 (1H, m), 7.40 (1H, dd, J = 1.6, 7.9 Hz), 7.56-7.64 (2H, m), 7.97-7.99 (1H, m), 8.07 (1H, s), 12.1 (1H, br.) | Ex. 1 |
| 862 | (3-chlorophenoxymethyl)phenyl triazole carbonitrile | 1H-NMR (CDCl3) δ: 5.14 (2H, s), 6.86-6.91 (1H, m), 6.94-7.02 (2H, m), 7.22 (1H, t, J = 8.1 Hz), 7.53-7.59 (2H, m), 7.93-7.99 (1H, m), 8.04 (1H, s), 12.1 (1H, br.) | Ex. 1 |
| 863 | (4-chlorophenoxymethyl)phenyl triazole carbonitrile | 1H-NMR (CDCl3) δ: 5.13 (2H, s), 6.90-6.95 (2H, m), 7.23-7.26 (2H, m), 7.55-7.58 (2H, m), 7.93-7.98 (1H, m), 8.04 (1H, s), 12.2 (1H, br.) | Ref. Ex. 499, Ex. 1 |

TABLE 4-continued

| | Structure | 1H-NMR | Ex. |
|---|---|---|---|
| 864 | 2,3-dichlorophenyl-O-CH2-phenyl-triazole-CN | 1H-NMR (CDCl3) δ: 5.24 (2H, s), 6.91 (1H, dd, J = 2.3, 7.4 Hz), 7.09-7.18 (2H, m), 7.54-7.66 (2H, m), 7.94-7.99 (1H, m), 8.06 (1H, s). | Ex. 1 |
| 865 | 2,4-dichlorophenyl-O-CH2-phenyl-triazole-CN | 1H-NMR (CDCl3) δ: 5.21 (2H, s), 6.92 (1H, d, J = 8.8 Hz), 7.18 (1H, dd, J = 2.5, 8.8 Hz), 7.40 (1H, d, J = 2.5 Hz), 7.54-7.64 (2H, m), 7.94-7.99 (1H, m), 8.05 (1H, s), 12.2 (1H, br). | Ex. 1 |
| 866 | 2,5-dichlorophenyl-O-CH2-phenyl-triazole-CN | 1H-NMR (CDCl3) δ: 5.19 (2H, s), 6.92 (1H, dd, J = 2.2, 8.4 Hz), 6.99 (1H, d, J = 2.2 Hz), 7.31 (1H, d, J = 8.4 Hz), 7.54-7.64 (2H, m), 7.95-7.98 (1H, m), 8.06 (1H, s). | Ex. 1 |
| 867 | 2,6-dichlorophenyl-O-CH2-phenyl-triazole-CN | 1H-NMR (CDCl3) δ: 5.13 (2H, s), 7.04 (1H, dd, J = 7.8, 8.3 Hz), 7.34 (2H, d, J = 8.0 Hz), 7.58 (1H, t, J = 7.7 Hz), 7.72 (1H, d, J = 7.7 Hz), 7.99 (1H, d, J = 7.7 Hz), 8.18 (1H, s), 12.2 (1H, br). | Ex. 1 |

TABLE 4-continued
| | | | |
|---|---|---|---|
| 868 |  | 1H-NMR (CDCl3) δ: 5.12 (2H, s), 6.85 (1H, dd, J = 2.9, 8.8 Hz), 7.10 (1H, d, J = 2.9 Hz), 7.34 (1H, d, J = 8.8 Hz), 7.53-7.60 (2H, m), 7.93-8.00 (1H, m), 8.04 (1H, s). | Ex. 1 |
| 869 | 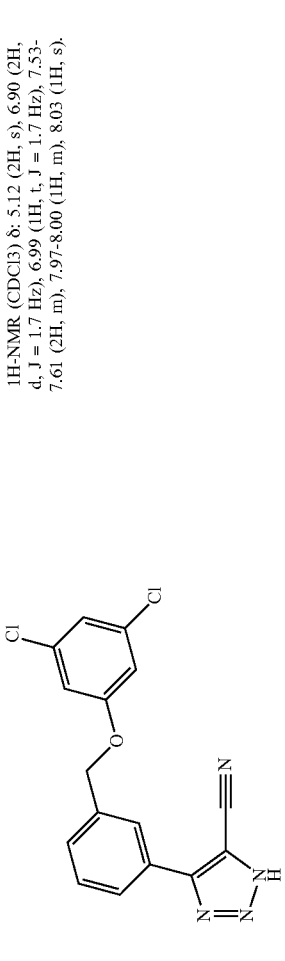 | 1H-NMR (CDCl3) δ: 5.12 (2H, s), 6.90 (2H, d, J = 1.7 Hz), 6.99 (1H, t, J = 1.7 Hz), 7.53-7.61 (2H, m), 7.97-8.00 (1H, m), 8.03 (1H, s). | Ex. 1 |
| 870 |  | 1H-NMR (CDCl3) δ: 5.10 (2H, s), 7.35 (2H, s), 7.58 (1H, t, J = 7.7 Hz), 7.69 (1H, d, J = 7.7 Hz), 7.99 (1H, d, J = 7.7 Hz), 8.16 (1H, s). | Ex. 1 |
| 871 |  | 1H-NMR (CDCl3) δ: 5.18 (2H, s), 6.73-6.83 (1H, m), 6.64-7.04 (2H, m), 7.52-7.61 (2H, m), 7.93-7.99 (1H, m), 8.04 (1H, s). | Ex. 1 |

TABLE 4-continued

| | | | |
|---|---|---|---|
| 872 | (structure: 2,4,6-trifluorophenyl-O-CH2-phenyl-triazole-CN) | 1H-NMR (CDCl3) δ: 5.18 (2H, s), 6.62-6.75 (2H, m), 7.75-7.63 (2H, m), 7.97 (1H, d, J = 7.2 Hz), 8.04 (1H, s), 12.3 (1H, br). | Ex. 1 |
| 873 | (structure: 3-CF3-phenyl-O-CH2-(5-Cl-phenyl)-triazole-CN) | 1H-NMR (CDCl3) δ: 5.16 (2H, s), 7.17 (1H, dd, J = 2.5, 8.4 Hz), 7.22-7.29 (2H, m), 7.43 (1H, t, J = 8.0 Hz), 7.59 (1H, s), 7.94-8.00 (2H, m). | Ex. 1 |
| 874 | (structure: 3-F-phenyl-O-CH2-(5-Cl-phenyl)-triazole-CN) | 1H-NMR (CDCl3) δ: 5.11 (2H, s), 6.69-6.80 (3H, m), 7.21-7.29 (1H, m), 7.57 (1H, s), 7.96 (2H, s), 12.3 (1H, br). | Ex. 1 |
| 875 | (structure: 2,4-diF-phenyl-O-CH2-(5-Cl-phenyl)-triazole-CN) | 1H-NMR (CDCl3) δ: 5.14 (2H, s), 6.74-6.84 (1H, m), 6.85-7.03 (2H, m), 7.59 (1H, s), 7.95 (2H, s), 12.3 (1H, br). | Ex. 1 |

TABLE 4-continued

| # | Structure | 1H-NMR | Ex. |
|---|---|---|---|
| 876 | (3-chloro-5-((2,4,6-trifluorophenoxy)methyl)phenyl triazole-carbonitrile) | 1H-NMR (CDCl3) δ: 5.15 (2H, s), 6.66-6.76 (2H, m), 7.60 (1H, s), 7.96 (2H, s), 12.3 (1H, br.). | Ex. 1 |
| 877 | (3-chloro-5-((2,4-bis(trifluoromethyl)phenoxy)methyl)phenyl triazole-carbonitrile) | 1H-NMR (CDCl3) δ: 5.30 (2H, s), 7.14 (1H, d, J = 8.7 Hz), 7.59 (1H, s), 7.79 (1H, d, J = 8.7 Hz), 7.89 (1H, s), 7.95 (1H, s), 7.98 (1H, s). | Ex. 1 |
| 878 | (3-chloro-5-((2,5-bis(trifluoromethyl)phenoxy)methyl)phenyl triazole-carbonitrile) | 1H-NMR (CDCl3) δ: 5.29 (2H, s), 7.31 (1H, s), 7.37 (1H, d, J = 8.2 Hz), 7.63 (1H, s), 7.77 (1H, d, J = 7.9 Hz), 7.99 (1H, s), 8.00 (1H, s). | Ex. 1 |
| 879 | (3-bromo-5-((3-(trifluoromethyl)phenoxy)methyl)phenyl triazole-carbonitrile) | 1H-NMR (CDCl3) δ: 5.17 (2H, s), 7.17 (1H, dd, J = 2.1, 8.0 Hz), 7.22-7.30 (2H, m), 7.43 (1H, t, J = 8.0 Hz), 7.75 (1H, s), 8.03 (1H, s), 8.12 (1H, s), 12.0 (1H, br.). | Ex. 1 |

TABLE 4-continued

| | Structure | NMR | Ex. |
|---|---|---|---|
| 880 | 3-bromo-5-[(3-fluorophenoxy)methyl]phenyl triazole with CN | 1H-NMR (CDCl3) δ: 5.11 (2H, s), 6.86-6.92 (3H, m), 7.21-7.31 (1H, m), 7.72 (1H, s), 8.00 (1H, s), 8.10 (1H, s), 12.2 (1H, br). | Ex. 1 |
| 881 | 3-[[2,5-bis(trifluoromethyl)phenoxy]methyl]phenyl triazole with CN | 1H-NMR (DMSO-d6) δ: 5.52 (2H, s), 7.51 (1H, d, J = 8.2 Hz), 7.64-7.69 (2H, m), 7.76 (1H, s), 7.87-7.92 (2H, m), 8.00 (1H, s). | Ex. 2 |
| 882 | 3-[(2,3-difluorophenoxy)methyl]phenyl triazole with CN | 1H-NMR (DMSO-d6) δ: 5.34 (2H, s), 7.01-7.05 (1H, m), 7.11-7.17 (2H, m), 7.66-7.67 (2H, m), 7.87-7.89 (1H, m), 8.00 (1H, s). | Ex. 2 |

TABLE 4-continued

| Ex. No. | STR | | ref. |
|---|---|---|---|
| 883 | ![structure: 2,5-dimethylpyridin-3-yl-phenyl-triazole-carbonitrile] | 1H-NMR (DMSO-d6) δ: 2.53 (3H, s), 2.57 (3H, s), 7.73-7.78 (1H, m), 7.81-7.85 (1H, m), 7.97-8.01 (1H, m), 8.12-8.13 (1H, m), 8.48 (1H, s). | Ex. 2 |
| 884 | ![structure: 3,5-dimethoxypyridin-2-yl-phenyl-triazole-carbonitrile] | 1H-NMR (DMSO-d6) δ: 4.04 (6H, s), 6.26 (1H, s), 7.77 (1H, t, J = 7.8 Hz), 8.07-8.09 (1H, m), 8.52-8.55 (1H, m), 9.07-9.08 (1H, m). | Ex. 2 |
| 885 | ![structure: 5-fluoropyridin-2-yl-phenyl-triazole-carbonitrile] | 1H-NMR (DMSO-d6) δ: 7.58 (1H, t, J = 7.8 Hz), 8.00 (1H, dt, J = 1.5, 7.8 Hz), 8.24 (1H, dt, J = 1.5, 7.8 Hz), 8.93 (1H, t, J = 1.5 Hz), 9.03 (2H, s). | Ex. 2 |

| Ex. No. | STR | m.p. | ref. |
|---|---|---|---|
| 886 | ![structure: benzofuran-chlorophenyl-triazole-carbonitrile] | 219-221 | Ex. 1 |

TABLE 4-continued
| | | | |
|---|---|---|---|
| 887 | 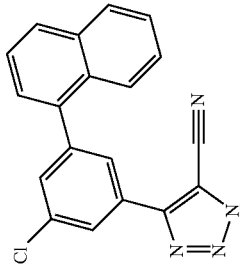 | 153-155 | Ex. 1 |
| 888 | 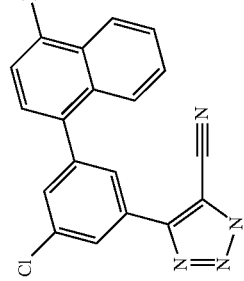 | 272-275 | Ex. 1 |
| 889 | 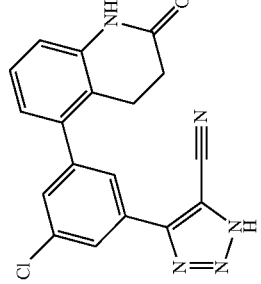 | 303-305 | Ex. 1 |
| 890 | 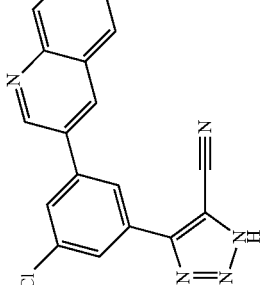 | 306-307 | Ex. 1 |

TABLE 4-continued
| | | | |
|---|---|---|---|
| 891 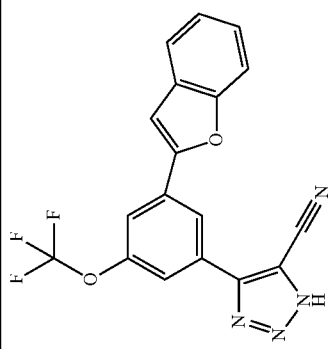 | 224 | Ex. 1 | |
| 892 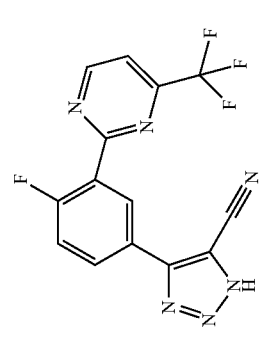 | 187-189 | Ex. 1 | |
| 893 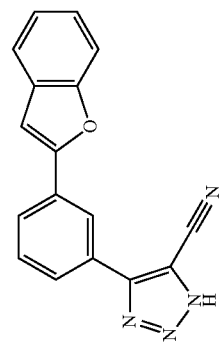 | 209 | Ex. 1 | |
| 894 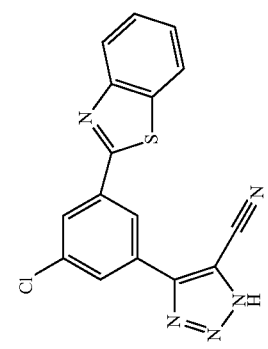 | 266-268 | Ex. 1 | |

TABLE 4-continued

| | | | |
|---|---|---|---|
| 895 | [6-chlorobenzothiazol-2-yl phenyl triazole carbonitrile structure] | 281–283 | Ex. 1 |
| 896 | [6-chlorobenzothiazol-2-yl (trifluoromethoxy)phenyl triazole carbonitrile structure] | 255–258 | Ex. 1 |
| 897 | [6-chlorobenzothiazol-2-yl chlorophenyl triazole carbonitrile structure] | 288–291 | Ex. 1 |

TABLE 4-continued
| | | | |
|---|---|---|---|
| 898 |  | 241 | Ex. 1 |
| 899 |  | 136-139 | Ex. 1 |
| 900 | 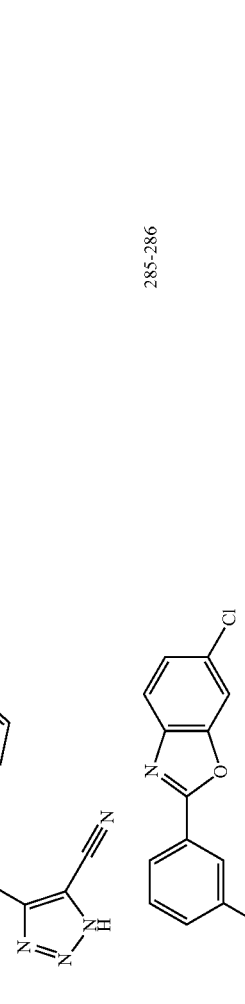 | 285-286 | Ex. 1 |

TABLE 4-continued

| | | | |
|---|---|---|---|
| 901 | [structure] | 122-123 | Ex. 1 |
| 902 | [structure] | 170-173 | Ex. 1 |
| 903 | [structure] | 170-171 | Ex. 1 |

TABLE 4-continued

| 904 | [structure] | 95-98 | Ex. 1 |
| 905 | [structure] | 153-154 | Ex. 1 |
| 906 | [structure] | 171-174 | Ex. 1 |

TABLE 4-continued

| | Structure | mp (°C) | Ex. |
|---|---|---|---|
| 907 | 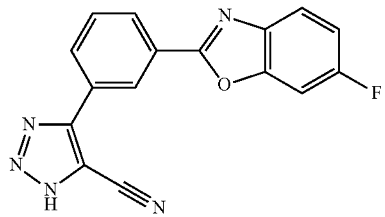 [SMILES: N#Cc1[nH]nnc1-c1cccc(-c2nc3ccc(F)cc3o2)c1] | 290 | Ex. 1 |
| 908 | 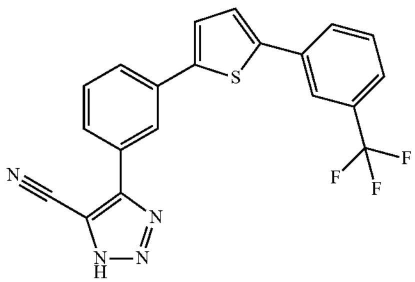 [SMILES: N#Cc1[nH]nnc1-c1cccc(-c2ccc(-c3cccc(C(F)(F)F)c3)s2)c1] | 173.0-174.5 | Ex. 2 |
| 909 | 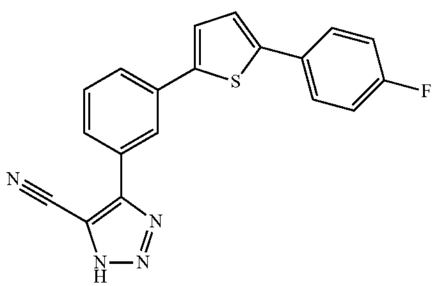 [SMILES: N#Cc1[nH]nnc1-c1cccc(-c2ccc(-c3ccc(F)cc3)s2)c1] | 192.0-194.0 | Ex. 2 |
| 910 | 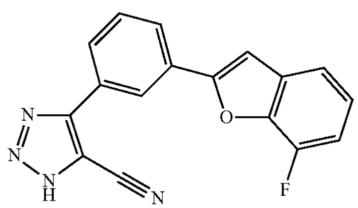 [SMILES: N#Cc1[nH]nnc1-c1cccc(-c2cc3cccc(F)c3o2)c1] | 248-249 | Ex. 1 |

TABLE 4-continued
| | | | |
|---|---|---|---|
| 911 | 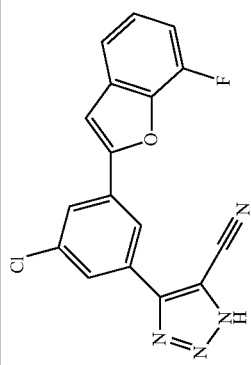 | 226 | Ex. 1 |
| 913 | 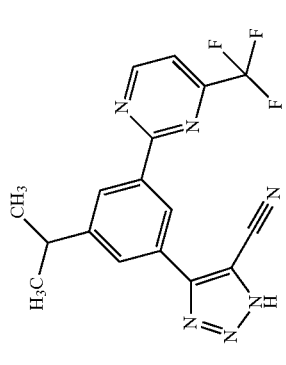 | 191 | Ex. 1 |
| 914 | 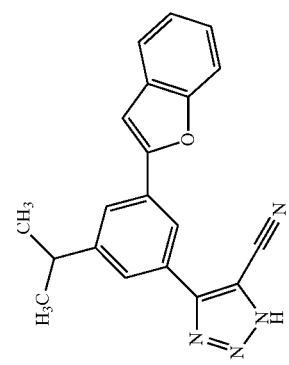 | 171-172 | Ex. 1 |

TABLE 4-continued

| | | | |
|---|---|---|---|
| 915 | [structure] | 186-187 | Ref. Ex. 91, Ex. 1 |
| 916 | [structure] | 175-180 | Ex. 1 |
| 917 | [structure] | 108-111 | Ex. 1 |

TABLE 4-continued
| | | | | |
|---|---|---|---|---|
| 918 | 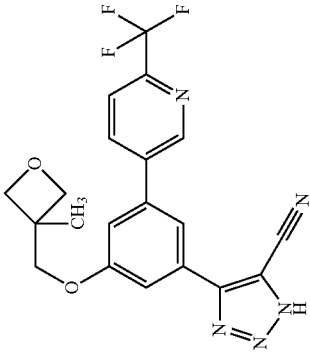 | 177-180 | Ex. 1 | |
| 919 | 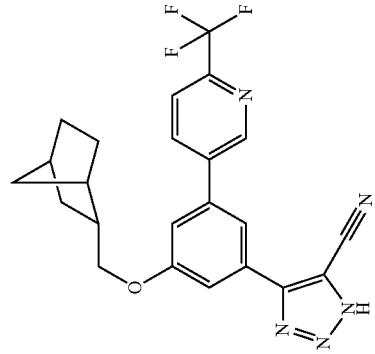 | 160-164 | Ex. 1 | |
| 920 | 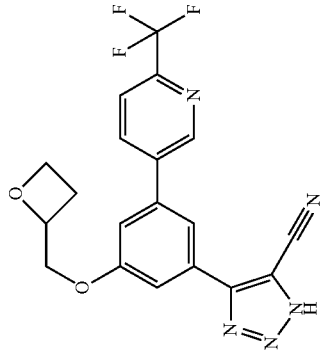 | 157-166 | Ex. 1 | |

TABLE 4-continued
| | | | |
|---|---|---|---|
| 921 | 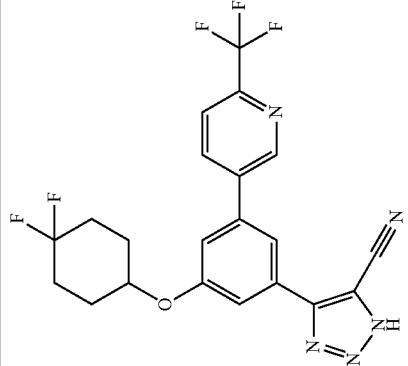 | 205-210 | Ex. 1 |
| 922 | 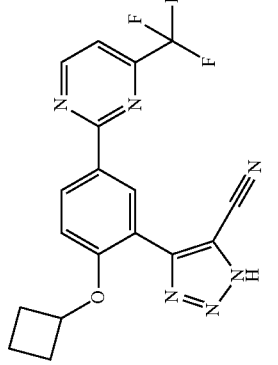 | 202-214 | Ex. 125 |
| 923 | 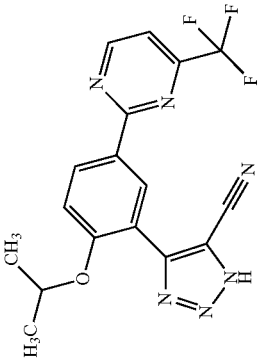 | 182-186 | Ex. 125 |

TABLE 4-continued

| Ex. No. | STR | 1H-NMR | ref. |
|---|---|---|---|
| 912 | (structure) | 1H-NMR (DMSO-d6) δ: 3.91 (3H, s), 7.23 (1H, dd, J = 4.7, 8.0 Hz), 7.68 (1H, t J = 7.8 Hz), 7.73-7.79 (1H, m), 7.86-7.92 (1H, m), 8.06 (1H, s), 8.21 (1H, s), 8.35-8.38 (1H, m), 8.42-8.46 (1H, m). | Ex. 1 |
| 924 | (structure) | 1H-NMR (DMSO-d6) δ: 7.86 (1H, t, J = 7.8 Hz), 8.07 (2H, dd, J = 1.8, 7.8 Hz), 8.44 (1H, t, J =1.8 Hz). | Ex. 125 |
| 925 | (structure) | 1H-NMR (CDCl3) δ: 7.60-7.62 (4H, m), 7.87-7.89 (4H, m), 8.10 (1H, s), 8.15 (2H, s). | Ex. 1 |

TABLE 4-continued

| | | | |
|---|---|---|---|
| 926 | [structure: 3-furyl and CF3 substituted phenyl-triazole-carbonitrile] | 1H-NMR (CDCl3) δ: 6.81-6.82 (1H, m), 7.56-7.57 (1H, m), 7.84 (1H, s), 7.90 (1H, s), 8.15 (1H, s), 8.34 (1H, s). | Ex. 1 |
| 927 | [structure: bis(3-thienyl) substituted phenyl-triazole-carbonitrile] | 1H-NMR (DMSO-d6) δ: 7.70-7.73 (2H, m), 7.74-7.76 (2H, m), 8.10-8.12 (4H, m), 8.24 (1H, s). | Ex. 1 |
| 928 | [structure: benzothiophen-3-yl and CF3 substituted phenyl-triazole-carbonitrile] | 1H-NMR (CDCl3) δ: 7.46-7.50 (2H, m), 7.61 (1H, s), 7.94-8.01 (3H, m), 8.29 (1H, s), 8.44 (1H, s). | Ex. 1 |

TABLE 4-continued

| | Structure | 1H-NMR | Ex. |
|---|---|---|---|
| 929 | (3-(1-methyl-1H-pyrazol-4-yl)-5-(trifluoromethyl)phenyl triazole-carbonitrile) | 1H-NMR (DMSO-d6) δ: 3.90 (3H, s), 7.97 (1H, s), 8.07 (1H, s), 8.10 (1H, s), 8.33 (1H, s), 8.40 (1H, s). | Ex. 1 |
| 930 | (3-(naphthalen-2-yl)-5-(trifluoromethyl)phenyl triazole-carbonitrile) | 1H-NMR (DMSO-d6) δ: 7.58-7.61 (2H, m), 7.96-8.12 (4H, m), 8.20 (1H, s), 8.33 (1H, s), 8.43 (1H, s), 8.59 (1H, s). | Ex. 2 |
| 931 | (3-(2,2-difluorobenzo[d][1,3]dioxol-5-yl)phenyl triazole-carbonitrile) | 1H-NMR (DMSO-d6) δ: 7.55-7.61 (2H, m), 7.72 (1H, t, J = 7.8 Hz), 7.82-7.90 (3H, m), 8.15 (1H, s). | Ex. 1 |
| 932 | (3-(2,2-difluorobenzo[d][1,3]dioxol-5-yl)-5-methylphenyl triazole-carbonitrile) | 1H-NMR (DMSO-d6) δ: 2.52 (3H, s), 7.56 (2H, s), 7.70 (2H, s), 7.79 (1H, s), 7.94 (1H, s). | Ex. 1 |

| | | | |
|---|---|---|---|
| 933 | [structure] | 1H-NMR (DMSO-d6) δ: 2.51 (3H, s), 7.37 (1H, t, J = 8.0 Hz), 7.45-7.56 (2H, m), 7.74 (1H, s), 7.79 (1H, s), 8.07 (1H, s). | Ex. 1 |
| 934 | [structure] | 1H-NMR (DMSO-d6) δ: 7.55-7.68 (2H, m), 7.84 (1H, s), 7.90 (2H, s), 8.19 (1H, s). | Ex. 1 |
| 935 | [structure] | 1H-NMR (CDCl3) δ: 7.19-7.26 (1H, m), 7.35-7.40 (2H, m), 7.88 (1H, s), 8.25 (1H, s), 8.35 (1H, s). | Ex. 2 |

TABLE 4-continued
| | | | |
|---|---|---|---|
| 936 | 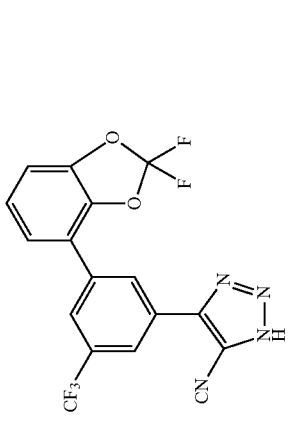 | 1H-NMR (CDCl3) δ: 7.12-7.15 (1H, m), 7.21-7.26 (1H, m), 7.36-7.39 (1H, m), 8.05 (1H, s), 8.29 (1H, s), 8.54 (1H, s). | Ex. 2 |
| 937 | 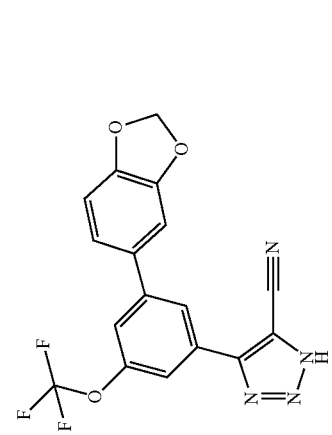 | 1H-NMR (DMSO-d6) δ: 6.11 (2H, s), 7.09 (1H, d, J = 8.1 Hz), 7.28-7.31 (1H, m), 7.40 (1H, d, J = 1.8 Hz), 7.76 (1H, s), 7.81 (1H, s), 8.14 (1H, t, J = 1.5 Hz). | Ex. 1 |
| 938 | 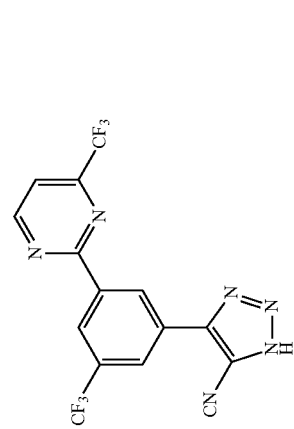 | 1H-NMR (DMSO-d6) δ: 8.08 (1H, d, J = 5.1 Hz), 8.38 (1H, s), 8.71 (1H, s), 9.17 (1H, s), 9.35 (1H, d, J = 5.1 Hz). | Ex. 2 |

TABLE 4-continued

| | Structure | NMR | Ex. |
|---|---|---|---|
| 939 | (5-(trifluoromethyl)pyrimidin-2-yl and trifluoromethoxy substituted phenyl-triazole-carbonitrile) | 1H-NMR (DMSO-d6) δ: 8.08-8.12 (2H, m), 8.40 (1H, s), 9.01 (1H, s), 9.38 (1H, d, J = 5.0 Hz). | Ex. 1 |
| 940 | (2,2-difluorobenzo[d][1,3]dioxine with chlorophenyl-triazole-carbonitrile) | 1H-NMR (DMSO-d6) δ: 7.66 (1H, d, J = 8.8 Hz), 7.94 (1H, d, J = 1.8 Hz), 8.08 (1H, d, J = 1.8 Hz), 8.18-8.23 (2H, m), 8.36 (1H, s). | Ex. 1 |
| 941 | (pyridin-2-yl and chloro substituted phenyl-triazole-carbonitrile) | 1H-NMR (DMSO-d6) δ: 7.58 (1H, t, J = 4.9 Hz), 8.09 (1H, t, J = 1.9 Hz), 8.51 (1H, t, J = 1.5 Hz), 8.92 (1H, t, J = 1.5 Hz), 9.00 (2H, d, J = 4.9 Hz). | Ex. 1 |

TABLE 4-continued

| | Structure | NMR | Ex. |
|---|---|---|---|
| 942 | 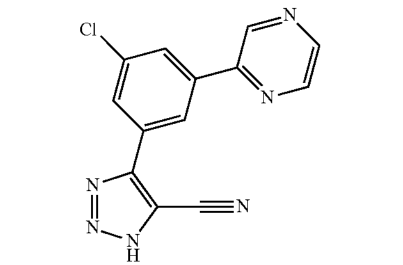 [SMILES: N#Cc1[nH]nnc1-c1cc(Cl)cc(-c2cnccn2)c1] | 1H-NMR (DMSO-d6) δ: 8.04 (1H, t, J = 1.7 Hz), 8.40 (1H, t, J = 1.7 Hz), 8.65 (1H, t, J = 1.5 Hz), 8.73 (1H, s), 8.80-8.81 (1H, m), 9.39 (1H, s). | Ex. 1 |
| 943 | 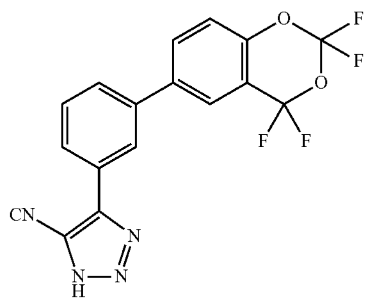 | 1H-NMR (CDCl3) δ: 7.24-7.26 (1H, m), 7.58-7.67 (2H, m), 7.84-7.89 (2H, m), 8.01-8.04 (1H, m), 8.18 (1H, s). | Ex. 1 |
| 944 | 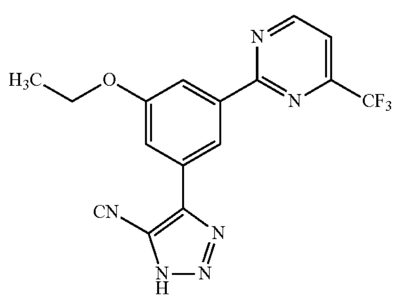 | 1H-NMR (DMSO-d6) δ: 1.42 (3H, t, J = 6.2 Hz), 4.22 (2H, q, J = 6.2 Hz), 7.63-7.64 (1H, m), 8.02-8.05 (1H, m), 8.17 (1H, s), 8.57 (1H, s), 9.31-9.33 (1H, m). | Ex. 1 |

TABLE 4-continued
| | | | |
|---|---|---|---|
| 945 | 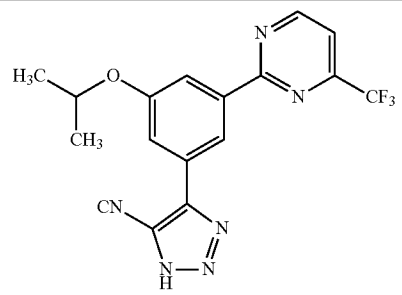 | 1H-NMR (DMSO-d6) δ: 1.37 (6H, d, J = 6.0 Hz), 4.73-4.85 (1H, m), 7.63-7.64 (1H, m), 8.01-8.04 (2H, m), 8.54 (1H, s), 9.32 (1H, d, J = 5.0 Hz). | Ex. 1 |
| 946 | 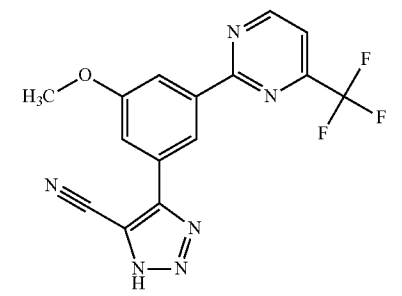 [SMILES: COc1cc(-c2nccc(C(F)(F)F)n2)cc(-c2nn[nH]c2C#N)c1] | 1H-NMR (DMSO-d6) δ: 3.95 (3H, s), 7.67-7.68 (1H, m), 8.04 (1H, d, J = 5.0 Hz), 8.07-8.08 (1H, m), 8.60-8.61 (1H, m), 9.34 (1H, d, J = 5.0 Hz). | Ex. 1 |
| 947 | 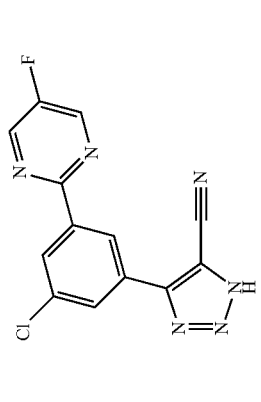 | 1H-NMR (DMSO-d6) δ: 8.05-8.09 (1H, m), 8.44 (1H, s), 8.85 (1H, s), 9.09 (2H, s). | Ex. 1 |
| 948 | 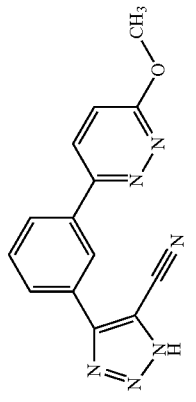 | 1H-NMR (DMSO-d6) δ: 4.10 (3H, s), 7.37 (1H, d, J = 9.3 Hz), 7.63 (1H, t, J = 7.8 Hz), 7.96-8.02 (2H, m), 8.18 (1H, d, J = 9.3 Hz), 8.59 (1H, t, J = 1.7 Hz). | Ex. 2 |

TABLE 4-continued

| | Structure | 1H-NMR | Ex. |
|---|---|---|---|
| 949 | (6-methylpyridazin-3-yl and methoxyphenyl substituted triazole-carbonitrile) | 1H-NMR (DMSO-d6) δ: 2.69 (3H, s), 3.95 (3H, s), 7.56-7.57 (1H, m), 7.73 (1H, d, J = 8.7 Hz), 7.83-7.84 (1H, m), 8.21 (1H, d, J = 8.7 Hz), 8.27-8.28 (1H, m). | Ex. 1 |
| 950 | (isoquinolinyl and chlorophenyl substituted triazole-carbonitrile) | 1H-NMR (DMSO-d6) δ: 7.73-7.90 (4H, m), 7.96-8.06 (2H, m), 8.27 (1H, d, J = 8.0 Hz), 8.54 (1H, d, J = 6.0 Hz), 9.46 (1H, s). | Ex. 1 |
| 951 | (naphthalenyl and chlorophenyl substituted triazole-carbonitrile) | 1H-NMR (DMSO-d6) δ: 7.56-7.62 (2H, m), 7.90-8.12 (6H, m), 8.28 (1H, s), 8.38 (1H, s). | Ex. 1 |
| 953 | (trifluoromethylpyrimidinyl and fluorophenyl substituted triazole-carbonitrile) | 1H-NMR (CDCl3) δ: 7.61 (1H, d, J = 6.0 Hz), 7.87-7.90 (1H, m), 8.35-8.38 (1H, m), 9.00 (1H, t, J = 1.3 Hz), 9.12 (1H, d, J = 5.0 Hz), 12.31 (1H, brs). | Ex. 2 |

TABLE 4-continued

| | Structure | NMR | Ref |
|---|---|---|---|
| 954 | (3-chloro-5-(indol-2-yl)phenyl with N-Boc-like tert-butyl carbamate and triazole-CN) | 1H-NMR (DMSO-d6) δ: 1.31 (9H, s), 6.92 (1H, s), 7.27-7.43 (2H, m), 7.67 (1H, d, J = 7.2 Hz), 7.79 (1H, t, J = 1.8 Hz), 7.92-7.97 (2H, m), 8.13-8.18 (1H, m). | Ex. 1 |
| 955 | (6-chloro-2-(2-fluoro-5-(triazol-CN)phenyl)benzothiazole) | 1H-NMR (DMSO-d6) δ: 7.65 (1H, dd, J = 2.2, 6.7 Hz), 7.73 (1H, dd, J = 8.7, 11.3 Hz), 8.09-8.15 (1H, m), 8.17 (1H, d, J = 8.7 Hz), 8.40 (1H, d, J = 2.2 Hz), 8.91 (1H, dd, J = 2.2, 7.0 Hz). | Ex. 1 |
| 956 | (3-(indolin-1-yl)phenyl-triazole-CN) | 1H-NMR (CDCl3) δ: 3.18 (2H, t, J = 8.4 Hz), 4.02 (2H, t, J = 8.4 Hz), 6.81 (1H, t, J = 7.3 Hz), 7.13 (1H, t, J = 7.7 Hz), 7.20 (1H, d, J = 7.0 Hz), 7.25-7.29 (1H, m), 7.35-7.53 (3H, m), 7.78 (1H, s). | Ex. 1 |
| 957 | (3-(5-chloroindol-1-yl)phenyl-triazole-CN) | 1H-NMR (CDCl3) δ: 6.67 (1H, dd, J = 0.7, 3.3 Hz), 7.22 (1H, dd, J = 2.0, 8.8 Hz), 7.42 (1H, d, J = 3.3 Hz), 7.54 (1H, d, J = 8.8 Hz), 7.60-7.74 (3H, m), 7.94-8.04 (1H, m), 8.11 (1H, s). | Ex. 1 |
| 958 | (3-(3,4-dihydroisoquinolin-2(1H)-yl)phenyl-triazole-CN) | 1H-NMR (CDCl3) δ: 3.03 (2H, t, J = 5.9 Hz), 3.66 (2H, t, J = 5.9 Hz), 4.51 (2H, s), 7.08 (1H, dd, J = 2.5, 8.2 Hz), 7.15-7.22 (4H, m), 7.31-7.36 (1H, m), 7.42 (1H, t, J = 7.9 Hz), 7.51 (1H, s). | Ex. 1 |

TABLE 4-continued

| | Structure | NMR | Ex. |
|---|---|---|---|
| 959 | (tetrahydroquinoline-phenyl-triazole-CN) | 1H-NMR (CDCl3) δ: 2.00-2.11 (2H, m), 2.85 (2H, t, J = 6.3 Hz), 3.70 (2H, t, J = 5.8 Hz), 6.76-6.83 (1H, m), 6.91-7.04 (2H, m), 7.07-7.12 (1H, m), 7.35-7.41 (1H, m), 7.45 (1H, t, J = 7.7 Hz), 7.57-7.63 (1H, m), 7.67 (1H, s), 12..2 (1H, br). | Ex. 1 |
| 960 | (trifluoromethoxy-benzothiophene-phenyl-triazole-CN) | 1H-NMR (DMSO-d6) δ: 7.52 (1H, d, J = 5.4 Hz), 7.76-7.84 (2H, m), 7.87 (1H, d, J = 5.4 Hz), 7.97 (1H, s), 8.04 (1H, d, J = 8.3 Hz), 8.29 (1H, s), 8.49 (1H, s). | Ex. 1 |
| 961 | (dimethylpyrazolopyridine-phenyl-triazole-CN) | 1H-NMR (DMSO-d6) δ: 2.63 (3H, s), 2.75 (3H, s), 4.02 (3H, s), 7.64 (1H, s), 7.76 (1H, t, J = 7.9 Hz), 7.99 (1H, t, J = 7.9 Hz), 8.35 (1H, t, J = 7.9 Hz), 8.84 (1H, s). | Ex. 2 |

TABLE 4-continued

| | Structure | 1H-NMR | Ex. |
|---|---|---|---|
| 962 | (imidazo[1,2-a]pyridin-3-yl-phenyl-triazole-carbonitrile) | 1H-NMR (DMSO-d6) δ: 7.06-7.09 (1H, m), 7.42-7.46 (1H, m), 7.74-7.96 (5H, m), 8.18 (1H, s), 8.73 (1H, d, J = 7.0 Hz). | Ex. 2 |
| 963 | (6-trifluoromethyl-imidazo[1,2-a]pyridin-2-yl-phenyl-triazole-carbonitrile) | 1H-NMR (DMSO-d6) δ: 7.53 (1H, dd, J = 1.5, 9.5 Hz), 7.73 (1H, t, J = 7.8 Hz), 7.83 (1H, d, J = 9.5 Hz), 7.88 (1H, d, J = 7.8 Hz), 8.17 (1H, d, J = 7.8 Hz), 8.55 (1H, s), 8.60 (1H, s), 9.29 (1H, s). | Ex. 2 |
| 964 | (imidazo[1,2-a]pyridin-2-yl-phenyl-triazole-carbonitrile) | 1H-NMR (DMSO-d6) δ: 6.93-6.97 (1H, m), 7.28-7.33 (1H, m), 7.63 (1H, d, J = 8.8 Hz), 7.69 (1H, t, J = 7.8 Hz), 7.83-7.86 (1H, m), 8.12-8.14 (1H, m), 8.50-8.53 (2H, m), 8.59-6.61 (1H, m). | Ex. 2 |

TABLE 4-continued

| | Structure | 1H-NMR | Ex. |
|---|---|---|---|
| 965 | [imidazo[1,2-a]pyridine-F, phenyl, triazole-CN] | 1H-NMR (DMSO-d6) δ: 7.36-7.42 (1H, m), 7.68-7.72 (2H, m), 7.84-7.86 (1H, m), 8.12-8.14 (1H, m), 8.50-8.52 (2H, m), 8.83-8.85 (1H, m). | Ex. 2 |
| 966 | [5-fluorobenzofuran, phenyl, triazole-CN] | 1H-NMR (DMSO-d6) δ: 7.16-7.24 (1H, m), 7.51-7.56 (2H, m), 7.67-7.74 (1H, m), 7.78 (1H, d, J = 7.7 Hz), 7.91-7.97 (1H, m), 8.09-8.14 (1H, m), 8.42 (1H, s). | Ex. 1 |
| 967 | [5-fluorobenzofuran, chlorophenyl, triazole-CN] | 1H-NMR (DMSO-d6) δ: 7.19-7.27 (1H, m), 7.55 (1H, dd, J = 2.5, 8.7 Hz), 7.68 (1H, s), 7.69-7.74 (1H, m), 7.94 (1H, s), 8.19 (1H, s), 8.36 (1H, s). | Ex. 1 |

| | | |
|---|---|---|
| 968 | [structure] | 1H-NMR (DMSO-d6) δ: 0.27-0.33 (2H, m), 0.53-0.60 (2H, m), 1.01-1.14 (1H, m), 2.75 (2H, d, J = 7.0 Hz), 8.02 (1H, d, J = 5.1 Hz), 8.06-8.08 (1H, m), 8.46 (1H, s), 8.84 (1H, t, J = 1.6 Hz), 8.34 (1H, d, J = 5.1 Hz). Ex. 1 |
| 969 | [structure] | 1H-NMR (DMSO-d6) δ: 4.20 (2H, s), 7.10-7.18 (2H, m), 7.33-7.40 (2H, m), 7.97-8.03 (2H, m), 8.42 (1H, s), 8.84 (1H, s), 9.31 (1H, d, J = 5.0 Hz). Ex. 1 |
| 970 | [structure] | 1H-NMR (DMSO-d6) δ: 4.11 (2H, s), 6.97-7.04 (2H, m), 7.18-7.25 (2H, m), 7.51-7.68 (3H, m), 7.75-7.84 (3H, m), 8.02-8.05 (1H, m). Ex. 1 |

TABLE 4-continued

| | | | |
|---|---|---|---|
| 971 | (structure: 4-fluorobenzyl and 5-(trifluoromethyl)pyridin-2-yl substituted phenyl triazole carbonitrile) | 1H-NMR (DMSO-d6) δ: 4.16 (2H, s), 7.10-7.18 (2H, m), 7.35-7.41 (2H, m), 7.89 (1H, s), 8.21-8.26 (2H, m), 8.34-8.40 (1H, m), 8.50-8.54 (1H, m), 9.07-9.11 (1H, m). | Ex. 1 |
| 972 | (structure: n-propyl and 4-(trifluoromethyl)pyrimidin-2-yl substituted phenyl triazole carbonitrile) | 1H-NMR (DMSO-d6) δ: 0.97 (3H, t, J = 7.3 Hz), 1.68-1.75 (2H, m), 2.79 (2H, t, J = 7.4 Hz), 7.96 (1H, s), 8.03 (1H, d, J = 5.0 Hz), 8.38 (1H, s), 8.83 (1H, s), 9.34 (1H, d, J = 5.0 Hz). | Ex. 1 |

| | | | |
|---|---|---|---|
| 973 | 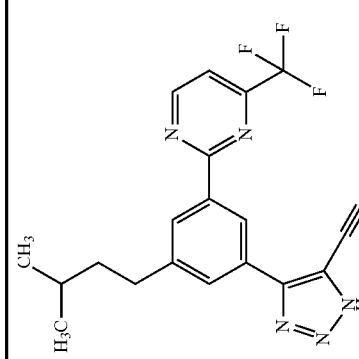 | 1H-NMR (DMSO-d6) δ: 0.95 (6H, d, J = 6.5 Hz), 1.55-1.66 (3H, m), 2.82 (2H, t, J = 7.5 Hz), 7.97 (1H, s), 8.03 (1H, d, J = 5.0 Hz), 8.40 (1H, s), 8.82 (1H, s), 9.34 (1H, d, J = 5.0 Hz). | Ex. 1 |
| 974 | 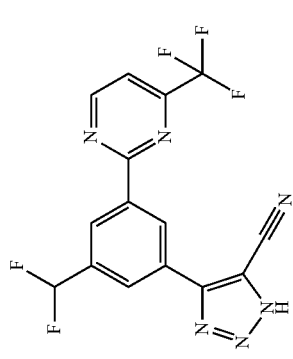 | 1H-NMR (DMSO-d6) δ: 7.36 (1H, t, J = 55.5 Hz), 8.10 (1H, d, J = 5.0 Hz), 8.33 (1H, s), 8.72 (1H, s), 9.16 (1H, s), 9.39 (1H, d, J = 5.0 Hz). | Ex. 1 |
| 975 | 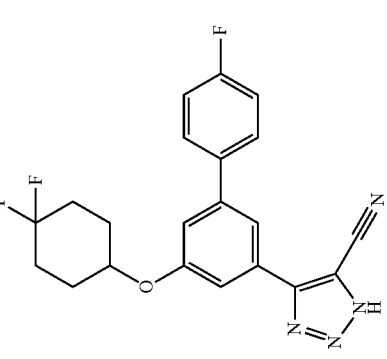 | 1H-NMR (DMSO-d6) δ: 1.84-2.16 (8H, m), 4.83 (1H, m), 7.34-7.38 (2H, m), 7.46 (2H, s), 7.72 (1H, s), 7.77-7.81 (2H, m). | Ex. 1 |

TABLE 4-continued

| | | | |
|---|---|---|---|
| 976 | structure with 4,4-difluoropiperidine, 3-chlorophenyl, triazole-CN | 1H-NMR (DMSO-d6) δ: 2.06-2.16 (4H, m), 3.45-3.49 (4H, m), 7.06 (1H, t, J = 2.0 Hz), 7.41-7.43 (2H, m). | Ex. 1 |
| 977 | structure with 4,4-difluoropiperidine, phenyl, triazole-CN | 1H-NMR (DMSO-d6) δ: 2.08-2.17 (4H, m), 3.43-3.47 (4H, m), 7.06-7.09 (1H, m), 7.39-7.46 (2H, m), 7.51-7.53 (1H, m). | Ex. 1 |
| 978 | structure with 4-fluoropiperidine, 3-chlorophenyl, triazole-CN | 1H-NMR (DMSO-d6) δ: 1.96-2.10 (4H, m), 3.30-3.36 (2H, m), 3.42-3.50 (2H, m), 4.80-4.95 (1H, m), 7.00 (1H, s), 7.35 (1H, s), 7.41 (1H, s). | Ex. 1 |
| 979 | structure with 4-(trifluoromethyl)piperidine, phenyl, triazole-CN | 1H-NMR (DMSO-d6) δ: 1.73-1.82 (2H, m), 1.98-2.04 (2H, m), 2.15-2.27 (1H, m), 2.77-2.85 (2H, m), 3.83-3.89 (2H, m), 7.06-7.09 (1H, m), 7.39-7.44 (2H, m), 7.51 (1H, s). | Ex. 1 |

TABLE 4-continued

| Ex. No. | STR | m.p. | ref. |
|---|---|---|---|
| 980 | 5-chlorothiophene-phenyl-triazole-carbonitrile | 243-244 | Ex. 1 |
| 981 | benzothiophene-phenyl-triazole-carbonitrile | 207 | Ex. 1 |

TABLE 4-continued
| | | | |
|---|---|---|---|
| 982 | 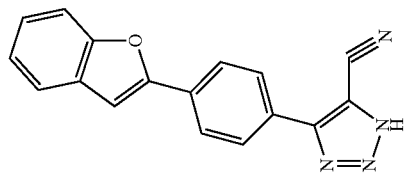 | 244-246 | Ex. 1 |
| 983 | 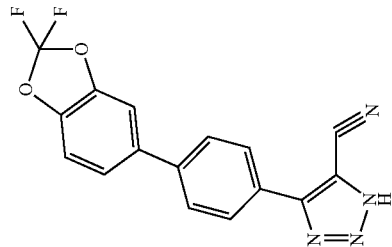 | 255 | Ex. 1 |

TABLE 4-continued
| | | | |
|---|---|---|---|
| 984 | 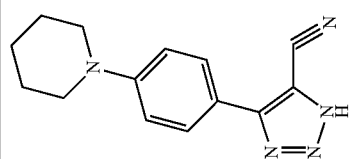 | 217 | Ex. 1 |
| 985 | 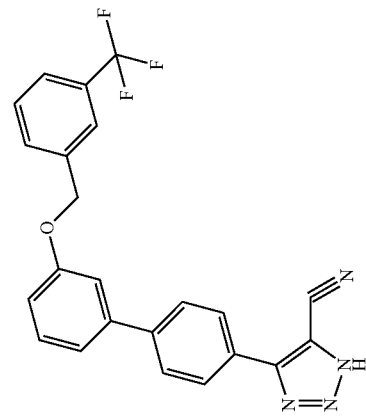 | 172-173 | Ex. 1 |
| 986 | 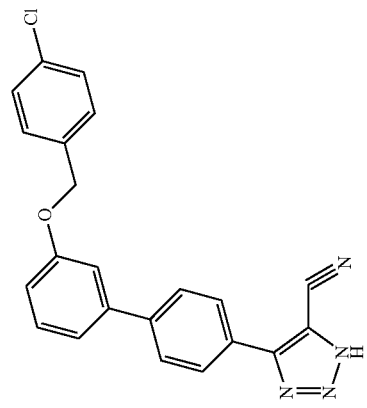 | 196 | Ex. 1 |

TABLE 4-continued
| | | | |
|---|---|---|---|
| 987 | 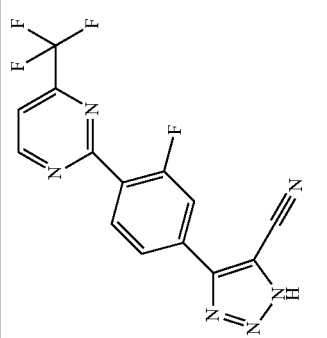 | 225-226 | Ex. 1 |
| 988 | 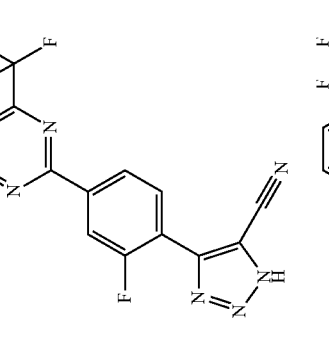 | 183-185 | Ex. 1 |
| 989 | 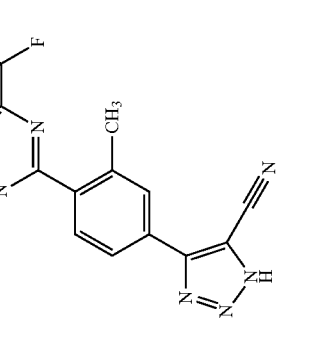 | 214-218 | Ex. 1 |

TABLE 4-continued

| Ex. No. | STR | | 1H-NMR | ref. |
|---|---|---|---|---|
| 990 | (structure: 4-(trifluoromethyl)pyrimidin-2-yl with difluorophenyl-triazole-carbonitrile) | 183-186 | | Ex. 1 |
| 991 | (structure: 4-(trifluoromethyl)pyrimidin-2-yl with chlorophenyl-triazole-carbonitrile) | 192-195 | | Ex. 1 |
| 992 | (structure: naphthalen-2-yl-phenyl-triazole-carbonitrile) | | 1H-NMR (CDCl3) δ: 7.56-7.59 (2H, m), 7.94-7.97 (2H, m), 8.03-8.10 (6H, m), 8.35 (1H, s). | Ex. 1 |

TABLE 4-continued
| | | | |
|---|---|---|---|
| 993 | 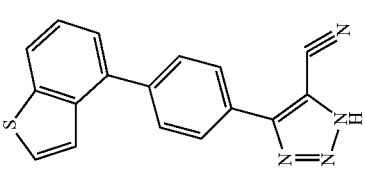 | 1H-NMR (DMSO-d6) δ: 7.46-7.52 (3H, m), 7.83-7.86 (3H, m), 8.05-8.10 (3H, m). | Ex. 1 |
| 994 | 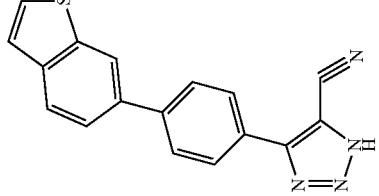 | 1H-NMR (DMSO-d6) δ: 7.52 (1H, d, J = 5.4 Hz), 7.78-7.84 (2H, m), 7.92-8.08 (5H, m), 8.45 (1H, s). | Ex. 1 |

TABLE 4-continued
| | | | |
|---|---|---|---|
| 995 | 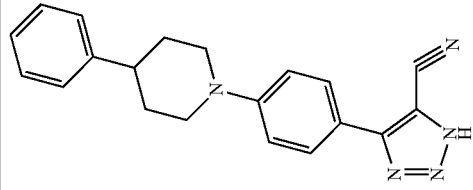 | 1H-NMR (DMSO-d6) δ: 1.69-1.77 (2H, m), 1.87-1.91 (2H, m), 2.74-2.79 (1H, m), 2.92 (2H, t, J = 10.8 Hz), 4.03-4.05 (2H, m), 7.16-7.21 (3H, m), 7.26-7.32 (4H, m), 7.74 (2H, d, J = 8.9 Hz). | Ex. 1 |
| 996 | 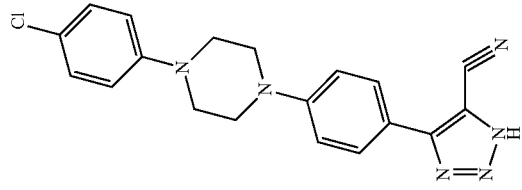 | 1H-NMR (DMSO-d6) δ: 3.29-3.31 (4H, m), 3.44-3.46 (4H, m), 7.01-7.04 (2H, m), 7.19 (2H, d, J = 9.0 Hz), 7.25-7.28 (2H, m), 7.76 (2H, d, J = 9.0 Hz). | Ex. 1 |

TABLE 4-continued

| | Structure | 1H-NMR | Ex. |
|---|---|---|---|
| 997 | 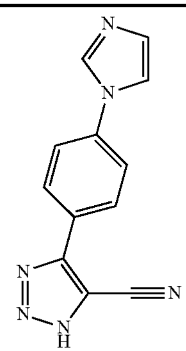 | 1H-NMR (DMSO-d6) δ: 7.25 (1H, s), 7.93-7.96 (3H, m), 8.01-8.04 (2H, m), 8.55 (1H, s). | Ex. 1 |
| 998 | 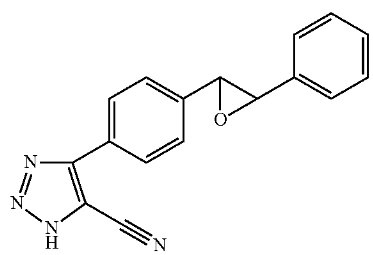 [SMILES: N#Cc1[nH]nnc1-c1ccc(C2OC2c2ccccc2)cc1] | 1H-NMR (CDCl3) δ: 3.89 (1H, d, J = 1.8 Hz), 3.94 (1H, d, J = 1.8 Hz), 7.33-7.42 (5H, m), 7.50 (2H, d, J = 8.3 Hz), 8.00 (2H, d, J = 8.3 Hz). | Ex. 1 |
| 999 | 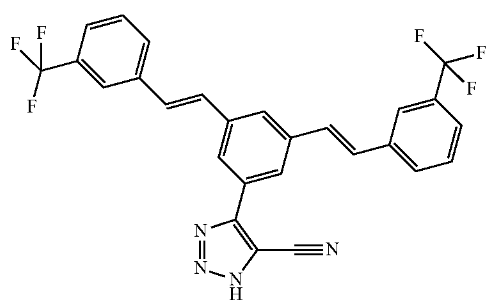 [SMILES: N#Cc1[nH]nnc1-c1cc(/C=C/c2cccc(C(F)(F)F)c2)cc(/C=C/c2cccc(C(F)(F)F)c2)c1] | 1H-NMR (DMSO-d6) δ: 7.55 (2H, d, J = 16.6 Hz), 7.61 (2H, d, J = 16.6 Hz), 7.64-7.69 (4H, m), 7.97-8.03 (6H, m), 8.18 (1H, s). | Ex. 1 |

TABLE 4-continued

| Ex. No. | STR | m.p. | ref. |
|---|---|---|---|
| 1000 | (structure) | 234-236 | Ex. 2 |
| 1001 | (structure) | 192-194 | Ex. 2 |
| 1002 | (structure) | 214-217 | Ex. 2 |

TABLE 4-continued

| | | | |
|---|---|---|---|
| 1003 | (structure) | 186-188 | Ex. 2 |
| 1005 | (structure) | 169-171 | Ex. 1 |
| 1007 | (structure) | 176-177 | Ex. 1 |

TABLE 4-continued

| Ex. No. | STR | 1H-NMR | ref. |
|---|---|---|---|
| 1004 | (3-(benzothiophen-2-yl-vinyl)phenyl triazole carbonitrile) | 1H-NMR (CDCl3-CD3OD) δ: 7.04 (1H, d, J = 16.1 Hz), 7.31-7.35 (3H, m), 7.44 (1H, d, J = 16.1 Hz), 7.53 (1H, t, J = 7.7 Hz), 7.61-7.65 (1H, m), 7.71-7.75 (1H, m), 7.78-7.81 (1H, m), 7.85-7.89 (1H, m), 8.09-8.11 (1H, m). | Ex. 1 |
| 1006 | (3-(quinolin-2-yl-vinyl)phenyl triazole carbonitrile) | 1H-NMR (DMSO-d6) δ: 7.56-7.61 (2H, m), 7.66 (1H, t, J = 7.6 Hz), 7.75-7.79 (1H, m), 7.85-8.04 (6H, m), 8.24 (1H, s), 8.39 (1H, d, J = 8.6 Hz). | Ex. 2 |
| 1008 | (3-chloro-5-(cyclohexyl-vinyl)phenyl triazole carbonitrile) | 1H-NMR (DMSO-d6) δ: 1.16-1.33 (5H, m), 1.71-1.80 (5H, m), 2.10-2.27 (1H, m), 6.45-6.47 (2H, m), 7.68 (1H, s), 7.72 (1H, s), 7.85 (1H, s). | Ex. 1 |

TABLE 4-continued
| | | | |
|---|---|---|---|
| 1009 | 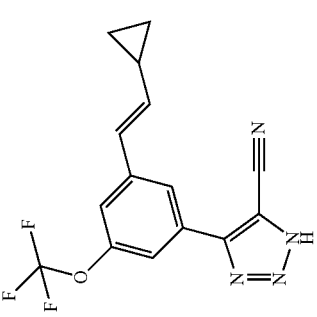 | 1H-NMR (DMSO-d6) δ: 0.57-0.60 (2H, m), 0.84-0.88 (2H, m), 1.62-1.67 (1H, m), 6.09 (1H, dd, J = 9.4, 15.8 Hz) 6.60 (1H, d, J = 15.8 Hz) 7.59 (1H, s), 7.61 (1H, s), 8.10 (1H, s). | Ex. 1 |
| 1010 | 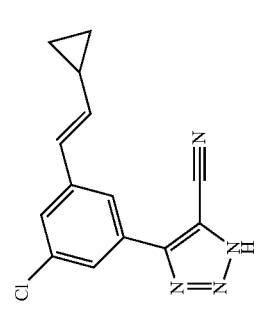 | 1H-NMR (DMSO-d6) δ: 0.56-0.59 (2H, m), 0.83-0.87 (2H, m), 1.62 (1H, m), 6.05 (1H, dd, J = 9.3, 15.8 Hz), 6.55 (1H, d, J = 15.8 Hz), 7.64 (1H, s), 7.68 (1H, s), 7.77 (1H, s). | Ex. 1 |
| 1011 | 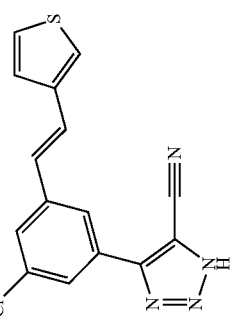 | 1H-NMR (DMSO-d6) δ: 7.18 (1H, d, J = 16.4 Hz), 7.47 (1H, d, J = 16.4 Hz), 7.52-7.67 (3H, m), 7.76 (1H, s), 7.84 (1H, s), 7.97 (1H, s). | Ex. 1 |

TABLE 4-continued

| | Structure | 1H-NMR | |
|---|---|---|---|
| 1012 | (3-(trifluoromethoxy)-5-(2-cyclohexylvinyl)phenyl triazole carbonitrile) | 1H-NMR (DMSO-d6) δ: 1.09-1.41 (5H, m), 1.58-1.85 (5H, m), 2.50 (1H, m), 6.50 (2H, m), 7.60 (1H, s), 7.65 (1H, s), 7.93 (1H, s). | Ex. 1 |
| 1013 | (3-chloro-5-(3-cyclopentylpropenyl)phenyl triazole carbonitrile) | 1H-NMR (DMSO-d6) δ: 1.11-1.28 (2H, m), 1.40-2.05 (7H, m), 2.22-2.26 (2H, m), 6.50-6.52 (2H, m), 7.69 (1H, s), 7.73 (1H, s), 7.85 (1H, s). | Ex. 1 |
| 1014 | (3-(trifluoromethyl)-5-(2-cyclopropylvinyl)phenyl triazole carbonitrile) | 1H-NMR (DMSO-d6) δ: 0.58-0.62 (2H, m), 0.85-0.89 (2H, m), 1.62-1.70 (1H, m), 6.15 (1H, dd, J = 9.4, 15.8 Hz), 6.66 (1H, d, J = 15.8 Hz), 7.90 (1H, s), 7.96 (1H, s), 8.10 (1H, s). | Ex. 2 |

| | | | |
|---|---|---|---|
| 1015 | [structure] | 1H-NMR (DMSO-d6) δ: 1.55-1.77 (4H, m), 2.10-2.31 (4H, m), 6.07 (1H, s), 6.58 (1H, d, J = 16.2 Hz), 7.07 (1H, d, J = 16.2 Hz), 7.63 (1H, s), 7.68 (1H, s), 7.99 (1H, s). | Ex. 1 |
| 1016 | [structure] | 1H-NMR (DMSO-d6) δ: 1.58-1.69 (4H, m), 2.18-2.23 (4H, m), 6.05 (1H, s), 6.53 (1H, d, J = 16.2 Hz), 7.05 (1H, d, J = 16.2 Hz), 7.71 (1H, s), 7.76 (1H, s), 7.90 (1H, s). | Ex. 1 |
| 1017 | [structure] | 1H-NMR (DMSO-d6) δ: 7.39-7.44 (4H, m), 7.65 (1H, t, J = 7.6 Hz), 7.77-7.82 (3H, m), 8.06 (1H, s). | Ex. 1 |
| 1018 | [structure] | 1H-NMR (DMSO-d6) δ: 7.52 (1H, d, J = 16.4 Hz), 7.67 (1H, t, J = 7.8 Hz), 7.76-7.87 (3H, m), 7.93 (1H, d, J = 7.6 Hz), 7.98 (1H, d, J = 8.0 Hz), 8.13 (1H, t, J = 7.8 Hz), 8.21 (1H, s). | Ref. Ex. 107, Ref. Ex. 91, Ex. 2 |

TABLE 4-continued

| | Structure | 1H-NMR | Ex. |
|---|---|---|---|
| 1019 | (3-(pyridin-2-yl-vinyl)phenyl triazole carbonitrile) | 1H-NMR (CDCl3-CD3OD) δ: 7.22-7.27 (1H, m), 7.28 (1H, d, J = 16.4 Hz), 7.53-7.59 (2H, m), 7.60 (1H, d, J = 16.4 Hz), 7.67-7.73 (1H, m), 7.76 (1H, dt, J = 1.8, 7.7 Hz), 7.90-7.95 (1H, m), 8.15 (1H, s), 8.55-8.58 (1H, m). | Ex. 1 |
| 1020 | (benzo[d][1,3]dioxol-5-yl-vinyl-phenyl triazole carbonitrile) | 1H-NMR (DMSO-d6) δ: 6.06 (2H, s), 6.95 (1H, d, J = 8.0 Hz), 7.07 (1H, dd, J = 1.8, 8.0 Hz), 7.21 (1H, d, J = 16.4 Hz), 7.29 (1H, d, J = 16.4 Hz), 7.34 (1H, d, J = 1.6 Hz), 7.60 (1H, t, J = 7.7 Hz), 7.71-7.78 (2H, m), 8.04 (1H, s). | Ex. 1 |
| 1021 | (2,2-difluorobenzo[d][1,3]dioxol-5-yl-vinyl-trifluoromethoxyphenyl triazole carbonitrile) | 1H-NMR (DMSO-d6) δ: 7.41-7.52 (4H, m), 7.72-7.81 (3H, m), 8.07 (1H, s). | Ex. 1 |
| 1022 | (2,2-difluorobenzo[d][1,3]dioxol-5-yl-vinyl-chlorophenyl triazole carbonitrile) | 1H-NMR (DMSO-d6) δ: 7.34-7.52 (4H, m), 7.79 (1H, s), 7.80 (1H, s), 7.89 (1H, s), 7.99 (1H, s). | Ex. 1 |

TABLE 4-continued

| Ex. No. | STR | 1H-NMR | ref. |
|---|---|---|---|
| 1023 | [structure: 5-chloro-3-(2,2,4,4-tetrafluoro-4H-benzo[d][1,3]dioxin-6-yl)vinyl phenyl triazole carbonitrile] | 1H-NMR (DMSO-d6) δ: 7.53-7.55 (3H, m), 7.82 (1H, t, J = 1.7 Hz), 7.92 (1H, t, J = 1.7 Hz), 8.02-8.08 (2H, m), 8.21 (1H, s). | Ex. 1 |
| 1024 | [structure: 3-chloro-5-[2-(4-trifluoromethylpyridin-2-yl)vinyl]phenyl triazole carbonitrile] | m.p. 230-233 | Ex. 1 |
| 1029 | [structure: 3-[2-(5-chlorothiophen-2-yl)vinyl]phenyl triazole carbonitrile] | 193-195 | Ex. 2 |

| Ex. No. | STR | 1H-NMR | ref. |
|---|---|---|---|
| 1025 | [structure: 3-[2-(furan-2-yl)vinyl]phenyl triazole carbonitrile] | 1H-NMR (CDCl3) δ: 6.96 (1H, d, J = 16.1 Hz), 7.03 (1H, dd, J = 3.6, 5.1 Hz), 7.12 (1H, d, J = 3.6 Hz), 7.24 (1H, d, J = 5.1 Hz), 7.34 (1H, d, J = 16.1 Hz), 7.51 (1H, t, J = 7.8 Hz), 7.59-7.62 (1H, m), 7.84-7.88 (1H, m), 8.06 (1H, s). | Ex. 1 |

TABLE 4-continued

| | Structure | NMR | Ex. |
|---|---|---|---|
| 1026 | (furan-stilbene-triazole-CN) | 1H-NMR (CDCl3) δ: 6.42 (1H, d, J = 3.3 Hz), 6.45 (1H, dd, J = 1.8, 3.3 Hz), 6.98 (1H, d, J = 16.2 Hz), 7.08 (1H, d, J = 16.2 Hz), 7.43-7.44 (1H, m), 7.50 (1H, t, J = 7.7 Hz), 7.57-7.62 (1H, m), 7.82-7.87 (1H, m), 8.06 (1H, s). | Ex. 1 |
| 1027 | (quinoline-stilbene-CF3-triazole-CN) | 1H-NMR (DMSO-d6) δ: 7.59-7.63 (1H, m), 7.75-7.82 (2H, m), 7.94 (1H, d, J = 8.9 Hz), 7.98-8.06 (3H, m), 8.14 (1H, s), 8.32 (1H, s), 8.43 (1H, d, J = 8.4 Hz), 8.53 (1H, s), | Ex. 2 |
| 1028 | (triazole-CN-phenyl-stilbene-phenyl-triazole-CN) | 1H-NMR (DMSO-d6) δ: 7.47 (2H, s), 7.66 (2H, t, J = 7.8 Hz), 7.80-7.87 (4H, m), 8.13 (2H, bs). | Ex. 2 |
| 1030 | (thiophene-stilbene-triazole-CN) | 1H-NMR (CDCl3) δ: 7.00 (1H, d, J = 16.2 Hz), 7.23 (1H, d, J = 16.2 Hz), 7.32-7.39 (3H, m), 7.51 (1H, t, J = 7.7 Hz), 7.61 (1H, d, J = 7.9 Hz), 7.85 (1H, d, J = 7.7 Hz), 8.06 (1H, s). | Ex. 1 |

TABLE 4-continued

| | Structure | 1H-NMR | |
|---|---|---|---|
| 1031 | 5-methylfuran-vinyl-phenyl-triazole-CN | 1H-NMR (CDCl3) δ: 2.37 (3H, s), 6.03 (1H, dd, J = 1.0, 3.1 Hz), 6.30 (1H, d, J = 3.1 Hz), 6.91 (1H, d, J = 16.2 Hz), 7.00 (1H, d, J = 16.2 Hz), 7.49 (1H, d, J = 7.7 Hz), 7.57 (1H, d, J = 7.9 Hz), 7.81 (1H, d, J = 7.5 Hz), 8.03 (1H, s). | Ex. 1 |
| 1032 | benzofuran-vinyl-phenyl-triazole-CN | 1H-NMR (CDCl3) δ: 6.75 (1H, s), 7.11 (1H, d, J = 16.2 Hz), 7.19-7.33 (2H, m), 7.37 (1H, d, J = 16.2 Hz), 7.47-7.57 (3H, m), 7.66 (1H, d, J = 7.7 Hz), 7.89 (1H, d, J = 7.5 Hz), 8.14 (1H, s), 12.2 (1H, br). | Ex. 1 |
| 1033 | 4-fluoronaphthyl-vinyl-(trifluoromethoxy)phenyl-triazole-CN | 1H-NMR (DMSO-d6) δ: 7.40-7.47 (2H, m), 7.70-7.74 (3H, m), 7.97-8.11 (3H, m), 8.12-8.26 (2H, m), 8.54-8.56 (1H, m). | Ex. 1 |

TABLE 4-continued

| | Structure | 1H-NMR | Ex. |
|---|---|---|---|
| 1034 | (benzothiophene-vinyl-phenyl-triazole-CN) | 1H-NMR (CDCl3) δ: 7.22 (1H, d, J = 16.1 Hz), 7.36-7.56 (4H, m), 7.61 (1H, s), 7.67 (1H, d, J = 7.8 Hz), 7.87-7.91 (2H, m), 8.03 (1H, d, J = 7.8 Hz), 8.15 (1H, s). | Ex. 1 |
| 1035 | (N-methylindole-vinyl-phenyl-triazole-CN) | 1H-NMR (CDCl3) δ: 3.82 (3H, s), 7.13 (1H, d, J = 16.4 Hz), 7.23-7.38 (4H, m), 7.41 (1H, d, J = 16.4 Hz), 7.50 (1H, t, J = 7.8 Hz), 7.62-7.65 (1H, m), 7.75-7.80 (1H, m), 7.98-8.02 (1H, m), 8.08 (1H, s). | Ex. 1 |
| 1036 | (6-trifluoromethylpyridine-vinyl-chlorophenyl-triazole-CN) | 1H-NMR (DMSO-d6) δ: 7.62 (1H, d, J = 16.1 Hz), 7.77-7.82 (2H, m), 7.86-7.87 (1H, m), 7.94 (1H, d, J = 7.9 Hz), 8.06-8.07 (1H, m), 8.12-8.16 (2H, m). | Ex. 2 |
| 1037 | (4-trifluoromethylpyrimidine-vinyl-ethoxyphenyl-triazole-CN) | 1H-NMR (DMSO-d6) δ: 1.39 (3H, t, J = 7.0 Hz), 4.20 (2H, q, J = 7.0 Hz), 7.42 (1H, s), 7.52 (1H, d, J = 15.7 Hz), 7.60 (1H, s), 7.85 (1H, s), 7.88 (1H, d, J = 5.0 Hz), 8.06 (1H, d, J = 15.7 Hz) 9.20 (1H, d, J = 5.0 Hz). | Ex. 2 |

TABLE 4-continued

| Ex. No. | STR | m.p. | ref. |
|---|---|---|---|
| 1038 | | | 1H-NMR (DMSO-d6) δ: 7.59 (1H, d, J = 16.2 Hz), 7.91-7.92 (2H, m), 8.08 (1H, d, J = 16.2 He), 8.18 (1H, s), 8.26 (1H, s), 9.22 (1H, d, J = 5.0 Hz). Ex. 2 |
| 1039 | | 167-168 | Ex. 1 |
| 1040 | | 156-158 | Ex. 1 |

TABLE 4-continued
| Ex. No. | STR | | ref. |
|---|---|---|---|
| 1041 | 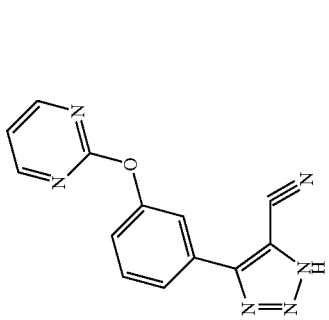 | 205-206 | Ex. 1 |
| | | 1H-NMR | |
| 1042 | 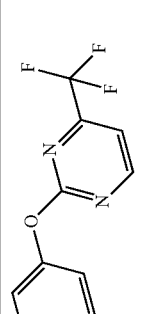 | 1H-NMR (DMSO-d6) δ: 7.36-7.43 (2H, m), 7.58-7.64 (1H, m), 7.89 (1H, s), 7.94-7.96 (1H, m), 8.80-8.81 (1H, m) | Ex. 1 |
| 1043 | 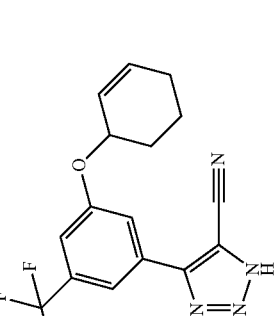 | 1H-NMR (CDCl3) δ: 1.70-2.16 (6H, m), 4.95 (1H, bs), 5.89-5.95 (1H, m), 6.04-6.10 (1H, m), 7.30 (1H, s), 7.75 (1H, s), 7.82 (1H, s). | Ex. 2 |

TABLE 4-continued

| | Structure | 1H-NMR | Ex. |
|---|---|---|---|
| 1044 | 2,3-dihydro-1H-inden-2-yl ether of 3-(CF₃)-5-(5-cyano-1H-1,2,3-triazol-4-yl)phenol | 1H-NMR (CDCl3) δ: 3.23 (2H, d, J = 16.9 Hz), 3.48 (2H, dd, J = 6.3, 16.9 Hz), 5.27-5.31 (1H, m), 7.20-7.29 (5H, m), 7.74 (1H, s), 7.83 (1H, s). | Ex. 191 |
| 1045 | 2,3-dihydro-1H-inden-1-yl ether of 3-(CF₃)-5-(5-cyano-1H-1,2,3-triazol-4-yl)phenol | 1H-NMR (CDCl3) δ: 2.27-2.31 (1H, m), 2.67-2.72 (1H, m), 3.02-3.06 (1H, m), 3.19-3.22 (1H, m), 5.90-5.93 (1H, m), 7.29-7.38 (4H, m), 7.47-7.49 (1H, m), 7.87 (2H, s). | Ex. 191 |
| 1046 | 1,2,3,4-tetrahydronaphthalen-1-yl ether of 3-(CF₃)-5-(5-cyano-1H-1,2,3-triazol-4-yl)phenol | 1H-NMR (CDCl3) δ: 1.84-1.89 (1H, m), 2.01-2.23 (3H, m), 2.81-2.93 (2H, m), 5.50-5.53 (1H, m), 7.13-7.43 (5H, m), 7.84 (2H, s). | Ex. 191 |
| 1047 | 4-(trifluoromethyl)pyrimidin-2-yl ether of 3-(CF₃)-5-(5-cyano-1H-pyrazol-4-yl)phenol | 1H-NMR (CDCl3) δ: 7.46 (1H, d, J = 4.9 Hz), 7.66 (1H, s), 8.14 (1H, s), 8.21 (1H, s), 8.85 (1H, d, J = 4.9 Hz). | Ex. 2 |

TABLE 4-continued

| Ex. No. | STR | m.p. | ref. |
|---|---|---|---|
| 1048 | (5-chloro-3-{4-(trifluoromethyl)pyridin-2-yloxy}phenyl)-triazole-carbonitrile | 1H-NMR (DMSO-d6) δ: 7.56-7.64 (3H, m), 7.68 (1H, t, J = 1.5 Hz), 7.82 (1H, t, J = 1.5 Hz), 8.45 (1H, d, J = 5.2 Hz). | Ex. 1 |
| 1049 | (3-methyl-5-{4-(trifluoromethyl)pyrimidin-2-yloxy}phenyl)-triazole-carbonitrile | 162-166 | Ex. 1 |
| 1050 | (3-{(4,4-difluorocyclohexyl)oxy}phenyl)-triazole-carbonitrile | 138-143 | Ex. 1 |

TABLE 4-continued
| Ex. No. | STR | 1H-NMR | ref. |
|---|---|---|---|
| 1051 | 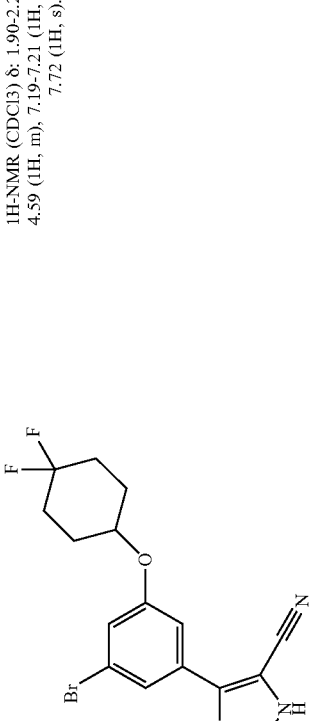 | 1H-NMR (CDCl3) δ: 1.90-2.20 (8H, m), 4.54-4.59 (1H, m), 7.19-7.21 (1H, m), 7.49 (1H, s), 7.72 (1H, s). | Ex. 1 |
| 1052 | 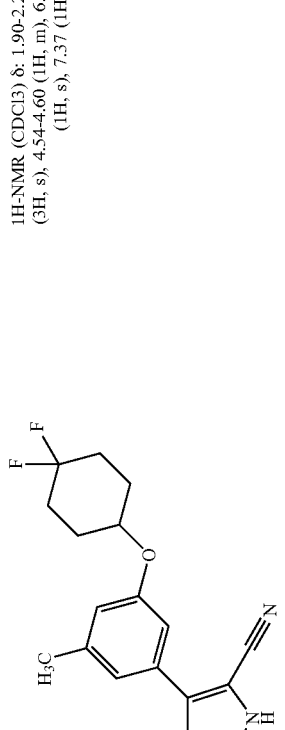 | 1H-NMR (CDCl3) δ: 1.90-2.20 (8H, m), 2.41 (3H, s), 4.54-4.60 (1H, m), 6.88 (1H, s), 7.32 (1H, s), 7.37 (1H, s). | Ex. 1 |
| 1053 | 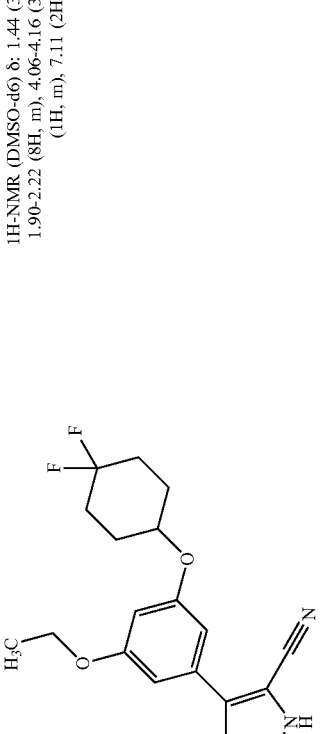 | 1H-NMR (DMSO-d6) δ: 1.44 (3H, t, J = 7.0 Hz), 1.90-2.22 (8H, m), 4.06-4.16 (3H, m), 6.58-6.59 (1H, m), 7.11 (2H, s). | Ex. 1 |

TABLE 4-continued
| | | | |
|---|---|---|---|
| 1054 |  | 1H-NMR (DMSO-d6) δ: 2.45 (2H, t, J = 7.2 Hz), 2.88 (2H, t, J = 7.2 Hz), 6.90-7.01 (3H, m), 7.14-7.17 (2H, m), 7.85-7.88 (2H, m), 10.1 (1H, s). | Ex. 1 |
| 1055 |  | 1H-NMR (DMSO-d6) δ: 2.44 (2H, t, J = 7.3 Hz), 2.77 (2H, t, J = 7.3 Hz), 6.67 (1H, d, J = 7.9 Hz), 6.78 (1H, d, J = 7.9 Hz), 7.13 (2H, d, J = 8.8 Hz), 7.21 (1H, t, J = 7.9 Hz), 7.87 (2H, d, J = 8.8 Hz), 10.3 (1H, s). | Ex. 1 |

TABLE 4-continued
| | | | |
|---|---|---|---|
| 1056 |  | 1H-NMR (DMSO-d6) δ: 2.55 (2H, t, J = 7.9 Hz), 2.88 (2H, t, J = 7.9 Hz), 3.27 (3H, s), 7.02-7.06 (2H, m), 7.14-7.20 (3H, m), 7.88 (2H, d, J = 8.3 Hz). | Ex. 1 |
| 1057 |  | 1H-NMR (DMSO-d6) δ: 2.51-2.55 (2H, m), 2.75-2.79 (2H, m), 3.29 (3H, s), 6.78-6.81 (1H, m), 7.04 (1H, d, J = 7.8 Hz), 7.12-7.16 (2H, m), 7.35 (1H, t, J = 8.2 Hz), 7.85-7.89 (2H, m). | Ex. 1 |

TABLE 4-continued
| Ex. No. | STR | m.p. | ref. |
|---|---|---|---|
| 1058 | 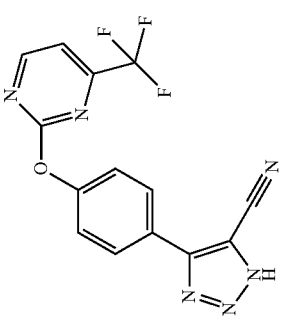 | 177-179 | Ex. 1 |
| 1059 | 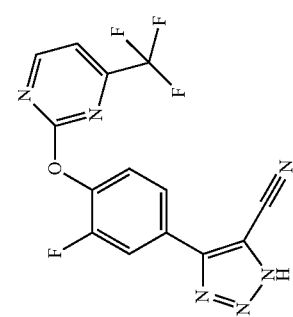 | 186-187 | Ex. 1 |
| 1060 | 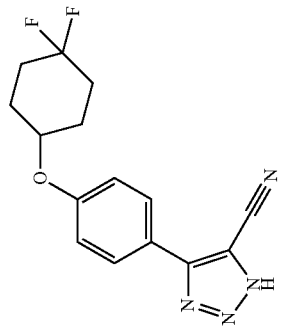 | 223-226 | Ex. 1 |

TABLE 4-continued
| | | | |
|---|---|---|---|
| 1061 |  | 241 | Ex. 1 |
| 1062 |  | 110-111 | Ex. 1 |
| 1063 |  | 116-117 | Ex. 1 |
| 1064 |  | 148-151 | Ex. 1 |

TABLE 4-continued

| Ex. No. | STR | | 1H-NMR | ref. |
|---|---|---|---|---|
| 1065 | (structure) | 167-168 | | Ex. 1 |
| 1066 | (structure) | 162-163 | | Ex. 1 |
| 1067 | (structure) | | 1H-NMR (CDCl3) δ: 5.43 (2H, s), 6.91 (1H, dt, J = 2.3, 11.0 Hz), 7.20-7.25 (1H, m), 7.41-7.42 (1H, m), 7.60-7.66 (1H, m), 7.72 (1H, d, J = 8.5 Hz), 7.77-7.83 (1H, m), 8.00-8.06 (2H, m), 8.45 (1H, d, J = 8.5 Hz). | Ex. 2 |
| 1068 | (structure) | | 1H-NMR (CDCl3) δ: 5.47 (2H, s), 7.27-7.31 (1H, m), 7.49-7.66 (4H, m), 7.72 (1H, d, J = 8.5 Hz), 7.78-7.83 (1H, m), 8.00-8.05 (2H, m), 8.45 (1H, d, J = 8.5 Hz). | Ex. 2 |

TABLE 4-continued

| | Structure | NMR | Ex. |
|---|---|---|---|
| 1069 | 4-[3-fluoro-5-[[trans-4-(trifluoromethyl)cyclohexyl]methoxy]phenyl]-1H-1,2,3-triazole-5-carbonitrile | 1H-NMR (DMSO-d6) δ: 1.08-1.21 (2H, m), 1.24-1.38 (2H, m), 1.76-1.83 (1H, m), 1.91-1.96 (4H, m), 2.21-2.28 (1H, m), 3.89 (2H, d, J = 6.4 Hz), 7.13-7.16 (1H, m), 7.42-7.47 (1H, m), 7.50-7.55 (1H, m). | Ex. 2 |
| 1070 | 4-[3-[[trans-4-(trifluoromethyl)cyclohexyl]methoxy]phenyl]-1H-1,2,3-triazole-5-carbonitrile | 1H-NMR (CDCl3) δ:1.09-1.22 (2H, m), 1.32-1.45 (2H, m), 1.79-1.89 (1H, m), 2.02-2.10 (5H, m), 3.86 (2H, d, J = 6.2 Hz), 7.01-7.05 (1H, m), 7.43 (1H, t, J = 8.0 Hz), 7.47 (1H, t, J = 2.0 Hz), 7.54-7.56 (1H, m). | Ex. 2 |
| 1071 | 4-[3-fluoro-5-[[trans-4-(trifluoromethyl)cyclohexyl]methoxy]phenyl]-1H-1,2,3-triazole-5-carbonitrile | 1H-NMR (CDCl3) δ: 1.60-1.72 (4H, m), 1.77-1.85 (4H, m), 2.17-2.19 (2H, m), 3.97 (2H, d, J = 7.2 Hz), 6.75 (1H, dt, J = 2.3, 10.4 Hz), 7.28-7.32 (1H, m), 7.33-7.34 (1H, m). | Ex. 2 |
| 1072 | 4-[3-[[trans-4-(trifluoromethyl)cyclohexyl]methoxy]phenyl]-1H-1,2,3-triazole-5-carbonitrile | 1H-NMR (CDCl3) δ: 1.62-1.72 (4H, m), 1.74-1.86 (4H, m), 2.13-2.20 (2H, m), 3.99 (2H, d, J = 7.2 Hz), 7.03-7.07 (1H, m), 7.44 (1H, J = 8.0 Hz), 7.49-7.50 (1H, m), 7.55-7.58 (1H, m). | Ex. 2 |

TABLE 4-continued
| Ex. No. | STR | | 1H-NMR | ref. |
|---|---|---|---|---|
| 1073 | 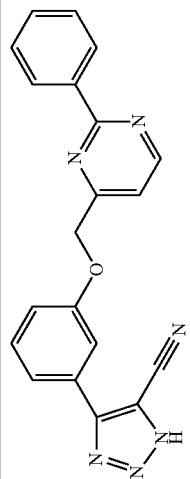 | | 1H-NMR (DMSO-d6) δ: 5.41 (2H, s), 7.29-7.33 (1H, m), 7.51-7.61 (7H, m), 8.39-8.44 (2H, m), 8.95 (1H, d, J = 4.8 Hz). | Ex. 2 |
| 1074 | 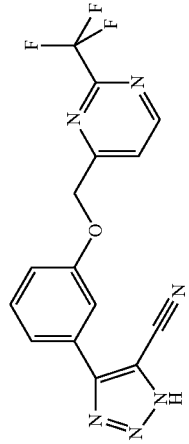 | | 1H-NMR (CDCl3) δ: 5.34 (2H, s), 7.13 (1H, dd, J = 2.1, 8.1 Hz), 7.50 (1H, t, J = 8.1 Hz), 7.62 (1H, t, J = 2.1 Hz), 7.68 (1H, d, J = 7.7 Hz), 7.84 (1H, d, J = 5.1 Hz), 8.95 (1H, d, J = 5.1 Hz), 12.26 (1H, brs). | Ex. 2 |
| Ex. No. | STR | m.p. | ref. |
|---|---|---|---|
| 1075 | 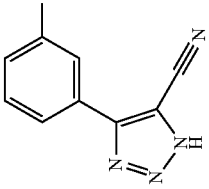 | 176 | Ex. 1 |

TABLE 4-continued

| | | | |
|---|---|---|---|
| 1076 | 145-147 | Ex. 1 | |
| 1077 | 115-117 | Ex. 1 | |
| 1078 | 168-170 | Ex. 1 | |
| 1079 | 205 | Ex. 1 | |

TABLE 4-continued
| | | | |
|---|---|---|---|
| 1081 | 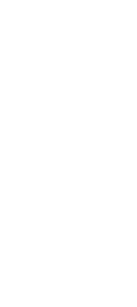 | 191 | Ex. 1 |
| 1082 |  | 185-186 | Ex. 1 |
| 1083 |  | 206-207 | Ex. 1 |
| 1085 |  | 97-100 | Ex. 1 |

TABLE 4-continued

| Ex. No. | STR | 126-132 1H-NMR | ref. |
|---|---|---|---|
| 1086 | (4,4-difluorocyclohexyl)methoxy-phenyl triazole carbonitrile structure | | Ex. 1 |
| 1080 | 6-(trifluoromethyl)pyridin-3-yl methoxy-phenyl triazole carbonitrile structure | 1H-NMR (DMSO-d6) δ: 6.39 (2H, s), 7.25-7.31 (1H, m), 7.49-7.61 (3H, m), 7.96 (1H, d, J = 8.1 Hz), 8.20 (1H, d, J = 7.8 Hz), 8.90 (1H, s). | Ex. 1 |
| 1084 | (2-methylthiazol-4-yl)methoxy-fluorophenyl triazole carbonitrile structure | 1H-NMR (DMSO-d6) δ: 2.67 (3H, s), 5.21 (2H, s), 7.18-7.22 (1H, m), 7.26-7.29 (1H, m), 7.36-7.37 (1H, m), 7.63 (1H, s). | Ex. 1 |
| 1087 | 2,5-bis(trifluoromethyl)phenyl butoxy-phenyl triazole carbonitrile structure | 1H-NMR (DMSO-d6) δ: 1.75-1.89 (4H, m), 2.91-2.94 (2H, m), 4.10 (2H, t, J = 6.1 Hz), 7.12-7.14 (1H, m), 7.42-7.54 (3H, m), 7.79 (1H, d, J = 8.2 Hz), 7.92 (1H, s), 7.93 (1H, s). | Ex. 1 |

TABLE 4-continued

| | Structure | 1H-NMR | Ex. |
|---|---|---|---|
| 1088 | (3-(pyridin-3-ylmethoxy)-5-(trifluoromethyl)phenyl triazole carbonitrile) | 1H-NMR (DMSO-d6) δ: 5.34 (2H, s), 7.44-7.48 (1H, m), 7.58 (1H, s), 7.79 (2H, s), 7.94 (1H, d, J = 7.8 Hz), 8.56-8.59 (1H, m), 8.72 (1H, s). | Ex. 1 |
| 1089 | (3-(pyridin-2-ylmethoxy)-5-(trifluoromethyl)phenyl triazole carbonitrile) | 1H-NMR (DMSO-d6) δ: 5.36 (2H, s), 7.35-7.36 (1H, m), 7.57-7.59 (2H, m), 7.78-7.86 (3H, m), 8.57-8.60 (1H, m). | Ex. 1 |
| 1090 | (3-(thiophen-3-ylmethoxy)-5-(trifluoromethyl)phenyl triazole carbonitrile) | 1H-NMR (DMSO-d6) δ: 5.29 (2H, s), 7.22-7.24 (1H, m), 7.56-7.60 (2H, m), 7.66 (1H, s), 7.78 (2H, s). | Ex. 1 |

TABLE 4-continued

| | Structure | 1H-NMR | Ex. |
|---|---|---|---|
| 1091 | (adamantylmethoxy-CF3-phenyl-triazole-CN) | 1H-NMR (CDCl3) δ: 1.70-1.82 (12H, m), 2.06 (3H, s), 3.63 (2H, s), 7.28 (1H, s), 7.71 (1H, s), 7.81 (1H, s). | Ex. 2 |
| 1092 | (1-methylcyclohexylmethoxy-CF3-phenyl-triazole-CN) | 1H-NMR (CDCl3) δ: 1.06 (3H, s), 1.26-1.52 (10H, m), 3.84 (2H, s), 7.26 (1H, s), 7.69 (1H, s), 7.79 (1H, s). | Ex. 191 |
| 1093 | (1-phenylcyclopropylmethoxy-CF3-phenyl-triazole-CN) | 1H-NMR (CDCl3) δ: 1.05 (4H, s), 4.15 (2H, s), 7.20-7.34 (4H, m), 7.41-7.44 (2H, m), 7.63 (1H, s), 7.77 (1H, s). | Ex. 191 |

TABLE 4-continued
| | | | |
|---|---|---|---|
| 1094 | 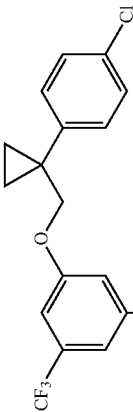 | 1H-NMR (CDCl3) δ: 0.99-1.08 (4H, m), 4.11 (2H, s), 7.19 (1H, s), 7.26-7.37 (4H, m), 7.63 (1H, s), 7.80 (1H, s). | Ex. 191 |
| 1095 | 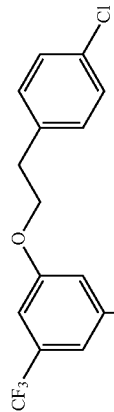 | 1H-NMR (CDCl3) δ: 3.12 (2H, t, J = 6.6 Hz), 4.28 (2H, t, J = 6.6 Hz), 7.23-7.32 (5H, m), 7.68 (1H, s), 7.82 (1H, s). | Ex. 185 |
| 1096 | 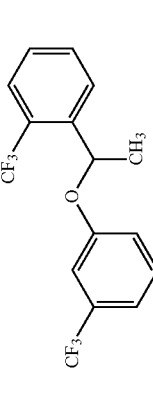 | 1H-NMR (CDCl3) δ: 1.71 (3H, d,J = 5.2 Hz), 5.78-5.84 (1H, m), 7.22 (1H, s), 7.39 (1H, t, J = 7.7 Hz), 7.55 (1H, t, J = 7.7 Hz), 7.67-7.74 (4H, m). | Ex. 2 |
| 1097 | 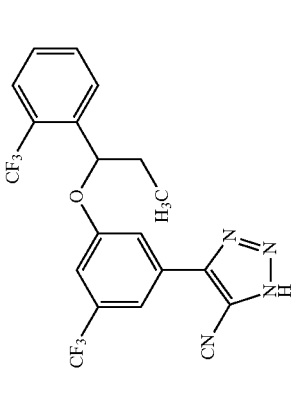 | 1H-NMR (CDCl3) δ: 1.15 (3H, t, J = 7.4 Hz), 1.91-2.00 (2H, m), 5.50-5.54 (1H, m), 7.22 (1H, s), 7.38 (1H, t, J = 7.8 Hz), 7.53 (1H, t, J = 7.8 Hz), 7.68-7.69 (3H, m), 7.74 (1H, s). | Ex. 2 |

TABLE 4-continued

| | Structure | NMR | Ex. |
|---|---|---|---|
| 1098 | (cyclohexyl-CH(CH3)-O-phenyl(CF3)-triazole-CN) | 1H-NMR (CDCl3) δ: 1.08-1.32 (9H, m), 1.68-1.95 (5H, m), 4.22-4.30 (1H, m), 7.23 (1H, s), 7.68 (1H, s), 7.77 (1H, s) | Ex. 191 |
| 1099 | (difluoromethylenedioxybenzyl-O-phenyl-triazole-CN) | 1H-NMR (DMSO-d6) δ: 5.20 (2H, s), 7.22 (1H, d, J = 7.9 Hz), 7.35 (1H, d, J = 7.9 Hz), 7.42-7.61 (5H, m). | Ex. 1 |
| 1100 | (difluoromethylenedioxybenzyl-O-phenyl(OCF3)-triazole-CN) | 1H-NMR (DMSO-d6) δ: 5.12 (2H, s), 5.95 (1H, s), 7.08 (1H, d, J = 8.1 Hz), 7.17-7.20 (2H, m), 7.53 (1H, s), 7.54 (1H, s). | Ex. 1 |

| | Structure | NMR | Ex. |
|---|---|---|---|
| 1101 | CF3-phenyl-triazole-CN with OCH2-C(CH3)(cyclopropyl) substituent | 1H-NMR (CDCl3) δ: 0.47-0.88 (4H, m), 1.26 (3H, s), 3.85 (2H, s), 7.26 (1H, s), 7.69 (1H, s), 7.81 (1H, s). | Ex. 191 |
| 1102 | CF3-phenyl-triazole-CN with OCH2-C(CF3)(cyclopropyl) substituent | 1H-NMR (CDCl3) δ: 0.95-1.00 (2H, m), 1.19-1.26 (2H, m), 4.19 (2H, s), 7.26 (1H, s), 7.70 (1H, s), 7.87 (1H, s). | Ex. 191 |
| 1103 | CF3-phenyl-triazole-CN with OCH2-(4,4-difluorocyclohexyl) substituent | 1H-NMR (CDCl3) δ: 1.40-1.56 (2H, m), 1.71-2.05 (5H, m), 2.13-2.19 (2H, m), 3.94 (2H, d, J = 5.9 Hz), 7.24 (1H, s), 7.70 (1H, s), 7.83 (1H, s). | Ex. 2 |

TABLE 4-continued

| | | | |
|---|---|---|---|
| 1104 | [structure] | 1H-NMR (DMSO-d6) δ: 5.22 (2H, s), 7.08 (1H, s), 7.27-7.46 (4H, m), 7.35 (1H, t, J = 73.5 Hz), 7.57 (1H, s). | Ex. 1 |
| 1105 | [structure] | 1H-NMR (CDCl3) δ: 2.43 (3H, s), 5.24 (2H, s), 6.95 (1H, s), 7.40 (1H, s), 7.45 (1H, s), 7.75 (1H, d, J = 7.9 Hz), 8.02 (1H, d, J = 7.9 Hz), 0.84 (1H, s), 12.0 (1H, br.). | Ex. 1 |
| 1106 | [structure] | 1H-NMR (DMSO-d6) δ: 3.90 (3H, s), 3.91 (3H, s), 5.16 (2H, s), 6.60 (1H, s), 7.23-7.27 (1H, m), 7.49-7.58 (3H, m). | Ex. 2 |
| 1107 | [structure] | 1H-NMR (DMSO-d6) δ: 1.31-1.41 (2H, m), 1.58-1.72 (2H, m), 2.03-2.09 (1H, m), 3.32-3.36 (2H, m), 3.87-3.91 (2H, m), 4.02 (2H, d, J = 6.5 Hz), 7.47 (1H, s), 7.72 (1H, s), 7.76 (1H, s). | Ex. 2 |

TABLE 4-continued

| Ex. No. | STR | m.p. | ref. |
|---|---|---|---|
| 1108 | (3,5-bis(trifluoromethyl)phenethoxy-phenyl triazole carbonitrile) | 1H-NMR (CDCl3) δ: 3.33-3.35 (2H, m), 4.38 (2H, t, J = 6.7 Hz), 7.14-7.17 (1H, m), 7.41-7.55 (3H, m), 7.97 (1H, s), 8.11 (2H, s). | Ex. 2 |
| 1109 | (benzothiophen-2-ylmethoxy-fluorophenyl triazole carbonitrile) | 1H-NMR (DMSO-d6) δ: 5.62 (2H, s), 7.34-7.41 (2H, m), 7.49-7.55 (2H, m), 7.60 (1H, s), 7.81-7.87 (2H, m), 7.95-8.00 (1H, m). | Ex. 1 |
| 1111 | (3-benzoylphenyl triazole carbonitrile) | 188 | Ex. 1 |
| 1112 | (3-(4-fluorobenzoyl)phenyl triazole carbonitrile) | 212-215 | Ex. 1 |

TABLE 4-continued

| | Structure | mp (°C) | Ex. |
|---|---|---|---|
| 1113 | 3-((3,5-bis(trifluoromethyl)benzyl)oxy)phenyl triazole carbonitrile | 84.0-87.7 | Ex. 2 |
| 1114 | 3-((3,5-difluorobenzyl)oxy)phenyl triazole carbonitrile | 87.6-88.0 | Ex. 2 |
| 1115 | 3-((3-(trifluoromethyl)benzyl)oxy)phenyl triazole carbonitrile | 89.4-90.5 | Ex. 2 |
| 1116 | 3-(2-(2,4,5-trifluorophenyl)ethyl)phenyl triazole carbonitrile | 138.6-139.0 | Ex. 2 |

TABLE 4-continued

| | | | |
|---|---|---|---|
| 1117 | [structure: 3-(2-(2,5-bis(trifluoromethyl)phenyl)ethyl)phenyl triazole carbonitrile] | 130.2-131.3 | Ex. 2 |
| 1118 | [structure: 3-(2-(3-fluoro-5-(trifluoromethyl)phenyl)ethyl)phenyl triazole carbonitrile] | 123.6-124.1 | Ex. 2 |
| 1119 | [structure: 3-((4-(trifluoromethyl)benzyloxy)methyl)phenyl triazole carbonitrile] | 92.5-93.0 | Ex. 2 |

TABLE 4-continued

| | | | |
|---|---|---|---|
| 1120 | (structure) | 146.3-149.3 | Ex. 2 |
| 1121 | (structure) | 156.7-157.1 | Ex. 2 |
| 1122 | (structure) | 87.2-88.4 | Ex. 2 |

TABLE 4-continued

| | | | |
|---|---|---|---|
| 1123 | (structure) | 138.4-138.8 | Ex. 2 |
| 1124 | (structure) | 142.9-143.0 | Ex. 2 |
| 1125 | (structure) | 109.1-109.2 | Ex. 2 |
| 1126 | (structure) | 144-146 | Ex. 1 |

TABLE 4-continued

| | | | |
|---|---|---|---|
| 1127 | ![structure: 3,5-bis(trifluoromethyl)phenyl-O-CH2CH2-phenyl-triazole-CN] | 149.5-150.5 | Ex. 2 |
| 1128 | ![structure: 6-(trifluoromethyl)pyridin-2-yl-O-CH2CH2-phenyl-triazole-CN] | 122.9-123.2 | Ex. 2 |
| 1129 | ![structure: 4-(trifluoromethyl)pyrimidin-2-yl-O-CH2CH2-phenyl-triazole-CN] | 139.9-140.4 | Ex. 2 |

TABLE 4-continued

| | | | |
|---|---|---|---|
| 1130 | [structure: 4-(trifluoromethyl)pyrimidin-2-yloxymethyl-phenyl triazole carbonitrile] | 136.7-137.0 | Ex. 2 |
| 1131 | [structure: 6-(trifluoromethyl)pyridin-2-yloxymethyl-phenyl triazole carbonitrile] | 147.3-147.4 | Ex. 2 |
| 1132 | [structure: 6-(trifluoromethyl)pyridin-3-ylmethyl-phenyl triazole carbonitrile] | 140-141 | Ex. 1 |

TABLE 4-continued

| Ex. No. | STR | 1H-NMR | ref. |
|---|---|---|---|
| 1177 | | 188-189 | Ex. 1 |
| 1133 | | 1H-NMR (DMSO-d6) δ: 0.33-0.64 (4H, m), 1.02-1.10 (1H, m), 3.22 (3H, s), 3.73 (1H, d, J = 8.0 Hz), 7.58 (1H, s), 7.83 (1H, s), 7.84 (1H, s). | Ex. 1 |
| 1134 | | 1H-NMR (DMSO-d6) δ: 7.42-7.45 (2H, m), 7.77 (1H, t, J = 7.8 Hz), 7.82-7.85 (2H, m), 8.09-8.44 (2H, m), 8.45 (1H, s), 10.56 (1H, s). | Ex. 1110 |
| 1135 | | 1H-NMR (DMSO-d6) δ: 3.11 (3H, s), 4.75 (2H, s), 6.90-6.94 (1H, m), 7.15 (1H, d, J = 7.6 Hz), 7.22 (1H, s), 7.37 (1H, t, J = 8.0 Hz), 7.50-7.62 (4H, m). | Ex. 1 |

TABLE 4-continued

| | Structure | 1H-NMR | Ex. |
|---|---|---|---|
| 1136 | 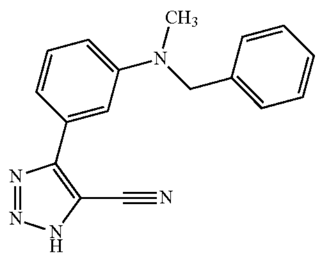 [SMILES: CN(Cc1ccccc1)c1cccc(-c2nn[nH]c2C#N)c1] | 1H-NMR (DMSO-d6) δ: 3.09 (3H, s), 4.65 (2H, s), 6.89-6.92 (1H, m), 7.13 (1H, d, J = 7.4 Hz), 7.22-7.38 (7H, m). | Ex. 1 |
| 1137 | 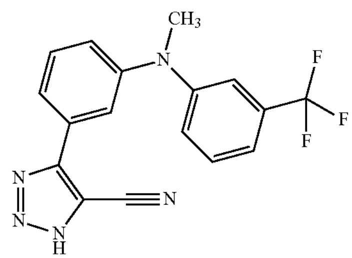 [SMILES: CN(c1cccc(-c2nn[nH]c2C#N)c1)c1cccc(C(F)(F)F)c1] | 1H-NMR (DMSO-d6) δ: 3.39 (3H, s), 7.25-7.33 (4H, m), 7.48-7.60 (4H, m). | Ex. 1 |
| 1138 | 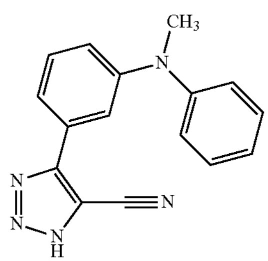 [SMILES: CN(c1ccccc1)c1cccc(-c2nn[nH]c2C#N)c1] | 1H-NMR (DMSO-d6) δ: 3.38 (3H, s), 7.03-7.19 (4H, m), 7.33-7.42 (5H, m). | Ex. 1 |
| 1139 | 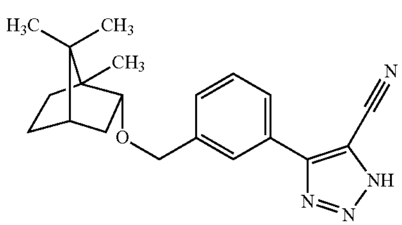 [SMILES: CC1(C)C2CCC1(C)C(OCc1cccc(-c3nn[nH]c3C#N)c1)C2] | 1H-NMR (CDCl3) δ: 0.85 (3H, s), 0.86 (3H, s), 0.93 (3H, s), 1.13 (1H, dd, J = 3.3, 13.0 Hz), 1.22-1.34 (2H, m), 1.65-1.77 (2H, m), 2.03-2.24 (2H, m), 3.72-3.78 (1H, m), 4.53 (1H, d, J = 12.5 Hz), 4.65 (1H, d, J = 12.5 Hz), 7.46-7.54 (2H, m), 7.83-7.90 (1H, m), 7.94 (1H, s). | Ex. 1 |

TABLE 4-continued

| | Structure | 1H-NMR | |
|---|---|---|---|
| 1140 | 3-cyanopyrazole with phenyl-CH2-O-adamantyl | 1H-NMR (CDCl3) δ: 1.50-1.91 (10H, m), 2.10-2.20 (4H, m), 3.64 (1H, s), 4.65 (2H, s), 7.46-7.53 (2H, m), 7.83-7.90 (1H, m), 8.00 (1H, s). | Ex. 1 |
| 1141 | 3-cyanopyrazole with phenyl-CH2-O-CH2-adamantyl | 1H-NMR (CDCl3) δ: 1.56-1.77 (12H, m), 1.95-2.00 (3H, m), 3.09 (2H, s), 4.58 (2H, s), 7.46-7.55 (2H, m), 7.85-7.91 (1H, m), 7.93 (1H, s). | Ex. 1 |
| 1142 | 3-cyanopyrazole with phenyl-CH2-O-menthyl (Chiral) | 1H-NMR (CDCl3) δ: 0.73 (3H, d, J = 7.0 Hz), 0.91 (3H, d, J = 7.0 Hz), 0.95 (3H, d, J = 6.5 Hz), 0.80-1.70 (7H, m), 2.17-2.34 (2H, m), 3.26 (1H, dt, J = 4.1, 10.5 Hz, 4.51 (1H, d, J = 11.5 Hz), 4.76 (1H, d, J = 11.5 Hz), 7.46-7.53 (2H, m), 7.84-7.92 (1H, m), 7.95 (1H, s). | Ex. 1 |
| 1143 | 3-cyanopyrazole with phenyl-CH2-O-menthyl (Chiral) | 1H-NMR (CDCl3) δ: 0.73 (3H, d, J = 7.0 Hz), 0.91 (3H, d, J = 7.0 Hz), 0.95 (3H, d, J = 6.5 Hz), 0.80-1.70 (7H, m), 2.17-2.34 (2H, m), 3.26 (1H, dt, J = 4.1, 10.5 Hz), 4.51 (1H, d, J = 11.5 Hz), 4.76 (1H, d, J = 11.5 Hz), 7.46-7.53 (2H, m), 7.84-7.92 (1H, m), 7.96 (1H, s). | Ex. 1 |

TABLE 4-continued

| | Structure | 1H-NMR | Ex. |
|---|---|---|---|
| 1144 | (3,4-dichlorophenyl-S-CH2-phenyl triazole-carbonitrile) | 1H-NMR (CDCl3) δ: 4.17 (2H, s), 7.12 (1H, dd, J = 2.2, 8.4 Hz), 7.31 (1H, d, J = 8.4 Hz), 7.37 (1H, d, J = 2.2 Hz), 7.39-7.44 (1H, m), 7.47 (1H, t, J = 7.7 Hz), 7.85-7.91 (2H, m). | Ex. 191 |
| 1146 | (2,2-difluoro-2-piperidinyl acetic acid CH2-phenyl triazole-carbonitrile) | 1H-NMR (CDCl3-CD3OD) δ: 1.40-1.80 (2H, m), 1.85-1.97 (4H, m), 2.67-3.48 (4H, m), 4.30 (2H, s), 7.55-7.67 (2H, m), 8.01 (1H, s), 8.06 (1H, d, J = 6.8 Hz). | Ex. 316 |
| 1147 | (N-methyl-N-(3-trifluoromethylbenzyl)-3-trifluoromethoxyphenyl triazole-carbonitrile) | 1H-NMR (DMSO-d6) δ: 3.16 (3H, s), 4.66 (2H, s), 6.61 (1H, s), 7.16 (1H, s), 7.43-7.53 (5H, m). | Ex. 1 |

TABLE 4-continued
| | | | |
|---|---|---|---|
| 1148 | 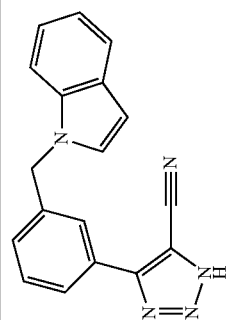 | 1H-NMR (CDCl3) δ: 5.42 (2H, s), 6.60 (1H, dd, J = 0.7, 3.2 Hz), 7.09-7.31 (5H, m), 7.46 (1H, t, J = 7.8 Hz), 7.64-7.73 (2H, m), 7.88 (1H, d, J = 7.8 Hz). | Ex. 1 |
| 1149 | 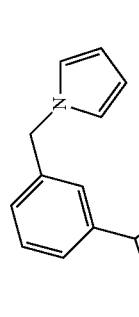 | 1H-NMR (CDCl3) δ: 5.15 (2H, s), 6.23 (2H, t, J = 2.1 Hz), 6.74 (2H, t, J = 2.1 Hz), 7.22-7.26 (1H, m), 7.49 (1H, t, J = 7.7 Hz), 7.66 (1H, s), 7.87-7.92 (1H, m). | Ex. 1 |
| 1150 | 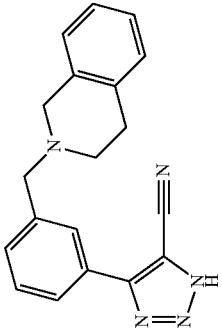 | 1H-NMR (CDCl3) δ: 3.10-3.30 (4H, m), 4.06 (2H, s), 4.08 (2H, s), 7.02-7.08 (1H, m), 7.15-7.32 (4H, m), 7.47 (1H, t, J = 7.8 Hz), 7.95-8.00 (1H, m), 8.47 (1H, s). | Ex. 1 |
| 1151 | 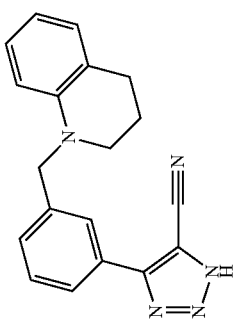 | 1H-NMR (CDCl3) δ: 2.01-2.12 (2H, m), 2.84 (2H, t, J = 6.1 Hz), 3.43 (2H, t, J = 5.7 Hz), 4.55 (2H, s), 6.46 (1H, d, J = 8.1 Hz), 6.56-6.63 (1H, m), 6.90-7.03 (2H, m), 7.39-7.52 (2H, m), 7.80-7.86 (2H, m). | Ex. 1 |

TABLE 4-continued

| | Structure | NMR | Ex. |
|---|---|---|---|
| 1152 | 3-(5-cyano-1H-1,2,3-triazol-4-yl)phenyl piperidinyl ketone | 1H-NMR (CDCl3) δ: 1.55-1.65 (2H, m), 1.70-1.80 (4H, m), 3.41-3.50 (2H, m), 3.81-3.89 (2H, m), 7.36-7.42 (1H, m), 7.49 (1H, t, J = 7.9 Hz), 7.97 (1H, br s), 8.20 (1H, br). | Ex. 1110 |
| 1153 | N-cyclohexyl-3-(5-cyano-1H-1,2,3-triazol-4-yl)benzamide | 1H-NMR (DMSO-d6) δ: 1.00-1.22 (1H, m), 1.22-1.42 (4H, m), 1.56-1.68 (1H, m), 1.68-1.93 (4H, m), 3.72-3.86 (1H, m), 7.70 (1H, t, J = 7.8 Hz), 7.97-8.04 (2H, m), 8.35 (1H, s), 8.40 (1H, d, J = 7.8 Hz). | Ex. 1110 |
| 1154 | N-(cyclohexylmethyl)-3-(5-cyano-1H-1,2,3-triazol-4-yl)benzamide | 1H-NMR (CDCl3) δ: 0.96-1.37 (5H, m), 1.58-1.87 (6H, m), 3.44 (2H, t, J = 6.5 Hz), 6.51 (1H, br t, J = 6.5 Hz), 7.60 (1H, t, J = 7.8 Hz), 7.73 (1H, d, J = 7.9 Hz), 8.23 (1H, d, J = 7.7 Hz), 8.75 (1H, s). | Ex. 1110 |
| 1155 | 3-(5-cyano-1H-1,2,3-triazol-4-yl)phenyl indolin-1-yl ketone | 1H-NMR (DMSO-d6) δ: 3.11 (2H, t, J = 8.2 Hz), 4.06 (2H, t, J = 8.2 Hz), 7.07 (1H, t, J = 7.3 Hz), 7.20 (1H, br.), 7.30 (1H, d, J = 7.3 Hz), 7.71-7.82 (2H, m), 7.91-8.21 (3H, m). | Ex. 1110 |

TABLE 4-continued
| | | |
|---|---|---|
| 1156 | 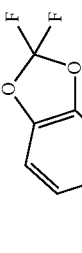 | 1H-NMR (DMSO-d6) δ: 4.08 (2H, s), 7.12-7.15 (1H, m), 7.32-7.37 (2H, m), 7.46 (1H, d, J = 7.7 Hz), 7.54 (1H, t, J = 7.7 Hz), 7.71-7.75 (2H, m). | Ex. 1 |
| 1157 | 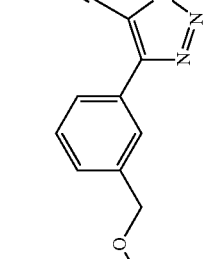 | 1H-NMR (CDCl3) δ: 1.42-1.76 (12H, m), 2.20-2.27 (2H, m), 3.18 (2H, s), 4.58 (2H, s), 7.39-7.45 (1H, m), 7.49 (1H, t, J = 7.6 Hz), 7.84-7.89 (1H, m), 7.96 (1H, s). | Ex. 1 |
| 1158 | 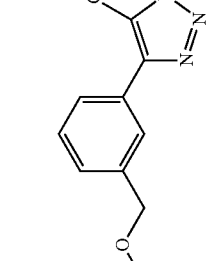 | 1H-NMR (CDCl3) δ: 1.44-1.82 (12H, m), 2.21-2.29 (2H, m), 3.17 (2H, s), 3.30 (3H, s), 4.58 (2H, s), 7.43 (1H, d, J = 7.6 Hz), 7.48 (1H, t, J = 7.6 Hz), 7.86 (1H, d, J = 7.6 Hz), 7.92 (1H, s). | Ex. 1 |
| 1159 | 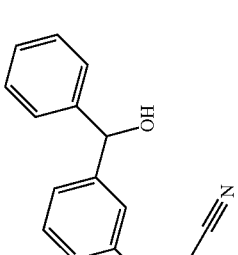 | 1H-NMR (DMSO-d6) δ: 5.78 (1H, s), 6.07 (1H, s), 7.17-7.34 (3H, m), 7.38-7.43 (2H, m), 7.50-7.53 (2H, m), 7.67-7.74 (1H, m), 7.96 (1H, s). | Ex. 1 |

TABLE 4-continued

| | Structure | 1H-NMR | |
|---|---|---|---|
| 1160 | (3-(2-(4-(trifluoromethyl)pyrimidin-2-yl)ethyl)phenyl)-triazole-carbonitrile | 1H-NMR (CDCl3) δ: 3.20-3.24 (4H, m), 7.45 (1H, d, J = 7.8 Hz), 7.51 (1H, t, J = 7.8 Hz), 7.69-7.72 (1H, m), 7.75 (1H, s), 7.87 (1H, d, J = 5.1 Hz), 9.13 (1H, d, J = 5.1 Hz). | Ex. 2 |
| 1161 | (3-chloro-5-(2-(3-(trifluoromethyl)phenyl)ethyl)phenyl)-triazole-carbonitrile | 1H-NMR (DMSO-d6) δ: 4.29 (4H, s), 7.50-7.61 (5H, m), 7.72-7.75 (2H, m). | Ex. 2 |
| 1162 | (3-((N-methyl-N-phenylamino)methyl)phenyl)-triazole-carbonitrile | 1H-NMR (DMSO-d6) δ: 3.07 (3H, s), 4.65 (2H, s), 6.61 (1H, t, J = 7.3 Hz), 6.73 (2H, d, J = 8.3 Hz), 7.13-7.16 (2H, m), 7.40 (1H, d, J = 7.6 Hz), 7.56 (1H, t, J = 8.3 Hz), 7.75-7.76 (2H, m). | Ex. 2 |

TABLE 4-continued

| | Structure | 1H-NMR | |
|---|---|---|---|
| 1163 | 4-(trifluoromethylphenyl)-S-CH2-phenyl-triazole-CN | 1H-NMR (DMSO-d6) δ: 4.48 (2H, s), 7.51-7.63 (6H, m), 7.76-7.78 (1H, m), 7.96 (1H, s). | Ex. 2 |
| 1164 | 2,5-bis(CF3)phenyl-CH2-O-CH2-phenyl-triazole-CN | 1H-NMR (CDCl3) δ: 4.75 (2H, s), 4.84 (2H, s), 7.54-7.56 (2H, m), 7.66 (1H, d, J = 8.1 Hz), 7.78 (1H, d, J = 8.1 Hz), 7.93-7.97 (1H, m), 8.00 (1H, s), 8.07 (1H, s). | Ex. 2 |
| 1165 | 3,4-dichlorophenyl-N(CH3)-CH2-phenyl-triazole-CN | 1H-NMR (DMSO-d6) δ: 3.10 (3H, s), 4.71 (2H, s), 6.70 (1H, dd, J = 3.0, 9.1 Hz), 6.88 (1H, d, J = 3.0 Hz), 7.31 (1H, d, J = 9.1 Hz), 7.39 (1H, d, J = 7.9 Hz), 7.58 (1H, t, J = 7.9 Hz), 7.71 (1H, s), 7.77 (1H, d, J = 7.9 Hz). | Ex. 2 |

TABLE 4-continued

| | Structure | 1H-NMR | |
|---|---|---|---|
| 1166 | 4-(trifluoromethyl)-N-methyl-N-benzyl aniline linked to phenyl-triazole-CN | 1H-NMR (DMSO-d6) δ: 3.17 (3H, s), 4.77 (2H, s), 6.83 (2H, d, J = 8.9 Hz), 7.40 (1H, d, J = 7.7 Hz), 7.44 (2H, d, J = 8.9 Hz), 7.58 (1H, t, J = 7.7 Hz), 7.74-7.78 (2H, m). | Ex. 2 |
| 1167 | benzothiophene-ethyl-phenyl-triazole-CN | 1H-NMR (DMSO-d6) δ: 3.13 (2H, t, J = 7.5 Hz), 3.27-3.31 (2H, m), 7.24-7.33 (3H, m), 7.47-7.54 (2H, m), 7.70-7.73 (2H, m), 7.03-7.82 (2H, m). | Ex. 2 |
| 1168 | 3,5-bis(trifluoromethyl)benzyl-S-CH2-phenyl-triazole-CN | 1H-NMR (DMSO-d6) δ: 3.86 (2H, s), 3.98 (2H, s), 7.40 (1H, d, J = 7.7 Hz), 7.46 (1H, t, J = 7.7 Hz), 7.66-7.69 (1H, m), 7.71 (1H, s), 7.81 (1H, s), 7.88 (2H, s). | Ex. 2 |

TABLE 4-continued

| | Structure | 1H-NMR | Ex. |
|---|---|---|---|
| 1169 | (4-tert-butylbenzyl thiomethyl-phenyl triazole carbonitrile) | 1H-NMR (DMSO-d6) δ: 1.26 (9H, s), 3.67 (2H, s), 3.77 (2H, s), 7.20-7.23 (2H, m), 7.30-7.34 (2H, s), 7.48 (1H, d, J = 7.7 Hz), 7.56 (1H, t, J = 7.7 Hz), 7.76 (1H, d, J = 7.7 Hz), 7.83 (1H, s). | Ex. 2 |
| 1170 | (3,5-bis(trifluoromethyl)benzyloxyethyl-phenyl triazole carbonitrile) | 1H-NMR (DMSO-d6) δ: 3.00 (2H, t, J = 6.4 Hz), 3.79 (2H, t, J = 6.4 Hz), 4.69 (2H, s), 7.46 (1H, d, J = 7.7 Hz), 7.53 (1H, t, J = 7.7 Hz), 7.74 (1H, d, J = 7.7 Hz), 7.80 (1H, s), 7.88 (2H, s), 7.97 (1H, s). | Ex. 2 |
| 1171 | (3-chloro-5-((6-trifluoromethylpyridin-3-yl)methyl)phenyl triazole carbonitrile) | 1H-NMR (DMSO-d6) δ: 4.21 (2H, s), 7.63 (1H, s), 7.74 (1H, s), 7.76 (1H, t, J = 1.8 Hz), 7.83 (1H, d, J = 8.0 Hz), 7.95-8.01 (1H, m), 8.76 (1H, d, J = 1.8 Hz). | Ex. 1 |

TABLE 4-continued

| # | Structure | 1H-NMR | Ex. |
|---|---|---|---|
| 1172 | 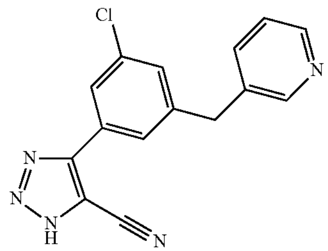 [SMILES: N#Cc1[nH]nnc1-c1cc(Cl)cc(Cc2cccnc2)c1] | 1H-NMR (DMSO-d6) δ: 4.11 (2H, s), 7.33-7.39 (1H, m), 7.57-7.59 (1H, m), 7.70-7.78 (3H, m), 8.43-8.49 (1H, m), 8.56-8.61 (1H, m). | Ex. 1 |
| 1173 | 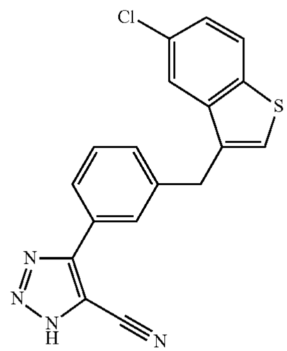 [SMILES: N#Cc1[nH]nnc1-c1cccc(Cc2csc3ccc(Cl)cc23)c1] | 1H-NMR (DMSO-d6) δ: 4.31 (2H, s), 7.37-7.42 (1H, m), 7.49-7.61 (3H, m), 7.72-7.77 (1H, m), 7.84 (1H, s), 7.88 (1H, d, J = 2.0 Hz), 8.03 (1H, d, J = 3.9 Hz). | Ex. 1 |
| 1174 | 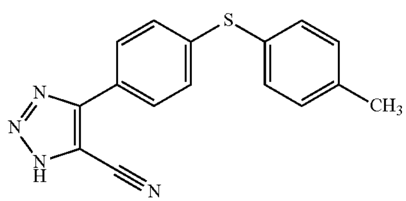 [SMILES: Cc1ccc(Sc2ccc(-c3nn[nH]c3C#N)cc2)cc1] | 1H-NMR (DMSO-d6) δ: 2.35 (3H, s), 7.27-7.32 (2H, m), 7.32-7.37 (2H, m), 7.39-7.44 (2H, m), 7.77-7.83 (2H, m). | Ex. 1 |
| 1175 | 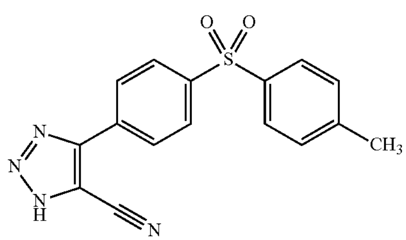 [SMILES: Cc1ccc(S(=O)(=O)c2ccc(-c3nn[nH]c3C#N)cc2)cc1] | 1H-NMR (CDCl3) δ: 2.41 (3H, s), 7.33 (2H, d, J = 6.0 Hz), 7.86 (2H, d, J = 8.0 Hz), 8.03-8.09 (2H, m), 8.09-8.15 (2H, m). | Ex. 1 |

TABLE 4-continued

| | Structure | 1H-NMR | Ex. |
|---|---|---|---|
| 1176 | (pyridine-CF3/benzyl-phenyl-triazole-CN) | 1H-NMR (DMSO-d6) δ: 4.19 (2H, s), 7.55 (2H, d, J = 7.8 Hz), 7.83 (2H, d, J = 7.8 Hz), 8.15 (1H, s), 8.84 (1H, s), 8.87 (1H, s). | Ex. 1 |
| 1178 | (thiophene/CF3-phenyl-triazole-CN) | 1H-NMR (CDCl3) δ: 6.81-6.84 (1H, m), 7.19-7.21 (1H, m), 7.33-7.35 (1H, m), 7.72 (1H, d, J = 7.7 Hz), 7.82-7.85 (2H, m). | Ex. 1 |
| 1179 | (furan/CF3-phenyl-triazole-CN) | 1H-NMR (CDCl3) δ: 6.17 (1H, s), 7.38-7.45 (2H, m), 7.68 (1H, d, J = 8.7 Hz), 7.81-7.84 (2H, m). | Ex. 1 |
| 1180 | (pyridine-CF3/vinyl-Cl-phenyl-triazole-CN) | 1H-NMR (DMSO-d6) δ: 7.48 (1H, d, J = 16.9 Hz), 7.65 (1H, d, J = 15.9 Hz), 7.71-7.78 (3H, m), 7.88 (1H, d, J = 8.0 Hz), 8.07-8.14 (2H, m). | Ex. 2 |

TABLE 4-continued

| | Structure | 1H-NMR | Ex. |
|---|---|---|---|
| 1181 | 4-(trifluoromethyl)phenyl-thiazole-triazole-CN | 1H-NMR (DMSO-d6) δ: 7.77 (2H, d, J = 8.2 Hz), 8.15-8.18 (3H, m). | Ex. 1 |
| 1182 | 2-(4-(trifluoromethyl)phenyl)-5-propyl-thiazole-triazole-CN | 1H-NMR (DMSO-d6) δ: 0.99 (3H, t, J = 7.3 Hz), 1.68-1.81 (2H, m), 3.24 (2H, t, J = 7.5 Hz), 7.92 (2H, d, J = 8.3 Hz), 8.19 (2H, d, J = 8.3 Hz). | Ex. 1 |
| 1183 | 2-(2-chloro-4-fluorophenyl)-thiazole-triazole-CN | 1H-NMR (DMSO-d6) δ: 7.48-7.53 (1H, m), 7.71 (1H, dd, J = 2.6, 8.8 Hz), 8.23 (1H, s), 8.43 (1H, dd, J = 6.3, 8.8 Hz). | Ex. 125 |
| 1184 | 2-(3-chloro-5-fluorophenyl)-thiazole-triazole-CN | 1H-NMR (DMSO-d6) δ: 7.65 (1H, d, J = 8.9 Hz), 7.86 (1H, d, J = 8.9 Hz), 7.97 (1H, s), 8.42 (1H, s). | Ex. 125 |

TABLE 4-continued

| | Structure | 1H-NMR | Ex. |
|---|---|---|---|
| 1185 | 2-(3-chloro-5-fluorophenyl)-5-methylthiazole-4-yl triazole carbonitrile | 1H-NMR (DMSO-d6) δ: 2.81 (3H, s), 7.57-7.60 (1H, m), 7.74-7.77 (1H, m), 7.86 (1H, t, J = 1.4 Hz). | Ex. 125 |
| 1186 | 2-(3-chloro-5-fluorophenyl)-5-ethylthiazole-4-yl triazole carbonitrile | 1H-NMR (DMSO-d6) δ: 1.32 (3H, t: J = 7.5 Hz), 3.30 (2H, q, J = 7.5 Hz), 7.57-7.51 (1H, m), 7.75-7.79 (1H, m), 7.88 (1H, s). | Ex. 125 |
| 1187 | 2-(3,5-difluorophenyl)-5-ethylthiazole-4-yl triazole carbonitrile | 1H-NMR (DMSO-d6) δ: 1.33 (3H, t, J = 7.5 Hz), 3.27 (2H, q, J = 7.5 Hz), 7.41-7.47 (1H, m), 7.65-7.72 (2H, m). | Ex. 125 |
| 1188 | 2-(3,5-difluorophenyl)thiazole-4-yl triazole carbonitrile | 1H-NMR (DMSO-d6) δ: 7.46-7.52 (1H, m), 7.74-7.80 (2H, m), 8.44 (1H, s). | Ex. 125 |
| 1189 | 5-chloro-2-(4-(trifluoromethyl)phenyl)thiazole-4-yl triazole carbonitrile | 1H-NMR (DMSO-d6) δ: 7.94 (2H, d, J = 8.2 Hz), 8.18 (2H, d, J = 8.1 Hz). | Ex. 108 |

TABLE 4-continued

| | | | |
|---|---|---|---|
| 1190 | *[4-fluoro-3-(trifluoromethyl)phenyl-thiazole-triazole-carbonitrile structure]* | 1H-NMR (DMSO-d6) δ: 7.76 (1H, t, J = 9.7 Hz), 8.38-8.43 (3H, m). | Ex. 1 |
| 1191 | *[3-chloro-5-(trifluoromethyl)phenyl-thiazole-triazole-carbonitrile structure]* | 1H-NMR (DMSO-d6) δ: 8.09 (1H, s), 8.35 (1H, s), 8.41 (1H, s), 8.48 (1H, s). | Ex. 1 |
| 1192 | *[3-methoxy-5-(trifluoromethyl)phenyl-thiazole-triazole-carbonitrile structure]* | 1H-NMR (DMSO-d6) δ: 3.95 (3H, s), 7.44 (1H, s), 7.86 (1H, s), 7.94 (1H, s), 8.43 (1H, s). | Ex. 1 |
| 1193 | *[4-methoxy-3-(trifluoromethyl)phenyl-thiazole-triazole-carbonitrile structure]* | 1H-NMR (DMSO-d6) δ: 4.00 (3H, s), 7.47 (1H, d, J = 9.5 Hz), 8.27-8.30 (2H, m), 8.33 (1H, s). | Ex. 1 |
| 1194 | *[3,4-difluorophenyl-thiazole-triazole-carbonitrile structure]* | 1H-NMR (DMSO-d6) δ: 7.63-7.72 (1H, m), 7.91-7.96 (1H, m), 8.06-8.13 (1H, m), 8.39 (1H, s). | Ex. 1 |

TABLE 4-continued

| | Structure | 1H-NMR | Ex. |
|---|---|---|---|
| 1195 | 3,5-bis(trifluoromethyl)phenyl-thiazole-triazole-CN | 1H-NMR (DMSO-d6) δ: 8.32 (1H, brs), 8.52 (1H, s), 8.67 (2H, brs). | Ex. 1 |
| 1196 | 4-fluorophenyl-thiazole-triazole-CN | 1H-NMR (DMSO-d6) δ: 7.40-7.46 (2H, m), 8.09-8.14 (2H, m), 8.34(1H, s). | Ex. 1 |
| 1197 | 4-methoxyphenyl-thiazole-triazole-CN | 1H-NMR (DMSO-d6) δ: 3.85 (3H, s), 7.10-7.15 (2H, m), 7.97-8.02 (2H, m), 8.24 (1H, s). | Ex. 1 |
| 1198 | 3-methoxyphenyl-thiazole-triazole-CN | 1H-NMR (DMSO-d6) δ: 3.88 (3H, s), 7.12-7.15 (1H, m), 7.46-7.51 (1H, m), 7.60-7.63 (2H, m), 8.34 (1H, s). | Ex. 1 |

TABLE 4-continued

| | Structure | 1H-NMR | |
|---|---|---|---|
| 1199 | 4-methylphenyl-thiazole-triazole-CN | 1H-NMR (DMSO-d6) δ: 2.39 (3H, s), 7.38 (2H, d, J = 8.0 Hz), 7.95 (2H, d, J = 8.1 Hz), 8.30 1H, s). | Ex. 1 |
| 1200 | 3-chlorophenyl-thiazole-triazole-CN | 1H-NMR (DMSO-d6) δ: 7.58-7.65 (2H, m), 7.99-8.03 (1H, m), 8.10-8.11 (1H, m), 8.40 (1H, s). | Ex. 1 |
| 1201 | 2,4-dichlorophenyl-thiazole-triazole-CN | 1H-NMR (DMSO-d6) δ: 7.86 (1H, d, J = 8.4 Hz), 8.03 (1H, dd, J= 2.1, 8.4 Hz), 8.28 (1H, d, J = 2.0 Hz), 8.42 (1H, s). | Ex. 1 |
| 1202 | 3,5-dichlorophenyl-thiazole-triazole-CN | 1H-NMR (DMSO-d6) δ: 7.83 (1H, t, J = 1 8 Hz), 8.09 (2H, d, J = 1.8 Hz), 8.45 (1H, s). | Ex. 1 |

TABLE 4-continued
| | | | |
|---|---|---|---|
| 1203 | 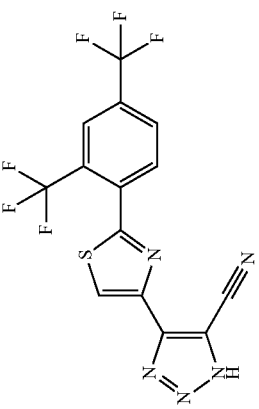 | 1H-NMR (DMSO-d6) δ: 8.12 (1H, d, J = 8.3 Hz), 8.26-8.29 (2H, m), 8.58 (1H, s). | Ex. 1 |
| 1204 | 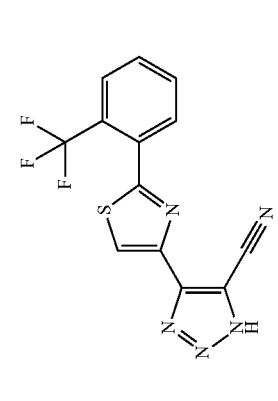 | 1H-NMR (DMSO-d6) δ: 7.80-7.88 (3H, m), 7.98 (1H, d, J = 7.4 Hz), 8.52 (1H, s). | Ex. 1 |
| 1205 | 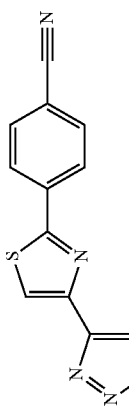 | 1H-NMR (DMSO-d6) δ: 8.05-8.08 (2H, m), 8.22-8.25 (2H, m), 8.48 (1H, s). | Ex. 1 |
| 1206 | 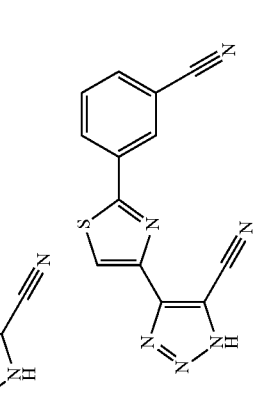 | 1H-NMR (DMSO-d6) δ: 7.50 (1H, t, J = 7.8 Hz), 8.03 (1H, dt, J = 7.8, 1.3 Hz), 8.36-8.39 (1H, m), 8.44 (1H, s), 8.48 (1H, t, J = 1.5 Hz). | Ex. 1 |

TABLE 4-continued
| | Structure | 1H-NMR | |
|---|---|---|---|
| 1207 | 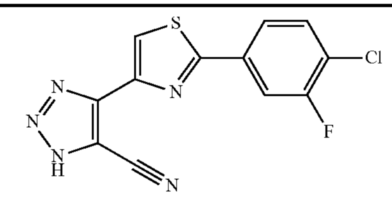 | 1H-NMR (DMSO-d6) δ: 7.83 (1H, t, J = 7.9 Hz), 7.93 (1H, dd, J = 2.1, 8.5 Hz), 8.06 (1H, dd, J = 2.0, 10.0 Hz), 8.42 (1H, s). | Ex. 1 |
| 1208 | 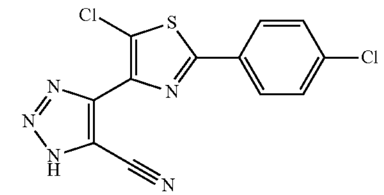 [SMILES: N#Cc1[nH]nnc1-c1nc(-c2ccc(Cl)cc2)sc1Cl] | 1H-NMR (DMSO-d6) δ: 7.64-7.68 (2H, m), 7.98-8.03 (2H, m). | Ex. 108 |
| 1209 | 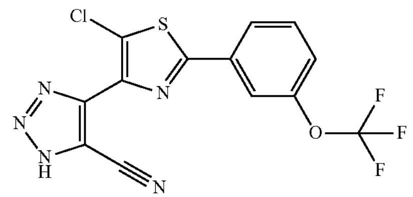 [SMILES: N#Cc1[nH]nnc1-c1nc(-c2cccc(OC(F)(F)F)c2)sc1Cl] | 1H-NMR (DMSO-d6) δ: 7.57-7.61 (1H, m), 7.72 (1H, t, J = 8.2 Hz), 7.99-8.01 (2H, m). | Ex. 1208 |
| 1210 | 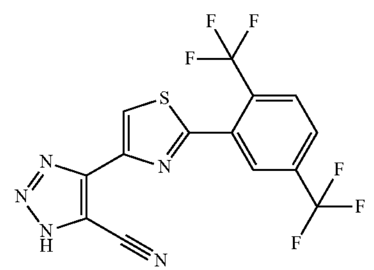 [SMILES: N#Cc1[nH]nnc1-c1csc(-c2cc(C(F)(F)F)ccc2C(F)(F)F)n1] | 1H-NMR (DMSO-d6) δ: 8.19-8.27 (3H, m), 8.59 (1H, s). | Ex. 1 |
| 1211 | 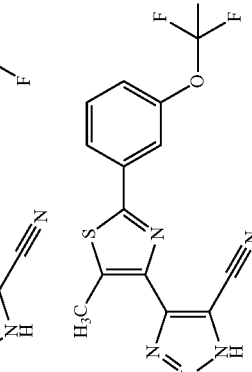 | 1H-NMR (DMSO-d6) δ: 2.80 (3H, s), 7.51-7.55 (1H, m), 7.69 (1H, t, J = 8.2 Hz), 7.95-7.98 (2H, m). | Ex. 1 |

TABLE 4-continued

| | Structure | 1H-NMR | Ex. |
|---|---|---|---|
| 1212 | 2-(3,4-dichlorophenyl)-5-methyl-thiazole-triazole-carbonitrile | 1H-NMR (DMSO-d6) δ: 2.79 (3H, s), 7.82 (1H, d, J = 11.2 Hz), 7.92 (1H, dd, J = 2.8, 11.2 Hz), 8.18 (1H, d, J = 2.7 Hz). | Ex. 1 |
| 1213 | 2-(4-chlorophenyl)-5-((dimethylamino)methyl)-thiazole-triazole-carbonitrile | 1H-NMR (DMSO-d6) δ: 2.87 (6H, s), 4.75 (2H, s), 7.62-7.67 (2H, m), 8.02-8.06 (2H m). | Ex. 1 |
| 1214 | 2-(4-chlorophenyl)-5-(dimethylamino)-thiazole-triazole-carbonitrile | 1H-NMR (DMSO-d6) δ: 2.88 (6H, s), 7.55-7.60 (2H, m), 7.89-7.93 (2H, m). | Ex. 1 |
| 1215 | 2-(4-chlorophenyl)-5-(ethoxy)-thiazole-triazole-carbonitrile | 1H-NMR (DMSO-d6) δ: 1.49 (3H, t, J = 7.0 Hz), 4.42 (2H, q, J = 6.9 Hz), 7.59-7.64 (2H, m), 7.91-7.95 (2H, m). | Ex. 1 |

TABLE 4-continued

| | Structure | 1H-NMR | Ex. |
|---|---|---|---|
| 1216 | 4-(trifluoromethyl)phenyl-thiazole-OMe-triazole-CN | 1H-NMR (DMSO-d6) δ: 4.22 (3H, s), 7.92 (2H, d, J = 8.5 Hz), 8.12 (2H, d, J = 8.2 Hz). | Ex. 1 |
| 1217 | 3-(trifluoromethyl)phenyl-thiazole-OMe-triazole-CN | 1H-NMR (DMSO-d6) δ: 4.22 (3H, s), 7.76-7.81 (1H, m), 7.87 (1H, d, J = 8.1 Hz), 8.18 (1H, d, J = 7.6 Hz), 8.27 (1H, s). | Ex. 1 |
| 1218 | 3-(trifluoromethoxy)phenyl-thiazole-OMe-triazole-CN | 1H-NMR (DMSO-d6) δ: 4.21 (3H, s), 7.50-7.52 (1H, m), 7.65-7.71 (1H, m), 7.90-7.92 (2H, m). | Ex. 1 |
| 1219 | 3,4-dichlorophenyl-thiazole-OMe-triazole-CN | 1H-NMR (DMSO-d6) δ: 4.20 (3H, s), 7.81 (1H, d, J = 8.4 Hz), 7.87 (1H, dd, J = 2.0, 8.4 Hz), 8.15 (1H, d, J = 2.0 Hz). | Ex. 1 |
| 1220 | 3-chloro-4-fluorophenyl-thiazole-Cl-triazole-CN | 1H-NMR (DMSO-d6) δ: 7.66 (1H, t, J = 8.9 Hz), 7.99-8.04 (1H, m), 8.20 (1H, dd, J = 2.2, 7.0 Hz). | Ex. 108 |

TABLE 4-continued

| | Structure | 1H-NMR | |
|---|---|---|---|
| 1222 | 2-(4-chlorophenyl)-5-(1-methylethyl)thiazol-4-yl triazole carbonitrile | 1H-NMR (DMSO-d6) δ: 1.37 (6H, d, J = 6.8 Hz), 3.96-4.07 (1H, m), 7.61-7.65 (2H, m), 7.99-8.04 (2H, m). | Ex. 1 |
| 1223 | 2-(3,5-di-tert-butyl-4-hydroxyphenyl)thiazol-4-yl triazole carbonitrile | 1H-NMR (DMSO-d6) δ: 1.44 (18H, s), 7.63 (1H, s), 7.83 (2H, s), 8.20 (1H, s). | Ex. 1 |
| 1224 | 2-(4-chlorophenyl)-5-(1-methylethenyl)thiazol-4-yl triazole carbonitrile | 1H-NMR (DMSO-d6) δ: 2.12 (3H, s), 5.35 (1H, s), 5.43 (1H, s), 7.62-7.65 (2H, m), 7.99-8.04 (2H, m). | Ex. 1 |
| 1225 | 2-(3-chloro-4-fluorophenyl)-5-(1-methylethyl)thiazol-4-yl triazole carbonitrile | 1H-NMR (DMSO-d6) δ: 1.37 (6H, d, J = 6.8 Hz), 3.97-4.06 (1H, m), 7.61 (1H, t, J = 8.9 Hz), 7.96-8.01 (1H, m), 8.18 (1H, dd, J = 2.0, 7.1 Hz). | Ex. 1 |

TABLE 4-continued

| | | | |
|---|---|---|---|
| 1226 | (4-chlorophenyl-thiazole with dinitrile-triazole structure) | 1H-NMR (DMSO-d6) δ: 7.70-7.75 (2H, m), 8.10-8.15 (2H, m). | Ex. 1 |
| 1227 | (3-trifluoromethoxyphenyl-thiazole with propyl and cyano-triazole) | 1H-NMR (DMSO-d6) δ: 0.99 (3H, t, J = 7.3 Hz), 1.68-1.80 (2H, m), 3.24 (2H, t, J = 7.6 Hz), 7.52 (1H, d, J = 8.4 Hz), 7.69 (1H, t, J = 8.3 Hz), 7.97-8.00 (2H, m). | Ex. 1 |
| 1228 | (3,4-dichlorophenyl-thiazole with methyl and cyano-triazole) | 1H-NMR (DMSO-d6) δ: 1.33 (3H, t, J = 7.4 Hz), 3.22-3.30 (2H, m), 7.81 (1H, d, J = 8.5 Hz), 7.91-7.94 (1H, m), 8.19 (1H, s). | Ex. 1 |
| 1229 | (3-chlorophenyl-thiazole with methyl and cyano-triazole) | 1H-NMR (DMSO-d6) δ: 1.34 (3H, t, J = 7.4 Hz), 3.23-3.30 (2H, m), 7.57-7.59 (2H, m), 7.91-7.94 (1H, m), 8.03-8.05 (1H, m). | Ex. 1 |
| 1230 | (4-trifluoromethylphenyl-thiazole with methyl and cyano-triazole) | 1H-NMR (DMSO-d6) δ: 1.35 (3H, t, J = 7.4 Hz), 3.24-3.31 (2H, m), 7.92 (2H, d, J = 8.3 Hz), 8.19 (2H, J = 8.2 Hz). | Ex. 1 |

TABLE 4-continued
| | | | |
|---|---|---|---|
| 1231 | 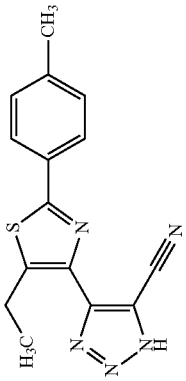 | 1H-NMR (DMSO-d6) δ: 1.32 (3H, t, J = 7.4 Hz), 2.37 (3H, s), 3.19-3.27 (2H, m), 7.35 (2H, d, J = 8.0 Hz), 7.88 (2H, d, J = 8.1 Hz). | Ex. 1 |
| 1232 | 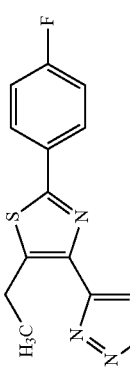 | 1H-NMR (DMSO-d6) δ: 1.33 (3H, t, J = 7.4 Hz), 3.21-3.28 (2H, m), 7.37-7.43 (2H, m), 8.02-8.06 (2H, m). | Ex. 1 |
| 1233 | 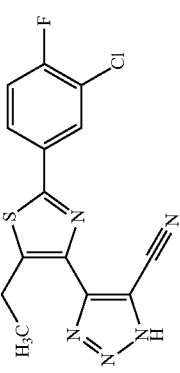 | 1H-NMR (DMSO-d6) δ: 1.33 (3H, t, J = 7.4 Hz), 3.22-3.30 (2H, m) 7.62 (1H, t, J = 8.9 Hz), 7.96-8.01 (1H, m), 8.16-8.19 (1H, m). | Ex. 1 |
| 1234 | 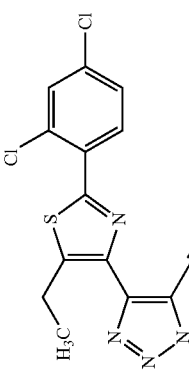 | 1H-NMR (DMSO-d6) δ: 1.33 (3H, t, J = 7.4 Hz), 3.22-3.30 (2H, m), 7.82 (1H, d, J = 8.4 Hz), 7.93 (1H, dd, J = 2.1, 8.4 Hz), 8.20 (1H, d, J = 2.0 Hz). | Ex. 1 |
| 1235 | 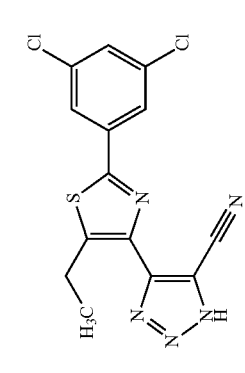 | 1H-NMR (DMSO-d6) δ: 1.33 (3H, t, J = 7.4 Hz), 3.22-3.30 (2H, m), 7.76 (1H, t, J = 1.9 Hz), 7.97 (2H, d, J = 1.9 Hz). | Ex. 1 |

TABLE 4-continued

| | Structure | 1H-NMR | Ex. |
|---|---|---|---|
| 1236 | (3-trifluoromethoxyphenyl-thiazole with ethyl and triazole-carbonitrile) | 1H-NMR (DMSO-d6) δ: 1.34 (3H, t, J = 7.4 Hz), 3.24-3.31 (2H, m), 7.51-7.54 (1H, m), 7.69 (1H, t, J = 8.3 Hz), 7.97-7.99 (2H, m). | Ex. 1 |
| 1237 | (3-trifluoromethyl-4-fluorophenyl-thiazole with ethyl and triazole-carbonitrile) | 1H-NMR (DMSO-d6) δ: 1.34 (3H, t, J = 7.4 Hz), 3.21-3.31 (2H, m), 7.69-7.75 (1H, m), 8.27-8.36 (2H, m) | Ex. 1 |
| 1238 | (3-chloro-4-fluorophenyl-thiazole with propyl and triazole-carbonitrile) | 1H-NMR (DMSO-d6) δ: 0.98 (3H, t, J = 7.3 Hz), 1.68-1.77 (2H, m), 3.19-3.23 (2H, m), 7.59-7.64 (1H, m), 7.95-8.00 (1H, m), 8.15-8.19 (1H, m). | Ex. 1 |
| 1239 | (3-chloro-4-fluorophenyl-thiazole with cyclopropylpropyl and triazole-carbonitrile) | 1H-NMR (DMSO-d6) δ: 0.08-0.11 (2H, m), 0.39-0.44 (2H, m), 0.75-0.82 (1H, m), 1.58-1.63 (2H, m), 3.31-3.34 (2H, m), 7.61 (1H, t, J = 8.9 Hz), 7.95-7.99 (1H, m), 8.16 (1H, dd, J = 2.1, 7.0 Hz). | Ex. 1 |

TABLE 4-continued

| | Structure | 1H-NMR | Ex. |
|---|---|---|---|
| 1240 | (2-(4-chlorophenyl)thiazole with cyclopropylpropyl and triazole-CN) | 1H-NMR (DMSO-d6) δ: 0.08-0.11 (2H, m), 0.39-0.43 (2H, m), 0.75-0.82 (1H, m), 1.58-1.63 (2H, m), 3.31-3.34 (2H, m), 7.61-7.64 (2H, m), 7.98-8.00 (2H, m). | Ex. 1 |
| 1241 | (2-(4-chlorophenyl)thiazole with tert-butyl-CH2CH2 and triazole-CN) | 1H-NMR (DMSO-d6) δ: 0.97 (9H, s), 1.58-1.61 (2H, m), 3.21-3.25 (2H, m), 7.83 (2H, d, J = 8.6 Hz), 7.99 (2H, d, J = 8.5 Hz). | Ex. 1 |
| 1242 | (2-(4-methoxyphenyl)thiazole with methyl and triazole-CN) | 1H-NMR (DMSO-d6) δ: 2.75 (3H, s), 3.84 (3H, s), 7.08-7.12 (2H, m), 7.90-7.93 (2H, m). | Ex. 1 |
| 1243 | (2-(4-methoxyphenyl)thiazole with ethyl and triazole-CN) | 1H-NMR (DMSO-d6) δ: 1.32 (3H, t, J = 7.4 Hz), 3.22 (2H, q, J = 7.4 Hz), 3.84 (3H, s), 7.03-7.12 (2H, m), 7.91-7.95 (2H, m). | Ex. 1 |
| 1244 | (2-(2-chloro-4-fluorophenyl)thiazole with methyl and triazole-CN) | 1H-NMR (DMSO-d6) δ: 2.81 (3H, s), 7.45-7.50 (1H, m), 7.67-7.69 (1H, m), 8.42 (1H, dd, J = 6.6, 8.7 Hz). | Ex. 125 |

| | | |
|---|---|---|
| 1245 | [structure: 2-(2-chloro-4-fluorophenyl)-5-ethyl-thiazole with triazole-carbonitrile] | 1H-NMR (DMSO-d6) δ: 1.34 (3H, t, J = 7.5 Hz), 3.27-3.33 (2H, m), 7.46-7.51 (1H, m), 7.70 (1H, dd, J = 2.6, 8.9 Hz), 8.42 (1H, dd, J = 6.3, 8.9 Hz). Ex. 125 |
| 1246 | [structure: 2-(2,4-dichlorophenyl)-5-methyl-thiazole with triazole-carbonitrile] | 1H-NMR (DMSO-d6) δ: 2.82 (3H, s), 7.63 (1H, dd, J = 2.2, 8.6 Hz), 7.83 (1H, d, J = 2.2 Hz), 8.41 (1H, d, J = 8.6 Hz). Ex. 125 |
| 1247 | [structure: 2-(4-chloro-2-fluorophenyl)-thiazole with triazole-carbonitrile] | 1H-NMR (DMSO-d6) δ: 7.58 (1H, dd, J = 2.0, 8.5 Hz), 7.75 (1H, dd, J = 2.0, 11.3 Hz), 8.31-8.40 (2H, m). Ex. 125 |
| 1248 | [structure: 2-(4-chloro-2-fluorophenyl)-5-ethyl-thiazole with triazole-carbonitrile] | 1H-NMR (DMSO-d6) δ: 1.33 (3H, t, J = 7.5 Hz), 3.24-3.30 (2H, m), 7.55 (1H, dd, J = 2.0, 8.5 Hz), 7.73 (1H, dd, J = 2.0, 11.3 Hz), 8.28 (1H, t, J = 8.5 Hz). Ex. 125 |
| 1249 | [structure: 2-(3-bromo-4-fluorophenyl)-thiazole with triazole-carbonitrile] | 1H-NMR (DMSO-d6) δ: 7.60 (1H, t, J = 8.6 Hz), 8.08-8.13 (1H, m), 8.36-8.38 (2H, m). Ex. 125 |

| | Structure | 1H-NMR | Ex. |
|---|---|---|---|
| 1250 | 2-(3-bromo-4-fluorophenyl)-5-methylthiazol-4-yl triazole carbonitrile | 1H-NMR (DMSO-d6) δ: 2.79 (3H, s), 7.58 (1H, t, J = 8.6 Hz), 7.98-8.02 (1H, m), 8.29 (1H, dd, J = 2.2, 6.6 Hz). | Ex. 125 |
| 1251 | 2-(3-bromo-4-fluorophenyl)-5-ethylthiazol-4-yl triazole carbonitrile | 1H-NMR (DMSO-d6) δ: 1.33 (3H, t, J = 7.5 Hz), 3.27 (2H, q, J = 7.5 Hz), 7.58 (1H, t, J = 8.7 Hz), 8.00-8.04 (1H, m), 8.30 (1H, dd, J = 2.2, 6.6 Hz). | Ex. 125 |
| 1252 | 2-(4-chloro-2-fluorophenyl)-5-methylthiazol-4-yl triazole carbonitrile | 1H-NMR (DMSO-d6) δ: 2.80 (3H, s), 7.56 (1H, dd, J = 2.0, 8.5 Hz), 7.74 (1H, dd, J = 2.0, 11.3 Hz), 8.28 (1H, t, J = 8.5 Hz). | Ex. 125 |
| 1253 | 2-(3,5-difluorophenyl)-5-methylthiazol-4-yl triazole carbonitrile | 1H-NMR (DMSO-d6) δ: 2.80 (3H, s), 7.39-7.45 (1H, m), 7.63-7.69 (2H m). | Ex. 125 |
| 1255 | 4-methyl-2-(4-(trifluoromethyl)phenyl)thiazol-5-yl triazole carbonitrile | 1H-NMR (DMSO-d6) δ: 2.65 (3H, s), 7.90 (2H, d, J = 8.3 Hz), 8.21 (2H, d, J = 8.1 Hz). | Ex. 1 |

TABLE 4-continued

| | Structure | 1H-NMR | |
|---|---|---|---|
| 1256 | 4-(trifluoromethyl)phenyl-thiazole-triazole-CN | 1H-NMR (DMSO-d6) δ: 7.92 (2H, d, J = 8.2 Hz), 8.26 (2H, d, J = 8.2 Hz), 8.50 (1H, s). | Ex. 1 |
| 1257 | 4-chlorophenyl-thiazole-triazole-CN | 1H-NMR (DMSO-d6) δ: 7.60-7.65 (2H, m), 8.04-8.08 (2H, m), 8.42 (1H,s). | Ex. 1 |
| 1258 | 4-(trifluoromethoxy)phenyl-thiazole-triazole-CN | 1H-NMR (DMSO-d6) δ: 7.54 (2H, d, J = 8.0 Hz), 8.13-8.18 (2H, m), 8.43 (1H, s). | Ex. 1 |
| 1259 | 3-chloro-4-fluorophenyl-thiazole-triazole-CN | 1H-NMR (DMSO-d6) δ: 7.62 (1H, t, J = 8.9 Hz), 8.04-8.09 (1H, m), 8.24 (1H, dd, J = 2.2, 7.0 Hz), 8.43 (1H, s). | Ex. 1 |
| 1260 | 4-chlorophenyl-4-(trifluoromethyl)thiazole-triazole-CN | 1H-NMR (DMSO-d6) δ: 7.66 (2H, d, J = 8.6 Hz), 8.08 (2H, d, J = 8.6 Hz). | Ex. 1 |

TABLE 4-continued

| | Structure | 1H-NMR | Ref. |
|---|---|---|---|
| 1261 | 2-(3-(trifluoromethyl)phenyl)-4-(trifluoromethyl)thiazol-5-yl triazole-carbonitrile | 1H-NMR (DMSO-d6) δ: 7.82 (1H, t, J = 7.8 Hz), 7.97 (1H, d, J = 8.6 Hz), 8.29-8.34 (2H, m). | Ex. 1 |
| 1262 | 4-ethyl-2-(4-(trifluoromethyl)phenyl)thiazol-5-yl triazole-carbonitrile | 1H-NMR (DMSO-d6) δ: 1.33 (3H, t, J = 7.5 Hz), 2.99 (2H, q, J = 7.5 Hz), 7.91 (2H, d, J = 8.3 Hz), 8.22 (2H, d, J = 8.3 Hz). | Ex. 1 |
| 1263 | 2-(4-chlorophenyl)-4-cyclopropylthiazol-5-yl triazole-carbonitrile | 1H-NMR (CDCl3-DMSO-d6) δ: 1.04-1.13 (2H, m), 1.15-1.26 (2H, m), 2.48-2.59 (1H, br.), 7.41 (2H, d, J = 8.5 Hz), 7.87 (2H, d, J = 8.5 Hz), 15.6 (1H, br.). | Ex. 1 |
| 1264 | 2-(3-chloro-4-fluorophenyl)-4-cyclopropylthiazol-5-yl triazole-carbonitrile | 1H-NMR (DMSO-d6) δ: 1.05-1.15 (4H, m), 2.39-2.47 (1H, br.), 7.57 (1H, t, J = 8.9 Hz), 7.92-7.99 (1H, m), 8.13 (1H, dd, J = 2.1, 7.0 Hz). | Ref. Ex. 63, Ex. 1 |

TABLE 4-continued

| | | | |
|---|---|---|---|
| 1265 | (structure: 2-(3-chloro-4-fluorophenyl)-5-(4-chlorophenyl)thiazole with triazole-carbonitrile) | 1H-NMR (DMSO-d6) δ: 7.55 (1H, t, J = 8.9 Hz), 7.60-7.66 (1H, m), 7.66-7.70 (2H, m), 7.93 (1H, dd, J = 2.1, 7.1 Hz), 8.05-8.09 (2H, m). | Ex. 1 |
| 1266 | (structure: 2-methyl-5-(4-trifluoromethylphenyl)thiazole with triazole-carbonitrile) | 1H-NMR (DMSO-d6) δ: 2.79 (3H, s), 7.67 (2H, d, J = 10.9 Hz), 7.80 (2H, d, J = 11.0 Hz). | Ex. 1 |
| 1267 | (structure: 2-(4-chlorophenyl)-5-(4-chlorobenzyl)thiazole with triazole-carbonitrile) | 1H-NMR (DMSO-d6) δ: 4.64 (2H, s), 7.36-7.41 (4H, m), 7.57-7.62 (2H, m), 7.96-8.00 (2H, m). | Ex. 1 |

TABLE 4-continued

| | Structure | 1H-NMR | Ex. |
|---|---|---|---|
| 1268 | (2-(4-chlorophenyl)-5-(4-(trifluoromethyl)benzyl)thiazol-4-yl triazole carbonitrile) | 1H-NMR (DMSO-d6) δ: 4.76 (2H, s), 7.55-7.62 (4H, m), 7.70 (2H, d, J = 8.1 Hz), 7.97-8.00 (2H, m). | Ex. 1 |
| 1269 | (2-bromo-5-(4-(trifluoromethyl)phenyl)thiazol-4-yl triazole carbonitrile) | 1H-NMR (CDCl3) δ: 7.54 (2H, d, J = 8.1 Hz), 7.72 (2H, d, J = 8.1 Hz). | Ex. 125 |
| 1270 | (2-(6-(trifluoromethyl)pyridin-3-yl)thiazol-4-yl triazole carbonitrile) | 1H-NMR (DMSO-d6) δ: 8.15 (1H, d, J = 8.3 Hz), 8.54 (1H, s), 8.68 (1H, dd, J = 2.1, 7.8 Hz), 9.41 (1H, d, J = 2.0 Hz). | Ex. 1 |
| 1271 | (5-methyl-2-(6-(trifluoromethyl)pyridin-3-yl)thiazol-4-yl triazole carbonitrile) | 1H-NMR (DMSO-d6) δ: 2.83 (3H, s), 8.11 (1H, d, J = 8.2 Hz), 8.57 (Hz, dd, J = 1.7, 8.2 Hz), 9.33 (1H, d, J = 1.7 Hz). | Ex. 1 |

TABLE 4-continued

| | Structure | 1H-NMR | Ref. |
|---|---|---|---|
| 1272 | 2-(5-chloropyridin-3-yl)thiazole with 5-methyl, linked to cyano-triazole | 1H-NMR (DMSO-d6) δ: 2.82 (3H, s), 8.42 (1H, t, J = 2.1 Hz), 8.77 (1H, d, J = 2.1 Hz), 9.13 (1H, d, J = 2.1 Hz). | Ex. 1 |
| 1273 | 2-(5-chloropyridin-3-yl)thiazole with 5-ethyl, linked to cyano-triazole | 1H-NMR (DMSO-d6) δ: 1.34 (3H, t, J = 7.5 Hz), 3.29 (2H, q, J = 7.5 Hz), 8.42 (1H, t, J = 2.1 Hz), 8.76 (1H, d, J = 2.1 Hz), 9.13 (1H, d, J = 2.1 Hz). | Ex. 1 |
| 1274 | 2-(6-chloropyridin-3-yl)thiazole with 5-methyl, linked to cyano-triazole | 1H-NMR (DMSO-d6) δ: 2.81 (3H, s), 7.74 (1H, dd, J = 0.6, 8.4 Hz), 8.36 (1H, dd, J = 2.5, 8.4 Hz), 8.99 (1H, dd, J = 0.6, 2.5 Hz). | Ex. 125 |
| 1275 | 2-(6-chloropyridin-3-yl)thiazole with 5-ethyl, linked to cyano-triazole | 1H-NMR (DMSO-d6) δ: 1.34 (3H, t, J = 7.4 Hz), 3.28 (2H, q, J = 7.4 Hz), 7.74 (1H, dd, J = 0.6, 8.4 Hz), 8.37 (1H, dd, J = 2.5, 8.4 Hz), 9.00 (1H, dd, J = 0.6, 2.5 Hz). | Ex. 125 |
| 1276 | 2-(6-chloropyridin-3-yl)thiazole linked to cyano-triazole | 1H-NMR (DMSO-d6) δ: 7.72 (1H, d, J = 8.3 Hz), 7.95 (1H, s), 8.40 (1H, dd, J = 2.4, 8.3 Hz), 9.02 (1H, d, J = 2.3 Hz). | Ex. 125 |

TABLE 4-continued
| | Structure | 1H-NMR | Ex. |
|---|---|---|---|
| 1277 | 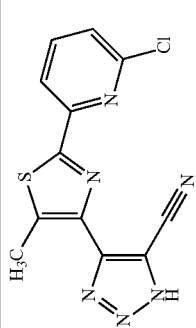 | 1H-NMR (DMSO-d6) δ: 2.80 (3H, s), 7.64-7.68 (1H, m), 8.09-8.14 (2H, m). | Ex. 125 |
| 1278 | 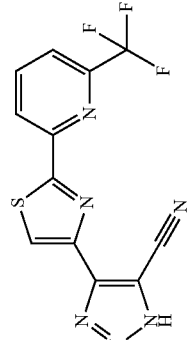 | 1H-NMR (DMSO-d6) δ: 8.09 (1H, dd, J = 1.3, 7.4 Hz), 8.37-8.45 (2H, m), 8.50 (1H, s). | Ex. 1 |
| 1279 | 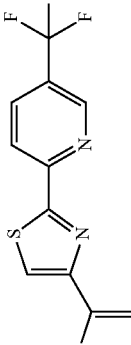 | 1H-NMR (DMSO-d6) δ: 8.35 (1H, d, J = 6.6 Hz), 8.52 (1H, s), 8.54 (1H, d, J = 1.4 Hz), 9.11 (1H, s). | Ex. 1 |
| 1280 | 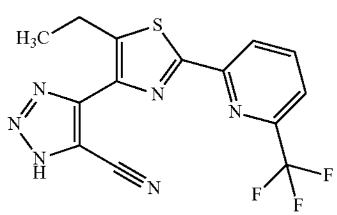 [SMILES: CCc1sc(-c2cccc(C(F)(F)F)n2)nc1-c1nn[nH]c1C#N] | 1H-NMR (DMSO-d6) δ: 1.34 (3H, t, J = 7.5 Hz), 3.25-3.31 (2H, m), 8.02 (1H, d, J = 6.7 Hz), 8.32-8.40 (2H, m). | Ex. 1 |
| 1281 | 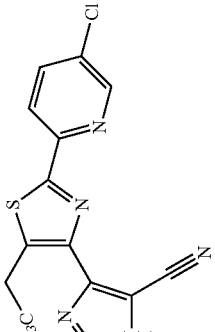 | 1H-NMR (DMSO-d6) δ: 1.34 (3H, t, J = 7.5 Hz), 3.26 (2H, q, J = 7.5 Hz), 8.13 (1H, dd, J = 0.5, 8.5 Hz), 8.21 (1H, dd, J = 2.4, 8.5 Hz), 8.73 (1H, dd, J = 0.5, 2.4 Hz). | Ex. 1 |

TABLE 4-continued

| | Structure | 1H-NMR | Ex. |
|---|---|---|---|
| 1282 | (2-(5-fluoropyridin-2-yl)-5-methylthiazol-4-yl triazole carbonitrile) | 1H-NMR (DMSO-d6) δ: 2.79 (3H, s), 7.96-8.04 (1H, m), 8.18 (1H, dd, J = 4.6, 8.8 Hz), 8.67 (1H, d, J = 2.8 Hz). | Ex. 1 |
| 1283 | (2-(5-fluoropyridin-2-yl)-5-ethylthiazol-4-yl triazole carbonitrile) | 1H-NMR (DMSO-d6) δ: 1.31 (3H, t, J = 7.4 Hz), 3.41-3.44 (2H, m), 7.95-8.00 (1H, m), 8.18 (1H, dd, J = 4.6, 8.9 Hz), 8.65 (1H, d, J = 2.8 Hz). | Ex. 1 |
| 1284 | (2-(2-chloropyridin-3-yl)-5-methylthiazol-4-yl triazole carbonitrile) | 1H-NMR (DMSO-d6) δ: 2.84 (3H, s), 7.92-7.93 (1H, m), 8.00 (1H, s), 8.59 (1H, d, J = 5.2 Hz). | Ex. 1 |
| 1285 | (2-(2-chloropyridin-3-yl)-5-ethylthiazol-4-yl triazole carbonitrile) | 1H-NMR (DMSO-d6) δ: 1.34 (3H, t, J = 7.4 Hz), 3.20-3.50 (2H, m), 7.93 (1H, d, J = 5.1 Hz), 8.01 (1H, s), 8.59 (1H, d, J = 5.1 Hz). | Ex. 1 |
| 1286 | (2-(4-chlorophenoxy)thiazol-4-yl triazole carbonitrile) | 1H-NMR (DMSO-d6) δ: 7.57 (4H, s), 7.84 (1H, s). | Ex. 1 |

TABLE 4-continued

| | Structure | 1H-NMR | |
|---|---|---|---|
| 1287 | 4-(trifluoromethoxy)phenoxy-thiazole-triazole-CN | 1H-NMR (DMSO-d6) δ: 7.49-7.52 (2H, m), 7.64-7.68 (2H, m), 7.85 (1H, s). | Ex. 1 |
| 1288 | 3-chloro-4-fluorophenoxy-thiazole-triazole-CN | 1H-NMR (DMSO-d6) δ: 7.52-7.58 (2H, m), 7.84 (1H, s), 7.90-7.93 (1H, m). | Ex. 1 |
| 1289 | 4-chlorophenoxy-5-chlorothiazole-triazole-CN | 1H-NMR (DMSO-d6) δ: 7.53-7.60 (4H, m). | Ex. 1 |
| 1290 | 3-(trifluoromethyl)phenoxy-5-chlorothiazole-triazole-CN | 1H-NMR (DMSO-d6) δ: 7.72-7.77 (2H, m), 7.86-7.89 (1H, m), 7.94 (1H, s). | Ex. 1 |
| 1291 | 4-chlorophenoxy-5-methylthiazole-triazole-CN | 1H-NMR (DMSO-d6) δ: 2.63 (3H, s), 7.69-7.87 (4H, m). | Ex. 1 |

TABLE 4-continued

| | Structure | 1H-NMR | |
|---|---|---|---|
| 1292 | (thiazole with 3-(trifluoromethyl)phenoxy and methyltriazole-carbonitrile) | 1H-NMR (DMSO-d6) δ: 2.63 (3H, s), 7.67-7.74 (2H, m), 7.84-7.87 (2H, m). | Ex. 1 |
| 1293 | (thiazole with 3-chloro-4-fluorophenylthio and triazole-carbonitrile) | 1H-NMR (DMSO-d6) δ: 7.61 (1H, t, J = 9.0 Hz), 7.81-7.86 (1H, m), 8.11 (1H, dd, J = 2.3, 6.9 Hz), 8.21 (1H, s). | Ex. 1 |
| 1294 | (thiazole with 3-(trifluoromethyl)phenylthio and triazole-carbonitrile) | 1H-NMR (DMSO-d6) δ: 7.77 (1H, t, J = 7.8 Hz), 7.92 (1H, d, J = 7.9 Hz), 8.09 (1H, s), 8.13 (1H, s), 8.25 (1H, s). | Ex. 1 |
| 1295 | (thiazole with 4-chlorophenylthio and methyltriazole-carbonitrile) | 1H-NMR (DMSO-d6) δ: 2.62 (3H, s), 7.58-7.61 (2H, m), 7.74-7.78 (2H, m). | Ex. 1 |
| 1296 | (thiazole with 3-chloro-4-fluorophenylthio and methyltriazole-carbonitrile) | 1H-NMR (DMSO-d6) δ: 2.63 (3H, s), 7.57 (1H, t, J = 9.0 Hz), 7.76-7.81 (1H, m), 8.05 (1H, dd, J = 2.3, 6.9 Hz). | Ex. 1 |

| | Structure | 1H-NMR | |
|---|---|---|---|
| 1297 | 4-(trifluoromethyl)styryl-thiazole-triazole-CN | 1H-NMR (DMSO-d6) δ: 7.76-7.80 (4H, m), 7.98 (2H, d, J = 8.1 Hz), 8.39 (1H, s). | Ex. 1 |
| 1298 | 4-(trifluoromethyl)phenyl-thiazole-triazole-CN | 1H-NMR (DMSO-d6) δ: 7.90 (2H, d, J = 8.3 Hz), 8.29 (2H, d, J = 8.1 Hz), 8.64 (1H, s). | Ex. 1 |
| 1299 | 4-chlorophenyl-thiazole-triazole-CN | 1H-NMR (DMSO-d6) δ: 7.58-7.62 (2H, m), 8.07-8.12 (2H, m), 8.46 (1H, s). | Ex. 1 |
| 1300 | 3-chloro-4-fluorophenyl-thiazole-triazole-CN | 1H-NMR (DMSO-d6) δ: 7.61 (1H, t, J = 9.0 Hz), 8.07-8.12 (1H, m), 8.29 (1H, dd, J = 2.2, 7.2 Hz), 8.53 (1H, s). | Ex. 1 |
| 1301 | piperidinyl-thiazole-triazole-CN | 1H-NMR (DMSO-d6) δ: 1.62 (6H, brs), 3.50 (4H, brs), 7.40 (1H, s). | Ex. 1 |

TABLE 4-continued

| | Structure | 1H-NMR | Ex. |
|---|---|---|---|
| 1302 | morpholine-thiazole-triazole-CN | 1H-NMR (DMSO-d6) δ: 3.48 (4H, t, J = 4.9 Hz), 3.74 (4H, t, J = 4.9 Hz), 7.49 (1H, s). | Ex. 1 |
| 1303 | 4-chlorophenoxymethyl-thiazole-triazole-CN | 1H-NMR (DMSO-d6) δ: 5.55 (2H, s), 7.13-7.19 (2H, m), 7.35-7.41 (2H, m), 8.34 (1H, s). | Ex. 1 |
| 1304 | 4-trifluoromethoxyphenoxymethyl-thiazole-triazole-CN | 1H-NMR (DMSO-d6) δ: 5.57 (2H, s), 7.21-7.26 (2H, m), 7.32-7.36 (2H, m), 8.35 (1H, s). | Ex. 1 |
| 1305 | 3-trifluoromethylphenoxymethyl-thiazole-triazole-CN | 1H-NMR (DMSO-d6) δ: 5.65 (2H, s), 7.37 (1H, d, J = 7.5 Hz), 7.44-7.47 (2H, m), 7.56-7.61 (1H, m), 8.35 (1H, s). | Ex. 1 |

TABLE 4-continued

| | Structure | 1H-NMR | |
|---|---|---|---|
| 1306 | N-methyl-N-(4-trifluoromethoxyphenyl)-thiazol-triazole-carbonitrile | 1H-NMR (DMSO-d6) δ: 3.57 (3H, s), 7.44-7.47 (3H, m), 7.73-7.78 (2H, m). | Ex. 1 |
| 1307 | N-(4-trifluoromethoxyphenyl)-thiazol-triazole-carbonitrile | 1H-NMR (DMSO-d6) δ: 7.26 (2H, d, J = 8.6 Hz), 7.58 (1H, s), 7.94-7.99 (2H, m), 10.71 (1H, s). | Ex. 1 |
| 1308 | N-(4-chlorophenyl)-thiazol-triazole-carbonitrile | 1H-NMR (DMSO-d6) δ: 7.30 (2H, d, J = 8.8 Hz), 7.57 (1H, s), 7.88 (2H, d, J = 9.8 Hz) 10.64 (1H, s). | Ex. 1 |
| 1309 | 2-(thiophen-3-yl)-thiazol-triazole-carbonitrile | 1H-NMR (DMSO-d6) δ: 7.67 (1H, dd, J = 1.3, 5.1 Hz), 7.79 (1H, dd, J = 2.9, 5.1 Hz), 8.27-8.28 (2H, m). | Ex. 1 |

TABLE 4-continued

| | Structure | 1H-NMR | |
|---|---|---|---|
| 1310 | (thiazole with 4-(trifluoromethyl)benzyl, triazole-CN) | 1H-NMR (DMSO-d6) δ: 4.57 (2H, s), 7.66 (2H, d, J = 8.2 Hz), 7.74 (2H, d, J = 8.3 Hz), 8.19 (1H, s). | Ex. 1 |
| 1311 | (thiazole with 4-chlorobenzyl, triazole-CN) | 1H-NMR (DMSO-d6) δ: 4.45 (2H, s), 7.41-7.48 (4H, m), 8.17 (1H, s). | Ex. 1 |
| 1312 | (thiazole with N-ethyl-N-(4-trifluoromethoxyphenyl)amino, triazole-CN) | 1H-NMR (DMSO-d6) δ: 1.24 (3H, t, J = 7.1 Hz), 4.05 (2H, q, J = 7.1 Hz), 7.38 (1H, s), 7.50 (2H, d, J = 8.2 Hz), 7.67-7.71 (2H, m). | Ex. 1 |
| 1313 | (thiazole with 2-(4-(trifluoromethyl)phenyl)ethyl, triazole-CN) | 1H-NMR (DMSO-d6) δ: 3.24 (2H t, J = 7.8 Hz), 3.45 (2H, t, J = 7.8 Hz), 7.54 (2H, d, J = 8.1 Hz), 7.65 (2H, d, J = 8.0 Hz), 8.14 (1H, s). | Ex. 1 |

TABLE 4-continued

| Ex. No. | STR | 1H-NMR | ref. |
|---|---|---|---|
| 1314 | (4-chlorobenzyl-N-methyl-aminothiazole triazole carbonitrile structure) | 1H-NMR (DMSO-d6) δ: 3.09 (3H, s), 4.77 (2H, s), 7.34-7.41 (5H, m). | Ex. 1 |
| 1315 | (trifluoromethyl-benzothiophene-thiazole-triazole carbonitrile structure) | m.p. 248-249 | Ex. 1 |
| 1316 | (furan-thiazole-triazole carbonitrile structure) | 1H-NMR (DMSO-d6) δ: 6.99 (1H, dd, J = 0.8, 1.8 Hz), 7.89 (1H, t, J = 1.7 Hz), 8.24 (1H, s), 8.46-8.48 (1H, m). | Ex. 1 |

TABLE 4-continued

| | Structure | 1H-NMR | Ex. |
|---|---|---|---|
| 1317 | 4-[4-(trifluoromethyl)phenyl]piperazinyl-thiazole-triazole-CN | 1H-NMR (DMSO-d6) δ: 3.48-3.52 (4H, m), 3.65-3.68 (4H, m), 7.15 (2H, d, J = 8.7 Hz), 7.50 (1H, s), 7.54 (2H, d, J = 8.8 Hz). | Ex. 1 |
| 1318 | 4-phenylpiperidinyl-thiazole-triazole-CN | 1H-NMR (DMSO-d6) δ: 1.68-1.82 (2H, m), 1.89-1.93 (2H, m), 2.78-2.86 (1H, m), 3.18-3.27 (2H, m), 4.09-4.13 (2H, m), 7.18-7.34 (5H, m), 7.44 (1H, s). | Ex. 1 |
| 1319 | 4-(4-chlorophenyl)piperazinyl-thiazole-triazole-CN | 1H-NMR (DMSO-d6) δ: 3.30-3.34 (4H, m), 3.53-3.66 (4H, m), 7.01-7.06 (2H, m), 7.24-7.29 (2H, m), 7.49 (1H, s). | Ex. 1 |
| 1320 | 2-tert-butyl-thiazole-triazole-CN | 1H-NMR (DMSO-d6) δ: 1.45 (9H, s), 8.15 (1H, s). | Ex. 1 |
| 1321 | 2-cyclohexyl-thiazole-triazole-CN | 1H-NMR (DMSO-d6) δ: 1.24-1.82 (8H, m), 2.10-2.14 (2H, m), 3.04-3.11 (1H, m), 8.16 (1H, s). | Ex. 1 |

TABLE 4-continued

| | Structure | 1H-NMR | Ex. |
|---|---|---|---|
| 1322 | (3-trifluoromethylbenzyl sulfonylmethyl-thiazole-triazole-CN) | 1H-NMR (DMSO-d6) δ: 4.94 (2H, s), 5.16 (2H, s), 7.66 (1H, t, J = 7.7 Hz), 7.76-7.84 (3H, m), 8.38 (1H, s). | Ex. 1 |
| 1323 | (4-chlorobenzyl-piperidine-thiazole-triazole-CN) | 1H-NMR (DMSO-d6) δ: 1.87-2.03 (2H, m), 2.15-2.25 (2H, m), 2.49-2.86 (4H, m), 3.18-3.27 (1H, m), 4.02 (2H, s), 7.45-7.52 4H, m), 7.88 (1H, s). | Ex. 1 |
| 1324 | (4-trifluoromethylbenzyl-piperidine-thiazole-triazole-CN) | 1H-NMR (DMSO-d6) δ: 1.85-1.98 (2H, m), 2.14-2.21 (2H, m), 2.49-2.74 (4H, m), 3.15-3.20 (1H, m), 4.01 (2H, s), 7.66 (2H, d, J = 8.1 Hz), 7.79 (2H, d, J = 8.1 Hz), 7.95 (1H, s). | Ex. 1 |
| 1325 | (4-chlorophenyl-piperidine-thiazole-triazole-CN) | 1H-NMR (DMSO-d6) δ: 1.79-1.94 (2H, m), 2.17-2.22 (2H, m), 2.85-2.94 (2H, m), 3.24-3.28 (1H, m), 3.76-3.81 (2H, m), 7.00 (2H, d, J = 8.8 Hz), 7.23 (2H, d, J = 8.6 Hz), 8.19 (1H, s). | Ex. 1 |
| 1326 | (4-trifluoromethylphenyl-piperidine-thiazole-triazole-CN) | 1H-NMR (DMSO-d6) δ: 1.77-1.91 (2H, m), 2.18-2.22 (2H, m), 3.00-3.10 (2H, m), 3.25-3.28 (1H, m), 3.95-4.00 (2H, m), 7.12 (2H, d, J = 8.6 Hz), 7.50 (2H, d, J = 8.9 Hz), 8.19 (1H, s). | Ex. 1 |

TABLE 4-continued

| | Structure | 1H-NMR | |
|---|---|---|---|
| 1327 | thiazole-CH2-O-CH2-C6H4-OCF3 connected to cyano-triazole | 1H-NMR (DMSO-d6) δ: 4.75 (2H, s), 4.95 (2H, s), 7.38 (2H, d, J = 8.0 Hz), 7.54 (2H, d, J = 8.6 Hz), 8.30 (1H, s). | Ex. 1 |
| 1328 | thiazole-CH2-O-CH2-C6H4-Cl connected to cyano-triazole | 1H-NMR (DMSO-d6) δ: 4.71 (2H, s), 4.93 (2H, s), 7.45 (4H, s), 8.30 (1H, s). | Ex. 1 |
| 1329 | thiazole-CH2-O-CH2-C6H4-CF3 connected to cyano-triazole | 1H-NMR (DMSO-d6) δ: 4.84 (2H, s), 4.98 (2H, s), 7.64 (2H, d, J = 8.1 Hz), 7.76 (2H, d, J = 8.2 Hz), 8.32 (1H, s). | Ex. 1 |
| 1330 | thiazole-CH2-(3,5-di-tert-butyl-4-hydroxyphenyl) connected to cyano-triazole | 1H-NMR (DMSO-d6) δ: 1.37 (18H, s), 4.29 (2H, s), 6.90 (1H, s), 7.14 (2H, s), 8.11 (1H, s). | Ex. 1 |

TABLE 4-continued

| | Structure | 1H-NMR | Ex. |
|---|---|---|---|
| 1331 | (indole-thiazole-triazole-CN) | 1H-NMR (DMSO-d6) δ: 7.16-7.27 (2H, m), 7.48-7.51 (1H, m), 8.10 (1H, s), 8.21 (1H, d, J = 2.9 Hz), 8.55 (1H, d, J = 7.1 Hz), 11.83 (1H, brs). | Ex. 1 |
| 1332 | (4-Cl-C6H4-C(O)NH-thiazole(CH3)-triazole-CN) | 1H-NMR (DMSO-d6) δ: 2.59 (3H, s), 7.62-7.64 (2H, m), 8.10-8.13 (2H, m), 12.79 (1H, s). | Ex. 125 |
| 1333 | (4-Cl-C6H4-CH2-NH-thiazole(CH3)-triazole-CN) | 1H-NMR (DMSO-d6) δ: 2.47 (3H, s), 4.48 (2H, d, J = 6.0 Hz), 7.37-7.43 (4H, m), 8.18 (1H, t, J = 6.0 Hz). | Ex. 125 |
| 1334 | (4-CF3-C6H4-CH2-NH-thiazole(CH3)-triazole-CN) | 1H-NMR (DMSO-d6) δ: 2.48 (3H, s), 4.59 (2H, d, J = 6.0 Hz), 7.61 (2H, d, J = 8.0 Hz), 7.69 (2H, d, J = 8.0 Hz), 8.27 (1H, t, J = 6.0 Hz). | Ex. 125 |

TABLE 4-continued

| | Structure | 1H-NMR | |
|---|---|---|---|
| 1335 | 4-(trifluoromethyl)benzyl-NH-thiazole(5-CH2CH3)-triazole-CN | 1H-NMR (DMSO-d6) δ: 1.17 (3H, t, J = 7.8 Hz), 2.96 (2H, q, J = 7.8 Hz), 4.60 (2H, d, J = 6.0 Hz), 7.61 (2H, d, J = 8.1 Hz), 7.69 (2H, d, J = 8.1 Hz), 8.30 (1H, t, J = 6.0 Hz). | Ex. 125 |
| 1336 | 4-chlorobenzoyl-N(CH3)-thiazole(5-CH2CH3)-triazole-CN | 1H-NMR (DMSO-d6) δ: 1.20 (3H, t, J = 7.5 Hz), 2.64 (2H, q, J = 7.5 Hz), 3.69 (3H, s), 7.54-7.58 (2H, m), 8.22-8.26 (2H, m). | Ex. 125 |
| 1337 | 1-(4-chlorophenyl)-4-piperazinyl-thiazole(5-(4-CF3-phenyl))-triazole-CN | 1H-NMR (DMSO-d6) δ: 3.33-3.35 (4H, m), 3.67-3.69 (4H, m), 7.02-7.06 (2H, m), 7.26-7.30 (2H, m), 7.63 (2H, d, J = 8.1 Hz), 7.74 (2H, d, J = 8.1 Hz). | Ex. 125 |
| 1339 | 2-(3-chloro-4-fluorophenyl)-thiazole(5-CHF2)-triazole-CN | 1H-NMR (DMSO-d6) δ: 7.70 (1H, t, J = 8.7 Hz), 7.82 (1H, t, J = 53.7 Hz), 8.10-8.15 (1H, m), 8.31 (1H, dd, J = 2.2, 7.0 Hz). | Ex. 125 |

TABLE 4-continued

| Ex. No. | STR | m.p. | ref. |
|---|---|---|---|
| 1340 | (2-(3-chloro-4-fluorophenyl)-5-(trifluoromethyl)thiazol-4-yl triazole carbonitrile) | 1H-NMR (DMSO-d6) δ: 7.71 (1H, t, J = 8.9 Hz), 8.13-8.17 (1H, m), 8.34 (1H, dd, J = 2.3, 7.0 Hz). | Ex. 125 |
| 1342 | (2-(4-chlorophenyl)-5-(difluoromethyl)thiazol-4-yl triazole carbonitrile) | 1H-NMR (DMSO-d6) δ: 7.81 (1H, t, J = 53.8 Hz), 7.68-7.71 (2H, m), 8.09-8.13 (2H, m). | Ex. 125 |
| 1341 | (2-(4-chlorophenyl)-5-(trifluoromethyl)thiazol-4-yl triazole carbonitrile) | 247.4-248.6 | Ex. 125 |
| 1343 | (2-(3-(trifluoromethyl)phenyl)-5-isopropyloxazol-4-yl triazole carbonitrile) | 211-212 | Ex. 2 |

TABLE 4-continued

| | | | |
|---|---|---|---|
| 1344 | (structure) | 229.3-231.4 | Ex. 2 |
| 1345 | (structure) | 271.2-271.6 | Ex. 2 |
| 1346 | (structure) | 201.8-203.4 | Ex. 2 |
| 1347 | (structure) | 241.1-243.0 | Ex. 2 |

TABLE 4-continued

| | | | |
|---|---|---|---|
| 1348 | (structure) | 147.6-151.6 | Ex. 2 |
| 1349 | (structure) | 236.1-239.0 | Ex. 2 |
| 1350 | (structure) | 266.9-269.1 | Ex. 2 |
| 1351 | (structure) | 228.3-230.3 | Ex. 2 |

TABLE 4-continued

| | | | |
|---|---|---|---|
| 1352 | (structure) | 216.6-220.0 | Ex. 2 |
| 1353 | (structure) | 205.5-207.8 | Ex. 2 |
| 1354 | (structure) | 193-196 | Ex. 1 |
| 1355 | (structure) | 148-167 | Ex. 1 |

TABLE 4-continued

| | | | |
|---|---|---|---|
| 1356 | (structure) | 151-169 | Ex. 1 |
| 1357 | (structure) | 209-215 | Ex. 1 |
| 1358 | (structure) | 190-204 | Ex. 1 |
| 1359 | (structure) | 176-188 | Ex. 1 |

TABLE 4-continued

| | | | |
|---|---|---|---|
| 1360 | [structure: 2-(3-chlorophenyl)-5-cyclobutyl-oxazole-triazole-carbonitrile] | 176-181 | Ex. 1 |
| 1361 | [structure: 2-(3-trifluoromethylphenyl)-5-cyclobutyl-oxazole-triazole-carbonitrile] | 186-193 | Ex. 1 |
| 1362 | [structure: 2-(3-chlorophenyl)-5-isobutyl-oxazole-triazole-carbonitrile] | 169-170 | Ex. 125 |
| 1363 | [structure: 2-(3-trifluoromethylphenyl)-5-isobutyl-oxazole-triazole-carbonitrile] | 176-182 | Ex. 125 |

TABLE 4-continued

| Ex. No. | STR | 1H-NMR | ref. |
|---|---|---|---|
| 1364 | (2-(3-trifluoromethylphenyl)oxazol-4-yl triazole carbonitrile) | 1H-NMR (DMSO-d6) δ: 7.88 (1H, t, J = 7.8 Hz), 8.00 (1H, d, J = 8.2 Hz), 8.29 (1H, s), 6.35 (1H, d, J = 7.9 Hz), 8.93 (1H, s). | Ex. 1 |
| 1365 | (2-(4-chlorophenyl)oxazol-4-yl triazole carbonitrile) | 1H-NMR (DMSO-d6) δ: 7.67-7.72 (2H, m), 8.04-8.08 (2H, m), 8.88 (1H, s). | Ex. 1 |
| 1366 | (2-(4-chlorophenyl)-5-ethyloxazol-4-yl triazole carbonitrile) | 1H-NMR (DMSO-d6) δ: 1.28 (3H, t, J = 7.5 Hz), 3.01 (2H, q, J = 7.5 Hz), 7.69-7.74 (2H, m), 7.98-8.03 (2H, m). | Ex. 2 |
| 1367 | (2-(4-chlorophenyl)-5-tert-butyloxazol-4-yl triazole carbonitrile) | 1H-NMR (DMSO-d6) δ: 1.42 (9H, s), 7.65-7.68 (2H, m), 8.00-8.03 (2H, m). | Ex. 2 |

TABLE 4-continued

| | Structure | 1H-NMR | |
|---|---|---|---|
| 1368 | 2-(3-chloro-4-fluorophenyl)-5-isopropyl oxazole-triazole-CN | 1H-NMR (DMSO-d6) δ: 1.35 (6H, d, J = 6.8 Hz), 3.63-3.70 (1H, m), 7.66 (1H, t, J = 9.2 Hz), 8.00-8.04 (1H, m), 8.14 (1H, m), dd, J = 2.2, 7.0 Hz). | Ex. 2 |
| 1369 | 2-(3,4-dichlorophenyl)-5-isopropyl oxazole-triazole-CN | 1H-NMR (DMSO-d6) δ: 1.36 (6H, d, J = 7.0 Hz), 3.64-3.71 (1H, m), 7.88 (1H, d, J = 8.5 Hz), 7.98 (1H, dd, J = 2.0, 8.5 Hz), 8.16 (1H, d, J = 2.0 Hz). | Ex. 2 |
| 1370 | 2-(3-trifluoromethylphenyl)-5-propyl oxazole-triazole-CN | 1H-NMR (DMSO-d6) δ: 0.98 (3H, t, J = 7.5 Hz), 1.76-1.82 (2H, m), 3.09 (2H, t, J = 7.5 Hz), 7.86 (1H, t, J = 7.9 Hz), 7.96 (1H, d, J = 7.9 Hz), 8.24 (1H, s), 8.30 (1H, d, J = 7.9 Hz). | Ex. 2 |
| 1371 | 2-(3-chloro-4-fluorophenyl)-5-propyl oxazole-triazole-CN | 1H-NMR (DMSO-d6) δ: 0.97 (3H, t, J = 7.4 Hz), 1.75-1.80 (2H, m), 3.07 (2H, t, J = 7.4 Hz), 7.65 (1H, t, J = 9.1 Hz), 7.99-8.03 (1H, m), 8.12 (1H, dd, J = 2.1, 7.0 Hz). | Ex. 2 |

TABLE 4-continued

| | Structure | 1H-NMR | |
|---|---|---|---|
| 1372 | (2-(3,4-difluorophenyl)oxazole with CH(CH3)2 and triazole-CN) | 1H-NMR (DMSO-d6) δ: 1.35 (6H, d, J = 6.9 Hz), 3.62-3.69 (1H, m), 7.65-7.72 (1H, m), 7.86-7.90 (1H, m), 7.96-8.01 (1H, m). | Ex. 2 |
| 1373 | (2-(4-chlorophenyl)oxazole with cyclopropyl and triazole-CN) | 1H-NMR (DMSO-d6) δ: 1.12-1.22 (4H, m), 2.58-2.63 (1H, m), 7.63-7.65 (2H, m), 7.96-7.98 (2H, m). | Ex. 2 |
| 1374 | (2-(4-chlorophenyl)oxazole with n-butyl and triazole-CN) | 1H-NMR (DMSO-d6) δ: 0.91 (3H, t, J = 7.4 Hz), 1.34-1.43 (2H, m), 1.69-1.77 (2H, m), 3.10 (2H, t, J = 7.4 Hz), 7.67 (2H, d, J = 8.6 Hz), 8.00 (2H, d, J = 8.6 Hz). | Ex. 2 |
| 1375 | (2-(4-trifluoromethylphenyl)oxazole with CH(CH3)2 and triazole-CN) | 1H-NMR (DMSO-d6) δ: 1.37 (6H, d, J = 6.9 Hz), 3.66-3.73 (1H, m), 7.97 (2H, d, J = 8.3 Hz), 8.22 (2H, d, J = 8.3 Hz). | Ex. 2 |

TABLE 4-continued
| | | | |
|---|---|---|---|
| 1376 | 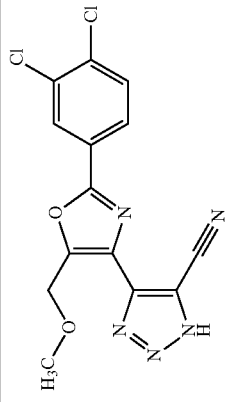 | 1H-NMR (DMSO-d6) δ: 3.34 (3H, s), 4.85 (2H, s), 7.90 (1H, d, J = 8.5 Hz), 8.00 (1H, dd, J = 2.0, 8.5 Hz), 8.17 (1H, d, J = 2.0 Hz). | Ex. 2 |
| 1377 | 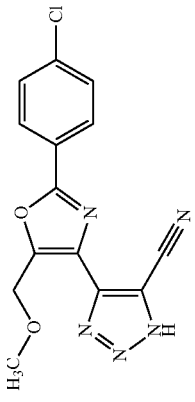 | 1H-NMR (DMSO-d6) δ: 3.34 (3H, s), 4.85 (2H, s), 7.69 (2H, d, J = 8.6 Hz), 8.05 (2H, d, J = 8.6 Hz). | Ex. 2 |
| 1378 | 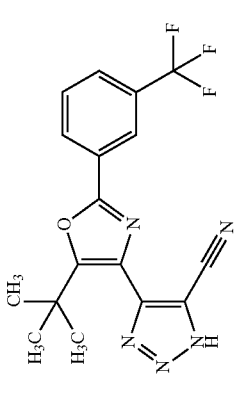 | 1H-NMR (CDCl3) δ: 1.46 (9H, s), 7.62 (1H, t, J = 7.5 Hz), 7.73 (1H, d, J = 7.5 Hz), 8.27-8.30 (2H, m). | Ex. 2 |
| 1379 | 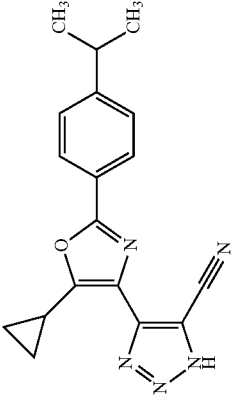 | 1H-NMR (DMSO-d6) δ: 1.09-1.24 (10H, m), 2.54-2.61 (1H, m), 2.93-3.00 (1H, m), 7.43 (2H, d, J = 8.1 Hz), 7.88 (2H, d, J = 8.1 Hz). | Ex. 2 |

TABLE 4-continued

| | | | |
|---|---|---|---|
| 1380 | [structure: 2-(2-fluoro-4-(trifluoromethyl)phenyl)-5-cyclopropyl oxazole-triazole-carbonitrile] | 1H-NMR (DMSO-d6) δ: 1.11-1.26 (4H, m), 2.62-2.68 (1H, m), 7.79 (1H, d, J = 8.1 Hz), 7.94 (1H, d, J = 10.0 Hz), 8.22 (1H, t, J = 7.7 Hz). | Ex. 2 |
| 1381 | [structure: 2-(5-fluoro-2-(trifluoromethyl)phenyl)-5-cyclopropyl oxazole-triazole-carbonitrile] | 1H-NMR (DMSO-d6) δ: 1.05-1.09 (2H, m), 1.19-1.26 (2H, m), 2.65-2.72 (1H, m), 7.63-7.69 (1H, m), 7.90-7.94 (1H, m), 8.03-8.07 (1H, m). | Ex. 1 |
| 1382 | [structure: 2-(3-fluoro-5-(trifluoromethyl)phenyl)-5-cyclopropyl oxazole-triazole-carbonitrile] | 1H-NMR (DMSO-d6) δ: 1.18-1.25 (4H, m), 2.60-2.67 (1H, m), 7.93 (1H, d, J = 8.6 Hz), 8.03-8.07 (2H, m). | Ex. 1 |

| | | | |
|---|---|---|---|
| 1383 | [structure: 2-(4-methylphenyl)-5-cyclopropyl-oxazole linked to cyano-triazole] | 1H-NMR (DMSO-d6) δ: 1.10-1.21 (4H, m), 2.38 (3H, s), 2.55-2.61 (1H, m), 7.37 (2H, d, J = 8.0 Hz), 7.86 (2H, d, J = 8.0 Hz). | Ex. 1 |
| 1384 | [structure: 2-(3-chlorophenyl)-5-cyclohexyl-oxazole linked to cyano-triazole] | 1H-NMR (DMSO-d6) δ: 1.30-1.44 (3H, m), 1.64-1.96 (8H, m), 7.61-7.67 (2H, m), 7.96-8.00 (2H, m). | Ex. 1 |
| 1385 | [structure: 2-(3-trifluoromethylphenyl)-5-cyclohexyl-oxazole linked to cyano-triazole] | 1H-NMR (DMSO-d6) δ: 1.30-1.45 (3H, m), 1.68-1.97 (8H, m), 7.85 (1H, t, J = 7.9 Hz), 7.98 (1H, d, J = 7.9 Hz), 8.25 (1H, s), 8.31 (1H, d, J = 7.9 Hz). | Ex. 1 |
| 1386 | [structure: 2-(3-chloro-4-fluorophenyl)-5-cyclopentyl-oxazole linked to cyano-triazole] | 1H-NMR (DMSO-d6) δ: 1.66-1.74 (2H, m), 1.80-1.90 (4H, m), 2.02-2.12 (2H, m), 3.72-3.78 (1H, m), 7.66 (1H, t, J = 9.0 Hz), 7.99-8.03 (1H, m), 8.12-8.15 (1H, m). | Ex. 1 |

| | | | |
|---|---|---|---|
| 1387 | (structure: 2-(3-chloro-4-fluorophenyl)-5-cyclobutyl-oxazole with triazole-carbonitrile) | 1H-NMR (DMSO-d6) δ: 1.90-2.10 (2H, m), 2.31-2.40 (2H, m), 2.42-2.48 (2H, m), 4.13-4.21 (1H, m), 7.87 (1H, t, J = 8.9 Hz), 8.04-8.08 (1H, m), 8.20 (1H, dd, J = 2.0, 7.0 Hz). | Ex. 125 |
| 1388 | (structure: 2-(3-chloro-4-fluorophenyl)-5-cyclohexyl-oxazole with triazole-carbonitrile) | 1H-NMR (DMSO-d6) δ: 1.29-1.44 (3H, m), 1.85-1.75 (3H, m), 1.80-1.94 (4H, m), 3.40-3.50 (1H, m), 7.63-7.68 (1H, m), 7.99-8.04 (1H, m), 8.13-8.16 (1H, m). | Ex. 125 |
| 1389 | (structure: 2-(3,5-bis(trifluoromethyl)phenyl)-5-cyclopropyl-oxazole with triazole-carbonitrile) | 1H-NMR (DMSO-d6) δ: 1.19-1.27 (4H, m), 2.62-2.70 (1H, m), 8.33 (1H, s), 8.50 (2H, s). | Ex. 125 |
| 1390 | (structure: 2-(3,4-difluorophenyl)-5-cyclopentyl-oxazole with triazole-carbonitrile) | 1H-NMR (DMSO-d6) δ: 1.67-1.74 (2H, m), 1.80-1.90 (4H, m), 2.02-2.10 (2H, m), 3.71-3.78 (1H, m), 7.64-7.71 (1H, m), 7.84-7.89 (1H, m), 7.94-7.99 (1H, m). | Ex. 125 |

TABLE 4-continued

| | Structure | 1H-NMR | Ref. |
|---|---|---|---|
| 1391 | 2-(3-chloro-4-fluorophenyl)-5-(2-methylpropyl)oxazole with triazole-carbonitrile | 1H-NMR (DMSO-d6) δ: 0.96 (6H, t, J = 6.7 Hz), 2.12-2.20 (1H, m), 3.00 (2H, d, J = 6.7 Hz), 7.66 (1H, t, J = 8.9 Hz), 7.98-8.03 (1H, m), 8.11 (1H, dd, J = 1.9, 7.1 Hz) | Ex. 125 |
| 1392 | 2-(3-trifluoromethylphenyl)-5-methyloxazole with triazole-carbonitrile | 1H-NMR (CDCl3) δ: 2.77 (3H, s), 7.63 (1H, t, J = 8.0 Hz), 7.74 (1H, d, J = 8.0 Hz), 8.27-8.37 (2H, m), 12.4 (1H, br.). | Ex. 125 |
| 1393 | 2-(3-chlorophenyl)-5-methyloxazole with triazole-carbonitrile | 1H-NMR (DMSO-d6) δ: 2.70 (3H, s), 7.61-7.67 (2H, m), 7.94-7.98 (2H, m). | Ref. Ex. 63, Ex. 125 |
| 1394 | 2-(3-chloro-4-fluorophenyl)-5-(tert-butyl)oxazole with triazole-carbonitrile | 1H-NMR (DMSO-d6) δ: 1.42 (9H, s), 7.66 (1H, d, J = 8.9 Hz), 7.99-8.04 (1H, m), 8.12-8.16 (1H, m). | Ex. 125 |

TABLE 4-continued

| | Structure | 1H-NMR | |
|---|---|---|---|
| 1395 | 2-(3,4-difluorophenyl)-5-tert-butyl-oxazole-triazole-carbonitrile | 1H-NMR (DMSO-d6) δ: 1.41 (9H, s), 7.64-7.71 (1H, m), 7.85-7.89 (1H, m), 7.96-8.01 (1H, m). | Ex. 125 |
| 1396 | 2-(3-trifluoromethylphenyl)-5-ethyl-oxazole-triazole-carbonitrile | 1H-NMR (DMSO-d6) δ: 1.33 (3H, t, J = 7.5 Hz), 3.12 (2H, q, J = 7.5 Hz), 7.86 (1H, t, J = 7.8 Hz), 7.97 (1H, d, J = 7.9 Hz), 8.25 (1H, s), 8.30 (1H, d, J = 7.8 Hz). | Ex. 125 |
| 1397 | 2-(3-trifluoromethylphenyl)-5-(2,2,2-trifluoroethyl)-oxazole-triazole-carbonitrile | 1H-NMR (DMSO-d6) δ: 4.38 (2H, q, J = 10.5 Hz), 7.90 (1H, t, J = 7.9 Hz), 8.02 (1H, d, J = 7.9 Hz), 8.24 (1H, s), 8.32 (1H, d, J = 7.9 Hz). | Ex. 125 |
| 1398 | 2-(4-chlorophenyl)-5-(2,2,2-trifluoroethyl)-oxazole-triazole-carbonitrile | 1H-NMR (DMSO-d6) δ: 4.35 (2H, q, J = 10.5 Hz), 7.70-7.72 (2H, m), 8.01-8.04 (2H, m). | Ex. 125 |

TABLE 4-continued

| | Structure | 1H-NMR | Ex. |
|---|---|---|---|
| 1399 | 2-(3-chloro-4-fluorophenyl)-oxazole with CH₂CF₃ and triazole-CN | 1H-NMR (DMSO-d6) δ: 4.35 (2H, q, J = 10.6 Hz), 7.70 (1H, t, J = 9.0 Hz), 8.01-8.04 (1H, m), 8.10-8.13 (1H, m). | Ex. 125 |
| 1400 | 2-(3,4-difluorophenyl)-oxazole with CH₂CF₃ and triazole-CN | 1H-NMR (DMSO-d6) δ: 4.34 (2H, q, J = 10.5 Hz), 7.69-7.78 (1H, m), 7.86-7.91 (1H, m), 7.93-8.00 (1H, m). | Ex. 125 |
| 1401 | 2-(3-chloro-4-fluorophenyl)-oxazole with CH₂CH₃ and triazole-CN | 1H-NMR (DMSO-d6) δ: 1.32 (3H, t, J = 7.6 Hz), 3.10 (2H, q, J = 7.6 Hz), 7.67 (1H, t J = 8.9 Hz), 7.99-8.03 (1H, m), 8.13 (1H, dd, J = 2.1, 7.0 Hz). | Ex. 125 |
| 1402 | 2-(3-chloro-4-fluorophenyl)-oxazole with CH₃ and triazole-CN | 1H-NMR (DMSO-d6) δ: 2.70 (3H, s), 7.66 (1H, t, J = 8.8 Hz), 7.98-8.02 (1H, m), 8.11 (1H, dd, J = 2.1, 7.0 Hz). | Ex. 125 |

TABLE 4-continued

| | Structure | 1H-NMR | Ex. |
|---|---|---|---|
| 1403 | 2-(4-(trifluoromethyl)phenyl)-5-ethyl-oxazole-triazole-carbonitrile | 1H-NMR (DMSO-d6) δ: 1.33 (3H, t, J = 7.5 Hz), 3.13 (2H, q, J = 7.5 Hz), 7.97 (2H, d, J = 8.3 Hz), 8.21 (2H, d, J = 8.3 Hz). | Ex. 125 |
| 1404 | 2-(4-(trifluoromethyl)phenyl)-5-methyl-oxazole-triazole-carbonitrile | 1H-NMR (DMSO-d6) δ: 2.73 (3H, s), 7.97 (2H, d, J = 8.5 Hz), 8.20 (2H, d, J = 8.5 Hz). | Ex. 125 |
| 1405 | 2-(3,4-dichlorophenyl)-5-methyl-oxazole-triazole-carbonitrile | 1H-NMR (DMSO-d6) δ: 2.70 (3H, s), 7.88 (1H, d, J = 8.4 Hz), 7.95 (1H, dd, J = 2.0, 8.4 Hz), 8.12 (1H, d, J = 2.0 Hz). | Ex. 125 |
| 1406 | 2-(3,4-dichlorophenyl)-5-ethyl-oxazole-triazole-carbonitrile | 1H-NMR (DMSO-d6) δ: 1.32 (3H, t, J = 7.5 Hz), 3.11 (2H, q, J = 7.5 Hz), 7.88 (1H, d, J = 8.5 Hz), 7.97 (1H, dd, J = 2.0, 8.6 Hz), 8.15 (1H, d, J = 2.0 Hz). | Ex. 125 |

TABLE 4-continued

| | Structure | 1H-NMR | Ex. |
|---|---|---|---|
| 1407 | 4-F-C6H4-oxazole(5-CH3)-triazole-CN | 1H-NMR (DMSO-d6) δ: 2.69 (3H, s), 7.41-7.47 (2H, m), 8.03-8.07 (2H, m). | Ex. 125 |
| 1408 | 3-Cl-C6H4-oxazole(5-CH2CH3)-triazole-CN | 1H-NMR (DMSO-d6) δ: 1.31 (3H, t, J = 7.6 Hz), 3.11 (2H, q, J = 7.6 Hz), 7.62-7.65 (2H, m), 7.96-7.99 (2H, m). | Ex. 125 |
| 1409 | 4-OCF3-C6H4-oxazole(5-CH3)-triazole-CN | 1H-NMR (DMSO-d6) δ: 2.70 (3H, s), 7.60 (2H, d, J = 8.5 Hz), 8.12 (2H, d, J = 8.5 Hz). | Ex. 125 |
| 1410 | 4-OCF3-C6H4-oxazole(5-CH2CH3)-triazole-CN | 1H-NMR (DMSO-d6) δ: 1.32 (3H, t, J = 7.5 Hz), 3.10 (2H, q, J = 7.5 Hz), 7.60 (2H, d, J = 8.2 Hz), 8.13 (2H, d, J = 8.2 Hz). | Ex. 125 |

TABLE 4-continued

| | Structure | 1H-NMR | Ex. |
|---|---|---|---|
| 1411 | 4-(trifluoromethyl)phenyl-oxazole-triazole-CN | 1H-NMR (DMSO-d6) δ: 8.00 (2H, d, J = 7.2 Hz), 8.28 (2H, d, J = 8.7 Hz), 8.93 (1H, s). | Ex. 125 |
| 1412 | 3-(trifluoromethoxy)phenyl-5-ethyl-oxazole-triazole-CN | 1H-NMR (DMSO-d6) δ: 1.32 (3H, t, J = 7.5 Hz), 3.11 (2H, q, J = 7.5 Hz), 7.60 (1H, d, J = 7.8 Hz), 7.75 (1H, t, J = 8.0 Hz), 7.90 (1H, s), 8.05 (1H, d, J = 7.8 Hz). | Ex. 125 |
| 1413 | 4-(difluoromethoxy)phenyl-oxazole-triazole-CN | 1H-NMR (CDCl3) δ: 6.61 (1H, t, J = 73.0 Hz), 7.26-7.28 (2H, m), 8.14 (2H, d, J = 8.8 Hz), 8.41 (1H, s). | Ex. 125 |
| 1414 | 2-(4-chlorophenyl)-5-(4-fluorophenyl)-oxazole-triazole-CN | 1H-NMR (DMSO-d6) δ: 7.40-7.44 (2H, m), 7.70-7.72 (2H, m), 8.13-8.21 (4H, m). | Ex. 2 |

TABLE 4-continued

| Ex. No. | STR | 1H-NMR | ref. |
|---|---|---|---|
| 1415 | (2,5-bis(4-chlorophenyl)oxazol-4-yl triazole carbonitrile structure) | 1H-NMR (DMSO-d6) δ: 7.62-7.73 (4H, m), 8.13-8.18 (4H, m). | Ex. 2 |
| 1416 | (2-(4-chlorophenyl)-5-(2-chlorophenyl)oxazol-4-yl triazole carbonitrile structure) | 1H-NMR (DMSO-d6) δ: 7.51-7.73 (5H, m), 7.79 (1H, dd, J = 1.7, 7.6 Hz), 8.08-8.11 (2H, m). | Ex. 2 |
| 1417 | (2-(3-chlorophenyl)-5-(furan-2-yl)oxazol-4-yl triazole carbonitrile structure) | 1H-NMR (DMSO-d6) δ: 6.80 (1H, s), 7.59 (1H, s), 7.64-7.72 (2H, m), 8.00 (1H, s), 8.03-8.07 (2H, m). | Ex. 125 |

| Ex. No. | STR | m.p. | ref. |
|---|---|---|---|
| 1418 | (5-(3-(trifluoromethyl)phenyl)oxazol-4-yl triazole carbonitrile structure) | 183.9-186.7 | Ex. 125 |

TABLE 4-continued

| Ex. No. | STR | 1H-NMR | ref. |
|---|---|---|---|
| 1419 | 5-(3-chlorophenyl)oxazol-4-yl triazole carbonitrile | 1H-NMR (DMSO-d6) δ: 7.56-7.59 (2H, m), 7.92 (1H, s), 8.14 (1H, s), 8.79 (1H, s). | Ex. 125 |
| 1420 | 5-(3-chloro-4-fluorophenyl)oxazol-4-yl triazole carbonitrile | 1H-NMR (DMSO-d6) δ: 7.61 (1H, t, J = 8.9 Hz), 7.98-8.04 (1H, m), 8.32-8.38 (1H, m), 8.76 (1H, s). | Ex. 125 |
| 1421 | 5-(3-chlorophenyl)-2-ethyloxazol-4-yl triazole carbonitrile | 1H-NMR (CDCl3) δ: 1.46 (3H, t, J = 7.6 Hz), 2.94 (2H, q, J = 7.6 Hz), 7.40 (2H, d, J = 5.1 Hz), 7.76 (1H, brs), 7.93 (1H, brs). | Ex. 125 |
| 1422 | 2-ethyl-5-(3-(trifluoromethyl)phenyl)oxazol-4-yl triazole carbonitrile | 1H-NMR (CDCl3) δ: 1.47 (3H, t, J = 7.6 Hz), 2.96 (2H, q, J = 7.6 Hz), 7.69 (1H, t, J = 7.8 Hz), 7.67 (1H, d, J = 7.8 Hz), 8.09 (1H, d, J = 7.8 Hz), 8.27 (1H, m). | Ex. 125 |

TABLE 4-continued

| # | Structure | 1H-NMR | Ex. |
|---|---|---|---|
| 1423 | (structure) | 1H-NMR (DMSO-d6) δ: 5.49 (2H, s), 7.36-7.43 (3H, m), 7.55-7.60 (1H, m), 8.78 (1H, s). | Ex. 1 |
| 1424 | (structure) | 1H-NMR (DMSO-d6) δ: 1.10- 1.20 (4H, m), 2.56 (1H, m), 6.14 (2H, s), 7.09 (1H, d, J = 8.2 Hz), 7.42 (1H, d, J = 1.6 Hz), 7.51 (1H, dd, J = 1.6, 8.2 Hz). | Ex. 1 |
| 1425 | (structure) | 1H-NMR (DMSO-d6) δ: 1.15-1.21 (4H, m), 2.56-2.62 (1H, m), 7.61 (1H, d, J = 8.5 Hz), 7.85 (1H, dd, J = 1.5, 8.5 Hz), 7.93 (1H, d, J = 1.5 Hz). | Ex. 1 |
| 1426 | (structure) | 1H-NMR (DMSO-d6) δ: 1.36 (6H, d, J = 7.0 Hz), 3.61-3.70 (1H, m), 7.64 (1H, d, J = 8.4 Hz), 7.90 (1H, d, J = 8.4 Hz), 7.96 (1H, s). | Ex. 1 |

TABLE 4-continued

| | Structure | 1H-NMR | Ex. |
|---|---|---|---|
| 1427 | [2-(6-(trifluoromethyl)pyridin-3-yl)-5-cyclopropyl-oxazol-4-yl triazole carbonitrile] | 1H-NMR (DMSO-d6) δ: 1.17-1.25 (4H, m), 2.62-2.70 (1H, m), 8.09-8.15 (1H, m), 8.55-8.59 (1H, m), 9.29 (1H, s). | Ex. 1 |
| 1428 | [2-(naphthalen-1-yl)-5-cyclopropyl-oxazol-4-yl triazole carbonitrile] | 1H-NMR (DMSO-d6) δ: 1.20-1.27 (4H, m), 2.65-2.73 (1H, m), 7.62-7.69 (3H, m), 8.04-8.07 (1H, m), 8.14 (1H, d, J = 8.3 Hz), 8.22-8.25 (1H, m), 9.50-9.54 (1H, m). | Ex. 1 |
| 1429 | [2-(6-(trifluoromethyl)benzothiophen-2-yl)-5-cyclopropyl-oxazol-4-yl triazole carbonitrile] | 1H-NMR (DMSO-d6) δ: 1.14-1.27 (4H, m), 2.62-2.68 (1H, m), 7.75-7.78 (1H, m), 8.18-8.21 (2H, m), 8.63 (1H, s). | Ex. 1 |
| 1430 | [2-(thiophen-2-yl)-5-cyclopropyl-oxazol-4-yl triazole carbonitrile] | 1H-NMR (CDCl3) δ: 1.13-1.29 (4H, m), 2.50-2.56 (1H, m), 7.11-7.15 (1H, m), 7.46-7.49 (1H, m), 7.65-7.69 (1H, m). | Ex. 1 |

TABLE 4-continued

| | Structure | 1H-NMR | |
|---|---|---|---|
| 1431 | 2,3-dihydrobenzofuran-5-yl / cyclopropyl oxazole-triazole-CN | 1H-NMR (DMSO-d6) δ: 1.08-1.19 (4H, m), 2.57 (1H, m), 3.25-3.30 (2H, m), 4.63 (2H, t, J = 6.7 Hz), 6.92 (1H, d, J = 8.4 Hz), 7.72-7.75 (1H, m), 7.82 (1H, s). | Ex. 1 |
| 1432 | 6-(trifluoromethyl)pyridin-3-yl / cyclobutyl oxazole-triazole-CN | 1H-NMR (DMSO-d6) δ: 1.94-2.14 (2H, m), 2.34-2.50 (4H, m), 4.15-4.23 (1H, m), 8.15 (1H, t, J = 8.3 Hz), 8.65 (1H, d, J = 8.3 Hz), 8.37 (1H, s). | Ex. 125 |
| 1433 | 5-(trifluoromethyl)pyridin-2-yl / cyclopropyl oxazole-triazole-CN | 1H-NMR (DMSO-d6) δ: 1.12-1.28 (4H, m), 2.65-2.72 (1H, m), 8.26 (1H, d, J = 8.3 Hz), 8.45 (1H, dd, J = 2.1, 8.3 Hz), 9.13 (1H, s). | Ex. 125 |
| 1434 | 5-(trifluoromethyl)pyridin-2-yl / isobutyl oxazole-triazole-CN | 1H-NMR (DMSO-d6) δ: 0.97 (6H, d, J = 6.7 Hz), 2.11-2.19 (1H, m), 3.06 (2H, d, J = 7.2 Hz), 8.29 (1H, d, J = 8.3 Hz), 8.46-8.49 (1H, m), 9.15 (1H, s). | Ex. 125 |

TABLE 4-continued
| | | | |
|---|---|---|---|
| 1435 |  | 1H-NMR (DMSO-d6) δ: 1.92-2.13 (2H, m), 2.32-2.54 (4H, m), 4.20 (1H, m), 8.68 (1H, s), 8.19 (1H, s), 9.49 (1H, d, J = 1.6 Hz). | Ex. 125 |
| 1436 | 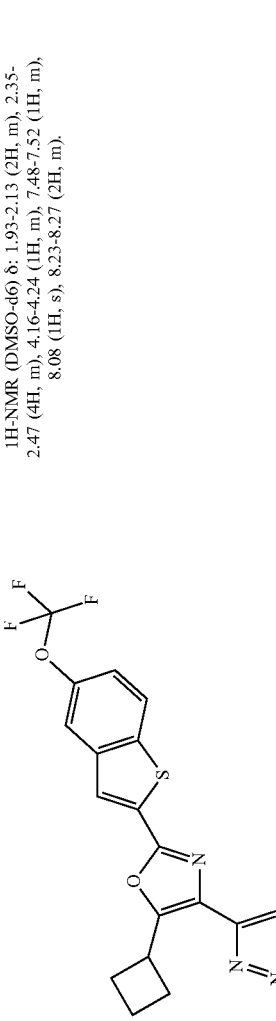 | 1H-NMR (DMSO-d6) δ: 1.93-2.13 (2H, m), 2.35-2.47 (4H, m), 4.16-4.24 (1H, m), 7.48-7.52 (1H, m), 8.08 (1H, s), 8.23-8.27 (2H, m). | Ex. 125 |
| 1437 | 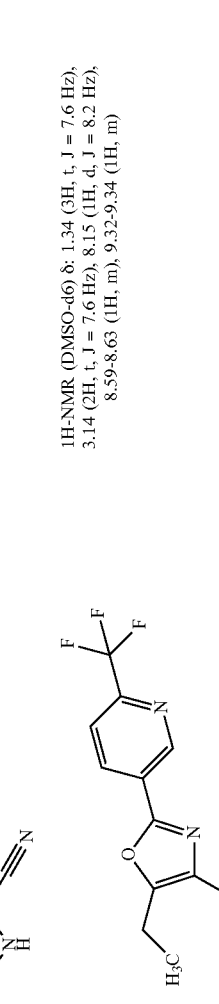 | 1H-NMR (DMSO-d6) δ: 1.34 (3H, t, J = 7.6 Hz), 3.14 (2H, t, J = 7.6 Hz), 8.15 (1H, d, J = 8.2 Hz), 8.59-8.63 (1H, m), 9.32-9.34 (1H, m) | Ex. 125 |

TABLE 4-continued

| | | | |
|---|---|---|---|
| 1438 | (structure) | 1H-NMR (DMSO-d6) δ: 2.69 (3H, s), 7.64 (1H, d, J = 6.4 Hz), 7.86-7.89 (1H, m), 7.91-8.93 (1H, m). | Ex. 125 |
| 1439 | (structure) | 1H-NMR (DMSO-d6) δ: 2.74 (3H, s), 8.14 (1H, d, J = 8.3 Hz), 8.80 (1H, dd, J = 1.8, 8.2 Hz), 9.31 (1H, d, J = 1.8 Hz). | Ex. 125 |
| 1440 | (structure) | 1H-NMR (DMSO-d6) δ: 1.93-2.01 (1H, m), 2.05-2.12 (1H, m), 2.35-2.47 (4H, m), 4.17-4.23 (1H, m), 7.52-7.57 (1H, m), 7.78-7.81 (1H, m), 8.28 (1H, d, J = 3.3 Hz). | Ex. 125 |
| 1441 | (structure) | 1H-NMR (DMSO-d6) δ: 7.67 (1H, d, J = 8.4 Hz), 7.93-7.96 (1H, m), 7.99-8.01 (1H, m), 8.86 (1H, s). | Ex. 125 |

TABLE 4-continued

| | Structure | 1H-NMR | Ex. |
|---|---|---|---|
| 1442 | (6-(trifluoromethyl)pyridin-3-yl-oxazole-triazole-CN) | 1H-NMR (DMSO-d6) δ: 8.15-8.18 (1H, m), 8.64-8.67 (1H, m), 9.02 (1H, s), 9.36-9.38 (1H, m). | Ex. 125 |
| 1444 | (2-cyclopropyl-oxazole-triazole-CN) | 1H-NMR (DMSO-d6) δ: 1.00-1.05 (2H, m), 1.09-1.16 (2H, m), 2.20-2.27 (1H, m), 8.54 (1H, s). | Ex. 1 |
| 1445 | (2-ethyl-oxazole-triazole-CN) | 1H-NMR (CDCl3) δ: 1.41 (3H, t, J = 7.6 Hz), 2.95 (2H, q, J = 7.6 Hz), 8.33 (1H, s). | Ex. 125 |
| 1448 | (2-(3-(trifluoromethyl)phenyl)-4-methyl-oxazole-triazole-CN) | 1H-NMR (DMSO-d6) δ: 2.51 (3H, s), 7.86 (1H, t, J = 7.8 Hz), 7.97 (1H, d, J = 7.8 Hz), 8.26-8.29 (2H, m). | Ex. 125 |

TABLE 4-continued

| | Structure | 1H-NMR | Ex. |
|---|---|---|---|
| 1449 | 2-(4-(trifluoromethyl)phenyl)-5-(trifluoromethyl)oxazole-triazole-carbonitrile | 1H-NMR (DMSO-d6) δ: 8.04 (2H, d, J = 8.3 Hz), 8.30 (2H, d, J = 8.3 Hz). | Ex. 125 |
| 1450 | 2-(4-(trifluoromethyl)phenyl)-5-(difluoromethyl)oxazole-triazole-carbonitrile | 1H-NMR (DMSO-d6) δ: 7.62 (1H, t, J = 51.4 Hz), 8.02 (2H, d, J = 8.3 Hz), 8.30 (2H, d, J = 8.3 Hz). | Ex. 125 |
| 1452 | 5-(3-(trifluoromethyl)phenyl)thiophene-triazole-carbonitrile | 1H-NMR (DMSO-d6) δ: 7.70-7.76 (3H, m), 7.87 (1H, d, J = 3.9 Hz), 8.04 (1H, d, J = 7.7 Hz), 8.06 (1H, s). | Ex. 1 |

TABLE 4-continued

| Ex. No. | STR | m.p. | ref. |
|---|---|---|---|
| 1443 | | 127-131 | Ex. 1 |
| 1447 | | 192.8-192.9 | Ex. 2 |
| 1451 | | 205 | Ex. 1 |
| 1453 | | 143-146 | Ex. 1 |

TABLE 4-continued
| Ex. No. | STR | Ex. | 162-164 | 1H-NMR | ref. |
|---|---|---|---|---|---|
| 1454 |  | Ex. 1 | | | |
| 1455 |  | Ex. 1 | | 1H-NMR (DMSO-d6) δ: 7.28 (1H, d, J = 4.0 Hz), 7.31 (1H, d, J = 4.0 Hz), 7.45 (1H, d, J = 4.0 Hz), 7.63 (1H, d, J = 4.0 Hz). | |
| 1456 |  | Ex. 1 | | 1H-NMR (DMSO-d6) δ: 7.49-7.52 (4H, m) 7.60 (1H, d, J = 3.8 Hz), 7.67 (1H, d, J = 3.8 Hz), 7.73 (2H, d, J = 8.4 Hz). | |

TABLE 4-continued
| | | | |
|---|---|---|---|
| 1457 |  | 1H-NMR (DMSO-d6) δ: 7.51-7.58 (2H, m), 7.70-7.73 (2H, m), 7.85-7.95 (1H, m). | Ex. 1 |
| 1458 |  | 1H-NMR (DMSO-d6) δ: 5.38 (2H, s), 7.17 (2H, d, J = 8.8 Hz), 7.58 (1H, d, J = 3.9 Hz), 7.68-7.73 (3H, m), 8.11 (1H, s), 8.20 (2H, s). | Ex. 1 |
| 1459 |  | 1H-NMR (DMSO-d6) δ: 5.16 (2H, s), 7.11 (2H, d, J = 6.9 Hz), 7.13-7.56 (4H, m), 7.67-7.70 (3H, m). | Ex. 1 |

TABLE 4-continued

| | | | |
|---|---|---|---|
| 1460 | [structure: 4-[(2,5-bis(trifluoromethyl)benzyl)oxy]phenyl-thiophene-triazole-carbonitrile] | 1H-NMR (DMSO-d6) δ: 5.39 (2H, s), 7.15 (2H, d, J = 8.9 Hz), 7.57 (1H, d, J = 3.9 Hz), 7.67-7.73 (3H, m), 8.00-8.10 (2H, m), 8.19 (1H, s). | Ex. 1 |
| 1461 | [structure: 3-[(2,5-bis(trifluoromethyl)benzyl)oxy]phenyl-thiophene-triazole-carbonitrile] | 1H-NMR (DMSO-d6) δ: 5.42 (2H, s), 7.07-7.10 (1H, m), 7.35-7.46 (3H, m), 7.70-7.73 (2H, m), 8.00-8.10 (2H, m), 8.22 (1H, s). | Ex. 1 |
| 1462 | [structure: 3-[(3,5-bis(trifluoromethyl)benzyl)oxy]phenyl-thiophene-triazole-carbonitrile] | 1H-NMR (DMSO-d6) δ: 6.41 (2H, s), 7.09-7.12 (1H, m), 7.34-7.46 (3H, m), 7.72 (2H, s), 8.11 (1H, s), 8.11 (1H, s), 8.22 (1H, s). | Ex. 1 |

TABLE 4-continued

| | | | |
|---|---|---|---|
| 1463 | [structure] | 1H-NMR (DMSO-d6) δ: 5.09 (2H, s), 6.92-7.02 (3H, m), 7.20 (1H, d, J = 5.1 Hz), 7.31-7.39 (3H, m), 7.47 (1H, s), 7.59 (1H, d, J = 5.1 Hz). | Ex. 1 |
| 1464 | [structure] | 1H-NMR (DMSO-d6) δ: 5.31 (2H, s), 6.82 (1H, d, J = 7.6 Hz), 7.01 (1H, s), 7.04 (1H, d, J = 8.5 Hz), 7.31 (1H, t, J = 7.0 Hz), 7.40 (1H, d, J = 3.9 Hz), 7.94 (1H, s), 8.09 (1H, s), 8.13 (2H, s). | Ex. 1 |
| 1465 | [structure] | 1H-NMR (DMSO-d6) δ: 7.75 (1H, d, J = 3.9 Hz), 8.06 (1H, d, J = 3.9 Hz), 8.10 (1H, s), 8.37 (2H, s). | Ex. 1 |

TABLE 4-continued

| | | 1H-NMR | Ex. |
|---|---|---|---|
| 1466 | (structure: 3,5-bis(trifluoromethyl)phenyl-thiophene-triazole-CN) | 1H-NMR (DMSO-d6) δ: 8.07 (1H, s), 8.30 (1H, s), 8.45 (2H, s), 8.58 (1H, s). | Ex. 1 |
| 1467 | (structure: 2,2-difluorobenzo[d][1,3]dioxole-thiophene-triazole-CN) | 1H-NMR (DMSO-d6) δ: 7.50 (1H, d, J = 8.4 Hz), 7.56-7.59 (1H, m), 7.66-7.73 (2H, m), 7.89 (1H, d, J = 1.8 Hz). | Ex. 1 |
| 1468 | (structure: 4-(trifluoromethyl)phenyl-thiophene-triazole-CN) | 1H-NMR (DMSO-d6) δ: 7.75-7.86 (4H, m), 7.97 (2H, d, J = 8.0 Hz). | Ex. 1 |

TABLE 4-continued

| | | | |
|---|---|---|---|
| 1469 | (3-trifluoromethoxyphenyl-thiophene-triazole-carbonitrile structure) | 1H-NMR (DMSO-d6) δ: 7.35-7.40 (1H, m), 7.57-7.64 (1H, m), 7.69-7.82 (4H, m). | Ex. 1 |
| 1470 | (4-trifluoromethoxyphenyl-thiophene-triazole-carbonitrile structure) | 1H-NMR (DMSO-d6) δ: 7.47 (2H, d, J = 8.6 Hz), 7.72 (2H, s), 7.88 (2H, d, J = 8.6 Hz). | Ex. 1 |
| 1471 | (methyl 4-benzoate-thiophene-triazole-carbonitrile structure) | 1H-NMR (DMSO-d6) δ: 3.88 (3H, s), 7.74 (1H, d, J = 3.9 Hz), 7.84 (1H, d, J = 3.9 Hz), 7.90 (2H, d, J = 8.4 Hz), 8.03 (2H, d, J = 8.4 Hz). | Ex. 1 |

TABLE 4-continued

| | | | |
|---|---|---|---|
| 1472 | [structure: 4-acetylphenyl-thiophene-triazole-carbonitrile] | 1H-NMR (DMSO-d6) δ: 2.61 (3H, s), 7.74 (1H, d, J = 4.0 Hz), 7.85 (1H, d, J = 4.0 Hz), 7.90 (2H, d, J = 8.5 Hz), 8.03 (2H, d, J = 8.6 Hz). | Ex. 1 |
| 1474 | [structure: 3,5-bis(trifluoromethyl)phenyl-4-methylthiophene-triazole-carbonitrile] | 1H-NMR (DMSO-d6) δ: 2.38 (3H, s), 7.63 (1H, s), 8.18 (3H, s). | Ex. 1 |
| 1475 | [structure: 3,5-bis(trifluoromethyl)styryl-thiophene-triazole-carbonitrile] | 1H-NMR (DMSO-d6) δ: 7.34 (1H, d, J = 16.3 Hz), 7.44 (1H, d, J = 3.8 Hz), 7.69 (1H, d, J = 3.8 Hz), 7.94-7.98 (2H, m), 8.36 (2H, s). | Ex. 1 |

TABLE 4-continued

| | Structure | 1H-NMR | Ex. |
|---|---|---|---|
| 1476 | (3-trifluoromethylphenyl-vinyl-4-methylthiophene-triazole-CN) | 1H-NMR (DMSO-d6) δ: 2.42 (3H, s), 7.11 (1H, d, J = 18.2 Hz), 7.60-7.62 (3H, m), 7.67 (1H, d, J = 16.2 Hz), 8.00-8.02 (1H, m), 8.09 (1H, s). | Ex. 1 |
| 1477 | (4-trifluoromethylphenyl-vinyl-thiophene-triazole-CN) | 1H-NMR (DMSO-d6) δ: 7.21 (1H, d, J = 16.3 Hz), 7.44 (1H, d, J = 3.9 Hz), 7.67 (1H, d, J = 3.9 Hz), 7.68-7.75 (4H, m), 7.85 (1H, d, J = 8.2 Hz). | Ex. 1 |
| 1478 | (4-trifluoromethylphenyl-vinyl-thiophene-triazole-CN isomer) | 1H-NMR (DMSO-d6) δ: 7.24 (1H, d, J = 16.5 Hz), 7.50 (1H, d, J = 16.5 Hz), 7.73 (2H, d, J = 8.4 Hz), 7.82 (2H, d, J = 8.4 Hz), 7.94 (1H, s), 7.99 (1H, s). | Ex. 1 |

TABLE 4-continued

| | Structure | 1H-NMR | Ex. |
|---|---|---|---|
| 1479 | (cyclopropyl-vinyl-thiophene-triazole-CN) | 1H-NMR (DMSO-d6) δ: 0.56-0.60 (2H, m), 0.80-0.86 (2H, m), 1.56-1.61 (1H, m), 5.78 (1H, dd, J = 9.1, 15.7 Hz), 6.71 (1H, d, J = 15.7 Hz), 7.08 (1H, d, J = 3.8 Hz), 7.56 (1H, d, J = 3.8 Hz). | Ex. 1 |
| 1480 | (4-fluorophenyl-vinyl-thiophene-triazole-CN) | 1H-NMR (DMSO-d6) δ: 7.13 (1H, d, J = 16.1 Hz), 7.23 (2H, t, J = 8.8 Hz), 7.35 (1H, d, J = 8.8 Hz), 7.49 (1H, d, J = 16.1 Hz), 7.64-7.71 (3H, m). | Ex. 1 |
| 1481 | (trifluoromethylphenyl-vinyl-thiophene-CN-triazole) | 1H-NMR (DMSO-d6) δ: 7.43 (1H, d, J = 16.3 Hz), 7.57 (1H, d, J = 16.3 Hz), 7.72-7.81 (5H, m), 7.90 (1H, d, J = 5.3 Hz). | Ex. 1 |
| 1482 | (thiophen-3-yl-vinyl-thiophene-triazole-CN) | 1H-NMR (DMSO-d6) δ: 7.14 (1H, d, J = 16.2 Hz), 7.30 (1H, d, J = 3.9 Hz), 7.35 (1H, d, J = 16.2 Hz), 7.50-7.52 (1H, m), 7.58-7.68 (3H, m). | Ex. 1 |

| | | 1H-NMR | Ex. |
|---|---|---|---|
| 1483 | 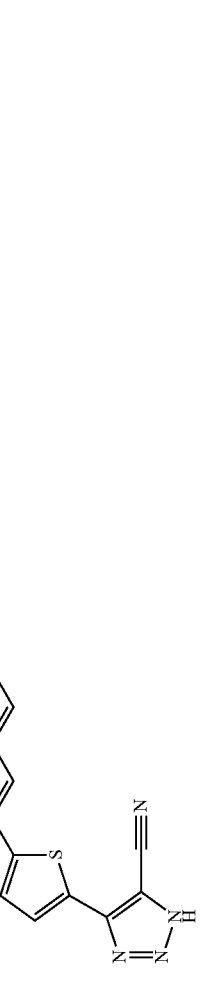 | 1H-NMR (DMSO-d6) δ: 2.38 (3H, s), 7.00 (1H, d, J = 16.1 Hz), 7.22 (2H, d, J = 8.9 Hz), 7.44 (1H, d, J = 16.1 Hz), 7.49 (1H, s), 7.72-7.77 (2H, m). | Ex. 1 |
| 1484 | 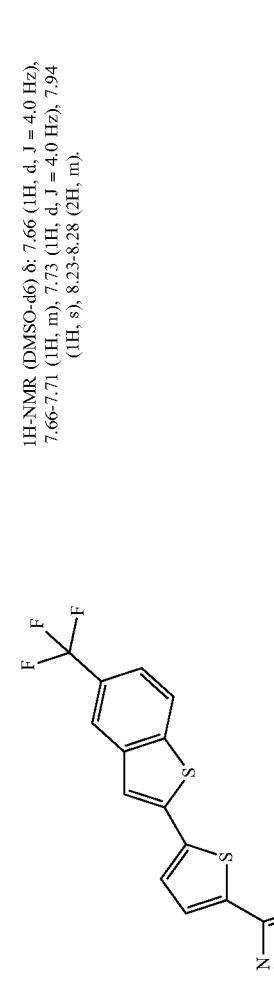 | 1H-NMR (DMSO-d6) δ: 7.66 (1H, d, J = 4.0 Hz), 7.66-7.71 (1H, m), 7.73 (1H, d, J = 4.0 Hz), 7.94 (1H, s), 8.23-8.28 (2H, m). | Ex. 1 |
| 1485 | 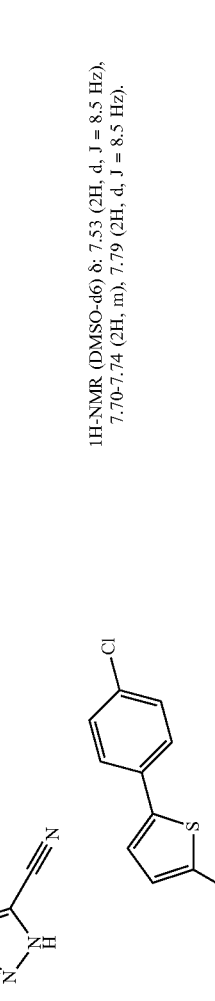 | 1H-NMR (DMSO-d6) δ: 7.53 (2H, d, J = 8.5 Hz), 7.70-7.74 (2H, m), 7.79 (2H, d, J = 8.5 Hz). | Ex. 1 |

TABLE 4-continued

| Ex. No. | STR | m.p. | 1H-NMR | ref. |
|---|---|---|---|---|
| 1486 | (5-fluorobenzothiophene-thiophene-triazole-CN) | | 1H-NMR (DMSO-d6) δ: 7.25-7.33 (1H, m), 7.63 (1H, d, J = 3.9 Hz), 7.66-7.74 (2H, m), 7.80 (1H, s), 8.01-8.08 (1H, m). | Ex. 1 |
| 1489 | (6-trifluoromethylpyridine-thiophene-triazole-CN) | | 1H-NMR (DMSO-d6) δ: 7.79 (1H, d, J = 3.9 Hz), 7.94-8.01 (2H, m), 8.38-8.45 (1H, m), 9.19 (1H, s). | Ex. 1 |
| 1487 | (4-fluoro-3-chlorophenyl-thiophene-triazole-CN) | 210-211 | | Ex. 1 |
| 1488 | (5-bromothiophene-triazole-CN) | 219-223 | | Ex. 1 |

TABLE 4-continued

| | | | |
|---|---|---|---|
| 1490 | [structure] | 251 | Ex. 1 |
| 1491 | [structure] | 256-259 | Ex. 1 |
| 1492 | [structure] | 207 | Ex. 1 |

TABLE 4-continued
| | | | |
|---|---|---|---|
| 1493 | 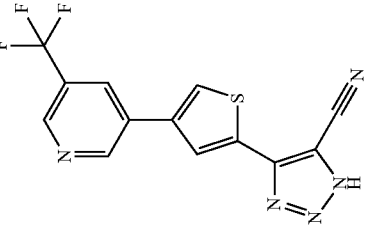 | 261-264 | Ex. 1 |
| 1495 |  | 208-209 | Ex. 1 |

TABLE 4-continued

| Ex. No. | STR | 1H-NMR | ref. |
|---|---|---|---|
| 1494 | [structure: 4-(trifluoromethyl)pyridine-thiophene-triazole-CN] | 1H-NMR (DMSO-d6) δ: 8.17 (1H, d, J = 8.6 Hz), 8.31 (1H, dd, J = 2.4, 8.6 Hz), 8.38 (1H, d, J = 1.2 Hz), 8.65 (1H, d, J = 1.2 Hz), 9.04 (1H, s). | Ex. 1 |
| 1496 | [structure: 6-(trifluoromethyl)pyridine-CH2-thiophene-triazole-CN] | 1H-NMR (DMSO-d6) δ: 4.18 (2H, s), 7.58 (2H, s), 7.86 (1H, d, J = 8.0 Hz), 7.95-8.00 (1H, m), 8.74 (1H, s). | Ref. Ex. 91, Ex. 1 |
| 1497 | [structure: 5-fluoropyridine-thiophene-triazole-CN] | 1H-NMR (DMSO-d6) δ: 7.75 (1H, d, J = 3.9 Hz), 7.90 (1H, d, J = 3.9 Hz), 8.17-8.20 (1H, m), 8.59 (1H, d, J = 2.6 Hz), 8.86-8.87 (1H, m). | Ex. 1 |

TABLE 4-continued

| | Structure | 1H-NMR | Ex. |
|---|---|---|---|
| 1498 | (2-(4-chlorophenyl)thiophen-3-yl triazole carbonitrile) | 1H-NMR (DMSO-d6) δ: 7.29 (2H, d, J = 8.5 Hz), 7.40 (1H, d, J = 5.2 Hz), 7.45 (2H, d, J = 8.5 Hz), 7.95 (1H, d, J = 5.2 Hz). | Ex. 1 |
| 1499 | (4-(4-(trifluoromethyl)phenyl)thiophen-3-yl triazole carbonitrile) | 1H-NMR (DMSO-d6) δ: 7.40 (2H, d, J = 8.1 Hz), 7.75 (2H, d, J = 8.1 Hz), 7.97 (1H, d, J = 3.1 Hz), 8.15 (1H, d, J = 3.1 Hz). | Ex. 1 |
| 1500 | (4-(4-(trifluoromethoxy)phenyl)thiophen-3-yl triazole carbonitrile) | 1H-NMR (DMSO-d6) δ: 7.27-7.32 (4H, m), 7.88 (1H, s), 8.10 (1H, s). | Ex. 1 |
| 1501 | (5-(4-(trifluoromethyl)phenyl)thiophen-3-yl triazole carbonitrile) | 1H-NMR (CDCl3) δ: 7.84 (2H, d, J = 8.3 Hz), 7.94 (2H, d, J = 8.3 Hz), 8.06 (1H, d, J = 1.4 Hz), 8.25 (1H, d, J = 1.4 Hz). | Ex. 125 |

TABLE 4-continued

| | Structure | 1H-NMR | Ex. |
|---|---|---|---|
| 1503 | 5-(3,5-bis(trifluoromethyl)phenyl)furan-2-yl triazole-carbonitrile | 1H-NMR (DMSO-d6) δ: 5.27 (1H, d, J = 3.7 Hz), 7.70 (1H, d, J = 3.7 Hz), 8.08 (1H, s), 8.47 (2H, s). | Ex. 1 |
| 1504 | (E)-2-(3,5-bis(trifluoromethyl)phenyl)vinyl-furan-triazole-carbonitrile | 1H-NMR (DMSO-d6) δ: 6.91 (1H, d, J = 3.5 Hz), 7.20 (1H, d, J = 3.6 Hz), 7.30 (1H, d, J = 16.4 Hz), 6.69 (1H, d, J = 16.4 Hz), 7.99 (1H, s), 8.30 (2H, s). | Ex. 1 |
| 1505 | (E)-2-(4-fluorophenyl)vinyl-furan-triazole-carbonitrile | 1H-NMR (DMSO-d6) δ: 6.80 (1H, d, J = 3.6 Hz), 7.13-7.27 (5H, m), 7.62-7.67 (2H, m). | Ex. 1 |

TABLE 4-continued
| | | | |
|---|---|---|---|
| 1506 | 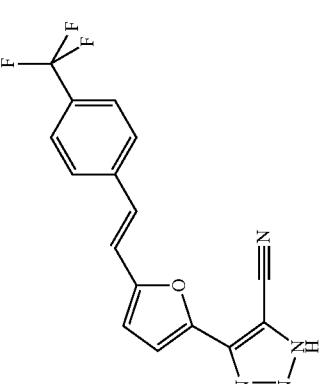 | 1H-NMR (DMSO-d6) δ: 6.90 (1H, d, J = 3.6 Hz), 7.19 (1H, d, J = 3.6 Hz), 7.22 (1H, d, J = 15.9 Hz), 7.43 (1H, d, J = 15.9 Hz), 7.73-7.82 (4H, m). | Ex. 1 |
| 1507 | 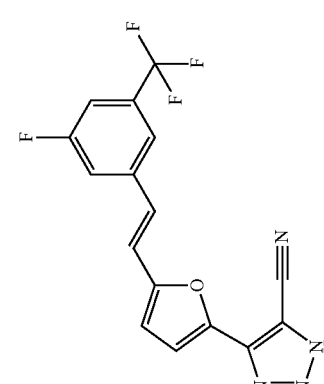 | 1H-NMR (DMSO-d6) δ: 6.89 (1H, d, J = 3.6 Hz), 7.19 (1H, d, J = 3.6 Hz), 7.21 (1H, d, J = 16.3 Hz), 7.53 (1H, d, J = 16.3 Hz), 7.59 (1H, d, J = 8.8 Hz), 7.79-7.85 (2H, m). | Ex. 1 |
| 1508 | 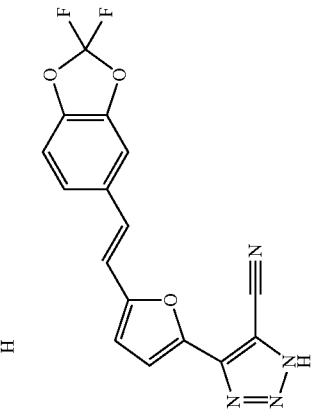 | 1H-NMR (DMSO-d6) δ: 6.81 (1H, d, J = 3.6 Hz), 7.14-7.34 (3H, m), 7.36-7.45 (2H, m), 7.78 (1H, s). | Ex. 1 |

TABLE 4-continued

| Ex. No. | STR | m.p. | ref. |
|---|---|---|---|
| 1509 | (structure: styryl-furan-triazole-CN) | 1H-NMR (DMSO-d6) δ: 6.81 (1H, d, J = 3.6 Hz), 7.16 (1H, d, J = 2.7 Hz), 7.19 (2H, d, J = 10.0 Hz), 7.23-7.34 (1H, m), 7.41 (2H, t, J = 7.1 Hz), 7.59 (2H, d, J = 7.1 Hz). | Ex. 1 |
| 1502 | (structure: 3-(trifluoromethyl)phenyl-furan-triazole-CN) | 209-212 | Ex. 125 |
| 1510 | (structure: 3-fluoro-5-methoxyphenyl styryl-furan-triazole-CN) | 198 | Ex. 1 |

TABLE 4-continued

| | | | |
|---|---|---|---|
| 1511 | (benzothiophene-furan-triazole-CN structure) | 257(dec.) | Ex. 1 |
| 1512 | (3-fluorostyryl-furan-triazole-CN structure) | 182(dec.) | Ex. 1 |
| 1513 | (3-methoxy-4,5-difluorostyryl-furan-triazole-CN structure) | 209-211 | Ex. 1 |

TABLE 4-continued

| | | | |
|---|---|---|---|
| 1514 | (structure) | 205-208 | Ex. 1 |
| 1515 | (structure) | 306-307 | Ex. 1 |
| 1516 | (structure) | 275-277 | Ex. 1 |
| 1517 | (structure) | 197-199 | Ex. 1 |

TABLE 4-continued

| | | | |
|---|---|---|---|
| 1518 | [5-(trifluoromethyl)benzothiophen-2-yl furan triazole carbonitrile structure] | 241-242 | Ex. 1 |
| 1519 | [3-chloro-4-fluorophenyl furan triazole carbonitrile structure] | 236-238 | Ex. 1 |
| 1521 | [4-chlorophenyl trifluoromethyl furan triazole carbonitrile structure] | 175.3-176.1 | Ex. 2 |

TABLE 4-continued

| Ex. No. | STR | 1H-NMR | ref. |
|---|---|---|---|
| 1520 | | 1H-NMR (DMSO-d6) δ: 7.30 (1H, d, J = 3.7 Hz), 7.61 (1H, d, J = 3.7 Hz), 8.07 (1H, d, J = 8.0 Hz), 8.42 (1H, d, J = 8.0 Hz), 8.23 (1H, s). | Ex. 1 |
| 1522 | | 1H-NMR (DMSO-d6) δ: 5.52 (2H, s), 6.28-6.31 (1H, m), 6.78 (1H, s), 6.96 (2H, d, J = 7.0 Hz), 7.18-7.22 (2H, m), 7.24-7.28 (2H, m), 16.2 (1H, br.). | Ex. 1 |
| 1523 | | 1H-NMR (DMSO-d6) δ: 5.61 (2H, s), 6.33-6.35 (1H, m), 6.80-6.82 (1H, m), 7.23-7.26 (2H, m), 7.30 (1H, s), 7.52 (1H, t, J = 7.7 Hz), 7.58 (1H, d, J = 7.9 Hz). | Ex. 1 |
| 1524 | | 1H-NMR (CDCl3) δ: 5.79 (2H, s), 6.45 (1H, dd, J = 2.7, 4.0 Hz), 6.67 (1H, s), 6.89 (1H, dd, J = 1.7, 2.7 Hz), 7.20-7.23 (1H, m), 7.61 (1H, d, J = 8.0 Hz), 7.81 (1H, d, J = 8.0 Hz), 11.5 (1H, br.). | Ex. 1 |

TABLE 4-continued

| | Structure | 1H-NMR | Ex. |
|---|---|---|---|
| 1525 | pyrrole-triazole with 4-chlorobenzyl | 1H-NMR (DMSO-d6) δ: 5.52 (2H, s), 6.29 (1H, dd, J = 2.8, 3.7 Hz), 6.77 (1H, dd, J = 1.6, 3.7 Hz), 6.98-7.01 (2H, m), 7.18 (1H, dd, J = 1.6, 2.8 Hz), 7.32-7.35 (2H, m). | Ex. 1 |
| 1526 | pyrrole-triazole with 3,4-dichlorobenzyl | 1H-NMR (DMSO-d6) δ: 5.52 (2H, s), 6.32 (1H, dd, J = 2.8, 3.7 Hz), 6.81 (1H, s), 6.92 (1H, d, J = 8.3 Hz), 7.23 (1H, s), 7.25 (1H, s), 7.55 (1H, d, J = 8.3 Hz). | Ex. 1 |
| 1527 | pyrrole-triazole with 2,5-dichlorobenzyl | 1H-NMR (CDCl3) δ: 5.57 (2H, s), 6.40-6.43 (2H, m), 6.87-6.89 (1H, m), 7.15-7.22 (2H, m), 7.31 (1H, d, J = 8.5 Hz), 11.6 (1H, br). | Ex. 1 |
| 1528 | pyrrole-triazole with 3,5-dichlorobenzyl | 1H-NMR (DMSO-d6) δ: 5.52 (2H, s), 5.34 (1H, dd, J = 2.8, 3.7 Hz), 6.81-6.83 (1H, m), 6.99 (2H, s), 7.24-7.26 (1H, m), 7.47-7.49 (1H, m), 16.0 (1H, br). | Ex. 1 |
| 1529 | pyrrole-triazole with 3,5-bis(trifluoromethyl)benzyl | 1H-NMR (DMSO-d6) δ: 5.68 (2H, s), 6.37 (1H, dd, J = 2.7, 3.7 Hz), 6.81-6.83 (1H, m), 7.31 (1H, dd, J = 1.7, 2.7 Hz), 7.61 (2H, s), 7.99 (1H, s). | Ex. 1 |

TABLE 4-continued

| | Structure | NMR | Ex. |
|---|---|---|---|
| 1530 | (pyrrole-N-CH2-3,5-dibromophenyl, triazole-CN) | 1H-NMR (DMSO-d6) δ: 5.50 (2H, s), 6.34 (1H, dd, J = 2.9, 3.5 Hz), 6.81-6.83 (1H, m), 7.17 (2H, s), 7.24-7.25 (1H, m), 7.69-7.71 (1H, m), 16.1 (1H, br). | Ex. 1 |
| 1531 | (pyrrole-N-CH2-4-trifluoromethylphenyl, triazole-CN) | 1H-NMR (CDCl3) δ: 5.61 (2H, s), 6.37-7.39 (1H, m), 6.90 (1H, s), 7.08 (2H, d, J = 8.0 Hz), 7.16 (1H, s), 7.53 (2H, d, J = 8.0 Hz), 11.8 (1H, br). | Ex. 1 |
| 1532 | (pyrrole-N-CH2-2,4-dichlorophenyl, triazole-CN) | 1H-NMR (CDCl3) δ: 5.57 (2H, s), 6.34 (1H, d, J = 8.3 Hz), 6.38-7.40 (1H, m), 6.86-6.88 (1H, m), 7.09 (1H, dd, J = 4.0, 8.3 Hz), 7.17 (1H, s), 7.39 (1H, d, J = 2.0 Hz), 11.8 (1H, br). | Ex. 1 |
| 1533 | (pyrrole-N-CH2-2,3-dichlorophenyl, triazole-CN) | 1H-NMR (CDCl3) δ: 5.62 (2H, s), 6.26 (1H, d, J = 7.7 Hz), 6.40 (1H, t, J = 3.3 Hz), 6.88 (1H, t, J = 1.9 Hz), 7.04 (1H, t, J = 7.9 Hz), 7.17 (1H, d, J = 2.7 Hz), 7.34 (1H, d, J = 8.1 Hz), 11.8 (1H, br). | Ex. 1 |
| 1534 | (pyrrole-N-CH2-3,5-dimethylphenyl, triazole-CN) | 1H-NMR (CDCl3) δ: 2.25 (6H, s), 5.43 (2H, s), 6.34-6.36 (1H, m), 6.63 (2H, s), 6.89 (2H, s), 7.07 (1H, s), 11.8 (1H, br). | Ex. 1 |

TABLE 4-continued

| | Structure | 1H-NMR | Ex. |
|---|---|---|---|
| 1535 | (pyrrole-triazole with 3-(trifluoromethoxy)benzyl) | 1H-NMR (CDCl3) δ: 5.55 (2H, s), 6.37 (1H, dd, J = 2.7, 3.9 Hz), 6.86-6.91 (3H, m), 7.05-7.14 (2H, m), 7.28-7.32 (1H, m), 11.8 (1H, br.). | Ex. 1 |
| 1536 | (pyrrole-triazole with 3-(1,1,2,2-tetrafluoroethoxy)benzyl) | 1H-NMR (CDCl3) δ: 5.54 (2H, s), 5.87 (1H, tt, J = 2.9, 53 Hz), 6.37 (1H, dd, J = 2.8, 3.9 Hz), 6.84-6.91 (3H, m), 6.87-6.89 (1H, m), 7.02 (2H, d, J = 8.8 Hz), 7.26-7.32 (1H, m), 11.8 (1H, br.). | Ex. 1 |
| 1537 | (pyrrole-triazole with 4-(trifluoromethoxy)benzyl) | 1H-NMR (CDCl3) δ: 5.54 (2H, s), 6.36 (1H, dd, J = 2.8, 3.9 Hz), 6.87-6.89 (1H, m), 7.02 (2H, d, J = 8.8 Hz), 7.10-7.15 (3H, m), 11.8 (1H, br.). | Ex. 1 |
| 1538 | (pyrrole-triazole with 4-tert-butylbenzyl) | 1H-NMR (CDCl3) δ: 1.28 (9H, s), 5.49 (2H, s), 6.32-6.35 (1H, m), 6.89 (1H, s), 6.95 (2H, d, J = 8.2 Hz), 7.07 (1H, s), 7.32 (2H, d, J = 8.2 Hz), 11.8 (1H, br.). | Ex. 1 |
| 1539 | (pyrrole-triazole with 4-(benzyloxy)benzyl) | 1H-NMR (CDCl3) δ: 5.02 (2H, s), 5.44 (2H, s), 6.31-6.34 (1H, m), 6.85-6.92 (3H, m), 6.97 (2H, d, J = 8.8 Hz), 7.06 (1H, s), 7.30-7.42 (5H, m), 11.7 (1H, br.). | Ex. 1 |

| | | | |
|---|---|---|---|
| 1540 | (structure: 1-([1,1'-biphenyl]-4-ylmethyl)pyrrole linked to cyano-triazole) | 1H-NMR (CDCl3) δ: 6.57 (2H, s), 6.37 (1H, dd, J = 2.8, 3.9 Hz), 6.92-6.95 (1H, m), 7.08 (2H, d, J = 8.4 Hz), 7.10-7.13 (1H, m), 7.30-7.36 (1H, m), 7.37-7.45 (2H, m), 7.49-7.56 (4H, m), 11.7 (1H, br.). | Ex. 1 |
| 1541 | (structure: 1-phenethylpyrrole linked to cyano-triazole) | 1H-NMR (CDCl3) δ: 3.01 (2H, t, J = 7.2 Hz), 4.48 (2H, br.s), 6.23-6.27 (1H, m), 6.76 (1H, s), 6.89-7.08 (3H, m), 7.20-7.29 (3H, m), 11.6 (1H, br.). | Ex. 1 |
| 1542 | (structure: 1-(4-(2,2,2-trifluoroethoxy)benzyl)pyrrole linked to cyano-triazole) | 1H-NMR (CDCl3) δ: 4.30 (2H, q, J = 8.0 Hz), 5.47 (2H, s), 6.34 (1H, dd, J = 2.8, 3.9 Hz), 6.82-6.89 (3H, m), 6.95-7.00 (2H, m), 7.06-7.10 (1H, m), 11.6 (1H, br.). | Ex. 1 |
| 1543 | (structure: 1-(4-(4,4,4-trifluorobutoxy)benzyl)pyrrole linked to cyano-triazole) | 1H-NMR (CDCl3) δ: 1.97-2.07 (2H, m), 2.20-2.37 (2H, m), 3.97 (2H, t, J = 6.0 Hz), 5.44 (2H, s), 6.31-6.35 (1H, m), 6.80 (2H, d, J = 8.7 Hz), 6.88 (1H, s), 6.96 (2H, d, J = 8.7 Hz), 7.07 (1H, s), 11.6 (1H, br.). | Ex. 1 |
| 1544 | (structure: 5-(3,4-difluorophenyl)-1-methylpyrrole linked to cyano-triazole) | 1H-NMR (DMSO-d6) δ: 3.76 (3H, s), 6.40 (1H, d, J = 4.0 Hz), 6.77 (1H, d, J = 4.0 Hz), 7.36-7.39 (1H, m), 7.51-7.67 (2H, m). | Ex. 2 |

TABLE 4-continued

| | Structure | 1H-NMR | |
|---|---|---|---|
| 1545 | (1-methylpyrrol-2-yl pyrazole carbonitrile) | 1H-NMR (DMSO-d6) δ: 3.82 (3H, s), 6.19-6.21 (1H, m), 6.68-6.70 (1H, m), 7.05-7.06 (1H, m). | Ex. 2 |
| 1546 | (4-trifluoromethoxyphenyl N-methylpyrrole pyrazole carbonitrile) | 1H-NMR (DMSO-d6) δ: 3.77 (3H, s), 6.45 (1H, d, J = 3.9 Hz), 6.79 (1H, d, J = 3.9 Hz), 7.48 (2H, d, J = 7.9 Hz), 7.64-7.67 (2H, m). | Ex. 2 |
| 1547 | (4-fluorophenyl N-methylpyrrole pyrazole carbonitrile) | 1H-NMR (DMSO-d6) δ: 3.74 (3H, s), 6.38 (1H, d, J = 3.9 Hz), 6.77 (1H, d, J = 3.9 Hz), 7.30-7.35 (2H, m), 7.54-7.58 (2H, m). | Ex. 2 |
| 1548 | (4-fluoro-2-trifluoromethylphenyl N-methylpyrrole pyrazole carbonitrile) | 1H-NMR (DMSO-d6) δ: 3.54 (3H, s), 6.30 (1H, d, J = 3.9 Hz), 6.80 (1H, d, J = 3.9 Hz), 7.53-7.59 (2H, m), 7.97-8.00 (1H, m). | Ex. 2 |
| 1549 | (3-trifluoromethoxyphenyl N-methylpyrrole pyrazole carbonitrile) | 1H-NMR (DMSO-d6) δ: 3.79 (3H, s), 6.49 (1H, d, J = 4.0 Hz), 6.78 (1H, d, J = 4.0 Hz), 7.39-7.41 (1H, m), 7.51 (1H, bs), 7.56-7.65 (2H, m). | Ex. 2 |

TABLE 4-continued

| | Structure | 1H-NMR | Ex. |
|---|---|---|---|
| 1550 | 4-(trifluoromethoxy)phenyl-pyrrole-triazole-CN | 1H-NMR (DMSO-d6) δ: 6.80-6.81 (1H, m), 7.55 (2H, d, J = 8.4 Hz), 7.64-7.65 (1H, m), 7.78-7.81 (2H, m), 7.93-7.94 (1H, m). | Ex. 2 |
| 1551 | 3-(trifluoromethyl)-5-methoxyphenyl-pyrrole-triazole-CN | 1H-NMR (DMSO-d6) δ: 3.94 (3H, s), 6.79-6.80 (1H, m), 7.24 (1H, s), 7.58 (1H, s), 7.54-7.55 (1H, m), 7.60 (1H, s), 7.78-7.79 (1H, m), 8.07-8.08 (1H, m). | Ex. 2 |
| 1552 | 2-(trifluoromethyl)phenyl-pyrrole-triazole-CN | 1H-NMR (DMSO-d6) δ: 6.78-6.79 (1H, m), 7.23-7.24 (1H, m), 7.58 (1H, s), 7.65 (1H, d, J = 7.7 Hz), 7.76 (1H, t, J = 7.7 Hz), 7.85-7.89 (1H, m), 7.96-7.98 (1H, m). | Ex. 2 |
| 1553 | 4-chlorophenyl-pyrrole-triazole-CN | 1H-NMR (DMSO-d6) δ: 6.79-6.80 (1H, m), 7.59-7.63 (3H, m), 7.70 (2H, d, J = 8.9 Hz), 7.92-7.93 (1H, m). | Ex. 2 |
| 1554 | 4-benzylphenyl-pyrrole-triazole-CN | 1H-NMR (DMSO-d6) δ: 4.00 (2H, s), 6.76-6.77 (1H, m), 7.18-7.33 (5H, m), 7.37-7.40 (2H, m), 7.54-7.56 (3H, m), 7.85-7.86 (1H, m), 16.31 (1H, bs). | Ex. 2 |

TABLE 4-continued

| | Structure | 1H-NMR | |
|---|---|---|---|
| 1555 | (4-benzoylphenyl pyrrole triazole carbonitrile) | 1H-NMR (DMSO-d6) δ: 6.85-6.86 (1H, m), 7.58-7.62 (2H, m), 7.69-7.73 (1H, m), 7.77-7.79 (3H, m), 7.86-7.93 (4H, m), 8.06-8.07 (1H, m), 16.31 (1H, bs). | Ex. 2 |
| 1556 | (4-phenoxyphenyl pyrrole triazole carbonitrile) | 1H-NMR (DMSO-d6) δ: 6.77-6.78 (1H, m), 7.06-7.09 (2H, m), 7.15-7.20 (3H, m), 7.41-7.45 (2H, m), 7.55-7.56 (1H, m), 7.64-7.67 (2H, m), 7.85-7.86 (1H, m). | Ex. 2 |
| 1557 | (3-bromo-5-(trifluoromethyl)phenyl pyrrole triazole carbonitrile) | 1H-NMR (DMSO-d6) δ: 6.80-6.81 (1H, m), 7.84-7.85 (1H, m), 7.95 (1H, s), 8.11 (1H, s), 8.15-8.16 (1H, m), 8.32 (1H, s). | Ex. 2 |
| 1558 | (3-chlorobenzyl pyrrole triazole carbonitrile) | 1H-NMR (DMSO-d6) δ: 5.26 (2H, s), 6.59-6.60 (1H, m), 7.11-7.12 (1H, m), 7.22-7.25 (1H, m), 7.36-7.43 (3H, m), 7.54-7.55 (1H, m), 16.08 (1H, bs). | Ex. 2 |
| 1559 | (2-chlorobenzyl pyrrole triazole carbonitrile) | 1H-NMR (DMSO-d6) δ: 5.35 (2H, s), 6.62 (1H, s), 7.10 (2H, s), 7.34-7.38 (2H, m), 7.51-7.53 (2H, m), 16.13 (1H, bs). | Ex. 2 |

TABLE 4-continued

| | | | |
|---|---|---|---|
| 1560 | [4-chlorobenzyl-pyrrole-triazole-CN structure] | 1H-NMR (DMSO-d6) δ: 5.24 (2H, s), 6.58-6.59 (1H, m), 7.08-7.09 (1H, m), 7.28-7.30 (2H, m), 7.43-7.45 (2H, m), 7.50-7.51 (1H, m). | Ex. 2 |
| 1561 | [3-benzylphenyl-pyrrole-triazole-CN structure] | 1H-NMR (DMSO-d6) δ: 4.03 (2H, s), 6.77-6.78 (1H, m), 7.18-7.23 (2H, m), 7.29-7.33 (4H, m), 7.42-7.48 (2H, m), 7.56-7.59 (2H, m), 7.88-7.89 (1H, m). | Ex. 2 |
| 1562 | [benzodioxole-ethyl-pyrrole-triazole-CN structure] | 1H-NMR (DMSO-d6) δ: 2.95 (2H, t, J = 7.3 Hz), 4.19 (2H, t, J = 7.3 Hz), 5.96 (2H, s), 6.51-6.52 (1H, m), 6.63 (1H, dd, J = 1.7, 7.9 Hz), 6.79 (1H, d, J = 7.9 Hz), 6.83 (1H, d, J = 1.7 Hz), 6.97-6.98 (1H, m), 7.37-7.38 (1H, m). | Ex. 2 |
| 1563 | [3,4-dichlorophenyl-ethyl-pyrrole-triazole-CN structure] | 1H-NMR (DMSO-d6) δ: 3.06 (2H, t, J = 7.3 Hz), 4.29 (2H, t, J = 7.3 Hz), 6.52 (1H, s), 6.98 (1H, bs), 7.18 (1H, dd, J = 2.0, 8.2 Hz), 7.39 (1H, s), 7.50 (1H, d, J = 2.0 Hz), 7.53 (1H, d, J = 8.2 Hz). | Ex. 2 |

TABLE 4-continued

| | Structure | 1H-NMR | |
|---|---|---|---|
| 1564 | (2,3-dihydro-1H-inden-1-yl pyrrole triazole carbonitrile) | 1H-NMR (DMSO-d6) δ: 2.15-2.20 (1H, m), 2.66-2.70 (1H, m), 2.93-2.97 (1H, m), 3.08-3.14 (1H, m), 5.84 (1H, t, J = 7.1 Hz), 6.59-6.60 (1H, m), 7.01 (1H, t, J = 2.5 Hz), 7.09 (1H, d, J = 7.5 Hz), 7.23 (1H, t, J = 7.2 Hz), 7.32 (1H, t, J = 7.2 Hz), 7.38-7.42 (2H, m). | Ex. 2 |
| 1565 | (2,3-dihydro-1H-inden-2-yl pyrrole triazole carbonitrile) | 1H-NMR (DMSO-d6) δ: 3.17 (2H, dd, J = 6.2, 16.0 Hz), 3.47 (2H, dd, J = 7.4, 16.0 Hz), 5.01-5.15 (1H, m), 6.55-6.56 (1H, m), 7.06-7.07 (1H, m), 7.21-7.24 (2H, m), 7.28-7.31 (2H, m), 7.45-7.46 (1H, m). | Ex. 2 |
| 1566 | (4-chlorobenzyl dimethylpyrrole triazole carbonitrile) | 1H-NMR (DMSO-d6) δ: 2.15 (3H, s), 2.27 (3H, s), 5.19 (2H, s), 6.25 (1H, bs), 6.96 (2H, d, J = 8.5 Hz), 7.42 (2H, d, J = 8.5 Hz). | Ex. 2 |
| 1567 | (3,5-bis(trifluoromethyl)benzyl dimethylpyrrole triazole carbonitrile) | 1H-NMR (CDCl3) δ: 2.19 (3H, s), 2.38 (3H, s), 5.21 (2H, s), 6.47 (1H, s), 7.36 (2H, s), 7.82 (1H, s). | Ex. 2 |

TABLE 4-continued

| | | | |
|---|---|---|---|
| 1568 | [structure: 2-(3,4-difluorophenyl)pyridine linked to triazole-carbonitrile] | 1H-NMR (DMSO-d6) δ: 7.57-7.64 (1H, m), 8.01 (1H, dd, J = 0.9, 7.7 Hz), 8.14 (1H, t, J = 7.7 Hz), 8.17-8.23 (2H, m), 8.42-8.48 (1H, m). | Ex. 1 |
| 1569 | [structure: 2-(3,5-bis(trifluoromethyl)phenyl)pyridine linked to triazole-carbonitrile] | 1H-NMR (DMSO-d6) δ: 8.10 (1H, d, J = 7.6 Hz), 8.18-8.24 (2H, m), 8.51 (1H, d, J = 7.6 Hz), 9.02 (2H, s). | Ex. 1 |
| 1570 | [structure: 2-(2-(3-(trifluoromethyl)phenyl)vinyl)pyridine linked to triazole-carbonitrile] | 1H-NMR (DMSO-d6) δ: 7.58-7.71 (4H, m), 7.90-8.02 (2H, m), 8.05 (1H, t, J = 7.8 Hz), 8.10-8.16 (2H, m). | Ex. 1 |

| | | | |
|---|---|---|---|
| 1571 | (structure: 3,5-bis(trifluoromethyl)phenyl-vinyl-pyridine-triazole-CN) | 1H-NMR (DMSO-d6) δ: 7.61 (1H, d, J = 7.7 Hz), 7.82 (1H, d, J = 15.9 Hz), 7.79-7.99 (1H, m), 8.03-8.09 (2H, m), 8.16 (1H, d, J = 15.9 Hz), 8.23 (2H, s). | Ex. 1 |
| 1572 | (structure: 4-(trifluoromethyl)phenyl-vinyl-pyridine-triazole-CN) | 1H-NMR (DMSO-d6) δ: 7.55-7.64 (2H, m), 7.78-7.82 (4H, m), 7.92 (1H, d, J = 7.3 Hz), 8.03-8.15 (2H, m). | Ex. 1 |
| 1575 | (structure: benzothiophene-pyridine-triazole-CN) | 1H-NMR (DMSO-d6) δ: 7.39-7.46 (2H, m), 7.89-8.05 (3H, m), 8.12 (1H, t, J = 7.0 Hz), 8.22 (1H, d, J = 8.0 Hz), 8.32 (1H, s). | Ex. 1 |
| 1577 | (structure: benzothiophene-fluoropyridine-triazole-CN) | 1H-NMR (DMSO-d6) δ: 7.24-7.32 (1H, m), 7.69-7.75 (2H, m), 7.82 (1H, s), 7.93 (1H, s), 8.04-8.10 (2H, m). | Ex. 1 |

TABLE 4-continued

| # | Structure | 1H-NMR | Ref |
|---|---|---|---|
| 1578 | 5-chlorobenzothiophene-pyridine-triazole-CN | 1H-NMR (DMSO-d6) δ: 7.43-7.45 (1H, m), 7.99-8.01 (2H, m), 8.07 (1H, d, J = 8.6 Hz), 8.15 (1H, t, J = 7.8 Hz), 8.23-8.24 (1H, m), 8.27 (1H, s). | Ex. 1 |
| 1579 | 5-fluoro-3-methylbenzothiophene-pyridine-triazole-CN | 1H-NMR (DMSO-d6) δ: 2.70 (3H, s), 7.29-7.37 (1H, m), 7.77 (1H, dd, J = 2.4, 10.2 Hz), 7.96-8.07 (3H, m), 8.18 (1H, t, J = 7.9 Hz). | Ref. Ex. 91, Ex. 1 |
| 1580 | 5-fluorobenzothiophene-pyridine-triazole-CN | 1H-NMR (DMSO-d6) δ: 7.27-7.35 (1H, m), 7.72 (1H, dd, J = 2.5, 9.7 Hz), 7.98-8.02 (1H, m), 8.04-8.18 (2H, m), 8.22-8.26 (1H, m), 8.29 (1H, s). | Ex. 1 |
| 1582 | benzofuran-pyridine-triazole-CN | 1H-NMR (DMSO-d6) δ: 7.29-7.44 (2H, m), 7.67-7.77 (3H, m), 8.15 (1H, d, J = 8.1 Hz), 8.49 (1H, dd, J = 1.9, 8.3 Hz), 9.34 (1H, d, J = 1.9 Hz). | Ex. 1 |

TABLE 4-continued

| Ex. No. | STR | m.p. | ref. |
|---|---|---|---|
| 1573 | (benzofuran-2-yl)-pyridine-triazole-carbonitrile | 230-233 | Ex. 1 |
| 1574 | (naphthalen-2-yl)-pyridine-triazole-carbonitrile | 236-239 | Ex. 1 |
| 1576 | (benzofuran-2-yl)-fluoropyridine-triazole-carbonitrile | 260-261 | Ex. 1 |
| 1581 | (5-trifluoromethyl-benzothiophen-2-yl)-pyridine-triazole-carbonitrile | 297 | Ex. 1 |

TABLE 4-continued

| Ex. No. | STR | | ref. |
|---|---|---|---|
| 1583 | (structure: 5-fluoro-3-methylbenzothiophene linked to fluoropyridine-triazole-carbonitrile) | 272-275 | Ex. 1 |
| 1584 | (structure: 6-trifluoromethylbenzothiophene linked to pyridine-triazole-carbonitrile) | 288 | Ex. 1 |

| Ex. No. | STR | 1H-NMR | ref. |
|---|---|---|---|
| 1585 | (structure: 3,5-bis(trifluoromethyl)benzyloxymethyl-pyridine-triazole-carbonitrile) | 1H-NMR (DMSO-d6) δ: 4.80 (2H, s), 4.90 (2H, s), 7.64 (1H, d, J = 7.7 Hz), 7.93 (1H, d, J = 7.3 Hz), 8.03-8.08 (4H, m). | Ex. 2 |
| 1586 | (structure: 4-(trifluoromethyl)benzyloxymethyl-pyridine-triazole-carbonitrile) | 1H-NMR (DMSO-d6) δ: 4.76 (2H, s), 4.81 (2H, s), 7.64-7.74 (5H, m), 7.94 (1H, d, J = 7.4 Hz), 8.07 (1H, t, J = 7.8 Hz). | Ex. 2 |

TABLE 4-continued

| | Structure | 1H-NMR | |
|---|---|---|---|
| 1587 | 2,4,5-trifluorobenzyl ether linked to pyridine-triazole-CN | 1H-NMR (DMSO-d6) δ: 4.70 (2H, s), 4.74 (2H, s), 7.54-7.68 (3H, m), 7.93 (1H, d, J = 7.4 Hz), 8.06 (1H, t, J = 7.7 Hz). | Ex. 2 |
| 1588 | 3,5-bis(trifluoromethyl)phenyl CH(CH3)O linked to pyridine-triazole-CN | 1H-NMR (CDCl3) δ: 1.65 (3H, d, J = 6.6 Hz), 4.62-4.85 (3H, m), 7.59 (1H, d, J = 7.8 Hz), 7.80 (3H, s), 7.95 (1H, t, J = 7.8 Hz), 8.06 (1H, d, J = 7.8 Hz). | Ex. 2 |
| 1589 | 2,4-bis(trifluoromethyl)benzyl ether linked to pyridine-triazole-CN | 1H-NMR (DMSO-d6) δ: 4.82 (2H, s), 4.96 (2H, s), 7.65 (1H, d, J = 7.6 Hz), 7.95 (1H, d, J = 7.6 Hz), 8.04-8.11 (4H, m). | Ex. 2 |

TABLE 4-continued

| | Structure | 1H-NMR | Ex. |
|---|---|---|---|
| 1590 | (2,5-bis(trifluoromethyl)benzyl ether-pyridine-triazole-CN) | 1H-NMR (DMSO-d6) δ: 4.84 (2H, s), 4.95 (2H, s), 7.61 (1H, s, J = 7.8 Hz), 7.92-7.95 (2H, m), 8.00 (1H, d, J = 8.0 Hz), 8.07 (1H, t, J = 8.0 Hz), 8.13 (1H, s) | Ex. 2 |
| 1591 | (1-(4-(trifluoromethyl)phenyl)ethoxy-pyridine-triazole-CN) | 1H-NMR (DMSO-d6) δ: 1.57 (3H, d, J = 6.5 Hz), 4.61-4.77 (3H, m), 7.60 (2H, d, J = 8.1 Hz), 7.66 (1H, d, J = 7.4 Hz), 7.71 (2H, d, J = 8.1 Hz), 7.92-7.94 (1H, m), 8.07 (1H, t, J = 7.4 Hz). | Ex. 2 |
| 1592 | (pyridine-2,6-bis(triazole-CN)) | 1H-NMR (DMSO-d6) δ: 8.10 (2H, d, J = 7.8 Hz), 8.27 (1H, t, J = 7.8 Hz). | Ex. 125 |
| 1593 | (2-(pyridin-2-yl)pyridine-triazole-CN) | 1H-NMR (DMSO-d6) δ: 7.50-7.53 (1H, m), 8.02 (1H, dt, J = 1.8, 7.8 Hz), 8.09 (1H, dd, J = 1.0, 7.8 Hz), 8.18 (1H, t, J = 7.8 Hz), 8.53 (1H, dd, J = 1.0, 7.8 Hz), 8.70 (1H, dt, J = 1.0, 7.8 Hz), 8.73-8.75 (1H, m). | Ex. 125 |

TABLE 4-continued

| Ex. No. | STR | m.p. | 1H-NMR (DMSO-d6) δ: 7.30-7.45 (2H, m), 7.68-7.78 (3H, m), 8.70 (1H, s), 9.07 (1H, s), 9.32 (1H, s). | ref. |
|---|---|---|---|---|
| 1595 | | | | Ex. 1 |
| 1594 | | 268 | | Ex. 1 |
| 1596 | | 242 | | Ex. 1 |

TABLE 4-continued

| Ex. No. | STR | 1H-NMR | ref. |
|---|---|---|---|
| 1597 | [structure: 3,5-bis(trifluoromethyl)phenyl-pyridine-triazole-CN] 280-281 | | Ex. 1 |
| 1598 | [structure: 1-benzyl-indole-triazole-CN] | 1H-NMR (CDCl3) δ: 5.80 (2H, s), 6.98 (2H, d, J = 7.3 Hz), 7.18-7.34 (6H, m), 7.46 (1H, s), 7.75 (1H, d, J = 8.0 Hz). | Ex. 1 |
| 1599 | [structure: 1-(3-trifluoromethylbenzyl)-indole-triazole-CN] | 1H-NMR (CDCl3) δ: 5.85 (2H, s), 7.01 (1H, d, J = 7.7 Hz), 7.20-7.24 (1H, m), 7.26-7.35 (3H, m), 7.43 (1H, s), 7.48 (1H, d, J = 7.7 Hz) 7.51 (1H, s), 7.7 (1H, d, J = 8.0 Hz), 11.8 (1H, br.). | Ex. 1 |
| 1600 | [structure: 1-(2,5-bis(trifluoromethyl)benzyl)-indole-triazole-CN] | 1H-NMR (CDCl3) δ: 6.00 (2H, s), 6.73 (1H, s), 7.17 (1H, d, J = 8.3 Hz), 7.21-7.33 (2H, m), 7.58 (1H, s), 7.60 (1H, d, J = 8.1 Hz), 7.80 (1H, d, J = 8.0 Hz), 7.87 (1H, d, J = 8.1 Hz), 11.8 (1H, br.). | Ex. 1 |

TABLE 4-continued

| | Structure | 1H-NMR | Ex. |
|---|---|---|---|
| 1601 | 2-(1-(4-chlorobenzyl)-1H-indol-2-yl)-1H-1,2,3-triazole-carbonitrile | 1H-NMR (CDCl3) δ: 5.77 (2H, s), 6.92 (2H, d, J = 8.2 Hz), 7.19-7.22 (3H, m), 7.27-7.30 (2H, m), 7.48 (1H, s), 7.74 (1H, dd, J = 0.7, 7.9 Hz), 11.9 (1H, br.). | Ex. 1 |
| 1602 | 2-(1-(3,4-dichlorobenzyl)-1H-indol-2-yl)-1H-1,2,3-triazole-carbonitrile | 1H-NMR (CDCl3) δ: 5.75 (2H, s), 6.77 (1H, dd, J = 1.4, 8.2 Hz), 7.17 (1H, d, J = 1.4 Hz), 7.22 (1H, t, J = 7.3 Hz), 7.26-7.33 (3H, m), 7.50 (1H, s), 7.77 (1H, d, J = 7.9 Hz), 11.9 (1H, br.). | Ex. 1 |
| 1603 | 2-(1-benzyl-5-chloro-1H-indol-2-yl)-1H-1,2,3-triazole-carbonitrile | 1H-NMR (CDCl3) δ: 5.78 (2H, s), 6.93-6.97 (2H, m), 7.20-7.28 (5H, m), 7.37 (1H, s), 7.70-7.72 (1H, m), 12.1 (1H, br.). | Ex. 1 |
| 1604 | 3-(1-phenyl-1H-indol-3-yl)-1H-1,2,3-triazole-carbonitrile | 1H-NMR (CDCl3) δ: 7.33-7.38 (2H, m), 7.45-7.48 (1H, m), 7.55-7.60 (5H, m), 8.16 (1H, s), 8.3 (1H, br.), 11.9 (1H, br.). | Ex. 1 |

TABLE 4-continued

| | | | |
|---|---|---|---|
| 1605 | (4-chlorophenyl-indole-triazole-CN structure) | 1H-NMR (CDCl3) δ: 7.34-7.38 (2H, m), 7.48-7.57 (5H, m), 8.11 (1H, s), 8.25 (1H, s), 12.0 (1H, br.). | Ex. 1 |
| 1606 | (benzyl-indole-triazole-CN structure) | 1H-NMR (CDCl3) δ: 5.43 (2H, s), 7.17 (2H, d, J = 7.2 Hz), 7.26-7.39 (6H, m), 8.00 (1H, s), 8.18 (1H, br.), 11.9 (1H, br.). | Ex. 1 |
| 1607 | (4-chlorobenzyl-indole-triazole-CN structure) | 1H-NMR (CDCl3) δ: 5.40 (2H, s), 7.09 (2H, d, J = 8.5 Hz), 7.26-7.34 (5H, m), 7.99 (1H, s), 8.18 (1H, br.), 12.0 (1H, br.). | Ex. 1 |
| 1608 | (thiophen-2-ylmethyl-indole-triazole-CN structure) | 1H-NMR (CDCl3) δ: 5.57 (2H, s), 6.96-6.97 (1H, m), 7.01-7.02 (1H, m), 7.24-7.26 (1H, m), 7.26-7.36 (2H, m), 7.46-7.50 (1H, m), 8.00 (1H, s), 8.20 (1H, s), 12.0 (1H, br.). | Ex. 1 |

TABLE 4-continued

| Ex. No. | STR | m.p. | 1H-NMR | ref. |
|---|---|---|---|---|
| 1609 | (1-cyclopropylmethyl-indol-3-yl-triazole-carbonitrile) | | 1H-NMR (CDCl3) δ: 0.43-0.47 (2H, m), 0.69-0.74 (2H, m), 1.33-1.37 (1H, m), 4.08 (2H, d, J = 7.0 Hz), 7.26-7.37 (2H, m), 7.47 (1H, d, J = 8.2 Hz), 8.09 (1H, s), 8.10 (1H, br.), 12.0 (1H, br.). | Ex. 1 |
| 1610 | (7-methyl-indol-3-yl-triazole-carbonitrile) | | 1H-NMR (CDCl3) δ: 2.53 (3H, s), 7.05-7.14 (2H, m), 7.74-7.88 (1H, br), 7.96 (1H, d, J = 2.9 Hz), 11.89 (1H, brs) | Ex. 1 |
| 1611 | (1-benzyl-indol-5-yl-triazole-carbonitrile) | 227-228 | | Ex. 1 |

TABLE 4-continued

| Ex. No. | STR | 162-164 | Ex. 1 |
|---|---|---|---|
| 1612 | (1-benzyl-indol-4-yl triazole carbonitrile structure) | | |
| Ex. No. | STR | 1H-NMR | ref. |
| 1613 | (1-(3-trifluoromethylphenyl)-indol-6-yl triazole carbonitrile structure) | 1H-NMR (CDCl3) δ: 6.78-6.82 (1H, m), 7.49 (1H, d, J = 3.3 Hz), 7.65-7.87 (6H, m), 8.12 (1H, s). | Ex. 1 |
| 1614 | (1-(3,4-difluorophenyl)-indol-6-yl triazole carbonitrile structure) | 1H-NMR (CDCl3) δ: 6.81 (1H, dd, J = 0.7, 3.3 Hz), 7.26-7.31 (1H, m), 7.32-7.42 (3H, m), 7.60 (1H, d, J = 8.7 Hz), 7.78-7.84 (1H, m), 8.31 (1H, s), 12.0 (1H, br.). | Ex. 1 |
| 1615 | (1-(3-trifluoromethylphenyl)-indol-6-yl triazole carbonitrile structure) | 1H-NMR (CDCl3) δ: 6.85 (1H, dd, J = 0.7, 3.3 Hz), 7.44 (1H, d, J = 3.3 Hz), 7.62-7.84 (6H, m), 8.32 (1H, d, J = 1.3 Hz), 12.0 (1H, br). | Ex. 1 |

TABLE 4-continued

| | Structure | 1H-NMR | Ex. |
|---|---|---|---|
| 1616 | 6-(3,4-difluorobenzyl)indole-triazole-CN | 1H-NMR (CDCl3) δ: 5.35 (2H, s), 6.64 (1H, dd, J = 0.8, 3.2 Hz), 6.90-6.99 (2H, m), 7.07-7.17 (1H, m), 7.26-7.30 (1H, m), 7.69 (1H, br.), 7.78 (1H, d, J = 8.2 Hz), 7.90 (1H, s), 12.0 (1H, br.). | Ex. 1 |
| 1617 | 6-(3-trifluoromethylbenzyl)indole-triazole-CN | 1H-NMR (CDCl3) δ: 5.45 (2H, s), 6.66 (1H, dd, J = 0.8, 3.2 Hz), 7.26-7.34 (2H, m), 7.41-7.49 (2H, m), 7.52-7.57 (1H, m), 7.70 (1H, br.), 7.79 (1H, d, J = 8.2 Hz), 7.92 (1H, s), 12.0 (1H, br.). | Ex. 1 |
| 1618 | 6-(4-methoxyphenyl)indole-triazole-CN | 1H-NMR (DMSO-d6) δ: 3.85 (3H, s), 6.78 (1H, dd, J = 0.7, 3.2 Hz), 7.13-7.20 (2H, m), 7.53-7.59 (2H, m), 7.65 (1H, dd, J = 1.5, 8.2 Hz), 7.78 (1H, d, J = 3.2 Hz), 7.88 (1H, d, J = 8.2 Hz), 8.01-8.05 (1H, m). | Ex. 1 |
| 1619 | 6-(benzo[1,3]dioxol-5-yl)indole-triazole-CN | 1H-NMR (DMSO-d6) δ: 6.16 (2H, s), 6.78 (1H, d, J = 3.2 Hz), 7.06-7.14 (2H, m), 7.26 (1H, d, J = 1.9 Hz), 7.64 (1H, dd, J = 1.4, 8.3 Hz), 7.77 (1H, d, J = 3.2 Hz), 7.86 (1H, d, J = 8.3 Hz), 8.05 (1H, s). | Ex. 1 |

TABLE 4-continued

| | Structure | 1H-NMR | |
|---|---|---|---|
| 1620 | 4-chlorophenyl-indole-triazole-CN | 1H-NMR (DMSO-d6) δ: 6.85 (1H, d, J = 3.3 Hz), 7.64-7.74 (5H, m), 7.86-7.92 (2H, m), 8.12 (1H, s). | Ex. 1 |
| 1621 | 3,5-difluorophenyl-indole-triazole-CN | 1H-NMR (CDCl3-CD3OD) δ: 6.78 (1H, dd, J = 0.7, 3.3 Hz), 6.82-6.91 (1H, m), 7.09-7.19 (2H, m), 7.44 (1H, d, J = 3.3 Hz), 7.75-7.84 (2H, m), 8 19-8.23 (1H, m). | Ex. 1 |
| 1622 | 3,4-difluorophenyl-indole-triazole-CN | 1H-NMR (DMSO-d6) δ: 7.00 (1H, d, J = 2.7 Hz), 7.43 (1H, t, J = 7.8 Hz), 7.49-7.57 (1H, m), 7.58-7.78 (3H, m), 7.80-7.91 (2H, m). | Ex. 1 |
| 1623 | 2,4,5-trifluorobenzyl-indole-triazole-CN | 1H-NMR (CDCl3) δ: 5.38 (2H, s), 6.60-6.71 (1H, m), 6.95-7.07 (2H, m), 7.31 (1H, d, J = 3.3 Hz), 7.33-7.39 (1H, m), 7.45 (1H, d, J = 8.2 Hz), 7.71-7.80 (1H, m), 12.3 (1H, br.). | Ex. 1 |

TABLE 4-continued

| | | | |
|---|---|---|---|
| 1624 | [structure] | 1H-NMR (DMSO-d6) δ: 7.36 (1H, d, J = 7.3 Hz), 7.47 (1H, t, J = 8.3 Hz), 7.52-7.60 (1H, m), 7.69 (1H, dd, J = 8.9, 10.4 Hz), 7.79 (1H, d, J = 8.3 Hz), 7.86-7.94 (1H, m), 8.07 (1H, s). | Ex. 1 |
| 1625 | [structure] | 1H-NMR (CDCl3) δ: 7.15-7.19 (1H, m), 7.40 (1H, dd, J = 7.5, 8.3 Hz), 7.49 (1H, d, J = 3.3 Hz), 7.63-7.75 (4H, m), 7 76-7.82 (2H, m). | Ex. 1 |
| 1626 | [structure] | 1H-NMR (CDCl3) δ:5.38 (2H, s), 6.64 (1H, dd, J = 0.7, 3.2 Hz), 6.73-6.83 (1H, m), 6.94-7.04 (1H, m), 7.29 (1H, d, J = 3.2 Hz), 7.66-7.72 (1H, m), 7.78 (1H, d, J = 8.2 Hz), 7.95 (1H, s), 12.5 (1H, br). | Ex. 1 |

TABLE 4-continued

| | Structure | 1H-NMR | Ex. |
|---|---|---|---|
| 1627 | 4-fluorophenyl-indole-triazole-CN | 1H-NMR (CDCl3-DMSO-d6) δ: 6.73 (1H, dd, J = 0.8, 3.2 Hz), 7.23-7.29 (2H, m), 7.42 (1H, d, J = 3.2 Hz), 7.49-7.57 (2H, m), 7.71-7.82 (2H, m), 8.12 (1H, s). | Ex. 1 |
| 1628 | 3-fluorophenyl-indole-triazole-CN | 1H-NMR (CDCl3-DMSO-d6) δ: 6.75 (1H, dd, J = 0.8, 3.2 Hz), 7.07-7.15 (1H, m), 7.29-7.41 (2H, m), 7.45 (1H, d, J = 3.2 Hz), 7.50-7.59 (1H, m), 7.79 (2H, s), 8.22 (1H, s). | Ex. 1 |
| 1629 | 4-trifluoromethylphenyl-indole-triazole-CN | 1H-NMR (CDCl3) δ: 6.79-6.82 (1H, m), 7.50 (1H, d, J = 3.2 Hz), 7.76-7.88 (6H, m), 8.23 (1H, s). | Ex. 1 |
| 1630 | 2,5-bis(trifluoromethyl)benzyl-indole-triazole-CN | 1H-NMR (CDCl3-DMSO-d6) δ: 5.61 (2H, s), 6.67 (1H, dd, J = 0.8, 3.2 Hz), 6.86 (1H, s), 7.20 (1H, d, J = 3.2 Hz), 7.62 (1H, d, J = 8.4 Hz), 7.74-7.77 (2H, m), 7.80-7.83 (1H, m), 7.87 (1H, d, J = 8.2 Hz). | Ex. 1 |

TABLE 4-continued

| | Structure | 1H-NMR | Ex. |
|---|---|---|---|
| 1631 | 4-methylphenyl-indole-triazole-CN | 1H-NMR (CDCl3) δ: 2.44 (3H, s), 6.73 (1H, dd, J = 0.7, 3.2 Hz), 7.33-7.39 (2H, m), 7.40-7.45 (2H, m), 7.46 (1H, d, J = 3.2 Hz), 7.66-7.72 (1H, m), 7.80 (1H, d, J = 8.3 Hz), 8.12 (1H, s). | Ex. 1 |
| 1632 | 3,5-bis(trifluoromethyl)benzyl-indole-triazole-CN | 1H-NMR (CDCl3) δ: 5.52 (2H, s), 6.70 (1H, dd, J = 0.8, 3.2 Hz), 7.28 (1H, d, J = 3.2 Hz), 7.59 (2H, s), 7.68-7.79 (1H, m), 7.79-7.85 (2H, m), 7.91 (1H, s). | Ex. 1 |
| 1633 | 2,4-difluorophenyl-indole-triazole-CN | 1H-NMR (CDCl3) δ: 6.78 (1H, d, J = 3.2 Hz), 7.06-7.17 (2H, m), 7.36-7.39 (1H, m), 7.49-7.59 (1H, m), 7.74 (1H, dd, J = 1.3, 8.3 Hz), 7.83 (1H, d, J = 8.3 Hz), 7.86 (1H, s), 12.0 (1H, br.). | Ex. 1 |
| 1634 | 2,5-difluorophenyl-indole-triazole-CN | 1H-NMR (CDCl3) δ: 6.79 (1H, d, J = 3.3 Hz), 7.09-7.18 (1H, m), 7.27-7.38 (2H, m), 7.39-7.43 (1H, m), 7.73-7.85 (2H, m), 7.94 (1H, s) 12.0 (1H, br). | Ex. 1 |

TABLE 4-continued

| | Structure | 1H-NMR | Ex. |
|---|---|---|---|
| 1635 | (4-trifluoromethylbenzyl-indole-triazole-CN) | 1H-NMR (CDCl3) δ: 5.47 (2H, s), 6.65 (1H, dd, J = 0.7, 3.1 Hz), 7.23-7.32 (3H, m), 7.57 (2H, d, J = 8.1 Hz), 7.64-7.71 (1H, m), 7.79 (1H, d, J = 8.2 Hz), 7.91 (1H, s), 12.4 (1H, br.). | Ex. 1 |
| 1636 | (cyclohexylmethyl-indole-triazole-CN) | 1H-NMR (CDCl3) δ: 0.94-1.11 (2H, m), 1.11-1.31 (3H, m), 1.56-1.77 (5H, m), 1.81-1.98 (1H, m), 4.02 (2H, d, J = 7.2 Hz), 6.54 (1H, dd, J = 0.7, 3.1 Hz), 7.21 (1H, d, J = 3.1 Hz), 7.51-7.70 (1H, m), 7.75 (1H, d, J = 8.2 Hz), 7.97 (1H, s), 12.5(1H, br.). | Ex. 1 |
| 1637 | (cyclobutylmethyl-indole-triazole-CN) | 1H-NMR (CDCl3) δ: 1.75-1.98 (4H, m), 2.00-2.16 (2H, m), 2.80-2.96 (1H, m), 4.22 (2H, d, J = 7.2 Hz), 6.55 (1H, dd, J = 0.7, 3.1 Hz), 7.24 (1H, d, J = 3.1 Hz), 7.55-7.67 (1H, m), 7.75 (1H, d, J = 8.2 Hz), 8.03 (1H, s). | Ex. 1 |
| 1638 | (cyclopropylmethyl-indole-triazole-CN) | 1H-NMR (CDCl3) δ: 0.38-0.47 (2H, m), 0.62-0.72 (2H, m), 1.23-1.40 (1H, m), 4.08 (2H, d, J = 6.8 Hz), 6.58 (1H, d, J = 3.1 Hz), 7.39 (1H, d, J = 3.1 Hz), 7.59-7.67 (1H, m), 7.77 (1H, d, J = 8.3 Hz), 8.03 (1H, s). | Ex. 1 |
| 1639 | (cyclopropylethyl-indole-triazole-CN) | 1H-NMR (CDCl3) δ: 0.00-0.08 (2H, m), 0.38-0.47 (2H, m), 0.54-0.69 (1H, m), 1.76 (2H, q, J = 6.8 Hz), 4.29 (2H, t, J = 6.8 Hz), 6.55 (1H, d, J = 3.1 Hz), 7.27 (1H, d, J = 3.1 Hz), 7.61 (1H, dd, J = 1.5, 8.3 Hz), 7.75 (1H, d, J = 8.3 Hz), 8.01 (1H, s). | Ex. 1 |

TABLE 4-continued

| | Structure | 1H-NMR | |
|---|---|---|---|
| 1640 | (1-(1-phenylethyl)-1H-indol-4-yl triazole carbonitrile) | 1H-NMR (CDCl3) δ: 1.97 (3H, d, J = 7.1 Hz), 5.72 (1H, q, J = 7.1 Hz), 6.94 (1H, d, J = 3.2 Hz), 7.10-7.16 (2H, m), 7.22-7.35 (4H, m), 7.40 (1H, d, J = 8.4 Hz), 7.47 (1H, d, J = 3.2 Hz), 7.67 (1H, d = 7.1 Hz). | Ex. 1 |
| 1641 | (1-(1-phenylethyl)-1H-indol-6-yl triazole carbonitrile) | 1H-NMR (CDCl3) δ: 1.97 (3H, d, J = 7.0 Hz), 5.76 (1H, q, J = 7.0 Hz), 6.63 (1H, dd, J = 0.7, 3.2 Hz), 7.17-7.35 (5H, m), 7.48 (1H, d, J = 3.2 Hz), 7.56-7.63 (1H, m), 7.75 (1H, d, J = 8.3 Hz), 7.88 (1H, s). | Ex. 1 |
| 1642 | (1-((tetrahydrofuran-2-yl)methyl)-1H-indol-6-yl triazole carbonitrile) | 1H-NMR (CDCl3) δ: 1.59-1.98 (3H, m), 2.02-2.17 (1H, m), 3.77-3.94 (2H, m), 4.18-4.45 (3H, m), 6.54 (1H, dd, J = 0.7, 3.1 Hz), 7.30 (1H, d, J = 3.1 Hz), 7.55 (1H, br.), 7.68 (1H, d, J = 8.2 Hz), 7.98 (1H, s). | Ex. 1 |
| 1643 | (5-bromobenzofuran-2-yl triazole carbonitrile) | 1H-NMR (DMSO-d6) δ: 7.55-7.61 (2H, m), 7.73 (1H, d, J = 8.8 Hz), 8.05 (1H, d, J = 2.0 Hz). | Ex. 1 |

TABLE 4-continued

| | | | |
|---|---|---|---|
| 1644 | [structure: 3-(trifluoromethyl)phenyl-vinyl-benzofuran-triazole-carbonitrile] | 1H-NMR (DMSO-d6) δ: 7.41 (1H, d, J = 16.4 Hz), 7.56-7.63 (6H, m), 7.77 (1H, s), 7.93-8.04 (2H, m). | Ex. 1 |
| 1645 | [structure: 3-(trifluoromethyl)phenyl-benzofuran-triazole-carbonitrile] | 1H-NMR (DMSO-d6) δ: 7.60 (1H, s), 7.74-7.84 (4H, m), 8.04-8.07 (2H, m), 8.20 (1H, s). | Ex. 1 |

TABLE 4-continued

| Ex. No. | STR | m.p. | ref. |
|---|---|---|---|
| 1646 | 4-fluorophenyl-benzofuran-triazole carbonitrile | 255-256 | Ex. 1 |
| 1647 | 3-(trifluoromethyl)phenyl-benzofuran-triazole carbonitrile | 176-179 | Ex. 1 |

TABLE 4-continued

| | | | |
|---|---|---|---|
| 1648 | ![structure] | 242-245 | Ex. 1 |
| 1649 | ![structure] | 257-259 | Ex. 1 |

TABLE 4-continued

| | | | |
|---|---|---|---|
| 1650 | [structure] | 265-267 | Ex. 1 |
| 1651 | [structure] | 232 | Ex. 1 |

TABLE 4-continued
| | | | |
|---|---|---|---|
| 1652 | 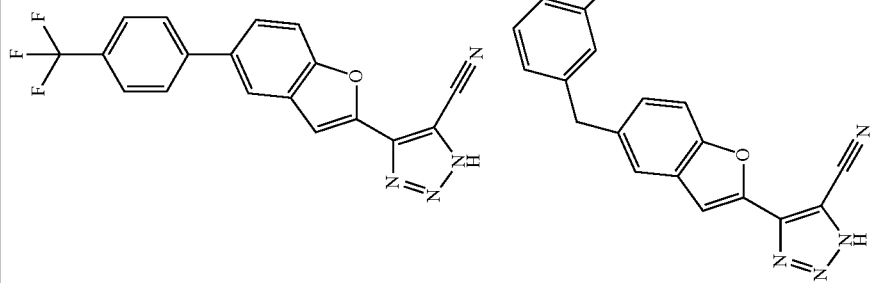 | 273-276 | Ex. 1 |
| 1654 | | 216-217 | Ex. 1 |

TABLE 4-continued
| | | | |
|---|---|---|---|
| 1655 | 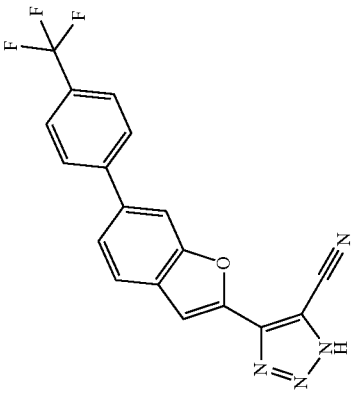 | 197-200 | Ex. 1 |
| 1656 | 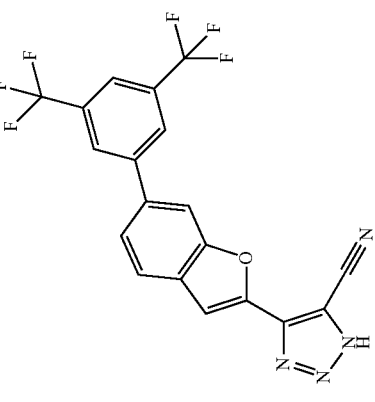 | 259 | Ex. 1 |
| 1657 | 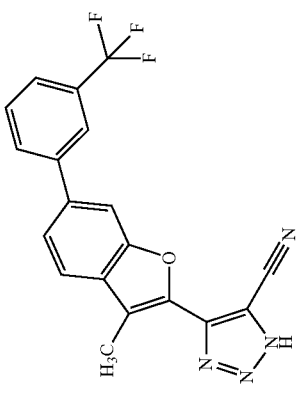 | 226-228 | Ex. 1 |

TABLE 4-continued

| Ex. No. | STR | 1H-NMR | ref. |
|---|---|---|---|
| 1653 | (4-trifluoromethoxyphenyl-benzofuran-triazole-carbonitrile structure) | 1H-NMR (DMSO-d6) δ: 7.49 (2H, d, J = 8.0 Hz), 7.60 (1H, d, J = 0.7 Hz), 7.75 (1H, dd, J = 1.9, 8.7 Hz), 7.81-7.87 (3H, m), 8.11 (1H, d, J = 1.9 Hz). | Ref. Ex. 260, Ex. 1 |
| 1658 | (4-fluorophenyl-methyl-benzofuran-triazole-carbonitrile structure) | 1H-NMR (DMSO-d6) δ: 2.57 (3H, s), 7.31 (2H, t, J = 8.9 Hz), 7.65-7.70 (1H, m), 7.80-7.88 (3H, m), 7.92-7.94 (1H, m). | Ex. 1 |

TABLE 4-continued
| Ex. No. | STR | m.p. | 1H-NMR | ref. |
|---|---|---|---|---|
| 1659 | 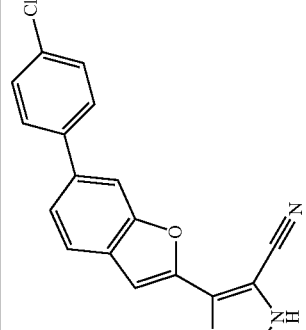 | | 1H-NMR (DMSO-d6) δ: 7.53-7.61 (3H, m), 7.67-7.72 (1H, m), 7.81-7.92 (3H, m), 8.04 (1H, s). | Ex. 1 |
| 1662 | 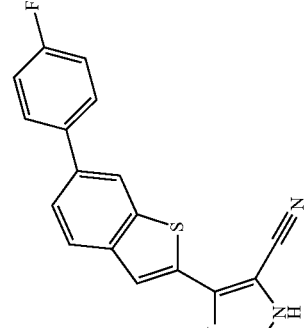 | | 1H-NMR (DMSO-d6) δ: 7.34 (2H, t, J = 8.8 Hz), 7.76 (1H, dd, J = 1.5, 8.4 Hz), 7.81-7.87 (2H, m), 8.07 (1H, s), 8.11 (1H, d, J = 8.4 Hz), 8.41 (1H, s). | Ex. 1 |
| 1660 | 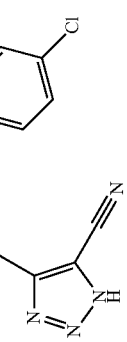 | 269-272 | | Ex. 1 |

TABLE 4-continued
| | | | |
|---|---|---|---|
| 1661 | 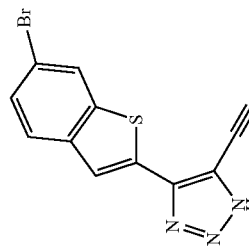 | 248-250 | Ex. 1 |
| 1663 | 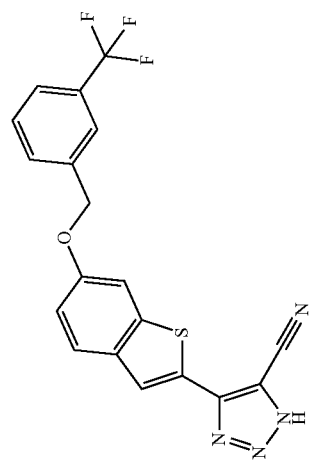 | 222 | Ex. 1 |
| 1664 | 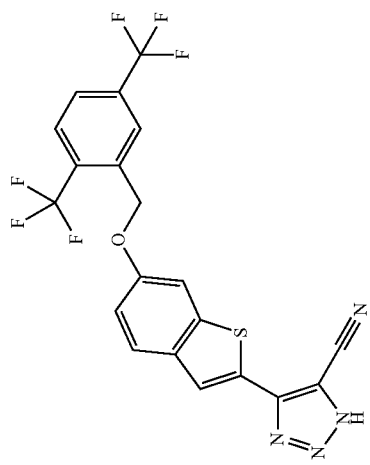 | 231 | Ex. 1 |

TABLE 4-continued
| | | | |
|---|---|---|---|
| 1665 | 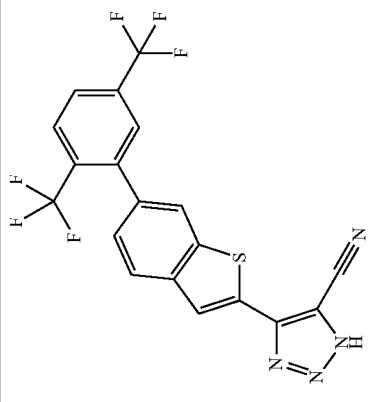 | 189-191 | Ex. 1 |
| 1666 | 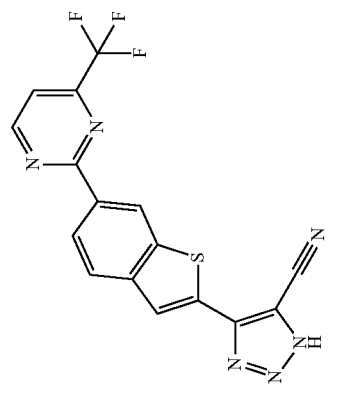 | 301 | Ex. 1 |
| 1667 | 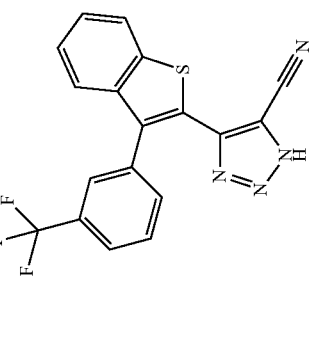 | 154-157 | Ex. 1 |

TABLE 4-continued

| Ex. No. | STR | | ref. |
|---|---|---|---|
| 1670 | (3-thienyl-benzothiophene-triazole-carbonitrile structure) | 248-250 | Ex. 1 |
| Ex. No. | STR | 1H-NMR | ref. |
| 1668 | (3-(3,5-bis(trifluoromethyl)phenyl)-benzothiophene-triazole-carbonitrile structure) | 1H-NMR (DMSO-d6) δ: 7.50-7.63 (3H, m), 8.14 (2H, s), 8.20-8.26 (2H, m). | Ex. 1 |
| 1669 | (5-(trifluoromethyl)-benzothiophene-triazole-carbonitrile structure) | 1H-NMR (DMSO-d6) δ: 7.76 (1H, dd, J = 1.5, 8.6 Hz), 8.21 (1H, s), 8.35 (1H, d, J = 8.6 Hz), 8.53 (1H, s). | Ex. 1 |

TABLE 4-continued

| | Structure | NMR | Ex. |
|---|---|---|---|
| 1671 | (6-[6-(trifluoromethyl)pyridin-3-yl]benzothiophen-2-yl triazole carbonitrile) | 1H-NMR (DMSO-d6) δ: 7.91-7.96 (1H, m), 8.04 (1H, d, J = 8.0 Hz), 8.11 (1H, s), 8.21 (1H, d, J = 8.0 Hz), 8.47-8.52 (1H, m), 8.63 (1H, s), 9.21-9.23 (1H, m). | Ex. 1 |
| 1672 | (6-piperidin-1-yl-2-phenylpyrimidin-4-yl triazole carbonitrile) | 1H-NMR (DMSO-d6) δ: 1.63-1.69 (6H, m), 3.80-3.82 (4H, m), 7.24 (1H, s), 7.48-7.52 (3H, m), 8.50-8.55 (2H, m). | Ex. 2 |
| 1673 | (2-phenylpyrimidin-4-yl triazole carbonitrile) | 1H-NMR (DMSO-d6) δ: 7.54-7.61 (3H, m), 7.95 (1H, d, J = 5.1 Hz), 8.59-8.62 (2H, m), 9.12 (1H, d, J = 5.1 Hz). | Ex. 2 |

TABLE 4-continued

| | Structure | 1H-NMR | |
|---|---|---|---|
| 1674 | 2-methyl-4-[(E)-2-(4-trifluoromethylphenyl)vinyl]pyrimidine with triazole-carbonitrile | 1H-NMR (DMSO-d6) δ: 2.65 (3H, s), 7.55 (1H, d, J = 15.6 Hz), 7.77-7.80 (2H, m), 7.90 (1H, s), 7.95-8.01 (3H, m). | Ex. 2 |
| 1675 | 2-methyl-4-[(E)-2-(4-fluorophenyl)vinyl]pyrimidine with triazole-carbonitrile | 1H-NMR (DMSO-d6) δ: 2.60 (3H, s), 7.22-7.28 (2H, m), 7.33 (1H, d, J = 16.0 Hz), 7.80-7.84 (3H, m), 7.90 (1H, d, J = 16.0 Hz). | Ex. 2 |
| 1676 | 6-pyrrolidin-1-yl-2-phenylpyrimidine with triazole-carbonitrile | 1H-NMR (CDCl3) δ: 2.61 (4H, brs), 3.49 (2H, brs), 3.82 (2H, brs), 6.92 (1H, s), 7.48-7.52 (3H, m), 8.45 (2H, d, J = 3.6 Hz). | Ex. 2 |

TABLE 4-continued

| | | | |
|---|---|---|---|
| 1677 | [structure: pyrrolidinyl-pyrimidine with 4-(trifluoromethyl)phenyl and cyano-triazole] | 1H-NMR (DMSO-d6) δ: 1.98-2.05 (4H, m), 3.48-3.49 (2H, m), 3.72-3.73 (2H, m), 6.99 (1H, s), 7.88 (2H, d, J = 8.2 Hz), 8.70 (2H, d, J = 8.2 Hz). | Ex. 2 |
| 1678 | [structure: morpholinyl-phenylpyrimidine with cyano-triazole] | 1H-NMR (DMSO-d6) δ: 3.95-4.00 (8H, m), 7.27 (1H, s), 7.48-7.55 (3H, m), 8.51-8.57 (2H, m). | Ex. 1 |
| 1679 | [structure: pyrrolidinyl-methoxy-pyrimidine with cyano-triazole] | 1H-NMR (DMSO-d6) δ: 1.90-1.99 (4H, m), 3.54 (2H, brs), 3.80 (2H, brs), 3.91 (3H, s), 5.52 (1H, s). | Ex. 2 |

TABLE 4-continued

| | Structure | 1H-NMR | |
|---|---|---|---|
| 1680 | 4-(trifluoromethyl)phenyl / 2-(trifluoromethyl)pyrimidine / triazole-carbonitrile | 1H-NMR (DMSO-d6) δ: 8.04 (2H, d, J = 8.3 Hz), 8.40 (2H, d, J = 8.3 Hz), 8.74 (1H, s). | Ex. 1 |
| 1681 | piperidinyl / 2-(trifluoromethyl)pyrimidine / triazole-carbonitrile | 1H-NMR (CDCl3) δ: 1.71-1.72 (4H, m), 1.74-1.83 (2H, m), 3.82 (4H, brs), 7.33 (1H, s). | Ex. 1 |
| 1682 | 3,5-bis(trifluoromethyl)phenyl / pyrrolidinyl-pyrimidine / triazole-carbonitrile | 1H-NMR (CDCl3) δ: 2.10 (2H, brs), 2.14 (2H, brs), 3.53 (2H, brs), 3.85 (2H, brs), 7.00 (1H, s), 7.97 (1H, s), 9.00 (2H, s). | Ex. 1 |

TABLE 4-continued

| | | | |
|---|---|---|---|
| 1683 | [structure] | 1H-NMR (DMSO-d6) δ: 7.95 (2H, d, J = 8.4 Hz), 7.98 (2H, d, J = 8.4 Hz), 8.49 (1H, s), 8.61 (2H, d, J = 8.1 Hz), 8.89 (2H, d, J = 8.1 Hz). | Ex. 1 |
| 1684 | [structure] | 1H-NMR (DMSO-d6) δ: 7.90-7.92 (3H, m), 8.76 (2H, d, J = 8.1 Hz), 8.95 (1H, d, J = 5.2 Hz). | Ex. 1 |
| 1685 | [structure] | 1H-NMR (DMSO-d6) δ: 2.00 (4H, brs), 3.68 (4H, t, J = 6.5 Hz), 7.90 (1H, s), 8.30 (1H, s), 8.80 (2H, s). | Ex. 1 |

TABLE 4-continued

| | Structure | 1H-NMR | Ex. |
|---|---|---|---|
| 1686 | 4-(trifluoromethyl)phenyl-6-(pyrrolidin-1-yl)pyrimidine-triazole-carbonitrile | 1H-NMR (DMSO-d6) δ: 1.99 (4H, t, J = 6.5 Hz), 3.66 (4H, t, J = 6.5 Hz), 7.68 (1H, s), 7.90 (2H, d, J = 8.3 Hz), 8.37 (2H, d, J = 8.3 Hz). | Ex. 1 |
| 1687 | 4-((4-(trifluoromethyl)benzyl)oxy)-7-methoxyquinoline-triazole-carbonitrile | 1H-NMR (DMSO-d6) δ: 3.96 (3H, s), 5.62 (2H, s), 7.30 (1H, dd, J = 2.5, 9.1 Hz), 7.34 (1H, d, J = 2.5 Hz), 7.58 (1H, s), 7.83 (4H, s), 8.17 (1H, J = 9.1 Hz). | Ex. 2 |
| 1688 | quinoline-triazole-carbonitrile | 1H-NMR (DMSO-d6) δ: 7.69-7.73 (1H, m), 7.86-7.90 (1H, m), 8.07 (1H, s), 8.09 (1H, d, J = 0.8 Hz), 8.14 (1H, d, J = 8.5 Hz), 8.61 (1H, d, J = 8.5 Hz). | Ex. 1 |

TABLE 4-continued

| | | | |
|---|---|---|---|
| 1689 | (structure: 7-methoxy-4-[4-(trifluoromethyl)phenyl]quinoline-2-yl triazole carbonitrile) | 1H-NMR (DMSO-d6) δ: 4.00 (3H, s), 7.35 (1H, dd, J = 2.6, 9.3 Hz), 7.48 (1H, d, J = 2.6 Hz), 7.70-7.78 (1H, m), 7.84-7.86 (2H, m), 7.92 (1H, s), 7.98-8.00 (2H, m). | Ex. 1 |
| 1690 | (structure: 4-(4-fluorophenyl)-7-methoxyquinoline-2-yl triazole carbonitrile) | 1H-NMR (DMSO-d6) δ: 3.99 (3H, s), 7.35 (1H, dd, J = 2.6, 9.2 Hz), 7.44-7.48 (3H, m), 7.65-7.69 (2H, m), 7.79 (1H, d, J = 9.2 Hz), 7.88 (1H, s). | Ex. 1 |
| 1691 | (structure: 7-methoxy-4-(thiophen-3-yl)quinoline-2-yl triazole carbonitrile) | 1H-NMR (DMSO-d6) δ: 3.99 (3H, s), 7.35 (1H, dd, J = 2.6, 9.3 Hz), 7.45 (1H, d, J = 2.6 Hz), 7.50 (1H, dd, J = 1.3, 4.9 Hz), 7.86 (1H, dd, J = 2.9, 4.9 Hz), 7.95 (1H, s), 8.01 (1H, dd, J = 1.3, 2.9 Hz), 8.03 (1H, d, J = 9.3 Hz). | Ex. 125 |

TABLE 4-continued

| | | | |
|---|---|---|---|
| 1692 | 4-(4-chlorophenyl)-7-methoxyquinolin-2-yl triazole carbonitrile structure | 1H-NMR (DMSO-d6) δ: 3.99 (3H, s), 7.35 (1H, dd, J = 2.6, 9.3 Hz), 7.47 (1H, d, J = 2.6 Hz), 7.63-7.65 (2H, m), 7.68-7.70 (2H, m), 7.79 (1H, d, J = 9.3 Hz), 7.88 (1H, s). | Ex. 1 |
| 1693 | 2-(pyrrolidin-1-yl)quinolin-3-yl triazole carbonitrile structure | 1H-NMR (DMSO-d6) δ: 1.80-1.83 (4H, m), 3.16 (4H, t, J = 6.5 Hz), 7.28-7.32 (1H, m), 7.63-7.70 (2H, m), 7.81 (1H, d, J = 7.9 Hz), 8.27 (1H, s). | Ex. 1 |
| 1694 | 2-(4-(trifluoromethyl)phenyl)quinolin-3-yl triazole carbonitrile structure | 1H-NMR (DMSO-d6) δ: 7.63 (2H, d, J = 8.2 Hz), 7.74-7.80 (3H, m), 7.93-7.99 (1H, m), 8.19 (2H, d, J = 8.2 Hz), 8.82 (1H, s). | Ex. 1 |

TABLE 4-continued

| | | | |
|---|---|---|---|
| 1695 | [structure] | 1H-NMR (CDCl3) δ: 3.37 (2H, t, J = 8.5 Hz), 3.98 (2H, t, J = 8.5 Hz), 6.90-6.99 (1H, m), 7.02-7.27 (5H, m), 12.2 (1H, br). | Ex. 1 |
| 1696 | [structure] | 1H-NMR (CDCl3) δ: 3.40 (2H, t, J = 8.4 Hz), 4.07 (2H, t, J = 8.5 Hz), 7.20-7.35 (4H, m), 7.40-7.52 (3H, m), 12.3 (1H, br). | Ex. 1 |
| 1697 | [structure] | 1H-NMR (DMSO-d6) δ: 3.20 (2H, t, J = 8.5 Hz), 3.4 (2H, t, J = 8.5 Hz), 4.45 (2H, s), 6.99 (1H, d, J = 1.4 Hz), 7.12 (1H, dd, J = 1.4, 7.6 Hz), 7.26 (1H, d, J = 7.6 Hz), 7.57-7.74 (4H, m). | Ex. 1 |
| 1698 | [structure] | 1H-NMR (CDCl3) δ: 3.08 (2H, t, J = 8.4 Hz), 3.48 (2H, t, J = 8.5 Hz), 4.33 (2H, s), 6.90-7.01 (2H, m), 7.15-7.31 (3H, m). | Ex. 1 |
| 1699 | [structure] | 1H-NMR (CDCl3) δ: 3.20 (2H, t, J = 8.5 Hz), 3.99 (2H, t, J = 8.5 Hz), 7.07-7.14 (2H, m), 7.22-7.31 (4H, m), 7.40-7.49 (1H, m), 12.4 (1H, br.). | Ex. 1 |

TABLE 4-continued

| | Structure | 1H-NMR | |
|---|---|---|---|
| 1700 | 3-(trifluoromethyl)phenyl-indoline-triazole-CN | 1H-NMR (CDCl3) δ: 3.24 (2H, t, J = 8.4 Hz), 4.08 (2H, t, J = 8.4 Hz), 7.22-7.26 (1H, m), 7.29-7.42 (3H, m), 7.46-7.53 (1H, m), 7.54-7.59 (1H, m), 7.63-7.68 (1H, m), 12.4 (1H, br.). | Ex. 1 |
| 1701 | 2,5-difluorophenyl-indoline-triazole-CN | 1H-NMR (CDCl3) δ: 3.24 (2H, t, J = 8.5 Hz), 4.02 (2H, t, J = 8.5 Hz), 6.75-6.85 (1H, m), 7.07-7.18 (3H, m), 7.30 (1H, d, J = 7.6 Hz), 7.34-7.41 (1H, m), 12.3 (1H, br.). | Ex. 1 |
| 1702 | Boc-piperidine-triazole-CN | 1H-NMR (CDCl3) δ: 1.48 (9H, s), 1.6-1.9 (2H, m), 1.9-2.03 (2H, m), 2.82-2.99 (2H, m), 3.01-3.17 (1H, m), 4.11-4.31 (2H, s), 12.9 (1H, br.). | Ex. 1 |
| 1703 | Cbz-piperidine-triazole-CN | 1H-NMR (CDCl3) δ: 1.72-1.95 (2H, br.), 1.95-2.06 (2H, m), 2.91-3.17(3H, m), 4.22-4.37 (2H, m), 5.16 (2H, s), 7.30-7.37 (5H, m), 12.7 (1H, br.). | Ex. 1 |

TABLE 4-continued

| | Structure | 1H-NMR | |
|---|---|---|---|
| 1704 | 3-(trifluoromethyl)benzyl-piperidinyl-triazole-carbonitrile | 1H-NMR (CDCl3) δ: 1.98-2.10 (4H, m), 2.25-2.38 (2H, m), 2.91-3.17 (3H, m), 3.75 (2H, s), 7.47 (1H, t, J = 7.6 Hz), 7.52-7.63 (3H, m). | Ex. 1 |
| 1705 | 4-(trifluoromethyl)benzoyl-piperidinyl-triazole-carbonitrile | 1H-NMR (CDCl3-CD3OD) δ: 1.71-2.26 (4H, m), 2.96-3.12 (1H, m), 3.17-3.31 (2H, m), 3.72-3.87 (1H, m), 4.71-4.85 (1H, m), 7.55 (2H, d, J = 8.0 Hz), 7.72 (2H, d, J = 8.0 Hz). | Ex. 1 |
| 1706 | benzoyl-piperidinyl-triazole-carbonitrile | 1H-NMR (CDCl3-CD3OD) δ: 1.69-2.22 (4H, m), 2.92-3.11 (1H, m), 3.14-3.30 (2H, m), 3.81-3.99 (1H, m), 4.68-4.85 (1H, m), 7.38-7.47 (5H, m). | Ex. 1 |
| 1707 | 4-methylphenylsulfonyl-piperidinyl-triazole-carbonitrile | 1H-NMR (CDCl3) δ: 1.94-2.12 (4H, m), 2.37-2.49 (2H, m), 2.47 (3H, s), 2.78-2.93 (1H, m), 3.85-3.96 (2H, m), 7.37 (2H, d, J = 8.0 Hz), 7.68 (2H, d, J = 8.0 Hz). | Ex. 1 |

TABLE 4-continued

| | Structure | 1H-NMR | |
|---|---|---|---|
| 1708 | 2,4,5-trifluorophenyl-piperidinyl-cyanotriazole | 1H-NMR (CDCl3) δ: 2.02-2.21 (4H, m), 2.74-2.89 (2H, m), 3.01-3.15 (1H, m), 3.41-3.53 (2H, m), 6.75-6.87 (1H, m), 6.87-6.99 (1H, m), 12.4 (1H, br.). | Ex. 1 |
| 1709 | 4-chlorophenyl-piperidinyl-cyanotriazole | 1H-NMR (CDCl3) δ: 1.95-2.21 (4H, m), 2.81-2.94 (2H, m), 3.01-3.15 (1H, m), 3.68-3.78 (2H, m), 6.85-6.94 (2H, m), 7.19-7.26 (2H, m). | Ex. 1 |
| 1710 | phenoxycarbonyl-piperidinyl-cyanotriazole | 1H-NMR (CD3OD) δ: 1.77-1.98 (2H, m), 2.04-2.17 (2H, m), 3.05-3.40 (3H, m), 4.21-4.34 (1H, m), 4.37-4.49 (1H, m), 7.08-7.15 (2H, m), 7.20-7.27 (1H, m), 7.35-7.44 (2H, m). | Ex. 1 |
| 1711 | (4-fluorophenyl)acetyl-piperidinyl-cyanotriazole | 1H-NMR (CDCl3-CD3OD) δ: 1.49-1.65 (1H, m), 1.66-1.83 (1H, m), 1.91-2.09 (2H, m), 2.74-2.87 (1H, m), 3.09-3.25 (2H, m), 3.75 (2H, s), 3.93-4.04 (1H, m), 4.62-4.73 (1H, m), 6.99-7.08 (2H, m), 7.18-7.26 (2H, m). | Ex. 1 |

TABLE 4-continued

| | Structure | 1H-NMR | |
|---|---|---|---|
| 1712 | 3-[1-[4-(trifluoromethyl)benzoyl]piperidin-3-yl]-1H-1,2,3-triazole-4-carbonitrile | 1H-NMR (DMSO-d6) δ: 1.53-1.93 (3H, m), 2.10-2.22 (1H, m), 2.90-3.81 (4H, m), 4.32-4.48 (0.4H, m), 4.58-4.74 (0.6H, m), 7.56-7.69 (2H, m), 7.74-7.88 (2H, m), 16.0 (1H, br.). | Ex. 1 |
| 1713 | 3-[1-(4-chlorophenyl)piperidin-3-yl]-1H-1,2,3-triazole-4-carbonitrile | 1H-NMR (DMSO-d6) δ: 1.64-1.90 (3H, m), 2.04-2.16 (1H, m), 2.77-2.87 (1H, m), 2.92-3.04 (1H, m), 3.16-3.31 (1H, m), 3.63-3.74 (1H, m), 3.84-3.94 (1H, m), 7.01-7.09 (2H, m), 7.22-7.30 (2H, m). | Ex. 1 |
| 1714 | 3-[1-(2,4,5-trifluorophenyl)piperidin-3-yl]-1H-1,2,3-triazole-4-carbonitrile | 1H-NMR (CDCl3) δ: 1.79-2.08 (2H, m), 2.20-2.37 (1H, m), 2.37-2.56 (1H, m), 3.40-3.60 (2H, m), 3.60-3.81 (2H, m), 3.91-4.07 (1H, m), 7.07-7.21 (1H, m), 7.91-8.18 (1H, m). | Ex. 1 |
| 1715 | 2-phenyl-1H-imidazol-5-yl triazole carbonitrile | 1H-NMR (DMSO-d6) δ: 7.42-7.45 (1H, m), 7.50-7.54 (2H, m), 7.86 (1H, s), 8.02-8.04 (2H, m), 13.23 (1H, brs). | Ex. 1 |
| 1716 | 4-methyl-5-[1-[4-(trifluoromethyl)benzyl]imidazol-5-yl]-1H-1,2,3-triazole-4-carbonitrile | 1H-NMR (DMSO-d6) δ: 2.21 (3H, s), 5.47 (2H, s), 7.19 (2H, d, J = 8.1 Hz), 7.64 (2H, d, J = 8.1 Hz), 8.60 (1H, brs). | Ex. 1 |

TABLE 4-continued

| | | | |
|---|---|---|---|
| 1717 | [structure: 4-(trifluoromethyl)benzyl-imidazole-methyl-triazole-carbonitrile] | 1H-NMR (CDCl3) δ: 2.49 (3H, s), 5.26 (2H, s), 7.26 (2H, d, J = 8.1 Hz), 7.67 (2H, d, J = 8.1 Hz), 7.94 (1H, s). | Ex. 1 |
| 1718 | [structure: 4-chlorophenyl-N-methyl-imidazole-methyl-triazole-carbonitrile] | 1H-NMR (DMSO-d6) δ: 2.23 (3H, s), 3.65 (3H, s), 7.62 (2H, d, J = 8.6 Hz), 7.78 (2H, d, J = 8.6 Hz). | Ex. 1 |
| 1719 | [structure: 4-fluorophenyl-N-methyl-imidazole-methyl-triazole-carbonitrile] | 1H-NMR (DMSO-d6) δ: 2.26 (3H, s), 3.66 (3H, s), 7.38-7.47 (2H, m), 7.82-7.85 (2H, m). | Ex. 1 |
| 1720 | [structure: 4-(trifluoromethyl)phenyl-N-methyl-imidazole-methyl-triazole-carbonitrile] | 1H-NMR (DMSO-d6) δ: 2.26 (3H, s), 3.70 (3H, s), 7.91 (2H, d, J = 8.2 Hz), 8.00 (2H, d, J = 8.2 Hz). | Ex. 1 |

TABLE 4-continued

| | Structure | NMR | Ex. |
|---|---|---|---|
| 1721 | (1-methyl-5-methyl-2-(4-trifluoromethylphenyl)imidazol-4-yl)-triazole-carbonitrile | 1H-NMR (CDCl3) δ: 2.59 (3H, s), 3.69 (3H, s), 7.75 (4H, s). | Ex. 1 |
| 1722 | (1-methyl-5-methyl-2-(4-chlorophenyl)imidazol-4-yl)-triazole-carbonitrile | 1H-NMR (CDCl3) δ: 2.56 (3H, s), 3.65 (3H, s), 7.42-7.46 (2H, m), 7.51-7.55 (2H, m). | Ex. 1 |
| 1723 | (1-methyl-5-methyl-2-(4-fluorophenyl)imidazol-4-yl)-triazole-carbonitrile | 1H-NMR (CDCl3) δ: 2.56 (3H, s), 3.64 (3H, s), 7.12-7.20 (2H, m), 7.55-7.60 (2H, m). | Ex. 1 |
| 1724 | (1-(4-chlorobenzyl)-2-ethyl-5-methylimidazol-4-yl)-triazole-carbonitrile | 1H-NMR (CDCl3) δ: 1.20 (3H, t, J = 7.5 Hz), 2.43 (3H, s), 2.68 (2H, q, J = 7.5 Hz), 5.12 (2H, s), 6.92 (2H, d, J = 8.5 Hz), 7.35 (2H, d, J = 8.5 Hz). | Ex. 1 |

TABLE 4-continued

| | Structure | 1H-NMR | Ex. |
|---|---|---|---|
| 1725 | 2-butyl-4-chloro-1-(4-chlorobenzyl)-imidazole linked to cyano-triazole | 1H-NMR (CDCl3) δ: 0.87 (3H, t, J = 7.4 Hz), 1.31-1.42 (2H, m), 1.85-1.72 (2H, m), 2.65 (2H, t, J = 7.8 Hz), 5.21 (2H, s), 6.87 (2H, d, J = 6.5 Hz), 7.25-7.32 (2H, m). | Ex. 1 |
| 1726 | 3-(trifluoromethyl)phenyl-pyrazole linked to cyano-triazole | 1H-NMR (CDCl3-CD3OD) δ: 7.11 (1H, d, J = 2.6 Hz), 7.59-7.70 (2H, m), 8.02-8.09 (2H, m), 8.18 (1H, d, J = 2.6 Hz). | Ex. 1 |
| 1727 | 4-chlorophenyl-pyrazole linked to cyano-triazole | 1H-NMR (CDCl3-CD3OD) δ: 7.07 (1H, d, J = 2.6 Hz), 7.45-7.51 (2H, m), 7.72-7.80 (2H, m), 8.05 (1H, d, J = 2.6 Hz). | Ex. 1 |
| 1728 | 3-(4-chlorophenyl)-1-methyl-pyrazole linked to cyano-triazole | 1H-NMR (DMSO-d6) δ: 4.09 (3H, s), 7.27 (1H, s), 7.47-7.54 (2H, m), 7.84-7.90 (2H, m). | Ex. 1 |
| 1729 | 1-(4-methoxybenzyl)-pyrazole linked to cyano-triazole | 1H-NMR (CDCl3) δ: 3.81 (3H, s), 5.32 (2H, s), 6.85-6.91 (2H, m), 6.95 (1H, d, J = 2.4 Hz), 7.16-7.22 (2H, m), 7.50 (1H, d, J = 2.4 Hz). | Ex. 1 |

TABLE 4-continued

| | | 1H-NMR | |
|---|---|---|---|
| 1730 | [structure: 3-(4-chlorophenyl)-1-propyl-pyrazole linked to cyano-triazole] | 1H-NMR (CDCl3) δ: 0.95 (3H, t, J = 7.5 Hz), 1.88-1.98 (2H, m), 4.54 (2H, t, J = 7.4 Hz), 7.38-7.42 (2H, m), 7.77-7.82 (2H, m), 12.8 (1H, br). | Ref. Ex. 63, Ex. 1 |
| 1731 | [structure: 3-(4-chlorophenyl)-1-(cyclopropylmethyl)-pyrazole linked to cyano-triazole] | 1H-NMR (CDCl3-CD3OD) δ: 0.40-4.44 (2H, m), 0.51-0.58 (2H, m), 1.34-1.44 (1H, m), 4.45 (2H, d, J = 7.1 Hz), 7.20 (1H, s), 7.39-7.42 (2H, m), 7.78-7.81 (2H, m). | Ex. 1 |
| 1732 | [structure: 3-(4-chlorophenyl)-1-(2-methylpropyl)-pyrazole linked to cyano-triazole] | 1H-NMR (CDCl3) δ: 0.85 (3H, t, J = 7.4 Hz), 1.82-1.91 (2H, m), 4.15 (2H, t, J = 7.3 Hz), 6.96 (1H, br), 7.35-7.39 (2H, m), 7.45-7.52 (2H, m), 19.2 (1H, br). | Ex. 1 |
| 1733 | [structure: 2-(4-chlorophenyl)-benzothiazole linked to cyano-triazole] | 1H-NMR (DMSO-d6) δ: 7.68 (2H, d, J = 8.5 Hz), 8.04-8.06 (1H, m), 8.17 (2H, d, J = 8.6 Hz), 8.27 (1H, d, J = 8.5 Hz), 8.69 (1H, s). | Ex. 1 |

TABLE 4-continued

| | Structure | 1H-NMR | Ex. |
|---|---|---|---|
| 1734 | 4-(trifluoromethyl)phenyl-benzothiazole-triazole-CN | 1H-NMR (DMSO-d6) δ: 7.97 (2H, d, J = 8.3 Hz), 8.06-8.09 (1H, m), 8.34 (1H, d, J = 8.7 Hz), 8.36 (2H, d, J = 8.3 Hz), 8.74 (1H, s). | Ex. 1 |
| 1735 | 6-(trifluoromethyl)pyridin-3-yl-benzothiazole-triazole-CN | 1H-NMR (DMSO-d6) δ: 8.08-8.11 (1H, m), 8.14 (1H, d, J = 8.3 Hz), 8.38 (1H, d, J = 8.3 Hz), 8.76-8.80 (2H, m), 9.50 (1H, s). | Ex. 1 |
| 1736 | 6-chlorobenzothiazole-triazole-CN | 1H-NMR (DMSO-d6) δ: 7.64 (1H, dd, J = 2.2, 8.8 Hz), 8.15 (1H, d, J = 8.8 Hz), 8.40 (1H, d, J = 2.2 Hz). | Ex. 125 |

TABLE 4-continued

| | Structure | 1H-NMR | Ex. |
|---|---|---|---|
| 1737 | 6-(trifluoromethyl)benzothiazol-2-yl triazole-carbonitrile | 1H-NMR (DMSO-d6) δ: 7.92 (1H, dd, J = 1.7, 8.6 Hz), 8.34 (1H, d, J = 8.6 Hz), 8.77 (1H, d, J = 1.7 Hz). | Ex. 125 |
| 1738 | 6-phenoxybenzothiazol-2-yl triazole-carbonitrile | 1H-NMR (DMSO-d6) δ: 7.11-7.14 (2H, m), 7.20-7.24 (1H, m), 7.29 (1H, dd, J = 2.5, 8.9 Hz), 7.43-7.47 (2H, m), 7.84 (1H, d, J = 2.5 Hz), 8.14 (1H, d, J = 8.9 Hz). | Ex. 125 |
| 1739 | 6-(4-(trifluoromethyl)phenyl)benzothiazol-2-yl triazole-carbonitrile | 1H-NMR (DMSO-d6) δ: 7.88 (2H, d, J = 8.3 Hz), 7.99 (1H, dd, J = 1.9, 8.6 Hz), 8.03 (2H, d, J = 8.3 Hz), 8.26 (1H, d, J = 8.6 Hz), 8.68 (1H, d, J = 1.9 Hz). | Ex. 125 |
| 1740 | 4-methoxybenzothiazol-2-yl triazole-carbonitrile | 1H-NMR (DMSO-d6) δ: 4.04 (3H, s), 7.15 (1H, dd, J = 0.6, 8.1 Hz), 7.50 (1H, J = 8.1 Hz), 7.76 (1H, d, J = 0.6, 8.1 Hz). | Ex. 125 |

TABLE 4-continued

| | Structure | 1H-NMR | Ex. |
|---|---|---|---|
| 1741 | 6-methoxy-benzothiazole-2-yl triazole-carbonitrile | 1H-NMR (DMSO-d6) δ: 3.88 (3H, s), 7.20 (1H, dd, J = 2.6, 9.0 Hz), 7.80 (1H, d, J = 2.6 Hz), 8.03 (1H, d, J = 9.0 Hz). | Ex. 125 |
| 1742 | 6-methoxy-benzothiazole-2-yl triazole-carbonitrile | 1H-NMR (DMSO-d6) δ: 3.90 (3H, s), 7.19 (1H, dd, J = 2.5, 8.8 Hz), 7.66 (1H, d, J = 2.5 Hz), 8.09 (1H, d, J = 8.8 Hz). | Ex. 125 |
| 1743 | 6-(4-trifluoromethylphenoxy)-benzothiazole-2-yl triazole-carbonitrile | 1H-NMR (DMSO-d6) δ: 7.26 (2H, d, J = 8.5 Hz), 7.40 (1H, dd, J = 2.5, 8.9 Hz), 7.79 (2H, d, J = 8.5 Hz), 8.02 (1H, d, J = 2.5 Hz), 8.20 (1H, d, J = 8.9 Hz). | Ex. 125 |

TABLE 4-continued
| | | | |
|---|---|---|---|
| 1744 | 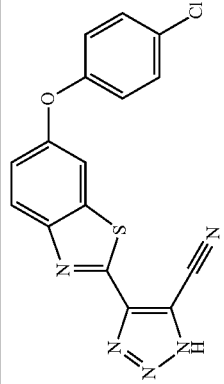 | 1H-NMR (DMSO-d6) δ: 7.14- 7.18 (2H, m), 7.33 (1H, dd, J = 2.5, 8.8 Hz), 7.47-7.51 (2H, m), 7.88 (1H, d, J = 2.5 Hz), 8.16 (1H, d, J = 8.8 Hz). | Ex. 125 |
| 1745 | 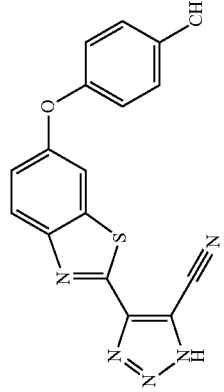 | 1H-NMR (DMSO-d6) δ: 2.32 (3H, s), 7.01-7.06 (2H, m), 7.25-7.27 (3H, m), 7.77 (1H, d, J = 2.5 Hz), 8.12 (1H, d, J = 8.9 Hz). | Ex. 125 |
| 1746 | 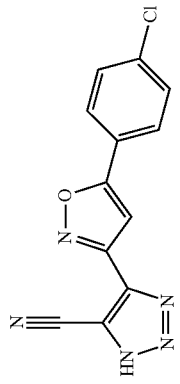 | 1H-NMR (DMSO-d6) δ: 7.64 (1H, s), 7.66-7.68 (2H, m), 8.02-8.05 (2H, m). | Ex. 2 |
| 1747 | 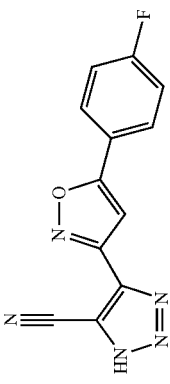 | 1H-NMR (DMSO-d6) δ: 7.43-7.47 (2H, m), 7.58 (1H, s), 8.07-8.10 (2H, m). | Ex. 2 |
| 1748 | 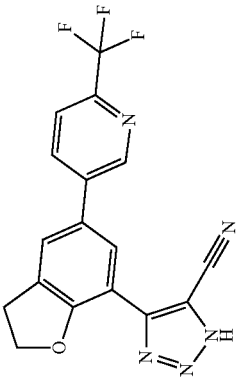 | 1H-NMR (DMSO-d6) δ: 3.40 (2H, t, J = 8.6 Hz), 4.78 (2H, t, J = 8.6 Hz), 7.92 (1H, s), 7.94 (1H, s), 8.00 (1H, d, J = 8.3 Hz), 8.35 (1H, dd, J = 1.9, 8.3 Hz), 9.09 (1H, d, J = 1.9 Hz). | Ex. 1 |

TABLE 4-continued

| | | | |
|---|---|---|---|
| 1751 | [structure: 3-(4-chlorophenyl)isothiazol-4-yl triazole carbonitrile] | 1H-NMR (DMSO-d6) δ: 7.41-7.43 (2H, m), 7.47-7.50 (2H, m), 9.56 (1H, s). | Ex. 125 |
| 1752 | [structure: 3-(4-chlorophenyl)isothiazol-5-yl triazole carbonitrile] | 1H-NMR (DMSO-d6) δ: 7.61 (2H, d, J = 8.6 Hz), 8.10 (2H, d, J = 8.6 Hz), 8.33 (1H, s). | Ex. 125 |
| 1753 | [structure: 3-(4-trifluoromethoxyphenyl)isothiazol-4-yl triazole carbonitrile] | 1H-NMR (DMSO-d6) δ: 7.41 (2H, d, J = 8.3 Hz), 7.54 (2H, d, J = 8.3 Hz), 9.58 (1H, s). | Ex. 125 |

TABLE 4-continued
| | | | |
|---|---|---|---|
| 1754 | 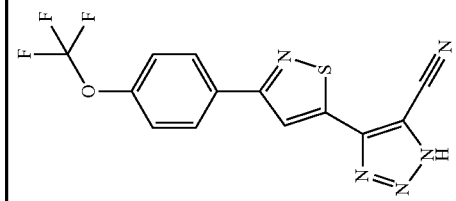 | 1H-NMR (DMSO-d6) δ: 7.54 (2H, d, J = 8.4 Hz), 8.21 (2H, d, J = 8.4 Hz), 8.37 (1H, s). | Ex. 125 |
| 1756 | 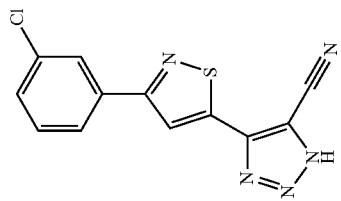 | 1H-NMR (DMSO-d6) δ: 7.56-7.59 (2H, m), 8.03-8.07 (1H, m), 8.14 (1H, s), 8.42 (1H, s). | Ex. 125 |

TABLE 4-continued
| | STR | | 1H-NMR | ref. |
|---|---|---|---|---|
| 1757 | 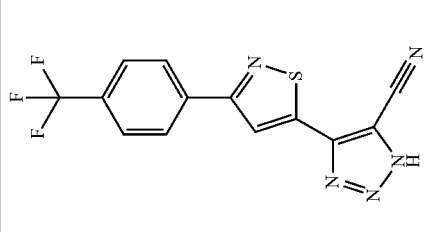 | | 1H-NMR (DMSO-d6) δ: 7.92 (2H, d, J = 8.3 Hz), 8.30 (2H, d, J = 8.3 Hz), 8.43 (1H, s). | Ex. 125 |
| 1758 | 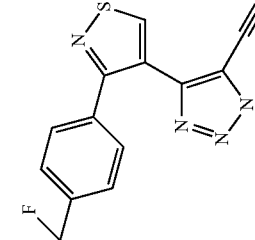 | | 1H-NMR (DMSO-d6) δ: 7.64 (2H, d, J = 8.1 Hz), 7.79 (2H, d, J = 8.1 Hz), 9.61 (1H, s). | Ex. 125 |
| Ex. No. | STR | m.p. | ref. |
|---|---|---|---|
| 1749 | 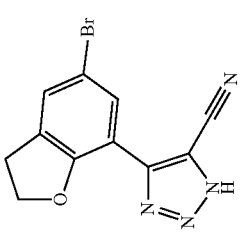 | 186-189 | Ex. 1 |

TABLE 4-continued

| | | | |
|---|---|---|---|
| 1750 | (5-(4-fluorophenyl)-2,3-dihydrobenzofuran-7-yl triazole carbonitrile) | 242-256 | Ex. 1 |
| 1755 | (3-(3-chlorophenyl)isothiazole triazole carbonitrile) | 189.1-191.1 | Ex. 125 |
| 1759 | (dibenzofuran triazole carbonitrile) | 224-226 | Ex. 1 |

TABLE 4-continued

| Ex. No. | STR | 1H-NMR | ref. |
|---|---|---|---|
| 1760 | | 1H-NMR (DMSO-d6) δ: 7.67 (1H, d, J = 8.4 Hz), 7.73-7.75 (1H, m), 7.86 (1H, s). | Ex. 1 |
| 1761 | | 1H-NMR (DMSO-d6) δ: 1.35 (3H, t, J = 7.0 Hz), 4.52 (2H, q, J = 7.0 Hz), 7.30 (1H, t, J = 7.5 Hz), 7.53-7.56 (1H, m), 7.70 (1H, d, J = 8.2 Hz), 7.87 (1H, d, J = 8.2 Hz), 7.95-7.97 (1H, m), 8.20 (1H, d, J = 7.5 Hz), 8.67 (1H, s). | Ex. 1 |

| Ex. No. | STR | m.p. | ref. |
|---|---|---|---|
| 1762 | | 197 | Ex. 1 |

TABLE 4-continued

| Ex. No. | STR | 1H-NMR | ref. |
|---|---|---|---|
| 1763 | | 1H-NMR (DMSO-d6) δ: 2.71-2.74 (2H, m), 2.93-2.96 (2H, m), 5.39 (2H, m), 7.18 (1H, d, J = 8.3 Hz), 7.24 (1H, d, J = 8.3 Hz), 7.37 (1H, t, J = 8.3 Hz), 7.95 (2H, s), 8.02 (1H, s). | Ex. 1 |
| 1764 | | 1H-NMR (DMSO-d6) δ: 7.25 (1H, d, J = 16.6 Hz), 7.37-7.54 (4H, m), 7.68-7.71 (2H, m). | Ex. 1 |
| 1765 | | 1H-NMR (DMSO-d6) δ: 5.41 (2H, s), 7.07-7.80 (6H, m), 8.01-8.10 (2H, m), 8.21 (1H, s). | Ex. 1 |

TABLE 4-continued

| | Structure | 1H-NMR | Ex. |
|---|---|---|---|
| 1766 | (benzyl-triazole-carbonitrile) | 1H-NMR (CDCl3) δ: 4.19 (2H, s), 7.26-7.36 (5H, m). | Ex. 2 |
| 1767 | (tert-butyl-triazole-carbonitrile) | 1H-NMR (CDCl3) δ: 1.28 (9H, s). | Ex. 2 |
| 1768 | (4-trifluoromethylphenyl-pyrimidinone-triazole-carbonitrile) | 1H-NMR (DMSO-d6) δ: 7.02 (1H, brs), 7.95 (2H, d, J = 8.4 Hz), 8.56-8.58 (2H, m), 13.17 (1H, brs). | Ex. 1 |
| 1769 | (4-chlorophenyl-cyclopropyl-triazole-carbonitrile) | 1H-NMR (CDCl3) δ: 1.44-1.47 (2H, m), 1.60-1.63 (2H, m), 7.33 (4H, s). | Ex. 2 |

TABLE 4-continued

| Ex. No. | STR | | ref. |
|---|---|---|---|
| 1770 | (4-phenoxyphenyl)methyl-triazole-carbonitrile structure | 1H-NMR (CDCl3) δ: 4.16 (2H, s), 6.90-6.92 (2H, m), 6.98-7.02 (3H, m), 7.10-7.14 (1H, m), 7.28-7.36 (3H, m). | Ex. 2 |
| 1771 | 3'-(trifluoromethyl)biphenyl-methyl-triazole-carbonitrile structure | m.p. 125.6-125.8 | Ex. 2 |
| 1772 | 4-((4-(trifluoromethyl)benzyloxy)phenyl)ethyl-triazole-carbonitrile structure | 1H-NMR (DMSO-d6) δ: 2.93 (2H, t, J = 7.5 Hz), 3.09 (2H, t, J = 7.5 Hz), 5.18 (2H, s), 6.92-6.95 (2H, m), 7.07-7.10 (2H, m), 7.85 (2H, d, J = 8.1 Hz), 7.75 (2H, d, J = 8.1 Hz). | Ex. 2 |

TABLE 4-continued

| | Structure | 1H-NMR | |
|---|---|---|---|
| 1773 | 4-(trifluoromethyl)benzyl ether-phenyl-CH2-triazole-CN | 1H-NMR (DMSO-d6) δ: 4.13 (2H, s), 5.21 (2H, s), 6.99-7.01 (2H, m), 7.10-7.12 (2H, m), 7.65 (2H, d, J = 8.0 Hz), 7.75 (2H, d, J = 8.0 Hz). | Ex. 2 |
| 1774 | 3,5-bis(trifluoromethyl)benzyl-triazole-CN | 1H-NMR (CDCl3) δ: 4.33 (2H, s), 7.77 (1H, s), 7.82 (2H, s). | Ex. 2 |
| 1775 | 4-(trifluoromethyl)benzyl ether-3-phenyl-CH2CH2-triazole-CN | 1H-NMR (CDCl3) δ: 3.04 (2H, t, J = 7.5 Hz), 3.18 (2H, t, J = 7.5 Hz), 5.11 (2H, s), 6.79-6.85 (3H, m), 7.22 (1H, d, J = 8.3 Hz), 7.54 (2H, d, J = 8.1 Hz), 7.65 (2H, d, J = 8.1 Hz). | Ex. 2 |

TABLE 4-continued

| | | | |
|---|---|---|---|
| 1776 | ![structure] | 1H-NMR (DMSO-d6) δ: 5.39 (2H, s), 7.22-7.25 (2H, m), 7.71 (2H, d, J = 8.2 Hz), 7.79 (2H, d, J = 8.2 Hz), 8.25-8.28 (2H, m). | Ex. 2 |
| 1777 | ![structure] | 1H-NMR (DMSO-d6) δ: 4.16 (2H, s), 7.27-7.30 (1H, m), 7.37-7.41 (3H, m), 7.50 (1H, s), 7.58 (1H, d, J = 7.7 Hz), 7.64 (1H, d, J = 7.7 Hz), 7.72 (1H, d, J = 7.7 Hz). | Ex. 2 |
| 1778 | ![structure] | 1H-NMR (DMSO-d6) δ: 4.16 (2H, s), 5.21 (2H, s), 6.84 (1H, d, J = 7.7 Hz), 6.93-6.95 (2H, m), 7.26-7.30 (1H, m), 7.75 (2H, d, J = 8.0 Hz), 7.66 (2H, d, J = 8.0 Hz). | Ex. 2 |

TABLE 4-continued

| | | | |
|---|---|---|---|
| 1780 | [structure] | 1H-NMR (DMSO-d6) δ: 3.03 (2H, t, J = 7.2 Hz), 3.14 (2H, t, J = 7.2 Hz), 6.24 (2H, s), 6.87 (1H, t, J = 7.6 Hz), 7.02-7.07 (2H, m), 7.18-7.22 (1H, m), 7.69 (2H, d, J = 8.0 Hz), 7.77 (2H, d, J = 8.0 Hz). | Ex. 2 |
| 1781 | [structure] | 1H-NMR (DMSO-d6) δ: 4.19 (2H, s), 5.23 (2H, s), 6.95 (1H, t, J = 7.3 Hz), 7.04 (1H, d, J = 8.2 Hz), 7.25-7.27 (2H, m), 7.49-7.51 (2H, m), 7.70 (2H, d, J = 8.1 Hz). | Ex. 2 |
| 1782 | [structure] | 1H-NMR (DMSO-d6) δ: 2.84-2.95 (4H, m), 7.19-7.21 (1H, m), 7.29-7.38 (3H, m), 7.55-7.58 (2H, m), 7.87 (1H, t, J = 7.7 Hz), 7.74 (1H, d, J = 7.7 Hz). | Ex. 2 |

TABLE 4-continued

| | Structure | 1H-NMR | |
|---|---|---|---|
| 1783 | (4-(trifluoromethyl)benzyloxy)phenyl cyclopropyl triazole carbonitrile | 1H-NMR (DMSO-d6) δ: 1.37-1.45 (4H, m), 5.21 (2H, s), 6.97-7.00 (2H, m), 7.22-7.25 (2H, m), 7.65 (2H, d, J = 8.0 Hz), 7.75 (2H, d, J = 8.0 Hz). | Ex. 2 |
| 1784 | 3'-(trifluoromethyl)biphenyl ethyl triazole carbonitrile | 1H-NMR (DMSO-d6) δ: 3.08 (2H, t, J = 7.2 Hz), 3.21 (2H, t, J = 7.2 Hz) 7.21 (1H, d, J = 7.5 Hz), 7.40 (1H, t, J = 8.0 Hz), 7.57-7.59 (2H, m), 7.68-7.75 (2H, m), 7.93-7.96 (2H, m). | Ex. 2 |

TABLE 4-continued

| | Structure | NMR | Ex. |
|---|---|---|---|
| 1785 | (4-(trifluoromethyl)phenyl)-imidazo[1,2-a]pyridine linked to cyano-triazole | 1H-NMR (DMSO-d6) δ: 7.42 (1H, dd, J = 1.7, 7.1 Hz), 7.83 (2H, d, J = 8.2 Hz), 8.15 (1H, s), 8.23 (2H, t, J = 8.2 Hz), 8.73 (1H, s), 8.77 (1H, d, J = 7.1 Hz). | Ex. 2 |
| 1786 | 2-(4-(trifluoromethyl)phenyl)imidazo[1,2-a]pyridin-8-yl cyano-triazole | 1H-NMR (DMSO-d6) δ: 7.18 (1H, t, J = 7.1 Hz), 7.81-7.85 (3H, m), 8.35 (2H, d, J = 8.2 Hz), 8.75 (1H, s), 8.77 (1H, d, J = 6.8 Hz). | Ex. 2 |
| 1787 | 4-(trifluoromethyl)benzyloxy-cyclohexyl cyano-triazole | 1H-NMR (CDCl3) δ: 1.53- 1.71 (4H, m), 2.05-2.28 (4H, m), 2.90-3.05 (1H, m), 3.43-3.50 (1H, m), 4.61-4.66 (2H, m), 7.46-7.50 (2H, m), 7.59-7.62 (2H, m). | Ex. 2 |

TABLE 4-continued

| Ex. No. | STR | 1H-NMR | ref. |
|---|---|---|---|
| 1788 | (5-(4-(trifluoromethyl)phenyl)-1,3,4-oxadiazol-2-yl triazole carbonitrile) | 1H-NMR (DMSO-d6) δ: 8.06 (2H, d, J = 8.2 Hz), 8.25 (2H, d, J = 8.2 Hz). | Ref. Ex. 159, Ex. 1 |
| 1789 | (benzodioxole pyridine-CF3 triazole carbonitrile) | 1H-NMR (DMSO-d6) δ: 6.26 (2H, s), 7.47 (1H, d, J = 1.4 Hz), 7.79 (1H, d, J = 1.4 Hz), 8.10 (1H, d, J = 8.3 Hz), 8.45 (1H, dd, J = 1.9, 8.3 Hz), 9.16 (1H, d, J = 1.9 Hz). | Ex. 1 |

| Ex. No. | STR | m.p. | ref. |
|---|---|---|---|
| 1790 | (3-chlorophenyl thiadiazole triazole carbonitrile) | 205.4-210.8 | Ex. 125 |

| Ex. No. | STR | 1H-NMR | ref. |
|---|---|---|---|
| 1791 | (benzyl pyrazole pyrazole carbonitrile) | 1H-NMR (DMSO-d6) δ: 5.75 (2H, s), 7.33-7.43 (5H, m), 8.80 (1H, s). | Ex. 125 |

TABLE 4-continued

| | Structure | 1H-NMR | Ex. |
|---|---|---|---|
| 1792 | 4-chlorophenyl-thiadiazole-triazole-CN | 1H-NMR (DMSO-d6) δ: 7.68-7.71 (2H, m), 8.28-8.31 (2H, m). | Ex. 125 |
| 1793 | 5-phenyl-benzoxazole-triazole-CN | 1H-NMR (DMSO-d6) δ: 7.39-7.43 (1H, m), 7.49-7.53 (2H, m), 7.77-7.80 (2H, m), 7.82 (1H, dd, J = 1.9, 8.6 Hz), 7.96 (1H, d, J = 8.6 Hz), 8.20 (1H, d, J = 1.9 Hz). | Ex. 125 |
| 1794 | 6-chloro-benzoxazole-triazole-CN | 1H-NMR (DMSO-d6) δ: 7.53 (1H, dd, J = 2.0, 8.6 Hz), 7.93 (1H, d, J = 8.6 Hz), 8.11 (1H, d, J = 2.0 Hz). | Ex. 125 |
| 1795 | 6-methoxy-benzoxazole-triazole-CN | 1H-NMR (DMSO-d6) δ: 3.87 (3H, s), 7.09 (1H, dd, J = 2.4, 8.8 Hz), 7.51 (1H, d, J = 2.4 Hz), 7.81 (1H, d, J = 8.8 Hz). | Ex. 125 |

TABLE 4-continued
| | | | |
|---|---|---|---|
| 1796 |  | 1H-NMR (DMSO-d6) δ: 2.47 (3H, s), 7.35 (1H, dd, J = 1.1, 8.4 Hz), 7.73-7.74 (1H, m), 7.76 (1H, d, J = 8.4 Hz). | Ex. 125 |
| 1797 |  | 1H-NMR (DMSO-d6) δ: 7.85 (1H, d, J = 8.4 Hz), 7.91 (1H, dd, J = 2.3, 8.4 Hz), 8.31 (1H, d, J = 1.9 Hz), 8.49 (1H, d, J = 2.3 Hz), 9.29 (1H, d, J = 1.9 Hz). | Ex. 125 |
| 1798 | 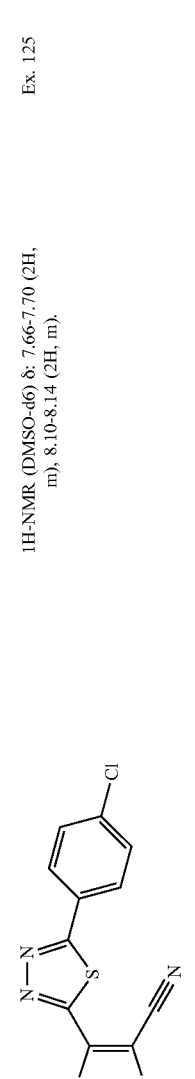 | 1H-NMR (DMSO-d6) δ: 7.66-7.70 (2H, m), 8.10-8.14 (2H, m). | Ex. 125 |
| 1799 | 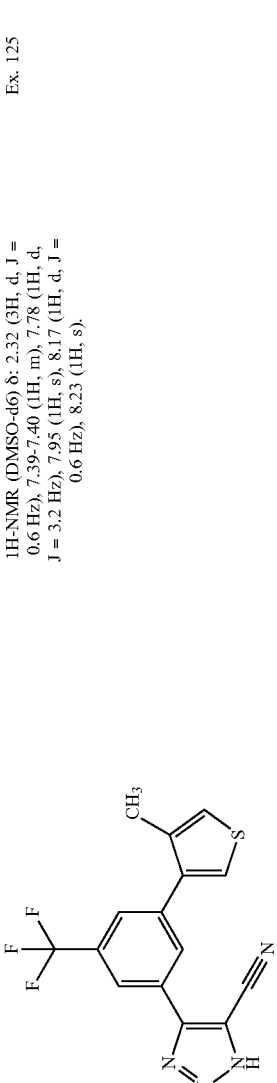 | 1H-NMR (DMSO-d6) δ: 2.32 (3H, d, J = 0.6 Hz), 7.39-7.40 (1H, m), 7.78 (1H, d, J = 3.2 Hz), 7.95 (1H, s), 8.17 (1H, d, J = 0.6 Hz), 8.23 (1H, s). | Ex. 125 |

TABLE 4-continued

| | Structure | NMR | Ex. |
|---|---|---|---|
| 1800 | 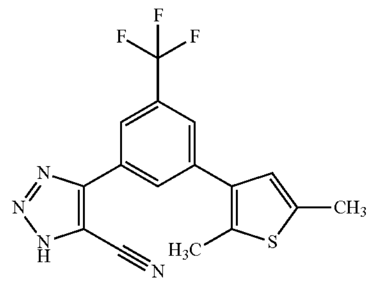 [SMILES: Cc1cc(-c2cc(-c3nn[nH]c3C#N)cc(C(F)(F)F)c2)c(C)s1] | 1H-NMR (DMSO-d6) δ: 2.43 (3H, s), 2.49 (3H, s), 6.98 (1H, d, J = 1.0 Hz), 7.89 (1H, s), 8.13 (1H, s), 8.19 (1H, s). | Ex. 125 |
| 1801 | 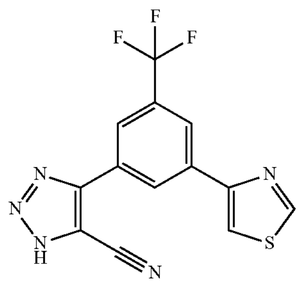 [SMILES: N#Cc1[nH]nnc1-c1cc(-c2cscn2)cc(C(F)(F)F)c1] | 1H-NMR (DMSO-d6) δ: 8.17 (1H, d, J = 0.3 Hz), 8.50 (1H, d, J = 0.3 Hz), 8.58 (1H, d, J = 1.8 Hz), 8.85 (1H, s), 9.32 (1H, d, J = 1.8 Hz). | Ex. 125 |
| 1803 | 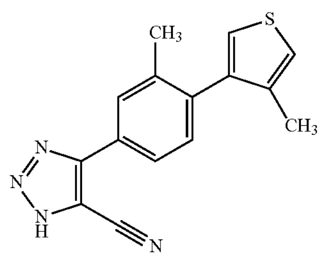 [SMILES: Cc1cc(-c2nn[nH]c2C#N)ccc1-c1cscc1C] | 1H-NMR (DMSO-d6) δ: 2.01 (3H, d, J = 0.5 Hz), 2.19 (3H, s), 7.32 (1H, dd, J = 1.1, 3.2 Hz), 7.37 (1H, d, J = 7.9 Hz), 7.41 (1H, d, J = 3.2 Hz), 7.75 (1H, dd, J = 1.7, 7.9 Hz), 7.83 (1H, d, J = 1.1 Hz). | Ex. 125 |

TABLE 4-continued
| Ex. No. | STR | m.p. | ref. |
|---|---|---|---|
| 1804 |  | | 1H-NMR (CDCl3) δ: 2.00-2.21 (4H, m), 4.27 (2H, t, J = 6.7 Hz), 6.65 (1H, dd, J = 0.7, 3.1 Hz), 7.18 (1H, d, J = 3.1 Hz), 7.45 (1H, d, J = 8.6 Hz), 7.68-7.85 (1H, m), 8.24 (1H, s), 12.2 (1H, br.). | Ex. 1 |
| 1805 | | 200.2-203.1 | Ex. 125 |

The compounds of Examples in Table 4 are shown as one tautomer, which are not limited, and the other two tautomers are also encompassed therein.

Example 1806

Synthesis of 3-(1-{4-[3-(2,5-bis-trifluoromethyl-benzyloxy)-phenyl]-5-cyano-2H-[1,2,3]triazol-2-yl}-ethoxycarbonyloxy)-2,2-dimethyl-propionic Acid

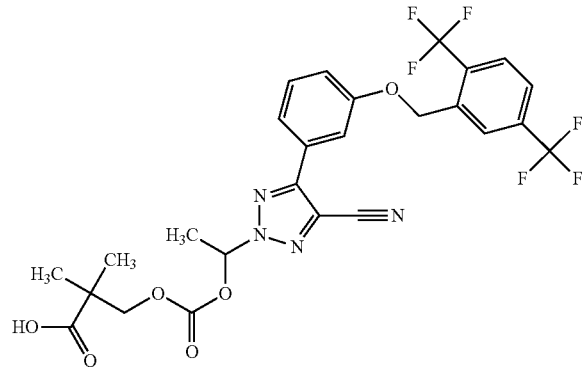 [SMILES: CC(OC(=O)OCC(C)(C)C(=O)O)n1nc(C#N)c(-c2cccc(OCc3cc(C(F)(F)F)ccc3C(F)(F)F)c2)n1]

4N HCl in AcOEt (6.02 ml, 24.08 mmol) was added to 3-(1-{4-[3-(2,5-bis-trifluoromethyl-benzyloxy)-phenyl]-5-cyano-2H-[1,2,3]triazol-2-yl}-ethoxycarbonyloxy)-2,2-dimethyl-propionic acid tert-butyl ester (316 mg, 0.48 mmol) at 0° C. The reaction mixture was stirred at room temperature overnight. Water was added to the reaction mixture, and the mixture was extracted twice with AcOEt. The combined organic layers were washed with brine, dried over $Na_2SO_4$, and concentrated in vacuo. The residue was purified by silica gel flash column chromatography (hexane:AcOEt=95:5-35:65) to give the title compound (255 mg, 88%) as a white amorphous.

$^1$H-NMR ($CDCl_3$) δ: 1.26 (6H, s), 2.01 (3H, d, J=6.3 Hz), 4.19 (1H, d, J=10.6 Hz), 4.30 (1H, d, J=10.6 Hz), 5.36 (2H, s), 6.99 (1H, q, J=6.3 Hz), 7.11 (1H, dd, J=8.3 Hz, 2.5 Hz), 7.46 (1H, t, J=8.0 Hz), 7.63 (1H, t, J=2.3 Hz), 7.67 (1H, d, J=7.8 Hz), 7.72 (1H, d, J=8.2 Hz), 7.85 (1H, d, J=8.2 Hz), 8.09 (1H, s).

Example 1807

Synthesis of 3-{1-[4-(5-chloro-4'-trifluoromethoxy-biphenyl-3-yl)-5-cyano-2H-[1,2,3]triazol-2-yl]-ethoxycarbonyloxy}-2,2-dimethyl-propionic Acid

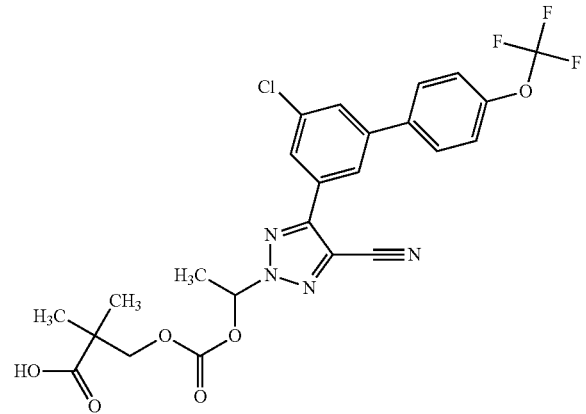 [SMILES: CC(OC(=O)OCC(C)(C)C(=O)O)n1nc(C#N)c(-c2cc(Cl)cc(-c3ccc(OC(F)(F)F)cc3)c2)n1]

To a stirred solution of 3-{1-[4-(5-chloro-4'-trifluoromethoxy-biphenyl-3-yl)-5-cyano-2H-[1,2,3]triazol-2-yl]-ethoxycarbonyloxy}-2,2-dimethyl-propionic acid benzyl ester (483 mg, 0.751 mmol) in ethanol (5 ml) were added, under nitrogen, 10% Pd—C (483 mg) followed by 1,4-cyclohexadiene (0.711 ml, 7.51 mmol). The suspension was stirred at room temperature for 30 min. The catalyst was removed by filtration through Celite, and the filtrate was concentrated in vacuo. The residue was purified by silica gel flash column chromatography (hexane:AcOEt=100:0-55:45) to give the title compound (188 mg, 45%) as a white amorphous.

$^1$H-NMR (DMSO-$d_6$) δ: 1.11 (3H, s), 1.12 (3H, s), 1.92 (3H, d, J=6.1 Hz), 4.14 (1H, d, J=10.2 Hz), 4.18 (1H, d, J=10.2 Hz), 7.10 (1H, q, J=6.1 Hz), 7.54 (2H, d, J=8.5 Hz), 7.91 (2H, d, J=8.5 Hz), 7.93 (1H, t, J=1.6 Hz), 8.00 (1H, t, J=1.6 Hz), 8.13 (1H, t, J=1.4 Hz).

Example 1808

Synthesis of 3-(1-{4-[3-chloro-5-(2,2-difluoro-benzo[1,3]dioxol-5-yl)-phenyl]-5-cyano-2H-[1,2,3]triazol-2-yl}-ethoxycarbonyloxy)-2,2-dimethyl-propionic Acid

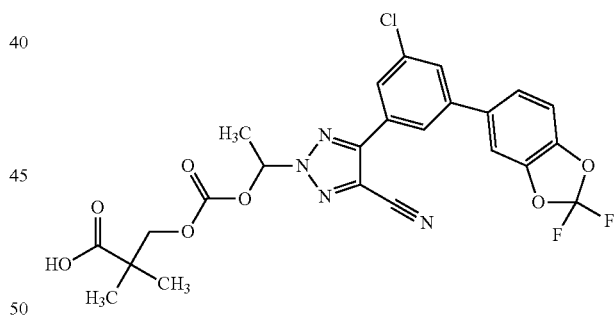

The title compound was obtained using 3-(1-{4-[3-chloro-5-(2,2-difluoro-benzo[1,3]dioxol-5-yl)-phenyl]-5-cyano-2H-[1,2,3]triazol-2-yl}-ethoxycarbonyloxy)-2,2-dimethyl-propionic acid tert-butyl ester in the same manner as in Example 1806.

white amorphous $^1$H-NMR ($CDCl_3$) δ: 1.27 (6H, s), 2.02 (3H, d, J=6.3 Hz), 4.20 (1H, d, J=10.5 Hz), 4.30 (1H, d, J=10.5 Hz), 7.00 (1H, q, J=6.3 Hz), 7.17 (1H, d, J=8.1 Hz), 7.30-7.34 (2H, m), 7.61 (1H, t, J=1.7 Hz), 7.97 (1H, t, J=1.7 Hz), 8.03 (1H, t, J=1.6 Hz).

Example 1809

Synthesis of 3-(1-{4-cyano-5-[3-methyl-5-(4-trifluoromethyl-pyrimidin-2-yl)-phenyl]-2H-[1,2,3]triazol-2-yl}-ethoxycarbonyloxy)-2,2-dimethyl-propionic Acid

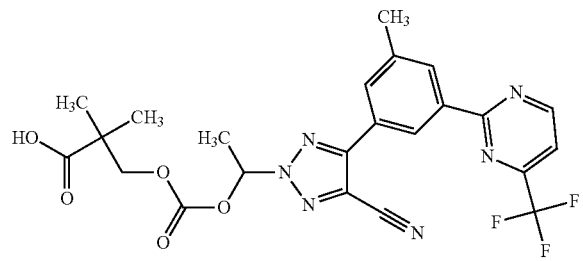 [SMILES: Cc1cc(-c2nccc(C(F)(F)F)n2)cc(-c2nn(C(C)OC(=O)OCC(C)(C)C(=O)O)nc2C#N)c1]

The title compound was obtained using 3-(1-{4-cyano-5-[3-methyl-5-(4-trifluoromethyl-pyrimidin-2-yl)-phenyl]-2H-[1,2,3]triazol-2-yl}-ethoxycarbonyloxy)-2,2-dimethyl-propionic acid benzyl ester in the same manner as in Example 1807.

white amorphous $^1$H-NMR (DMSO-$d_6$) δ: 1.11 (3H, s), 1.12 (3H, s), 1.93 (3H, d, J=6.1 Hz), 2.54 (3H, s), 4.15 (1H, d, J=10.2 Hz), 4.19 (1H, d, J=10.2 Hz), 7.10 (1H, q, J=6.1 Hz), 7.97 (1H, s), 8.04 (1H, d, J=5.0 Hz), 8.41 (1H, s), 8.83 (1H, s), 9.34 (1H, d, J=4.9 Hz).

Example 1810

Synthesis of 3-(1-{4-[3-chloro-5-(4-trifluoromethyl-pyrimidin-2-yl)-phenyl]-5-cyano-2H-[1,2,3]triazol-2-yl}-ethoxycarbonyloxy)-2,2-dimethyl-propionic Acid

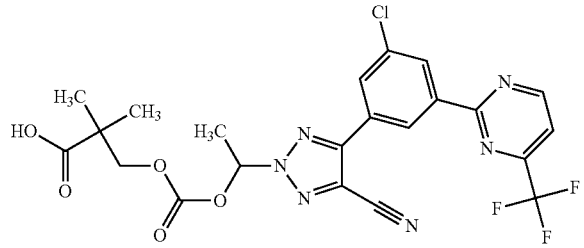 [SMILES: CC(OC(=O)OCC(C)(C)C(=O)O)n1nc(C#N)c(-c2cc(Cl)cc(-c3nccc(C(F)(F)F)n3)c2)n1]

The title compound was obtained using 3-(1-{4-[3-chloro-5-(4-trifluoromethyl-pyrimidin-2-yl)-phenyl]-5-cyano-2H-[1,2,3]triazol-2-yl}-ethoxycarbonyloxy)-2,2-dimethyl-propionic acid tert-butyl ester in the same manner as in Example 1806.

white amorphous $^1$H-NMR (CDCl$_3$) δ: 1.27 (3H, s), 1.29 (3H, s), 2.03 (3H, d, J=6.2 Hz), 4.23 (1H, d, J=10.5 Hz), 4.29 (1H, d, J=10.5 Hz), 7.00 (1H, q, J=6.2 Hz), 7.62 (1H, d, J=5.0 Hz), 8.15 (1H, t, J=1.8 Hz), 8.62 (1H, t, J=1.8 Hz), 9.02 (1H, t, J=1.5 Hz), 9.17 (1H, d, J=5.0 Hz).

Example 1811

Synthesis of 3-[1-(4-{3-chloro-5-[(E)-2-(3-trifluoromethyl-phenyl)-vinyl]-phenyl}-5-cyano-2H-[1,2,3]triazol-2-yl)-ethoxycarbonyloxy]-2,2-dimethyl-propionic Acid

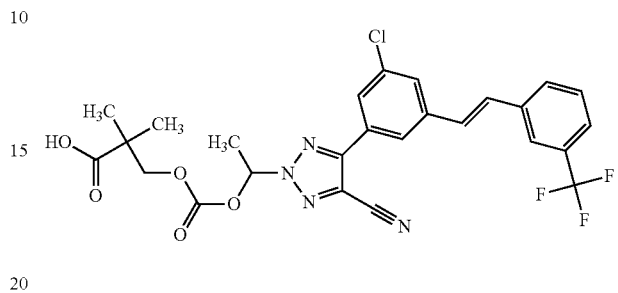

The title compound was obtained using 3-[1-(4-{3-chloro-5-[(E)-2-(3-trifluoromethyl-phenyl)-vinyl]-phenyl}-5-cyano-2H-[1,2,3]triazol-2-yl)-ethoxycarbonyloxy]-2,2-dimethyl-propionic acid tert-butyl ester in the same manner as in Example 1806.

white amorphous $^1$H-NMR (CDCl$_3$) δ: 1.27 (6H, s), 2.02 (3H, d, J=6.2 Hz), 4.21 (1H, d, J=10.5 Hz), 4.30 (1H, d, J=10.5 Hz), 7.00 (1H, q, J=6.2 Hz), 7.15 (1H, d, J=16.3 Hz), 7.22 (1H, d, J=16.3 Hz), 7.50 (1H, t, J=7.7 Hz), 7.56 (1H, d, J=7.8 Hz), 7.62 (1H, s), 7.70 (1H, d, J=7.7 Hz), 7.78 (1H, s), 7.90 (1H, t, J=1.5 Hz), 8.03 (1H, s).

Example 1812

Synthesis of 3-(1-{4-cyano-5-[3-methoxy-5-(4-trifluoromethyl-pyridin-2-yl)-phenyl]-2H-[1,2,3]triazol-2-yl}-ethoxycarbonyloxy)-2,2-dimethyl-propionic Acid

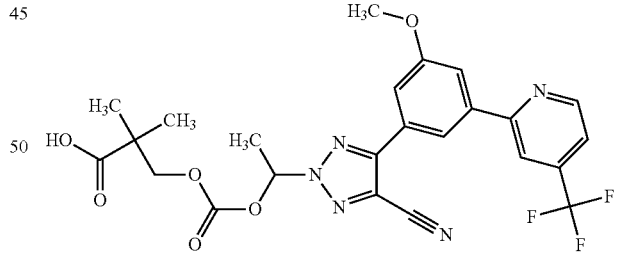

The title compound was obtained using 3-(1-{4-cyano-5-[3-methoxy-5-(4-trifluoromethyl-pyridin-2-yl)-phenyl]-2H-[1,2,3]triazol-2-yl}-ethoxycarbonyloxy)-2,2-dimethyl-propionic acid benzyl ester in the same manner as in Example 1814.

colorless powder

1H-NMR (CDCl$_3$) δ: 1.26 (3H, s), 1.34 (3H, s), 2.00 (3H, d, J=6.2 Hz), 3.98 (3H, s), 4.00 (1H, d, J=10.3 Hz), 4.52 (1H, d, J=10.3 Hz), 6.89 (1H, q, J=6.2 Hz), 7.48-7.52 (1H, m), 7.57-7.59 (1H, m), 7.71-7.72 (1H, m), 7.97 (1H, s), 8.25 (1H, t, J=1.5 Hz), 9.11 (1H, d, J=5.2 Hz).

Example 1813

Synthesis of 3-[1-(4-cyano-5-{3-trifluoromethyl-5-[(E)-2-(6-trifluoromethyl-pyridin-2-yl)-vinyl]-phenyl}-2H-[1,2,3]triazol-2-yl)-ethoxycarbonyloxy]-2,2-dimethyl-propionic Acid

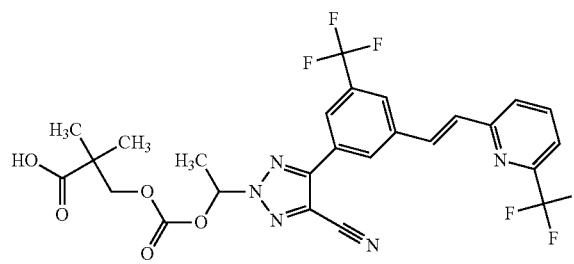

The title compound was obtained using 3-[1-(4-cyano-5-{3-trifluoromethyl-5-[(E)-2-(6-trifluoromethyl-pyridin-2-yl)-vinyl]-phenyl}-2H-[1,2,3]triazol-2-yl)-ethoxycarbonyloxy]-2,2-dimethyl-propionic acid allyl ester in the same manner as in Example 1815.

white powder $^1$H-NMR (CDCl$_3$) δ: 1.27 (3H, s), 1.29 (3H, s), 2.03 (3H, d, J=6.2 Hz), 4.26 (2H, s), 7.01 (1H, q, J=6.2H), 7.39 (1H, d, d=16.1 Hz), 7.59 (1H, d, J=7.7 Hz), 7.64 (1H, J=8.0 Hz), 7.81 (1H, d, J=16.1 Hz), 7.90 (1H, t, J=7.8 Hz), 7.94 (1H, s), 8.21 (1H, s), 8.42 (1H, s).

Example 1814

Synthesis of 3-(1-{4-[2-(4-chloro-phenyl)-thiazol-4-yl]-5-cyano-2H-[1,2,3]triazol-2-yl}-ethoxycarbonyloxy)-2,2-dimethyl-propionic Acid

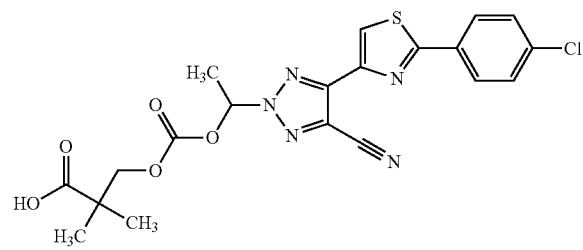 [SMILES: CC(OC(=O)OCC(C)(C)C(=O)O)n1nc(C#N)c(-c2csc(-c3ccc(Cl)cc3)n2)n1]

To a solution of 3-(1-{4-[2-(4-chloro-phenyl)-thiazol-4-yl]-5-cyano-2H-[1,2,3]triazol-2-yl}-ethoxycarbonyloxy)-2,2-dimethyl-propionic acid benzyl ester (325.3 mg, 0.575 mmol) in AcOEt (15 ml) under nitrogen was added 10% Pd/C (dry) (150 mg). The reaction mixture was stirred at room temperature for 3 hr under hydrogen. After filtration, 10% Pd/C (dry) (150 mg) was added to the filtrate. The reaction mixture was stirred at room temperature for 2 hr under hydrogen. After filtration, the filtrate was concentrated in vacuo. The residue was purified by silica gel flash column chromatography (AcOEt/hexane=0% to 40%). The obtained oil was precipitated with hexane, and recrystallized from AcOEt/hexane (Recrystallization was repeated twice) to give the title compound (75 mg, 27%) as colorless prisms.

$^1$H-NMR (CDCl$_3$) δ: 1.26 (3H, s), 1.27 (3H, s), 2.02 (3H, d, J=6.2 Hz), 4.21 (1H, d, J=10.5 Hz), 4.32 (1H, d, J=10.5 Hz), 6.99 (1H, q, J=6.2 Hz), 7.43-7.47 (2H, m), 7.92-8.02 (3H, m).

Example 1815

Synthesis of 3-[1-(4-cyano-5-{3-[(E)-2-(4-trifluoromethyl-pyridin-2-yl)-vinyl]-phenyl}-2H-[1,2,3]triazol-2-yl)-ethoxycarbonyloxy]-2,2-dimethyl-propionic Acid

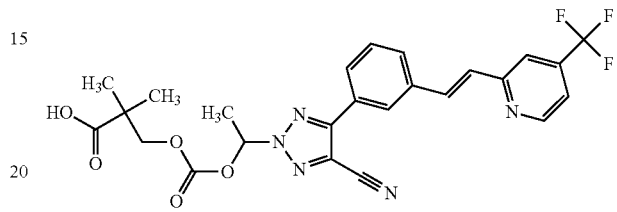

To a solution of 3-[1-(4-cyano-5-{3-[(E)-2-(4-trifluoromethyl-pyridin-2-yl)-vinyl]-phenyl}-2H-[1,2,3]triazol-2-yl)-ethoxycarbonyloxy]-2,2-dimethyl-propionic acid allyl ester (207.8 mg, 0.365 mmol) in THF (4 ml) were added AcOH (0.418 ml, 7.30 mmol), triphenylphosphine (9.57 mg, 0.036 mmol) and Pd(Ph$_3$P)$_4$ (21.08 mg, 0.018 mmol) in argon, and the reaction mixture was stirred for 2.5 hr at room temperature. The reaction mixture was concentrated in vacuo. The residue was purified by silica gel flash column chromatography (hexane/AcOEt=0% to 50%), and recrystallized (AcOEt-hexane) to give the title compound (136 mg, 70%) as a white powder.

$^1$H-NMR (CDCl$_3$) δ: 1.27 (3H, s), 1.41 (3H, s), 1.99 (3H, d, J=6.2 Hz), 3.90 (1H, d, J=10.4 Hz), 4.63 (1H, d, J=10.4 Hz), 6.89 (1H, q, J=6.2 Hz), 7.43-7.46 (1H, m), 7.52-7.57 (2H, m), 7.58 (1H, d, J=16.5 Hz), 7.75 (1H, d, J=16.5 Hz), 7.89 (1H, s), 7.97-8.00 (1H, m), 8.44 (1H, s), 8.79 (1H, d, J=5.0 Hz).

Example 1816

Synthesis of 3-[1-(4-cyano-5-{3-[(E)-2-(4-trifluoromethyl-pyrimidin-2-yl)-vinyl]-phenyl}-2H-[1,2,3]triazol-2-yl)-ethoxycarbonyloxy]-2,2-dimethyl-propionic Acid

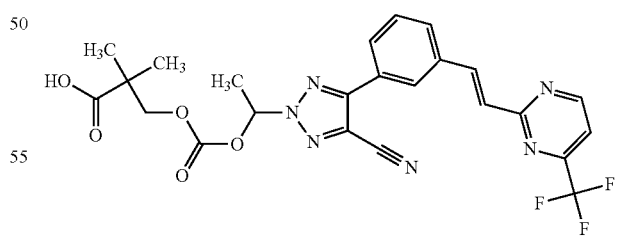

The title compound was obtained using 3-[1-(4-cyano-5-{3-[(E)-2-(4-trifluoromethyl-pyrimidin-2-yl)-vinyl]-phenyl}-2H-[1,2,3]triazol-2-yl)-ethoxycarbonyloxy]-2,2-dimethyl-propionic acid allyl ester in the same manner as in Example 1815.

colorless powder $^1$H-NMR (CDCl$_3$) δ: 1.27 (3H, s), 1.35 (3H, s), 2.00 (3H, d, J=6.2 Hz), 4.07 (1H, d, J=10.4 Hz), 4.46 (1H, d, J=10.4

Hz), 6.94 (1H, q, J=6.2 Hz), 7.49 (1H, d, J=5.0 Hz), 7.56 (1H, t, J=7.8 Hz), 7.62 (1H, d, J=15.9 Hz), 7.68 (1H, d, J=7.8 Hz), 8.00-8.03 (1H, m), 8.17 (1H, d, J=15.9 Hz), 8.38 (1H, s), 8.95 (1H, d, J=5.0 Hz).

Example 1817

Synthesis of 3-(1-{4-[5-chloro-2-(3-trifluoromethyl-phenyl)-thiazol-4-yl]-5-cyano-2H-[1,2,3]triazol-2-yl}-ethoxycarbonyloxy)-2,2-dimethyl-propionic Acid

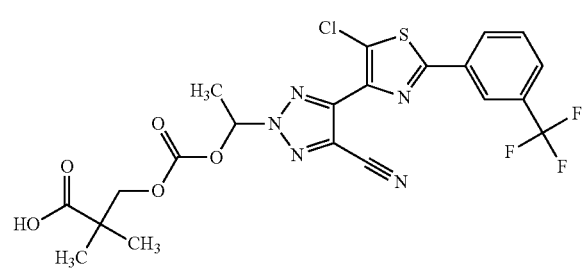 [SMILES: CC(OC(=O)OCC(C)(C)C(=O)O)n1nc(C#N)c(-c2nc(-c3cccc(C(F)(F)F)c3)sc2Cl)n1]

The title compound was obtained using 3-(1-{4-[5-chloro-2-(3-trifluoromethyl-phenyl)-thiazol-4-yl]-5-cyano-2H-[1,2,3]triazol-2-yl}-ethoxycarbonyloxy)-2,2-dimethyl-propionic acid allyl ester in the same manner as in Example 1815.

pale brown powder $^1$H-NMR (DMSO-d$_6$) δ: 1.11 (3H, s), 1.12 (3H, s), 1.93 (3H, d, J=6.1 Hz), 4.15 (1H, d, J=10.3 Hz), 4.19 (1H, d, J=10.3 Hz), 7.10 (1H, q, J=6.2 Hz), 7.83 (1H, t, J=7.8 Hz), 7.95 (1H, d, J=7.8 Hz), 8.27 (1H, d, J=7.8 Hz), 8.35 (1H, s), 12.52 (1H, brs).

Example 1819

Synthesis of 3-(1-{4-cyano-5-[2-(3-trifluoromethoxy-phenyl)-thiazol-4-yl]-2H-[1,2,3]triazol-2-yl}-ethoxycarbonyloxy)-2,2-dimethyl-propionic Acid

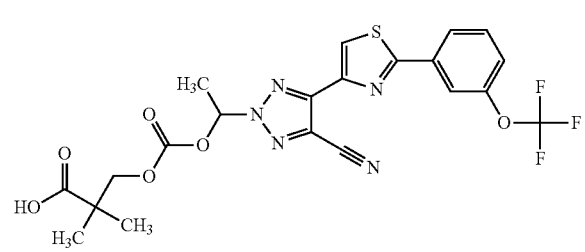 [SMILES: CC(OC(=O)OCC(C)(C)C(=O)O)n1nc(C#N)c(-c2csc(-c3cccc(OC(F)(F)F)c3)n2)n1]

The title compound was obtained using 3-(1-{4-cyano-5-[2-(3-trifluoromethoxy-phenyl)-thiazol-4-yl]-2H-[1,2,3]triazol-2-yl}-ethoxycarbonyloxy)-2,2-dimethyl-propionic acid benzyl ester in the same manner as in Example 1814.

colorless powder $^1$H-NMR (DMSO-d$_6$) δ: 1.11 (6H, s), 1.92 (3H, d, J=6.1 Hz), 4.15 (1H, d, J=10.3 Hz), 4.18 (1H, d, J=10.3 Hz), 7.08 (1H, q, J=6.1 Hz), 7.56-7.58 (1H, m), 7.72 (1H, t, J=8.0 Hz), 8.04-8.08 (2H, m), 8.49 (1H, s).

Example 1819

Synthesis of 3-(1-{4-cyano-5-[2-(3,4-dichloro-phenyl)-thiazol-4-yl]-2H-[1,2,3]triazol-2-yl}-ethoxycarbonyloxy)-2,2-dimethyl-propionic Acid

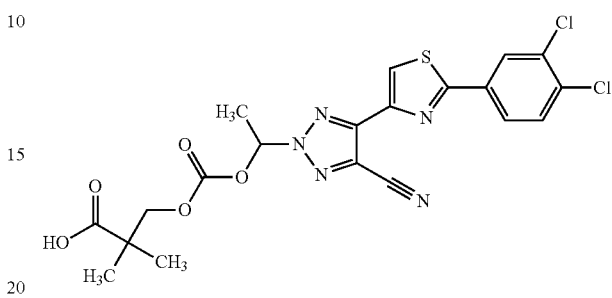

The title compound was obtained using 3-(1-{4-cyano-5-[2-(3,4-dichloro-phenyl)-thiazol-4-yl]-2H-[1,2,3]triazol-2-yl}-ethoxycarbonyloxy)-2,2-dimethyl-propionic acid allyl ester in the same manner as in Example 1815.

pale brown powder $^1$H-NMR (DMSO-d$_6$) δ: 1.11 (3H, s), 1.12 (3H, s), 1.92 (3H, d, J=6.1 Hz), 4.14 (1H, d, J=10.3 Hz), 4.18 (1H, d, J=10.3 Hz), 7.07 (1H, q, J=6.1 Hz), 7.86 (1H, d, J=8.4 Hz), 8.03 (1H, dd, J=2.1, 8.4 Hz), 8.27 (1H, d, J=2.1 Hz), 12.54 (1H, brs).

Example 1820

Synthesis of 3-(1-{4-cyano-5-[5-methyl-2-(4-trifluoromethyl-phenyl)-thiazol-4-yl]-2H-[1,2,3]triazol-2-yl}-ethoxycarbonyloxy)-2,2-dimethyl-propionic Acid

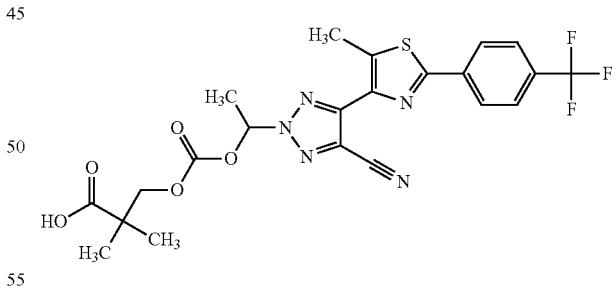

The title compound was obtained using 3-(1-{4-cyano-5-[5-methyl-2-(4-trifluoromethyl-phenyl)-thiazol-4-yl]-2H-[1,2,3]triazol-2-yl}-ethoxycarbonyloxy)-2,2-dimethyl-propionic acid benzyl ester in the same manner as in Example 1814.

white powder $^1$H-NMR (CDCl$_3$) δ: 1.26 (3H, s), 1.27 (3H, s), 2.03 (3H, d, J=6.2 Hz), 2.81 (3H, s), 4.22 (1H, d, J=10.6 Hz), 4.27 (1H, d, J=10.6 Hz), 7.01 (1H, q, J=6.2 Hz), 7.72 (2H, d, J=8.3 Hz), 7.85 (2H, d, J=8.3 Hz).

Example 1821

Synthesis of 3-(1-{4-cyano-5-[3-(4-trifluoromethyl-pyridin-2-yloxymethyl)-phenyl]-2H-[1,2,3]triazol-2-yl}-ethoxycarbonyloxy)-2,2-dimethyl-propionic Acid

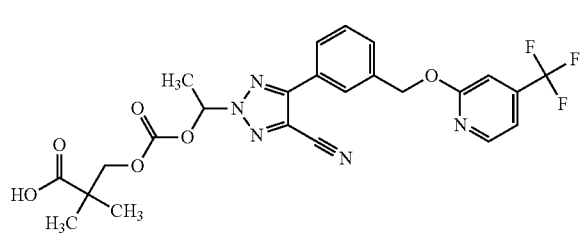 [SMILES: CC(OC(=O)OCC(C)(C)C(=O)O)n1nc(C#N)c(-c2cccc(COc3cc(C(F)(F)F)ccn3)c2)n1]

The title compound was obtained using 3-(1-{4-cyano-5-[3-(4-trifluoromethyl-pyridin-2-yloxymethyl)-phenyl]-2H-[1,2,3]triazol-2-yl}-ethoxycarbonyloxy)-2,2-dimethyl-propionic acid allyl ester in the same manner as in Example 1815.

colorless oil $^1$H-NMR (CDCl$_3$) δ: 1.26 (3H, s), 1.27 (3H, s), 2.01 (3H, d, J=6.2 Hz), 4.23 (1H, d, J=10.5 Hz), 4.27 (1H, d, J=10.5 Hz), 5.50 (2H, s), 6.98 (1H, q, J=6.2 Hz), 7.06-7.07 (1H, m), 7.10-7.11 (1H, m), 7.52 (1H, t, J=7.6 Hz), 7.56-7.58 (1H, m), 7.96-7.98 (1H, m), 8.11 (1H, s), 8.35 (1H, d, J=5.3 Hz).

Example 1822

Synthesis of 3-(1-{4-[2-(4-chloro-phenyl)-5-isopropyl-oxazol-4-yl]-5-cyano-2H-[1,2,3]triazol-2-yl}-ethoxycarbonyloxy)-2,2-dimethyl-propionic Acid

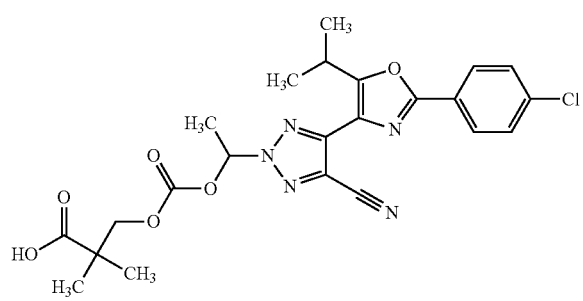 [SMILES: CC(C)c1oc(-c2ccc(Cl)cc2)nc1-c1nn(C(C)OC(=O)OCC(C)(C)C(=O)O)nc1C#N]

The title compound was obtained using 3-(1-{4-[2-(4-chloro-phenyl)-5-isopropyl-oxazol-4-yl]-5-cyano-2H-[1,2,3]triazol-2-yl}-ethoxycarbonyloxy)-2,2-dimethyl-propionic acid benzyl ester in the same manner as in Example 1807.

white powder $^1$H-NMR (DMSO-d$_6$) δ: 1.10 (3H, s), 1.11 (3H, s), 1.35 (3H, d, J=2.0 Hz), 1.36 (3H, d, J=2.0 Hz), 1.91 (3H, d, J=6.1 Hz), 3.61-3.68 (1H, m), 4.11-4.19 (2H, m), 7.07 (1H, q, J=6.1 Hz), 7.68 (2H, d, J=8.6 Hz), 8.03 (2H, d, J=8.6 Hz).

Example 1823

Synthesis of 3-(1-{4-[2-(3-chloro-4-fluoro-phenyl)-5-methyl-thiazol-4-yl]-5-cyano-2H-[1,2,3]triazol-2-yl}-ethoxycarbonyloxy)-2,2-dimethyl-propionic Acid

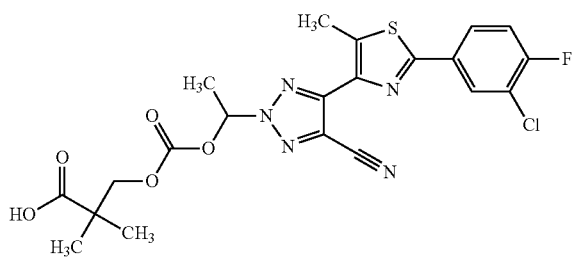 [SMILES: Cc1sc(-c2ccc(F)c(Cl)c2)nc1-c1nn(C(C)OC(=O)OCC(C)(C)C(=O)O)nc1C#N]

The title compound was obtained using 3-(1-{4-[2-(3-chloro-4-fluoro-phenyl)-5-methyl-thiazol-4-yl]-5-cyano-2H-[1,2,3]triazol-2-yl}-ethoxycarbonyloxy)-2,2-dimethyl-propionic acid benzyl ester in the same manner as in Example 1814.

colorless powder $^1$H-NMR (DMSO-d$_6$) δ: 1.11 (3H, s), 1.12 (3H, s), 1.93 (3H, d, J=6.1 Hz), 2.79 (3H, s), 4.15 (1H, d, J=10.3 Hz), 4.18 (1H, d, J=10.3 Hz), 7.08 (1H, q, J=6.1 Hz), 7.63 (1H, t, J=8.9 Hz), 7.96-7.99 (1H, m), 8.16 (1H, dd, J=2.2, 7.0 Hz), 12.54 (1H, brs).

Example 1824

Synthesis of 3-(1-{4-cyano-5-[5-cyclopropyl-2-(3-trifluoromethyl-phenyl)-oxazol-4-yl]-2H-[1,2,3]triazol-2-yl}-ethoxycarbonyloxy)-2,2-dimethyl-propionic Acid

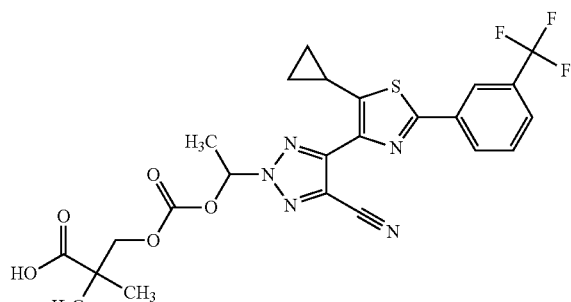

The title compound was obtained using 3-(1-{4-cyano-5-[5-cyclopropyl-2-(3-trifluoromethyl-phenyl)-oxazol-4-yl]-2H-[1,2,3]triazol-2-yl}-ethoxycarbonyloxy)-2,2-dimethyl-propionic acid benzyl ester in the same manner as in Example 1814.

colorless powder $^1$H-NMR (DMSO-d$_6$) δ: 1.09 (3H, s), 1.10 (3H, s), 1.22-1.25 (4H, m), 1.92 (3H, d, J=6.1 Hz), 2.59-2.64 (1H, m), 4.14 (1H, d, J=10.2 Hz), 4.16 (1H, d, J=10.2 Hz), 7.06 (1H, q, J=6.1 Hz), 7.83 (1H, t, J=7.8 Hz), 7.94 (1H, d, J=7.8 Hz), 8.21 (1H, s), 8.26 (1H, d, J=7.8 Hz).

Example 1825

Synthesis of 3-(1-{4-cyano-5-[3-methyl-5-(6-trifluoromethyl-pyridin-3-yl)-phenyl]-2H-[1,2,3]triazol-2-yl}-ethoxycarbonyloxy)-2,2-dimethyl-propionic Acid

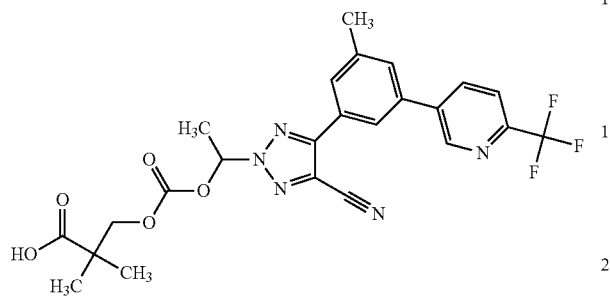

The title compound was obtained using 3-(1-{4-cyano-5-[3-methyl-5-(6-trifluoromethyl-pyridin-3-yl)-phenyl]-2H-[1,2,3]triazol-2-yl}-ethoxycarbonyloxy)-2,2-dimethyl-propionic acid benzyl ester in the same manner as in Example 1807.

white amorphous $^1$H-NMR (CDCl$_3$) δ: 1.26 (3H, s), 1.27 (3H, s), 2.02 (3H, d, J=6.3 Hz), 2.54 (3H, s), 4.25 (2H, s), 7.00 (1H, q, J=6.2 Hz), 7.53 (1H, s), 7.79 (1H, d, J=8.1 Hz), 7.90 (1H, s), 8.04 (1H, s), 8.11 (1H, dd, J=8.1, 2.0 Hz), 9.03 (1H, d, J=1.8 Hz).

Example 1826

Synthesis of 3-(1-{4-cyano-5-[5-ethyl-2-(5-trifluoromethyl-pyridin-2-yl)-thiazol-4-yl]-2H-[1,2,3]triazol-2-yl}-ethoxycarbonyloxy)-2,2-dimethyl-propionic Acid

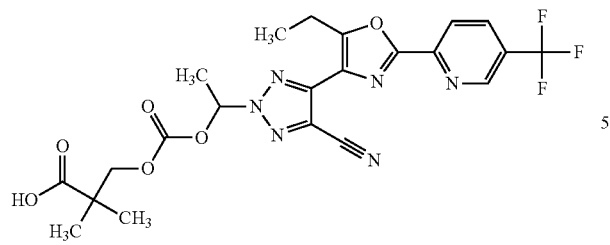

The title compound was obtained using 3-(1-{4-cyano-5-[5-ethyl-2-(5-trifluoromethyl-pyridin-2-yl)-thiazol-4-yl]-2H-[1,2,3]triazol-2-yl}-ethoxycarbonyloxy)-2,2-dimethyl-propionic acid benzyl ester in the same manner as in Example 1814.

colorless powder

1H-NMR (CDCl$_3$) δ: 1.27 (6H, s), 1.42 (3H, t, J=7.5 Hz), 2.03 (3H, d, J=6.2 Hz), 3.30 (2H, q, J=7.5 Hz), 4.21 (1H, d, J=10.5 Hz), 4.29 (1H, d, J=10.5 Hz), 7.02 (1H, q, J=6.2 Hz), 8.04-8.06 (1H, m), 8.44 (1H, d, J=8.2 Hz), 8.84 (1H, s).

Example 1827

Synthesis of 3-(1-{4-[3-(2,5-bis-trifluoromethylbenzyloxy)phenyl]-5-cyano-2H-[1,2,3]triazol-2-yl}ethoxycarbonyloxy)-3-methylbutyric Acid

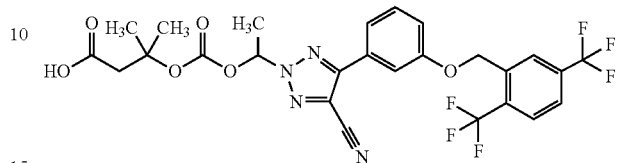

The title compound was obtained using 3-(1-{4-[3-(2,5-bis-trifluoromethyl-benzyloxy)-phenyl]-5-cyano-2H-([1,2,3]triazol-2-yl}-ethoxycarbonyloxy)-3-methyl-butyric acid benzyl ester in the same manner as in Example 1814.

colorless powder

Melting point 90.1-94.2° C.

$^1$H-NMR (CDCl$_3$) δ: 1.59 (6H, s), 1.99 (3H, d, J=6.2 Hz), 2.91 (1H, d, J=14.6 Hz), 2.96 (1H, d, J=14.6 Hz), 5.36 (2H, s), 6.95 (1H, q, J=6.2 Hz), 7.09-7.12 (1H, m), 7.46 (1H, t, J=8.0 Hz), 7.63-7.64 (1H, m), 7.67-7.69 (1H, m), 7.72 (1H, d, J=8.3 Hz), 7.85 (1H, d, J=8.3 Hz), 8.09 (1H, s).

Example 1828

Synthesis of carbonic Acid 1-{4-[3-(2,5-bis-trifluoromethylbenzyloxy)phenyl]-5-cyano-2H-[1,2,3]triazol-2-yl}ethyl ester 2-hydroxyethyl ester

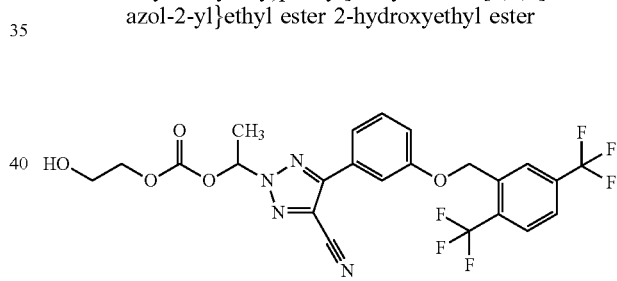

To a solution of carbonic acid 1-{4-[3-(2,5-bis-trifluoromethyl-benzyloxy)-phenyl]-5-cyano-2H-[1,2,3]triazol-2-yl}-ethyl ester 2-(tetrahydro-pyran-2-yloxy)-ethyl ester (0.79 g, 1.257 mmol) in THF (8 ml) was added 1N HCl (3.77 ml, 3.77 mmol). The reaction mixture was stirred at room temperature overnight. The organic solution was concentrated. Water was added to the reaction mixture, and the mixture was extracted with AcOEt. The combined organic layers were washed with brine, dried over magnesium sulfate, and concentrated in vacuo. The residue was purified by silica gel flash column chromatography (8%-66% AcOEt/hexane) to give colorless oil. The oil was dissolved in AcOEt and precipitated with hexane then recrystallized from AcOEt/hexane to give the title compound (0.35 g, 51%) as a colorless powder.

Melting point 70.1-73.0° C.

$^1$H-NMR (CDCl$_3$) δ: 1.81 (1H, t, J=6.2 Hz), 3.02 (3H, d, J=6.2 Hz), 3.85-3.89 (2H, m), 4.26-4.38 (2H, m), 5.37 (2H, s), 7.01 (1H, q, J=6.2 Hz), 7.10-7.13 (1H, m), 7.46 (1H, t, J=8.0 Hz), 7.63-7.64 (1H, m), 7.67-7.69 (1H, m), 7.72 (1H, d, J=8.0 Hz), 7.85 (1H, d, J=8.0 Hz), 8.09 (1H, s).

Example 1829

Synthesis of acetic Acid 4-cyano-5-[3-methyl-5-(4-trifluoromethylpyrimidin-2-yl)phenyl]-2H-[1,2,3]triazol-2-ylmethyl ester

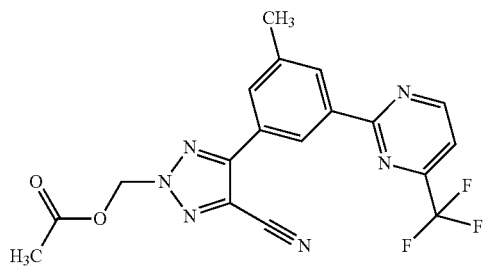 [SMILES: CC(=O)OCn1nc(C#N)c(-c2cc(C)cc(-c3nccc(C(F)(F)F)n3)c2)n1]

To a stirred solution of 5-[3-methyl-5-(4-trifluoromethyl-pyrimidin-2-yl)-phenyl]-3H-[1,2,3]triazole-4-carbonitrile (250 mg, 0.757 mmol) in DMF (10 ml) was added NaH (36.3 mg, 0.833 mmol) at 0° C. After the reaction mixture was stirred at the same temperature for 15 minutes, chloromethyl acetate (123 mg, 1.135 mmol) was added thereto, and the mixture was stirred at room temperature for 5 hr. Saturated NH$_4$Cl solution was added to the reaction mixture at 0° C., and the precipitate was collected by filtration, washed with water, and dried at 60° C. The crude product was purified by recrystallization from CH$_3$CN to give the title compound (205 mg, 67%) as a colorless powder.

$^1$H-NMR (DMSO-d$_6$) δ: 2.15 (3H, s), 2.54 (3H, s), 6.48 (2H, s), 7.97 (1H, s), 8.04 (1H, d, J=5.0 Hz), 8.41 (1H, s), 8.83 (1H, s), 9.34 (1H, d, J=5.0 Hz).

Example 1830

Synthesis of acetic Acid 4-{3-chloro-5-[(E)-2-(3-trifluoromethylphenyl)vinyl]phenyl}-5-cyano-2H-[1,2,3]triazol-2-ylmethyl ester

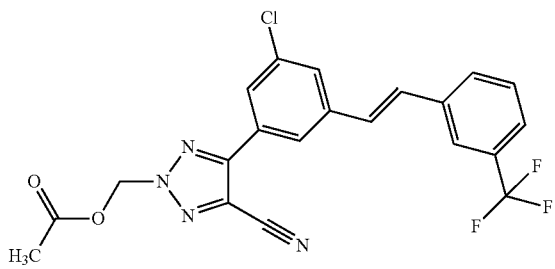 [SMILES: CC(=O)OCn1nc(C#N)c(-c2cc(Cl)cc(/C=C/c3cccc(C(F)(F)F)c3)c2)n1]

The title compound was obtained using 5-{3-chloro-5-[(E)-2-(3-trifluoromethyl-phenyl)-vinyl]-phenyl}-3H-[1,2,3]triazole-4-carbonitrile and chloromethyl acetate in the same manner as in Example 1829.

white powder $^1$H-NMR (DMSO-d$_6$) δ: 2.15 (3H, s), 6.47 (2H, s), 7.60 (2H, s), 7.64-7.69 (2H, m), 7.83 (1H, t, J=1.6 Hz), 7.96 (1H, d, J=7.1 Hz), 8.00 (1H, t, J=1.6 Hz), 8.04 (1H, s), 8.04-8.06 (1H, m).

Example 1831

Synthesis of butyric acid 4-{3-chloro-5-[(E)-2-(3-trifluoromethyl-phenyl)-vinyl]-phenyl}-5-cyano-2H-[1,2,3]triazol-2-ylmethyl ester

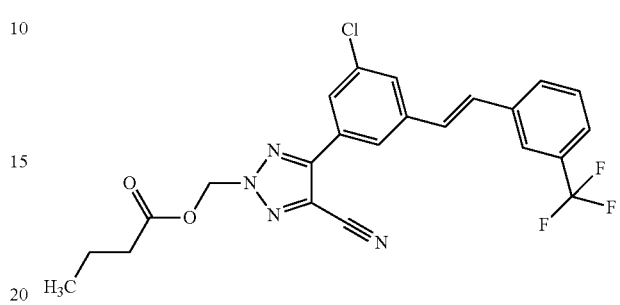

The title compound was obtained using 5-{3-chloro-5-[(E)-2-(3-trifluoromethyl-phenyl)-vinyl]-phenyl}-3H-[1,2,3]triazole-4-carbonitrile and chloromethyl butyrate in the same manner as in Example 1829.

white powder $^1$H-NMR (DMSO-d$_6$) δ: 0.88 (3H, t, J=7.4 Hz), 1.53-1.61 (2H, m), 2.42 (2H, t, J=7.3 Hz), 6.49 (2H, s), 7.59 (2H, s), 7.62-7.69 (2H, m), 7.82-7.83 (1H, m), 7.96 (1H, d, J=6.7 Hz), 7.98-8.00 (1H, m), 8.03 (1H, s), 8.04-8.06 (1H, m).

Example 1832

Synthesis of butyric acid 4-[3-chloro-5-(4-trifluoromethyl-pyrimidin-2-yl)-phenyl]-5-cyano-2H-[1,2,3]triazol-2-ylmethyl ester

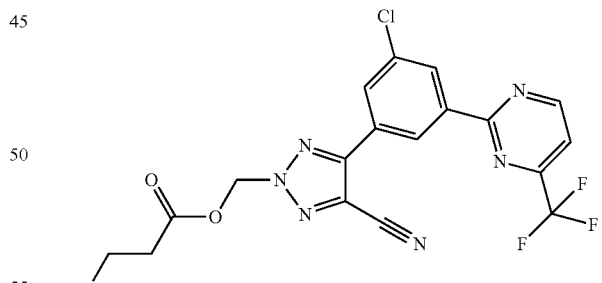

The title compound was obtained using 5-[3-chloro-5-(4-trifluoromethyl-pyrimidin-2-yl)-phenyl]-3H-[1,2,3]triazole-4-carbonitrile and chloromethyl butyrate in the same manner as in Example 1829.

white powder $^1$H-NMR (DMSO-d$_6$) δ: 0.88 (3H, t, J=7.4 Hz), 1.53-1.61 (2H, m), 2.42 (2H, t, J=7.3 Hz), 6.52 (2H, s), 8.10 (1H, d, J=5.0 Hz), 8.15-8.17 (1H, m), 8.51-8.53 (1H, m), 8.91-8.93 (1H, m), 9.37 (1H, d, J=5.0 Hz).

Example 1833

Synthesis of butyric acid 1-{4-cyano-5-[3-methyl-5-(4-trifluoromethylpyrimidin-2-yl)phenyl]-2H-[1,2,3]triazol-2-yl}ethyl ester

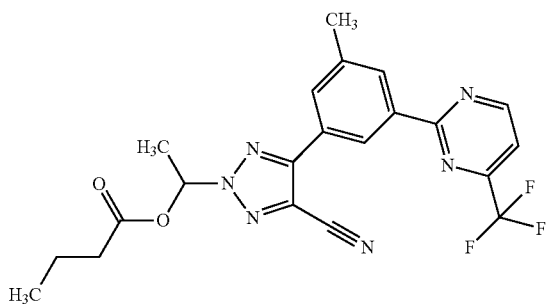 [SMILES: CCCC(=O)OC(C)n1nc(C#N)c(-c2cc(C)cc(-c3nccc(C(F)(F)F)n3)c2)n1]

To a stirred solution of 5-[3-methyl-5-(4-trifluoromethyl-pyrimidin-2-yl)-phenyl]-3H-[1,2,3]triazole-4-carbonitrile (350 mg, 1.060 mmol) in DMF (8 ml) were added $K_2CO_3$ (439 mg, 3.18 mmol) and 1-iodoethyl butyrate (641 mg, 2.65 mmol). The reaction mixture was stirred at 80° C. overnight. Water was added to the reaction mixture at 0° C., and the precipitate was collected by filtration, washed with water, and dried at 60° C. The crude product was purified by silica gel flash column chromatography (hexane:AcOEt=100:0-75:25) and recrystallization from $CH_3CN$ to give the title compound (187 mg, 40%) as a white powder.

$^1$H-NMR (CDCl$_3$) δ: 0.95 (3H, t, J=7.5 Hz), 1.65-1.72 (2H, m), 1.97 (3H, d, J=6.2 Hz), 2.38 (2H, t, J=7.4 Hz), 2.55 (3H, s), 7.17 (1H, q, J=6.2 Hz), 7.56 (1H, d, J=4.9 Hz), 7.97 (1H, s), 8.45 (1H, s), 8.95 (1H, s), 9.09 (1H, d, J=4.9 Hz).

Example 1834

Synthesis of isobutyric Acid 1-(4-{3-chloro-5-[(E)-2-(3-trifluoromethyl-phenyl)-vinyl]-phenyl}-5-cyano-2H-[1,2,3]triazol-2-yl)-ethyl ester

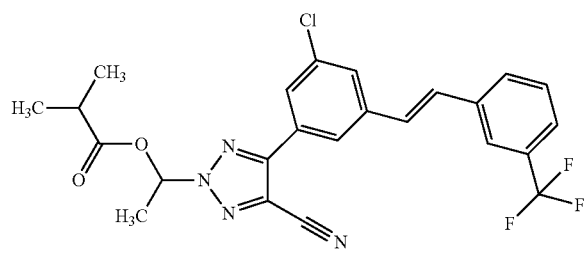 [SMILES: CC(C)C(=O)OC(C)n1nc(C#N)c(-c2cc(Cl)cc(/C=C/c3cccc(C(F)(F)F)c3)c2)n1]

The title compound was obtained using 5-{3-chloro-5-[(E)-2-(3-trifluoromethyl-phenyl)-vinyl]-phenyl}-3H-[1,2,3]triazole-4-carbonitrile and 1-chloroethyl isobutyrate in the same manner as in Example 1833.

white powder $^1$H-NMR (DMSO-d$_6$) δ: 1.07 (3H, d, J=7.0 Hz), 1.12 (3H, d, J=7.0 Hz), 1.90 (3H, d, J=6.2 Hz), 2.60-2.66 (1H, m), 7.18 (1H, q, J=6.2 Hz), 7.59 (2H, s), 7.63-7.69 (2H, m), 7.83 (1H, t, J=1.6 Hz), 7.96 (1H, d, J=7.0 Hz), 7.99-8.00 (1H, m), 8.03 (1H, s), 8.04-8.06 (1H, m).

Example 1835

Synthesis of isobutyric Acid 1-{4-cyano-5-[5-cyclopropyl-2-(3-trifluoromethyl-phenyl)-oxazol-4-yl]-2H-[1,2,3]triazol-2-yl}-ethyl ester

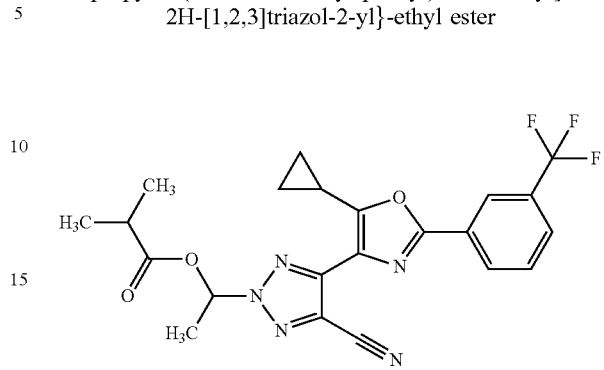

The title compound was obtained using 5-[5-cyclopropyl-2-(3-trifluoromethyl-phenyl)-oxazol-4-yl]-3H-[1,2,3]triazole-4-carbonitrile and 1-chloroethyl isobutyrate in the same manner as in Example 1833.

white powder $^1$H-NMR (DMSO-d$_6$) δ: 1.07 (3H, d, J=6.9 Hz), 1.11 (3H, d, J=6.9 Hz), 1.20-1.25 (4H, m), 1.89 (3H, d, J=6.2 Hz), 2.59-2.66 (2H, m), 7.17 (1H, q, J=6.2 Hz), 7.83 (1H, t, J=7.9 Hz), 7.94 (1H, d, J=7.9 Hz), 8.21 (1H, s), 8.26 (1H, d, J=7.9 Hz).

Example 1836

Synthesis of 3-(1-{4-[3-(2,5-bis-trifluoromethyl-benzyloxy)-phenyl]-5-cyano-2H-[1,2,3]triazol-2-yl}-ethoxycarbonyloxy)-2,2-dimethyl-propionic Acid tert-butyl ester

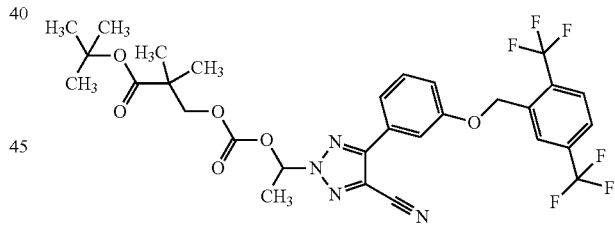

To a solution of 5-[3-(2,5-bis-trifluoromethyl-benzyloxy)-phenyl]-3H-[1,2,3]triazole-4-carbonitrile (500 mg, 1.213 mmol) in DMF (2.5 ml) were added sodium bicarbonate (408 mg, 4.85 mmol) and 3-(1-chloro-ethoxycarbonyloxy)-2,2-dimethyl-propionic acid tert-butyl ester (375 mg, 1.334 mmol). The reaction mixture was stirred at 60° C. overnight. Water was added to the reaction mixture, and the mixture was extracted twice with AcOEt. The combined organic layers were washed with water, brine, dried over $Na_2SO_4$, and concentrated in vacuo. The residue was purified by silica gel flash column chromatography (hexane:AcOEt=100:0-75:25) to give the title compound (316 mg, 40%) as a colorless oil.

$^1$H-NMR (CDCl$_3$) δ: 1.18 (3H, s), 1.19 (3H, s), 1.39 (9H, s), 2.01 (3H, d, J=6.2 Hz), 4.20 (2H, s), 5.36 (2H, s), 7.00 (1H, q, J=6.2 Hz), 7.11 (1H, dd, J=8.3 Hz, 2.5 Hz), 7.46 (1H, t, J=8.0 Hz), 7.63 (1H, t, J=2.3 Hz), 7.68 (1H, d, J=7.8 Hz), 7.72 (1H, d, J=8.2 Hz), 7.86 (1H, d, J=8.2 Hz), 8.09 (1H, s).

Example 1837

Synthesis of 3-{1-[4-(5-chloro-4'-trifluoromethoxy-biphenyl-3-yl)-5-cyano-2H-[1,2,3]triazol-2-yl]-ethoxycarbonyloxy}-2,2-dimethyl-propionic Acid benzyl ester

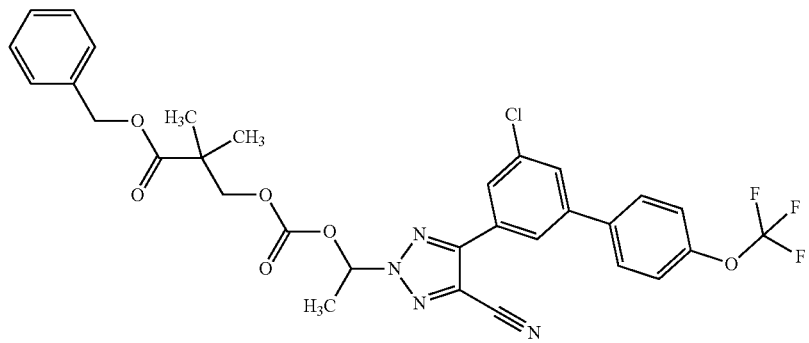 [SMILES: CC(OC(=O)OCC(C)(C)C(=O)OCc1ccccc1)n1nc(C#N)c(-c2cc(Cl)cc(-c3ccc(OC(F)(F)F)cc3)c2)n1]

The title compound was obtained using 5-(5-chloro-4'-trifluoromethoxy-biphenyl-3-yl)-3H-[1,2,3]triazole-4-carbonitrile and 3-(1-chloro-ethoxycarbonyloxy)-2,2-dimethyl-propionic acid benzyl ester in the same manner as in Example 1836.

colorless oil $^1$H-NMR (CDCl$_3$) δ: 1.26 (6H, s), 2.00 (3H, d, J=6.2 Hz), 4.22 (1H, d, J=10.5 Hz), 4.31 (1H, d, J=10.5 Hz), 5.10 (1H, d, J=12.4 Hz), 5.13 (1H, d, J=12.4 Hz), 6.96 (1H, q, J=6.2 Hz), 7.27-7.36 (7H, m), 7.62-7.67 (3H, m), 7.97 (1H, t, J=1.5 Hz), 8.07 (1H, t, J=1.5 Hz).

Example 1838

Synthesis of 3-(1-{4-[3-chloro-5-(2,2-difluoro-benzo[1,3]dioxol-5-yl)-phenyl]-5-cyano-2H-[1,2,3]triazol-2-yl}-ethoxycarbonyloxy)-2,2-dimethyl-propionic Acid tert-butyl ester

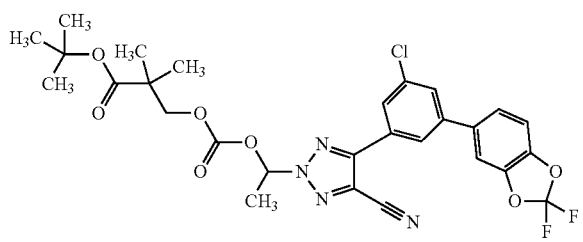 [SMILES: CC(OC(=O)OCC(C)(C)C(=O)OC(C)(C)C)n1nc(C#N)c(-c2cc(Cl)cc(-c3ccc4c(c3)OC(F)(F)O4)c2)n1]

The title compound was obtained using 5-[3-chloro-5-(2,2-difluoro-benzo[1,3]dioxol-5-yl)-phenyl]-3H-[1,2,3]triazole-4-carbonitrile and 3-(1-chloro-ethoxycarbonyloxy)-2,2-dimethyl-propionic acid tert-butyl ester in the same manner as in Example 1836.

colorless oil $^1$H-NMR (CDCl$_3$) δ: 1.18 (3H, s), 1.19 (3H, s), 1.40 (9H, s), 2.02 (3H, d, J=6.3 Hz), 4.21 (2H, s), 7.00 (1H, q, J=6.3 Hz), 7.17 (1H, d, J=8.1 Hz), 7.31-7.35 (2H, m), 7.60-7.62 (1H, m), 7.96-7.98 (1H, m), 8.02-8.04 (1H, m).

Example 1839

Synthesis of 3-(1-{4-cyano-5-[3-methyl-5-(4-trifluoromethyl-pyrimidin-2-yl)-phenyl]-2H-[1,2,3]triazol-2-yl}-ethoxycarbonyloxy)-2,2-dimethyl-propionic Acid benzyl ester

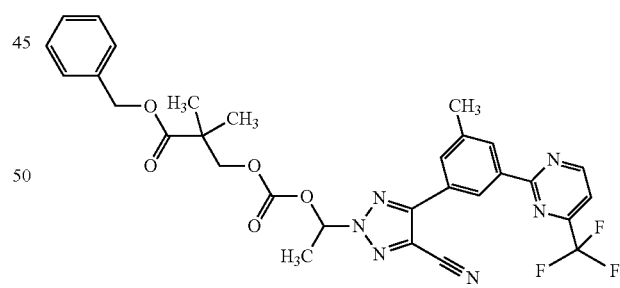

The title compound was obtained using 5-[3-methyl-5-(4-trifluoromethyl-pyrimidin-2-yl)-phenyl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil $^1$H-NMR (CDCl$_3$) δ: 1.25 (3H, s), 1.26 (3H, s), 2.01 (3H, d, J=6.3 Hz), 2.55 (3H, s), 4.22 (1H, d, J=10.6 Hz), 4.32 (1H, d, J=10.6 Hz), 5.10 (1H, d, J=12.5 Hz), 5.14 (1H, d, J=12.5 Hz), 6.98 (1H, q, J=6.3 Hz), 7.27-7.36 (5H, m), 7.55 (1H, d, J=5.0 Hz), 7.96 (1H, s), 8.45 (1H, s), 8.95 (1H, s), 9.08 (1H, d, J=5.0 Hz).

Example 1840

Synthesis of 3-(1-{4-[3-chloro-5-(4-trifluoromethyl-pyrimidin-2-yl)-phenyl]-5-cyano-2H-[1,2,3]triazol-2-yl}-ethoxycarbonyloxy)-2,2-dimethyl-propionic Acid tert-butyl ester

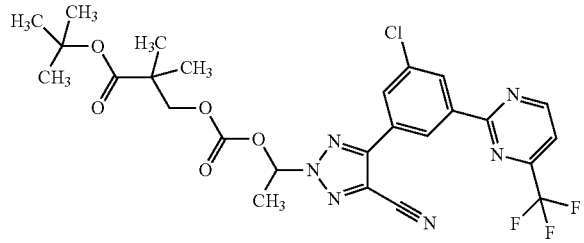 [SMILES: CC(OC(=O)OCC(C)(C)C(=O)OC(C)(C)C)n1nc(C#N)c(-c2cc(Cl)cc(-c3nccc(C(F)(F)F)n3)c2)n1]

The title compound was obtained using 5-[3-chloro-5-(4-trifluoromethyl-pyrimidin-2-yl)-phenyl]-3H-[1,2,3]triazole-4-carbonitrile and 3-(1-chloro-ethoxycarbonyloxy)-2,2-dimethyl-propionic acid tert-butyl ester in the same manner as in Example 1836.

colorless oil $^1$H-NMR (CDCl$_3$) δ: 1.18 (3H, s), 1.19 (3H, s), 1.40 (9H, s), 2.03 (3H, d, J=6.2 Hz), 4.21 (2H, s), 7.03 (1H, q, J=6.2 Hz), 7.61 (1H, d, J=5.0 Hz), 8.14 (1H, t, J=1.9 Hz), 8.63 (1H, d, J=1.9 Hz), 9.07-9.08 (1H, m), 9.12 (1H, d, J=4.9 Hz).

Example 1841

Synthesis of 3-[1-(4-{3-chloro-5-[(E)-2-(3-trifluoromethyl-phenyl)-vinyl]-phenyl}-5-cyano-2H-[1,2,3]triazol-2-yl)-ethoxycarbonyloxy]-2,2-dimethyl-propionic Acid tert-butyl ester

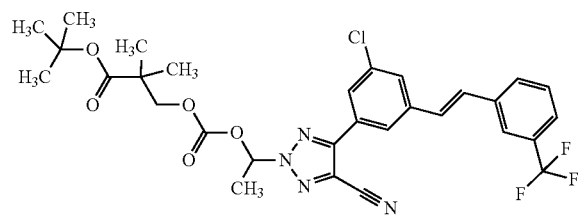 [SMILES: CC(OC(=O)OCC(C)(C)C(=O)OC(C)(C)C)n1nc(C#N)c(-c2cc(Cl)cc(/C=C/c3cccc(C(F)(F)F)c3)c2)n1]

The title compound was obtained using 5-{3-chloro-5-[(E)-2-(3-trifluoromethyl-phenyl)-vinyl]-phenyl}-3H-[1,2,3]triazole-4-carbonitrile and 3-(1-chloro-ethoxycarbonyloxy)-2,2-dimethyl-propionic acid tert-butyl ester in the same manner as in Example 1836.

colorless oil $^1$H-NMR (CDCl$_3$) δ: 1.18 (3H, s), 1.19 (3H, s), 1.40 (9H, s), 2.02 (3H, d, J=6.2 Hz), 4.21 (2H, s), 7.01 (1H, q, J=6.2 Hz), 7.16 (1H, d, J=16.3 Hz), 7.23 (1H, d, J=16.3 Hz), 7.51 (1H, t, J=7.8 Hz), 7.56 (1H, d, J=7.9 Hz), 7.63 (1H, s), 7.71 (1H, d, J=7.6 Hz), 7.79 (1H, s), 7.91 (1H, t, J=1.5 Hz), 8.04 (1H, s).

Example 1842

Synthesis of 3-(1-{4-cyano-5-[5-methyl-2-(4-trifluoromethyl-phenyl)-thiazol-4-yl]-2H-[1,2,3]triazol-2-yl}-ethoxycarbonyloxy)-2,2-dimethyl-propionic Acid benzyl ester

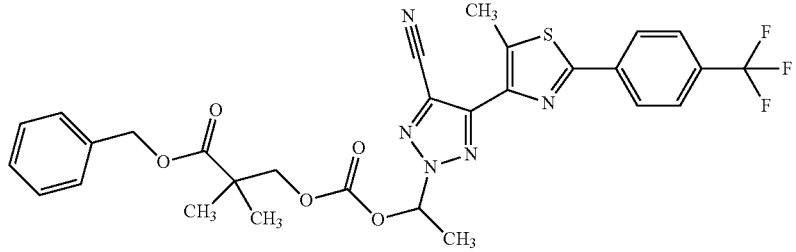 [SMILES: Cc1sc(-c2ccc(C(F)(F)F)cc2)nc1-c1nn(C(C)OC(=O)OCC(C)(C)C(=O)OCc2ccccc2)nc1C#N]

The title compound was obtained using 5-[5-methyl-2-(4-trifluoromethyl-phenyl)-thiazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil $^1$H-NMR (CDCl$_3$) δ: 1.26 (6H, s), 2.00 (3H, d, J=6.3 Hz), 2.81 (3H, s), 4.21 (1H, d, J=10.4 Hz), 4.31 (1H, d, J=10.4 Hz), 5.11 (1H, d, J=12.6 Hz), 5.14 (1H, d, J=12.6 Hz), 6.98 (1H, q, J=6.3 Hz), 7.27-7.36 (5H, m), 7.71 (2H, d, J=8.3 Hz), 8.11 (2H, d, J=8.3 Hz).

Example 1843

Synthesis of 3-(1-{4-[2-(4-chloro-phenyl)-5-isopropyl-oxazol-4-yl]-5-cyano-2H-[1,2,3]triazol-2-yl}-ethoxycarbonyloxy)-2,2-dimethyl-propionic Acid benzyl ester

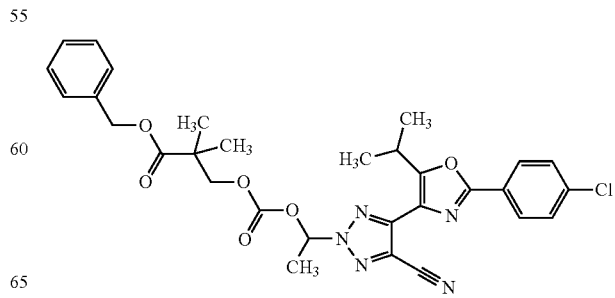

The title compound was obtained using 5-[2-(4-chloro-phenyl)-5-isopropyl-oxazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.25 (3H, s), 1.26 (3H, s), 1.37 (3H, d, J=1.8 Hz), 1.38 (3H, d, J=1.8 Hz), 1.98 (3H, d, J=6.3 Hz), 3.62-3.70 (1H, m), 4.20 (1H, d, J=10.4 Hz), 4.32 (1H, d, J=10.4 Hz), 5.11-5.15 (2H, m), 6.96 (1H, q, J=6.3 Hz), 7.28-7.37 (5H, m), 7.45 (2H, d, J=8.6 Hz), 8.03 (2H, d, J=8.6 Hz).

Example 1844

Synthesis of 3-(1-{4-[2-(3-chloro-4-fluoro-phenyl)-5-methyl-thiazol-4-yl]-5-cyano-2H-[1,2,3]triazol-2-yl}-ethoxycarbonyloxy)-2,2-dimethyl-propionic Acid benzyl ester

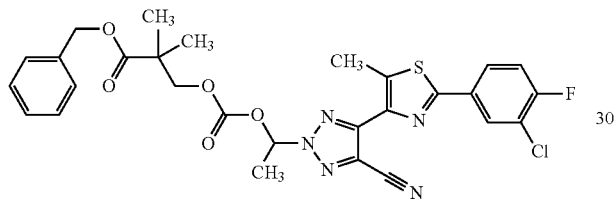

The title compound was obtained using 5-[2-(3-chloro-4-fluoro-phenyl)-5-methyl-thiazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.26 (6H, s), 2.00 (3H, d, J=6.2 Hz), 2.78 (3H, s), 4.21 (1H, d, J=10.4 Hz), 4.31 (1H, d, J=10.4 Hz), 5.10 (1H, d, J=12.5 Hz), 5.15 (1H, d, J=12.5 Hz), 6.98 (1H, q, J=6.2 Hz), 7.23 (1H, t, J=8.6 Hz), 7.27-7.37 (5H, m), 7.90-7.94 (1H, m), 8.00 (1H, dd, J=2.2, 6.9 Hz).

Example 1845

Synthesis of 3-(1-{4-cyano-5-[5-cyclopropyl-2-(3-trifluoromethyl-phenyl)-oxazol-4-yl]-2H-[1,2,3]triazol-2-yl}-ethoxycarbonyloxy)-2,2-dimethyl-propionic Acid benzyl ester

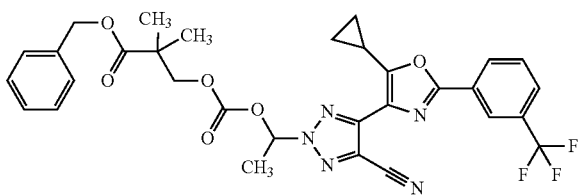 [SMILES: CC(OC(=O)OCC(C)(C)C(=O)OCc1ccccc1)n1nc(C#N)c(-c2nc(-c3cccc(C(F)(F)F)c3)oc2C2CC2)n1]

The title compound was obtained using 5-[5-cyclopropyl-2-(3-trifluoromethyl-phenyl)-oxazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.16-1.22 (4H, m), 1.24 (6H, s), 1.99 (3H, d, J=6.2 Hz), 2.59-2.65 (1H, m), 4.22 (1H, d, J=10.4 Hz), 4.31 (1H, d, J=10.4 Hz), 5.11 (1H, d, J=12.5 Hz), 5.15 (1H, d, J=12.5 Hz), 6.97 (1H, q, J=6.2 Hz), 7.28-7.37 (5H, m), 7.59 (1H, t, J=7.8 Hz), 7.69 (1H, d, J=7.8 Hz), 8.19 (1H, s), 8.26 (1H, d, J=7.8 Hz).

Example 1846

Synthesis of 3-(1-{4-cyano-5-[3-methyl-5-(6-trifluoromethyl-pyridin-3-yl)-phenyl]-2H-[1,2,3]triazol-2-yl}-ethoxycarbonyloxy)-2,2-dimethyl-propionic Acid benzyl ester

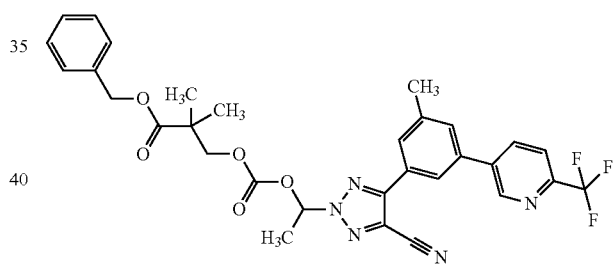

The title compound was obtained using 5-[3-methyl-5-(6-trifluoromethyl-pyridin-3-yl)-phenyl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.26 (6H, s), 2.00 (3H, d, J=6.2 Hz), 2.54 (3H, s), 4.22 (1H, d, J=10.5 Hz), 4.30 (1H, d, J=10.5 Hz), 5.11 (2H, d, J=4.0 Hz), 6.97 (1H, q, J=6.2 Hz), 7.27-7.37 (5H, m), 7.53 (1H, s), 7.78 (1H, d, J=8.1 Hz), 7.90 (1H, s), 8.01 (1H, s), 8.09 (1H, dd, J=8.1, 2.1 Hz), 8.98 (1H, d, J=1.9 Hz).

Example 1847

Synthesis of 3-(1-{4-[3-(2,5-bis-trifluoromethyl-benzyloxy)-phenyl]-5-cyano-2H-[1,2,3]triazol-2-yl}-ethoxycarbonyloxy)-3-methyl-butyric Acid benzyl ester

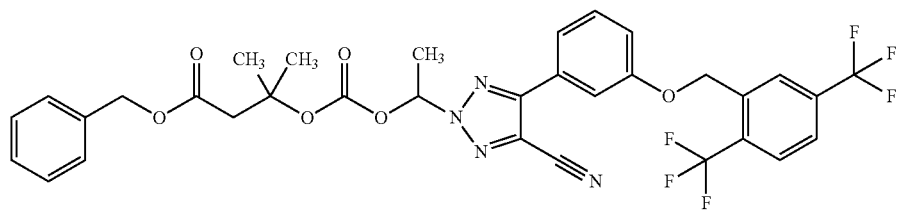 [SMILES: CC(OC(=O)OC(C)(C)CC(=O)OCc1ccccc1)n1nc(C#N)c(-c2cccc(OCc3cc(C(F)(F)F)ccc3C(F)(F)F)c2)n1]

The title compound was obtained using 5-[3-(2,5-bis-trifluoromethyl-benzyloxy)-phenyl]-3H-[1,2,3]triazole-4-carbonitrile and 3-(1-chloro-ethoxycarbonyloxy)-3-methyl-butyric acid benzyl ester in the same manner as in Example 1836.

colorless oil $^1$H-NMR (CDCl$_3$) δ: 1.56 (3H, s), 1.57 (3H, s), 1.92 (3H, d, J=6.3 Hz), 2.89 (1H, d, J=14.4 Hz), 3.02 (1H, d, J=14.4 Hz), 5.09 (2H, s), 5.35 (2H, s), 6.90 (1H, q, J=6.3 Hz), 7.10 (1H, dd, J=2.3, 8.0 Hz), 7.27-7.36 (5H, m), 7.45 (1H, t, J=8.0 Hz), 7.63 (1H, t, J=2.3 Hz), 7.66 (1H, d, J=8.1 Hz), 7.72 (1H, d, J=8.1 Hz), 7.85 (1H, d, J=8.1 Hz), 8.09 (1H, s).

Example 1848

Synthesis of carbonic Acid 1-{-4-[3-(2,5-bis-trifluoromethyl-benzyloxy)-phenyl]-5-cyano-2H-[1,2,3]triazol-2-yl}-ethyl ester 2-(tetrahydro-pyran-2-yloxy)-ethyl ester

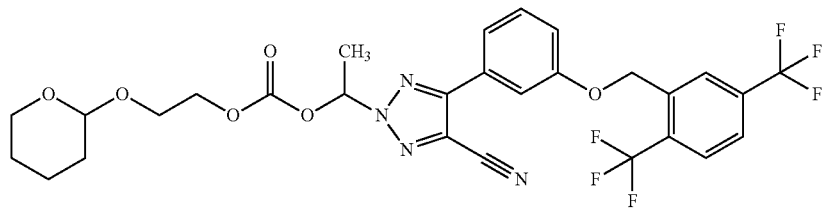 [SMILES: CC(OC(=O)OCCOC1CCCCO1)n1nc(C#N)c(-c2cccc(OCc3cc(C(F)(F)F)ccc3C(F)(F)F)c2)n1]

The title compound was obtained using 5-[3-(2,5-bis-trifluoromethyl-benzyloxy)-phenyl]-3H-[1,2,3]triazole-4-carbonitrile and carbonic acid 1-chloro-ethyl ester 2-(tetrahydro-2H-pyran-2-yloxy)-ethyl ester in the same manner as in Example 1836.

pale yellow oil $^1$H-NMR (CDCl$_3$) δ: 1.48-1.52 (2H, m), 1.53-1.63 (2H, m), 1.64-1.73 (1H, m), 1.74-1.82 (1H, m), 2.01 (3H, d, J=6.2 Hz), 3.47-3.51 (1H, m), 3.64-3.69 (1H, m), 3.79-3.83 (1H, m), 3.89-3.96 (1H, m), 4.32-4.43 (2H, m), 4.61-4.63 (1H, m), 5.36 (2H, s), 7.01 (1H, q, J=6.2 Hz), 7.10-7.13 (1H, m), 7.46 (1H, t, J=8.0 Hz), 7.63-7.64 (1H, m), 7.67-7.69 (1H, m), 7.72 (1H, d, J=8.1 Hz), 7.85 (1H, d, J=8.1 Hz), 8.09 (1H, s).

Example 1849

Synthesis of 3-[1-(4-cyano-5-{3-trifluoromethyl-5-[(E)-2-(6-trifluoromethyl-pyridin-2-yl)-vinyl]-phenyl}-2H-[1,2,3]triazol-2-yl)-ethoxycarbonyloxy]-2,2-dimethyl-propionic Acid allyl ester

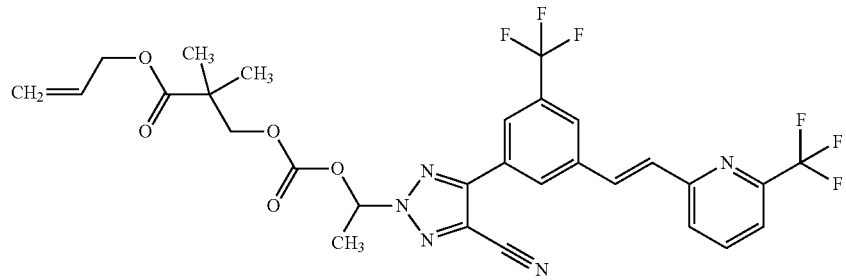 [SMILES: C=CCOC(=O)C(C)(C)COC(=O)OC(C)n1nc(C#N)c(-c2cc(/C=C/c3cccc(C(F)(F)F)n3)cc(C(F)(F)F)c2)n1]

The title compound was obtained using 5-{3-trifluoromethyl-5-[(E)-2-(6-trifluoromethyl-pyridin-2-yl)-vinyl]-phenyl}-3H-[1,2,3]triazole-4-carbonitrile and 3-(1-chloro-ethoxycarbonyloxy)-2,2-dimethyl-propionic acid allyl ester in the same manner as in Example 1836.

colorless oil $^1$H-NMR (CDCl$_3$) δ: 1.26 (6H, s), 2.04 (3H, d, J=6.2 Hz), 4.24 (1H, d, J=10.5 Hz), 4.30 (1H, d, J=10.5 Hz), 4.56-4.60 (2H, m), 5.19-5.23 (1H, m), 5.25-5.31 (1H, m), 5.82-5.93 (1H, m), 7.01 (1H, q, J=6.2 Hz), 7.36 (1H, d, J=16.1 Hz), 7.59 (1H, d, J=7.7 Hz), 7.62 (1H, J=7.8 Hz), 7.83 (1H, d, J=16.1 Hz), 7.99 (1H, t, J=7.8 Hz), 7.96 (1H, s), 8.20 (1H, s), 8.41 (1H, s).

Example 1850

Synthesis of 3-(1-{4-[2-(4-chloro-phenyl)-thiazol-4-yl]-5-cyano-2H-[1,2,3]triazol-2-yl}-ethoxycarbonyloxy)-2,2-dimethyl-propionic Acid benzyl ester

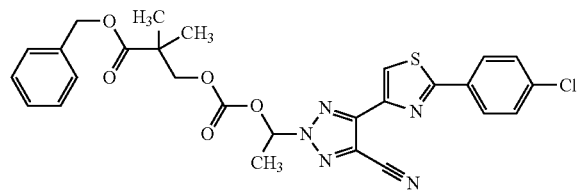 [SMILES: CC(OC(=O)OCC(C)(C)C(=O)OCc1ccccc1)n1nc(C#N)c(-c2csc(-c3ccc(Cl)cc3)n2)n1]

The title compound was obtained using 5-[2-(4-chlorophenyl)-thiazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil $^1$H-NMR (CDCl$_3$) δ: 1.26 (6H, s), 1.99 (3H, d, J=6.2 Hz), 4.22 (1H, d, J=10.5 Hz), 4.30 (1H, d, J=10.5 Hz), 5.10 (1H, d, J=12.5 Hz), 5.14 (1H, d, J=12.5 Hz), 6.97 (1H, q, J=6.2 Hz), 7.26-7.36 (5H, m), 7.43-7.47 (2H, m), 7.49 (1H, s), 7.99-8.02 (2H, m).

Example 1851

Synthesis of 3-[1-(4-cyano-5-{3-[(E)-2-(4-trifluoromethyl-pyridin-2-yl)-vinyl]-phenyl}-2H-[1,2,3]triazol-2-yl)-ethoxycarbonyloxy]-2,2-dimethyl-propionic Acid allyl ester

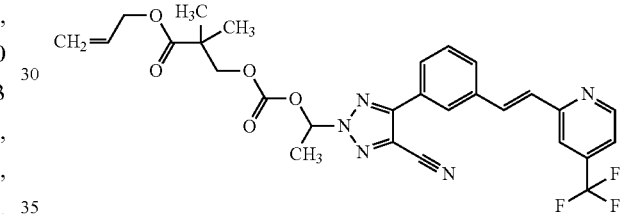

The title compound was obtained using 5-{3-[(E)-2-(4-trifluoromethyl-pyridin-2-yl)-vinyl]-phenyl}-3H-[1,2,3]triazole-4-carbonitrile and 3-(1-chloro-ethoxycarbonyloxy)-2,2-dimethyl-propionic acid allyl ester in the same manner as in Example 1836.

colorless oil $^1$H-NMR (CDCl$_3$) δ: 1.26 (6H, s), 2.03 (3H, d, J=6.2 Hz), 4.23 (1H, d, J=10.5 Hz), 4.30 (1H, d, J=10.5 Hz), 4.56-4.60 (2H, m), 5.17-5.22 (1H, m), 5.25-5.31 (1H, m), 5.82-5.91 (1H, m), 7.00 (1H, q, J=6.2 Hz), 7.31 (1H, d, J=16.1 Hz), 7.38-7.40 (1H, m), 7.55 (1H, t, J=7.8 Hz), 7.62 (1H, s), 7.69-7.72 (1H, m), 7.81 (1H, d, J=16.1 Hz), 7.96-8.00 (1H, m), 8.24 (1H, s), 8.79 (1H, d, J=5.0 Hz).

Example 1852

Synthesis of 3-(1-{4-cyano-5-[2-(3,4-dichloro-phenyl)-thiazol-4-yl]-2H-[1,2,3]triazol-2-yl}-ethoxycarbonyloxy)-2,2-dimethyl-propionic Acid allyl ester

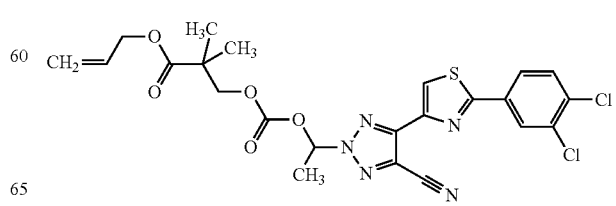

The title compound was obtained using 5-[2-(3,4-dichloro-phenyl)-thiazol-4-yl]-3H-[1,2,3]triazole-4-carbonitrile and 3-(1-chloro-ethoxycarbonyloxy)-2,2-dimethyl-propionic acid allyl ester in the same manner as in Example 1836.

colorless oil

¹H-NMR (CDCl₃) δ: 1.25 (6H, s), 2.02 (3H, d, J=6.2 Hz), 4.22 (1H, d, J=10.4 Hz), 4.29 (1H, d, J=10.4 Hz), 4.57-4.59 (2H, m), 5.19-5.23 (1H, m), 5.26-5.31 (1H, m), 5.82-5.92 (1H, m), 7.00 (1H, q, J=6.2 Hz), 7.56 (1H, d, J=8.4 Hz), 7.93 (1H, dd, J=2.1, 8.4 Hz), 7.99 (1H, s), 8.12 (1H, d, J=2.1 Hz).

Example 1853

Synthesis of 3-(1-{4-[5-chloro-2-(3-trifluoromethyl-phenyl)-thiazol-4-yl]-5-cyano-2H-[1,2,3]triazol-2-yl}-ethoxycarbonyloxy)-2,2-dimethyl-propionic Acid allyl ester

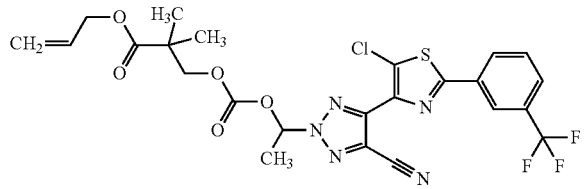 [SMILES: C=CCOC(=O)C(C)(C)COC(=O)OC(C)n1nc(C#N)c(-c2nc(-c3cccc(C(F)(F)F)c3)sc2Cl)n1]

The title compound was obtained using 5-[5-chloro-2-(3-trifluoromethyl-phenyl)-thiazol-4-yl]-3H-[1,2,3]triazole-4-carbonitrile and 3-(1-chloro-ethoxycarbonyloxy)-2,2-dimethyl-propionic acid allyl ester in the same manner as in Example 1836.

colorless oil

¹H-NMR (CDCl₃) δ: 1.26 (6H, s), 2.04 (3H, d, J=6.2 Hz), 4.22 (1H, d, J=10.4 Hz), 4.30 (1H, d, J=10.4 Hz), 4.58-4.60 (2H, m), 5.20-5.23 (1H, m), 5.26-5.32 (1H, m), 5.83-5.93 (1H, m), 7.04 (1H, q, J=6.2 Hz), 7.63 (1H, t, J=7.8 Hz), 7.74 (1H, d, J=7.8 Hz), 8.14 (1H, s), 8.23 (1H, d, J=7.8 Hz).

Example 1854

Synthesis of 3-(1-{4-cyano-5-[3-methoxy-5-(4-trifluoromethyl-pyridin-2-yl)-phenyl]-2H-[1,2,3]triazol-2-yl}-ethoxycarbonyloxy)-2,2-dimethyl-propionic Acid benzyl ester

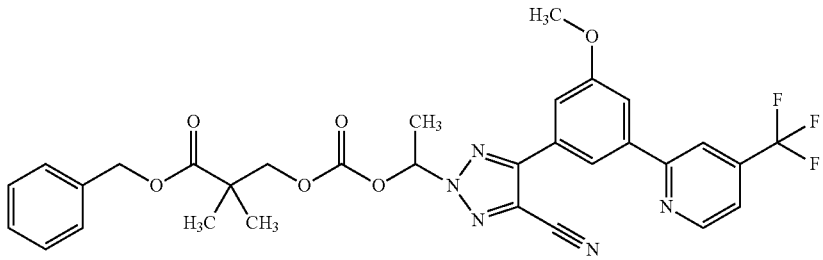 [SMILES: COc1cc(-c2cc(C(F)(F)F)ccn2)cc(-c2nn(C(C)OC(=O)OCC(C)(C)C(=O)OCc3ccccc3)nc2C#N)c1]

The title compound was obtained using 5-[3-methoxy-5-(4-trifluoromethyl-pyridin-2-yl)-phenyl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.26 (6H, s), 2.00 (3H, d, J=6.2 Hz), 3.97 (3H, s), 4.23 (1H, d, J=10.5 Hz), 4.32 (1H, d, J=10.5 Hz), 5.10 (1H, d, J=12.4 Hz), 5.14 (1H, d, J=12.4 Hz), 6.98 (1H, q, J=6.2 Hz), 7.28-7.36 (5H, m), 7.51 (1H, dd, J=0.7, 5.0 Hz), 7.64 (1H, dd, J=1.5, 2.4 Hz), 7.74 (1H, dd, J=1.5, 2.4 Hz), 7.98 (1H, s), 8.22 (1H, t, J=1.5 Hz), 8.90 (1H, d, J=5.0 Hz).

Example 1855

Synthesis of 3-(1-{4-cyano-5-[2-(3-trifluoromethoxy-phenyl)-thiazol-4-yl]-2H-[1,2,3]triazol-2-yl}-ethoxycarbonyloxy)-2,2-so dimethyl-propionic Acid benzyl ester

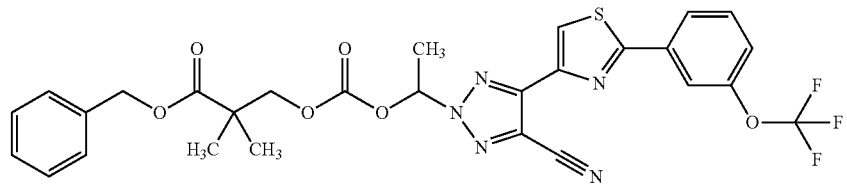 [SMILES: CC(OC(=O)OCC(C)(C)C(=O)OCc1ccccc1)n1nc(C#N)c(-c2csc(-c3cccc(OC(F)(F)F)c3)n2)n1]

The title compound was obtained using 5-[2-(3-trifluoromethoxy-phenyl)-thiazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.
colorless oil
¹H-NMR (CDCl₃) δ: 1.59 (6H, s), 2.00 (3H, d, J=6.2 Hz), 4.22 (1H, d, J=10.5 Hz), 4.31 (1H, d, J=10.5 Hz), 5.12 (2H, d, J=2.5 Hz), 6.97 (1H, q, J=6.2 Hz), 7.28-7.40 (6H, m), 7.52 (1H, t, J=8.0 Hz), 7.91 (1H, s), 7.98 (1H, s), 8.00-8.03 (1H, m).

Example 1856

Synthesis of 3-(1-{4-cyano-5-[3-(4-trifluoromethyl-pyridin-2-yloxymethyl)-phenyl]-2H-[1,2,3]triazol-2-yl}-ethoxycarbonyloxy)-2,2-dimethyl-propionic Acid allyl ester

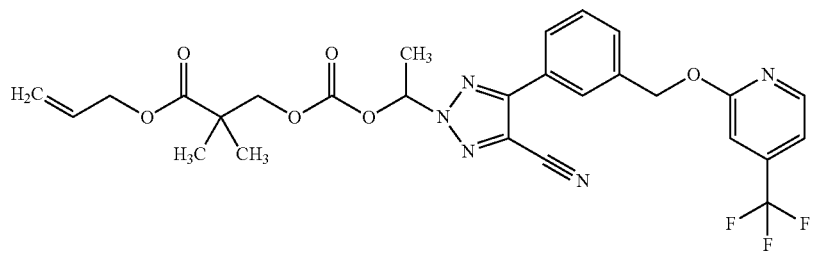 [SMILES: C=CCOC(=O)C(C)(C)COC(=O)OC(C)n1nc(C#N)c(-c2cccc(COc3cc(C(F)(F)F)ccn3)c2)n1]

The title compound was obtained using 5-[3-(4-trifluoromethyl-pyridin-2-yloxymethyl)-phenyl]-3H-[1,2,3]triazole-4-carbonitrile and 3-(1-chloro-ethoxycarbonyloxy)-2,2-dimethyl-propionic acid allyl ester in the same manner as in Example 1836.
colorless oil
¹H-NMR (CDCl₃) δ: 1.25 (6H, s), 2.00 (3H, d, J=6.2 Hz), 4.22 (1H, d, J=10.5 Hz), 4.29 (1H, d, J=10.5 Hz), 4.57 (1H, t, J=1.4 Hz), 4.58 (1H, t, J=1.4 Hz), 5.18-5.23 (1H, m), 5.25-5.33 (1H, m), 5.50 (2H, s), 5.81-5.93 (1H, m), 6.99 (1H, q, J=6.2 Hz), 7.07-7.08 (1H, m), 7.10-7.11 (1H, m), 7.49-7.55 (1H, m), 7.57-7.59 (1H, m), 7.96-7.99 (1H, m), 8.11-8.12 (1H, m), 8.34 (1H, d, J=5.3 Hz).

Example 1857

Synthesis of 3-(1-{4-cyano-5-[5-ethyl-2-(5-trifluoromethyl-pyridin-2-yl)-thiazol-4-yl]-2H-[1,2,3]triazol-2-yl}-ethoxycarbonyloxy)-2,2-dimethyl-propionic Acid benzyl ester

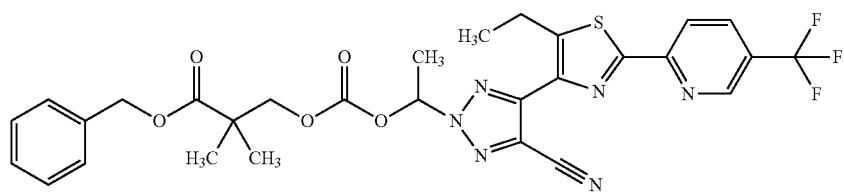 [SMILES: CCc1sc(-c2ccc(C(F)(F)F)cn2)nc1-c1nn(C(C)OC(=O)OCC(C)(C)C(=O)OCc2ccccc2)nc1C#N]

The title compound was obtained using 5-[5-ethyl-2-(5-trifluoromethyl-pyridin-2-yl)-thiazol-4-yl]-3H-[1,2,3]triazole-4-carbonitrile and 3-(1-chloro-ethoxycarbonyloxy)-2,2-dimethyl-propionic acid benzyl ester in the same manner as in Example 1836.

colorless oil

¹H-NMR (CDCl₃) δ: 1.26 (6H, s), 1.42 (3H, t, J=7.5 Hz), 2.00 (3H, d, J=6.2 Hz), 3.30 (2H, q, J=7.5 Hz), 4.21 (1H, d, J=10.4 Hz), 4.32 (1H, d, J=10.4 Hz), 5.13 (2H, d, J=2.4 Hz), 6.99 (1H, q, J=6.2 Hz), 7.28-7.36 (5H, m), 8.05 (1H, dd, J=1.9, 8.4 Hz), 8.45 (1H, d, J=8.4 Hz), 8.84-8.85 (1H, m).

Example 1858

Synthesis of 3-[1-(4-cyano-5-{3-[(E)-2-(4-trifluoromethyl-pyrimidin-2-yl)-vinyl]-phenyl}-2H-[1,2,3]triazol-2-yl)-ethoxycarbonyloxy]-2,2-dimethyl-propionic Acid allyl ester

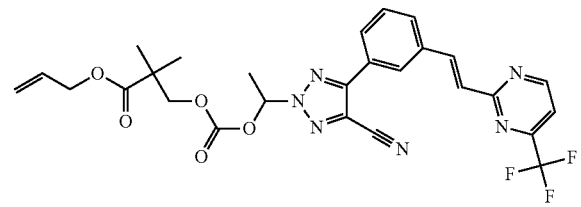 [SMILES: C=CCOC(=O)C(C)(C)COC(=O)OC(C)n1nc(C#N)c(-c2cccc(/C=C/c3nccc(C(F)(F)F)n3)c2)n1]

The title compound was obtained using 5-{3-[(E)-2-(4-trifluoromethyl-pyrimidin-2-yl)-vinyl]-phenyl}-3H-[1,2,3]triazole-4-carbonitrile and 3-(1-chloro-ethoxycarbonyloxy)-2,2-dimethyl-propionic acid allyl ester in the same manner as in Example 1836.
colorless oil
¹H-NMR (CDCl₃) δ: 1.26 (6H, s), 2.03 (3H, d, J=6.2 Hz), 4.23 (1H, d, J=10.5 Hz), 4.30 (1H, d, J=10.5 Hz), 4.57 (1H, t, J=1.4 Hz), 4.59 (1H, t, J=1.4 Hz), 5.18-5.22 (1H, m), 5.25-5.31 (1H, m), 5.82-5.92 (1H, m), 7.00 (1H, q, J=6.2 Hz), 7.40 (1H, d, J=16.0 Hz), 7.46 (1H, d, J=4.9 Hz), 7.57 (1H, t, J=7.8 Hz), 7.77 (1H, d, J=7.8 Hz), 7.99-8.03 (1H, m), 8.16 (1H, d, J=16.0 Hz), 8.27 (1H, s), 8.97 (1H, d, J=4.9 Hz).

Example 1859

Synthesis of carbonic Acid 1-[4-cyano-5-(3-(thiophen-3-yl)-5-trifluoromethylphenyl)-2H-[1,2,3]triazol-2-yl]ethyl ester ethyl ester

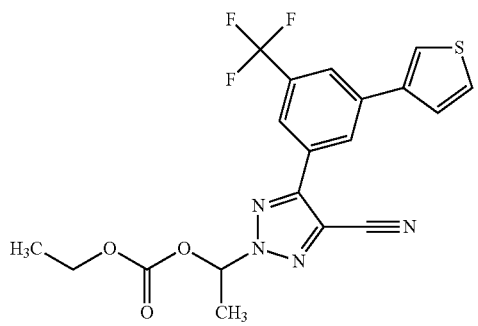 [SMILES: CCOC(=O)OC(C)n1nc(C#N)c(-c2cc(-c3ccsc3)cc(C(F)(F)F)c2)n1]

To a solution of 5-(3-(thiophen-3-yl)-5-trifluoromethylphenyl)-3H-[1,2,3]triazole-4-carbonitrile (0.19 g, 0.593 mmol) in DMF (1 ml) was added 1-chloroethyl ethyl carbonate (0.120 ml, 0.890 mmol) and sodium bicarbonate (0.150 g, 1.780 mmol). The reaction mixture was stirred at 50° C. for 6 h. Water was added to the reaction mixture, and the mixture was extracted with AcOEt. The combined organic layers were washed with brine, dried over magnesium sulfate, and concentrated in vacuo. The residue was purified by flash column chromatography (3%-30% AcOEt/hexane) to give colorless oil. The oil was precipitated with hexane and recrystallized from hexane to give the title compound (40 mg, 15%) as a colorless powder.

Melting point 79.7-83.3° C.

$^1$H-NMR (CDCl$_3$) δ: 1.34 (3H, t, J=7.1 Hz), 2.03 (3H, d, J=6.2 Hz), 4.20-4.34 (2H, m), 7.03 (1H, q, J=6.2 Hz), 7.48 (2H, d, J=2.2 Hz), 7.65 (1H, t, J=2.2 Hz), 7.93-7.94 (1H, m), 8.16-8.17 (1H, m), 8.43-8.44 (1H, m).

Example 1860

Synthesis of carbonic Acid 1-[4-cyano-5-(3-(thiophen-3-yl)-5-trifluoromethylphenyl)-2H-[1,2,3]triazol-2-yl]ethyl ester 2-hydroxyethyl ester

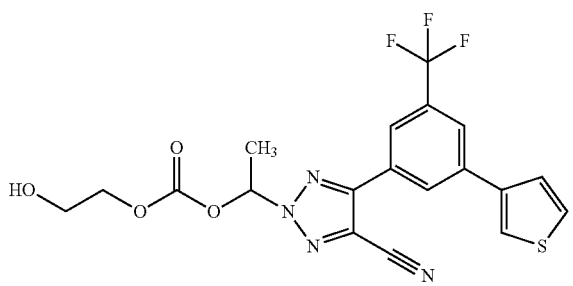 [SMILES: CC(OC(=O)OCCO)n1nc(C#N)c(-c2cc(-c3ccsc3)cc(C(F)(F)F)c2)n1]

To a solution of carbonic acid 1-[4-cyano-5-(3-(thiophen-3-yl)-5-trifluoromethyl-phenyl)-2H-[1,2,3]triazol-2-yl]- ethyl ester 2-(tetrahydro-pyran-2-yloxy)-ethyl ester (0.20 g, 0.373 mmol) in THF (2 ml) was added 1N HCl aqueous (1.118 ml, 1.118 mmol). The reaction mixture was stirred at room temperature overnight. The organic solution was concentrated. Water was added to the reaction mixture, and the mixture was extracted with AcOEt. The combined organic layers were washed with brine, dried over magnesium sulfate, and concentrated in vacuo. The residue was purified by flash column chromatography (8%-66% AcOEt/hexane) to give colorless oil. The oil was dissolved in AcOEt, precipitated with hexane, and recrystallised from AcOEt/hexane to give the title compound (60 mg, 36%) as a colorless powder.

Melting point 101.0-104.9° C.

$^1$H-NMR (CDCl$_3$) δ: 1.81 (1H, s), 2.05 (3H, d, J=6.2 Hz), 3.89 (2H, d, J=3.6 Hz), 4.27-4.41 (2H, m), 7.04 (1H, q, J=6.2 Hz), 7.48 (2H, d, J=2.2 Hz), 7.65 (1H, t, J=2.2 Hz), 7.94 (1H, d, J=0.6 Hz), 8.16 (1H, d, J=0.6 Hz), 8.42-8.44 (1H, m).

Example 1863

Synthesis of acetic Acid 4-cyano-5-(3-(thiophen-3-yl)-5-trifluoromethylphenyl)-2H-[1,2,3]triazol-2-ylmethyl ester

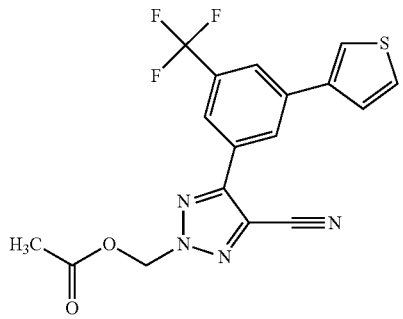 [SMILES: CC(=O)OCn1nc(C#N)c(-c2cc(-c3ccsc3)cc(C(F)(F)F)c2)n1]

To a solution of 5-(3-(thiophen-3-yl)-5-trifluoromethylphenyl)-3H-[1,2,3]triazole-4-carbonitrile (300 mg, 0.937 mmol) in DMF (3 ml) was added NaH (49.0 mg, 1.124 mmol) at 0° C. The reaction mixture was stirred at 0° C. for 0.5 hr. The reaction mixture was added chloromethyl acetate (0.278 ml, 2.81 mmol) at 0° C., and stirred at room temperature overnight. Water was added to the reaction mixture, and the resulting suspension was filtered. The obtained solid was purified by flash column chromatography (3%-30% AcOEt/hexane) to give a colorless solid. The solid was recrystallized from AcOEt/hexane to give the title compound (0.15 g, 41%) as a colorless powder.

Melting point 126.4-127.9° C.

$^1$H-NMR (CDCl$_3$) δ: 2.20 (3H, s), 6.37 (2H, s), 7.48 (2H, d, J=2.2 Hz), 7.65 (1H, t, J=2.2 Hz), 7.94-7.95 (1H, m), 8.16-8.17 (1H, m), 8.44 (1H, brs).

Example 1864

Synthesis of {1-[4-cyano-5-(3-(thiophen-3-yl)-5-trifluoromethylphenyl)-2H-[1,2,3]triazol-2-yl]ethoxycarbonylamino}acetic Acid ethyl ester

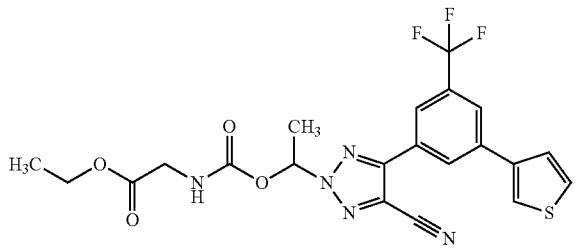 [SMILES: CCOC(=O)CNC(=O)OC(C)n1nc(C#N)c(-c2cc(-c3ccsc3)cc(C(F)(F)F)c2)n1]

To a solution of glycine ethyl ester hydrochloride (0.351 g, 2.52 mmol) in $CH_2Cl_2$ (6 ml) were added $Et_3N$ (0.702 ml, 5.04 mmol) and 1-chloroethyl chloroformate (0.228 ml, 2.098 mmol) at 0° C. The reaction mixture was stirred at 0° C. for 1.5 hr. To the reaction mixture were added 5-(3-(thiophen-3-yl)-5-trifluoromethyl-phenyl)-3H-[1,2,3]triazole-4-carbonitrile (0.470 g, 1.469 mmol), DMF (3 ml) and sodium bicarbonate (0.370 g, 4.41 mmol) at 0° C., and the reaction mixture was stirred at room temperature overnight. Water was added to the reaction mixture, and the mixture was extracted with AcOEt. The combined organic layers were washed with brine, dried over magnesium sulfate, and concentrated in vacuo. The residue was purified by flash column chromatography (6%-30% AcOEt/hexane), and then purified by thin layer chromatography (AcOEt:Hexane=1:3, twice) to give the title compound (40 mg, 4%) as a pale yellow solid.

$^1$H-NMR (CDCl$_3$) δ: 1.28 (3H, t, J=7.1 Hz), 1.98 (3H, d, J=6.2 Hz), 3.89-4.06 (2H, m), 4.22 (2H, q, J=7.1 Hz), 5.42 (1H, t, J=5.1 Hz), 7.13 (1H, q, J=6.2 Hz), 7.46-7.49 (2H, m), 7.64-7.66 (1H, m), 7.92-7.93 (1H, m), 8.16-8.17 (1H, m), 8.43 (1H, s).

Example 1889

Synthesis of carbonic Acid 1-{4-[3-(2,5-bis-trifluoromethylbenzyloxy)phenyl]-5-cyano-2H-[1,2,3]triazol-2-yl}ethyl ester ethyl ester

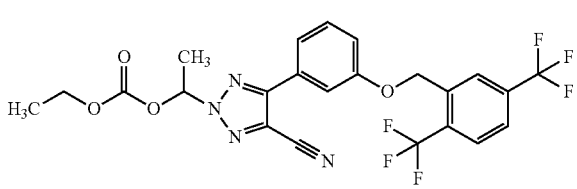 [SMILES: CCOC(=O)OC(C)n1nc(C#N)c(-c2cccc(OCc3cc(C(F)(F)F)ccc3C(F)(F)F)c2)n1]

To a solution of 5-[3-(2,5-bis-trifluoromethyl-benzyloxy)-phenyl]-3H-[1,2,3]triazole-4-carbonitrile (1 g, 2.425 mmol) in DMF (3 ml) were added 1-chloroethyl ethyl carbonate (0.652 ml, 4.85 mmol) and sodium bicarbonate (0.611 g, 7.28 mmol). The reaction mixture was stirred at 60° C. for 4 hr. After cooling to room temperature, the precipitate was filtered and washed with 20% AcOEt/Hex. The obtained solid was recrystallized from IPA to give carbonic acid 1-{4-[3-(2,5-bis-trifluoromethylbenzyloxy)phenyl]-5-cyano-2H-[1,2,3]triazol-2-yl}ethyl ester ethyl ester (0.48 g, 37%) as a colorless powder.

The filtrate of the reaction mixture was concentrated in vacuo. The obtained residue was purified by flash column chromatography (3%-28% AcOEt/hexane) to give carbonic acid 1-{4-[3-(2,5-bis-trifluoromethyl-benzyloxy)-phenyl]-5-cyano-1H-[1,2,3]triazol-1-yl}-ethyl ester ethyl ester (0.10 g, 8%) as a colorless powder and carbonic acid 1-{5-[3-(2,5-bis-trifluoromethyl-benzyloxy)-phenyl]-4-cyano-1H-[1,2,3]triazol-1-yl}-ethyl ester ethyl ester (71 mg, 6%) as a colorless oil.

carbonic Acid 1-{4-[3-(2,5-bis-trifluoromethylbenzyloxy)phenyl]-5-cyano-2H-[1,2,3]triazol-2-yl}ethyl ester ethyl ester $^1$H-NMR (CDCl$_3$) δ: 1.33 (3H, t, J=7.1 Hz), 2.01 (3H, d, J=6.2 Hz), 4.21-4.31 (2H, m), 5.36 (2H, s), 7.00 (1H, q, J=6.2 Hz), 7.10-7.13 (1H, m), 7.46 (1H, t, J=8.0 Hz), 7.63-7.64 (1H, m), 7.67-7.69 (1H, m), 7.72 (1H, d, J=8.3 Hz), 7.85 (1H, d, J=8.3 Hz), 8.09 (1H, s).

carbonic Acid 1-{4-[3-(2,5-bis-trifluoromethyl-benzyloxy)-phenyl]-5-cyano-1H-[1,2,3]triazol-1-yl}-ethyl ester ethyl ester $^1$H-NMR (CDCl$_3$) δ: 1.33 (3H, t, J=7.2 Hz), 2.10 (3H, d, J=6.3 Hz), 4.20-4.33 (2H, m), 5.37 (2H, s), 7.04 (1H, q, J=6.3 Hz), 7.11-7.16 (1H, m), 7.47 (1H, t, J=8.0 Hz), 7.71-7.72 (1H, m), 7.73-7.75 (2H, m), 7.86 (1H, d, J=8.2 Hz), 8.09 (1H, s).

carbonic Acid 1-(5-[3-(2,5-bis-trifluoromethyl-benzyloxy)-phenyl]-4-cyano-1H-[1,2,3]triazol-1-yl)-ethyl ester ethyl ester $^1$H-NMR (CDCl$_3$) δ: 1.27 (3H, t, J=7.1 Hz), 1.93 (3H, d, J=6.3 Hz), 4.14-4.24 (2H, m), 5.37 (2H, s), 6.74 (1H, q, J=6.3 Hz), 7.14-7.17 (1H, m), 7.20-7.21 (1H, m), 7.23-7.26 (1H, m), 7.56 (1H, t, J=8.0 Hz), 7.74 (1H, d, J=8.2 Hz), 7.87 (1H, d, J=8.2 Hz), 8.09 (1H, s).

Example 1899

Synthesis of 3-(1-{4-cyano-5-[4-(4-trifluoromethylpyrimidin-2-yl)phenyl]-2H-[1,2,3]triazol-2-yl}ethoxycarbonyloxy)-3-methylbutyric Acid

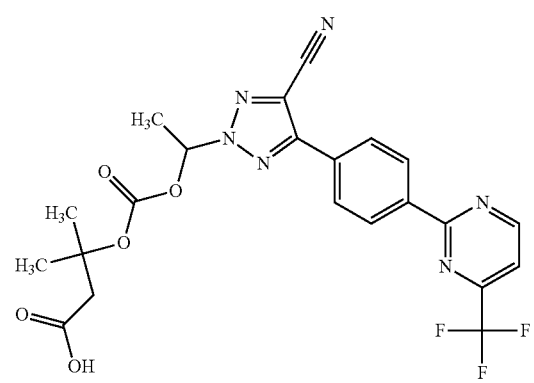 [SMILES: CC(OC(=O)OC(C)(C)CC(=O)O)n1nc(C#N)c(-c2ccc(-c3nccc(C(F)(F)F)n3)cc2)n1]

To a solution of 5-[4-(4-trifluoromethylpyrimidin-2-yl)phenyl]-3H-[1,2,3]triazole-4-carbonitrile (0.30 g, 0.949 mmol) in DMF (1.5 ml) were added 3-(1-chloroethoxycarbonyloxy)-3-methylbutyric acid benzyl ester (0.448 g, 1.423 mmol) and sodium bicarbonate (0.239 g, 2.85 mmol). The reaction mixture was stirred at 60° C. for 6 hr. Water was added to the reaction mixture, and the mixture was extracted with AcOEt. The combined organic layers were washed with brine, dried over magnesium sulfate, and concentrated in vacuo. The residue was purified by flash column chromatography (3%-30% AcOEt/hexane) to give 3-(1-{4-cyano-5-[4-(4-trifluoromethylpyrimidin-2-yl)phenyl]-2H-[1,2,3]triazol-2-yl}ethoxycarbonyloxy)-3-methylbutyric acid benzyl ester (0.36 g, 64%) as a colorless oil.

To a solution of 3-(1-{4-cyano-5-[4-(4-trifluoromethylpyrimidin-2-yl)phenyl]-2H-[1,2,3]triazol-2-yl}ethoxycarbonyloxy)-3-methylbutyric acid benzyl ester (0.35 g, 0.589 mmol) in AcOEt (4 ml) under $N_2$ was added 10% Pd/C (dry) (70 mg). The reaction mixture was stirred at room temperature for 2 hr under hydrogen. After filtration, the filtrate was concentrated to give pale yellow oil. The oil was dissolved in AcOEt, precipitated with hexane, and recrystallized from AcOEt/hexane to give the title compound (0.21 g, 71%) as a pale yellow powder.

Melting point 119.3-127.1° C.

$^1$H-NMR (CDCl$_3$) δ: 1.59 (3H, s), 1.60 (3H, s), 2.01 (3H, d, J=6.2 Hz), 2.94 (2H, s), 6.98 (1H, q, J=6.2 Hz), 7.56 (1H, d, J=5.0 Hz), 9.15-8.18 (2H, m), 8.62-8.67 (2H, m), 9.09 (1H, d, J=5.0 Hz).

The following compounds were synthesized in the same manner as in the above-mentioned Examples. The structures and physical property thereof (melting point, $^1$H-NMR data, mass spectrum etc.) are shown in the following Table 5. The "ref." in Table 5 means "Example No." or "Reference Example No." which the compound was synthesized in reference to.

TABLE 5

| Ex. No. | STR | 1H-NMR | ref. |
|---|---|---|---|
| 1861 | | 1H-NMR (CDCl3) δ: 1.28 (3H, t, J = 7.2 Hz), 2.08 (3H, d, J = 6.2 Hz), 4.19-431 (2H, m), 4.64 (1H, d, J = 15.9 Hz), 4.71 (1H, d, J = 15.9 Hz), 7.05 (1H, q, J = 6.2 Hz), 7.45-7.49 (2H, m), 7.66 (1H, t, J = 2.2 Hz), 7.94 (1H, brs), 8.17 (1H, brs), 8.44 (1H, brs). | Ex. 1859 |
| 1862 | | 1H-NMR (CDCl3) δ: 2.03 (3H, d, J = 6.2 Hz), 3.38 (3H, s), 3.63 (2H, t, J = 4.6 Hz), 4.29-4.43 (2H, m), 7.03 (1H, q, J = 6.2 Hz), 7.48 (2H, d, J = 2.2 Hz), 7.65 (1H, t, J = 2.2 Hz 7.94 (1H, d, J = 0.7 Hz), 8.16 (1H, J = 0.7 Hz), 8.43 (1H, s). | Ex. 1859 |
| 1865 | | 1H-NMR (DMSO-d6) 1.22 (3H, t, J = 7.1 Hz), 1.92.(3H, d, J = 6.1 Hz), 2.51 (3H, s), 4.15-4.22 (2H, m), 7.09 (1H, q, J = 6.2 Hz), 7.82 (1H, s), 7.87 (1H, s), 8.06 (1H, d, J = 8.2 Hz), 8.09 (1H, s), 8.41 (1H, dd, J = 8.3, 2.1 Hz), 9.13 (1H, d, J = 2.1 Hz). | Ex. 1859 |
| 1866 | | 1H-NMR (CDCl3) δ: 1.20-1.60 (6H, m ), 1.69-1.80 (2H, m), 1.87-1.99 (2H, m), 2.02 (3H, d, J = 6.2 Hz), 2.54 (3H, s), 4.65-4.70 (1H, m), 7.00 (1H, q, J = 6.1 Hz), 7.53 (1H, s), 7.79 (1H , J = 8.2 Hz), 7.91 (1H, s), 8.02 (1H, s), 8.10 (1H, dd, J = 8.1, 2.1 Hz), 6.98 (1H, d, J = 1.8 Hz). | Ex. 1859 |

TABLE 5-continued

| Ex. No. | STR | 1H-NMR | ref. |
|---|---|---|---|
| 1867 | | 1H-NMR (DMSO-d6) δ: 3.14 (3H, s), 5.09 (1H, dd, J =10.4, 7.3 Hz), 5.17 (1H, dd, J = 10.4, 2.9 Hz), 7.27 (1H, dd, J = 7.3, 2.8 Hz), 7.84 (1H, s), 7.90 (1H, s), 8.07 (1H, d, J = 8.2 Hz), 8.12 (1H, s), 8.42 (1H, dd, J = 8.1 Hz, 2.0 Hz), 8.14 (1H, d, J = 2.0 Hz). | Ex. 1863 |
| 1868 | | 1H-NMR (CDCl3) δ: 2.54 (3H, s), 6.81 (2H, s), 7.45-7.50 (2H, m), 7.54 (1H, s), 7.50-7.65 (1H, m), 7.79 (1H, d, J = 8.0 Hz), 7.91 (1H, d, J = 0.6 Hz), 8.03 (1H, s), 8.08-8.11 (3H, m), 8.98 (1H, d, J = 2.0 Hz). | Ex. 1863 |
| 1869 | | 1H-NMR (DMSO-d6) δ: 1.22 (3H, t, J = 7.1 Hz), 1.92 (3H, d, J = 6.1 Hz), 4.16-4.23 (2H, m), 7.11 (1H, q, J = 6.1 Hz), 7.85 (1 H, t, J = 7.8 Hz), 8.05 (1H , d, J = 5.3 Hz), 8.15-8.18 (1H, m), 8.57-8.60 (1H, m), 9.01 (1H, t, J = 1.6 Hz), 9.36 (1H, d, J = 5.1 Hz). | Ex. 1859 |
| 1870 | | 1H-NMR (DMSO-d6) δ: 1.93 (3H, d, J = 6.1 Hz), 3.23 (3H, s), 3.53 (2H, t, J = 4.5 Hz), 4.22-4.30 (2H, m), 7.12 (1H, q, J = 6.1 Hz), 7.85 (1H, t, J = 7.9 Hz), 8.05 (1H, d, J = 5.1 Hz), 6.15-8.18 (1H, m), 8.58-8.60 (1H, m), 9.00-9.02 (1H, m), 9.38 (1H, d, J = 5.1 Hz). | Ex. 1859 |
| 1871 | | 1H-NMR (DMSO-d6) δ: 1.17-1.49 (6H, m), 1.58-1.69 (2H, m), 1.77-1.90 (2H, m), 1.92 (3H, d, J = 6.1 Hz), 4.57-4.63 (1H, m), 7.10 (1H, q, J = 6.1 Hz), 7.85 (1H, t, J = 7.9 Hz), 8.05 (1H , d, J = 5.1 Hz), 8.15-8.18 (1H, m), 8.57-8.61 (1H, m), 9.01 (1H, t, J = 1.6 Hz), 9.35 (1H, d, J = 6.0 Hz). | Ex. 1859 |
| 1872 | | 1H-NMR (DMSO-d6) δ: 2.15 (3H, s), 6.49 (2H, s), 7.85 (1H, t, J = 7.9 Hz), 8.05 (1H, d, J = 5.0 Hz), 8.15-8.18 (1H, m), 8.57-8.60 (1H, m), 9.01 (1H, t, J = 1.7 Hz), 8.35 (1H, d, J = 5.0 Hz). | Ex. 1863 |

TABLE 5-continued

| Ex. No. | STR | 1H-NMR | ref. |
|---|---|---|---|
| 1873 | | 1H-NMR (DMSO-d6) δ: 1.18 (9H, s), 6.62 (2H, s), 7.85 (1H, t, J = 7.7 Hz), 8.15-8.18 (1H, m), 8.05 (1H, d, J = 5.0 Hz), 8.58-8.60 (1H, m), 9.01 (1H, t, J = 1.7 Hz), 9.35 (1H, d, J = 5.0 Hz). | Ex. 1863 |
| 1874 | | 1H-NMR (DMSO-d6) δ: 0.88 (3H, t, J = 7.4 Hz), 1.53-1.61 (2H, m), 2.42 (2H, t, J = 7.2 Hz), 6.52 (2H, s), 7.85 (1H, t, J = 7.9 Hz), 8.05 (1H, d, J = 5.1 Hz), 8.14-8.18 (1H, m), 8.59 (1H, dt, J = 8.1, 1.4 Hz), 9.01 (1H, t, J = 1.7 Hz), 9.35 (1H, d, J = 5.0 Hz). | Ex. 1863 |
| 1875 | | 1H-NMR (DMSO-d6) δ: 1.22 (3H, t, J = 7.1 Hz), 1.92 (3H, d, J = 6.2 Hz), 2.54 (3H, s), 4.14-4.24 (2H, m), 7.10 (1H, q, J = 6.2 Hz), 7.97 (1H, s), 8.04 (1H, d, J = 4.9 Hz), 8.41 (1H, s), 8.83 (1H, s), 9.34 (1H, d, J = 4.9 Hz). | Ex. 1859 |
| 1876 | | 1H-NMR (DMSO-d6) δ: 1.16-1.50 (6H, m), 1.58-1.69 (2H, m), 1.77-1.90 (2H, m), 1.92 (3H, d, J = 6.2 Hz), 2.54 (3H, s), 4.57-4.64 (1H, m), 7.09 (1H, q, J = 6.2 Hz), 7.97 (1H, s), 8.04 (1H, d, J = 5.0 Hz), 8.41 (1H, s), 8.83 (1H, s), 9.34 (1H, d, (J = 4.9 Hz). | Ex. 1859 |
| 1877 | | 1H-NMR (DMSO-d6) δ: 2.55 (3H, s), 5.09 (1H, dd, J = 10.4, 7.1 Hz), 5.16 (1H, dd, J = 10.4, 2.8 Hz), 7.30 (1H, dd, J = 7.1, 2.8 Hz), 7.98 (1H, s), 8.04 (1H, d, J = 5.0 Hz), 8.43 (1H, s), 8.84 (1H, s), 9.34 (1H, d, J = 5.0 Hz). | Ex. 1863 |
| 1878 | | 1H-NMR (DMSO-d6) δ: 2.15 (3H, s), 2.54 (3H, s), 6.48 (2H, s), 7.97 (1H, s), 8.04 (1H, d, J = 5.0 Hz), 6.41 (1H, s), 8.83 (1H, s), 9.34 (1H, d, J = 5.0 Hz). | Ex. 1863 |

TABLE 5-continued

| Ex. No. | STR | 1H-NMR | ref. |
|---|---|---|---|
| 1880 | | 1H-NMR (CDCl3) δ: 1.33 (3H, t, J = 7.1 Hz), 1.99 (3H, d, J = 6.3 Hz), 4.04 (2H, s), 4.21-4.31 (2H, m), 6.97-7.04 (3H, m), 7.12 (1H, s), 7.15-7.19 (2H, m), 7.70 (1H, s), 7.76 (1H, s). | Ex. 1859 |
| 1881 | | 1H-NMR (CDCl3) δ: 1.21-1.58 (6H, m), 1.70-1.80 (2H, m), 1.86-1.97 (2H, m), 1.99 (3H, d, J = 6.3 Hz), 4.04 (2H, s), 4.63-4.70 (1H, m), 6.94-7.04 (3H, m), 7.12 (1H, s), 7.15-7.19 (2H, m), 7.70 (1H, s), 7.77 (1H, s). | Ex. 1859 |
| 1882 | | 1H-NMR (CDCl3) δ: 4.04 (2H, s), 6.58 (2H, s), 7.01 (2H, t, J = 8.7 Hz), 7.13 (1H, s), 7.14-7.18 (1H, m), 7.44-7.50 (3H, m), 7.62 (1H, t, J = 7.5 Hz), 7.71 (1H, s), 7.77 (1H, s), 8.05-8.09 (2H, m). | Ex. 1863 |
| 1883 | | 1H-NMR (CDCl3) δ: 0.95 (3H, t, J = 7.4 Hz), 1.65-1.72 (2H, m), 2.40 (2H, t, J = 7.4 Hz), 4.04 (2H, s), 6.33 (2H, s), 7.02 (2H, t, J = 8.6 Hz), 7.13 (1H, s), 7.15-7.19 (2H, m), 7.70 (1H, s), 7.76 (1H, s). | Ex. 1863 |
| 1884 | | 1H-NMR (DMSO-d6) δ: 1.22 (3H, t, J = 7.0 Hz), 1.92 (3H, d, J = 6.1 Hz), 4.14-4.24 (2H, m), 7.08 (1H, q, J = 6.1 Hz), 7.60 (2H, s), 7.63-7.68 (2H, m), 7.84 (1H, t, J = 1.6 Hz), 7.96 (1H, d, J = 7.1 Hz), 8.00 (1H, t, J = 1.6 Hz), 8.03-8.06 (2H, m). | Ex.1859 |

TABLE 5-continued

| Ex. No. | STR | 1H-NMR | ref. |
|---|---|---|---|
| 1885 | | 1H-NMR (DMSO-d6) δ: 1.17-1.50 (6H, m), 1.59-1.69 (2H, m), 1.77-1.90 (2H, m), 1.92 (3H, d, J = 6.1 Hz), 4.57-4.64 (1H, m), 7.07 (1H, q, J = 6.1 Hz), 7.59 (2H, s), 7.62-7.69 (2H, m), 7.83 (1H, t, J = 1.6 Hz), 7.96 (1H, d, J = 6.9 Hz), 8.00 (1H, t, J = 1.6 Hz), 8.03 (1H, s), 8.05 (1H, t, J = 1.4 Hz). | Ex. 1859 |
| 1886 | | 1H-NMR (DMSO-d6) δ: 5.10 (1H, dd, J = 10.3, 7.3 Hz), 5.17 (1H, dd, J = 10.3, 2.9 Hz), 7.27 (1H, dd, J = 7.2, 2.8 Hz), 7.6 (2H, s), 7.63-7.70 (2H, m), 7.85-7.87 (1H, m), 7.96 (1H, d, J = 8.9 Hz), 8.02-8.07 (3H, m). | Ex. 1863 |
| 1887 | | 1H-NMR (DMSO-d6) δ: 2.15 (3H, s), 6.47 (2H, s), 7.60 (2H, s), 7.64-7.69 (2H, m), 7.83 (1H, t, J = 1.6 Hz), 7.96 (1H, d, J = 7.1 Hz), 8.00 (1H, t, J = 1.6 Hz), 8.04 (1H, s), 8.04-8.06 (1H, m). | Ex. 1863 |
| 1888 | | 1H-NMR (DMSO-d6) δ: 6.76 (2H, s), 7.57 (2H, d, J = 7.7 Hz), 7.59 (2H, s), 7.62-7.69 (2H, m), 7.73 (1H, t, J = 7.4 Hz), 7.64 (1H, s), 7.96 (1H, d, J = 6.8 Hz), 8.00 (1H, s), 8.01-8.05 (3H, m), 8.06 (1H, s). | Ex. 1863 |
| 1892 | | 1H-NMR (CDCl3) δ: 2.02 (3H, d, J = 6.2 Hz), 2.50 (4H, brs), 2.66 (2H, brs), 3.69 (4H, brs), 4.33 (2H, brs), 5.36 (2H, s), 7.00 (1H, q, J = 6.2 Hz), 7.10-7.13 (1H, m), 7.46 (1H, t, J = 8.0 Hz), 7.63-7.64 (1H, m), 7.56-7.69 (1H, m), 7.73 (1H, d, J = 8.0 Hz), 7.86 (1H, d, J = 8.0 Hz), 8.09 (1H, s). | Ex. 1864 |
| 1893 | | 1H-NMR (CDCl3) δ: 1.27 (3H, t, J = 7.1 Hz), 2.05 (3H, d, J = 6.2 Hz), 4.24 (2H, q, J = 7.1 Hz), 4.62 (1H, d, J = 15.8 Hz), 4.72 (1H, d, J = 15.8 Hz), 5.37 (2H, s), 7.02 (1H, q, J = 6.2 Hz), 7.10-7.13 (1H, m), 7.46 (1H, t, J = 8.0 Hz), 7.64 (1H, t, J = 1.6 Hz), 7.67-7.69 (1H, m), 7.72-7.74 (1H, m), 7.85 (1H, d, J = 8.2 Hz), 8.09 (1H, s). | Ex. 1859 |

TABLE 5-continued

| Ex. No. | STR | 1H-NMR | ref. |
|---|---|---|---|
| 1894 | | 1H-NMR (CDCl3) δ: 2.02 (3H, d, J = 6.2 Hz), 3.38 (3H, s), 3.62 (2H, t, J = 4.6 Hz), 4.26-4.42 (2H, m), 5.36 (2H, s), 7.00 (1H, q, J = 6.2 Hz), 7.10-7.13 (1H, m), 7.46 (1H, t, J = 8.0 Hz), 7.62-7.63 (1H, m), 7.67-7.69 (1H, m), 7.73 (1H, d, J = 8.4 Hz), 7.86 (1H, d, J = 8.4 Hz), 8.09 (1H, s). | Ex. 1859 |
| 1895 | | 1H-NMR (CDCl3) δ: 2.28 (1H, t, J = 6.3 Hz), 4.21-4.29 (2H, m), 4.64-4.71 (2H, m), 5.36 (2H, s), 7.09-7.12 (1H, m), 7.46 (1H, t, J = 8.0 Hz), 7.60-7.61 (1H, m), 7.65-7.67 (1H, m), 7.72 (1H, d, J = 8.2 Hz), 7.85 (1H, d, J = 8.2 Hz), 8.09 (1H, s). | Ex. 1863 |
| 1896 | | 1H-NMR (CDCl3) δ: 4.31 (3H, s), 5.36 (2H, s), 7.09-7.11 (1H, m), 7.46 (1H, t, J = 8.1 Hz), 7.61 (1H, s), 7.65 (1H, d, J = 7.7 Hz), 7.73 (1H, d, J = 7.7 Hz), 7.86 (1H, d, J = 8.1 Hz), 8.10 (1H, s). | Ex. 1863 |
| 1897 | | 1H-NMR (CDCl3) δ: 1.34 (3H, t, J = 7.1 Hz), 2.02 (3H, d, J = 6.2 Hz), 4.21-4.31 (2H, m), 7.03 (1H, q, J = 6.2 Hz), 7.56 (1H, d, J = 5.0 Hz), 8.16-8.19 (2H, m), 8.64-8.68 (2H, m), 9.09 (1H, d, J = 5.0 Hz). | Ex. 1859 |
| 1898 | | 1H-NMR (CDCl3) δ: 1.27 (6H, s), 2.03 (3H, d, J = 6.2 Hz), 4.21 (1H, d, J = 10.5 Hz), 4.31 (1H, d, J = 10.5 Hz), 7.01 (1H, q, J = 6.2 Hz), 7.57 (1H, d, J = 5.0 Hz), 8.15-8.18 (2H, m), 8.64-8.68 (2H, m), 9.09 (1H, d, J = 5.0 Hz). | Ex. 1899 |

TABLE 5-continued

| Ex. No. | STR | 1H-NMR | ref. |
| --- | --- | --- | --- |
| 1900 | | 1H-NMR (CDCl3) δ: 4.34 (3H, s), 7.56 (1H, d, J = 5.0 Hz), 8.08-8.22 (2H, m), 6.58-6.71 (2H, m), 9.08 (1H, d, J = 5.0 Hz). | Ex. 1863 |
| 1901 | | 1H-NMR (CDCl3) δ: 2.20 (3H, s), 6.38 (2H, s), 7.57 (1H, d, J = 5.0 Hz), 8.16-8.19 (2H, m), 8.68-8.69 (2H, m), 9.10 (1H, d, J = 5.0 Hz). | Ex. 1863 |
| 1902 | | 1H-NMR (CDCl3) δ: 1.33 (3H, t, J = 7.1 Hz), 2.02 (3H, d, J = 6.2 Hz), 2.83 (3H, s), 4.22-4.32 (2H, m), 7.03 (1H, q, J = 6.2 Hz), 7.71 (2H, d, J = 8.2 Hz), 8.11 (2H, d, J = 8.2 Hz). | Ex. 1859 |
| 1903 | | 1H-NMR (CDCl3) δ: 1.26 (3H, s), 1.27 (3H, s), 2.03 (3H, d, J = 6.2 Hz), 2.81 (3H, s), 4.22 (1H, d, J = 10.6 Hz), 4.27 (1H, d, J = 10.6 Hz), 7.01 (1H, q, J = 6.3 Hz), 7.72 (2H, d, J = 8.3 Hz), 7.85 (2H, d, J = 8.3 Hz). | Ex. 1899 |
| 1904 | | 1H-NMR (CDCl3) δ: 1.16 (3H, t, J = 7.3 Hz), 1.94 (3H, d, J = 6.2 Hz), 3.19-3.33 (2H, m), 4.64 (1H, s), 7.12 (1H, q, J = 6.2 Hz), 7.56 (1H, d, J = 5.0 Hz), 8.16-8.18 (2H, m), 8.64-8.97 (2H, m), 9.09 (1H, d, J = 5.0 Hz). | Ex. 1864 |

TABLE 5-continued

| Ex. No. | STR | 1H-NMR | ref. |
|---|---|---|---|
| 1905 | | 1H-NMR (DMSO-d6) δ: 1.12-1.43 (6H, m), 1.50-1.68 (3H, m), 1.74-1.86 (2H, m), 1.89 (3H, d, J = 6.1 Hz), 2.81 (3H, s), 7.19 (1H, q, J = 6.1 Hz), 7.94 (2H, d, J = 8.2 Hz), 8.19 (2H, d, J = 8.2 Hz). | Ex. 1559 |
| 1906 | | 1H-NMR (DMSO-d6) δ: 2.15 (3H, s), 2.82 (3H, s), 6.47 (2H, s), 7.94 (2H, d, J = 8.3 Hz), 8.19 (2H, d, J = 8.3 Hz). | Ex. 1863 |
| 1907 | | 1H-NMR (DMSO-d6) δ: 0.97 (3H, t, J = 7.5 Hz), 1.52-1.60 (2H, m), 2.42 (2H, t, J = 7.2 Hz), 2.81 (3H, s), 8.50 (2H, s), 7.94 (2H, d, J = 8.4 Hz), 8.19 (2H, d, J = 8.4 Hz). | Ex. 1863 |
| 1908 | | 1H-NMR (DMSO-d6) δ: 1.19-1.25 (7H, m), 1.91 (3H, d, J = 6.2 Hz), 2.58-2.65 (1H, m), 4.14-4.23 (2H, m), 7.06 (1H, q, J = 6.2 Hz), 7.58-7.65 (2H, m), 7.91-7.97 (2H, m). | Ex. 1859 |
| 1909 | | 1H-NMR (DMSO-d6) δ: 1.16-1.50 (10H, m), 1.58-1.69 (2H, m), 1.75-1.89 (2H, m), 1.90 (3H, d, J = 6.1 Hz), 2.57-2.65 (1H, m), 4.56-4.63 (1H, m), 7.05 (1H, q, J = 6.1 Hz), 7.59-7.65 (2H, m), 7.91-7.97 (2H, m). | Ex. 1859 |
| 1910 | | 1H-NMR (DMSO-d6) δ: 1.19-1.26 (4H, m), 2.14 (3H, s), 2.57-2.65 (1H, m), 6.44 (2H, s), 7.59-7.65 (2H, m), 7.91-7.96 (2H, m). | Ex. 1863 |

TABLE 5-continued

| Ex. No. | STR | 1H-NMR | ref. |
|---|---|---|---|
| 1911 | | 1H-NMR (DMSO-d6) δ: 1.18-1.24 (4H, m), 2.58-2.65 (1H, m), 6.73 (2H, s), 7.54-7.65 (4H, m), 7.71-7.78 (1H, m), 7.91-7.97 (2H, m), 8.00-8.05 (2H, m). | Ex. 1863 |
| 1912 | | 1H-NMR (DMSO-d6) δ: 1.12-1.42 (9H, m), 1.51-1.69 (3H, m), 1.74-1.85 (2H, m), 1.88 (3H, d, J = 6.1 Hz), 2.35-2.46 (1H, m), 2.56-2.65 (1H, m), 7.14-7.19 (1H, m), 7.59-7.66 (2H, m), 7.90-7.97 (2H, m). | Ex. 1859 |
| 1913 | | 1H-NMR (DMSO-d6) δ: 1.20 (3H, t, J = 7.1 Hz), 1.75 (3H, d, J = 6.2 Hz), 4.09-4.19 (2H, m), 6.94 (1H, q, J = 6.2 Hz), 7.58 (1H, d, J = 5.2 Hz), 8.03-8.06 (3H, m), 8.12 (1H, s). | Ex. 1859 |
| 1914 | | 1H-NMR (DMSO-d6) δ: 1.16-1.50 (6H, m), 1.58-1.67 (2H, m), 1.75 (3H, d, J = 6.1 Hz), 1.77-1.87 (2H, m), 4.52-4.58 (1H, m), 6.94 (1H, q, J = 6.1 Hz), 7.59 (1H, d, J = 5.2 Hz), 8.02-8.06 (3H, m), 8.12 (1H, s). | Ex. 1859 |

TABLE 5-continued
| Ex. No. | STR | 1H-NMR | ref. |
|---|---|---|---|
| 1915 | 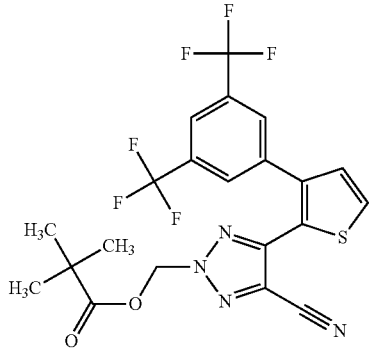 | 1H-NMR (DMSO-d6) δ: 1.12 (9H, s), 6.40 (2H, s), 7.60 (1H, d, J = 5.2 Hz), 8.00 (2H, s), 8.06 (1H, d, J = 5.2 Hz), 8.13 (1H, s). | Ex. 1863 |
| 1916 | 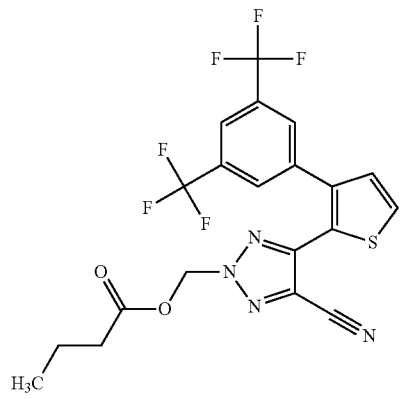 | 1H-NMR (DMSO-d6) δ: 0.85 (3H, t, J = 7.4 Hz), 1.49-1.56 (2H, m), 2.35 (2H, t, J = 7.3 Hz), 6.38 (2H, s), 7.59 (1H, d, J = 7.1 Hz), 8.03 (2H, s), 8.05 (1H, d, J = 5.0 Hz), 8.12 (1H, s). | Ex. 1863 |
| 1917 | 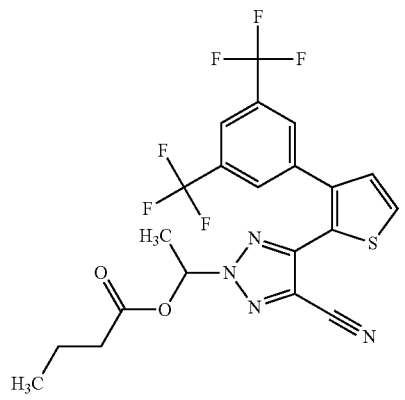 | 1H-NMR (DMSO-d6) δ: 0.92 (3H, t, J = 7.4 Hz), 1.59-1.67 (2H, m), 1.82 (3H, d, J = 6.2 Hz), 2.29-2.33 (2H, m), 7.03 (1H, q, J = 6.2 Hz), 7.27 (1H, d, J = 5.2 Hz), 7.64 (1H, d, J = 5.2 Hz), 7.82 (2H, s), 7.86 (1H, s). | Ex. 1859 |
| 1918 | 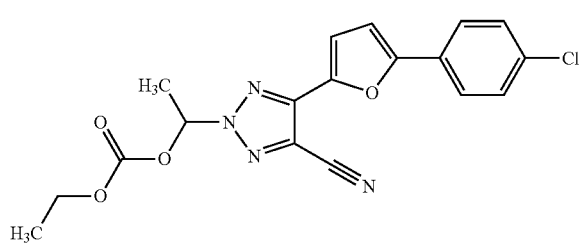 | 1H-NMR (DMSO-d6) δ: 1.22 (3H, t, J = 7.1 Hz), 1.89 (3H, d, J = 6.2 Hz), 4.15-4.22 (2H, m), 7.05 (1H, d, J = 6.2 Hz), 7.30 (1H, d, J = 3.6 Hz), 7.32 (1H, d, J = 3.6 Hz), 7.58 (2H, d, J = 8.6 Hz), 7.85 (2H, d, J = 8.6 Hz). | Ex. 1859 |

TABLE 5-continued

| Ex. No. | STR | 1H-NMR | ref. |
| --- | --- | --- | --- |
| 1919 | | 1H-NMR (DMSO-d6) δ: 1.18-1.50 (6H, m), 1.58-1.68 (2H, m), 1.76-1.87 (2H, m), 1.88 (3H, d, J = 6.2 Hz), 4.56-4.62 (1H, m), 7.03 (1H, q, J = 6.2 Hz), 7.29 (1H, d, J = 3.7 Hz), 7.33 (1H, d, J = 3.7 Hz), 7.58 (2H, d, J = 8.6 Hz), 7.85 (2H, d, J = 8.6 Hz). | Ex. 1859 |
| 1920 | | 1H-NMR (DMSO-d6) δ: 1.16 (9H, s), 6.47 (2H, s), 7.29 (1H, d, J = 3.6 Hz), 7.33 (1H, d, J = 3.6 Hz), 7.59 (2H, d, J = 8.5 Hz), 7.85 (2H, d, J = 8.5 Hz). | Ex. 1863 |
| 1921 | | 1H-NMR (DMSO-d6) δ: 0.87 (3H, t, J = 7.4 Hz), 1.52-1.59 (2H, m), 2.41 (2H, t, J = 7.2 Hz), 6.46 (2H, s), 7.29 (1H, d, J = 3.6 Hz), 7.33 (1H, d, J = 3.6 Hz), 7.59 (2H, d, J = 8.6 Hz), 7.86 (2H, d, J = 8.6 Hz). | Ex. 1863 |
| 1922 | | 1H-NMR (CDCl3) δ: 2.20 (1H, brs), 4.26 k(2H, t, J = 5.0 Hz), 4.67-4.74 (2H, m), 7.47 (2H, d, J = 2.2 Hz), 7.64 (1H, t, J = 2.2 Hz), 7.90-7.93 (1H, m), 8.13-8.14 (1H, m), 8.41-8.43 (1H, m). | Ex. 1863 |
| 1923 | | 1H-NMR (CDCl3) δ: 1.16 (3H, t, J = 7.3 Hz), 1.94 (3H, d, J = 6.2 Hz), 3.18-3.33 (2H, m), 4.85 (1H, s), 7.12 (1H, q, J = 6.2 Hz), 7.48 (2H, d, J = 2.2 Hz), 7.64 (1H, t, J = 2.2 Hz), 7.93 (1H, s), 8.13-8.16 (1H, m), 8.43 (1H, s). | Ex. 1854 |

TABLE 5-continued

| Ex. No. | STR | 1H-NMR | ref. |
|---|---|---|---|
| 1924 | | 1H-NMR (CDCl3) δ: 2.31 (1H, brs), 4.25 (2H, t, J = 4.8 Hz), 4.66-4.75 (2H, m), 7.57 (1H, d, J = 4.9 Hz), 8.10-8.16 (2H, m), 8.65-8.68 (2H, m), 9.09 (1H, d, J = 4.9 Hz). | Ex. 1863 |
| 1925 | | 1H-NMR (DMSO) δ: 2.80 (3H, s), 4.37 (3H, s), 7.92 (2H, d, J = 8.3 Hz), 8.16 (2H, d, J = 8.3 Hz). | Ex. 1863 |
| 1926 | | 1H-NMR (CDCl3) δ: 1.57 (3H, s), 1.58 (3H, s), 1.95 (3H, d, J = 6.2 Hz), 2.90 (1H, d, J = 14.4 Hz), 3.03 (1H, d, J = 14.4 Hz), 5.10 (2H, s), 6.93 (1H, q, J = 6.2 Hz), 7.30-7.38 (5H, m), 7.56 (1H, d, J = 5.0 Hz), 8.13-8.18 (2H, m), 8.64-8.68 (2H, m), 9.09 (1H, d, J = 5.0 Hz). | Ex. 1859 |
| 1927 | | 1H-NMR (CDCl3) δ: 1.26 (6H, s), 2.00 (3H, d, J = 6.2 Hz), 4.22 (1H, d, J = 10.4 Hz), 4.32 (1H, d, J = 10.4 Hz), 5.13 (2H, d, J = 2.3 Hz), 6.98 (1H, q, J = 6.2 Hz), 7.28-7.44 (5H, m), 7.57 (1H, d, J = 4.9 Hz), 8.15-8.18 (2H, m), 8.64-8.68 (2H, m), 9.09 (1H, d, J = 4.9 Hz). | Ex. 1859 |
| 1928 | | 1H-NMR (CDCl3) δ: 1.42-1.52 (2H, m), 1.53-1.59 (2H, m), 1.66-1.86 (2H, m), 2.04 (3H, d, J = 6.2 Hz), 3.47-3.52 (1H, m), 3.63-3.75 (1H, m), 3.76-3.84 (1H, m), 3.88-3.99 (1H, m), 4.32-4.47 (2H, m), 4.61-4.63 (1H, m), 7.04 (1H, q, J = 6.2 Hz), 7.45-7.50 (2H, m), 7.55 (1H, t, J = 2.2 Hz), 7.94 (1H, s), 8.16 (1H, d, J = 0.4 Hz), 8.44 (1H, s). | Ex. 1859 |
| 1929 | | 1H-NMR (CDCl3) δ: 4.13 (2H, s), 7.07-7.17 (7H, m), 7.26-7.44 (13H, m), 7.81-7.85 (2H, m). | Ex. 1833 |

TABLE 5-continued

| Ex. No. | STR | 1H-NMR | ref. |
|---|---|---|---|
| 1930 | | 1H-NMR (CDCl3) δ: 5.36 (2H, s), 5.76 (2H, s), 7.10-7.13 (1H, m), 7.46 (1H, t, J = 8.2 Hz), 7.56 (1H, s), 7.64-7.73 (2H, m), 7.84-7.92 (4H, m), 8.08 (1H, s). | Ex. 1829 |
| 1931 | | 1H-NMR (CDCl3) δ: 5.93 (1H, bs), 7.13-7.16 (7H, m), 7.28-7.39 (9H, m), 7.61 (1H, s), 7.75 (1H, s). | Ex. 1859 |
| 1932 | | 1H-NMR (CDCl3) δ: 5.20 (2H, s), 7.11-7.14 (6H, m), 7.26-7.39 (10H, m), 7.53-7.57 (2H, m), 7.64-7.67 (2H, m), 7.72 (1H, s), 7.78 (1H, s). | Ex. 1859 |
| 1933 | | 1H-NMR (CDCl3) δ: 7.12-7.17 (6H, m), 7.26-7.40 (9H, m), 7.62-7.67 (1H, m), 7.95-8.00 (1H, m), 8.20-8.25 (1H, m), 8.40 (1H, s), 10.06 (1H, s) | Ex. 1859 |

TABLE 5-continued

| Ex. No. | STR | 1H-NMR | ref. |
|---|---|---|---|
| 1934 | | 1H-NMR (CDCl3) δ: 1.77 (1H, br. s), 4.75 (2H, br. s), 7.10-7.18 (6H, m), 7.29-7.39 (9H, m), 7.44-7.49 (2H, m), 7.85-7.93 (2H, m). | Ref. Ex. 19 |
| 1935 | | 1H-NMR (CDCl3) δ: 2.99 (3H, s), 5.28 (2H, s), 7.11-7.16 (6H, m), 7.32-7.42 (9H, m), 7.48-7.54 (2H, m), 7.95 (1H, s), 7.96-7.99 (1H, m). | Ref. Ex. 103 |
| 1936 | | 1H-NMR (CDCl3) δ: 3.23 (2H, d, J = 16.8 Hz), 3.47 (2H, dd, J = 6.1, 16.8 Hz), 5.26 (1H, bs), 7.15-7.43 (20H, m), 7.70 (1H, s), 7.76 (1H, s). | Ref. Ex. 80 |
| 1937 | | 1H-NMR (CDCl3) δ: 2.21-2.23 (1H, m), 2.60-2.72 (1H, m), 2.98-3.07 (1H, m), 3.18-3.28 (1H, m), 5.87-5.91 (1H, m), 7.16-7.19 (6H, m), 7.33-7.40 (14H, ml), 7.81 (2H, s). | Ref. Ex. 80 |

TABLE 5-continued

| Ex. No. | STR | 1H-NMR | ref. |
|---|---|---|---|
| 1938 | | 1H-NMR (CDCl3) δ: 1.05 (3H, s), 1.36-1.55 (10H, m), 3.72 (2H, s), 7.12-7.20 (7H, m), 7.33-7.39 (9H, m), 7.64 (1H, s), 7.71 (1H, s). | Ref. Ex. 80 |
| 1939 | | 1H-NMR (CDCl3) δ: 0.97-1.05 (4H, m), 4.06 (2H, s), 7.11-7.14 (7H, m), 7.24-7.40 (13H, m), 7.57 (1H, s), 7.67 (1H, s). | Ref. Ex. 80 |
| 1940 | | 1H-NMR (CDCl3) δ: 1.04 (4H, s), 4.12 (2H, s), 7.12-7.15 (8H, m), 7.30-7.42 (13H, m), 7.60 (1H, s), 7.71 (1H, s). | Ref. Ex. 80 |
| 1941 | | 1H-NMR (CDCl3) δ: 1.80-1.89 (1H, m), 2.02-2.20 (3H, m), 2.82-2.92 (2H, m), 5.46-5.49 (1H, m), 7.13-7.38 (20H, m), 7.78 (2H, s). | Ref. Ex. 80 |

TABLE 5-continued
| Ex. No. | STR | 1H-NMR | ref. |
|---|---|---|---|
| 1942 | 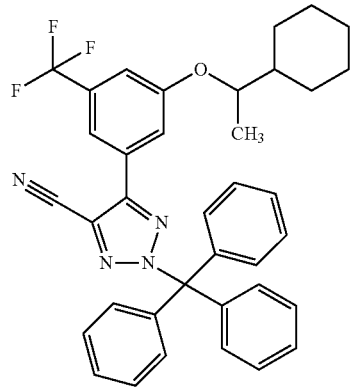 | 1H-NMR (CDCl3) δ: 1.07-1.31 (11H, m), 1.68-1.93 (3H, m), 4.18-4.25 (1H, m), 7.13-7.16 (7H, m), 7.26-7.37 (9H, m), 7.61 (1H, s), 7.69 (1H, s). | Ref. Ex. 80 |
| 1943 | 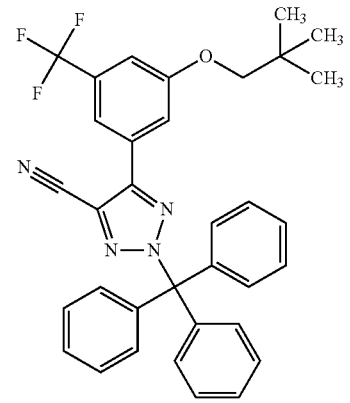 | 1H-NMR (CDCl3) δ: 1.07 (9H, s), 3.69 (2H, s), 7.14-7.17 (7H, m), 7.30-7.40 (9H, m), 7.68 (1H, s), 7.74 (1H, s). | Ref. Ex. 80 |
| 1944 | 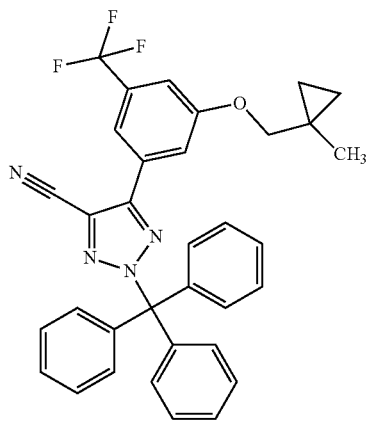 | 1H-NMR (CDCl3) δ: 0.47-0.57 (4H, m), 1.27 (3H, s), 3.81 (2H, s) 7.13-7.16 (7H, m), 7.33-7.39 (9H, m), 7.65 (1H, s), 7.73 (1H, s). | Ref. Ex. 80 |

TABLE 5-continued

| Ex. No. | STR | 1H-NMR | ref. |
|---|---|---|---|
| 1945 | | 1H-NMR (CDCl3) δ: 1.13-1.22 (4H, m), 4.15 (2H, s), 7.13-7.16 (7H, m), 7.30-7.40 (9H, m), 7.64 (1H, s), 7.78 (1H, s). | Ref. Ex. 80 |

The following compounds were synthesized in the same manner as in the above-mentioned Examples. The structures and physical property thereof (melting point, ¹H-NMR data, mass spectrum etc.) are shown in the following Table 6. The "ref." in Table 6 means "Example No." or "Reference Example No." which the compound was synthesized in reference to.

TABLE 6

| Ex. No. | STR | MS (M + H) |
|---|---|---|
| 1946 | | 185 |
| 1947 | | 189 |
| 1948 | | 263 |
| 1949 | | 277 |

TABLE 6-continued

| Ex. No. | STR | MS (M + H) |
|---|---|---|
| 1950 | | 221 |
| 1951 | | 217 |
| 1952 | | 293 |
| 1953 | | 224 |
| 1954 | | 201 |
| 1955 | | 231 |

TABLE 6-continued

| Ex. No. | STR | MS (M + H) |
|---|---|---|
| 1956 | | 215 |
| 1957 | | 229 |
| 1958 | | 213 |
| 1959 | | 227 |
| 1960 | | 279 |
| 1961 | | 215 |

TABLE 6-continued

| Ex. No. | STR | MS (M + H) |
|---|---|---|
| 1962 | | 259 |
| 1963 | | 242 |
| 1964 | | 272 |
| 1965 | | 205 |
| 1966 | | 189 |
| 1967 | | 239 |

TABLE 6-continued
| Ex. No. | STR | MS (M + H) |
|---|---|---|
| 1968 | 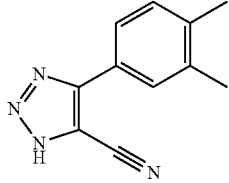 | 199 |
| 1969 | 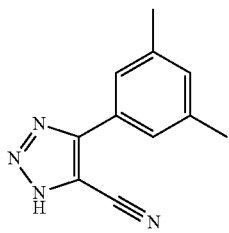 | 199 |
| 1970 |  | 199 |
| 1971 | 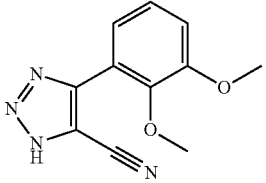 | 231 |
| 1972 | 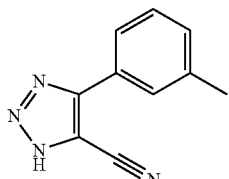 | 185 |
| 1973 | 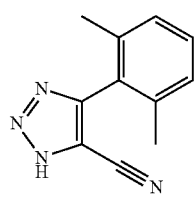 | 199 |
| 1974 | 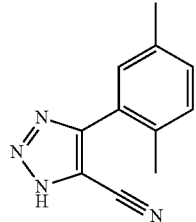 | 199 |

TABLE 6-continued

| Ex. No. | STR | MS (M + H) |
|---|---|---|
| 1975 | | 261 |
| 1976 | | 261 |
| 1977 | | 307 |
| 1978 | | 383 |
| 1979 | | 383 |

TABLE 6-continued

| Ex. No. | STR | MS (M + H) |
|---|---|---|
| 1980 | | 277 |
| 1981 | | 307 |
| 1982 | | 344 |
| 1983 | | 311 |
| 1984 | | 300 |

TABLE 6-continued

| Ex. No. | STR | MS (M + H) |
|---|---|---|
| 1985 | | 327 |
| 1986 | | 339 |
| 1987 | | 199 |
| 1988 | | 187 |
| 1989 | | 191 |
| 1990 | | 172 |

TABLE 6-continued
| Ex. No. | STR | MS (M + H) |
|---|---|---|
| 1991 | 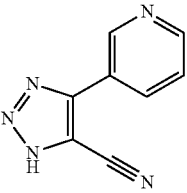 | 172 |
| 1992 | 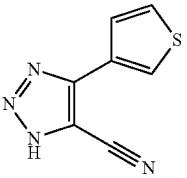 | 177 |
| 1993 | 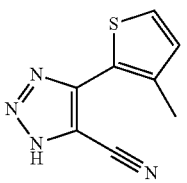 | 191 |
| 1994 | 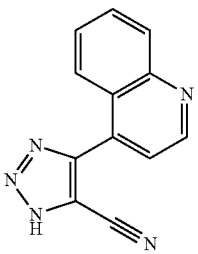 | 222 |
| 1995 | 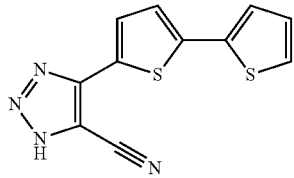 | 259 |
| 1996 | 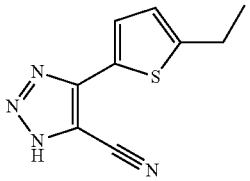 | 205 |
| 1997 | 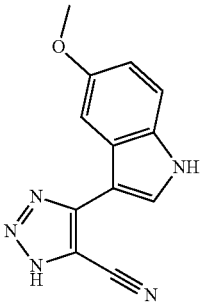 | 240 |

TABLE 6-continued

| Ex. No. | STR | MS (M + H) |
|---|---|---|
| 1998 | | 269 |
| 1999 | | 205 |
| 2000 | | 213 |
| 2001 | | 250 |
| 2002 | | 228 |
| 2003 | | 240 |

TABLE 6-continued

| Ex. No. | STR | MS (M + H) |
|---|---|---|
| 2004 | | 311 |
| 2005 | | 297 |
| 2006 | | 222 |
| 2007 | | 160 |
| 2008 | | 161 |
| 2009 | | 175 |

TABLE 6-continued
| Ex. No. | STR | MS (M + H) |
|---|---|---|
| 2010 | 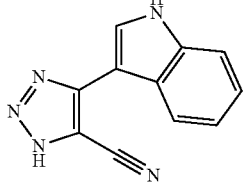 | 210 |
| 2011 | 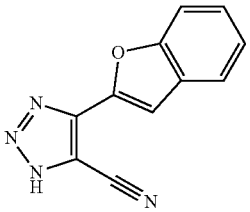 | 211 |
| 2012 | 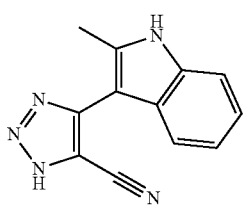 | 224 |
| 2013 | 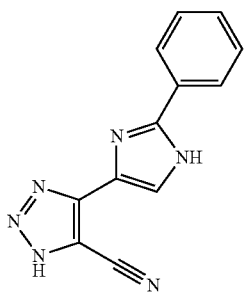 | 237 |
| 2014 | 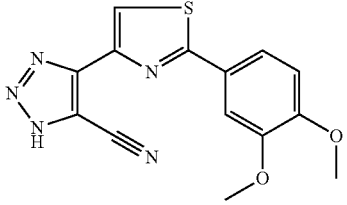 | 314 |
| 2015 | 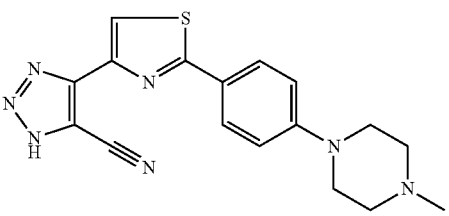 | 352 |

TABLE 6-continued

| Ex. No. | STR | MS (M + H) |
|---|---|---|
| 2016 | | 224 |
| 2017 | | 364 |
| 2018 | | 306 |
| 2019 | | 211 |
| 2020 | | 254 |
| 2021 | | 330 |

TABLE 6-continued

| Ex. No. | STR | MS (M + H) |
|---|---|---|
| 2022 | | 270 |
| 2023 | | 189 |
| 2024 | | 241 |
| 2025 | | 271 |
| 2026 | | 305 |
| 2027 | | 339 |

TABLE 6-continued

| Ex. No. | STR | MS (M + H) |
|---|---|---|
| 2028 | | 225 |
| 2029 | | 177 |
| 2030 | | 285 |
| 2031 | | 286 |
| 2032 | | 338 |
| 2033 | | 210 |

TABLE 6-continued

| Ex. No. | STR | MS (M + H) |
|---|---|---|
| 2034 | | 287 |
| 2035 | | 314 |
| 2036 | | 325 |
| 2037 | | 209 |
| 2038 | | 242 |
| 2039 | | 278 |

TABLE 6-continued

| Ex. No. | STR | MS (M + H) |
|---|---|---|
| 2040 | | 260 |
| 2041 | | 314 |
| 2042 | | 260 |
| 2043 | | 260 |
| 2044 | | 227 |
| 2045 | | 227 |

TABLE 6-continued

| Ex. No. | STR | MS (M + H) |
|---|---|---|
| 2046 | | 264 |
| 2047 | | 302 |
| 2048 | | 306 |
| 2049 | | 485 |
| 2050 | | 223 |
| 2051 | | 279 |

TABLE 6-continued

| Ex. No. | STR | MS (M + H) |
|---|---|---|
| 2052 | 4-cyanophenyl triazole carbonitrile | 196 |
| 2053 | pyridin-4-yl triazole carbonitrile | 172 |
| 2054 | 2,6-dichlorophenyl triazole carbonitrile | 239 |
| 2055 | 4-(trifluoromethoxy)phenyl triazole carbonitrile | 255 |
| 2056 | 2-((4-bromophenyl)thio)phenyl triazole carbonitrile | 357 |
| 2057 | 2-(4-chlorophenoxy)phenyl triazole carbonitrile | 297 |

TABLE 6-continued

| Ex. No. | STR | MS (M + H) |
|---|---|---|
| 2058 | | 331 |
| 2059 | | 293 |
| 2060 | | 277 |
| 2061 | | 281 |
| 2062 | | 255 |

TABLE 6-continued

| Ex. No. | STR | MS (M + H) |
|---|---|---|
| 2063 | | 200 |
| 2064 | | 265 |
| 2065 | | 331 |
| 2066 | | 307 |
| 2067 | | 265 |
| 2068 | | 265 |
| 2069 | | 315 |

TABLE 6-continued

| Ex. No. | STR | MS (M + H) |
|---|---|---|
| 2070 | | 261 |
| 2071 | | 261 |
| 2072 | | 281 |
| 2073 | | 289 |
| 2074 | | 303 |
| 2075 | | 277 |
| 2076 | | 289 |

TABLE 6-continued
| Ex. No. | STR | MS (M + H) |
|---|---|---|
| 2077 | 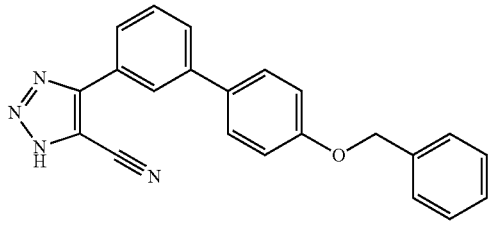 | 353 |
| 2078 | 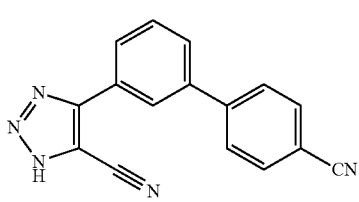 | 272 |
| 2079 | 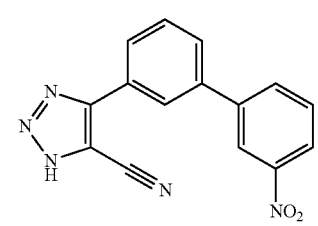 | 292 |
| 2080 | 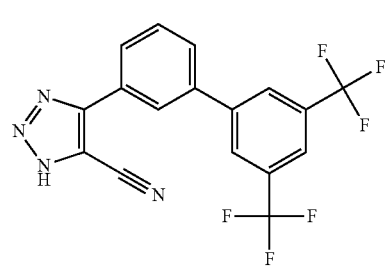 | 481 |
| 2081 | 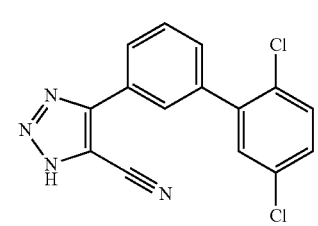 | 315 |
| 2082 | 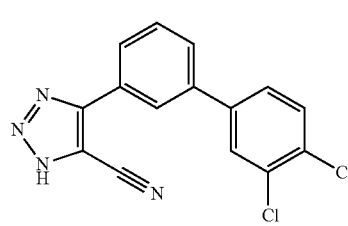 | 315 |
| 2083 | 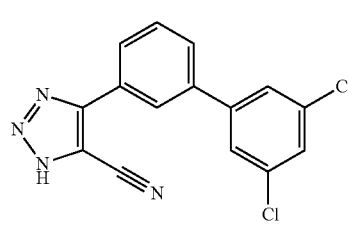 | 315 |

TABLE 6-continued

| Ex. No. | STR | MS (M + H) |
|---|---|---|
| 2084 | | 299 |
| 2085 | | 323 |
| 2086 | | 303 |
| 2087 | | 293 |
| 2088 | | 293 |
| 2089 | | 277 |

TABLE 6-continued

| Ex. No. | STR | MS (M + H) |
|---|---|---|
| 2090 | | 339 |
| 2091 | | 295 |
| 2092 | | 275 |
| 2093 | | 291 |
| 2094 | | 305 |
| 2095 | | 301 |
| 2096 | | 277 |

TABLE 6-continued
| Ex. No. | STR | MS (M + H) |
|---|---|---|
| 2097 | 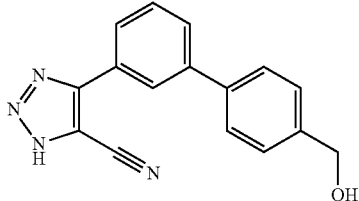 | 277 |
| 2098 | 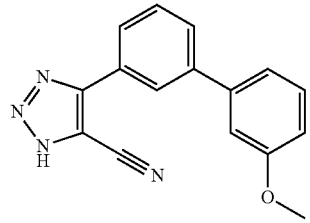 | 277 |
| 2099 | 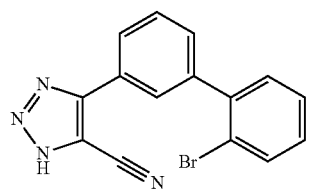 | 325 |
| 2100 | 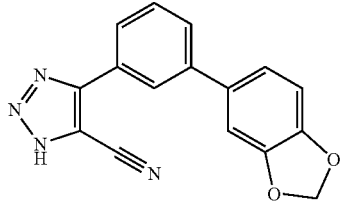 | 291 |
| 2101 | 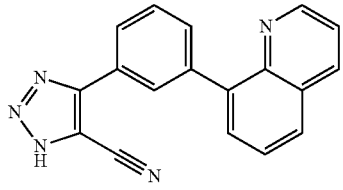 | 298 |
| 2102 | 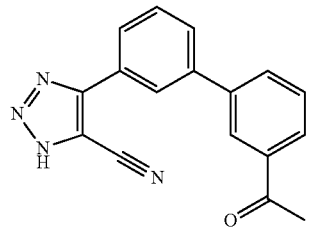 | 289 |
| 2103 | 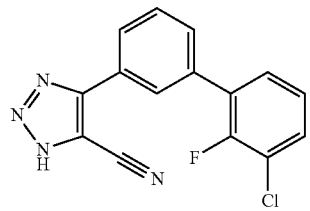 | 299 |

TABLE 6-continued

| Ex. No. | STR | MS (M + H) |
|---|---|---|
| 2104 | | 298 |
| 2105 | | 298 |
| 2106 | | 289 |
| 2107 | | 298 |
| 2108 | | 280 |
| 2109 | | 284 |
| 2110 | | 261 |

TABLE 6-continued

| Ex. No. | STR | MS (M + H) |
|---|---|---|
| 2111 | | 289 |
| 2112 | | 287 |
| 2113 | | 305 |
| 2114 | | 303 |
| 2115 | | 300 |
| 2116 | | 318 |
| 2117 | | 298 |

TABLE 6-continued
| Ex. No. | STR | MS (M + H) |
|---|---|---|
| 2118 | 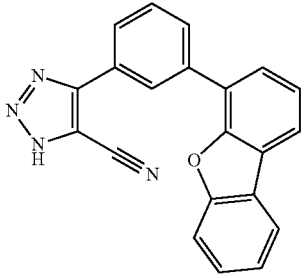 | 337 |
| 2119 | 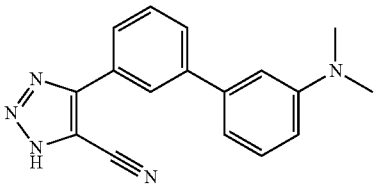 | 290 |
| 2120 | 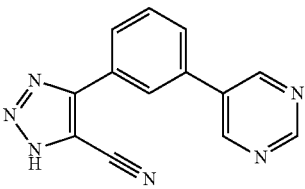 | 249 |
| 2121 | 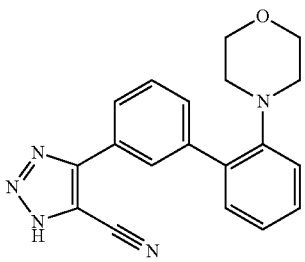 | 332 |
| 2122 | 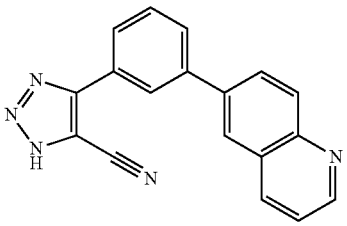 | 296 |
| 2123 | 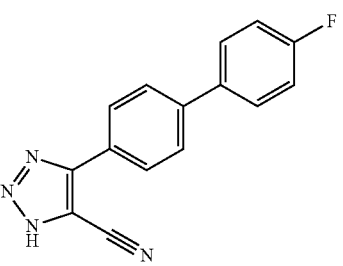 | 265 |

TABLE 6-continued
| Ex. No. | STR | MS (M + H) |
|---|---|---|
| 2124 | 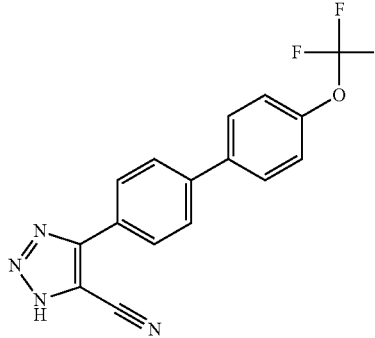 | 331 |
| 2125 | 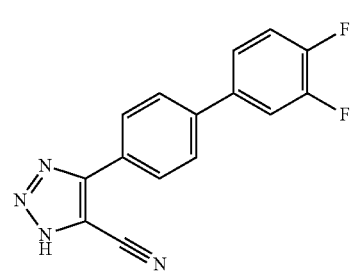 | 283 |
| 2126 | 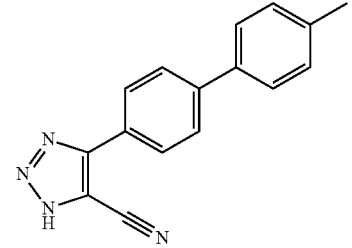 | 261 |
| 2127 | 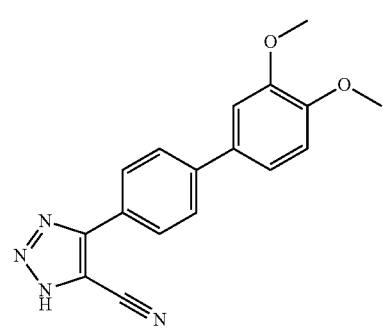 | 307 |
| 2128 | 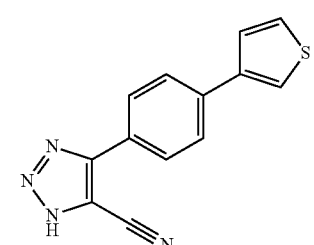 | 253 |

TABLE 6-continued

| Ex. No. | STR | MS (M + H) |
|---|---|---|
| 2129 | | 265 |
| 2130 | | 265 |
| 2131 | | 261 |
| 2132 | | 281 |
| 2133 | | 289 |

TABLE 6-continued
| Ex. No. | STR | MS (M + H) |
|---|---|---|
| 2134 | 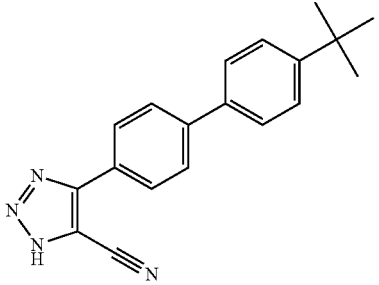 | 303 |
| 2135 | 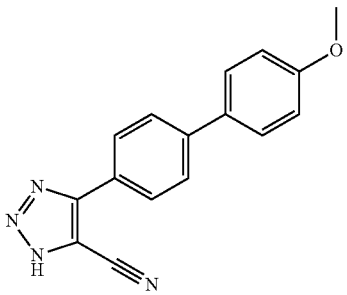 | 277 |
| 2136 | 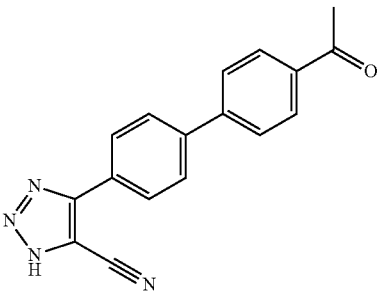 | 289 |
| 2137 | 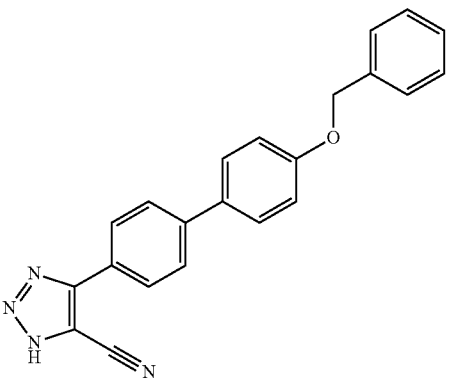 | 353 |
| 2138 | 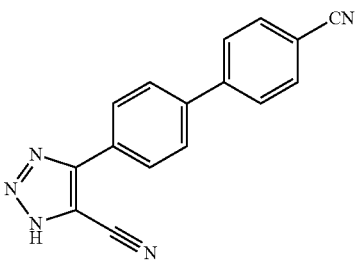 | 272 |

TABLE 6-continued
| Ex. No. | STR | MS (M + H) |
|---|---|---|
| 2139 | 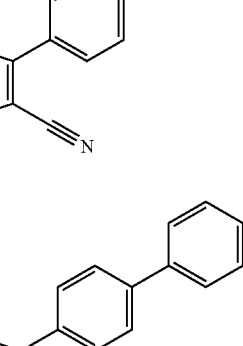 | 325 |
| 2140 | 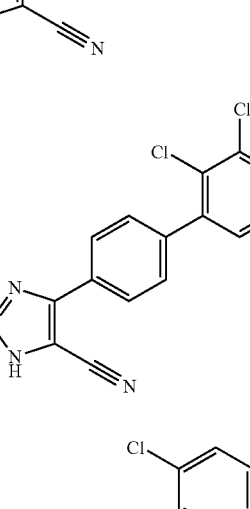 | 292 |
| 2141 | 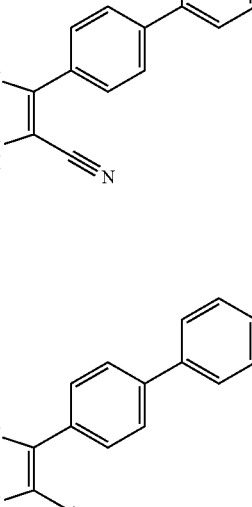 | 315 |
| 2142 | 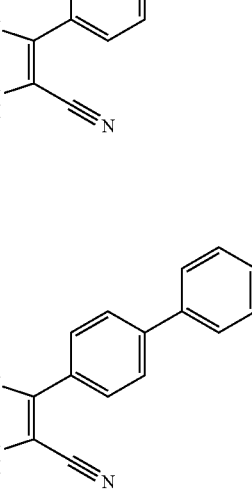 | 315 |
| 2143 | 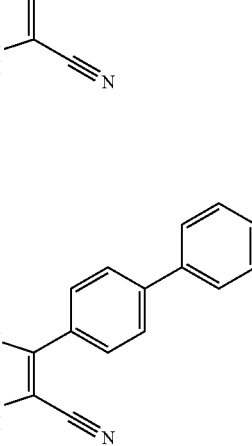 | 315 |

TABLE 6-continued

| Ex. No. | STR | MS (M + H) |
|---|---|---|
| 2144 | | 275 |
| 2145 | | 297 |
| 2146 | | 303 |
| 2147 | | 293 |
| 2148 | | 293 |

TABLE 6-continued
| Ex. No. | STR | MS (M + H) |
|---|---|---|
| 2149 | 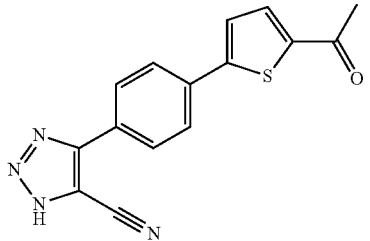 | 295 |
| 2150 | 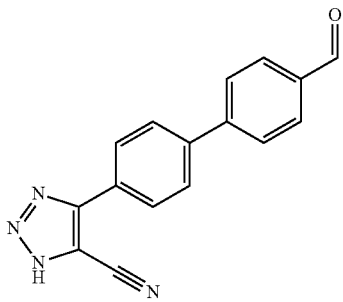 | 275 |
| 2151 | 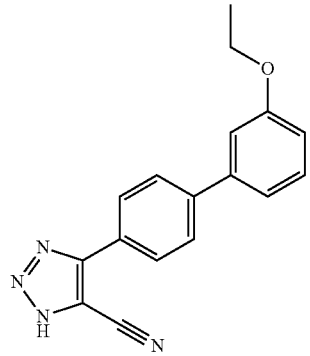 | 291 |
| 2152 | 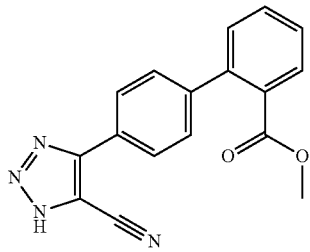 | 305 |
| 2153 | 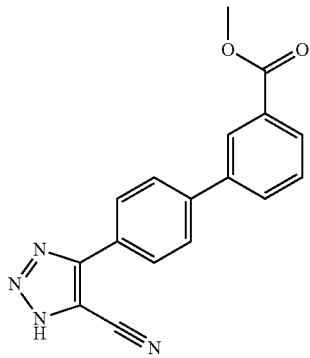 | 305 |

TABLE 6-continued

| Ex. No. | STR | MS (M + H) |
|---------|-----|------------|
| 2154 | 4'-(5-cyano-1H-1,2,3-triazol-4-yl)-[1,1'-biphenyl]-4-carboxylic acid methyl ester | 305 |
| 2155 | 4-(3'-(hydroxymethyl)-[1,1'-biphenyl]-4-yl)-1H-1,2,3-triazole-5-carbonitrile | 277 |
| 2156 | 4-(4'-(hydroxymethyl)-[1,1'-biphenyl]-4-yl)-1H-1,2,3-triazole-5-carbonitrile | 277 |
| 2157 | 4-(3'-methoxy-[1,1'-biphenyl]-4-yl)-1H-1,2,3-triazole-5-carbonitrile | 277 |
| 2158 | 4-(4-(pyridin-4-yl)phenyl)-1H-1,2,3-triazole-5-carbonitrile | 248 |

TABLE 6-continued

| Ex. No. | STR | MS (M + H) |
|---|---|---|
| 2159 | | 291 |
| 2160 | | 298 |
| 2161 | | 289 |
| 2162 | | 299 |
| 2163 | | 298 |

TABLE 6-continued

| Ex. No. | STR | MS (M + H) |
|---|---|---|
| 2164 | | 298 |
| 2165 | | 269 |
| 2166 | | 298 |
| 2167 | | 345 |
| 2168 | | 280 |
| 2169 | | 261 |

TABLE 6-continued
| Ex. No. | STR | MS (M + H) |
|---|---|---|
| 2170 | 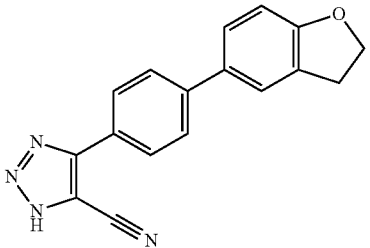 | 289 |
| 2171 | 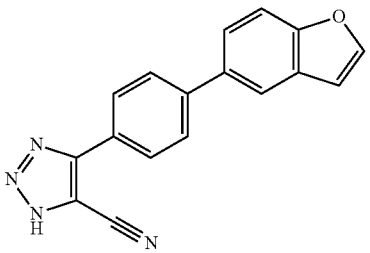 | 287 |
| 2172 | 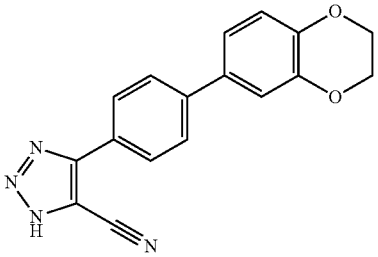 | 305 |
| 2173 | 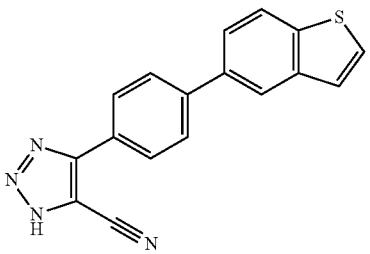 | 303 |
| 2174 | 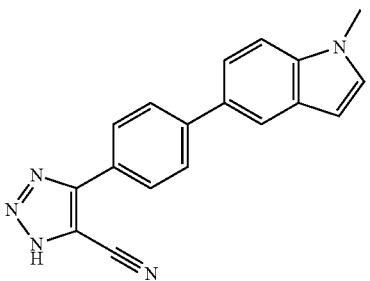 | 300 |

TABLE 6-continued

| Ex. No. | STR | MS (M + H) |
|---|---|---|
| 2175 | | 318 |
| 2176 | | 298 |
| 2177 | | 337 |
| 2178 | | 339 |
| 2179 | | 290 |

TABLE 6-continued

| Ex. No. | STR | MS (M + H) |
|---|---|---|
| 2180 | | 249 |
| 2181 | | 332 |
| 2182 | | 298 |
| 2183 | | 315 |
| 2184 | | 237 |
| 2185 | | 261 |

TABLE 6-continued

| Ex. No. | STR | MS (M + H) |
|---|---|---|
| 2186 | | 315 |
| 2187 | | 275 |
| 2188 | | 286 |
| 2189 | | 297 |
| 2190 | | 339 |
| 2191 | | 266 |
| 2192 | | 262 |

TABLE 6-continued
| Ex. No. | STR | MS (M + H) |
|---|---|---|
| 2193 | 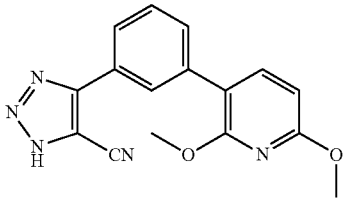 | 308 |
| 2194 | 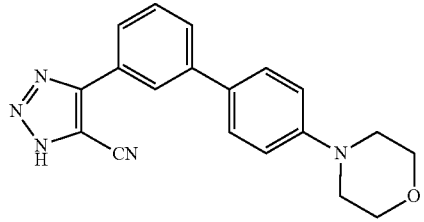 | 332 |
| 2195 | 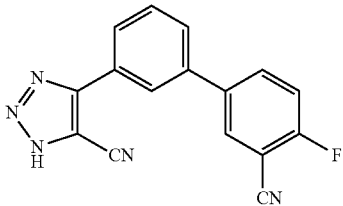 | 290 |
| 2196 | 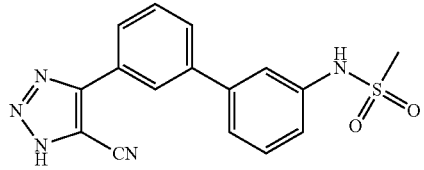 | 340 |
| 2197 | 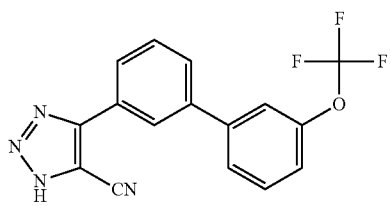 | 331 |
| 2198 | 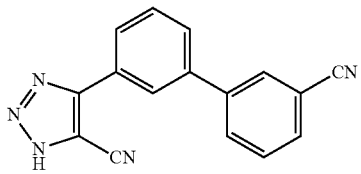 | 272 |
| 2199 | 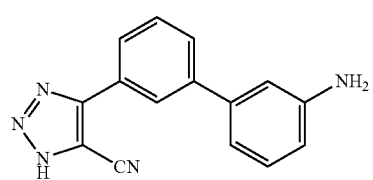 | 262 |

TABLE 6-continued
| Ex. No. | STR | MS (M + H) |
|---|---|---|
| 2200 | 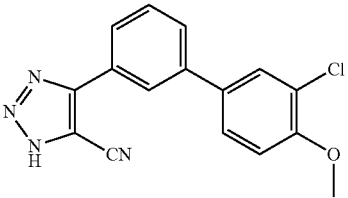 | 311 |
| 2201 | 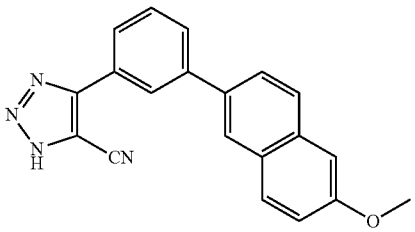 | 327 |
| 2202 | 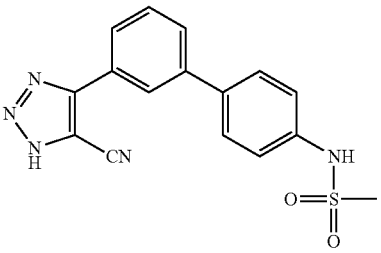 | 340 |
| 2203 | 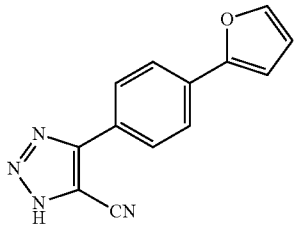 | 237 |
| 2204 | 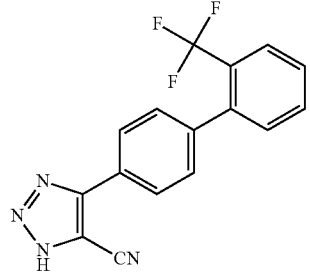 | 315 |
| 2205 | 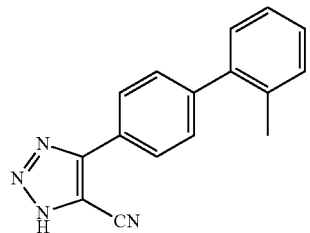 | 261 |

TABLE 6-continued

| Ex. No. | STR | MS (M + H) |
|---|---|---|
| 2206 | | 315 |
| 2207 | | 299 |
| 2208 | | 286 |
| 2209 | | 277 |
| 2210 | | 266 |
| 2211 | | 282 |

TABLE 6-continued

| Ex. No. | STR | MS (M + H) |
|---|---|---|
| 2212 | | 308 |
| 2213 | | 332 |
| 2214 | | 340 |
| 2215 | | 262 |
| 2216 | | 311 |

TABLE 6-continued

| Ex. No. | STR | MS (M + H) |
|---|---|---|
| 2217 | | 327 |
| 2218 | | 340 |
| 2219 | | 381 |
| 2220 | | 396 |
| 2221 | | 413 |

TABLE 6-continued

| Ex. No. | STR | MS (M + H) |
|---------|-----|------------|
| 2222 | | 423 |
| 2223 | | 429 |
| 2224 | | 397 |
| 2225 | | 366 |
| 2226 | | 437 |

TABLE 6-continued

| Ex. No. | STR | MS (M + H) |
|---|---|---|
| 2227 | | 469 |
| 2228 | | 427 |
| 2229 | | 371 |
| 2230 | | 327 |
| 2231 | | 395 |

TABLE 6-continued

| Ex. No. | STR | MS (M + H) |
|---|---|---|
| 2232 | | 399 |
| 2233 | | 399 |
| 2234 | | 496 |
| 2235 | | 425 |
| 2236 | | 462 |

TABLE 6-continued

| Ex. No. | STR | MS (M + H) |
|---|---|---|
| 2237 | | 353 |
| 2238 | | 337 |
| 2239 | | 429 |
| 2240 | | 409 |
| 2241 | | 451 |

TABLE 6-continued
| Ex. No. | STR | MS (M + H) |
|---|---|---|
| 2242 | 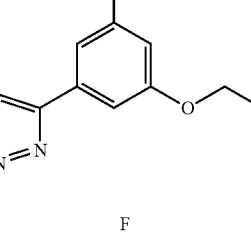 | 379 |
| 2243 | 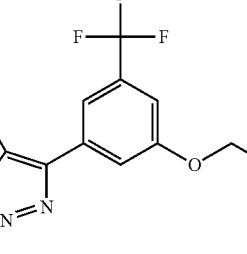 | 385 |
| 2244 | 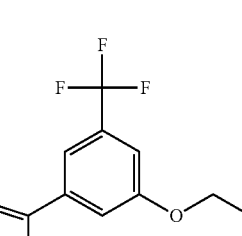 | 414 |
| 2245 | 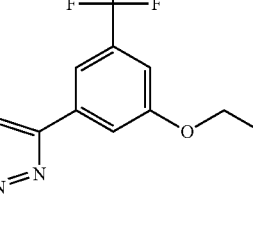 | 485 |
| 2246 | 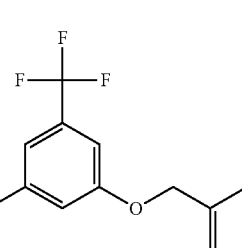 | 435 |

TABLE 6-continued
| Ex. No. | STR | MS (M + H) |
|---|---|---|
| 2247 | 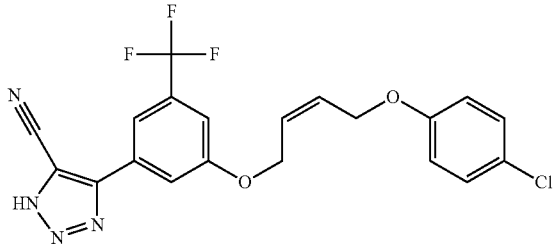 | 435 |
| 2248 | 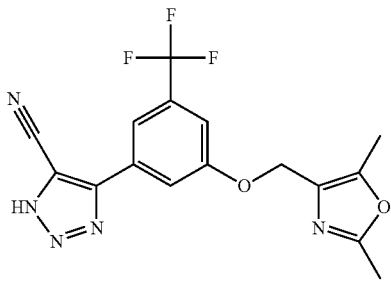 | 364 |
| 2249 | 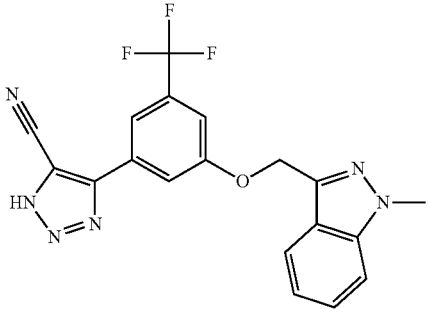 | 399 |
| 2250 | 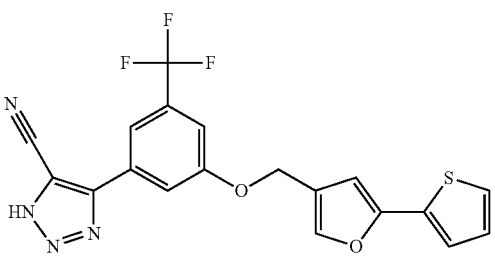 | 418 |
| 2251 | 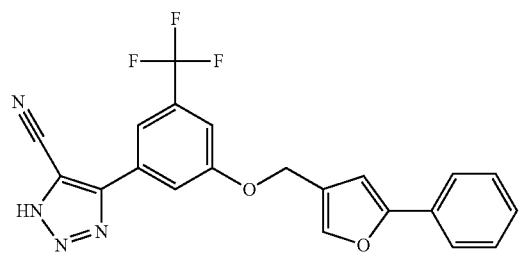 | 412 |

TABLE 6-continued
| Ex. No. | STR | MS (M + H) |
|---|---|---|
| 2252 | 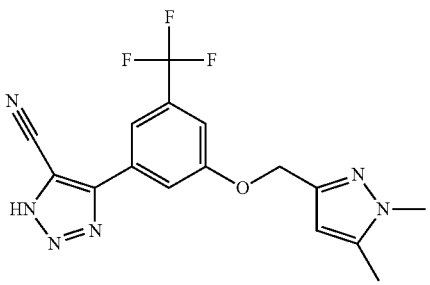 | 363 |
| 2253 | 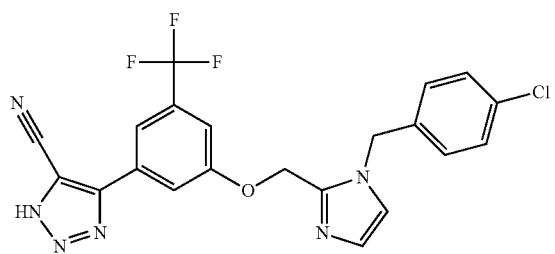 | 459 |
| 2254 | 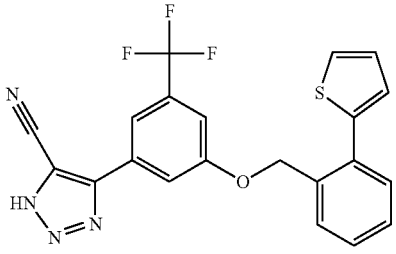 | 427 |
| 2255 | 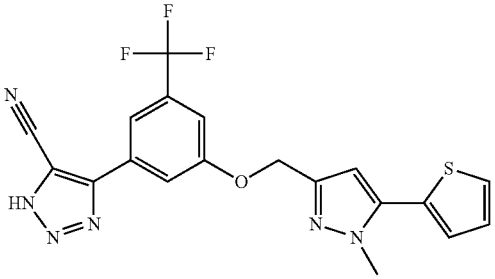 | 431 |
| 2256 | 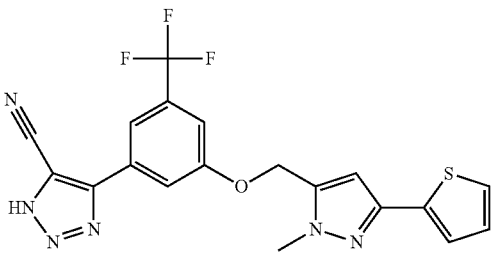 | 431 |

TABLE 6-continued
| Ex. No. | STR | MS (M + H) |
|---|---|---|
| 2257 | 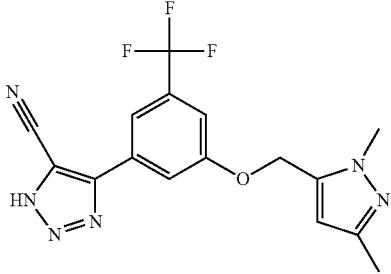 | 363 |
| 2258 | 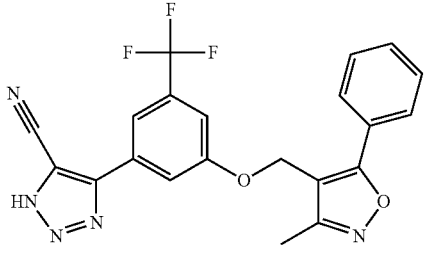 | 426 |
| 2259 | 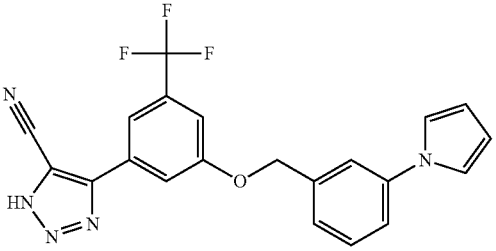 | 410 |
| 2260 | 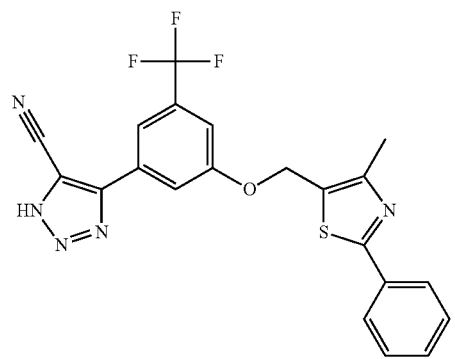 | 442 |
| 2261 | 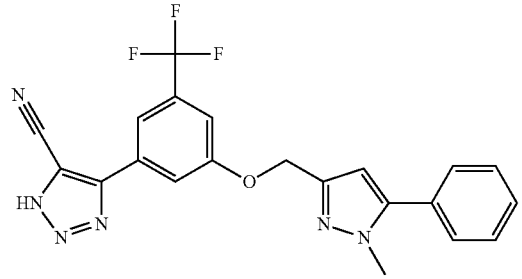 | 425 |

TABLE 6-continued

| Ex. No. | STR | MS (M + H) |
|---|---|---|
| 2262 | | 427 |
| 2263 | | 423 |
| 2264 | | 434 |
| 2265 | | 425 |
| 2266 | | 428 |
| 2267 | | 445 |

TABLE 6-continued

| Ex. No. | STR | MS (M + H) |
|---|---|---|
| 2268 | | 413 |
| 2269 | | 415 |
| 2270 | | 425 |
| 2271 | | 510 |
| 2272 | | 509 |

TABLE 6-continued

| Ex. No. | STR | MS (M + H) |
|---|---|---|
| 2273 | | 481 |
| 2274 | | 439 |
| 2275 | | 443 |
| 2276 | | 443 |
| 2277 | | 453 |

TABLE 6-continued

| Ex. No. | STR | MS (M + H) |
|---|---|---|
| 2278 | | 493 |
| 2279 | | 427 |
| 2280 | | 427 |
| 2281 | | 415 |
| 2282 | | 425 |

TABLE 6-continued

| Ex. No. | STR | MS (M + H) |
|---------|-----|------------|
| 2283 | | 427 |
| 2284 | | 490 |
| 2285 | | 427 |
| 2286 | | 410 |
| 2287 | | 442 |

TABLE 6-continued
| Ex. No. | STR | MS (M + H) |
|---|---|---|
| 2288 | 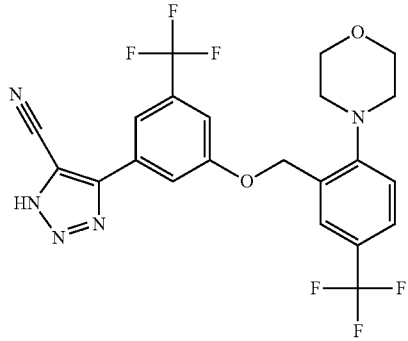 | 498 |
| 2289 | 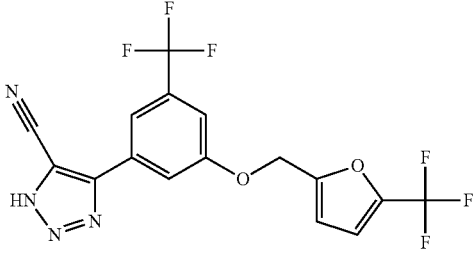 | 403 |
| 2290 | 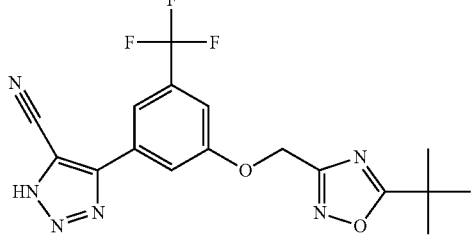 | 393 |
| 2291 | 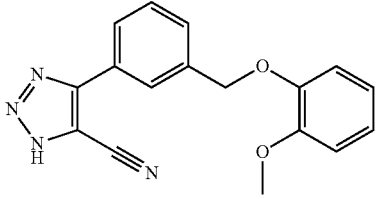 | 307 |
| 2292 | 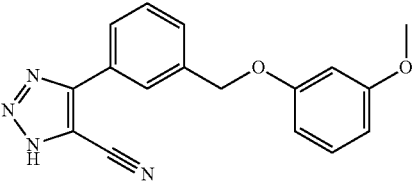 | 307 |
| 2293 | 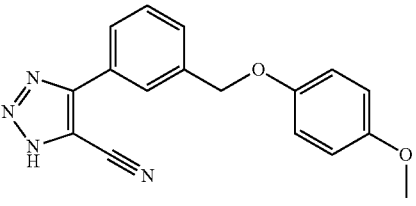 | 307 |

TABLE 6-continued

| Ex. No. | STR | MS (M + H) |
|---|---|---|
| 2294 | | 337 |
| 2295 | | 321 |
| 2296 | | 291 |
| 2297 | | 291 |
| 2298 | | 291 |
| 2299 | | 305 |
| 2300 | | 305 |

TABLE 6-continued

| Ex. No. | STR | MS (M + H) |
|---|---|---|
| 2301 | | 295 |
| 2302 | | 295 |
| 2303 | | 313 |
| 2304 | | 313 |
| 2305 | | 327 |
| 2306 | | 327 |
| 2307 | | 361 |

TABLE 6-continued
| Ex. No. | STR | MS (M + H) |
|---|---|---|
| 2308 |  | 361 |
| 2309 |  | 361 |
| 2310 |  | 334 |
| 2311 |  | 344 |
| 2312 |  | 335 |
| 2313 |  | 373 |
| 2314 |  | 309 |

TABLE 6-continued
| Ex. No. | STR | MS (M + H) |
|---|---|---|
| 2315 | 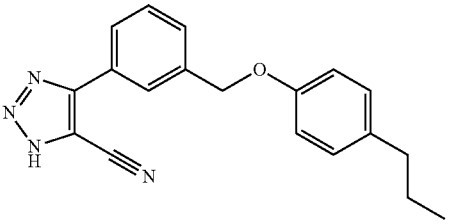 | 319 |
| 2316 | 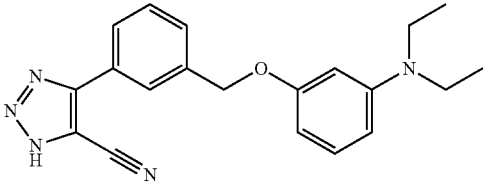 | 348 |
| 2317 | 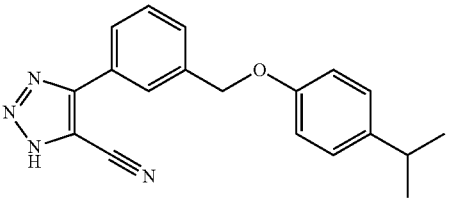 | 319 |
| 2318 | 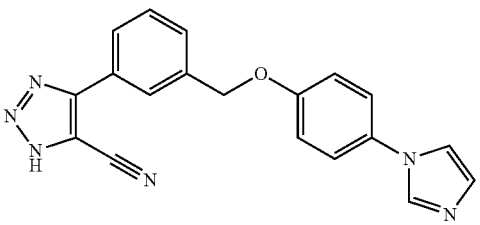 | 343 |
| 2319 | 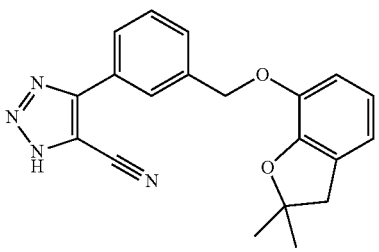 | 347 |
| 2320 | 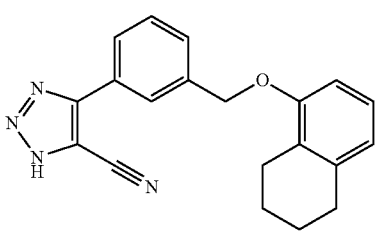 | 331 |
| 2321 | 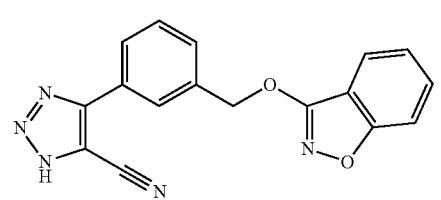 | 321 |

TABLE 6-continued

| Ex. No. | STR | MS (M + H) |
|---|---|---|
| 2322 | | 317 |
| 2323 | | 342 |
| 2324 | | 345 |
| 2325 | | 343 |
| 2326 | | 343 |
| 2327 | | 361 |

TABLE 6-continued
| Ex. No. | STR | MS (M + H) |
|---|---|---|
| 2328 |  | 374 |
| 2329 |  | 361 |
| 2330 |  | 360 |
| 2331 |  | 346 |
| 2332 |  | 350 |
| 2333 |  | 376 |

TABLE 6-continued
| Ex. No. | STR | MS (M + H) |
|---|---|---|
| 2334 |  | 348 |
| 2335 |  | 362 |
| 2336 |  | 360 |
| 2337 |  | 346 |
| 2338 |  | 346 |
| 2339 |  | 374 |

TABLE 6-continued

| Ex. No. | STR | MS (M + H) |
|---|---|---|
| 2340 | | 347 |
| 2341 | | 378 |
| 2342 | | 325 |
| 2343 | | 331 |
| 2344 | | 320 |
| 2345 | | 342 |

TABLE 6-continued
| Ex. No. | STR | MS (M + H) |
|---|---|---|
| 2346 |  | 306 |
| 2347 | 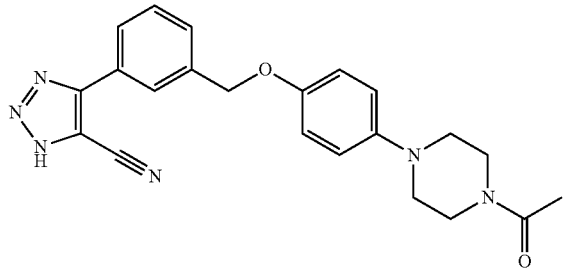 | 403 |
| 2348 | 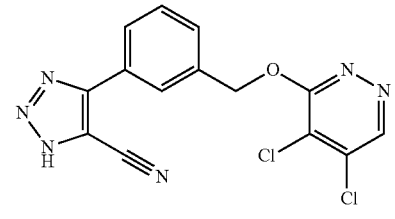 | 347 |
| 2349 | 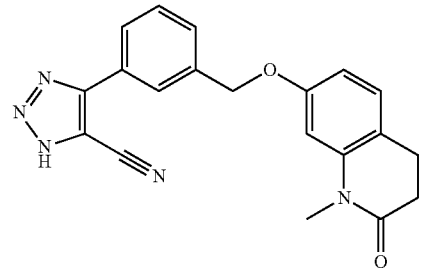 | 360 |
| 2350 | 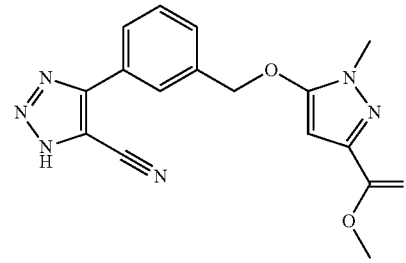 | 339 |
| 2351 | 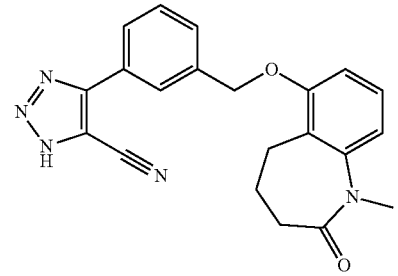 | 374 |

TABLE 6-continued

| Ex. No. | STR | MS (M + H) |
|---|---|---|
| 2352 | | 317 |
| 2353 | | 360 |
| 2354 | | 335 |
| 2355 | | 360 |
| 2356 | | 360 |
| 2357 | | 360 |

TABLE 6-continued

| Ex. No. | STR | MS (M + H) |
|---|---|---|
| 2358 | | 376 |
| 2359 | | 325 |
| 2360 | | 391 |
| 2361 | | 379 |
| 2362 | | 331 |
| 2363 | | 329 |
| 2364 | | 335 |

TABLE 6-continued

| Ex. No. | STR | MS (M + H) |
|---|---|---|
| 2365 | | 303 |
| 2366 | | 243 |
| 2367 | | 255 |
| 2368 | | 311 |
| 2369 | | 257 |
| 2370 | | 239 |
| 2371 | | 297 |

TABLE 6-continued

| Ex. No. | STR | MS (M + H) |
|---|---|---|
| 2372 | | 343 |
| 2373 | | 408 |
| 2374 | | 342 |
| 2375 | | 345 |
| 2376 | | 379 |

TABLE 6-continued
| Ex. No. | STR | MS (M + H) |
|---|---|---|
| 2377 | 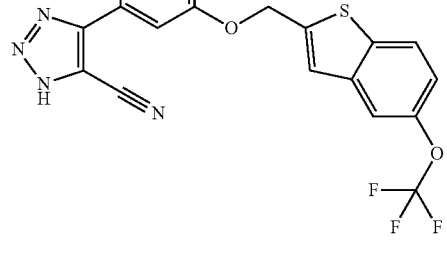 | 417 |
| 2378 | 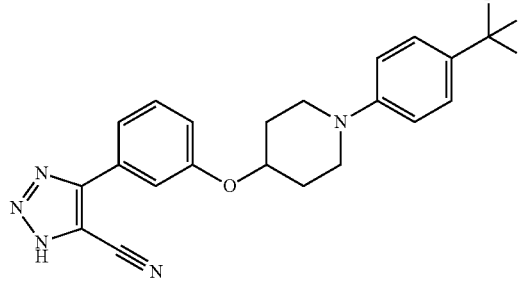 | 414 |
| 2379 | 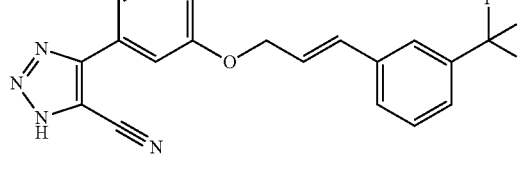 | 371 |
| 2380 | 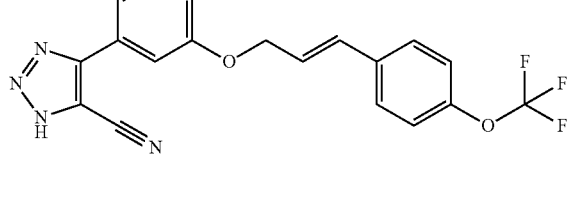 | 387 |
| 2381 | 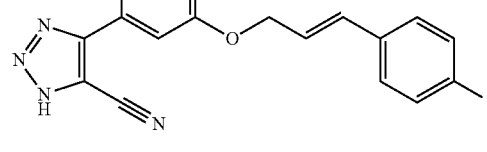 | 387 |
| 2382 | 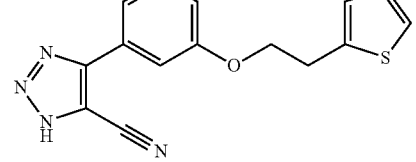 | 297 |

TABLE 6-continued
| Ex. No. | STR | MS (M + H) |
|---|---|---|
| 2383 | 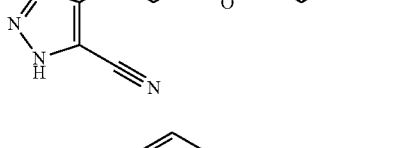 | 297 |
| 2384 | 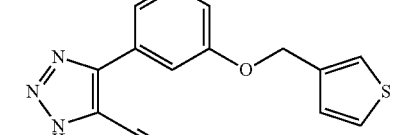 | 283 |
| 2385 | 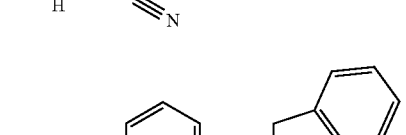 | 303 |
| 2386 | 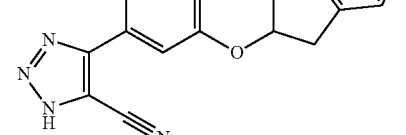 | 229 |
| 2387 | 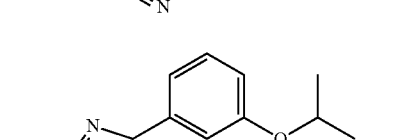 | 394 |
| 2388 | 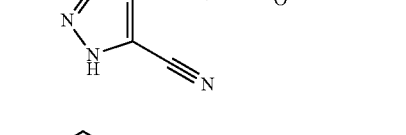 | 364 |
| 2389 | 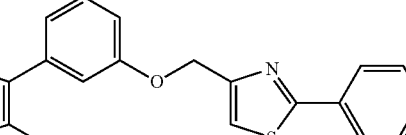 | 428 |

TABLE 6-continued
| Ex. No. | STR | MS (M + H) |
|---|---|---|
| 2390 | 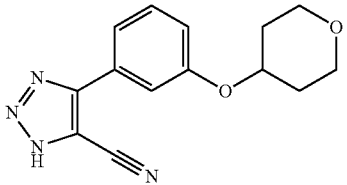 | 271 |
| 2391 | 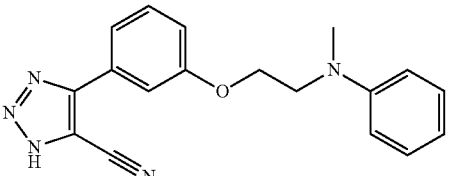 | 320 |
| 2392 | 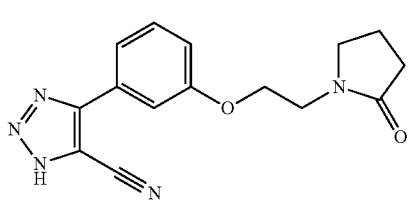 | 298 |
| 2393 | 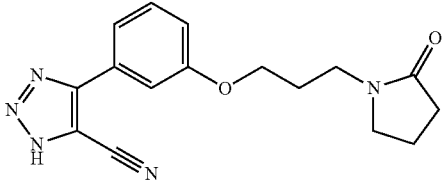 | 312 |
| 2394 | 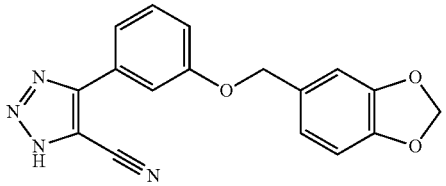 | 321 |
| 2395 | 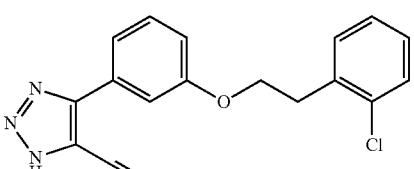 | 325 |
| 2396 | 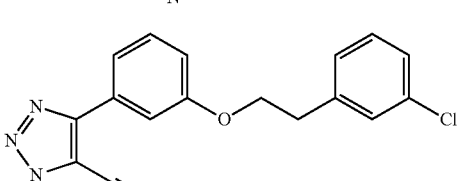 | 325 |
| 2397 | 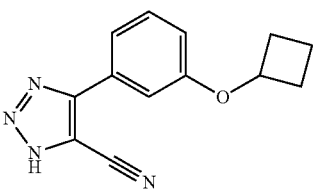 | 241 |

TABLE 6-continued

| Ex. No. | STR | MS (M + H) |
|---|---|---|
| 2398 | | 333 |
| 2399 | | 333 |
| 2400 | | 333 |
| 2401 | | 281 |
| 2402 | | 354 |
| 2403 | | 343 |
| 2404 | | 331 |

TABLE 6-continued
| Ex. No. | STR | MS (M + H) |
|---|---|---|
| 2405 | 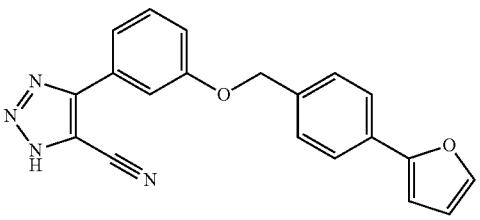 | 343 |
| 2406 | 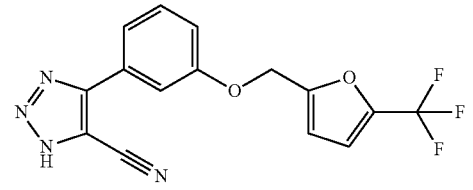 | 335 |
| 2407 | 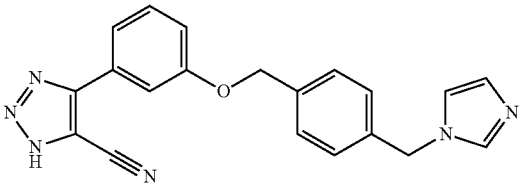 | 357 |
| 2408 | 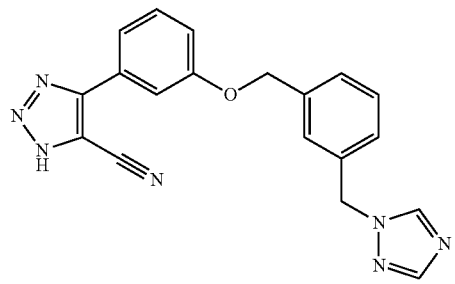 | 358 |
| 2409 | 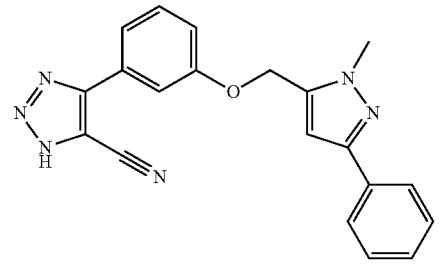 | 357 |
| 2410 | 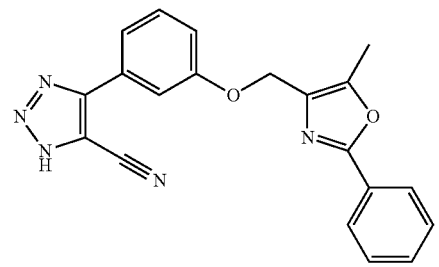 | 358 |

TABLE 6-continued

| Ex. No. | STR | MS (M + H) |
|---|---|---|
| 2411 | | 357 |
| 2412 | | 360 |
| 2413 | | 378 |
| 2414 | | 378 |
| 2415 | | 355 |
| 2416 | | 378 |

TABLE 6-continued

| Ex. No. | STR | MS (M + H) |
|---|---|---|
| 2417 | | 312 |
| 2418 | | 271 |
| 2419 | | 317 |
| 2420 | | 297 |
| 2421 | | 309 |
| 2422 | | 273 |
| 2423 | | 309 |

TABLE 6-continued
| Ex. No. | STR | MS (M + H) |
|---|---|---|
| 2424 | 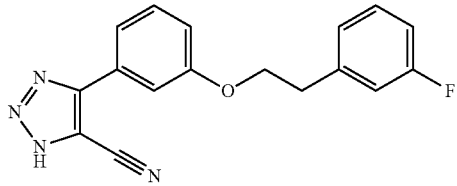 | 309 |
| 2425 | 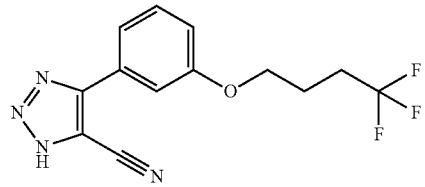 | 297 |
| 2426 | 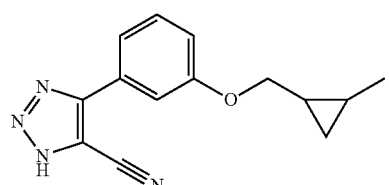 | 255 |
| 2427 | 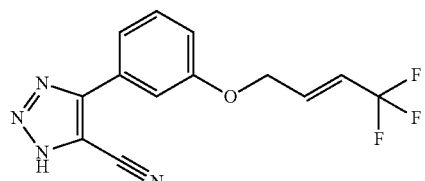 | 295 |
| 2428 | 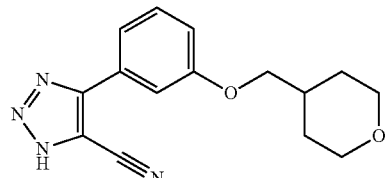 | 285 |
| 2429 | 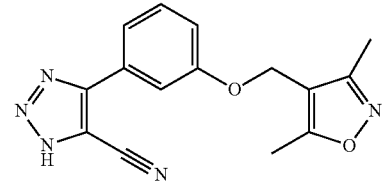 | 296 |
| 2430 | 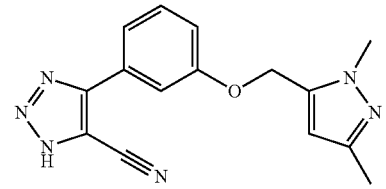 | 295 |
| 2431 | 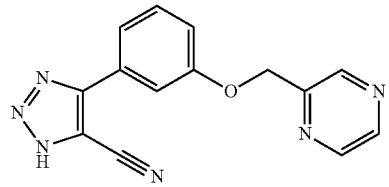 | 279 |

TABLE 6-continued

| Ex. No. | STR | MS (M + H) |
|---|---|---|
| 2432 | | 284 |
| 2433 | | 295 |
| 2434 | | 282 |
| 2435 | | 312 |
| 2436 | | 330 |
| 2437 | | 388 |
| 2438 | | 402 |

TABLE 6-continued

| Ex. No. | STR | MS (M + H) |
|---|---|---|
| 2439 | | 399 |
| 2440 | | 373 |
| 2441 | | 360 |
| 2442 | | 355 |
| 2443 | | 404 |
| 2444 | | 302 |
| 2445 | | 241 |

TABLE 6-continued

| Ex. No. | STR | MS (M + H) |
|---|---|---|
| 2446 | | 379 |
| 2447 | | 360 |
| 2448 | | 359 |
| 2449 | | 296 |
| 2450 | | 317 |
| 2451 | | 333 |
| 2452 | | 342 |

TABLE 6-continued

| Ex. No. | STR | MS (M + H) |
|---|---|---|
| 2453 | | 374 |
| 2454 | | 296 |
| 2455 | | 360 |
| 2456 | | 331 |
| 2457 | | 330 |
| 2458 | | 281 |
| 2459 | | 425 |

TABLE 6-continued

| Ex. No. | STR | MS (M + H) |
|---|---|---|
| 2460 | | 442 |
| 2461 | | 347 |
| 2462 | | 357 |
| 2463 | | 341 |
| 2464 | | 341 |
| 2465 | | 325 |

TABLE 6-continued

| Ex. No. | STR | MS (M + H) |
|---|---|---|
| 2466 | | 302 |
| 2467 | | 284 |
| 2468 | | 284 |
| 2469 | | 268 |
| 2470 | | 328 |
| 2471 | | 298 |
| 2472 | | 323 |

TABLE 6-continued

| Ex. No. | STR | MS (M + H) |
|---|---|---|
| 2473 | | 358 |
| 2474 | | 357 |
| 2475 | | 355 |
| 2476 | | 339 |
| 2477 | | 292 |
| 2478 | | 337 |
| 2479 | | 267 |

TABLE 6-continued
| Ex. No. | STR | MS (M + H) |
|---|---|---|
| 2480 | 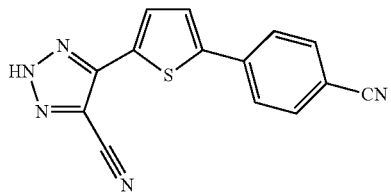 | 278 |
| 2481 | 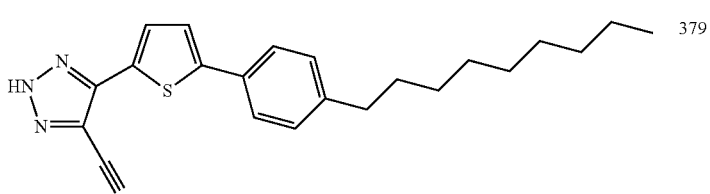 | 379 |
| 2482 | 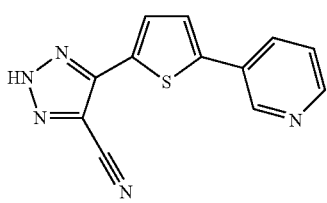 | 254 |
| 2483 | 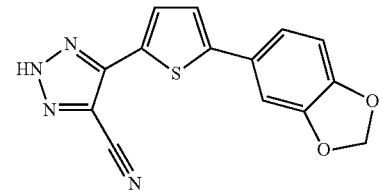 | 297 |
| 2484 | 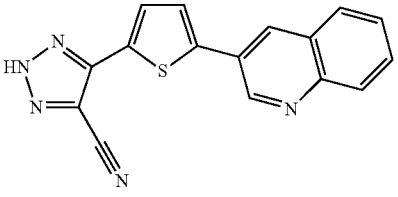 | 304 |
| 2485 | 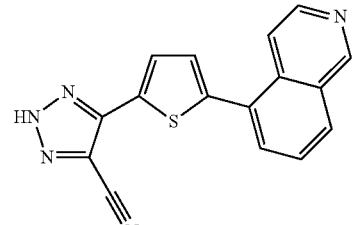 | 304 |
| 2486 | 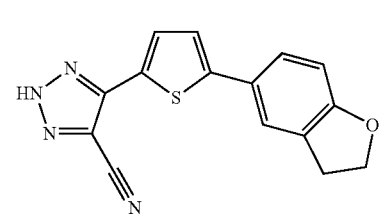 | 295 |

TABLE 6-continued
| Ex. No. | STR | MS (M + H) |
|---|---|---|
| 2487 | 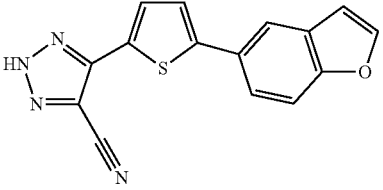 | 293 |
| 2488 | 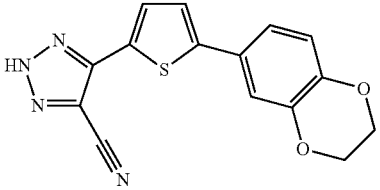 | 311 |
| 2489 | 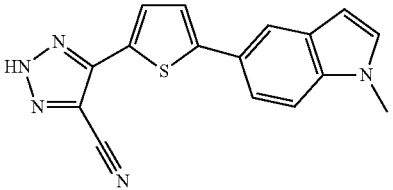 | 306 |
| 2490 | 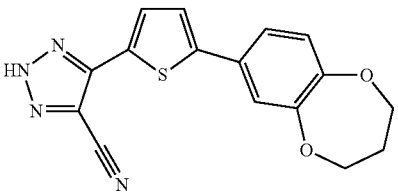 | 325 |
| 2491 | 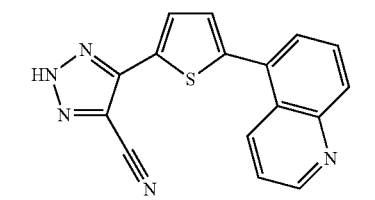 | 304 |
| 2492 | 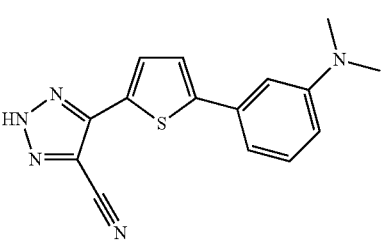 | 296 |
| 2493 | 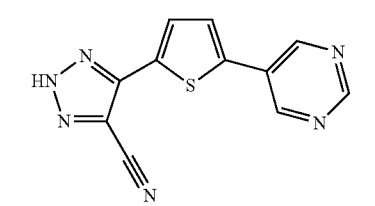 | 255 |

TABLE 6-continued
| Ex. No. | STR | MS (M + H) |
|---|---|---|
| 2494 |  | 304 |
| 2495 |  | 338 |
| 2496 |  | 346 |
| 2497 |  | 278 |
| 2498 |  | 346 |
| 2499 |  | 335 |
| 2500 |  | 347 |

TABLE 6-continued

| Ex. No. | STR | MS (M + H) |
|---|---|---|
| 2501 | | 372 |
| 2502 | | 265 |
| 2503 | | 313 |
| 2504 | | 360 |
| 2505 | | 324 |
| 2506 | | 333 |
| 2507 | | 310 |

TABLE 6-continued
| Ex. No. | STR | MS (M + H) |
|---|---|---|
| 2508 | 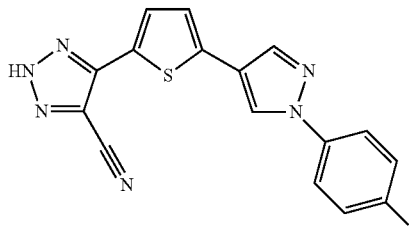 | 337 |
| 2509 | 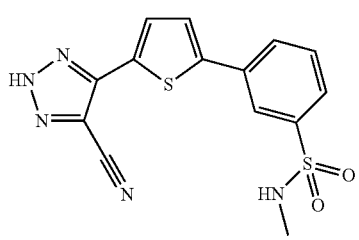 | 346 |
| 2510 | 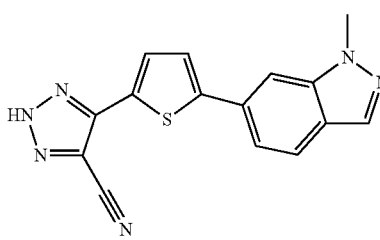 | 307 |
| 2511 | 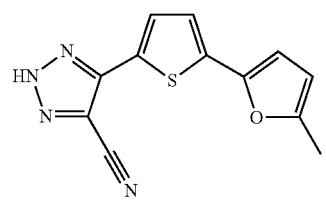 | 257 |
| 2512 | 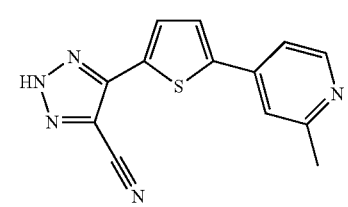 | 268 |
| 2513 | 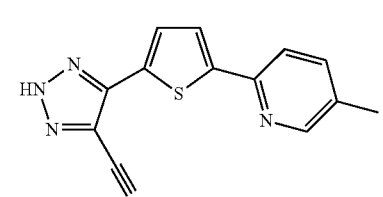 | 268 |
| 2514 | 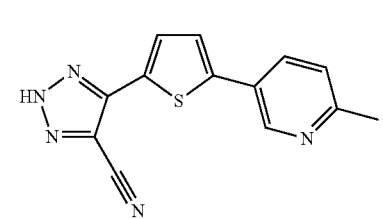 | 268 |

TABLE 6-continued

| Ex. No. | STR | MS (M + H) |
|---|---|---|
| 2515 | | 331 |
| 2516 | | 271 |
| 2517 | | 306 |
| 2518 | | 257 |
| 2519 | | 309 |
| 2520 | | 339 |
| 2521 | | 271 |

TABLE 6-continued
| Ex. No. | STR | MS (M + H) |
|---|---|---|
| 2522 | 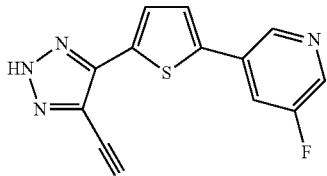 | 272 |
| 2523 | 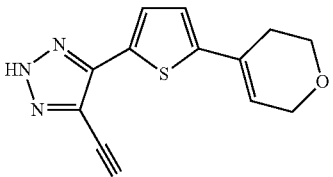 | 259 |
| 2524 | 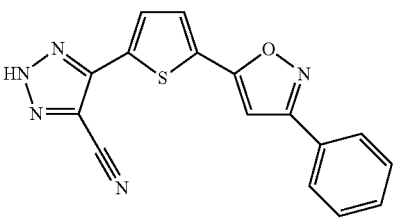 | 320 |
| 2525 | 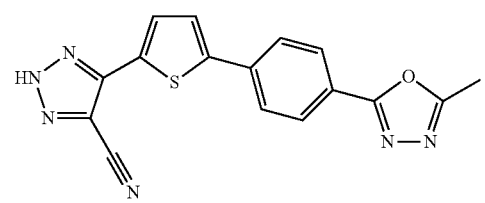 | 335 |
| 2526 | 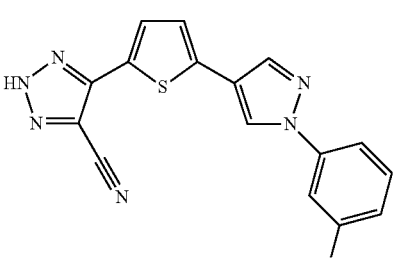 | 353 |
| 2527 | 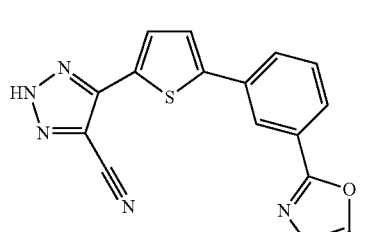 | 335 |
| 2528 | 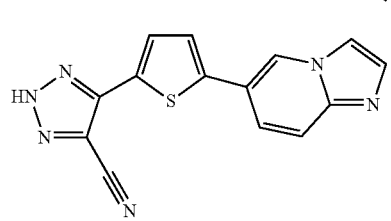 | 293 |

TABLE 6-continued
| Ex. No. | STR | MS (M + H) |
|---|---|---|
| 2529 | 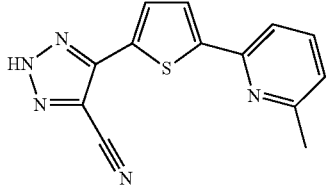 | 268 |
| 2530 | 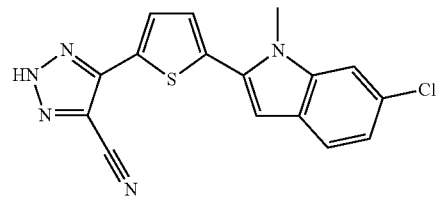 | 340 |
| 2531 | 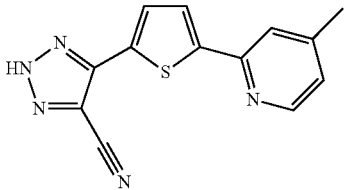 | 268 |
| 2532 | 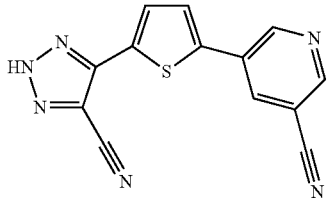 | 279 |
| 2533 | 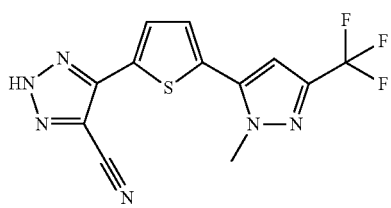 | 325 |
| 2534 | 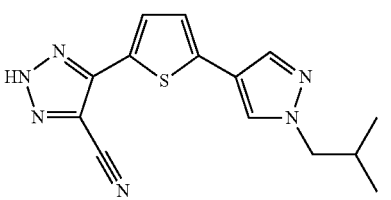 | 299 |
| 2535 | 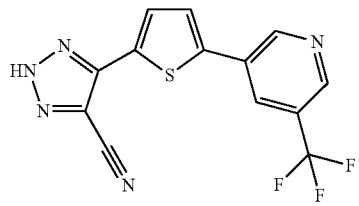 | 322 |

TABLE 6-continued

| Ex. No. | STR | MS (M + H) |
| --- | --- | --- |
| 2536 | | 297 |
| 2537 | | 322 |
| 2538 | | 268 |
| 2539 | | 256 |
| 2540 | | 165 |
| 2541 | | 149 |
| 2542 | | 199 |

TABLE 6-continued

| Ex. No. | STR | MS (M + H) |
|---|---|---|
| 2543 | | 151 |
| 2544 | | 151 |
| 2545 | | 165 |
| 2546 | | 215 |
| 2547 | | 225 |
| 2548 | | 193 |
| 2549 | | 267 |

TABLE 6-continued

| Ex. No. | STR | MS (M + H) |
|---|---|---|
| 2550 | | 203 |
| 2551 | | 169 |
| 2252 | | 193 |

The compounds of Examples in Table 6 are shown as one tautomer, which are not limited and the other two tautomers are also encompassed therein.

Experimental Example 1

Effects on Type 2 Diabetes: Meal Load Test

To evaluate whether a cyanotriazol compound improves diabetes or not, especially related to postprandial blood glucose, meal load test was performed using one of type 2 diabetic model rats, the Zucker Diabetic Fatty (ZDF) rat (Charles river, Japan). About 24 animals fasted overnight (17 h) were taken blood samples from the tail veins, and measured blood glucose levels (Pre BG) and body weights (BW). Proper animals were selected and divided into two groups (n=6) based on the Pre BG and BW using SAS Statistical Analysis System (SAS institute Japan Ltd. Release 9.1). The compounds to be tested (10 or 30 mg/kg body weight in 5% Arabia gum) or Arabia gum solution only (vehicle group) were orally administrated via gavage two hours prior to or just before meal loading (50 kcal/kg body weight). The meal suspension was prepared by mixing purified AIN-93G (Norsan Corp, Yokohama, Japan) and distilled water (2:3, w/v). One-hour after meal loading, blood glucose (BG1h) of each animal was measured. Effectiveness of each compound was shown by $\Delta$BG1h (BG1h difference between compound group and vehicle group). Although a set of 24 animals was used several times (from 13 weeks to 21 weeks of age), at least a one-week interval was placed from one to another test. The results are shown in Table 7.

TABLE 7

| Example No. | Dose (mg/kg) | $\Delta$BG1h |
|---|---|---|
| 11 | 10 | −93.2 |
| 14 | 10 | −79.2 |
| 15 | 10 | −50.5 |
| 21 | 10 | −95.7 |
| 22 | 10 | −108.5 |
| 23 | 10 | −137.0 |
| 29 | 10 | −37.3 |
| 41 | 10 | −158.0 |
| 47 | 10 | −89.7 |
| 49 | 10 | −78.7 |
| 50 | 10 | −120.0 |
| 51 | 10 | −79.0 |
| 52 | 10 | −120.4 |
| 55 | 10 | −110.2 |
| 60 | 10 | −132.0 |
| 70 | 10 | −137.2 |
| 75 | 10 | −83.2 |
| 77 | 10 | −61.3 |
| 78 | 10 | −93.7 |
| 79 | 10 | −51.0 |
| 90 | 10 | −119.0 |
| 92 | 10 | −69.2 |
| 98 | 10 | −87.9 |
| 100 | 10 | −100.5 |
| 108 | 10 | −101.9 |
| 120 | 10 | −114.3 |
| 122 | 10 | −75.5 |
| 137 | 10 | −162.6 |
| 146 | 10 | −94.9 |
| 147 | 10 | −80.5 |
| 220 | 10 | −85.6 |
| 275 | 10 | −83.3 |
| 276 | 10 | −71.4 |
| 298 | 10 | −62.8 |
| 423 | 10 | −87.6 |
| 504 | 10 | −69.1 |

TABLE 7-continued

| Example No. | Dose (mg/kg) | ΔBG1h |
|---|---|---|
| 600 | 10 | −74.0 |
| 607 | 10 | −106.8 |
| 610 | 10 | −86.8 |
| 613 | 10 | −138.8 |
| 617 | 10 | −113.3 |
| 620 | 10 | −159.7 |
| 623 | 10 | −111.2 |
| 627 | 10 | −85.2 |
| 639 | 10 | −58.5 |
| 640 | 10 | −62.0 |
| 644 | 10 | −131.0 |
| 645 | 10 | −121.6 |
| 646 | 10 | −89.3 |
| 649 | 10 | −99.4 |
| 657 | 10 | −120.5 |
| 659 | 10 | −161.2 |
| 663 | 10 | −149.5 |
| 718 | 10 | −147.5 |
| 790 | 10 | −61.5 |
| 807 | 10 | −94.5 |
| 931 | 10 | −76.4 |
| 934 | 10 | −87.2 |
| 944 | 10 | −125.1 |
| 989 | 10 | −116.0 |
| 1004 | 10 | −89.8 |
| 1017 | 10 | −124.6 |
| 1018 | 10 | −59.2 |
| 1248 | 10 | −82.2 |
| 1505 | 10 | −123.5 |
| 1573 | 10 | −132.7 |
| 1672 | 10 | −94.8 |
| 1676 | 10 | −49.5 |
| 1806 | 30 | −86.3 |
| 1808 | 30 | −76.0 |
| 1810 | 30 | −53.2 |
| 1811 | 30 | −84.5 |
| 1812 | 30 | −111.8 |
| 1813 | 30 | −73.0 |
| 1814 | 30 | −108.7 |
| 1815 | 30 | −63.2 |
| 1816 | 30 | −45.5 |
| 1817 | 30 | −106.5 |
| 1818 | 30 | −33.0 |
| 1819 | 30 | −54.3 |
| 1820 | 30 | −77.0 |
| 1822 | 30 | −36.0 |
| 1823 | 30 | −63.3 |
| 1824 | 30 | −70.5 |
| 1825 | 30 | −48.3 |
| 1826 | 30 | −91.3 |
| 1827 | 30 | −82.5 |
| 1828 | 30 | −69.3 |
| 1829 | 30 | −93.7 |
| 1830 | 30 | −52.5 |
| 1831 | 30 | −61.0 |

Experimental Example 2

Assay of the Citric Acid Cycle Activation
(1) Construction of the Human NaCT Expression Vector pME-NaCT The human NaCT (also called SLC13A5 or NAC2; GenBank accession No. NM_177550) cDNA was inserted into the EcoRI-NotI site of the mammalian expression vector pME18S (GenBank accession No. AB009864) and purified by Qiagen Plasmid Maxi Kit (Qiagen).
(2) Establishment of NaCT Stably Expressed CHO Cells The pME-NaCT vector and the pcDNA™3.1 vector containing the neomycin resistance gene (Life Technologies) were co-transfected into CHO-K1 cells (ATCC) by Lipofectaimine 2000 reagent (Life Technologies). The next day the cells were subcultured in Nutrient Mixture F-12 Ham (Sigma-Aldrich) with 10% FBS (Biological Industries), and Geneticin (Life Technologies) was added (final concentration 350 µg/mL) in the following day. CHO cell clones stably expressing NaCT were given by neomycin resistant cell screening and limiting dilution method. Established cell lines (named NaCT-CHO) were also maintained in culture medium (Nutrient Mixture F-12 Ham) with 10% FBS and 350 µg/mL Geneticin. For control cells (named pME-CHO) preparation, the naive pME18S were also transfected instead of pME-NaCT into CHO-K1 cells.
(3) Assay of the Citric Acid Cycle Activation NaCT-CHO and pME-CHO were plated at 20,000 cells/well into white CulturPlate™-96 (PerkinElmer) two days before the assay. Prior to assay incubation, the cultured plates were washed twice with washing buffer, 10 mM HEPES-Tris(pH7.4) containing 140 mM choline chloride, 2 mM KCl, 1 mM $CaCl_2$, 1 mM $MgCl_2$. The compounds to be tested were dissolved and diluted in DMSO (Wako Pure Chemical industries) to 1,000 times of a final concentration, and further diluted to two times as high as the final concentration in assay buffer, 10 mM HEPES-Tris(pH7.4) containing 140 mM NaCl, 2 mM KCl, 1 mM $CaCl_2$, 1 mM $MgCl_2$. The range of final concentrations was properly determined based on the test compounds activity. Each 25 µL compound solution was added to well and subsequently 25 µL radiolabeled substrate solution containing 0.4 mM (0.4 MBq/mL) [1,5-$^{14}$C]-citric acid (PerkinElmer) in the assay buffer was added. After 1 hour incubation at 37° C., the reaction mixture was discarded and washed three times with pre-chilled washing buffer and then 0.1 mL MicroScint 20 (PerkinElmer) was added to well. The plate was sealed with TopSeal-A (PerkinElmer) and the radioactivity was measured using a TopCount (PerkinElmer). Non-specific activity (NS cpm) and total radio activity (Total cpm) were determined by counting of pME-CHO plated wells and NaCT-CHO plated wells without compounds, respectively. Diffusion of [$^{14}$C]—$CO_2$ was able to be estimated from residual radioactivity (R cpm) by an equation (Total−R)/(Total−NS)×100(%). The difference of Total and R was disappeared in the presence of 0.1 µM antimycin A. $EC_{50}$ values were calculated by regression analysis using SAS Statistical Analysis System (SAS institute Japan Ltd. Release 9.1). The results are shown in Table 8.

TABLE 8

| Ex. No | EC50 (µM) |
|---|---|
| 1 | 0.5 |
| 2 | 0.28 |
| 3 | 0.26 |
| 4 | 0.24 |
| 5 | 0.2 |
| 6 | 0.4 |
| 7 | 0.17 |
| 8 | 0.29 |
| 9 | 0.23 |
| 10 | 0.07 |
| 11 | 0.67 |
| 12 | 0.69 |
| 13 | 0.87 |
| 14 | 0.5 |
| 15 | 0.49 |
| 16 | 0.67 |
| 17 | 0.52 |
| 18 | 0.57 |
| 19 | 0.53 |
| 20 | 1.62 |
| 21 | 0.77 |
| 22 | 0.65 |
| 23 | 0.45 |
| 24 | 0.48 |

TABLE 8-continued

| Ex. No | EC50 (μM) |
| --- | --- |
| 25 | 0.54 |
| 26 | 0.69 |
| 27 | 0.89 |
| 28 | 0.37 |
| 29 | 0.68 |
| 30 | 0.64 |
| 31 | 0.38 |
| 32 | 0.74 |
| 33 | 0.27 |
| 34 | 0.46 |
| 35 | 0.34 |
| 36 | 0.45 |
| 37 | 0.12 |
| 38 | 0.42 |
| 39 | 0.71 |
| 40 | 0.55 |
| 41 | 0.39 |
| 42 | 0.59 |
| 43 | 0.67 |
| 44 | 0.69 |
| 45 | 0.91 |
| 46 | 0.98 |
| 47 | 1.07 |
| 48 | 0.43 |
| 49 | 0.48 |
| 50 | 0.44 |
| 51 | 0.76 |
| 52 | 0.58 |
| 53 | 0.48 |
| 54 | 0.43 |
| 55 | 0.65 |
| 56 | 0.73 |
| 57 | 0.48 |
| 58 | 0.72 |
| 59 | 0.50 |
| 60 | 0.30 |
| 61 | 0.44 |
| 62 | 0.6 |
| 63 | 0.96 |
| 64 | 0.24 |
| 65 | 0.79 |
| 66 | 0.66 |
| 67 | 0.49 |
| 68 | 0.46 |
| 69 | 0.53 |
| 70 | 0.51 |
| 71 | 0.59 |
| 72 | 0.3 |
| 73 | 0.73 |
| 74 | 2.91 |
| 75 | 0.88 |
| 76 | 0.59 |
| 77 | 0.91 |
| 78 | 0.51 |
| 79 | 0.62 |
| 80 | 0.87 |
| 81 | 0.99 |
| 82 | 0.76 |
| 83 | 1.08 |
| 84 | 1.5 |
| 85 | 0.69 |
| 86 | 0.67 |
| 87 | 0.90 |
| 88 | 0.62 |
| 89 | 0.76 |
| 90 | 0.56 |
| 91 | 0.7 |
| 92 | 0.82 |
| 93 | 0.58 |
| 94 | 0.79 |
| 95 | 0.74 |
| 96 | 0.67 |
| 97 | 0.50 |
| 98 | 0.59 |
| 99 | 0.54 |
| 100 | 0.54 |
| 101 | 0.85 |
| 102 | 0.36 |

TABLE 8-continued

| Ex. No | EC50 (μM) |
| --- | --- |
| 103 | 0.23 |
| 104 | 0.70 |
| 105 | 1.91 |
| 106 | 0.84 |
| 107 | 2.56 |
| 108 | 0.42 |
| 109 | 0.67 |
| 110 | 3.23 |
| 111 | 0.75 |
| 112 | 0.79 |
| 113 | 0.79 |
| 114 | 0.45 |
| 115 | 0.65 |
| 116 | 4.13 |
| 117 | 1.59 |
| 119 | 0.71 |
| 120 | 0.89 |
| 121 | 0.99 |
| 122 | 0.51 |
| 123 | 0.68 |
| 124 | 0.92 |
| 125 | 0.54 |
| 126 | 0.26 |
| 127 | 0.74 |
| 128 | 0.56 |
| 129 | 0.44 |
| 130 | 0.73 |
| 131 | 0.44 |
| 132 | 0.32 |
| 133 | 0.19 |
| 134 | 0.085 |
| 135 | 1.57 |
| 136 | 0.68 |
| 137 | 0.57 |
| 138 | 0.062 |
| 139 | 0.21 |
| 140 | 0.8 |
| 141 | 0.71 |
| 142 | 0.58 |
| 143 | 1.02 |
| 144 | 0.79 |
| 145 | 0.37 |
| 146 | 0.41 |
| 147 | 1.66 |
| 148 | 0.92 |
| 149 | 0.7 |
| 150 | 0.86 |
| 220 | 0.35 |
| 275 | 1.04 |
| 276 | 0.85 |
| 298 | 0.74 |
| 423 | 0.92 |
| 504 | 1.47 |
| 600 | 0.43 |
| 607 | 0.45 |
| 610 | 1.74 |
| 613 | 0.43 |
| 617 | 0.48 |
| 620 | 1.45 |
| 623 | 0.69 |
| 627 | 0.74 |
| 639 | 1.21 |
| 640 | 0.67 |
| 644 | 2.35 |
| 645 | 1.09 |
| 646 | 0.62 |
| 649 | 2.47 |
| 657 | 1.16 |
| 659 | 0.81 |
| 663 | 1.25 |
| 718 | 1.51 |
| 790 | 0.98 |
| 807 | 1.1 |
| 931 | 0.69 |
| 934 | 0.51 |
| 944 | 1.01 |
| 989 | 0.80 |
| 1004 | 1.80 |

TABLE 8-continued

| Ex. No | EC50 (μM) |
|---|---|
| 1017 | 1.00 |
| 1018 | 1.17 |
| 1248 | 3.05 |
| 1505 | 0.42 |
| 1573 | 1.03 |
| 1672 | 1.29 |
| 1676 | 2.22 |

Experimental Example 3

Measurement of Carbon Dioxide Evolution Rate and Oxygen Consumption Rate

Figure 2:
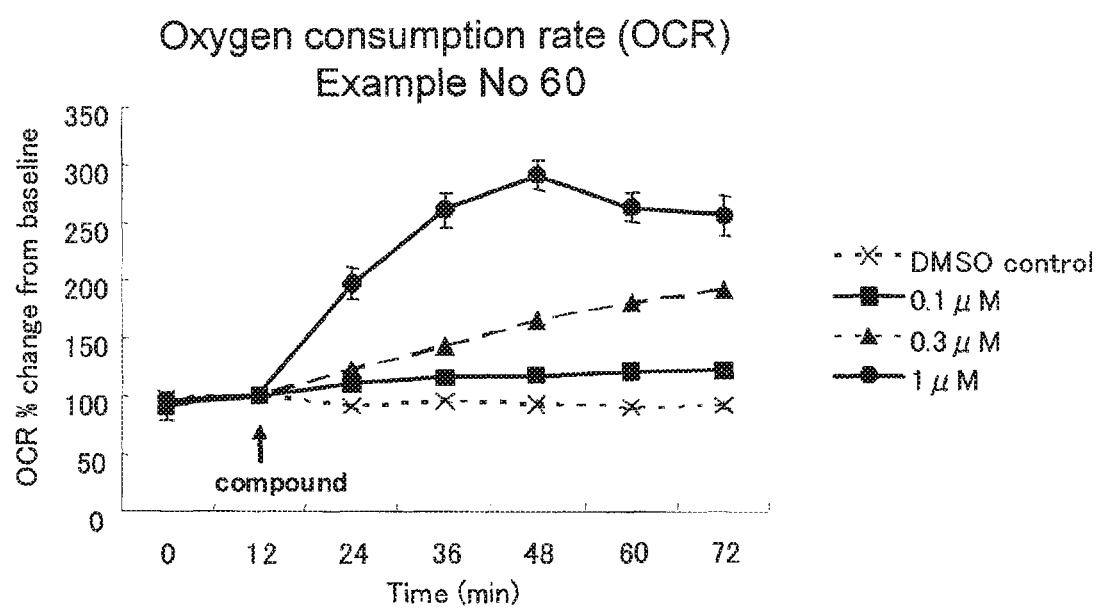
FIG. 2 shows oxygen consumption rate (OCR) of the compound of Example 60.

Carbon dioxide evolution rate (CDER) and oxygen consumption rate (OCR) were measured using an extracellular flux analyzer (XF24-3; Seahorse Bioscience). Measurements were conducted in Krebs-Henseleit HEPES Buffer (KHHB) containing 111 mM NaCl, 4.7 mM KCl, 2 mM $MgSO_4$, 1.2 mM $Na_2HPO_4$, 25 mM glucose, 1 mM sodium pyruvate, 20 mM HEPES (pH7.1). NaCT-CHO was maintained in culture medium (Nutrient Mixture F-12 Ham with 10% FBS and 350 μg/mL geneticin). The day before XF24 assay, the cells in a 100 μL volume of culture medium were seeded at 100,000 cells/well in an XF24 cell culture microplate (Seahorse Bioscience), allowed to attach for 4-5 hours, and then 150 μL of culture medium was added to each well. XF24-3 assay cartridge sensors (Seahorse Bioscience) were hydrated with XF Calibration solution (Seahorse Bioscience) and were incubated at 37° C. for overnight. Next day the plate was incubated at 37° C. for 1 hour prior to assay. After washing the plate twice with KHHB, 675 μL of KHHB was added to each well and then the plate was incubated for another 30 min. The compounds to be tested were first dissolved in DMSO (Wako Pure Chemical industries) at 1,000 times as high as a final concentration required for the assay and followed by further dilution with KHHB to 10 times of the final concentration. Injection port was loaded with the 75 μL of KHHB containing compounds. After a 13-min equilibration periods, a round of measurement which consisted of a 6.5-min mixing periods, a 0.5-min waiting period and a 4-min measuring periods, was repeated twice for basal measurement, and followed by the compounds injection. After the injection, a 5-round measurement was conducted for evaluating compound efficacy on CDER and OCR. CDER and OCR raw data were transformed using the "(LEVEL) Curve Fit" algorithm and "(LEVEL) Direct (AKOS)" algorithm, respectively, which are components of the Seahorse XF24 1.8.0.14 software package. The results are shown in FIGS. 1 and 2.

INDUSTRIAL APPLICABILITY

Since Compound (1) stimulates the citric acid cycle activity and/or improves hyperglycemia, it is useful for treating and/or preventing diseases or disorders on which citric acid cycle activation and/or improvement of hyperglycemia has a prophylactic and/or therapeutic effect, for example, diabetes, impaired glucose tolerance, insulin resistance, diabetic complications, obesity, dyslipidemia, hepatic steatosis, atherosclerosis and/or cardiovascular disease, as well as diseases or disorders that would benefit from stimulating energy expenditure.

This application is based on provisional patent application Nos. 61/847,268, 61/885,254 and 61/928,267 filed in USA, the contents of which are encompassed in full herein.

The invention claimed is:
1. A cyanotriazole compound represented by the formula (1aa):

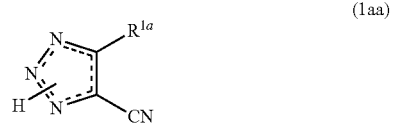

wherein $R^{1a}$ is one of the following (1-1) to (1-13):
(1-1) a phenyl group substituted with one or more members selected from the group consisting of the following (1-1-1) to (1-1-36):
(1-1-1) a lower alkyl group optionally substituted with one or more halogen atoms,
(1-1-2) a lower alkoxy group optionally substituted with one or more halogen atoms,
(1-1-3) a lower alkoxy lower alkyl group,
(1-1-4) a cycloalkyl group,
(1-1-5) a cycloalkoxy group,
(1-1-6) a cycloalkyl lower alkyl group,
(1-1-7) a cycloalkyl lower alkoxy group,
(1-1-8) a cycloalkyl lower alkoxy lower alkyl group,
(1-1-9) a halogen atom,
(1-1-10) a cyano group,
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group substituted on the phenyl ring with one or more lower alkyl groups substituted with one or more halogen atoms,
(1-1-14) a phenoxy group optionally substituted with one or more lower alkyl groups optionally substituted with one or more halogen atoms,
(1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms,
(1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
(1-1-17) a phenylthio group optionally substituted with one or more halogen atoms,
(1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms, (1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms,
(1-2) a thiazolyl group substituted with one or more members selected from the group consisting of the following (1-2-1) to (1-2-11):
(1-2-1) a lower alkyl group optionally substituted with one or more halogen atoms,
(1-2-2) a lower alkoxy group,
(1-2-3) a cycloalkyl group,
(1-2-4) a halogen atom,
(1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-2-6) a styryl group optionally substituted on the phenyl ring with one or more lower alkyl groups optionally substituted with one or more halogen atoms,
(1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
(1-2-8) a benzyloxy group optionally substituted on the phenyl ring with one or more halogen atoms,
(1-2-9) a phenylthio group optionally substituted with one or more members selected from the group consisting of a halogen atom; and a lower alkyl group optionally substituted with one or more halogen atoms,
(1-2-10) an N-lower alkyl-N-phenyl amino group optionally substituted on the phenyl ring with one or more members selected from the group consisting of a halogen atom; and a lower alkyl group optionally substituted with one or more halogen atoms, and
(1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
(1-3-1) a lower alkyl group,
(1-3-2) a cycloalkyl group, and
(1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group substituted with one or more members selected from the group consisting of the following (1-4-1) to (1-4-5):
(1-4-1) a lower alkyl group optionally substituted with one or more halogen atoms,
(1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
(1-4-3) a benzyl group optionally substituted on the phenyl ring with one or more halogen atoms,
(1-4-4) a phenoxy group optionally substituted with one or more lower alkyl groups optionally substituted with one or more halogen atoms, and
(1-4-5) a styryl group optionally substituted on the phenyl ring with one or more lower alkyl groups optionally substituted with one or more halogen atoms,
(1-5) a furyl group substituted with one or more members selected from the group consisting of the following (1-5-1) to (1-5-2):
(1-5-1) a phenyl group optionally substituted with one or more halogen atoms, and
(1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of the following (1-6-1) to (1-6-3):
(1-6-1) a lower alkyl group,
(1-6-2) a phenyl group optionally substituted with one or more members selected from the group consisting of a halogen atom; and a lower alkyl group optionally substituted with one or more halogen atoms, and
(1-6-3) a phenyl lower alkyl group optionally substituted on the phenyl ring with one or more lower alkyl groups optionally substituted with one or more halogen atoms,
(1-7) a pyridyl group substituted with one or more members selected from the group consisting of the following (1-7-1) to (1-7-3):

(1-7-1) a benzyloxy lower alkyl group optionally substituted on the phenyl ring with one or more lower alkyl groups optionally substituted with one or more halogen atoms,
(1-7-2) a phenyl group optionally substituted with one or more lower alkyl groups optionally substituted with one or more halogen atoms, and
(1-7-3) a benzofuryl group,
(1-8) a piperidyl group substituted with one or more members selected from the group consisting of the following (1-8-1) to (1-8-2):
(1-8-1) a phenyl group optionally substituted with one or more lower alkyl groups optionally substituted with one or more halogen atoms, and
(1-8-2) a benzyl group optionally substituted on the phenyl ring with one or more halogen atoms,
(1-9) an indolyl group optionally substituted with one or more members selected from the group consisting of the following (1-9-1) to (1-9-2):
(1-9-1) a lower alkyl group optionally substituted with one or more halogen atoms, and
(1-9-2) a phenyl group optionally substituted with one or more halogen atoms,
(1-10) a benzofuryl group optionally substituted with one or more members selected from the group consisting of the following (1-10-1) to (1-10-2):
(1-10-1) a halogen atom, and
(1-10-2) a phenyl group optionally substituted with one or more halogen atoms,
(1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
(1-12-1) a phenyl group optionally substituted with one or more lower alkyl groups optionally substituted with one or more halogen atoms; and
(1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
(1-13-1) a phenyl group,
(1-13-2) a pyrrolidinyl group, and
(1-13-3) a piperidyl group; provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
5-{4-[2-(thiophen-2-yl)vinyl]phenyl}-1,2,3-triazole-4-carbonitrile;
5-{4-[2-(benzofuran-2-yl)vinyl]phenyl}-1,2,3-triazole-4-carbonitrile;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole;
4-(4-fluoro-3-phenoxyphenyl)-5-cyano-1,2,3-triazole;
4-(2-fluorophenyl)-1,2,3-triazole-5-carbonitrile;
4-(4-fluoro-3-methoxyphenyl)-1,2,3-triazole-5-carbonitrile;
4-(2-methoxyphenyl)-1H-1,2,3-triazole-5-carbonitrile;
4-(2,4-dimethoxyphenyl)-1H-1,2,3-triazole-5-carbonitrile;
4-(2,6-dichlorophenyl)-1H-1,2,3-triazole-5-carbonitrile;
4-(3-bromo-6-methoxyphenyl)-1H-1,2,3-triazole-5-carbonitrile;
4-(2-chloro-6-fluorophenyl)-1H-1,2,3-triazole-5-carbonitrile;
4-(4'-methoxy-biphenyl-4-yl)-1H-1,2,3-triazole-5-carbonitrile;
4-(4-trifluoromethoxyphenyl)-1H-1,2,3-triazole-5-carbonitrile;
4-(4'-chlorobiphenyl-4-yl)-1H-1,2,3-triazole-5-carbonitrile;
4-(3-trifluoromethylphenyl)-1H-1,2,3-triazole-5-carbonitrile;
4-(2,4-dichlorophenyl)-1H-1,2,3-triazole-5-carbonitrile;
4-(2,4,6-trimethylphenyl)-1H-1,2,3-triazole-5-carbonitrile;
4-(2,6-difluorophenyl)-1H-1,2,3-triazole-5-carbonitrile;
4-(4'-(trifluoromethyl)biphenyl-4-yl)-1H-1,2,3-triazole-5-carbonitrile;
4-(3,5-di-tert-butyl-2-methoxyphenyl)-1H-1,2,3-triazole-5-carbonitrile;
4-(4'-methylbiphenyl-2-yl)-1H-1,2,3-triazole-5-carbonitrile;
4-(4-ethylphenyl)-1H-1,2,3-triazole-5-carbonitrile; and
4-(4-tert-butylphenyl)-1H-1,2,3-triazole-5-carbonitrile;
are excluded,
or a salt thereof.
2. The compound or salt according to claim 1, wherein $R^{1a}$ is the following (1-1):
(1-1) a phenyl group substituted with one or more members selected from the group consisting of the following (1-1-1) to (1-1-36):
(1-1-1) a lower alkyl group optionally substituted with one or more halogen atoms,
(1-1-2) a lower alkoxy group optionally substituted with one or more halogen atoms,
(1-1-3) a lower alkoxy lower alkyl group,
(1-1-4) a cycloalkyl group,
(1-1-5) a cycloalkoxy group,
(1-1-6) a cycloalkyl lower alkyl group,
(1-1-7) a cycloalkyl lower alkoxy group,
(1-1-8) a cycloalkyl lower alkoxy lower alkyl group,
(1-1-9) a halogen atom,
(1-1-10) a cyano group,
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms, (1-1-12) a phenyl lower alkyl group optionally substituted on the phenyl ring with one or more members selected from the group consisting of a halogen atom; and a lower alkyl group optionally substituted with one or more halogen atoms, (1-1-13) a styryl group substituted on the phenyl ring with one or more lower alkyl groups substituted with one or more halogen atoms, (1-1-14) a phenoxy group optionally substituted with one or more lower alkyl groups optionally substituted with one or more halogen atoms, (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms, (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms, (1-1-17) a phenylthio group optionally substituted with one or more halogen atoms, (1-1-18) a benzylthio lower alkyl group optionally substituted on the phenyl ring with one or more lower alkoxy groups optionally substituted with one or more halogen atoms, (1-1-19) an N-lower alkyl-N-phenyl amino lower alkyl group optionally substituted on the phenyl ring with one or more halogen atoms, (1-1-20) an N-benzyl-N-lower alkyl amino group optionally substituted on the phenyl ring with one or more lower alkyl groups optionally substituted with one or more halogen atoms, (1-1-21) a pyridyl group optionally substituted with one or more lower alkyl groups optionally substituted with one or more halogen atoms, (1-1-22) a pyridyl lower alkyl group optionally substituted on the pyridine ring with one or more lower alkyl groups optionally substituted with one or more halogen atoms, (1-1-23) a pyridyloxy lower alkyl group optionally substituted on the pyridine ring with one or more lower alkyl groups optionally substituted with one or more halogen atoms, (1-1-24) a pyridylvinyl group optionally substituted on the pyridine ring with one or more lower alkyl groups optionally substituted with one or more halogen atoms, (1-1-25) a pyrimidinyl group optionally substituted with one or more lower alkyl groups optionally substituted with one or more halogen atoms, (1-1-26) a pyrimidinylvinyl group optionally substituted on the pyrimidine ring with one or more lower alkyl groups optionally substituted with one or more halogen atoms, (1-1-27) a piperidyl group optionally substituted with one or more lower alkyl groups optionally substituted with one or more halogen atoms, (1-1-28) a benzoxazolyl group optionally substituted on the phenyl ring with one or more halogen atoms, (1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms,
(1-1-34) an indolinyl lower alkyl group,
(1-1-35) a benzothienylvinyl group, and
(1-1-36) a benzo[1,3]dioxolylvinyl group optionally substituted on the benzo[1,3]dioxole ring with one or more halogen atoms;

provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole;
4-(4-fluoro-3-phenoxyphenyl)-5-cyano-1,2,3-triazole;
4-(2-fluorophenyl)-1,2,3-triazole-5-carbonitrile;
4-(4-fluoro-3-methoxyphenyl)-1,2,3-triazole-5-carbonitrile;
4-(2-methoxyphenyl)-1H-1,2,3-triazole-5-carbonitrile;
4-(2,4-dimethoxyphenyl)-1H-1,2,3-triazole-5-carbonitrile;
4-(2,6-dichlorophenyl)-1H-1,2,3-triazole-5-carbonitrile;
4-(3-bromo-6-methoxyphenyl)-1H-1,2,3-triazole-5-carbonitrile;
4-(2-chloro-6-fluorophenyl)-1H-1,2,3-triazole-5-carbonitrile;
4-(4'-methoxy-biphenyl-4-yl)-1H-1,2,3-triazole-5-carbonitrile;
4-(4-trifluoromethoxyphenyl)-1H-1,2,3-triazole-5-carbonitrile;
4-(4'-chlorobiphenyl-4-yl)-1H-1,2,3-triazole-5-carbonitrile;
4-(3-trifluoromethylphenyl)-1H-1,2,3-triazole-5-carbonitrile;
4-(2,4-dichlorophenyl)-1H-1,2,3-triazole-5-carbonitrile;
4-(2,4,6-trimethylphenyl)-1H-1,2,3-triazole-5-carbonitrile;
4-(2,6-difluorophenyl)-1H-1,2,3-triazole-5-carbonitrile;
4-(4'-(trifluoromethyl)biphenyl-4-yl)-1H-1,2,3-triazole-5-carbonitrile;
4-(3,5-di-tert-butyl-2-methoxyphenyl)-1H-1,2,3-triazole-5-carbonitrile;
4-(4'-methylbiphenyl-2-yl)-1H-1,2,3-triazole-5-carbonitrile;

4-(4-ethylphenyl)-1H-1,2,3-triazole-5-carbonitrile; and
4-(4-tert-butylphenyl)-1H-1,2,3-triazole-5-carbonitrile;
are excluded.

3. The compound or salt according to claim 1, wherein $R^{1a}$ is one of the following (1-2) to (1-13):

(1-2) a thiazolyl group substituted with one or more members selected from the group consisting of the following (1-2-1) to (1-2-11):
  (1-2-1) a lower alkyl group optionally substituted with one or more halogen atoms,
  (1-2-2) a lower alkoxy group,
  (1-2-3) a cycloalkyl group,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-2-6) a styryl group optionally substituted on the phenyl ring with one or more lower alkyl groups optionally substituted with one or more halogen atoms,
  (1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
  (1-2-8) a benzyloxy group optionally substituted on the phenyl ring with one or more halogen atoms,
  (1-2-9) a phenylthio group optionally substituted with one or more members selected from the group consisting of a halogen atom; and a lower alkyl group optionally substituted with one or more halogen atoms,
  (1-2-10) an N-lower alkyl-N-phenyl amino group optionally substituted on the phenyl ring with one or more members selected from the group consisting of a halogen atom; and a lower alkyl group optionally substituted with one or more halogen atoms, and
  (1-2-11) a pyridyl group optionally substituted with one or more members selected from the group consisting of a halogen atom; and a lower alkyl group optionally substituted with one or more halogen atoms, (1-3) an oxazolyl group optionally substituted with one or more members selected from the group consisting of the following (1-3-1) to (1-3-3):
  (1-3-1) a lower alkyl group,
  (1-3-2) a cycloalkyl group, and
  (1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms, (1-4) a thienyl group substituted with one or more members selected from the group consisting of the following (1-4-1) to (1-4-5):
  (1-4-1) a lower alkyl group optionally substituted with one or more halogen atoms,
  (1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
  (1-4-3) a benzyl group optionally substituted on the phenyl ring with one or more halogen atoms,
  (1-4-4) a phenoxy group optionally substituted with one or more lower alkyl groups optionally substituted with one or more halogen atoms, and
  (1-4-5) a styryl group optionally substituted on the phenyl ring with one or more lower alkyl groups optionally substituted with one or more halogen atoms, (1-5) a furyl group substituted with one or more members selected from the group consisting of the following (1-5-1) to (1-5-2):
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms, (1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms, (1-7) a pyridyl group substituted with one or more members selected from the group consisting of the following (1-7-1) to (1-7-3):
  (1-7-1) a benzyloxy lower alkyl group optionally substituted on the phenyl ring with one or more lower alkyl groups optionally substituted with one or more halogen atoms,
  (1-7-2) a phenyl group optionally substituted with one or more lower alkyl groups optionally substituted with one or more halogen atoms, and
  (1-7-3) a benzofuryl group, (1-8) a piperidyl group substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms, (1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms, (1-10) a benzofuryl group optionally substituted with one or more members selected from the group consisting of the following (1-10-1) to (1-10-2):
  (1-10-1) a halogen atom, and
  (1-10-2) a phenyl group optionally substituted with one or more halogen atoms, (1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms; and
  (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
  (1-13-1) a phenyl group,
  (1-13-2) a pyrrolidinyl group, and
  (1-13-3) a piperidyl group.

4. The compound or salt according to claim 1, wherein $R^{1a}$ is one of the following (1-1) to (1-7), (1-9), (1-10), (1-12) and (1-13):
(1-1) a phenyl group substituted with one or more members selected from the group consisting of
  (1-1-1) a lower alkyl group optionally substituted with one or more halogen atoms,
  (1-1-2) a lower alkoxy group optionally substituted with one or more halogen atoms, (1-1-9) a halogen atom,
  (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
  (1-1-12) a phenyl lower alkyl group optionally substituted on the phenyl ring with one or more members selected from the group consisting of a halogen atom; and a lower alkyl group optionally substituted with one or more halogen atoms,
  (1-1-13) a styryl group substituted on the phenyl ring with one or more lower alkyl groups substituted with one or more halogen atoms,
  (1-1-14) a phenoxy group,
  (1-1-16) a phenyl lower alkoxy group optionally substituted on the phenyl ring with one or more lower alkyl groups optionally substituted with one or more halogen atoms,
  (1-1-19) an N-lower alkyl-N-phenyl amino lower alkyl group optionally substituted on the phenyl ring with one or more halogen atoms,
  (1-1-20) an N-benzyl-N-lower alkyl amino group optionally substituted on the phenyl ring with one or more lower alkyl groups optionally substituted with one or more halogen atoms,
  (1-1-21) a pyridyl group optionally substituted with one or more lower alkyl groups optionally substituted with one or more halogen atoms,
  (1-1-23) a pyridyloxy lower alkyl group optionally substituted on the pyridine ring with one or more lower alkyl groups optionally substituted with one or more halogen atoms,
  (1-1-24) a pyridylvinyl group optionally substituted on the pyridine ring with one or more lower alkyl groups optionally substituted with one or more halogen atoms,
  (1-1-25) a pyrimidinyl group optionally substituted with one or more lower alkyl groups optionally substituted with one or more halogen atoms,
  (1-1-26) a pyrimidinylvinyl group optionally substituted on the pyrimidine ring with one or more lower alkyl groups optionally substituted with one or more halogen atoms,
  (1-1-27) a piperidyl group optionally substituted with one or more lower alkyl groups optionally substituted with one or more halogen atoms,
  (1-1-31) a thienyl group,
  (1-1-32) a benzothienyl group,
  (1-1-33) a benzo[1,3]dioxolyl group optionally substituted with one or more halogen atoms,
  (1-1-35) a benzothienylvinyl group, and
  (1-1-36) a benzo[1,3]dioxolylvinyl group optionally substituted on the benzo[1,3]dioxole ring with one or more halogen atoms,
(1-2) a thiazolyl group substituted with one or more members selected from the group consisting of
  (1-2-1) a lower alkyl group optionally substituted with one or more halogen atoms,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
  (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of
  (1-3-1) a lower alkyl group,
  (1-3-2) a cycloalkyl group, and
  (1-3-3) a phenyl group optionally substituted with one or more members selected from the group consisting of a halogen atom; and a lower alkyl group optionally substituted with one or more halogen atoms,
(1-4) a thienyl group substituted with one or more members selected from the group consisting of
  (1-4-2) a phenyl group optionally substituted with one or more lower alkyl groups optionally substituted with one or more halogen atoms,
(1-5) a furyl group substituted with one or more members selected from the group consisting of
  (1-5-1) a phenyl group optionally substituted with one or more halogen atoms, and
  (1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of
  (1-6-1) a lower alkyl group, and
  (1-6-2) a phenyl group optionally substituted with one or more members selected from the group consisting of a halogen atom; and a lower alkyl group optionally substituted with one or more halogen atoms,
(1-7) a pyridyl group substituted with one or more members selected from the group consisting of
  (1-7-3) a benzofuryl group,
(1-9) an indolyl group optionally substituted with one or more members selected from the group consisting of (1-9-1) a lower alkyl group optionally substituted with one or more halogen atoms,
(1-10) a benzofuryl group optionally substituted with one or more members selected from the group consisting of
(1-10-2) a phenyl group optionally substituted with one or more halogen atoms,
(1-12) a phenyl lower alkyl group optionally substituted on the phenyl ring with one or more members selected from the group consisting of
(1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of
(1-13-1) a phenyl group,
(1-13-2) a pyrrolidyl group, and
(1-13-3) a piperidyl group.

5. The compound or salt according to claim 4, wherein $R^{1a}$ is the following (1-1):
(1-1) a phenyl group substituted with one or more members selected from the group consisting of
(1-1-1) a lower alkyl group optionally substituted with one or more halogen atoms,
(1-1-2) a lower alkoxy group optionally substituted with one or more halogen atoms,
(1-1-9) a halogen atom,
(1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-1-12) a phenyl lower alkyl group optionally substituted on the phenyl ring with one or more members selected from the group consisting of a halogen atom; and a lower alkyl group optionally substituted with one or more halogen atoms,
(1-1-13) a styryl group substituted on the phenyl ring with one or more lower alkyl groups substituted with one or more halogen atoms,
(1-1-14) a phenoxy group,
(1-1-16) a phenyl lower alkoxy group optionally substituted on the phenyl ring with one or more lower alkyl groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-31) a thienyl group,
(1-1-32) a benzothienyl group,
(1-1-33) a benzo[1,3]dioxolyl group optionally substituted with one or more halogen atoms,
(1-1-35) a benzothienylvinyl group, and
(1-1-36) a benzo[1,3]dioxolylvinyl group optionally substituted on the benzo[1,3]dioxole ring with one or more halogen atoms;
provided that
5-(4-styrylphenyl)-1,2,3-triazole-4-carbonitrile;
5-[4-(4-methylstyryl)phenyl]-1,2,3-triazole-4-carbonitrile;
5-[4-(4-methoxystyryl)phenyl]-1,2,3-triazole-4-carbonitrile;
5-[4-(3,4,5-trimethoxystyryl)phenyl]-1,2,3-triazole-4-carbonitrile;
5-[4-(4-chlorostyryl)phenyl]-1,2,3-triazole-4-carbonitrile;
5-[4-(3-chlorostyryl)phenyl]-1,2,3-triazole-4-carbonitrile;
5-[4-(4-cyanostyryl)phenyl]-1,2,3-triazole-4-carbonitrile;
5-{4-[2-(pyridin-4-yl)vinyl]phenyl}-1,2,3-triazole-4-carbonitrile;
4-(4-methylphenyl)-5-cyano-1,2,3-triazole;
4-(4-isopropylphenyl)-5-cyano-1,2,3-triazole;
4-(4-methoxyphenyl)-5-cyano-1,2,3-triazole;
4-(2,3-dimethoxyphenyl)-5-cyano-1,2,3-triazole;
4-(3,4-dimethoxyphenyl)-5-cyano-1,2,3-triazole;
4-(3,4,5-trimethoxyphenyl)-5-cyano-1,2,3-triazole;
4-(4-fluorophenyl)-5-cyano-1,2,3-triazole;
4-(4-chlorophenyl)-5-cyano-1,2,3-triazole;
4-(4-bromophenyl)-5-cyano-1,2,3-triazole;
4-(4-phenoxyphenyl)-5-cyano-1,2,3-triazole;
4-(3-fluoro-4-phenoxyphenyl)-5-cyano-1,2,3-triazole;
4-(3-phenoxyphenyl)-5-cyano-1,2,3-triazole; and
4-(4-fluoro-3-phenoxyphenyl)-5-cyano-1,2,3-triazole;
4-(2-fluorophenyl)-1,2,3-triazole-5-carbonitrile; 4-(4-fluoro-3-methoxyphenyl)-1,2,3-triazole-5-carbonitrile;
4-(2-methoxyphenyl)-1H-1,2,3-triazole-5-carbonitrile;
4-(2,4-dimethoxyphenyl)-1H-1,2,3-triazole-5-carbonitrile;
4-(2,6-dichlorophenyl)-1H-1,2,3-triazole-5-carbonitrile;
4-(3-bromo-6-methoxyphenyl)-1H-1,2,3-triazole-5-carbonitrile;
4-(2-chloro-6-fluorophenyl)-1H-1,2,3-triazole-5-carbonitrile;
4-(4'-methoxy-biphenyl-4-yl)-1H-1,2,3-triazole-5-carbonitrile;
4-(4-trifluoromethoxyphenyl)-1H-1,2,3-triazole-5-carbonitrile;
4-(4'-chlorobiphenyl-4-yl)-1H-1,2,3-triazole-5-carbonitrile;
4-(3-trifluoromethylphenyl)-1H-1,2,3-triazole-5-carbonitrile;
4-(2,4-dichlorophenyl)-1H-1,2,3-triazole-5-carbonitrile;
4-(2,4,6-trimethylphenyl)-1H-1,2,3-triazole-5-carbonitrile;

4-(2,6-difluorophenyl)-1H-1,2,3-triazole-5-carbonitrile;
4-(4'-(trifluoromethyl)biphenyl-4-yl)-1H-1,2,3-triazole-5-carbonitrile;
4-(3,5-di-tert-butyl-2-methoxyphenyl)-1H-1,2,3-triazole-5-carbonitrile;
4-(4'-methylbiphenyl-2-yl)-1H-1,2,3-triazole-5-carbonitrile;
4-(4-ethylphenyl)-1H-1,2,3-triazole-5-carbonitrile; and
4-(4-tert-butylphenyl)-1H-1,2,3-triazole-5-carbonitrile;
are excluded.

6. The compound or salt according to claim 4, wherein $R^{1a}$ is one of the following (1-2) to (1-7), (1-9), (1-10), (1-12) and (1-13):
(1-2) a thiazolyl group substituted with one or more members selected from the group consisting of
   (1-2-1) a lower alkyl group optionally substituted with one or more halogen atoms,
   (1-2-4) a halogen atom,
   (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
   (1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of
   (1-3-1) a lower alkyl group,
   (1-3-2) a cycloalkyl group, and
   (1-3-3) a phenyl group optionally substituted with one or more members selected from the group consisting of a halogen atom; and a lower alkyl group optionally substituted with one or more halogen atoms,
(1-4) a thienyl group substituted with one or more members selected from the group consisting of
   (1-4-2) a phenyl group optionally substituted with one or more lower alkyl groups optionally substituted with one or more halogen atoms,
(1-5) a furyl group substituted with one or more members selected from the group consisting of
   (1-5-1) a phenyl group optionally substituted with one or more halogen atoms, and
   (1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of
   (1-6-1) a lower alkyl group, and
   (1-6-2) a phenyl group optionally substituted with one or more members selected from the group consisting of a halogen atom; and a lower alkyl group optionally substituted with one or more halogen atoms,
(1-7) a pyridyl group substituted with one or more members selected from the group consisting of
   (1-7-3) a benzofuryl group,
(1-9) an indolyl group optionally substituted with one or more members selected from the group consisting of
   (1-9-1) a lower alkyl group optionally substituted with one or more halogen atoms,
(1-10) a benzofuryl group optionally substituted with one or more members selected from the group consisting of
   (1-10-2) a phenyl group optionally substituted with one or more halogen atoms,
(1-12) a phenyl lower alkyl group optionally substituted on the phenyl ring with one or more members selected from the group consisting of
   (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of
   (1-13-1) a phenyl group,
   (1-13-2) a pyrrolidyl group, and
   (1-13-3) a piperidyl group.

7. A cyanotriazole compound represented by the formula (1bb):

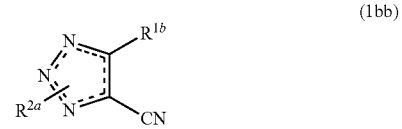

wherein
$R^{1b}$ is one of the following (1-1) to (1-13):
(1-1) a phenyl group optionally substituted with one or more members selected from the group consisting of the following (1-1-1) to (1-1-34):
   (1-1-1) a lower alkyl group optionally substituted with one or more halogen atoms,
   (1-1-2) a lower alkoxy group optionally substituted with one or more halogen atoms,
   (1-1-3) a lower alkoxy lower alkyl group,
   (1-1-4) a cycloalkyl group,
   (1-1-5) a cycloalkoxy group,
   (1-1-6) a cycloalkyl lower alkyl group,
   (1-1-7) a cycloalkyl lower alkoxy group,
   (1-1-8) a cycloalkyl lower alkoxy lower alkyl group,
   (1-1-9) a halogen atom,
   (1-1-10) a cyano group,
   (1-1-11) a phenyl group optionally substituted with one or more members selected from the group consisting of a halogen atom; a lower alkyl group optionally substituted with one or more halogen atoms; and a lower alkoxy group optionally substituted with one or more halogen atoms,
   (1-1-12) a phenyl lower alkyl group optionally substituted on the phenyl ring with one or more members selected from the group consisting of a halogen atom; and a lower alkyl group optionally substituted with one or more halogen atoms,
   (1-1-13) a styryl group substituted on the phenyl ring with one or more lower alkyl groups substituted with one or more halogen atoms,
   (1-1-14) a phenoxy group optionally substituted with one or more lower alkyl groups optionally substituted with one or more halogen atoms,
   (1-1-15) a phenoxy lower alkyl group optionally substituted on the phenyl ring with one or more members selected from the group consisting of a lower alkyl group optionally substituted with one or more halogen atoms; and a lower alkoxy group optionally substituted with one or more halogen atoms, (1-1-16) a phenyl lower alkoxy group optionally substituted on the phenyl ring with one or more members selected from the group consisting of a halogen atom; a lower alkoxy group; and a lower alkyl group optionally substituted with one or more halogen atoms,
(1-1-17) a phenylthio group optionally substituted with one or more halogen atoms,
(1-1-18) a benzylthio lower alkyl group optionally substituted on the phenyl ring with one or more lower alkoxy groups optionally substituted with one or more halogen atoms,
(1-1-19) an N-lower alkyl-N-phenyl amino lower alkyl group optionally substituted on the phenyl ring with one or more halogen atoms,
(1-1-20) an N-benzyl-N-lower alkyl amino group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-22) a pyridyl lower alkyl group optionally substituted on the pyridine ring with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-27) a piperidyl group optionally substituted with one or more lower alkyl groups optionally substituted with one or more halogen atoms,
(1-1-28) a benzoxazolyl group optionally substituted on the phenyl ring with one or more halogen atoms,
(1-1-29) a benzofuryl group,
(1-1-30) a benzofuryl lower alkoxy group,
(1-1-31) a thienyl group,
(1-1-32) a benzothienyl group,
(1-1-33) a benzo[1,3]dioxolyl group optionally substituted with one or more halogen atoms, and
(1-1-34) an indolinyl lower alkyl group,
(1-2) a thiazolyl group optionally substituted with one or more members selected from the group consisting of the following (1-2-1) to (1-2-11):
(1-2-1) a lower alkyl group optionally substituted with one or more halogen atoms,
(1-2-2) a lower alkoxy group,
(1-2-3) a cycloalkyl group,
(1-2-4) a halogen atom,
(1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-2-6) a styryl group optionally substituted on the phenyl ring with one or more lower alkyl groups optionally substituted with one or more halogen atoms,
(1-2-7) a phenoxy group optionally substituted with one or more members selected from the group consisting of a halogen atom; a lower alkyl group optionally substituted with one or more halogen atoms; and a lower alkoxy group optionally substituted with one or more halogen atoms,
(1-2-8) a benzyloxy group optionally substituted on the phenyl ring with one or more halogen atoms,
(1-2-9) a phenylthio group optionally substituted with one or more members selected from the group consisting of a halogen atom; and a lower alkyl group optionally substituted with one or more halogen atoms,
(1-2-10) an N-lower alkyl-N-phenyl amino group optionally substituted on the phenyl ring with one or more members selected from the group consisting of a halogen atom; and a lower alkyl group optionally substituted with one or more halogen atoms, and
(1-2-11) a pyridyl group optionally substituted with one or more members selected from the group consisting of a halogen atom; and a lower alkyl group optionally substituted with one or more halogen atoms,
(1-3) an oxazolyl group optionally substituted with one or more members selected from the group consisting of the following (1-3-1) to (1-3-3):
(1-3-1) a lower alkyl group,
(1-3-2) a cycloalkyl group, and
(1-3-3) a phenyl group optionally substituted with one or more members selected from the group consisting of a halogen atom; a lower alkyl group optionally substituted with one or more halogen atoms; and a lower alkoxy group optionally substituted with one or more halogen atoms,
(1-4) a thienyl group optionally substituted with one or more members selected from the group consisting of the following (1-4-1) to (1-4-5):
(1-4-1) a lower alkyl group optionally substituted with one or more halogen atoms,
(1-4-2) a phenyl group optionally substituted with one or more members selected from the group consisting of a halogen atom; a lower alkyl group optionally substituted with one or more halogen atoms; and a benzyloxy group optionally substituted on the phenyl ring with one or more lower alkyl groups optionally substituted with one or more halogen atoms,
(1-4-3) a benzyl group optionally substituted on the phenyl ring with one or more halogen atoms,
(1-4-4) a phenoxy group optionally substituted with one or more lower alkyl groups optionally substituted with one or more halogen atoms, and
(1-4-5) a styryl group optionally substituted on the phenyl ring with one or more lower alkyl groups optionally substituted with one or more halogen atoms,
(1-5) a furyl group optionally substituted with one or more members selected from the group consisting of the following (1-5-1) to (1-5-2):
(1-5-1) a phenyl group optionally substituted with one or more halogen atoms, and
(1-5-2) a styryl group optionally substituted on the phenyl ring with one or more members selected from the group consisting of a halogen atom; and a lower alkyl group optionally substituted with one or more halogen atoms,
(1-6) a pyrrolyl group optionally substituted with one or more members selected from the group consisting of the following (1-6-1) to (1-6-3):
  (1-6-1) a lower alkyl group,
  (1-6-2) a phenyl group optionally substituted with one or more members selected from the group consisting of a halogen atom; and a lower alkyl group optionally substituted with one or more halogen atoms, and
  (1-6-3) a phenyl lower alkyl group optionally substituted on the phenyl ring with one or more lower alkyl groups optionally substituted with one or more halogen atoms,
(1-7) a pyridyl group optionally substituted with one or more members selected from the group consisting of the following (1-7-1) to (1-7-2):
  (1-7-1) a benzyloxy lower alkyl group optionally substituted on the phenyl ring with one or more lower alkyl groups optionally substituted with one or more halogen atoms, and
  (1-7-2) a phenyl group optionally substituted with one or more lower alkyl groups optionally substituted with one or more halogen atoms,
(1-8) a piperidyl group optionally substituted with one or more members selected from the group consisting of the following (1-8-1) to (1-8-2):
  (1-8-1) a phenyl group optionally substituted with one or more lower alkyl groups optionally substituted with one or more halogen atoms, and
  (1-8-2) a benzyl group optionally substituted on the phenyl ring with one or more halogen atoms,
(1-9) an indolyl group optionally substituted with one or more members selected from the group consisting of the following (1-9-1) to (1-9-2):
  (1-9-1) a lower alkyl group optionally substituted with one or more halogen atoms, and
  (1-9-2) a phenyl group optionally substituted with one or more halogen atoms,
(1-10) a benzofuryl group optionally substituted with one or more phenyl groups optionally substituted with one or more halogen atoms,
(1-11) a benzothienyl group optionally substituted with one or more phenyl groups optionally substituted with one or more halogen atoms,
(1-12) a phenyl lower alkyl group optionally substituted on the phenyl ring with one or more members selected from the group consisting of the following (1-12-1) to (1-12-2):
  (1-12-1) a phenyl group optionally substituted with one or more lower alkyl groups optionally substituted with one or more halogen atoms, and
  (1-12-2) a benzyloxy group optionally substituted on the phenyl ring with one or more lower alkyl groups optionally substituted with one or more halogen atoms, and
(1-13) a pyrimidinyl group optionally substituted with one or more members selected from the group consisting of the following (1-13-1) to (1-13-3):
  (1-13-1) a phenyl group,
  (1-13-2) a pyrrolidyl group, and
  (1-13-3) a piperidyl group; and
$R^{2a}$ is one of the following (2-1) to (2-3):
(2-1) a lower alkyl group optionally substituted with one or more members selected from the group consisting of a hydroxy group; and a phenyl group optionally substituted with one or more lower alkyl groups optionally substituted with one or more halogen atoms,
(2-2) a 2-oxo-1,3-dioxolanyl group, and
(2-3) a group represented by the formula:

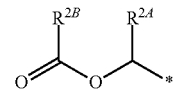

wherein
* is a bonding site;
$R^{2A}$ is one of the following (2A-1) to (2A-2):
  (2A-1) a hydrogen atom, and
  (2A-2) a lower alkyl group; and
$R^{2B}$ is one of the following (2B-1) to (2B-6):
  (2B-1) a lower alkoxy group optionally substituted with one or more members selected from the group consisting of a lower alkoxy group; a carboxy group; a lower alkoxy-carbonyl group; a hydroxy group; a phenyl lower alkoxy-carbonyl group; a lower alkenyloxy-carbonyl group; a morpholinyl group; a benzyloxycarbonyl group; and a tetrahydropyran-2-yloxy group,
  (2B-2) a lower alkyl group;
  (2B-3) a lower alkylamino group optionally substituted with one or more lower alkoxy-carbonyl groups;
  (2B-4) a cycloalkyl group;
  (2B-5) a cycloalkoxy group; and
  (2B-6) a phenyl group;
provided that
2-butyl-5-(pyridin-3-yl)-2H-[1,2,3]triazole-4-carbonitrile;
2-butyl-5-phenyl-2H-[1,2,3]triazole-4-carbonitrile; and
2-methyl-5-phenyl-2H-[1,2,3]triazole-4-carbonitrile are excluded,
or a salt thereof.

8. The cyanotriazole compound or salt according to claim 7, which is a compound represented by the formula (1bbA):

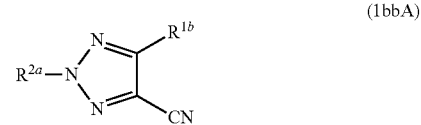

wherein each symbol is as defined in claim 7, or a salt thereof.

9. The cyanotriazole compound or salt according to claim 7,
wherein
$R^{1b}$ is one of the following (1-1) to (1-5):
(1-1) a phenyl group optionally substituted with one or more members selected from:
  (1-1-1) a lower alkyl group optionally substituted with one or more halogen atoms,
  (1-1-2) a lower alkoxy group optionally substituted with one or more halogen atoms,
  (1-1-9) a halogen atom,
  (1-1-11) a phenyl group optionally substituted with one or more lower alkoxy groups optionally substituted with one or more halogen atoms,
  (1-1-12) a phenyl lower alkyl group optionally substituted on the phenyl ring with one or more halogen atoms, (1-1-13) a styryl group substituted on the phenyl ring with one or more lower alkyl groups substituted with one or more halogen atoms,
(1-1-16) a phenyl lower alkoxy group optionally substituted on the phenyl ring with one or more lower alkyl groups optionally substituted with one or more halogen atoms,
(1-1-21) a pyridyl group optionally substituted with one or more lower alkyl groups optionally substituted with one or more halogen atoms,
(1-1-23) a pyridyloxy lower alkyl group optionally substituted on the pyridine ring with one or more lower alkyl groups optionally substituted with one or more halogen atoms,
(1-1-24) a pyridylvinyl group optionally substituted on the pyridine ring with one or more lower alkyl groups optionally substituted with one or more halogen atoms,
(1-1-25) a pyrimidinyl group optionally substituted with one or more lower alkyl groups optionally substituted with one or more halogen atoms,
(1-1-26) a pyrimidinylvinyl group optionally substituted on the pyrimidine ring with one or more lower alkyl groups optionally substituted with one or more halogen atoms,
(1-1-31) a thienyl group, and
(1-1-33) a benzo[1,3]dioxolyl group optionally substituted with one or more halogen atoms,
(1-2) a thiazolyl group optionally substituted with one or more members selected from:
  (1-2-1) a lower alkyl group optionally substituted with one or more halogen atoms,
  (1-2-4) a halogen atom,
  (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
  (1-2-11) a pyridyl group optionally substituted with one or more lower alkyl groups optionally substituted with one or more halogen atoms,
(1-3) an oxazolyl group optionally substituted with one or more members selected from:
  (1-3-1) a lower alkyl group,
  (1-3-2) a cycloalkyl group, and
  (1-3-3) a phenyl group optionally substituted with one or more members selected from the group consisting of a halogen atom; and a lower alkyl group optionally substituted with one or more halogen atoms,
(1-4) a thienyl group optionally substituted with one or more members selected from:
  (1-4-2) a phenyl group optionally substituted with one or more lower alkyl groups optionally substituted with one or more halogen atoms, and
(1-5) a furyl group optionally substituted with one or more members selected from:
  (1-5-1) a phenyl group optionally substituted with one or more halogen atoms; and
$R^{2a}$ is one of the following groups:
a 1-(((2-carboxy-2,2-dimethylethoxy)carbonyl)oxy)ethyl group;
a 1-(((2-carboxy-1,1-dimethylethoxy)carbonyl)oxy)ethyl group;
a 1-(((2-hydroxyethoxy)carbonyl)oxy)ethyl group;
a 1-(butyryloxy)ethyl group;
a 1-(isobutyryloxy)ethyl group;
an acetoxymethyl group; and
a butyryloxymethyl group.

10. A cyanotriazole compound selected from the group consisting of following compounds:
5-[3-methyl-5-(6-trifluoromethyl-pyridin-3-yl)-phenyl]-3H-[1,2,3]triazole-4-carbonitrile,
5-[3-methyl-5-(6-trifluoromethyl-pyridin-3-yl)-phenyl]-2H-[1,2,3]triazole-4-carbonitrile,
5-[3-methyl-5-(6-trifluoromethyl-pyridin-3-yl)-phenyl]-1H-[1,2,3]triazole-4-carbonitrile,
5-[3-trifluoromethyl-5-(6-trifluoromethyl-pyridin-2-yl)-phenyl]-3H-[1,2,3]triazole-4-carbonitrile,
5-[3-trifluoromethyl-5-(6-trifluoromethyl-pyridin-2-yl)-phenyl]-2H-[1,2,3]triazole-4-carbonitrile,
5-[3-trifluoromethyl-5-(6-trifluoromethyl-pyridin-2-yl)-phenyl]-1H-[1,2,3]triazole-4-carbonitrile,
5-[3-methoxy-5-(4-trifluoromethyl-pyridin-2-yl)-phenyl]-3H-[1,2,3]triazole-4-carbonitrile,
5-[3-methoxy-5-(4-trifluoromethyl-pyridin-2-yl)-phenyl]-2H-[1,2,3]triazole-4-carbonitrile,
5-[3-methoxy-5-(4-trifluoromethyl-pyridin-2-yl)-phenyl]-1H-[1,2,3]triazole-4-carbonitrile,
5-[3-(4-trifluoromethyl-pyrimidin-2-yl)-phenyl]-3H-[1,2,3]triazole-4-carbonitrile,
5-[3-(4-trifluoromethyl-pyrimidin-2-yl)-phenyl]-2H-[1,2,3]triazole-4-carbonitrile,
5-[3-(4-trifluoromethyl-pyrimidin-2-yl)-phenyl]-1H-[1,2,3]triazole-4-carbonitrile,
5-[3-methyl-5-(4-trifluoromethyl-pyrimidin-2-yl)-phenyl]-3H-[1,2,3]triazole-4-carbonitrile,
5-[3-methyl-5-(4-trifluoromethyl-pyrimidin-2-yl)-phenyl]-2H-[1,2,3]triazole-4-carbonitrile,
5-[3-methyl-5-(4-trifluoromethyl-pyrimidin-2-yl)-phenyl]-1H-[1,2,3]triazole-4-carbonitrile,
5-[3-chloro-5-(4-trifluoromethyl-pyrimidin-2-yl)-phenyl]-3H-[1,2,3]triazole-4-carbonitrile,
5-[3-chloro-5-(4-trifluoromethyl-pyrimidin-2-yl)-phenyl]-2H-[1,2,3]triazole-4-carbonitrile,
5-[3-chloro-5-(4-trifluoromethyl-pyrimidin-2-yl)-phenyl]-1H-[1,2,3]triazole-4-carbonitrile,
5-(5-chloro-4'-trifluoromethoxy-biphenyl-3-yl)-3H-[1,2,3]triazole-4-carbonitrile,
5-(5-chloro-4'-trifluoromethoxy-biphenyl-3-yl)-2H-[1,2,3]triazole-4-carbonitrile,
5-(5-chloro-4'-trifluoromethoxy-biphenyl-3-yl)-1H-[1,2,3]triazole-4-carbonitrile,
5-{3-[(E)-2-(4-cyano-phenyl)-vinyl]-phenyl}-3H-[1,2,3]triazole-4-carbonitrile,
5-{3-[(E)-2-(4-cyano-phenyl)-vinyl]-phenyl}-2H-[1,2,3]triazole-4-carbonitrile,
5-{3-[(E)-2-(4-cyano-phenyl)-vinyl]-phenyl}-1H-[1,2,3]triazole-4-carbonitrile,
5-{3-chloro-5-[(E)-2-(3-trifluoromethyl-phenyl)-vinyl]-phenyl}-3H-[1,2,3]triazole-4-carbonitrile,
5-{3-chloro-5-[(E)-2-(3-trifluoromethyl-phenyl)-vinyl]-phenyl}-2H-[1,2,3]triazole-4-carbonitrile,
5-{3-chloro-5-[(E)-2-(3-trifluoromethyl-phenyl)-vinyl]-phenyl}-1H-[1,2,3]triazole-4-carbonitrile,
5-{3-[(E)-2-(5-trifluoromethyl-pyridin-3-yl)-vinyl]-phenyl}-3H-[1,2,3]triazole-4-carbonitrile,
5-{3-[(E)-2-(5-trifluoromethyl-pyridin-3-yl)-vinyl]-phenyl}-2H-[1,2,3]triazole-4-carbonitrile,
5-{3-[(E)-2-(5-trifluoromethyl-pyridin-3-yl)-vinyl]-phenyl}-1H-[1,2,3]triazole-4-carbonitrile,
5-{3-[(E)-2-(4-trifluoromethyl-pyridin-2-yl)-vinyl]-phenyl}-3H-[1,2,3]triazole-4-carbonitrile, 5-{3-[(E)-2-(4-trifluoromethyl-pyridin-2-yl)-vinyl]-phenyl}-2H-[1,2,3]triazole-4-carbonitrile,
5-{3-[(E)-2-(4-trifluoromethyl-pyridin-2-yl)-vinyl]-phenyl}-1H-[1,2,3]triazole-4-carbonitrile,
5-{3-trifluoromethyl-5-[(E)-2-(6-trifluoromethyl-pyridin-2-yl)-vinyl]-phenyl}-3H-[1,2,3]triazole-4-carbonitrile,
5-{3-trifluoromethyl-5-[(E)-2-(6-trifluoromethyl-pyridin-2-yl)-vinyl]-phenyl}-2H-[1,2,3]triazole-4-carbonitrile,
5-{3-trifluoromethyl-5-[(E)-2-(6-trifluoromethyl-pyridin-2-yl)-vinyl]-phenyl}-1H-[1,2,3]triazole-4-carbonitrile,
5-{3-[(E)-2-(4-trifluoromethyl-pyrimidin-2-yl)-vinyl]-phenyl}-3H-[1,2,3]triazole-4-carbonitrile,
5-{3-[(E)-2-(4-trifluoromethyl-pyrimidin-2-yl)-vinyl]-phenyl}-2H-[1,2,3]triazole-4-carbonitrile,
5-{3-[(E)-2-(4-trifluoromethyl-pyrimidin-2-yl)-vinyl]-phenyl}-1H-[1,2,3]triazole-4-carbonitrile,
5-[3-(4-trifluoromethyl-pyridin-2-yloxymethyl)-phenyl]-3H-[1,2,3]triazole-4-carbonitrile,
5-[3-(4-trifluoromethyl-pyridin-2-yloxymethyl)-phenyl]-2H-[1,2,3]triazole-4-carbonitrile,
5-[3-(4-trifluoromethyl-pyridin-2-yloxymethyl)-phenyl]-1H-[1,2,3]triazole-4-carbonitrile,
5-[3-(2,5-bis-trifluoromethyl-benzyloxy)-phenyl]-3H-[1,2,3]triazole-4-carbonitrile,
5-[3-(2,5-bis-trifluoromethyl-benzyloxy)-phenyl]-2H-[1,2,3]triazole-4-carbonitrile,
5-[3-(2,5-bis-trifluoromethyl-benzyloxy)-phenyl]-1H-[1,2,3]triazole-4-carbonitrile,
5-[4-(4-trifluoromethyl-pyrimidin-2-yl)-phenyl]-3H-[1,2,3]triazole-4-carbonitrile,
5-[4-(4-trifluoromethyl-pyrimidin-2-yl)-phenyl]-2H-[1,2,3]triazole-4-carbonitrile,
5-[4-(4-trifluoromethyl-pyrimidin-2-yl)-phenyl]-1H-[1,2,3]triazole-4-carbonitrile,
5-[2-(4-chloro-phenyl)-thiazol-4-yl]-3H-[1,2,3]triazole-4-carbonitrile,
5-[2-(4-chloro-phenyl)-thiazol-4-yl]-2H-[1,2,3]triazole-4-carbonitrile,
5-[2-(4-chloro-phenyl)-thiazol-4-yl]-1H-[1,2,3]triazole-4-carbonitrile,
5-[2-(3,4-dichloro-phenyl)-thiazol-4-yl]-3H-[1,2,3]triazole-4-carbonitrile,
5-[2-(3,4-dichloro-phenyl)-thiazol-4-yl]-2H-[1,2,3]triazole-4-carbonitrile,
5-[2-(3,4-dichloro-phenyl)-thiazol-4-yl]-1H-[1,2,3]triazole-4-carbonitrile,
5-[2-(3-trifluoromethyl-phenyl)-thiazol-4-yl]-3H-[1,2,3]triazole-4-carbonitrile,
5-[2-(3-trifluoromethyl-phenyl)-thiazol-4-yl]-2H-[1,2,3]triazole-4-carbonitrile,
5-[2-(3-trifluoromethyl-phenyl)-thiazol-4-yl]-1H-[1,2,3]triazole-4-carbonitrile,
5-[2-(3-trifluoromethoxy-phenyl)-thiazol-4-yl]-3H-[1,2,3]triazole-4-carbonitrile,
5-[2-(3-trifluoromethoxy-phenyl)-thiazol-4-yl]-2H-[1,2,3]triazole-4-carbonitrile,
5-[2-(3-trifluoromethoxy-phenyl)-thiazol-4-yl]-1H-[1,2,3]triazole-4-carbonitrile,
5-[2-(3-chloro-4-fluoro-phenyl)-5-methyl-thiazol-4-yl]-3H-[1,2,3]triazole-4-carbonitrile,
5-[2-(3-chloro-4-fluoro-phenyl)-5-methyl-thiazol-4-yl]-2H-[1,2,3]triazole-4-carbonitrile,
5-[2-(3-chloro-4-fluoro-phenyl)-5-methyl-thiazol-4-yl]-1H-[1,2,3]triazole-4-carbonitrile,
5-[5-methyl-2-(4-trifluoromethyl-phenyl)-thiazol-4-yl]-3H-[1,2,3]triazole-4-carbonitrile,
5-[5-methyl-2-(4-trifluoromethyl-phenyl)-thiazol-4-yl]-2H-[1,2,3]triazole-4-carbonitrile,
5-[5-methyl-2-(4-trifluoromethyl-phenyl)-thiazol-4-yl]-1H-[1,2,3]triazole-4-carbonitrile,
5-[2-(4-chloro-phenyl)-5-ethyl-thiazol-4-yl]-3H-[1,2,3]triazole-4-carbonitrile,
5-[2-(4-chloro-phenyl)-5-ethyl-thiazol-4-yl]-2H-[1,2,3]triazole-4-carbonitrile,
5-[2-(4-chloro-phenyl)-5-ethyl-thiazol-4-yl]-1H-[1,2,3]triazole-4-carbonitrile,
5-[5-ethyl-2-(5-trifluoromethyl-pyridin-2-yl)-thiazol-4-yl]-3H-[1,2,3]triazole-4-carbonitrile,
5-[5-ethyl-2-(5-trifluoromethyl-pyridin-2-yl)-thiazol-4-yl]-2H-[1,2,3]triazole-4-carbonitrile,
5-[5-ethyl-2-(5-trifluoromethyl-pyridin-2-yl)-thiazol-4-yl]-1H-[1,2,3]triazole-4-carbonitrile,
5-[5-chloro-2-(3-trifluoromethyl-phenyl)-thiazol-4-yl]-3H-[1,2,3]triazole-4-carbonitrile,
5-[5-chloro-2-(3-trifluoromethyl-phenyl)-thiazol-4-yl]-2H-[1,2,3]triazole-4-carbonitrile,
5-[5-chloro-2-(3-trifluoromethyl-phenyl)-thiazol-4-yl]-1H-[1,2,3]triazole-4-carbonitrile,
5-[5-cyclopropyl-2-(3-trifluoromethyl-phenyl)-oxazol-4-yl]-3H-[1,2,3]triazole-4-carbonitrile,
5-[5-cyclopropyl-2-(3-trifluoromethyl-phenyl)-oxazol-4-yl]-2H-[1,2,3]triazole-4-carbonitrile,
5-[5-cyclopropyl-2-(3-trifluoromethyl-phenyl)-oxazol-4-yl]-1H-[1,2,3]triazole-4-carbonitrile,
5-[2-(4-chloro-phenyl)-5-isopropyl-oxazol-4-yl]-3H-[1,2,3]triazole-4-carbonitrile,
5-[2-(4-chloro-phenyl)-5-isopropyl-oxazol-4-yl]-2H-[1,2,3]triazole-4-carbonitrile,
5-[2-(4-chloro-phenyl)-5-isopropyl-oxazol-4-yl]-1H-[1,2,3]triazole-4-carbonitrile,
5-{5-[(E)-2-(3-trifluoromethyl-phenyl)-vinyl]-furan-2-yl}-3H-[1,2,3]triazole-4-carbonitrile,
5-{5-[(E)-2-(3-trifluoromethyl-phenyl)-vinyl]-furan-2-yl}-2H-[1,2,3]triazole-4-carbonitrile,
5-{5-[(E)-2-(3-trifluoromethyl-phenyl)-vinyl]-furan-2-yl}-1H-[1,2,3]triazole-4-carbonitrile,
5-[1-(4,4,4-trifluoro-butyl)-1H-indol-6-yl]-3H-[1,2,3]triazole-4-carbonitrile,
5-[1-(4,4,4-trifluoro-butyl)-1H-indol-6-yl]-2H-[1,2,3]triazole-4-carbonitrile,
5-[1-(4,4,4-trifluoro-butyl)-1H-indol-6-yl]-1H-[1,2,3]triazole-4-carbonitrile,
5-[6-(4-fluoro-phenyl)-benzofuran-2-yl]-3H-[1,2,3]triazole-4-carbonitrile,
5-[6-(4-fluoro-phenyl)-benzofuran-2-yl]-2H-[1,2,3]triazole-4-carbonitrile,
5-[6-(4-fluoro-phenyl)-benzofuran-2-yl]-1H-[1,2,3]triazole-4-carbonitrile,
5-(5'-fluoro-3'-trifluoromethyl-biphenyl-3-yl)-3H-[1,2,3]triazole-4-carbonitrile,
5-(5'-fluoro-3'-trifluoromethyl-biphenyl-3-yl)-2H-[1,2,3]triazole-4-carbonitrile,
5-(5'-fluoro-3'-trifluoromethyl-biphenyl-3-yl)-1H-[1,2,3]triazole-4-carbonitrile,
5-(5-chloro-3',5'-bis-trifluoromethyl-biphenyl-3-yl)-3H-[1,2,3]triazole-4-carbonitrile,
5-(5-chloro-3',5'-bis-trifluoromethyl-biphenyl-3-yl)-2H-[1,2,3]triazole-4-carbonitrile,
5-(5-chloro-3',5'-bis-trifluoromethyl-biphenyl-3-yl)-1H-[1,2,3]triazole-4-carbonitrile, 5-(5-chloro-3'-fluoro-4'-trifluoromethoxy-biphenyl-3-yl)-3H-[1,2,3]triazole-4-carbonitrile,
5-(5-chloro-3'-fluoro-4'-trifluoromethoxy-biphenyl-3-yl)-2H-[1,2,3]triazole-4-carbonitrile,
5-(5-chloro-3'-fluoro-4'-trifluoromethoxy-biphenyl-3-yl)-1H-[1,2,3]triazole-4-carbonitrile,
5-(3'-fluoro-5,4'-bis-trifluoromethoxy-biphenyl-3-yl)-3H-[1,2,3]triazole-4-carbonitrile,
5-(3'-fluoro-5,4'-bis-trifluoromethoxy-biphenyl-3-yl)-2H-[1,2,3]triazole-4-carbonitrile,
5-(3'-fluoro-5,4'-bis-trifluoromethoxy-biphenyl-3-yl)-1-H-[1,2,3]triazole-4-carbonitrile,
5-[3-(3,4-bis-trifluoromethyl-benzyloxy)-phenyl]-3H-[1,2,3]triazole-4-carbonitrile,
5-[3-(3,4-bis-trifluoromethyl-benzyloxy)-phenyl]-2H-[1,2,3]triazole-4-carbonitrile,
5-[3-(3,4-bis-trifluoromethyl-benzyloxy)-phenyl]-1H-[1,2,3]triazole-4-carbonitrile,
5-[3-(2,5-bis-trifluoromethyl-benzyloxy)-5-trifluoromethoxy-phenyl]-3H-[1,2,3]triazole-4-carbonitrile,
5-[3-(2,5-bis-trifluoromethyl-benzyloxy)-5-trifluoromethoxy-phenyl]-2H-[1,2,3]triazole-4-carbonitrile,
5-[3-(2,5-bis-trifluoromethyl-benzyloxy)-5-trifluoromethoxy-phenyl]-1H-[1,2,3]triazole-4-carbonitrile,
5-{3-[(E)-2-(4-fluoro-2-trifluoromethyl-phenyl)-vinyl]-phenyl}-3H-[1,2,3]triazole-4-carbonitrile,
5-{3-[(E)-2-(4-fluoro-2-trifluoromethyl-phenyl)-vinyl]-phenyl}-2H-[1,2,3]triazole-4-carbonitrile,
5-{3-[(E)-2-(4-fluoro-2-trifluoromethyl-phenyl)-vinyl]-phenyl}-1H-[1,2,3]triazole-4-carbonitrile,
5-{3-[(E)-2-(4-fluoro-3-methyl-phenyl)-vinyl]-phenyl}-3H-[1,2,3]triazole-4-carbonitrile,
5-{3-[(E)-2-(4-fluoro-3-methyl-phenyl)-vinyl]-phenyl}-2H-[1,2,3]triazole-4-carbonitrile,
5-{3-[(E)-2-(4-fluoro-3-methyl-phenyl)-vinyl]-phenyl}-1H-[1,2,3]triazole-4-carbonitrile,
5-{3-[(E)-2-(3,5-bis-trifluoromethyl-phenyl)-vinyl]-5-chloro-phenyl}-3H-[1,2,3]triazole-4-carbonitrile,
5-{3-[(E)-2-(3,5-bis-trifluoromethyl-phenyl)-vinyl]-5-chloro-phenyl}-2H-[1,2,3]triazole-4-carbonitrile,
5-{3-[(E)-2-(3,5-bis-trifluoromethyl-phenyl)-vinyl]-5-chloro-phenyl}-1H-[1,2,3]triazole-4-carbonitrile,
5-{3-[(E)-2-(3-trifluoromethyl-phenyl)-vinyl]-phenyl}-3H-[1,2,3]triazole-4-carbonitrile,
5-{3-[(E)-2-(3-trifluoromethyl-phenyl)-vinyl]-phenyl}-2H-[1,2,3]triazole-4-carbonitrile,
5-{3-[(E)-2-(3-trifluoromethyl-phenyl)-vinyl]-phenyl}-1H-[1,2,3]triazole-4-carbonitrile,
5-{3-[(E)-2-(4-trifluoromethyl-phenyl)-vinyl]-phenyl}-3H-[1,2,3]triazole-4-carbonitrile,
5-{3-[(E)-2-(4-trifluoromethyl-phenyl)-vinyl]-phenyl}-2H-[1,2,3]triazole-4-carbonitrile,
5-{3-[(E)-2-(4-trifluoromethyl-phenyl)-vinyl]-phenyl}-1H-[1,2,3]triazole-4-carbonitrile,
5-{3-trifluoromethyl-5-[(E)-2-(3-trifluoromethyl-phenyl)-vinyl]-phenyl}-3H-[1,2,3]triazole-4-carbonitrile,
5-{3-trifluoromethyl-5-[(E)-2-(3-trifluoromethyl-phenyl)-vinyl]-phenyl}-2H-[1,2,3]triazole-4-carbonitrile,
5-{3-trifluoromethyl-5-[(E)-2-(3-trifluoromethyl-phenyl)-vinyl]-phenyl}-1H-[1,2,3]triazole-4-carbonitrile,
5-{3-chloro-5-[(E)-2-(4-fluoro-phenyl)-vinyl]-phenyl}-3H-[1,2,3]triazole-4-carbonitrile,
5-{3-chloro-5-[(E)-2-(4-fluoro-phenyl)-vinyl]-phenyl}-2H-[1,2,3]triazole-4-carbonitrile,
5-{3-chloro-5-[(E)-2-(4-fluoro-phenyl)-vinyl]-phenyl}-1H-[1,2,3]triazole-4-carbonitrile,
5-{3-[(E)-2-(4-fluoro-phenyl)-vinyl]-5-methyl-phenyl}-3H-[1,2,3]triazole-4-carbonitrile,
5-{3-[(E)-2-(4-fluoro-phenyl)-vinyl]-5-methyl-phenyl}-2H-[1,2,3]triazole-4-carbonitrile,
5-{3-[(E)-2-(4-fluoro-phenyl)-vinyl]-5-methyl-phenyl}-1H-[1,2,3]triazole-4-carbonitrile,
5-{3-[(E)-2-(4-fluoro-phenyl)-vinyl]-5-trifluoromethoxy-phenyl}-3H-[1,2,3]triazole-4-carbonitrile,
5-{3-[(E)-2-(4-fluoro-phenyl)-vinyl]-5-trifluoromethoxy-phenyl}-2H-[1,2,3]triazole-4-carbonitrile,
5-{3-[(E)-2-(4-fluoro-phenyl)-vinyl]-5-trifluoromethoxy-phenyl}-1H-[1,2,3]triazole-4-carbonitrile,
5-{3-[(E)-2-(4-fluoro-phenyl)-vinyl]-phenyl}-3H-[1,2,3]triazole-4-carbonitrile,
5-{3-[(E)-2-(4-fluoro-phenyl)-vinyl]-phenyl}-2H-[1,2,3]triazole-4-carbonitrile,
5-{3-[(E)-2-(4-fluoro-phenyl)-vinyl]-phenyl}-1H-[1,2,3]triazole-4-carbonitrile,
5-{3-ethoxy-5-[(E)-2-(3-trifluoromethyl-phenyl)-vinyl]-phenyl}-3H-[1,2,3]triazole-4-carbonitrile,
5-{3-ethoxy-5-[(E)-2-(3-trifluoromethyl-phenyl)-vinyl]-phenyl}-2H-[1,2,3]triazole-4-carbonitrile,
5-{3-ethoxy-5-[(E)-2-(3-trifluoromethyl-phenyl)-vinyl]-phenyl}-1H-[1,2,3]triazole-4-carbonitrile,
5-{3-[(E)-2-(2,4-difluoro-phenyl)-vinyl]-5-trifluoromethyl-phenyl}-3H-[1,2,3]triazole-4-carbonitrile,
5-{3-[(E)-2-(2,4-difluoro-phenyl)-vinyl]-5-trifluoromethyl-phenyl}-2H-[1,2,3]triazole-4-carbonitrile,
5-{3-[(E)-2-(2,4-difluoro-phenyl)-vinyl]-5-trifluoromethyl-phenyl}-1H-[1,2,3]triazole-4-carbonitrile,
5-{3-[(E)-2-(2,4-difluoro-phenyl)-vinyl]-phenyl}-3H-[1,2,3]triazole-4-carbonitrile,
5-{3-[(E)-2-(2,4-difluoro-phenyl)-vinyl]-phenyl}-2H-[1,2,3]triazole-4-carbonitrile,
5-{3-[(E)-2-(2,4-difluoro-phenyl)-vinyl]-phenyl}-1H-[1,2,3]triazole-4-carbonitrile,
5-{3-chloro-5-[(E)-2-(3-trifluoromethoxy-phenyl)-vinyl]-phenyl}-3H-[1,2,3]triazole-4-carbonitrile,
5-{3-chloro-5-[(E)-2-(3-trifluoromethoxy-phenyl)-vinyl]-phenyl}-2H-[1,2,3]triazole-4-carbonitrile,
5-{3-chloro-5-[(E)-2-(3-trifluoromethoxy-phenyl)-vinyl]-phenyl}-1H-[1,2,3]triazole-4-carbonitrile,
5-{3-methoxy-5-[(E)-2-(3-trifluoromethyl-phenyl)-vinyl]-phenyl}-3H-[1,2,3]triazole-4-carbonitrile,
5-{3-methoxy-5-[(E)-2-(3-trifluoromethyl-phenyl)-vinyl]-phenyl}-2H-[1,2,3]triazole-4-carbonitrile,
5-{3-methoxy-5-[(E)-2-(3-trifluoromethyl-phenyl)-vinyl]-phenyl}-1H-[1,2,3]triazole-4-carbonitrile,
5-{3-[(E)-2-(3-fluoro-5-trifluoromethyl-phenyl)-vinyl]-phenyl}-3H-[1,2,3]triazole-4-carbonitrile,
5-{3-[(E)-2-(3-fluoro-5-trifluoromethyl-phenyl)-vinyl]-phenyl}-2H-[1,2,3]triazole-4-carbonitrile,
5-{3-[(E)-2-(3-fluoro-5-trifluoromethyl-phenyl)-vinyl]-phenyl}-1H-[1,2,3]triazole-4-carbonitrile,
5-{3-[(E)-2-(4-fluoro-3-trifluoromethyl-phenyl)-vinyl]-phenyl}-3H-[1,2,3]triazole-4-carbonitrile,
5-{3-[(E)-2-(4-fluoro-3-trifluoromethyl-phenyl)-vinyl]-phenyl}-2H-[1,2,3]triazole-4-carbonitrile,
5-{3-[(E)-2-(4-fluoro-3-trifluoromethyl-phenyl)-vinyl]-phenyl}-1H-[1,2,3]triazole-4-carbonitrile,
5-(3-benzo[b]thiophen-2-yl-5-chloro-phenyl)-3H-[1,2,3]triazole-4-carbonitrile,
5-(3-benzo[b]thiophen-2-yl-5-chloro-phenyl)-2H-[1,2,3]triazole-4-carbonitrile,
5-(3-benzo[b]thiophen-2-yl-5-chloro-phenyl)-1H-[1,2,3]triazole-4-carbonitrile, 5-[3-(4-trifluoromethyl-pyridin-2-yl)-phenyl]-3H-[1,2,3]triazole-4-carbonitrile,
5-[3-(4-trifluoromethyl-pyridin-2-yl)-phenyl]-2H-[1,2,3]triazole-4-carbonitrile,
5-[3-(4-trifluoromethyl-pyridin-2-yl)-phenyl]-1H-[1,2,3]triazole-4-carbonitrile,
5-[3-methyl-5-(5-trifluoromethyl-pyridin-2-yl)-phenyl]-3H-[1,2,3]triazole-4-carbonitrile,
5-[3-methyl-5-(5-trifluoromethyl-pyridin-2-yl)-phenyl]-2H-[1,2,3]triazole-4-carbonitrile,
5-[3-methyl-5-(5-trifluoromethyl-pyridin-2-yl)-phenyl]-1H-[1,2,3]triazole-4-carbonitrile,
5-[3-(2,2-difluoro-benzo[1,3]dioxol-5-yl)-phenyl]-3H-[1,2,3]triazole-4-carbonitrile,
5-[3-(2,2-difluoro-benzo[1,3]dioxol-5-yl)-phenyl]-2H-[1,2,3]triazole-4-carbonitrile,
5-[3-(2,2-difluoro-benzo[1,3]dioxol-5-yl)-phenyl]-1H-[1,2,3]triazole-4-carbonitrile,
5-[3-(2,2-difluoro-benzo[1,3]dioxol-5-yl)-5-trifluoromethoxy-phenyl]-3H-[1,2,3]triazole-4-carbonitrile,
5-[3-(2,2-difluoro-benzo[1,3]dioxol-5-yl)-5-trifluoromethoxy-phenyl]-2H-[1,2,3]triazole-4-carbonitrile,
5-[3-(2,2-difluoro-benzo[1,3]dioxol-5-yl)-5-trifluoromethoxy-phenyl]-1H-[1,2,3]triazole-4-carbonitrile,
5-[3-ethoxy-5-(4-trifluoromethyl-pyrimidin-2-yl)-phenyl]-3H-[1,2,3]triazole-4-carbonitrile,
5-[3-ethoxy-5-(4-trifluoromethyl-pyrimidin-2-yl)-phenyl]-2H-[1,2,3]triazole-4-carbonitrile,
5-[3-ethoxy-5-(4-trifluoromethyl-pyrimidin-2-yl)-phenyl]-1H-[1,2,3]triazole-4-carbonitrile,
5-[3-methyl-4-(4-trifluoromethyl-pyrimidin-2-yl)-phenyl]-3H-[1,2,3]triazole-4-carbonitrile,
5-[3-methyl-4-(4-trifluoromethyl-pyrimidin-2-yl)-phenyl]-2H-[1,2,3]triazole-4-carbonitrile,
5-[3-methyl-4-(4-trifluoromethyl-pyrimidin-2-yl)-phenyl]-1H-[1,2,3]triazole-4-carbonitrile,
5-[3-((E)-2-benzo[b]thiophen-2-yl-vinyl)-phenyl]-3H-[1,2,3]triazole-4-carbonitrile,
5-[3-((E)-2-benzo[b]thiophen-2-yl-vinyl)-phenyl]-2H-[1,2,3]triazole-4-carbonitrile,
5-[3-((E)-2-benzo[b]thiophen-2-yl-vinyl)-phenyl]-1H-[1,2,3]triazole-4-carbonitrile,
5-{3-[(E)-2-(2,2-difluoro-benzo[1,3]dioxol-5-yl)-vinyl]-phenyl}-3H-[1,2,3]triazole-4-carbonitrile,
5-{3-[(E)-2-(2,2-difluoro-benzo[1,3]dioxol-5-yl)-vinyl]-phenyl}-2H-[1,2,3]triazole-4-carbonitrile,
5-{3-[(E)-2-(2,2-difluoro-benzo[1,3]dioxol-5-yl)-vinyl]-phenyl}-1H-[1,2,3]triazole-4-carbonitrile,
5-{3-[(E)-2-(6-trifluoromethyl-pyridin-2-yl)-vinyl]-phenyl}-3H-[1,2,3]triazole-4-carbonitrile,
5-{3-[(E)-2-(6-trifluoromethyl-pyridin-2-yl)-vinyl]-phenyl}-2H-[1,2,3]triazole-4-carbonitrile,
5-{3-[(E)-2-(6-trifluoromethyl-pyridin-2-yl)-vinyl]-phenyl}-1H-[1,2,3]triazole-4-carbonitrile,
5-[2-(4-chloro-2-fluoro-phenyl)-5-ethyl-thiazol-4-yl]-3H-[1,2,3]triazole-4-carbonitrile,
5-[2-(4-chloro-2-fluoro-phenyl)-5-ethyl-thiazol-4-yl]-2H-[1,2,3]triazole-4-carbonitrile,
5-[2-(4-chloro-2-fluoro-phenyl)-5-ethyl-thiazol-4-yl]-1H-[1,2,3]triazole-4-carbonitrile,
5-{5-[(E)-2-(4-fluoro-phenyl)-vinyl]-furan-2-yl}-3H-[1,2,3]triazole-4-carbonitrile,
5-{5-[(E)-2-(4-fluoro-phenyl)-vinyl]-furan-2-yl}-2H-[1,2,3]triazole-4-carbonitrile,
5-{5-[(E)-2-(4-fluoro-phenyl)-vinyl]-furan-2-yl}-1H-[1,2,3]triazole-4-carbonitrile,
5-(6-(benzofuran-2-yl)-pyridin-2-yl)-3H-[1,2,3]triazole-4-carbonitrile,
5-(6-(benzofuran-2-yl)-pyridin-2-yl)-2H-[1,2,3]triazole-4-carbonitrile,
5-(6-(benzofuran-2-yl)-pyridin-2-yl)-1H-[1,2,3]triazole-4-carbonitrile,
5-(2-phenyl-6-(piperidin-1-yl)-pyrimidin-4-yl)-3H-[1,2,3]triazole-4-carbonitrile,
5-(2-phenyl-6-(piperidin-1-yl)-pyrimidin-4-yl)-2H-[1,2,3]triazole-4-carbonitrile,
5-(2-phenyl-6-(piperidin-1-yl)-pyrimidin-4-yl)-1H-[1,2,3]triazole-4-carbonitrile,
5-(2-phenyl-6-(pyrrolidin-1-yl)-pyrimidin-4-yl)-3H-[1,2,3]triazole-4-carbonitrile,
5-(2-phenyl-6-(pyrrolidin-1-yl)-pyrimidin-4-yl)-2H-[1,2,3]triazole-4-carbonitrile,
5-(2-phenyl-6-(pyrrolidin-1-yl)-pyrimidin-4-yl)-1H-[1,2,3]triazole-4-carbonitrile,
3-(1-{4-[3-(2,5-bis-trifluoromethyl-benzyloxy)-phenyl]-5-cyano-2H-[1,2,3]triazol-2-yl}-ethoxycarbonyloxy)-2,2-dimethyl-propionic acid,
3-(1-{4-[3-chloro-5-(2,2-difluoro-benzo[1,3]dioxol-5-yl)-phenyl]-5-cyano-2H-[1,2,3]triazol-2-yl}-ethoxycarbonyloxy)-2,2-dimethyl-propionic acid,
3-(1-{4-[3-chloro-5-(4-trifluoromethyl-pyrimidin-2-yl)-phenyl]-5-cyano-2H-[1,2,3]triazol-2-yl}-ethoxycarbonyloxy)-2,2-dimethyl-propionic acid,
3-[1-(4-{3-chloro-5-[(E)-2-(3-trifluoromethyl-phenyl)-vinyl]-phenyl}-5-cyano-2H-[1,2,3]triazol-2-yl)-ethoxycarbonyloxy]-2,2-dimethyl-propionic acid,
3-(1-{4-cyano-5-[3-methoxy-5-(4-trifluoromethyl-pyridin-2-yl)-phenyl]-2H-[1,2,3]triazol-2-yl}-ethoxycarbonyloxy)-2,2-dimethyl-propionic acid,
3-[1-(4-cyano-5-{3-trifluoromethyl-5-[(E)-2-(6-trifluoromethyl-pyridin-2-yl)-vinyl]-phenyl}-2H-[1,2,3]triazol-2-yl)-ethoxycarbonyloxy]-2,2-dimethyl-propionic acid,
3-(1-{4-[2-(4-chloro-phenyl)-thiazol-4-yl]-5-cyano-2H-[1,2,3]triazol-2-yl}-ethoxycarbonyloxy)-2,2-dimethyl-propionic acid,
3-[1-(4-cyano-5-{3-[(E)-2-(4-trifluoromethyl-pyridin-2-yl)-vinyl]-phenyl}-2H-[1,2,3]triazol-2-yl)-ethoxycarbonyloxy]-2,2-dimethyl-propionic acid,
3-[1-(4-cyano-5-{3-[(E)-2-(4-trifluoromethyl-pyrimidin-2-yl)-vinyl]-phenyl}-2H-[1,2,3]triazol-2-yl)-ethoxycarbonyloxy]-2,2-dimethyl-propionic acid,
3-(1-{4-[5-chloro-2-(3-trifluoromethyl-phenyl)-thiazol-4-yl]-5-cyano-2H-[1,2,3]triazol-2-yl}-ethoxycarbonyloxy)-2,2-dimethyl-propionic acid,
3-(1-{4-cyano-5-[2-(3-trifluoromethoxy-phenyl)-thiazol-4-yl]-2H-[1,2,3]triazol-2-yl}-ethoxycarbonyloxy)-2,2-dimethyl-propionic acid,
3-(1-{4-cyano-5-[2-(3,4-dichloro-phenyl)-thiazol-4-yl]-2H-[1,2,3]triazol-2-yl}-ethoxycarbonyloxy)-2,2-dimethyl-propionic acid,
3-(1-{4-cyano-5-[5-methyl-2-(4-trifluoromethyl-phenyl)-thiazol-4-yl]-2H-[1,2,3]triazol-2-yl}-ethoxycarbonyloxy)-2,2-dimethyl-propionic acid,
3-(1-{4-[2-(4-chloro-phenyl)-5-isopropyl-oxazol-4-yl]-5-cyano-2H-[1,2,3]triazol-2-yl}-ethoxycarbonyloxy)-2,2-dimethyl-propionic acid,
3-(1-{4-[2-(3-chloro-4-fluoro-phenyl)-5-methyl-thiazol-4-yl]-5-cyano-2H-[1,2,3]triazol-2-yl}-ethoxycarbonyloxy)-2,2-dimethyl-propionic acid,
3-(1-{4-cyano-5-[5-cyclopropyl-2-(3-trifluoromethyl-phenyl)-oxazol-4-yl]-2H-[1,2,3]triazol-2-yl}-ethoxycarbonyloxy)-2,2-dimethyl-propionic acid, 3-(1-{4-cyano-5-[3-methyl-5-(6-trifluoromethyl-pyridin-3-yl)-phenyl]-2H-[1,2,3]triazol-2-yl}-ethoxycarbonyloxy)-2,2-dimethyl-propionic acid, 3-(1-{4-cyano-5-[5-ethyl-2-(5-trifluoromethyl-pyridin-2-yl)-thiazol-4-yl]-2H-[1,2,3]triazol-2-yl}-ethoxycarbonyloxy)-2,2-dimethyl-propionic acid, 3-(1-{4-[3-(2,5-bis-trifluoromethylbenzyloxy)phenyl]-5-cyano-2H-[1,2,3]triazol-2-yl}ethoxycarbonyloxy)-3-methylbutyric acid, carbonic acid 1-{4-[3-(2,5-bis-trifluoromethylbenzyloxy)phenyl]-5-cyano-2H-[1,2,3]triazol-2-yl}ethyl ester-2-hydroxyethyl ester, acetic acid 4-cyano-5-[3-methyl-5-(4-trifluoromethylpyrimidin-2-yl)phenyl]-2H-[1,2,3]triazol-2-ylmethyl ester, acetic acid 4-{3-chloro-5-[(E)-2-(3-trifluoromethylphenyl) vinyl]phenyl}-5-cyano-2H-[1,2,3]triazol-2-ylmethyl ester, and butyric acid 4-{3-chloro-5-[(E)-2-(3-trifluoromethyl-phenyl)-vinyl]-phenyl}-5-cyano-2H-[1,2,3]triazol-2-ylmethyl ester, or a salt thereof.

11. The cyanotriazole compound or salt according to claim 8, wherein $R^{1b}$ is one of the following (1-1) to (1-5):

(1-1) a phenyl group optionally substituted with one or more members selected from:
- (1-1-1) a lower alkyl group optionally substituted with one or more halogen atoms,
- (1-1-2) a lower alkoxy group optionally substituted with one or more halogen atoms,
- (1-1-9) a halogen atom,
- (1-1-11) a phenyl group optionally substituted with one or more lower alkoxy groups optionally substituted with one or more halogen atoms,
- (1-1-12) a phenyl lower alkyl group optionally substituted on the phenyl ring with one or more halogen atoms,
- (1-1-13) a styryl group substituted on the phenyl ring with one or more lower alkyl groups substituted with one or more halogen atoms,
- (1-1-16) a phenyl lower alkoxy group optionally substituted on the phenyl ring with one or more lower alkyl groups optionally substituted with one or more halogen atoms,
- (1-1-21) a pyridyl group optionally substituted with one or more lower alkyl groups optionally substituted with one or more halogen atoms,
- (1-1-23) a pyridyloxy lower alkyl group optionally substituted on the pyridine ring with one or more lower alkyl groups optionally substituted with one or more halogen atoms,
- (1-1-24) a pyridylvinyl group optionally substituted on the pyridine ring with one or more lower alkyl groups optionally substituted with one or more halogen atoms,
- (1-1-25) a pyrimidinyl group optionally substituted with one or more lower alkyl groups optionally substituted with one or more halogen atoms,
- (1-1-26) a pyrimidinylvinyl group optionally substituted on the pyrimidine ring with one or more lower alkyl groups optionally substituted with one or more halogen atoms,
- (1-1-31) a thienyl group, and
- (1-1-33) a benzo[1,3]dioxolyl group optionally substituted with one or more halogen atoms, (1-2) a thiazolyl group optionally substituted with one or more members selected from:
- (1-2-1) a lower alkyl group optionally substituted with one or more halogen atoms,
- (1-2-4) a halogen atom,
- (1-2-5) a phenyl group optionally substituted with one or more members selected from the group consisting of a halogen atom; a lower alkyl group optionally substituted with one or more halogen atoms; and a lower alkoxy group optionally substituted with one or more halogen atoms, and
- (1-2-11) a pyridyl group optionally substituted with one or more lower alkyl groups optionally substituted with one or more halogen atoms, (1-3) an oxazolyl group optionally substituted with one or more members selected from:
- (1-3-1) a lower alkyl group,
- (1-3-2) a cycloalkyl group, and
- (1-3-3) a phenyl group optionally substituted with one or more members selected from the group consisting of a halogen atom; and a lower alkyl group optionally substituted with one or more halogen atoms, (1-4) a thienyl group optionally substituted with one or more members selected from:
- (1-4-2) a phenyl group optionally substituted with one or more lower alkyl groups optionally substituted with one or more halogen atoms, and (1-5) a furyl group optionally substituted with one or more members selected from:
- (1-5-1) a phenyl group optionally substituted with one or more halogen atoms; and $R^{2a}$ is one of the following groups:

a 1-(((2-carboxy-2,2-dimethylethoxy)carbonyl)oxy)ethyl group;

a 1-(((2-carboxy-1,1-dimethylethoxy)carbonyl)oxy)ethyl group;

a 1-(((2-hydroxyethoxy)carbonyl)oxy)ethyl group;

a 1-(butyryloxy)ethyl group;

a 1-(isobutyryloxy)ethyl group;

an acetoxymethyl group; and a butyryloxymethyl group.

* * * * *